(12) United States Patent
Brown et al.

(10) Patent No.: US 8,030,354 B2
(45) Date of Patent: Oct. 4, 2011

(54) SUBSTITUTED BIPHENYL GPR40 MODULATORS

(75) Inventors: Sean P. Brown, San Francisco, CA (US); Qiong Cao, Daly City, CA (US); Paul John Dransfield, San Francisco, CA (US); Xiaohui Du, Belmont, CA (US); Zice Fu, Foster City, CA (US); Jonathan Houze, San Mateo, CA (US); Xian Yun Jiao, Belmont, CA (US); Yong-Jae Kim, Foster City, CA (US); Todd J. Kohn, San Mateo, CA (US); SuJen Lai, Burlingame, CA (US); An-Rong Li, San Mateo, CA (US); Daniel Lin, Redwood City, CA (US); Jiwen Liu, Foster City, CA (US); Jian Luo, Albany, CA (US); Julio C. Medina, San Carlos, CA (US); Jeffrey D. Reagan, Woodside, CA (US); Vatee Pattaropong, Burlingame, CA (US); Margrit Schwarz, San Carlos, CA (US); Wang Shen, San Mateo, CA (US); Yongli Su, Foster City, CA (US); Gayathri Swaminath, Fremont, CA (US); Marc Vimolratana, San Mateo, CA (US); Yingcai Wang, Millbrae, CA (US); Yumei Xiong, San Bruno, CA (US); Li Yang, San Francisco, CA (US); Ming Yu, Foster City, CA (US); Jie Zhang, Sunnyvale, CA (US); Liusheng Zhu, Foster City, CA (US)

(73) Assignee: Amgen Inc., Thousand Oaks, CA (US)

( * ) Notice: Subject to any disclaimer, the term of this patent is extended or adjusted under 35 U.S.C. 154(b) by 488 days.

(21) Appl. No.: 12/287,036

(22) Filed: Oct. 3, 2008

(65) Prior Publication Data
US 2009/0137561 A1    May 28, 2009

Related U.S. Application Data

(60) Provisional application No. 60/998,786, filed on Oct. 10, 2007, provisional application No. 61/068,724, filed on Mar. 6, 2008.

(51) Int. Cl.
*A61K 31/192* (2006.01)
*C07C 53/134* (2006.01)

(52) U.S. Cl. ........ 514/570; 562/496; 562/512; 546/342; 514/357

(58) Field of Classification Search .................. 514/570, 514/357; 562/496, 512; 546/342
See application file for complete search history.

(56) References Cited

U.S. PATENT DOCUMENTS

| | | | |
|---|---|---|---|
| 3,507,881 A | 4/1970 | Sandberg et al. | |
| 4,760,089 A | 7/1988 | Chambers et al. | |
| 5,312,960 A | 5/1994 | Krämer et al. | |
| 6,037,367 A | 3/2000 | Christensen, IV et al. | |
| 6,506,757 B1 | 1/2003 | Tajima et al. | |
| 6,620,832 B2 | 9/2003 | Eastwood | |
| 6,645,939 B1 | 11/2003 | Durette et al. | |
| 6,710,063 B1 | 3/2004 | Chao et al. | |
| 6,723,740 B2 | 4/2004 | Chao et al. | |
| 6,875,780 B2 | 4/2005 | Auerbach et al. | |
| 6,906,046 B2 | 6/2005 | Jackson et al. | |
| 6,939,875 B2 | 9/2005 | Auerbach et al. | |
| 6,964,983 B2 | 11/2005 | Auerbach et al. | |
| 7,326,732 B2 | 2/2008 | Oxford et al. | |
| 7,338,960 B2 | 3/2008 | Bell et al. | |
| 7,345,068 B2 | 3/2008 | Endou et al. | |
| 7,456,218 B2 * | 11/2008 | Yasuma et al. | 514/568 |
| 2004/0058965 A1 | 3/2004 | Momose et al. | |
| 2005/0089866 A1 | 4/2005 | Hinuma et al. | |
| 2005/0119256 A1 | 6/2005 | Endo et al. | |
| 2006/0003344 A1 | 1/2006 | Houseknecht et al. | |
| 2006/0004012 A1 | 1/2006 | Akerman et al. | |

(Continued)

FOREIGN PATENT DOCUMENTS
AU         A 27141/77         1/1979

(Continued)

OTHER PUBLICATIONS

U.S. Appl. No. 12/082,645, filed Apr. 10, 2008, Brown et al.

(Continued)

*Primary Examiner* — Charanjit Aulakh
(74) *Attorney, Agent, or Firm* — Bernard P. Friedrichsen

(57) ABSTRACT

The present invention provides compounds useful, for example, for treating metabolic disorders in a subject. Such compounds have the general formula I:

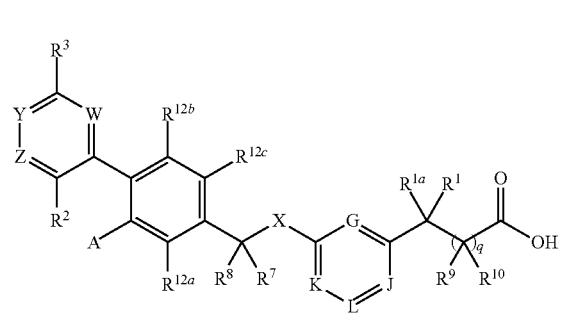

I where the definitions of the variables are provided herein. The present invention also provides compositions that include, and methods for using, the compounds in preparing medicaments and for treating metabolic disorders such as, for example, type II diabetes.

96 Claims, 11 Drawing Sheets

U.S. PATENT DOCUMENTS

| | | | |
|---|---|---|---|
| 2006/0270724 | A1 | 11/2006 | Houze et al. |
| 2007/0066647 | A1 | 3/2007 | Akerman et al. |
| 2007/0149608 | A1 | 6/2007 | Yasuma et al. |
| 2007/0244155 | A1 | 10/2007 | Sharma et al. |
| 2007/0265332 | A1 | 11/2007 | Ge et al. |
| 2008/0090840 | A1 | 4/2008 | Beck et al. |
| 2008/0119511 | A1 | 5/2008 | Brown et al. |
| 2010/0144806 | A1 | 6/2010 | Yasuma et al. |

FOREIGN PATENT DOCUMENTS

| | | |
|---|---|---|
| AU | A 52306/93 | 6/1994 |
| CA | 2111035 | 6/1994 |
| DE | 199 41 567 A1 | 4/2000 |
| DE | 199 41567 A1 | 4/2000 |
| EP | 0 250 264 A1 | 12/1987 |
| EP | 0 414 289 B1 | 2/1994 |
| EP | 1 357 115 A1 | 10/2003 |
| EP | 1 380 562 A1 | 1/2004 |
| EP | 1 535 915 A1 | 6/2005 |
| EP | 1 559 422 A1 | 8/2005 |
| EP | 1 630 152 A1 | 3/2006 |
| EP | 1 731 505 A1 | 12/2006 |
| JP | 10316641 A | 2/1998 |
| JP | 2001242165 | 9/2001 |
| JP | 2002003368 | 1/2002 |
| WO | WO 93/23040 | 11/1993 |
| WO | WO 93/23041 | 11/1993 |
| WO | WO 95/01326 | 1/1995 |
| WO | WO 95/01348 | 1/1995 |
| WO | WO 97/12867 | 4/1997 |
| WO | WO 99/11255 | 3/1999 |
| WO | WO 00/63196 | 10/2000 |
| WO | WO 01/00603 A1 | 1/2001 |
| WO | WO 01/36351 A2 | 5/2001 |
| WO | WO 01/36365 A2 | 5/2001 |
| WO | WO 02/057783 A2 | 7/2002 |
| WO | WO 02/062774 A1 | 8/2002 |
| WO | WO 02/100403 A1 | 12/2002 |
| WO | WO 03/074050 A1 | 9/2003 |
| WO | WO 03/099793 A1 | 12/2003 |
| WO | WO 04/000315 A1 | 12/2003 |
| WO | WO 2004/092117 A1 | 10/2004 |
| WO | WO 2004/106276 A1 | 12/2004 |
| WO | WO 2005/051890 A1 | 6/2005 |
| WO | WO 2005/058848 A1 | 6/2005 |
| WO | WO 2005/063725 A1 | 7/2005 |
| WO | WO 2005/063729 A1 | 7/2005 |
| WO | WO 2005/086661 A2 | 9/2005 |
| WO | WO 2005/087710 A1 | 9/2005 |
| WO | WO 2006/001092 A1 | 1/2006 |
| WO | WO 2006/011615 A1 | 2/2006 |
| WO | WO 2006/083612 A1 | 8/2006 |
| WO | WO 2006/083781 A1 | 8/2006 |
| WO | WO 2007/008541 A2 | 1/2007 |
| WO | WO 2007/013689 A1 | 2/2007 |
| WO | WO 2007/049050 A2 | 5/2007 |
| WO | WO 2007/123225 A1 | 11/2007 |
| WO | WO 2007/131619 A1 | 11/2007 |
| WO | WO 2007/131620 A1 | 11/2007 |
| WO | WO 2007/131622 A1 | 11/2007 |
| WO | WO 2008/001931 A2 | 1/2008 |
| WO | WO 2008/054675 A2 | 5/2008 |
| WO | WO 2008/130514 A1 | 10/2008 |

OTHER PUBLICATIONS

International Search Report and Written Opinion from co-pending PCT Application No. PCT/US2008/011422 mailed on Feb. 27, 2009.
Bachmann, W. E. et al., "The Synthesis of an Analog of the Sex Hormones," *J. Am. Chem. Soc.*, 64, 94-97 (1942).
Berthelot et al., "Synthesis and Pharmacological Evaluation of y-Aminobutyric Acid Analogues. New Ligand for $GABA_B$ Sites," *J. Med. Chem.*, 30, 743-746 (1987).
Booth, C. J. et al., "The Synthesis and Transition Temperatures of Novel Low Molar Mass Chosesteric materials Derives from (R)-2-(4-Hydroxyphenoxy)propanoic Acid," Mol. Cryst. Liq. Cryst., vol. 210, pp. 31-57 (1992).
Booth, C. J. et al., "The Influence of the Liquid Crystalline Core Geometry on the Mesogenicity of Novel Chiral 2-(4-Substituted-phenoxy)propanonitriles," Liquid Crystals, vol. 16(6), pp. 925-940, (1994).
Boyle, Thomas F. et al., "Applications of the Spiroannulation of Tetralins with Alkynes; Towards New Anti-Estrogenic Compounds," *J. Chem. Soc. Perkin Trans. 1: Organic and Bioorganic Chem.*, 18, 2707-2711 (1997).
Briscoe et al., "The Orphan G Protein-Coupled Receptor GPR40 is Activated by Medium and Long Chain Fatty Acids," *J. of Biol. Chem.*, 278(13), 11303-11311 (2003).
Briscoe, C. P. et al., "Pharmacological Regulation of Insulin Secretion in MIN6 Cells Through the Fatty Acid Receptor GPR40: Identification of Agonist and Antagonist Small Molecules," *Brit. J. of Pharmacology*, 148, 619-628 (2006).
Burnop, V.C.E. et al., "Fused Carbon Rings. Part XIX. Experiments on the Synthesis of Tetracyclic Compounds of the Sexual Hormonal Type," *J. Chem. Soc.*, 727-735 (1940).
Chatterjee, A., et al., "Studies on Nucleophilic Ring Opening of Some Epoxides in Polar Protic Solvents," *Tetrahedron*, 33, 85-94 (1977).
Collins, David J. et al., "The Structure and Function of Oestrogens. IX*. Synthesis of the trans Isomer of 5,5,10b-Trimtehyl-4b,5,6,10b,11,12-hexahydrocvhrysene-2,8-diol," *Aust. J. Chem.*, 41, 735-744 (1988).
Deb, Soumitra et al., "A Stereocontrolled Synthesis of (1'RS,2'SR)-3-oxo-3',4'-dihydrospiro[cyclopentane-1,1'(2'H)-naphthalen]-2-yl Acetic Acid and its Methoxy Derivatives," *J. Chem. Res. Synops.*, 12, 406 (1985).
DeWolf et al., "Inactivation of Dopamine β-Hydroxylase by β-Ethynyltyramine: Kinetic Characterization and Covalent Modification of an Active Site Peptide," *Biochemistry*, 28, 3833-3842 (1989).
Egan, R. W. et al., "Naphthalenes as Inhibitors of Myeloperoxidase: Direct and Indirect Mechanisms of Inhibition," *Agents and Actions*, 29 3/4 266-276 (1990).
Frey et al., "Total Synthesis of Pentacyclic Diterpenoid Tropone Hainanolidol," *Aust. J. Chem.*, 53, 819-830 (2000).
Galemmo et al., "The Development of a Novel Series of (Quinolin-2-ylmethoxy) phenyl-Containing Compounds as High-Affinity Leukotriene Receptor Antagonists. 3. Structural Variation of the Acidic Side Chain to Give Antagonists of Enhanced Potency," *J. Med. Chem.*, 33, 2828-2841 (1990).
Garrido, D. M., et al., "Synthesis and Activity of Small Molecule GPR40 Agonists," *Bioorg. and Med. Chem. Lett.*, 16, 1840-1845 (2006).
Ghosal, Probir Kumar, et al., "Stereospecific Synthesis of 9bβ-Carbomethoxy-7-methoxy-2,3,3aα,4,5,9bβ-Hexahydro-1H-Benz[e]-Inden-2-one; An Intermediate Towards Physiologically Active Compounds," *Tet. Lett.*, 17, 1463-1464 (1977).
Guthrie, R. W. et al., "Synthesis in the Series of Diterpene Alkaloids VI. A Simple Synthesis of Atisine," *Tet. Lett.*, 38, 4645-4654 (1966).
Haigh et al., "Non-thiazolidinedione Antihyperglycaemic Agents. Part 3: The Effects of Stereochemistry on the Potency of α-Methoxy-β-phenylpropanoic Acids," *Bioorg. and Med. Chem.*, 7, 821-830 (1999).
Hares, Owen et al., "Sythetic Studies of Tricyclospirodienones: Model Chemistry for Novel Mimics of Steroid Substrates," *J. Chem. Soc. Perkin Trans. 1: Organic and Bioorganic Chem.*, 13, 1481-1492 (1993).
Houze, J. et al., "Beta-substituted Carboxylic Acids as Potent, Bioavailable Agonists of GPR40", 234th ACS National Meeting Boston, MA Aug. 19-23, 2007.
Iizuka et al., "β-Substituted Phenethylamines as High Affinity Mechanism-Based Inhibitors of Dopamine β-Hydroxylase," *J. Med. Chem.*, 31, 704-706 (1988).
Ishikawa et al., "Actions of the Novel Oral Antidiabetic Agent HQL-975 in Insulin-Resistant Non-Insulin—Dependent Diabetes Mellitus Model Animals," *Diabetes Res. and Clin. Pract.*, 41, 101-111 (1998).
Ishikawa et al., "Effects of the Novel Oral Antidiabetic Agent HQL-975 on Glucose and Lipid Metabolism in Diabetic db/db Mice," *Arzneim. Forsch. Drug Res.*, 48(3), 245-250 (1998).

Itoh et al., "Free Fatty Acids Regulate Insulin Secretion from Pancreatic β Cells Through GPR40," *Nature*, 422, 173-176 (2003).

Johns, William F. et al., "Total Synthesis of Estrajervatetraene," *J. Org. Chem.*, 44(6), 958-961 (1979).

Kao et al., "One-Pot Synthesis of the Hydroximoyl Chlorides and [3.3.0] Bicyclic Compounds from the Reactions of β-Nitrostyrenese with Stabilized Nucleophiles," *Tetrahedron*, 54(46), 13997-14014 (1998).

Kolasa et al., "Symmetrical Bis (heteroarylmethoxyphenyl) alkylcarboxylic Acids as Inhibitors of Leukotriene Biosynthesis," *J. Med. Chem.*, 43, 3322-3334 (2000).

Kotarsky et al., "A Human Cell Surface Receptor Activated by Free Fatty Acids and Thiazolidinedione Drugs", *Biochem. and Biophys. Res. Comm.*, 301, 406-410 (2003).

Kuchar et al., "Benzyloxyarylaliphatic Acids: Synthesis and Quantitative Relations Between Structure and Antiinflammatory Activity," *Collection Czechoslovak Chem, Comm.*, 47, 2514-2524 (1982).

Kuchar et al., "The Effects of Lopophilicity on the Inhibition of Denaturation of Serum Albumin and on the Activation of Fibrionolysis Observed with a Serixes of Benzyloxyarylaliphatic Acids," *Collection Czechoslovak Chem, Comm.*, 48, 1077-1088 (1983).

Lin, Llnus S. et al., "The Discovery of Acylated β-Amino Acids as Potent and Orally Bioavailable VLA-4 Antagonists," *Bioorg. and Med. Chem. Lett.*, 12, 611-614 (2002).

Liu et al., "Synthesis and Biological Activity of L-Tyrosine-based PPARγ Agonists with Reduced Molecular Weight," *Bioorg. and Med. Chem. Lett.*, 11, 3111-3113 (2001).

McKeown, S.C. et al., "Solid Phase Synthesis and SAR of Small Molecule Agonists for the GPR40 Receptor," Bioorg. and Med. Chem. Lett., 17, pp. 1584-1589 (2007).

Nilsson, N. E. et al., "Identification of a Free Fatty Acid Receptor, $FFA_2R$, Expressed on Leukocytes and Activated by Short-Chain Fatty Acids, " *Biochem. and Biophys. Res. Comm.*, 303 1047-1052 (2003).

Oliver et al., "A Selective Peroxisome Proliferator-Activated Receptor δ Agonist Promotes Reverse Cholesterol Transport," *PNAS*, 98(9), 5306-5311 (2001).

Poitout, Vincent, "The Ins and Outs of Fatty Acids on the Pancreatic β Cells," *Trends in Endocrinology and Metabolism*, 14(5), 201-203 (2003).

Ray, Chhanda et al., "Synthesis of some angularly cyclopentanone fused hydrophenanthrene and hydrofluorene derivatives by acid-catalyzed intramolecular C-alkylation of γ, δ -unsaturated α'-diazomethyl ketones," *Synthetic Commun.*, 21(10-11), 1223-1242 (1991).

Sandberg, Rune et al., "N-Aminoalkylsuccinimides as Local Anaesthetics," *Acta Pharmaceutica Suecica*, 17(4) 169-176 (1980).

Sanyal, Utpal et al., "A Novel Synthesis of a Tricyclo $(7.5.0^{1,5}.0^{1,9})$ Tetradecane Ring System Related to Gascardic Acid," *Tet. Lett.*, 25, 2187-2190 (1978).

Sarma, Aluru Sudarsana et al., "Synthetic Studies on Terpenoids. Parts XVIII. Stereocontrolled Synthesis of (+/−)-1,2,3,4,4a,9,10,10aα-Octahydro-1α-methylenephenanthrene-1β,4aβ-dicarboxylic acid and the 7-Methoxy Analog: A Potential Intermediate for Diterpinoid Synthesis," *J. Chem. Soc. Perkin Trans. I: Organic and Bioorganic Chem.*, 7, 722-727 (1976).

Sawzdargo et al., "A Cluster of Four Novel Human G Protein-Coupled Receptor Genes Occurring in Close Proximity to CD22 Gene on Chromosome 19q13.1", *Biochem. and Biophys. Res. Comm.*, 239, 543-547 (1997).

Shaw et al., "Enantioselective Synthesis of (+)-(2S, 3S)-3-Ethyltyrosine," *Tet. Lett.*, 31(35), 5081-84 (1990).

Shiotani, Shunsaku et al., "Synthesis of 1,3-Bridged 1,2,3,4,5,6-Hexahydro-2,6-methano-3-benzazocine Derivatives," *Chem. Pharm. Bull.*, 28(6), 1928-1931 (1980).

Song, F. et al., "Synthesis and Biological Evaluation of 3-Aryl-3-(4-phenoxy)-propionic Acid as a Novel Series of G Protein-Coupled REceptor 40 Agonists," J. Med. Chem. 50 pp. 2807-2817 (2007).

Waid et al., "Constrained Amino Acids. An Approach to the Synthesis of 3-Substituted Prolines," *Tet. Lett.*, 37(24), 4091-4094 (1996).

\* cited by examiner

SUBSTITUTED BIPHENYL GPR40 MODULATORS

1. CROSS REFERENCES TO RELATED APPLICATIONS

This application claims the benefit of U.S. Provisional Application No. 60/998,786, filed on Oct. 10, 2007, and U.S. Provisional Application No. 61/068,724, filed on Mar. 6, 2008, both of which are hereby incorporated by reference in their entireties and for all purposes as if specifically and fully set forth herein.

2. FIELD OF THE INVENTION

The present invention relates to compounds capable of modulating the G-protein-coupled receptor GPR40 and/or stimulating GLP-1 secretion, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

3. BACKGROUND OF THE INVENTION

The production of insulin is central to the regulation of carbohydrate and lipid metabolism. Insulin imbalances lead to conditions such as type II diabetes mellitus, a serious metabolic disease that afflicts around 5% of the population in Western Societies and over 150 million people worldwide. Insulin is secreted from pancreatic β cells in response to elevated plasma glucose which is augmented by the presence of fatty acids. The recent recognition of the function of the G-protein coupled receptor GPR40 in modulating insulin secretion has provided insight into regulation of carbohydrate and lipid metabolism in vertebrates, and further provided targets for the development of therapeutic agents for disorders such as obesity, diabetes, cardiovascular disease and dyslipidemia.

GPR40 is a member of the gene superfamily of G-protein coupled receptors ("GPCRs"). GPCRs are membrane proteins characterized as having seven putative transmembrane domains that respond to a variety of molecules by activating intra-cellular signaling pathways critical to a diversity of physiological functions. GPR40 was first identified as an orphan receptor (i.e., a receptor without a known ligand) from a human genomic DNA fragment. Sawzdargo et al. (1997) Biochem. Biophys. Res. Commun. 239: 543-547. GPR40 is highly expressed in pancreatic β cells and insulin-secreting cell lines. GPR40 activation is linked to modulation of the $G_q$ family of intra-cellular signaling proteins and concomitant induction of elevated calcium levels. It has been recognized that fatty acids serve as ligands for GPR40, and that fatty acids regulate insulin secretion through GPR40. Itoh et al. (2003) Nature 422:173-176; Briscoe et al. (2003) J. Biol. Chem. 278: 11303-11311; Kotarsky et al. (2003) Biochem. Biophys. Res. Commun. 301: 406-410.

Various documents have disclosed compounds reportedly having activity with respect to GPR40. For example, WO 2004/041266 and EP 1559422 disclose compounds that purportedly act as GPR40 receptor function regulators. WO 2004/106276 and EP 1630152 are directed to condensed ring compounds that purportedly possess GPR40 receptor function modulating action. More recently, WO 2005/086661 U.S. Patent Publication No. 2006/0004012, US Patent Publication No. 2006/0270724, and US Patent Publication No. 2007/0066647 disclose compounds useful for modulating insulin levels in subjects and useful for treating type II diabetes.

Although a number of compounds have been disclosed that reportedly modulate GPR40 activity, the prevalence of type II diabetes, obesity, hypertension, cardiovascular disease and dyslipidemia underscores the need for new therapies to effectively treat or prevent these conditions.

Glucagon-like peptide 1 (GLP-1) is a peptide that is secreted from the enteroendocrine L-cells of the gut in response to an oral glucose load or food ingestion. The active forms of GLP-1 are processed from a precursor and are denoted GLP-1(7-37) and GLP-1(7-36) amide. GLP-1 has many effects on peripheral tissues. GLP-1 activates its cognate receptor GLP-1R (GLP-1 receptor) on pancreatic beta cells and potentiates glucose stimulated insulin secretion. Additionally, GLP-1 decreases glucagon levels, increases insulin biosynthesis, increases beta cell mass, decreases beta cell apoptosis and inhibits gastric emptying. These activities contribute to an improvement in hyperglycemia, and GLP-1 and GLP-1 mimetics have proven useful in the treatment of type 2 diabetes. GLP-1 has also been found to decrease body weight. Therefore, GLP-1 secretagogues may be useful in treating obesity and preparing medicaments for treating obesity. The decrease in body weight may result from the activities of GLP-1 to inhibit gastric emptying and to increase satiety. The GLP-1 receptor is also expressed in the heart and GLP-1 has been demonstrated to have cardioprotective effects and may be useful in the treatment of cardiovascular disease. The importance of GLP-1 with respect to diabetes, obesity and cardioprotection underscores a need for new therapies and compounds that stimulate GLP-1 secretion.

4. SUMMARY OF THE INVENTION

Provided herein are compounds, pharmaceutical compositions, and methods useful for treating a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema.

In one aspect, the present invention provides a compound having the formula I or a pharmaceutically acceptable salt, stereoisomer, $C_1$-$C_6$ alkyl ester, or mixture thereof:

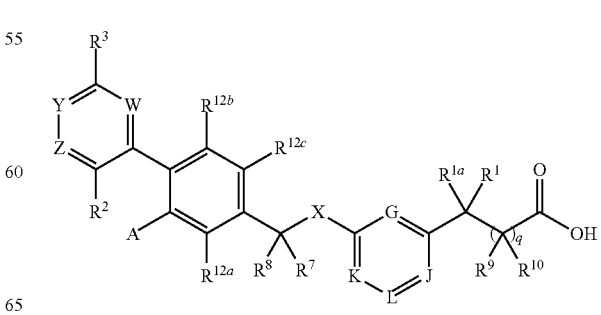

where
G is selected from N or $CR^{11a}$;
J is selected from N or $CR^{11b}$;
L is selected from N or $CR^{11c}$;
K is selected from N or $CR^{11d}$;
wherein 0 or 1 of G, J, L, and K is N;

A is selected from —$(C_1-C_{12})$alkyl; —$(C_2-C_{12})$alkenyl; —$(C_1-C_{12})$alkyl-O—$(C_1-C_4)$alkyl; —$(C_1-C_{12})$alkyl-OH; —$(C_1-C_{12})$alkyl-O—$(C_2-C_4)$alkenyl; —$(C_2-C_{12})$alkenyl-O—$(C_1-C_4)$alkyl; —$(C_2-C_{12})$alkenyl-OH; —$(C_2-C_{12})$alkenyl-O—$(C_2-C_4)$alkenyl; —O—$(C_1-C_{12})$alkyl; —O—$(C_2-C_{12})$alkenyl; —O—$(C_1-C_4)$alkyl-aryl; —S—$(C_1-C_{12})$alkyl; —S—$(C_2-C_{12})$alkenyl; —S(O)—$(C_1-C_{12})$alkyl; —S(O)—$(C_2-C_{12})$alkenyl; —S(O)$_2$—$(C_1-C_{12})$alkyl; —S(O)$_2$—$(C_2-C_{12})$alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 $(C_1-C_2)$alkyl groups; a —$(C_1-C_4)$alkyl-heterocyclyl wherein the heterocyclyl of the —$(C_1-C_4)$alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 $(C_1-C_2)$alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 $(C_1-C_2)$alkyl groups; further wherein the alkyl and alkenyl groups of —$(C_1-C_{12})$alkyl, —$(C_2-C_{12})$alkenyl, —$(C_1-C_{12})$alkyl-O—$(C_1-C_4)$alkyl, —$(C_1-C_{12})$alkyl-O—H, —$(C_1-C_{12})$alkyl-O—$(C_2-C_4)$alkenyl, —$(C_2-C_{12})$alkenyl-O—$(C_1-C_4)$alkyl, —$(C_2-C_{12})$alkenyl-OH, —$(C_2-C_{12})$alkenyl-O—$(C_2-C_4)$alkenyl, —O—$(C_1-C_{12})$alkyl, —O—$(C_2-C_{12})$alkenyl, and —O—$(C_1-C_4)$alkyl-aryl are unsubstituted or are substituted with from 1 to 4 substituents selected from —F, —Cl, —OH, (=O), —NH$_2$, NH$(C_1-C_4)$alkyl, —N$((C_1-C_4)$alkyl$)_2$, aryl, unsubstituted —$(C_1-C_2)$alkyl, or unsubstituted —O—$(C_1-C_2)$alkyl;

X is O, S, or NR$^a$ wherein R$^a$ is selected from —H or —$(C_1-C_6)$alkyl groups;

W, Y, and Z are selected from N or $CR^{13}$; wherein 0, 1, or 2 of W, Y, and Z is N; and further wherein Z is not N if R$^2$ is —F;

R$^1$ is selected from —H, —$(C_1-C_6)$alkyl, —$(C_2-C_6)$alkenyl, —$(C_2-C_6)$alkynyl, —$(C_1-C_4)$alkyl-O—$(C_1-C_4)$alkyl, heterocyclyl, aryl, or heteroaryl;

R$^{1a}$ is selected from —H and —$(C_1-C_4)$alkyl;

or R$^1$ and R$^{1a}$ may join together to form a 3 to 7 membered ring with 0, 1, or 2 heteroatoms selected from O, N, or S;

R$^2$ is selected from —H, —F, —CF$_3$, or —O—$(C_1-C_6)$alkyl;

R$^3$ is —H, —F, —Cl, —OH, —$(C_1-C_4)$alkyl, —O—$(C_1-C_3)$alkyl, or —S—$(C_1-C_2)$alkyl;

R$^7$ and R$^8$ are independently selected from —H and —$(C_1-C_4)$alkyl;

R$^9$ and R$^{10}$ are independently selected from —H and —$(C_1-C_4)$alkyl;

each of R$^{11a}$, R$^{11b}$, R$^{11c}$, and R$^{11d}$ is independently selected from —H, —F, —Cl, —$(C_1-C_4)$alkyl, or —O—$(C_1-C_4)$alkyl; and R$^{11a}$ is absent if G is N; R$^{11b}$ is absent if J is N, R$^{11c}$ is absent if L is N; or R$^{11d}$ is absent if K is N;

each of R$^{12a}$, R$^{12b}$, and R$^{12c}$ is independently selected from —H, —F, —Cl, —$(C_1-C_4)$alkyl, or —O—$(C_1-C_4)$alkyl;

R$^{13}$ is selected from —H, —F, —$(C_1-C_4)$alkyl, and —O—$(C_1-C_4)$alkyl; and q is 1 or 2.

In another aspect, the invention provides a compound of formula I or a pharmaceutically acceptable salt, stereoisomer, $C_1-C_6$ alkyl ester, or mixture thereof, wherein
G is selected from N or $CR^{11a}$;
J is selected from N or $CR^{11b}$;
L is selected from N or $CR^{11c}$;
K is selected from N or $CR^{11d}$;
wherein 0 or 1 of G, J, L, and K is N;

A is selected from $(C_1-C_{12})$alkyl, $(C_2-C_{12})$alkenyl, —O—$(C_1-C_{12})$alkyl, —O—$(C_2-C_{12})$alkenyl, —O—$(C_1-C_4)$alkyl-aryl, or a heterocycle comprising 4 to 7 ring members of which 1 or 2 are heteroatoms selected from N or O, wherein the heterocycle has 0 or 1 double bond between ring members;

X is O or S;

W, Y, and Z are selected from N or $CR^{13}$; wherein 0 or 1 of W, Y, and Z is N; and further wherein Z is not N if R$^2$ is F;

R$^1$ is selected from H, $(C_1-C_6)$alkyl, $(C_2-C_6)$alkenyl, $(C_2-C_6)$alkynyl, —$(C_1-C_4)$alkyl-O—$(C_1-C_4)$alkyl, heterocyclyl, aryl, or heteroaryl;

R$^{1a}$ is selected from H and $(C_1-C_4)$alkyl;

R$^2$ is selected from H, F, CF$_3$, or $(C_1-C_6)$alkoxy;

R$^3$ is H, —OH, —O—$(C_1-C_2)$alkyl, or —S—$(C_1-C_2)$alkyl;

R$^7$ and R$^8$ are independently selected from H and $(C_1-C_4)$alkyl;

R$^9$ and R$^{10}$ are independently selected from H and $(C_1-C_4)$alkyl;

each of R$^{11a}$, R$^{11b}$, R$^{11c}$, and R$^{11d}$ is independently selected from H, F, Cl, $(C_1-C_4)$alkyl, or $(C_1-C_4)$alkoxy; and R$^{11a}$ is absent if G is N; R$^{11b}$ is absent if J is N, R$^{11c}$ is absent if L is N; or R$^{11d}$ is absent if K is N;

each of R$^{12a}$, R$^{12b}$, and R$^{12c}$ is independently selected from H, F, Cl, $(C_1-C_4)$alkyl, or $(C_1-C_4)$alkoxy;

R$^{13}$ is selected from H, F, $(C_1-C_4)$alkyl, and —O—$(C_1-C_4)$alkyl; and
q is 1 or 2.

In some embodiments, X is O. In other embodiments, X is S. In still further embodiments X is NR$^a$. In some embodiments X is NR$^a$ and R$^a$ is selected from H or methyl. In still other embodiments, X is NR$^a$ and R$^a$ is H. In some embodiments, the compound of formula I is a compound of formula II or a pharmaceutically acceptable salt, stereoisomer, $C_1-C_6$ alkyl ester, or mixture thereof. The compound of formula II has the following structure where each of the variables has any of the values of any of the embodiments described herein:

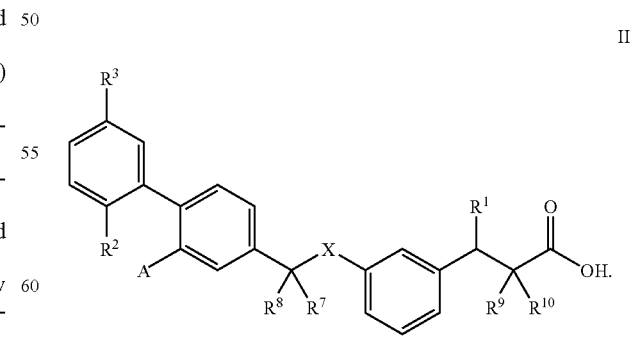

II

In some embodiments, the compound of formula II is a compound of formula II' or a pharmaceutically acceptable salt, stereoisomer, $C_1-C_6$ alkyl ester, or mixture thereof. The compound of formula II' has the following structure where each of the variables has any of the values of any of the embodiments described herein:

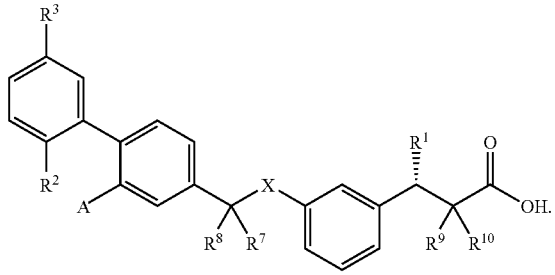

II'

In some embodiments, the compound of formula II is a compound of formula II″ or a pharmaceutically acceptable salt, stereoisomer, $C_1$-$C_6$ alkyl ester, or mixture thereof. The compound of formula II' has the following structure where each of the variables has any of the values of any of the embodiments described herein:

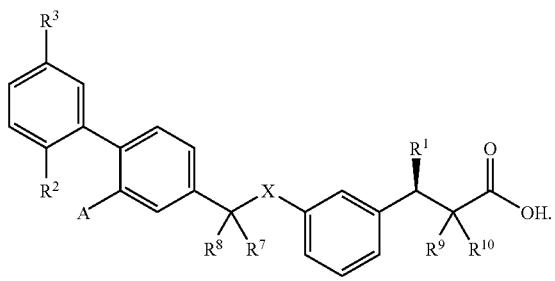

II″

In some embodiments of the compound of formula I, W and Z are CH and Y is N such that the compound of formula I has the formula III or is a pharmaceutically acceptable salt, stereoisomer, $C_1$-$C_6$ alkyl ester, or mixture thereof. The compound of formula III has the following structure where each of the variables has any of the values of any of the embodiments described herein:

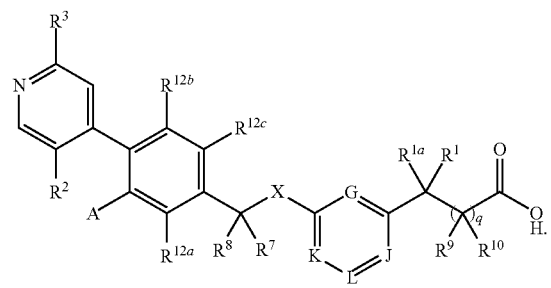

III

In some embodiments, the compound of formula III is a compound of formula III' or a pharmaceutically acceptable salt, stereoisomer, $C_1$-$C_6$ alkyl ester, or mixture thereof. The compound of formula III' has the following structure where each of the variables has any of the values of any of the embodiments described herein:

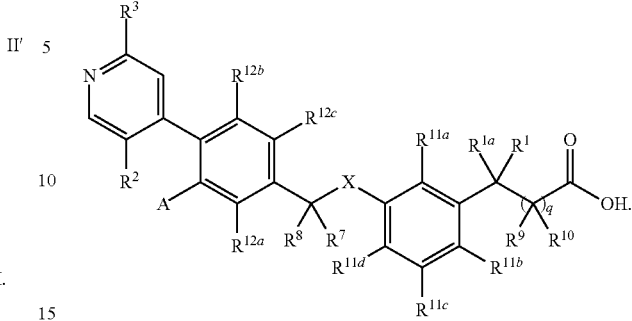

III'

In some embodiments, the compound of formula III is a compound of formula III″ or a pharmaceutically acceptable salt, stereoisomer, $C_1$-$C_6$ alkyl ester, or mixture thereof. The compound of formula III″ has the following structure where each of the variables has any of the values of any of the embodiments described herein:

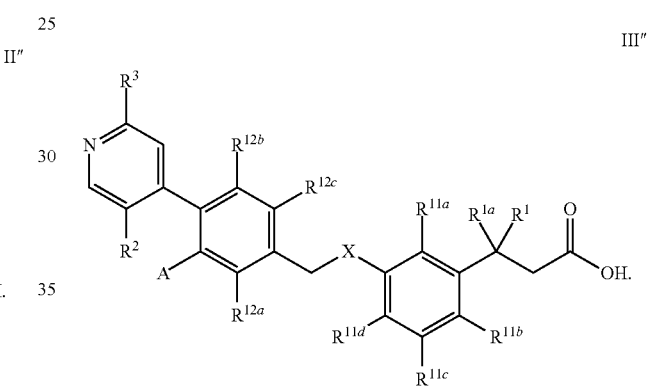

III″

In some embodiments, the compound of any of the embodiments is a salt. In other embodiments, the compound of any of the embodiments is a $C_1$-$C_6$ alkyl ester. In some such embodiments, the $C_1$-$C_6$ alkyl ester is a $C_1$-$C_6$ alkyl ester such as a methyl, ethyl, propyl, butyl, isopropyl, pentyl, or hexyl ester. In other such embodiments, the $C_1$-$C_6$ alkyl ester is a methyl, ethyl, propyl, or butyl ester. In some such embodiments, the ester is a methyl or ethyl ester.

In some embodiments, where two or more chiral centers are present, the compound is a mixture of diastereomers. In some such embodiments, the percentage of one diastereomer is greater than 75%, greater than 80%, greater than 85%, greater than 90%, greater than 95%, greater than 98%, or greater than 99% based on the total diastereomers present in the mixture. In other embodiments, the compound is one specific diastereomer. In some embodiments, the compound is a mixture of enantiomers. In some such embodiments, the mixture comprises both enantiomers where the percent of one enantiomer with respect to both enantiomers is greater than 75%, greater than 80%, greater than 85%, greater than 90%, greater than 95%, greater than 98%, or greater than 99%. In other embodiments, the compound is a pure single enantiomer. In some embodiments with a single chiral center, the compound comprises a stereomerically pure S-enantiomer. In other embodiments with a single chiral center, the compound comprises a stereomerically pure R-enantiomer. In yet other embodiments with a single chiral center, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

In another aspect, the invention provides methods for treating a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. Such methods include administering to a subject in need thereof, a therapeutically effective amount of a compound of any of the embodiments. In some such embodiments, the disease or condition is type II diabetes. In some embodiments, a compound of any of the embodiments is administered in combination with a second therapeutic agent. In some such embodiments, the second therapeutic agent is metformin, is a thiazolidinedione, is a DPP-IV inhibitor or is a GLP-1 analog. The second therapeutic agent may be administered before, during, or after administration of the compound of any of the embodiments.

In another aspect, the invention provides methods for treating a disease or condition responsive to the modulation of GPR40. Such methods include administering to a subject in need thereof, a therapeutically effective amount of a compound of any of the embodiments.

In another aspect, the invention provides methods for treating a disease or condition mediated, regulated, or influenced by pancreatic β cells. Such methods include administering to a subject in need thereof, a therapeutically effective amount of a compound of any of the embodiments.

In another aspect, the invention provides methods for modulating GPR40 function in a cell. Such methods include contacting a cell with a compound of any of the embodiments.

In another aspect, the invention provides methods for modulating GPR40 function. Such methods include contacting GPR40 with a compound of any of the embodiments.

In another aspect, the invention provides methods for modulating circulating insulin concentration in a subject. Such methods include administering a compound of any of the embodiments to the subject. In some such embodiments, the circulating insulin concentration is increased in the subject after administration whereas in other such embodiments, the circulating insulin concentration is decreased in the subject after administration.

In another aspect, the invention provides the use of a compound of any of the embodiments for treating a disease or condition or for preparing a medicament for treating a disease or condition where the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes. The compounds of the invention may also be used to prepare medicaments that include a second therapeutic agent such as metformin, a thiazolidinedione, or a DPP-IV inhibitor.

In another aspect, the invention provides the use of a compound of any of the embodiments for modulating GPR40 or for use in the preparation of a medicament for modulating GPR40.

In another aspect, the invention provides a therapeutic composition that includes a compound of any of the embodiments and a second therapeutic agent such as those described herein, for example, metformin a thiazolidinedione, or a DPP-IV inhibitor, as a combined preparation for simultaneous, separate, or sequential use in the treatment of a disease or condition mediated by GPR40. In some such embodiments, the disease or condition is type II diabetes. In some embodiments, the compound of any of the embodiments and the second therapeutic agent are provided as a single composition, whereas in other embodiments they are provided separately as parts of a kit.

In some embodiments, the invention provides a compound of any of the embodiments described herein for use as a medicament.

In other embodiments, the invention provides a compound of any of the embodiments described herein for use in modulating GPR40.

In still other embodiments, the invention provides a compound of any of the embodiments described herein for use in a method for treating a disease or condition selected from type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, or edema.

The compounds of the invention have been found to stimulate GLP-secretion. Cells contacted with compounds of the invention have been found to increase GLP-1 secretion. Therefore, in some embodiments, the invention provides a method of stimulating GLP-1 secretion by cells. Such methods typically include contacting a cell capable of producing GLP-1 with a compound of any of the embodiments set forth herein. Administration of the compounds of the invention to subjects has also been found to provide increased levels of GLP-1 in the blood plasma of such subjects. Therefore, in some embodiments, a compound of any of the embodiments described herein may be used to stimulate GLP-1 secretion and increase the blood plasma level of GLP-1 in a subject. In some such embodiments, the compounds of the invention both stimulate GLP-1 secretion and activate GPR40. Therefore, in some embodiments, the compounds of the invention both stimulate GLP-1 secretion and display incretin effect by activating GPR40.

In some embodiments, the invention further provides a method for increasing GLP-1 levels in the blood plasma of a subject. Such methods typically include administering a compound of any of the embodiments to a subject. In some such embodiments, the subject is a diabetic patient. In other such embodiments, the subject is an obese patient. In some embodiments, the invention provides a method for stimulating weight loss in a subject. In such embodiments, a compound of any of the embodiments is administered to a subject in an effective amount to stimulate weight loss in the subject. The compounds of the invention may be administered in the fasted or non-fasted state. Therefore, in some embodiments, a compound of any of the embodiments is administered to a subject prior to a meal. In some such embodiments, the compound is administered 2 hours, 1, hour, 30 minutes, or 15 minutes before a meal. In other embodiments, a compound of any embodiments set forth herein is administered to a subject during a meal. In other embodiments, a compound of any of the embodiments described herein is administered to a subject within 2 hours, within 1 hour, within 30 minutes, or within 15 minutes of a meal.

In another aspect the invention provide a process for hydrogenating a compound of formula V, the method comprising: (a) reacting a compound of formula V with $H_2$ in the presence of a transition metal or a transition metal complex to form a compound of formula VIA, a compound of formula VIB or mixture of the compound of formula VIA and the compound of formula VIB. The compounds of formula V, VIA, and VIB have the following structures:

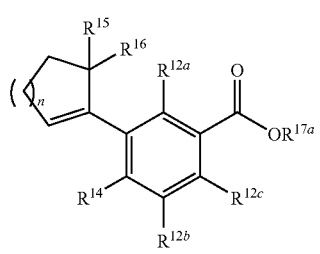

V

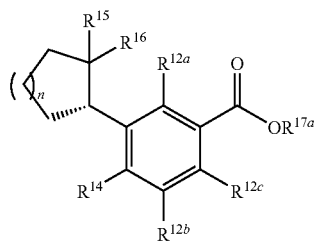

VIA

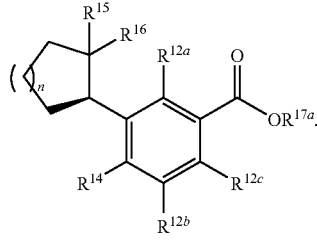

VIB wherein,
$R^{12a}$ is selected from —H, halo, a —($C_1$-$C_6$)alkyl group, or a —O—($C_1$-$C_6$)alkyl group;
$R^{12b}$ is selected from —H, halo, a —($C_1$-$C_6$)alkyl group, or a —O—($C_1$-$C_6$)alkyl group;
$R^{12c}$ is selected from —H, halo, a —($C_1$-$C_6$)alkyl group, or a —O—($C_1$-$C_6$)alkyl group;
$R^{14}$ is —H or —OH;
$R^{15}$ is selected from —H, or a —($C_1$-$C_6$)alkyl group;
$R^{16}$ is selected from —H, or a —($C_1$-$C_6$)alkyl group;
$R^{17a}$ is a —($C_1$-$C_6$)alkyl group; and
the subscript n is 1, 2, or 3;
wherein at least one of $R^{15}$ or $R^{16}$ is a —($C_1$-$C_6$)alkyl group.

In another aspect, the invention provides a compound of formula V, VIA, and/or VIB. In such an aspect, the variables have the definitions provided herein with respect to the process for hydrogenating a compound of formula V. In various embodiments of this aspect, the variables have any of the definitions provided with respect to any of the embodiments of the process for hydrogenating a compound of formula V. For example, in some embodiments, $R^{14}$ is OH. In other such embodiments, $R^{15}$ and $R^{16}$ are both methyl groups.

In some embodiments of the process for hydrogenating the compound of formula V, the transition metal or transition metal complex comprises palladium, platinum, nickel, or rhodium. For example, the reduction may be accomplished using palladium on carbon, Raney nickel, $PtO_2$ or various rhodium compounds. In some such embodiments, the transition metal or transition metal complex is palladium, and in some such embodiments is palladium on carbon. Various supported catalysts known to those skilled in the art may be used in conjunction with this process.

In some embodiments of the process for hydrogenating the compound of formula V, the process is an enantioselective process. In such embodiments, the method includes reacting a compound of formula V with $H_2$ in the presence of a transition metal or a transition metal complex and a phosphine ligand to form a compound of formula VIA, a compound of formula VIB, or a mixture of the compound of formula VIA and the compound of formula VIB. In such embodiments, the phosphine ligand comprises at least one chiral center.

In some embodiments of the process for hydrogenating a compound of formula V, $R^{14}$ is —OH.

In some embodiments of the process for hydrogenating a compound of formula V, $R^{15}$ and $R^{16}$ are both —$CH_3$.

In some embodiments of the process for hydrogenating a compound of formula V, the subscript n is 1.

In some embodiments of the process for hydrogenating a compound of formula V, $R^{12b}$ and $R^{12c}$ are both —H.

In some embodiments of the process for hydrogenating a compound of formula V, $R^{12a}$ is H or halo. Thus, in some embodiments $R^{12a}$ is H whereas in other embodiments, $R^{12a}$ is F.

In some embodiments of the process for hydrogenating a compound of formula V, the transition metal or the transition metal complex comprises rhodium. For example, in some such embodiments, the transition metal complex is generated from $Rh(COD)_2BF_4$, $Rh(COD)_2SbF_6$, or $Rh(NBD)_2BF_4$ where COD represents the 1,5-cyclooctadiene ligand and NBD represents the norbornadiene ligand.

In some embodiments of the process for hydrogenating a compound of formula V, the phosphine is a diphosphine. In some such embodiments, the diphosphine comprises a ferrocene group. In some such embodiments, the diphosphine is selected from

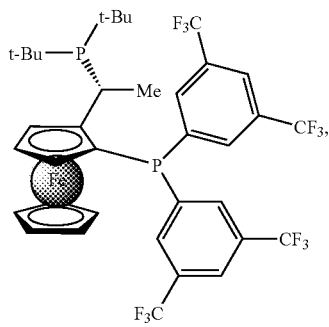

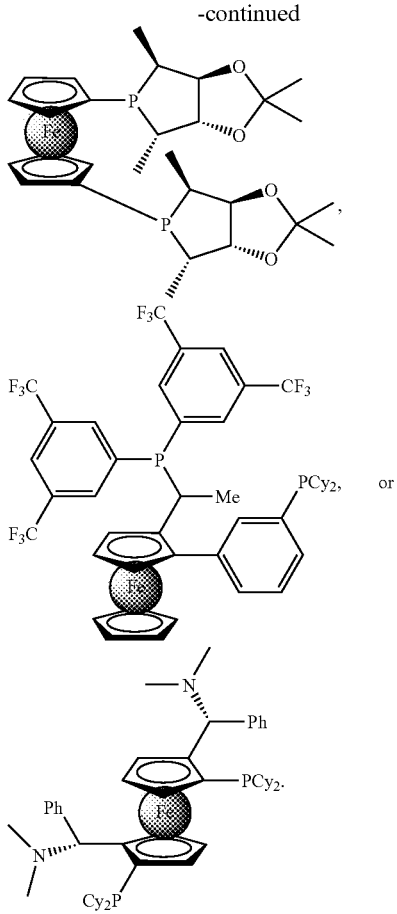

In some such embodiments, the diphosphine is

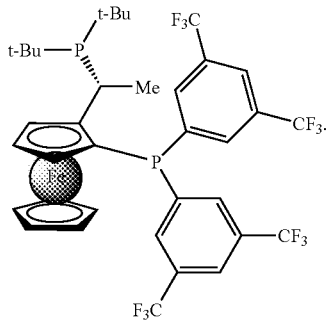

In other such embodiments, the diphosphine is an enantiomer of one of the compounds shown above.

In some embodiments of the process for hydrogenating a compound of formula V, the compound of formula V is reacted with $H_2$ at a pressure of from 15 to 1400 psi. In some such embodiments, the pressure ranges from 50 to 400 psi.

In some embodiments of the process for hydrogenating a compound of formula V, the compound of formula V is reacted with $H_2$ in a mixture comprising at least one solvent selected from an ethereal solvent, an ester solvent, an aromatic solvent, a halogenated hydrocarbon solvent, a ketone solvent, or a $C_1$-$C_4$ alcohol solvent. In some such embodiments, the at least one solvent comprises an ethereal solvent selected from tetrahydrofuran, 1,4-dioxane, 1,2-dimethoxyethane, 1,2-diethoxyethane, tetrahydropyran, diethylether, dipropylether, or dibutylether. In other such embodiments, the at least one solvent comprises tetrahydrofuran. In other such embodiments, the at least one solvent comprises at least one of tetrahydrofuran, toluene, acetone, methyl ethyl ketone, ethanol, or methanol.

In some embodiments, the transition metal complex is mixed with the phosphine in a solvent prior to adding the compounds of formula V. In some such embodiments, the solvent is an ethereal solvent such as tetrahydrofuran, and the transition metal complex is selected from $Rh(COD)_2BF_4$, $Rh(COD)_2SbF_6$, or $Rh(NBD)_2BF_4$. In some such embodiments, the phosphine is a diphosphine comprising a ferrocenyl group such as one of those described herein.

In some embodiments of the process for hydrogenating a compound of formula V, the compound of formula I is reacted with $H_2$ at a temperature ranging from 15° C. to 60° C. In some such embodiments, the temperature ranges from 20° C. to 45° C.

In some embodiments of the process for hydrogenating a compound of formula V, the enantiomeric excess of one of the products is greater than 50%, greater than 60%, greater than 75%, greater than 85%, greater than 90%, greater than 95%, or greater than 98%.

In some embodiments of the process for hydrogenating a compound of formula V, the conversion of the compound of formula V to the compound of formula VIA, the compound of formula VIB, or the mixture of the compound of formula VIA and the compound of formula VIB is greater than 50%, greater than 70%, greater than 80%, or greater than 95%.

Other objects, features and advantages of the invention will become apparent to those skilled in the art from the following description and claims.

5. BRIEF DESCRIPTION OF THE DRAWINGS

FIG. 1 is a graph showing displacement of $^3$H-labeled Comparative Compound 1 by various unlabeled compounds, including Examples 9 and 14. Unlabeled Comparative Compound 1 displaced the $^3$H-labeled Comparative Compound. In direct contrast, Examples 9 and 14 enhanced the total binding of $^3$H-labeled Comparative Compound 1. These results indicate that Examples 9 and 14 interact with the GPR40 receptor in a manner that is different from Comparative Compound 1.

Figure 5:
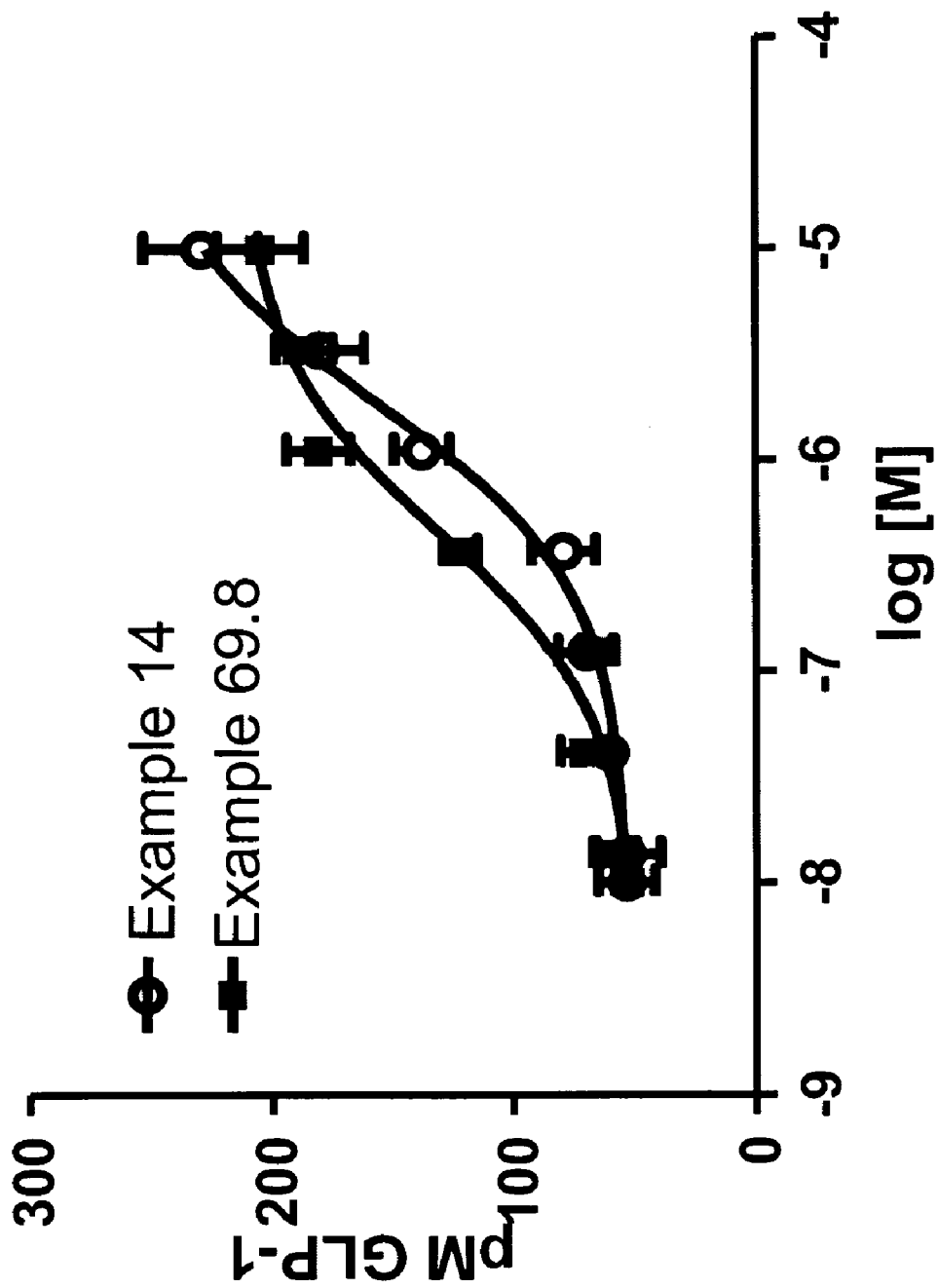

FIG. 5 is a graph showing the concentration of GLP-1 secreted into culture medium as a function of the amount of Example compounds 14 and 69.8. The GLP-1 was secreted from fetal rat intestinal cells isolated from E19 rat embryos. The cultured cells were treated with serial dilutions of the indicated compounds, and GLP-1 secreted into the culture medium was determined. These results indicate that these compounds significantly stimulated GLP-1 secretion.

Figure 6:
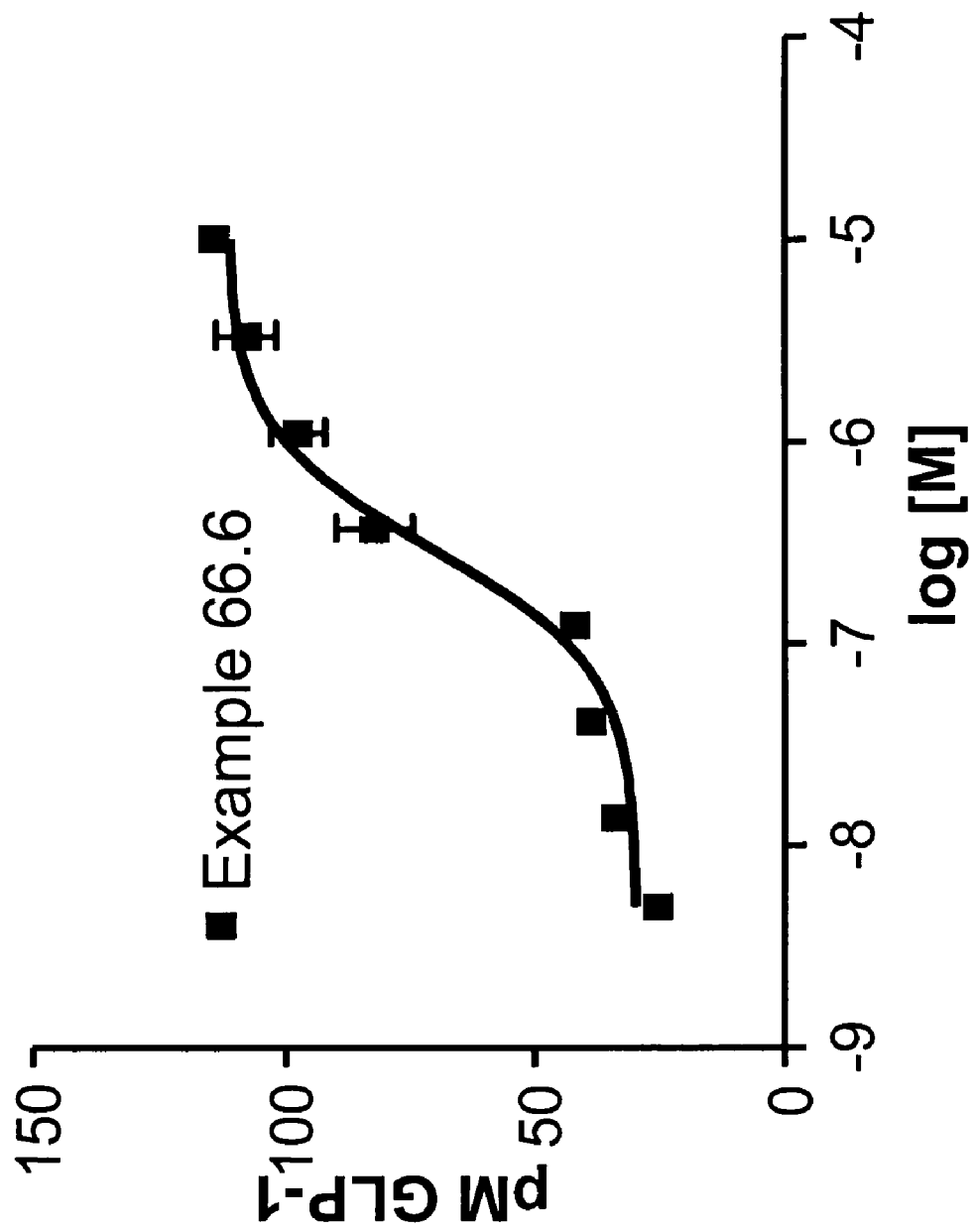

FIG. 6 is a graph showing the concentration of GLP-1 secreted into culture medium as a function of the amount of Example compound 66.6. The GLP-1 was secreted from fetal rat intestinal cells isolated from E19 rat embryos. The cultured cells were treated with serial dilutions of the indicated compound, and GLP-1 secreted into the culture medium was determined. These results indicate that this compound significantly stimulated GLP-1 secretion.

Figure 7:
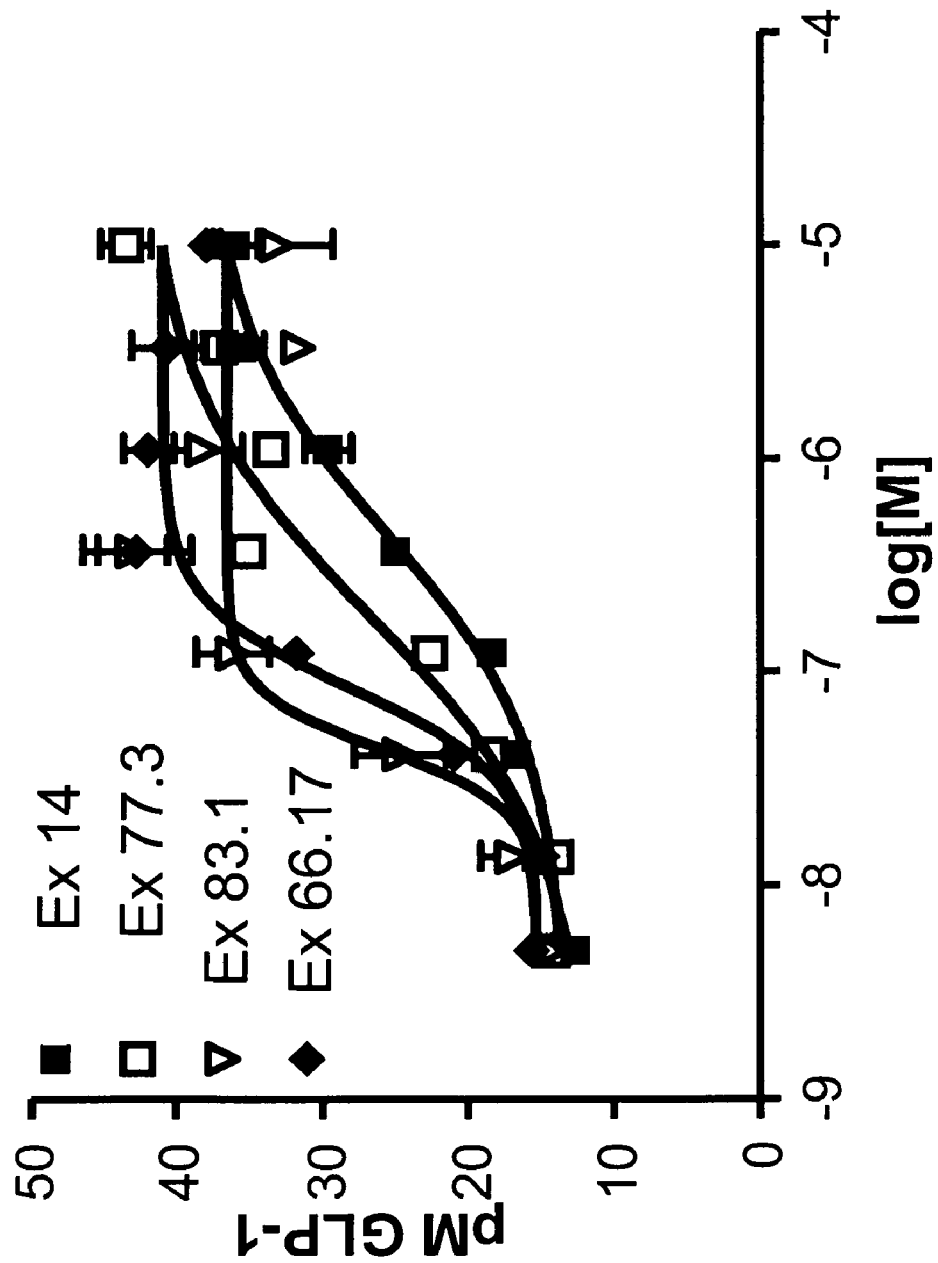

FIG. 7 is a graph showing the concentration of GLP-1 secreted into culture medium as a function of the amount of Example compounds 14, 66.17, 77.3, and 83.1. The GLP-1 was secreted from fetal rat intestinal cells isolated from E19 rat embryos. The cultured cells were treated with serial dilutions of the indicated compounds, and GLP-1 secreted into the culture medium was determined. These results indicate that these compounds significantly stimulated GLP-1 secretion.

Figure 8:
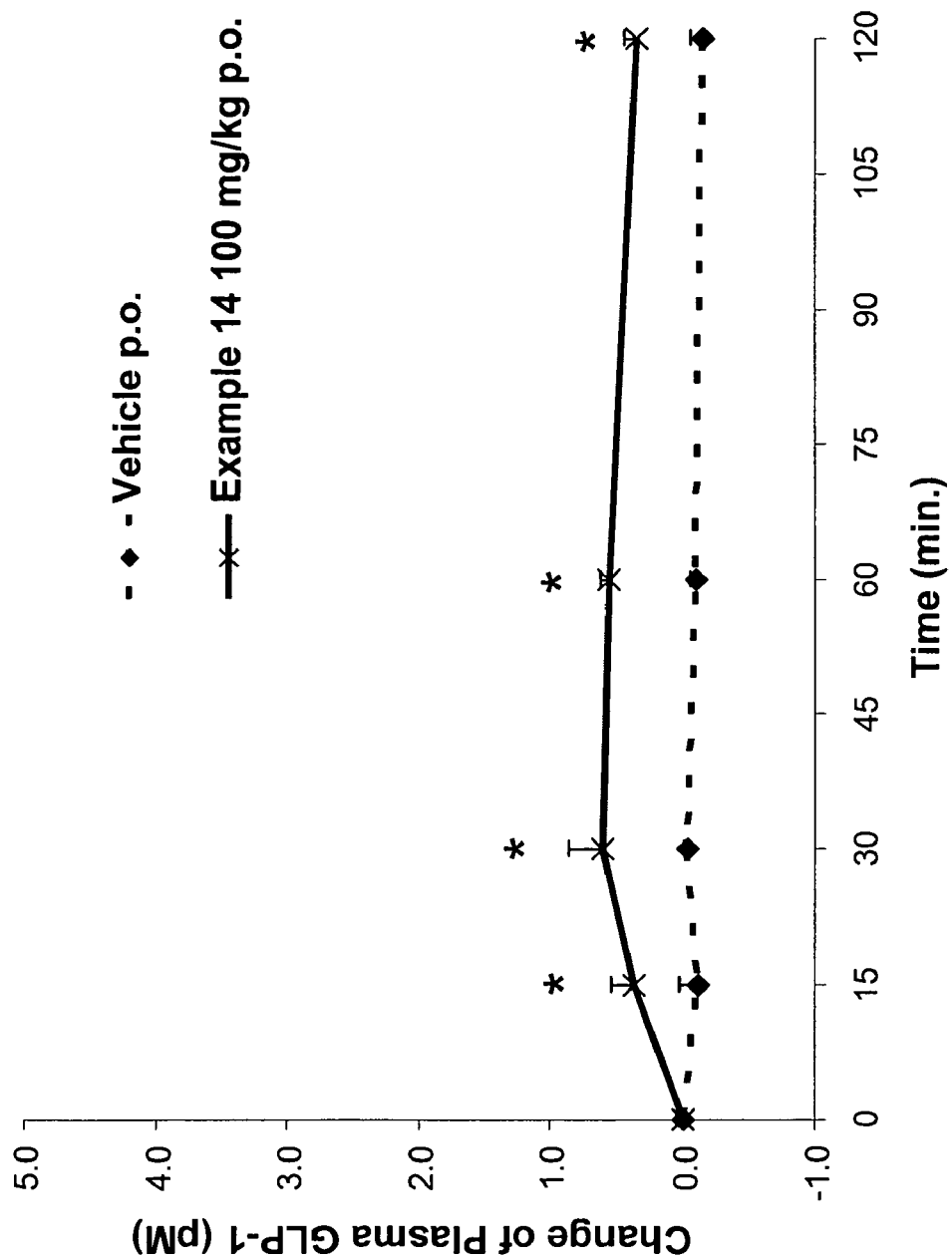

FIG. 8 is a graph showing GLP-1 plasma levels in C57BL6 mice under overnight fast condition after administration of vehicle and Example 14 (100 mg/kg). Each group had 12 mice. The * symbol indicates that for this point $p<0.05$ (student's t-test) when treatment with example compound is compared with vehicle control. Only the top part of the error bars is shown.

Figure 9:
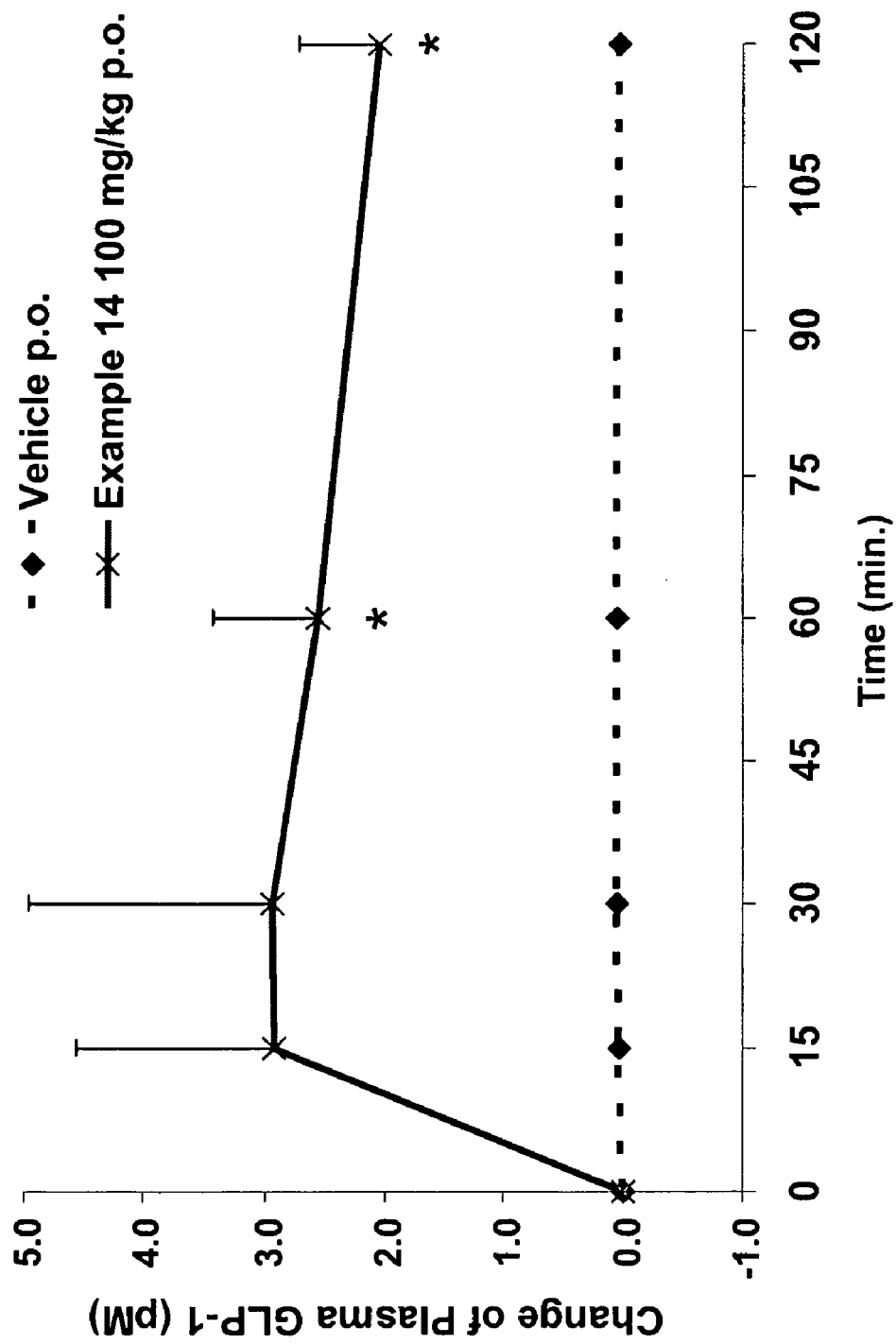

FIG. 9 is a graph showing GLP-1 plasma levels in C57BL6 mice under non-fasted condition after administration of vehicle and Example 14 (100 mg/kg). Each group had 12 mice. The * symbol indicates that for this point $p<0.05$ (student's t-test) when treatment with example compound is compared with vehicle control. Only the top part of the error bars is shown.

Figure 10:
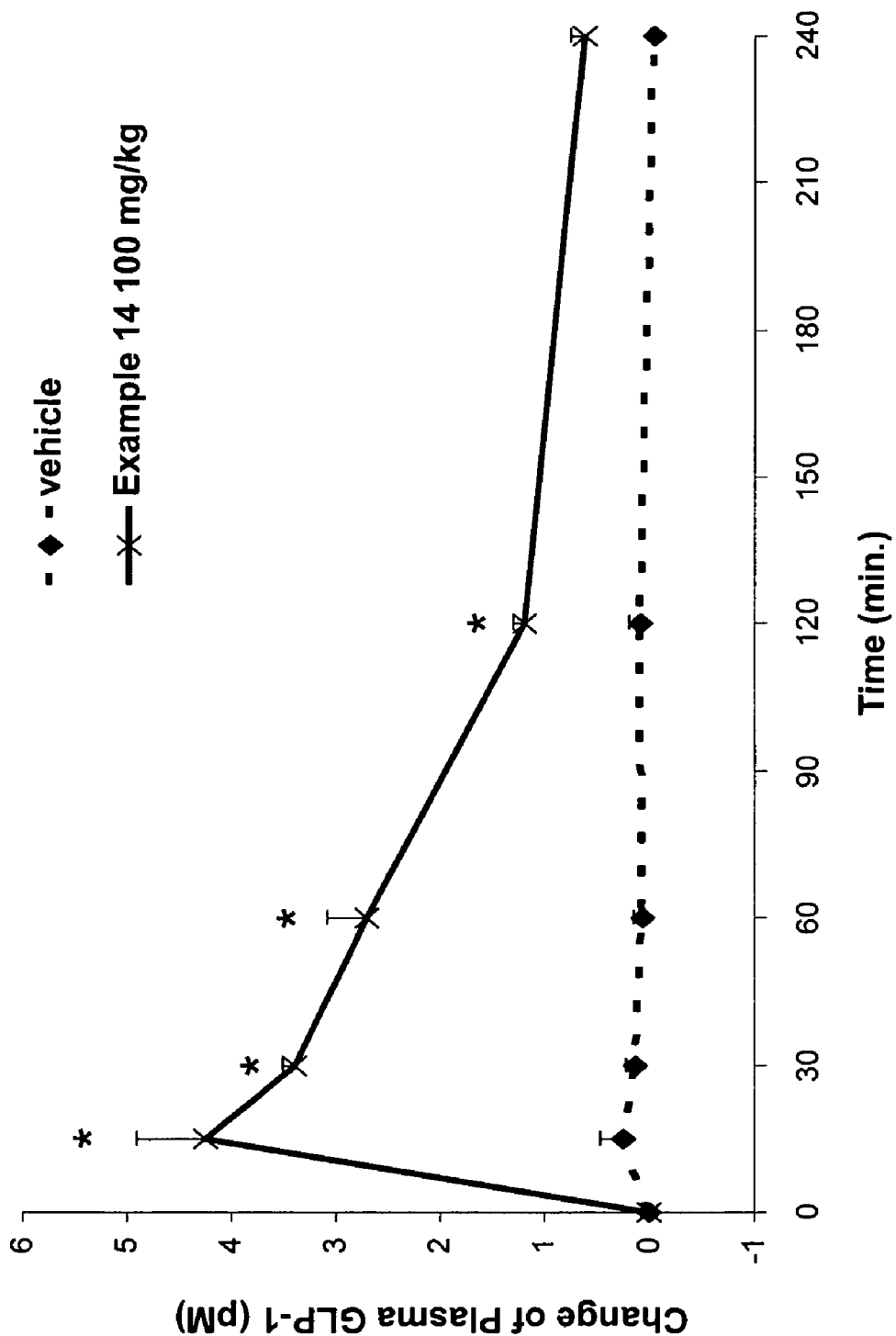

FIG. 10 is a graph showing GLP-1 plasma levels in HF/STZ mice under non-fasted condition after administration of vehicle and Example 14 (100 mg/kg). Each group had 12 mice. The * symbol indicates that for this point $p<0.05$ (student's t-test) when treatment with example compound is compared with vehicle control. Only the top part of the error bars is shown.

Figure 11:
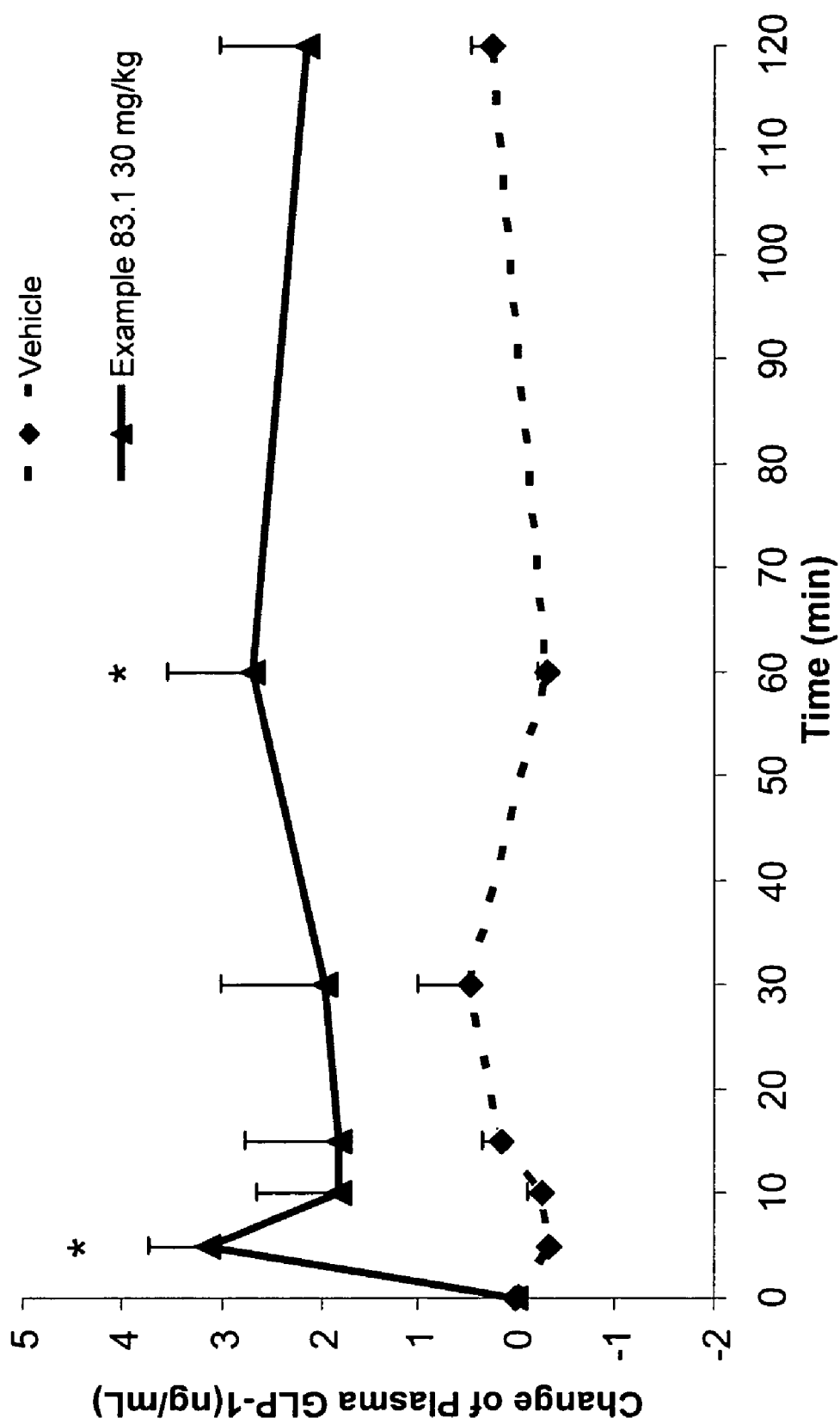

FIG. 11 is a graph showing GLP-1 plasma levels in HF/STZ mice under non-fasted condition after administration of vehicle and Example 83.1 (30 mg/kg). Each group had 12 mice. The * symbol indicates that for this point $p<0.05$ (student's t-test) when treatment with example compound is compared with vehicle control. Only the top part of the error bars is shown.

6. DETAILED DESCRIPTION OF THE INVENTION

6.1 Abbreviations and Definitions

The terms "treat", "treating" and "treatment", as used herein, are meant to include alleviating or abrogating a condition or disease and/or its attendant symptoms. In some instances treating may also involve prevention of symptoms. The terms "prevent", "preventing" and "prevention", as used herein, refer to a method of delaying or precluding the onset of a condition or disease and/or its attendant symptoms, barring a subject from acquiring a condition or disease, or reducing a subject's risk of acquiring a condition or disease.

The term "therapeutically effective amount" refers to that amount of the compound that will elicit the biological or medical response of a tissue, system, or subject that is being sought. The term "therapeutically effective amount" includes that amount of a compound that, when administered, is sufficient to prevent development of, or alleviate to some extent, one or more of the symptoms of the condition or disorder being treated in a subject. The therapeutically effective amount in a subject will vary depending on the compound, the disease and its severity, and the age, weight, etc., of the subject to be treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "modulate", "modulation" and the like refer to the ability of a compound to increase or decrease the function or activity of GPR40 either directly or indirectly. Inhibitors are compounds that, for example, bind to, partially or totally block stimulation, decrease, prevent, delay activation, inactivate, desensitize, or down regulate signal transduction, such as, for instance, antagonists. Activators are compounds that, for example, bind to, stimulate, increase, activate, facilitate, enhance activation, sensitize or up regulate signal transduction, such as agonists for instance. Modulation may occur in vitro or in vivo.

As used herein, the phrases "GPR40-mediated condition or disorder", "disease or condition mediated by GPR40", and the like refer to a condition or disorder characterized by inappropriate, for example, less than or greater than normal, GPR40 activity. A GPR40-mediated condition or disorder may be completely or partially mediated by inappropriate GPR40 activity. However, a GPR40-mediated condition or disorder is one in which modulation of GPR40 results in some effect on the underlying condition or disease (e.g., a GPR40 modulator results in some improvement in patient well-being in at least some patients). Exemplary GPR40-mediated conditions and disorders include cancer and metabolic disorders, e.g., diabetes, type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, ketoacidosis, hypoglycemia, thrombotic disorders, metabolic syndrome, syndrome X and related disorders, e.g., cardiovascular disease, atherosclerosis, kidney disease, nephropathy, diabetic neuropathy, diabetic retinopathy, sexual dysfunction, dermatopathy, dyspepsia, and edema.

The term "alkyl", by itself or as part of another substituent, means, unless otherwise stated, a straight or branched chain, or cyclic hydrocarbon radical, or combination thereof, which is fully saturated, having the number of carbon atoms designated (e.g., $C_1$-$C_{10}$ means one to ten carbons). Examples of alkyl groups include, but are not limited to, methyl, ethyl, n-propyl, isopropyl, n-butyl, t-butyl, isobutyl, sec-butyl, pentyl, cyclohexyl, (cyclohexyl)methyl, methylcyclohexyl, dimethylcyclohexyl, cyclopropyl, cyclopropylmethyl, methylcyclopropyl, cyclobutyl, cyclobutylmethyl, methylcyclobutyl, cyclopentyl, methylcyclopentyl, cyclopentylmethyl, dimethylcyclopentyl, and homologs and isomers thereof, for example, n-pentyl, n-hexyl, n-heptyl, n-octyl, and the like. Alkyl groups may be substituted or unsubstituted.

The term "alkenyl", by itself or as part of another substituent, means a straight or branched chain, or cyclic hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include, but are not limited to, vinyl, 2-propenyl, crotyl, 2-isopentenyl, 2-(butadienyl), 2,4-pentadienyl, 3-(1,4-pentadienyl), cyclopentenyl, cyclohexenyl, 5,5-dimethylcycopentenyl, 6,6-dimethylcyclohexenyl, cycloheptenyl, cycloheptadienyl, and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include, but are not limited to, ethynyl, 1- and 3-propynyl, 3-butynyl, and higher homologs and isomers thereof.

The term "alkoxy" refers to a group of formula —O-alkyl where alkyl has the definition provided above. An alkoxy group can have a specified number of carbon atoms. For example, a methoxy group (—$OCH_3$) is a $C_1$ alkoxy group. Alkoxy groups typically have from 1 to 10 carbon atoms. Examples of alkoxy group include, but are not limited to, methoxy, ethoxy, propoxy, butoxy, pentoxy, hexoxy, heptoxy, and the like.

The term "cycloalkyl" by itself, or in combination with other terms, represents, unless otherwise stated, a cyclic type of "alkyl" in which 3 or more carbon atoms form a ring. Thus, the term "cycloalkyl" is meant to be included in the term "alkyl". Examples of cycloalkyl include cyclopropyl, cyclobutyl, cyclopentyl, cyclohexyl, cycloheptyl, and the like. Cycloalkyl groups typically include from 3 to 14 or 3 to 10 ring members. Cycloalkyl groups may be monocyclic, bicyclic, or multicyclic. Therefore, in addition to the groups described above, cycloalkyl groups include norbornyl and adamantyl groups.

The term "cycloalkenyl" by itself, or in combination with other terms, represents, unless otherwise stated, a cyclic type of "alkenyl" in which 3 or more carbon atoms form a ring that includes at least one carbon-carbon double bond. Thus, the term "cycloalkenyl" is meant to be included in the term "alkenyl". Examples of cycloalkenyl include cyclopropenyl, cyclobutenyl, cyclopentenyl, cyclohexenyl, cycloheptenyl, and the like. Cycloalkenyl groups typically include from 3 to 14 or 3 to 10 ring members. Cycloalkenyl groups may be monocyclic, bicyclic, or multicyclic.

The term "heterocyclyl" by itself or in combination with other terms, represents, unless otherwise stated, a ring system in which one ore more ring members is a heteroatom selected from N, O, or S. The heteroatom can occupy the position at which the heterocycle is attached to the remainder of the molecule. A heterocyclyl group can also be attached to the remainder of the molecule through a carbon atom of the ring. Heterocyclyl groups typically include from 3 to 10 ring members of which 1, 2, or 3 are heteroatoms. Heterocyclyl groups can be saturated or may include some unsaturation. Heterocyclyl groups may also be substituted or unsubstituted. Examples of heterocyclyl groups include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, 4,5-dihydroisoxazol-3-yl, and the like.

The term "heteroalkyl," by itself or in combination with another term, means, unless otherwise stated, a stable straight or branched chain, or cyclic hydrocarbon radical, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S may be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, and —$CH_2$—CH=N—$OCH_3$. Up to two heteroatoms may be consecutive, such as, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group is a oxyalkyl group. For instance, ($C_2$-$C_5$)oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2OH$, and the like.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m'+1), where m' is the total number of carbon atoms in the alkyl group. For example, the term "halo ($C_1$-$C_4$)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms). The term "perhaloalkyl" means, unless otherwise stated, alkyl substituted with (2m'+1) halogen atoms, where m' is the total number of carbon atoms in the alkyl group. For example, the term "perhalo($C_1$-$C_4$)alkyl", is meant to include trifluoromethyl, pentachloroethyl, 1,1,1-trifluoro-2-bromo-2-chloroethyl, and the like.

The term "aryl" means, unless otherwise stated, a polyunsaturated, aromatic, hydrocarbon substituent which can be a single ring or multiple rings (up to three rings) which are fused together or linked covalently. The term "heteroaryl" refers to aryl groups (or rings) that contain from one to four heteroatom ring members selected from the group consisting of N, O and S, wherein the nitrogen and sulfur atoms are optionally oxidized, and the nitrogen atom(s) are optionally quaternized. Heteroaryl groups can be unsubstituted or substituted. In some embodiments, a heteroaryl group includes 1 or 2 heteroatoms. A heteroaryl group can be attached to the remainder of the molecule through a heteroatom or through a carbon atom of the ring. Non-limiting examples of aryl and heteroaryl groups include phenyl, 1-naphthyl, 2-naphthyl, 4-biphenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, dibenzofuryl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, 2-benzoxazolyl, 5-benzoxazolyl, benzo[c][1,2,5]oxadiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl. Typically an aryl group refers to an aromatic group that includes from 6-10 ring members such that it is a ($C_6$-$C_{10}$)aryl group. Typically, heteroaryl groups include 5 to 10 ring members of which 1 or 2 is selected from O, N, or S.

Preferably, the term "aryl" refers to a phenyl or naphthyl group which is unsubstituted or substituted. Preferably, the term "heteroaryl" refers to a pyrrolyl, pyrazolyl, imidazolyl, pyrazinyl, oxazolyl, oxadiazolyl, isoxazolyl, thiazolyl, furyl, thienyl (thiophenyl), pyridyl, pyrimidyl, benzothiazolyl, purinyl, benzimidazolyl, indolyl, isoquinolyl, triazolyl, tetrazolyl, quinoxalinyl, or quinolyl group which is unsubstituted or substituted.

For brevity, the term "aryl" when used in combination with other terms (e.g., aryloxy, arylalkoxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). As another example, the term "aryl($C_1$-$C_4$)alkoxy" is mean to include radicals in which an aryl group is attached to an alkyl group having 1 to 4 carbon atoms that is bonded to an O which is attached to the rest of the molecule. Examples include substituted and unsubstituted phenylmethoxy, phenylethoxy, phenylpropoxy, pyridylmethoxy, and the like.

Each of the above terms (e.g., "alkyl," "alkenyl," "aryl," "heterocyclyl" and "heteroaryl") is meant to include both substituted and unsubstituted forms of the indicated radical, unless otherwise indicated. Preferred substituents for each type of radical are provided below.

Substituents for the alkyl radicals (as well as those groups referred to as alkenyl, alkynyl, cycloalkyl, and heterocyclyl) can be a variety of groups selected from: —OR', =O, =NR', =N—OR', —NR'R", R', —SR', halogen, —OC(O)R', —C(O)R', —$CO_2$R', —CONR'R", —OC(O)NR'R", —NR"C(O)R', —NR'—C(O)NR"R'", —NR'—$SO_2$NR"R'", —NR"$CO_2$R', —NH—C($NH_2$)=NH, —NR'C($NH_2$)=NH, —NH—C($NH_2$)=NR', —SiR'R"R'", —S(O)R', —$SO_2$R', —$SO_2$NR'R", —NR"$SO_2$R, —CN, —($C_2$-$C_5$)alkynyl, —($C_2$-$C_5$)alkenyl, and —$NO_2$, in a number ranging from zero to three, with those groups having zero, one or two substituents being particularly preferred. R', R" and R'" each independently refer to hydrogen; unsubstituted ($C_1$-$C_8$)alkyl, ($C_2$-$C_8$)alkenyl, and heteroalkyl; unsubstituted aryl; unsubstituted heterocyclyl; heterocyclyl substituted with up to three unsubstituted ($C_1$-$C_2$)alkyl groups; aryl substituted with one to three halogens, unsubstituted ($C_1$-$C_2$)alkyl, —O—($C_1$-$C_4$)alkyl, and —S—($C_1$-$C_4$)alkyl groups; unsubstituted halo($C_1$-$C_4$)alkyl; unsubstituted —($C_1$-$C_4$)alkyl-O—($C_1$-$C_4$)alkyl; unsubstituted —($C_1$-$C_4$)alkyl-aryl; or unsubstituted aryl-($C_1$-$C_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl.

Typically, an alkyl group will have from zero to three substituents, with those groups having two or fewer substituents being preferred in the present invention. More preferably, an alkyl radical will be unsubstituted or monosubstituted. Most preferably, an alkyl radical will be unsubstituted. From the above discussion of substituents, one of skill in the art will understand that the term "alkyl" is meant to include groups such as trihaloalkyl (e.g., —$CF_3$ and —$CH_2CF_3$).

Preferred substituents for the alkyl radicals are selected from: —OR', =O, —NR'R", —SR', halogen, —OC(O)R', —C(O)R', —$CO_2$R', —CONR'R", —OC(O)NR'R", —NR"C(O)R', —NR"$CO_2$R', —NR'—$SO_2$NR"R'", —S(O)R', —$SO_2$R', —$SO_2$NR'R", —NR"$SO_2$R, —CN, —($C_2$-$C_5$)alkynyl, —($C_2$-$C_5$)alkenyl, R', and —$NO_2$, where R' and R" are as defined above. Further preferred substituents are selected from: —OR', =O, —NR'R", halogen, —OC(O)R', —$CO_2$R', —CONR'R", —OC(O)NR'R", —NR"C(O)R', —NR"$CO_2$R', —NR'—$SO_2$NR"R'", —$SO_2$R', —$SO_2$NR'R", —NR"$SO_2$R, —CN, —($C_2$-$C_5$)alkynyl, —($C_2$-$C_5$)alkenyl, and —$NO_2$.

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, unsubstituted ($C_1$-$C_8$)alkyl and heteroalkyl; unsubstituted aryl and heteroaryl; unsubstituted aryl-($C_1$-$C_4$)alkyl; unsubstituted aryl-O—($C_1$-$C_4$)alkyl; unsubstituted —($C_2$-$C_5$) alkynyl; and unsubstituted —($C_2$-$C_5$)alkenyl.

Two of the substituents on adjacent atoms of the aryl or heteroaryl ring may optionally be replaced with a substituent of the formula -T-C(O)—($CH_2$)$_q$—U—, wherein T and U are independently —NH—, —O—, —$CH_2$—, or a single bond, and q is an integer of from 0 to 2. Alternatively, two of the substituents on adjacent atoms of the aryl or heteroaryl ring may optionally be replaced with a substituent of the formula -A-($CH_2$)$_r$—B—, wherein A and B are independently —$CH_2$—, —O—, —NH—, —S—, —S(O)—, —S(O)$_2$—, —S(O)$_2$NR'—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —($CH_2$)$_s$—X—($CH_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl. Otherwise, R' is as defined above.

As used herein, the term "heteroatom" is meant to include oxygen (O), nitrogen (N), and sulfur (S).

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein, "solvate" refers to a compound of the present invention or a salt thereof, that further includes a stoichiometric or non-stoichiometric amount of solvent bound by non-covalent intermolecular forces. Where the solvent is water, the solvate is a hydrate. In some embodiments, the compounds, salts of the compounds, tautomers of the compound, and salts of the tautomers may include a solvent or water such that the compound or salt is a solvate or hydrate.

Certain compounds of the invention may exist in multiple crystalline or amorphous forms. In general, all physical forms are equivalent for the uses contemplated by the invention and are intended to be within the scope of the invention.

As known by those skilled in the art, certain compounds of the invention may exist in one or more tautomeric forms. Because one chemical structure may only be used to represent one tautomeric form, it will be understood that convenience, referral to a compound of a given structural formula includes tautomers of the structure represented by the structural formula.

Certain compounds of the invention possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., GPR40 assay reagents, and diagnostic agents, e.g., in vivo imaging agents. All isotopic variations of the compounds of the invention, whether radioactive or not, are intended to be encompassed within the scope of the invention. For example, if a variable is said to be H, this means that variable may also be deuterium (D) or tritium (T).

6.2 Embodiments of the Invention

In one aspect, a class of compounds that modulates GPR40 is described herein. Depending on the biological environment (e.g., cell type, pathological condition of the subject, etc.), these compounds can modulate, e.g., activate or inhibit, the actions of GPR40. By modulating GPR40, the compounds find use as therapeutic agents capable of regulating insulin levels in a subject. The compounds find use as therapeutic agents for modulating diseases and conditions responsive to modulation of GPR40 and/or mediated by GPR40 and/or mediated by pancreatic β cells. As noted above, examples of such diseases and conditions include diabetes, obesity, hyperglycemia, glucose intolerance, insulin resistance, cancer, hyperinsulinemia, hypercholesterolemia, hypertension, hyperlipoproteinemia, hyperlipidemia, hypertriglylceridemia, dyslipidemia, ketoacidosis, hypoglycemia, metabolic syndrome, syndrome X, cardiovascular disease, atherosclerosis, kidney disease, nephropathy, thrombotic disorders, diabetic neuropathy, diabetic retinopathy, dermatopathy, dyspepsia and edema. Additionally, the compounds are useful for the treatment and/or prevention of complications of these diseases and disorders (e.g., type II diabetes, sexual dysfunction, dyspepsia and so forth).

While the compounds of the invention are believed to exert their effects by interacting with GPR40, the mechanism of action by which the compounds act is not a limiting embodiment of the invention.

Compounds contemplated by the invention include, but are not limited to, the exemplary compounds provided herein.

6.2.1 Compounds

In one aspect, the present invention provides a compound having the formula I or a pharmaceutically acceptable salt, stereoisomer, $C_1$-$C_6$ alkyl ester, or mixture thereof:

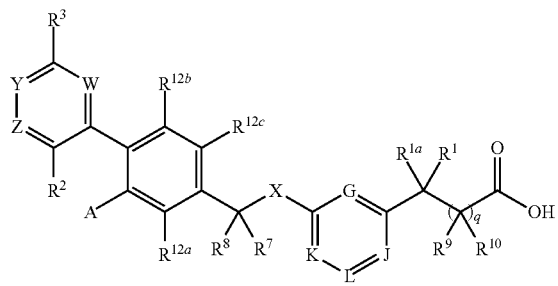

I where
G is selected from N or $CR^{11a}$;
J is selected from N or $CR^{11b}$;
L is selected from N or $CR^{11c}$;
K is selected from N or $CR^{11d}$;
wherein 0 or 1 of G, J, L, and K is N;
A is selected from —($C_1$-$C_{12}$)alkyl; —($C_2$-$C_{12}$)alkenyl; —($C_1$-$C_{12}$)alkyl-O—($C_1$-$C_4$)alkyl; —($C_1$-$C_{12}$)alkyl-OH; —($C_1$-$C_{12}$)alkyl-O—($C_2$-$C_4$)alkenyl; —($C_2$-$C_{12}$)alkenyl-O—($C_1$-$C_4$)alkyl; —($C_2$-$C_{12}$)alkenyl-OH; —($C_2$-$C_{12}$)alkenyl-O—($C_2$-$C_4$)alkenyl; —O—($C_1$-$C_{12}$)alkyl; —O—($C_2$-$C_{12}$)alkenyl; —O—($C_1$-$C_4$)alkyl-aryl; —S—($C_1$-$C_{12}$)alkyl; —S—($C_2$-$C_{12}$)alkenyl; —S(O)—($C_1$-$C_{12}$)alkyl; —S(O)—($C_2$-$C_{12}$)alkenyl; —S(O)$_2$—($C_1$-$C_{12}$)alkyl; —S(O)$_2$—($C_2$-$C_{12}$)alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$)alkyl groups; a —($C_1$-$C_4$)alkyl-heterocyclyl wherein the heterocyclyl of the —($C_1$-$C_4$)alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 ($C_1$-$C_2$)alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$)alkyl groups; further wherein the alkyl and alkenyl groups of —($C_1$-$C_{12}$)alkyl, —($C_2$-$C_{12}$)alkenyl, —($C_1$-$C_{12}$)alkyl-O—($C_1$-$C_4$)alkyl, —($C_1$-$C_{12}$)alkyl-O—H, —($C_1$-$C_{12}$)alkyl-O—($C_2$-$C_4$)alkenyl, —($C_2$-$C_{12}$)alkenyl-O—($C_1$-$C_4$)alkyl, —($C_2$-$C_{12}$)alkenyl-OH, —($C_2$-$C_{12}$)alkenyl-O—($C_2$-$C_4$)alkenyl, —O—($C_1$-$C_{12}$)alkyl, —O—($C_2$-$C_{12}$)alkenyl, and —O—($C_1$-$C_4$)alkyl-aryl are unsubstituted or are substituted with from 1 to 4 substituents selected from —F, —Cl, —OH, (=O), —NH$_2$, NH($C_1$-$C_4$)alkyl, —N(($C_1$-$C_4$)alkyl)$_2$, aryl, unsubstituted —($C_1$-$C_2$)alkyl, or unsubstituted —O—($C_1$-$C_2$)alkyl;

X is O, S, or NR$^a$ wherein R$^a$ is selected from —H or —($C_1$-$C_6$)alkyl groups;

W, Y, and Z are selected from N or CR$^{13}$; wherein 0, 1, or 2 of W, Y, and Z is N; and further wherein Z is not N if R$^2$ is —F;

R$^1$ is selected from —H, —($C_1$-$C_6$)alkyl, —($C_2$-$C_6$)alkenyl, —($C_2$-$C_6$)alkynyl, —($C_1$-$C_4$)alkyl-O—($C_1$-$C_4$)alkyl, heterocyclyl, aryl, or heteroaryl;

R$^{1a}$ is selected from —H and —($C_1$-$C_4$)alkyl;

or R$^1$ and R$^{1a}$ may join together to form a 3 to 7 membered ring with 0, 1, or 2 heteroatoms selected from O, N, or S;

R$^2$ is selected from —H, —F, —CF$_3$, or —O—($C_1$-$C_6$) alkyl;

R$^3$ is —H, —F, —Cl, —OH, —($C_1$-$C_4$)alkyl, —O—($C_1$-$C_3$)alkyl, or —S—($C_1$-$C_2$)alkyl;

R$^7$ and R$^8$ are independently selected from —H and —($C_1$-$C_4$)alkyl;

R$^9$ and R$^{10}$ are independently selected from —H and —($C_1$-$C_4$)alkyl;

each of R$^{11a}$, R$^{11b}$, R$^{11c}$, and R$^{11d}$ is independently selected from —H, —F, —Cl, —($C_1$-$C_4$)alkyl, or —O—($C_1$-$C_4$)alkyl; and R$^{11a}$ is absent if G is N; R$^{11b}$ is absent if J is N, R$^{11c}$ is absent if L is N; or R$^{11d}$ is absent if K is N;

each of R$^{12a}$, R$^{12b}$, and R$^{12c}$ is independently selected from —H, —F, —Cl, —($C_1$-$C_4$)alkyl, or —O—($C_1$-$C_4$)alkyl;

R$^{13}$ is selected from —H, —F, —($C_1$-$C_4$)alkyl, and —O—($C_1$-$C_4$)alkyl; and q is 1 or 2.

In another aspect, the invention provides a compound of formula I or a pharmaceutically acceptable salt, stereoisomer, $C_1$-$C_6$ alkyl ester, or mixture thereof, wherein
G is selected from N or CR$^{11a}$;
J is selected from N or CR$^{11b}$;
L is selected from N or CR$^{11c}$;
K is selected from N or CR$^{11d}$;
wherein 0 or 1 of G, J, L, and K is N;
A is selected from ($C_1$-$C_{12}$)alkyl, ($C_2$-$C_{12}$)alkenyl, —O—($C_1$-$C_{12}$)alkyl, —O—($C_2$-$C_{12}$)alkenyl, —O—($C_1$-$C_4$)alkyl-aryl, or a heterocycle comprising 4 to 7 ring members of which 1 or 2 are heteroatoms selected from N or O, wherein the heterocycle has 0 or 1 double bond between ring members;

X is O, S, or NR$^a$ wherein R$^a$ is selected from H or ($C_1$-$C_6$) alkyl groups;

W, Y, and Z are selected from N or CR$^{13}$; wherein 0 or 1 of W, Y, and Z is N; and further wherein Z is not N if R$^2$ is F;

R$^1$ is selected from H, ($C_1$-$C_6$)alkyl, ($C_2$-$C_6$)alkenyl, ($C_2$-$C_6$)alkynyl, —($C_1$-$C_4$)alkyl-O—($C_1$-$C_4$)alkyl, heterocyclyl, aryl, or heteroaryl;

R$^{1a}$ is selected from H and ($C_1$-$C_4$)alkyl;

R$^2$ is selected from H, F, CF$_3$, or ($C_1$-$C_6$)alkoxy;

R$^3$ is H, —OH, —O($C_1$-$C_2$)alkyl, or —S($C_1$-$C_2$)alkyl;

R$^7$ and R$^8$ are independently selected from H and ($C_1$-$C_4$) alkyl;

R$^9$ and R$^{10}$ are independently selected from H and ($C_1$-$C_4$) alkyl;

each of R$^{11a}$, R$^{11b}$, R$^{11c}$, and R$^{11d}$ is independently selected from H, F, Cl, ($C_1$-$C_4$)alkyl, or ($C_1$-$C_4$)alkoxy; and R$^{11a}$ is absent if G is N; R$^{11b}$ is absent if J is N, R$^{11c}$ is absent if L is N; or R$^{11d}$ is absent if K is N;

each of $R^{12a}$, $R^{12b}$, and $R^{12c}$ is independently selected from H, F, Cl, $(C_1$-$C_4)$alkyl, or $(C_1$-$C_4)$alkoxy;

$R^{13}$ is selected from H, F, $(C_1$-$C_4)$alkyl, and —O—$(C_1$-$C_4)$alkyl; and q is 1 or 2.

In another aspect, the invention provides a compound of formula I or a pharmaceutically acceptable salt, stereoisomer, $C_1$-$C_6$ alkyl ester, or mixture thereof, wherein G is selected from N or $CR^{11a}$;
J is selected from N or $CR^{11b}$;
L is selected from N or $CR^{11c}$;
K is selected from N or $CR^{11d}$;
wherein 0 or 1 of G, J, L, and K is N;

A is selected from $(C_1$-$C_{12})$alkyl, $(C_2$-$C_{12})$alkenyl, —O—$(C_1$-$C_{12})$alkyl, —O—$(C_2$-$C_{12})$alkenyl, —O—$(C_1$-$C_4)$alkyl-aryl, or a heterocycle comprising 4 to 7 ring members of which 1 or 2 are heteroatoms selected from N or O, wherein the heterocycle has 0 or 1 double bond between ring members;

X is O or S;

W, Y, and Z are selected from N or $CR^{13}$; wherein 0 or 1 of W, Y, and Z is N; and further wherein Z is not N if $R^2$ is F;

$R^1$ is selected from H, $(C_1$-$C_6)$alkyl, $(C_2$-$C_6)$alkenyl, $(C_2$-$C_6)$alkynyl, —$(C_1$-$C_4)$alkyl-O—$(C_1$-$C_4)$alkyl, heterocyclyl, aryl, or heteroaryl;

$R^{1a}$ is selected from H and $(C_1$-$C_4)$alkyl;

$R^2$ is selected from H, F, $CF_3$, or $(C_1$-$C_6)$alkoxy;

$R^3$ is H, —OH, —O—$(C_1$-$C_2)$alkyl, or —S—$(C_1$-$C_2)$alkyl;

$R^7$ and $R^8$ are independently selected from H and $(C_1$-$C_4)$alkyl;

$R^9$ and $R^{10}$ are independently selected from H and $(C_1$-$C_4)$alkyl;

each of $R^{11a}$, $R^{11b}$, $R^{11c}$, and $R^{11d}$ is independently selected from H, F, Cl, $(C_1$-$C_4)$alkyl, or $(C_1$-$C_4)$alkoxy; and $R^{11a}$ is absent if G is N; $R^{11b}$ is absent if J is N, $R^{11c}$ is absent if L is N; or $R^{11d}$ is absent if K is N;

each of $R^{12a}$, $R^{12b}$, and $R^{12c}$ is independently selected from H, F, Cl, $(C_1$-$C_4)$alkyl, or $(C_1$-$C_4)$alkoxy;

$R^{13}$ is selected from H, F, $(C_1$-$C_4)$alkyl, and —O—$(C_1$-$C_4)$alkyl; and q is 1 or 2.

In some embodiments,

X is O, S, or $NR^a$ wherein $R^a$ is selected from H or unsubstituted $(C_1$-$C_6)$alkyl groups;

$R^1$ is selected from H, unsubstituted —$(C_1$-$C_6)$alkyl, unsubstituted —$(C_2$-$C_6)$alkenyl, unsubstituted —$(C_2$-$C_6)$alkynyl, —$(C_1$-$C_4)$alkyl-O—$(C_1$-$C_4)$alkyl, heterocyclyl, aryl, heteroaryl, —$(C_1$-$C_6)$alkyl substituted with from 1 to 3 substituents selected from —F or —OH, or —$(C_2$-$C_6)$alkenyl substituted with from 1 to 3 substituents selected from —F or —OH;

$R^{1a}$ is selected from H, unsubstituted —$(C_1$-$C_4)$alkyl, or —$(C_1$-$C_4)$alkyl substituted with from 1 to 3 substituents selected from F and OH;

or $R^1$ and $R^{1a}$ may join together to form a 3 to 7 membered ring with 0, 1, or 2 heteroatoms selected from O, N, or S;

$R^2$ is selected from —H, —F, —$CF_3$, or —O—$(C_1$-$C_6)$alkyl;

$R^3$ is —H, —F, —Cl, —OH, —S$(C_1$-$C_2)$alkyl, unsubstituted —$(C_1$-$C_4)$alkyl, unsubstituted —O$(C_1$-$C_3)$alkyl, —$(C_1$-$C_4)$alkyl substituted with from 1 to 3 substituents selected from —F, —OH, (=O), or —O$(C_1$-$C_2)$alkyl, or substituted —O$(C_1$-$C_3)$alkyl, wherein the alkyl group of the substituted —O$(C_1$-$C_3)$alkyl is substituted with from 1 to 3 substituents selected from —F, —OH, or —O$(C_1$-$C_2)$alkyl;

$R^7$ and $R^8$ are independently selected from H and unsubstituted —$(C_1$-$C_4)$alkyl;

$R^9$ and $R^{10}$ are independently selected from H and unsubstituted —$(C_1$-$C_4)$alkyl;

each of $R^{11a}$, $R^{11b}$, $R^{11c}$, and $R^{11d}$ is independently selected from —H, —F, —Cl, —$(C_1$-$C_4)$alkyl, —O$(C_1$-$C_4)$alkyl, or —$CF_3$; and $R^{11a}$ is absent if G is N; $R^{11b}$ is absent if J is N, $R^{11c}$ is absent if L is N; or $R^{11d}$ is absent if K is N;

each of $R^{12a}$, $R^{12b}$, and $R^{12c}$ is independently selected from —H, —F, —Cl, unsubstituted —$(C_1$-$C_4)$alkyl, $CF_3$, or —O$(C_1$-$C_4)$alkyl; and $R^{13}$ is selected from —H, —F, —$(C_1$-$C_4)$alkyl, and —O—$(C_1$-$C_4)$alkyl. In some such embodiments, q is 1.

In some embodiments, $R^1$ is selected from H, unsubstituted —$(C_1$-$C_6)$alkyl, unsubstituted —$(C_2$-$C_6)$alkenyl, unsubstituted —$(C_2$-$C_6)$alkynyl, —$(C_1$-$C_4)$alkyl-O—$(C_1$-$C_4)$alkyl, heterocyclyl, aryl, heteroaryl, —$(C_1$-$C_6)$alkyl substituted with from 1 to 3 substituents selected from —F or —OH, or —$(C_2$-$C_6)$alkenyl substituted with from 1 to 3 substituents selected from —F or —OH.

In some embodiments, $R^{1a}$ is selected from H, unsubstituted —$(C_1$-$C_4)$alkyl, or —$(C_1$-$C_4)$alkyl substituted with from 1 to 3 substituents selected from F and OH; or $R^1$ and $R^{1a}$ may join together to form a 3 to 7 membered ring with 0, 1, or 2 heteroatoms selected from O, N, or S.

In some embodiments, $R^3$ is —H, —F, —Cl, —OH, —S$(C_1$-$C_2)$alkyl, unsubstituted —$(C_1$-$C_4)$alkyl, unsubstituted —O$(C_1$-$C_3)$alkyl, —$(C_1$-$C_4)$alkyl substituted with from 1 to 3 substituents selected from —F, —OH, (=O), or —O$(C_1$-$C_2)$alkyl, or substituted —O$(C_1$-$C_3)$alkyl, wherein the alkyl group of the substituted —O$(C_1$-$C_3)$alkyl is substituted with from 1 to 3 substituents selected from —F, —OH, or —O$(C_1$-$C_2)$alkyl.

In some embodiments, $R^7$ and $R^8$ are independently selected from H and unsubstituted —$(C_1$-$C_4)$alkyl.

In some embodiments, $R^9$ and $R^{10}$ are independently selected from H and unsubstituted —$(C_1$-$C_4)$alkyl.

In some embodiments, each of $R^{11a}$, $R^{11b}$, $R^{11c}$, and $R^{11d}$ is independently selected from —H, —F, —Cl, —$(C_1$-$C_4)$alkyl, —O$(C_1$-$C_4)$alkyl, or —$CF_3$; and $R^{11a}$ is absent if G is N; $R^{11b}$ is absent if J is N, $R^{11c}$ is absent if L is N; or $R^{11d}$ is absent if K is N.

In some embodiments, each of $R^{12a}$, $R^{12b}$, and $R^{12c}$ is independently selected from —H, —F, —Cl, unsubstituted —$(C_1$-$C_4)$alkyl, $CF_3$, or —O$(C_1$-$C_4)$alkyl.

In some embodiments, $R^{13}$ is selected from —H, —F, —$(C_1$-$C_4)$alkyl, and —O—$(C_1$-$C_4)$alkyl.

In some embodiments, A is selected from —$(C_4$-$C_{12})$alkyl, —$(C_4$-$C_{12})$alkenyl, —$(C_3$-$C_{12})$alkyl-O—$(C_1$-$C_4)$alkyl, —$(C_3$-$C_{12})$alkyl-OH, —$(C_3$-$C_{12})$alkenyl-O—$(C_1$-$C_4)$alkyl, —$(C_3$-$C_{12})$alkenyl-OH, —O—$(C_4$-$C_{12})$alkyl, —O—$(C_4$-$C_{12})$alkenyl, a heterocycle comprising 4 to 7 ring members of which 1 or 2 are heteroatoms selected from N or O, wherein the heterocycle has 0 or 1 double bond between ring members and is unsubstituted or is substituted with from 1 to 4 $(C_1$-$C_2)$ alkyl groups, a —$(C_1$-$C_4)$alkyl-heterocyclyl wherein the heterocyclyl of the —$(C_1$-$C_4)$alkyl-heterocyclyl comprises 4 to 7 ring members of which 1 or 2 are heteroatoms selected from N or O, wherein the heterocycle has 0 or 1 double bond between ring members and is unsubstituted or is substituted with from 1 to 4 $(C_1$-$C_2)$alkyl groups, or a —O-heterocyclyl wherein the heterocyclyl of the —O-heterocyclyl comprises 4 to 7 ring members of which 1 or 2 are heteroatoms selected from N or O, wherein the heterocycle has 0 or 1 double bond between ring members and is unsubstituted or is substituted with from 1 to 4 $(C_1$-$C_2)$alkyl groups, further wherein the alkyl and alkenyl groups of —$(C_4$-$C_{12})$alkyl, —$(C_4$-$C_{12})$alkenyl, —$(C_3$-$C_{12})$alkyl-O—$(C_1$-$C_4)$alkyl, —$(C_3$-$C_{12})$alkyl-O—H, —$(C_3$-$C_{12})$alkenyl-O—$(C_1$-$C_4)$alkyl, —$(C_3$-$C_{12})$alkenyl-OH, —O—(C$_4$-C$_{12}$)alkyl, or —O—(C$_4$-C$_{12}$)alkenyl are unsubstituted or are substituted with from 1 to 4 substituents selected from —F, —Cl, —OH, (=O), —NH$_2$, NH(C$_1$-C$_4$)alkyl, —N((C$_1$-C$_4$)alkyl)$_2$, aryl, unsubstituted —O—(C$_1$-C$_2$)alkyl, or unsubstituted —(C$_1$-C$_2$)alkyl. In some such embodiments, A is selected from —(C$_4$-C$_{12}$)alkyl, —(C$_4$-C$_{12}$)alkenyl, —(C$_3$-C$_{12}$)alkyl-O—(C$_1$-C$_4$)alkyl, —(C$_3$-C$_{12}$)alkyl-OH, —(C$_3$-C$_{12}$)alkenyl-O—(C$_1$-C$_4$)alkyl, —(C$_3$-C$_{12}$)alkenyl-OH, —O—(C$_4$-C$_{12}$)alkyl, or —O—(C$_4$-C$_{12}$)alkenyl, wherein the alkyl and alkenyl groups of —(C$_4$-C$_{12}$)alkyl, —(C$_4$-C$_{12}$)alkenyl, —(C$_3$-C$_{12}$)alkyl-O—(C$_1$-C$_4$)alkyl, —(C$_3$-C$_{12}$)alkyl-O—H, —(C$_3$-C$_{12}$)alkenyl-O—(C$_1$-C$_4$)alkyl, —(C$_3$-C$_{12}$)alkenyl-OH, —O—(C$_4$-C$_{12}$)alkyl, or —O—(C$_4$-C$_{12}$)alkenyl are unsubstituted or are substituted with from 1 to 4 substituents selected from —F, —Cl, —OH, (=O), —NH$_2$, NH(C$_1$-C$_4$)alkyl, or N((C$_1$-C$_4$)alkyl)$_2$, unsubstituted —O—(C$_1$-C$_2$)alkyl, or unsubstituted —(C$_1$-C$_2$)alkyl. In some such embodiments, A is selected from —(C$_4$-C$_{12}$)alkyl, —(C$_4$-C$_{12}$)alkenyl, —(C$_3$-C$_{12}$)alkyl-O—(C$_1$-C$_4$)alkyl, —(C$_3$-C$_{12}$)alkyl-OH, —(C$_3$-C$_{12}$)alkenyl-O—(C$_1$-C$_4$)alkyl, —(C$_3$-C$_{12}$)alkenyl-OH, wherein the alkyl and alkenyl groups of —(C$_4$-C$_{12}$)alkyl, —(C$_4$-C$_{12}$)alkenyl, —(C$_3$-C$_{12}$)alkyl-O—(C$_1$-C$_4$)alkyl, —(C$_3$-C$_{12}$)alkyl-O—H, —(C$_3$-C$_{12}$)alkenyl-O—(C$_1$-C$_4$)alkyl, or —(C$_3$-C$_{12}$)alkenyl-OH, are unsubstituted or are substituted with from 1 to 4 substituents selected from —F, —OH, unsubstituted —O—(C$_1$-C$_2$)alkyl, or unsubstituted —(C$_1$-C$_2$)alkyl. In some such embodiments, A is selected from —(C$_4$-C$_{12}$)alkyl, —(C$_4$-C$_{12}$)alkenyl, —(C$_3$-C$_{12}$)alkyl-O—(C$_1$-C$_4$)alkyl, —(C$_3$-C$_{12}$)alkyl-OH, —(C$_3$-C$_{12}$)alkenyl-O—(C$_1$-C$_4$)alkyl, —(C$_3$-C$_{12}$)alkenyl-OH, wherein the alkyl and alkenyl groups of —(C$_4$-C$_{12}$)alkyl, —(C$_4$-C$_{12}$)alkenyl, —(C$_3$-C$_{12}$)alkyl-O—(C$_1$-C$_4$)alkyl, —(C$_3$-C$_{12}$)alkyl-O—H, —(C$_3$-C$_{12}$)alkenyl-O—(C$_1$-C$_4$)alkyl, or —(C$_3$-C$_{12}$)alkenyl-OH, are unsubstituted or are substituted with 1 to 4 substituent selected from —F, —OH, unsubstituted —O—(C$_1$-C$_2$)alkyl, or unsubstituted —(C$_1$-C$_2$)alkyl. In some such embodiments, A is a 5 to 7 membered cycloalkyl or cycloalkenyl group comprising from 1 to 4 methyl groups. In other embodiments, A is a —(C$_3$-C$_{12}$)alkyl-O—(C$_1$-C$_4$)alkyl, —(C$_3$-C$_{12}$)alkyl-OH, —(C$_3$-C$_{12}$)alkenyl-O—(C$_1$-C$_4$)alkyl, or —(C$_3$-C$_{12}$)alkenyl-OH. In some embodiments, each of the alkyl and alkenyl groups of the —(C$_3$-C$_{12}$)alkyl-O—(C$_1$-C$_4$)alkyl, —(C$_3$-C$_{12}$)alkyl-OH, —(C$_3$-C$_{12}$)alkenyl-O—(C$_1$-C$_4$)alkyl, or —(C$_3$-C$_{12}$)alkenyl-OH are unsubstituted whereas in other embodiments, each is substituted with 1 to 4 substituents selected from —OH, unsubstituted —O—(C$_1$-C$_2$)alkyl, or unsubstituted —(C$_1$-C$_2$)alkyl. In some embodiments, A is a —(C$_4$-C$_8$)alkyl-O—(C$_1$-C$_2$)alkyl, —(C$_4$-C$_8$)alkyl-OH, —(C$_4$-C$_8$)alkenyl-O—(C$_1$-C$_2$)alkyl, or —(C$_4$-C$_8$)alkenyl-OH and each of the alkyl and alkenyl groups of —(C$_4$-C$_8$)alkyl-O—(C$_1$-C$_2$)alkyl, —(C$_4$-C$_8$)alkyl-OH, —(C$_4$-C$_8$)alkenyl-O—(C$_1$-C$_2$)alkyl, or —(C$_4$-C$_8$)alkenyl-OH are unsubstituted or are substituted with 1 substituent selected from —OH, unsubstituted —O—(C$_1$-C$_2$)alkyl, or unsubstituted —(C$_1$-C$_2$)alkyl. In some such embodiments, at least one of the alkyl or alkenyl groups is branched or comprises a C$_3$-C$_7$ cycloalkyl ring. Therefore, in some embodiments, A is selected from

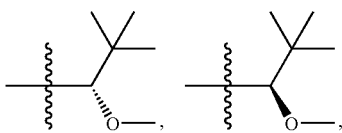

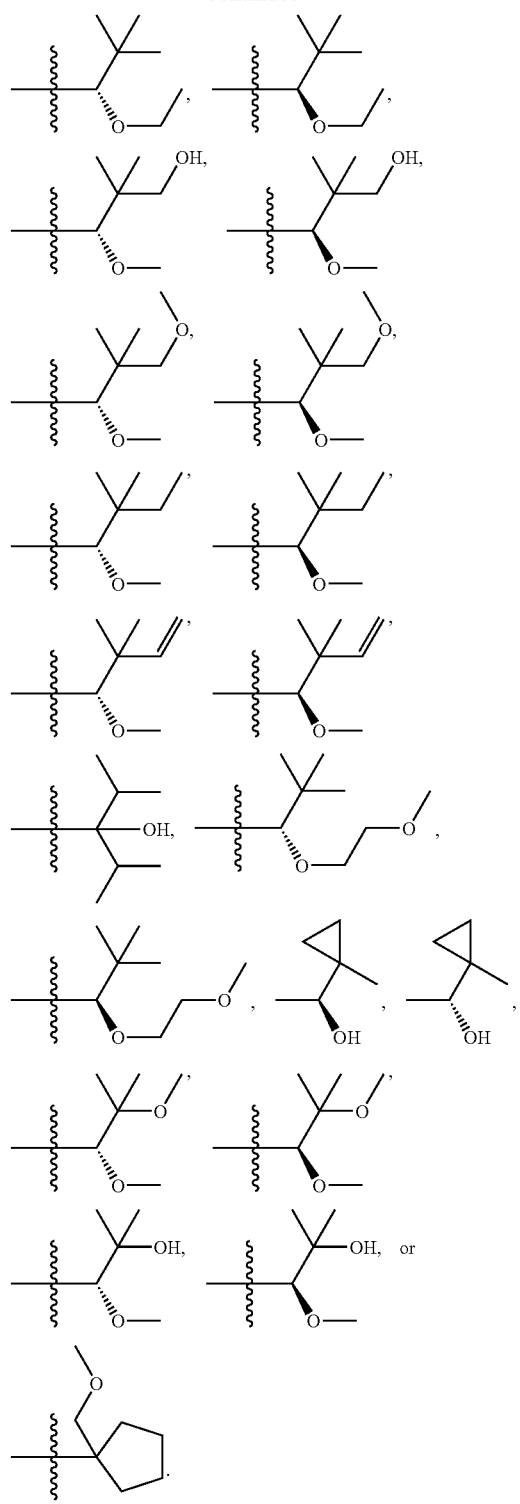

In some embodiments, X is O. In other embodiments, X is S. In still further embodiments X is NR$^a$. In some embodiments X is NR$^a$ and R$^a$ is selected from H or methyl. In still other embodiments, X is NR$^a$ and R$^a$ is H.

In some embodiments, the compound of formula I is a compound of formula I' or a pharmaceutically acceptable salt, stereoisomer, C$_1$-C$_6$ alkyl ester, or mixture thereof,

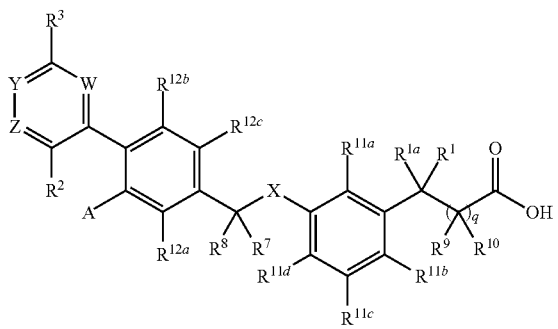

where the variables have the values described above with respect to the compound of formula I.

In some embodiments, the compound of formula I is a compound of formula I" or a pharmaceutically acceptable salt, stereoisomer, $C_1$-$C_6$ alkyl ester, or mixture thereof:

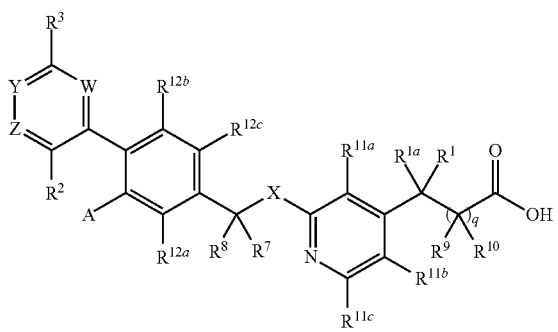

where the variables have the values described above with respect to the compound of formula I.

In some embodiments, G is $CR^{11a}$; J is $CR^{11b}$; L is $CR^{11c}$; and K is $CR^{11d}$. In some such embodiments, each of $R^{11a}$, $R^{11b}$, $R^{11c}$, and $R^{11d}$ is H. In some such embodiments, each of $R^{12a}$, $R^{12b}$, and $R^{12c}$ is H. In other such embodiments, $R^{12a}$ and $R^{12b}$ are H and $R^{12c}$ is F. In still other such embodiments, $R^{12b}$ and $R^{12c}$ are H and $R^{12a}$ is F. In yet other such embodiments, $R^{12a}$ and $R^{12c}$ are H and $R^{12b}$ is F. In other such embodiments, $R^{11a}$ is F and each of $R^{11b}$, $R^{11c}$, and $R^{11d}$ is H. In other such embodiments, $R^{11b}$ is F and each of $R^{11a}$, $R^{11c}$, and $R^{11d}$ is H. In other such embodiments, $R^{11c}$ is F and each of $R^{11a}$, $R^{11b}$, and $R^{11d}$ is H. In other such embodiments, $R^{11d}$ is F and each of $R^{11a}$, $R^{11b}$, and $R^{11c}$ is H. In other embodiments, where $R^{11a}$, $R^{11b}$, $R^{11c}$, and $R^{11d}$ is H or where $R^{11a}$ is F and each of $R^{11b}$, $R^{11c}$, and $R^{11d}$ is H, $R^{12c}$ is F, $R^{12a}$ is H, and $R^{12b}$ is H.

In some embodiments, G is $CR^{11a}$; J is $CR^{11b}$; L is $CR^{11c}$; and K is N. In some such embodiments, each of $R^{11a}$, $R^{11b}$, and $R^{11c}$ is H. In some such embodiments, each of $R^{12a}$, $R^{12b}$, and $R^{12c}$ is H. In some such embodiments $R^{1a}$ is H; W is C—H; Y, is C—H; Z is C—H; $R^7$ is H; $R^8$ is H; $R^9$ is H; $R^{10}$ is H; X is O, and q is 1. In still other such embodiments, $R^2$ is F. In some such embodiments, $R^3$ is methoxy or ethoxy.

In some embodiments, G is N; J is $CR^{11b}$; L is $CR^{11c}$; and K is $CR^{11d}$. In some such embodiments, each of $R^{11b}$, $R^{11c}$, and $R^{11d}$ is H. In some such embodiments, each of $R^{12a}$, $R^{12b}$, and $R^{12c}$ is H.

In some embodiments, G is $CR^{11a}$; J is N; L is $CR^{11c}$; and K is $CR^{11d}$. In some such embodiments, each of $R^{11a}$, $R^{11c}$, and $R^{11d}$ is H. In some such embodiments, each of $R^{12a}$, $R^{12b}$, and $R^{12c}$ is H.

In some embodiments, G is $CR^{11a}$; J is $CR^{11b}$; L is N; and K is $CR^{11d}$. In some such embodiments, each of $R^{11a}$, $R^{11b}$, and $R^{11d}$ is H. In some such embodiments, each of $R^{12a}$, $R^{12b}$, and $R^{12c}$ is H.

In some embodiments, G is $CR^{11a}$; J is $CR^{11b}$; L is $CR^{11c}$; K is $CR^{11d}$; $R^{11a}$, $R^{11b}$, $R^{11c}$, and $R^{11d}$ are H; $R^{1a}$ is H; W is C—H; Z is C—H; $R^2$ is F; $R^3$ is methoxy; $R^7$ is H; $R^8$ is H; $R^9$ is H; $R^{10}$ is H; X is O; q is 1; and two of $R^{12a}$, $R^{12b}$, and $R^{12c}$ are H and the other of $R^{12a}$, $R^{12b}$, and $R^{12c}$ is F. In some such embodiments, Y is N.

In some embodiments of the compound of formula I or I', $R^2$ is selected from F, $CF_3$, or ($C_1$-$C_6$)alkoxy. In some such embodiments, $R^2$ is selected from F, $CF_3$, or ($C_4$-$C_6$)alkoxy. In some such embodiments, $R^2$ is H or F. In other embodiments, $R^2$ is F. In still other embodiments, $R^2$ is H. In other embodiments, $R^2$ is propoxy, butoxy, or pentoxy. In some such embodiments, $R^2$ is butoxy.

In some embodiments, A is selected from ($C_1$-$C_{12}$)alkyl, ($C_2$-$C_{12}$)alkenyl, —O—($C_1$-$C_{12}$)alkyl, —O—($C_2$-$C_{12}$)alkenyl, or —O—($C_1$-$C_4$)alkyl-aryl.

In some embodiments, $R^2$ is H or F, and A is selected from a branched ($C_4$-$C_{10}$)alkyl group, a ($C_4$-$C_{10}$)alkenyl group, a bicyclic ($C_7$-$C_{12}$)alkyl group, an unsubstituted or a substituted ($C_5$-$C_7$)cycloalkyl group, or an unsubstituted or a substituted ($C_5$-$C_7$)cycloalkenyl group. In some embodiments, A is a an unsubstituted ($C_5$-$C_7$)cycloalkyl group, a ($C_5$-$C_7$)cycloalkyl group substituted with 1, 2, 3, or 4 methyl groups, an unsubstituted ($C_5$-$C_7$)cycloalkenyl group, or a ($C_5$-$C_7$)cycloalkenyl group substituted with 1, 2, 3, or 4 methyl groups. In some such embodiments, $R^1$ is selected from methyl, ethyl, propyl, cyclopropyl, cyclobutyl, or cyclopropylmethyl. In some such embodiments, $R^3$ is methoxy. In some such embodiments, A is selected from

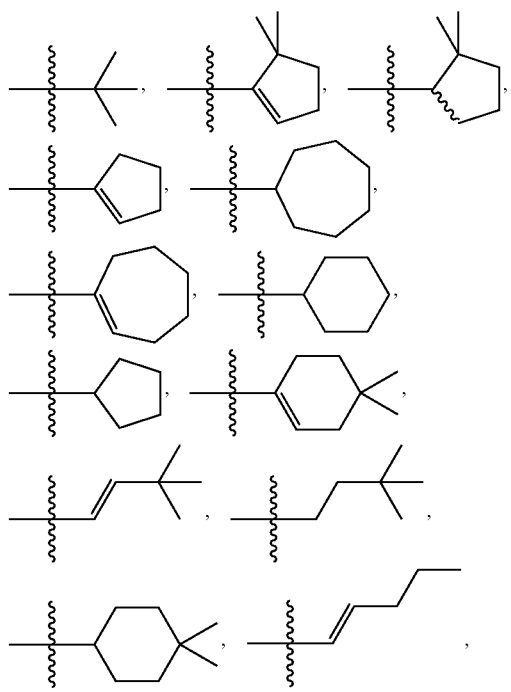

-continued

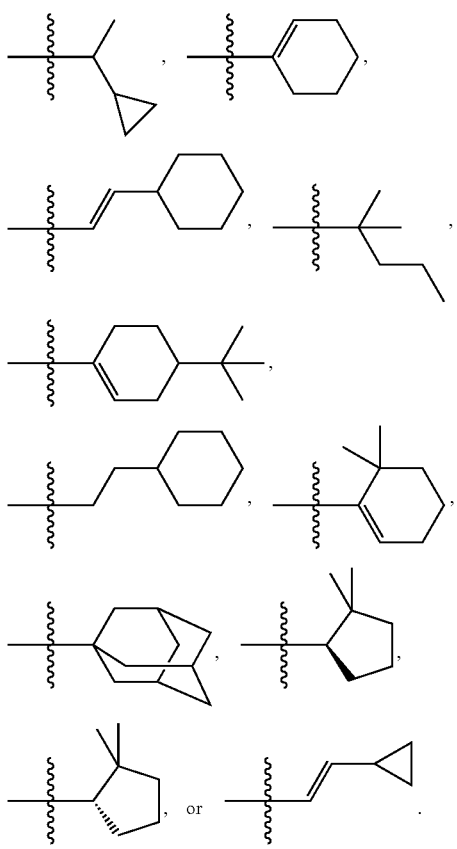

In some such embodiments, A is selected from

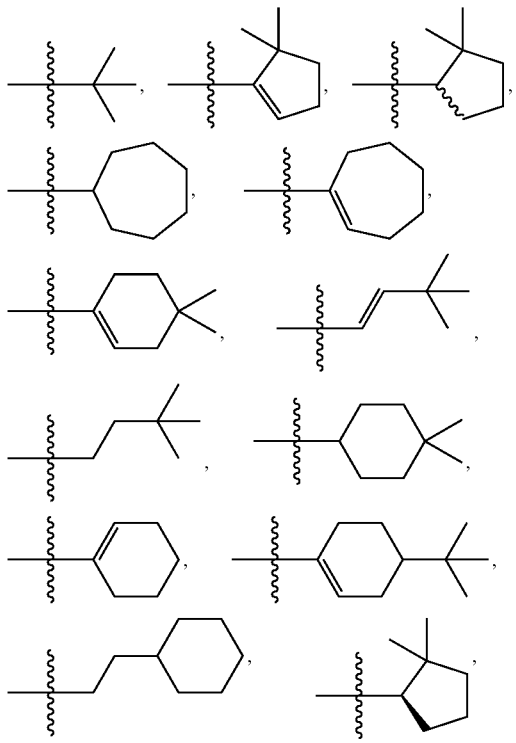

-continued

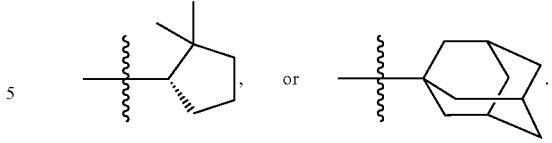

In some embodiments of the compound of formula I or I', $R^3$ is selected from —OH, —O($C_1$-$C_2$)alkyl, or —S($C_1$-$C_2$) alkyl. In some such embodiments, $R^3$ is selected from —O($C_1$-$C_2$)alkyl or —S($C_1$-$C_2$)alkyl. In some embodiments, $R^3$ is selected from —O-Me or —S-Me. In other such embodiments $R^3$ is —O-Et. In still other such embodiments, $R^3$ is selected from —O—($C_1$-$C_2$)haloalkyl. Examples of some such groups include —OCF$_3$ and —OCH$_2$CF$_3$. In some embodiments, $R^3$ is selected from methoxy or ethoxy. In other embodiments, $R^3$ is a substituted ($C_1$-$C_2$)alkyl group such as a —CHF$_2$ or —CF$_3$ group. In other embodiments, $R^3$ is a ($C_1$-$C_3$)alkyl group that is substituted with a group such as —OH or with an oxo group. Examples of such groups include, but are not limited to, —C(CH$_3$)$_2$OH and —C(=O)—CH$_3$. In some embodiments, $R^3$ is selected from —F, —Cl, —OH, —OCH$_3$, —SCH$_3$, —OCH$_2$CH$_3$, —OCHF$_2$, —OCF$_3$, —OCH$_2$CF$_3$, —O-cyclopropyl, —CHF$_2$, —CF$_3$, —C(=O)—CH$_3$, —CH(CH$_3$)$_2$OH, or —CH$_2$CH$_3$. In some such embodiments, $R^3$ is selected from —OCH$_3$, —OCH$_2$CH$_3$, —OCHF$_2$, —OCF$_3$, —OCH$_2$CF$_3$, —O-cyclopropyl, —CHF$_2$, or —CF$_3$. In some embodiments, $R^3$ is selected from —F, —Cl, —OCHF$_2$, —OCH$_2$CF$_3$, —OCF$_3$, —O-cyclopropyl, —CF$_3$, or —CHF$_2$. In some embodiments, $R^3$ is selected from —OCHF$_2$, —OCH$_2$CF$_3$, —OCF$_3$, —O-cyclopropyl, —CF$_3$, or —CHF$_2$.

In some embodiments of the compound of formula I or I', q is 1.

In some embodiments of the compound of formula I or I', $R^{1a}$ is H or methyl. In some such embodiments, $R^{1a}$ is H.

In some embodiments of the compound of formula I or I', $R^1$ and $R^{1a}$ join together to form a ring having 3 to 7 ring members. In some such embodiments, $R^1$ and $R^{1a}$ join to form a cycloalkyl ring such as a cyclopropyl, cyclobutyl, cyclopentyl, cyclohexyl, or cycloheptyl ring. In other embodiments, the ring has 3 to 7 ring members and includes 1 heteroatom selected from O, S, or N.

In some embodiments of the compound of formula I or I', W, Y, and Z are all C—H. In other embodiments W and Z are C—H and Y is N.

In some embodiments of the compound of formula I or I', A is selected from ($C_3$-$C_{10}$)alkyl or ($C_4$-$C_{10}$)alkenyl. In some such embodiments, A is t-butyl. In other such embodiments, A is an unsubstituted or substituted cyclopentyl, cyclohexyl, or cycloheptyl group. In some such embodiments, A is an unsubstituted cyclopentyl, cyclohexyl, or cycloheptyl group. In some such embodiments, A is a cyclopentyl, cyclohexyl, or cycloheptyl group optionally substituted with 1, 2, 3, or 4 ($C_1$-$C_4$)alkyl groups. In some such embodiments, A is a cyclopentyl, cyclohexyl, or cycloheptyl group substituted with a t-butyl group. In other such embodiments A is a cyclopentyl, cyclohexyl, or cycloheptyl group substituted with 1 or 2 methyl groups. In some such embodiments, A is an unsubstituted or substituted cyclopentenyl, cyclohexenyl, or cycloheptenyl group. In some such embodiments, A is an unsubstituted cyclopentenyl, cyclohexenyl, or cycloheptenyl group. In some such embodiments, A is a cyclopentenyl, cyclohexenyl, or cycloheptenyl group optionally substituted with 1, 2, 3, or 4 ($C_1$-$C_4$)alkyl groups. In some such embodiments, A is a cyclopentenyl, cyclohexenyl, or cycloheptenyl group substituted with a t-butyl group. In other such embodiments A is a cyclopentenyl, cyclohexenyl, or cycloheptenyl group substituted with 1 or 2 methyl groups.
In some embodiments of the compound of formula I or I', A is selected from
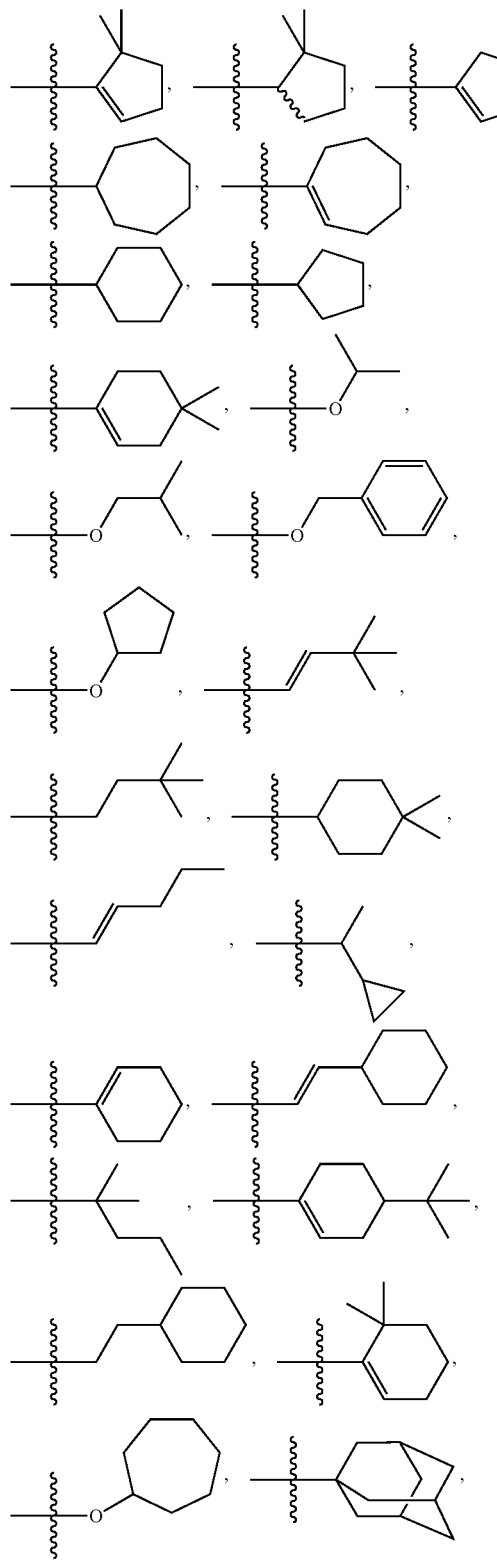
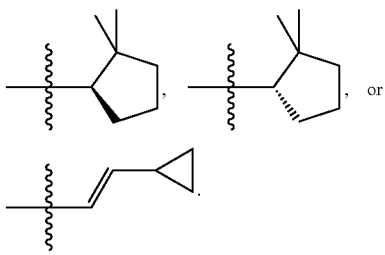
In some embodiments of the compound of formula I or I', A is selected from any one or more of 33
-continued
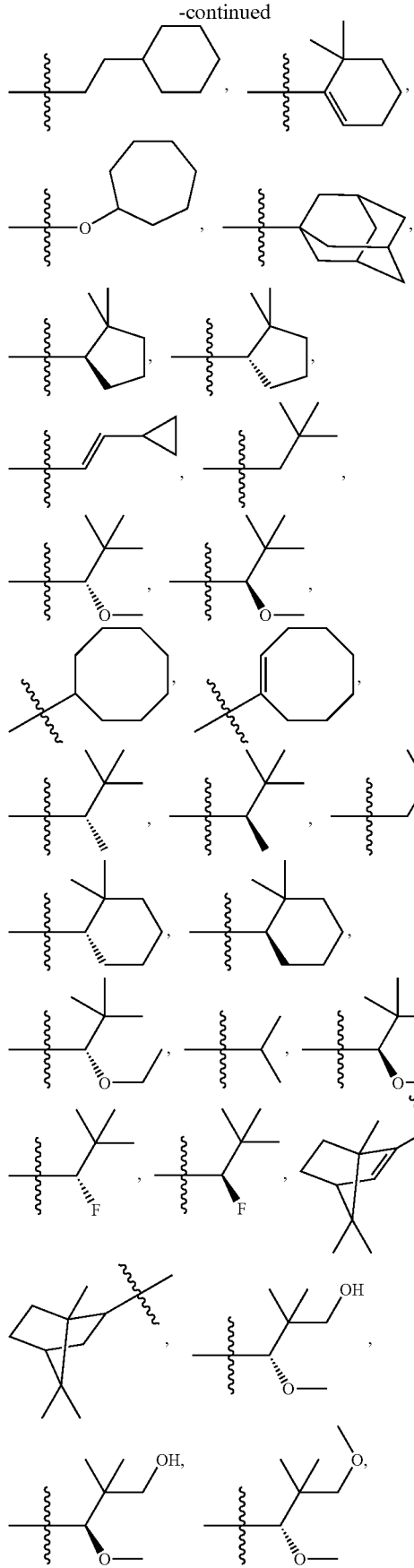
34
-continued
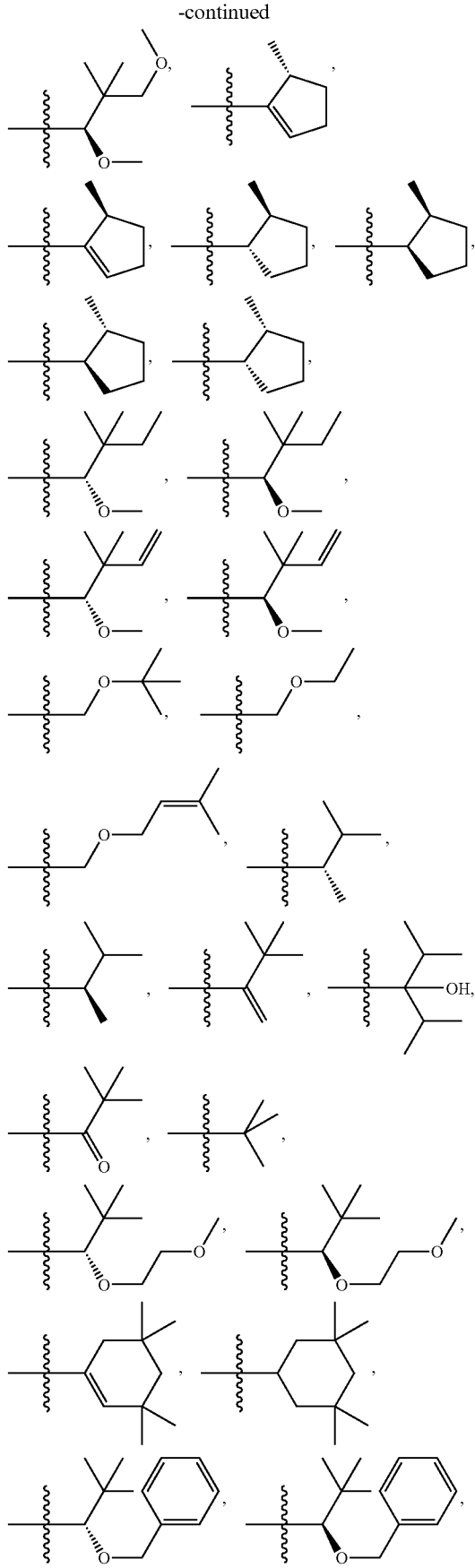

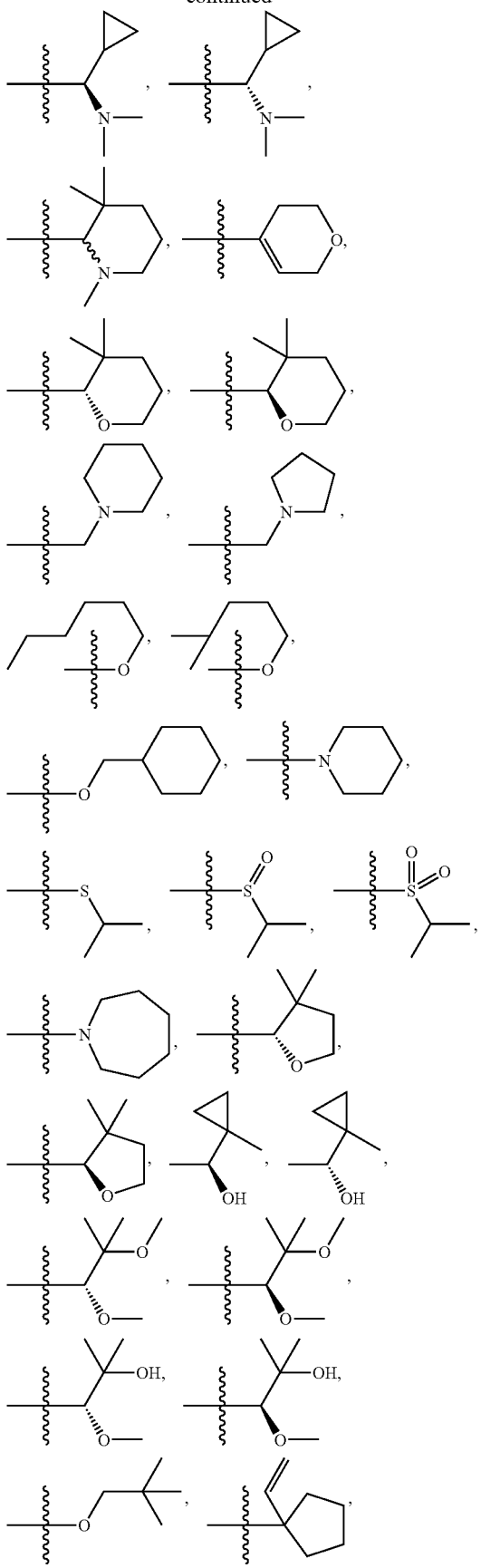

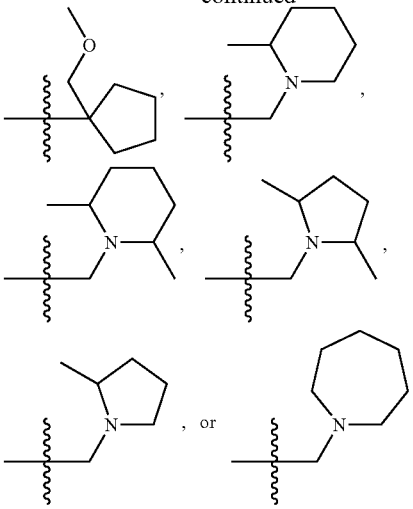

In some embodiments of the compound of formula I or I', A is a group of formula A'.

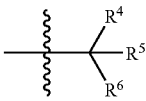

where the wavy line indicates the point of attachment and $R^4$, $R^5$, and $R^6$ are independently selected from H, F, $(C_1-C_4)$ alkyl, and two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring. In some such embodiments, $R^4$, $R^5$, and $R^6$ are independently selected from H and $(C_1-C_4)$ alkyl groups and at least two of $R^4$, $R^5$, and $R^6$ are $(C_1-C_4)$ alkyl groups. In some such embodiments, all three of $R^4$, $R^5$, and $R^6$ are independently selected from $(C_1-C_4)$alkyl groups. In some such embodiments, two of $R^4$, $R^5$, and $R^6$ are methyl groups. In some such embodiments, each of $R^4$, $R^5$, and $R^6$ is a methyl group. In other embodiments, $R^4$, $R^5$, and $R^6$ are independently selected from H, $(C_1-C_4)$alkyl groups, or a substituted $(C_1-C_4)$alkyl group selected from $(C_1-C_4)$haloalkyl groups, $(C_1-C_4)$perhaloalkyl groups, or $(C_1-C_4)$ alkoxy$(C_1-C_4)$alkyl groups. In some such embodiments, at least one of $R^4$, $R^5$, and $R^6$ is a $CF_3$ group. In other embodiments at least one of $R^4$, $R^5$, and $R^6$ is a methoxymethyl group.

In some embodiments of the compound of formula I or I', A is a group of formula A' where the wavy line indicates the point of attachment and $R^4$, $R^5$, and $R^6$ are independently selected from H, F, OH, —O—$(C_1-C_3)$alkyl, $(C_1-C_6)$alkyl and $(C_2-C_6)$alkenyl, and two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring. In some such embodiments, $R^4$, $R^5$, and $R^6$ are independently selected from H, OH, OMe, OEt, $(C_1-C_6)$alkyl, and $(C_2-C_6)$alkenyl groups and at least two of $R^4$, $R^5$, and $R^6$ are $(C_1-C_4)$alkyl groups. In some such embodiments, all three of $R^4$, $R^5$, and $R^6$ are independently selected from $(C_1-C_4)$alkyl groups. In some such embodiments, two of $R^4$, $R^5$, and $R^6$ are methyl groups. In some such embodiments, each of $R^4$, $R^5$, and $R^6$ is a methyl group. In other embodiments, $R^4$, $R^5$, and $R^6$ are independently selected from H, $(C_1-C_4)$alkyl groups, or a substituted $(C_1-C_4)$alkyl group selected from $(C_1-C_4)$haloalkyl groups, $(C_1-C_4)$perhaloalkyl groups, or $(C_1-C_4)$alkoxy$(C_1-C_4)$alkyl groups. In some such embodiments, at least one of $R^4$, $R^5$, and $R^6$ is a $CF_3$ group. In other embodiments at least one of $R^4$, $R^5$, and $R^6$ is a methoxymethyl group. In other embodiments, at least one of $R^4$, $R^5$, and $R^6$ is selected from OH, methoxy, or is ethoxy. In some such embodiments one of $R^4$, $R^5$, and $R^6$ is a methoxy. In other such embodiments one of $R^4$, $R^5$, and $R^6$ is OH. In other such embodiments one of $R^4$, $R^5$, and $R^6$ is ethoxy.

In some embodiments of the compound of formula I or I' where A is a group of formula A', two of $R^4$, $R^5$, and $R^6$, together with the C atom to which they are attached, join to form a 3-8 or 3-7 membered ring, and the other of $R^4$, $R^5$, and $R^6$ is selected from H, an unsubstituted $(C_1-C_4)$alkyl, or a substituted $(C_1-C_4)$alkyl. In some embodiments the ring is a carbocyclic ring which may be a fully saturated cycloalkyl ring. In some such embodiments, the 3-8 membered ring is a 5-7 membered ring, a 3-6 membered ring, or a 3-5 membered ring. Examples of such rings include cyclopropyl, cyclobutyl, cyclopentyl, cyclohexyl, and cycloheptyl rings. In some such embodiments, two of $R^4$, $R^5$, and $R^6$ join to form a cyclopropyl ring. In some such embodiments, the other of $R^4$, $R^5$, and $R^6$ is H. In some embodiments two of $R^4$, $R^5$, and $R^6$, together with the C atom to which they are attached, join to form an optionally substituted saturated or partially unsaturated 3-8 or 3-7 membered ring which may be monocyclic or bicyclic, and the other of $R^4$, $R^5$, and $R^6$ is selected from H, an unsubstituted $(C_1-C_4)$alkyl, or a substituted $(C_1-C_4)$alkyl. In some embodiments the ring only includes carbon ring members. In some such embodiments, the ring includes 0 or 1 double bonds between ring members. In some such embodiments, the 3-7 membered ring is a 3-6, or a 3-5 membered ring. Examples of such rings include cyclopropyl, cyclobutyl, cyclobutenyl, cyclopentyl, cyclopentenyl, cyclohexyl, cyclohexenyl, cycloheptyl, and cycloheptenyl rings. In some such embodiments, two of $R^4$, $R^5$, and $R^6$ join to form an optionally substituted cyclopropyl ring. In some such embodiments, the other of $R^4$, $R^5$, and $R^6$ is H. In some such embodiments, two of $R^4$, $R^5$, and $R^6$ join to form an optionally substituted cyclopentenyl, cyclohexenyl, or cycloheptenyl ring. In some such embodiments, the other of $R^4$, $R^5$, and $R^6$ is H. In some embodiments all three of $R^4$, $R^5$, and $R^6$, together with the C atom to which they are attached, join to form an optionally substituted saturated or partially unsaturated 3-8 membered ring bicyclic ring system. For example, in some embodiments, A may comprise an adamantyl or another bicyclic ring system such as, but not limited to bicyclo[3.2.1]octane, bicyclo[2.2.1]heptane, and the like. In some such embodiments the ring only includes carbon ring members. In some such embodiments, the ring includes 0 or 1 double bonds between ring members. In some embodiments, A is a branched chain $(C_4-C_8)$alkyl group such as a t-butyl group. In other such embodiments, A is an optionally substituted $(C_5-C_7)$cycloalkyl group or an optionally substituted $(C_5-C_7)$cycloalkenyl group. In some such embodiments, the $(C_5-C_7)$cycloalkyl group or the $(C_5-C_7)$cycloalkenyl group are substituted with 1, 2, 3, or 4 methyl groups. In some other such embodiments, A has the formula

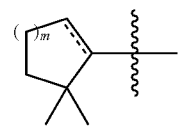

wherein m is 1, 2, or 3, and the dashed line indicates a single or double bond. In some such embodiments, A has the formula

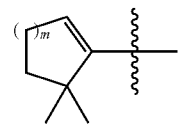

wherein m is 1, 2, or 3. In other such embodiments, A has the formula

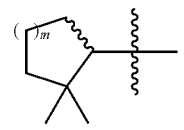

wherein m is 1, 2, or 3 and the wavy line indicates that the compound has the R stereochemistry, the S stereochemistry, or a mixture of the R and S stereochemistry with respect to the carbon attached to the rest of the molecule. In some such embodiments, A has the formula

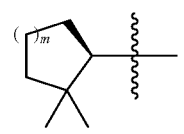

wherein m is 1, 2, or 3. In other embodiments, A has the formula

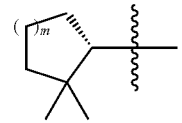

wherein m is 1, 2, or 3. In some embodiments, A is an $-OR^{4a}$ group. In some such embodiments, $R^{4a}$ is selected from a methyl, ethyl, propyl, butyl, pentyl, hexyl, isopropyl, t-butyl, or an isomer thereof. In some embodiments, $R^{4a}$ is selected from such an alkyl group that is substituted. For example, in some embodiments, $R^{4a}$ may a trihaloalkyl group such as a $CF_3$ group or another perhaloalkyl group.

In some embodiments, A is

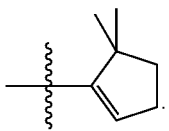

In some embodiments, A is selected from

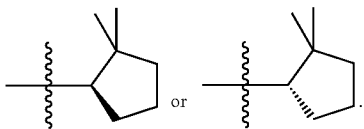

In some embodiments, A is

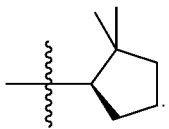

In some embodiments, A is

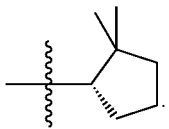

In some embodiments of the compound of formula I or I', A is a $(C_1-C_{12})$alkyl or is a $(C_2-C_{12})$alkenyl group and the $(C_1-C_{12})$alkyl or the $(C_2-C_{12})$alkenyl group is substituted with at least one A'' group where A'' is selected from —F, —OH, —O—$(C_1-C_4)$alkyl, —O$(C_1-C_4)$alkyl-aryl, —O$(C_2-C_8)$alkenyl, or —O—$(C_1-C_4)$alkyl-O—$(C_1-C_4)$alkyl. Therefore, in some embodiments A is selected from any one or all of:

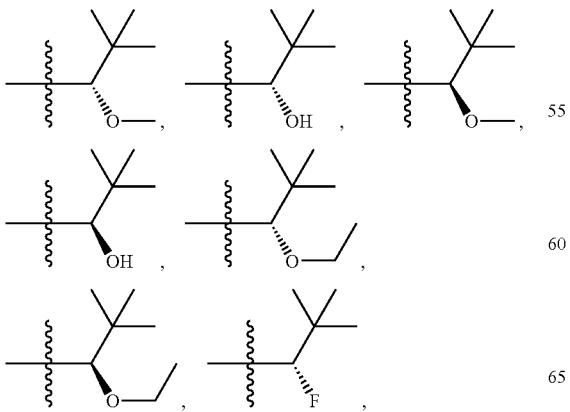

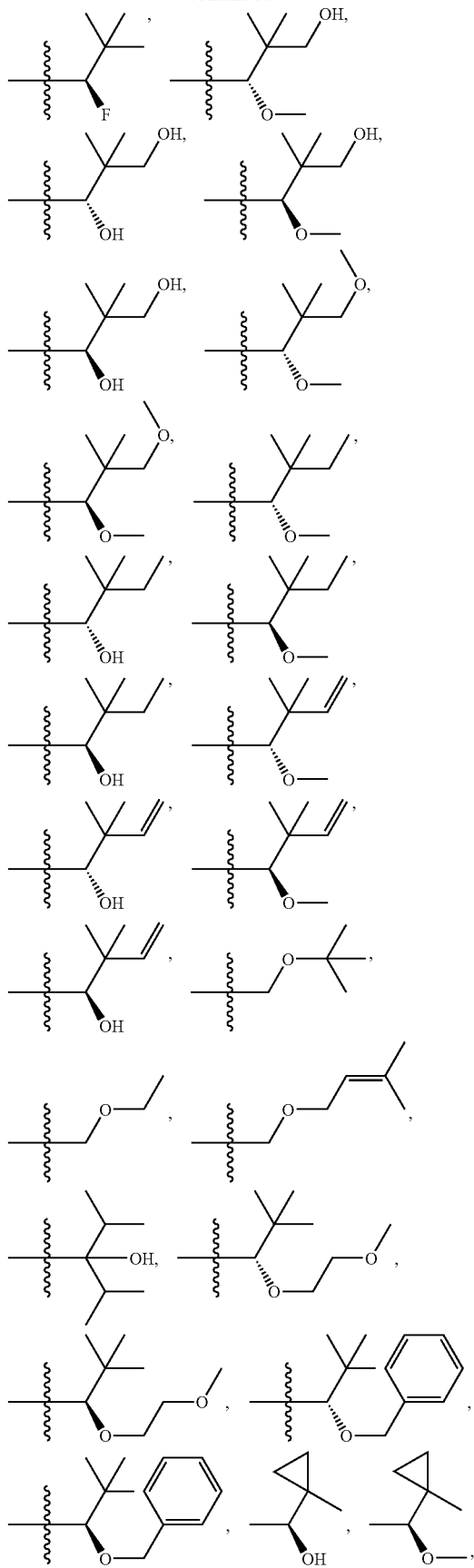

-continued

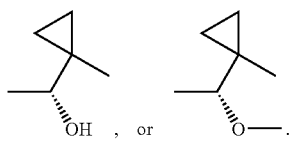

In some embodiments, A is selected from

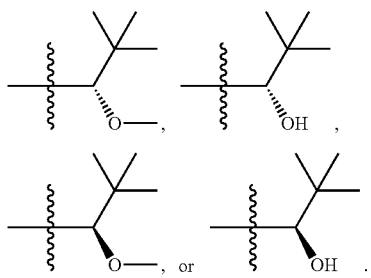

In some embodiments, A is selected from

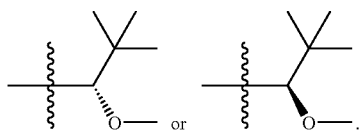

In some embodiments, A is

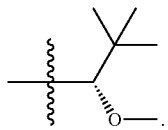

In some embodiments, A is

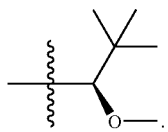

In some embodiments, A is selected from

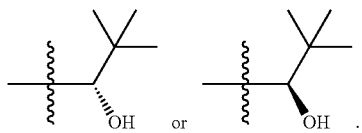

In some embodiments, A is

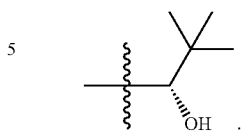

In some embodiments, A is

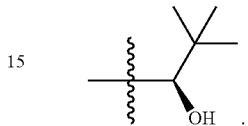

In some embodiments of the compound of formula I or I', $R^2$ is F or butoxy. In some such embodiments, $R^2$ is F whereas in other such embodiments, $R^2$ is butoxy. In still other embodiments, $R^2$ is propoxy, pentoxy, or hexoxy. In still further embodiments, $R^2$ is selected from F or $(C_3-C_4)$alkoxy. In some embodiments, $R^2$ is a —$CF_3$ group.

In some embodiments of the compound of formula I or I', $R^3$ is methoxy or ethoxy. In some such embodiments, $R^3$ is methoxy.

In some embodiments of the compound of formula I or I', $R^3$ is a substituted or unsubstituted —$O(C_1-C_2)$alkyl group. In some such embodiments, $R^3$ is a —$OCHF_2$ group.

In some embodiments of the compound of formula I or I', X is O. In other embodiments, X is S.

In some embodiments of the compound of formula I or I', $R^7$ and $R^8$ are both H. In some embodiments one of $R^7$ and $R^8$ is H and the other of $R^7$ and $R^8$ is methyl. Therefore, in some embodiments $R^7$ and $R^8$ are independently selected from H and methyl.

In some embodiments of the compound of formula I or I', $R^9$ and $R^{10}$ are both H. In other embodiments, $R^9$ and $R^{10}$ are selected from H and methyl. In some such embodiments, one of $R^9$ and $R^{10}$ is H and the other of $R^9$ and $R^{10}$ is methyl.

In some embodiments of the compound of formula I or I', $R^1$ is selected from $(C_1-C_6)$alkyl, $(C_2-C_6)$alkenyl, $(C_2-C_6)$alkynyl, heterocyclyl, or heteroaryl. In some such embodiments, $R^1$ is a $(C_1-C_4)$alkyl. In some such embodiments, $R^1$ is a methyl, ethyl, propyl, or butyl group. In some such embodiments, $R^1$ is a methyl, ethyl, or propyl. In some such embodiments, $R^1$ is a propyl group. In some embodiments, $R^1$ is a $(C_3-C_6)$alkyl group that is a cycloalkyl group such as cyclopropyl, cyclobutyl, or cyclopentyl group. In some embodiments, $R^1$ is a $CF_3$ group. In other embodiments, $R^1$ is a —$CH_2CF_3$ group. In still other embodiments, $R^1$ is a —$CH_2CH_2CF_3$ group. In some embodiments, $R^1$ is a cyclopropyl group or a cyclobutyl group that is optionally substituted. In some such embodiments, $R^1$ is selected from a cyclopropyl group that is optionally substituted with one or two methyl groups. In other embodiments, $R^1$ is a cyclobutyl group that is optionally substituted with one or two methyl groups. In still other embodiments, $R^1$ is a cyclopropylmethyl (—$CH_2$(cyclopropyl)) group. In yet other embodiments, $R^1$ is a cyclobutylmethyl (—$CH_2$(cyclobutyl)) group. In some embodiments, $R^1$ is a —$CH_3$, —$CH_2CH_3$, —$CH_2CH_2CH_3$, —$CH_2CH_2CH_2CH_3$, —$C(H)(CH_3)_2$, —$CH$=$CH_2$, —$C(CH_3)$=$CH_2$, —$CH_2C(H)$=$CH_2$, —$CF_3$, —$CH_2CH_2CF_3$, -cyclopropyl, -cyclobutyl, —$CH_2$-cyclopropyl, —$CH_2$-cyclobutyl, —$CH_2$—O—$CH_3$, —CH=CHCH$_2$CH$_3$, or —CH$_2$CH(CH$_3$)$_2$. In some such embodiments, R$^{1a}$ is —H whereas in other such embodiments, R$^{1a}$ is —CH$_3$.

In some embodiments of the compound of formula I or I', R$^1$ is a cis(C$_2$-C$_6$)alkenyl group whereas in other embodiments R$^1$ is a trans(C$_2$-C$_6$)alkenyl group. In some embodiments, R$^1$ is a mixture of cis and trans(C$_2$-C$_6$)alkenyl groups. In other embodiments, R$^1$ is a (C$_2$-C$_4$)alkenyl group. In some embodiments R$^1$ is a cis(C$_2$-C$_4$) alkenyl group whereas in other embodiments R$^1$ is a trans(C$_2$-C$_4$)alkenyl group. In some embodiments, R$^1$ is a mixture of cis and trans(C$_2$-C$_4$) alkenyl groups. In some embodiments, R$^1$ is selected from —CH=CH$_2$, —CH=CH—CH$_3$, —CH=CH—CH$_2$—CH$_3$, or —CH$_2$—CH=CH$_2$. In some such embodiments, R$^1$ is —CH$_2$—CH=CH$_2$. In some such embodiments, R$^1$ is —CH=CH—CH$_3$. In some such embodiments, R$^1$ has the formula

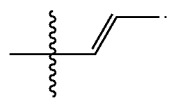

In other such embodiments, R$^1$ has the formula

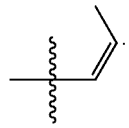

In some embodiments of the compound of formula I or I', R$^1$ is a (C$_2$-C$_4$) alkynyl. For example, in some embodiments, R$^1$ is —C≡C—CH$_3$.

In some embodiments of the compound of formula I, G is CR$^{11a}$; J is CR$^{11b}$; L is CR$^{11c}$; K is CR$^{11d}$; R$^{11a}$, R$^{11b}$, R$^{11c}$, R$^{11d}$, R$^{12a}$, R$^{12b}$, and R$^{12c}$ are all H; R$^{1a}$ is H; W is C—H; Y, is C—H; Z is C—H; R$^2$ is F; R$^3$ is methoxy; R$^7$ is H; R$^8$ is H; R$^9$ is H; R$^{10}$ is H; X is O, and q is 1. In some such embodiments, A is a branched chain (C$_4$-C$_8$)alkyl group such as a t-butyl, —CH$_2$CH$_2$C(CH$_3$)$_3$, —CH$_2$CH$_2$CH(CH$_3$)$_2$, —CH(CH$_3$)(cyclopropyl), or —C(CH$_3$)$_2$CH$_2$CH$_2$CH$_3$ group. In some such embodiments, A is a t-butyl group. In other such embodiments, A is an optionally substituted (C$_5$-C$_7$)cycloalkyl group or an optionally substituted (C$_5$-C$_7$)cycloalkenyl group. In some such embodiments, the (C$_5$-C$_7$)cycloalkyl group or the (C$_5$-C$_7$)cycloalkenyl group are substituted with 1, 2, 3, or 4 methyl groups. In some other such embodiments, A has the formula

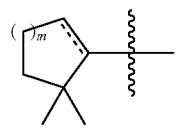

wherein m is 1, 2, or 3, and the dashed line indicates a single or double bond. In some such embodiments, A has the formula

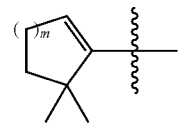

wherein m is 1, 2, or 3. In other such embodiments, A has the formula

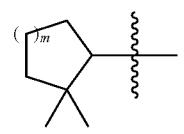

wherein m is 1, 2, or 3. In some such embodiments, A is a (C$_4$-C$_{10}$)alkenyl group. In some such embodiments, A is selected from —CH=CH—C(CH$_3$)$_3$, —CH=CH—CH$_2$CH$_2$CH$_3$, —CH=CH-cyclopropyl, or —CH=CH-cyclohexyl groups.

In some embodiments of the compound of formula I, G is CR$^{11a}$; J is CR$^{11b}$; L is CR$^{11c}$; K is CR$^{11d}$; R$^{11a}$, R$^{11b}$, R$^{11c}$, R$^{11d}$, R$^{12a}$, R$^{12b}$, and R$^{12c}$ are all H; R$^{1a}$ is H; W is C—H; Y, is C—H; Z is C—H; R$^2$ is F; R$^3$ is methoxy; R$^7$ is H; R$^8$ is H; R$^9$ is H; R$^{10}$ is H; X is O, q is 1, and A is —O—(C$_1$-C$_{12}$)alkyl, —O—(C$_2$-C$_{12}$)alkenyl, or —O—(C$_1$-C$_4$)alkyl-aryl. In some such embodiments, A is a —OCH$_2$-phenyl. In other embodiments, A is a —O—CF$_3$. In other such embodiments, A is a —O—(C$_3$-C$_{10}$)alkyl or —O—(C$_3$-C$_{10}$)alkenyl group. In other such embodiments, A is —O—(C$_3$-C$_8$)cycloalkyl optionally substituted with 1 or 2 methyl groups. In some such embodiments, A is an unsubstituted —O—(C$_3$-C$_8$)cycloalkyl group. In some such embodiments, A is a cyclopropyloxy, a cyclobutyloxy, a cyclopentyloxy, a cyclohexyloxy, or a cycloheptyloxy group. In some embodiments, A is a —O—CH$_2$CH$_2$CH$_3$, —O—CH$_2$CH$_2$CH$_2$CH$_3$, —O—CH$_2$CH$_2$CH$_2$CH$_2$CH$_3$, —O—CH(CH$_3$)$_2$, or —O—CH$_2$CH(CH$_3$)$_2$.

In some embodiments of the compound of formula I or I', R$^{11a}$, R$^{11b}$, R$^{11c}$, R$^{11d}$, R$^{12a}$, R$^{12b}$, and R$^{12c}$ are all H; R$^{1a}$ is H; W is C—H; Y, is C—H; Z is C—H; R$^7$ is H; R$^8$ is H; R$^9$ is H; R$^{10}$ is H; X is O; and A is —OR$^{4a}$. In some such embodiments, q is 1.

In some embodiments of the compound of formula I or I', G is CR$^{11a}$; J is CR$^{11b}$; L is CR$^{11c}$; K is CR$^{11d}$; R$^{11a}$ is H or F; R$^{11b}$, R$^{11c}$, and R$^{11d}$ are H; R$^{1a}$ is H; W is C—H; Z is C—H; R$^2$ is F; R$^3$ is methoxy; R$^7$ is H; R$^8$ is H; R$^9$ is H; R$^{10}$ is H; X is O; q is 1; and two of R$^{12a}$, R$^{12b}$, and R$^{12c}$ are H and the other of R$^{12a}$, R$^{12b}$, and R$^{12c}$ is F. In some such embodiments, R$^{11a}$ is H whereas in other such embodiments, R$^{11a}$ is F.

In some embodiments, the compound of formula I or I' is a compound of formula II or a pharmaceutically acceptable salt, stereoisomer, C$_1$-C$_6$ alkyl ester, or mixture thereof. The compound of formula II has the following structure where each of the variables has any of the values of any of the embodiments described herein:

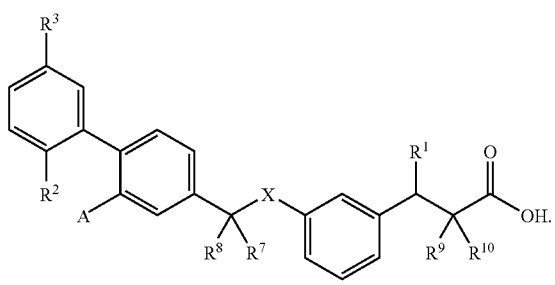

II

In some embodiments, the compound of formula II is a compound of formula II' or a pharmaceutically acceptable salt, stereoisomer, $C_1$-$C_6$ alkyl ester, or mixture thereof. The compound of formula II' has the following structure where each of the variables has any of the values of any of the embodiments described herein:

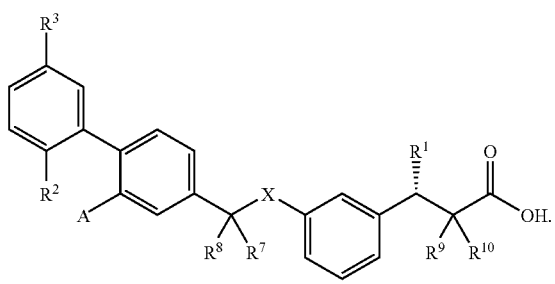

II'

In some embodiments, the compound of formula II is a compound of formula II" or a pharmaceutically acceptable salt, stereoisomer, $C_1$-$C_6$ alkyl ester, or mixture thereof. The compound of formula II' has the following structure where each of the variables has any of the values of any of the embodiments described herein:

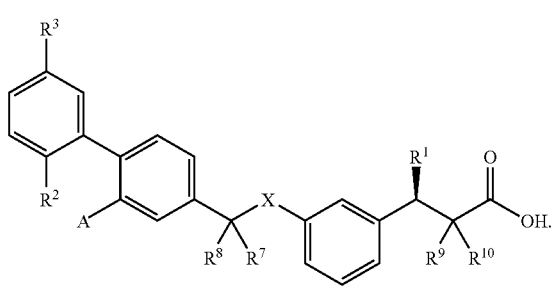

II"

In some embodiments of the compound of formula I, W and Z are CH and Y is N such that the compound of formula I has the formula III or is a pharmaceutically acceptable salt, stereoisomer, $C_1$-$C_6$ alkyl ester, or mixture thereof. The compound of formula III has the following structure where each of the variables has any of the values of any of the embodiments described herein:

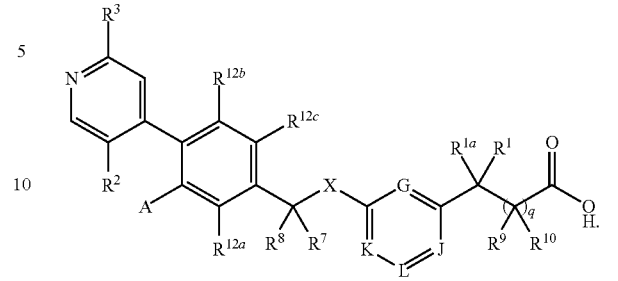

III

In some embodiments, the compound of formula III is a compound of formula III' or a pharmaceutically acceptable salt, stereoisomer, $C_1$-$C_6$ alkyl ester, or mixture thereof. The compound of formula III' has the following structure where each of the variables has any of the values of any of the embodiments described herein:

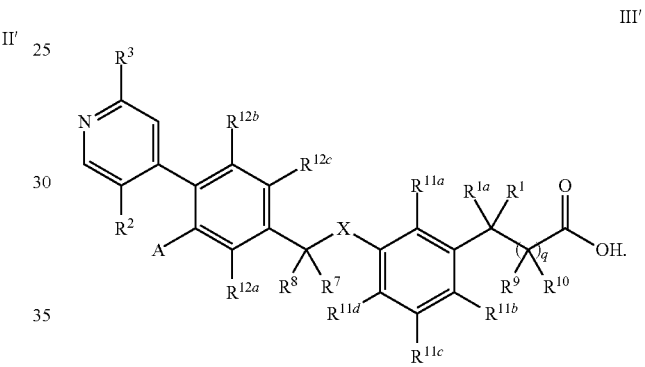

III'

In some embodiments, the compound of formula III is a compound of formula III" or a pharmaceutically acceptable salt, stereoisomer, $C_1$-$C_6$ alkyl ester, or a mixture thereof. The compound of formula III" has the following structure where each of the variables has any of the values of any of the embodiments described herein:

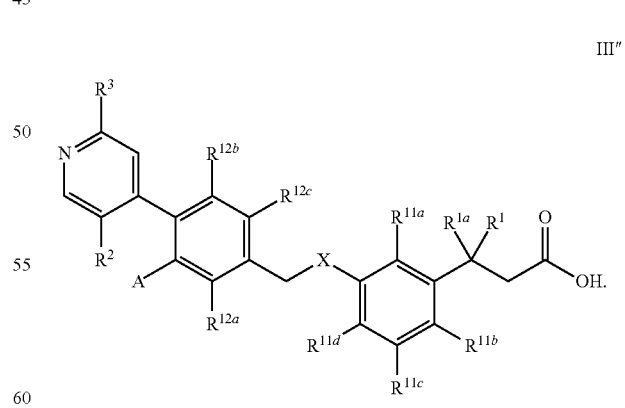

III"

In some embodiments of the compound of formula III, formula III', or formula III", $R^{11a}$ is selected from H or F. In some such embodiments, $R^{11a}$ is H whereas in other such embodiments $R^{11a}$ is F. In some embodiments, $R^{11b}$, $R^{11c}$, and $R^{11d}$ are each H. In still other embodiments, $R^{11a}$ is F, $R^{11b}$ is H, $R^{11c}$ is H, and $R^{11d}$ is H whereas in other embodiments $R^{11a}$ is H, $R^{11b}$ is H, $R^{11c}$ is H, and $R^{11d}$ is H. In still other such embodiments $R^2$ is F. In still other such embodiments, $R^3$ is methoxy (—OCH$_3$). In still further such embodiments, one of $R^{12a}$, $R^{12b}$, and $R^{12c}$ is F and the other two of $R^{12a}$, $R^{12b}$, and $R^{12c}$ are H. In some such embodiments, $R^{12c}$ is F, $R^{12a}$ is H, and $R^{12b}$ is H. In other embodiments, each of $R^{12a}$, $R^{12b}$, and $R^{12c}$ is H. In some embodiments, X is selected from O or S. Therefore, in some embodiments, X is O whereas in other embodiments, X is S.

In some embodiments, the compound of formula I is selected from a group that includes each, all, or any one of the compounds in any of the tables or is a pharmaceutically acceptable salt, or $C_1$-$C_6$ alkyl ester thereof. In some such embodiments where the compound has a chiral center, the compound exists as a single enantiomer whereas in other embodiments, the compound is a mixture of enantiomers of the compounds shown above. In some such embodiments, the compound of formula I is one of the compounds in any of the tables or is a pharmaceutically acceptable salt, or $C_1$-$C_6$ alkyl ester thereof. In other embodiments, the compound is an enantiomer or diastereomer of one of the compounds in any of the tables or is a pharmaceutically acceptable salt, or $C_1$-$C_6$ alkyl ester thereof.

In some embodiments, the compound of formula I is a $C_1$-$C_6$ alkyl ester. Such esters typically have the formula IE where each of the variables has any of the values set forth herein with respect to any of the embodiments, and Alk is a $C_1$-$C_6$ alkyl group. In some such embodiments, Alk is a methyl or ethyl group such that the compound is a methyl or ethyl ester.

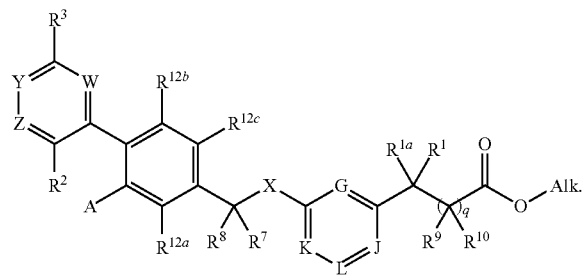

IE

In some embodiments, the compound is selected from any of those in any of the tables. Furthermore, in some embodiments, the compound of formula I has a variable corresponding to any of the groups in the compounds of any of the tables. For example, if a compound in any of the tables has a group corresponding to the A group, then in some embodiments of the compound of formula I, the A group will correspond to that set forth in the compound(s) in any of the tables.

In some embodiments, the compound of any of the embodiments described herein does not displace a compound of the following formula that is bound to the GPR40 receptor

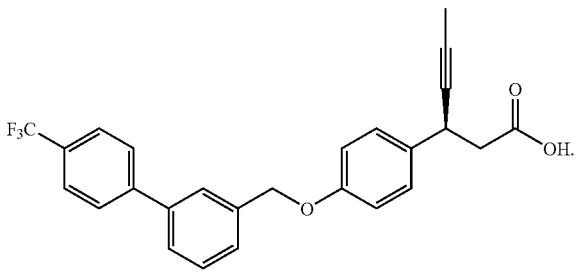

In some embodiments, the compound of any one of the embodiments described herein binds to a different site on the GPR40 receptor than does a compound of formula

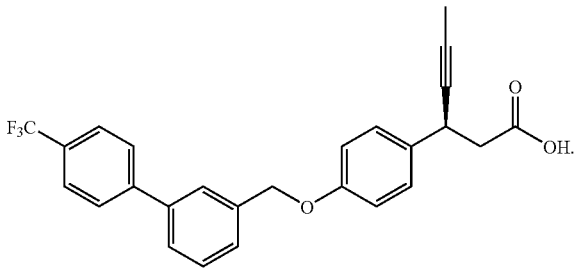

In one aspect, the invention provides a compound that binds to a different site on the GPR40 receptor than does the following compound

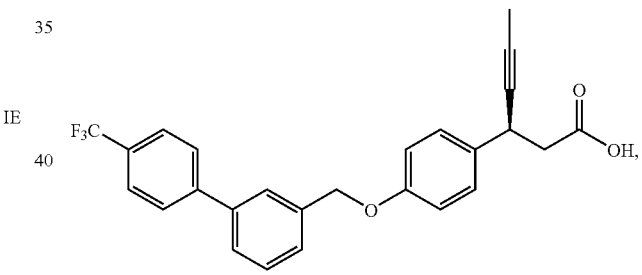

wherein the compound is a synthetic compound that does not occur naturally in the body of an animal. In some such embodiments, the compound comprises a biphenyl group. In other such embodiments, the compound comprises a biphenyl group and a phenyl group that is not part of the biphenyl group. In some such embodiments, the compound further comprises a carboxylic acid group or a salt of such a group. In still other such compounds, the phenyl group that is not part of the biphenyl group is meta substituted.

In some embodiments, the compound of any of the embodiments is a salt. In other embodiments, the compound of any of the embodiments is a $C_1$-$C_6$ alkyl ester. In some such embodiments, the $C_1$-$C_6$ alkyl ester is a $C_1$-$C_6$ alkyl ester such as a methyl, ethyl, propyl, butyl, isopropyl, pentyl, or hexyl ester. In other embodiments, the $C_1$-$C_6$ alkyl ester is a methyl, ethyl, propyl, or butyl ester. In some such embodiments, the ester is a methyl or ethyl ester.

In some embodiments, the compound comprises a stereomerically pure S-enantiomer. In other embodiments, the compound comprises a stereomerically pure R-enantiomer. In yet other embodiments, the compound comprises a mixture of S- and R-enantiomers.

In another aspect, the invention provides pharmaceutical compositions comprising a pharmaceutically acceptable carrier, diluent, or excipient, and a compound of any of the embodiments of the invention.

In another aspect, a compound of any of the embodiments described herein is used to prepare a medicament.

In yet another aspect, the invention provides a therapeutic composition that includes a compound of any of the embodiments and a second therapeutic agent as a combined preparation for simultaneous, separate, or sequential use in the treatment of a disease or condition mediated by GPR40. In some such embodiments, the disease or condition is type II diabetes. In some embodiments, the second therapeutic agent is selected from metformin, a thiazolidinedione, or a DPP-IV inhibitor. In some embodiments, the compound of any of the embodiments described herein and the second therapeutic agent are provided as single composition. In other embodiments, the compound of any of the embodiments described herein and the second therapeutic agent are provided separately as parts of a kit.

In some embodiments, the invention provides a compound of any of the embodiments described herein for use as a medicament.

In some embodiments, the invention provides a compound of any of the embodiments described herein for use in modulating GPR40.

In some embodiments, the invention provides a compound of any of the embodiments described herein for use in treating a disease or condition selected from type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, or edema. In some such embodiments, the compound is used for treating type II diabetes.

The compounds of the invention have been found to stimulate GLP-secretion. Cells contacted with compounds of the invention have been found to increase GLP-1 secretion. Therefore, in some embodiments, the invention provides a method of stimulating GLP-1 secretion by cells. Such methods typically include contacting a cell capable of producing GLP-1 with a compound of any of the embodiments set forth herein. Administration of the compounds of the invention to subjects has also been found to provide increased levels of GLP-1 in the blood plasma of such subjects. Therefore, in some embodiments, a compound of any of the embodiments described herein may be used to stimulate GLP-1 secretion and increase the blood plasma level of GLP-1 in a subject. In some such embodiments, the compounds of the invention both stimulate GLP-1 secretion and activate GPR40. Therefore, in some embodiments, the compounds of the invention both stimulate GLP-1 secretion and display incretin effect by activating GPR40.

In some embodiments, the invention further provides a method for increasing GLP-1 levels in the blood plasma of a subject. Such methods typically include administering a compound of any of the embodiments to a subject. In some such embodiments, the subject is a diabetic patient. In other such embodiments, the subject is an obese patient. The compounds of the invention may be administered in the fasted or non-fasted state. Therefore, in some embodiments, a compound of any of the embodiments is administered to a subject prior to a meal. In some embodiments, the compound is administered 2 hours, 1, hour, 30 minutes, or 15 minutes before a meal. In other embodiments, a compound of any embodiments set forth herein is administered to a subject during a meal. In other embodiments, a compound of any of the embodiments described herein is administered to a subject within 2 hours, within 1 hour, within 30 minutes, or within 15 minutes of a meal.

In another aspect the invention provide a process for hydrogenating a compound of formula V, the method comprising: (a) reacting a compound of formula V with $H_2$ in the presence of a transition metal or a transition metal complex to form a compound of formula VIA, a compound of formula VIB or mixture of the compound of formula VIA and the compound of formula VIB. The compounds of formula V, VIA, and VIB have the following structures:

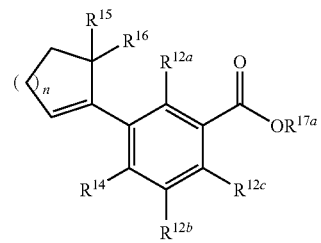

V

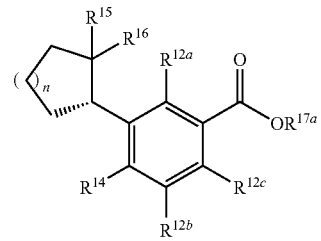

VIA

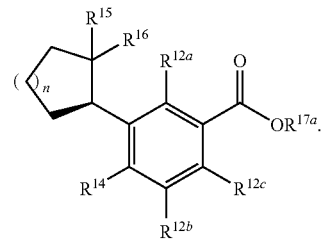

VIB wherein,
$R^{12a}$ is selected from —H, halo, a —($C_1$-$C_6$)alkyl group, or a —O—($C_1$-$C_6$)alkyl group;
$R^{12b}$ is selected from —H, halo, a —($C_1$-$C_6$)alkyl group, or a —O—($C_1$-$C_6$)alkyl group;
$R^{12c}$ is selected from —H, halo, a —($C_1$-$C_6$)alkyl group, or a —O—($C_1$-$C_6$)alkyl group;
$R^{14}$ is —H or —OH;
$R^{15}$ is selected from —H, or a —($C_1$-$C_6$)alkyl group;
$R^{16}$ is selected from —H, or a —($C_1$-$C_6$)alkyl group;
$R^{17a}$ is a —($C_1$-$C_6$)alkyl group; and
the subscript n is 1, 2, or 3;
wherein at least one of $R^{15}$ or $R^{16}$ is a —($C_1$-$C_6$)alkyl group.

In another aspect, the invention provides a compound of formula V, VIA, and/or VIB. In such an aspect, the variables have the definitions provided herein with respect to the process for hydrogenating a compound of formula V. In various embodiments of this aspect, the variables have any of the definitions provided with respect to any of the embodiments of the process for hydrogenating a compound of formula V. For example, in some embodiments, $R^{14}$ is OH. In other such embodiments, $R^{15}$ and $R^{16}$ are both methyl groups.

In some embodiments of the process for hydrogenating the compound of formula V, the transition metal or transition metal complex comprises palladium, platinum, nickel, or rhodium. For example, the reduction may be accomplished using palladium on carbon, Raney nickel, $PtO_2$ or various rhodium compounds. In some such embodiments, the transition metal or transition metal complex is palladium, and in some such embodiments is palladium on carbon. Various supported catalysts known to those skilled in the art may be used in conjunction with this process.

In some embodiments of the process for hydrogenating the compound of formula V, the process is an enantioselective process. In such embodiments, the method includes reacting a compound of formula V with $H_2$ in the presence of a transition metal or a transition metal complex and a phosphine ligand to form a compound of formula VIA, a compound of formula VIB, or a mixture of the compound of formula VIA and the compound of formula VIB. In such embodiments, the phosphine ligand comprises at least one chiral center.

In some embodiments of the process for hydrogenating a compound of formula V, $R^{14}$ is —OH.

In some embodiments of the process for hydrogenating a compound of formula V, $R^{15}$ and $R^{16}$ are both —$CH_3$.

In some embodiments of the process for hydrogenating a compound of formula V, the subscript n is 1.

In some embodiments of the process for hydrogenating a compound of formula V, $R^{12b}$ and $R^{12c}$ are both —H.

In some embodiments of the process for hydrogenating a compound of formula V, $R^{12a}$ is H or halo. Thus, in some embodiments $R^{12a}$ is H whereas in other embodiments, $R^{12a}$ is F.

In some embodiments of the process for hydrogenating a compound of formula V, the transition metal or the transition metal complex comprises rhodium. For example, in some such embodiments, the transition metal complex is generated from $Rh(COD)_2BF_4$, $Rh(COD)_2SbF_6$, or $Rh(NBD)_2BF_4$ where COD represents the 1,5-cyclooctadiene ligand and NBD represents the norbornadiene ligand.

In some embodiments of the process for hydrogenating a compound of formula V, the phosphine is a diphosphine. In some such embodiments, the diphosphine comprises a ferrocene group. In some such embodiments, the diphosphine is selected from

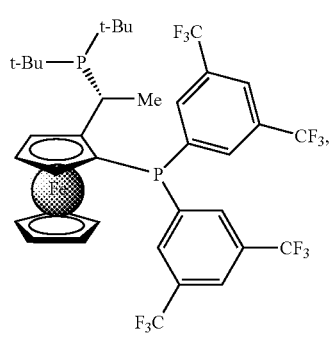

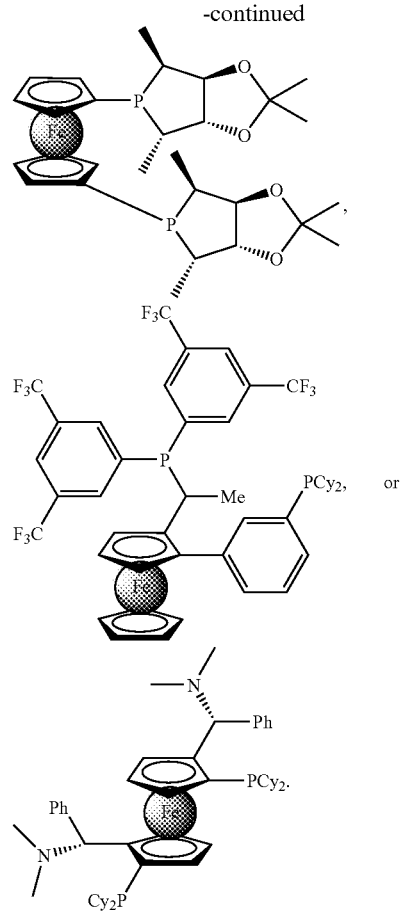

In some such embodiments, the diphosphine is

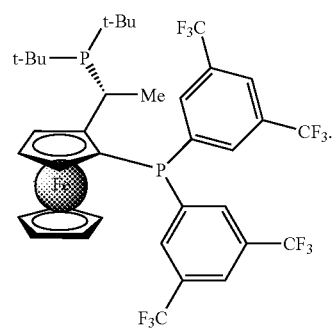

In other such embodiments, the diphosphine is an enantiomer of one of the compounds shown above.

In some embodiments of the process for hydrogenating a compound of formula V, the compound of formula V is reacted with $H_2$ at a pressure of from 15 to 1400 psi. In some such embodiments, the pressure ranges from 50 to 400 psi.

In some embodiments of the process for hydrogenating a compound of formula V, the compound of formula V is reacted with $H_2$ in a mixture comprising at least one solvent selected from an ethereal solvent, an ester solvent, an aromatic solvent, a halogenated hydrocarbon solvent, a ketone solvent, or a $C_1$-$C_4$ alcohol solvent. In some such embodiments, the at least one solvent comprises an ethereal solvent selected from tetrahydrofuran, 1,4-dioxane, 1,2-dimethoxyethane, 1,2-diethoxyethane, tetrahydropyran, diethylether, dipropylether, or dibutylether. In other such embodiments, the at least one solvent comprises tetrahydrofuran. In other such embodiments, the at least one solvent comprises at least one of tetrahydrofuran, toluene, acetone, methyl ethyl ketone, ethanol, or methanol.

In some embodiments, the transition metal complex is mixed with the phosphine in a solvent prior to adding the compounds of formula V. In some such embodiments, the solvent is an ethereal solvent such as tetrahydrofuran, and the transition metal complex is selected from $Rh(COD)_2BF_4$, $Rh(COD)_2SbF_6$, or $Rh(NBD)_2BF_4$. In some such embodiments, the phosphine is a diphosphine comprising a ferrocenyl group such as one of those described herein.

In some embodiments of the process for hydrogenating a compound of formula V, the compound of formula I is reacted with $H_2$ at a temperature ranging from 15° C. to 60° C. In some such embodiments, the temperature ranges from 20° C. to 45° C.

In some embodiments of the process for hydrogenating a compound of formula V, the enantiomeric excess of one of the products is greater than 50%, greater than 60%, greater than 75%, greater than 85%, greater than 90%, greater than 95%, or greater than 98%.

In some embodiments of the process for hydrogenating a compound of formula V, the conversion of the compound of formula V to the compound of formula VIA, the compound of formula VIB, or the mixture of the compound of formula VIA and the compound of formula VIB is greater than 50%, greater than 70%, greater than 80%, or greater than 95%.

6.2.2 Preparation of the Compounds

The compounds of the invention can be prepared by a variety of synthetic or semisynthetic techniques. Scheme 1 provides a general synthetic scheme for exemplary compounds of the invention utilizing ester A where the variables in Scheme 1 have any of the values described above with respect to any of the embodiments, V is a OH or a halogen such as, but not limited to a Cl, Br, or I, or sulfonate ester such as, but not limited to OTs (tosylate) or OTf (triflate); and Alk is a straight or branched chain alkyl group having from 1-8 carbon atoms. It will be understood that the phenolic OH group of A can be replaced with an SH and reacted with a compound where V is a halogen to produce the analogous S-containing derivative (X=S) to the compounds shown. The synthesis of various chloromethyl and hydroxymethyl biphenyl tail group compounds and phenol carboxylic acid head group compounds is described herein. Appropriate starting materials can be prepared by techniques known or apparent to those of skill in the art or the starting materials may be commercially available. One of skill in the art will understand that the synthetic routes can be modified to use different starting materials or alternative reagents and that suitable adjustments in conditions (e.g., temperatures, solvents, etc.) can be made to accomplish the desired transformations. One of skill in the art will recognize that protecting groups may be necessary for the preparation of certain compounds and will be aware of those conditions compatible with a selected protecting group. Examples of such protecting groups include, for example, those set forth in Protective Groups in Organic Synthesis, Greene, T. W.; Wuts, P. G. M., John Wiley & Sons, New York, N.Y., (3rd Edition, 1999). Accordingly, the exemplary methods and the examples described herein are illustrative of the present invention and are not to be construed as limiting the scope thereof.

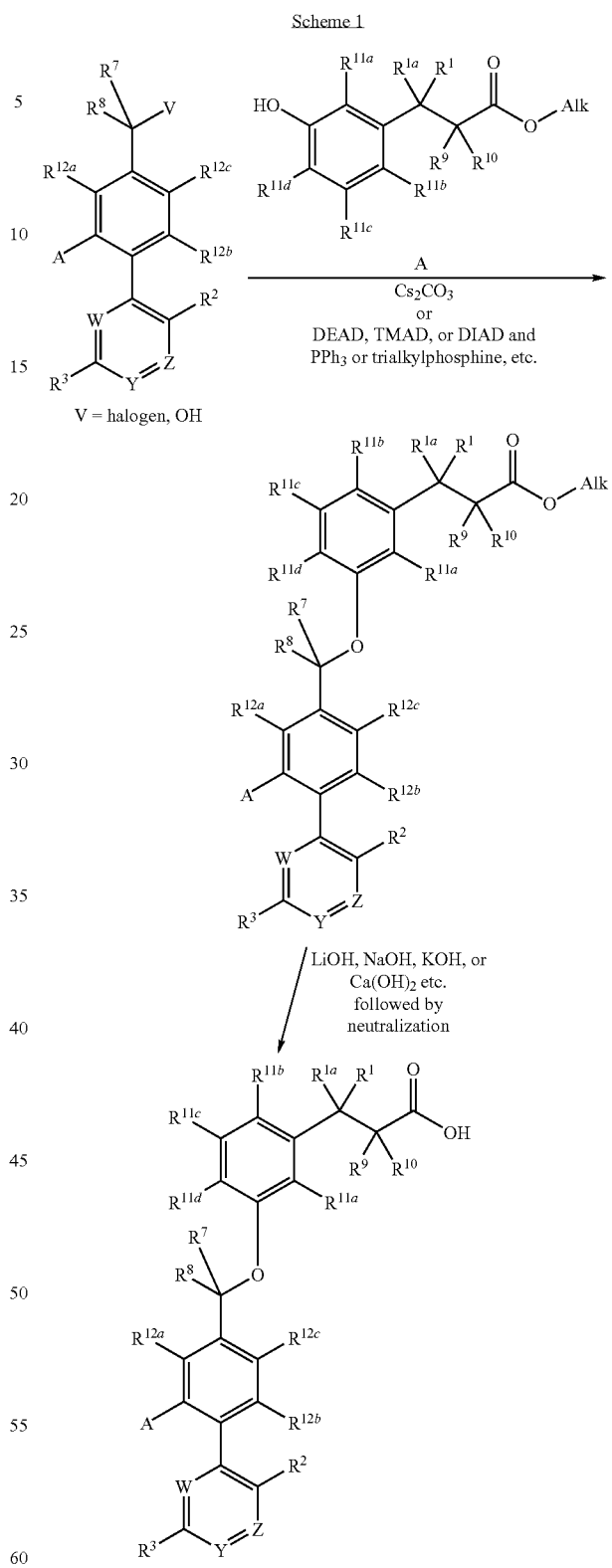

Certain compounds of the invention that include a compound with an A group that is a cycloalkyl ring possessing a chiral center can be produced using a hydrogenation process that has been discovered. For example, as shown in Scheme 2, a cycloalkenyl aryl compound such as a compound of formula V can be hydrogenated to provide the two cycloalkyl enantiomers VIA and VIB. Typically, the process includes: (a) reacting a compound of formula V with $H_2$ in the presence of a transition metal or a transition metal complex to form a mixture of a compound of formula VIA and a compound of formula VIB. The compounds of formula V, VIA, and VIB have the structures shown below with respect to the enantioselective hydrogenation process.

In some embodiments of the process for hydrogenating the compound of formula V, the transition metal or transition metal complex comprises palladium, platinum, nickel, or rhodium. For example, the reduction may be accomplished using palladium on carbon, Raney nickel, $PtO_2$ or various rhodium compounds. Various supported catalysts known to those skilled in the art may be used in conjunction with this process.

Certain compounds of the invention that include a compound with an A group that is a cycloalkyl ring possessing a chiral center can also be produced using an enantioselective hydrogenation process that has been discovered. For example, as shown in Scheme 2, a cycloalkenyl aryl compound such as a compound of formula V can be hydrogenated to provide the two cycloalkyl enantiomers VIA and VIB. Typically, the method includes reacting a compound of formula V with $H_2$ in the presence of a transition metal or a transition metal complex and a phosphine ligand to form a compound of formula VIA, a compound of formula VIB, or a mixture of a compound of formula VIA and a compound of formula VIB.

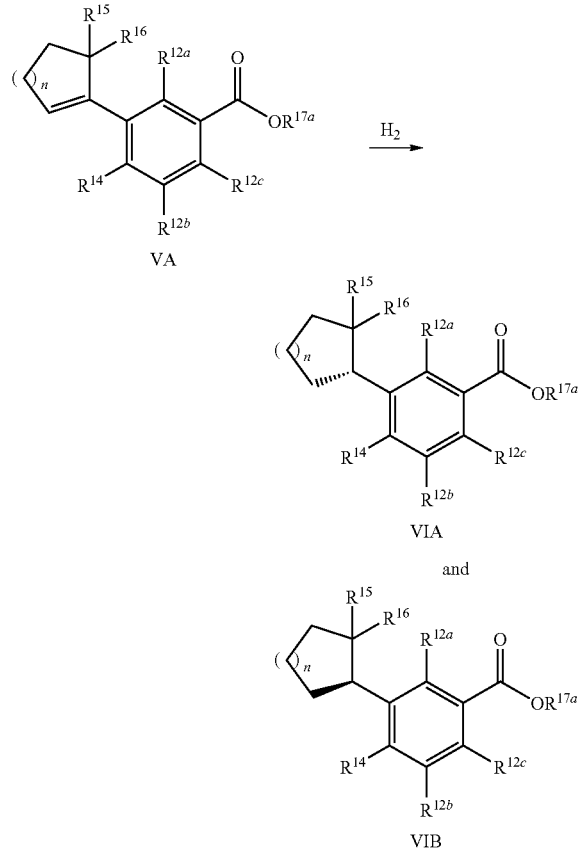

Scheme 2

In the compounds of formula VA, VIA, and VIB, $R^{12a}$ is selected from —H, halo, a —$(C_1$-$C_6)$alkyl group, or a —O—$(C_1$-$C_6)$alkyl group; $R^{12b}$ is selected from —H, halo, a —$(C_1$-$C_6)$alkyl group, or a —O—$(C_1$-$C_6)$alkyl group; $R^{12c}$ is selected from —H, halo, a —$(C_1$-$C_6)$alkyl group, or a —O—$(C_1$-$C_6)$alkyl group; $R^{14}$ is —H or —OH; $R^{15}$ is selected from —H, or a —$(C_1$-$C_6)$alkyl group; $R^{16}$ is selected from —H, or a —$(C_1$-$C_6)$alkyl group; $R^{17a}$ is a —$(C_1$-$C_6)$alkyl group; and the subscript n is 1, 2, or 3. Generally, at least one of $R^{15}$ or $R^{16}$ is a —$(C_1$-$C_6)$alkyl group. In some embodiments of the process for hydrogenating a compound of formula V, $R^{15}$ and $R^{16}$ are both —$CH_3$. In some embodiments of the process for hydrogenating a compound of formula V, the subscript n is 1. In some embodiments of the process for hydrogenating a compound of formula V, $R^{12b}$ and $R^{12c}$ are both —H. In some embodiments of the process for hydrogenating a compound of formula V, $R^{12a}$ is H or halo. Thus, in some embodiments $R^{12a}$ is H whereas in other embodiments, $R^{12a}$ is F.

Various solvents and mixtures thereof can be used in the enantioselective hydrogenation process. Typical solvents for the reaction include ethereal solvents, ester solvents, aromatic solvents, halogenated hydrocarbon solvents, ketone solvents, and $C_1$-$C_4$ alcohol solvents. Examples of ethereal solvents include, but are not limited to cyclic and non-cyclic ethers including, but not limited to, tetrahydrofuran, 1,4-dioxane, 1,2-dimethoxyethane, 1,2-diethoxyethane, tetrahydropyran, diethylether, dipropylether, and dibutylether. Tetrahydrofuran is an example of one solvent that has been found to function particularly well, but other solvents such as toluene, acetone, methyl ethyl ketone, dichloromethane, ethanol, and methanol may be employed in the reduction.

The enantioselective hydrogenation process may be conducted at various temperatures. For example, in some embodiments of the process for hydrogenating a compound of formula V, the compound of formula V is reacted with $H_2$ at a temperature ranging from 15° C. to 60° C. In some such embodiments, the temperature ranges from 20° C. to 45° C.

The enantioselective hydrogenation process may also be conducted at various pressures of $H_2$. For example, in some embodiments of the process for hydrogenating a compound of formula V, the compound of formula V is reacted with $H_2$ at a pressure of from 15 to 1400 psi. In some such embodiments, the pressure is from 50 to 400 psi whereas in other embodiments, the pressure ranges from 80 to 400 psi, from 100 to 400 psi, or from 100 to 200 psi.

In some embodiments of the process for hydrogenating a compound of formula V, the phosphine is a diphosphine. In some such embodiments, the diphosphine comprises a ferrocene group. Examples of diphosphines comprising a ferrocene group include, but are not limited to,

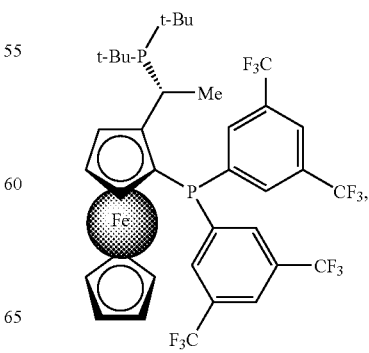

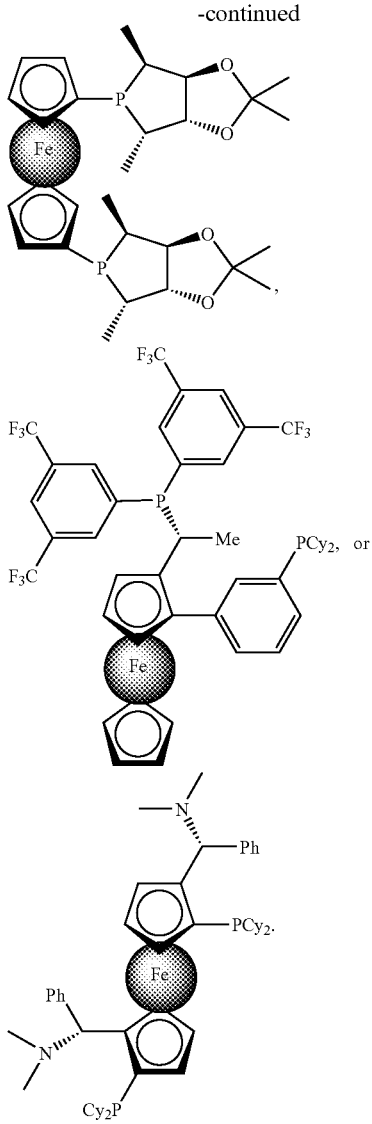

The following diphosphine has been fount to be particularly effective. Therefore, in some embodiments, the diphosphine is

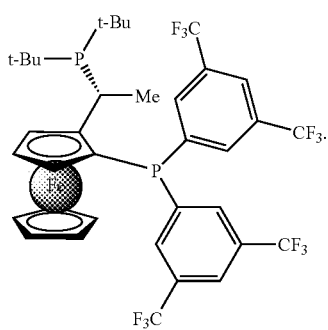

Enantiomers of the diphosphines shown above may be used to generate the other enantiomer as the majority product. Therefore, in some embodiments, the diphosphine is an enantiomer of one of those shown above.

Various transition metals and transition metal complexes may be used to hydrogenate compounds of formula V. However, rhodium has been found to produce particularly good results. Therefore in some embodiments for hydrogenating a compound of formula V, the transition metal or the transition metal complex comprises rhodium. For example, in some such embodiments, the transition metal or transition metal complex is generated from $Rh(COD)_2BF_4$, $Rh(COD)_2SbF_6$, or $Rh(NBD)_2BF_4$.

Generally, the transition metal complex is mixed with the phosphine in a solvent prior to adding the compounds of formula V. In some such embodiments, the solvent is an ethereal solvent such as tetrahydrofuran, and the transition metal complex is selected from $Rh(COD)_2BF_4$, $Rh(COD)_2SbF_6$, or $Rh(NBD)_2BF_4$. In some such embodiments, the phosphine is a diphosphine comprising a ferrocenyl group such as one of those described herein.

The enantioselective hydrogenation process has been found to provide compounds of formula VIA and VIB in good yield with excellent enantiomeric excess. Scheme 3 shows a general method for hydrogenating two compounds of formula V.

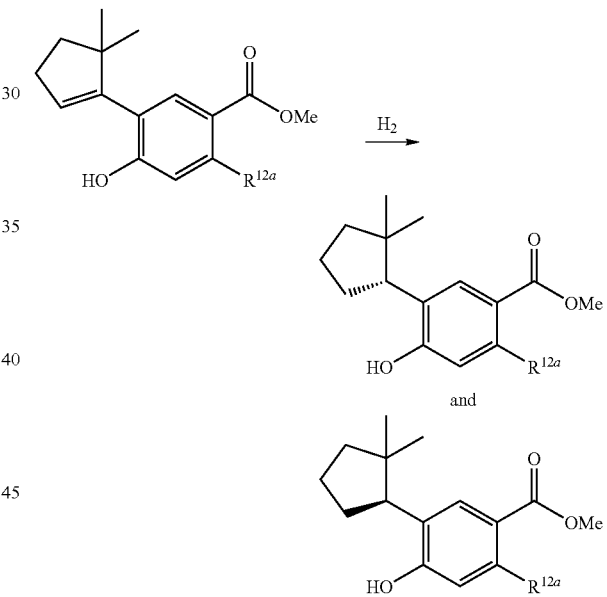

Scheme 3

Referring to Scheme 3, when $R^{12a}$ is H, the cycloalkene was hydrogenated to provide the cyclopentyl compounds in good yield and with excellent enantiomeric excess. For example, a yield of 99% and a 99% enantiomeric excess was achieved after 2 hours at room temperature under 200 psi $H_2$ when the compound shown in Scheme 3 ($R^{12a}$=H) and triethylamine were added to the mixture prepared by mixing $Rh(COD)_2BF_4$ and (R)-1-[(S)-2-(R)-(ditertbutylphosphino) ferrocenyl]ethyl-bis-(3,5-bistrifluoromethylphenyl)phosphine in tetrahydrofuran. Good yields and enantiomeric excesses were also observed for compounds where $R^{12a}$ is F. For example, a yield of 83% and a 99.3% enantiomeric excess was achieved after 2 hours at room temperature under 200 psi $H_2$ when the compound shown in Scheme 3 ($R^{12a}$=F) and triethylamine were added to the mixture prepared by mixing $Rh(COD)_2BF_4$ and (R)-1-[(S)-2-(R)-(ditertbutylphosphino) ferrocenyl]ethyl-bis-(3,5-bistrifluoromethylphenyl)phosphine in tetrahydrofuran. The presence of a trialkyl amine base such as triethylamine was found to slightly improve the enantiomeric excess in these reactions. While the trialkylamine was not required for the reaction to proceed with good enantioselectivity, it was found to improve the ee in cases where the starting material may have contained small amounts of impurities.

In some embodiments of the process for hydrogenating a compound of formula V, the enantiomeric excess of one of the products is greater than 50%, greater than 60%, greater than 75%, greater than 85%, greater than 90%, greater than 95%, or greater than 98%.

In some embodiments of the process for hydrogenating a compound of formula V, the conversion of the compound of formula V to the compound of formula VIA, the compound of formula VIB, or the mixture of the compound of formula VIA and the compound of formula VIB is greater than 50%, greater than 70%, greater than 80%, or greater than 95%.

Compounds of formula VIA and VIB may be used to synthesize the biphenyl tail groups used to prepare the example compounds of the present invention. Therefore, in some embodiments, where $R^{14}$ is —OH (compounds of formula VIA' and VIB') compounds of formula VIA' and/or VIB' are converted to compounds of VIIA and/or VIIB as shown in Scheme 4 by reacting them with N-phenyl-bis(trifluoromethanesulfonimide) or with trifluoromethanesulfonic anhydride. Typically, this reaction is accomplished in a suitable solvent such as dichloromethane with triethylamine and dimethylaminopyridine. Therefore, in some embodiments, the process further includes reacting a compound of formula VIA' and/or VIB' with N-phenyl-bis(trifluoromethanesulfonimide) or with trifluoromethanesulfonic an hydride to form a compound of formula VIIA or VIIB where the variables have any of the values set forth herein.

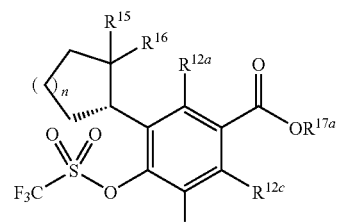

VIIA or

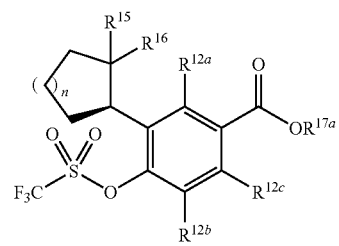

VIIB

Compounds of formula VIIA and VIIB are very useful intermediates and can be used to synthesize numerous biphenyl or phenylpyridyl compounds that may be used to construct the compounds of the invention. For example, as shown in Scheme 5, compounds VIIA and VIIB can be reacted with boronic acids or boronates (VIIIA or VIIIB) to provide biphenyl compounds IXA or IXB using the conditions set forth herein. Therefore, in some embodiments, the process further includes reacting a compound of formula VIIA and/or VIIB with a compound of formula VIIIA or VIIIB to form a compound of formula IXA or IXB where the variables have any of the values set forth herein.

Scheme 4

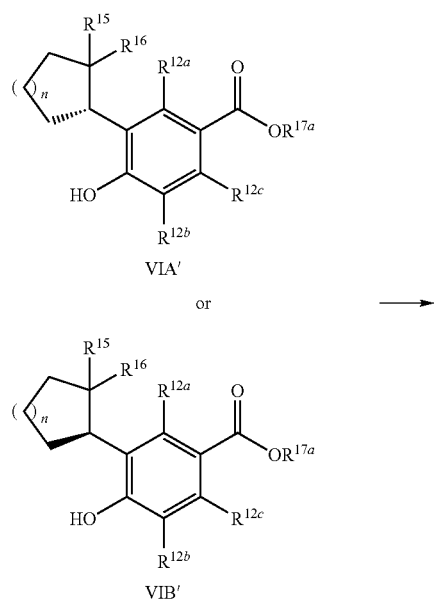

Scheme 5

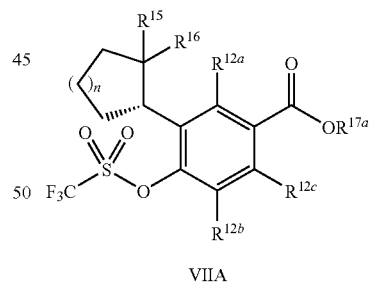

VIIA or +

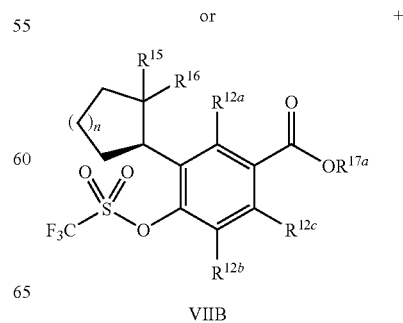

VIIB

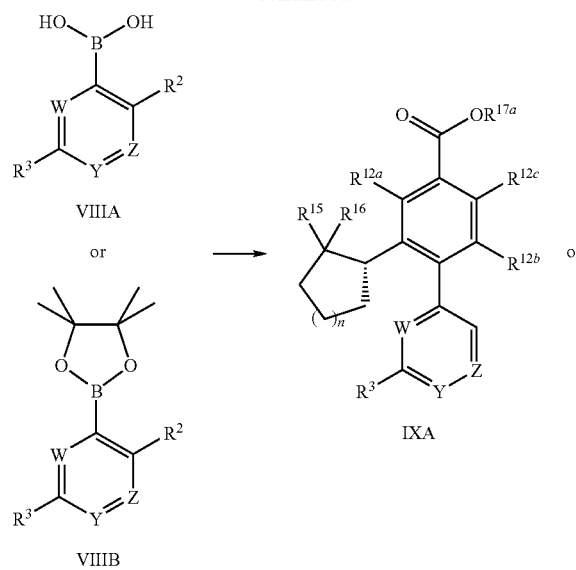

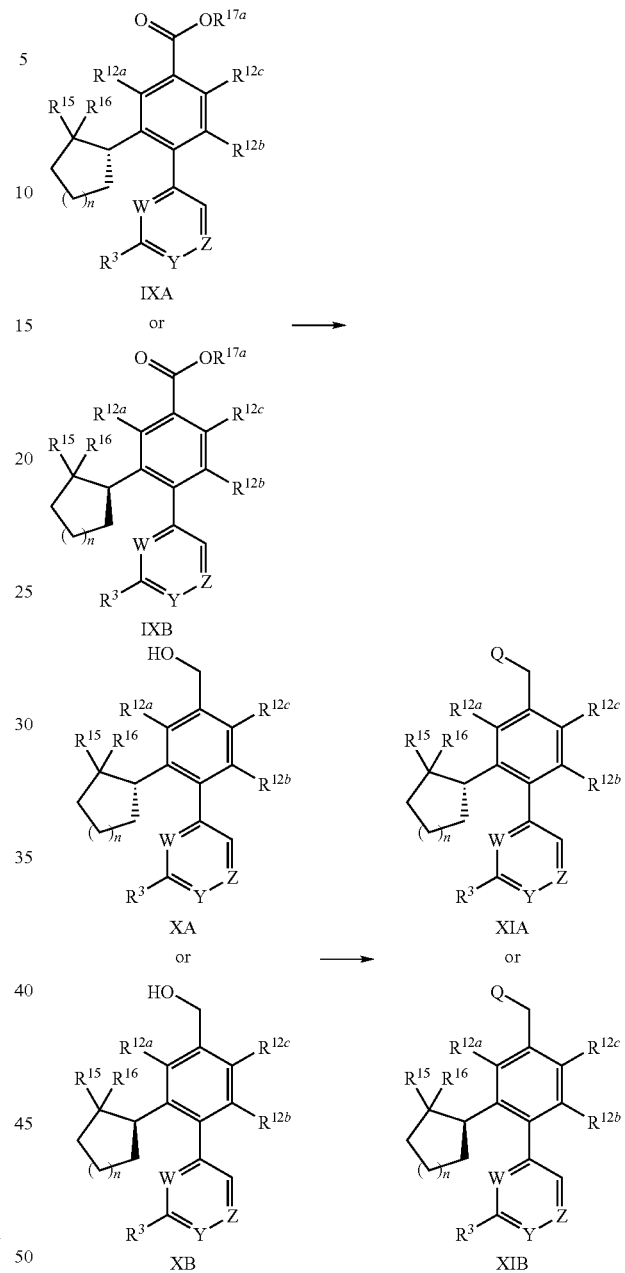

Scheme 6

Esters of formula IXA and IXB are also useful intermediates and can be used to synthesize compounds of the invention after reduction to the hydroxymethyl compounds XA or XB or subsequent conversion to the chloromethyl or bromomethyl compounds XIA or XIB where Q=Cl or Br. For example, as shown in Scheme 6, compounds IXA and IXB can be reduced with reducing agents such as lithium aluminum hydride using the conditions set forth herein to provide hydroxymethyl compounds XA or XB which may then be converted to halomethyl compounds with reagents such as thionyl chloride to provide compounds such as XIA or XIB where the variables have any of the values set forth herein. Therefore, in some embodiments, the method further comprising reducing a compound of formula IXA or IXB with a reducing agent such as LAH to form a compound of formula XA or XB. In some such embodiments, the method further comprises converting the hydroxyl functional group of a compound of formula XA or XB to a chloride or a bromide to form a compound of formula XIA or XIB.

Hydroxymethyl compounds XA or XB and chloromethyl or bromomethyl compounds XIA or XIB may be reacted with ester compounds of formula XII to form compounds of formula XIIIA or XIIIB using the reaction conditions set forth herein where $R^{18}$ is a $(C_1-C_6)$alkyl group and the other variables have any of the values set forth herein. Therefore, in some embodiments, the method further includes reacting a compound of formula XA or XB or a compound of formula XIA or XIB with a compound of formula XII to form a compound of formula XIIIA or XIIIB. Esters XIIIA and XIIIB, which are compounds of formula I, can then be saponified using the conditions described herein to form compounds of formula XIVA and XIVB where the variables have any of the values set forth herein. Therefore, some embodiments include saponifying a compound of formula XIIIA or XIIIB to form a compound of formula XIVA or XIVB where $R^{18}$ is a $(C_1-C_6)$alkyl group and the other variables have any of the values set forth herein.

XII
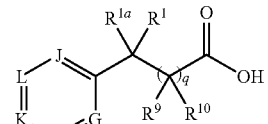

XIIIA
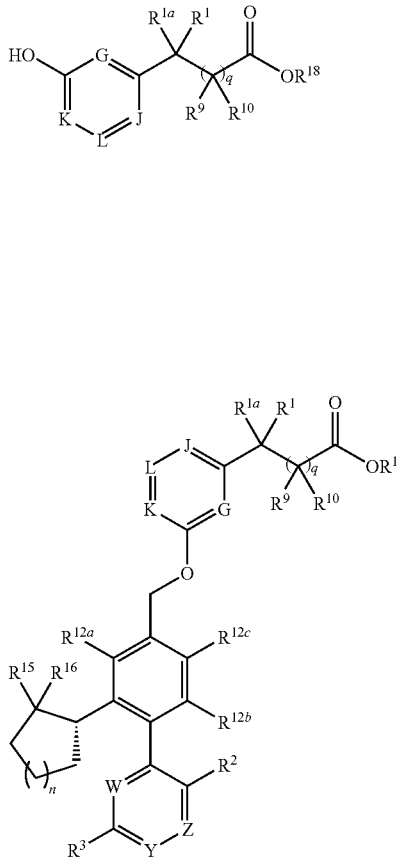

XIIIB
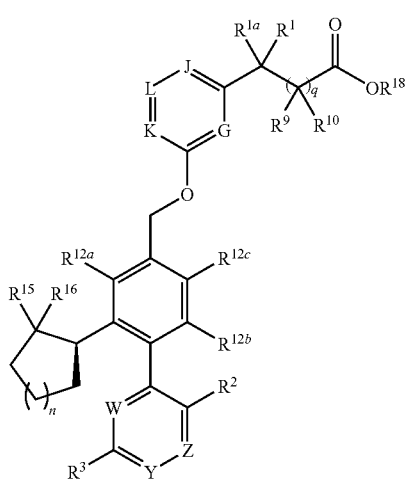

XIVA
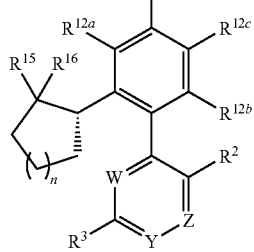

XIVB
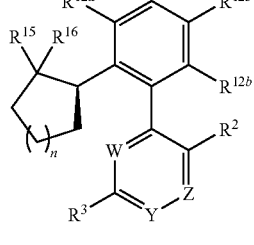

6.2.3 Compositions

In another aspect, the invention provides pharmaceutical compositions suitable for pharmaceutical use comprising one or more compounds of the invention and a pharmaceutically acceptable carrier, excipient, or diluent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

6.2.4 Methods of Use

In another aspect, the invention provides methods of treating a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. The methods comprise administering to a subject in need thereof, a therapeutically effective amount of a compound or composition of any of the embodiments of the invention.

In one embodiment, the disease or condition is type II diabetes.

In another aspect, the present invention provides a method for treating a disease or condition responsive to the modulation of GPR40. Such methods comprise administering to a subject in need thereof a therapeutically effective amount of a compound or composition of the invention.

In some embodiments, the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In certain embodiments, the disease or condition is type II diabetes.

In some embodiments, the disease or condition is obesity.

In some embodiments, the disease or condition is hypertension.

In some embodiments of administering the compounds or compositions of the invention, the compound or composition is administered orally, parenterally, or topically. In some embodiments, the compound or composition is administered orally. In other embodiments, the compound or composition is administered parenterally. In other embodiments, the compound or composition is administered topically.

The compounds of the invention may be administered alone or in combination with one or more other therapeutic agents. Therefore, in some embodiments, the compound or composition of any of the embodiments is administered in combination with a second therapeutic agent. In some such embodiments, the second therapeutic agent is an insulin sensitizing agent, such as metformin or a thiazolidinedione, for example. In some embodiments, the second therapeutic agent is a GLP-1 analog. In some embodiments, the second therapeutic agent is an inhibitor of DPP-IV such as, but not limited to, sitagliptin.

In another aspect, the invention provides methods of treating a disease or disorder responsive to modulation of GPR40 comprising administering to a subject having such a disease or disorder, a therapeutically effective amount of one or more of the subject compounds or compositions.

In yet another aspect, the invention provides methods of treating a GPR40-mediated condition, disease or disorder comprising administering to a subject having such a condition, disease or disorder, a therapeutically effective amount of one or more of the subject compounds or compositions.

In yet another aspect, the invention provides methods of modulating GPR40 comprising contacting a cell with one or more of the subject compounds or compositions.

For example, in some embodiments, a cell that constitutively expresses GPR40 is contacted with one or more of the subject compounds or compositions.

In certain embodiments, a cell to be contacted can be made to express or overexpress GPR40, for example, by expressing GPR40 from heterologous nucleic acid introduced into the cell or, as another example, by upregulating the expression of GPR40 from nucleic acid endogenous to the cell.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the treatment or prevention type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema or other conditions or disorders associated with GPR40, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day. For oral administration, the compositions are preferably provided in the form of tablets containing from 1.0 to 1000 milligrams of the active ingredient, particularly 1.0, 3.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such other agents, or drugs, may be administered, by a route and in an amount commonly used therefore, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

The compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition mediated by GPR40. In some embodiments, therapeutic compositions are provided that include a compound of the invention and a second therapeutic agent as a combined preparation for simultaneous, separate or sequential use in the prophylactic treatment of a subject at risk for a disease or condition mediated by GPR40. In some such embodiments, the components are provided as a single composition. In other embodiments, the compound and the second therapeutic agent are provided separately as parts of a kit.

Examples of other therapeutic agents that may be combined with a compound of the invention, either administered separately or in the same pharmaceutical compositions, include, but are not limited to: (a) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors and vasodilators (e.g., sodium nitroprusside, nicardipine hydrochloride, nitroglycerin and enaloprilat); and (c) antidiabetic agents such as insulin and insulin mimetics, sulfonylureas (e.g., glyburide, meglinatide), biguanides, e.g., metformin (GLUCOPHAGE®), α-glucosidase inhibitors (acarbose), insulin sensitizers, e.g., thiazolidinone compounds, rosiglitazone (AVANDIA®), troglitazone (REZULIN®), ciglitazone, pioglitazone (ACTOS®) and englitazone, DPP-IV inhibitors, e.g., vildagliptin (Galvus®), sitagliptin (Januvia™), and GLP-I analogs, e.g., exenatide (Byetta®). In some embodiments, a compound of the invention may be administered along with a DPP-IV inhibitor or a GLP-I analog. In some embodiments, a compound of the invention is administered with any of the DPP-IV inhibitors set forth in U.S. Patent Publication No. 2006/0270701 which is hereby incorporated by reference in its entirety and for all purposes as if specifically set forth herein.

The weight ratio of the compound of the invention to the second active ingredient may be varied and will depend upon the effective dose of each ingredient. Generally, an effective dose of each will be used. Combinations of a compound of the invention and other active ingredients will generally also be within the aforementioned range, but in each case, an effective dose of each active ingredient should be used.

In another aspect, the present invention provides a method for modulating circulating insulin concentration in a subject, comprising administering a compound or composition of the invention.

In some embodiments, the insulin concentration is increased after the compound is administered to the subject.

In other embodiments, the insulin concentration is decreased after the compound is administered to the subject.

The compounds and compositions described herein may be used to treat a variety of disease states and conditions. Therefore, in some embodiments, a compound of composition of any of the described embodiments is used for treating a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes.

The compounds of the invention may also be used to modulate GPR 40. Therefore, in some embodiments, a compound or composition of any of the embodiments is used for modulating GPR40.

The compounds of any of the embodiments described herein may be used to prepare medicaments for treating the diseases or conditions described herein such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and/or edema. In some embodiment, the disease or condition is type II diabetes. The compounds of any of the embodiments may also be used to prepare medicaments for modulating GPR40 in a subject such as in a mammalian subject with type II diabetes.

The following examples are offered by way of illustration and are not intended to limit the scope of the invention. Those of skill in the art will readily recognize a variety of noncritical parameters that could be modified to yield essentially similar results.

7. EXAMPLES

Unless otherwise stated, all compounds were obtained from commercial sources or were prepared using the methods and experimental procedures described herein. Various procedures are also set forth in published U.S. Patent Application No. 2006/0004012 which is hereby incorporated by reference in its entirety and for all purposes as if set forth herein. The following abbreviations are used to refer to various reagents, solvents, experimental procedures, or analytical techniques that are described in the examples:

ACN Acetonitrile
COD 1,5-Cyclooctadiene
Cy Cyclohexyl
DBU 1,8-Diazabicyclo[5.4.0]undec-7-ene DCE 1,2-Dichloroethane
DCM Dichloromethane
DMF N,N-Dimethylformamide
DMAP 4-Dimethylaminopyridine
DME Dimethoxyethane
DMSO Dimethylsulfoxide
ESI Electrospray Ionization
EtOAc Ethyl acetate
EtOH Ethanol
HPLC High Performance Liquid Chromatography
HSA Human Serum Albumin
IPA Isopropanol
LAH Lithium Aluminum Hydride
LDA Lithium Diisopropylamide
MeCN Acetonitrile
MeOH Methanol
MS Mass Spectrometry
NBD Norbornadiene
NMR Nuclear Magnetic Resonance
—PCy$_2$-P(cyclohexyl)$_2$
PPTS Pyridinium p-Toluenesulfonate
TEA Triethylamine
TEMPO 2,2,6,6-Tetramethyl-1-piperidinyloxy free radical
TFA Trifluoroacetic acid
THF Tetrahydrofuran
THP Tetrahydropyran
SPA Scintilliation Proximity Assay

7.1 Intermediate A

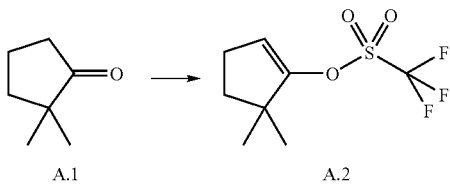

A.1  →  A.2

5,5-Dimethylcyclopent-1-enyl trifluoromethanesulfonate (A.2). To a solution of 2,2-dimethylcyclopentanone A.1 (available from ChemSampCo) (3.00 g, 26.75 mmol) in THF (100 mL), was slowly added LDA (14.7 mL, 2.0 M, in heptane) at −78° C. The resulting mixture was stirred at −78° C. for 1 hour. A solution of N-phenyltriflimide (10.00 g, 28.00 mmol) was added to the mixture at −78° C., and stirring was continued at 0° C. for 2 hours and then at room temperature overnight. The reaction mixture was extracted with hexane (80×2 mL). The organic layer was washed with saturated Na$_2$CO$_3$ (30 mL), brine (20 mL), and dried with MgSO$_4$. The solvent was removed, and the crude product was purified by CombiFlash (eluant was EtOAc and hexane) to give A.2. $^1$H NMR (CDCl$_3$) δ ppm 1.16 (s, 6H), 1.86 (t, J=7.1 Hz, 2H), 2.36 (t, J=7.1 Hz, 2H), 5.56 (m, 1H).

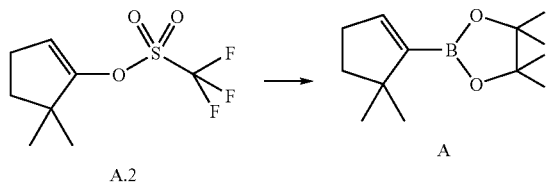

A.2  →  A 2-(5,5-Dimethylcyclopent-1-enyl)-4,4,5,5-tetramethyl-1,3,2-dioxaborolane (A). PdCl$_2$(PPh$_3$)$_2$ (0.56 g, 0.80 mmol), PPh$_3$ (0.63 g, 2.40 mmol), bis(pinacolato)diboron (6.80 g, 26.75 mmol) and KOPh (fine powder, 5.30 g, 40.10 mmol) were added to a flask. The flask was flushed with nitrogen and charged with toluene (100 mL) and with A.2 (6.53 g, 26.75 mmol). The mixture was stirred at 50° C. for 2 hours. The reaction mixture was treated with water at room temperature and extracted with benzene (60×2 mL). The organic layer was dried over MgSO$_4$. The product was then purified by CombiFlash to give Intermediate A. $^1$H NMR (CDCl$_3$) δ ppm 1.04 (s, 6H), 1.18 (s, 12H), 1.57 (t, J=7.1 Hz, 2H), 2.29 (t, J=7.1 Hz, 2H), 6.29 (m, 1H).

Example 1

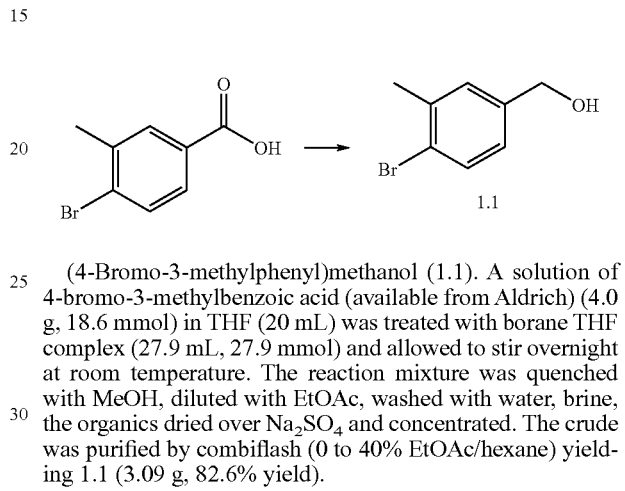

(4-Bromo-3-methylphenyl)methanol (1.1). A solution of 4-bromo-3-methylbenzoic acid (available from Aldrich) (4.0 g, 18.6 mmol) in THF (20 mL) was treated with borane THF complex (27.9 mL, 27.9 mmol) and allowed to stir overnight at room temperature. The reaction mixture was quenched with MeOH, diluted with EtOAc, washed with water, brine, the organics dried over Na$_2$SO$_4$ and concentrated. The crude was purified by combiflash (0 to 40% EtOAc/hexane) yielding 1.1 (3.09 g, 82.6% yield).

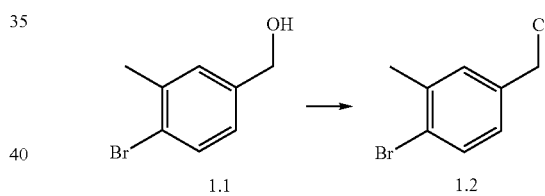

1.1  →  1.2

1-Bromo-4-(chloromethyl)-2-methylbenzene (1.2). To a stirred solution of 1.1 (2.0 g, 9.947 mmol) in DCM (50 mL) at 23° C. was added thionyl chloride (1.451 mL, 19.89 mmol) and allowed to stir overnight. The reaction was concentrated and then purified by combiflash (0 to 10% EtOAc/hexanes) to provide 1.2 (1.9940 g, 91.32% yield).

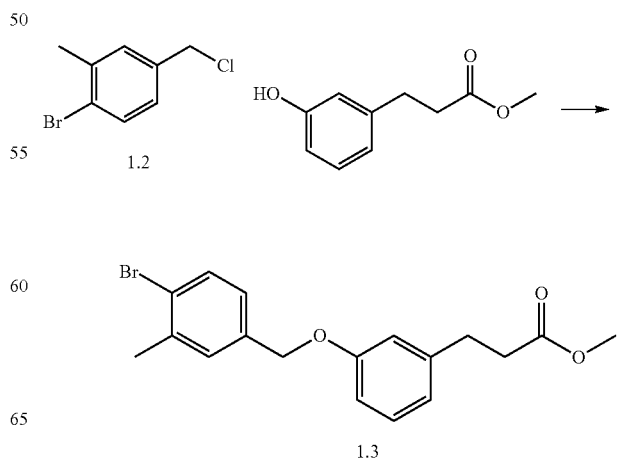

1.2

Methyl 3-(3-(((4-bromo-3-methylphenyl)methyl)oxy) phenyl)propanoate (1.3). To flask containing methyl 3-(3-hydroxyphenyl)propanoate (available from Aagile Labs Division of Tyger Scientific) (0.25 g, 1.387 mmol) and cesium carbonate (0.5876 g, 1.804 mmol) in DMF (8 mL), was added 1.2 (0.3654 g, 1.665 mmol). The resulting mixture was then stirred overnight. The reaction was diluted with water and extracted with EtOAc. The organic layers were washed with brine, dried over $Na_2SO_4$, filtered, concentrated, and then purified by combiflash (0 to 20% EtOAc/hexane) to provide 1.3 (0.4575 g, 90.78% yield). MS ESI (pos.) m/e: 382.0 $(M+H_2O)^+$.

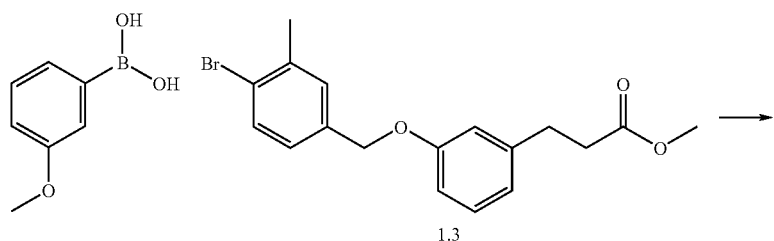

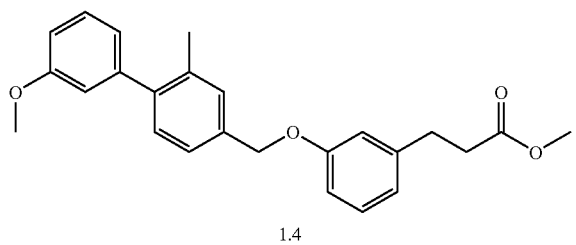

1.4

Methyl 3-(3-(((2-methyl-3'-(methyloxy)-1,1'-biphenyl-4-yl)methyl)oxy)phenyl)propanoate (1.4). To a 2 dram vial charged with methyl ester 1.3 (0.0700 g, 0.193 mmol), tetrakis(triphenylphosphine)palladium (0) (0.0445 g, 0.0385 mmol), cesium fluoride (0.0356 mL, 0.964 mmol), and 3-methoxyphenylboronic acid (available from Aldrich) (0.0878 g, 0.578 mmol), was added DME (1 mL). The resulting mixture was then heated at 85° C. overnight. The reaction was allowed to cool and then filtered and concentrated. The crude product was purified by combiflash (0 to 20% EtOAc/hexanes) yielding 1.4 (0.0624 g, 82.9% yield). MS ESI (pos.) m/e: 391.1 $(M+H)^+$.

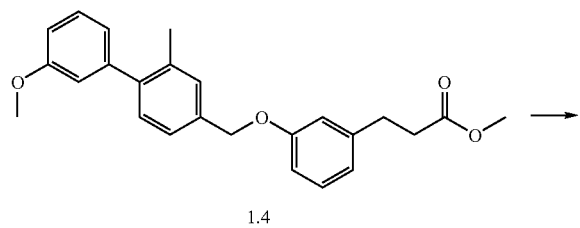

1.4

-continued

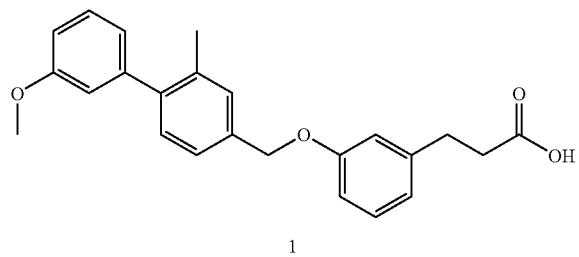

1

3-(3-(((2-Methyl-3'-(methyloxy)-1,1'-biphenyl-4-yl)methyl)oxy)phenyl)propanoic acid (1). To a solution of 1.4 (0.0532 g, 0.136 mmol) in THF/MeOH (2/1) (1.5 mL) was added LiOH (0.50 mL, 0.500 mmol). The resulting mixture was stirred overnight at 23° C., quenched with excess 1N HCl, and extracted with EtOAc. The combined organic layers were dried over $Na_2SO_4$ and concentrated. The crude residue was purified by combiflash (0 to 40% EtOAc/hexane) to afford 1 (0.0426 g, 83.1% yield). MS ESI (neg.) m/e: 375.1 $(M-H)^+$. $^1H$ NMR (400 MHz, $CDCl_3$) δ ppm 7.32-7.39 (3H, m), 7.24-7.31 (2H, m), 6.85-6.95 (6H, m), 5.08 (2H, s), 3.87 (3H, s), 2.99 (2H, t, J=7.8 Hz), 2.73 (2H, t, J=7.8 Hz), 2.34 (3H, s).

Example 2

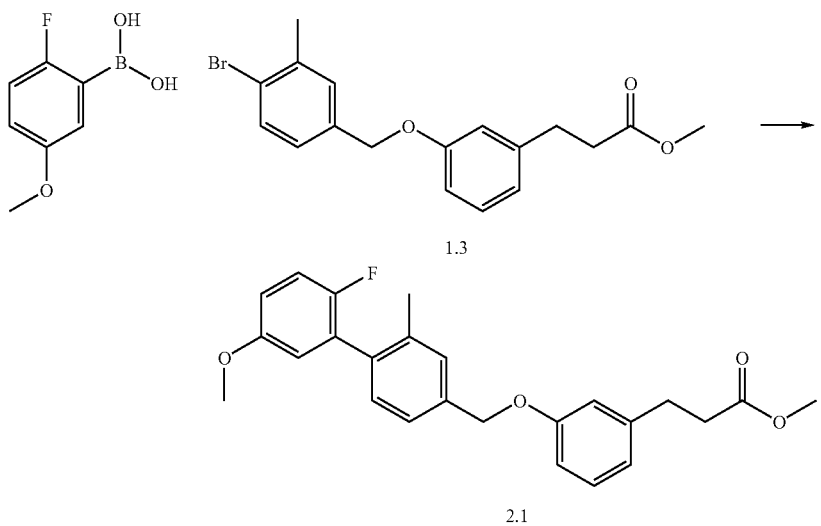

Methyl 3-(3-(((2-methyl-3'-(methyloxy)-1,1'-biphenyl-4-yl)methyl)oxy)phenyl)propanoate (2.1). Compound 1.3 (0.070 g, 0.193 mmol) was coupled with 2-fluoro-5-methoxyphenylboronic acid (available from Aldrich) (0.0982 g, 0.578 mmol) according to the method reported for preparation of 1.4 to afford 2.1 (0.070 g, 89%) as a colorless oil.

3-(3-(((2'-Fluoro-2-methyl-5'-(methyloxy)-1,1'-biphenyl-4-yl)methyl)oxy)phenyl)propanoic acid (2). To a solution of 2.1 (0.0560 g, 0.137 mmol) in THF/MeOH (2/1) (1.5 mL) was added LiOH (0.50 mL, 0.500 mmol). The resulting mixture was stirred overnight at 23° C., quenched with excess 1N HCl, and extracted with EtOAc. The combined organic layers were dried over $Na_2SO_4$ and concentrated. The crude residue was purified by combiflash (0 to 40% EtOAc/hexanes) to afford 2 (0.0395 g, 73.0% yield). MS ESI (neg.) m/e: 393.1 (M−H)$^+$. $^1$H NMR (400 MHz, CDCl$_3$) δ ppm 7.32-7.41 (2H, m), 7.24-7.29 (2H, m), 7.08 (1H, t, J=9.0 Hz), 6.85-6.92 (4H, m), 6.79 (1H, dd, J=5.9, 3.1 Hz), 5.08 (2H, s), 3.83 (3H, s), 2.98 (2H, t, J=7.8 Hz), 2.72 (2H, t, J=7.6 Hz), 2.27 (3H, s).

Example 3

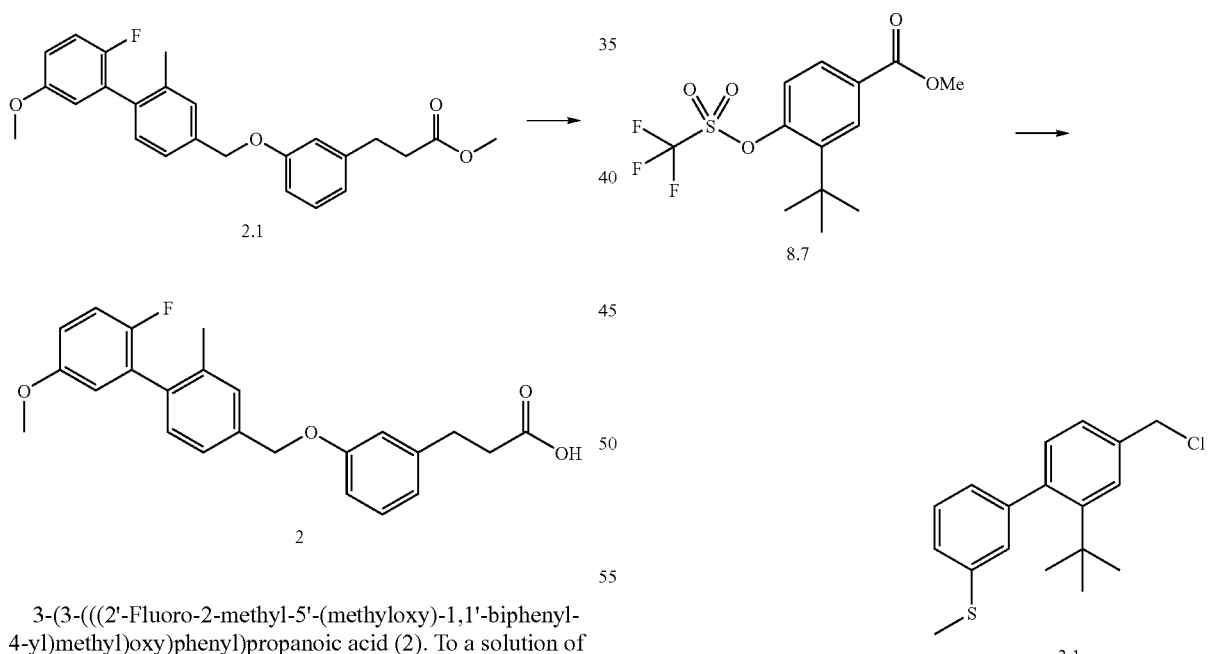

4-(Chloromethyl)-2-(1,1-dimethylethyl)-3'-(methylsulfanyl)-1,1'-biphenyl (3.1). The title compound was synthesized in a similar manner as 12.3 starting from 8.7 and 3-thiomethylphenylboronic acid (available from Aldrich). $^1$H NMR (500 MHz, CDCl$_3$) δ ppm 7.54 (1H, d, J=2.0 Hz), 7.28 (4H, m), 7.15 (1H, t, J=1.7 Hz), 7.05 (2H, m), 4.65 (2H, s), 2.49 (3H, s), 1.22 (9H, s).

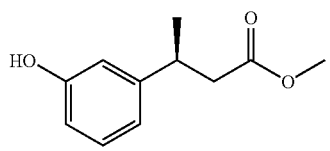

or +

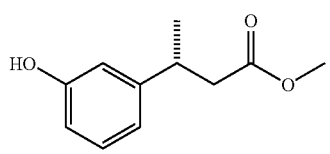

5,7

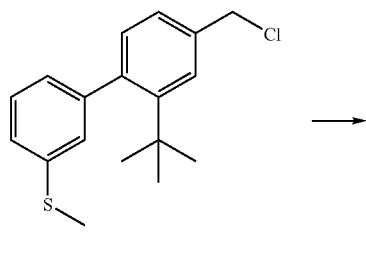

3.1

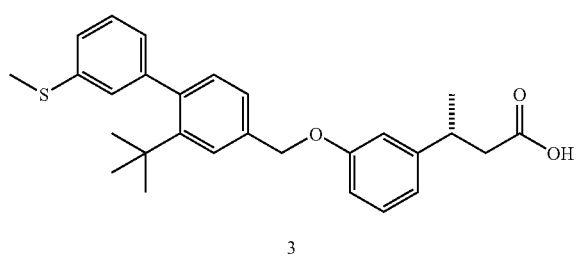

or

3

(3R)-3-(3-(((2-(1,1-Dimethylethyl)-3'-(methylsulfanyl)-1,1'-biphenyl-4-yl)methyl)oxy)phenyl)butanoic acid or (3S)-3-(3-(((2-(1,1-dimethylethyl)-3'-(methylsulfanyl)-1,1'-biphenyl-4-yl)methyl)oxy)phenyl)butanoic acid (3). Compound 3 was prepared from 5.7 and 3.1 using the coupling and hydrolysis techniques for preparing compounds reported in US 2006/0004012. (MS ESI (neg.) m/e: 447.1 (M–H). $^1$H NMR (500 MHz) (CDCl$_3$) δ ppm 7.62 (1H, d, J=1.2 Hz), 7.32 (4H, m), 7.20 (1H, s), 7.10 (2H, m), 6.95 (2H, m), 6.89 (1H, d, J=7.6 Hz), 5.11 (2H, s), 3.35 (1H, m), 2.76 (1H, m), 2.65 (1H, m), 2.51 (3H, s), 1.36 (3H, d, J=7.1 Hz), 1.25 (9H, s).

Example 4

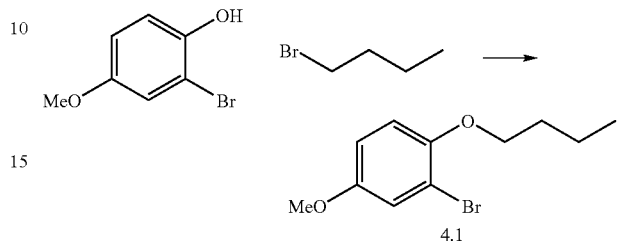

4.1

2-Bromo-1-butoxy-4-methoxybenzene (4.1). A mixture of 2-bromo-4-methoxyphenol (available from Betapharma Inc.) (1.50 g, 7.39 mmol), 1-bromobutane (available from Aldrich) (0.95 mL, 8.87 mmol), and cesium carbonate (3.13 g, 9.60 mmol) in DMF (40 mL) was stirred overnight at room temperature. The mixture was diluted with EtOAc, washed with water and brine, dried over Na$_2$SO$_4$, and concentrated. The crude product was purified by silica gel flash chromatography (0-20% EtOAc/hexane) to afford compound 4.1 (1.49 g, 78% yield) as a colorless oil. $^1$H NMR (400 MHz, CDCl$_3$) δ ppm 7.15 (d, J=2.7 Hz, 1H), 6.84 (d, J=9.0 Hz, 1H), 6.80 (dd, J=3.1, 9.0 Hz, 1H), 3.97 (t, J=6.5 Hz, 2H), 3.76 (s, 3H), 1.79 (m, 2H), 1.53 (m, 2H), 0.98 (t, J=7.2 Hz, 3H).

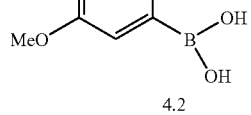

4.1

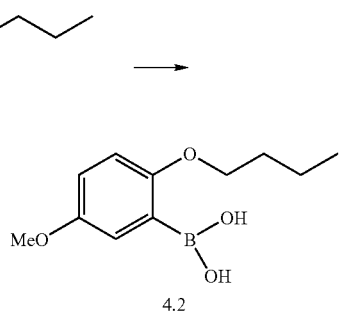

4.2

2-Butoxy-5-methoxyphenylboronic acid (4.2). To a −78° C. solution of 2-bromo-1-butoxy-4-methoxybenzene 4.1 (250 mg, 965 μmol) in THF (8.0 mL) was added tert-butyllithium, 1.7 M solution in pentane (1248 μL, 2122 μmol) dropwise under a blanket of nitrogen. The pale yellow solution was stirred for 0.5 h at −78° C. before dropwise addition of neat trimethyl borate (175 μL, 1544 μmol) at the same temperature. The resulting mixture was stirred for 1 hour at −78° C., warmed to 25° C., and stirred for an additional hour. The reaction was quenched with saturated aqueous ammonium chloride and concentrated. The resulting residue was suspended in water/acetic acid (pH=3) and extracted with DCM. The combined organic layers were washed with saturated aqueous sodium bicarbonate and brine, dried (MgSO$_4$), and concentrated to afford a light brown solid. The product was purified by trituration with hexane to afford 2-butoxy-5-methoxyphenylboronic acid 4.2 (67.2 mg, 31.1% yield) as a white powder.

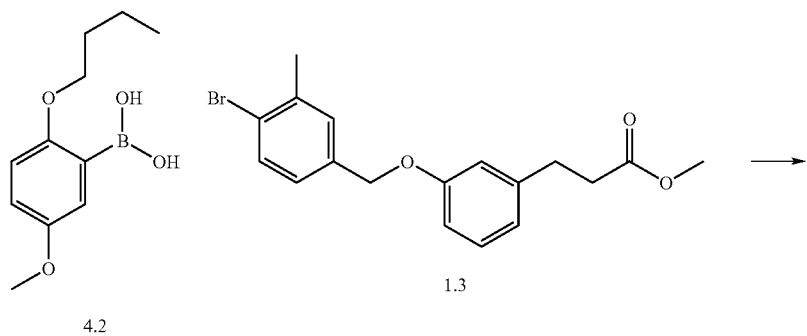

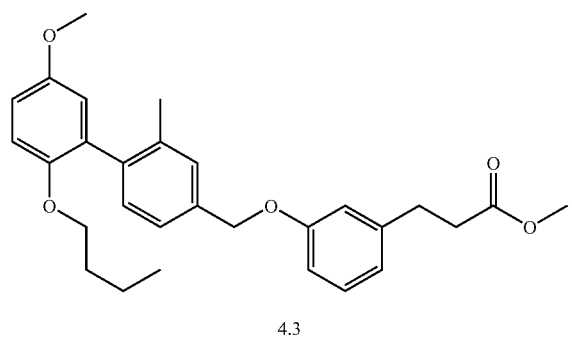

Methyl 3-(3-(((2'-(butyloxy)-2-methyl-5'-(methyloxy)-1,1'-biphenyl-4-yl)methyl)oxy)phenyl)propanoate (4.3). To a 2 dram vial charged with 1.3 (0.0200 g, 0.0551 mmol), tetrakis(triphenylphosphine)palladium (0) (0.0127 g, 0.0110 mmol), cesium fluoride (0.0102 mL, 0.275 mmol), and 2-butoxy-5-methoxyphenylboronic acid 4.2 (0.0247 g, 0.110 mmol), was added DME (1 mL). The resulting mixture was then heated at 85° C. overnight. The reaction was allowed to cool and then filtered and concentrated. The crude was purified by combiflash (0 to 20% EtOAc/hexanes) yielding 4.3 (0.0241 g, 95% yield).

solution of 4.3 (0.0241 g, 0.0521 mmol) in THF/MeOH (2/1) (1.5 mL) was added LiOH (0.50 mL, 0.500 mmol). The resulting mixture was stirred overnight at 23° C., quenched with excess 1N HCl, and extracted with EtOAc. The combined organic layers were dried over $Na_2SO_4$ and concentrated. The crude residue was purified by combiflash (0 to 40% EtOAc/hexanes) to afford 4 (0.0166 g, 71.0% yield). MS ESI (neg.) m/e: 393.1 (M−H)+. $^1$H NMR (400 MHz, $CDCl_3$) δ ppm 7.32 (1H, s), 7.20-7.29 (4H, m), 6.83-6.92 (5H, m), 6.74 (1H, d, J=2.9 Hz), 5.07 (2H, s), 3.83 (2H, t, J=6.6 Hz), 3.79 (3H, s), 2.97 (2H, t, J=7.8 Hz), 2.68-2.73 (2H, m), 2.19 (3H, s), 1.53-1.60 (2H, m), 1.22-1.31 (2H, m), 0.83 (3H, t, J=7.3 Hz).

Example 5

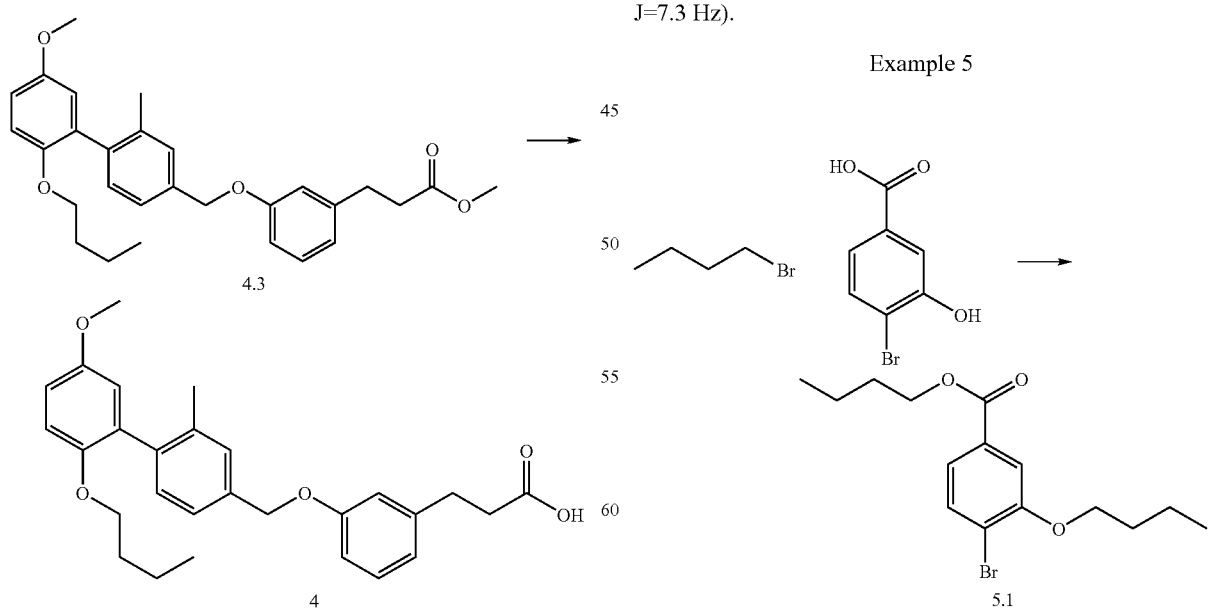

3-(3-(((2'-(Butyloxy)-2-methyl-5'-(methyloxy)-1,1'-biphenyl-4-yl)methyl)oxy)phenyl)propanoic acid (4). To a Butyl 4-bromo-3-(butyloxy)benzoate (5.1). To a flask containing 4-bromo-3-hydroxybenzoic acid (available from Combi-Blocks Inc.) (2.40 g, 11.06 mmol) and cesium carbonate (8.287 g, 25.44 mmol) in DMF (40 mL), was added 1-bromobutane (available from Aldrich) (2.494 mL, 23.22 mmol), and the mixture was stirred overnight. The reaction was diluted with water and extracted with EtOAc. The organic layers were washed with brine, dried over Na₂SO₄, filtered, concentrated, and then purified by combiflash (0 to 20% EtOAc/Hexanes) to provide 5.1 (2.4326 g, 66.81% yield).

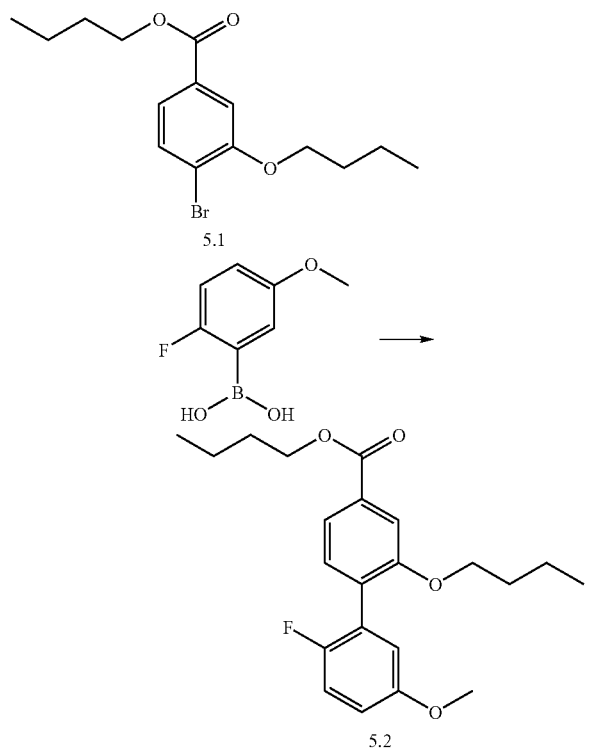

Butyl 2-(butyloxy)-2'-fluoro-5'-(methyloxy)-1,1'-biphenyl-4-carboxylate (5.2). To a 2 dram vial charged with 2-fluoro-5-methoxyphenylboronic acid (available from Aldrich) (2.323 g, 13.67 mmol), tetrakis(triphenylphosphine)palladium(0) (0.7897 g, 0.6834 mmol), cesium fluoride (0.8409 mL, 22.78 mmol), and 5.1 (1.50 g, 4.556 mmol), was added DME (20 mL), and the mixture was then heated at 90° C. overnight. The reaction was allowed to cool and then filtered and concentrated. The crude product was purified by combiflash (0 to 10% EtOAc/hexanes) yielding 5.2 (1.1530 g, 67.58% yield).

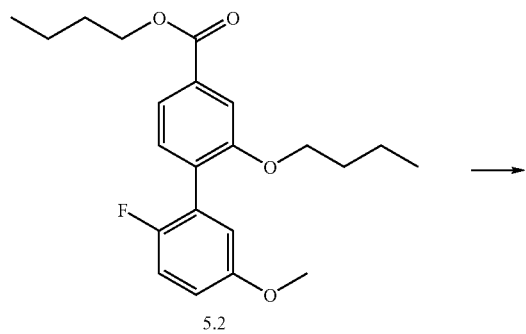

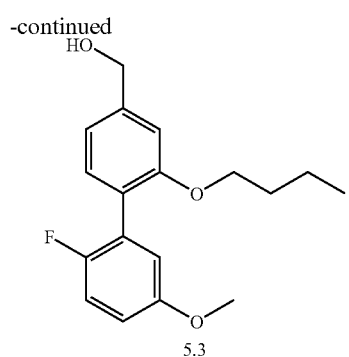

(2-(Butyloxy)-2'-fluoro-5'-(methyloxy)-1,1'-biphenyl-4-yl)methanol (5.3). To 5.2 (1.1530 g, 3.079 mmol) in THF (10 mL) at 0° C. was added LAH (1.0 M solution in THF (4.619 mL, 4.619 mmol)). The reaction was stirred for one hour and then carefully diluted with water, extracted with EtOAc, washed with brine, dried over sodium sulfate, filtered, and concentrated to provide 5.3 (0.9050 g, 96.57% yield).

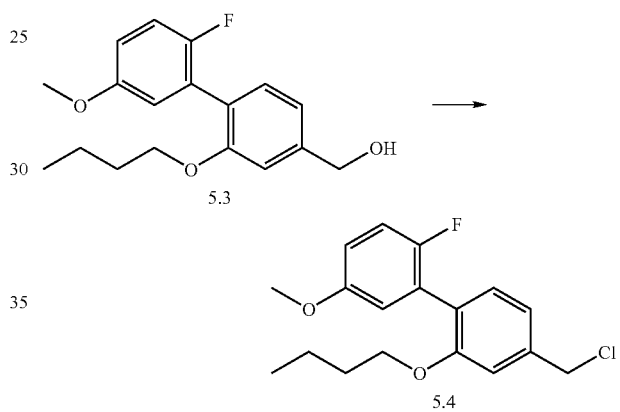

2-(Butyloxy)-4-(chloromethyl)-2'-fluoro-5'-(methyloxy)-1,1'-biphenyl (5.4). To a stirred solution of 5.3 (0.8800 g, 2.891 mmol) in DCM (15 mL) at 23° C. was added thionyl chloride (0.4218 mL, 5.783 mmol). The reaction mixture was then stirred overnight. The reaction was concentrated and then purified by combiflash (0 to 10% EtOAc/Hexanes) to provide 5.4 (0.7980 g, 85.50% yield).

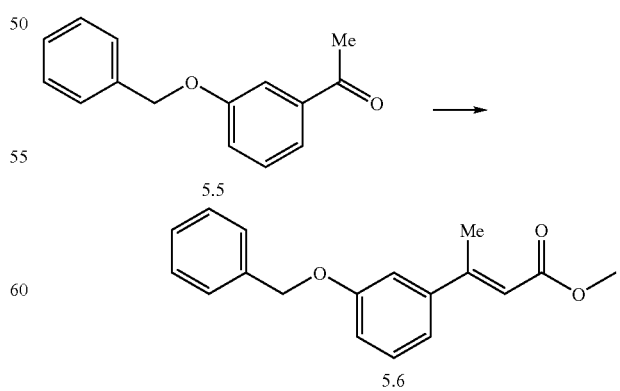

Methyl (2E)-3-(3-((phenylmethyl)oxy)phenyl)-2-butenoate (5.6). To a suspension of lithium chloride (0.28 g, 6.6 mmol) in MeCN (9 mL) were added trimethyl phosphonoacetate (0.76 mL, 5.3 mmol), 1,8-diazabicyclo[5.4.0]undec-7-ene (0.79 mL, 5.3 mmol), and 3-benzyloxyacetophenone (available from Aldrich) (1.00 g, 4.4 mmol). The mixture was stirred overnight at reflux (100° C.), cooled to room temperature, diluted with EtOAc, washed with water and brine, dried (MgSO$_4$), and concentrated. The crude product was chromatographed on silica gel (0-10% EtOAc/hexane) to afford 5.6 (0.45 g, 36%) as a colorless oil.

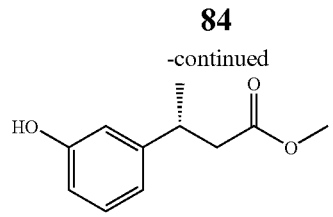

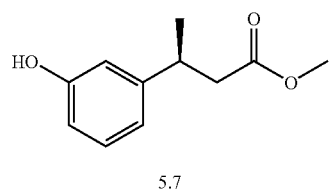

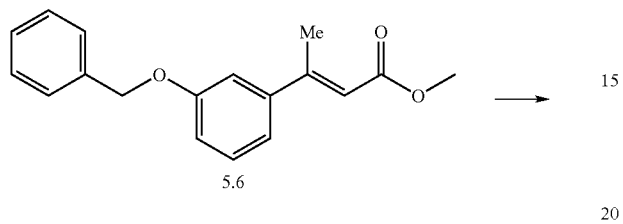

Methyl (3R)-3-(3-hydroxyphenyl)butanoate and methyl (3S)-3-(3-hydroxyphenyl)butanoate (5.7 and 5.8). To a solution of 5.6 (0.44 g, 1.56 mmol) in 1:1 EtOAc/MeOH (10.0 mL), was added 10% Pd/C (0.25 g, 0.23 mmol) under a blanket of N$_2$. The mixture was sparged with H$_2$, stirred overnight under a H$_2$ balloon, filtered through silica gel (EtOAc), and concentrated. The resulting racemate was resolved by chiral HPLC (Chiralcel OD column, 3% IPA/hexane, 220 nm) to afford 5.7 (0.14 g, 22.7 minutes) and 5.8 (0.14 g, 36.1 minutes) as pale yellow oils.

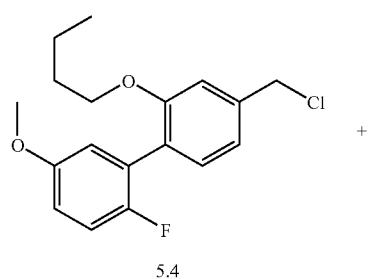

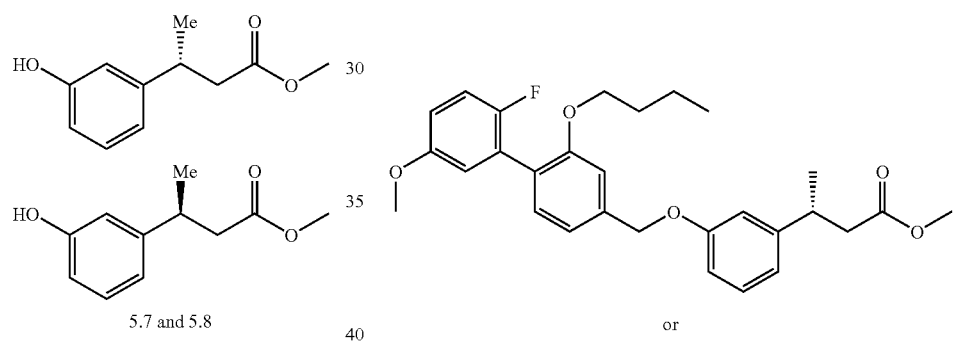

Methyl (3R)-3-(3-(((2-(butyloxy)-2'-fluoro-5'-(methyloxy)-1,1'-biphenyl-4-yl)methyl)oxy)phenyl)butanoate or methyl (3S)-3-(3-(((2-(butyloxy)-2'-fluoro-5'-(methyloxy)-1,1'-biphenyl-4-yl)methyl)oxy)phenyl)butanoate (5.9). To flask containing 5.7 (0.0250 g, 0.129 mmol) and cesium carbonate (0.0545 g, 0.167 mmol) in DMF (1 mL) was added 5.4 (0.0499 g, 0.154 mmol). The resulting mixture was then stirred overnight. The reaction was diluted with water and extracted with EtOAc. The organic layers were washed with brine, dried over Na$_2$SO$_4$, filtered, concentrated, and then purified by combiflash (0 to 20% EtOAc/Hexanes) to provide 5.9.

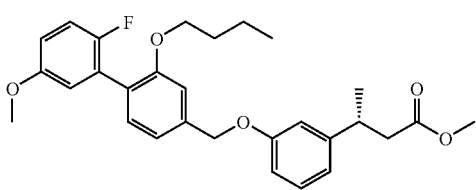

or

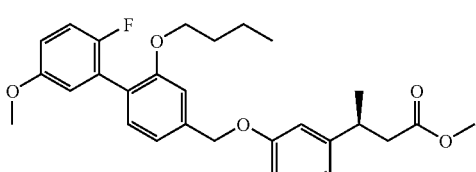

5-9

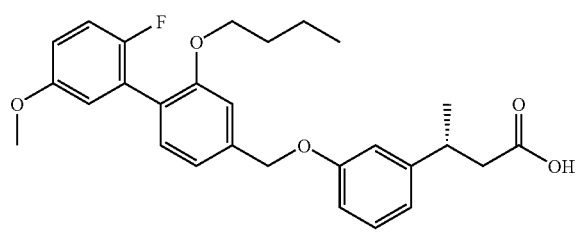

or

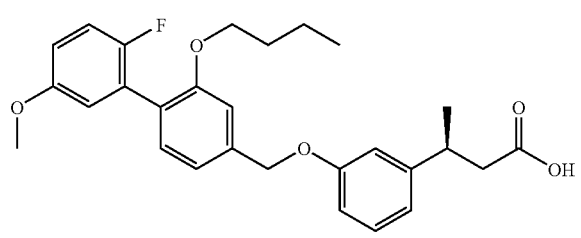

5

(3R)-3-(3-(((2Butyloxy)-2'-fluoro-5'-(methyloxy)-1,1'-biphenyl-4-yl)methyl)oxy)phenyl)butanoic acid or (3S)-3-(3-(((2-(butyloxy)-2'-fluoro-5'-(methyloxy)-1,1'-biphenyl-4-yl)methyl)oxy)phenyl)butanoic acid (5). To a solution of 5.9 (0.0620 g, 0.129 mmol) in THF/MeOH (2/1) (1.5 mL), was added lithium hydroxide (0.500 mL, 0.500 mmol). The resulting mixture was stirred overnight at 23° C., quenched with excess 1N HCl, and extracted with EtOAc. The combined organic layers were dried over Na$_2$SO$_4$ and concentrated. The crude residue was purified by combiflash (0 to 40% EtOAc/hexanes) to afford 5 (0.0519 g, 86.2% yield). MS ESI (neg.) m/e: 465.2 (M−H)$^+$. $^1$H NMR (500 MHz, CDCl$_3$) δ ppm 7.25-7.32 (2H, m), 7.02-7.10 (3H, m), 6.83-6.92 (5H, m), 5.09 (2H, s), 4.01 (2H, t, J=6.5 Hz), 3.81 (3H, s), 3.25-3.32 (1H, m) 2.68-2.73 (1H, m), 2.57-2.63 (1H, m), 1.66-1.72 (2H, m), 1.33-1.42 (5H, m), 0.91 (3H, t, J=7.5 Hz).

Example 6

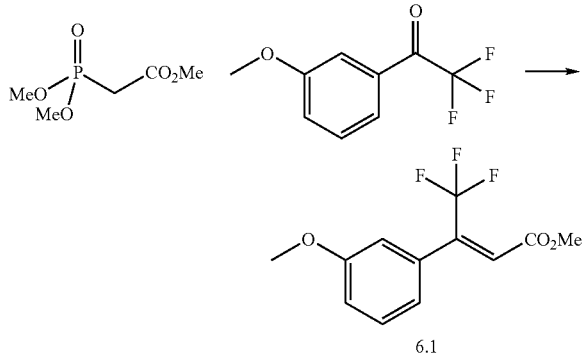

6.1

Methyl (2Z)-4,4,4-trifluoro-3-(3-(methyloxy)phenyl)-2-butenoate (6.1). To a suspension of lithium chloride (0.623 g, 14.7 mmol) in MeCN (20 mL), were added trimethylphosphonoacetate (available from Aldrich) (1.70 mL, 11.8 mmol), DBU (1.76 mL, 11.8 mmol), and 2,2,2-trifluoro-1-(3-methoxyphenyl)ethanone (available from Oakwood Products Inc.) (2.0 g, 9.80 mmol) at room temperature. The pale yellow mixture was heated to reflux and stirred overnight. The mixture was partitioned between water and EtOAc. The layers were separated, and the aqueous phase was extracted with additional EtOAc. The combined organic layers were washed with 1 N HCl and brine, dried over Na$_2$SO$_4$, and concentrated. The crude product was purified by silica gel flash chromatography (0-10% EtOAc/hexane) to afford 6.1 (2.49 g, 97.7% yield) as a colorless oil.

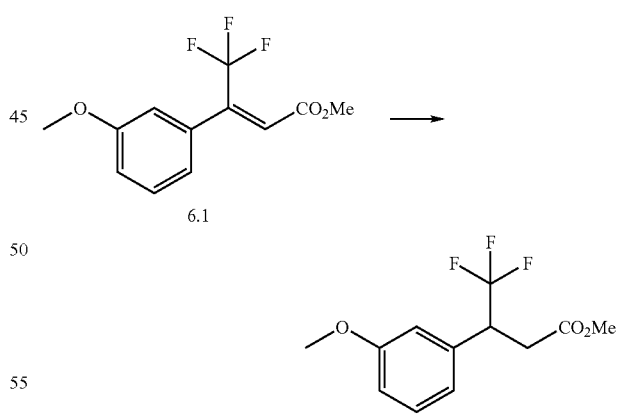

Methyl 4,4,4-trifluoro-3-(3-(methyloxy)phenyl)butanoate (6.2). A 250 mL flask containing a solution of 6.1 (2.20 g, 8.5 mmol) in 1:1 EtOAc/MeOH (40 mL) was purged with N$_2$. To the mixture was added palladium, 10 wt. % (dry), on carbon powder, wet (0.90 g, 0.85 mmol). The vial was then purged with H$_2$, and the contents were stirred overnight under a H$_2$ balloon. The black mixture was filtered through a pad of Celite and concentrated to afford 6.2 (2.19 g, 99% yield).

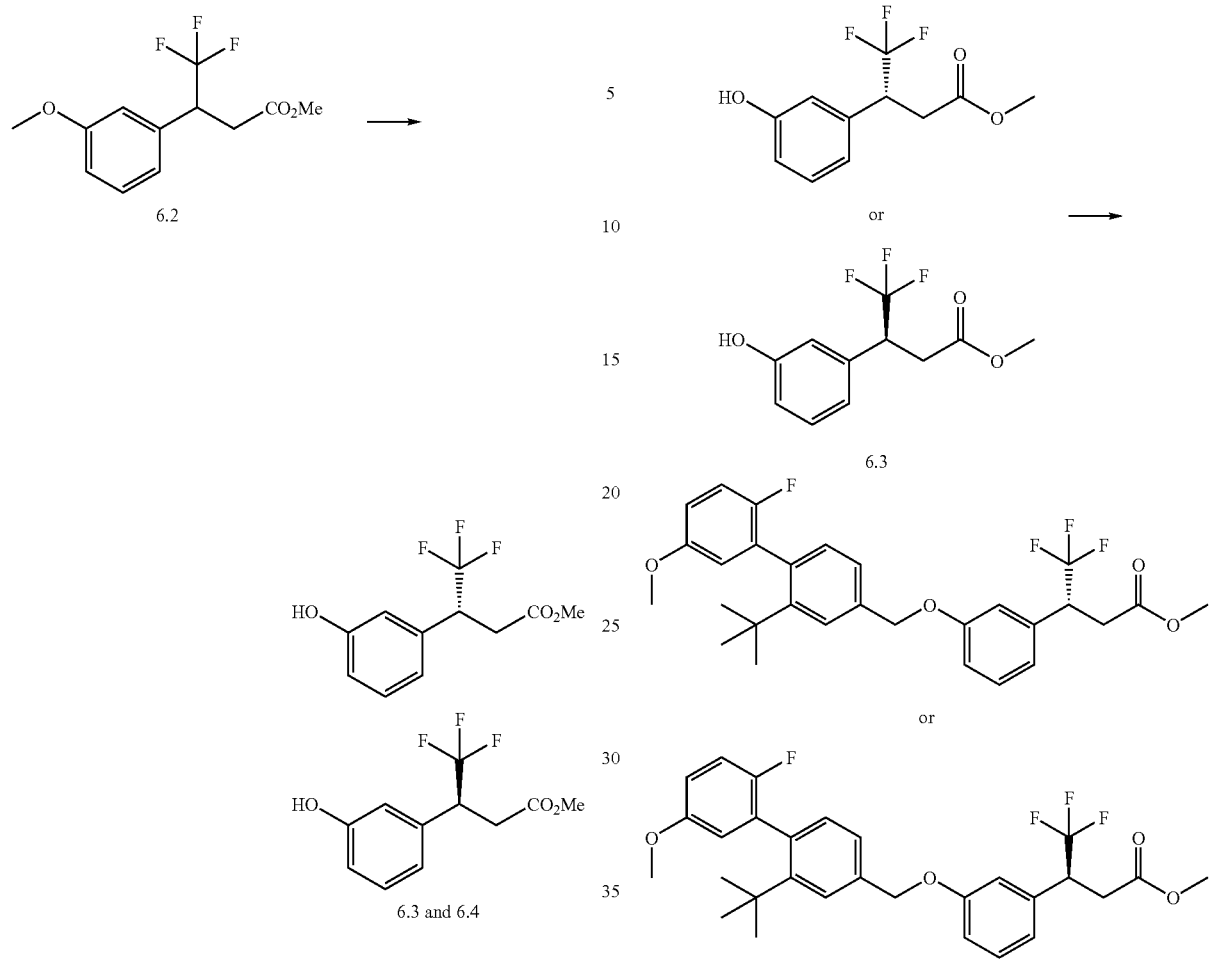

Methyl (3R)-4,4,4-trifluoro-3-(3-hydroxyphenyl)butanoate and methyl (3S)-4,4,4-trifluoro-3-(3-hydroxyphenyl)butanoate (6.3 and 6.4). To a solution of methyl ether 6.2 (1.9546 g, 7.45 mmol) in DCE (60 mL), was added 1,2-ethanedithiol (9.99 mL, 119 mmol) followed by anhydrous aluminum chloride (7.95 g, 59.6 mmol) at 0° C. The reaction mixture was allowed to slowly warm to room temperature over four hours and then was quenched with saturated Rochelle's salt solution. The mixture was extracted (2×50 mL) with DCM. The combined organic layers were washed with water (1×40 mL) and brine (1×40 mL) and dried over magnesium sulfate. The filtrate was concentrated, and the residue was purified by chromatography (silica, 0 to 30% EtOAc:hexanes) and then the enantiomers were resolved by chiral HPLC (Chiralcel OD-H column, 3% IPA/hexane, 220 nm) to afford 6.3 (28 minutes) and 6.4 (45 minutes).

Methyl (3R)-3-(3-(((2-(1,1-dimethylethyl)-2'-fluoro-5'-(methyloxy)-1,1'-biphenyl-4-yl)methyl)oxy)phenyl)-4,4,4-trifluorobutanoate or methyl (3S)-3-(3-(((2-(1,1-dimethylethyl)-2'-fluoro-5'-(methyloxy)-1,1'-biphenyl-4-yl)methyl)oxy)phenyl)-4,4,4-trifluorobutanoate (6.5). To flask containing 6.3 (0.0300 g, 0.121 mmol) and cesium carbonate (0.0512 g, 0.157 mmol) in DMF (1 mL), was added 8.10 (0.0445 g, 0.145 mmol). The resulting mixture was stirred overnight. The reaction was diluted with water and extracted with EtOAc. The organic layers were washed with brine, dried over Na$_2$SO$_4$, filtered, concentrated, and then purified by combiflash (0 to 20% EtOAc/Hexanes) to provide 6.5.

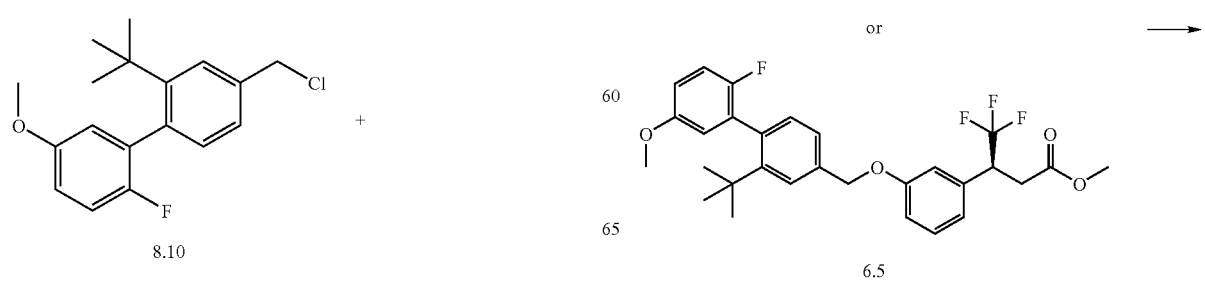

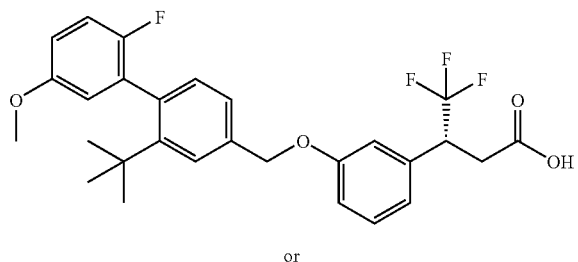

or

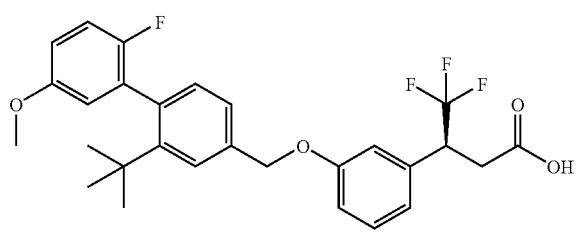

6

(3R)-3-(3-(((2-(1,1-Dimethylethyl)-2'-fluoro-5'-(methyloxy)-1,1'-biphenyl-4-yl)methyl)oxy)phenyl)-4,4,4-trifluorobutanoic acid or (3S)-3-(3-(((2-(1,1-dimethylethyl)-2'-fluoro-5'-(methyloxy)-1,1'-biphenyl-4-yl)methyl)oxy)phenyl)-4,4,4-trifluorobutanoic acid (6). To a solution of 6.4 (0.0627 g, 0.121 mmol) in THF/MeOH (2/1) (1.5 mL), was added lithium hydroxide (0.50 mL, 0.500 mmol). The resulting mixture was stirred overnight at 23° C., quenched with excess 1N HCl, and extracted with EtOAc. The combined organic layers were dried over $Na_2SO_4$ and concentrated. The crude residue was purified by combiflash (0 to 40% EtOAc/hexanes) to afford 6 (0.0449 g, 73.6% yield). MS ESI (neg.) m/e: 503.2 (M−H)+. 1H NMR (400 MHz, CDCl3) δ ppm 7.61 (1H, d, J=1.6 Hz), 7.28-7.34 (2H, m), 7.07 (1H, d, J=7.4 Hz), 6.94-7.04 (4H, m), 6.87 (1H, dd, J=7.6, 4.5 Hz), 6.79 (1H, dd, J=5.9, 3.1 Hz), 5.09 (2H, s), 3.87 (1H, s), 3.80 (3H, s), 3.06 (1H, dd, J=5.1, 16.8 Hz), 2.96 (1H, dd, J=9.4, 16.8 Hz), 1.25 (9H, s).

Example 7

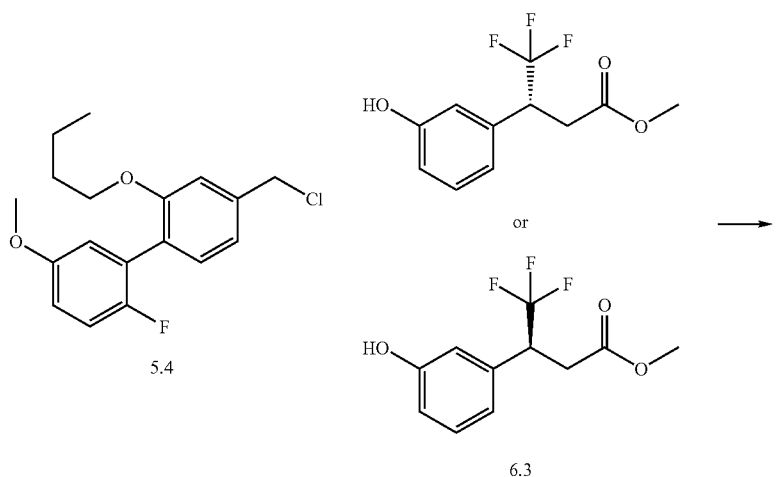

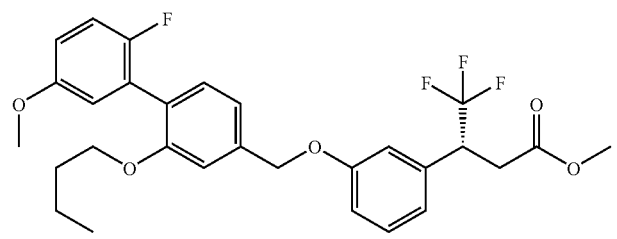

or

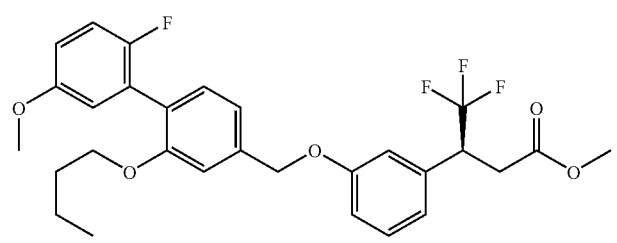

7.1

Methyl (3R)-3-(3-(((2-(butyloxy)-2'-fluoro-5'-(methyloxy)-1,1'-biphenyl-4-yl)methyl)oxy)phenyl)-4,4,4-trifluorobutanoate or methyl (3S)-3-(3-(((2-(butyloxy)-2'-fluoro-5'-(methyloxy)-1,1'-biphenyl-4-yl)methyl)oxy)phenyl)-4,4,4-trifluorobutanoate (7.1). To a flask containing 6.3 (0.0300 g, 0.121 mmol) and cesium carbonate (0.0512 g, 0.157 mmol) in DMF (1 mL), was added 5.4 (0.0468 g, 0.145 mmol). The resulting mixture was stirred overnight. The reaction was diluted with water and extracted with EtOAc. The organic layers were washed with brine, dried over Na₂SO₄, filtered, concentrated, and then purified by combiflash (0 to 20% EtOAc/hexanes) to provide 7.1.

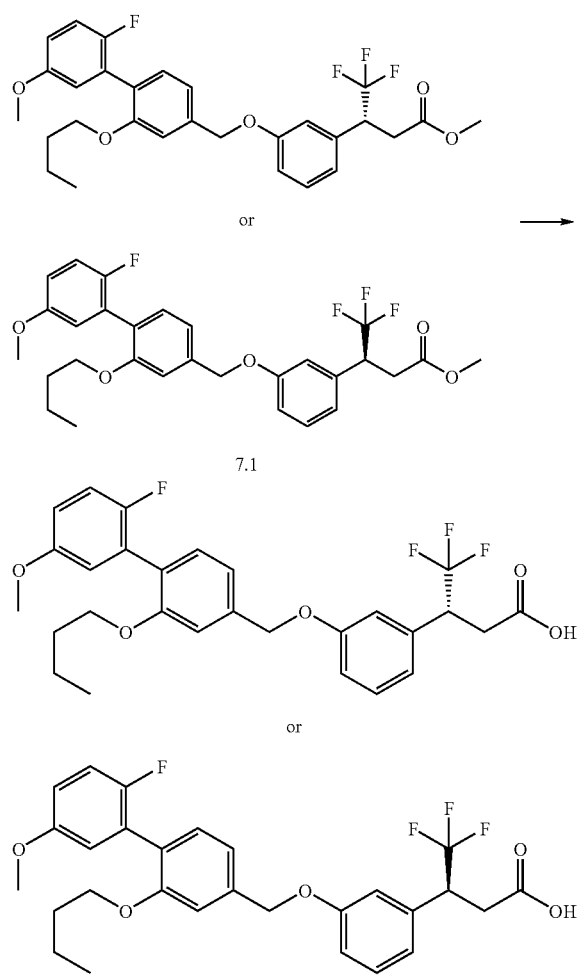

(3R)-3-(3-(((2-(Butyloxy)-2'-fluoro-5'-(methyloxy)-1,1'-biphenyl-4-yl)methyl)oxy)phenyl)-4,4,4-trifluorobutanoic acid or (3S)-3-(3-(((2-(butyloxy)-2'-fluoro-5'-(methyloxy)-1,1'-biphenyl-4-yl)methyl)oxy)phenyl)-4,4,4-trifluorobutanoic acid (7). To a solution of 7.1 (0.0647 g, 0.121 mmol) in THF/MeOH (2/1) (1.5 mL), was added lithium hydroxide (0.500 mL, 0.500 mmol). The resulting mixture was stirred overnight at 23° C., quenched with excess 1N HCl, and extracted with EtOAc. The combined organic layers were dried over Na₂SO₄ and concentrated. The crude residue was purified by combiflash (0 to 40% EtOAc/hexanes) to afford 7. MS ESI (neg.) m/e: 519.2 (M−H)⁺. ¹H NMR (400 MHz, CDCl₃) δ ppm 7.28-7.33 (2H, m), 7.04-7.09 (3H, m), 6.93-7.02 (3H, m), 6.83-6.91 (2H, m), 5.08 (2H, s), 4.00 (2H, t, J=6.5 Hz), 3.88 (1H, td, J=9.2, 4.7 Hz), 3.81 (3H, s), 3.04-3.11 (1H, m), 2.90-2.98 (1H, m), 1.64-1.72 (2H, m), 1.34-1.44 (2H, m), 0.90 (3H, t, J=7.2 Hz).

Example 8

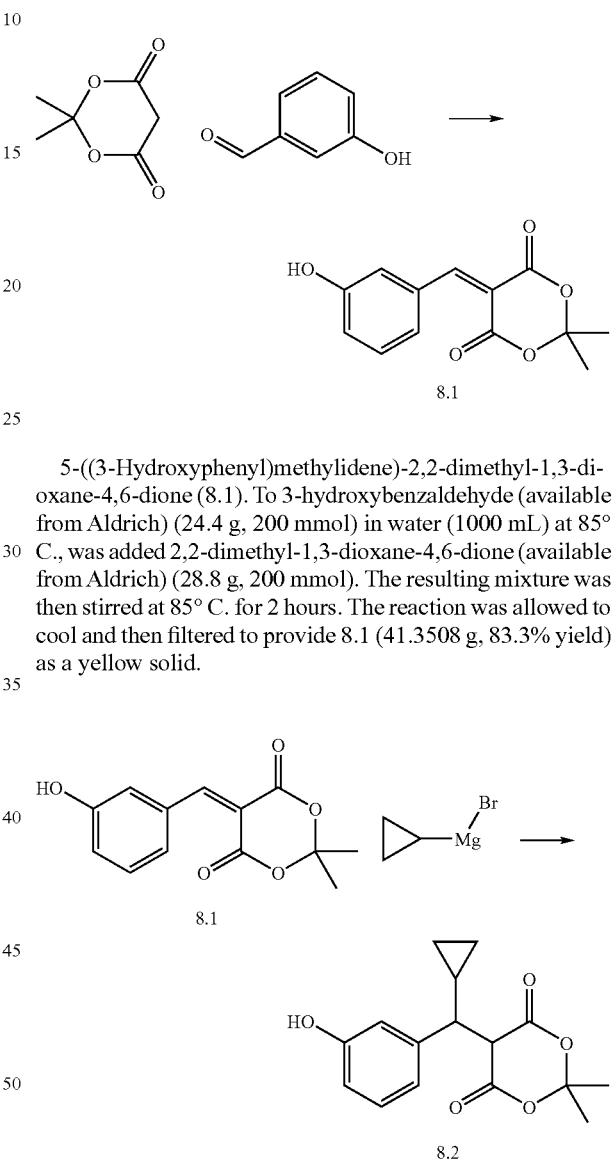

5-((3-Hydroxyphenyl)methylidene)-2,2-dimethyl-1,3-dioxane-4,6-dione (8.1). To 3-hydroxybenzaldehyde (available from Aldrich) (24.4 g, 200 mmol) in water (1000 mL) at 85° C., was added 2,2-dimethyl-1,3-dioxane-4,6-dione (available from Aldrich) (28.8 g, 200 mmol). The resulting mixture was then stirred at 85° C. for 2 hours. The reaction was allowed to cool and then filtered to provide 8.1 (41.3508 g, 83.3% yield) as a yellow solid.

5-(Cyclopropyl(3-hydroxyphenyl)methyl)-2,2-dimethyl-1,3-dioxane-4,6-dione (8.2). To a solution of 8.1 (2.0 g, 8.06 mmol) in THF, was added cyclopropylmagnesium bromide (available from Aldrich) (96.7 mL, 48.3 mmol) via cannula at 0° C. The resulting heterogeneous mixture was warmed to room temperature, stirred for 30 minutes, and quenched with 1 N aq. HCl. The aqueous layer was extracted with EtOAc. The combined organic layers were washed with brine, dried sodium sulfate, filtered, and concentrated. The crude product was purified by silica gel flash chromatography (10-35% EtOAc/hexane) to afford 8.2 (2.04 g, 87.2% yield) as a yellow oil.

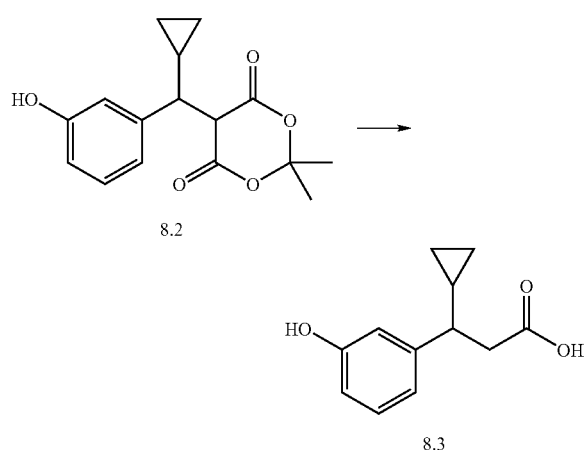

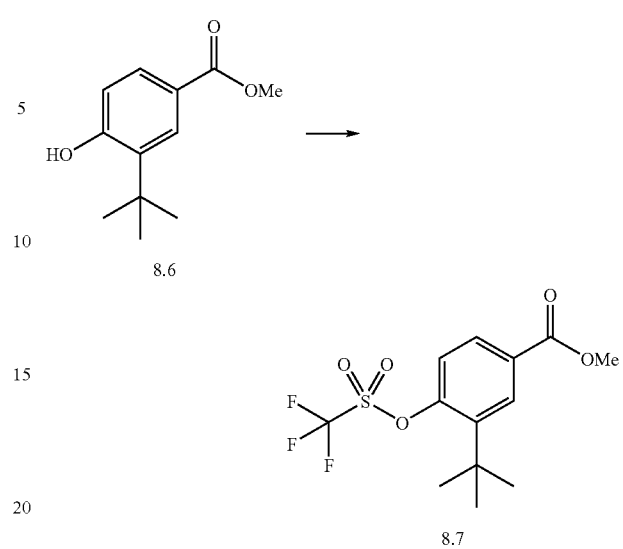

3-Cyclopropyl-3-(3-hydroxyphenyl)propanoic acid (8.3). Compound 8.2 (1.71 g, 5.89 mmol) in DMF/water (10/1) (22 mL) was heated at 90° C. overnight. The reaction was diluted with water and extracted with EtOAc. The organic layers were washed with brine, dried over $Na_2SO_4$, filtered, and concentrated to provide 8.3, which was used in the next step without further purification.

Methyl 3-tert-butyl-4-(trifluoromethylsulfonyloxy)benzoate (8.7). To a stirred solution of methyl 3-tert-butyl-4-hydroxybenzoate (available from Apin Chemical Ltd, United Kingdom) (0.100 g, 0.48 mmol) in DCM (10 mL, 155 mmol) at 23° C., was added TEA (0.080 mL, 0.58 mmol) and DMAP (0.0059 g, 0.048 mmol), followed by triflic anhydride (0.097 mL, 0.58 mmol). The dark solution was stirred at room temperature and monitored by TLC and LC-MS. After 19 hours, the reaction was concentrated in vacuo. The residue was then purified by flash chromatography ($SiO_2$ gel 60, eluted with 0%-10% EtOAc in hexanes). Fractions containing the desired product were combined and concentrated to provide 8.7 as a colorless oil (0.16 g, 98%). MS ESI (pos.) m/e: 341.0 $(M+H)^+$.

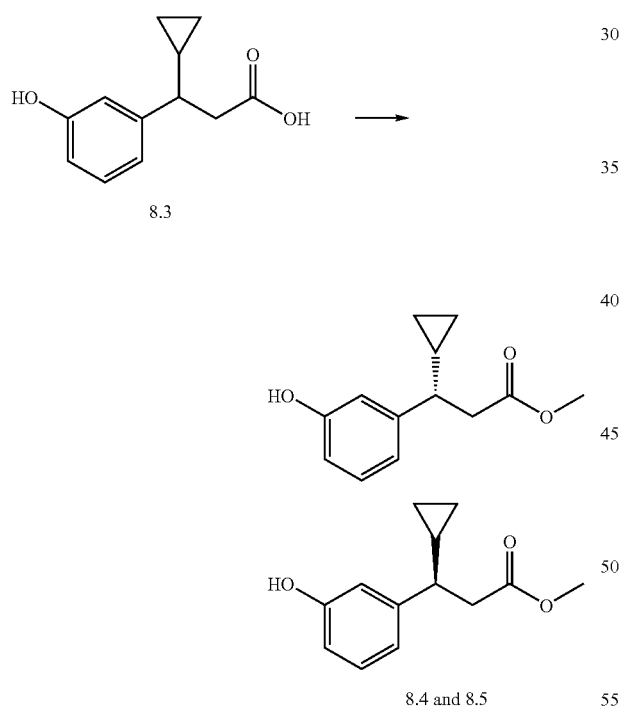

Methyl (3S)-3-cyclopropyl-3-(3-hydroxyphenyl)propanoate and methyl (3R)-3-cyclopropyl-3-(3-hydroxyphenyl)propanoate (8.4 and 8.5). To a flask containing 8.3 (1.2 g, 5.8 mmol) in MeOH (15 mL), was added $H_2SO_4$ (0.31 mL, 5.8 mmol). The resulting mixture was stirred overnight at reflux. The reaction was concentrated and then purified by combiflash (0 to 30% EtOAc/hexanes), and the enantiomers were resolved by chiral HPLC (Chiralcel OD-H column, 3% IPA/hexane, 220 nm) to afford 8.4 (40 minutes) and 8.5 (60 minutes).

Methyl 2-(1,1-dimethylethyl)-2'-fluoro-5'-(methyloxy)-1,1'-biphenyl-4-carboxylate (8.8). To a stirred solution of 8.7 (0.100 g, 0.29 mmol) in DMF (2.00 mL, 26 mmol) at 23° C., was added 2-fluoro-5-methoxyphenylboronic acid (available from Aldrich) (0.100 g, 0.59 mmol), potassium carbonate (0.12 g, 0.88 mmol), followed by tetrakis(triphenylphosphine)palladium (0.034 g, 0.029 mmol). The mixture was heated to 100° C. After 2 hours, the reaction was cooled to room temperature and diluted with water. The mixture was extracted with EtOAc (3×50 mL) and concentrated in vacuo. The residue was then purified by flash chromatography (SiO$_2$ gel 60, eluted with 0%-15% EtOAc in hexanes). Fractions containing the desired product were combined and concentrated to provide 8.8 as a colorless oil (0.85 g, 71%). MS ESI (pos.) m/e: 317.2 (M+H)$^+$.

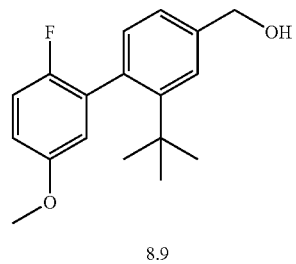

8.8

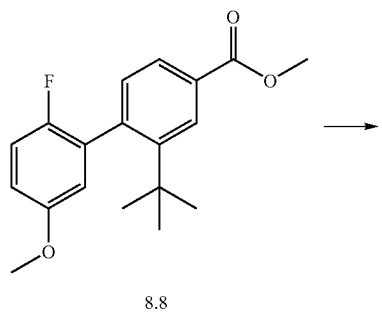

8.9

(2-(1,1-Dimethylethyl)-2'-fluoro-5'-(methyloxy)-1,1'-biphenyl-4-yl)methanol (8.9). To a cooled solution of 8.8 (0.85 g, 2.69 mmol) in dry THF (10.0 mL, 2.69 mmol) at 0° C., was added LAH (1.0 M solution in THF (6.0 mL, 6.0 mmol)). Upon complete addition, the reaction was allowed to warm to room temperature and monitored by TLC and LCMS. Upon completion, 1N NaOH (5 mL) was carefully added to quench the reaction. The resulting solution was extracted with EtOAc (3×10 mL). The combined organic layers were dried over MgSO$_4$, filtered, and concentrated in vacuo. The residue was then purified by flash chromatography (SiO$_2$ gel 60, eluted with 0%-40% EtOAc in hexanes). Fractions containing the desired product were combined and concentrated to provide 8.9 as a colorless oil (0.56 g, 72%). MS ESI (pos.) m/e: 311.2 (M+Na)$^+$.

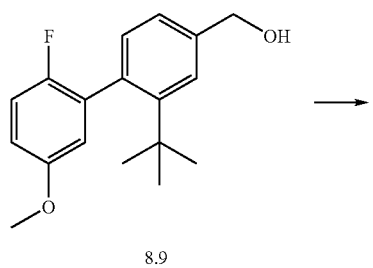

8.9

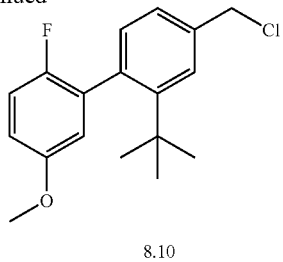

8.10

4-(Chloromethyl)-2-(1,1-dimethylethyl)-2'-fluoro-5'-(methyloxy)-1,1'-biphenyl (8.10). To a cooled solution of 8.9 (0.56 g, 1.93 mmol) in dry DCM (3.60 mL, 1.93 mmol) at 0° C., was added thionyl chloride (0.40 mL, 5.48 mmol) dropwise. Upon complete addition of thionyl chloride, the mixture was allowed to warm to room temperature. After 18 hours, the reaction was concentrated in vacuo. The residue was then purified by flash chromatography (SiO$_2$ gel 60, eluted with 0%-15% EtOAc in hexanes). Fractions containing the desired product were combined and concentrated to provide 8.10 as a colorless solid (0.44 g, 74%). $^1$H NMR (500 MHz, CDCl$_3$) δ ppm 7.56 (1H, s), 7.25 (5H, dd, J=7.7, 1.6 Hz), 7.01 (2H, m), 6.86 (1H, dd, J=9.0, 3.2 Hz), 6.77 (1H, dd, J=5.9, 3.2 Hz), 4.65 (3H, s), 3.79 (3H, s), 1.24 (9H, s).

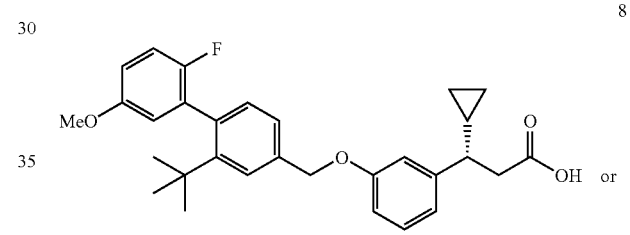

8

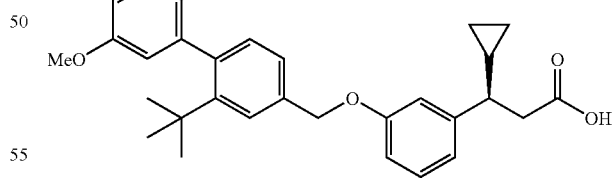

(3S)-3-Cyclopropyl-3-(3-(((2-(1,1-dimethylethyl)-2'-fluoro-5'-(methyloxy)-1,1'-biphenyl-4-yl)methyl)oxy)phenyl)propanoic acid or (3R)-3-cyclopropyl-3-(3-(((2-(1,1-dimethylethyl)-2'-fluoro-5'-(methyloxy)-1,1'-biphenyl-4-yl)methyl)oxy)phenyl)propanoic acid (8). Example 8 was synthesized by a method analogous to the method used for compound 7 from 8.4 and 8.10. MS ESI (neg.) m/e: 475.2 (M−H)$^+$. $^1$H NMR (400 MHz, CDCl$_3$) δ ppm 7.62 (1H, s), 7.24-7.32 (2H, m), 6.98-7.08 (2H, m), 6.84-6.92 (4H, m), 6.78 (1H, dd, J=5.9, 3.1 Hz), 5.09 (2H, s), 3.79 (3H, s), 2.80

(2H, dd, J=7.6, 4.5 Hz), 2.38 (1H, m), 1.25 (9H, s), 1.04 (1H, m), 0.60 (1H, m), 0.44 (1H, m), 0.30 (1H, m), 0.17 (1H, m).

Example 9

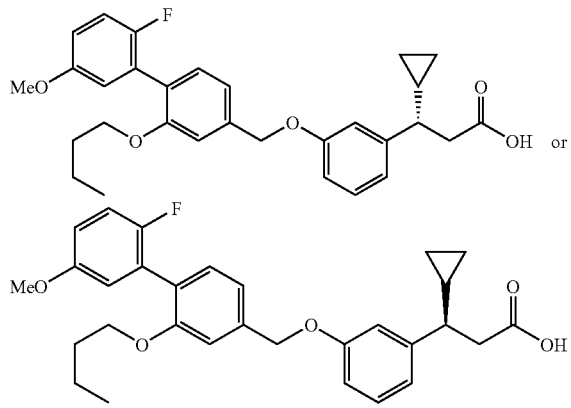

(3S)-3-(3-(((2-(Butyloxy)-2'-fluoro-5'-(methyloxy)-1,1'-biphenyl-4-yl)methyl)oxy)phenyl)-3-cyclopropylpropanoic acid or (3R)-3-(3-(((2-(butyloxy)-2'-fluoro-5'-(methyloxy)-1,1'-biphenyl-4-yl)methyl)oxy)phenyl)-3-cyclopropylpropanoic acid (9). Example 9 was synthesized analogous to the method for compound 7 from 8.4 and 5.4. MS ESI (neg.) m/e: 491.2 (M−H)$^+$. $^1$H NMR (400 MHz, CDCl$_3$) δ ppm 7.23-7.31 (2H, m), 7.01-7.09 (3H, m), 6.82-6.92 (5H, m), 5.08 (2H, s), 4.00 (2H, t, J=6.5 Hz), 3.81 (3H, s), 2.79 (2H, dd, J=7.2, 5.3 Hz), 2.35-2.41 (1H, m), 1.64-1.71 (2H, m), 1.34-1.43 (2H, m), 0.98-1.08 (1H, m), 0.90 (3H, t, J=7.2 Hz), 0.56-0.63 (1H, m), 0.45 (1H, m), 0.27-0.34 (1H, m), 0.14-0.20 (1H, m).

Example 10

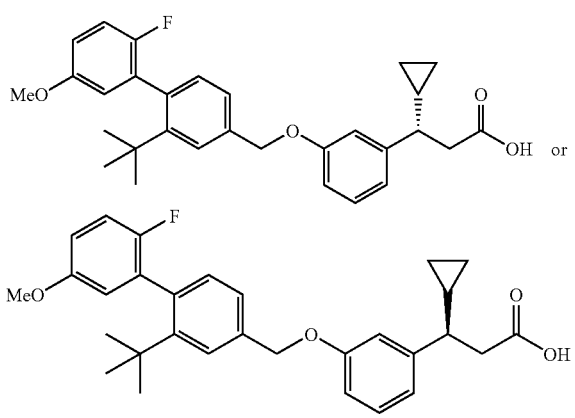

(3R)-3-Cyclopropyl-3-(3-(((2-(1,1-dimethylethyl)-2'-fluoro-5'-(methyloxy)-1,1'-biphenyl-4-yl)methyl)oxy)phenyl)propanoic acid or (3S)-3-cyclopropyl-3-(3-(((2-(1,1-dimethylethyl)-2'-fluoro-5'-(methyloxy)-1,1'-biphenyl-4-yl)methyl)oxy)phenyl)propanoic acid (10). Example 10 was synthesized from 8.5 and 8.10 using a method analogous to the method used to prepare compound 7. MS ESI (neg.) m/e: 475.2 (M−H)$^+$. $^1$H NMR (400 MHz, CDCl$_3$) δ ppm 7.61 (1H, m), 7.28 (2H, m), 7.03 (2H, m), 6.88 (4H, m), 6.77 (1H, m), 5.08 (2H, s), 3.79 (3H, s), 2.80 (2H, m), 2.38 (1H, m), 1.25 (9H, s), 1.04 (1H, m), 0.60 (1H, m), 0.45 (1H, m), 0.32 (1H, m), 0.18 (1H, m).

Example 11

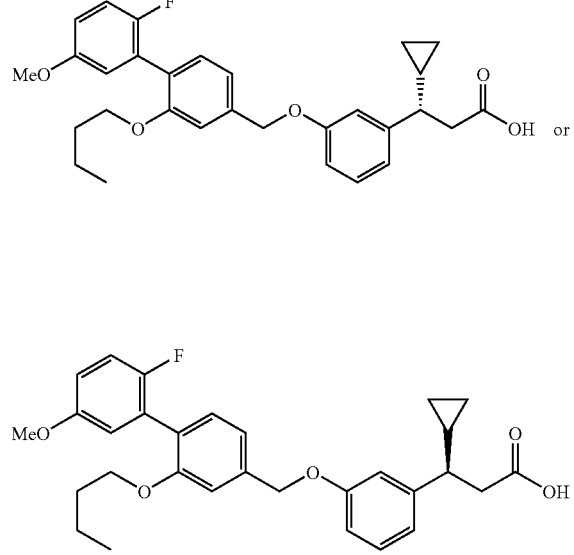

(3R)-3-(3-(((2-(Butyloxy)-2'-fluoro-5'-(methyloxy)-1,1'-biphenyl-4-yl)methyl)oxy)phenyl)-3-cyclopropylpropanoic acid or (3S)-3-(3-(((2-(butyloxy)-2'-fluoro-5'-(methyloxy)-1,1'-biphenyl-4-yl)methyl)oxy)phenyl)-3-cyclopropylpropanoic acid (11). Example 11 was synthesized from 8.5 and 5.4 using a method analogous to the method used to prepare compound 7. MS ESI (neg.) m/e: 491.2 (M−H)$^+$. $^1$H NMR (400 MHz, CDCl$_3$) δ ppm 7.23-7.31 (2H, m), 7.01-7.09 (3H, m), 6.82-6.92 (5H, m), 5.08 (2H, s), 4.00 (2H, t, J=6.5 Hz), 3.81 (3H, s), 2.79 (2H, dd, J=7.2, 5.3 Hz), 2.35-2.41 (1H, m), 1.64-1.71 (2H, m), 1.34-1.43 (2H, m), 0.98-1.08 (1H, m), 0.90 (3H, t, J=7.2 Hz), 0.56-0.63 (1H, m), 0.45 (1H, m), 0.27-0.34 (1H, m), 0.14-0.20 (1H, m).

Example 12

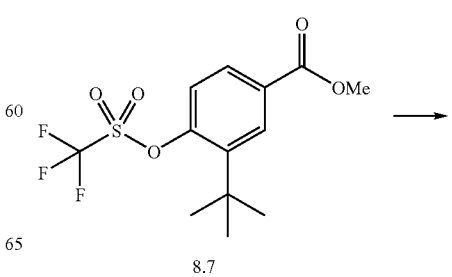

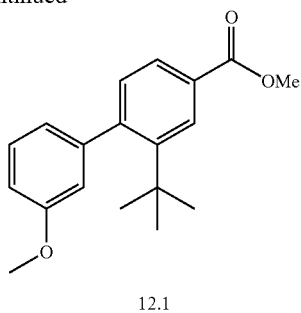

12.1

Methyl 2-(1,1-dimethylethyl)-3'-(methyloxy)-1,1'-biphenyl-4-carboxylate (12.1). A dry round bottom flask containing 8.7 (1.40 g, 4.1 mmol), 3-methoxyphenylboronic acid (available from Aldrich) (1.27 g, 8.34 mmol), tetrakis(triphenylphosphine)palladium (0.49 g, 0.42 mmol), and potassium carbonate (1.71 g, 12.36 mmol) was evacuated and backfilled three times with argon. Dry DMF (12.0 mL) was added via syringe under argon, and the mixture was then heated to 100° C. and monitored by TLC. After 2 hours, the reaction was cooled to room temperature and diluted with water. The mixture was extracted three times with EtOAc and then concentrated under reduced pressure. The residue was then purified by flash chromatography (SiO$_2$ gel 60, eluted with 0%-15% EtOAc in hexanes). Fractions containing the desired product were combined and concentrated to provide 12.1 as a colorless oil (1.01, 82%). MS ESI (pos.) m/e: 299.2 (M+H)$^+$.

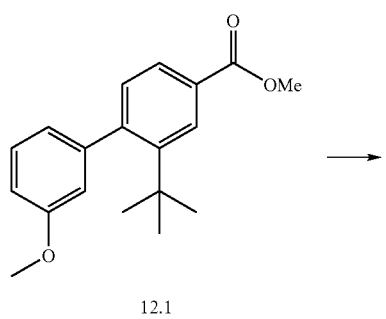

(2-(1,1-Dimethylethyl)-3'-(methyloxy)-1,1'-biphenyl-4-yl)methanol (12.2). To a cooled solution of 12.1 (1.01 g, 3.38 mmol) in dry THF (10.0 mL) at 0° C., was added LAH (1.0 M solution in THF (6.7 mL, 6.7 mmol)). Upon complete addition, the reaction was allowed to warm to room temperature and monitored by TLC and LCMS. Upon completion, 1N NaOH (5 mL) was carefully added to quench the reaction. The resulting solution was extracted with EtOAc (3×10 mL), dried over MgSO$_4$, filtered and concentrated in vacuo. The residue was then purified by flash chromatography (SiO$_2$ gel 60, eluted with 0%-40% EtOAc in hexanes). Fractions containing the desired product were combined and concentrated to provide 12.2 as a colorless oil (0.82, 90%). $^1$H NMR (500 MHz, CDCl$_3$) δ ppm 7.56 (1H, s), 7.29 (1H, t, J=3.8 Hz), 7.24 (1H, m), 7.07 (1H, d, J=7.6 Hz), 6.93 (2H, m), 6.86 (1H, d, J=1.5 Hz), 4.77 (2H, s), 3.85 (3H, s), 1.72 (1H, s), 1.26 (9H, s).

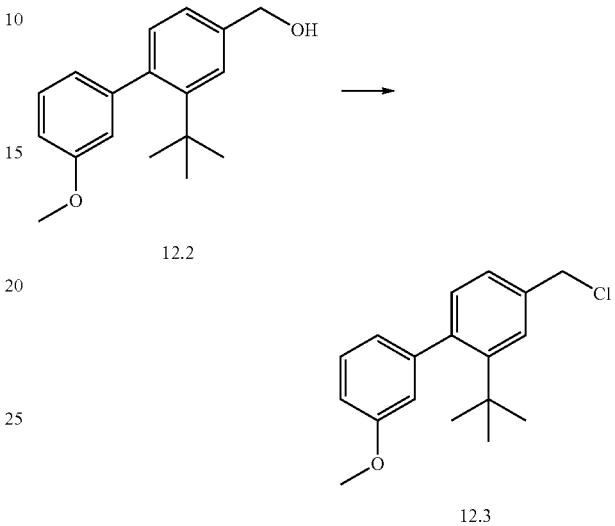

4-(Chloromethyl)-2-(1,1-dimethylethyl)-3'-(methyloxy)-1,1'-biphenyl (12.3). A dry, round bottom flask containing 12.2 (0.82 g, 3.04 mmol) and DCM (8.5 mL) was cooled to 0° C. After 15 minutes, thionyl chloride (1.50 mL, 20.56 mmol) was carefully added dropwise at 0° C. Upon complete addition of thionyl chloride, the mixture was allowed to warm to room temperature and stirred overnight. After 25 hours, the reaction was concentrated under reduced pressure. The residue was then purified by flash chromatography (SiO$_2$ gel 60, eluted with 0%-15% EtOAc in hexanes). Fractions containing the desired product were combined and concentrated to provide 12.3 as a colorless oil (0.82, 93%). $^1$H NMR (500 MHz, CDCl$_3$) δ ppm 7.53 (1H, d, J=1.7 Hz), 7.28 (3H, m), 7.03 (1H, d, J=7.8 Hz), 6.90 (3H, m), 4.65 (2H, s), 3.82 (3H, s), 1.23 (9H, s).

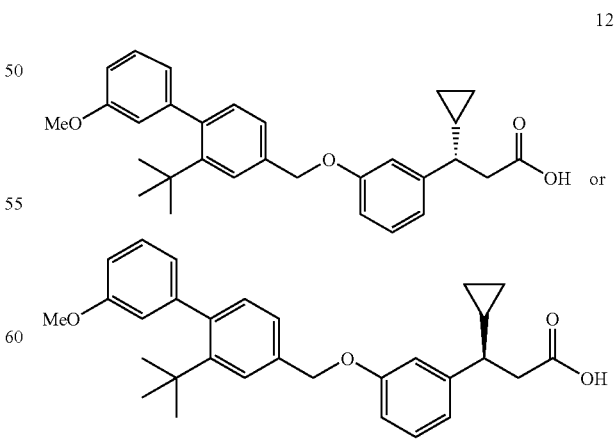

12

(3S)-3-Cyclopropyl-3-(3-(((2-(1,1-dimethylethyl)-3'-(methyloxy)-1,1'-biphenyl-4-yl)methyl)oxy)phenyl)propanoic acid or (3R)-3-cyclopropyl-3-(3-(((2-(1,1-dimethylethyl)-3'-(methyloxy)-1,1'-biphenyl-4-yl)methyl)oxy)phenyl)propanoic acid (12). Compound 12 was synthesized from 8.4 and 12.3 by a method analogous to the method used to prepare compound 7. MS ESI (neg.) m/e: 457.1 (M–H)+. ¹H NMR (400 MHz, CDCl₃) δ ppm 7.58 (1H, d, J=1.6 Hz), 7.23-7.27 (3H, m), 7.05 (1H, d, J=7.6 Hz), 6.82-6.92 (6H, m), 5.07 (2H, s), 3.81 (3H, s), 2.79 (2H, dd, J=7.4, 4.1 Hz), 2.37 (1H, m), 1.22 (9H, s), 1.03 (1H, m), 0.59 (1H, m), 0.43 (1H, m), 0.30 (1H, m), 0.16 (1H, m).

Example 13

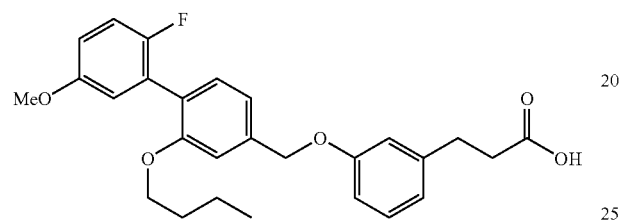

13

3-(3-(((2-(Butyloxy)-2'-fluoro-5'-(methyloxy)-1,1'-biphenyl-4-yl)methyl)oxy)phenyl)propanoic acid (13). Compound 13 was synthesized from methyl 3-(3-hydroxyphenyl)propanoate (available from Aagile Labs Division of Tyger Scientific) and 5.4 by a method analogous to the method used to prepare compound 7. ESI (neg.) m/e: 451.1 (M–H)+. ¹H NMR (400 MHz, CDCl₃) δ ppm 7.22-7.32 (2H, m), 7.01-7.09 (3H, m), 6.82-6.91 (5H, m), 5.08 (2H, s), 4.00 (2H, t, J=6.5 Hz), 3.81 (3H, s), 2.97 (2H, t, J=7.8 Hz), 2.71 (2H, t, J=7.8 Hz), 1.64-1.72 (2H, m), 1.34-1.43 (2H, m), 0.90 (3H, t, J=7.3 Hz).

Example 14

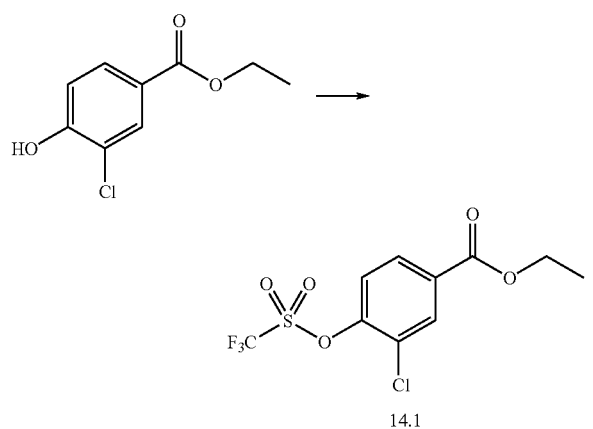

Ethyl 3-chloro-4-(((trifluoromethyl)sulfonyl)oxy)benzoate (14.1) A mixture of ethyl 3-chloro-4-hydroxybenzoate (available from Aldrich) (5.00 g, 25.0 mmol), N-phenyltriflimide (9.30 g, 26.0 mmol) and TEA (4.2 mL, 30.0 mmol) in DCM (40 mL) with a catalytic amount of DMAP, was stirred at ambient temperature overnight. DCM (150 mL) was added, and the reaction mixture was washed with brine (30×3 mL), dried over MgSO₄, and the solvent was removed under reduced pressure. The product 14.1 was used in the next step without further purification. MS ESI (pos.) m/e: 335.0 (M+Na)+.

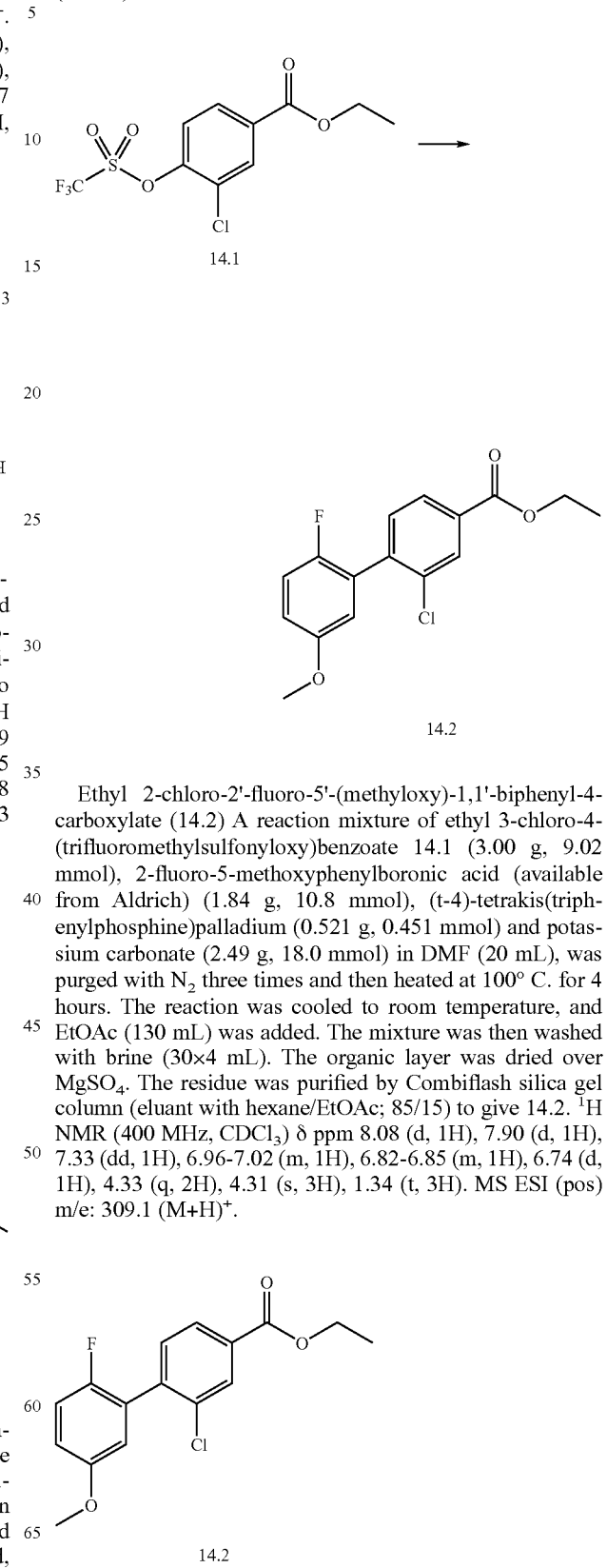

Ethyl 2-chloro-2'-fluoro-5'-(methyloxy)-1,1'-biphenyl-4-carboxylate (14.2) A reaction mixture of ethyl 3-chloro-4-(trifluoromethylsulfonyloxy)benzoate 14.1 (3.00 g, 9.02 mmol), 2-fluoro-5-methoxyphenylboronic acid (available from Aldrich) (1.84 g, 10.8 mmol), (t-4)-tetrakis(triphenylphosphine)palladium (0.521 g, 0.451 mmol) and potassium carbonate (2.49 g, 18.0 mmol) in DMF (20 mL), was purged with N₂ three times and then heated at 100° C. for 4 hours. The reaction was cooled to room temperature, and EtOAc (130 mL) was added. The mixture was then washed with brine (30×4 mL). The organic layer was dried over MgSO₄. The residue was purified by Combiflash silica gel column (eluant with hexane/EtOAc; 85/15) to give 14.2. ¹H NMR (400 MHz, CDCl₃) δ ppm 8.08 (d, 1H), 7.90 (d, 1H), 7.33 (dd, 1H), 6.96-7.02 (m, 1H), 6.82-6.85 (m, 1H), 6.74 (d, 1H), 4.33 (q, 2H), 4.31 (s, 3H), 1.34 (t, 3H). MS ESI (pos) m/e: 309.1 (M+H)+.

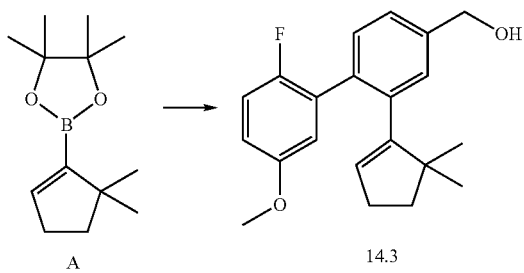
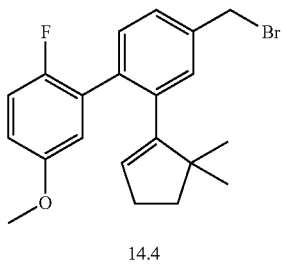

(2-(5,5-Dimethyl-1-cyclopenten-1-yl)-2'-fluoro-5'-(methyloxy)-1,1'-biphenyl-4-yl)methanol (14.3) A reaction mixture of compound 14.2 (1.80 g, 5.80 mmol), 2-(5,5-dimethylcyclopent-1-enyl)-4,4,5,5-tetramethyl-1,3,2-dioxaborolane A (1.40 g, 6.4 mmol), S-Phos (0.48 g, 1.20 mmol), tripotassium phosphate (3.10 g, 15.0 mmol) and palladium acetate (0.13 g, 0.58 mmol) in DMF (10.0 mL) and water (1.0 mL), was purged with N₂ three times. The resulting mixture was heated at 100° C. overnight. EtOAc (120 mL) was added, and the mixture was washed with brine (25×2 mL). The organic layer was dried with MgSO4. The residue was purified by Combiflash silica gel, eluant with hexane/EtOAc, 9/1 to give Suzuki coupling product as an intermediate, ethyl 2-(5,5-dimethyl-1-cyclopenten-1-yl)-2'-fluoro-5'-(methyloxy)-1,1'-biphenyl-4-carboxylate. MS ESI (pos.) m/e: 369.1 (M+H)⁺. To a solution of ethyl 2-(5,5-dimethyl-1-cyclopenten-1-yl)-2'-fluoro-5'-(methyloxy)-1,1'-biphenyl-4-carboxylate (1.00 g, 3.0 mmol) in THF (10.0 mL), was slowly added LAH, (1.0M solution in diethyl ether, 4.0 mL, 4.0 mmol) at 0° C. After the addition, the reaction mixture was stirred at 40° C. for 1.5 hours, and then at room temperature for 2 hours. A mixture of water (0.22 mL) in THF (2.0 mL) was slowly added and then 15% sodium hydroxide (0.22 mL) was added at 0° C. Finally, water (0.65 mL) was added at room temperature. The solid was removed by filtration, and the solvent was removed under reduced pressure. The residue was purified by Combiflash (silica gel column, eluant with hexane/EtOAc, 90/10 to 70/30) to give the title compound 14.3. ¹H NMR (400 MHz, CDCl₃) δ ppm. 7.24 (s, 2H), 7.09-7.21 (m, 1H), 6.84-6.96 (m, 1H), 6.68-6.72 (m, 2H), 5.43 (s, 1H), 4.65 (s, 2H), 3.66 (s, 3H), 2.17 (td, 2H), 1.77 (b, 1H), 1.58 (t, 2H), 0.78 (s, 6H). MS ESI (pos.) m/e: 309.1 (M–HO)⁺, 345.2 (M+H₃O)⁺.

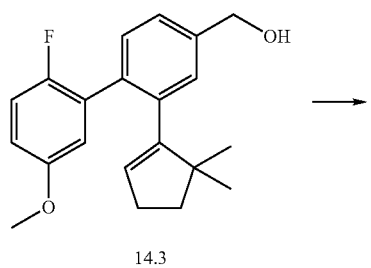

4-(Bromomethyl)-2-(5,5-dimethyl-1-cyclopenten-1-yl)-2'-fluoro-5'-1,1'-biphenyl (14.4) To a solution of triphenylphosphine (0.13 g, 0.51 mmol) in DCM (1.0 mL), was slowly added bromine (0.081 g, 0.51 mmol, 0.25 mL, 2M in CCl₄) at 0° C. The resulting mixture was stirred at 0° C. for 15 minutes and then a mixture of compound 14.3 (0.15 g, 0.46 mmol) and anhydrous pyridine (0.041 mL, 0.51 mmol) in DCM (3.0 mL) was added to the mixture. The reaction mixture was stirred at room temperature for 2 hours. DCM (80 mL) was added, and the mixture was washed with water (20×2 mL), and dried over Na₂SO₄. The solvent was removed under reduced pressure. The crude product 14.4 was used in the next step without further purification. ¹H NMR (400 MHz, CDCl₃) δ ppm. 7.16-7.29 (m, 3H), 6.88 (t, 1H), 6.72 (m, 2H), 5.45 (s, 1H), 4.46 (s, 2H), 3.68 (s, 3H), 2.16-2.19 (m, 2H), 1.59 (t, 2H), 0.78 (s, 6H).

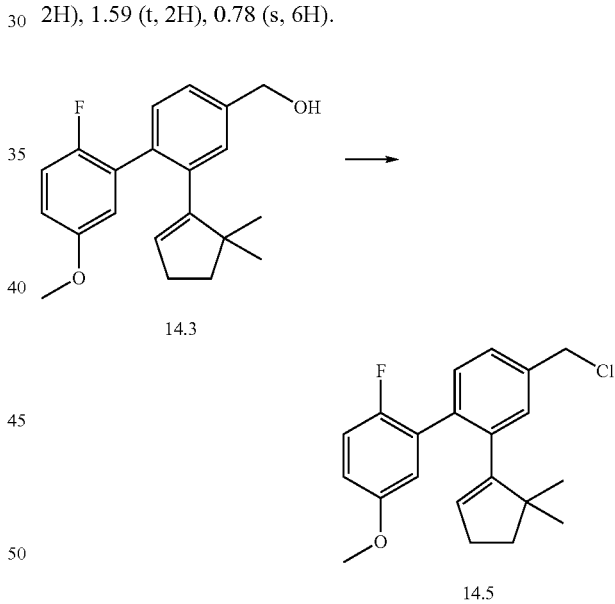

4-(Chloromethyl)-2-(5,5-dimethyl-1-cyclopenten-1-yl)-2'-fluoro-5'-(methyloxy)-1,1'-biphenyl (14.5) To a solution of compound 14.3 (1.10 g, 3.37 mmol) and a catalytic amount of DMF (0.10 mL) in DCM (12.0 mL), was slowly added thionyl chloride (0.802 g, 6.74 mmol) at 0° C. After addition, the reaction mixture was stirred at room temperature for 1 hour. The solvent was removed under reduced pressure, and the resulting residue was purified by Combiflash (silica gel column eluted with hexane/EtOAc, 100/0 to 95/5) to give the title compound 14.5 (1.15 g). ¹H NMR (400 MHz, CDCl₃) δ ppm. 7.32-7.39 (m, 2H), 7.28-7.29 (m. 1H), 6.88 (t, 1H), 6.80-6.82 (m, 2H), 5.56 (s, 1H), 4.66 (s, 2H), 3.78 (s, 3H), 2.27-2.29 (m, 2H), 1.69 (t, 2H), 0.89 (s, 6H).

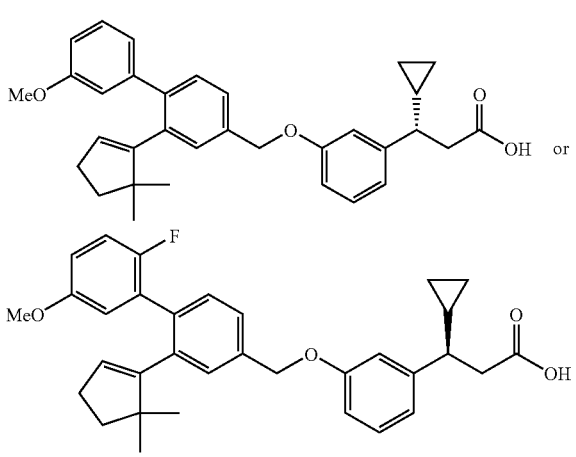

(3S)-3-Cyclopropyl-3-(3-(((2-(5,5-dimethyl-1-cyclopenten-1-yl)-2'-fluoro-5'-(methyloxy)-1,1'-biphenyl-4-yl)methyl)oxy)phenyl)propanoic acid or (3R)-3-cyclopropyl-3-(3-(((2-(5,5-dimethyl-1-cyclopenten-1-yl)-2'-fluoro-5'-(methyloxy)-1,1'-biphenyl-4-yl)methyl)oxy)phenyl)propanoic acid (14). Compound 14 was synthesized from 8.4 and 14.5 by a method analogous to that used to prepare compound 7. ESI (neg.) m/e: 513.3 (M–H)⁺. ¹H NMR (400 MHz, CDCl₃) δ ppm 7.39-7.42 (1H, m), 7.30-7.36 (2H, m), 7.23-7.28 (2H, m), 6.97 (1H, m), 6.84-6.91 (3H, m), 6.80 (2H, ddd, J=6.1, 2.5, 2.3 Hz), 5.53 (1H, s), 5.10 (2H, s), 3.75-3.81 (3H, m), 2.79 (2H, dd, J=7.2, 4.5 Hz), 2.38 (1H, m), 2.25 (2H, m), 1.66 (2H, t, J=7.0 Hz), 0.97-1.07 (1H, m), 0.86 (6H, s), 0.56-0.63 (1H, m), 0.44 (1H, m), 0.27-0.33 (1H, m), 0.13-0.20 (1H, m).

Example 15

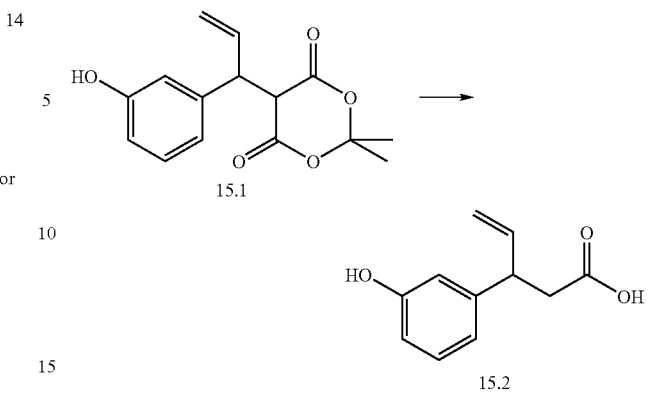

3-(3-Hydroxyphenyl)-4-pentenoic acid (15.2). 8.1 in DMF/water (10/1) (66 mL) was overnight heated at 90° C. The reaction was diluted with water and extracted with EtOAc. The organic layers were washed with brine, dried over Na₂SO₄, filtered, and concentrated to provide compound 15.2.

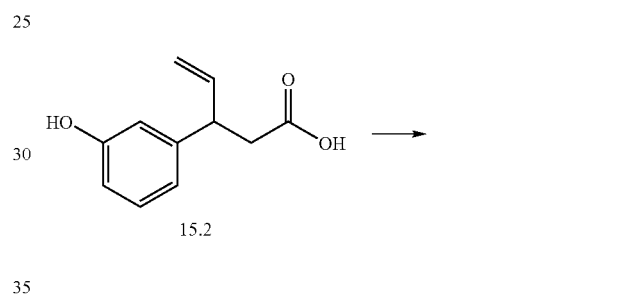

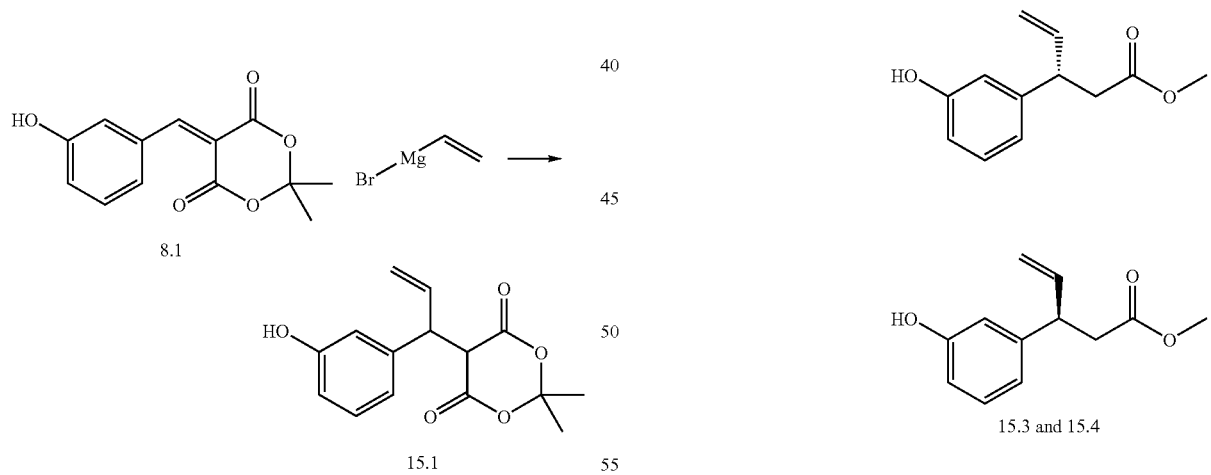

5-(1-(3-Hydroxyphenyl)-2-propenyl)-2,2-dimethyl-1,3-dioxane-4,6-dione (15.1). To a solution of 8.1 (6.0 g, 24.17 mmol) in THF, was added vinylmagnesium bromide (available from Aldrich) (207.2 mL, 145.0 mmol) via cannula at 0° C. The resulting heterogeneous mixture was warmed to room temperature, stirred for 30 minutes, and quenched with 1 N aq. HCl. The aqueous layer was extracted with EtOAc. The combined organic layers were washed with brine, dried over Na₂SO₄, filtered, and concentrated to provide 15.1 as a yellow oil which was used in the next step without further purification.

Methyl (3S)-3-(3-hydroxyphenyl)-4-pentenoate and methyl (3R)-3-(3-hydroxyphenyl)-4-pentenoate (15.3 and 15.4). To flask containing 15.2 in MeOH (50 mL), was added H₂SO₄ (0.0129 mL, 0.242 mmol). The resulting mixture was stirred at reflux overnight. The reaction was concentrated and then purified by combiflash (0 to 30% EtOAc/Hexanes). The enantiomers were resolved by chiral HPLC (Chiralcel OD-H column, 3% IPA/hexane, 220 nm wavelength used to observe the compound peaks) to afford 15.3 (0.400 g, 16.0% yield from 8.1) (28 minutes) and 15.4 (0.400 g, 16.0% yield from 8.1) (45 minutes).

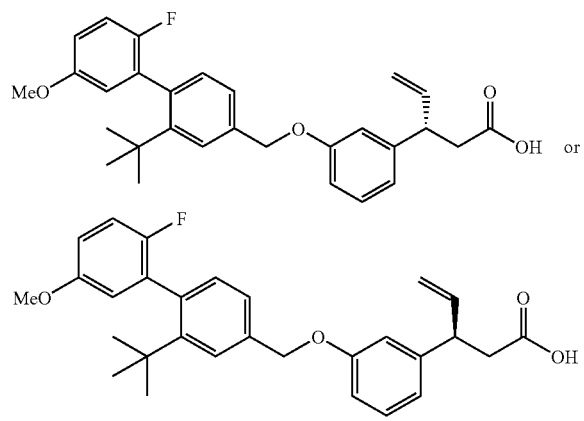

(3S)-3-(3-(((2-(1,1-Dimethylethyl)-2'-fluoro-5'-(methyloxy)-1,1'-biphenyl-4-yl)methyl)oxy)phenyl)-4-pentenoic acid or (3R)-3-(3-(((2-(1,1-dimethylethyl)-2'-fluoro-5'-(methyloxy)-1,1'-biphenyl-4-yl)methyl)oxy)phenyl)-4-pentenoic acid (15). Compound 15 was synthesized from 15.3 and 8.10 by a method analogous to that used to prepare compound 7. ESI (neg.) m/e: 461.2 (M−H)+. 1H NMR (500 MHz, CDCl3) δ ppm 7.61 (1H, s), 7.30 (1H, dd, J=7.7, 1.1 Hz), 7.27 (1H, m), 6.99-7.07 (2H, m), 6.85-6.92 (4H, m), 6.79 (1H, dd, J=5.9, 3.2 Hz), 5.98 (1H, m), 5.08-5.14 (4H, m), 3.87 (1H, m), 3.80 (3H, s), 2.79 (2H, t, J=7.5 Hz), 1.25 (9H, s).

Example 16

16

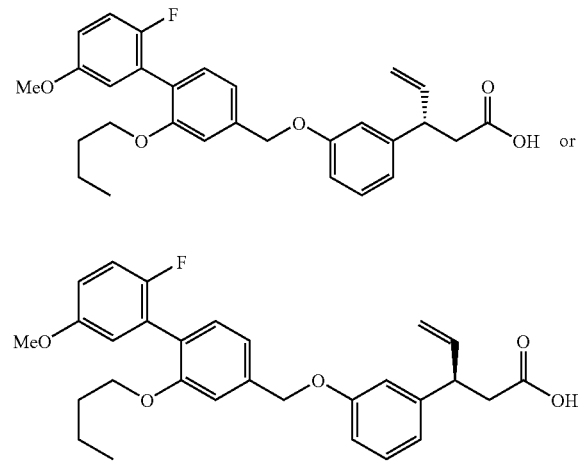

(3S)-3-(3-(((2-(Butyloxy)-2'-fluoro-5'-(methyloxy)-1,1'-biphenyl-4-yl)methyl)oxy)phenyl)-4-pentenoic acid or (3R)-3-(3-(((2-(butyloxy)-2'-fluoro-5'-(methyloxy)-1,1'-biphenyl-4-yl)methyl)oxy)phenyl)-4-pentenoic acid (16). Compound 16 was synthesized from 15.3 and 5.4 by a method analogous to that used to prepare compound 7. ESI (neg.) m/e: 477.2 (M−H)+. 1H NMR (500 MHz, CDCl3) δ ppm 7.24-7.31 (2H, m), 7.01-7.09 (3H, m), 6.83-6.90 (5H, m), 5.99 (1H, ddd, J=17.4, 10.1, 7.0 Hz), 5.07-5.14 (4H, m), 4.00 (2H, t, J=6.4 Hz), 3.83-3.89 (1H, m), 3.81 (3H, s), 2.74-2.84 (2H, m), 1.65-1.71 (2H, m), 1.35-1.42 (2H, m), 0.90 (3H, t, J=7.3 Hz).

Example 17

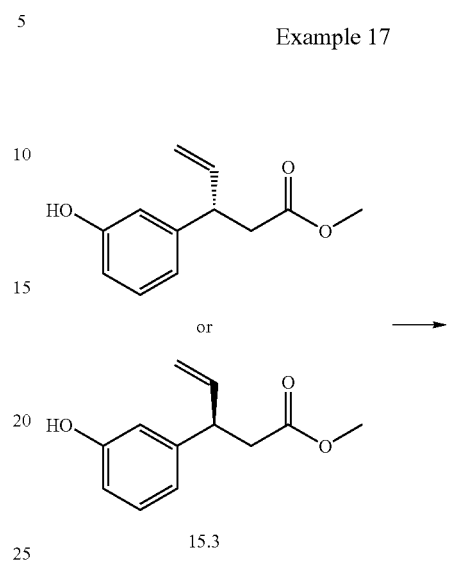

15.3 or 17.1

Methyl (3R)-3-(3-hydroxyphenyl)pentanoate or methyl (3S)-3-(3-hydroxyphenyl)pentanoate (17.1). A 50 mL flask containing a solution of 15.3 (100 mg, 485 μmol) in EtOAc (10 mL) was purged with N2. To the flask was added palladium, 10 wt. % (dry), on carbon powder, wet (103 mg, 97.0 μmol). The flask was then purged with H2, and the contents were stirred overnight under a H2 balloon. The black mixture was filtered through a pad of Celite and concentrated to afford a pink oil. The crude product was purified by combiflash (0 to 10% EtOAc/hexanes) yielding 17.1.

17

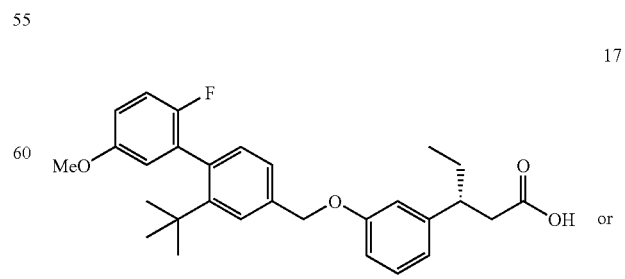

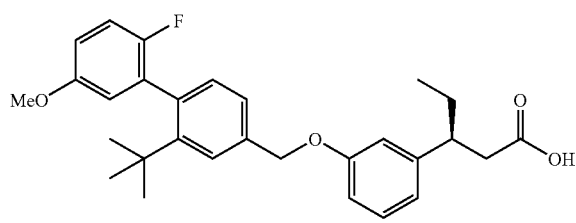

(3R)-3-(3-(((2-(1,1-Dimethylethyl)-2'-fluoro-5'-(methyloxy)-1,1'-biphenyl-4-yl)methyl)oxy)phenyl)pentanoic acid or (3S)-3-(3-(((2-(1,1-dimethylethyl)-2'-fluoro-5'-(methyloxy)-1,1'-biphenyl-4-yl)methyl)oxy)phenyl)pentanoic acid (17). Compound 17 was synthesized from 17.1 and 8.10 using a method analogous to that used to prepare compound 7. EI (neg.) m/e: 463.1 (M−H)+. $^1$H NMR (400 MHz, CDCl$_3$) δ ppm 7.62 (1H, d, J=1.6 Hz), 7.23-7.32 (3H, m), 7.03 (2H, m), 6.81-6.90 (4H, m), 6.78 (1H, dd, J=6.0, 3.2 Hz), 5.08 (2H, s), 3.79 (3H, s), 3.00 (1H, m), 2.65 (2H, dd, J=7.3, 4.6 Hz), 1.74 (1H, m), 1.62 (1H, m), 1.25 (9H, s), 0.81 (3H, t, J=7.3 Hz).

Example 18

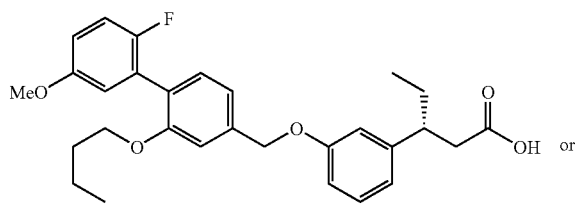

(3R)-3-(3-(((2-(Butyloxy)-2'-fluoro-5'-(methyloxy)-1,1'-biphenyl-4-yl)methyl)oxy)phenyl)pentanoic acid or (3S)-3-(3-(((2-(butyloxy)-2'-fluoro-5'-(methyloxy)-1,1'-biphenyl-4-yl)methyl)oxy)phenyl)pentanoic acid (18). Compound 18 was synthesized from 17.1 and 5.4 by a method analogous to that used to prepare compound 7. ESI (neg.) m/e: 479.2 (M−H)+. $^1$H NMR (400 MHz, CDCl$_3$) δ ppm 7.22-7.31 (3H, m), 7.01-7.09 (3H, m), 6.81-6.90 (5H, m), 5.08 (2H, s), 4.00 (2H, t, J=6.6 Hz), 3.81 (3H, s), 2.96-3.03 (1H, m), 2.65 (2H, dd, J=7.4, 5.7 Hz), 1.63-1.74 (3H, m), 1.34-1.43 (2H, m), 0.90 (3H, t, J=7.3 Hz), 0.81 (3H, t, J=7.3 Hz).

Example 19

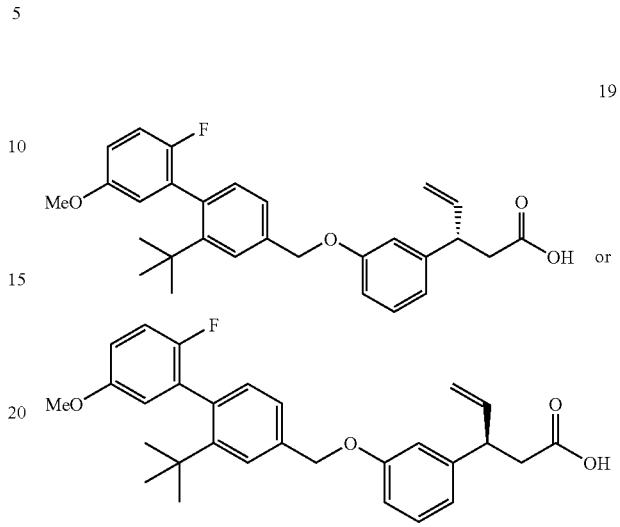

(3R)-3-(3-(((2-(1,1-Dimethylethyl)-2'-fluoro-5'-(methyloxy)-1,1'-biphenyl-4-yl)methyl)oxy)phenyl)-4-pentenoic acid or (3S)-3-(3-(((2-(1,1-dimethylethyl)-2'-fluoro-5'-(methyloxy)-1,1'-biphenyl-4-yl)methyl)oxy)phenyl)-4-pentenoic acid (19). Compound 19 was synthesized from 15.4 and 8.10 by a method analogous to that used to prepare compound 7. ESI (neg.) m/e: 460.7 (M−H)+. $^1$H NMR (500 MHz, CDCl$_3$) δ ppm 7.61 (1H, s), 7.30 (1H, dd, J=7.7, 1.1 Hz), 7.27 (1H, m), 6.99-7.07 (2H, m), 6.85-6.92 (4H, m), 6.79 (1H, dd, J=5.9, 3.2 Hz), 5.98 (1H, m), 5.08-5.14 (4H, m), 3.87 (1H, m), 3.80 (3H, s), 2.79 (2H, t, J=7.5 Hz), 1.25 (9H, s).

Example 20

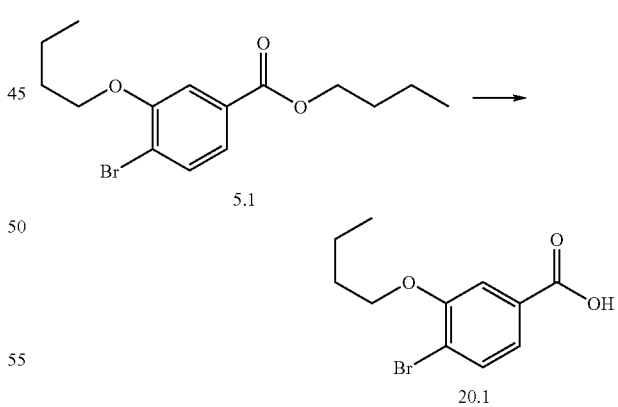

4-Bromo-3-(butyloxy)benzoic acid (20.1). To a solution of 5.1 (0.90 g, 2.7 mmol) in THF/MeOH (2/1) (18 mL), was added lithium hydroxide (6.0 mL, 6.0 mmol). The resulting mixture was stirred overnight at 23° C. and then quenched with excess 1N HCl. The mixture was then extracted with EtOAc. The combined organic layers were dried over Na$_2$SO$_4$ and concentrated. The crude residue was purified by combiflash (0 to 40% EtOAc/hexanes) to afford a 20.1 (0.68 g, 91% yield).

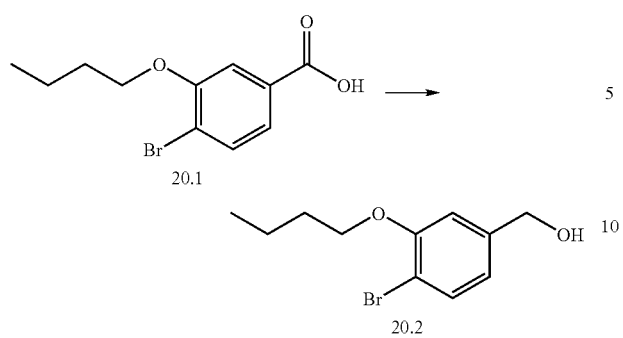

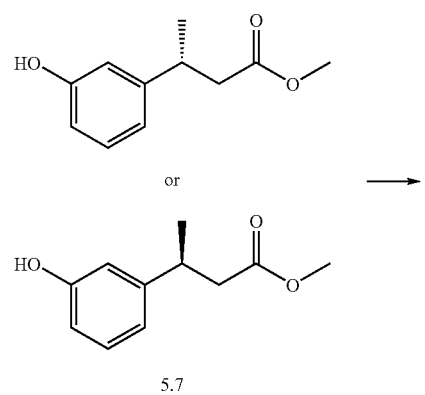

(4-Bromo-3-(butyloxy)phenyl)methanol (20.2). A solution of 20.1 (0.68 g, 2490 μmol) in THF (5 mL) was treated with borane THF complex (4979 μL, 4979 μmol) and stirred overnight at 65° C. The reaction mixture was quenched with MeOH, diluted with EtOAc, and washed with water and brine. The organic layer was dried over Na₂SO₄ and concentrated. The crude product was purified by combiflash (10 to 50% EtOAc/hexanes) yielding 20.2 (659.3 mg, 102% yield).

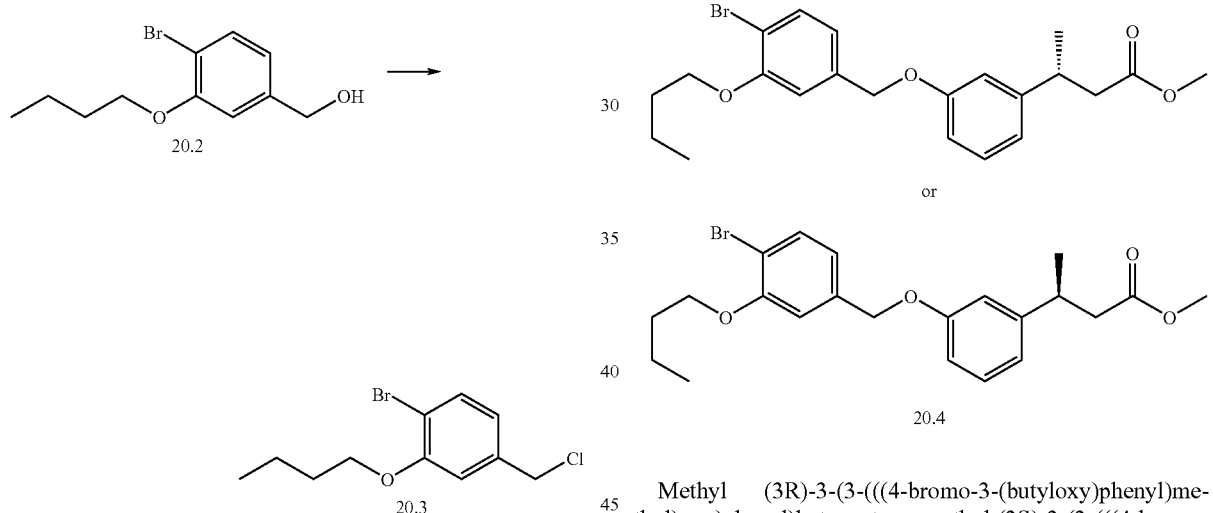

2-Bromo-5-(chloromethyl)phenyl butyl ether (20.3). To a stirred solution of 20.2 (659.3 mg, 2544 μmol) in DCM (15 mL) at 23° C., was added thionyl chloride (371 μL, 5088 μmol). The resulting mixture was stirred overnight. The reaction was concentrated and then purified by combiflash (0 to 10% EtOAc/Hexanes) to provide 20.3 (650 mg, 92.0% yield).

Methyl (3R)-3-(3-(((4-bromo-3-(butyloxy)phenyl)methyl)oxy)phenyl)butanoate or methyl (3S)-3-(3-(((4-bromo-3-(butyloxy)phenyl)methyl)oxy)phenyl)butanoate (20.4). To a flask containing 5.7 (125.0 g, 643.6 mmol) and cesium carbonate (272.6 g, 836.6 mmol) in DMF (1 mL), was added 20.3 (214.4 g, 772.3 mmol), and the resulting mixture was stirred overnight. The reaction was diluted with water and extracted with EtOAc. The organic layers were washed with brine, dried over Na₂SO₄, filtered, concentrated, and then purified by combiflash (0 to 20% EtOAc/Hexanes) to provide 20.4.

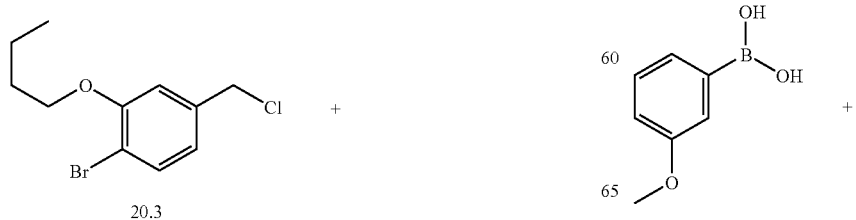

113

-continued

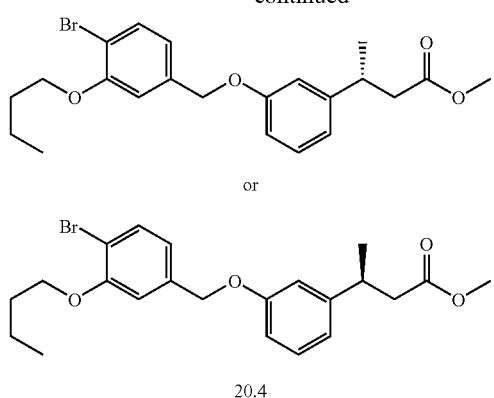

20.4

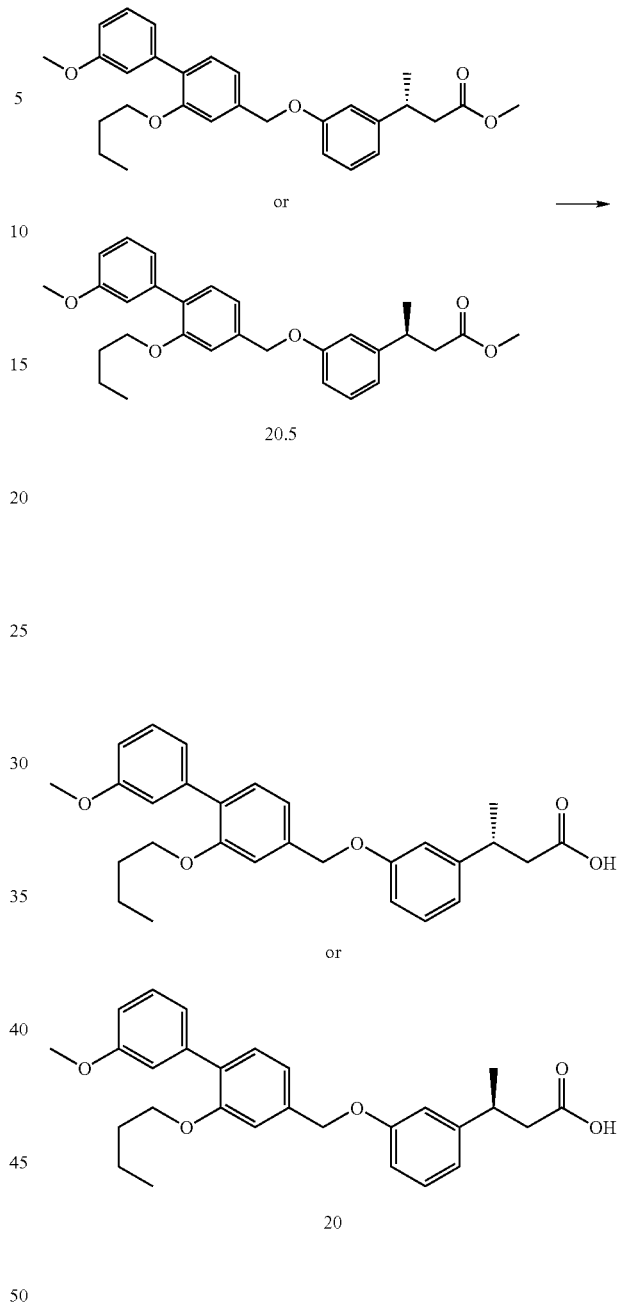

Methyl (3R)-3-(3-(((2-(butyloxy)-3'-(methyloxy)-1,1'-biphenyl-4-yl)methyl)oxy)phenyl)butanoate or methyl (3S)-3-(3-(((2-(butyloxy)-3'-(methyloxy)-1,1'-biphenyl-4-yl)methyl)oxy)phenyl)butanoate (20.5). To a 2 dram vial charged with 20.4 (25.0 mg, 57.4 µmol), tetrakis(triphenylphosphine) palladium (0) (13.3 mg, 11.5 µmol), cesium fluoride (10.6 µL, 287 µmol), and 3-methoxybenzeneboronic acid (available from Aldrich) (26.2 mg, 172 µmol), was added DME (1 mL). The resulting mixture was then heated at 85° C. overnight. The reaction was allowed to cool and then filtered and concentrated. The crude product was purified by combiflash (0 to 20% EtOAc/hexanes) yielding 20.5.

(3R)-3-(3-(((2-(Butyloxy)-3'-(methyloxy)-1,1'-biphenyl-4-yl)methyl)oxy)phenyl)butanoic acid or (3S)-3-(3-(((2-(butyloxy)-3'-(methyloxy)-1,1'-biphenyl-4-yl)methyl)oxy)phenyl)butanoic acid (20). To a solution of 20.5 (26.6 mg, 57.4 µmol) in THF/MeOH (2/1) (1.5 mL), was added lithium hydroxide (0.500 mL, 500 µmol). The resulting mixture was stirred overnight at 23° C., quenched with excess 1N HCl, and extracted with EtOAc. The combined organic layers were dried over $Na_2SO_4$ and concentrated. The crude residue was purified by combiflash (0 to 40% EtOAc/hexanes) to afford 20 (16.2 mg, 62.9% yield). ESI (neg.) m/e: 446.8 (M−H)+. $^1$H NMR (500 MHz, $CDCl_3$) δ ppm 7.34 (2H, m), 7.23-7.26 (1H, m), 7.13-7.15 (2H, m), 7.07-7.09 (2H, m), 6.89-6.91 (2H, m), 6.85-6.88 (2H, m), 5.07 (2H, s), 4.00 (2H, t, J=6.5 Hz), 3.85

(3H, s), 3.24-3.31 (1H, m), 2.67-2.72 (1H, m), 2.56-2.62 (1H, m), 1.70-1.76 (2H, m), 1.41-1.48 (2H, m), 1.34 (3H, d, J=7.1 Hz), 0.93 (3H, t, J=7.3 Hz).

Example 21

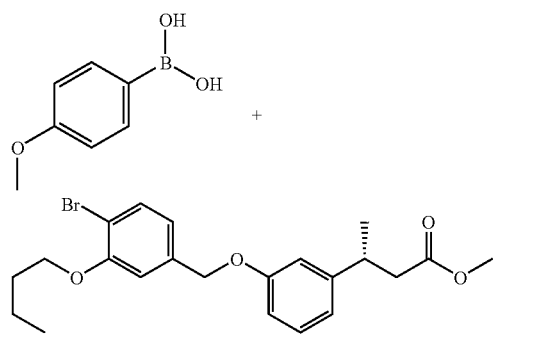

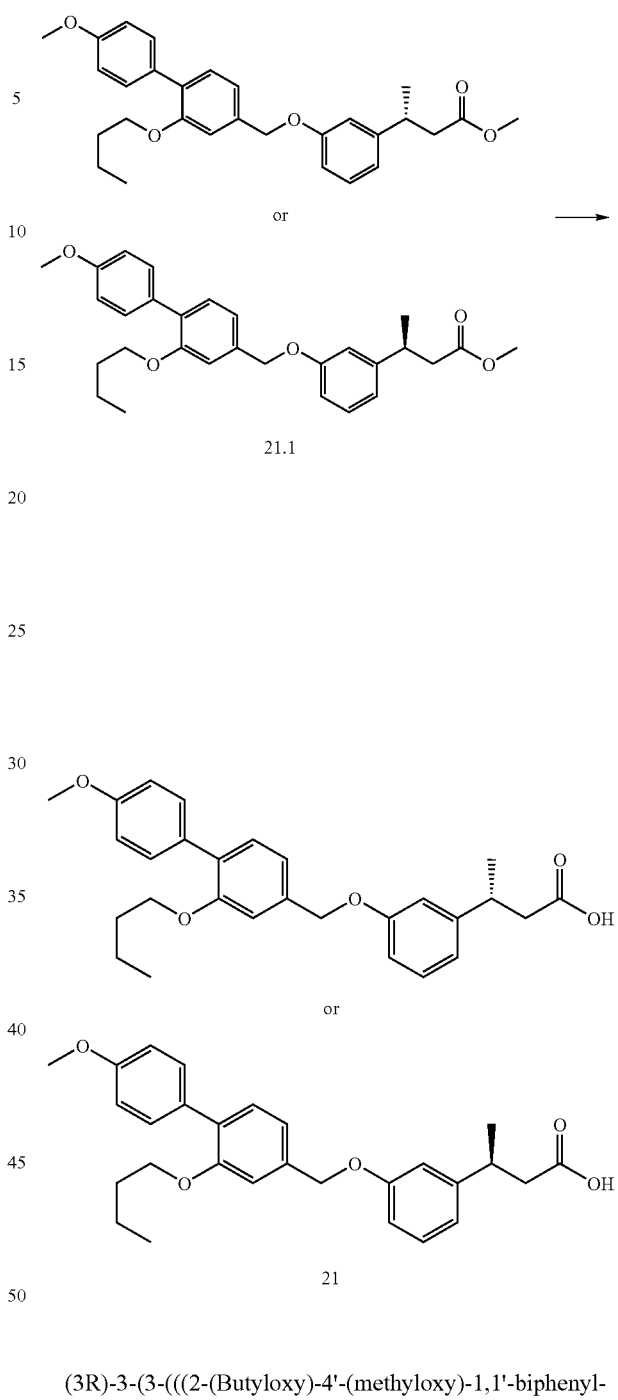

Methyl (3R)-3-(3-(((2-(butyloxy)-4'-(methyloxy)-1,1'-biphenyl-4-yl)methyl)oxy)phenyl)butanoate or methyl (3S)-3-(3-(((2-(butyloxy)-4'-(methyloxy)-1,1'-biphenyl-4-yl)methyl)oxy)phenyl)butanoate (21.1). To a 2 dram vial charged with 20.4 (25.0 mg, 57.4 μmol), tetrakis(triphenylphosphine) palladium(0) (13.3 mg, 11.5 μmol), cesium fluoride (10.6 μL, 287 μmol), and 4-methoxyphenylboronic acid (available from Aldrich) (26.2 mg, 172 μmol), was added DME (1 mL). The resulting mixture was then heated at 85° C. overnight. The reaction was allowed to cool and then filtered and concentrated. The crude product was purified by combiflash (0 to 20% EtOAc/hexanes) yielding 21.1.

(3R)-3-(3-(((2-(Butyloxy)-4'-(methyloxy)-1,1'-biphenyl-4-yl)methyl)oxy)phenyl)butanoic acid or (3S)-3-(3-(((2-(butyloxy)-4'-(methyloxy)-1,1'-biphenyl-4-yl)methyl)oxy)phenyl)butanoic acid (21). To a solution of 21.1 (26.6 mg, 57.4 μmol) in THF/MeOH (2/1) (1.5 mL) was added lithium hydroxide (0.500 mL, 500 μmol). The resulting mixture was stirred overnight at 23° C., quenched with excess 1N HCl, and extracted with EtOAc. The combined organic layers were dried over $Na_2SO_4$ and concentrated. The crude residue was purified by combiflash (5 to 25% EtOAc/hexanes) to afford 21 (19.3 mg, 75.0% yield). ESI (neg.) m/e: 446.8 (M−H)+. $^1$H NMR (400 MHz, $CDCl_3$) δ ppm 7.49-7.53 (2H, m), 7.33 (1H, d, J=8.2 Hz), 7.23-7.26 (1H, m), 7.05-7.08 (2H, m), 6.85-6.98 (5H, m), 5.06 (2H, s), 4.00 (2H, t, J=6.5 Hz), 3.86 (3H, s), 3.23-3.32 (1H, m), 2.68 (1H, m), 2.55-2.62 (1H, m), 1.69-1.76 (2H, m), 1.40-1.49 (2H, m), 1.34 (3H, d, J=7.0 Hz), 0.94 (3H, t, J=7.3 Hz).

Example 22

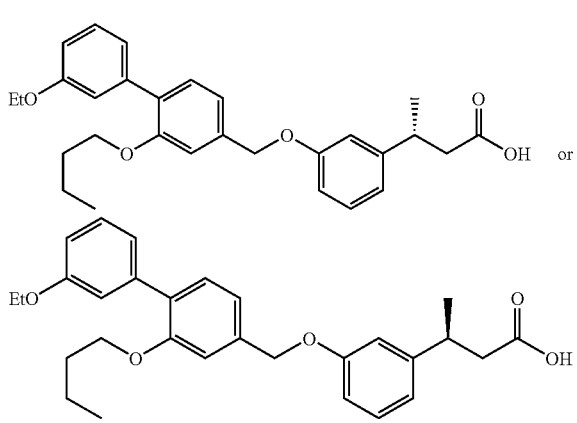

22

(3R)-3-(3-(((2-(Butyloxy)-3'-(ethyloxy)-1,1'-biphenyl-4-yl)methyl)oxy)phenyl)butanoic acid or (3S)-3-(3-(((2-(butyloxy)-3'-(ethyloxy)-1,1'-biphenyl-4-yl)methyl)oxy)phenyl)butanoic acid (22). Compound 22 was synthesized from 20.4 by a method analogous to that used to prepare compound 21. 3-Ethoxyphenylboronic acid is available from Aldrich. ESI (neg.) m/e: 460.7 (M−H)+. 1H NMR (400 MHz, CDCl3) δ ppm 7.36-7.39 (1H, m), 7.25-7.34 (2H, m), 7.08-7.16 (4H, m), 6.87-6.93 (4H, m), 5.09 (2H, s), 4.10 (2H, q, J=7.0 Hz), 4.01 (2H, t, J=6.5 Hz), 3.25-3.33 (1H, m), 2.68-2.74 (1H, m), 2.57-2.64 (1H, m), 1.70-1.78 (2H, m), 1.41-1.50 (5H, m), 1.35 (3H, d, J=6.8 Hz), 0.94 (3H, t, J=7.4 Hz).

Example 23

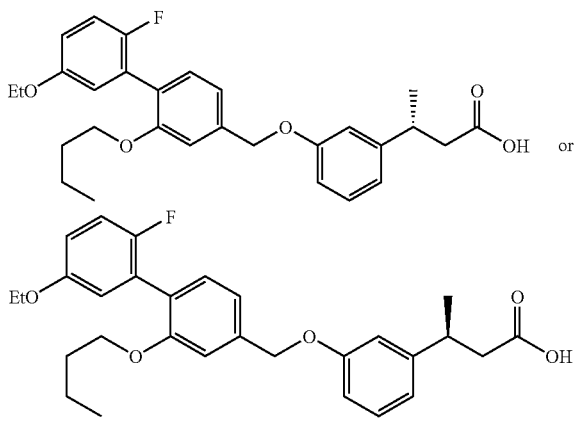

(3R)-3-(3-(((2-(Butyloxy)-5'-(ethyloxy)-2'-fluoro-1,1'-biphenyl-4-yl)methyl)oxy)phenyl)butanoic acid or (3S)-3-(3-(((2-(butyloxy)-5'-(ethyloxy)-2'-fluoro-1,1'-biphenyl-4-yl)methyl)oxy)phenyl)butanoic acid (23). Compound 23 was synthesized from 20.4 by a method analogous to that used to prepare compound 21. ESI (neg.) m/e: 478.7 (M−H)+. 1H NMR (500 MHz, CDCl3) δ ppm 7.23-7.31 (3H, m), 7.00-7.09 (3H, m), 6.82-6.91 (5H, m), 5.08 (2H, s), 3.98-4.05 (4H, m), 3.24-3.31 (1H, m), 2.66-2.72 (1H, m), 2.56-2.62 (1H, m), 1.65-1.70 (2H, m), 1.36-1.43 (5H, m), 1.34 (3H, d, J=6.8 Hz), 0.87-0.92 (3H, m).

Example 24

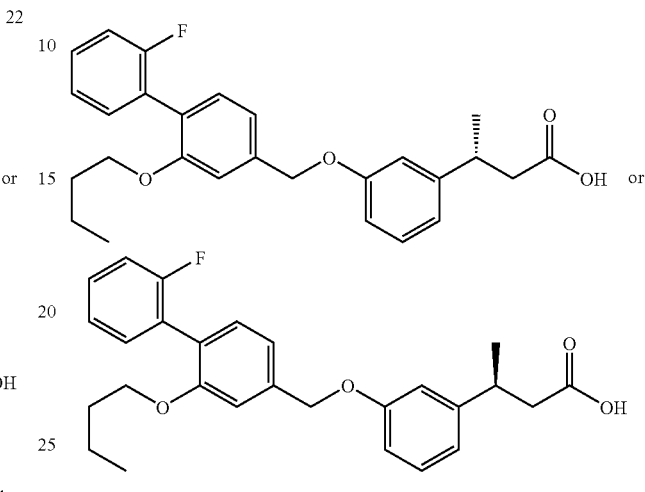

24

(3R)-3-(3-(((2-(Butyloxy)-2'-fluoro-1,1'-biphenyl-4-yl)methyl)oxy)phenyl)butanoic acid or (3S)-3-(3-(((2-(butyloxy)-2'-fluoro-1,1'-biphenyl-4-yl)methyl)oxy)phenyl)butanoic acid (24). Compound 24 was synthesized from 20.4 by a method analogous to that used to prepare compound 21. 2-Fluorophenylboronic acid is available from Aldrich. ESI (neg.) m/e: 434.8 (M−H)+. 1H NMR (500 MHz, CDCl3) δ ppm 7.29-7.38 (3H, m), 7.24-7.27 (2H, m), 7.18 (1H, td, J=7.5, 1.1 Hz), 7.07-7.14 (3H, m), 6.89 (2H, m), 6.87 (1H, m), 5.08 (2H, s), 4.00 (2H, t, J=6.4 Hz), 3.24-3.32 (1H, m), 2.66-2.72 (1H, m), 2.55-2.62 (1H, m), 1.63-1.69 (2H, m), 1.32-1.40 (5H, m), 0.89 (3H, t, J=7.3 Hz).

Example 25

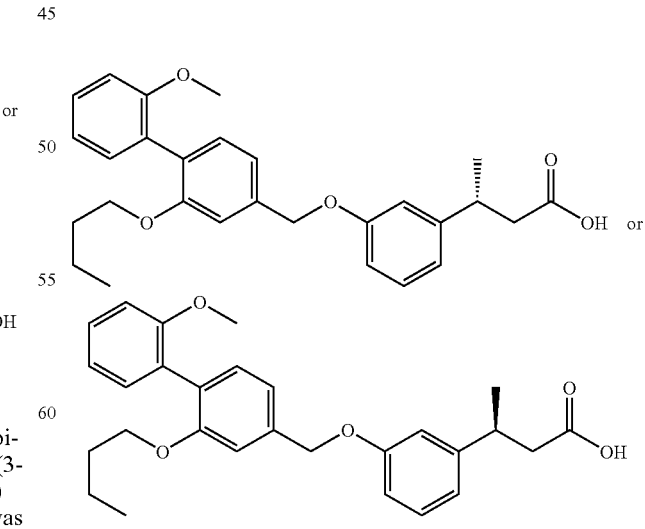

25

(3R)-3-(3-(((2-(Butyloxy)-2'-(methyloxy)-1,1'-biphenyl-4-yl)methyl)oxy)phenyl)butanoic acid or (3S)-3-(3-(((2-(butyloxy)-2'-(methyloxy)-1,1'-biphenyl-4-yl)methyl)oxy)phenyl)butanoic acid (25). Compound 25 was synthesized from 20.4 by a method analogous to that used to prepare compound 21. 2-Methoxyphenylboronic acid is available from Aldrich. ESI (neg.) m/e: 446.8 (M–H)+.

Example 26

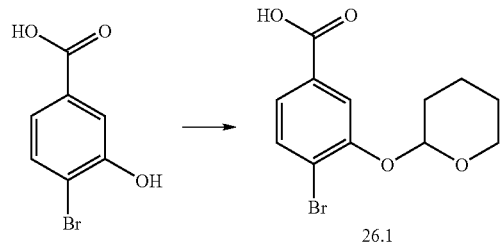

4-Bromo-3-(tetrahydro-2H-pyran-2-yloxy)benzoic acid 4-bromo-3-(tetrahydro-2H-pyran-2-yloxy)benzoic acid (26.1). To solution of 4-bromo-3-hydroxybenzoic acid (available from Combi-Blocks Inc.) (2.50 g, 11.5 mmol) in DCM (100 mL) at 23° C., was added 3,4-dihydro-2H-pyran (available from Aldrich) (2.10 mL, 23.0 mmol) followed by PPTS (0.289 g, 1.15 mmol). The reaction gave a mixture of bis THP protected compound and 26.1.

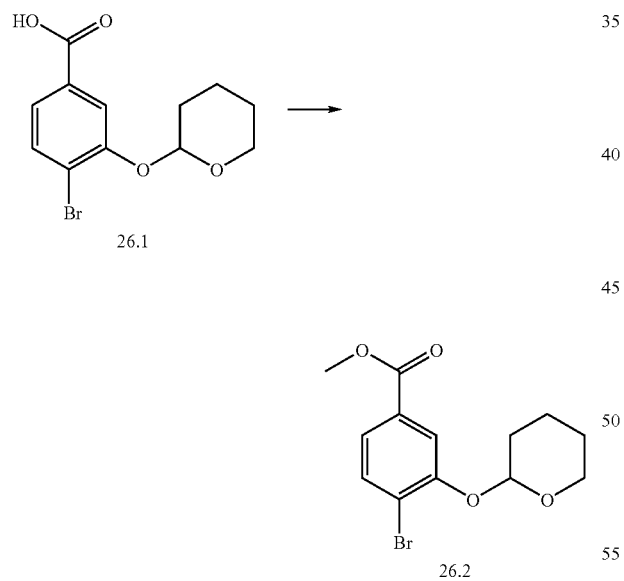

Methyl 4-bromo-3-(tetrahydro-2H-pyran-2-yloxy)benzoate (26.2). To flask containing 26.1 (2.15 g, 7.14 mmol) and cesium carbonate (3.95 g, 12.1 mmol) in acetone (50 mL), was added iodomethane (0.667 mL, 10.7 mmol). The resulting mixture was stirred overnight. The reaction was diluted with water and extracted with EtOAc. The organic layers were washed with brine, dried over $Na_2SO_4$, filtered, concentrated, and then purified by combiflash (0 to 20% EtOAc/Hexanes) to provide methyl 26.2 (2.25 g, 99% yield).

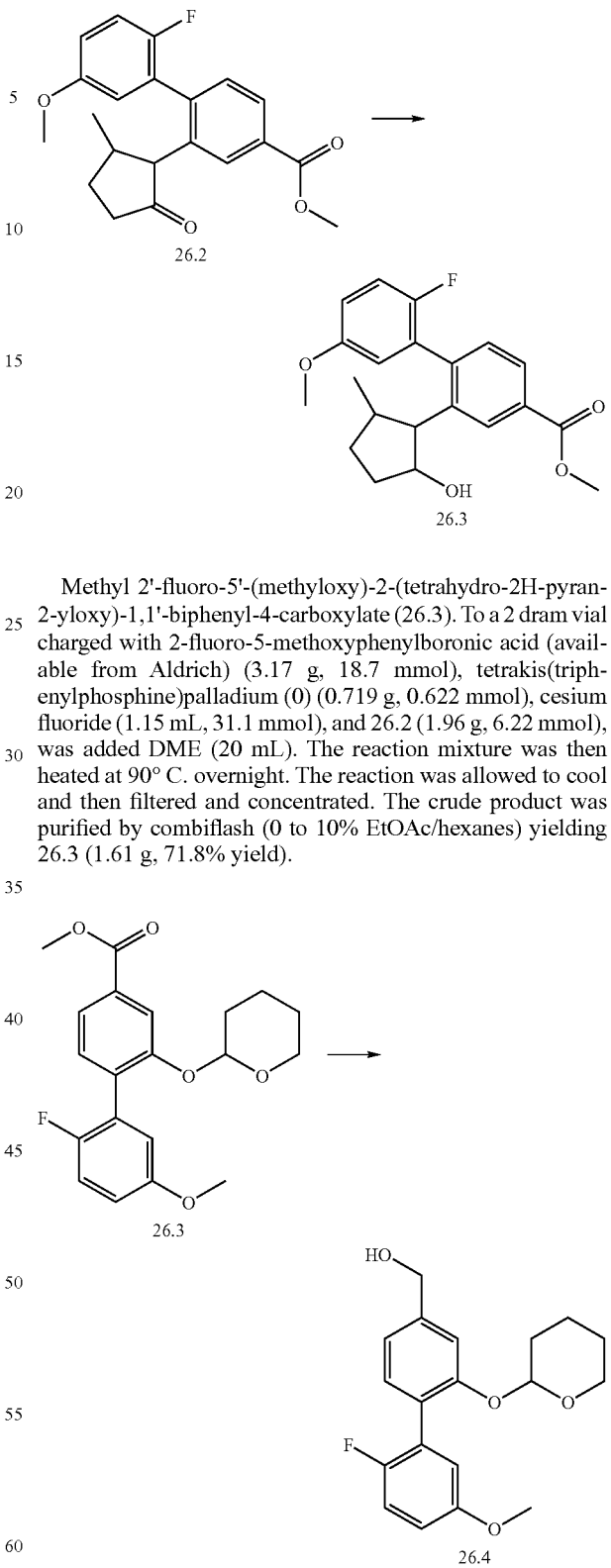

Methyl 2'-fluoro-5'-(methyloxy)-2-(tetrahydro-2H-pyran-2-yloxy)-1,1'-biphenyl-4-carboxylate (26.3). To a 2 dram vial charged with 2-fluoro-5-methoxyphenylboronic acid (available from Aldrich) (3.17 g, 18.7 mmol), tetrakis(triphenylphosphine)palladium (0) (0.719 g, 0.622 mmol), cesium fluoride (1.15 mL, 31.1 mmol), and 26.2 (1.96 g, 6.22 mmol), was added DME (20 mL). The reaction mixture was then heated at 90° C. overnight. The reaction was allowed to cool and then filtered and concentrated. The crude product was purified by combiflash (0 to 10% EtOAc/hexanes) yielding 26.3 (1.61 g, 71.8% yield).

(2'-Fluoro-5'-(methyloxy)-2-(tetrahydro-2H-pyran-2-yloxy)-1,1'-biphenyl-4-yl)methanol (26.4). To 26.3 (1.61 g, 4.47 mmol) in THF (10 mL) at 0° C., was added LAH (1.0M solution in THF, 6.70 mL, 6.70 mmol). The reaction was stirred for one hour and then carefully diluted with water, extracted with EtOAc, washed with brine, dried over sodium sulfate, filtered, and concentrated to provide 26.4 (0.990 g, 66.7% yield).

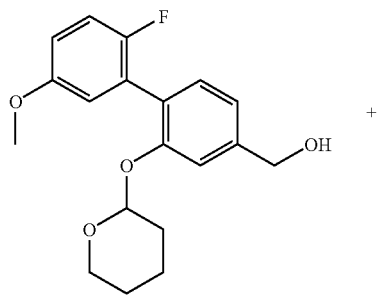

26.4

+

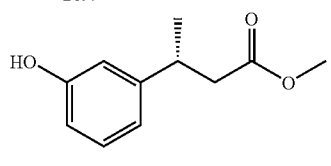

or

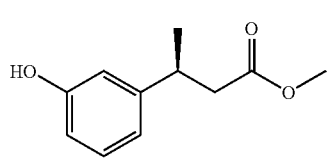

5.7

→

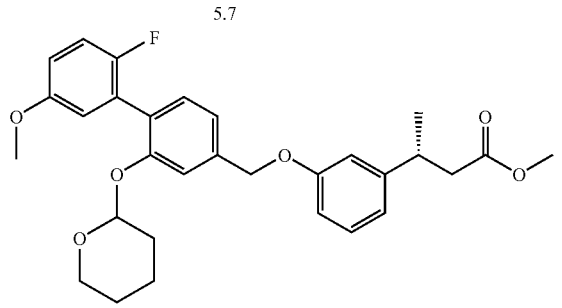

or

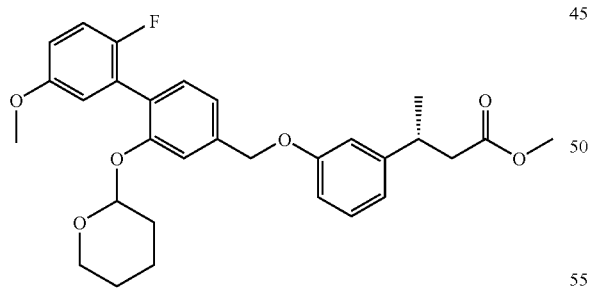

26.5

Methyl (3R)-3-(3-(((2'-fluoro-5'-(methyloxy)-2-(tetrahydro-2H-pyran-2-yloxy)-1,1'-biphenyl-4-yl)methyl)oxy)phenyl)butanoate or methyl (3S)-3-(3-(((2'-fluoro-5'-(methyloxy)-2-(tetrahydro-2H-pyran-2-yloxy)-1,1'-biphenyl-4-yl)methyl)oxy)phenyl)butanoate (26.5). To a flask containing 5.7 (150.0 mg, 772.3 µmol), 26.4 (308.0 mg, 926.8 µmol), and polymer supported triphenylphosphine (386.1 mg, 1158 µmol) in DCM (3 mL) was added diethyl azodicarboxylate (182.4 µL, 1158 µmol) at 0° C. The reaction mixture was allowed to warm to room temperature and stirred for 1 hour. The reaction was concentrated and then purified by combi-flash (0 to 20% EtOAc/hexanes) to provide 26.5 (253.9 mg, 64.64% yield).

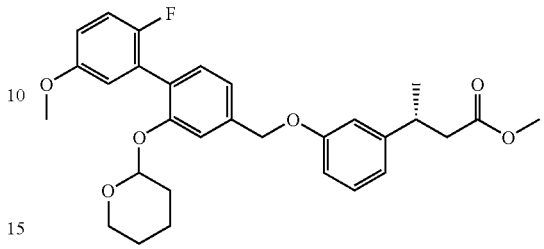

or

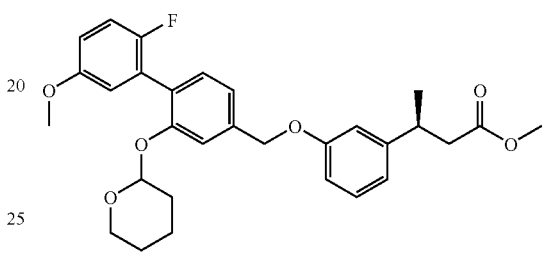

26.5

→

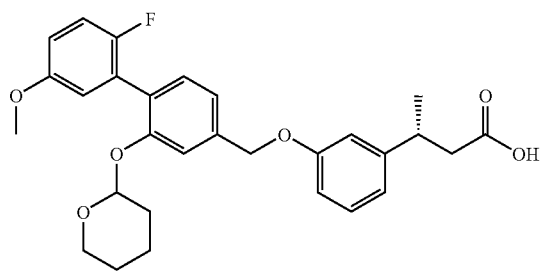

or

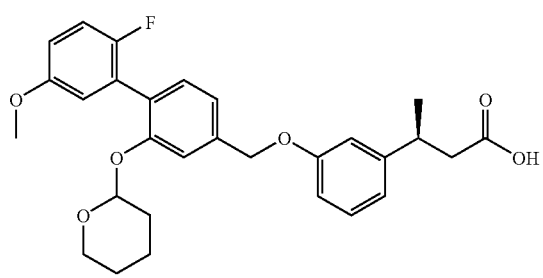

26

(3R)-3-(3-(((2'-Fluoro-5'-(methyloxy)-2-(tetrahydro-2H-pyran-2-yloxy)-1,1'-biphenyl-4-yl)methyl)oxy)phenyl)butanoic acid or (3S)-3-(3-(((2'-fluoro-5'-(methyloxy)-2-(tetrahydro-2H-pyran-2-yloxy)-1,1'-biphenyl-4-yl)methyl)oxy)phenyl)butanoic acid (26). To a solution of 26.5 (20.0 mg, 39.3 µmol) in THF/MeOH (2/1) (1.5 mL) was added lithium hydroxide (0.500 mL, 500 µmol). The resulting mixture was stirred overnight at 23° C., quenched with excess 1N HCl, and extracted with EtOAc. The combined organic layers were dried over Na$_2$SO$_4$ and concentrated. The crude residue was purified by combiflash (0 to 40% EtOAc/hexanes) to afford 26 (16.0 mg, 82.3% yield). ESI (neg.) m/e: 493.1 (M−H)⁺.

Example 27

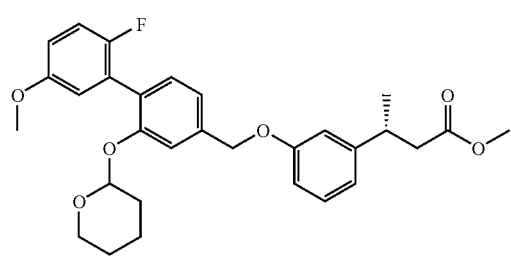

26.5 or

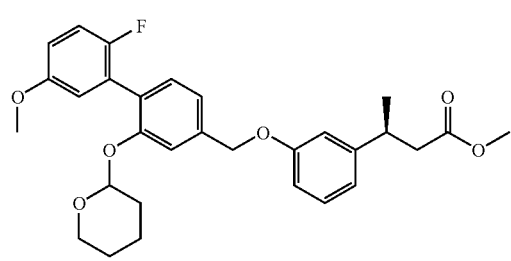

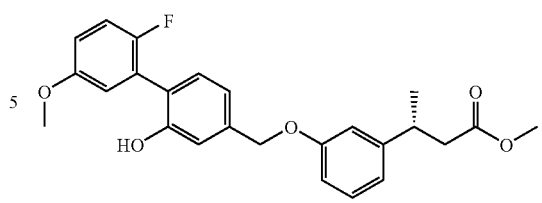

or


27.1

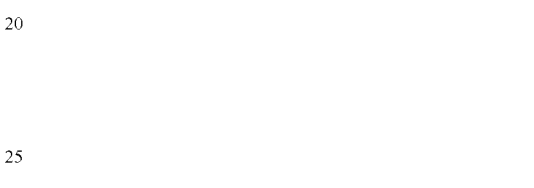

or

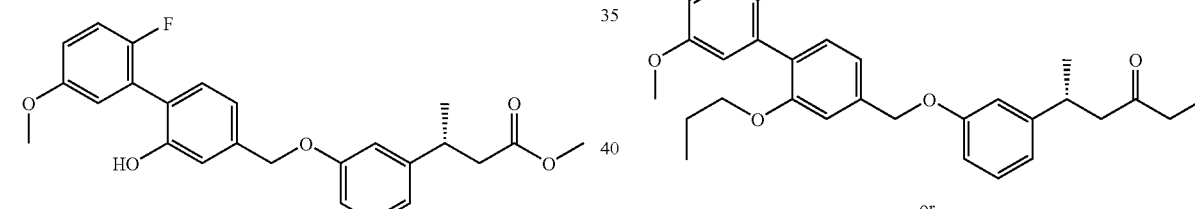

27.1

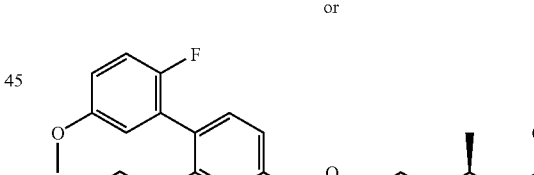

or

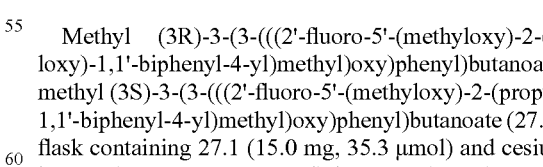

27.2

Methyl (3R)-3-(3-(((2'-fluoro-2-hydroxy-5'-(methyloxy)-1,1'-biphenyl-4-yl)methyl)oxy)phenyl)butanoate or methyl (3S)-3-(3-(((2'-fluoro-2-hydroxy-5'-(methyloxy)-1,1'-biphenyl-4-yl)methyl)oxy)phenyl)butanoate (27). To a solution of 26.5 (250 mg, 492 μmol) in MeOH (2.5 mL), was added PPTS (12.4 mg, 49.2 μmol) at room temperature. The mixture was heated overnight, cooled to room temperature, diluted with EtOAc, washed with water and brine, dried (MgSO₄), and concentrated. The crude product was purified by silica gel flash chromatography (0-25% EtOAc/hexane) to afford 27.1 (179.1 mg, 85.8% yield) as a colorless oil.

Methyl (3R)-3-(3-(((2'-fluoro-5'-(methyloxy)-2-(propyloxy)-1,1'-biphenyl-4-yl)methyl)oxy)phenyl)butanoate or methyl (3S)-3-(3-(((2'-fluoro-5'-(methyloxy)-2-(propyloxy)-1,1'-biphenyl-4-yl)methyl)oxy)phenyl)butanoate (27.2). To a flask containing 27.1 (15.0 mg, 35.3 μmol) and cesium carbonate (23.0 mg, 70.7 μmol) in DMF (1 mL), was added 1-bromopropane (5.78 μL, 63.6 μmol), and the resulting mixture was stirred overnight. The reaction was diluted with water and extracted with EtOAc. The organic layers were washed with brine, dried over Na₂SO₄, filtered, concentrated, and then purified by combiflash (0 to 20% EtOAc/Hexanes) to provide 27.2.

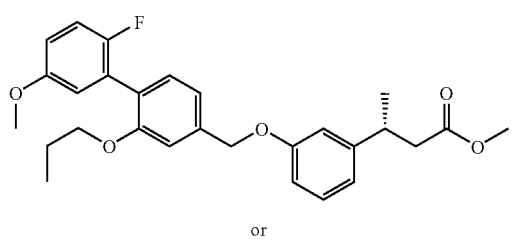

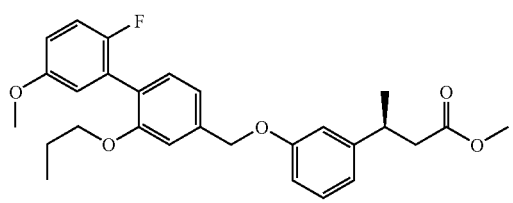

27.2

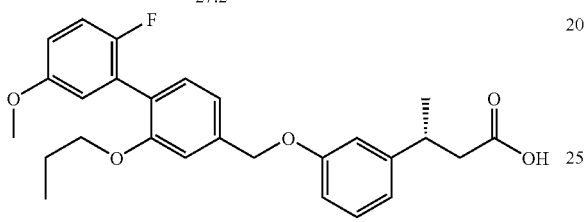

or

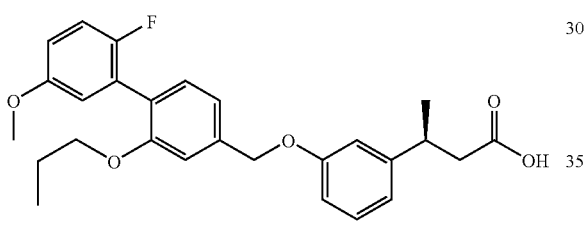

27

(3R)-3-(3-(((2'-Fluoro-5'-(methyloxy)-2-(propyloxy)-1,1'-biphenyl-4-yl)methyl)oxy)phenyl)butanoic acid or (3S)-3-(3-(((2'-fluoro-5'-(methyloxy)-2-(propyloxy)-1,1'-biphenyl-4-yl)methyl)oxy)phenyl)butanoic acid (27). To a solution of 27.2 (16.5 mg, 35.3 μmol) in THF/MeOH (2/1) (1.5 mL) was added lithium hydroxide (0.500 mL, 500 μmol). The resulting mixture was stirred overnight at 23° C., quenched with excess 1N HCl, and extracted with EtOAc. The combined organic layers were dried over Na$_2$SO$_4$ and concentrated. The crude residue was purified by combiflash (5 to 25% EtOAc/hexanes) to afford a 27 (12.5 mg, 78.3% yield). ESI (neg.) m/e: 451.1 (M−H)$^+$.

Example 28

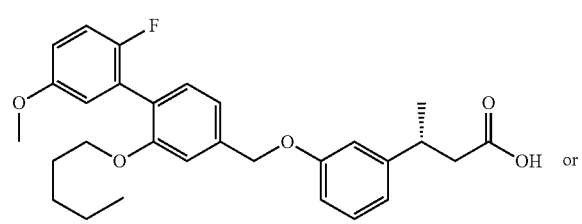

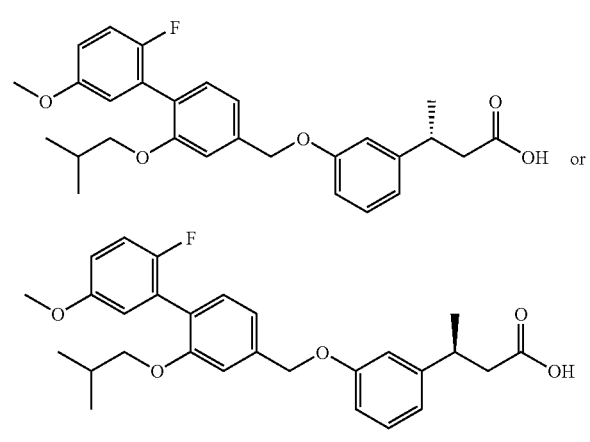

28

(3R)-3-(3-(((2'-Fluoro-5'-(methyloxy)-2-(pentyloxy)-1,1'-biphenyl-4-yl)methyl)oxy)phenyl)butanoic acid or (3S)-3-(3-(((2'-fluoro-5'-(methyloxy)-2-(pentyloxy)-1,1'-biphenyl-4-yl)methyl)oxy)phenyl)butanoic acid (28). Compound 28 was synthesized from 27.1 by a method analogous to that used to prepare compound 27. ESI (neg.) m/e: 479.2 (M−H)$^+$.

Example 29

29

(3R)-3-(3-(((2'-Fluoro-5'-(methyloxy)-2-((2-methylpropyl)oxy)-1,1'-biphenyl-4-yl)methyl)oxy)phenyl)butanoic acid or (3S)-3-(3-(((2'-fluoro-5'-(methyloxy)-2-((2-methylpropyl)oxy)-1,1'-biphenyl-4-yl)methyl)oxy)phenyl)butanoic acid (29). Compound 29 was synthesized from 27.1 by a method analogous to that used to prepare compound 27. ESI (neg.) m/e: 465.2 (M−H)$^+$.

Example 30

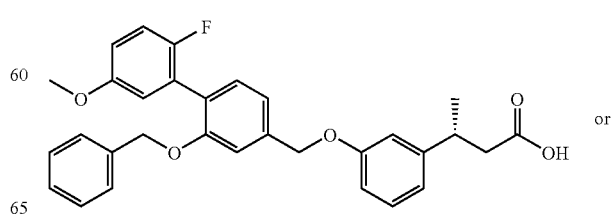

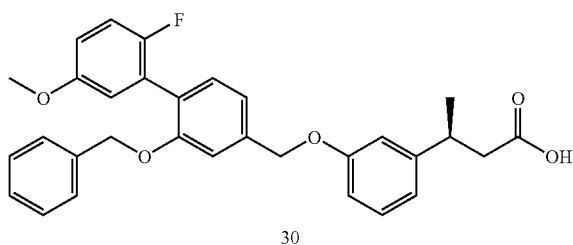

30

(3R)-3-(3-(((2'-Fluoro-5'-(methyloxy)-2-((phenylmethyl)oxy)-1,1'-biphenyl-4-yl)methyl)oxy)phenyl)butanoic acid or (3S)-3-(3-(((2'-fluoro-5'-(methyloxy)-2-((phenylmethyl)oxy)-1,1'-biphenyl-4-yl)methyl)oxy)phenyl)butanoic acid (30). Compound 30 was synthesized from 27.1 using a method analogous to that used to prepare compound 27. ESI (neg.) m/e: 499.1 (M–H)$^+$.

Example 31

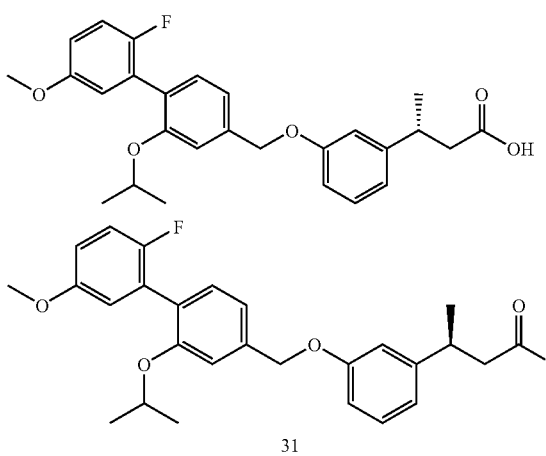

31

(3R)-3-(3-(((2'-Fluoro-2-((1-methylethyl)oxy)-5'-(methyloxy)-1,1'-biphenyl-4-yl)methyl)oxy)phenyl)butanoic acid or (3S)-3-(3-(((2'-fluoro-2-((1-methylethyl)oxy)-5'-(methyloxy)-1,1'-biphenyl-4-yl)methyl)oxy)phenyl)butanoic acid (31). Example 31 was synthesized from 27.1 by a method analogous to that used to prepare compound 27. ESI (neg.) m/e: 451.1 (M–H)$^+$.

Example 32

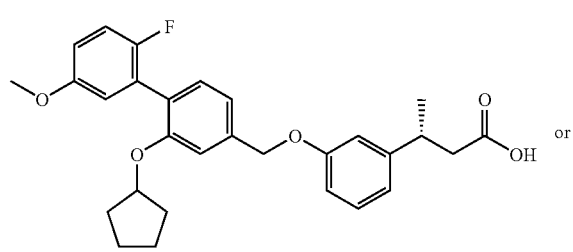

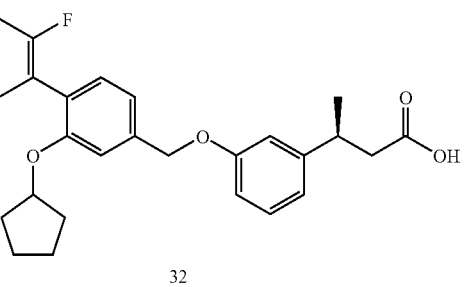

32

(3R)-3-(3-(((2-(Cyclopentyloxy)-2'-fluoro-5'-(methyloxy)-1,1'-biphenyl-4-yl)methyl)oxy)phenyl)butanoic acid or (3S)-3-(3-(((2-(cyclopentyloxy)-2'-fluoro-5'-(methyloxy)-1,1'-biphenyl-4-yl)methyl)oxy)phenyl)butanoic acid (32). Example 32 was synthesized from 27.1 by a method analogous to that used to prepare compound 27. ESI (neg.) m/e: 477.2 (M–H)$^+$.

Example 33

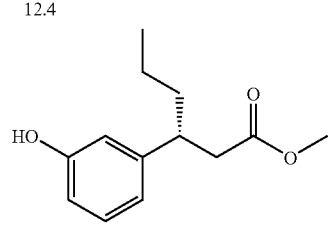

12.4

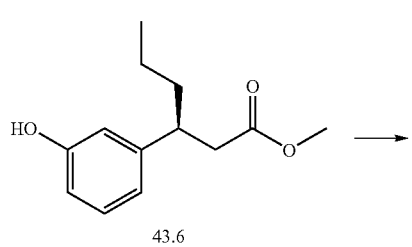

43.6

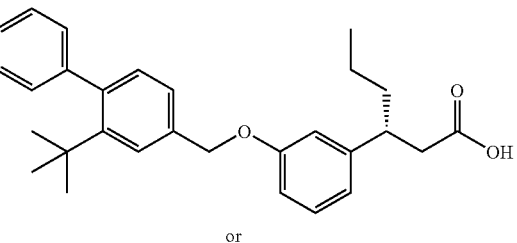

or

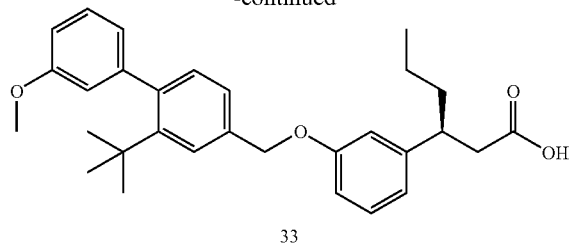

33

(3R)-3-(3-(((2-(1,1-Dimethylethyl)-3'-(methyloxy)-1,1'-biphenyl-4-yl)methyl)oxy)phenyl)hexanoic acid or (3S)-3-(3-(((2-(1,1-dimethylethyl)-3'-(methyloxy)-1,1'-biphenyl-4-yl)methyl)oxy)phenyl)hexanoic acid (33). Compound 43.6 (0.015 g, 0.067 mmol) was coupled with 12.4 (0.021 g, 0.074 mmol) according to the method described for preparation of 42 to afford 33 (0.025 g, 81%) as a colorless oil. $^1$H NMR (400 MHz, CDCl$_3$) δ ppm 7.57 (d, 1H), 7.24 (m, 3H), 7.05 (d, 1H), 6.87 (m, 4H), 6.82 (m, 2H), 5.06 (s, 2H), 3.81 (s, 3H), 3.08 (m, 1H), 2.63 (m, 2H), 1.61 (m, 2H), 1.22 (s, 9H), 1.19 (m, 2H), 0.86 (t, 3H).

Example 34

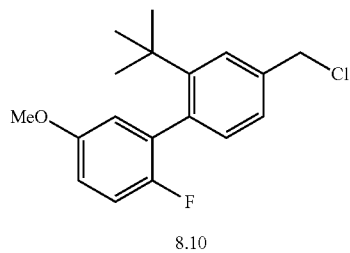

8.10

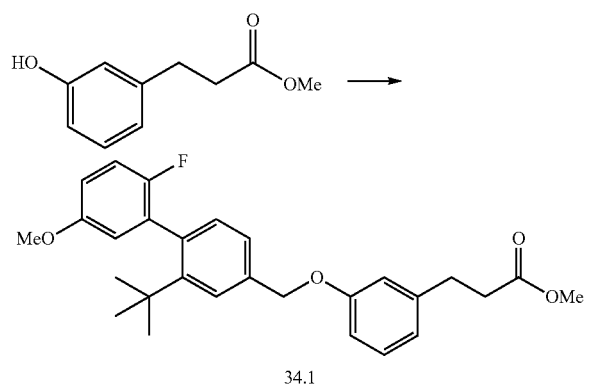

34.1

Methyl 3-(3-(((2-(1,1-dimethylethyl)-2'-fluoro-5'-(methyloxy)-1,1'-biphenyl-4-yl)methyl)oxy)phenyl)propanoate (34.1). Methyl 3-(3-hydroxyphenyl)propanoate (commercially available from Aagile Labs Division of Tyger Scientific) (0.025 g, 0.14 mmol) was alkylated by reaction with compound 8.10 (0.043 g, 0.14 mmol) according to the method given in Example 1 to give compound 34.1 as a clear oil (0.052 g, 83% yield). MS ESI (pos.) m/e: 473.2 (M+Na)$^+$, 468.2 (M+H$_2$O)$^+$.

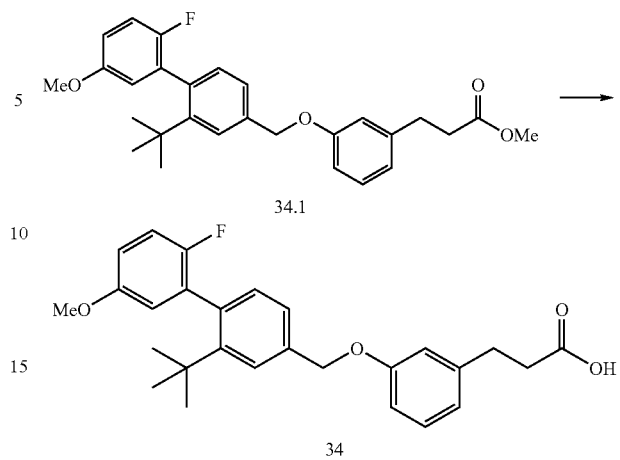

34.1

34

3-(3-(((2-(1,1-Dimethylethyl)-2'-fluoro-5'-(methyloxy)-1,1'-biphenyl-4-yl)methyl)oxy)phenyl)propanoic acid (34). Compound 34.1 (0.052 g, 0.12 mmol) was hydrolyzed according to the method reported for Example 1 to give compound 34 as a clear oil (0.0376 g, 75% yield). $^1$H NMR (400 MHz, CDCl$_3$) δ ppm 7.61 (1H, d, J=1.6 Hz), 7.31-7.23 (2H, m), 7.06 (1H, d, J=8.2 Hz), 7.00 (1H, t, J=8.6 Hz), 6.91-6.83 (4H, m), 6.78 (1H, dd, J=5.9, 3.1 Hz), 5.08 (2H, s), 3.79 (3H, s), 2.97 (2H, t, J=7.8 Hz), 2.71 (2H, t, J=7.8 Hz), 1.24 (9H, s). MS ESI (neg.) m/e: 871.5 (2M–H)$^+$, 543.2 (M–H)$^+$.

Example 35

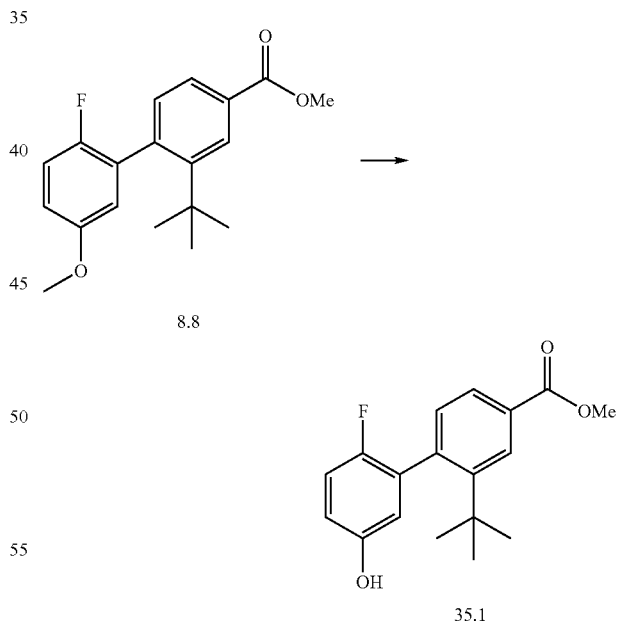

8.8

35.1

Methyl 2-(1,1-dimethylethyl)-2'-fluoro-5'-hydroxy-1,1'-biphenyl-4-carboxylate (35.1). To a cooled solution of 8.8 (0.500 g, 2.00 mmol) in dry DCM (32.0 mL) at 0° C. was added boron tribromide (7.00 mL, 7.00 mmol). Stirring was continued for 6 hours, and the reaction was monitored by TLC and LCMS. Upon completion, pH 7 buffer was added to the mixture at 0° C. The resulting solution was extracted with DCM (3×20 mL). The combined organic layers were dried over MgSO₄, filtered, and concentrated in vacuo. The residue was then purified by flash chromatography (SiO₂ gel 60, eluted with 0%-20% EtOAc in hexanes). Fractions containing the desired product were combined and concentrated to provide 35.1 as a colorless oil (0.29 g, 61%). MS ESI (pos.) m/e: 335.1 (M+Na)⁺, 320.1 (M+H₂O)⁺, 303.1 (M+H)⁺.

desired product were combined and concentrated to provide 35. 2 as a colorless oil (0.100 g, 100%). MS ESI (pos.) m/e: 795.4 (2M+Na)⁺.

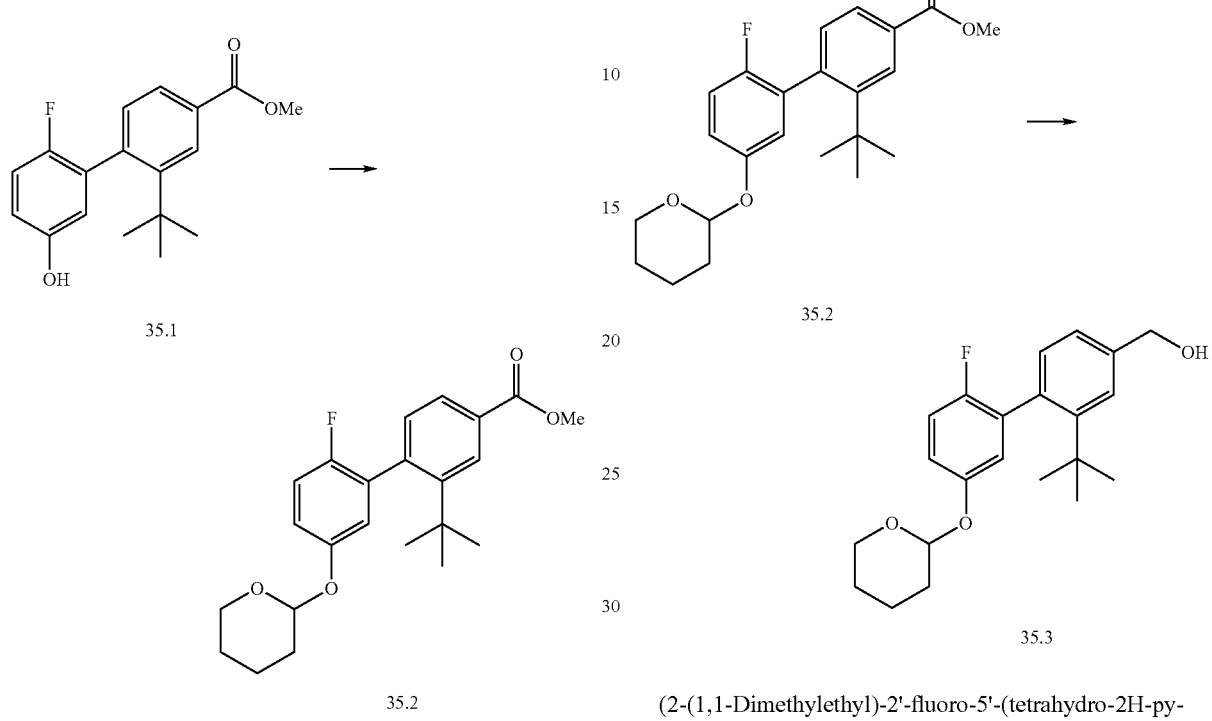

Methyl 2-(1,1-dimethylethyl)-2'-fluoro-5'-(tetrahydro-2H-pyran-2-yloxy)-1,1'-biphenyl-4-carboxylate (35.2). To a stirred solution of 35.1 (0.080 g, 0.30 mmol) in dry DCM (1.00 mL) at 23° C., was added 3,4-dihydro-2H-pyran (available from Aldrich) (0.04 g, 0.50 mmol), followed by PPTS (0.007 g, 0.03 mmol). Stirring was continued for 14 hours. The resulting solution was concentrated in vacuo. Water was added, and the resulting mixture was extracted with EtOAc (3×10 mL). The combined organic layers were dried over MgSO₄, filtered, and concentrated in vacuo. The residue was then purified by flash chromatography (SiO₂ gel 60, eluted with 0%-20% EtOAc in hexanes). Fractions containing the (2-(1,1-Dimethylethyl)-2'-fluoro-5'-(tetrahydro-2H-pyran-2-yloxy)-1,1'-biphenyl-4-yl)methanol (35.3). To a cooled solution of 35.2 (0.080 g, 0.30 mmol) in THF (3.00 mL) at 0° C., was added LAH (1.0 M solution in THF, 0.60 mL, 0.60 mmol). Stirring was continued for 1 hour. 1N NaOH (5 mL) was carefully added to quench the reaction. The resulting solution was extracted with EtOAc (3×10 mL). The combined organic layers were dried over MgSO₄, filtered, and concentrated in vacuo. The residue was then purified by flash chromatography (SiO₂ gel 60, eluted with 0%-30% EtOAc in hexanes). Fractions containing the desired product were combined and concentrated to provide 35.3 as a colorless oil (0.055 g, 54%). MS ESI (pos.) m/e: 739.3 (2M+Na)⁺, 376.1 (M+H₂O)⁺.

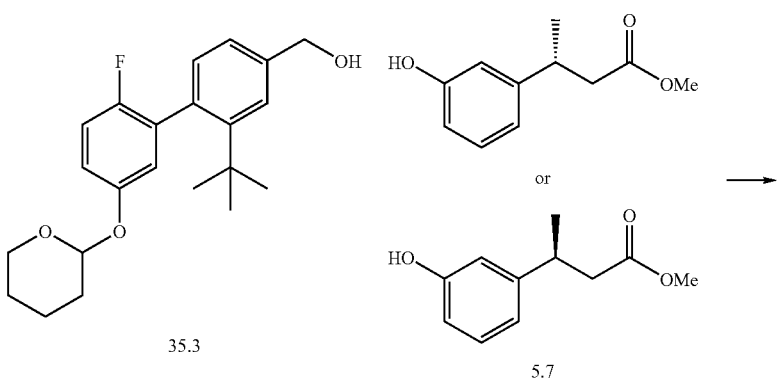

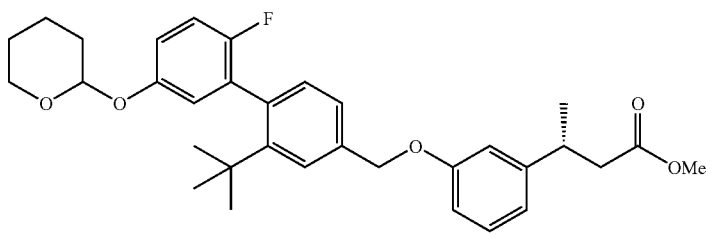

or

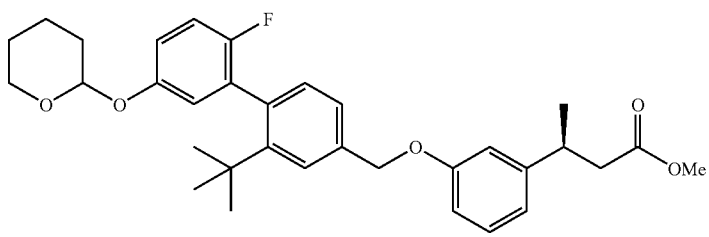

35.4

Methyl (3R)-3-(3-(((2-(1,1-dimethylethyl)-2'-fluoro-5'-(tetrahydro-2H-pyran-2-yloxy)-1,1'-biphenyl-4-yl)methyl)oxy)phenyl) butanoate or methyl (3S)-3-(3-(((2-(1,1-dimethylethyl)-2'-fluoro-5'-(tetrahydro-2H-pyran-2-yloxy)-1,1'-biphenyl-4-yl)methyl)oxy)phenyl)butanoate (35.4). To a stirred solution of compound 5.7 (0.015 g, 0.077 mmol) in THF (0.77 mL) at 0° C., was added 35.3 (0.030 g, 0.085 mmol) and polymer based triphenylphosphine (0.030 g, 0.12 mmol) followed by diethyl azodicarboxylate (0.018 mL, 0.12 mmol). Stirring continued at 23° C. for 19 hours. Water (5 mL) was added to quench the reaction, and the resulting solution was extracted with EtOAc (3×10 mL). The combined organic layers were dried over MgSO$_4$, filtered and concentrated in vacuo. The residue was then purified by flash chromatography (SiO$_2$ gel 60, eluted with 0%-20% EtOAc in hexanes). Fractions containing the desired product were combined and concentrated to provide 35.4 as a colorless oil (0.028 g, 68%). MS ESI (pos.) m/e: 557.3 (M+Na)$^+$.

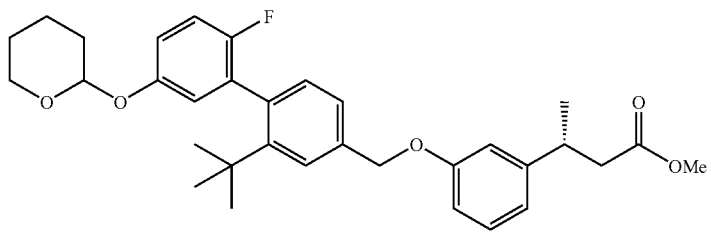

or

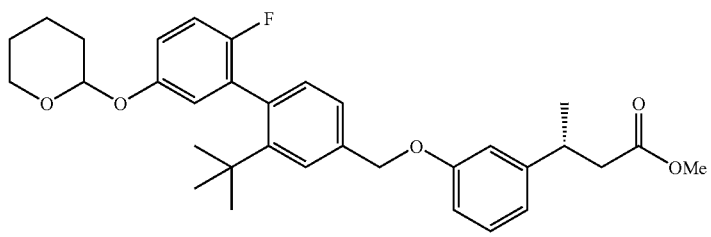

35.4

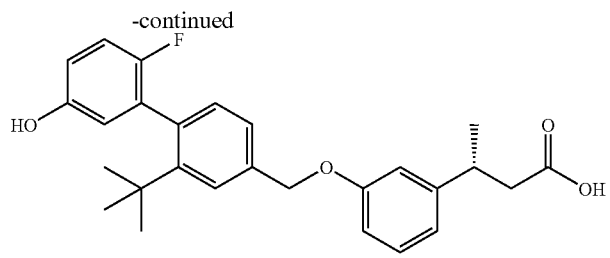

or

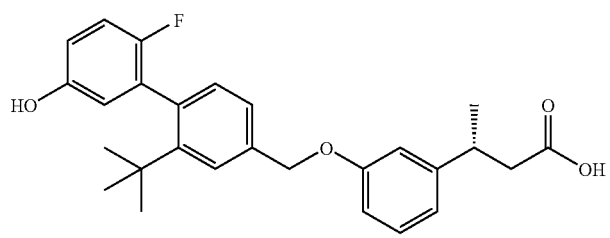

35

(3R)-3-(3-(((2-(1,1-Dimethylethyl)-2'-fluoro-5'-hydroxy-1,1'-biphenyl-4-yl)methyl)oxy)phenyl)butanoic acid or (3S)-3-(3-(((2-(1,1-dimethylethyl)-2'-fluoro-5'-hydroxy-1,1'-biphenyl-4-yl)methyl)oxy)phenyl)butanoic acid (35). To a stirred solution of compound 35.4 (0.028 g, 0.052 mmol) in THF (2.00 mL) and EtOH (2.00 mL) at 23° C. was added a solution of lithium hydroxide (1N, 1.00 mL). Stirring was continued for 16 hours. The resulting mixture was concentrated in vacuo. 1 N HCl (5 mL) was added to the solution, and stirring was continued for 24 hours. The mixture was extracted with EtOAc (3×10 mL). The combined organic layers were dried over $MgSO_4$, filtered, and concentrated in vacuo. The residue was then purified by flash chromatography ($SiO_2$ gel 60, eluted with 0%-40% EtOAc in hexanes). Fractions containing the desired product were combined and concentrated to provide compound 35 as a colorless oil (0.010 g, 45%). $^1$H NMR (400 MHz, $CDCl_3$) δ ppm 7.60 (1H, d, J=1.6 Hz), 7.30-7.23 (2H, m), 7.04 (1H, dd, J=7.8, 1.3 Hz), 6.95 (1H, t, J=8.8 Hz), 6.89-6.85 (3H, m), 6.79 (1H, m), 6.71 (1H, dd, J=5.9, 3.1 Hz), 5.08 (2H, s), 3.27 (1H, m), 2.71-2.65 (1H, dd, J=15.4, 6.6, 2.0 Hz), 2.61-2.55 (1H, dd, J=15.4, 8.1 Hz), 1.33 (3H, d, J=7.0 Hz), 1.24 (9H, s). MS ESI (pos.) m/e: 871.3 $(2M-H)^+$, 435.1 $(M-H)^+$.

Example 36

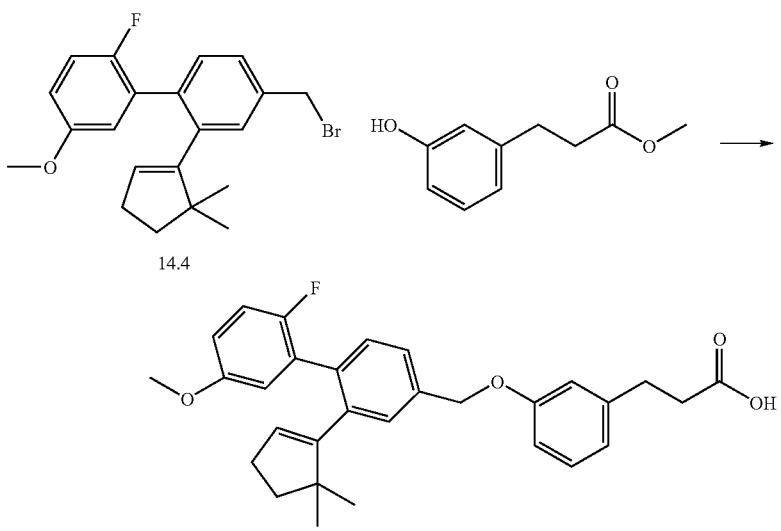

3-(3-(((2-(5,5-Dimethyl-1-cyclopenten-1-yl)-2'-fluoro-5'-(methyloxy)-1,1'-biphenyl-4-yl)methyl)oxy)phenyl)propanoic acid (36). A reaction mixture of compound 14.4 (36.0 mg, 0.093 mmol), commercially available methyl 3-(3-hydroxyphenyl)propanoate (available from Aagile Labs Division of Tyger Scientific) (18.3 mg, 0.093 mmol) and cesium carbonate (60.3 mg, 0.185 mmol) in DMSO (1.0 mL) was stirred at room temperature overnight. LC-MS results indicated the benzylation reaction was completed. MS ESI (pos.)

m/e: 511.1 (M+Na)⁺. Lithium hydroxide (18.0 mg, 0.74 mmol, 0.3 mL, 3.33M in water) and DMSO (1.0 mL) were added. Stirring was continued overnight. 1 N HCl was then added to reach a pH of about 3. The reaction mixture was purified by HPLC (reversed phase) to give the title compound 36. ¹H NMR (400 MHz, CD₃CN) δ ppm 7.44 (dd, 1H), 7.30-7.38 (m, 2H), 7.24 (t, 1H), 7.05 (t, 1H), 6.85-6.94 (m, 5H), 5.54 (s, 1H), 5.16 (s, 2H), 3.77 (s, 3H), 2.89 (t, 2H), 2.62 (t, 2H), 2.22-2.31 (m, 2H), 1.66-1.71 (m, 2H), 0.87 (s, 6H) MS ESI (neg.) m/e: 473.2 (M−H)⁺.

Example 37

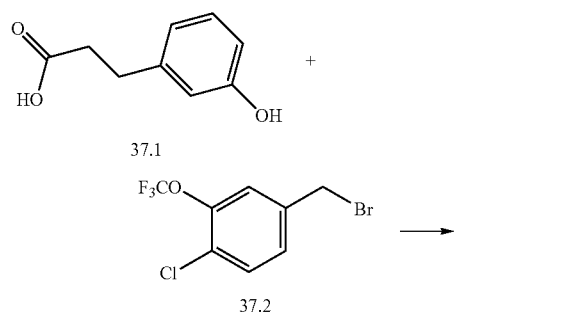

3-(3-(4-Chloro-3-(trifluoromethoxy)benzyloxy)phenyl)-propanoic acid (37.3). Compound 37.3 was synthesized using the alkylation and hydrolysis procedure of Example 13 above using compounds 37.1 and 37.2. 3-(3-Hydroxyphenyl)propanoic acid is available from Alfa Aesar Avocado, and Lancaster). 4-(Bromomethyl)-1-chloro-2-(trifluoromethoxy)benzene is available from Alfa Aesar, Lancaster, and Avocado. MS ESI (neg.) m/e: 373 (M−H).

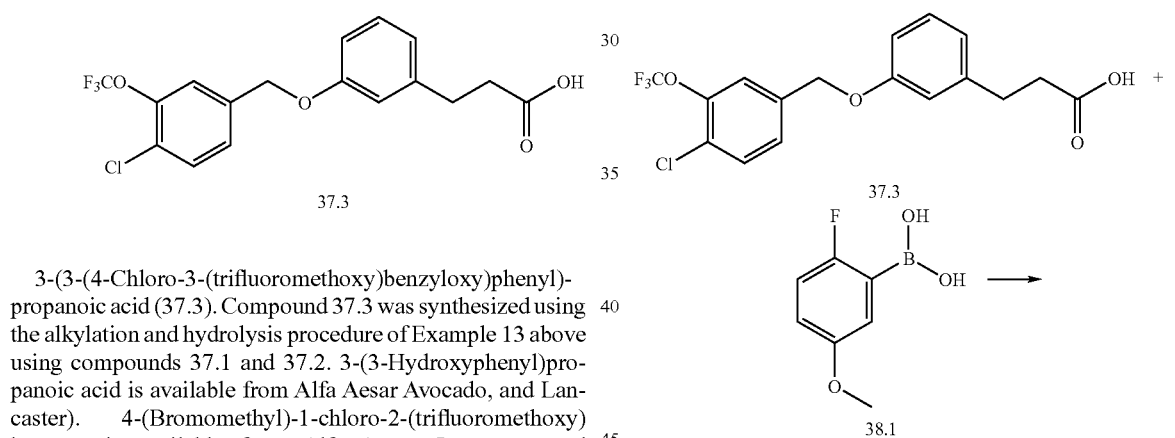

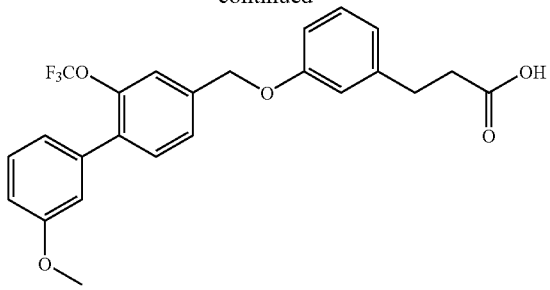

3-[3-(3'-Methoxy-2-trifluoromethoxy-biphenyl-4-yl-methoxy)-phenyl]-propionic acid (37). Compound 37 was synthesized using the procedure above for preparing 13.3 using compound 37.3 and 3-methoxyphenylboronic acid 37.4 (available from Aldrich). MS ESI (neg.) m/e: 445 (M−H). ¹H NMR (400 MHz, CD₃CN) δ ppm 7.51 (3H, s), 7.38 (1H, s), 7.22 (1H, s), 7.05 (2H, s), 6.98 (1H, s), 6.87 (3H, s), 5.15 (2H, s), 3.81 (3H, s), 2.86 (2H, s), 2.59 (2H, s).

Example 38

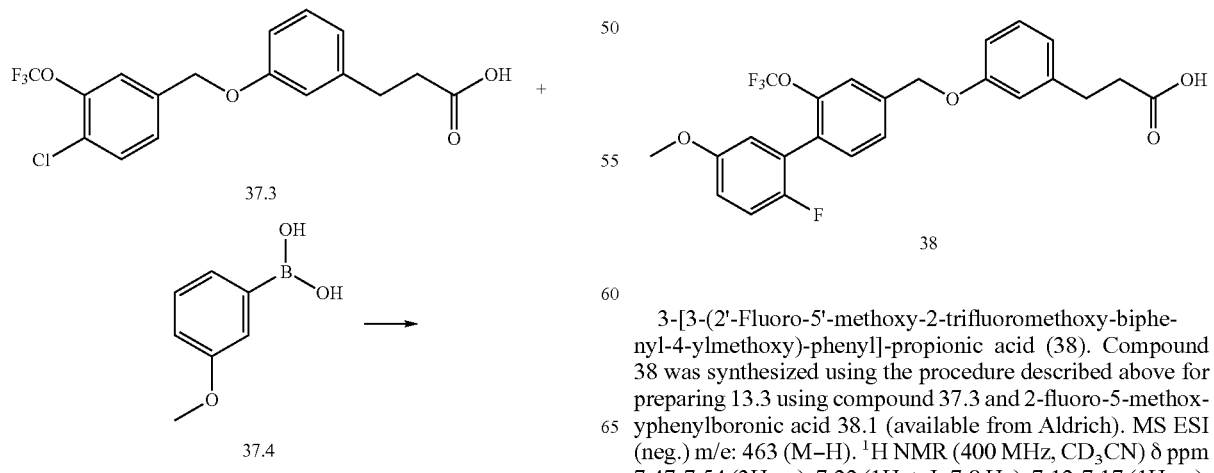

3-[3-(2'-Fluoro-5'-methoxy-2-trifluoromethoxy-biphenyl-4-ylmethoxy)-phenyl]-propionic acid (38). Compound 38 was synthesized using the procedure described above for preparing 13.3 using compound 37.3 and 2-fluoro-5-methoxyphenylboronic acid 38.1 (available from Aldrich). MS ESI (neg.) m/e: 463 (M−H). ¹H NMR (400 MHz, CD₃CN) δ ppm 7.47-7.54 (3H, m), 7.22 (1H, t, J=7.8 Hz), 7.12-7.17 (1H, m), 6.98 (1H, dt, J=9.0, 3.5 Hz), 6.90-6.93 (2H, m), 6.85 (2H, dd, J=8.0, 2.2 Hz), 5.16 (2H, s), 3.79 (3H, s), 2.86 (2H, s), 2.56-2.62 (2H, m).

Example 39

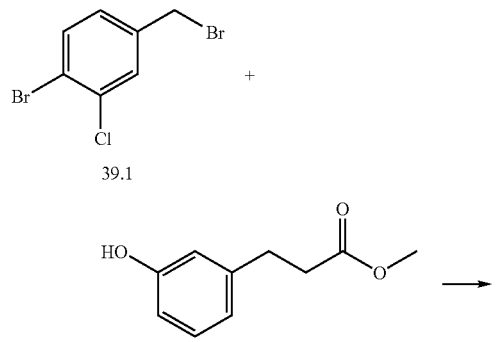

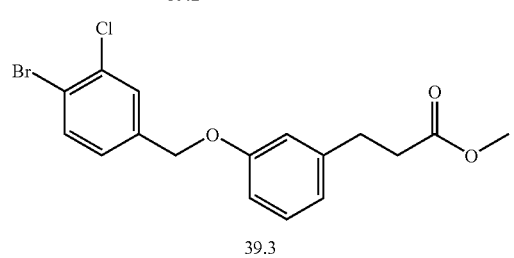

39.2

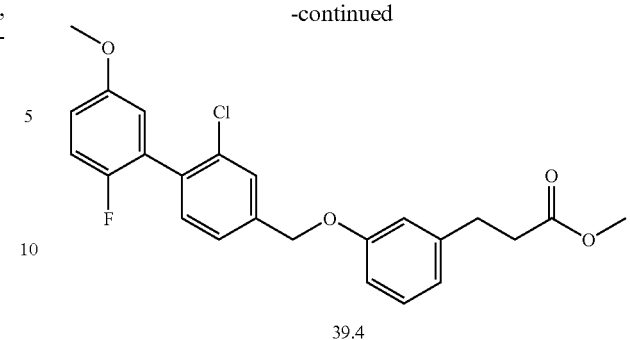

39.4

3-[3-(2-Chloro-2'-fluoro-5'-methoxy-biphenyl-4-yl-methoxy)-phenyl]-propionic acid methyl ester (39.4). Compound 39.4 was synthesized using the procedure described above for preparing 13.2 using compound 39.3 and 38.1. MS ESI (pos.) m/e: 451 (M+Na).

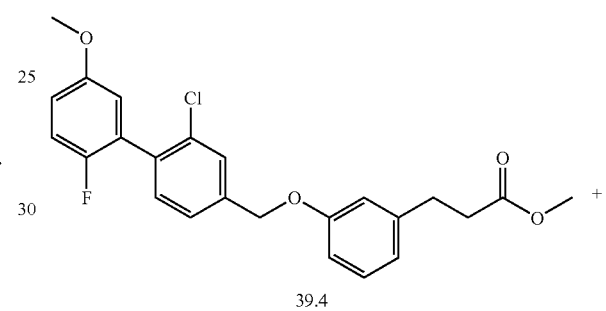

39.4

Methyl 3-(3-(4-bromo-3-chlorobenzyloxy)phenyl)propanoate (39.3). Compound 39.3 was synthesized using the procedure described above for preparing 1.1 using 1-bromo-4-(bromomethyl)-2-chlorobenzene 39.1 (available from Metina AB) and methyl 3-(3-hydroxyphenyl)propanoate 39.2 (available from Aagile Labs Division of Tyger Scientific). ¹H NMR (400 MHz, CDCl₃) δ ppm 7.63 (1H, d, J=8.2 Hz), 7.55 (1H, d, J=2.0 Hz), 7.17-7.24 (2H, m), 6.78-6.85 (3H, m), 4.99 (2H, s), 3.68 (3H, s) 2.94 (2H, t, J=7.8 Hz), 2.64 (2H, t, J=7.8 Hz).

39.3

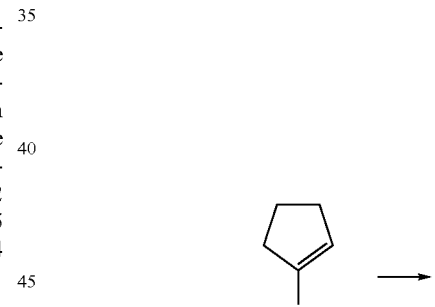

39.5

38.1

39.6

3-[3-(2-Cyclopent-1-enyl-2'-fluoro-5'-methoxy-biphenyl-4-ylmethoxy)-phenyl]-propionic acid methyl ester (39.6). Compound 39.6 was synthesized using the procedure described above for preparing 13.3 using compound 39.4 and 39.5. MS ESI (pos.) m/e: 483 (M+Na).

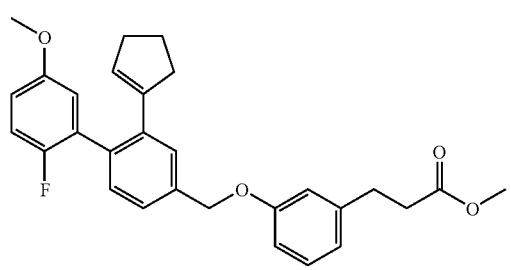

39.6

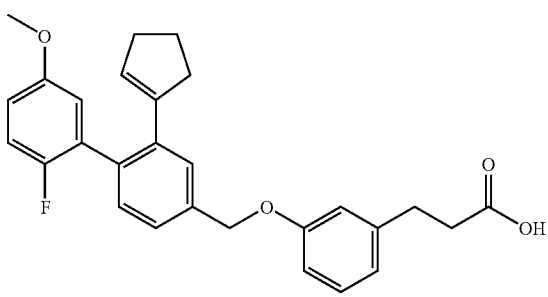

39

3-[3-(2-Cyclopent-1-enyl-2'-fluoro-5'-methoxy-biphenyl-4-ylmethoxy)-phenyl]-propionic acid (39). Compound 39 was synthesized using the procedure described above for preparing Example 1 using compound 39.6. MS ESI (neg.) m/e: 445 (M–H). $^1$H NMR (400 MHz, CD$_3$CN) δ ppm 7.45 (1H, s), 7.37 (1H, dd, J=7.8, 2.0 Hz), 7.27 (1H, d, J=7.8 Hz), 7.18-7.23 (1H, m), 7.03 (1H, t, J=9.2 Hz), 6.82-6.90 (4H, m), 6.82 (1H, d, J=3.5 Hz), 5.46 (1H, t, J=2.2 Hz), 5.10 (2H, s), 3.75 (3H, s), 2.85 (2H, t, J=7.6 Hz), 2.58 (2H, t, J=7.8 Hz), 2.34-2.38 (2H, m), 2.34 (1H, d, J=2.0 Hz), 2.27 (2H, ddd, J=9.9, 5.0, 2.3 Hz), 1.76-1.84 (2H, m).

Example 40

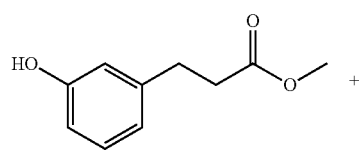

+

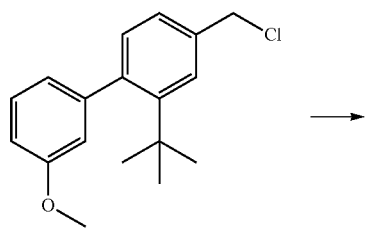

12.3

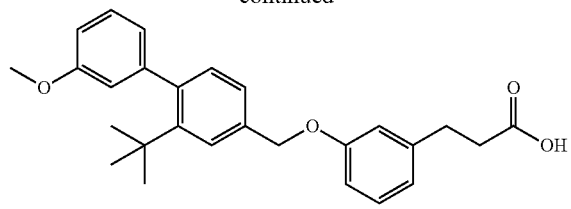

40

3-(3-(((2-(1,1-Dimethylethyl)-3'-(methyloxy)-1,1'-biphenyl-4-yl)methyl)oxy)phenyl)propanoic acid (40). Compound 40 was prepared from commercially available methyl 3-(3-hydroxyphenyl)propanoate (available from Aagile Labs Division of Tyger Scientific) and 12.3 by a method based on that reported in US 2006/0004012. (MS ESI (neg.) m/e: 417.1 (M–H). $^1$H NMR (400 MHz) (CDCl$_3$) δ ppm 7.59 (1H, d, J=1.6 Hz), 7.29 (3H, m), 7.07 (1H, d, J=7.8 Hz), 6.92 (6H, m), 5.08 (2H, s), 3.83 (3H, s), 2.98 (2H, t, J=7.8 Hz), 2.75 (2H, m), 1.24 (9H, s).

Example 41

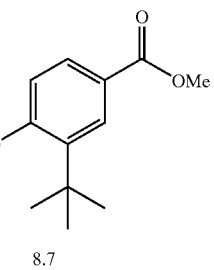

8.7

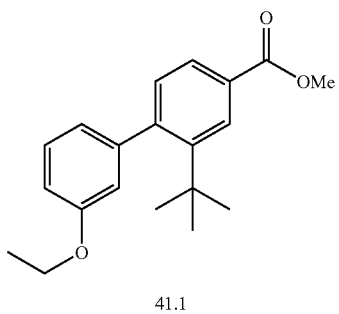

41.1

Methyl 2-(1,1-dimethylethyl)-3'-(ethyloxy)-1,1'-biphenyl-4-carboxylate (41.1). A dry round bottom flask containing 8.7 (1.13 g, 3.31 mmol), 3-ethoxyphenylboronic acid (available from Aldrich) (1.10 g, 6.63 mmol), tetrakis(triphenylphosphine)palladium (0.39 g, 0.340 mmol), and potassium carbonate (1.41 g, 10.20 mmol) was evacuated and backfilled three times with argon. Dry DMF (10.000 mL) was then added via syringe under argon. The mixture was then heated at 80° C. and monitored with TLC. After 20 hours, the reaction was cooled to room temperature and diluted with water. The mixture was extracted three times with EtOAc and then concentrated under reduced pressure. The residue was then purified by flash chromatography (SiO$_2$ gel 60, eluted with 0%-25% EtOAc in hexanes). Fractions containing the desired product were combined and concentrated to provide 41.1 as a colorless oil (0.87, 84%). MS ESI (pos.) m/e: 313.1 (M+H)$^+$.

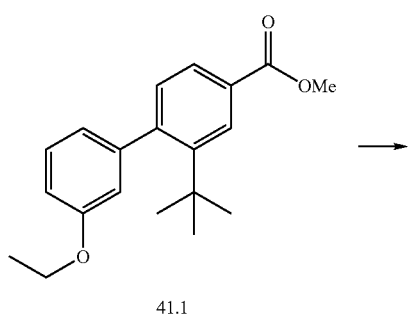

41.1

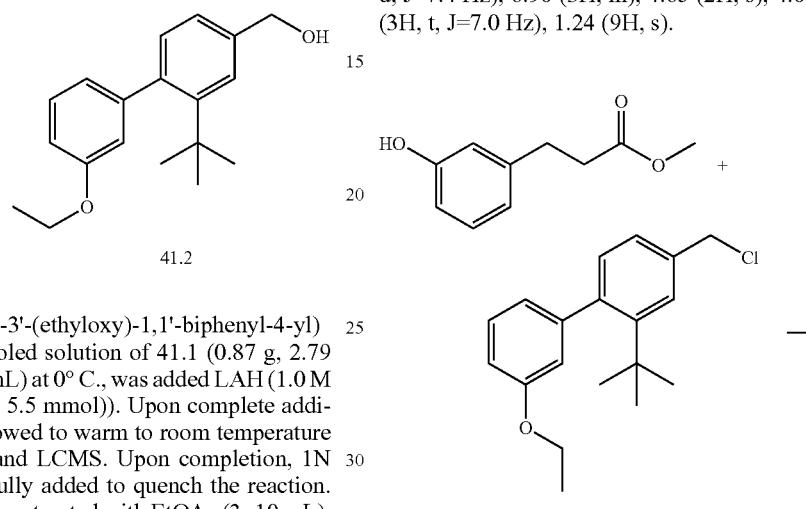

(2-(1,1-Dimethylethyl)-3'-(ethyloxy)-1,1'-biphenyl-4-yl) methanol (41.2). To a cooled solution of 41.1 (0.87 g, 2.79 mmol) in dry THF (10.0 mL) at 0° C., was added LAH (1.0 M solution in THF (5.5 mL, 5.5 mmol)). Upon complete addition, the reaction was allowed to warm to room temperature and monitored by TLC and LCMS. Upon completion, 1N NaOH (5 mL) was carefully added to quench the reaction. The resulting solution was extracted with EtOAc (3×10 mL). The combined organic layers were dried over MgSO₄, filtered, and concentrated in vacuo. The residue was then purified by flash chromatography (SiO₂ gel 60, eluted with 0%-40% EtOAc in hexanes). Fractions containing the desired product were combined and concentrated to provide 41.2 as a colorless oil (0.72, 91%). ¹H NMR (500 MHz, CDCl₃) δ ppm 7.53 (1H, d, J=1.5 Hz), 7.26 (1H, m), 7.19 (1H, dd, J=7.7, 1.8 Hz), 7.04 (1H, d, J=7.6 Hz), 6.89 (3H, m), 4.74 (2H, d, J=3.2 Hz), 4.08 (2H, m), 1.71 (1H, s), 1.42 (3H, t, J=7.0 Hz), 1.23 (9H, s).

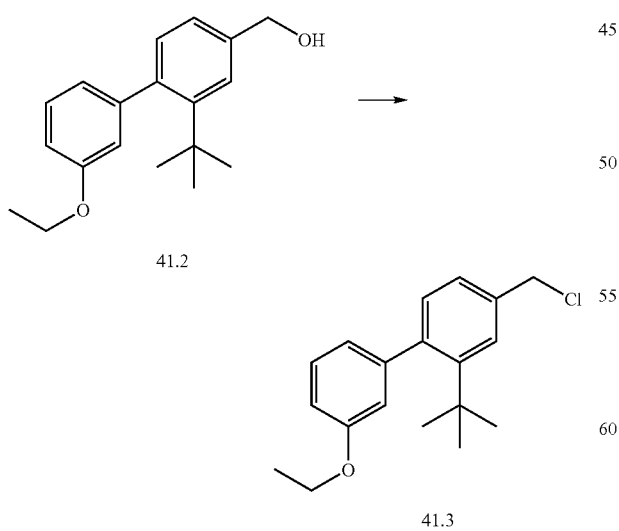

4-(Chloromethyl)-2-(1,1-dimethylethyl)-3'-(ethyloxy)-1,1'-biphenyl (41.3). A dry, round bottom flask containing 41.2 (0.72 g, 2.53 mmol) and DCM (9.0 mL) was cooled to 0° C. After 15 minutes, thionyl chloride (1.0 mL, 13.7 mmol) was carefully added dropwise at 0° C. Upon complete addition of thionyl chloride, the mixture was allowed to warm to room temperature and stirred overnight. After 20 hours, the reaction was concentrated under reduced pressure. The residue was then purified by flash chromatography (SiO₂ gel 60, eluted with 0%-15% EtOAc in hexanes). Fractions containing the desired product were combined and concentrated to provide 41.3 as a colorless oil (0.57, 74%). ¹H NMR (500 MHz, CDCl₃) δ ppm 7.54 (1H, d, J=2.0 Hz), 7.25 (2H, m), 7.04 (1H, d, J=7.4 Hz), 6.90 (3H, m), 4.65 (2H, s), 4.05 (2H, m), 1.43 (3H, t, J=7.0 Hz), 1.24 (9H, s).

3-(3-(((2-(1,1-Dimethylethyl)-3'-(ethyloxy)-1,1'-biphenyl-4-yl)methyl)oxy)phenyl)propanoic acid (41). Compound 41 was prepared from commercially available methyl 3-(3-hydroxyphenyl)propanoate (available from Aagile Labs Division of Tyger Scientific) and 41.3 by a method based on that reported in US 2006/0004012. (MS ESI (neg.) m/e: 431.2 (M−H). ¹H NMR (400 MHz) (CDCl₃) δ ppm 7.62 (1H, d, J=1.6 Hz), 7.32 (3H, m), 7.09 (1H, d, J=7.8 Hz), 6.95 (5H, m), 6.87 (1H, s), 5.10 (2H, s), 4.07 (2H, dd, J=6.5, 4.5 Hz), 3.00 (2H, t, J=7.8 Hz), 2.74 (2H, t, J=7.8 Hz), 1.45 (3H, t, J=6.8 Hz), 1.30 (9H, s).

Example 42

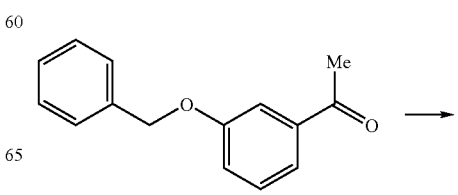

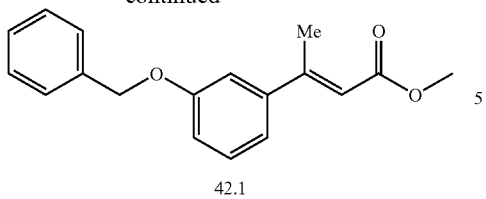

42.1

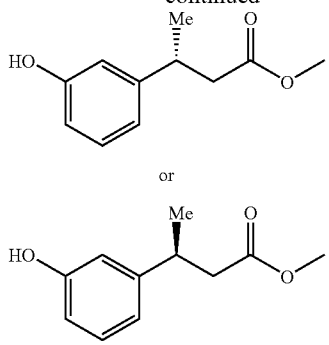

5.7 or

Methyl (2E)-3-(3-((phenylmethyl)oxy)phenyl)-2-butenoate (42.1). To a suspension of lithium chloride (0.28 g, 6.6 mmol) in MeCN (9 mL), were added trimethyl phosphonoacetate (available from Aldrich) (0.76 mL, 5.3 mmol), DBU (0.79 mL, 5.3 mmol), and 3-benzyloxyacetophenone (available from Aldrich) (1.00 g, 4.4 mmol). The mixture was stirred overnight at reflux (100° C.), cooled to room temperature, diluted with EtOAc, washed with water and brine, dried (MgSO₄), and concentrated. The crude product was chromatographed on silica gel (0-10% EtOAc/hexane) to afford 42.1 (0.45 g, 36%) as a colorless oil.

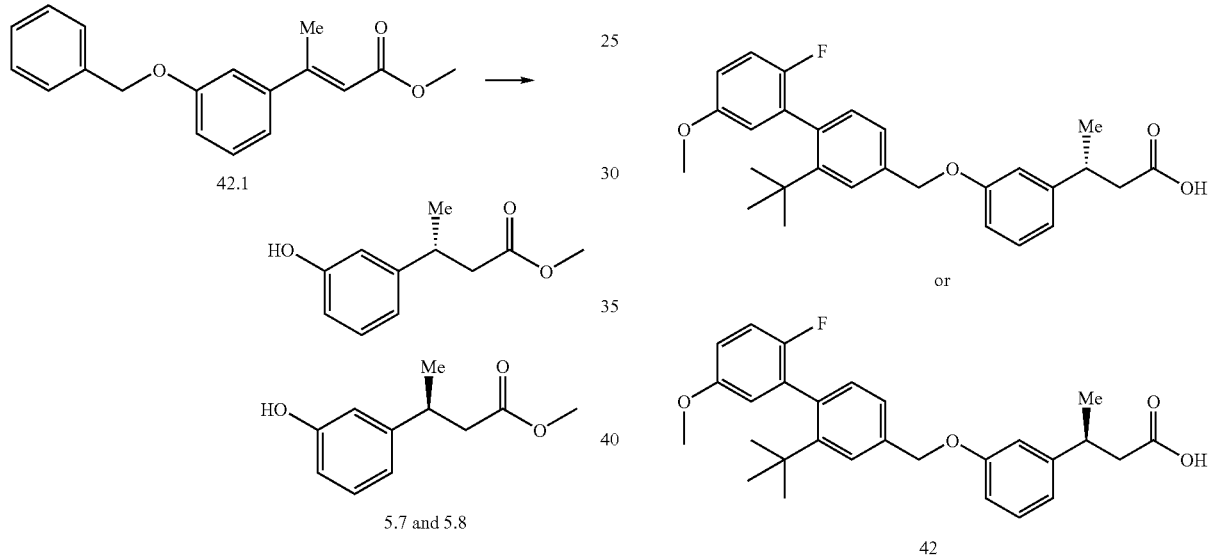

Methyl (3R)-3-(3-hydroxyphenyl)butanoate (5.7) and methyl (3S)-3-(3-hydroxyphenyl)butanoate (5.8). To a solution of 42.1 (0.44 g, 1.56 mmol) in 1:1 EtOAc/MeOH (10.0 mL) was added 10% Pd/C (0.25 g, 0.23 mmol) under a blanket of N₂. The mixture was sparged with H₂, stirred overnight under a H₂ balloon, filtered through silica gel (EtOAc), and concentrated. The resulting racemate was resolved by chiral HPLC (Chiralcel OD column, 3% IPA/hexane, 220 nm) to afford 5.7 (0.14 g, 22.7 minutes) and 5.8 (0.14 g, 36.1 minutes) as pale yellow oils.

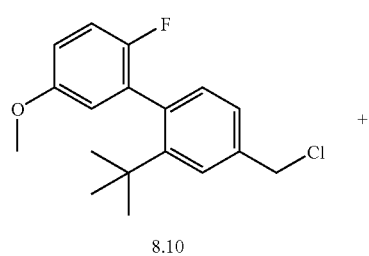

8.10

(3R)-3-(3-(((2-(1,1-Dimethylethyl)-2'-fluoro-5'-(methyloxy)-1,1'-biphenyl-4-yl)methyl)oxy)phenyl)butanoic acid or (3S)-3-(3-(((2-(1,1-dimethylethyl)-2'-fluoro-5'-(methyloxy)-1,1'-biphenyl-4-yl)methyl)oxy)phenyl)butanoic acid (42). A screw-cap vial was charged with 5.7 (0.010 g, 0.051 mmol), 8.10 (0.017 g, 0.057 mmol), cesium carbonate (0.025 g, 0.077 mmol), and DMF (1.0 mL). The mixture was stirred overnight at room temperature, diluted with water, and extracted with EtOAc. The combined organic layers were dried (MgSO₄) and concentrated, and the residue was chromatographed on silica gel (0-15% EtOAc/hexane) to afford a colorless oil. The oil was dissolved in 2:1 THF/MeOH (1.5 mL), and 1 N LiOH (0.5 mL) was added. The mixture was stirred overnight at room temperature, quenched with 1 N HCl (0.6 mL), and extracted with EtOAc. The combined organics were dried (MgSO₄) and concentrated. The crude product was chromatographed on silica gel (0-30% EtOAc/hexane to afford 42 (0.019 g, 83%) as a colorless oil. ¹H NMR (400 Mhz, CDCl₃) δ ppm 7.60 (d, 1H), 7.29 (dd, 1H), 7.25 (t, 1H), 7.05 (d, 1H), 6.99 (t, 1H), 6.86 (m, 4H), 6.77 (dd, 1H), 5.07 (s, 2H), 3.78 (s, 3H), 3.27 (m, 1H), 2.68 (dd, 1H), 2.58 (dd, 1H), 1.32 (d, 3H), 1.23 (s, 9H).

Example 43

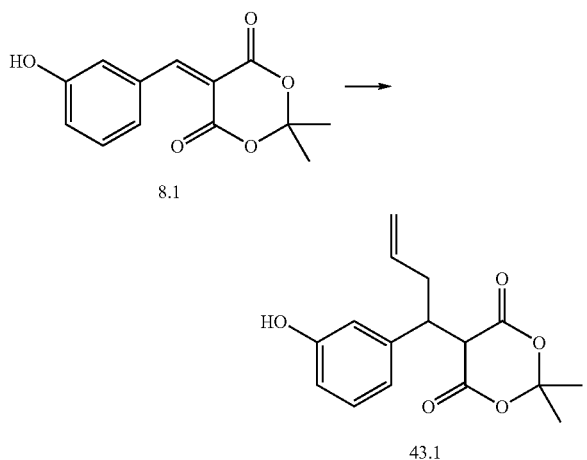

5-(1-(3-Hydroxyphenyl)-3-butenyl)-2,2-dimethyl-1,3-dioxane-4,6-dione (43.1). To a solution of 8.1 (8.00 g, 32 mmol) in THF (100 mL) was added allylmagnesium chloride (available from Aldrich) (2.0 M in THF) (97 mL, 193 mmol) dropwise at 0° C. over 1 hour. When the addition was complete, the reaction was quenched with 1 N HCl and extracted with EtOAc. The combined organic layers were washed with brine, dried (MgSO$_4$), and concentrated. The crude product was chromatographed on silica gel (20-30% EtOAc/hexane) to afford 43.1 (3.4 g, 36%) as a pale yellow oil.

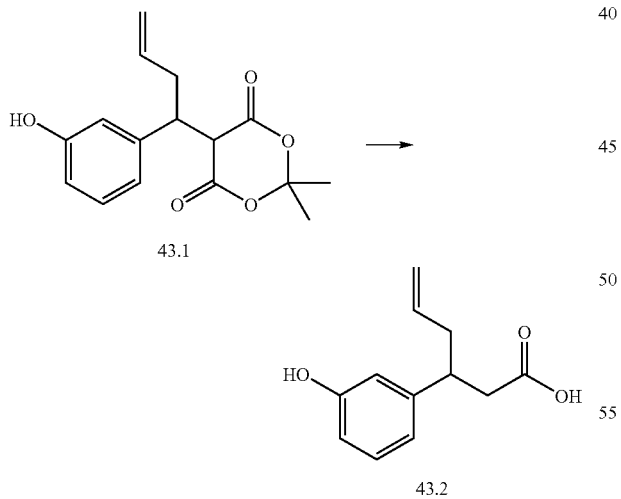

3-(3-Hydroxyphenyl)-5-hexenoic acid (43.2). A solution of 43.1 (3.4 g, 12 mmol) in 10:1 DMF/water (48 mL) was stirred overnight at 90° C. The mixture was cooled to room temperature, diluted with EtOAc, washed with 1 N HCl and brine, dried (MgSO$_4$), and concentrated to afford 43.2 (2.4 g) as a pink oil. The crude product was used without further purification.

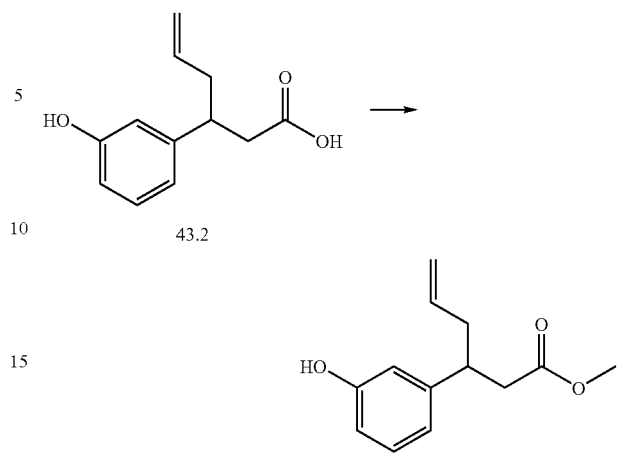

Methyl 3-(3-hydroxyphenyl)-5-hexenoate (43.3). To a solution of 43.2 (2.4 g, 12 mmol) in MeOH (25 mL) was added five drops of sulfuric acid. The mixture was stirred overnight at reflux, cooled to room temperature, diluted with EtOAc, washed with water and brine, dried (MgSO$_4$), and concentrated. The crude product was chromatographed on silica gel (0-25% EtOAc/hexane) to afford 43.3 (2.2 g, 84%) as a colorless oil.

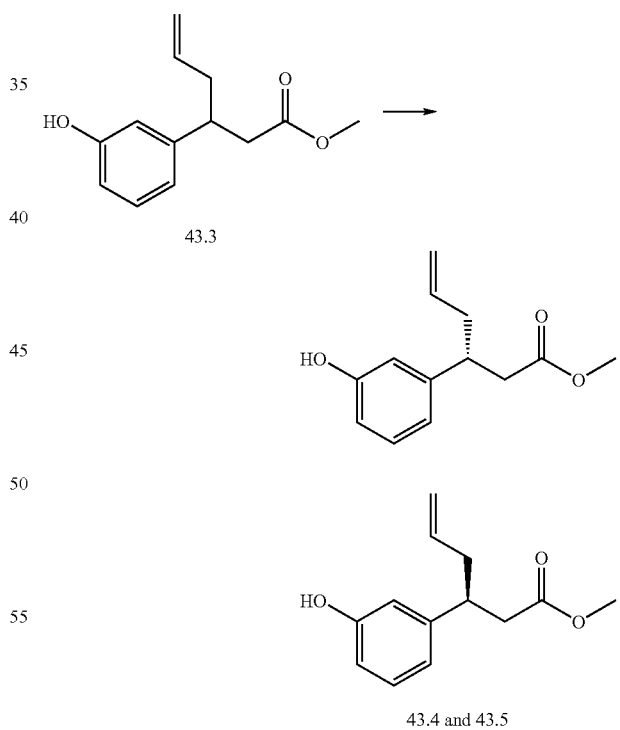

Methyl (3R)-3-(3-hydroxyphenyl)-5-hexenoate and methyl (3S)-3-(3-hydroxyphenyl)-5-hexenoate (43.4 and 43.5). Racemate 43.3 (2.16 g, 9.81 mmol) was resolved by chiral HPLC (Chiralcel OD column, 3% IPA/hexane, 220 nm) to afford 43.4 (1.04 g, 17.8 minutes) and 43.5 (1.00 g, 26.2 minutes) as colorless oils.

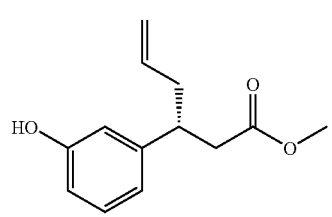

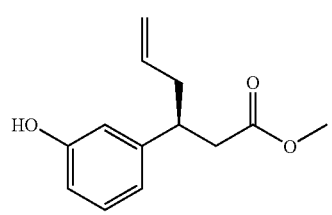

43.4

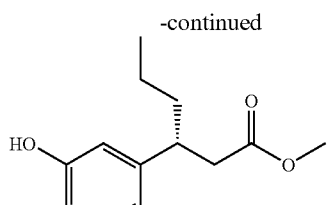

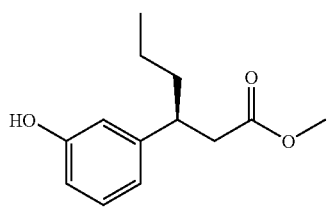

43.6

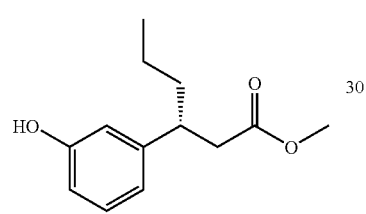

or

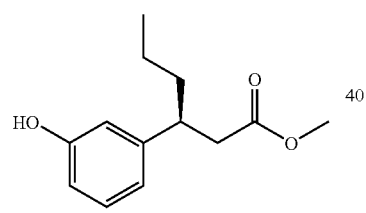

43.6

Methyl (3R)-3-(3-hydroxyphenyl)hexanoate or methyl (3S)-3-(3-hydroxyphenyl)hexanoate (43.6). To a solution of 43.4 (0.47 g, 2.1 mmol) in EtOAc (10 mL) was added 10% Pd/C (0.11 g, 0.11 mmol) under a blanket of $N_2$. The mixture was sparged with $H_2$, stirred overnight under a $H_2$ balloon, filtered through silica gel (EtOAc), and concentrated to afford 43.6 (0.47 g, 99%) as a colorless oil.

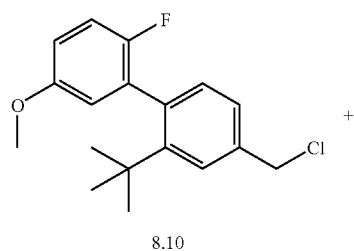

8.10

+

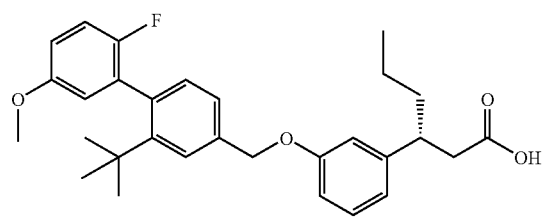

or

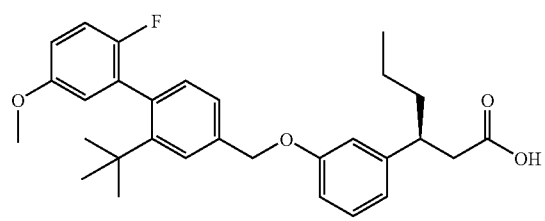

43

(3R)-3-(3-(((2-(1,1-Dimethylethyl)-2'-fluoro-5'-(methyloxy)-1,1'-biphenyl-4-yl)methyl)oxy)phenyl)hexanoic acid or (3S)-3-(3-(((2-(1,1-dimethylethyl)-2'-fluoro-5'-(methyloxy)-1,1'-biphenyl-4-yl)methyl)oxy)phenyl)hexanoic acid (43). Compound 43.6 (0.010 g, 0.045 mmol) was coupled with 8.10 (0.015 g, 0.049 mmol) according to the method described for preparation of 42 to afford 43 (0.018 g, 84%) as a colorless oil. $^1$H NMR (400 MHz, CDCl$_3$) δ ppm 7.60 (d, 1H), 7.29 (dd, 1H), 7.23 (t, 1H), 7.05 (d, 1H), 6.99 (t, 1H), 6.85 (m, 4H), 6.77 (dd, 1H), 5.07 (s, 2H), 3.78 (s, 3H), 3.08 (m, 1H), 2.63 (m, 2H), 1.61 (m, 2H), 1.23 (s, 9H), 1.19 (m, 2H), 0.86 (t, 3H).

Example 44

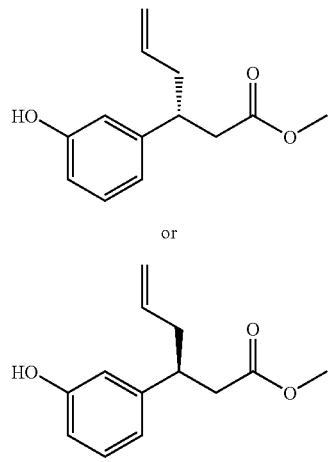

43.5

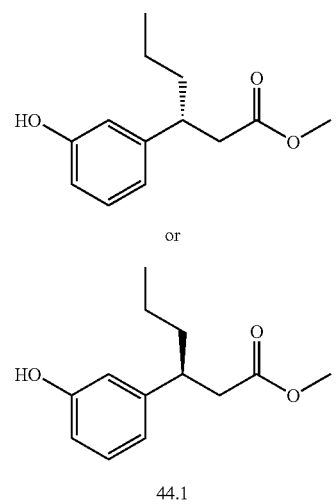

44.1

Methyl (3S)-3-(3-hydroxyphenyl)hexanoate or methyl (3R)-3-(3-hydroxyphenyl)hexanoate (44.1). Compound 43.5 (0.47 g, 2.1 mmol) was hydrogenated according to the method described for preparation of 43.6 to afford 44.1 (0.47 g, 99%) as a colorless oil.

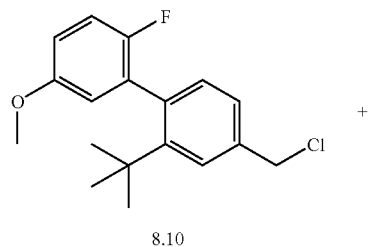

8.10

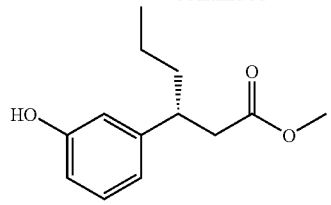

or

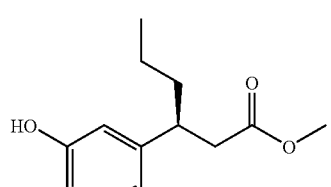

44.1

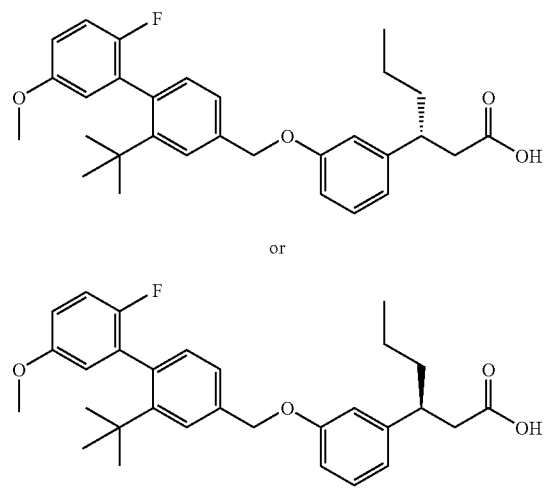

44

(3S)-3-(3-(((2-(1,1-Dimethylethyl)-2'-fluoro-5'-(methyloxy)-1,1'-biphenyl-4-yl)methyl)oxy)phenyl)hexanoic acid or (3R)-3-(3-(((2-(1,1-dimethylethyl)-2'-fluoro-5'-(methyloxy)-1,1'-biphenyl-4-yl)methyl)oxy)phenyl)hexanoic acid (44). Compound 44.1 (0.010 g, 0.045 mmol) was coupled with 8.10 (0.015 g, 0.049 mmol) according to the method described for preparation of 42 to afford 44 (0.020 g, 93%) as a colorless oil. $^1$H NMR (400 MHz, CDCl$_3$) δ ppm 7.60 (d, 1H), 7.29 (d, 1H), 7.23 (t, 1H), 7.05 (d, 1H), 6.99 (t, 1H), 6.84

(m, 4H), 6.77 (dd, 1H), 5.07 (s, 2H), 3.78 (s, 3H), 3.08 (m, 1H), 2.63 (m, 2H), 1.61 (m, 2H), 1.23 (s, 9H), 1.19 (m, 2H), 0.85 (t, 3H).

6.86 (m, 4H), 6.77 (dd, 1H), 5.07 (s, 2H), 3.78 (t, 3H), 3.27 (m, 1H), 2.68 (dd, 1H), 2.58 (dd, 1H), 1.33 (d, 3H), 1.24 (s, 9H).

Example 45

Example 46

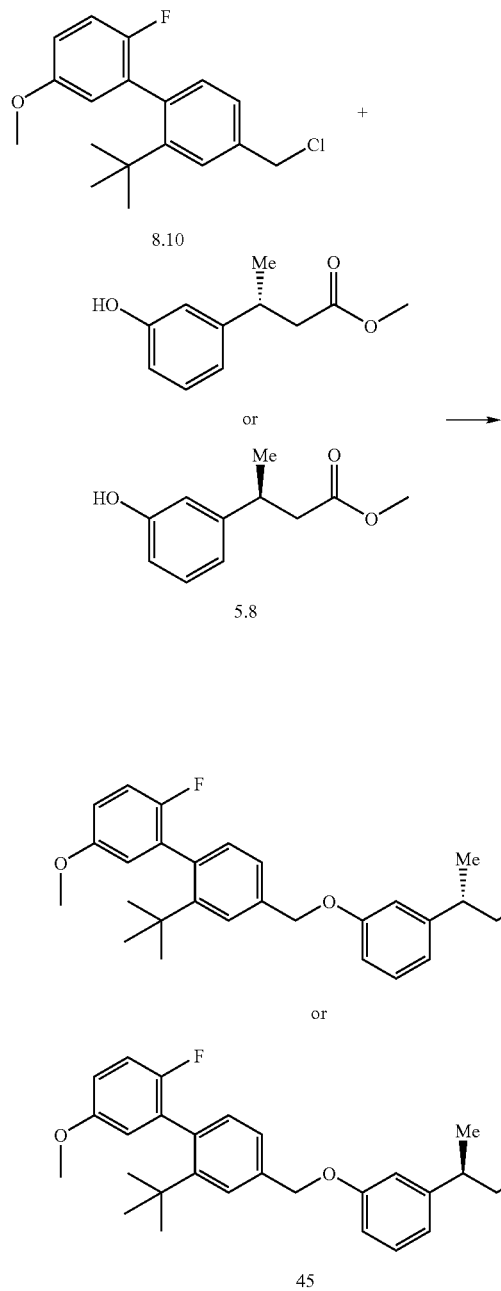

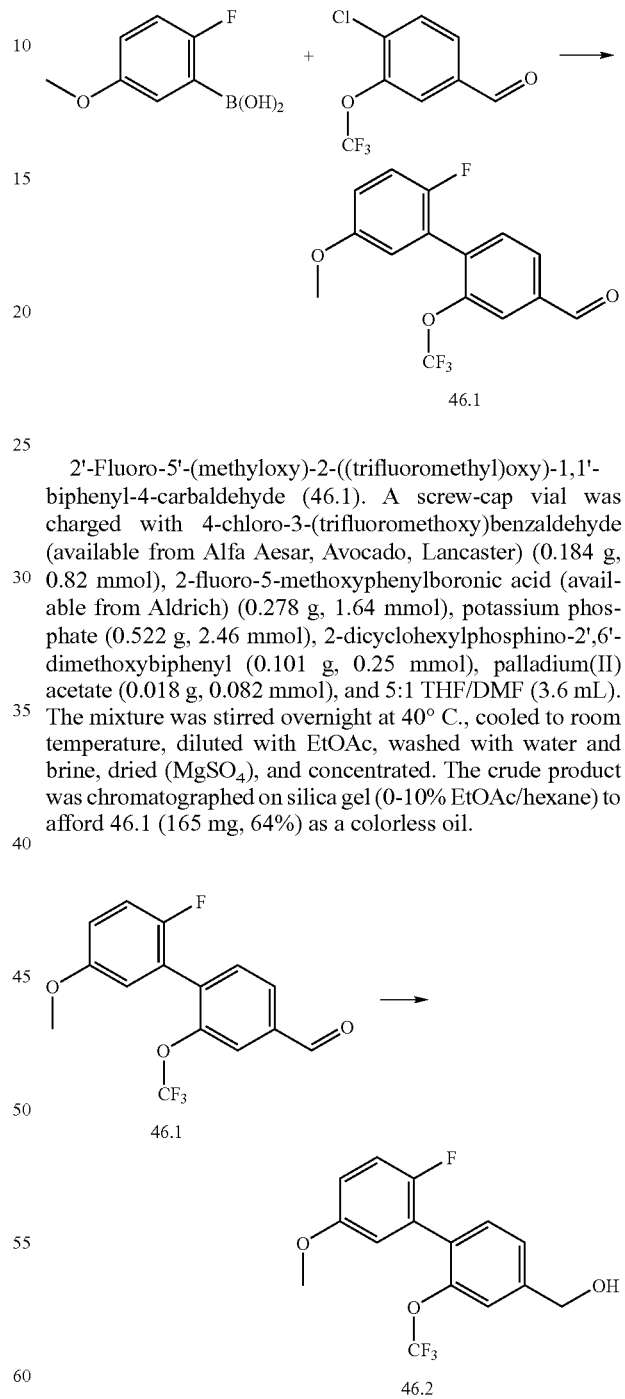

2'-Fluoro-5'-(methyloxy)-2-((trifluoromethyl)oxy)-1,1'-biphenyl-4-carbaldehyde (46.1). A screw-cap vial was charged with 4-chloro-3-(trifluoromethoxy)benzaldehyde (available from Alfa Aesar, Avocado, Lancaster) (0.184 g, 0.82 mmol), 2-fluoro-5-methoxyphenylboronic acid (available from Aldrich) (0.278 g, 1.64 mmol), potassium phosphate (0.522 g, 2.46 mmol), 2-dicyclohexylphosphino-2',6'-dimethoxybiphenyl (0.101 g, 0.25 mmol), palladium(II) acetate (0.018 g, 0.082 mmol), and 5:1 THF/DMF (3.6 mL). The mixture was stirred overnight at 40° C., cooled to room temperature, diluted with EtOAc, washed with water and brine, dried (MgSO₄), and concentrated. The crude product was chromatographed on silica gel (0-10% EtOAc/hexane) to afford 46.1 (165 mg, 64%) as a colorless oil.

(3S)-3-(3-(((2-(1,1-Dimethylethyl)-2'-fluoro-5'-(methyloxy)-1,1'-biphenyl-4-yl)methyl)oxy)phenyl)butanoic acid or (3R)-3-(3-(((2-(1,1-dimethylethyl)-2'-fluoro-5'-(methyloxy)-1,1'-biphenyl-4-yl)methyl)oxy)phenyl)butanoic acid (45). Compound 5.8 (0.010 g, 0.051 mmol) was coupled with 8.10 (0.017 g, 0.057 mmol) according to the method described for preparation of 42 to afford 45 (0.022 g, 96%) as a colorless oil. ¹H NMR (400 MHz, CDCl₃) δ ppm 7.60 (d, 1H), 7.29 (dd, 1H), 7.25 (t, 1H), 7.05 (d, 1H), 7.00 (t, 1H), (2'-Fluoro-5'-(methyloxy)-2-((trifluoromethyl)oxy)-1,1'-biphenyl-4-yl)methanol (46.2). To a solution of 46.1 (0.165 g, 0.53 mmol) in MeOH (6 mL) was added sodium borohydride (0.040 g, 1.05 mmol) in one portion at room temperature. The mixture was stirred for 30 minutes, quenched with 1 N HCl, and extracted with EtOAc. The combined organic layers were washed with water and brine, dried (MgSO$_4$), and concentrated. The crude product was chromatographed on silica gel (0-30% EtOAc/hexane) to afford 46.2 (0.164 g, 99%) as a colorless oil.

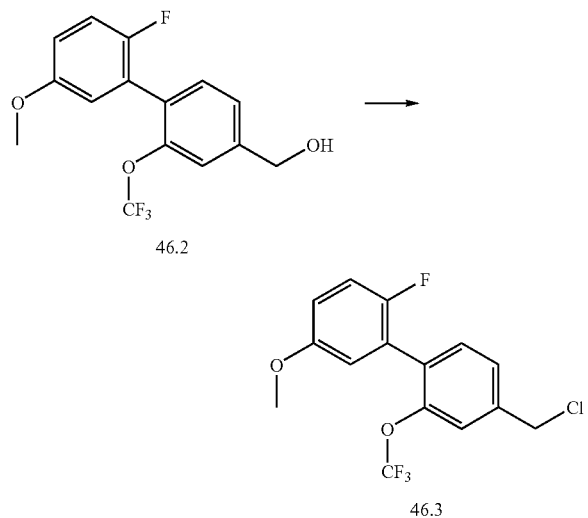

4-(Chloromethyl)-2'-fluoro-5'-(methyloxy)-2-((trifluoromethyl)oxy)-1,1'-biphenyl (46.3). To a solution of 46.2 (0.164 g, 0.52 mmol) in DCM (5 mL) was added thionyl chloride (76 µL, 1.04 mmol) in one portion at room temperature. The mixture was stirred overnight and concentrated. The crude product was chromatographed on silica gel (0-10% EtOAc/hexane) to afford 46.3 (0.009 g, 5%) as a colorless oil.

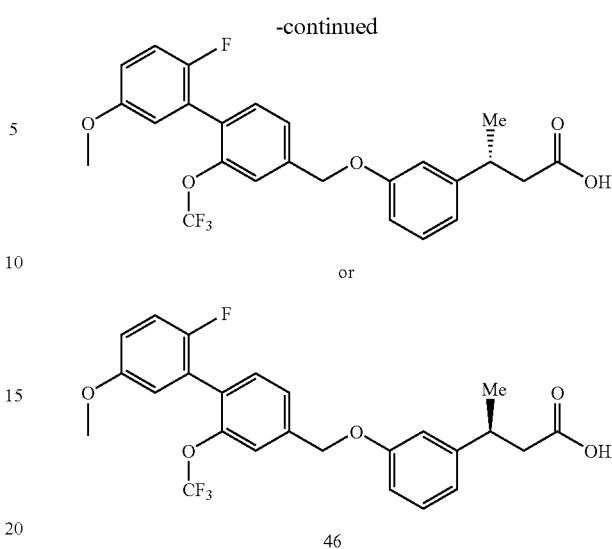

(3R)-3-(3-(((2'-Fluoro-5'-(methyloxy)-2-((trifluoromethyl)oxy)-1,1'-biphenyl-4-yl)methyl)oxy)phenyl)butanoic acid or (3S)-3-(3-(((2'-fluoro-5'-(methyloxy)-2-((trifluoromethyl)oxy)-1,1'-biphenyl-4-yl)methyl)oxy)phenyl)butanoic acid (46). Compound 5.7 (0.006 g, 0.029 mmol) was coupled with 46.3 (0.009 g, 0.026 mmol) according to the method described for preparation of 42 to afford 46 (0.009 g, 69%) as a colorless oil. $^1$H NMR (400 MHz, CDCl$_3$) δ ppm 7.44 (m, 3H), 7.25 (t, 1H), 7.07 (t, 1H), 6.86 (m, 5H), 5.11 (s, 2H), 3.81 (s, 3H), 3.27 (m, 1H), 2.68 (dd, 1H), 2.58 (dd, 1H), 1.32 (d, 3H).

Example 47

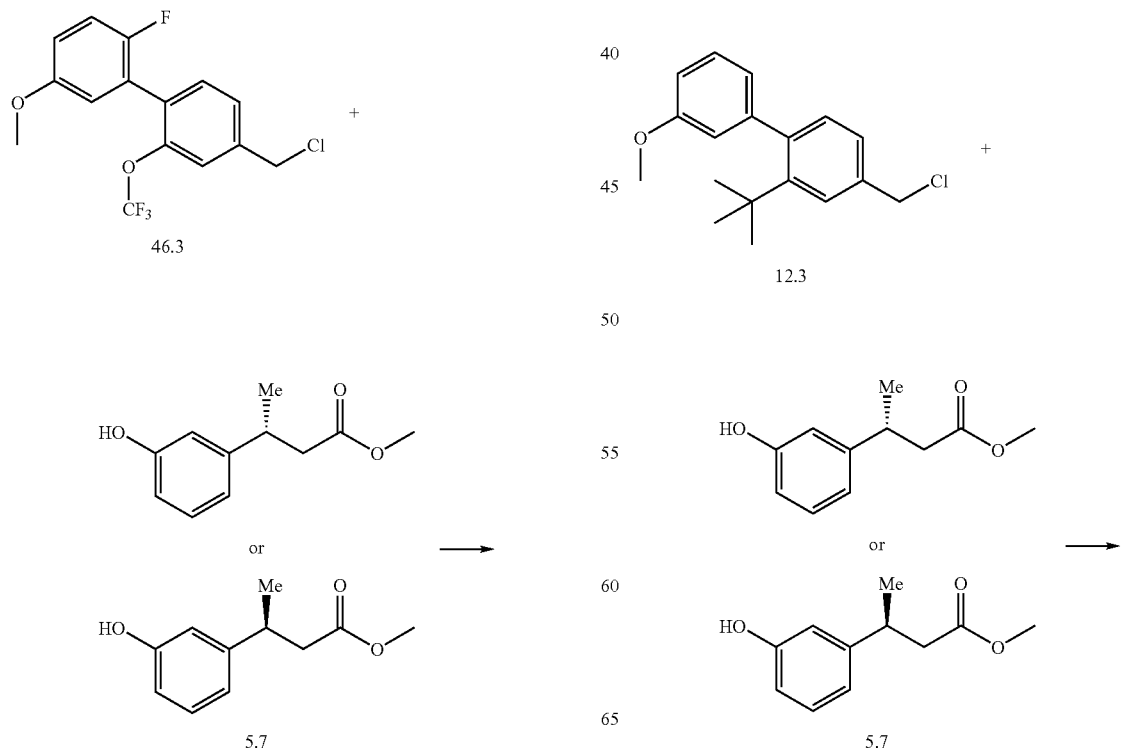

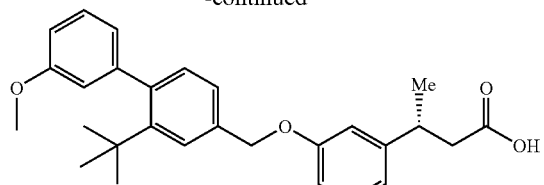

or

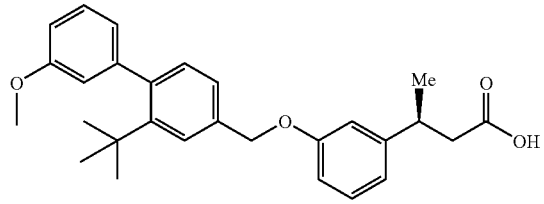

47

(3R)-3-(3-(((2-(1,1-Dimethylethyl)-3'-(methyloxy)-1,1'-biphenyl-4-yl)methyl)oxy)phenyl)butanoic acid or (3S)-3-(3-(((2-(1,1-dimethylethyl)-3'-(methyloxy)-1,1'-biphenyl-4-yl)methyl)oxy)phenyl)butanoic acid (47). Compound 5.7 (0.021 g, 0.11 mmol) was coupled with 12.3 (0.034 g, 0.12 mmol) according to the method described for preparation of 42 to afford 47 (0.042 g, 90%) as a colorless oil. $^1$H NMR (400 MHz, CDCl$_3$) δ ppm 7.58 (d, 1H), 7.25 (t, 3H), 7.06 (d, 1H), 6.87 (m, 6H), 5.07 (s, 2H), 3.81 (s, 3H), 3.27 (m, 1H), 2.69 (dd, 1H), 2.58 (dd, 1H), 1.33 (d, 3H), 1.22 (s, 9H).

Example 48

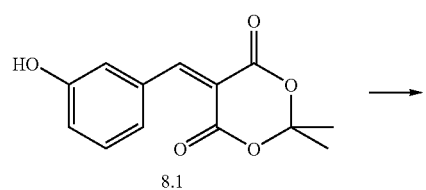

8.1

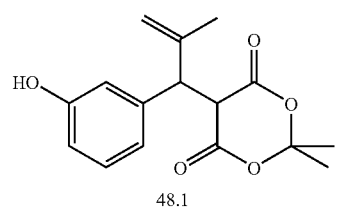

48.1

5-(1-(3-Hydroxyphenyl)-2-methyl-2-propenyl)-2,2-dimethyl-1,3-dioxane-4,6-dione (48.1). Compound 8.1 (2.00 g, 8.1 mmol) was treated with isopropenylmagnesium bromide (available from Aldrich) (0.5 M in THF) (97 mL, 48 mmol) according to the method described for preparation of 43.1 to afford 48.1 (0.88 g, 38%) as a yellow oil.

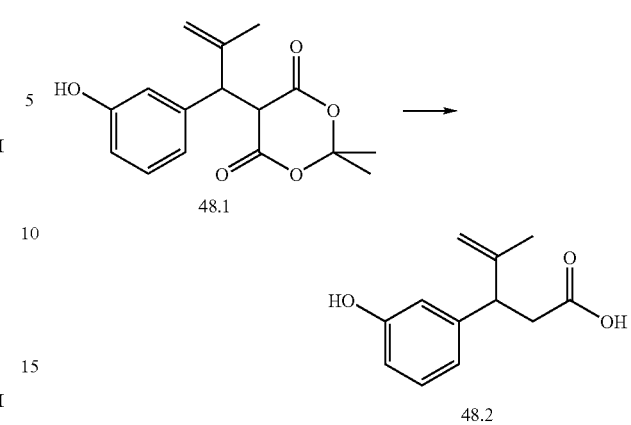

3-(3-Hydroxyphenyl)-4-methyl-4-pentenoic acid (48.2). Compound 48.1 (0.88 g, 3.0 mmol) was hydrolyzed according to the method described for preparation of 43.2 to afford 48.2 (0.63 g).

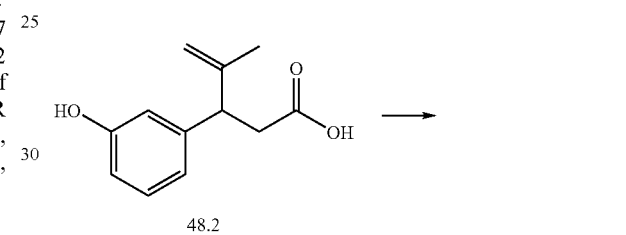

48.2

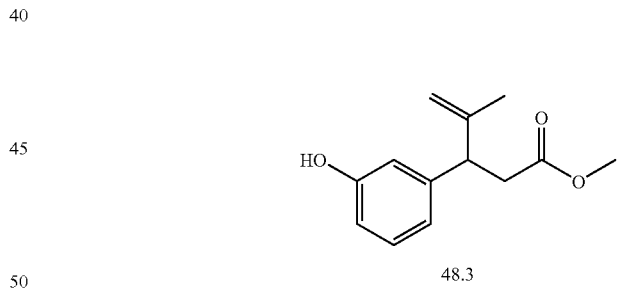

48.3

Methyl 3-(3-hydroxyphenyl)-4-methyl-4-pentenoate (48.3). Compound 48.2 (0.63 g, 3.1 mmol) was esterified according to the method described for preparation of 43.3 to afford 48.3 (0.56 g, 83%) as a colorless oil.

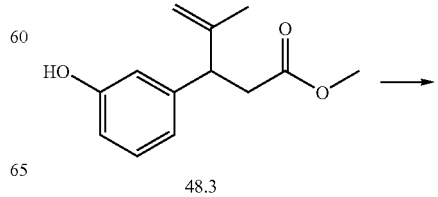

48.3

-continued

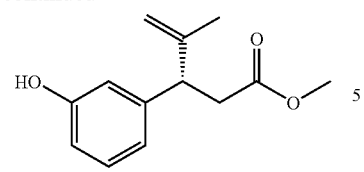

or

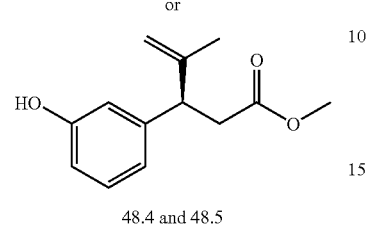

48.4 and 48.5

Methyl (3S)-3-(3-hydroxyphenyl)-4-methyl-4-pentenoate and methyl (3R)-3-(3-hydroxyphenyl)-4-methyl-4-pentenoate (48.4 and 48.5). Racemate 48.3 (0.56 g, 2.5 mmol) was resolved by chiral HPLC (Chiralcel OD column, 3% IPA/hexane, 220 nm) to afford 48.4 (0.25 g, 19.0 minutes) and 48.5 (0.26 g, 23.8 minutes) as colorless oils.

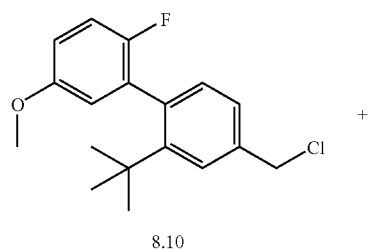

8.10

-continued

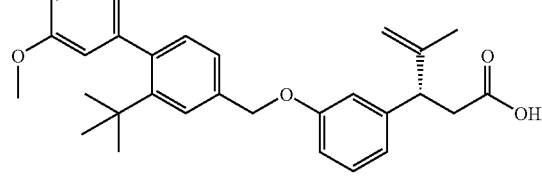

or

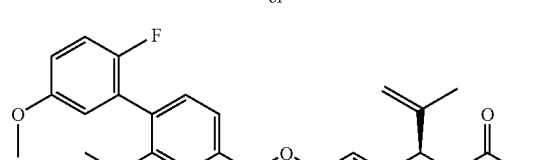

48

(3R)-3-(3-(((2-(1,1-Dimethylethyl)-2'-fluoro-5'-(methyloxy)-1,1'-biphenyl-4-yl)methyl)oxy)phenyl)-4-methyl-4-pentenoic acid or (3S)-3-(3-(((2-(1,1-dimethylethyl)-2'-fluoro-5'-(methyloxy)-1,1'-biphenyl-4-yl)methyl)oxy) phenyl)-4-methyl-4-pentenoic acid (48). Compound 48.5 (0.015 g, 0.068 mmol) was coupled with 8.10 (0.023 g, 0.075 mmol) according to the method described for preparation of 42 to afford 48 (0.032 g, 99%) as a colorless oil. $^1$H NMR (400 MHz, CDCl$_3$) δ ppm 7.59 (d, 1H), 7.28 (dd, 1H), 7.24 (t, 1H), 7.04 (d, 1H), 6.99 (t, 1H), 6.86 (m, 4H), 6.76 (dd, 1H), 5.07 (s, 2H), 4.93 (s, 1H), 4.90 (bt, 1H), 3.78 (s, 3H), 3.76 (t, 1H), 2.89 (dd, 1H), 2.75 (dd, 1H), 1.62 (s, 3H), 1.23 (s, 9H).

Example 49

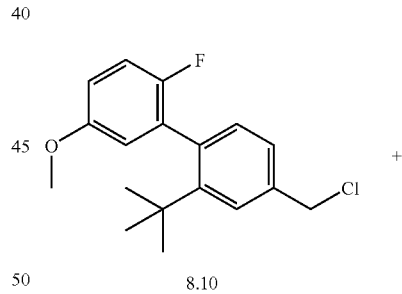

8.10

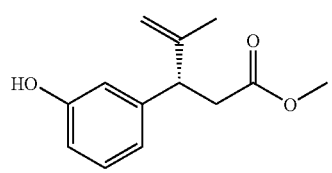

or

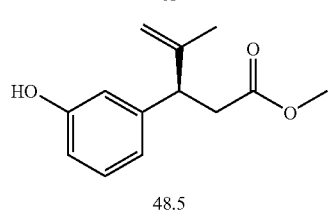

48.4


or

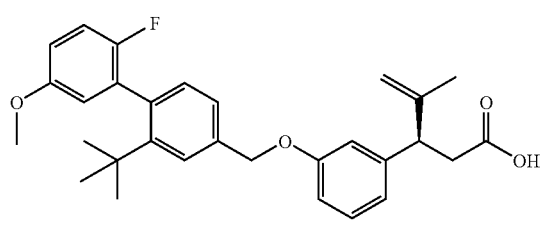

49

(3S)-3-(3-(((2-(1,1-Dimethylethyl)-2'-fluoro-5'-(methyloxy)-1,1'-biphenyl-4-yl)methyl)oxy)phenyl)-4-methyl-4-pentenoic acid or (3R)-3-(3-(((2-(1,1-dimethylethyl)-2'-fluoro-5'-(methyloxy)-1,1'-biphenyl-4-yl)methyl)oxy)phenyl)-4-methyl-4-pentenoic acid (49). Compound 48.4 (0.015 g, 0.068 mmol) was coupled with 8.10 (0.023 g, 0.075 mmol) according to the method described for preparation of 42 to afford 49 (0.024 g, 74%) as a colorless oil. $^1$H NMR (400 MHz, CDCl$_3$) δ ppm 7.59 (d, 1H), 7.28 (dd, 1H), 7.24 (t, 1H), 7.04 (d, 1H), 6.99 (t, 1H), 6.86 (m, 4H), 6.76 (dd, 1H), 5.07 (s, 2H), 4.93 (s, 1H), 4.90 (bt, 1H), 3.78 (s, 3H), 3.76 (t, 1H), 2.89 (dd, 1H), 2.75 (dd, 1H), 1.62 (s, 3H), 1.23 (s, 9H).

Example 50

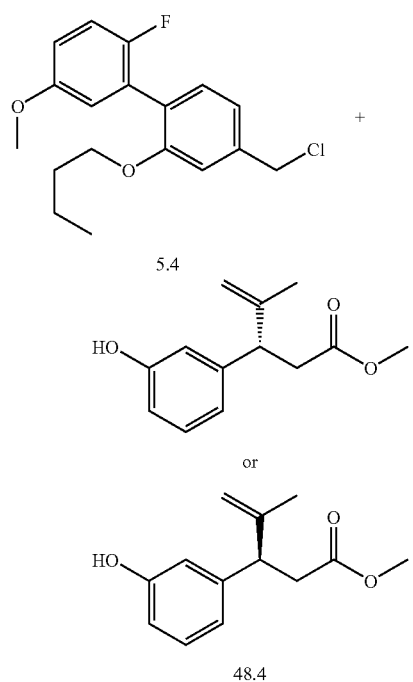

(3S)-3-(3-(((2-(Butyloxy)-2'-fluoro-5'-(methyloxy)-1,1'-biphenyl-4-yl)methyl)oxy)phenyl)-4-methyl-4-pentenoic acid or (3R)-3-(3-(((2-(butyloxy)-2'-fluoro-5'-(methyloxy)-1,1'-biphenyl-4-yl)methyl)oxy)phenyl)-4-methyl-4-pentenoic acid (50). Compound 48.4 (0.014 g, 0.064 mmol) was coupled with 5.4 (0.023 g, 0.070 mmol) according to the method described for preparation of 42 to afford 50 (0.027 g, 87%) as a colorless oil. $^1$H NMR (400 MHz, CDCl$_3$) δ ppm 7.28 (d, 1H), 7.23 (t, 1H), 7.06 (m, 2H), 7.02 (t, 1H), 6.85 (m, 5H), 5.06 (s, 2H), 4.93 (s, 1H), 4.90 (s, 1H), 3.98 (t, 2H), 3.79 (s, 3H), 3.76 (t, 1H), 2.88 (dd, 1H), 2.75 (dd, 1H), 1.66 (m, 2H), 1.62 (s, 3H), 1.37 (m, 2H), 0.88 (t, 3H).

Example 51

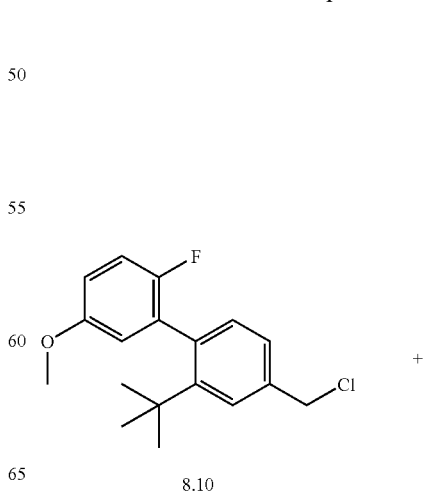

163

-continued

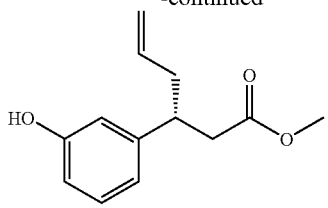

or

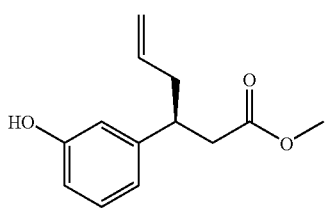

43.4

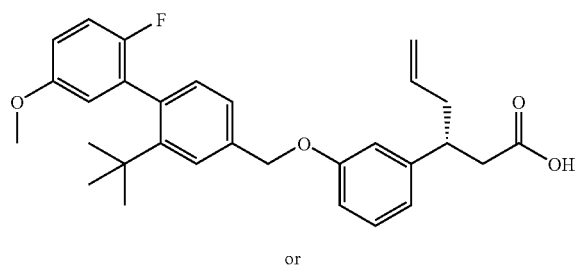

or

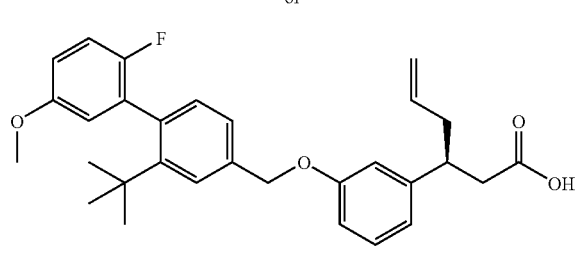

51

(3R)-3-(3-(((2-(1,1-Dimethylethyl)-2'-fluoro-5'-(methyloxy)-1,1'-biphenyl-4-yl)methyl)oxy)phenyl)-5-hexenoic acid or (3S)-3-(3-(((2-(1,1-dimethylethyl)-2'-fluoro-5'-(methyloxy)-1,1'-biphenyl-4-yl)methyl)oxy)phenyl)-5-hexenoic acid (51). Compound 43.4 (0.015 g, 0.068 mmol) was coupled with 8.10 (0.023 g, 0.075 mmol) according to the method described for preparation of 42 to afford 51 (0.029 g, 89%) as a colorless oil. $^{1}$H NMR (400 MHz, CDCl$_3$) δ ppm 7.60 (d, 1H), 7.29 (dd, 1H), 7.24 (t, 1H), 7.05 (d, 1H), 7.00 (t, 1H), 6.84 (m, 4H), 6.77 (dd, 1H), 5.65 (m, 1H), 5.07 (s, 2H),

164

5.00 (m, 2H), 3.78 (s, 3H), 3.19 (m, 1H), 2.72 (dd, 1H), 2.61 (dd, 1H), 2.39 (t, 2H), 1.23 (s, 9H).

Example 52


or


48.4

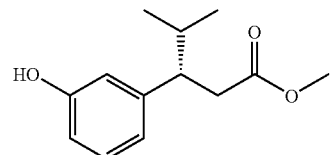

or

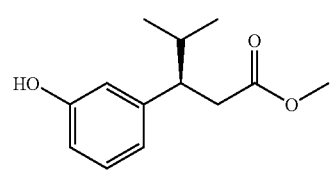

52.1

Methyl (3S)-3-(3-hydroxyphenyl)-4-methylpentanoate or methyl (3R)-3-(3-hydroxyphenyl)-4-methylpentanoate (52.1). Compound 48.4 (0.10 g, 0.45 mmol) was hydrogenated according to the method described for preparation of 43.6 to afford 52.1 (0.10 g, 99%) as a colorless oil.

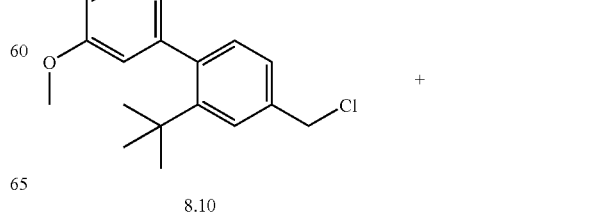

8.10

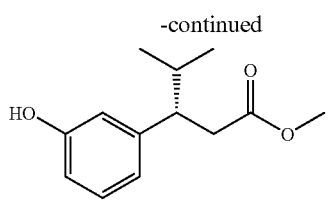

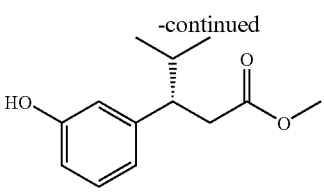

or

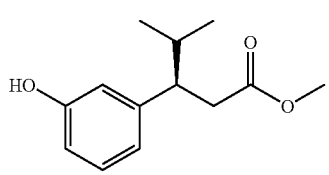

52.1

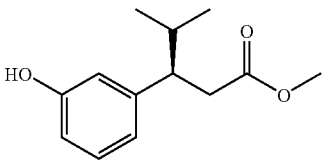

52.1

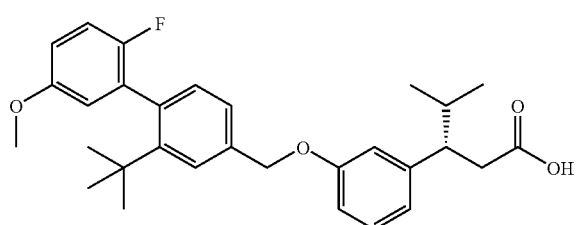

or

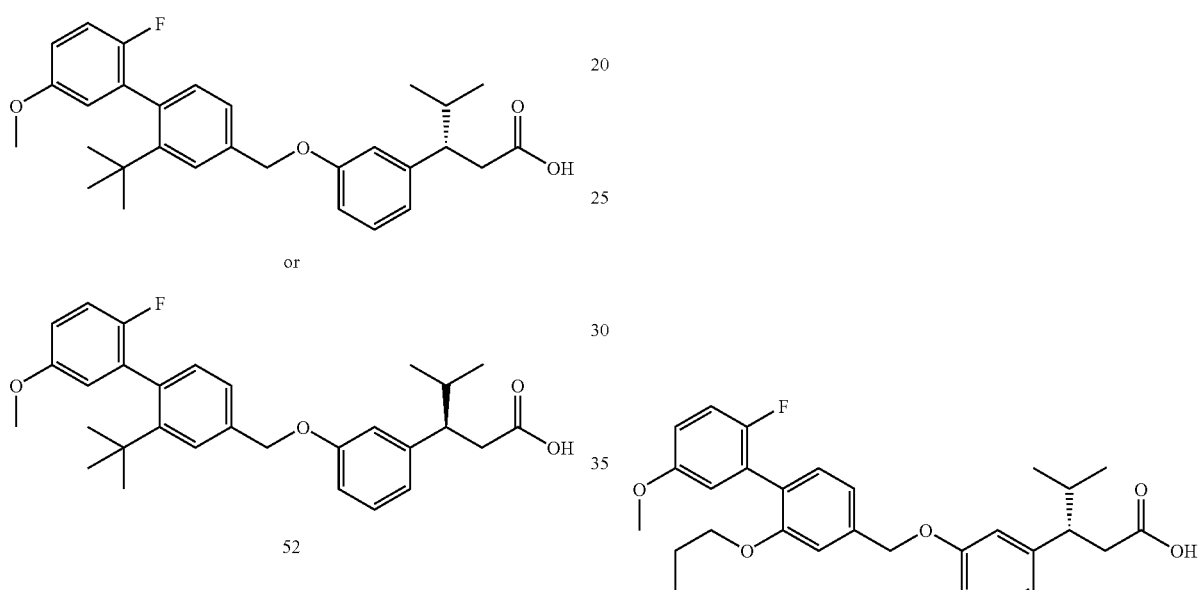

52

Compound (52). Compound 52.1 (0.015 g, 0.067 mmol) was coupled with 8.10 (0.023 g, 0.074 mmol) according to the method described for preparation of 42 to afford 52 (0.028 g, 87%) as a colorless oil. $^1$H NMR (400 MHz, CDCl$_3$) δ ppm 7.60 (d, 1H), 7.29 (dd, 1H), 7.21 (t, 1H), 7.04 (d, 1H), 6.99 (t, 1H), 6.85 (m, 2H), 6.78 (m, 3H), 5.07 (s, 2H), 3.78 (s, 3H), 2.86 (m, 1H), 2.79 (dd, 1H), 2.62 (dd, 1H), 1.84 (m, 1H), 1.23 (s, 9H), 0.93 (d, 3H), 0.76 (d, 3H).

Example 53

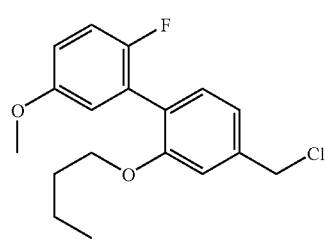

5.4

+

(3S)-3-(3-(((2-(1,1-Dimethylethyl)-2'-fluoro-5'-(methyloxy)-1,1'-biphenyl-4-yl)methyl)oxy)phenyl)-4-methylpentanoic acid or (3R)-3-(3-(((2-(1,1-dimethylethyl)-2'-fluoro-5'-(methyloxy)-1,1'-biphenyl-4-yl)methyl)oxy)phenyl)-4-methylpentanoic acid (53). Compound 52.1 (0.015 g, 0.067 mmol) was coupled with 5.4 (0.024 g, 0.074 mmol) according to the method described for preparation of 42 to afford 53 (0.028 g, 83%) as a colorless oil. $^1$H NMR (400 MHz, CDCl$_3$) δ ppm 7.28 (d, 1H), 7.21 (t, 1H), 7.06 (m, 2H), 7.02 (t, 1H), 6.82 (m, 5H), 5.06 (s, 2H), 3.98 (t, 2H), 3.79 (s, 3H), 2.86 (m, 1H), 2.79 (dd, 1H), 2.61 (dd, 1H), 1.85 (m, 1H), 1.66 (m, 2H), 1.37 (m, 2H), 0.93 (d, 3H), 0.88 (t, 3H), 0.76 (d, 3H).

Example 54

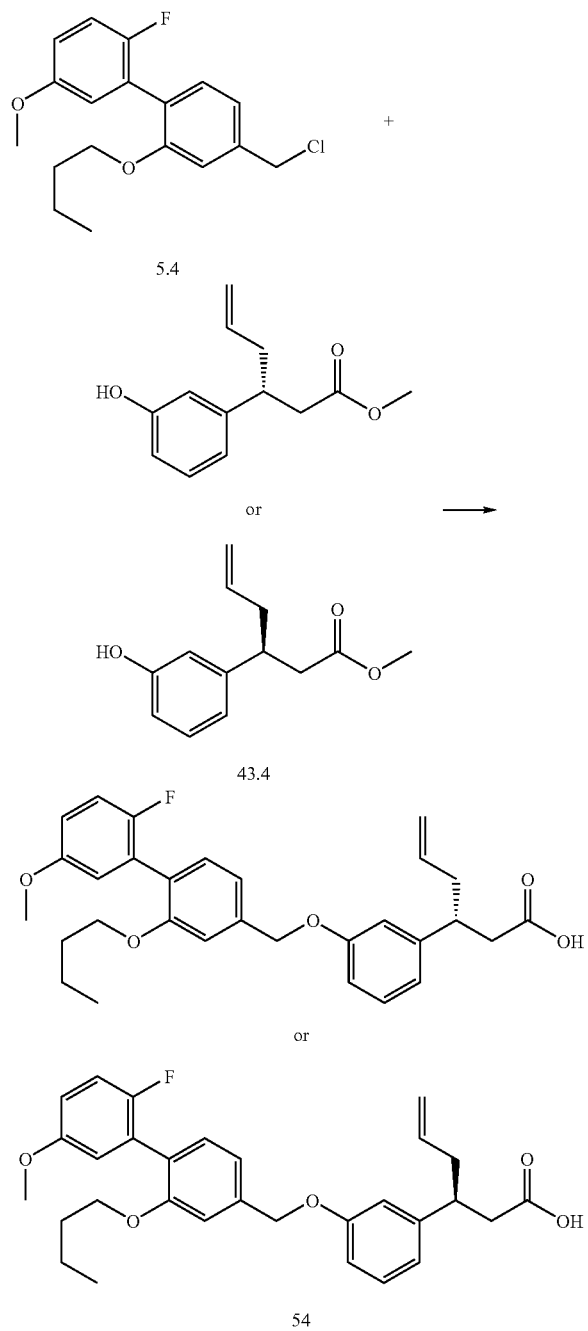

54

(3R)-3-(3-(((2-(Butyloxy)-2'-fluoro-5'-(methyloxy)-1,1'-biphenyl-4-yl)methyl)oxy)phenyl)-5-hexenoic acid or (3S)-3-(3-(((2-(butyloxy)-2'-fluoro-5'-(methyloxy)-1,1'-biphenyl-4-yl)methyl)oxy)phenyl)-5-hexenoic acid (54). Compound 43.4 (0.015 g, 0.068 mmol) was coupled with 5.4 (0.024 g, 0.075 mmol) according to the method described for preparation of 42 to afford 54 (0.026 g, 79%) as a colorless oil. $^1$H NMR (400 MHz, CDCl$_3$) δ ppm 7.29 (d, 1H), 7.23 (t, 1H), 7.06 (m, 2H), 7.02 (t, 1H), 6.85 (m, 5H), 5.65 (m, 1H), 5.06 (s, 2H), 5.00 (m, 2H), 3.99 (t, 2H), 3.79 (s, 3H), 3.18 (m, 1H), 2.72 (dd, 1H), 2.60 (dd, 1H), 2.39 (t, 2H), 1.66 (m, 2H), 1.37 (m, 2H), 0.88 (t, 3H).

Example 55

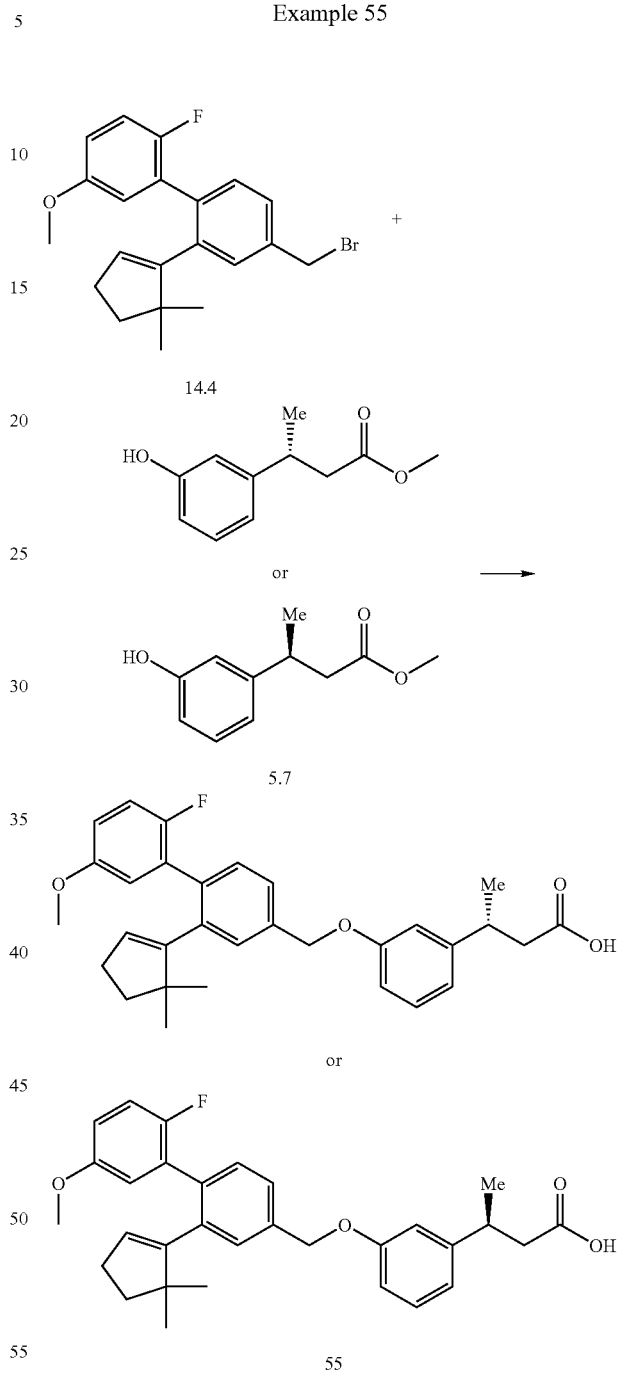

55

(3R)-3-(3-(((2-(5,5-Dimethyl-1-cyclopenten-1-yl)-2'-fluoro-5'-(methyloxy)-1,1'-biphenyl-4-yl)methyl)oxy)phenyl)butanoic acid or (3S)-3-(3-(((2-(5,5-dimethyl-1-cyclopenten-1-yl)-2'-fluoro-5'-(methyloxy)-1,1'-biphenyl-4-yl)methyl)oxy)phenyl)butanoic acid (55). Compound 5.7 (0.012 g, 0.062 mmol) was coupled with 14.4 (0.026 g, 0.068 mmol) according to the method described for preparation of 42 to afford 55 (0.021 g, 71%) as a colorless oil. $^1$H NMR (400 MHz, CDCl$_3$) δ ppm 7.39 (dd, 1H), 7.33 (d, 1H), 7.29 (bd, 1H), 7.24 (t, 1H), 6.96 (t, 1H), 6.86 (m, 3H), 6.79 (m, 2H), 5.52 (bt, 1H), 5.08 (s, 2H), 3.75 (s, 3H), 3.26 (m, 1H), 2.68 (dd, 1H), 2.57 (dd, 1H), 2.24 (dt, 2H), 1.65 (t, 2H), 1.32 (d, 3H), 0.85 (s, 6H).

2H), 4.93 (s, 1H), 4.90 (bt, 1H), 3.81 (s, 3H), 3.76 (t, 1H), 2.89 (dd, 1H), 2.75 (dd, 1H), 1.62 (s, 3H), 1.22 (s, 9H).

Example 56

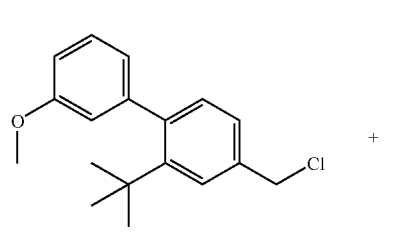

12.3

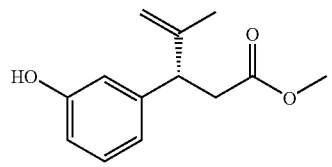

or

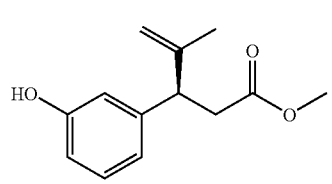

48.4

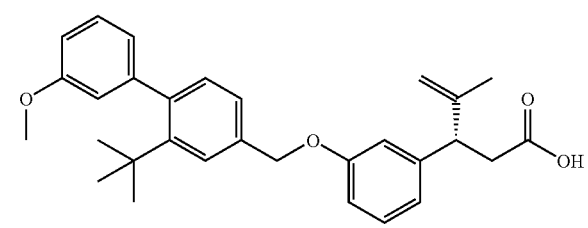

or

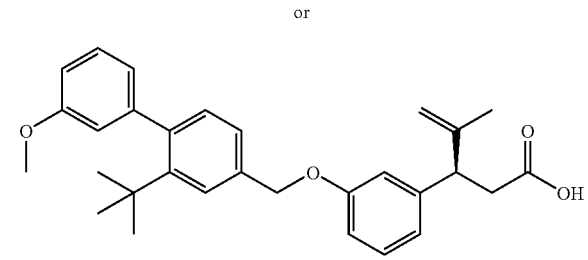

56

Example 57

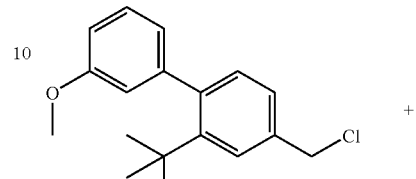

12.3

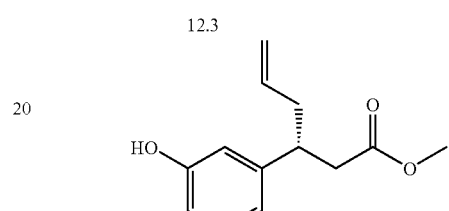

or

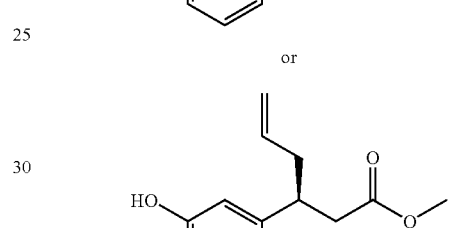

43.4

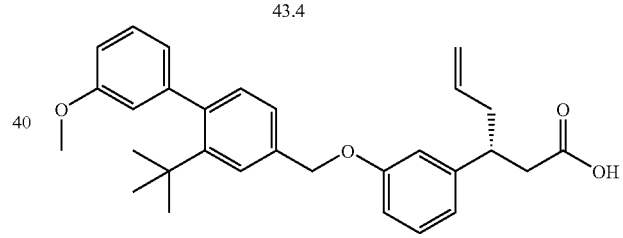

or

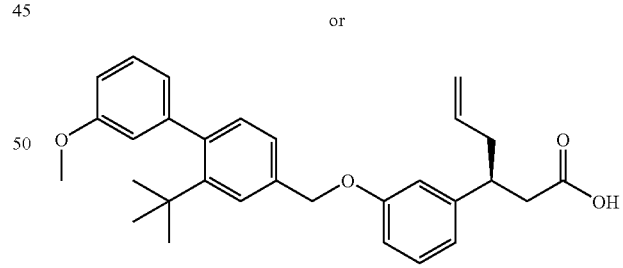

57

(3S)-3-(3-(((2-(1,1-Dimethylethyl)-3'-(methyloxy)-1,1'-biphenyl-4-yl)methyl)oxy)phenyl)-4-methyl-4-pentenoic acid or (3R)-3-(3-(((2-(1,1-dimethylethyl)-3'-(methyloxy)-1,1'-biphenyl-4-yl)methyl)oxy)phenyl)-4-methyl-4-pentenoic acid (56). Compound 48.4 (0.015 g, 0.068 mmol) was coupled with 12.3 (0.022 g, 0.075 mmol) according to the method described for preparation of 42 to afford 56 (0.028 g, 89%) as a colorless oil. $^1$H NMR (400 MHz, CDCl$_3$) δ ppm 7.56 (d, 1H), 7.24 (m, 3H), 7.05 (d, 1H), 6.86 (m, 6H), 5.06 (s, (3R)-3-(3-(((2-(1,1-dimethylethyl)-3'-(methyloxy)-1,1'-biphenyl-4-yl)methyl)oxy)phenyl)-5-hexenoic acid or (3S)-3-(3-(((2-(1,1-dimethylethyl)-3'-(methyloxy)-1,1'-biphenyl-4-yl)methyl)oxy)phenyl)-5-hexenoic acid (57). Compound 43.4 (0.015 g, 0.068 mmol) was coupled with 12.3 (0.022 g, 0.075 mmol) according to the method described for preparation of 42 to afford 57 (0.027 g, 88%) as a colorless oil. $^1$H NMR (400 MHz, CDCl$_3$) δ ppm 7.57 (d, 1H), 7.24 (m, 3H), 7.05 (d, 1H), 6.87 (m, 4H), 6.82 (m, 2H), 5.65 (m, 1H), 5.06

(s, 2H), 5.00 (m, 2H), 3.81 (s, 3H), 3.19 (m, 1H), 2.72 (dd, 1H), 2.61 (dd, 1H), 2.39 (t, 2H), 1.22 (s, 9H).

6.81 (m, 2H), 6.77 (d, 1H), 5.06 (s, 2H), 3.81 (s, 3H), 2.87 (m, 1H), 2.79 (dd, 1H), 2.62 (dd, 1H), 1.85 (m, 1H), 1.21 (s, 9H), 0.93 (d, 3H), 0.76 (d, 3H).

Example 58

Example 59

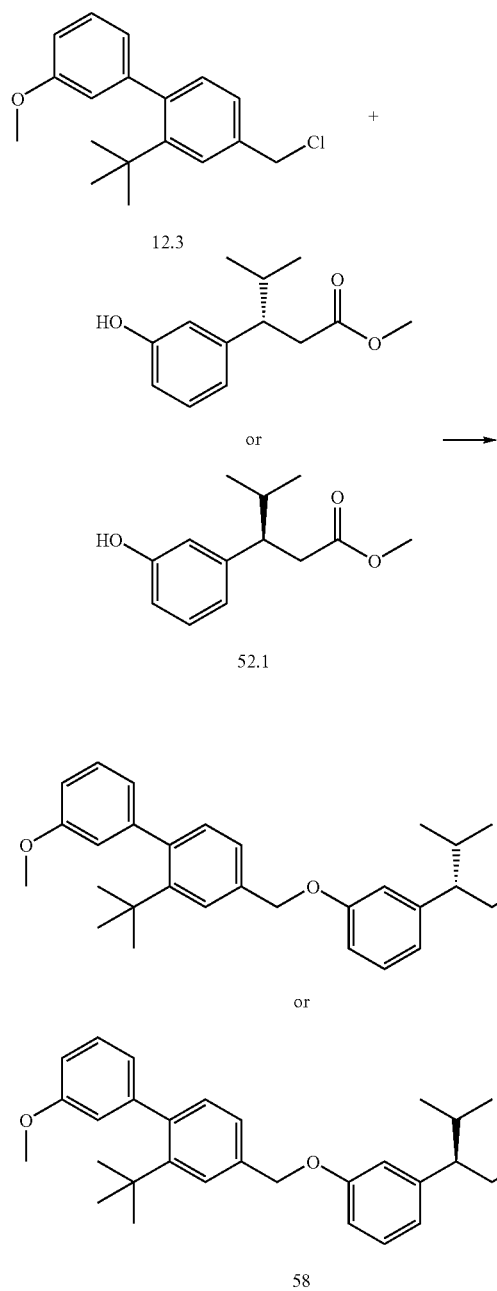

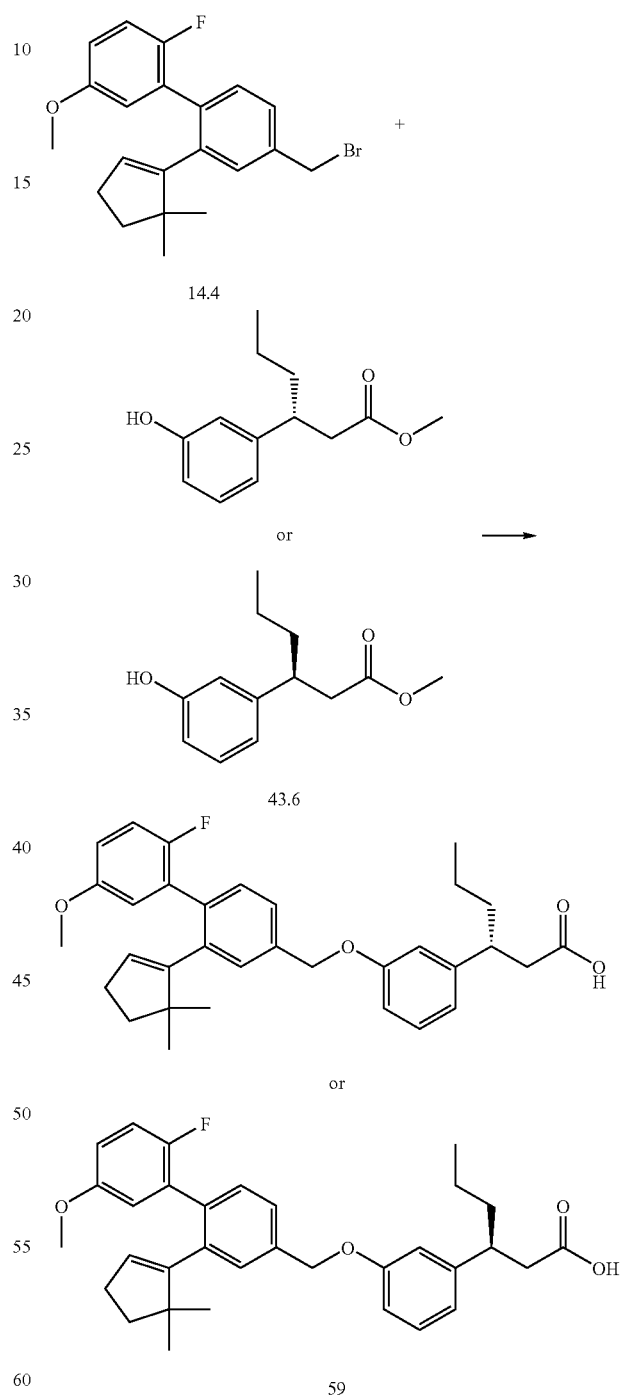

(3S)-3-(3-(((2-(1,1-Dimethylethyl)-3'-(methyloxy)-1,1'-biphenyl-4-yl)methyl)oxy)phenyl)-4-methylpentanoic acid or (3R)-3-(3-(((2-(1,1-dimethylethyl)-3'-(methyloxy)-1,1'-biphenyl-4-yl)methyl)oxy)phenyl)-4-methylpentanoic acid (58). Compound 52.1 (0.015 g, 0.067 mmol) was coupled with 12.3 (0.021 g, 0.074 mmol) according to the method described for preparation of 42 to afford 58 (0.028 g, 91%) as a colorless oil. $^1$H NMR (400 MHz, CDCl$_3$) δ ppm 7.57 (d, 1H), 7.25 (m, 2H), 7.21 (t, 1H), 7.04 (d, 1H), 6.87 (m, 3H), (3R)-3-(3-(((2-(5,5-Dimethyl-1-cyclopenten-1-yl)-2'-fluoro-5'-(methyloxy)-1,1'-biphenyl-4-yl)methyl)oxy)phenyl)hexanoic acid or (3S)-3-(3-(((2-(5,5-dimethyl-1-cyclopenten-1-yl)-2'-fluoro-5'-(methyloxy)-1,1'-biphenyl-4-yl)methyl)oxy)phenyl)hexanoic acid (59). Compound 43.6

(0.015 g, 0.067 mmol) was coupled with 14.4 (0.029 g, 0.074 mmol) according to the method described for preparation of 42 to afford 59 (0.020 g, 58%) as a colorless oil. $^1$H NMR (400 MHz, CDCl$_3$) δ ppm 7.39 (dd, 1H), 7.33 (d, 1H), 7.29 (d, 1H), 7.22 (t, 1H), 6.96 (t, 1H), 6.82 (m, 5H), 5.52 (bt, 1H), 5.08 (s, 2H), 3.75 (s, 3H), 3.07 (m, 1H), 2.62 (m, 2H), 2.24 (dt, 2H), 1.65 (t, 2H), 1.60 (m, 2H), 1.18 (m, 2H), 0.85 (m, 9H).

Example 60

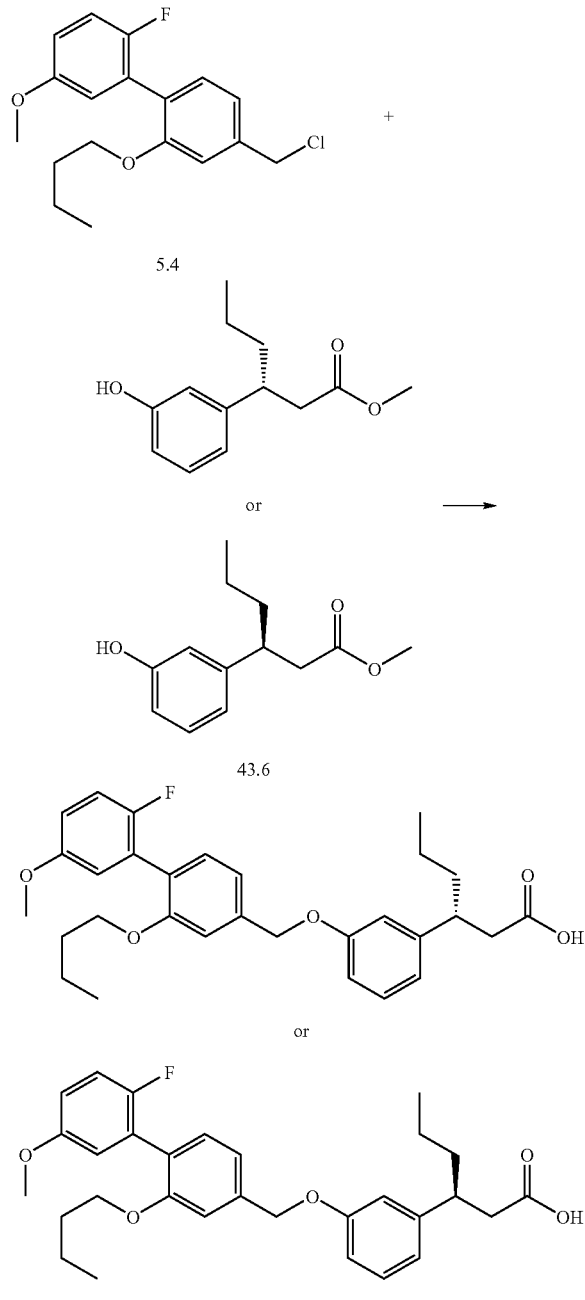

(3R)-3-(3-(((2-(Butyloxy)-2'-fluoro-5'-(methyloxy)-1,1'-biphenyl-4-yl)methyl)oxy)phenyl)hexanoic acid or (3S)-3-(3-(((2-(butyloxy)-2'-fluoro-5'-(methyloxy)-1,1'-biphenyl-4-yl)methyl)oxy)phenyl)hexanoic acid (60). Compound 43.6 (0.015 g, 0.067 mmol) was coupled with 5.4 (0.024 g, 0.074 mmol) according to the method described for preparation of 42 to afford 60 (0.027 g, 83%) as a colorless oil. $^1$H NMR (400 MHz, CDCl$_3$) δ ppm 7.29 (d, 1H), 7.23 (t, 1H), 7.06 (m, 2H), 7.02 (t, 1H), 6.84 (m, 5H), 5.07 (s, 2H), 3.99 (t, 2H), 3.79 (s, 3H), 3.08 (m, 1H), 2.63 (m, 2H), 1.65 (m, 2H), 1.61 (m, 2H), 1.37 (m, 2H), 1.18 (m, 2H), 0.88 (t, 3H), 0.85 (t, 3H).

Example 61

The following compounds were prepared from commercially available methyl 3-(3-hydroxyphenyl)propanoate (available from Aagile Labs Division of Tyger Scientific) and the appropriate halomethyl or hydroxymethyl compound according to the methods described herein.

TABLE 1

| Compound | TG |
|---|---|
| 61.1 | 2-(2,2-dimethylcyclopentyl)-2'-fluoro-5'-methoxybiphenyl |
| 61.2 | 2-(2,2-dimethylcyclopentyl)biphenyl |
| 61.3 | 2-(2,2-dimethylcyclopentyl)-3'-methoxybiphenyl |
| 61.4 | 2-tert-butyl-3'-(methylthio)biphenyl |

3-(3-(((2-(2,2-Dimethylcyclopentyl)-2'-fluoro-5'-(methyloxy)-1,1'-biphenyl-4-yl)methyl)oxy)phenyl)propanoic acid (61.1). MS ESI (neg.) m/e: 475.1 (M–H).

3-(3-(((2-(2,2-Dimethylcyclopentyl)-1,1'-biphenyl-4-yl)methyl)oxy)phenyl)propanoic acid (61.2). MS ESI (neg) m/e: 425.2 (M–H).

3-(3-(((2-(2,2-Dimethylcyclopentyl)-3'-(methyloxy)-1,1'-biphenyl-4-yl)methyl)oxy)phenyl)propanoic acid (61.3). MS ESI (neg.) m/e: 455.3 (M–H).

3-(3-(((2-(1,1-Dimethylethyl)-3'-(methylsulfanyl)-1,1'-biphenyl-4-yl)methyl)oxy)phenyl)propanoic acid (61.4). MS ESI (neg.) m/e: 433.1 (M–H).

Example 62

Synthesis of methyl (2R)-3-(3-hydroxyphenyl)-2-methylpropanoate (62) and methyl (2S)-3-(3-hydroxyphenyl)-2-methylpropanoate (63)

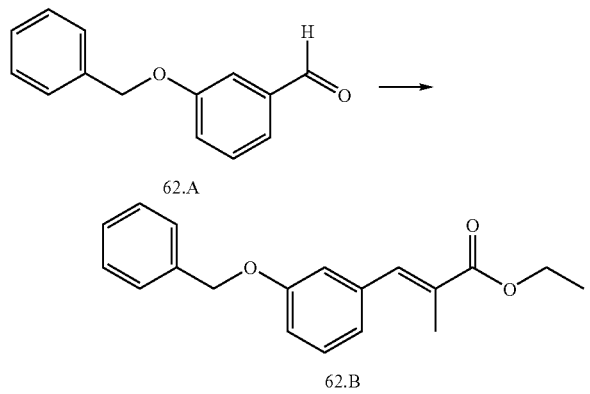

(E)-Ethyl 3-(3-(benzyloxy)phenyl)-2-methylacrylate (62.B). To a solution of (carbethoxyethylidene)triphenylphosphorane (available from Aldrich) (5.50 g, 15.2 mmol) in THF (25 mL) was added 3-(benzyloxy)benzaldehyde (available from Aldrich) (2.93 g, 13.8 mmol) in THF (10 mL) under nitrogen at –78° C. The reaction was allowed to slowly warm to room temperature and stirred for 2 hours. EtOAc (100 mL) was added, and the mixture was washed with brine (30×2 mL). The organic layer was dried over MgSO$_4$. The solvent was removed by evaporation. The crude product was purified by passing through a short silica gel column, eluting with hexane/EtOAc (85/15) to give (E)-ethyl 3-(3-(benzyloxy)phenyl)-2-methylacrylate 62.B.

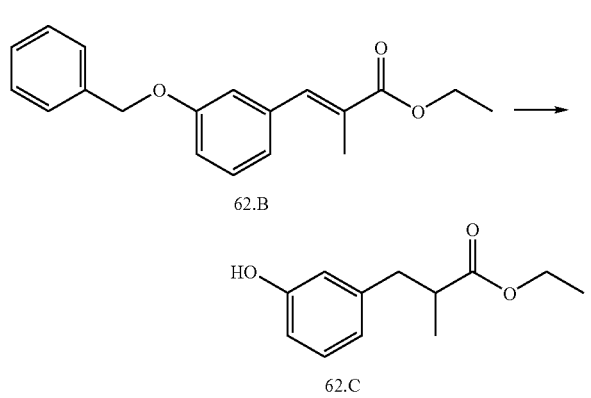

Ethyl 3-(3-hydroxyphenyl)-2-methylpropanoate (62.C). A mixture of (E)-ethyl 3-(3-(benzyloxy)phenyl)-2-methylacrylate 62.B (0.93 g, 3.1 mmol) and palladium on charcoal (10%, 0.1 g) in EtOH (25.0 mL) was flushed with hydrogen three times. The reaction mixture was stirred at room temperature for 2-3 hours. The catalyst was filtered away, and the solvent was removed. The residue, ethyl 3-(3-hydroxyphenyl)-2-methylpropanoate 62.C was used in the next step without further purification.

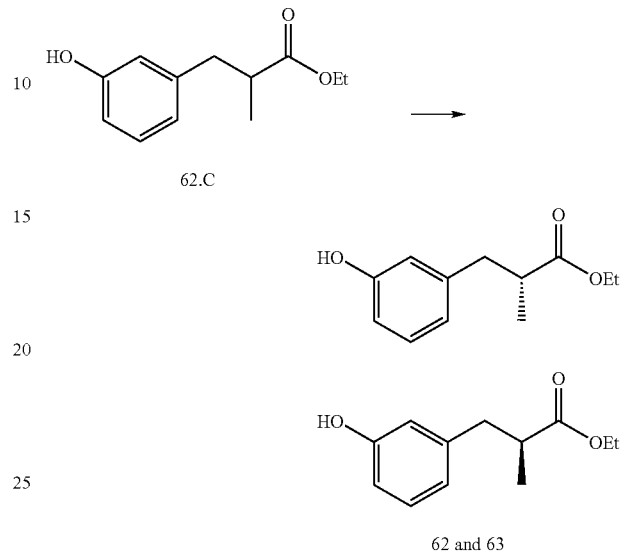

Methyl (2R)-3-(3-hydroxyphenyl)-2-methylpropanoate (62) and methyl (2S)-3-(3-hydroxyphenyl)-2-methylpropanoate (63). Racemic ethyl 3-(3-hydroxyphenyl)-2-methylpropanoate 62.C (0.40 g) was separated by ChiralPak OJ-H column, eluted with 10% isopropanol in hexane to give the separated enantiomers; (R)-ethyl 3-(3-hydroxyphenyl)-2-methylpropanoate and (S)-ethyl 3-(3-hydroxyphenyl)-2-methylpropanoate 62 and 63. MS ESI (pos.) m/e: 209.1 (M+H)$^+$.

The following compounds were prepared from 62 and the appropriate halomethyl or hydroxymethyl compound according to the methods described herein. Both of the compounds in the following table were prepared using the same enantiomer of the phenol.

TABLE 2

| Compound | TG |
|---|---|
| 62.1 | ![structure with F, cyclopentenyl, dimethyl] |

TABLE 2-continued

| | |
|---|---|
| 62.2 | 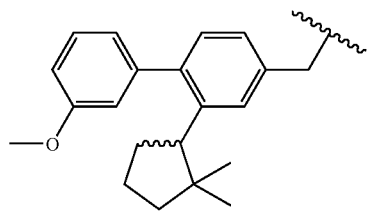 |

(2R)-3-(3-(((2-(5,5-Dimethyl-1-cyclopenten-1-yl)-2'-fluoro-5'-(methyloxy)-1,1'-biphenyl-4-yl)methyl)oxy)phenyl)-2-methylpropanoic acid or (2S)-3-(3-(((2-(5,5-dimethyl-1-cyclopenten-1-yl)-2'-fluoro-5'-(methyloxy)-1,1'-biphenyl-4-yl)methyl)oxy)phenyl)-2-methylpropanoic acid (62.1). MS ESI (neg.) m/e: 487.1 (M–H).

(2R)-3-(3-(((2-(2,2-Dimethylcyclopentyl)-2'-fluoro-5'-(methyloxy)-1,1'-biphenyl-4-yl)methyl)oxy)phenyl)-2-methylpropanoic acid or (2S)-3-(3-(((2-(2,2-dimethylcyclopentyl)-2'-fluoro-5'-(methyloxy)-1,1'-biphenyl-4-yl)methyl)oxy)phenyl)-2-methylpropanoic acid (62.2). MS ESI (neg.) m/e: 489.2 (M–H).

Example 63

The following compounds were prepared from 63 and the appropriate halomethyl or hydroxymethyl compound according to the methods described herein. Both of the compounds in the following table were prepared using the same enantiomer of the phenol.

TABLE 3

(2S)-3-(3-(((2-(5,5-Dimethyl-1-cyclopenten-1-yl)-2'-fluoro-5'-(methyloxy)-1,1'-biphenyl-4-yl)methyl)oxy)phenyl)-2-methylpropanoic acid or (2R)-3-(3-(((2-(5,5-dimethyl-1-cyclopenten-1-yl)-2'-fluoro-5'-(methyloxy)-1,1'-biphenyl-4-yl)methyl)oxy)phenyl)-2-methylpropanoic acid (63.1). MS ESI (neg.) m/e: 487.1 (M–H).

(2S)-3-(3-(((2-(2,2-Dimethylcyclopentyl)-2'-fluoro-5'-(methyloxy)-1,1'-biphenyl-4-yl)methyl)oxy)phenyl)-2-methylpropanoic acid or (2R)-3-(3-(((2-(2,2-dimethylcyclopentyl)-2'-fluoro-5'-(methyloxy)-1,1'-biphenyl-4-yl)methyl)oxy)phenyl)-2-methylpropanoic acid (63.2). MS ESI (neg.) m/e: 489.2 (M–H).

Example 64

The following compounds were prepared from 5.7 and the appropriate halomethyl or hydroxymethyl compound according to the methods described herein. Each of the compounds in the following table were prepared using the same enantiomer of the phenol.

TABLE 4

TABLE 4-continued
64.4 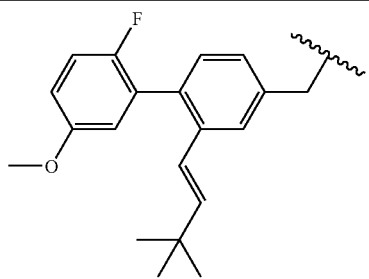
64.5 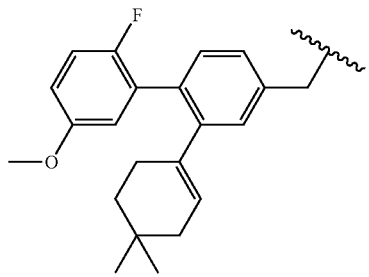
64.6 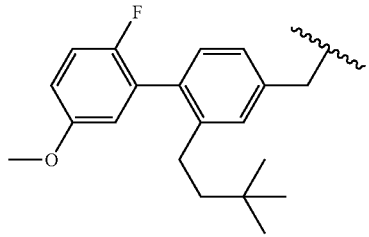
64.7 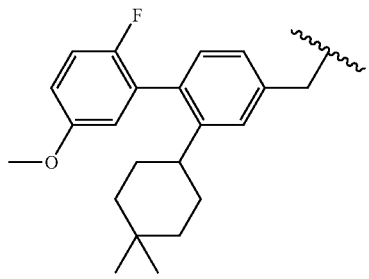
64.8 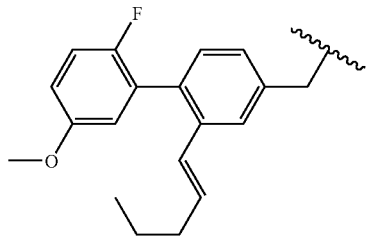
64.9 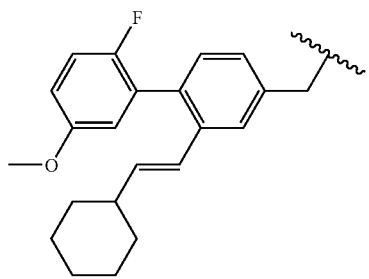
TABLE 4-continued
64.10 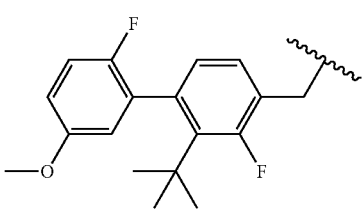
64.11 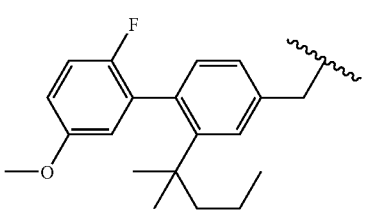
64.12 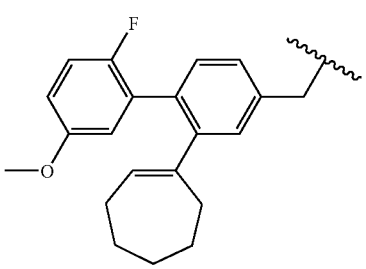
64.13 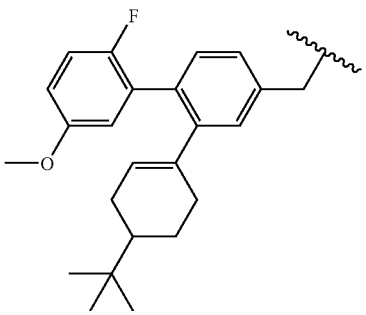
64.14 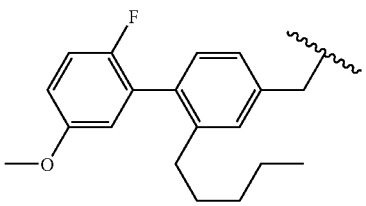
64.15 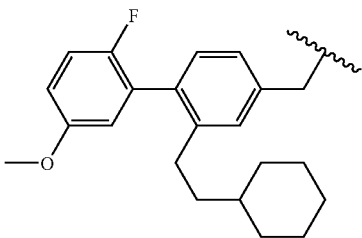

TABLE 4-continued

| | |
|---|---|
| 64.16 | 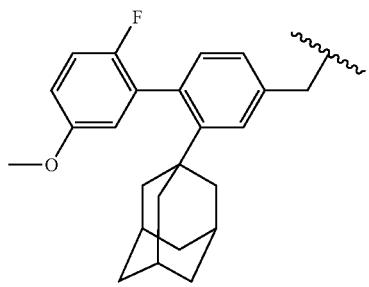 |
| 64.17 | 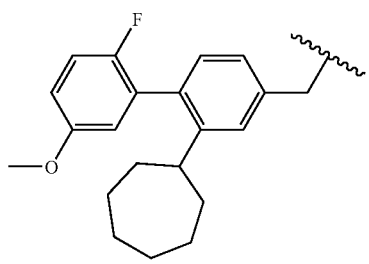 |
| 64.18 | 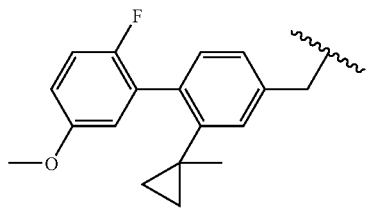 |
| 64.19 | 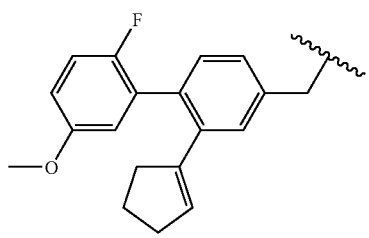 |
| 64.20 | 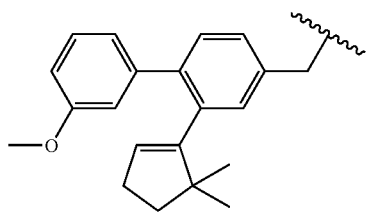 |
| 64.21 | 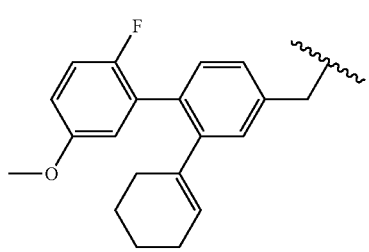 |

TABLE 4-continued

| | |
|---|---|
| 64.22 | 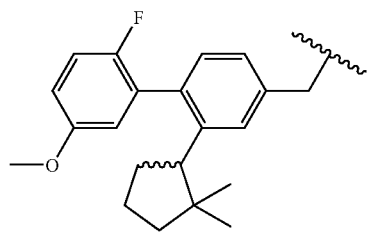 |
| 64.23 | 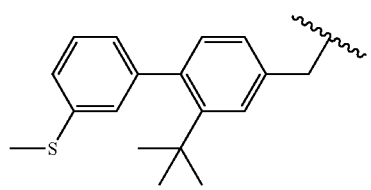 |
| 64.24 | 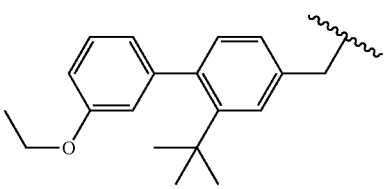 |
| 64.25 | 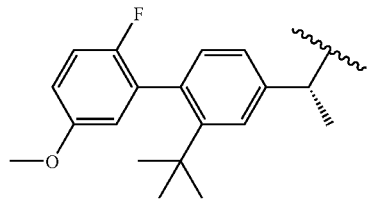 |
| | or |
| | 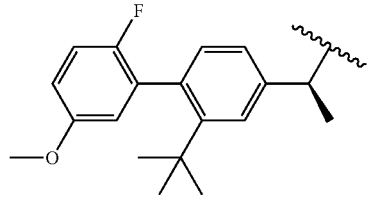 |
| 64.26 | 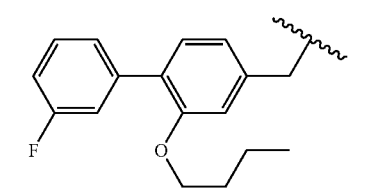 |

(3R)-3-(3-(((2-((2,2-Dimethylpropyl)oxy)-2'-fluoro-5'-(methyloxy)-1,1'-biphenyl-4-yl)methyl)oxy)phenyl)butanoic acid or (3S)-3-(3-(((2-((2,2-dimethylpropyl)oxy)-2'-fluoro-5'-(methyloxy)-1,1'-biphenyl-4-yl)methyl)oxy)phenyl)butanoic acid (64.1). Example 64.1 was synthesized from 27.1 by a method analogous to that used to prepare compound 27 using 1-bromo-2,2-dimethylpropane (commercially available from Aldrich). MS ESI (neg.) m/e: 479.2 (M−H).

(3R)-3-(3-(((2-(Butyloxy)-3'-(methylsulfanyl)-1,1'-biphenyl-4-yl)methyl)oxy)phenyl)butanoic acid or (3S)-3-(3-(((2-(butyloxy)-3'-(methylsulfanyl)-1,1'-biphenyl-4-yl)methyl)oxy)phenyl)butanoic acid (64.2). Example 64.2 was synthesized from 20.4 by a method analogous to that used to prepare compound 21 using 3-(methylthio)phenylboronic acid (commercially available from Aldrich). MS ESI (neg.) m/e: 463.1 (M−H).

(3R)-3-(3-(((2-(1,1-Dimethylethyl)-2'-fluoro-5-methyl-5'-(methyloxy)-1,1'-biphenyl-4-yl)methyl)oxy)phenyl)butanoic acid or (3S)-3-(3-(((2-(1,1-dimethylethyl)-2'-fluoro-5-methyl-5'-(methyloxy)-1,1'-biphenyl-4-yl)methyl)oxy) phenyl)butanoic acid (64.3). MS ESI (neg.) m/e: 463.1 (M−H).

(3R)-3-(3-(((2-((1E)-3,3-Dimethyl-1-butenyl)-2'-fluoro-5'-(methyloxy)-1,1'-biphenyl-4-yl)methyl)oxy)phenyl)butanoic acid or (3S)-3-(3-(((2-((1E)-3,3-dimethyl-1-butenyl)-2'-fluoro-5'-(methyloxy)-1,1'-biphenyl-4-yl)methyl)oxy) phenyl)butanoic acid (64.4). MS ESI (neg.) m/e: 951.4 (2M−H)$^+$, 475.1 (M−H)$^+$.

(3R)-3-(3-(((2-(4,4-Dimethyl-1-cyclohexen-1-yl)-2'-fluoro-5'-(methyloxy)-1,1'-biphenyl-4-yl)methyl)oxy)phenyl)butanoic acid or (3S)-3-(3-(((2-(4,4-dimethyl-1-cyclohexen-1-yl)-2'-fluoro-5'-(methyloxy)-1,1'-biphenyl-4-yl) methyl)oxy)phenyl)butanoic acid (64.5). MS ESI (neg.) m/e: 501.2 (M−H)$^+$.

(3R)-3-(3-(((2-(3,3-Dimethylbutyl)-2'-fluoro-5'-(methyloxy)-1,1'-biphenyl-4-yl)methyl)oxy)phenyl)butanoic acid or (3S)-3-(3-(((2-(3,3-dimethylbutyl)-2'-fluoro-5'-(methyloxy)-1,1'-biphenyl-4-yl)methyl)oxy)phenyl)butanoic acid (64.6). MS ESI (neg.) m/e: 955.5 (2M−H)$^+$, 477.2 (M−H)$^+$.

(3R)-3-(3-(((2-(4,4-Dimethylcyclohexyl)-2'-fluoro-5'-(methyloxy)-1,1'-biphenyl-4-yl)methyl)oxy)phenyl)butanoic acid or (3S)-3-(3-(((2-(4,4-dimethylcyclohexyl)-2'-fluoro-5'-(methyloxy)-1,1'-biphenyl-4-yl)methyl)oxy) phenyl)butanoic acid (64.7). MS ESI (neg.) m/e: 503.2 (M−H)$^+$.

(3R)-3-(3-(((2'-Fluoro-5'-(methyloxy)-2-((1E)-1-pentenyl)-1,1'-biphenyl-4-yl)methyl)oxy)phenyl)butanoic acid or (3S)-3-(3-(((2'-fluoro-5'-(methyloxy)-2-((1E)-1-pentenyl)-1,1'-biphenyl-4-yl)methyl)oxy)phenyl)butanoic acid (64.8). MS ESI (neg.) m/e: 923.3 (2M−H)$^+$, 461.2 (M−H)$^+$.

(3R)-3-(3-(((2-((E)-2-Cyclohexylethenyl)-2'-fluoro-5'-(methyloxy)-1,1'-biphenyl-4-yl)methyl)oxy)phenyl)butanoic acid or (3S)-3-(3-(((2-((E)-2-cyclohexylethenyl)-2'-fluoro-5'-(methyloxy)-1,1'-biphenyl-4-yl)methyl)oxy) phenyl)butanoic acid (64.9). MS ESI (neg.) m/e: 501.1 (M−H)$^+$.

(3R)-3-(3-(((2-(1,1-Dimethylethyl)-2',3-difluoro-5'-(methyloxy)-1,1'-biphenyl-4-yl)methyl)oxy)phenyl)butanoic acid or (3S)-3-(3-(((2-(1,1-dimethylethyl)-2',3-difluoro-5'-(methyloxy)-1,1'-biphenyl-4-yl)methyl)oxy)phenyl)butanoic acid (64.10). MS ESI (neg.) m/e: 935.3 (2M−H)$^+$, 467.2 (M−H)$^+$.

(3R)-3-(3-(((2-(1,1-Dimethylbutyl)-2'-fluoro-5'-(methyloxy)-1,1'-biphenyl-4-yl)methyl)oxy)phenyl)butanoic acid or (3S)-3-(3-(((2-(1,1-dimethylbutyl)-2'-fluoro-5'-(methyloxy)-1,1'-biphenyl-4-yl)methyl)oxy)phenyl)butanoic acid (64.11). MS ESI (neg.) m/e: 955.5 (2M−H)$^+$, 477.2 (M−H)$^+$.

(3R)-3-(3-(((2-(1-Cyclohepten-1-yl)-2'-fluoro-5'-(methyloxy)-1,1'-biphenyl-4-yl)methyl)oxy)phenyl)butanoic acid or (3S)-3-(3-(((2-(1-cyclohepten-1-yl)-2'-fluoro-5'-(methyloxy)-1,1'-biphenyl-4-yl)methyl)oxy)phenyl)butanoic acid (64.12). MS ESI (neg.) m/e: 975.4 (2M−H)$^+$, 487.2 (M−H)$^+$.

(3R)-3-(3-(((2-(4-(1,1-Dimethylethyl)-1-cyclohexen-1-yl)-2'-fluoro-5'-(methyloxy)-1,1'-biphenyl-4-yl)methyl)oxy) phenyl)butanoic acid or (3S)-3-(3-(((2-(4-(1,1-dimethylethyl)-1-cyclohexen-1-yl)-2'-fluoro-5'-(methyloxy)-1,1'-biphenyl-4-yl)methyl)oxy)phenyl)butanoic acid (64.13). MS ESI (neg.) m/e: 529.3 (M−H)$^+$.

(3R)-3-(3-(((2'-Fluoro-5'-(methyloxy)-2-pentyl-1,1'-biphenyl-4-yl)methyl)oxy)phenyl)butanoic acid or (3S)-3-(3-(((2'-fluoro-5'-(methyloxy)-2-pentyl-1,1'-biphenyl-4-yl)methyl)oxy)phenyl)butanoic acid (64.14). MS ESI (neg.) m/e: 927.4 (2M−H)$^+$, 463.1 (M−H)$^+$.

(3R)-3-(3-(((2-(2-Cyclohexylethyl)-2'-fluoro-5'-(methyloxy)-1,1'-biphenyl-4-yl)methyl)oxy)phenyl)butanoic acid or (3S)-3-(3-(((2-(2-cyclohexylethyl)-2'-fluoro-5'-(methyloxy)-1,1'-biphenyl-4-yl)methyl)oxy)phenyl)butanoic acid (64.15). MS ESI (neg.) m/e: 503.2 (M−H)$^+$.

(3R)-3-(3-(((2'-Fluoro-5'-(methyloxy)-2-tricyclo[3.3.1.1~3,7~]dec-1-yl-1,1'-biphenyl-4-yl)methyl)oxy)phenyl)butanoic acid or (3S)-3-(3-(((2'-fluoro-5'-(methyloxy)-2-tricyclo[3.3.1.1~3,7~]dec-1-yl-1,1'-biphenyl-4-yl)methyl) oxy)phenyl)butanoic acid (64.16). MS ESI (neg.) m/e: 527.2 (M−H)$^+$.

(3R)-3-(3-(((2-Cycloheptyl-2'-fluoro-5'-(methyloxy)-1,1'-biphenyl-4-yl)methyl)oxy)phenyl)butanoic acid or (3S)-3-(3-(((2-cycloheptyl-2'-fluoro-5'-(methyloxy)-1,1'-biphenyl-4-yl)methyl)oxy)phenyl)butanoic acid (64.17). MS ESI (neg.) m/e: 979.5 (2M−H)$^+$, 489.2 (M−H)$^+$.

(3R)-3-(3-(((2'-Fluoro-2-(1-methylcyclopropyl)-5'-(methyloxy)-1,1'-biphenyl-4-yl)methyl)oxy)phenyl)butanoic acid or (3S)-3-(3-(((2'-fluoro-2-(1-methylcyclopropyl)-5'-(methyloxy)-1,1'-biphenyl-4-yl)methyl)oxy)phenyl)butanoic acid (64.18). MS ESI (neg.) m/e: 895.5 (2M−H)$^+$, 447.3 (M−H)$^+$.

(3R)-3-(3-(((2-(1-Cyclopenten-1-yl)-2'-fluoro-5'-(methyloxy)-1,1'-biphenyl-4-yl)methyl)oxy)phenyl)butanoic acid or (3S)-3-(3-(((2-(1-cyclopenten-1-yl)-2'-fluoro-5'-(methyloxy)-1,1'-biphenyl-4-yl)methyl)oxy)phenyl)butanoic acid (64.19). MS ESI (neg.) m/e: 459.1 (M−H).

(3R)-3-(3-(((2-(5,5-Dimethyl-1-cyclopenten-1-yl)-3'-(methyloxy)-1,1'-biphenyl-4-yl)methyl)oxy)phenyl)butanoic acid or (3S)-3-(3-(((2-(5,5-dimethyl-1-cyclopenten-1-yl)-3'-(methyloxy)-1,1'-biphenyl-4-yl)methyl)oxy)phenyl) butanoic acid (64.20). MS ESI (neg.) m/e: 469.3 (M−H).

(3R)-3-(3-(((2-(1-Cyclohexen-1-yl)-2'-fluoro-5'-(methyloxy)-1,1'-biphenyl-4-yl)methyl)oxy)phenyl)butanoic acid or (3S)-3-(3-(((2-(1-cyclohexen-1-yl)-2'-fluoro-5'-(methyloxy)-1,1'-biphenyl-4-yl)methyl)oxy)phenyl)butanoic acid (64.21). MS ESI (neg.) m/e: 473.2 (M−H).

(3R)-3-(3-(((2-(2,2-Dimethylcyclopentyl)-2'-fluoro-5'-(methyloxy)-1,1'-biphenyl-4-yl)methyl)oxy)phenyl)butanoic acid or (3S)-3-(3-(((2-(2,2-dimethylcyclopentyl)-2'-fluoro-5'-(methyloxy)-1,1'-biphenyl-4-yl)methyl)oxy) phenyl)butanoic acid (64.22). MS ESI (neg.) m/e: 489.2 (M−H).

(3R)-3-(3-(((2-(1,1-Dimethylethyl)-3'-(methylsulfanyl)-1,1'-biphenyl-4-yl)methyl)oxy)phenyl)butanoic acid or (3S)-3-(3-(((2-(1,1-dimethylethyl)-3'-(methylsulfanyl)-1,1'-biphenyl-4-yl)methyl)oxy)phenyl)butanoic acid (64.23). MS ESI (neg.) m/e: 447.1 (M−H). $^1$H NMR (500 MHz) (CDCl$_3$) δ ppm 7.62 (1H, d, J=1.2 Hz), 7.32 (4H, m), 7.20 (1H, s), 7.10 (2H, m), 6.95 (2H, m), 6.89 (1H, d, J=7.6 Hz), 5.11 (2H, s), 3.35 (1H, m), 2.76 (1H, m), 2.65 (1H, m), 2.51 (3H, s), 1.36 (3H, d, J=7.1 Hz), 1.25 (9H, s).

(3R)-3-(3-(((2-(1,1-Dimethylethyl)-3'-(ethyloxy)-1,1'-biphenyl-4-yl)methyl)oxy)phenyl)butanoic acid or (3S)-3-(3-(((2-(1,1-dimethylethyl)-3'-(ethyloxy)-1,1'-biphenyl-4-yl) methyl)oxy)phenyl)butanoic acid (64.24). MS ESI (neg.) m/e: 445.1 (M−H). $^1$H NMR (500 MHz) (CDCl$_3$) δ ppm 7.60 (1H, d, J=1.2 Hz), 7.29 (3H, m), 7.07 (1H, d, J=7.8 Hz), 6.93 (5H, m), 6.84 (1H, d, J=1.7 Hz), 5.09 (2H, s), 4.06 (2H, ddd, J=13.4, 6.6, 6.4 Hz), 3.33 (1H, m), 2.74 (1H, m), 2.63 (1H, m), 1.44 (3H, t, J=7.0 Hz), 1.35 (3H, d, J=7.1 Hz), 1.25 (9H, s).

Example 64.25

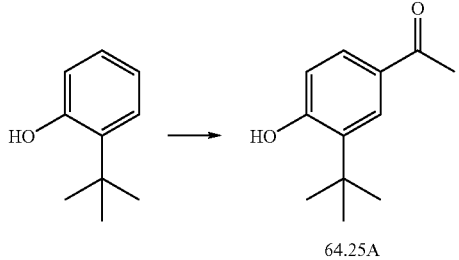

64.25A 1-(3-(1,1-Dimethylethyl)-4-hydroxyphenyl)ethanone (64.25 A). To a dry, round bottom flask was added aluminum chloride (4.402 g, 33.0 mmol). The flask was then cooled to −45° C. After 10 minutes, dry toluene (80 mL) was added followed by dropwise addition of 2-tert-butylphenol (5.00 mL, 32.7 mmol) (commercially available from Aldrich). The mixture was stirred and maintained at −4° C. After 1.5 hours, acetyl chloride (2.40 mL, 33.8 mmol) was carefully added dropwise. The mixture was allowed to warm to room temperature and monitored with TLC and LC-MS. After 18 hours, the mixture was slowly poured onto crushed ice. This mixture was stirred at room temperature and the crystals were collected by filtration. The light yellow solid was identified as 64.25 A (4.2589 g, 68%). MS ESI (pos.) m/e: 193.1 (M+H)$^+$.

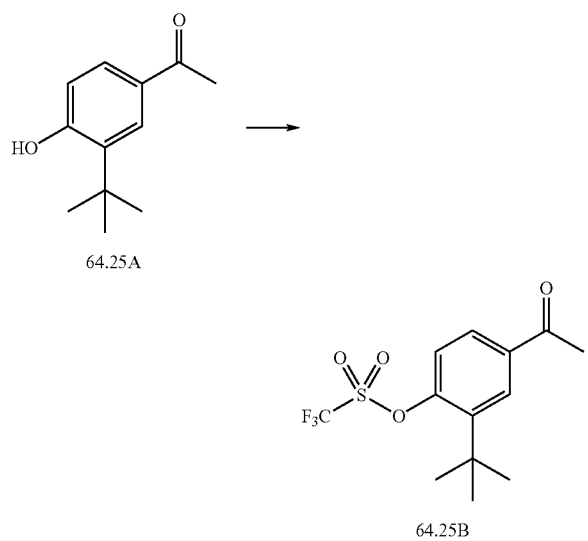

4-Acetyl-2-(1,1-dimethylethyl)phenyl trifluoromethanesulfonate (64.25 B). To a stirred solution of 64.25 A (2.0006 g, 10.41 mmol) in dry DCM (37 mL) was added TEA (3.0 mL, 21.57 mmol) and DMAP (0.1309 g, 1.071 mmol). After 20 minutes, N-phenyltrifluoromethanesulfonimide (5.5846 g, 15.63 mmol) was added in portions. Upon complete addition, the solution was stirred at room temperature and monitored with TLC and LC-MS. After 4.5 hours, the reaction was diluted with brine and extracted three times with DCM. After drying over anhydrous magnesium sulfate and filtration, the solvent was removed under reduced pressure. The residue was purified by silica gel flash chromatography (0-20% EtOAc/hexane) to yield 64.25 B (3.0227 g, 90% yield). MS ESI (pos.) m/e: 325.1 (M+H)$^+$.

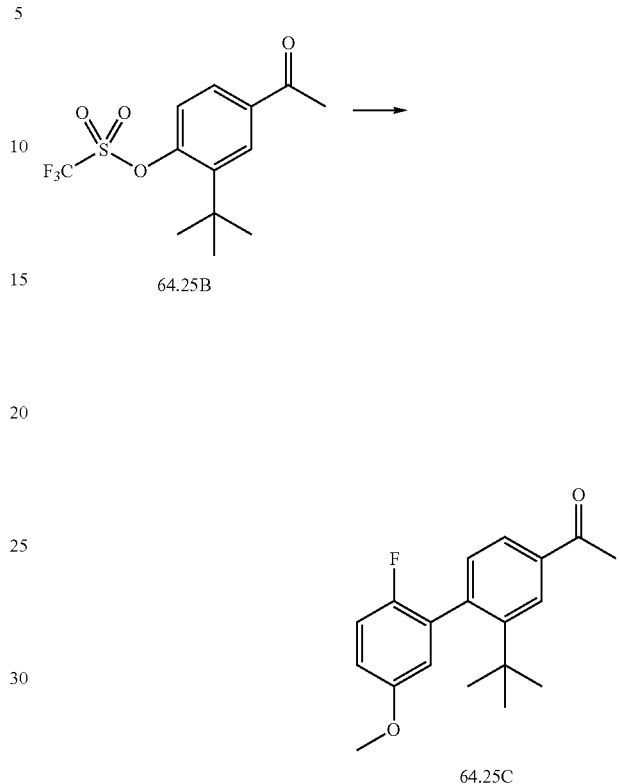

1-(2-(1,1-Dimethylethyl)-2'-fluoro-5'-(methyloxy)-1,1'-biphenyl-4-yl)ethanone (64.25 C). A dry round bottom containing 64.25 B (3.0227 g, 9.3202 mmol), 2-fluoro-5-methoxyphenylboronic acid (2.4005 g, 14.125 mmol) (commercially available from Aldrich), tetrakis(triphenylphosphine)palladium (1.0853 g, 0.93920 mmol), and potassium carbonate (3.9996 g, 28.940 mmol) was evacuated and backfilled three times with argon. Dry DMF (25 mL) was added via syringe under argon, then the mixture was heated to 100° C. and monitored with TLC. After 3 hours, the reaction was cooled to room temperature, then diluted with water. The mixture was extracted three times with EtOAc then concentrated under reduced pressure. The residue was purified by silica gel flash chromatography (0-15% EtOAc/hexane) to yield 64.25 C (2.6053 g, 93% yield). MS ESI (pos.) m/e: 301.1 (M+H)$^+$.

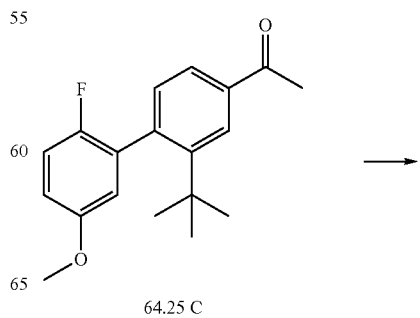

64.25 C

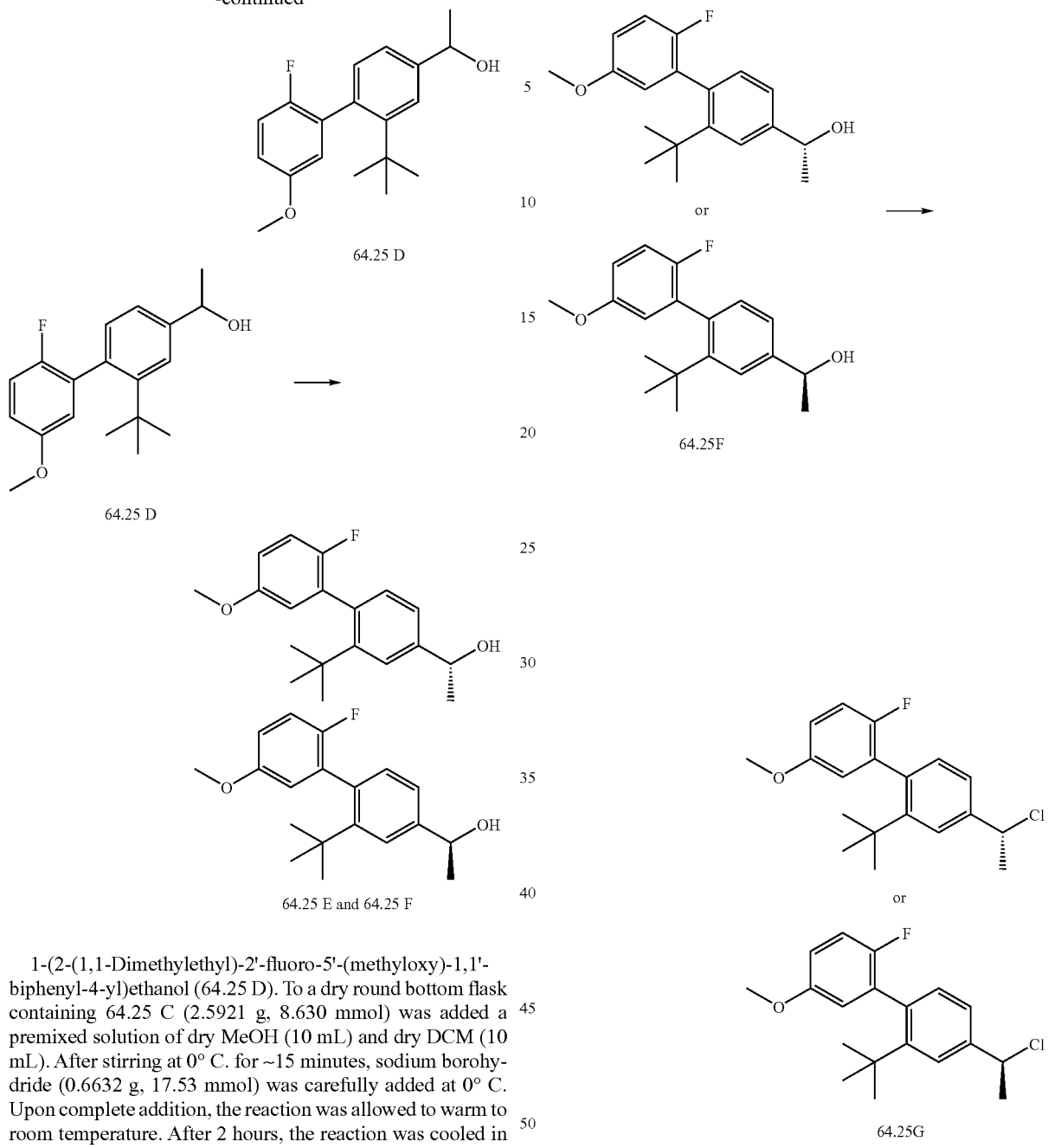

1-(2-(1,1-Dimethylethyl)-2'-fluoro-5'-(methyloxy)-1,1'-biphenyl-4-yl)ethanol (64.25 D). To a dry round bottom flask containing 64.25 C (2.5921 g, 8.630 mmol) was added a premixed solution of dry MeOH (10 mL) and dry DCM (10 mL). After stirring at 0° C. for ~15 minutes, sodium borohydride (0.6632 g, 17.53 mmol) was carefully added at 0° C. Upon complete addition, the reaction was allowed to warm to room temperature. After 2 hours, the reaction was cooled in an ice bath, then carefully quenched with water and extracted three times with DCM. After drying over anhydrous magnesium sulfate and filtration, the organic solvent was removed under reduced pressure. The residue was purified by silica gel flash chromatography (0-15% EtOAc/hexane) to yield 64.25 D (2.5329 g, 97% yield). MS ESI (pos.) m/e: 285.1 $(M—H_2O)^+$. Chiral separation of 64.25 D was accomplished using SFC with 9 g/min MeOH (0.6% DEA)+81 g/min $CO_2$ on a 250×30 mm OD-H column. The outlet pressure of the system was set to 140 bar, temperature at 25° C. and detector wavelength was 220 nm. Sample was dissolved to 54 mg/mL in MeOH and separations on 13.5 mg injections were performed at a rate of one injection per 1.65 minutes to provide 64.25 E (peak 1) and 64.25 F (peak 2). Both enantiomers were used to synthesize example compounds, and both enantiomers gave active compounds.

4-((1S)-1-Chloroethyl)-2-(1,1-dimethylethyl)-2'-fluoro-5'-(methyloxy)-1,1'-biphenyl or 4-((1R)-1-chloroethyl)-2-(1,1-dimethylethyl)-2'-fluoro-5'-(methyloxy)-1,1'-biphenyl (64.25 G). A dry, round bottom flask containing 64.25 F (1.0221 g, 3.380 mmol) was evacuated and backfilled with argon. Dry DCM (14 mL) was added under argon, and the homogeneous solution was cooled to 0° C. After 15 minutes, thionyl chloride (1.0 mL, 13.71 mmol) was carefully added dropwise at 0° C. Upon complete addition of thionyl chloride, the mixture was allowed to warm to room temperature and stirred overnight. After 2.5 hours, the reaction was concentrated under reduced pressure. The residue was purified by silica gel flash chromatography (0-15% EtOAc/hexane) to yield 64.25 G (744.7 mg, 69% yield). MS ESI (pos.) m/e: 338.2 $(M+H_2O)^+$.

189

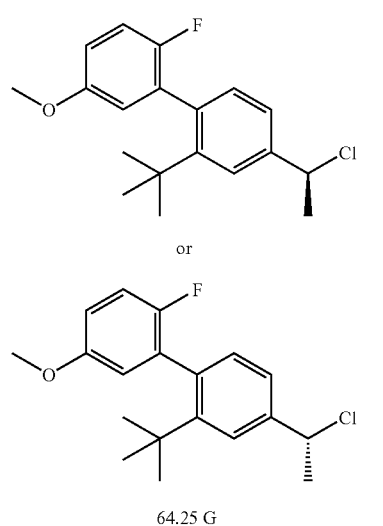

64.25 G

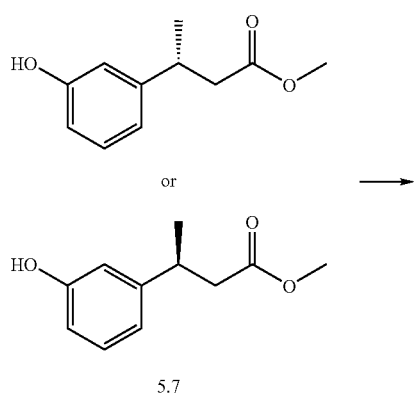

5.7

190

-continued

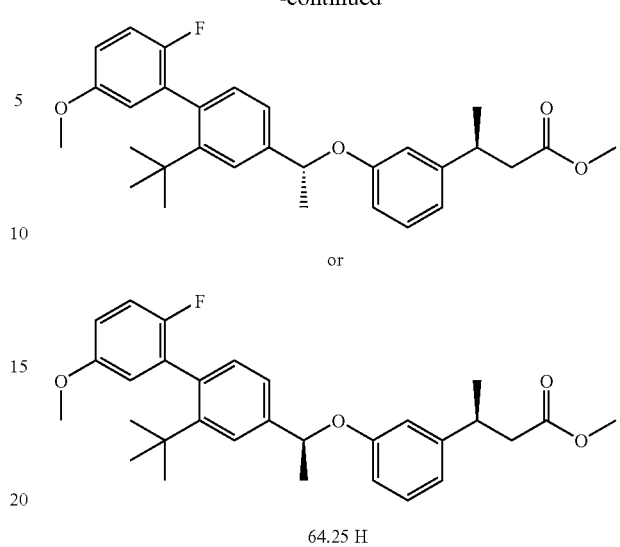

64.25 H

Methyl (3R)-3-(3-(((1R)-1-(2-(1,1-dimethylethyl)-2'-fluoro-5'-(methyloxy)-1,1'-biphenyl-4-yl)ethyl)oxy)phenyl)butanoate or methyl (3R)-3-(3-(((1S)-1-(2-(1,1-dimethylethyl)-2'-fluoro-5'-(methyloxy)-1,1'-biphenyl-4-yl)ethyl)oxy)phenyl)butanoate or methyl (3S)-3-(3-(((1R)-1-(2-(1,1-dimethylethyl)-2'-fluoro-5'-(methyloxy)-1,1'-biphenyl-4-yl)ethyl)oxy)phenyl)butanoate or methyl (3S)-3-(3-(((1S)-1-(2-(1,1-dimethylethyl)-2'-fluoro-5'-(methyloxy)-1,1'-biphenyl-4-yl)ethyl)oxy)phenyl)butanoate (64.25 H). To a round bottom flask containing 5.7 (0.0276 g, 0.142 mmol) in 2.0 mL dry DMF was added cesium carbonate (0.0510 g, 0.157 mmol). The mixture was stirred at room temperature for 15 minutes, then 64.25 G (0.0508 g, 0.158 mmol) was added. After 18 hours, the reaction was diluted with water then extracted five times with EtOAc. The organic extraction was then washed one time with brine and dried over anhydrous magnesium sulfate. The solid was filtered off, and the solvent was concentrated. The residue was purified by silica gel flash chromatography (0-40% EtOAc/hexane) to yield 64.25 H (41.5 mg, 61% yield). MS ESI (pos.) m/e: 501.2 (M+Na)$^+$.

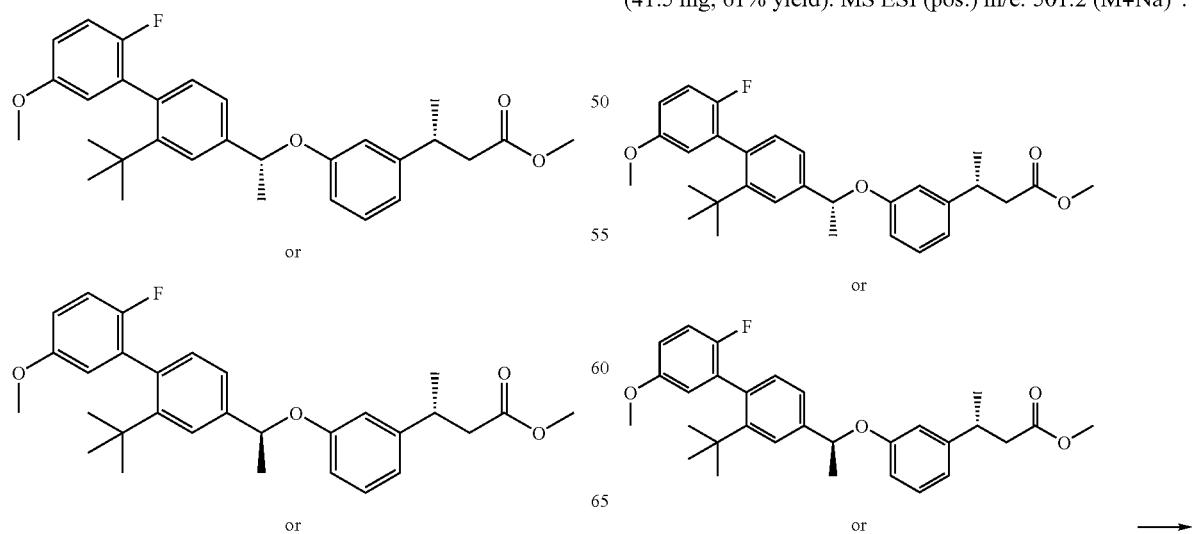

-continued

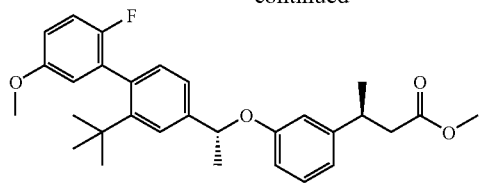

or

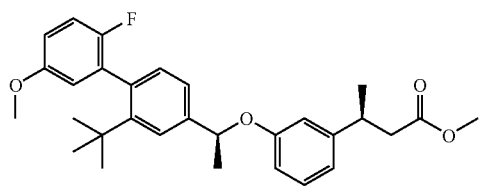

64.25 H

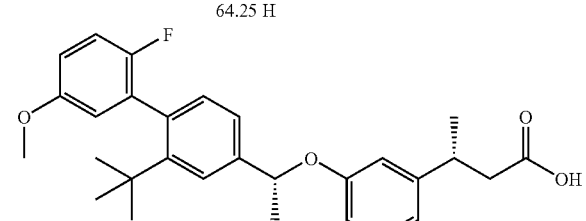

or

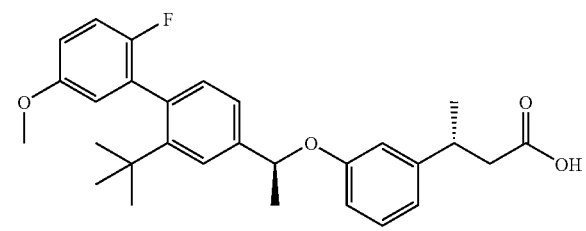

or

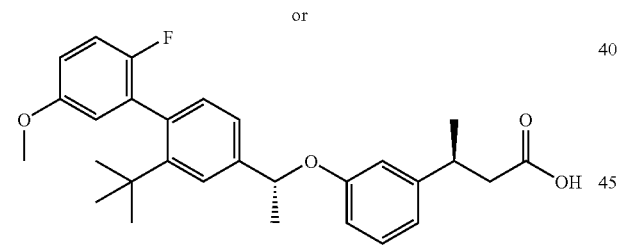

or

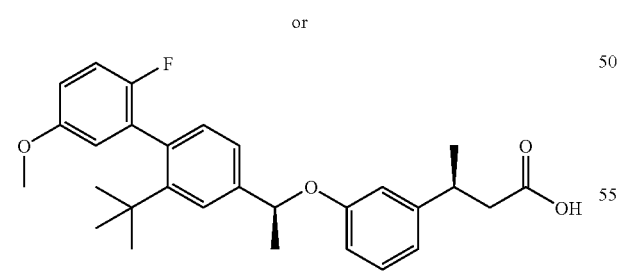

64.25

(3R)-3-(3-(((1R)-1-(2-(1,1-Dimethylethyl)-2'-fluoro-5'-(methyloxy)-1,1'-biphenyl-4-yl)ethyl)oxy)phenyl)butanoic acid, (3R)-3-(3-(((1S)-1-(2-(1,1-dimethylethyl)-2'-fluoro-5'-(methyloxy)-1,1'-biphenyl-4-yl)ethyl)oxy)phenyl)butanoic acid, (3S)-3-(3-(((1R)-1-(2-(1,1-dimethylethyl)-2'-fluoro-5'-(methyloxy)-1,1'-biphenyl-4-yl)ethyl)oxy)phenyl)butanoic acid, or (3S)-3-(3-(((1S)-1-(2-(1,1-dimethylethyl)-2'-fluoro-5'-(methyloxy)-1,1'-biphenyl-4-yl)ethyl)oxy)phenyl)butanoic acid (64.25). A pre-mixed solution of 2M sodium hydroxide (1 mL, 2.0 mmol), MeOH (1 mL), and THF (1 mL, 0.087 mmol) was added to a round bottom flask containing 64.25 H (0.0415 g, 0.087 mmol). The resulting solution was stirred at room temperature and monitored with TLC and LC-MS. After 24 hours, the mixture was diluted with water and acidified with 2M HCl to a pH 6. The mixture was then extracted five times with EtOAc. The organic phase was dried over anhydrous magnesium sulfate then filtered and concentrated in vacuo. The residue was purified by silica gel flash chromatography (0-100% EtOAc/hexane) to yield 64.25 (31.1 mg, 77% yield). (MS ESI (neg.) m/e: 445.1 (M−H). $^1$H NMR (500 MHz) (CDCl$_3$) δ ppm 7.60 (1H, d, J=1.2 Hz), 7.29 (3H, m), 7.07 (1H, d, J=7.8 Hz), 6.93 (5H, m), 6.84 (1H, d, J=1.7 Hz), 5.09 (2H, s), 4.06 (2H, ddd, J=13.4, 6.6, 6.4 Hz), 3.33 (1H, m), 2.74 (1H, m), 2.63 (1H, m), 1.44 (3H, t, J=7.0 Hz), 1.35 (3H, d, J=7.1 Hz), 1.25 (9H, s).

(3R)-3-(3-(((2-(butyloxy)-3'-fluoro-1,1'-biphenyl-4-yl)methyl)oxy)phenyl)butanoic acid or (3S)-3-(3-(((2-(butyloxy)-3'-fluoro-1,1'-biphenyl-4-yl)methyl)oxy)phenyl)butanoic acid (64.26). Example 64.26 was synthesized from 20.4 by a method analogous to that used to prepare compound 21 using 3-fluorophenylboronic acid (commercially available from Aldrich). MS ESI (neg.) m/e: 435.2 (M−H).

Example 65

The following compounds were prepared from 17.1 and the appropriate halomethyl or hydroxymethyl compound according to the methods described herein. Both of the compounds in the following table were prepared using the same enantiomer of the phenol.

TABLE 5

| Compound | TG |
|---|---|
| 65.1 | |

TABLE 5-continued 65.2
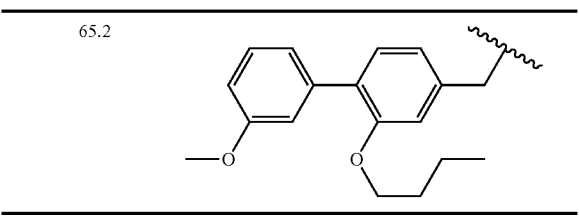

(3R)-3-(3-(((2-(5,5-Dimethyl-1-cyclopenten-1-yl)-2'-fluoro-5'-(methyloxy)-1,1'-biphenyl-4-yl)methyl)oxy)phenyl)pentanoic acid or (3S)-3-(3-(((2-(5,5-dimethyl-1-cyclopenten-1-yl)-2'-fluoro-5'-(methyloxy)-1,1'-biphenyl-4-yl)methyl)oxy)phenyl)pentanoic acid (65.1). MS ESI (neg.) m/e: 501.2 (M–H).

(3R)-3-(3-(((2-(Butyloxy)-3'-(methyloxy)-1,1'-biphenyl-4-yl)methyl)oxy)phenyl)pentanoic acid or (3S)-3-(3-(((2-(butyloxy)-3'-(methyloxy)-1,1'-biphenyl-4-yl)methyl)oxy)phenyl)pentanoic acid (65.2). MS ESI (neg.) m/e: 461.2 (M–H).

Example 66

The following compounds were prepared from 8.4 or 66.6X and the appropriate halomethyl or hydroxymethyl compound according to the methods described herein. Each of the compounds in the following table were prepared using the same enantiomer of the phenol.

TABLE 6

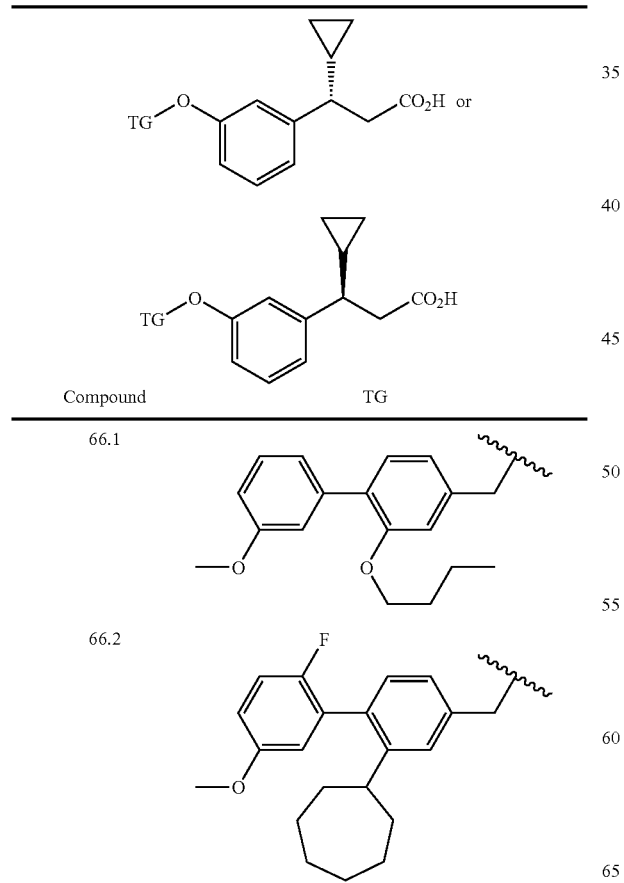

| Compound | TG |
| --- | --- |
| 66.1 | 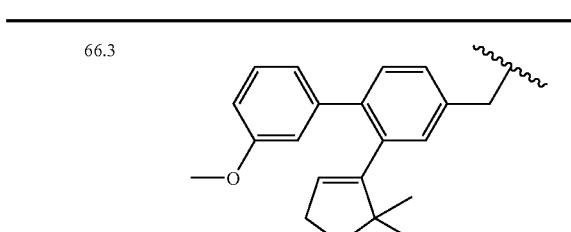 |
| 66.2 | 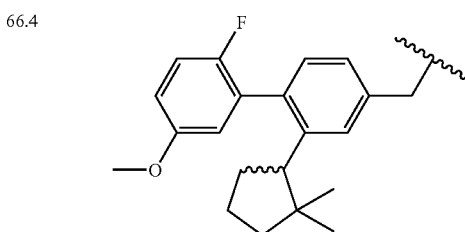 |
| 66.3 | 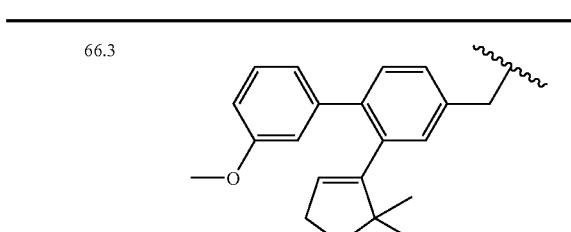 |
| 66.4 | 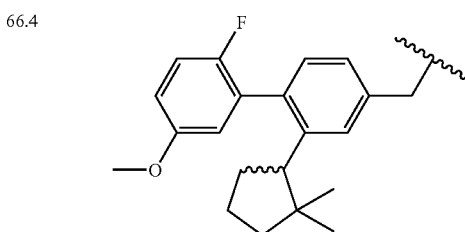 |
| 66.5 | 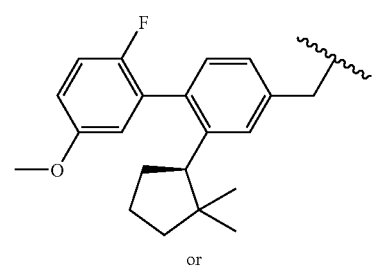 or 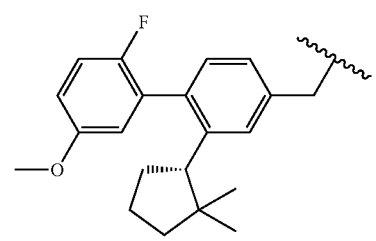 |
| 66.6 | 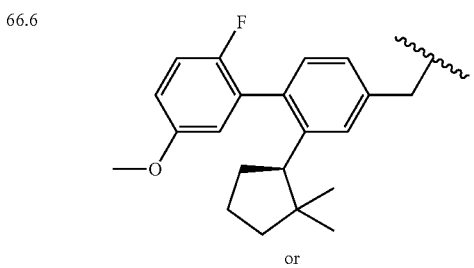 or 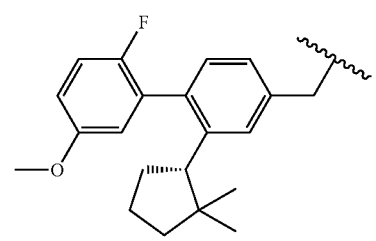 but not the same one as 66.5 |

TABLE 6-continued
66.7 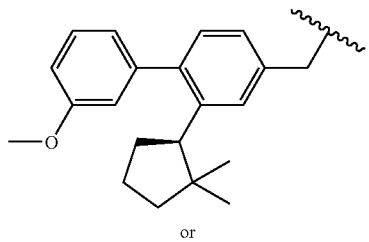
or
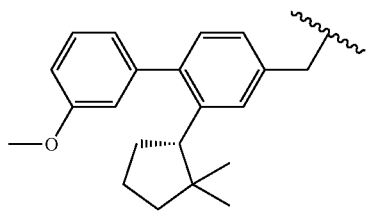
66.8 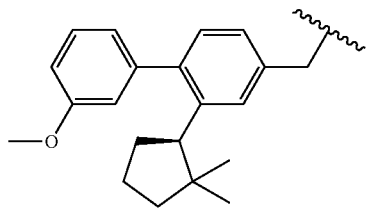
or
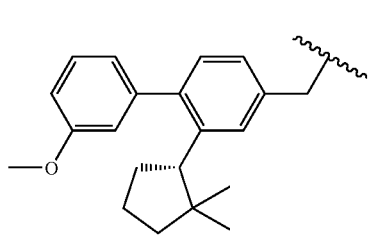
but not the same one as 66.7
66.9 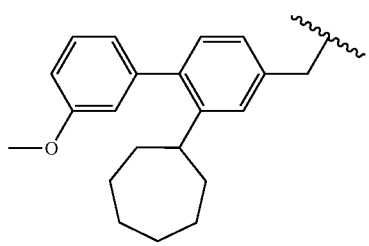
66.10 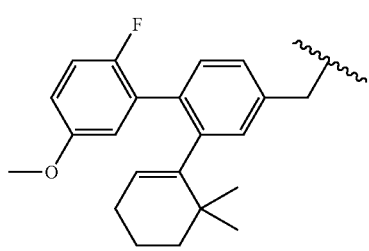
TABLE 6-continued
66.11 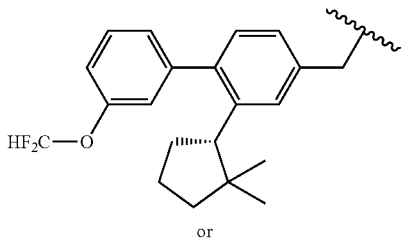
or
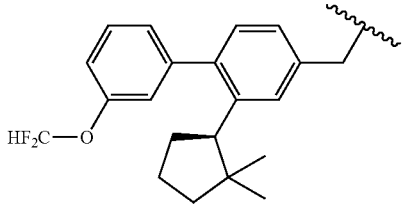
66.12 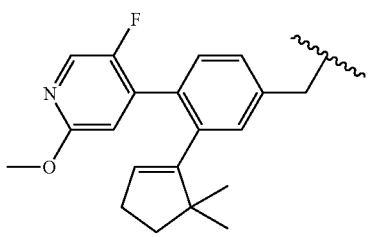
66.13 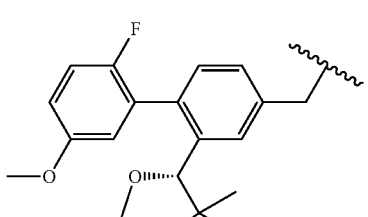
or
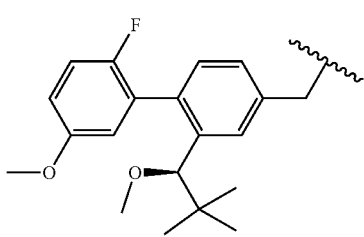
66.14 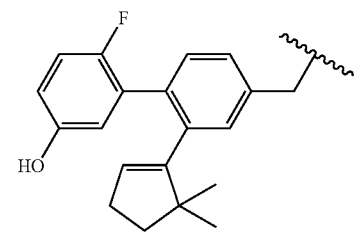

TABLE 6-continued
| | | |
|---|---|---|
| 66.15 |  | |
| 66.16 | 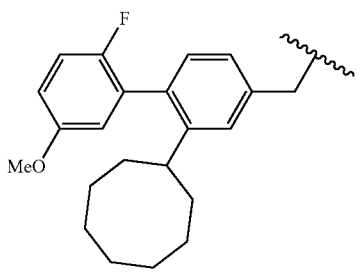 | |
| 66.17 | 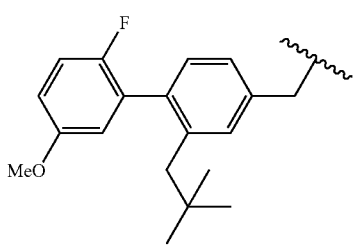 | |
| 66.18 | 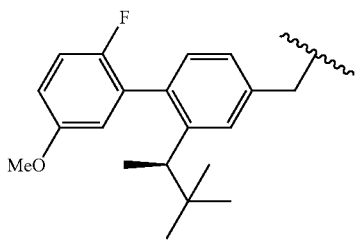 or | |
| 66.19 | 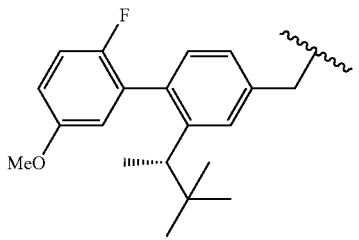 or | |
TABLE 6-continued
| | | |
|---|---|---|
| | 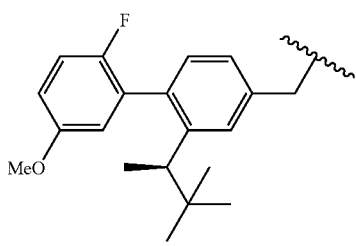 but not the same one as 66.18 | |
| 66.20 | 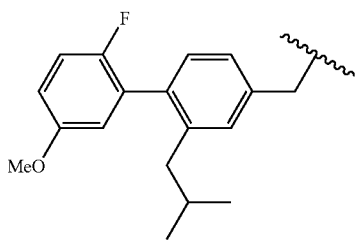 | |
| 66.21 | 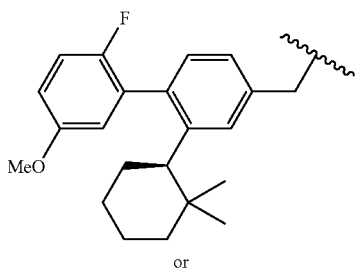 or | |
| | 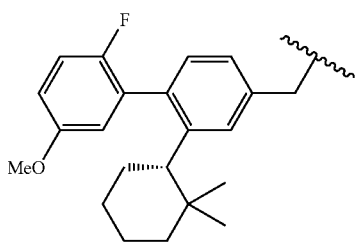 | |
| 66.22 | 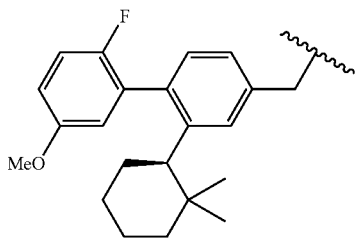 or | |
| | 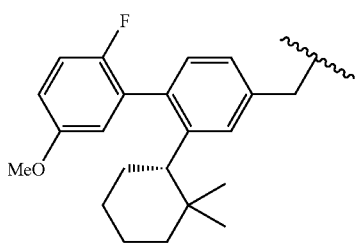 but not the same one as 66.21 | |

TABLE 6-continued
66.23 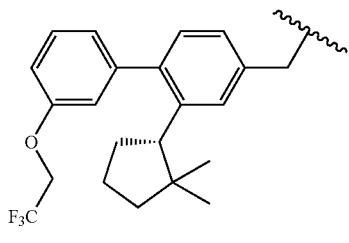
or
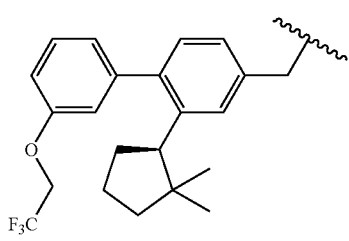
66.24 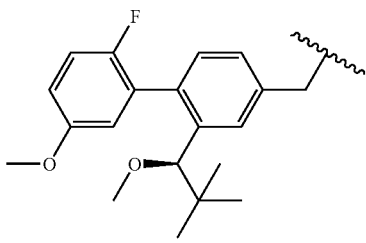
or
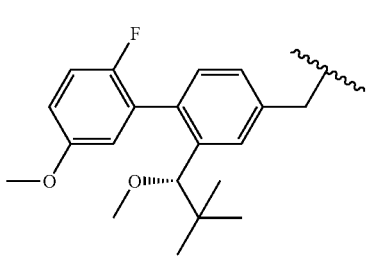
but not the same one as 66.13
66.25 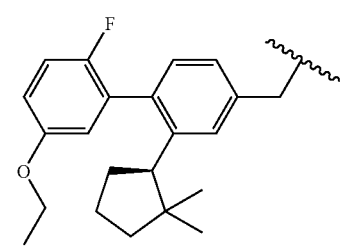
or
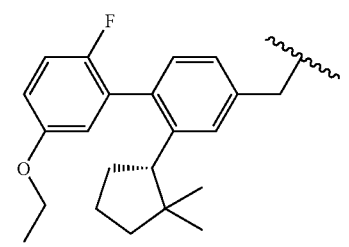
TABLE 6-continued
66.26 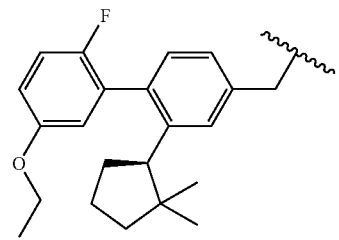
or
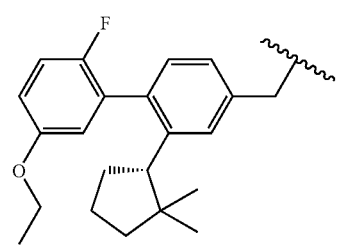
but not the same one as 66.25
66.27 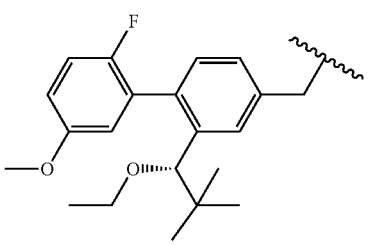
or
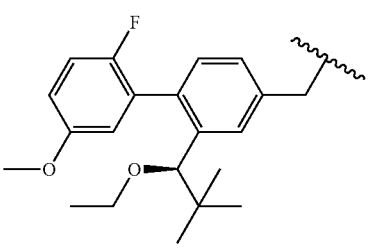
66.28 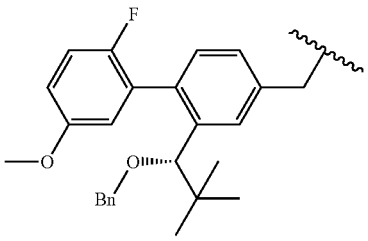
or
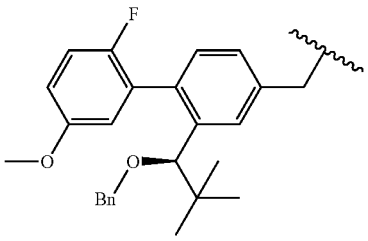
Bn = benzyl TABLE 6-continued
66.29 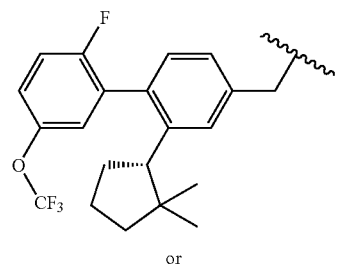
or
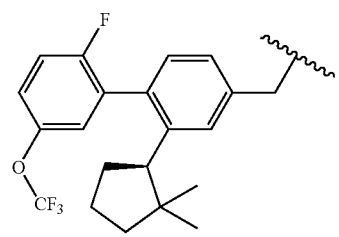
66.30 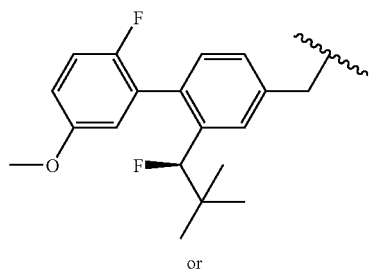
or
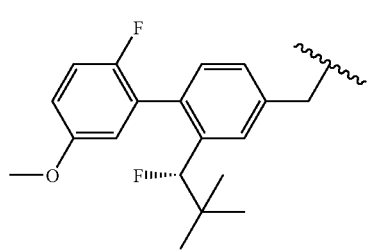
66.31 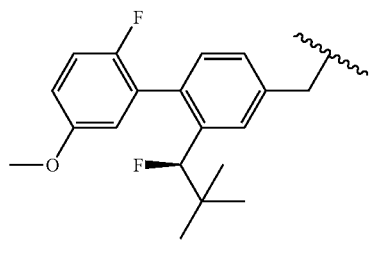
or
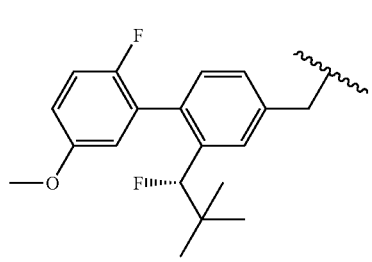
but not the same one as 66.30
TABLE 6-continued
66.32 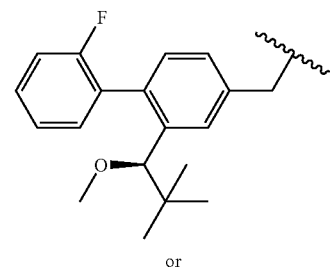
or
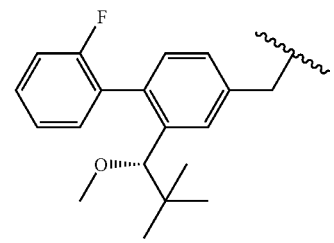
66.33 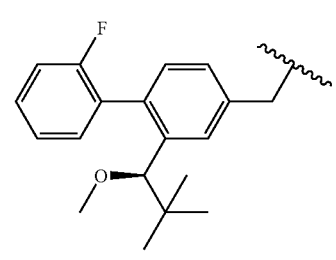
or
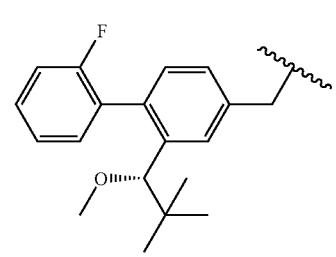
but not the same one as 66.32
66.34 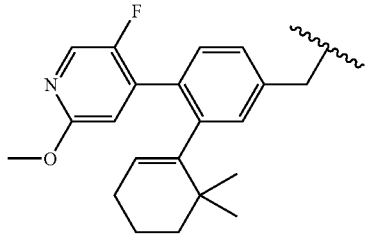
66.35 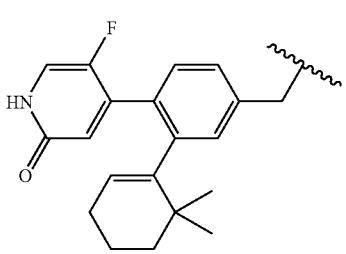

TABLE 6-continued
| | |
|---|---|
| 66.36 | 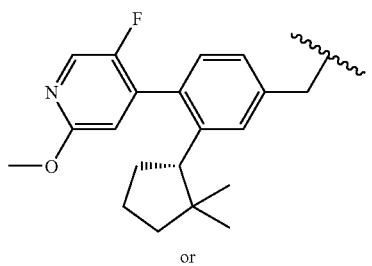
or
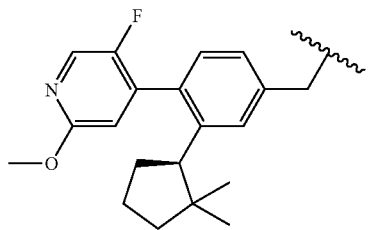 |
| 66.37 | 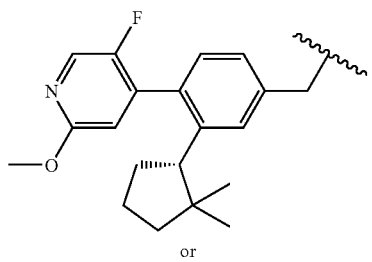
or
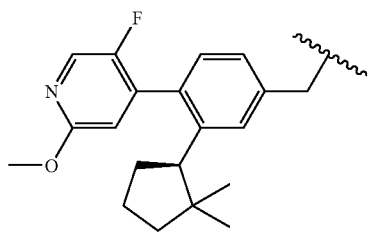
but not the same one as 66.36 |
| 66.38 | 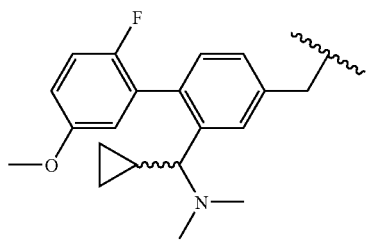 |
| 66.39 | No compound associated with this number |
| 66.40 | 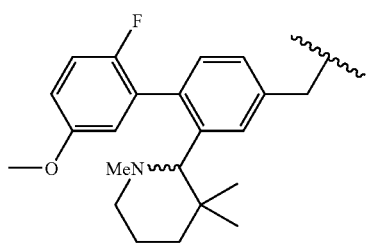 |
TABLE 6-continued
| | |
|---|---|
| 66.41 | 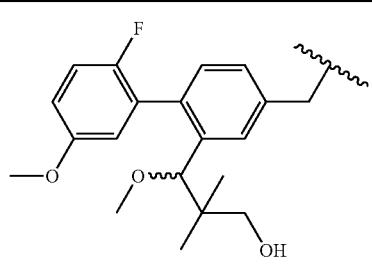 |
| 66.42 | 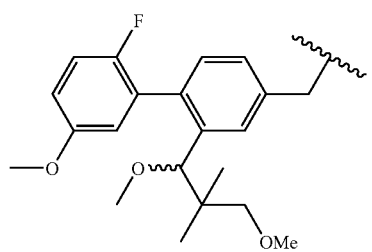 |
| 66.43 | 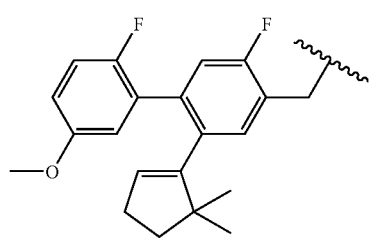 |
| 66.44 | 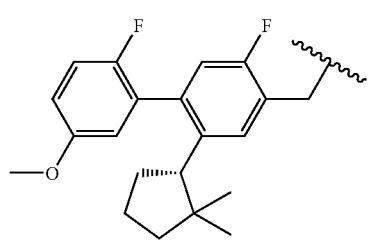
or
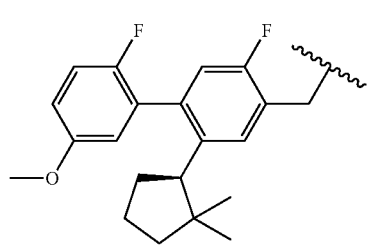
or
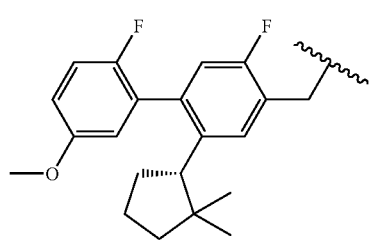
or |
| 66.45 | |

TABLE 6-continued
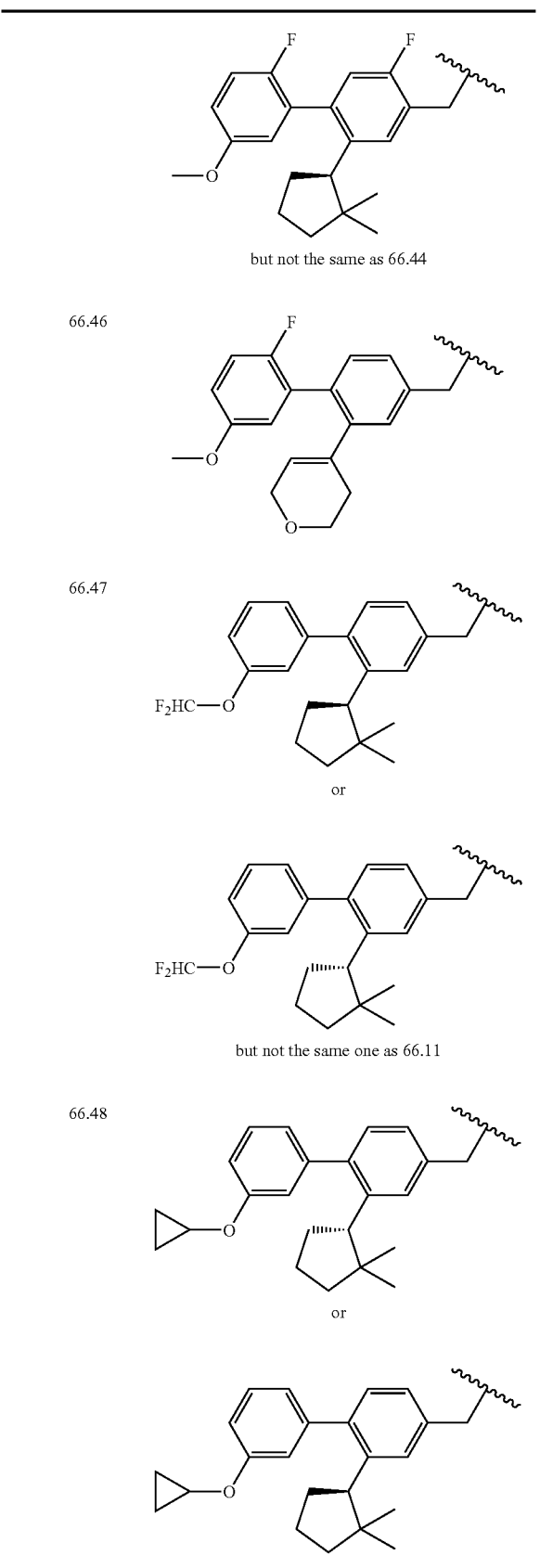
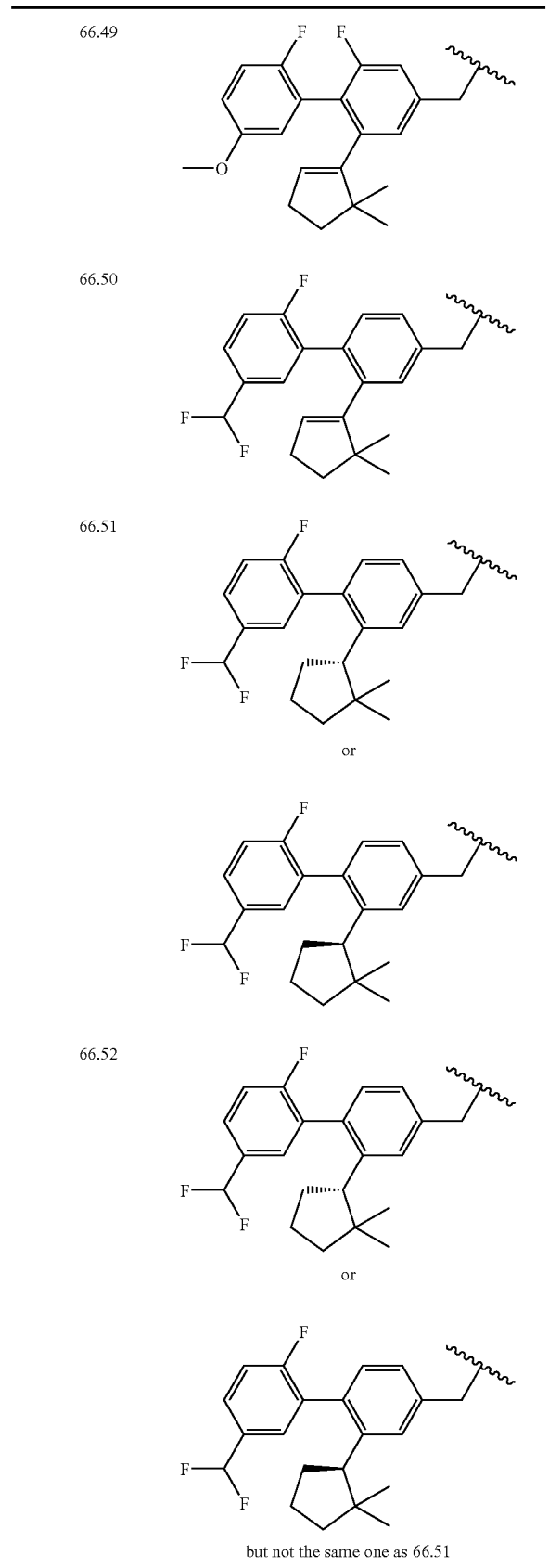

TABLE 6-continued
66.53 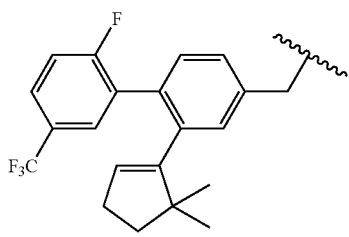
66.54 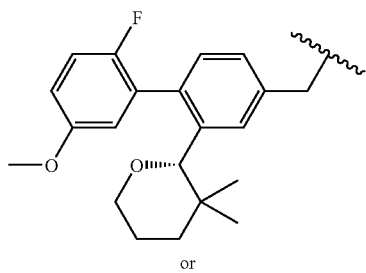
or

66.55 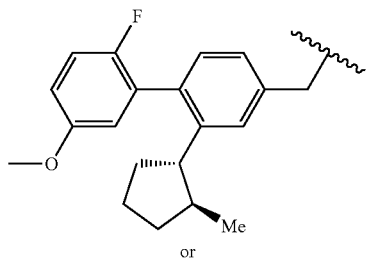
or
TABLE 6-continued
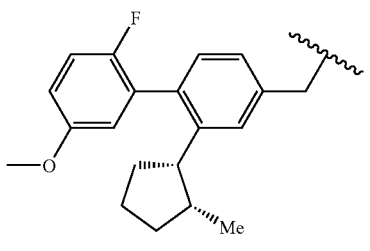
or
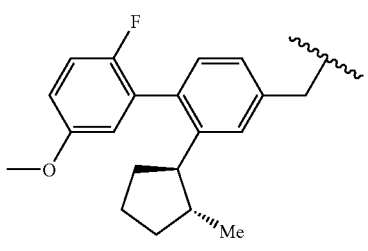
or
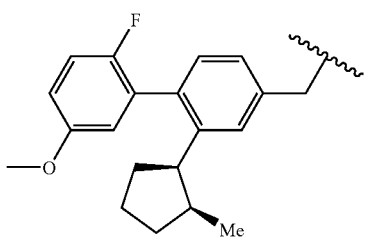
66.57 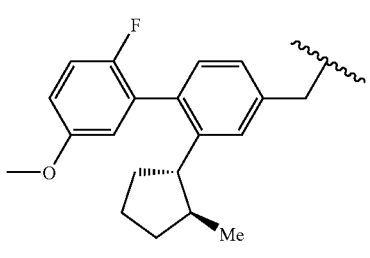
or
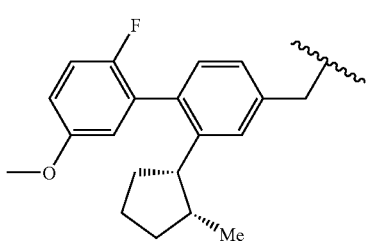
or
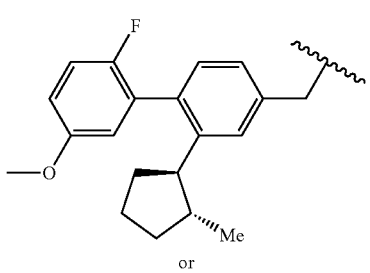
or
but not the same one as 66.54
66.56 (image continues)
or TABLE 6-continued
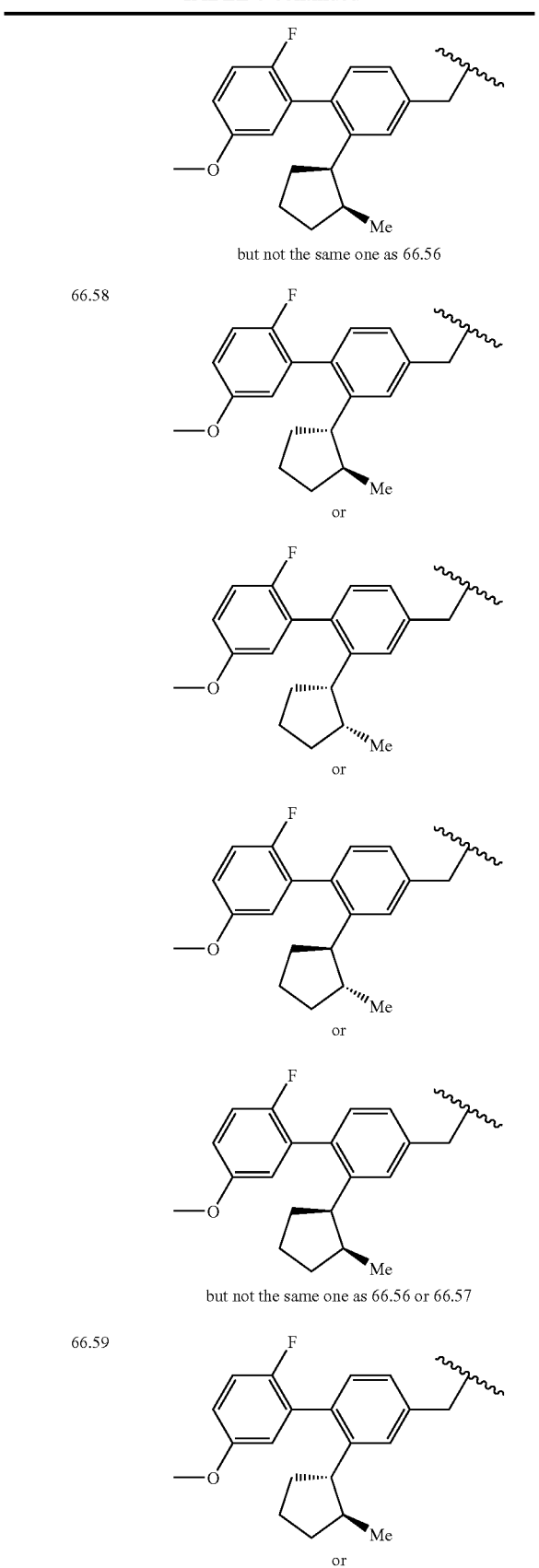
66.58
66.59
TABLE 6-continued
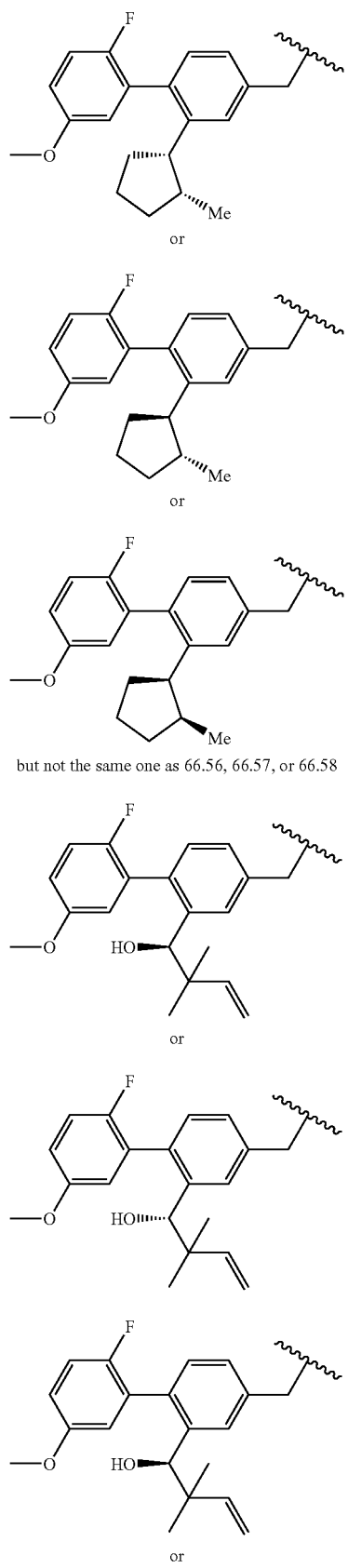
66.60
66.61

TABLE 6-continued
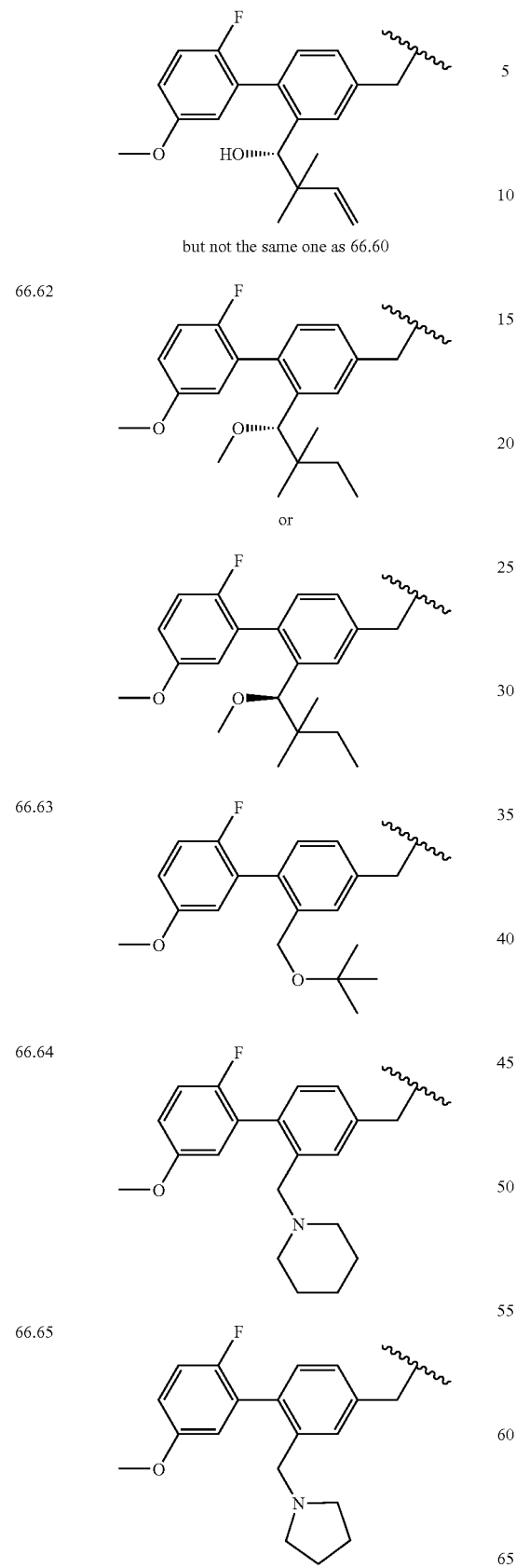
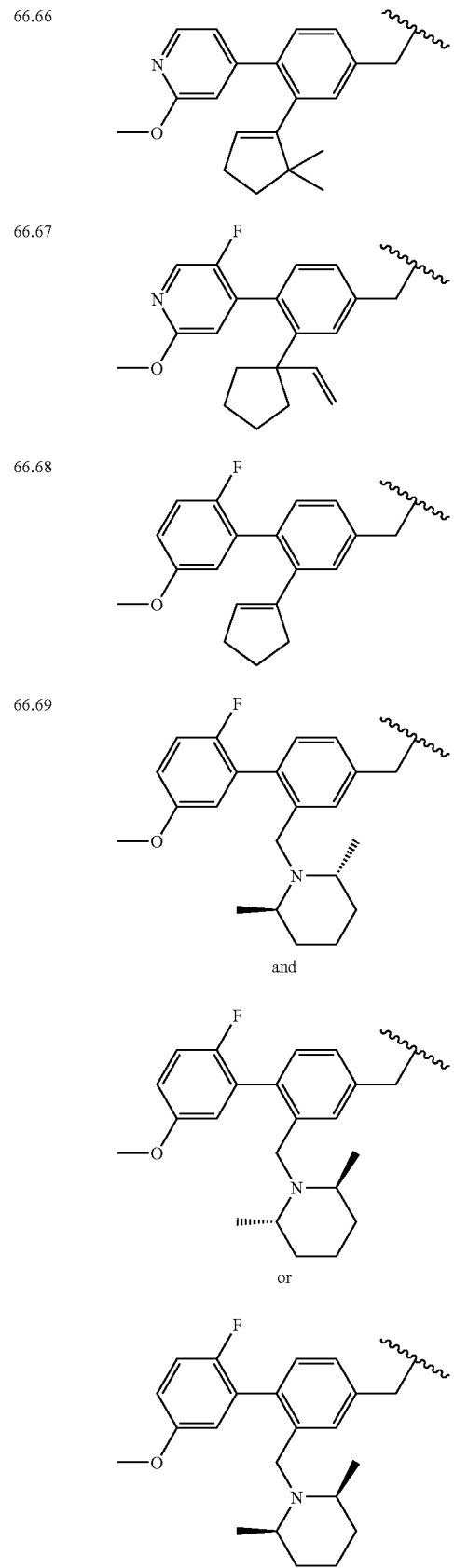

TABLE 6-continued
66.70 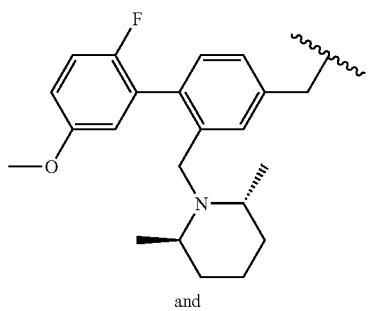
and
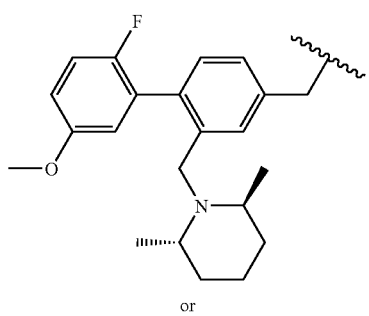
or
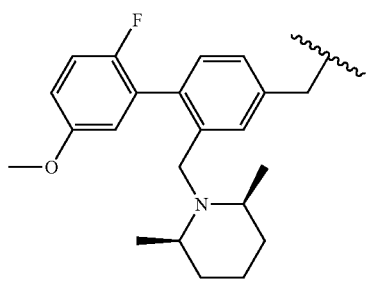
but not the same as 66.69
66.71 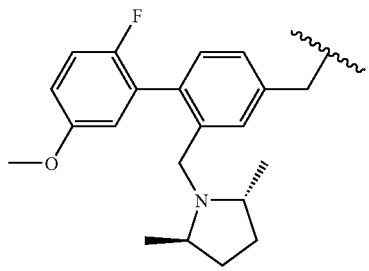
66.72 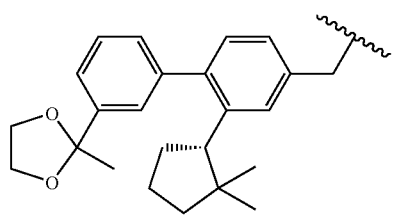
or
TABLE 6-continued
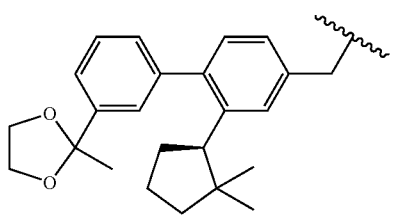
66.73 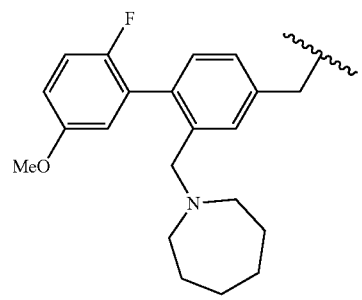
66.74 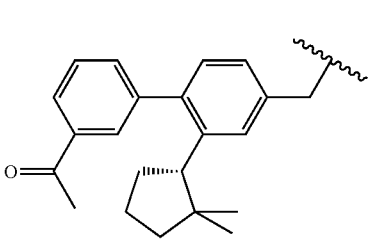
66.75 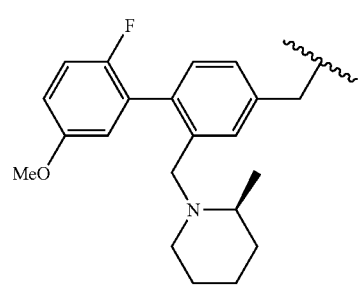
66.76 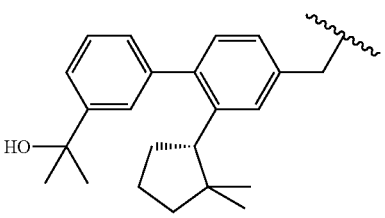
or
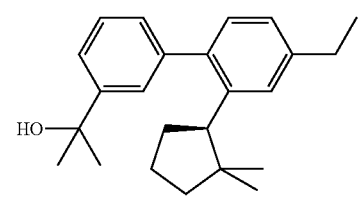

TABLE 6-continued

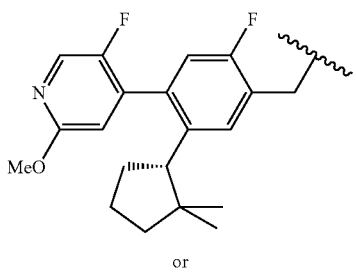

66.77 or

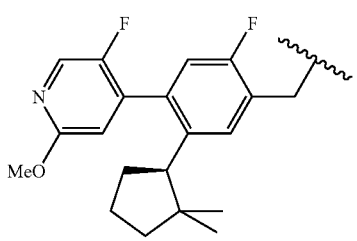

(3S)-3-(3-(((2-(Butyloxy)-3'-(methyloxy)-1,1'-biphenyl-4-yl)methyl)oxy)phenyl)-3-cyclopropylpropanoic acid or (3R)-3-(3-(((2-(butyloxy)-3'-(methyloxy)-1,1'-biphenyl-4-yl)methyl)oxy)phenyl)-3-cyclopropylpropanoic acid (66.1). MS ESI (neg.) m/e: 473.2 (M–H).

(3S)-3-(3-(((2-Cycloheptyl-2'-fluoro-5'-(methyloxy)-1,1'-biphenyl-4-yl)methyl)oxy)phenyl)-3-cyclopropylpropanoic acid or (3R)-3-(3-(((2-cycloheptyl-2'-fluoro-5'-(methyloxy)-1,1'-biphenyl-4-yl)methyl)oxy)phenyl)-3-cyclopropylpropanoic acid (66.2). MS ESI (neg.) m/e: 515.2 (M–H)⁺.

(3S)-3-Cyclopropyl-3-(3-(((2-(5,5-dimethyl-1-cyclopenten-1-yl)-3'-(methyloxy)-1,1'-biphenyl-4-yl)methyl)oxy)phenyl)propanoic acid or (3R)-3-cyclopropyl-3-(3-(((2-(5,5-dimethyl-1-cyclopenten-1-yl)-3'-(methyloxy)-1,1'-biphenyl-4-yl)methyl)oxy)phenyl)propanoic acid (66.3). MS ESI (neg.) m/e: 991.5 (2M–H)⁺, 495.2 (M–H)⁺.

(3S)-3-Cyclopropyl-3-(3-(((2-(2,2-dimethylcyclopentyl)-2'-fluoro-5'-(methyloxy)-1,1'-biphenyl-4-yl)methyl)oxy)phenyl)propanoic acid or (3R)-3-cyclopropyl-3-(3-(((2-(2,2-dimethylcyclopentyl)-2'-fluoro-5'-(methyloxy)-1,1'-biphenyl-4-yl)methyl)oxy)phenyl)propanoic acid (66.4). MS ESI (neg.) m/e: 515.3 (M–H).

(3S)-3-Cyclopropyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3S)-3-cyclopropyl-3-(3-(((2-((S)-2,2-dimethylcyclopentyl)-2'-fluoro-5'-(methyloxy)-1,1'-biphenyl-4-yl)methyl)oxy)phenyl)propanoic acid or (3R)-3-cyclopropyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3R)-3-cyclopropyl-3-(3-(((2-((1S)-2,2-dimethylcyclopentyl)-2'-fluoro-5'-(methyloxy)-1,1'-biphenyl-4-yl)methyl)oxy)phenyl)propanoic acid (66.5). MS ESI (neg.) m/e: 515.3 (M–H)⁺.

Example 66.6

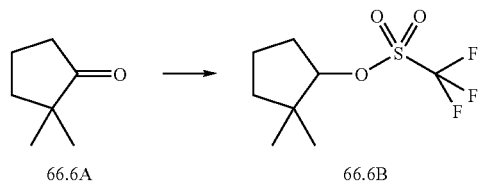

66.6A → 66.6B 5,5-Dimethylcyclopent-1-enyl trifluoromethanesulfonate (66.6B). To a solution of 2,2-dimethylcyclopentanone 66.6A (available from ChemSampCo) (3.00 g, 26.75 mmol) in THF (100 mL), was slowly added LDA (14.7 mL, 2.0 M, in heptane) at −78° C. The resulting mixture was stirred at −78° C. for 1 hour. A solution of N-phenyltriflimide (10.00 g, 28.00 mmol) was added to the mixture at −78° C., and stirring was continued at 0° C. for 2 hours and then at room temperature overnight. The reaction mixture was extracted with hexane (80×2 mL). The organic layer was washed with saturated Na₂CO₃ (30 mL), brine (20 mL), and dried with MgSO₄. The solvent was removed, and the crude product was purified by CombiFlash (eluant was EtOAc and hexane) to give 66.6B. ¹H NMR (CDCl₃) δ ppm 1.16 (s, 6H), 1.86 (t, J=7.1 Hz, 2H), 2.36 (t, J=7.1 Hz, 2H), 5.56 (m, 1H).

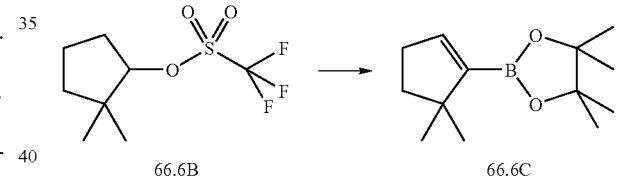

66.6B → 66.6C 2-(5,5-Dimethylcyclopent-1-enyl)-4,4,5,5-tetramethyl-1,3,2-dioxaborolane (66.6C). KOPh was prepared by dissolving commercially available phenol (100 g, 1063 mmol) in MeOH (300 mL) and then adding a mixture of potassium hydroxide (20 mL, 1052 mmol) dissolved in MeOH (80 mL) and water (80 mL). The resulting solution was mixed well and flushed with nitrogen. The solvent was then removed by rotary evaporator at 50-60° C. The resulting product was ground to fine powders and pumped on at high vacuum at 60° C. for 1 hour to give KOPh as an off white solid. PdCl₂(PPh₃)₂ (0.56 g, 0.80 mmol), PPh₃ (0.63 g, 2.40 mmol), bis(pinacolato)diboron (6.80 g, 26.75 mmol) and KOPh (fine powder, 5.30 g, 40.10 mmol) were added to a flask. The flask was flushed with nitrogen and charged with toluene (100 mL) and with 66.6B (6.53 g, 26.75 mmol). The mixture was stirred at 50° C. for 2 hours. The reaction mixture was treated with water at room temperature and extracted with benzene (60×2 mL). The organic layer was dried over MgSO₄. The product was then purified by CombiFlash to give intermediate 66.6C. ¹H NMR (CDCl₃) δ ppm 1.04 (s, 6H), 1.18 (s, 12H), 1.57 (t, J=7.1 Hz, 2H), 2.29 (t, J=7.1 Hz, 2H), 6.29 (m, 1H).

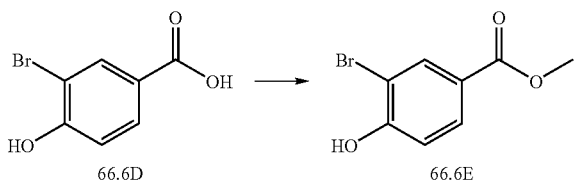

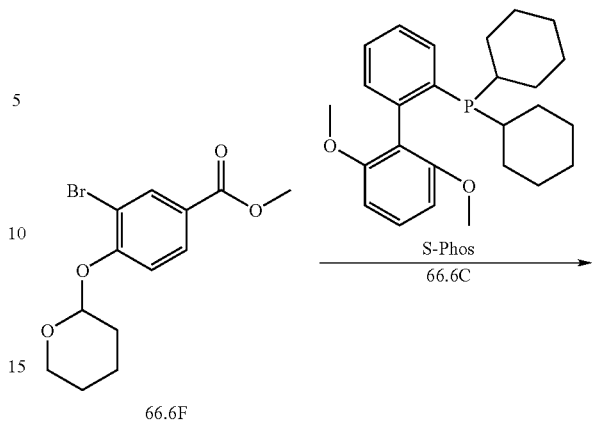

Methyl 3-bromo-4-hydroxybenzoate (66.6E). To a stirred solution of 3-bromo-4-hydroxybenzoic acid (66.6D) (available from Alfa Aesar, Avocado, Lancaster) (50.0 g, 231 mmol) in MeOH (300 mL) was added a cold solution of sulfuric acid (2.50 mL, 47 mmol). The mixture was heated to 80° C. and monitored by TLC. After 16.5 hours, the solvent was removed and the reaction mixture was diluted with EtOAc. The organic phase was washed carefully two times with saturated aqueous NaHCO$_3$, once with brine, and then dried over anhydrous sodium sulfate. After filtration, the organic solvent was removed in vacuo to yield 66.6E as a white solid (yield 100%) that was used without purification.

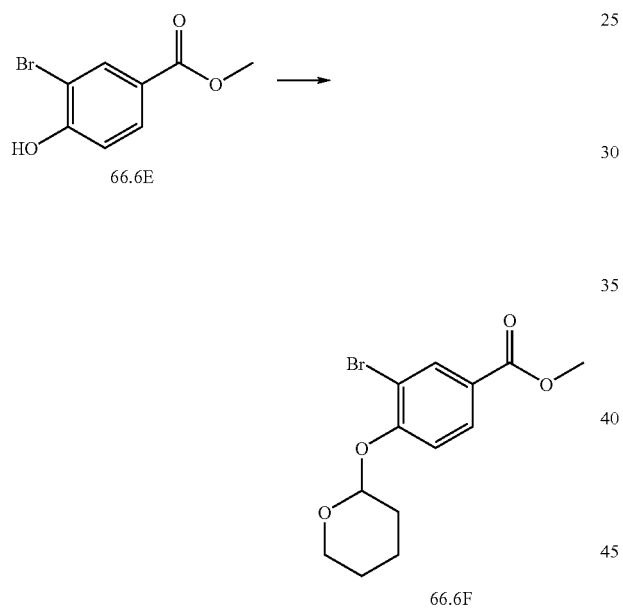

Methyl 3-bromo-4-(tetrahydro-2H-pyran-2-yloxy)benzoate (66.6F). To a stirred solution of 66.6E (38 g, 164 mmol) and 3,4-dihydro-2H-pyran (45 mL, 493 mmol) in DCM (355 mL,) was added 4-methylbenzenesulfonic acid hydrate (0.63 g, 3.30 mmol). The mixture was stirred at room temperature and monitored by TLC. After 2 hours, the solution was washed with a mixed aqueous solution of saturated aqueous sodium bicarbonate/brine/water (1:1:2). The aqueous layer was extracted three times with ether. After drying over anhydrous sodium sulfate and then filtering, the organic solvent was removed under reduced pressure. The crude material was purified on silica gel (0-10% EtOAc in hexanes) to yield a white solid. The product was recrystallized from MeOH to provide 66.6F (yield 90%). $^1$H NMR (400 MHz, CDCl$_3$) δ ppm 8.24 (1H, d, J=2.0 Hz), 7.93 (1H, dd, J=8.6, 2.0 Hz), 7.17 (1H, d, J=8.6 Hz), 5.62 (1H, t, J=2.5 Hz), 3.90 (3H, s), 3.83 (1H, td, J=11.1, 2.9 Hz), 3.66 (1H, m), 2.18 (1H, m), 2.04 (1H, m), 1.94 (1H, m), 1.79 (2H, m), 1.67 (1H, m).)

Methyl 3-(5,5-dimethylcyclopent-1-enyl)-4-(tetrahydro-2H-pyran-2-yloxy)benzoate (66.6G). A stirred mixture of 66.6F (10.1 g, 31.9 mmol), grounded S-Phos (2.62 g, 6.39 mmol), palladium acetate (0.72 g, 3.2 mmol), and potassium phosphate, tribasic (17.0 g, 80.2 mmol) in DMF (70 mL) and water (3.5 mL) was purged three times with argon and placed under vacuum three times. Before heating, 2-(5,5-dimethyl-cyclopent-1-enyl)-4,4,5,5-tetramethyl-1,3,2-dioxaborolane (66.6C) (8.50 g, 38.3 mmol) was added via syringe. The resulting mixture was then heated to 75° C. After 21 hours (black solution), the reaction was cooled to room temperature, diluted with water, and extracted three times with EtOAc. The organic layers were combined and washed twice with brine. After drying over anhydrous sodium sulfate and filtering, the organic solvent was removed under reduced pressure. The residue was purified on silica gel (0-20% EtOAc in hexanes) to yield 66.6G as a colorless oil that solidified (yield 80%). $^1$H NMR (400 MHz) (CDCl$_3$) δ ppm 7.91 (1H, dd, J=8.6, 2.3 Hz), 7.74 (1H, d, J=2.3 Hz), 7.15 (1H, d, J=8.6 Hz), 5.55 (1H, t, J=2.3 Hz), 5.49 (1H, t, J=2.9 Hz), 3.88 (3H, s), 3.82 (1H, td, J=11.1, 2.9 Hz), 3.64 (1H, m), 2.43 (2H, td, J=7.0, 2.3 Hz), 1.92 (5H, m), 1.69 (1H, m), 1.61 (2H, m), 1.09 (6H, d, J=13.7 Hz).

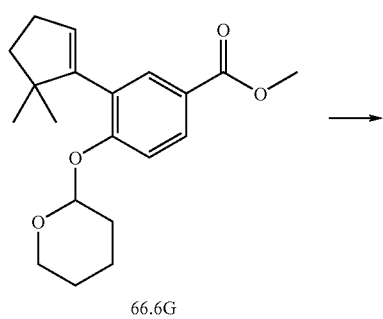

66.6G

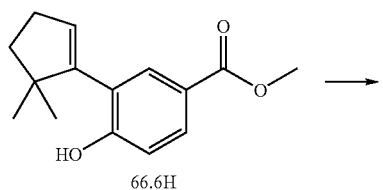

66.6H

Methyl 3-(5,5-dimethylcyclopent-1-enyl)-4-hydroxybenzoate (66.6H). To a stirred solution of 66.6G (19.0 g, 57.6 mmol) in MeOH (150 mL) was added PPTS (1.46 g, 5.80 mmol). The mixture was heated to 50° C. and monitored with TLC. After 19 hours, the organic solvent was removed under reduced pressure and the product was then purified on silica gel (0-15% EtOAc in hexanes) to yield 66.6H as a white solid (yield 90%). $^1$H NMR (400 MHz) (CDCl$_3$) δ ppm 7.89 (1H, dd, J=8.6, 2.0 Hz), 7.79 (1H, d, J=2.3 Hz), 6.97 (1H, d, J=8.6 Hz), 5.87 (1H, s), 5.81 (1H, t, J=2.3 Hz), 3.89 (3H, s), 2.51 (2H, td, J=7.1, 2.5 Hz), 1.94 (2H, t, J=7.0 Hz), 1.12 (6H, s).

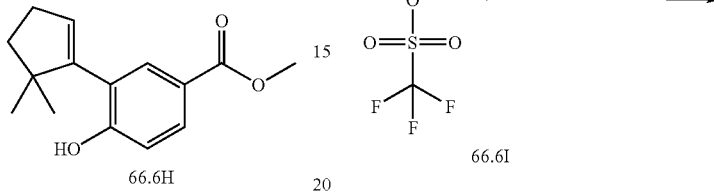

66.6H

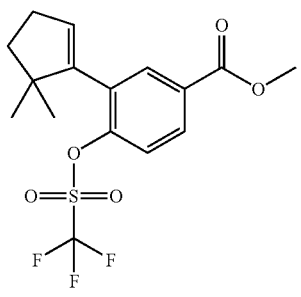

66.6I

Methyl 3-(5,5-dimethylcyclopent-1-enyl)-4-(trifluoromethylsulfonyloxy)benzoate (66.6I). To a stirred solution of 66.6H (6.00 g, 24.4 mmol) in dry DCM (35 mL) was added TEA (6.80 mL, 48.9 mmol) and 4-dimethylaminopyridine (0.30 g, 2.5 mmol). After about 20 minutes, N-phenyl bis-trifluoromethane sulfonimide (10.5 g, 29.3 mmol) was added in portion. Upon complete addition, the solution was stirred at room temperature and monitored with TLC. After 3 hours, the reaction was diluted with brine and extracted three times with DCM. After drying over anhydrous magnesium sulfate and filtering, the organic solvent was removed under reduced pressure and the product was then purified on silica gel (0-10% EtOAc in hexanes) to yield 66.61 as a colorless oil (yield 88%). $^1$H NMR (400 MHz, CDCl$_3$) δ ppm 8.02 (1H, dd, J=8.6, 2.0 Hz), 7.94 (1H, d, J=2.0 Hz), 7.35 (1H, d, J=8.6 Hz), 5.80 (1H, t, J=2.5 Hz), 3.94 (3H, s), 2.48 (2H, td, J=7.0, 2.3 Hz), 1.91 (2H, t, J=7.0 Hz), 1.09 (6H, s).

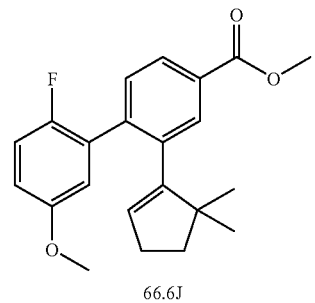

66.6I

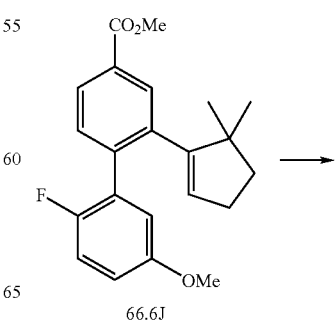

66.6J

Synthesis of 66.6J. To a stirred solution of 66.6I (8.71 g, 23.0 mmol) in DMF (20 mL) at 23° C. was added 2-fluoro-5-methoxyphenylboronic acid (7.84 g, 46.1 mmol) and potassium carbonate (9.56 g, 69.1 mmol) followed by tetrakis(triphenylphosphine)palladium (0) (2.67 g, 2.31 mmol). The mixture was heated to 90° C. After 15 hours, LCMS-showed that the reaction was complete. The mixture was then cooled to room temperature and then diluted with water. After extracting three times with EtOAc, the mixture was concentrated in vacuo and then purified on silica gel (0%-10% EtOAc/hexane) to give 66.6J as a clear oil that solidified (yield 91%). $^1$H NMR (400 MHz, CDCl$_3$) δ ppm 7.98 (1H, dd, J=8.0, 1.8 Hz), 7.91 (1H, d, J=2.0 Hz), 7.40 (1H, d, J=7.8 Hz), 6.98 (1H, t, J=8.8 Hz), 6.85 (2H, m), 5.55 (1H, s), 3.95 (3H, s), 3.77 (3H, s), 2.27 (2H, td, J=7.0, 2.7 Hz), 1.68 (2H, t, J=7.0 Hz), 0.87 (6H, s).

-continued

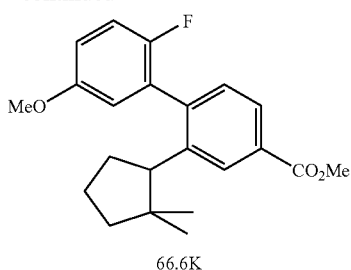
66.6K

-continued

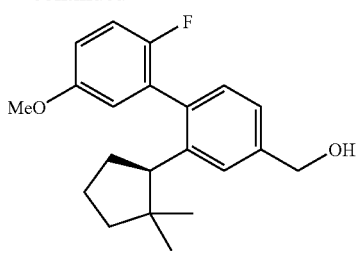
66.6M and 66.6N

Synthesis of 66.6K. To a stirred solution of 66.6J (0.660 g, 1.86 mmol) in MeOH (20.00 mL, 1.86 mmol) at 23° C. was added Pd/C (0.0198 g, 0.186 mmol). The reaction was stirred under an atmosphere of hydrogen (0.00375 g, 1.86 mmol) for 16 hours. The reaction mixture was then filtered and concentrated in vacuo to give 66.6K as a clear oil (0.600 g, 90.4% yield).

Synthesis of 66.6L, 66.6M, and 66.6N. To a stirred solution of 66.6K (0.500 g, 1.4 mmol) in THF (7.0 mL, 1.4 mmol) at 0° C. was added LAH (1.4 mL, 1.4 mmol). After addition, the reaction was stirred for 1.5 hours. 1N NaOH (aq) was then added to quench the reaction, and the mixture was then extracted with EtOAc. The organic layers were dried over magnesium sulfate, filtered, and concentrated in vacuo. The resulting product was then purified on silica gel (0%-20% EtOAc/hexane) to give 66.6L (0.442 g, 96% yield). Chiral separation of 66.6L was accomplished on Chiracel-OD (3% IPA in hexane) to provide 66.6M and 66.6N. Both enantiomers were used to synthesize example compounds, and both enantiomers gave active example compounds. However, the enantiomer corresponding to peak 2 provided the most active example compounds. Analytical column (Chiracel-OD (2% IPA in hexane, 45 min run) Peak 1-15.5 mins, Peak 2-38.0 mins).[1]

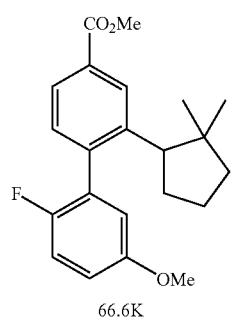
66.6K

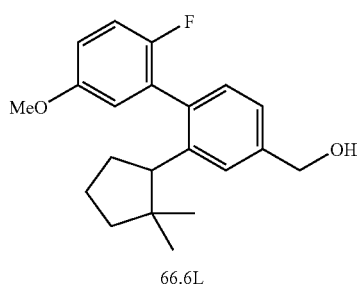
66.6L

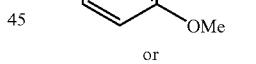

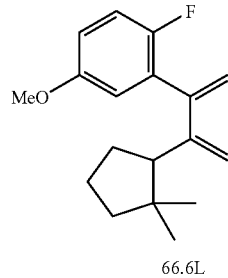
66.6L

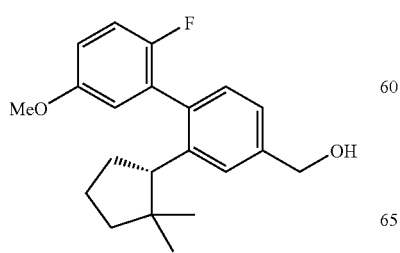
66.6M or 66.6N

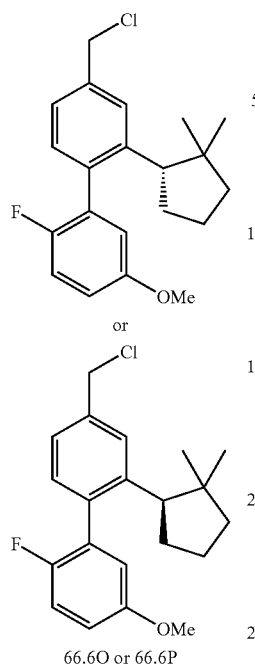

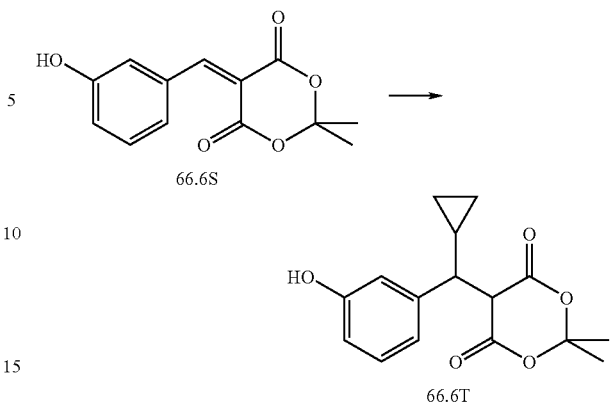

4-(Chloromethyl)-2-((1R)-2,2-dimethylcyclopentyl)-2'-fluoro-5'-(methyloxy)-1,1'-biphenyl (66.6O) or 4-(chloromethyl)-2-((1S)-2,2-dimethylcyclopentyl)-2'-fluoro-5'-methyloxy)-1,1'-biphenyl (66.6P). Thionyl chloride (1.5 mL, 20 mmol) was added to a stirred solution of 66.6M or 66.6N (3.280 g, 10.0 mmol) in DCM (100 mL, 10.0 mmol) and DMF (0.77 mL, 10.0 mmol) at 0° C. Stirring was continued at room temperature for 2 hours. The reaction mixture was then concentrated in vacuo and purified on silica gel (0-10% EtOAc in hexane) to give the desired product 66.6O or 66.6P (3.00 g, 87% yield) as a clear oil.

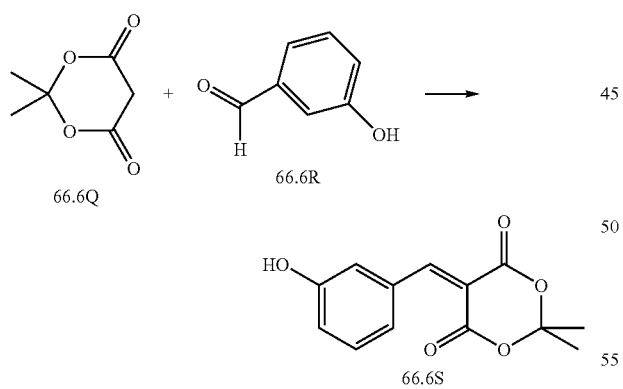

5-(3-Hydroxybenzylidene)-2,2-dimethyl-1,3-dioxane-4,6-dione (66.6S). 2,2-Dimethyl-1,3-dioxane-4,6-dione 66.6Q (available from Aldrich) (28.8 g, 200 mmol) was added to a mixture of 3-hydroxybenzaldehyde 66.6R (available from Aldrich) (24.4 g, 200 mmol) in water (1000 mL) at 85° C. The resulting mixture was stirred at 85° C. for 2 hours. The reaction was allowed to cool and then filtered to provide 5-(3-hydroxybenzylidene)-2,2-dimethyl-1,3-dioxane-4,6-dione 66.6S (41.4 g, 83% yield) as a yellow solid.

5-(Cyclopropyl(3-hydroxyphenyl)methyl)-2,2-dimethyl-1,3-dioxane-4,6-dione (66.6T). To a solution of 5-(3-hydroxybenzylidene)-2,2-dimethyl-1,3-dioxane-4,6-dione 66.6S (2.00 g, 8.06 mmol) in THF (25 mL) was added cyclopropylmagnesium bromide (available from Aldrich) (0.5M, 96.7 mL, 48.3 mmol) via cannula at 0° C. The resulting heterogeneous mixture was warmed to room temperature, stirred for 30 minutes, and quenched with 1 N aqueous HCl. The aqueous layer was extracted with EtOAc. The combined organic layers were washed with brine, dried over sodium sulfate, filtered, and concentrated. The residue was purified by silica gel flash chromatography (10-35% EtOAc/hexane) to afford 5-(cyclopropyl(3-hydroxyphenyl)methyl)-2,2-dimethyl-1,3-dioxane-4,6-dione 66.6T (2.04 g, 87% yield) as a yellow oil.

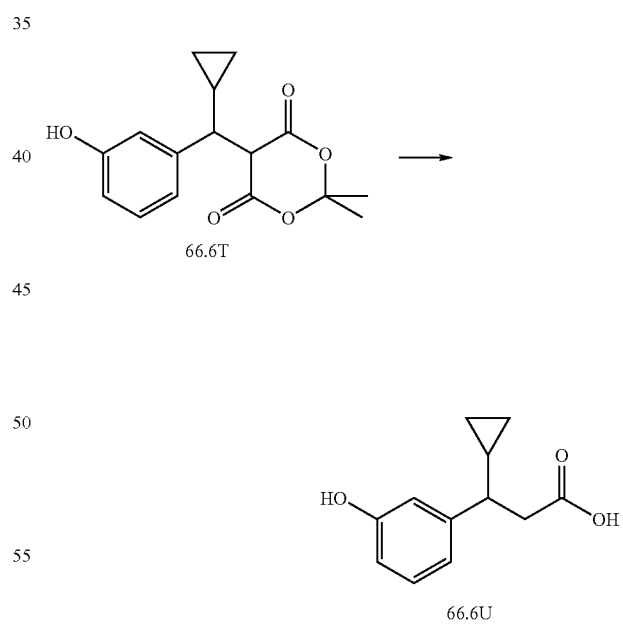

3-Cyclopropyl-3-(3-hydroxyphenyl)propanoic acid (66.6U). 5-(Cyclopropyl(3-hydroxyphenyl)methyl)-2,2-dimethyl-1,3-dioxane-4,6-dione 66.6T (14.64 g, 50.43 mmol) in DMF/water (10/1) (220 mL) was heated at 90° C. overnight. The reaction was then diluted with water and extracted with EtOAc. The combined organic layers were washed with brine, dried over Na$_2$SO$_4$, filtered, and concentrated to give 66.6U as a clear oil (10.40 g, 100%).

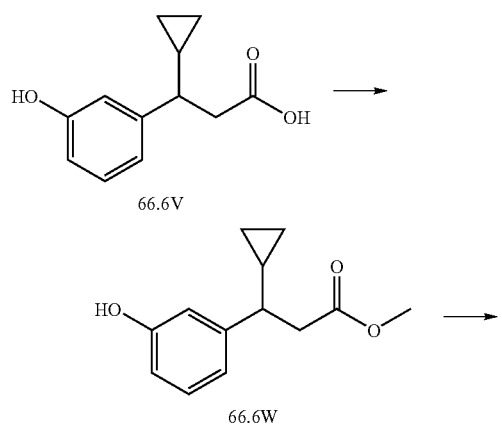

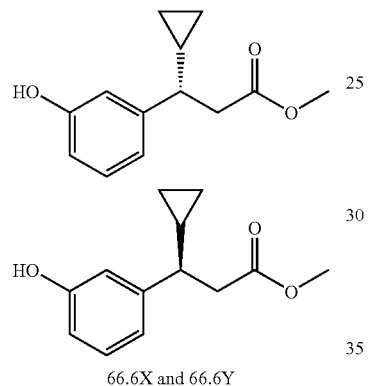

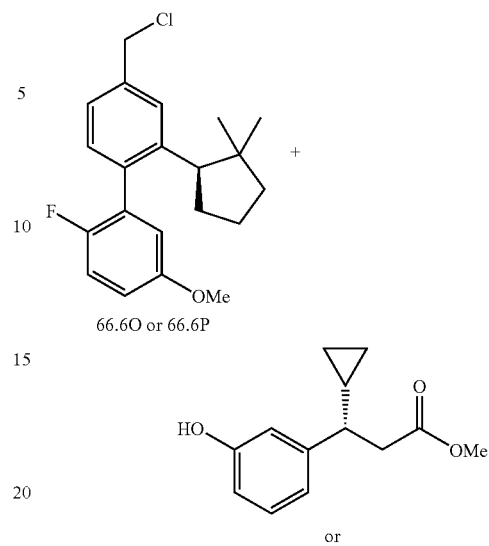

Methyl 3-cyclopropyl-3-(3-hydroxyphenyl)propanoate (66.6W, 66.6X, and 66.6Y). To a flask containing 3-cyclopropyl-3-(3-hydroxyphenyl)propanoic acid 66.6V (1.2 g, 5.8 mmol) in MeOH (15 mL) was added $H_2SO_4$ (0.31 mL, 5.8 mmol). The resulting mixture was stirred at reflux overnight. The reaction was concentrated and purified by combiflash chromatography (0 to 30% EtOAc/Hexanes) to provide methyl 3-cyclopropyl-3-(3-hydroxyphenyl)propanoate 66.6W (1.2 g, 94%). Chiral separation was accomplished on Chiracel-OD (3% IPA in hexane) to provide 66.6X and 66.6Y. Peak 1 was the desired enantiomer. Analytical column (Chiracel-OD (2% IPA in hexane-45 min run) Peak 1-22.5 mins, Peak 2-34.0 mins).

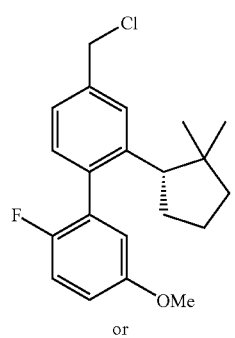

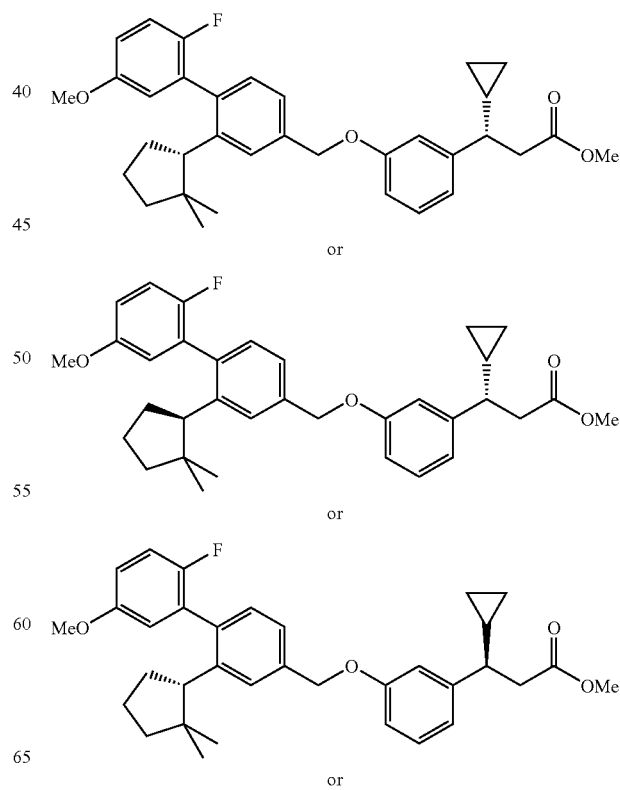

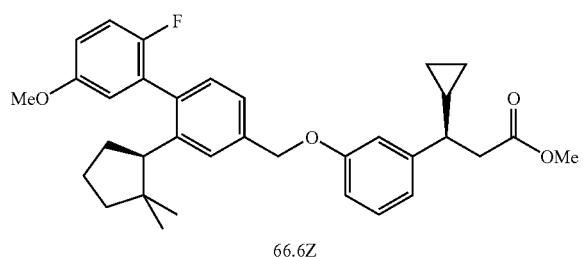

66.6Z

Methyl (3S)-3-cyclopropyl-3-(3-(((2-((1S)-2,2-dimethylcyclopentyl)-2'-fluoro-5'-(methyloxy)-1,1'-biphenyl-4-yl)methyl)oxy)phenyl)propanoate or methyl (3S)-3-cyclopropyl-3-(3-(((2-((1R)-2,2-dimethylcyclopentyl)-2'-fluoro-5'-(methyloxy)-1,1'-biphenyl-4-yl)methyl)oxy)phenyl)propanoate or methyl (3R)-3-cyclopropyl-3-(3-(((2-((1S)-2,2-dimethylcyclopentyl)-2'-fluoro-5'-(methyloxy)-1,1'-biphenyl-4-yl)methyl)oxy)phenyl)propanoate or methyl (3R)-3-cyclopropyl-3-(3-(((2-((1R)-2,2-dimethylcyclopentyl)-2'-fluoro-5'-(methyloxy)-1,1'-biphenyl-4-yl)methyl)oxy)phenyl)propanoate (66.6Z). To a stirred solution of 66.6X (0.350 g, 1.59 mmol) in DMF (20.00 mL, 1.59 mmol) at 23° C. was added 66.6O or 66.6P (0.551 g, 1.59 mmol) followed by cesium carbonate (1.04 g, 3.18 mmol). The resulting mixture was stirred for 20 hours. Water was then added to the reaction, and the resulting mixture was extracted with EtOAc. The combined organic layers were dried over magnesium sulfate, filtered and concentrated in vacuo. The residue was purified on silica gel (0%-20% EtOAc/hexane) to give Product 66.6Z (0.843 g, 100.0% yield).

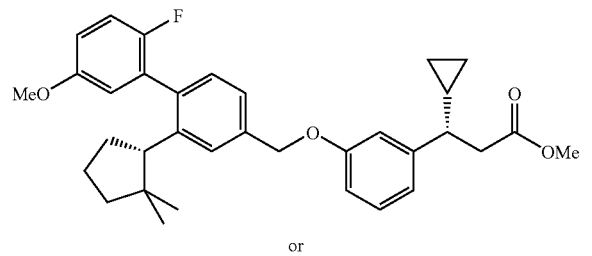

or

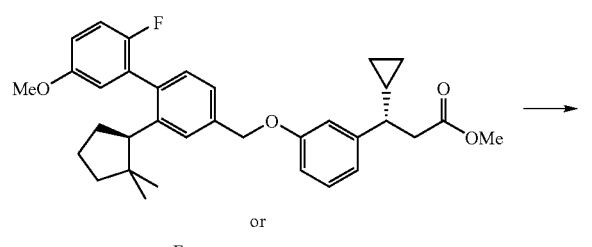

or

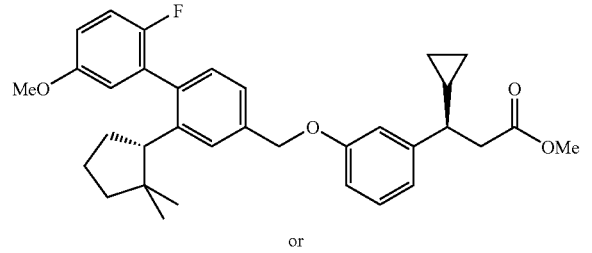

or

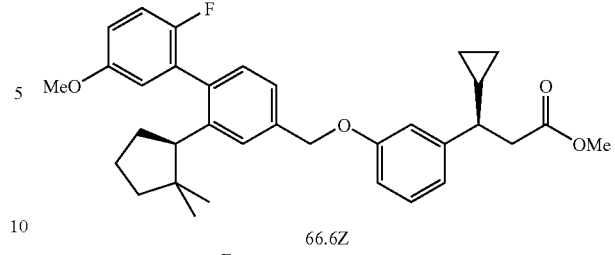

66.6Z

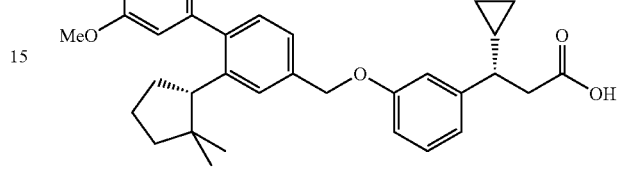

or

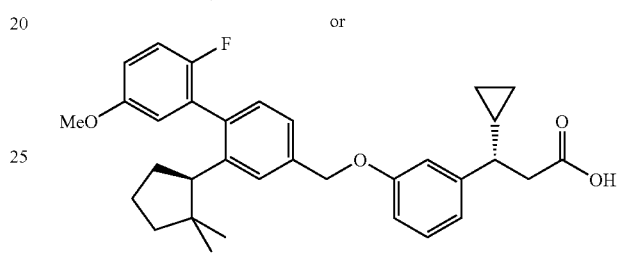

or

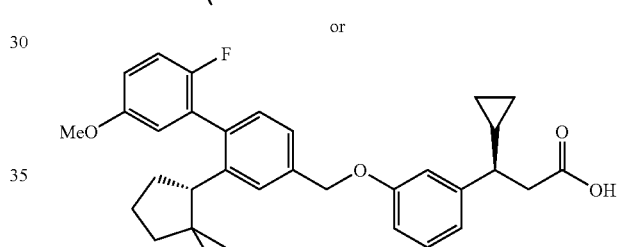

or

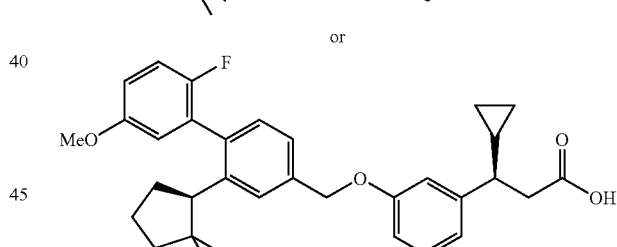

or

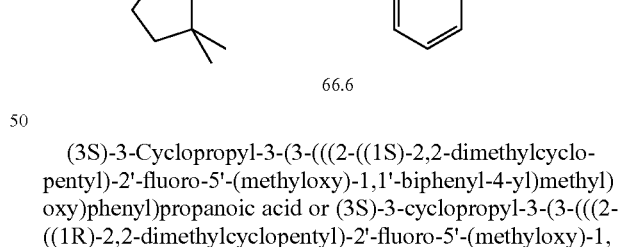

66.6

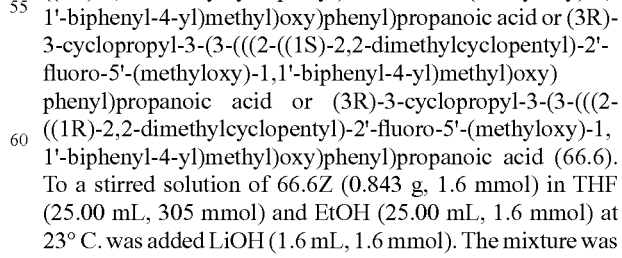

(3S)-3-Cyclopropyl-3-(3-(((2-((1S)-2,2-dimethylcyclopentyl)-2'-fluoro-5'-(methyloxy)-1,1'-biphenyl-4-yl)methyl)oxy)phenyl)propanoic acid or (3S)-3-cyclopropyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3R)-3-cyclopropyl-3-(3-(((2-((1S)-2,2-dimethylcyclopentyl)-2'-fluoro-5'-(methyloxy)-1,1'-biphenyl-4-yl)methyl)oxy)phenyl)propanoic acid or (3R)-3-cyclopropyl-3-(3-(((2-((1R)-2,2-dimethylcyclopentyl)-2'-fluoro-5'-(methyloxy)-1,1'-biphenyl-4-yl)methyl)oxy)phenyl)propanoic acid (66.6). To a stirred solution of 66.6Z (0.843 g, 1.6 mmol) in THF (25.00 mL, 305 mmol) and EtOH (25.00 mL, 1.6 mmol) at 23° C. was added LiOH (1.6 mL, 1.6 mmol). The mixture was stirred at 23° C. for 16 hours. The reaction mixture was concentrated in vacuo. 1N HCl was then added to the mixture, and the resulting mixture was extracted with EtOAc. The combined organic layers were dried over magnesium sulfate, filtered and concentrated in vacuo. The residue was purified on silica gel (0%-30% EtOAc/hexane) to give 66.6 (0.7422 g, 90% yield). MS ESI (neg.) m/e: 515.2 (M−H)⁺. Compound 66.5 is a diastereomer of 66.6 because the same head group was used to synthesize it that was used to prepare 66.6, but the tail groups used were different.

Asymmetric synthesis of 66.6O or 66.6P. The following procedures were used to synthesize 66.6O or 66.6P using a highly enantioselective procedure to hydrogenate 66.6H to form 66.6AA or 66.6AB.

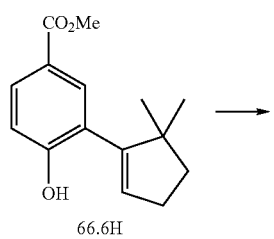
66.6H

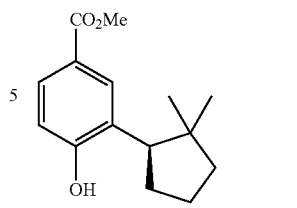
or
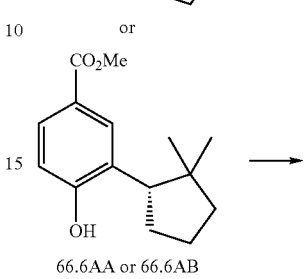
66.6AA or 66.6AB

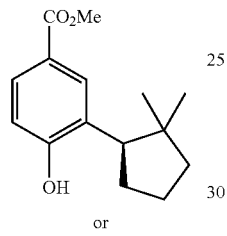
or
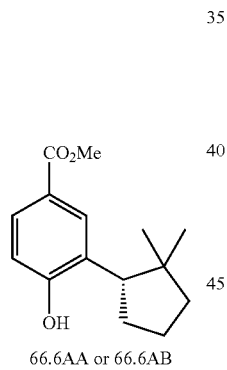
66.6AA or 66.6AB (R)-methyl 3-(2,2-dimethylcyclopentyl)-4-hydroxybenzoate (66.6AA) or (S)-methyl 3-(2,2-dimethylcyclopentyl)-4-hydroxybenzoate (66.6AB). A mixture of Rh(COD)₂BF₄ (Stern Chemical, 35138-22-8, 137.2 mg, 0.338 mmol) and (R)-1-[(S)-2-(R)-(ditertbutylphosphino)ferrocenyl]ethyl-bis-(3,5-bistrifluoromethylphenyl)phosphine (Solvias, SL-J210-1, 302 mg, 0.3718 mmol) was stirred in THF (300 mL) under N₂ for 60 minutes and a dark red solution formed. To the resulting solution was added methyl 3-(5,5-dimethyl-cyclopent-1-enyl)-4-hydroxybenzoate 66.6H (41.64 g, 168.98 mmol) and TEA (10 mol %, 2.35 mL, 16.9 mmol). The resulting solution was filled with H₂ (200 psi) three times and stirred at room temperature/200 psi for 2 hours. The reaction mixture was then passed through a short plug of silica gel, eluting with 1:1 hexane/EtOAc, followed by concentration afforded the desired product as a white solid (98.9A % conversion, 99% yield (41.6 g), 99% ee).

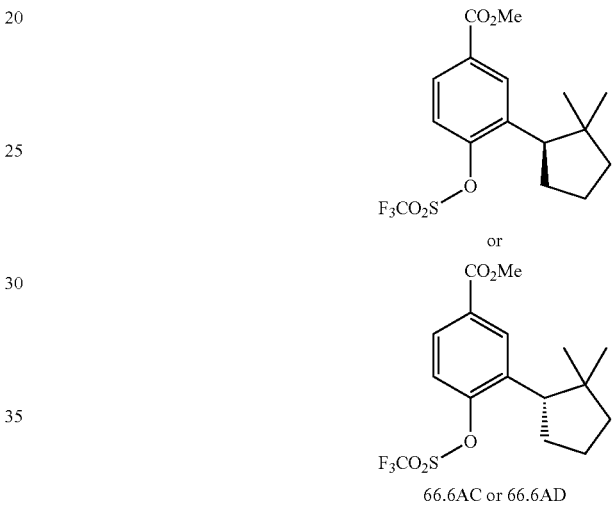
66.6AC or 66.6AD (R)-methyl 3-(2,2-dimethylcyclopentyl)-4-(trifluoromethylsulfonyloxy)benzoate or (S)-methyl 3-(2,2-dimethylcyclopentyl)-4-(trifluoromethylsulfonyloxy)benzoate (66.6AC or 66.6AD). To a stirred solution of (R)-methyl 3-(2,2-dimethylcyclopentyl)-4-hydroxybenzoate or (S)-methyl 3-(2,2-dimethylcyclopentyl)-4-hydroxybenzoate (66.6AA or 66.6AB) (18.00 g, 72 mmol) in DCM (181 mL, 72 mmol) at 23° C. was added TEA (12 mL, 87 mmol) and a catalytic amount of DMAP. N-phenyltriflimide (28 g, 80 mmol) was then added to the mixture and stirring was continued at room temperature for 16 hours. The reaction was concentrated in vacuo. The residue was purified on silica gel (0-10% EtOAc in hexanes) to yield 66.6AC or 66.6AD as a colorless oil (27.7 g, 100% yield). MS ESI (pos.) m/e: 381.1 (M+H)⁺.

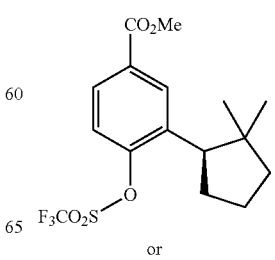
or

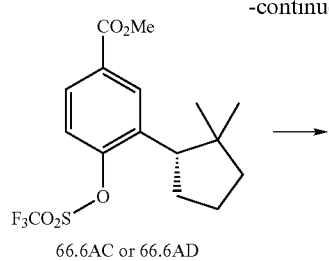

66.6AC or 66.6AD

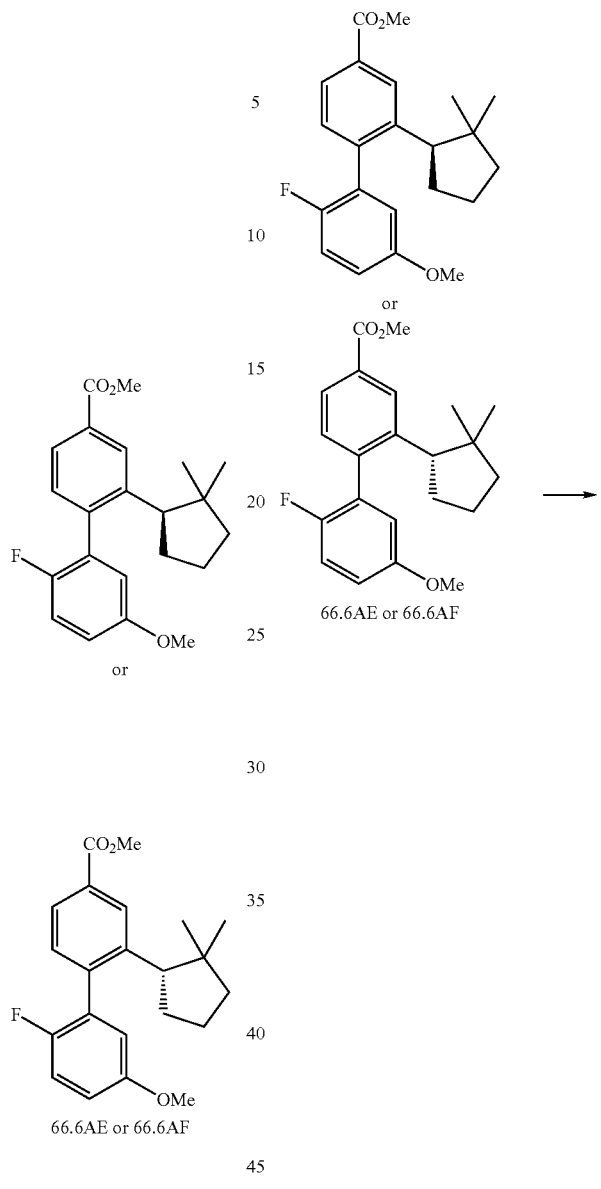

Methyl 2-((1R)-2,2-dimethylcyclopentyl)-2'-fluoro-5'-(methyloxy)-1,1'-biphenyl-4-carboxylate or methyl 2-((1S)-2,2-dimethylcyclopentyl)-2'-fluoro-5'-(methyloxy)-1,1'-biphenyl-4-carboxylate (66.6AE or 66.6AF). To a stirred solution of (S)-methyl 3-(2,2-dimethylcyclopentyl)-4-(trifluoromethylsulfonyloxy)benzoate or (R)-methyl 3-(2,2-dimethylcyclopentyl)-4-(trifluoromethylsulfonyloxy)benzoate (66.6AC or 66.6AD) (28.5 g, 75 mmol) in DMF (375 mL, 75 mmol) at 23° C. was added 2-fluoro-5-methoxyphenylboronic acid (19 g, 112 mmol) (commercially available from Aldrich), potassium carbonate (31 g, 225 mmol), and then tetrakis(triphenylphosphine)palladium (4 g, 4 mmol). The mixture was heated to 90° C. Stirring was continued for 20 hours, after which, the reaction was cooled to room temperature, diluted with water, and extracted three times with EtOAc. The organic layers were combined and washed twice with brine. After drying over anhydrous sodium sulfate and filtering, the organic solvent was removed under reduced pressure. The residue was purified on silica gel (0-10% EtOAc in hexanes) to yield 66.6AE or 66.6AF as a colorless oil (25.00 g, 94% yield). MS ESI (pos.) m/e: 357.1 (M+H)$^+$.

(2-((1R)-2,2-Dimethylcyclopentyl)-2'-fluoro-5'-(methyloxy)-1,1'-biphenyl-4-yl)methanol or (2-((1S)-2,2-dimethylcyclopentyl)-2'-fluoro-5'-(methyloxy)-1,1'-biphenyl-4-yl)methanol (66.6AG or 66.6AF). To a stirred solution of methyl 2-((1R)-2,2-dimethylcyclopentyl)-2'-fluoro-5'-(methyloxy)-1,1'-biphenyl-4-carboxylate or methyl 2-((1S)-2,2-dimethylcyclopentyl)-2'-fluoro-5'-(methyloxy)-1,1'-biphenyl-4-carboxylate (66.6AE or 66.6AF) (29.50 g, 83 mmol) in THF (414 mL, 83 mmol) at 0° C. was added LAH (124 mL, 124 mmol). Stirring was continued for 2 hours. Aqueous 1N NaOH was then added to quench the reaction, and the mixture was then extracted with EtOAc. The combined organic layers were dried over magnesium sulfate, filtered, and concentrated in vacuo. The residue was purified on silica gel (0-20% EtOAc in hexanes) to yield 66.6AG or 66.6AH as a colorless oil (23.66 g, 87% yield). MS ESI (pos.) m/e: 346.1 (M+H$_2$O)$^+$.

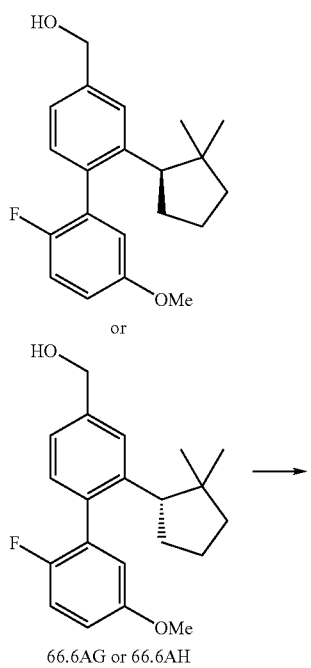

66.6AG or 66.6AH

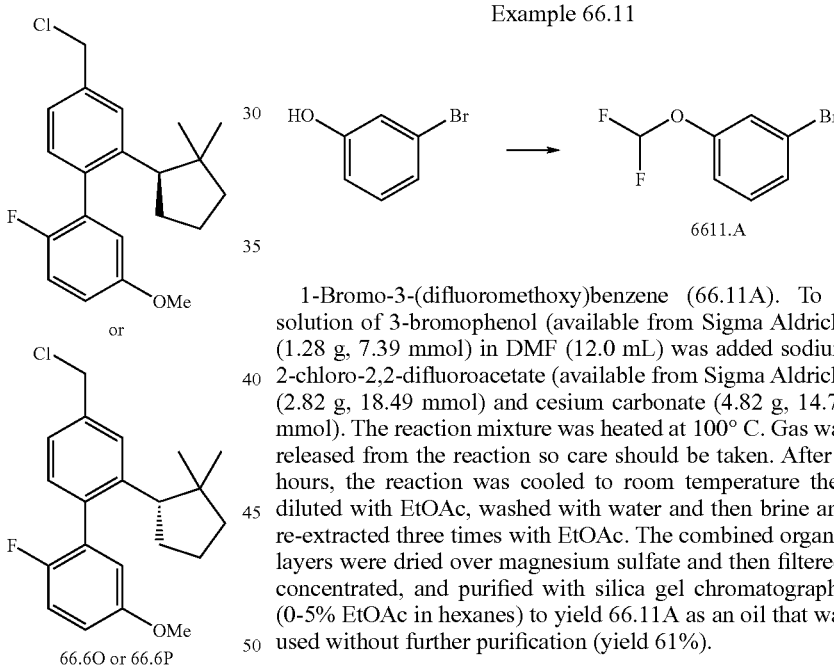

66.6O or 66.6P 4-(Chloromethyl)-2-((1R)-2,2-dimethylcyclopentyl)-2'-fluoro-5'-(methyloxy)-1,1'-biphenyl or 4-(chloromethyl)-2-((1S)-2,2-dimethylcyclopentyl)-2'-fluoro-5'-(methyloxy)-1,1'-biphenyl (66.6O or 66.6P). To a stirred solution of (2-((1R)-2,2-dimethylcyclopentyl)-2'-fluoro-5'-(methyloxy)-1,1'-biphenyl-4-yl)methanol or (2-((1S)-2,2-dimethylcyclopentyl)-2'-fluoro-5'-(methyloxy)-1,1'-biphenyl-4-yl)methanol (66.6AG or 66.6AH) (23.66 g, 72 mmol) in DCM (360 mL, 72 mmol) and DMF (0.56 mL, 7.2 mmol) at 0° C. was added thionyl chloride (11 mL, 144 mmol). Stirring was continued at room temperature for 1 hour. The reaction as then concentrated in vacuo, and the residue was purified on silica gel (0-10% EtOAc in hexanes) to yield 66.6O or 66.6P as a colorless oil (23.0 g, 92% yield). MS ESI (pos.) m/e: 364.1 (M+H$_2$O)$^+$.

(3S)-3-Cyclopropyl-3-(3-(((2-((1R)-2,2-dimethylcyclopentyl)-3'-(methyloxy)-1,1'-biphenyl-4-yl)methyl)oxy)phenyl)propanoic acid or (3S)-3-cyclopropyl-3-(3-(((2-((1S)-2,2-dimethylcyclopentyl)-3'-(methyloxy)-1,1'-biphenyl-4-yl)methyl)oxy)phenyl)propanoic acid or (3R)-3-cyclopropyl-3-(3-(((2-((1R)-2,2-dimethylcyclopentyl)-3'-(methyloxy)-1,1'-biphenyl-4-yl)methyl)oxy)phenyl)propanoic acid or (3R)-3-cyclopropyl-3-(3-(((2-((1S)-2,2-dimethylcyclopentyl)-3'-(methyloxy)-1,1'-biphenyl-4-yl)methyl)oxy)phenyl)propanoic acid (66.7). MS ESI (neg.) m/e: 995.5 (2M–H)$^+$, 497.3 (M–H)$^+$.

Diastereomer of 66.7 (66.8). MS ESI (neg.) m/e: 995.5 (2M–H)$^+$, 497.4 (M–H)$^+$.

(3S)-3-(3-(((2-Cycloheptyl-3'-(methyloxy)-1,1'-biphenyl-4-yl)methyl)oxy)phenyl)-3-cyclopropylpropanoic acid or (3R)-3-(3-(((2-cycloheptyl-3'-(methyloxy)-1,1'-biphenyl-4-yl)methyl)oxy)phenyl)-3-cyclopropylpropanoic acid (66.9). MS ESI (neg.) m/e: 995.5 (2M–H)$^+$, 497.3 (M–H)$^+$.

(3S)-3-Cyclopropyl-3-(3-(((2-(6,6-dimethyl-1-cyclohexen-1-yl)-2'-fluoro-5'-(methyloxy)-1,1'-biphenyl-4-yl)methyl)oxy)phenyl)propanoic acid or (3R)-3-cyclopropyl-3-(3-(((2-(6,6-dimethyl-1-cyclohexen-1-yl)-2'-fluoro-5'-(methyloxy)-1,1'-biphenyl-4-yl)methyl)oxy)phenyl)propanoic acid (66.10). MS ESI (neg.) m/e: 527.2 (M–H)$^+$.

Example 66.11

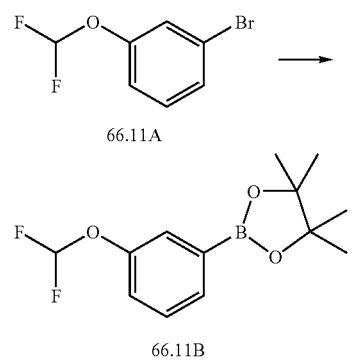

6611.A

1-Bromo-3-(difluoromethoxy)benzene (66.11A). To a solution of 3-bromophenol (available from Sigma Aldrich) (1.28 g, 7.39 mmol) in DMF (12.0 mL) was added sodium 2-chloro-2,2-difluoroacetate (available from Sigma Aldrich) (2.82 g, 18.49 mmol) and cesium carbonate (4.82 g, 14.79 mmol). The reaction mixture was heated at 100° C. Gas was released from the reaction so care should be taken. After 2 hours, the reaction was cooled to room temperature then diluted with EtOAc, washed with water and then brine and re-extracted three times with EtOAc. The combined organic layers were dried over magnesium sulfate and then filtered, concentrated, and purified with silica gel chromatography (0-5% EtOAc in hexanes) to yield 66.11A as an oil that was used without further purification (yield 61%).

2-(3-(Difluoromethoxy)phenyl)-4,4,5,5-tetramethyl-1,3,2-dioxaborolane (66.11B). A stirred mixture of 66.11A (1.00 g, 4.50 mmol), bis(pinacolato)diboron (1.26 g, 4.95 mmol), potassium acetate (1.34 g, 13.70 mmol), and dichloro[1,1'-bis(diphenylphosphino)ferrocene]dichloride palladium(II) DCM adduct (0.17 g, 0.23 mmol) in dry 1,4-dioxane (10.0 mL) was purged three times with argon and placed under vacuum three times. The mixture was heated to 100° C. and monitored with LC-MS and TLC. After 21 hours, the reaction was cooled to room temperature and then filtered through Celite. The organic solvent was removed under reduced pressure, and the residue was purified on silica gel (0-10% EtOAc in hexanes) to yield 66.11B as a colorless oil (0.41 g, 34%). $^1$H NMR (400 MHz, CDCl$_3$) δ ppm 7.67 (1H, d, J=7.4 Hz), 7.56 (1H, d, J=2.3 Hz), 7.41 (1H, m), 7.22 (1H, dd, J=7.8, 2.3 Hz), 6.73 (1H, t, J=74 Hz), 1.36 (12H, s).

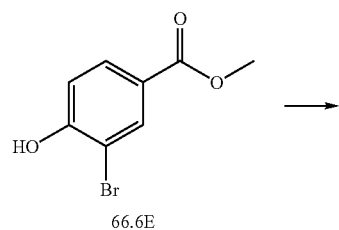

66.6E

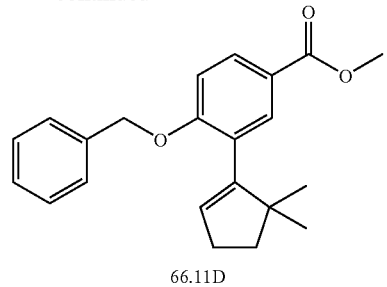

66.11D

Methyl 4-(benzyloxy)-3-(5,5-dimethylcyclopent-1-enyl)benzoate (66.11D). A stirred mixture of 66.11C (3.75 g, 11.66 mmol), ground S-Phos (0.96 g, 2.33 mmol), palladium acetate (0.26 g, 1.17 mmol), and potassium phosphate, tribasic (6.19 g, 29.17 mmol) in DMF (28.0 mL) and water (1.50 mL) was purged three times with argon and placed under vacuum three times. Before heating, 2-(5,5-dimethylcyclopent-1-enyl)-4,4,5,5-tetramethyl-1,3,2-dioxaborolane (66.6C) (3.11 g, 13.99 mmol) was added via syringe, then the mixture was heated to 75° C. After 21 hours (black solution), the reaction was cooled to room temperature, diluted with water, and extracted three times with EtOAc. The combined organic layers were washed twice with brine. After drying over anhydrous sodium sulfate and filtration, the organic solvent was removed under reduced pressure. The residue was purified on silica gel (0-10% EtOAc in hexanes) to yield 66.11D as a colorless oil (3.03 g, 77%). MS ESI (pos.) m/e: 337.0 (M+H)$^+$.

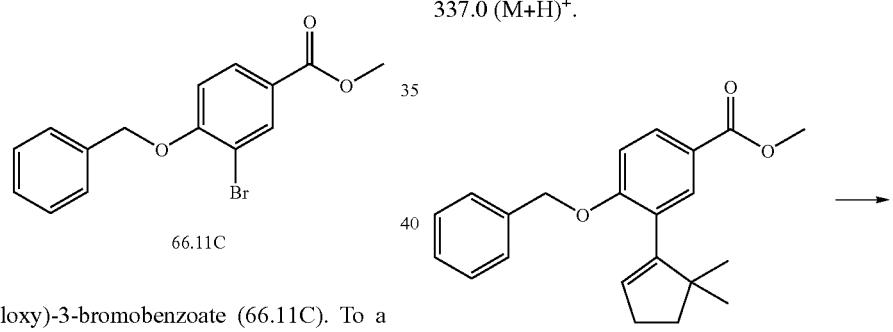

66.11C 66.11D 66.11E

Methyl 4-(benzyloxy)-3-bromobenzoate (66.11C). To a solution of 66.6E (53.2 g, 230 mmol) in DMSO (45.0 mL) was added 1-(bromomethyl)benzene (35.6 mL, 299 mmol). After cooling in an ice water bath, cesium carbonate (128 g, 391 mmol) was carefully added to the mixture, and the mixture was allowed to warm to room temperature. After overnight stirring, the mixture was diluted with water and extracted three times with EtOAc. The organic layers were combined and then washed with brine. After drying over anhydrous magnesium sulfate and filtration, the organic solvent was removed under reduced pressure to yield 66.11C as a white solid.

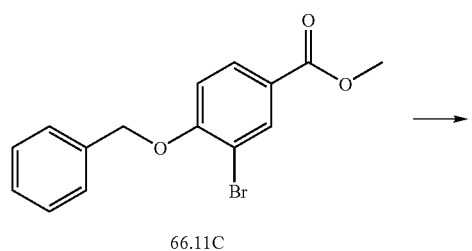

66.11C

Methyl 3-(2,2-dimethylcyclopentyl)-4-hydroxybenzoate (66.11E). To a flask containing 66.11D (3.03 g, 9.0 mmol) in MeOH (25.0 mL) was added palladium, 10% wt. on activated carbon (0.48 g, 0.45 mmol). After purging, the mixture was stirred under an atmosphere of hydrogen at room temperature. The reaction was monitored with TLC and LC-MS. After 27.5 hours, the reaction was filtered through Celite. After concentration, the residue was purified on silica gel using 0-50% EtOAc in hexanes to yield 66.11E as a colorless oil that solidified (1.99 g, 89%). $^1$H NMR (400 MHz, CDCl$_3$)

δ ppm 7.91 (1H, d, J=2.3 Hz), 7.79 (1H, dd, J=8.4, 2.2 Hz), 6.82 (1H, d, J=8.2 Hz), 5.54 (1H, s), 3.90 (3H, s), 3.17 (1H, dd, J=10.4, 8.0 Hz), 2.17 (1H, m), 2.04 (1H, m), 1.92 (1H, m), 1.81 (1H, m), 1.68 (2H, m), 1.06 (3H, s), 0.72 (3H, s).

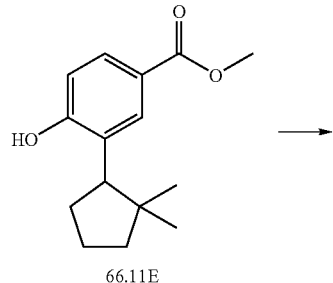

66.11E

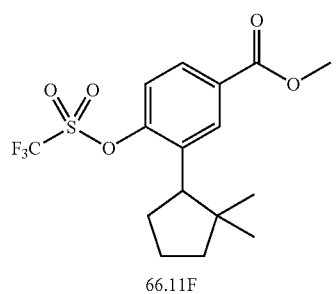

66.11F

Methyl 3-(2,2-dimethylcyclopentyl)-4-(trifluoromethylsulfonyloxy)benzoate (66.11F). To a stirred solution of 66.11E (0.93 g, 3.74 mmol) in dry DCM (10.0 mL) was added TEA (1.1 mL, 7.89 mmol) and 4-(dimethylamino)pyridine (46.2 mg, 0.378 mmol). After about 20 minutes, N-phenyl-bis(trifluoromethanesulfonimide) (1.61 g, 4.51 mmol) was added in portions. Upon complete addition, the solution was stirred at room temperature and monitored with TLC and LC-MS. After 3.5 hours, the reaction was diluted with brine and extracted three times with DCM. After drying over anhydrous magnesium sulfate and filtration, the organic solvent was removed under reduced pressure and the residue was purified with silica gel chromatography using 0-10% EtOAc in hexanes to yield 66.11F as a colorless oil (1.21 g, 85%). ¹H NMR (400 MHz, CDCl₃) δ ppm 8.08 (1H, d, J=2.2 Hz), 7.95 (1H, dd, J=8.6, 2.2 Hz), 7.35 (1H, d, J=8.6 Hz), 3.95 (3H, s), 3.21 (1H, dd, J=9.8, 8.4 Hz), 2.14 (2H, m), 1.95 (1H, m), 1.86 (1H, m), 1.69 (2H, m), 1.02 (3H, s), 0.70 (3H, s).

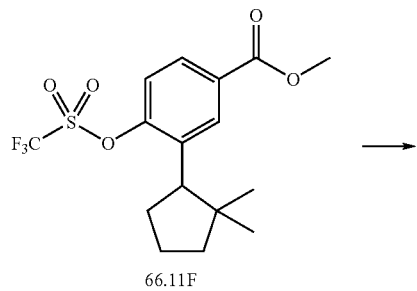

66.11F

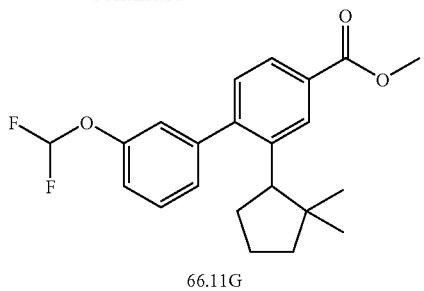

66.11G

Methyl 3'-((difluoromethyl)oxy)-2-(2,2-dimethylcyclopentyl)-1,1'-biphenyl-4-carboxylate (66.11G). A stirred mixture of 66.11F (0.48 g, 1.26 mmol), ground S-Phos (104.8 mg, 0.255 mmol), palladium acetate (29.1 mg, 0.130 mmol), and potassium phosphate tribasic (0.6727 g, 3.17 mmol) in dry DMF (5.0 mL) was purged with argon and placed under vacuum (repeated three times). Before heating, 66.11B (0.512 g, 1.89 mmol) was added via syringe, and then the mixture was heated to 75° C. After 16 hours, the reaction was cooled to room temperature, diluted with water and extracted three times with EtOAc. The combined organic layers were washed twice with brine. After drying over anhydrous sodium sulfate and filtration, the organic solvent was removed under reduced pressure. The residue was purified on silica gel (0-20% EtOAc in hexanes) to yield 66.11G as a colorless oil (308.9 mg, 65%). ¹H NMR (500 MHz, CDCl₃) δ ppm 8.11 (1H, d, J=1.7 Hz), 7.90 (1H, dd, J=7.9, 1.8 Hz), 7.44 (1H, m), 7.28 (1H, m), 7.16 (2H, m), 7.07 (1H, s), 6.57 (1H, t, J=75 Hz), 3.97 (3H, s), 3.10 (1H, t, J=9.4 Hz), 2.13 (2H, m), 1.90 (1H, m), 1.73 (1H, m), 1.61 (1H, m), 1.38 (1H, ddd, J=12.6, 9.4, 7.6 Hz), 0.75 (3H, s), 0.58 (3H, s).

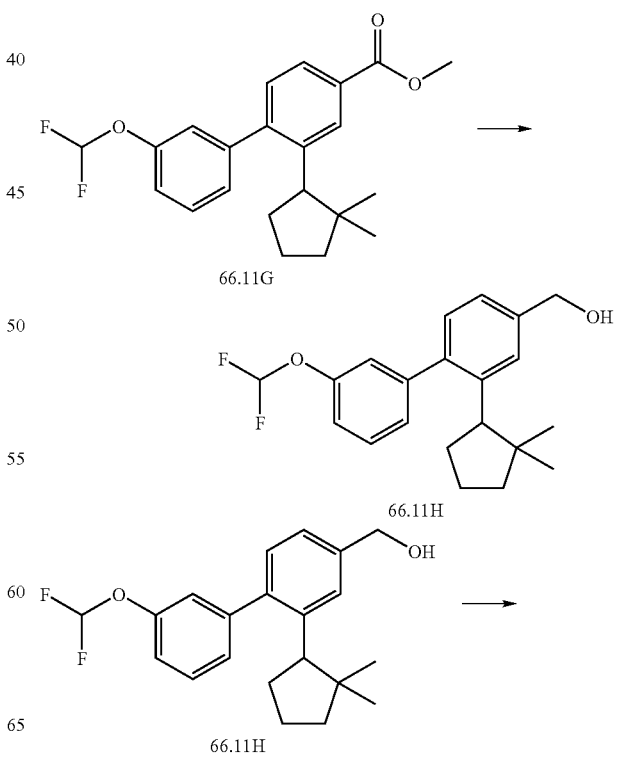

66.11G 66.11H 66.11H

-continued

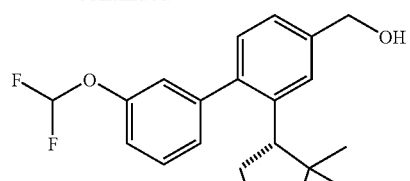

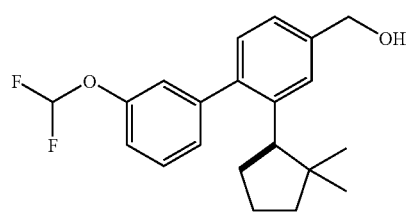

66.11I and 66.11J (3'-((Difluoromethyl)oxy)-2-(2,2-dimethylcyclopentyl)-1,1'-biphenyl-4-yl)methanol (66.11H). To a cooled solution of 66.11G (308.9 mg, 0.82 mmol) in dry THF (8.0 mL) at 0° C. was added LAH, 1.0 M in THF (1.70 mL, 1.70 mmol) dropwise. Upon complete addition, the reaction was maintained at 0° C. and was monitored by TLC and LCMS. After 45 minutes, 1N NaOH was added to quench the reaction. The resulting solution was extracted three times with EtOAc. After drying over anhydrous magnesium sulfate, filtration, and concentration, the residue was purified by flash chromatography ($SiO_2$ gel 60, eluted with 0%-50% EtOAc in hexanes). Fractions containing the desired product were combined and concentrated to yield 66.11H as a colorless oil (261.6 mg, 92%). $^1$H NMR (500 MHz, $CDCl_3$) δ ppm 7.41 (2H, m), 7.26 (1H, m), 7.21 (1H, m), 7.14 (2H, m), 7.05 (1H, s), 6.55 (1H, t, J=75 Hz), 4.76 (2H, m), 3.07 (1H, dd, J=10.3, 8.6 Hz), 2.10 (2H, m), 1.86 (1H, m), 1.71 (1H, m), 1.55 (1H, ddd, J=12.7, 8.1, 4.9 Hz), 1.37 (1H, ddd, J=12.5, 9.5, 7.6 Hz), 0.75 (3H, s), 0.60 (3H, s). Chiral separation of 66.11H was accomplished on Chiracel-OD (3% IPA in hexane) to provide 66.11I (peak 1) and 66.11J (peak 2). Both enantiomers were used to synthesize example compounds, and both enantiomers gave active compounds. The enantiomer corresponding to peak 2 provided the more active example compound.

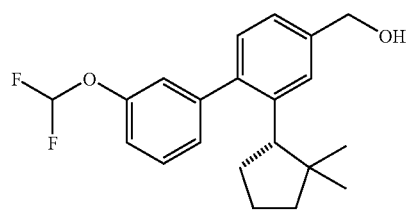

or

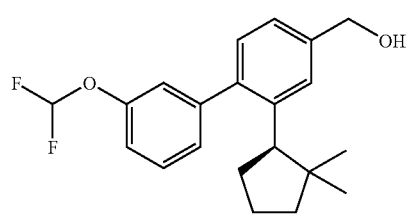

66.11J

-continued

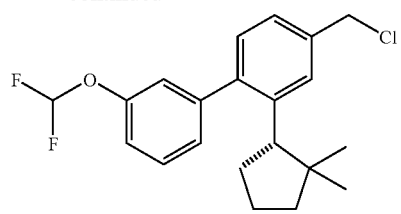

or

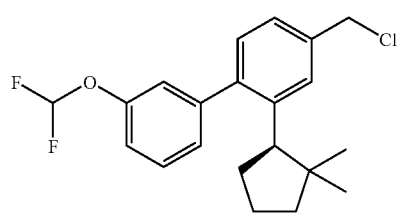

66.11K 4-(Chloromethyl)-3'-((difluoromethyl)oxy)-2-((1S)-2,2-dimethylcyclopentyl)-1,1'-biphenyl or 4-(chloromethyl)-3'-((difluoromethyl)oxy)-2-((1R)-2,2-dimethylcyclopentyl)-1,1'-biphenyl (66.11K). To a solution of 66.11J (112.7 mg, 0.325 mmol) in dry DCM (4.0 mL) and dry DMF (0.03 mL) was added thionyl chloride (0.06 mL, 0.823 mmol) at 0° C. The resulting solution was warmed to room temperature and monitored with TLC and LCMS. After 45 minutes, the reaction was concentrated then purified by silica gel flash chromatography (0-5% EtOAc/hexane) to yield 66.11K (99.5 mg, 84%). $^1$H NMR (400 MHz, $CDCl_3$) δ ppm 7.42 (2H, m), 7.25 (1H, d, J=2.0 Hz), 7.19 (1H, m), 7.11 (2H, dd, J=7.8, 2.0 Hz), 7.03 (1H, s), 6.54 (1H, t, J=74 Hz), 4.66 (2H, m), 3.04 (1H, dd, J=10.4, 8.4 Hz), 2.14 (2H, m), 1.88 (1H, m), 1.73 (1H, m), 1.54 (2H, ddd, J=12.7, 8.2, 4.9 Hz), 1.41 (1H, m), 0.73 (3H, s), 0.56 (3H, s).

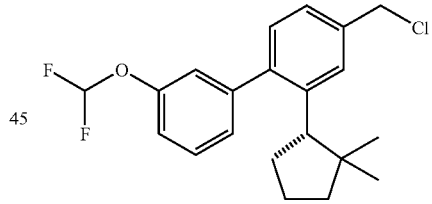

or

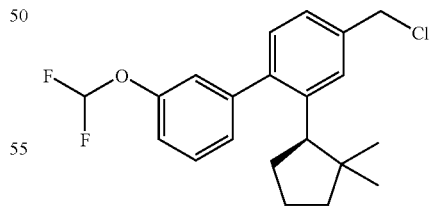

66.11K

+

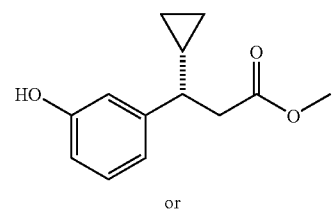

or

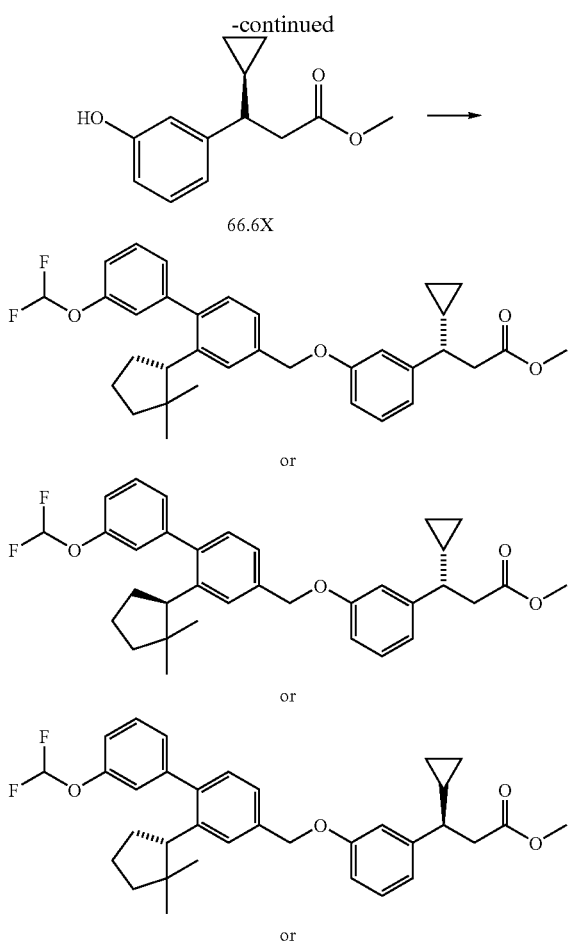

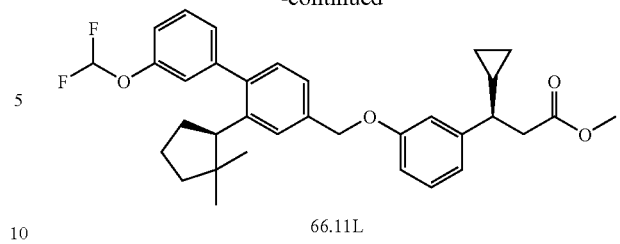

Methyl (3S)-3-cyclopropyl-3-(3-(((3'-((difluoromethyl)oxy)-2-((1S)-2,2-dimethylcyclopentyl)-1,1'-biphenyl-4-yl)methyl)oxy)phenyl)propanoate or methyl (3S)-3-cyclopropyl-3-(3-(((3'-((difluoromethyl)oxy)-2-((1R)-2,2-dimethylcyclopentyl)-1,1'-biphenyl-4-yl)methyl)oxy)phenyl)propanoate or methyl (3R)-3-cyclopropyl-3-(3-(((3'-((difluoromethyl)oxy)-2-((1S)-2,2-dimethylcyclopentyl)-1,1'-biphenyl-4-yl)methyl)oxy)phenyl)propanoate or methyl (3R)-3-cyclopropyl-3-(3-(((3'-((difluoromethyl)oxy)-2-((1R)-2,2-dimethylcyclopentyl)-1,1'-biphenyl-4-yl)methyl)oxy)phenyl)propanoate (66.11L). To a vial containing 66.6X (0.0156 g, 0.0708 mmol) in dry DMF (1.0 mL) was added cesium carbonate (0.0299 g, 0.0918 mmol). The mixture was stirred at room temperature for 10 minutes, then 66.11K (0.0297 g, 0.0814 mmol) was added. After 22 hours, the reaction was diluted with water then extracted five times with EtOAc. The combined organic layers were then washed one time with brine and dried over anhydrous magnesium sulfate. The solid was filtered off, and the solvent was concentrated. The residue was purified by silica gel flash chromatography (0-50% EtOAc/hexane) to yield 66.11L (20.5 mg, 53%).

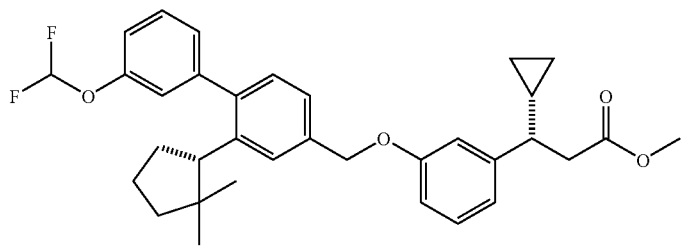

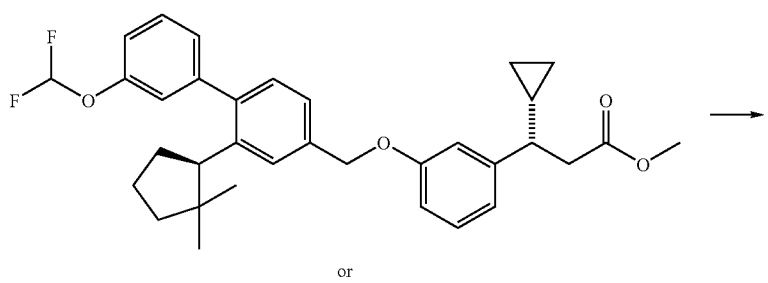

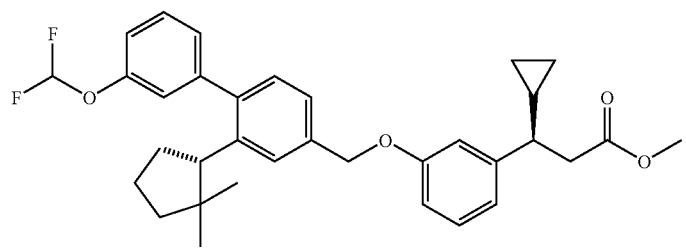
or
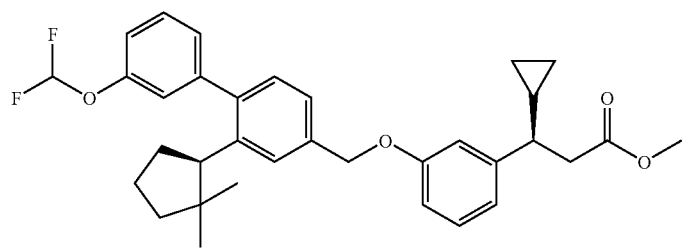
66.11L
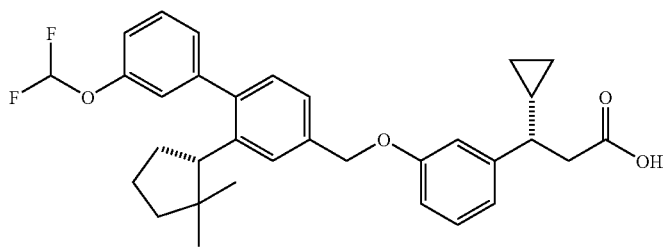
or
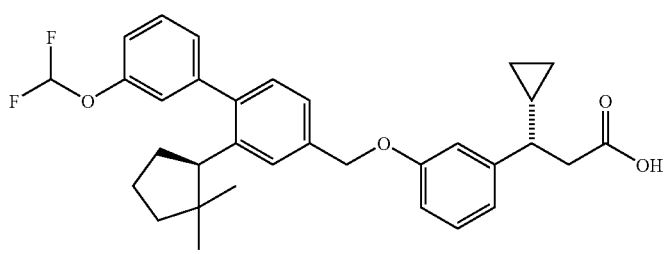
or
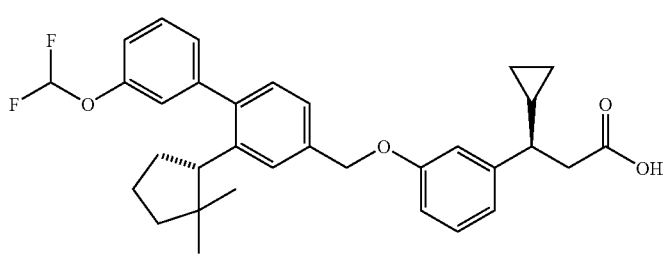
or
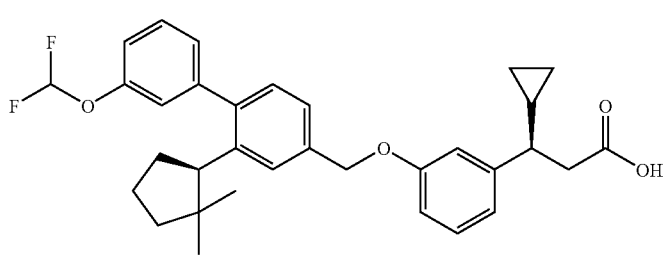
66.11

(3S)-3-Cyclopropyl-3-(3-(((3'-((difluoromethyl)oxy)-2-((1S)-2,2-dimethylcyclopentyl)-1,1'-biphenyl-4-yl)methyl)oxy)phenyl)propanoic acid or (3S)-3-cyclopropyl-3-(3-(((3'-((difluoromethyl)oxy)-2-((1R)-2,2-dimethylcyclopentyl)-1,1'-biphenyl-4-yl)methyl)oxy)phenyl)propanoic acid or (3R)-3-cyclopropyl-3-(3-(((3'-((difluoromethyl)oxy)-2-((1S)-2,2-dimethylcyclopentyl)-1,1'-biphenyl-4-yl)methyl)oxy)phenyl)propanoic acid or (3R)-3-cyclopropyl-3-(3-(((3'-((difluoromethyl)oxy)-2-((1R)-2,2-dimethylcyclopentyl)-1,1'-biphenyl-4-yl)methyl)oxy)phenyl)propanoic acid (66.11). A pre-mixed solution of 2M NaOH (0.3 mL), THF (0.5 mL), and MeOH (0.5 mL) was added to a vial containing 66.11L (0.0205 g, 0.0374 mmol). This solution was stirred at room temperature and monitored with TLC and LC-MS. After 24 hours, the mixture was diluted with water and acidified with 1M aqueous HCl solution, then extracted five times with EtOAc. The organic phase was dried over anhydrous magnesium sulfate, filtered and concentrated. The residue was purified by silica gel flash chromatography (0-40% EtOAc/hexane) to yield 66.11 (12.8 mg, 64%). $^1$H NMR (400 MHz, CDCl$_3$) δ ppm 7.45 (2H, m), 7.32 (1H, dd, J=7.8, 2.0 Hz), 7.28 (3H, m), 7.15 (2H, m), 7.04 (1H, s), 6.93 (3H, m), 6.54 (1H, t, J=78 Hz), 5.10 (2H, s), 3.05 (1H, dd, J=10.4, 8.4 Hz), 2.86 (2H, m), 2.44 (1H, m), 2.13 (2H, m), 1.87 (1H, m), 1.73 (1H, m), 1.52 (1H, ddd, J=12.7, 8.2, 4.9 Hz), 1.40 (1H, m), 1.09 (1H, m), 0.69 (3H, s), 0.65 (4H, m), 0.49 (1H, m), 0.30 (1H, dq, J=9.7, 4.8 Hz), 0.16 (1H, dq, J=9.9, 4.8 Hz). MS ESI (neg.) m/e: 532.9 (M−H)$^+$.

Example 66.12

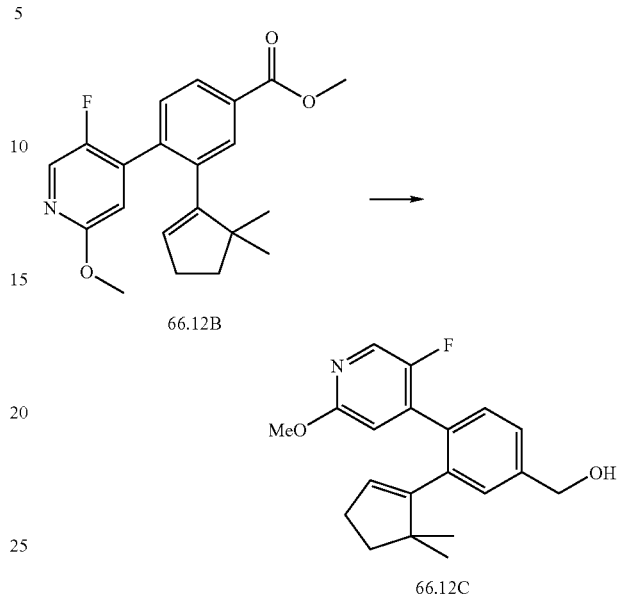

Methyl 3-(5,5-dimethylcyclopent-1-enyl)-4-(5-fluoro-2-methoxypyridin-4-yl)benzoate (66.12B). To a flask with methyl 3-(5,5-dimethylcyclopent-1-enyl)-4-(trifluoromethylsulfonyloxy)benzoate 66.61 (404 mg, 1068 μmol) was added Pd(PPh$_3$)$_4$ (123 mg, 107 μmol), potassium carbonate (443 mg, 3203 μmol), 5-fluoro-2-methoxypyridin-4-ylboronic acid 66.12A (456 mg, 2669 μmol, commercially available from Asymchem). The mixture was then degassed, and DMF (3 mL) was added. The reaction was stirred overnight at 87° C. and worked up with EtOAc and water. Silica gel chromatography (0-50% EtOAc/Hexanes) afforded methyl 3-(5,5-dimethylcyclopent-1-enyl)-4-(5-fluoro-2-methoxypyridin-4-yl)benzoate 66.12B 295 mg (78%).

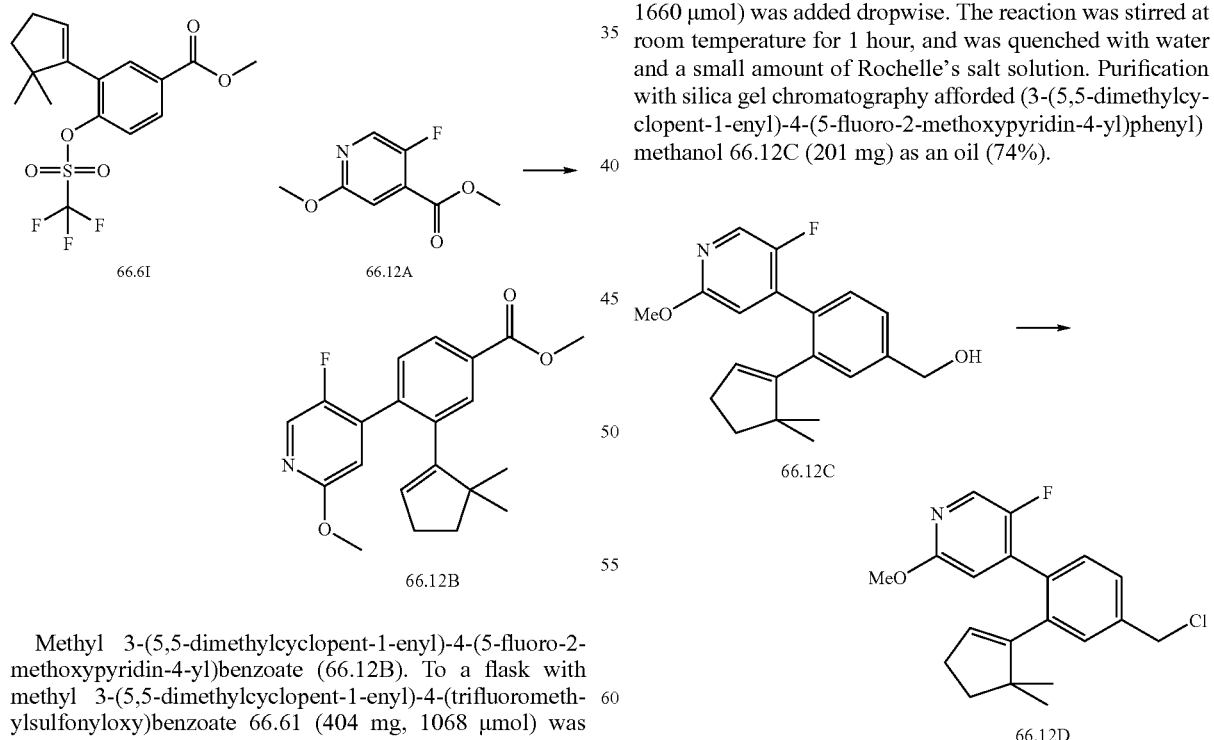

(3-(5,5-Dimethylcyclopent-1-enyl)-4-(5-fluoro-2-methoxypyridin-4-yl)phenyl)methanol (66.12C). To methyl 3-(5,5-dimethylcyclopent-1-enyl)-4-(5-fluoro-2-methoxypyridin-4-yl)benzoate 66.12B (295 mg, 830 μmol) was added THF. The mixture was cooled to 0° C., and LAH (1660 μL, 1660 μmol) was added dropwise. The reaction was stirred at room temperature for 1 hour, and was quenched with water and a small amount of Rochelle's salt solution. Purification with silica gel chromatography afforded (3-(5,5-dimethylcyclopent-1-enyl)-4-(5-fluoro-2-methoxypyridin-4-yl)phenyl)methanol 66.12C (201 mg) as an oil (74%).

4-(4-(Chloromethyl)-2-(5,5-dimethylcyclopent-1-enyl)phenyl)-5-fluoro-2-methoxypyridine (66.12D). To (3-(5,5-dimethylcyclopent-1-enyl)-4-(5-fluoro-2-methoxypyridin-4-yl)phenyl)methanol 66.12C (34.5 mg, 105 μmol) was added DCM (1.1 mL) and DMF (8.2 μL, 105 μmol) followed by thionyl chloride (15 μL, 211 μmol) in an ice bath. The reaction was then stirred at room temperature for 1 hour. The reaction was concentrated and directly purified on silica gel to afford 4-(4-(chloromethyl)-2-(5,5-dimethylcyclopent-1-enyl)phenyl)-5-fluoro-2-methoxypyridine 66.12D (36 mg) as an oil (99%).

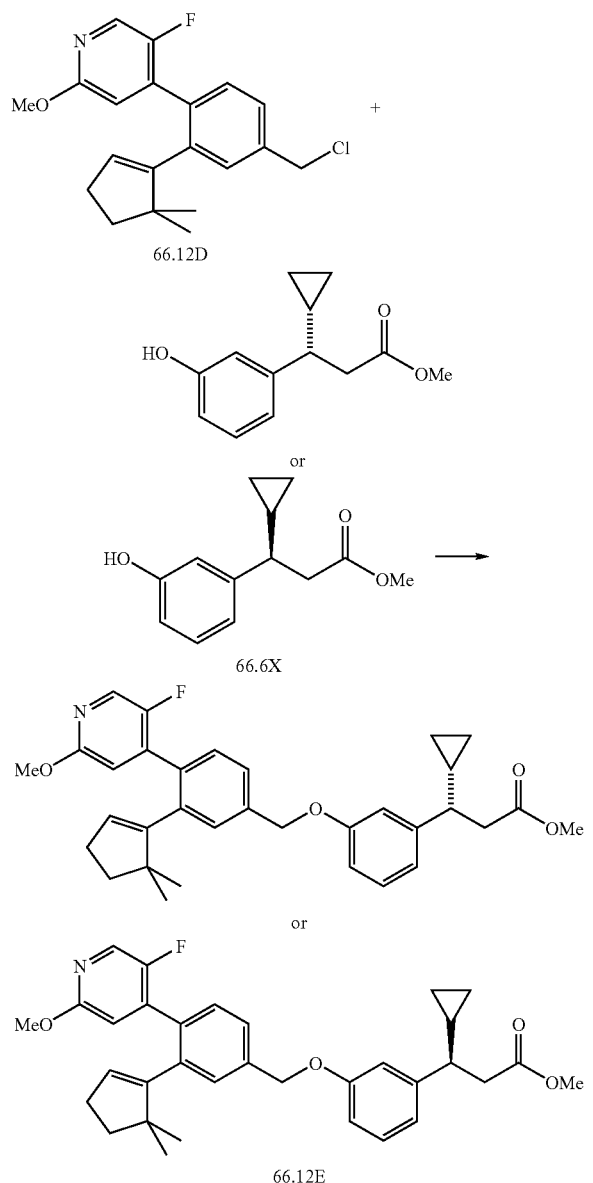

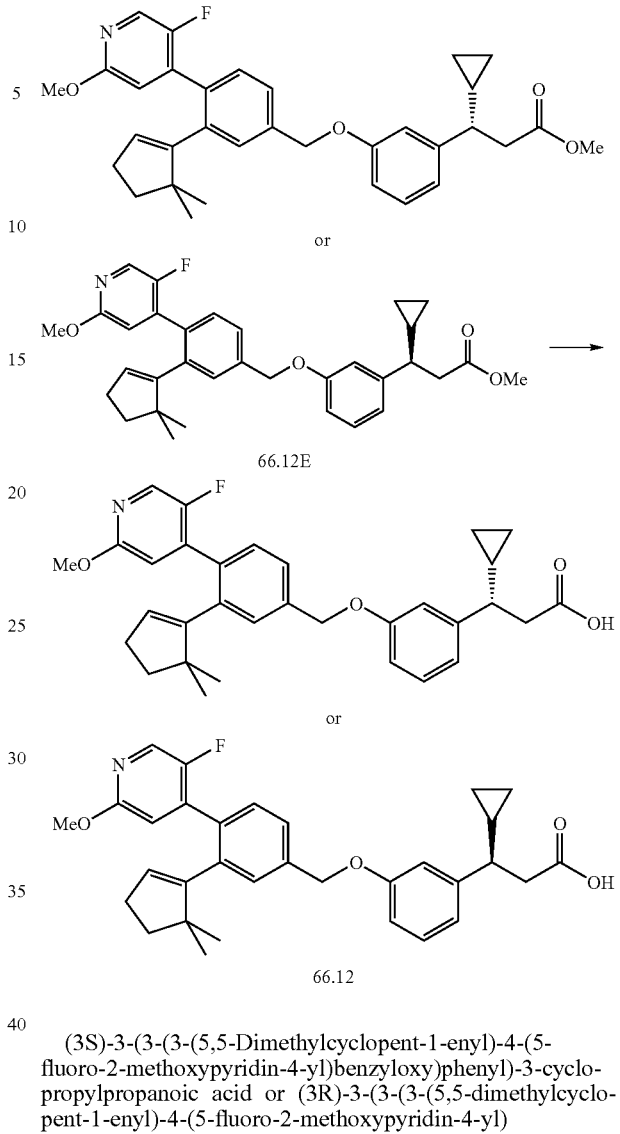

(3S)-Methyl 3-(3-(3-(5,5-dimethylcyclopent-1-enyl)-4-(5-fluoro-2-methoxypyridin-4-yl)benzyloxy)phenyl)-3-cyclopropylpropanoate or (3R)-methyl 3-(3-(3-(5,5-dimethylcyclopent-1-enyl)-4-(5-fluoro-2-methoxypyridin-4-yl)benzyloxy)phenyl)-3-cyclopropylpropanoate (66.12E). To a flask with 4-(4-(chloromethyl)-2-(5,5-dimethylcyclopent-1-enyl)phenyl)-5-fluoro-2-methoxypyridine 66.12D (36 mg, 104 μmol) and cesium carbonate (41 mg, 125 μmol) was added a DMF solution of 66.6X (23 mg, 104 μmol). The reaction was stirred overnight at room temperature. Water was added followed by extraction with EtOAc. The product was purified by silica gel chromatography to afford 66.12E 53 mg an oil (96%).

(3S)-3-(3-(3-(5,5-Dimethylcyclopent-1-enyl)-4-(5-fluoro-2-methoxypyridin-4-yl)benzyloxy)phenyl)-3-cyclopropylpropanoic acid or (3R)-3-(3-(3-(5,5-dimethylcyclopent-1-enyl)-4-(5-fluoro-2-methoxypyridin-4-yl)benzyloxy)phenyl)-3-cyclopropylpropanoic acid (66.12). To a flask with 66.12E was added 1 mL THF, 0.5 mL MeOH and 0.5 mL 1N LiOH. The mixture was stirred overnight. 1N HCl was added to adjust the pH to about 4. The reaction was then extracted with EtOAc. The product was purified by silica gel chromatography to afford 66.12 (46 mg) as a white solid (89%). MS ESI (neg.) m/e: 514.2 (M–H)+.

Example 66.13

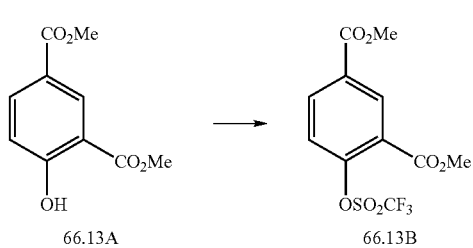

Dimethyl 4-(trifluoromethylsulfonyloxy)isophthalate (66.13B). To a stirred solution of dimethyl 4-hydroxyisophthalate 66.13A (commercially available from Chem Service) (37.7 g, 179 mmol) in DCM (256 mL, 179 mmol) at 23° C. was added TEA (30 mL, 215 mmol), and a catalytic amount of DMAP. N-phenyltriflimide (70 g, 197 mmol) was then added, and stirring was continued at room temperature for 21 hours. The solvent was removed, and the residue was purified on silica gel (0-10% EtOAc in hexanes) to yield 66.13B dimethyl 4-(trifluoromethylsulfonyloxy)isophthalate as a colorless oil (59.00 g, 96% yield). MS ESI (pos.) m/e: 360.0 $(M+H_2O)^+$, 343.0 $(M+H)^+$.

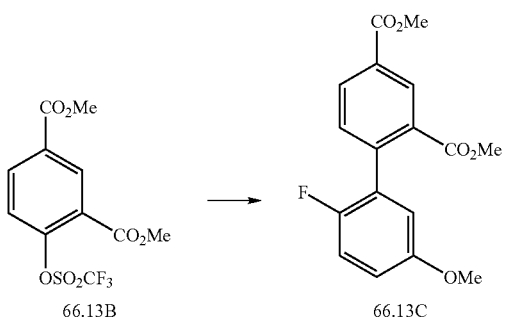

Dimethyl 2'-fluoro-5'-(methyloxy)-1,1'-biphenyl-2,4-dicarboxylate (66.13C). To a stirred solution of dimethyl 4-(trifluoromethylsulfonyloxy)isophthalate 66.13B (39.00 g, 114 mmol) in DMF (228 mL, 114 mmol) at 23° C. was added 2-fluoro-5-methoxyphenylboronic acid (29 g, 171 mmol) (commercially available from Aldrich), potassium carbonate (47 g, 342 mmol), followed by tetrakis(triphenylphosphine)palladium (9.2 g, 8.0 mmol). The mixture was heated to 90° C. and stirring was continued for 18 hours. The reaction was cooled to room temperature. Water was added to the reaction, and the resulting mixture was extracted with EtOAc. The organic layer was dried over $MgSO_4$ and concentrated. The crude product was purified by silica gel flash chromatography (0-20% EtOAc/hexane) to afford dimethyl 2'-fluoro-5'-(methyloxy)-1,1'-biphenyl-2,4-dicarboxylate 66.13C as a clear oil (32.00 g, 88% yield). MS ESI (pos.) m/e: 319.1 $(M+H)^+$.

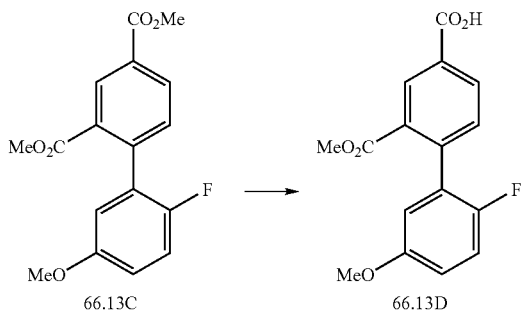

2'-Fluoro-5'-(methyloxy)-2-((methyloxy)carbonyl)-1,1'-biphenyl-4-carboxylic acid (66.13D). To a stirred solution of 66.13C (36.50 g, 115 mmol) in THF (70.0 mL, 854 mmol) and MeOH (70.0 mL, 1730 mmol) at 0° C. was added potassium hydroxide (63 mL, 126 mmol) slowly to maintain the temperature below 6° C. The reaction mixture was allowed to warm to room temperature and stirring was continued for 15 hours. The reaction mixture was concentrated in vacuo. 1N HCl was added to the aqueous phase and the resulting mixture was extracted with EtOAc. The organic layer was dried over $MgSO_4$, and concentrated in vacuo to give 2'-fluoro-5'-(methyloxy)-2-((methyloxy)carbonyl)-1,1'-biphenyl-4-carboxylic acid 66.13D as a white solid (35.00 g, 100% yield). MS ESI (pos.) m/e: 322.1 $(M+H_2O)^+$, 305.0 $(M+H)^+$.

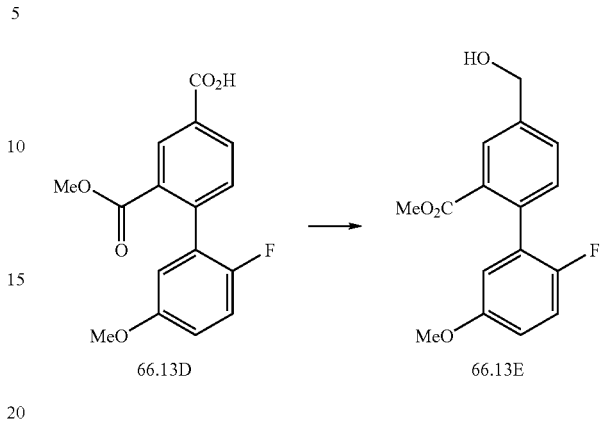

Methyl 2'-fluoro-4-(hydroxymethyl)-5'-(methyloxy)-1,1'-biphenyl-2-carboxylate (66.13E). To a stirred solution of 2'-fluoro-5'-(methyloxy)-2-((methyloxy)carbonyl)-1,1'-biphenyl-4-carboxylic acid 66.13D (35.60 g, 117 mmol) in THF (1170 mL, 117 mmol) at 0° C. was added borane-THF (234 mL, 234 mmol). The reaction was warmed to 23° C. and stirring was continued for 6 hours. The mixture was then concentrated in vacuo. 1 N HCl was added to the reaction, and the mixture was extracted with EtOAc. The combined organic layers were dried over $MgSO_4$, filtered and concentrated in vacuo. The residue was purified on silica gel (0-40% EtOAc in hexane) to give methyl 2'-fluoro-4-(hydroxymethyl)-5'-(methyloxy)-1,1'-biphenyl-2-carboxylate 66.13E as a clear oil (30.00 g, 88% yield). MS ESI (pos.) m/e: 308.0 $(M+H_2O)^+$, 291.1 $(M+H)^+$.

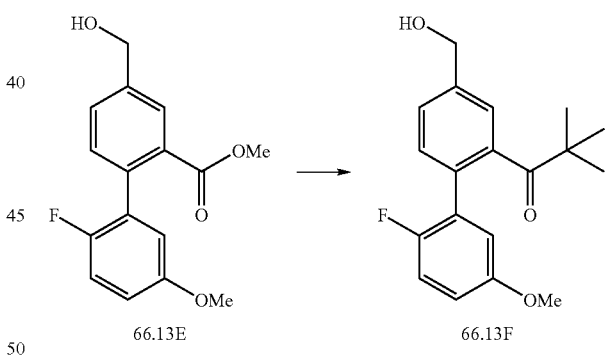

1-(2'-Fluoro-4-(hydroxymethyl)-5'-(methyloxy)-1,1'-biphenyl-2-yl)-2,2-dimethyl-1-propanone (66.13F). To a stirred solution of methyl 2'-fluoro-4-(hydroxymethyl)-5'-(methyloxy)-1,1'-biphenyl-2-carboxylate 66.13E (2.00 g, 7 mmol) in THF (138 mL, 7 mmol) at −78° C. was added t-butyllithium (1.7 M in pentane, 9 mL, 14 mmol). Stirring was continued for 3 hours. A saturated solution of ammonium chloride was added to quench the reaction, and the resulting mixture was extracted with EtOAc. The combined organic layers were dried over $MgSO_4$, filtered, and concentrated in vacuo to give the crude product. The crude product was purified by silica gel flash chromatography (0-20% EtOAc/hexane) to afford 1-(2'-Fluoro-4-(hydroxymethyl)-5'-(methyloxy)-1,1'-biphenyl-2-yl)-2,2-dimethyl-1-propanone 66.13F as a clear oil (2.00 g, 92% yield). MS ESI (pos.) m/e: 334.1 $(M+H_2O)^+$, 317.2 $(M+H)^+$.

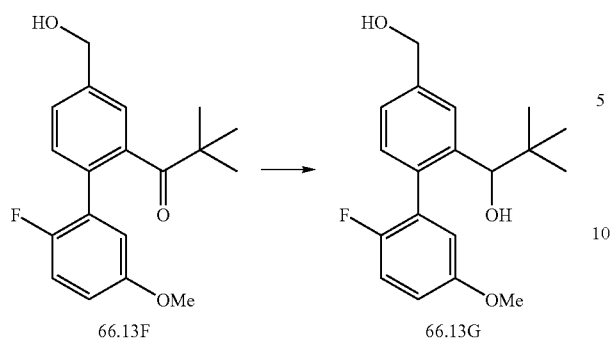
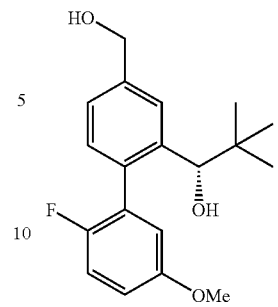
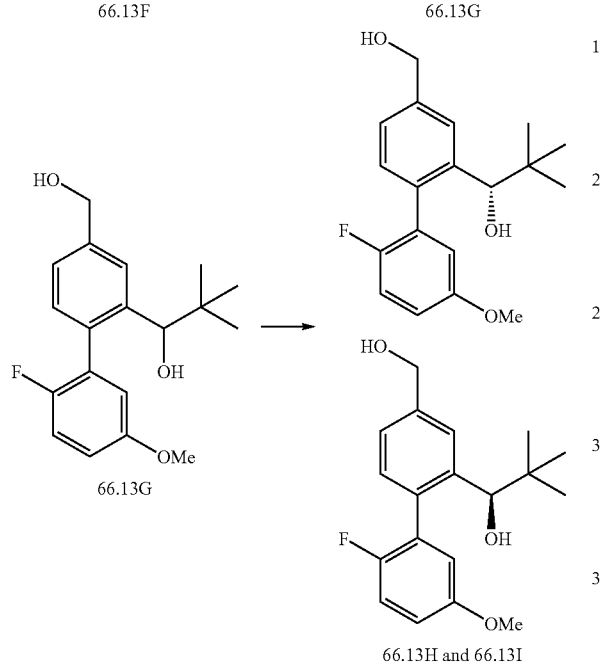
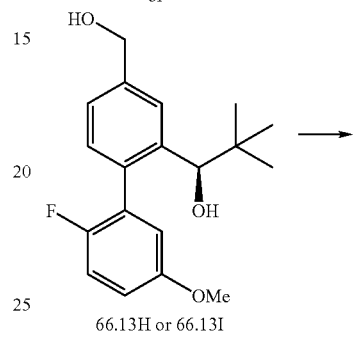

1-(2'-Fluoro-4-(hydroxymethyl)-5'-(methyloxy)-1,1'-biphenyl-2-yl)-2,2-dimethyl-1-propanol (66.13G), and (1R)-1-(2'-fluoro-4-(hydroxymethyl)-5'-(methyloxy)-1,1'-biphenyl-2-yl)-2,2-dimethyl-1-propanol and (1S)-1-(2'-fluoro-4-(hydroxymethyl)-5'-(methyloxy)-1,1'-biphenyl-2-yl)-2,2-dimethyl-1-propanol (66.13H and 66.13I). To a stirred solution of 1-(2'-fluoro-4-(hydroxymethyl)-5'-(methyloxy)-1,1'-biphenyl-2-yl)-2,2-dimethyl-1-propanone 66.13F (2.00 g, 6.3 mmol) in THF (63 mL, 6.3 mmol) at 0° C. was added LAH (1.0 M in THF, 13 mL, 13 mmol). Stirring was continued for 2 hours. 1N NaOH (aq) was added to the mixture, and the resulting mixture was extracted with EtOAc. The combined organic layers were dried over $MgSO_4$, filtered, and concentrated in vacuo to give the crude product. The crude product was purified by silica gel flash chromatography (0-30% EtOAc/hexane) to afford 1-(2'-fluoro-4-(hydroxymethyl)-5'-(methyloxy)-1,1'-biphenyl-2-yl)-2,2-dimethyl-1-propanol 66.13G (1.50 g, 75% yield) as a white solid. MS ESI (pos.) m/e: 336.2 $(M+H_2O)^+$. Chiral separation of 66.13G was accomplished on Chiracel-OD (4% IPA in hexane) to provide 66.13H and 66.13I. Both enantiomers were used to synthesize example compounds, and both enantiomers gave active example compounds. However, the enantiomer corresponding to peak 2 provided the most active example compounds. Analytical column (Chiracel-OD (4% IPA in hexane, 45 min run) Peak 1-18.5 mins, Peak 2-24.5 mins).[1]

(1S)-1-(4-((((1,1-Dimethylethyl)(dimethyl)silyl)oxy)methyl)-2'-fluoro-5'-(methyloxy)-1,1'-biphenyl-2-yl)-2,2-dimethyl-1-propanol or (1R)-1-(4-((((1,1-dimethylethyl)(dimethyl)silyl)oxy)methyl)-2'-fluoro-5'-(methyloxy)-1,1'-biphenyl-2-yl)-2,2-dimethyl-1-propanol (66.13J or 66.13K). To a stirred solution of (1R)-1-(2'-fluoro-4-(hydroxymethyl)-5'-(methyloxy)-1,1'-biphenyl-2-yl)-2,2-dimethyl-1-propanol or (1S)-1-(2'-fluoro-4-(hydroxymethyl)-5'-(methyloxy)-1,1'-biphenyl-2-yl)-2,2-dimethyl-1-propanol (66.13H or 66.13I) (0.300 g, 0.9 mmol) in DCM (10.00 mL, 155 mmol) at 23° C. was added tert-butyldimethylsilyl chloride (0.2 mL, 1 mmol), followed by TEA (0.2 mL, 1 mmol) and DMAP (0.01 g, 0.09 mmol). Stirring was continued for 16 hours. The mixture was then concentrated in vacuo to give the crude product. The crude product was purified by silica gel flash chromatography (0-10% EtOAc/hexane) to afford (1S)-1-(4-((((1,1-dimethylethyl)(dimethyl)silyl)oxy)methyl)-2'-fluoro-5'-(methyloxy)-1,1'-biphenyl-2-yl)-2,2-dimethyl-1-propanol or (1R)-1-(4-((((1,1-dimethylethyl)(dimethyl)silyl)oxy)methyl)-2'-fluoro-5'-(methyloxy)-1,1'-biphenyl-2-yl)-2,2-dimethyl-1-propanol 66.13J or 66.13K (0.375 g, 92% yield). MS ESI (pos.) m/e: 450.2 (M+H₂O)⁺.

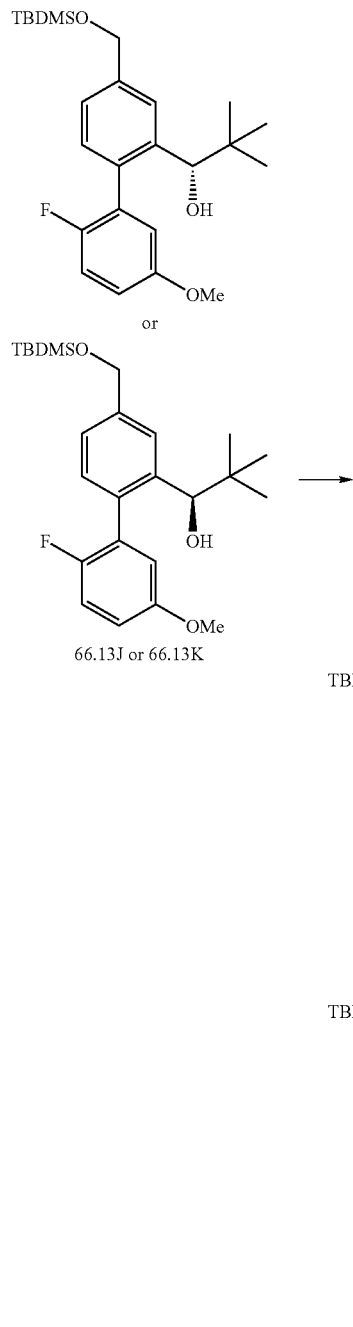

was added iodomethane (0.069 g, 0.50 mmol), followed by sodium hydride (0.012 g, 0.50 mmol). Stirring was continued at 50° C. for 21 hours. Water was added to the mixture, and the resulting mixture was extracted with EtOAc. The combined organic layers were dried over MgSO₄, filtered, and concentrated in vacuo to give the crude product. The crude product was purified by silica gel flash chromatography (0-5% EtOAc/hexane) to afford 66.13L or 66.13M (0.051 g, 45% yield).

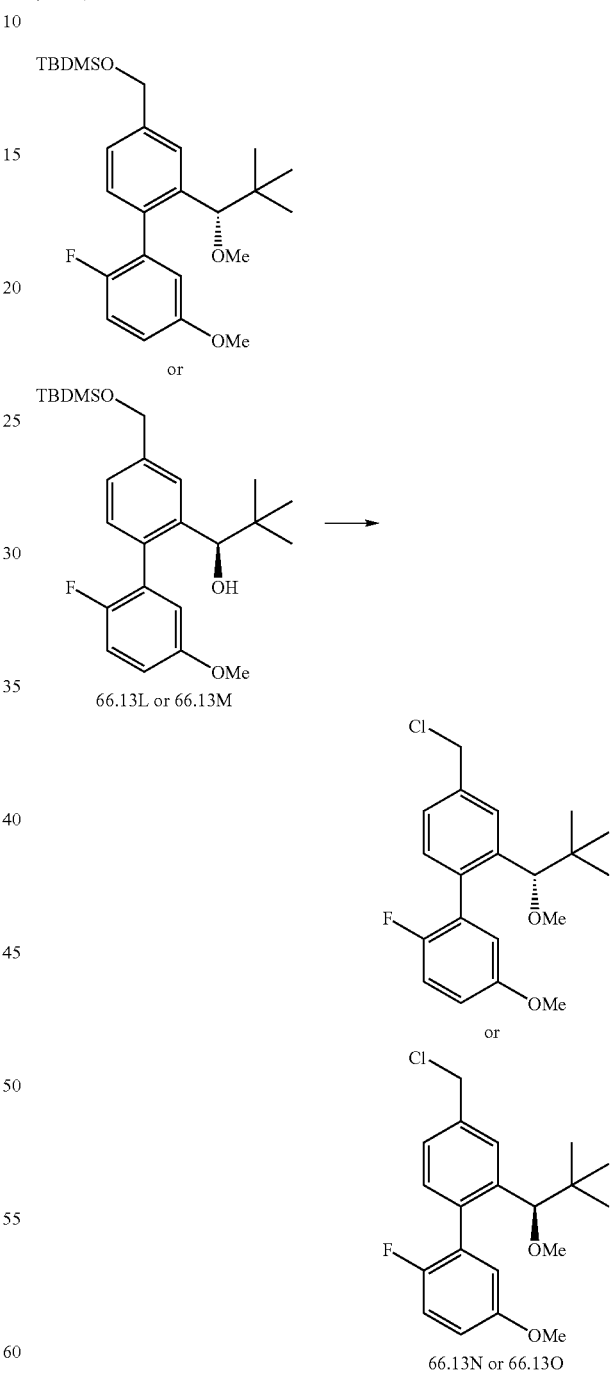

(1,1-Dimethylethyl)(((2-((1S)-2,2-dimethyl-1-(methyloxy)propyl)-2'-fluoro-5'-(methyloxy)-1,1'-biphenyl-4-yl)methyl)oxy)dimethylsilane or (1,1-dimethylethyl)(((2-((1R)-2,2-dimethyl-1-(methyloxy)propyl)-2'-fluoro-5'-(methyloxy)-1,1'-biphenyl-4-yl)methyl)oxy)dimethylsilane (66.13L or 66.13M). To a stirred solution of 66.13J or 66.13K (0.110 g, 0.25 mmol) in DMF (2.00 mL, 26 mmol) at 23° C.

4-(Chloromethyl)-2-((1S)-2,2-dimethyl-1-(methyloxy)propyl)-2'-fluoro-5'-(methyloxy)-1,1'-biphenyl or 4-(chloromethyl)-2-((1R)-2,2-dimethyl-1-(methyloxy)propyl)-2'-fluoro-5'-(methyloxy)-1,1'-biphenyl (66.13N or 66.13O). To a stirred solution of 66.13L or 66.13M (0.082 g, 0.18 mmol)

in DCM (2.00 mL, 31 mmol) at 23° C. was added DMF (0.0014 mL, 0.018 mmol) followed by thionyl chloride (0.027 mL, 0.37 mmol). Stirring was continued for one hour. The reaction mixture was then concentrated in vacuo. The residue was purified by silica gel flash chromatography (0-5% EtOAc/hexane) to afford 66.13N or 66.13O (0.063 g, 98% yield).

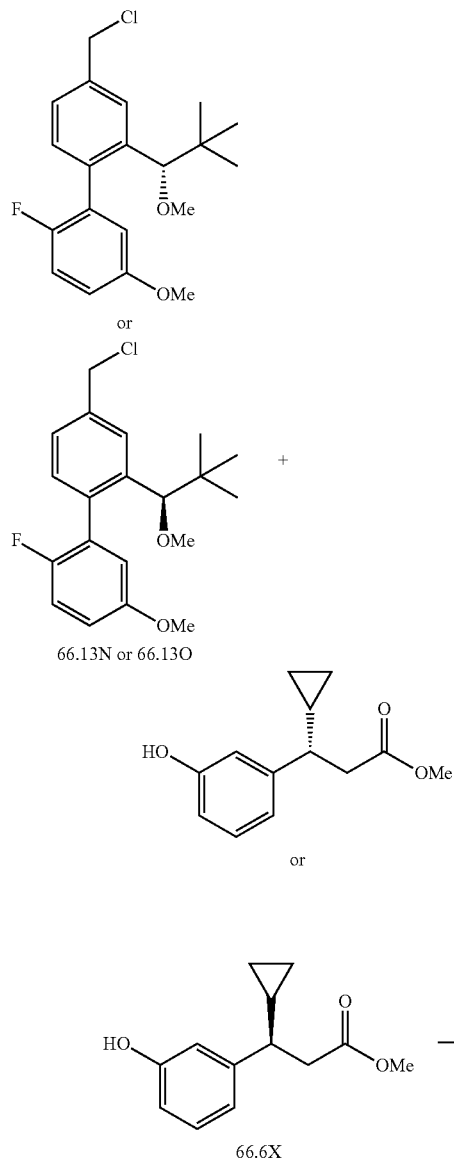

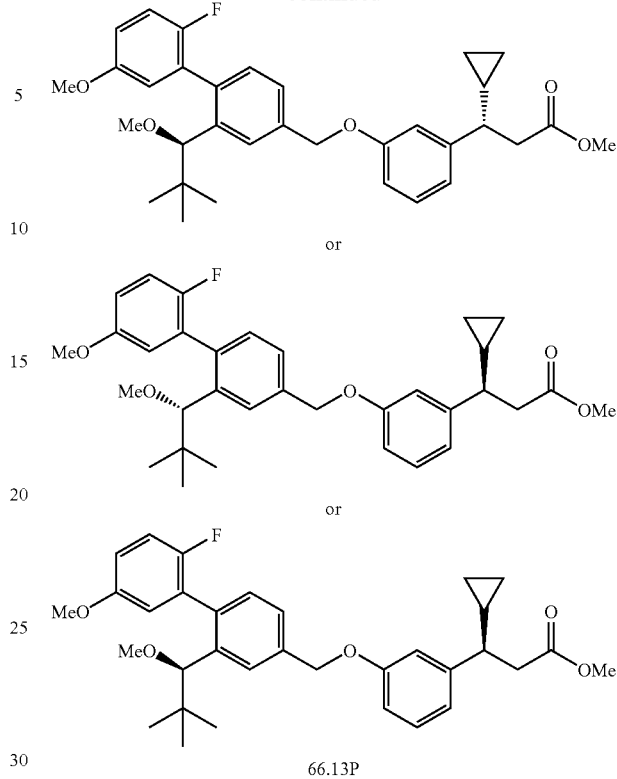

66.13P

Synthesis of methyl (3S)-3-cyclopropyl-3-(3-(((2-((1S)-2,2-dimethyl-1-(methyloxy)propyl)-2'-fluoro-5'-(methyloxy)-1,1'-biphenyl-4-yl)methyl)oxy)phenyl)propanoate or methyl (3S)-3-cyclopropyl-3-(3-(((2-((1R)-2,2-dimethyl-1-(methyloxy)propyl)-2'-fluoro-5'-(methyloxy)-1,1'-biphenyl-4-yl)methyl)oxy)phenyl)propanoate or methyl (3R)-3-cyclopropyl-3-(3-(((2-((1S)-2,2-dimethyl-1-(methyloxy)propyl)-2'-fluoro-5'-(methyloxy)-1,1'-biphenyl-4-yl)methyl)oxy)phenyl)propanoate or methyl (3R)-3-cyclopropyl-3-(3-(((2-((1R)-2,2-dimethyl-1-(methyloxy)propyl)-2'-fluoro-5'-(methyloxy)-1,1'-biphenyl-4-yl)methyl)oxy)phenyl)propanoate (66.13P). To a stirred solution of 66.6X (0.020 g, 0.091 mmol) in DMF (2.00 mL, 0.091 mmol) at 23° C. was added 66.13N or 66.13O (0.032 g, 0.091 mmol) followed by cesium carbonate (0.059 g, 0.18 mmol). Stirring was continued for 16 hours. Water was added to the reaction, and the resulting mixture was extracted with EtOAc. The combined organic layers were dried over magnesium sulfate, filtered and concentrated in vacuo. The residue was purified on silica gel (0%-20% EtOAc/hexane) to give 66.13P (0.048 g, 100% yield). MS ESI (pos.) m/e: 557.3 (M+Na)+.

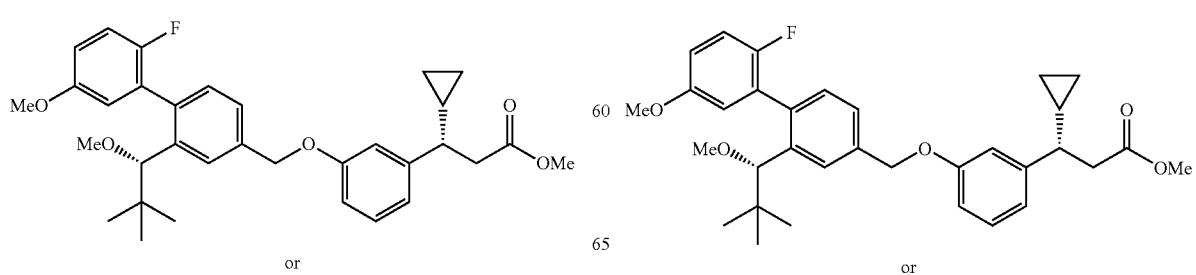

-continued

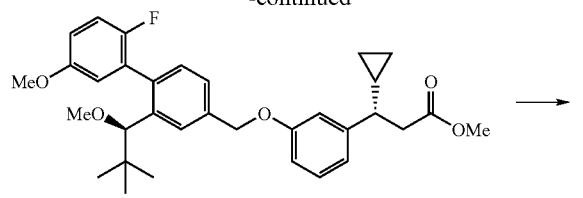

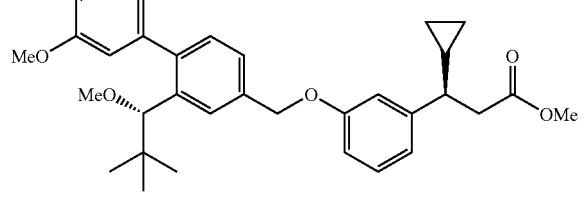

or

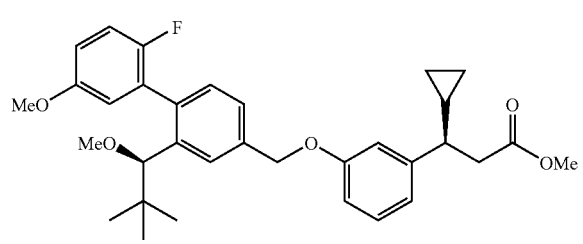

66.13P

-continued

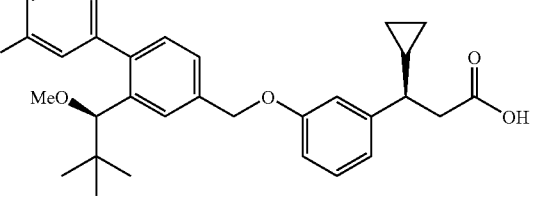

66.13

(3S)-3-Cyclopropyl-3-(3-(((2-((1S)-2,2-dimethyl-1-(methyloxy)propyl)-2'-fluoro-5'-(methyloxy)-1,1'-biphenyl-4-yl)methyl)oxy)phenyl)propanoic acid or (3S)-3-cyclopropyl-3-(3-(((2-((1R)-2,2-dimethyl-1-(methyloxy)propyl)-2'-fluoro-5'-(methyloxy)-1,1'-biphenyl-4-yl)methyl)oxy) phenyl)propanoic acid or (3R)-3-cyclopropyl-3-(3-(((2-((1S)-2,2-dimethyl-1-(methyloxy)propyl)-2'-fluoro-5'-(methyloxy)-1,1'-biphenyl-4-yl)methyl)oxy)phenyl) propanoic acid or (3R)-3-cyclopropyl-3-(3-(((2-((1R)-2,2-dimethyl-1-(methyloxy)propyl)-2'-fluoro-5'-(methyloxy)-1,1'-biphenyl-4-yl)methyl)oxy)phenyl)propanoic acid (66.13). To a stirred solution of 66.13P (0.049 g, 0.092 mmol) in THF (2.00 mL, 24 mmol) and EtOH (2.00 mL, 0.092 mmol) at 23° C. was added LiOH (0.092 mL, 0.092 mmol). Stirring was continued at 23° C. for 16 hours. The reaction mixture was then concentrated in vacuo. 1N HCl was added to the mixture, and the resulting mixture was extracted with EtOAc. The combined organic layers were dried over magnesium sulfate, filtered and concentrated in vacuo. The residue was purified on silica gel (0%-20% EtOAc/hexane) to 66.13 (0.0343 g, 72% yield). MS ESI (neg.) m/e: 519.2 (M–H)$^+$.

Asymmetric Synthesis of 66.13H or 66.13I

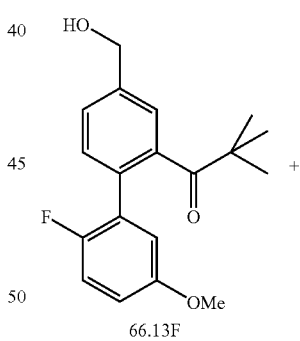

66.13F

+

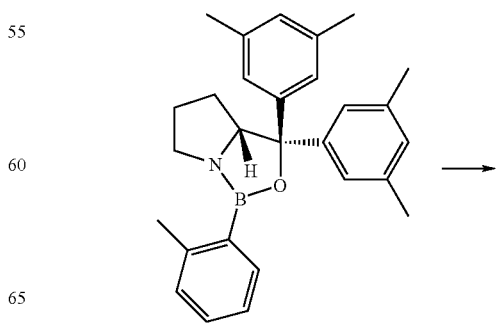

-continued

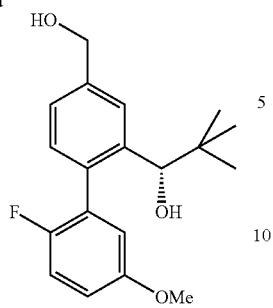

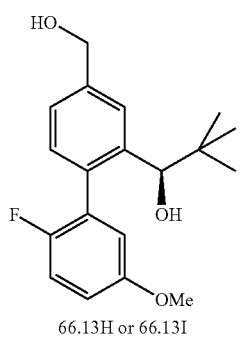

66.13H or 66.13I (1R)-1-(2'-Fluoro-4-(hydroxymethyl)-5'-(methyloxy)-1,1'-biphenyl-2-yl)-2,2-dimethyl-1-propanol and (1S)-1-(2'-fluoro-4-(hydroxymethyl)-5'-(methyloxy)-1,1'-biphenyl-2-yl)-2,2-dimethyl-1-propanol (66.13H and 66.13I). To a stirred solution of 66.13F (0.050 g, 0.2 mmol) in THF (2 ml, 0.2 mmol) at 0° C. was added (R)-3,3-bis(3,5-dimethylphenyl)-1-o-tolyl-hexahydropyrrolo[1,2-c][1,3,2]oxazaborole in toluene (0.02 ml, 0.02 mmol, 1.0M, commercially available from Aldrich), followed by dropwise addition of borane in THF (0.2 ml, 0.2 mmol). The reaction was then stirred at 23° C. for 4 hours. The reaction was then quenched with 1N HCl (aq). The reaction mixture was extracted with EtOAc, dried over MgSO$_4$, filtered, and concentrated in vacuo. The residue was purified on silica gel (0%-20% EtOAc/hexane) to yield 66.13H or 66.13I (0.045 g, 89% yield). Chiral HPLC determined that the major product was the desired more potent enantiomer with an enantiomeric excess of 85%.

Example 66.14

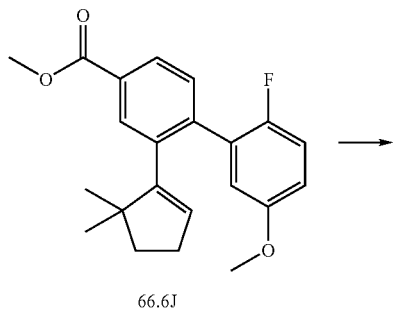

66.6J

-continued

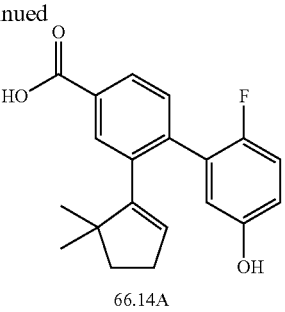

66.14A 2-(5,5-Dimethyl-1-cyclopenten-1-yl)-2'-fluoro-5'-hydroxy-1,1'-biphenyl-4-carboxylic acid (66.14A). To a stirred solution of 66.6J (300.0 mg, 846 µmol) in DCM (10 mL) at 0° C. was added boron tribromide (3809 µL, 3809 µmol). The reaction was stirred for two hours and then pH 7 buffer was added to the mixture at 0° C., and the mixture was extracted with DCM. The combined organic layers were dried over MgSO$_4$, concentrated in vacuo, and the residue was purified on silica gel (0%-20% EtOAc/hexane) to give 66.14A.

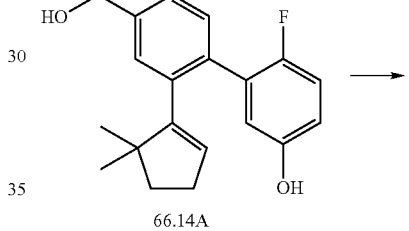

66.14A

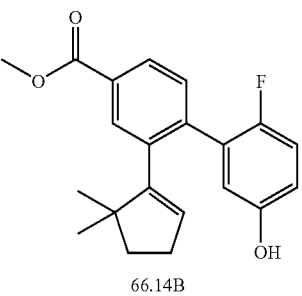

66.14B

Methyl 2-(5,5-dimethyl-1-cyclopenten-1-yl)-2'-fluoro-5'-hydroxy-1,1'-biphenyl-4-carboxylate (66.14B). To a flask containing 66.14A (75 mg, 230 µmol) in MeOH (2 mL) was added sulfuric acid (0.61 µL, 11 µmol), and the mixture was stirred at reflux overnight. The reaction was concentrated and then purified by silica gel chromatography (0 to 30% EtOAc/Hexanes) to provide 66.14B (77.0 mg, 98% yield).

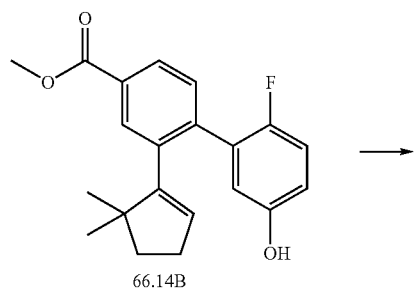

66.14B

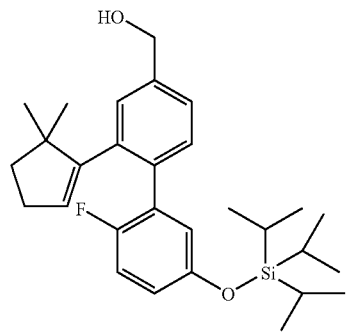

66.14D (2-(5,5-Dimethyl-1-cyclopenten-1-yl)-2'-fluoro-5'-((tris(1,1-dimethylethyl)silyl)oxy)-1,1'-biphenyl-4-yl)methanol (66.14D). To 66.14C (90.0 mg, 167 μmol) in THF (1 mL) at 0° C. was added LAH (1.0M solution in THF) (251 μL, 251 μmol). The reaction was stirred for one hour and then carefully diluted with water, extracted with EtOAc, washed with brine, dried over sodium sulfate, filtered, and concentrated to provide 66.14D (64.0 mg, 75.0% yield).

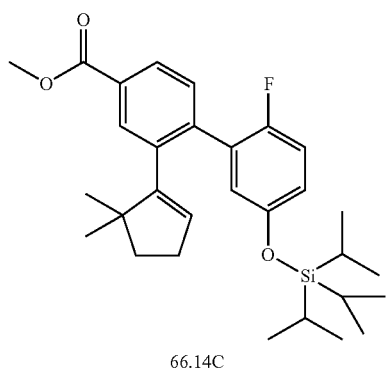

66.14C

Methyl 2-(5,5-dimethyl-1-cyclopenten-1-yl)-2'-fluoro-5'-((tris(1-methylethyl)silyl)oxy)-1,1'-biphenyl-4-carboxylate (66.14C). To 66.14B (77.0 mg, 226 μmol) in DMF (10 mL) was added imidazole (30.8 mg, 452 μmol) and then triisopropylsilyl chloride (58.1 μL, 271 μmol). The resulting mixture was then stirred for 4 hours. The reaction was diluted with EtOAc and washed with 1N HCl, water, and brine. The organic phase was dried over sodium sulfate, filtered, concentrated, and purified by silica gel chromatography (0 to 10% EtOAc/Hexanes) to provide 66.14C (90.0 mg, 80.1% yield).

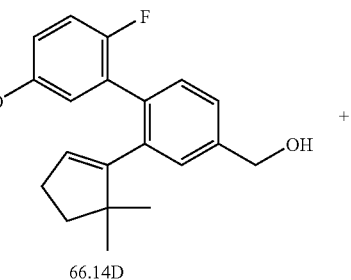

66.14D

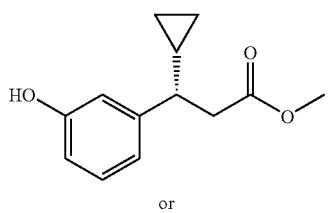

or

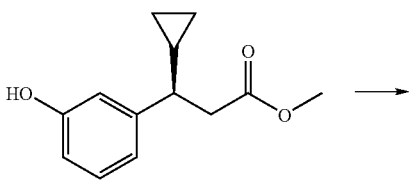

8.4

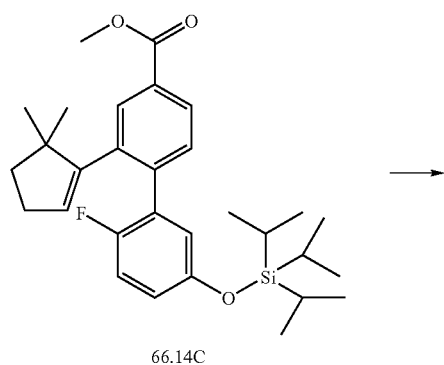

66.14C

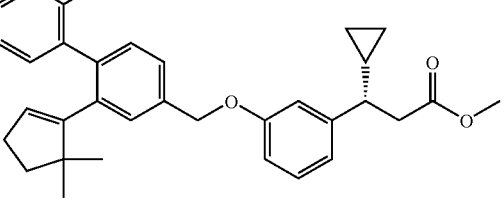

or

-continued

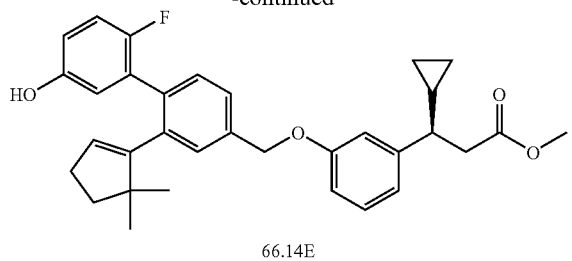

66.14E

Methyl (3S)-3-cyclopropyl-3-(3-(((2-(5,5-dimethyl-1-cyclopenten-1-yl)-2'-fluoro-5'-hydroxy-1,1'-biphenyl-4-yl)methyl)oxy)phenyl)propanoate or methyl (3R)-3-cyclopropyl-3-(3-(((2-(5,5-dimethyl-1-cyclopenten-1-yl)-2'-fluoro-5'-hydroxy-1,1'-biphenyl-4-yl)methyl)oxy)phenyl)propanoate (66.14E). To a flask containing 8.4 (30.1 mg, 137 µmol), 66.14D (64.0 mg, 137 µmol), and triphenylphosphine (polymer supported) (68.3 mg, 205 µmol) in DCM (1 mL) was added diethyl azodicarboxylate (32.3 µL, 205 µmol) at 0° C. The reaction was then allowed to warm to room temperature and stirred for 1 hour. The reaction was concentrated and then purified by silica gel chromatography (0 to 20% EtOAc/Hexanes) to provide 66.14E (66.3 mg, 94.4% yield).

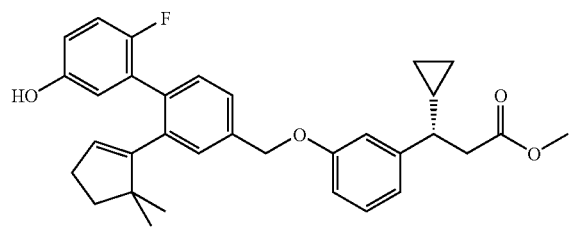

or

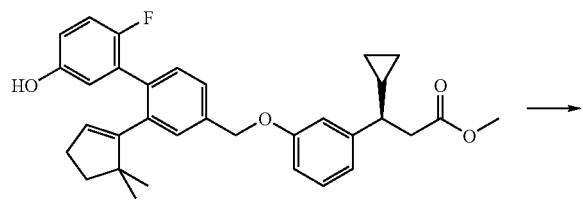

66.14E

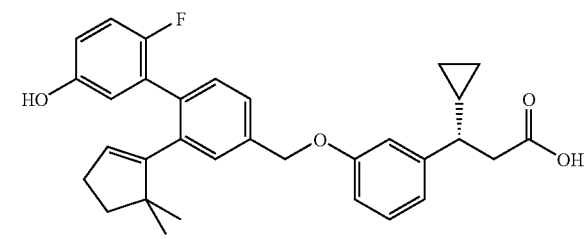

or

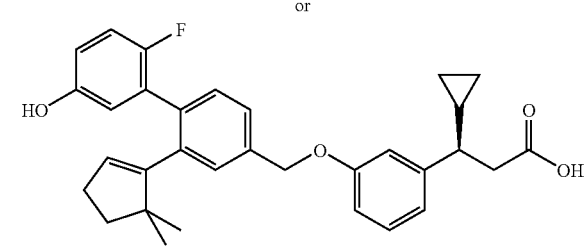

66.14

(3S)-3-Cyclopropyl-3-(3-(((2-(5,5-dimethyl-1-cyclopenten-1-yl)-2'-fluoro-5'-hydroxy-1,1'-biphenyl-4-yl)methyl)oxy)phenyl)propanoic acid or (3R)-3-cyclopropyl-3-(3-(((2-(5,5-dimethyl-1-cyclopenten-1-yl)-2'-fluoro-5'-hydroxy-1,1'-biphenyl-4-yl)methyl)oxy)phenyl)propanoic acid (66.14). To a solution of 66.14E (5.1 mg, 9.9 µmol) in THF/MeOH (2/1) (1.5 mL) was added LiOH (0.500 mL, 500 µmol). The resulting mixture was stirred overnight at 23° C., quenched with excess 1N HCl, and extracted with EtOAc. The combined organic layers were dried over Na$_2$SO$_4$ and concentrated. The residue was purified by silica gel chromatography (0 to 40% EtOAc/hexanes) to afford a 66.14 (4.5 mg, 91% yield). MS ESI (neg.) m/e: 499.1 (M–H).

Example 66.15

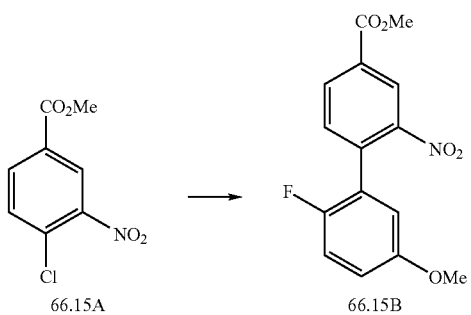

66.15A → 66.15B

Methyl 2'-fluoro-5'-(methyloxy)-2-nitro-1,1'-biphenyl-4-carboxylate (66.15B). To a stirred solution of methyl 4-chloro-3-nitrobenzoate (10.00 g, 46 mmol) (commercially available from Aldrich) in DMF (15.00 mL, 194 mmol) at 23° C. was added 2-fluoro-5-methoxyphenylboronic acid (12 g, 70 mmol) (commercially available from Aldrich), and potassium carbonate (19 g, 139 mmol). Tetrakis(triphenylphosphine)palladium (2.1 g, 1.9 mmol) was then added to the mixture, and the mixture was heated at 90° C. for 18 hours. The mixture was then cooled to room temperature, diluted with brine and extracted three times with EtOAc. After drying over anhydrous magnesium sulfate and filtering, the organic solvent was removed under reduced pressure and the product was purified on silica gel (0-40% EtOAc in hexanes) to yield 66.15B as a colorless oil (14.00 g, 99% yield).

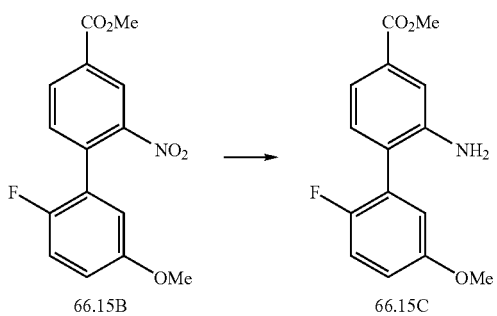

66.15B → 66.15C

Methyl 2-amino-2'-fluoro-5'-(methyloxy)-1,1'-biphenyl-4-carboxylate (66.15C). To a stirred solution of 66.15B (1.00 g, 3.3 mmol) in acetic acid (2.00 mL, 35 mmol) at 23° C. was added DME (15.00 mL, 144 mmol), EtOH (10.00 mL), followed by tin(II) chloride (4.7 g, 25 mmol). The mixture was heated at 60° C. for 17 hours. After which, the reaction was cooled to room temperature. The reaction was diluted with water and extracted three times with EtOAc. After drying over anhydrous magnesium sulfate and filtering, the organic solvent was removed under reduced pressure to give the product 66.15C (0.90 g, 100% yield).

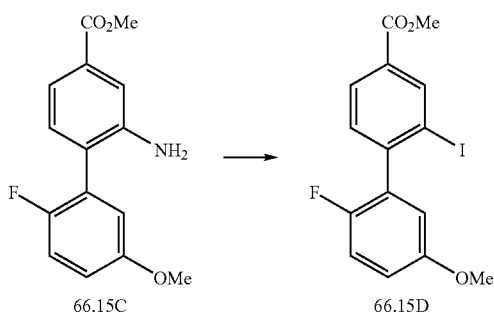

Methyl 2'-fluoro-2-iodo-5'-(methyloxy)-1,1'-biphenyl-4-carboxylate (66.15D). To a stirred solution of 66.15C (1.00 g, 3.6 mmol) in DME (10.00 mL, 96 mmol) at 23° C. was added sulfuric acid (0.19 mL, 3.6 mmol) in water (8 mL), followed by dropwise addition of a solution of sodium nitrite (0.38 g, 5.4 mmol) in water (2 mL) at 0° C. over 30 minutes. The reaction was then stirred for 20 minutes. To the mixture was added a solution of sodium iodide (3.0 g, 20 mmol) in water (7 mL) at 0° C. The resulting mixture was then stirred for 1 hour. The reaction was quenched with sodium thiosulfate and extracted three times with diethyl ether. After drying over anhydrous magnesium sulfate and filtering, the organic solvent was removed under reduced pressure and the product was purified on silica gel (0-40% EtOAc in hexanes) to yield a colorless solid 66.15D (0.820 g, 58% yield).

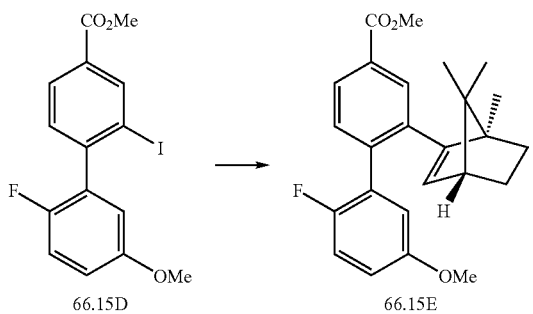

Methyl 2'-fluoro-5'-(methyloxy)-2-((1R,4R)-1,7,7-trimethylbicyclo[2.2.1]hept-2-en-2-yl)-1,1'-biphenyl-4-carboxylate (66.15E). To a stirred solution of 66.15D (0.200 g, 0.52 mmol) in DMF (4.00 mL, 52 mmol) at 23° C. was added (1S,4R)-1,7,7-trimethylbicyclo[2.2.1]hept-2-en-2-ylboronic acid (0.19 g, 1.0 mmol, commercially available from Combi-Blocks, Cat. No. BB-2567), potassium carbonate (0.21 g, 1.6 mmol), and then tetrakis(triphenylphosphine)palladium (0.060 g, 0.052 mmol). The mixture was heated at 90° C. for 19 hours and then cooled to room temperature. The reaction was diluted with brine and extracted three times with EtOAc. After drying over anhydrous magnesium sulfate and filtering, the organic solvent was removed under reduced pressure and the product was purified on silica gel (0-10% EtOAc in hexanes) to yield 66.15E as a colorless oil (0.165 g, 81% yield).

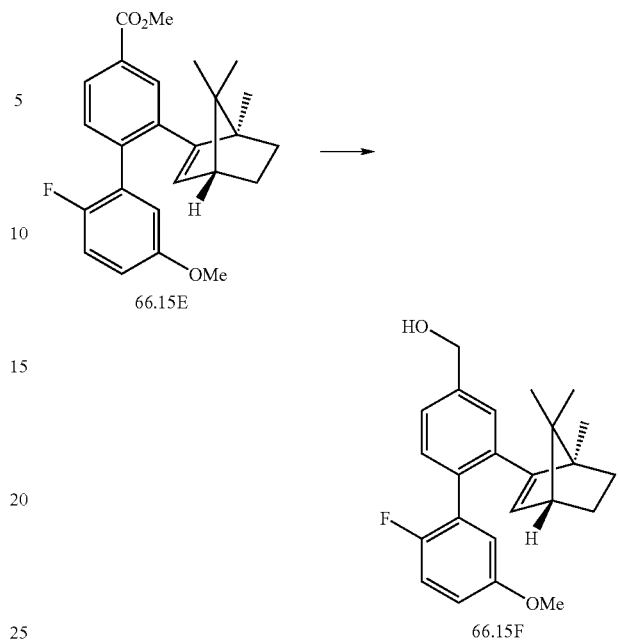

(2'-Fluoro-5'-(methyloxy)-2-((1R,4R)-1,7,7-trimethylbicyclo[2.2.1]hept-2-en-2-yl)-1,1'-biphenyl-4-yl)methanol (66.15F). To a stirred solution of 66.15E (0.050 g, 0.1 mmol) in THF (4 mL) at 0° C. was added LAH in THF (0.3 mL, 0.3 mmol, 1.0M). The resulting mixture was stirred for 2 hours. 1N NaOH(aq) was added to the mixture to quench it. The reaction was then extracted three times with EtOAc. After drying over anhydrous magnesium sulfate and filtering, the organic solvent was removed under reduced pressure and the product was purified on silica gel (0-20% EtOAc in hexanes) to yield 66.15F as a colorless oil (0.035 g, 75% yield).

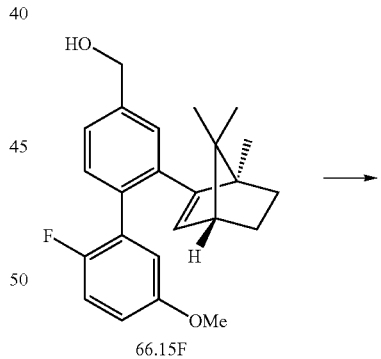

4'-(Chloromethyl)-6-fluoro-2'-((1R,4R)-1,7,7-trimethylbicyclo[2.2.1]hept-2-en-2-yl)-1,1'-biphenyl-3-yl methyl ether (66.15G). To a stirred solution of 66.15F (0.035 g, 0.10 mmol) in DCM (2.00 mL) and DMF (0.01 mL) at 0° C. was added thionyl chloride (0.01 g, 0.10 mmol). The reaction was then stirred at room temperature for 2 hours and was then concentrated in vacuo. The resulting product was then purified on silica gel (0-10% EtOAc in hexanes) to yield 66.15G as a colorless oil (0.035 g, 95% yield).

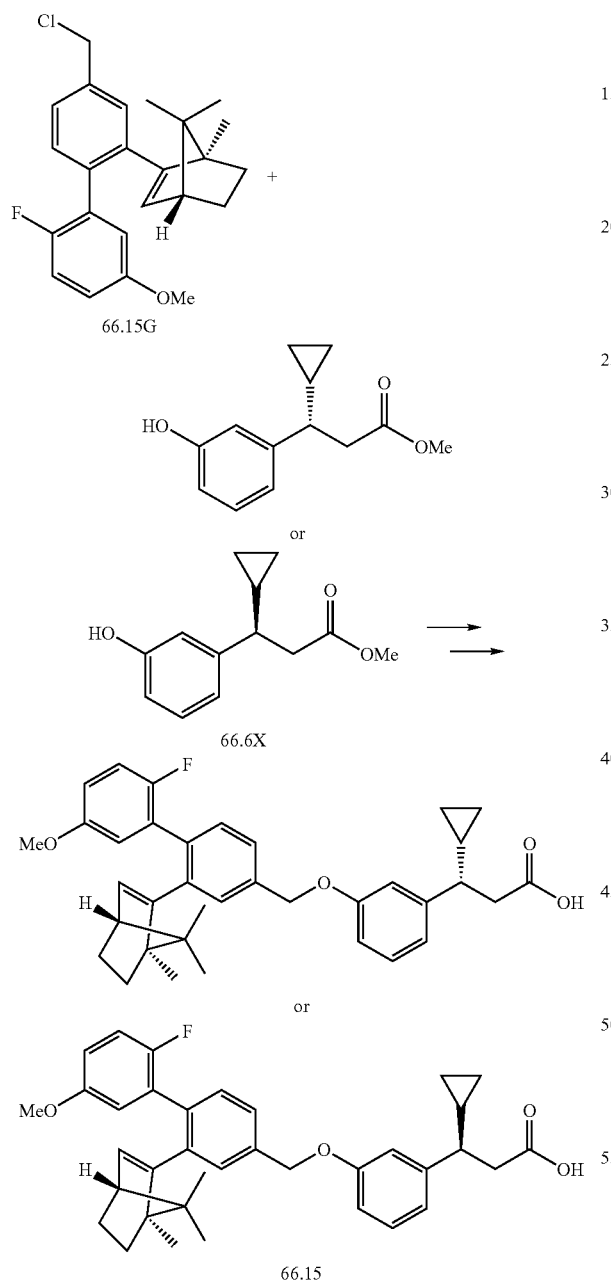

(3S)-3-Cyclopropyl-3-(3-(((2'-fluoro-5'-(methyloxy)-2-((1R,4R)-1,7,7-trimethylbicyclo[2.2.1]hept-2-en-2-yl)-1,1'-biphenyl-4-yl)methyl)oxy)phenyl)propanoic acid or (3R)-3-cyclopropyl-3-(3-(((2'-fluoro-5'-(methyloxy)-2-((1R,4R)-1,7,7-trimethylbicyclo[2.2.1]hept-2-en-2-yl)-1,1'-biphenyl-4-yl)methyl)oxy)phenyl)propanoic acid (66.15). The alkylation and hydrolysis were conducted in an analogous manner to Example 66.6 (described herein) to yield 66.15 (0.0303 g, 61% yield over two steps). MS ESI (neg.) m/e: 515.2 (M–H)+.

Example 66.16

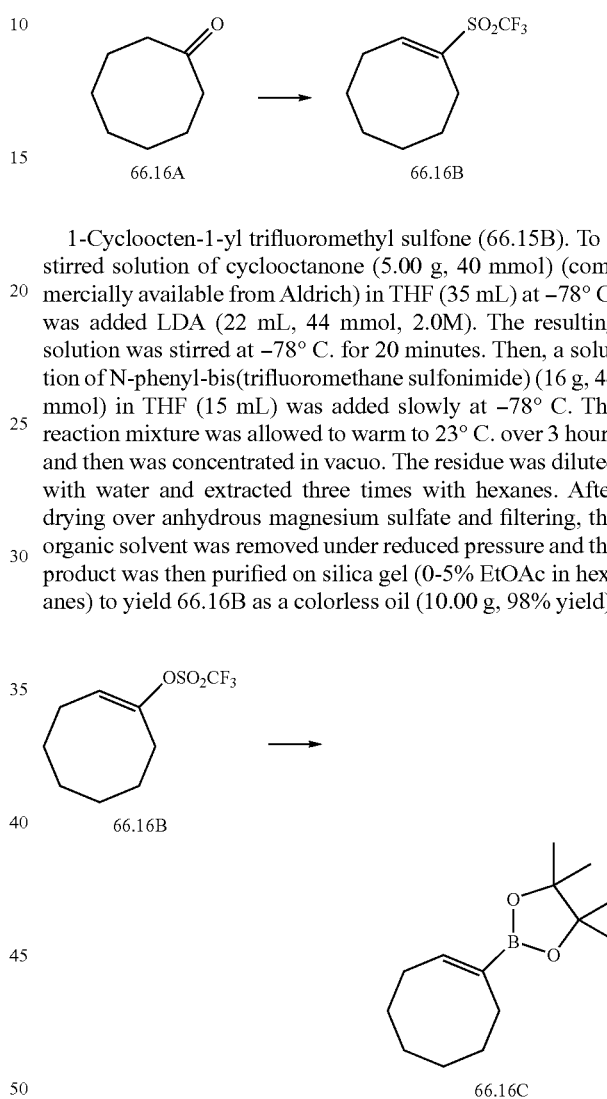

1-Cycloocten-1-yl trifluoromethyl sulfone (66.15B). To a stirred solution of cyclooctanone (5.00 g, 40 mmol) (commercially available from Aldrich) in THF (35 mL) at –78° C. was added LDA (22 mL, 44 mmol, 2.0M). The resulting solution was stirred at –78° C. for 20 minutes. Then, a solution of N-phenyl-bis(trifluoromethane sulfonimide) (16 g, 44 mmol) in THF (15 mL) was added slowly at –78° C. The reaction mixture was allowed to warm to 23° C. over 3 hours and then was concentrated in vacuo. The residue was diluted with water and extracted three times with hexanes. After drying over anhydrous magnesium sulfate and filtering, the organic solvent was removed under reduced pressure and the product was then purified on silica gel (0-5% EtOAc in hexanes) to yield 66.16B as a colorless oil (10.00 g, 98% yield).

2-(1-Cycloocten-1-yl)-4,4,5,5-tetramethyl-1,3,2-dioxaborolane (66.16C). A mixture of triphenylphosphine (1 g, 4 mmol), potassium phenolate (7 g, 54 mmol), 4,4,5,5-tetramethyl-2-(4,4,5,5-tetramethyl-1,3,2-dioxaborolan-2-yl)-1,3,2-dioxaborolane (10 g, 39 mmol) and 66.16B (10.00 g, 39 mmol) in toluene (194 mL) was degassed with nitrogen. Then, dichlorobis(triphenylphosphine)palladium(II) (1 g, 2 mmol) was added and the mixture was further degassed with nitrogen. The reaction mixture was stirred at 50° C. for 3.5 hours. The reaction mixture was diluted with water and extracted three times with EtOAc. After drying over anhydrous magnesium sulfate and filtering, the organic solvent was removed under reduced pressure and the product was then purified on silica gel (0-5% EtOAc in hexanes) to yield 66.16C as a colorless oil (7.00 g, 77% yield).

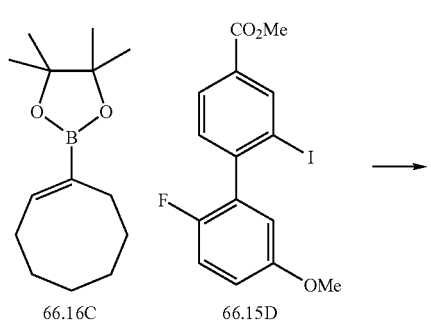

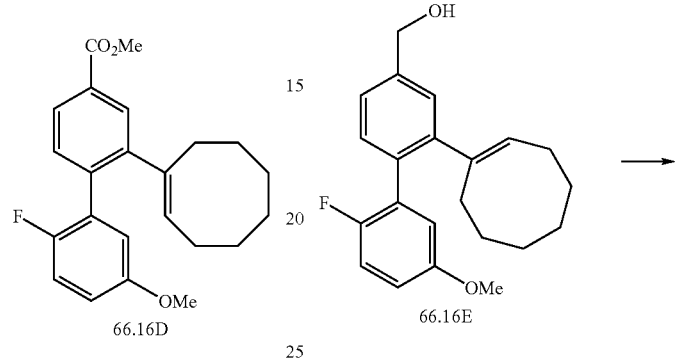

Methyl 2-(1-cycloocten-1-yl)-2'-fluoro-5'-(methyloxy)-1,1'-biphenyl-4-carboxylate (66.16D). To a stirred solution of 66.15D (0.750 g, 1.9 mmol) in DMF (4.00 mL, 52 mmol) at 23° C. was added (Z)-2-cyclooctenyl-4,4,5,5-tetramethyl-1,3,2-dioxaborolane 66.16C (0.92 g, 3.9 mmol), potassium carbonate (0.81 g, 5.8 mmol), and then tetrakis(triphenylphosphine)palladium (0.22 g, 0.19 mmol). The mixture was heated at 90° C. for 19 hours and then cooled to room temperature. The reaction was diluted with brine and extracted three times with EtOAc. After drying over anhydrous magnesium sulfate and filtering, the organic solvent was removed under reduced pressure and the product was purified on silica gel (0-10% EtOAc in hexanes) to yield 66.16D as a colorless oil (0.35 g, 49% yield).

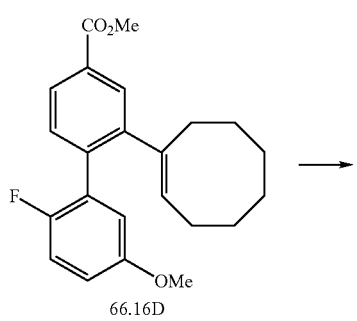

(2-(1-Cycloocten-1-yl)-2'-fluoro-5'-(methyloxy)-1,1'-biphenyl-4-yl)methanol (66.16E). To a stirred solution of 66.16D (0.350 g, 0.9 mmol) in THF (9 mL, 0.9 mmol) at 0° C. was added LAH in THF (2 mL, 2 mmol, 1.0M). The reaction was stirred for 1 hour. 1N NaOH(aq) was then added to quench the reaction. The reaction was extracted three times with EtOAc. After drying over anhydrous magnesium sulfate and filtering, the organic solvent was removed under reduced pressure and the product was then purified on silica gel (0-20% EtOAc in hexanes) to yield 66.16E as a colorless oil (0.387 g, 120% yield).

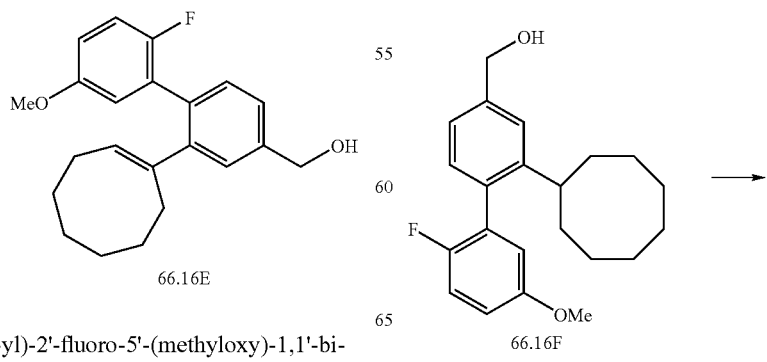

(2-Cyclooctyl-2'-fluoro-5'-(methyloxy)-1,1'-biphenyl-4-yl)methanol (66.16F). To a stirred solution of 66.16E (0.387 g, 1 mmol) in EtOAc (11 mL) at 23° C. was added palladium on carbon (0.1 g, 1 mmol). The reaction was placed under an atmosphere of hydrogen and stirred for 2 hours. The reaction mixture was then filtered and concentrated in vacuo. The residue was purified on silica gel (0-20% EtOAc in hexanes) to yield 66.16F as a colorless oil (0.13 g, 33% yield).

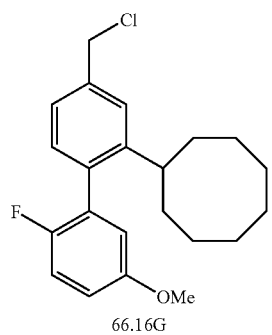

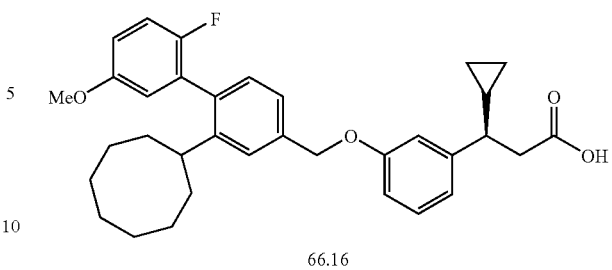

4-(Chloromethyl)-2'-fluoro-5'-(methyloxy)-2-cyclooctyl-1,1'-biphenyl (66.16G). To a stirred solution of 66.16F (0.130 g, 0.4 mmol) in DCM (2.00 mL) and DMF (0.03 mL) at 0° C. was added thionyl chloride (0.06 mL, 0.8 mmol). The reaction was stirred at room temperature for 2 hours. After which, the reaction was concentrated in vacuo and the product was then purified on silica gel (0-10% EtOAc in hexanes) to yield 66.16G as a colorless oil (0.130 g, 95% yield).

(3S)-3-(3-(((2-Cyclooctyl-2'-fluoro-5'-(methyloxy)-1,1'-biphenyl-4-yl)methyl)oxy)phenyl)-3-cyclopropylpropanoic acid or (3R)-3-(3-(((2-cyclooctyl-2'-fluoro-5'-(methyloxy)-1,1'-biphenyl-4-yl)methyl)oxy)phenyl)-3-cyclopropylpropanoic acid (66.16). The alkylation and hydrolysis were conducted in an analogous manner to Example 66.6 (described herein) to yield 66.16 (0.0227 g, 63% yield over two steps). MS ESI (neg.) m/e: 529.3 (M−H)+.

Example 66.17

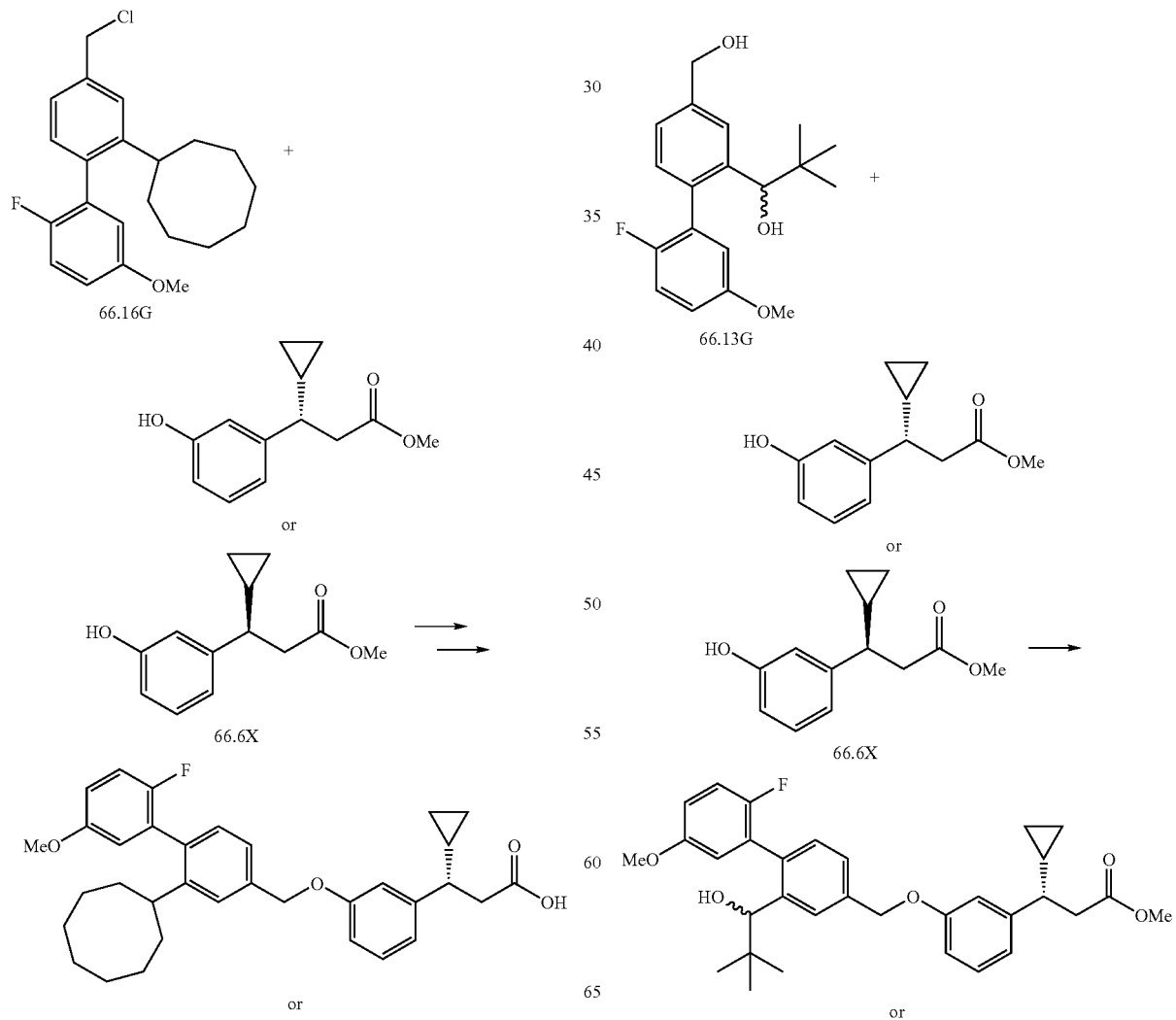

-continued

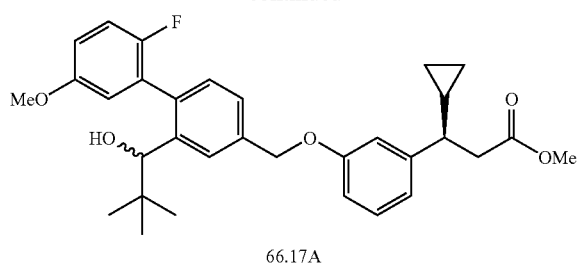

66.17A

Methyl (3S)-3-cyclopropyl-3-(3-(((2'-fluoro-2-(1-hydroxy-2,2-dimethylpropyl)-5'-(methyloxy)-1,1'-biphenyl-4-yl)methyl)oxy)phenyl)propanoate or methyl (3R)-3-cyclopropyl-3-(3-(((2'-fluoro-2-(1-hydroxy-2,2-dimethylpropyl)-5'-(methyloxy)-1,1'-biphenyl-4-yl)methyl)oxy)phenyl)propanoate (66.17A). To a stirred solution of 66.6X (0.730 g, 3.3 mmol) in THF (20.00 mL) at 23° C. was added 66.13G (1.1 g, 3.3 mmol), triphenylphosphine (1.3 g, 5.0 mmol), and then DEAD (0.79 mL, 5.0 mmol) over two hours. The reaction was further stirred for 21 hours, and then was diluted with water and extracted three times with EtOAc. After drying over anhydrous magnesium sulfate and filtering, the organic solvent was removed under reduced pressure and the product was then purified on silica gel (0-20% EtOAc in hexanes) to yield 66.17A as a colorless oil (1.40 g, 81% yield).

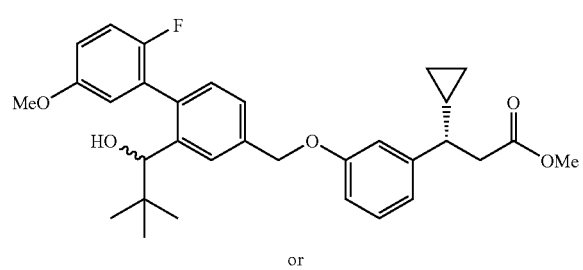

66.17A or

-continued

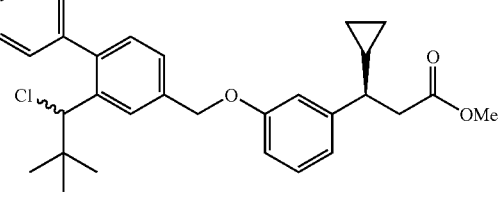

66.17B

Methyl (3S)-3-(3-(((2-(1-chloro-2,2-dimethylpropyl)-2'-fluoro-5'-(methyloxy)-1,1'-biphenyl-4-yl)methyl)oxy)phenyl)-3-cyclopropylpropanoate or methyl (3R)-3-(3-(((2-(1-chloro-2,2-dimethylpropyl)-2'-fluoro-5'-(methyloxy)-1,1'-biphenyl-4-yl)methyl)oxy)phenyl)-3-cyclopropylpropanoate (66.17B). To a stirred solution of 66.17A (1.400 g, 2.7 mmol) in DCM (20.00 mL) at 23° C. was added DMF (0.021 mL) followed by thionyl chloride (0.39 mL, 5.4 mmol). The reaction was stirred for 45 minutes, and then was concentrated in vacuo. The resulting product was purified on silica gel (0-10% EtOAc in hexanes) to yield 66.17B as a colorless oil (1.300 g, 90% yield).

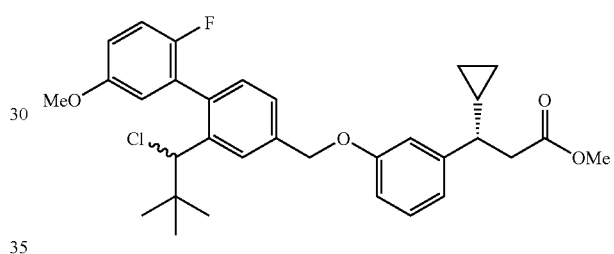

or

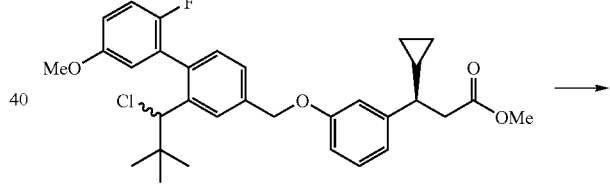

66.17B

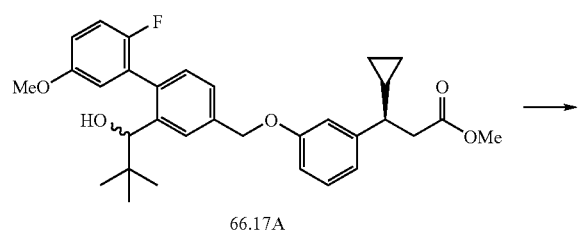

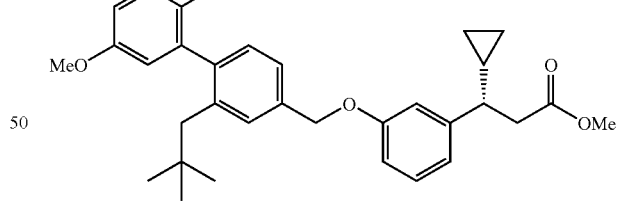

or

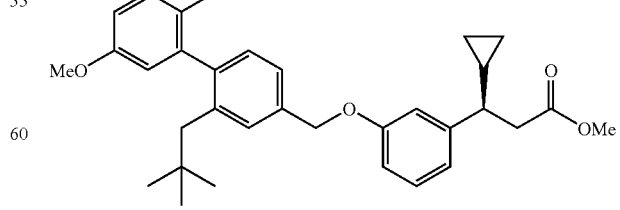

66.17C

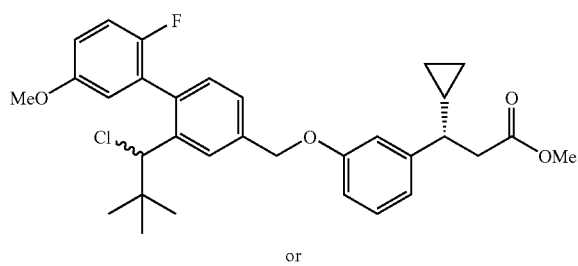

or

Methyl (3S)-3-cyclopropyl-3-(3-(((2-(2,2-dimethylpropyl)-2'-fluoro-5'-(methyloxy)-1,1'-biphenyl-4-yl)methyl)

oxy)phenyl)propanoate or methyl (3R)-3-cyclopropyl-3-(3-(((2-(2,2-dimethylpropyl)-2'-fluoro-5'-(methyloxy)-1,1'-biphenyl-4-yl)methyl)oxy)phenyl)propanoate (66.17C). To a stirred solution of 66.17B (1.30 g, 2.4 mmol) in toluene (10.00 mL) at 23° C. was added AIBN (0.040 g, 0.24 mmol) followed by tri-n-butyltin hydride (1.9 mL, 7.2 mmol). The reaction mixture was heated to 100° C. and stirred for 1 hour. The reaction mixture was then concentrated in vacuo, and the residue was purified on silica gel (0-15% EtOAc in hexanes) to yield 66.17C as a colorless oil (1.10 g, 90% yield).

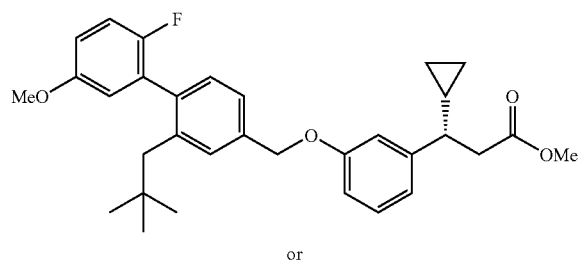

or

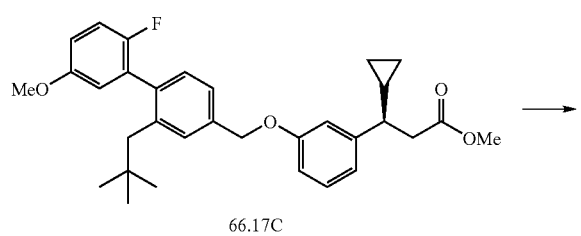

66.17C

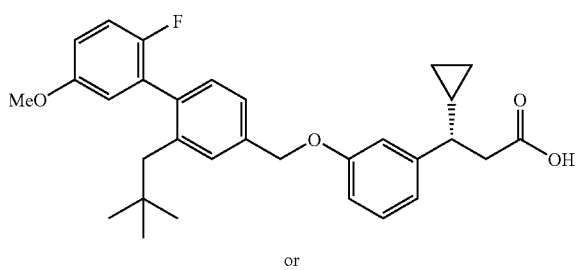

or

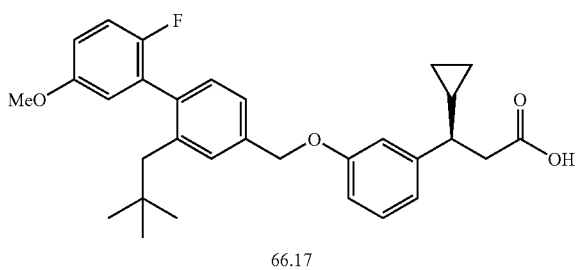

66.17

(3S)-3-Cyclopropyl-3-(3-(((2-(2,2-dimethylpropyl)-2'-fluoro-5'-(methyloxy)-1,1'-biphenyl-4-yl)methyl)oxy)phenyl)propanoic acid or (3R)-3-cyclopropyl-3-(3-(((2-(2,2-dimethylpropyl)-2'-fluoro-5'-(methyloxy)-1,1'-biphenyl-4-yl)methyl)oxy)phenyl)propanoic acid (66.17). The hydrolysis of 66.17C was conducted in an analogous manner to Example 66.6 (described herein) to yield 66.17 (0.900 g, 84%). MS ESI (neg.) m/e: 489.2 (M−H)+.

Example 66.18

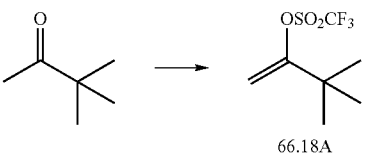

66.18A

Synthesis of 66.18A. To a solution of 3,3-dimethylbutan-2-one (5.00 g, 50 mmol, commercially available from Aldrich) in THF (71 mL) at −78° C. was added dropwise a solution of LDA (28 mL, 56 mmol). The resulting solution was stirred at −78° C. for 20 minutes. A solution of N-phenyl-bis(trifluoromethane sulfonimide) (20 g, 55 mmol) in THF (15 mL) was then added slowly at −78° C. The reaction mixture was allowed to room temperature over 3 hours. The reaction was concentrated in vacuo. The reaction was then diluted with water and extracted three times with EtOAc. After drying over anhydrous magnesium sulfate and filtering, the organic solvent was removed under reduced pressure and the product was purified on silica gel (0-5% EtOAc in hexanes) to yield 66.18A as a colorless oil (10.00 g, 86% yield)

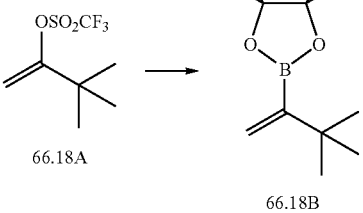

Synthesis of 66.18B. A mixture of triphenylphosphine (0.90 g, 3.4 mmol), potassium phenolate (6.4 g, 48 mmol), 4,4,5,5-tetramethyl-2-(4,4,5,5-tetramethyl-1,3,2-dioxaborolan-2-yl)-1,3,2-dioxaborolane (8.7 g, 34 mmol) and 66.18A (8.00 g, 34 mmol) in toluene (172 mL) was degassed by N₂. Then dichlorobis(triphenylphosphine)palladium(II) (1.2 g, 1.7 mmol) was added, and the reaction mixture was further degassed with N₂. The reaction was then stirred at 50° C. for 3.5 hours. The reaction was then filtered and concentrated in vacuo. The product was purified on silica gel (0-5% EtOAc in hexanes) to yield 66.18B as a colorless oil (5.0 g, 69% yield).

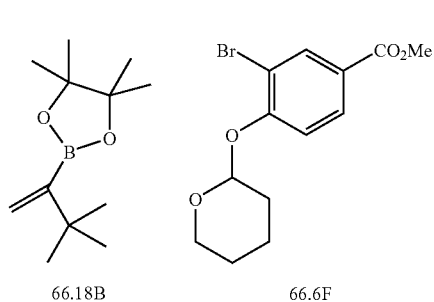

66.18B          66.6F

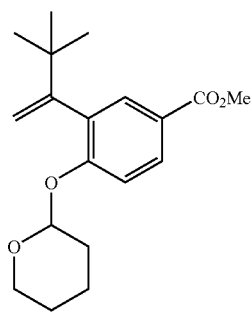

66.18C

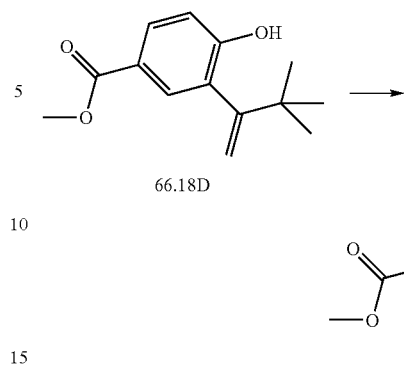

66.18D

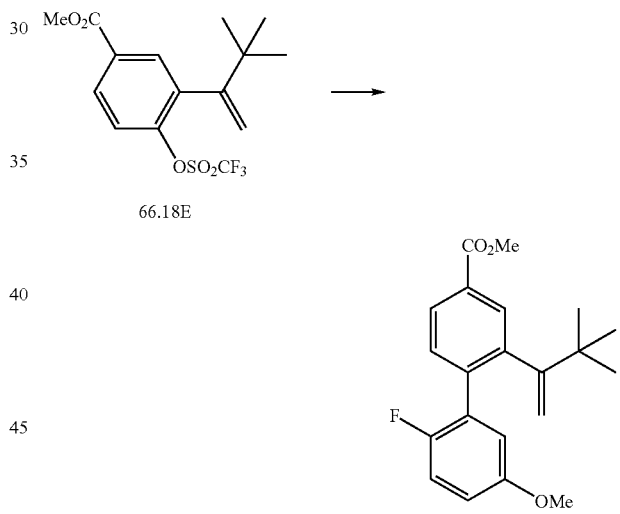

66.18E

Methyl 3-(1-(1,1-dimethylethyl)ethenyl)-4-(tetrahydro-2H-pyran-2-yloxy)benzoate (66.18C). A stirred solution of methyl 3-bromo-4-(tetrahydro-2H-pyran-2-yloxy)benzoate 66.6F (2.50 g, 7.9 mmol), palladium acetate (0.18 g, 0.79 mmol), S-Phos (0.65 g, 1.6 mmol), tripotassium phosphate (1.6 mL, 20 mmol) in DMF (15.00 mL, 194 mmol) and water (0.600 mL, 33 mmol) was purged 3 times with nitrogen and placed under vacuum and the process repeated three times. Before heating, 66.18B (2.0 g, 9.5 mmol) was added, and the mixture was heated to 70° C. and stirred for 19 hours. The resulting mixture was then cooled to room temperature, diluted with water and extracted three times with EtOAc. After drying over anhydrous magnesium sulfate and filtering, the organic solvent was removed under reduced pressure and the product was then purified on silica gel (0-20% EtOAc in hexanes) to yield 66.18C as a colorless oil (2.50 g, 99% yield).

Methyl 3-(1-(1,1-dimethylethyl)ethenyl)-4-(((trifluoromethyl)sulfonyl)oxy)benzoate (66.18E). To a stirred solution of 66.18D (0.500 g, 2 mmol) in DCM (11 mL) at 23° C. was added TEA (0.4 mL, 3 mmol), DMAP (catalytic), and then N-phenyltriflimide (0.8 g, 2 mmol). The reaction was further stirred for 19 hours and then concentrated in vacuo. The product was purified on silica gel (0-10% EtOAc in hexanes) to yield 66.18E as a colorless oil (0.1 g, 13% yield).

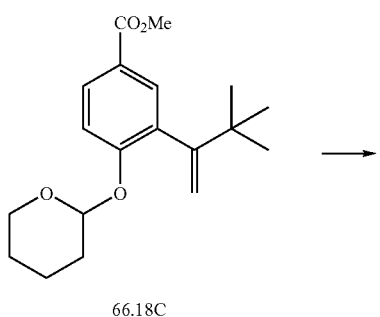

66.18C

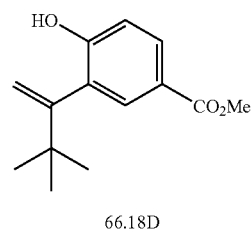

66.18D

Methyl 3-(1-(1,1-dimethylethyl)ethenyl)-4-hydroxybenzoate (66.18D). To a stirred solution of 66.18C (2.500 g, 7.85 mmol) in MeOH (10.00 mL, 7.85 mmol) at 23° C. was added PPTS (0.197 g, 0.785 mmol). The reaction was heated to 60° C. and stirred for 19 hours. The reaction was then concentrated in vacuo to give a clear oil. The product was then purified on silica gel (0-20% EtOAc in hexanes) to yield 66.18D as a colorless oil (1.50 g, 81.5% yield).

Methyl 2-(1-(1,1-dimethylethyl)ethenyl)-2'-fluoro-5'-(methyloxy)-1,1'-biphenyl-4-carboxylate (66.18F). To a stirred solution of 66.18E (0.550 g, 1.5 mmol) in DMF (3.0 mL, 1.5 mmol) at 23° C. was added 2-fluoro-5-methoxyphenylboronic acid (0.38 g, 2.3 mmol) (commercially available from Aldrich), potassium carbonate (0.62 g, 4.5 mmol) and then tetrakis(triphenylphosphine)palladium (0.12 g, 0.11 mmol). The mixture was heated to 90° C. and stirred for 17 hours. The resulting mixture was then cooled to room temperature, diluted with water and extracted three times with EtOAc. After drying over anhydrous magnesium sulfate and filtering, the organic solvent was removed under reduced pressure and the product was then purified on silica gel (0-10% EtOAc in hexanes) to yield 66.18F as a colorless oil (0.100 g, 19% yield).

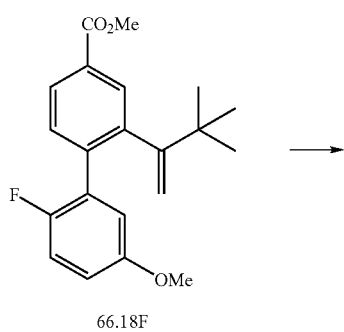

66.18F

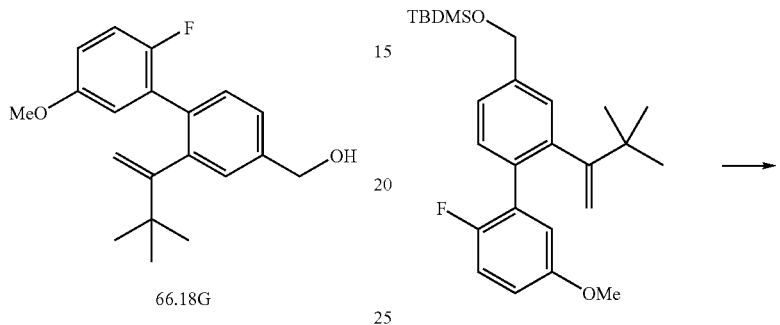

(2-(1-(1,1-Dimethylethyl)ethenyl)-2'-fluoro-5'-(methyloxy)-1,1'-biphenyl-4-yl)methanol (66.18G). To a stirred solution of 66.18F (0.400 g, 1 mmol) in THF (6 mL) at 0° C. was added LAH in THF (2 mL, 2 mmol, 1.0M). The resulting mixture was stirred for 2 hours. 1N NaOH(aq) was then added to the mixture, and the resulting mixture was extracted three times with EtOAc. After drying over anhydrous magnesium sulfate and filtering, the organic solvent was removed under reduced pressure and the product was then purified on silica gel (0-20% EtOAc in hexanes) to yield 66.18G as a colorless oil (0.273 g, 74% yield).

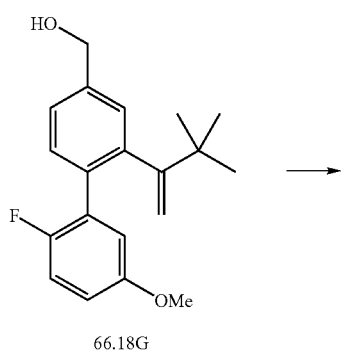

66.18G (1,1-Dimethylethyl)(((2-(1-(1,1-dimethylethyl)ethenyl)-2'-fluoro-5'-(methyloxy)-1,1'-biphenyl-4-yl)methyl)oxy)dimethylsilane (66.18H). To a stirred solution of 66.18G (0.273 g, 0.9 mmol) in DCM (2.00 mL) at 23° C. was added tert-butyldimethylsilyl chloride (0.2 mL, 1 mmol), followed by TEA (0.1 mL, 1 mmol) and DMAP (0.01 g, 0.09 mmol). The resulting mixture was then stirred for 16 hours and then was concentrated in vacuo to give the product. The product was purified on silica gel (0-5% EtOAc in hexanes) to yield 66.16H as a colorless oil (0.374 g, 100% yield).

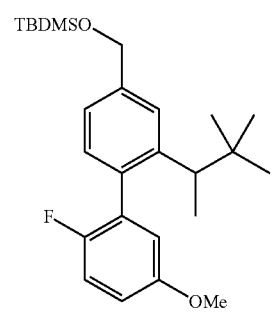

66.18H

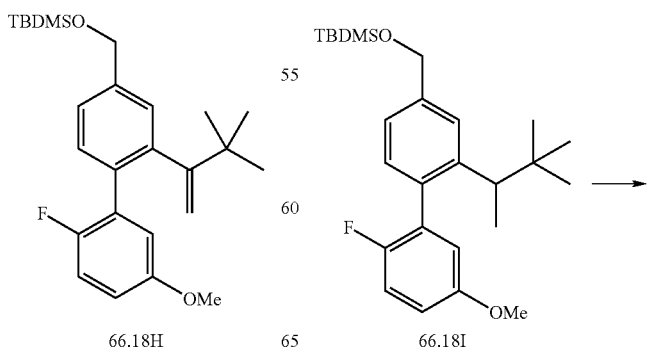

66.18I (1,1-Dimethylethyl)(((2'-fluoro-5'-(methyloxy)-2-(1,2,2-trimethylpropyl)-1,1'-biphenyl-4-yl)methyl)oxy)dimethylsilane (66.18I). To a stirred solution of 66.18H (0.400 g, 0.93 mmol) in EtOAc (2.00 mL) at 23° C. was added palladium on carbon (0.0099 g, 0.093 mmol). The resulting mixture was stirred under an atmosphere of hydrogen for 21 hours and then was filtered and concentrated in vacuo. The product was purified on silica gel (0-5% EtOAc in hexanes) to yield 66.18I as a colorless oil (0.400 g, 100% yield).

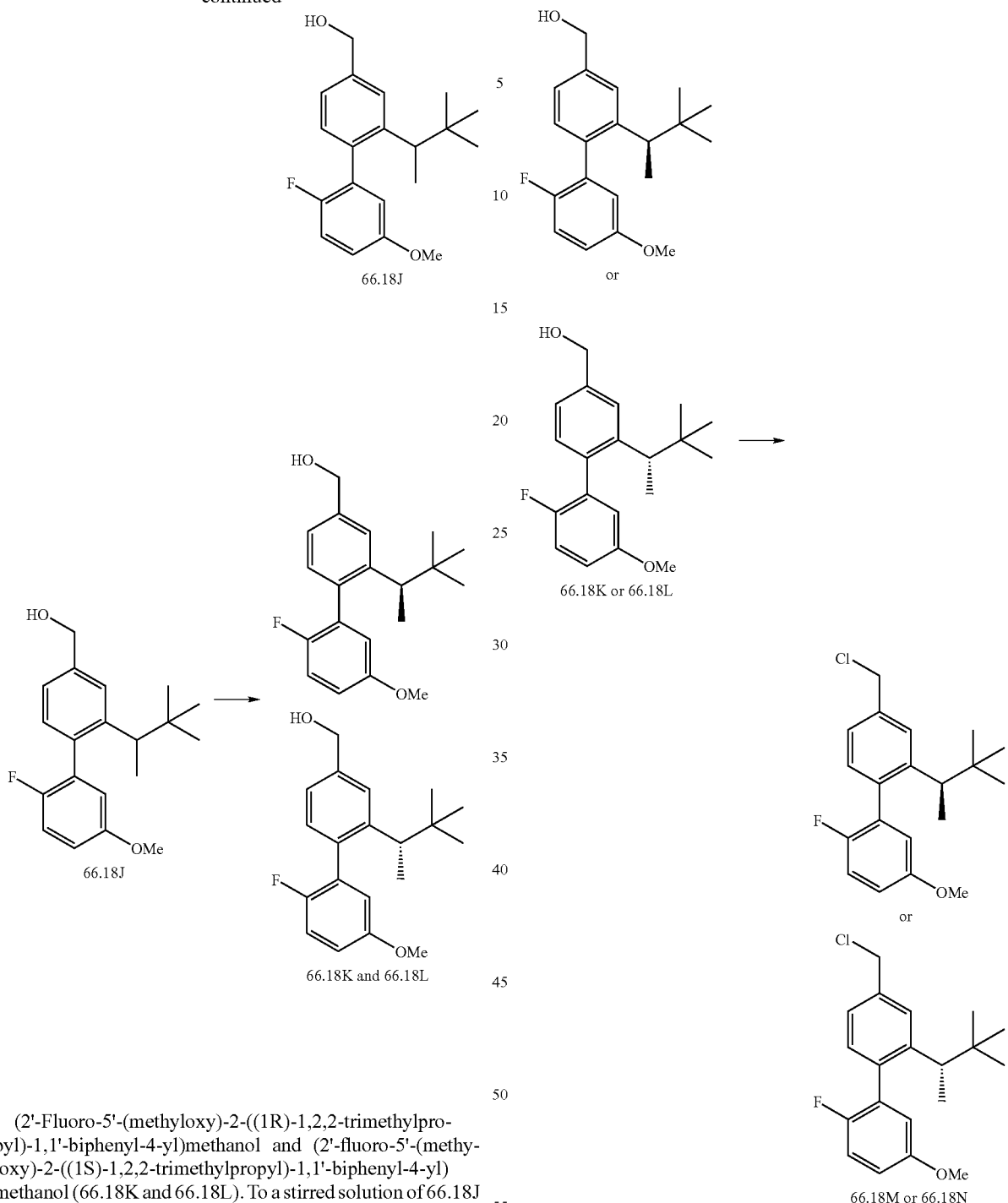

(2'-Fluoro-5'-(methyloxy)-2-((1R)-1,2,2-trimethylpropyl)-1,1'-biphenyl-4-yl)methanol and (2'-fluoro-5'-(methyloxy)-2-((1S)-1,2,2-trimethylpropyl)-1,1'-biphenyl-4-yl)methanol (66.18K and 66.18L). To a stirred solution of 66.18J (0.400 g, 0.929 mmol) in MeOH (10.00 mL, 0.929 mmol) at 23° C. was added PPTS (0.0233 g, 0.0929 mmol). The mixture was stirred for 19 hours and then was concentrated in vacuo to give a clear oil. The product was then purified on silica gel (0-20% EtOAc in hexanes) to yield 66.16J as a colorless oil (0.250 g, 85% yield). Chiral separation of 66.18J was accomplished on Chiracel-OD (3% IPA in hexane) to provide 66.18K (peak one) and 66.18L (peak two). Both enantiomers were used to synthesize example compounds, and both enantiomers gave active example compounds. However, the enantiomer corresponding to peak 2 provided the most active example compounds.

4-(Chloromethyl)-2'-fluoro-5'-(methyloxy)-2-((1R)-1,2,2-trimethylpropyl)-1,1'-biphenyl or 4-(chloromethyl)-2'-fluoro-5'-(methyloxy)-2-((1S)-1,2,2-trimethylpropyl)-1,1'-biphenyl (66.18M or 66.18N). To a stirred solution of 66.18K or 66.18L (0.050 g, 0.16 mmol) in DCM (2.00 mL) at 23° C. was added DMF (0.0012 mL) followed by thionyl chloride (0.023 mL, 0.32 mmol). The mixture was stirred for one hour and then was concentrated in vacuo. The resulting product was purified on silica gel (0-10% EtOAc in hexanes) to yield 66.18M or 66.18N as a colorless oil (0.050 g, 94% yield).

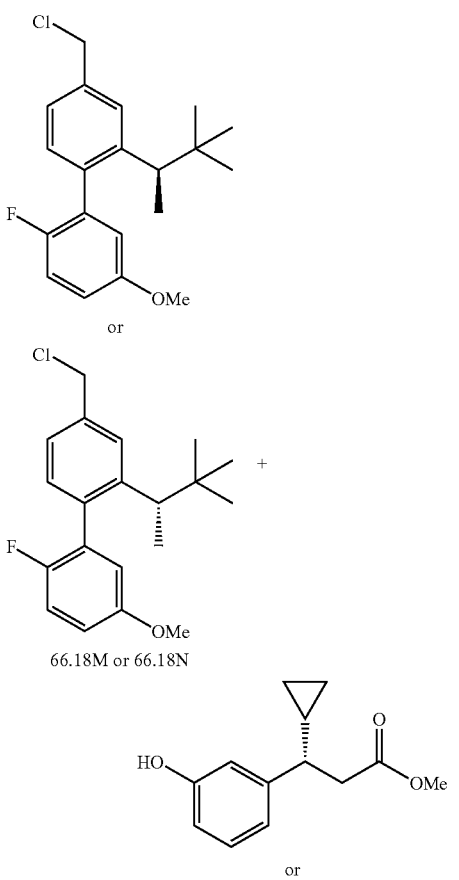

66.18M or 66.18N or

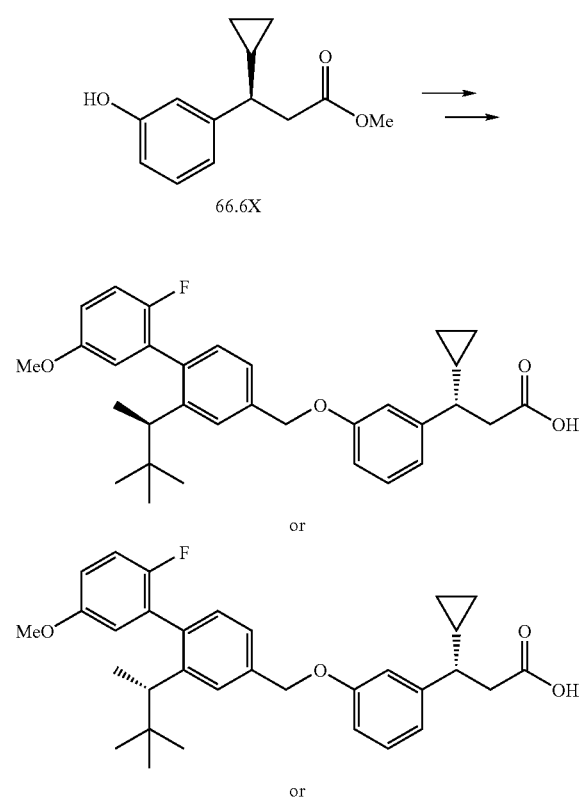

66.6X or

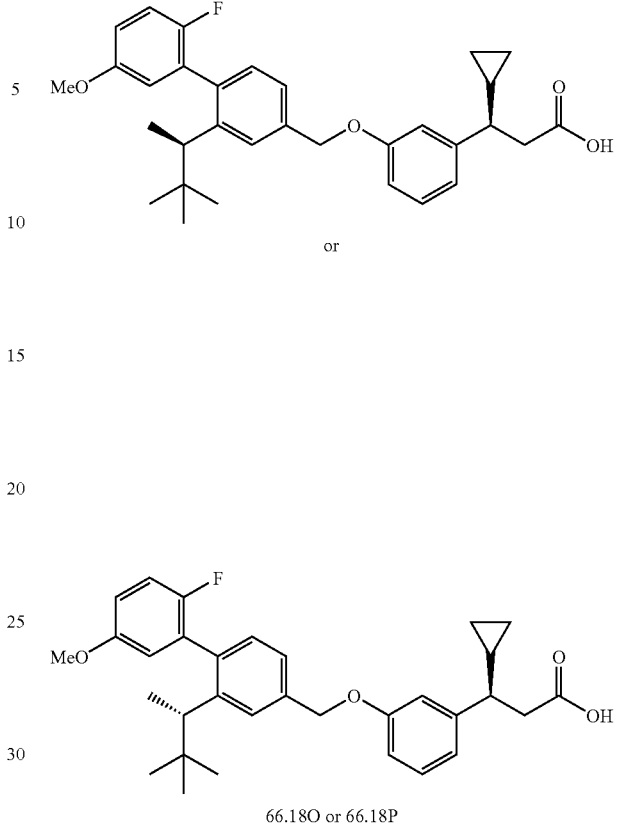

66.18O or 66.18P (3S)-3-Cyclopropyl-3-(3-(((2'-fluoro-5'-(methyloxy)-2-((1R)-1,2,2-trimethylpropyl)-1,1'-biphenyl-4-yl)methyl)oxy)phenyl)propanoic acid or (3S)-3-cyclopropyl-3-(3-(((2'-fluoro-5'-(methyloxy)-2-((1S)-1,2,2-trimethylpropyl)-1,1'-biphenyl-4-yl)methyl)oxy)phenyl)propanoic acid or (3R)-3-cyclopropyl-3-(3-(((2'-fluoro-5'-(methyloxy)-2-((1R)-1,2,2-trimethylpropyl)-1,1'-biphenyl-4-yl)methyl)oxy)phenyl)propanoic acid or (3R)-3-cyclopropyl-3-(3-(((2'-fluoro-5'-(methyloxy)-2-((1S)-1,2,2-trimethylpropyl)-1,1'-biphenyl-4-yl)methyl)oxy)phenyl)propanoic acid (66.18). The alkylation and hydrolysis were conducted in an analogous manner to Example 66.6 (using the chloromethyl compound derived from peak one from the chiral separation of 66.18J on the OD-column, described herein) to yield 66.18 (0.0334 g, 73% yield over the two steps). MS ESI (neg.) m/e: 503.2 (M−H)$^+$.

(3S)-3-cyclopropyl-3-(3-(((2'-fluoro-5'-(methyloxy)-2-((1R)-1,2,2-trimethylpropyl)-1,1'-biphenyl-4-yl)methyl)oxy)phenyl)propanoic acid or (3S)-3-cyclopropyl-3-(3-(((2'-fluoro-5'-(methyloxy)-2-((1S)-1,2,2-trimethylpropyl)-1,1'-biphenyl-4-yl)methyl)oxy)phenyl)propanoic acid or (3R)-3-cyclopropyl-3-(3-(((2'-fluoro-5'-(methyloxy)-2-((1R)-1,2,2-trimethylpropyl)-1,1'-biphenyl-4-yl)methyl)oxy)phenyl)propanoic acid or (3R)-3-cyclopropyl-3-(3-(((2'-fluoro-5'-(methyloxy)-2-((1S)-1,2,2-trimethylpropyl)-1,1'-biphenyl-4-yl)methyl)oxy)phenyl)propanoic acid (66.19). The alkylation and hydrolysis were conducted in an analogous manner to Example 66.6 (using the chloromethyl compound derived from peak two from the chiral separation of 66.18J on the OD-column, described herein) to yield 66.19A or 66.19B (0.0305 g, 66% yield over two steps). MS ESI (neg.) m/e: 503.2 (M−H)⁺.

Example 66.20

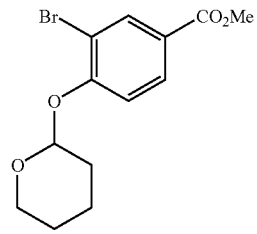

66.6F

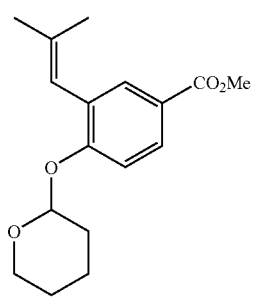

66.20A

Methyl 3-(2-methyl-1-propenyl)-4-(tetrahydro-2H-pyran-2-yloxy)benzoate (66.20A). A mixture of methyl 3-bromo-4-(tetrahydro-2H-pyran-2-yloxy)benzoate 66.6F (0.500 g, 1.6 mmol), palladium acetate (0.036 g, 0.16 mmol), S-Phos (0.13 g, 0.32 mmol) and tripotassium phosphate (0.32 mL, 4.0 mmol) in DMF (10.00 mL, 129 mmol) and water (0.40 mL, 22 mmol) was stirred. The mixture was purged with nitrogen and placed under vacuum and the process repeated three times. Before heating, 2-methylprop-1-enylboronic acid (0.24 g, 2.4 mmol, commercially available from Synthonix, Cat. No. D3007G1) was added, and the mixture was heated to 70° C. and stirred for 23 hours. The mixture was then cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield 66.20A as a colorless oil (0.460 g, 100% yield).

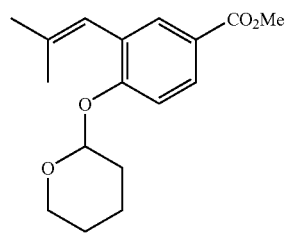

66.20A

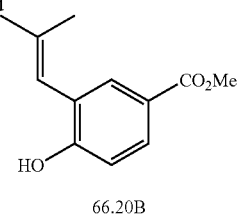

66.20B

Methyl 4-hydroxy-3-(2-methyl-1-propenyl)benzoate (66.20B). To a stirred mixture of 66.20A (0.460 g, 2 mmol) in MeOH (8 mL) was added PPTS (0.04 g, 0.2 mmol). The reaction mixture was then stirred for 24 hours and then concentrated in vacuo. The residue was purified on silica gel (0-20% EtOAc in hexanes) to yield 66.20B as a colorless oil (0.320 g, 98% yield).

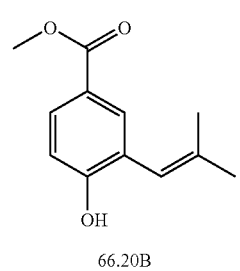

66.20B

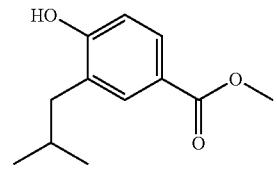

66.20C

Methyl 4-hydroxy-3-(2-methylpropyl)benzoate (66.20C). To a stirred solution of methyl 4-hydroxy-3-(2-methylprop-1-enyl)benzoate 66.20B (0.320 g, 1.6 mmol) in EtOAc (2.00 mL, 20 mmol) at 23° C. was added palladium on carbon (0.017 g, 0.16 mmol). The reaction was stirred under an atmosphere of hydrogen (0.0031 g, 1.6 mmol) for 16 hours. The reaction mixture was then filtered and concentrated in vacuo to give a clear oil. The residue was purified on silica gel (0-20% EtOAc in hexanes) to yield 66.20C as a colorless oil (0.256 g, 79% yield)

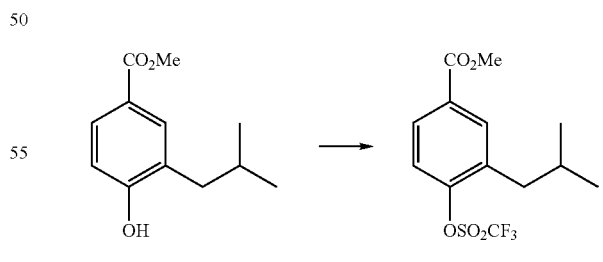

66.20C          66.20D

Methyl 3-(2-methylpropyl)-4-(((trifluoromethyl)sulfonyl)oxy)benzoate (66.20D). To a stirred solution of 66.20C (0.256 g, 1 mmol) in DCM (12 mL, 1 mmol) at 0° C. was added TEA (0.2 mL, 1 mmol), and a catalytic amount of DMAP. N-phenyltriflimide (0.5 g, 1 mmol) was then added and the mixture was stirred at room temperature for 20 hours.

The reaction was concentrated in vacuo, and the residue was purified on silica gel (0-10% EtOAc in hexanes) to yield 66.20D as a colorless oil (0.400 g, 96% yield).

with EtOAc. After drying over anhydrous magnesium sulfate and filtering, the organic solvent was removed under reduced pressure and the product was then purified on silica gel (0-20% EtOAc in hexanes) to yield 66.20F as a colorless oil (0.260 g, 97% yield).

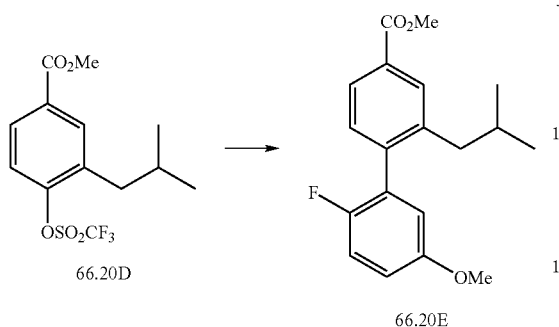

Methyl 2'-fluoro-5'-(methyloxy)-2-(2-methylpropyl)-1,1'-biphenyl-4-carboxylate (66.20E). To a stirred solution of 66.20D (0.400 g, 1.2 mmol) in DMF (4.00 mL, 52 mmol) at 23° C. was added 2-fluoro-5-methoxyphenylboronic acid (0.40 g, 2.4 mmol) (commercially available from Aldrich), potassium carbonate (0.49 g, 3.5 mmol), and then tetrakis(triphenylphosphine)palladium (0.14 g, 0.12 mmol). The mixture was heated to 90° C. and stirred for 22 hours. The mixture was cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield 66.20E as a colorless oil (0.293 g, 79% yield).

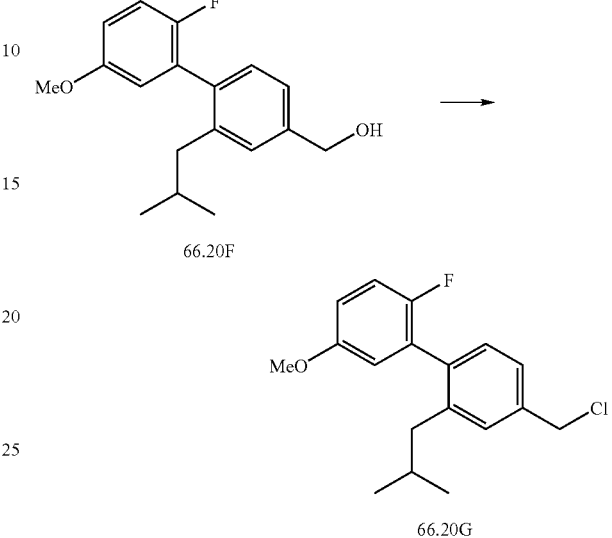

4-(Chloromethyl)-2'-fluoro-5'-(methyloxy)-2-(2-methylpropyl)-1,1'-biphenyl 66.20G. To a stirred solution of 66.20F (0.260 g, 0.90 mmol) in DCM (2.00 mL, 31 mmol) at 23° C. was added DMF (0.0070 mL, 0.090 mmol) followed by thionyl chloride (0.13 mL, 1.8 mmol). The reaction was stirred for one hour and then the reaction was concentrated in vacuo. The residue was then purified on silica gel (0-10% EtOAc in hexanes) to yield 66.20G as a colorless oil (0.252 g, 91% yield).

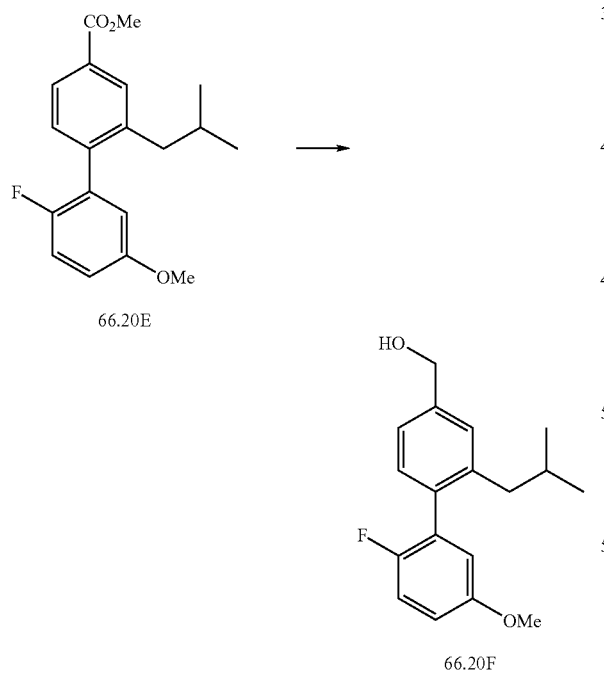

(2'-Fluoro-5'-(methyloxy)-2-(2-methylpropyl)-1,1'-biphenyl-4-yl)methanol (66.20E). To a stirred solution of 66.20E (0.293 g, 0.9 mmol) in THF (5 mL, 0.9 mmol) at 0° C. was added LAH in THF (2 mL, 2 mmol, 1.0M). The reaction was stirred for one hour and then 1N NaOH(aq) was added to quench the mixture. The reaction was extracted three times

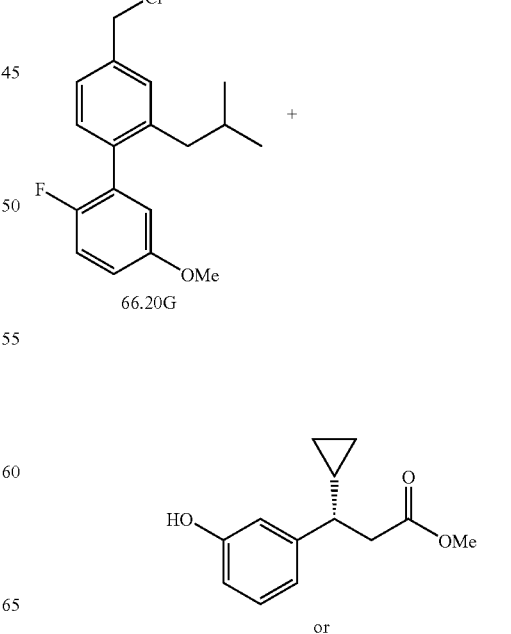

or

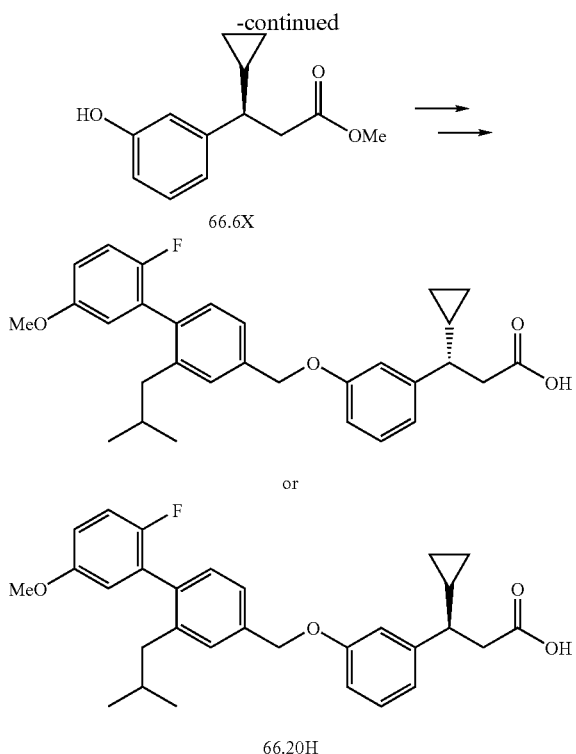

(3S)-3-Cyclopropyl-3-(3-(((2'-fluoro-5'-(methyloxy)-2-(2-methylpropyl)-1,1'-biphenyl-4-yl)methyl)oxy)phenyl)propanoic acid or (3R)-3-cyclopropyl-3-(3-(((2'-fluoro-5'-(methyloxy)-2-(2-methylpropyl)-1,1'-biphenyl-4-yl)methyl)oxy)phenyl)propanoic acid (66.20). The alkylation and hydrolysis were conducted in an analogous manner to Example 66.6 to yield 66.20H (0.0312 g, 72% yield over two steps). MS ESI (neg.) m/e: 951.4 (2M−H), 475.1 (M−H)⁺.

Example 66.21

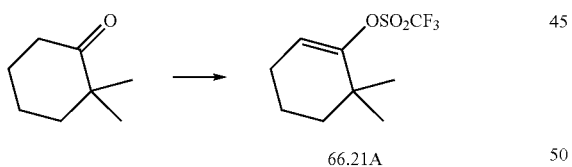

6,6-Dimethyl-1-cyclohexen-1-yl trifluoromethanesulfonate (66.21A). To a solution of 2,2-dimethylcyclohexanone (2.00 g, 16 mmol, commercially available from Aldrich) in THF (35 mL) at −78° C. was added dropwise LDA (9 mL, 18 mmol, 2.0 M). The resulting solution was stirred at −78° C. for 20 minutes. A solution of N-phenyl-bis(trifluoromethane sulfonimide) (6 g, 17 mmol) in THF (15 mL) was then added slowly at −78° C. The reaction mixture was allowed to warm to 23° C. over 3 hours and the reaction was then concentrated in vacuo. The reaction was diluted with brine and extracted three times with EtOAc. After drying over anhydrous magnesium sulfate and filtering, the organic solvent was removed under reduced pressure and the product was then purified on silica gel (0-10% EtOAc in hexanes) 66.21A as a clear oil (4.1 g, 100%).

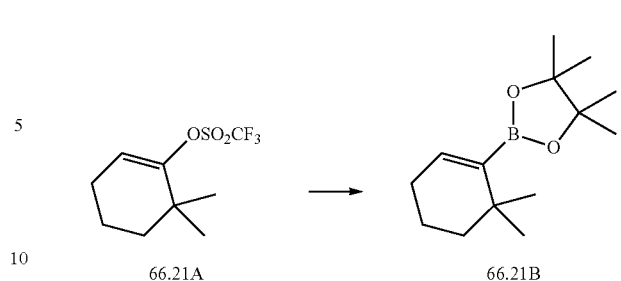

2-(6,6-Dimethyl-1-cyclohexen-1-yl)-4,4,5,5-tetramethyl-1,3,2-dioxaborolane (66.21B). A mixture of triphenylphosphine (0.4 g, 2 mmol), potassium phenolate (3 g, 22 mmol), 4,4,5,5-tetramethyl-2-(4,4,5,5-tetramethyl-1,3,2-dioxaborolan-2-yl)-1,3,2-dioxaborolane (4 g, 16 mmol) and 66.21A (4.1 g, 16 mmol) in toluene (79 mL, 16 mmol) was degassed using N₂. Then dichlorobis(triphenylphosphine)-palladium (II) (0.6 g, 0.8 mmol) was added. The reaction mixture was further degassed with N₂. The reaction was stirred at 50° C. for 3.5 hours, and then it was diluted with brine and extracted three times with EtOAc. After drying over anhydrous magnesium sulfate and filtering, the organic solvent was removed under reduced pressure and the product was then purified on silica gel (0-10% EtOAc in hexanes) to yield 66.21B as a colorless oil (3.00 g, 80% yield).

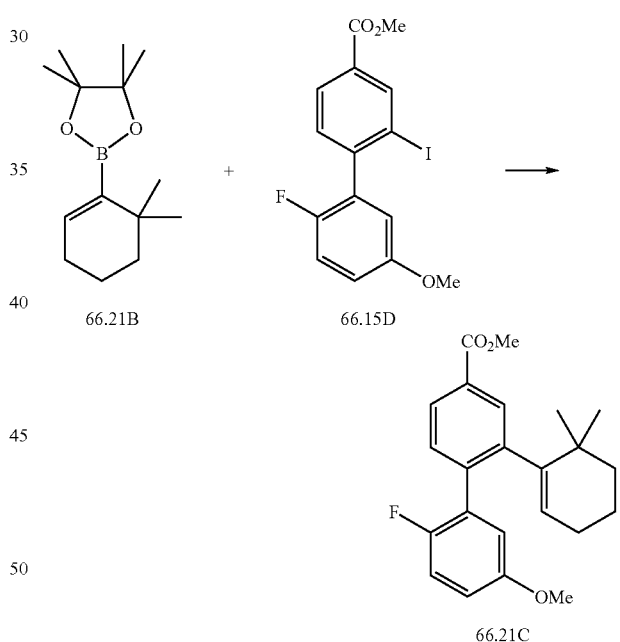

Methyl 2-(6,6-dimethyl-1-cyclohexen-1-yl)-2'-fluoro-5'-(methyloxy)-1,1'-biphenyl-4-carboxylate (66.21C). To a stirred solution of 66.15D (0.750 g, 1.9 mmol) in DMF (4.00 mL, 52 mmol) at 23° C. was added 66.21B (0.92 g, 3.9 mmol), potassium carbonate (0.81 g, 5.8 mmol), and then tetrakis(triphenylphosphine)palladium (0.22 g, 0.19 mmol). The mixture was heated to 90° C. and stirred for 24 hours. The reaction was then cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield 66.21C as a colorless oil (0.34 g, 48% yield).

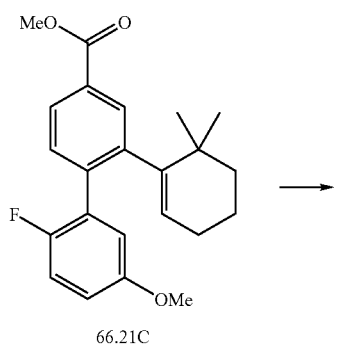

66.21C

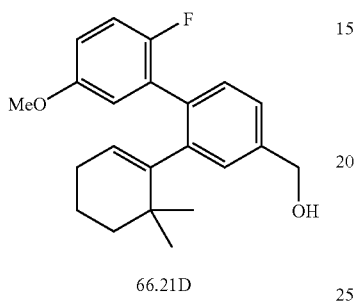

66.21D (2-(6,6-Dimethyl-1-cyclohexen-1-yl)-2'-fluoro-5'-(methyloxy)-1,1'-biphenyl-4-yl)methanol (66.21D). To a stirred solution of 66.21C (0.300 g, 0.814 mmol) in THF (0.0587 g, 0.814 mmol) at 0° C. was added LAH in THF (1.63 mL, 1.63 mmol, 1.0M). The reaction was stirred for 4.5 hours and then 1N NaOH(aq) was added to quench the mixture. The reaction was extracted three times with EtOAc. After drying over anhydrous magnesium sulfate and filtering, the organic solvent was removed under reduced pressure and the product was then purified on silica gel (0-20% EtOAc in hexanes) to yield 66.21D as a colorless oil (0.250 g, 90.2% yield).

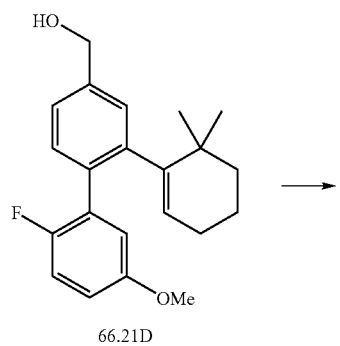

66.21D

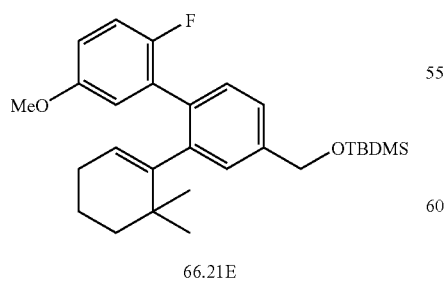

66.21E (((2-(6,6-Dimethyl-1-cyclohexen-1-yl)-2'-fluoro-5'-(methyloxy)-1,1'-biphenyl-4-yl)methyl)oxy)(1,1-dimethylethyl)dimethylsilane (66.21 E). To a stirred solution of 66.21D (0.160 g, 0.5 mmol) in DCM (10.00 mL, 155 mmol) at 23° C. was added tert-butyldimethylsilyl chloride (0.09 mL, 0.6 mmol), followed by TEA (0.08 mL, 0.6 mmol) and DMAP (0.006 g, 0.05 mmol). The reaction was stirred for one hour and then concentrated in vacuo. The crude product was then purified on silica gel (0-5% EtOAc in hexanes) to yield 66.21E as a colorless oil (0.198 g, 93% yield).

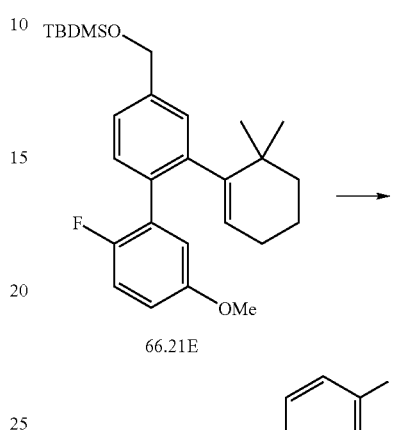

66.21E

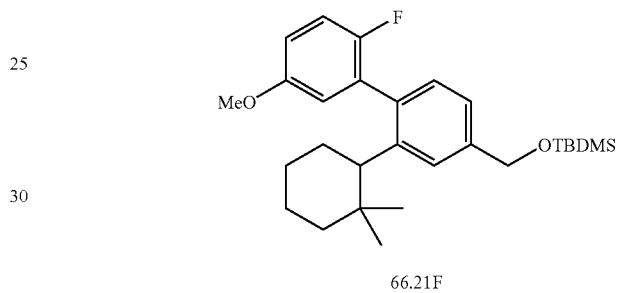

66.21F

Synthesis of 66.21F. To a stirred solution of 66.21E (0.090 g, 0.20 mmol) in EtOAc (2.00 mL, 20 mmol) at 23° C. was added palladium on carbon (0.0021 g, 0.020 mmol). The resulting mixture was stirred under an atmosphere of hydrogen for 4 days. The reaction mixture was filtered, and the filtrate was concentrated in vacuo to yield 66.21F as a colorless oil (0.090 g, 100% yield)

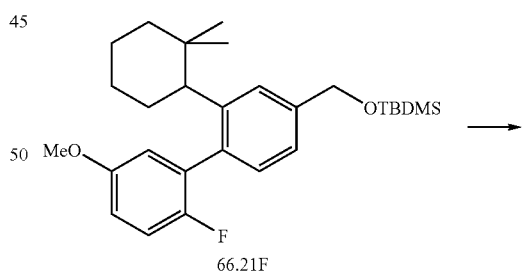

66.21F

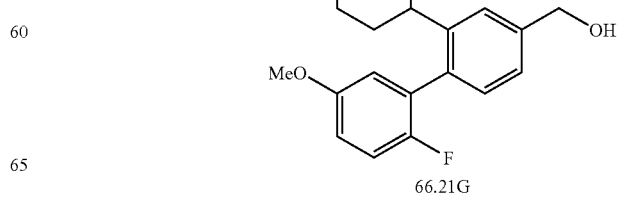

66.21G

-continued

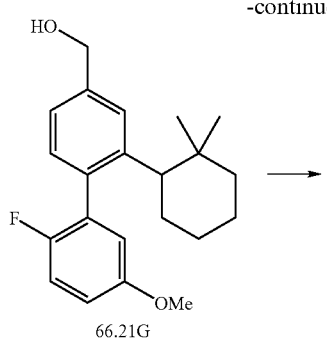
66.21G

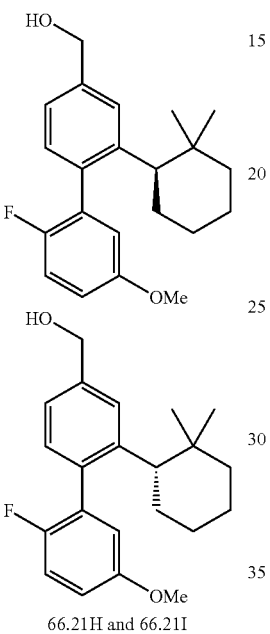
66.21H and 66.21I

-continued

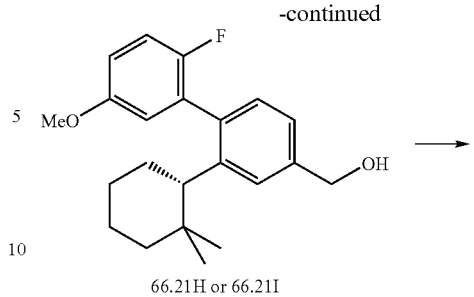
66.21H or 66.21I

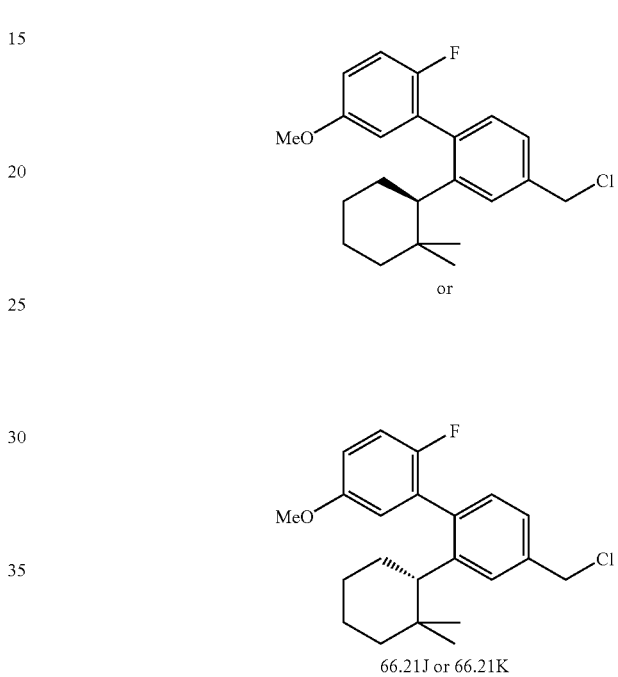
66.21J or 66.21K (2-((1R)-2,2-dimethylcyclohexyl)-2'-fluoro-5'-(methyloxy)-1,1'-biphenyl-4-yl)methanol and (2-((1S)-2,2-dimethylcyclohexyl)-2'-fluoro-5'-(methyloxy)-1,1'-biphenyl-4-yl)methanol (66.21H and 66.21I). To a stirred mixture of 66.21F (0.090 g, 0.20 mmol) in MeOH (0.99 mL, 0.20 mmol) was added PPTS (0.0050 g, 0.020 mmol). The resulting mixture was stirred for 4.5 hours and then was concentrated in vacuo. The residue was purified on silica gel (0-15% EtOAc in hexanes) to yield a colorless oil (0.067 g, 99% yield). Chiral separation of 66.21G was accomplished on Chiracel-OD (3% IPA in hexane) to provide 66.21H (peak one) and 66.21I (peak two). Both enantiomers were used to synthesize example compounds, and both enantiomers gave active example compounds. However, the enantiomer corresponding to peak 2 provided the most active example compounds.[1]

4-(Chloromethyl)-2-((1R)-2,2-dimethylcyclohexyl)-2'-fluoro-5'-(methyloxy)-1,1'-biphenyl or 4-(chloromethyl)-2-((1S)-2,2-dimethylcyclohexyl)-2'-fluoro-5'-(methyloxy)-1,1'-biphenyl (66.21 J or 66.21K). To a stirred solution of 66.21H or 66.21I (0.035 g, 0.10 mmol) in DCM (2.00 mL, 31 mmol) at 23° C. was added DMF (0.00079 mL, 0.010 mmol) followed by thionyl chloride (0.015 mL, 0.20 mmol). The reaction was stirred for one hour. After which, the reaction mixture was concentrated in vacuo. The crude product was then purified on silica gel (0-10% EtOAc in hexanes) to yield 66.21J or 66.12K as a colorless oil (0.025 g, 68% yield).

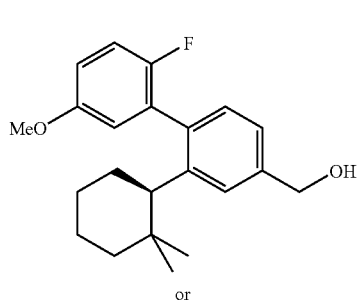
or

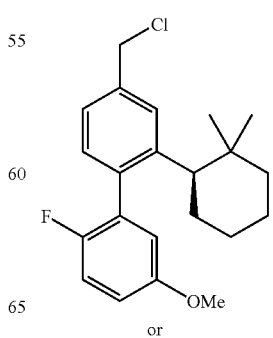
or

295
-continued

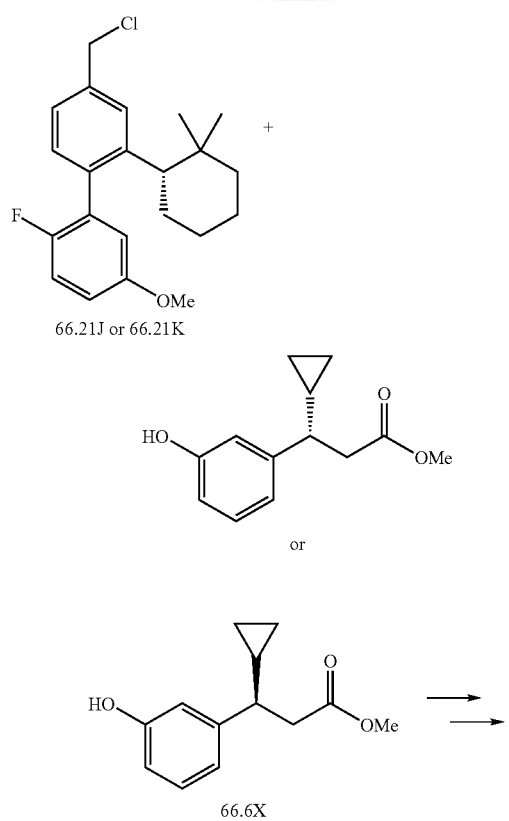

66.21J or 66.21K

296
-continued

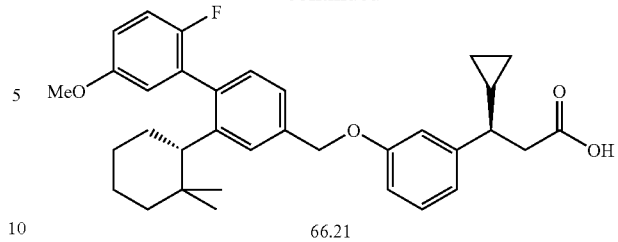

66.21

(3S)-3-Cyclopropyl-3-(3-(((2-((1R)-2,2-dimethylcyclohexyl)-2'-fluoro-5'-(methyloxy)-1,1'-biphenyl-4-yl)methyl)oxy)phenyl)propanoic acid or (3S)-3-cyclopropyl-3-(3-(((2-((1S)-2,2-dimethylcyclohexyl)-2'-fluoro-5'-(methyloxy)-1,1'-biphenyl-4-yl)methyl)oxy)phenyl)propanoic acid or (3R)-3-cyclopropyl-3-(3-(((2-((1R)-2,2-dimethylcyclohexyl)-2'-fluoro-5'-(methyloxy)-1,1'-biphenyl-4-yl)methyl)oxy)phenyl)propanoic acid or (3R)-3-cyclopropyl-3-(3-(((2-((1S)-2,2-dimethylcyclohexyl)-2'-fluoro-5'-(methyloxy)-1,1'-biphenyl-4-yl)methyl)oxy)phenyl)propanoic acid (66.21). The alkylation and hydrolysis were conducted in an analogous manner to Example 66.6 (using peak one from the chiral separation of 66.21G on the OD-column, described herein) to yield 66.21 (0.0305 g, 10% yield over two steps). MS ESI (neg.) m/e: 529.3 (M–H)$^+$.

Example 66.22

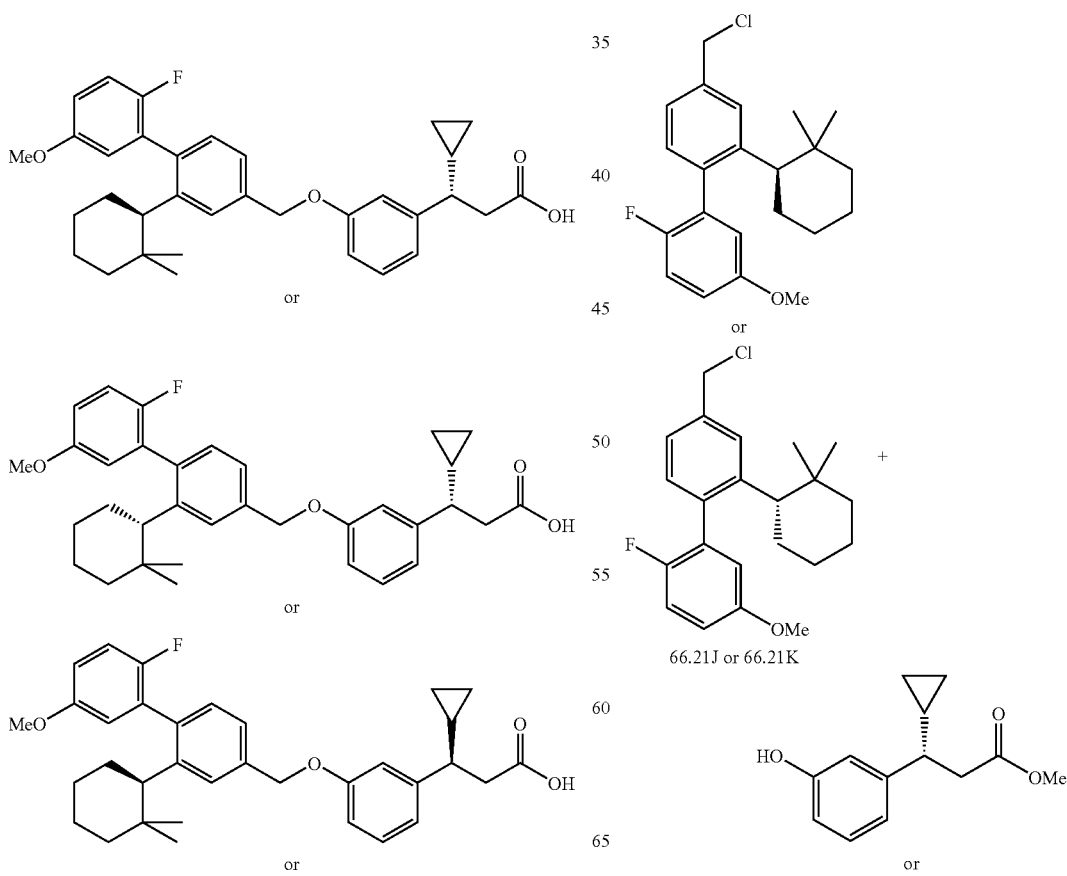

297

-continued

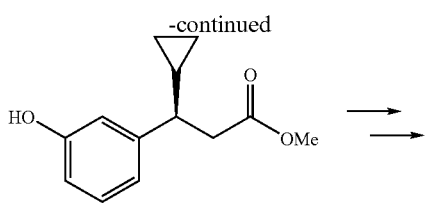

66.6X

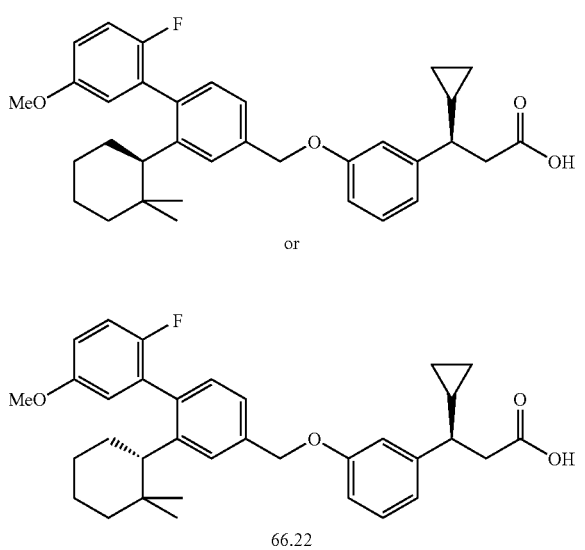

66.22

(3S)-3-Cyclopropyl-3-(3-(((2-((1R)-2,2-dimethylcyclohexyl)-2'-fluoro-5'-(methyloxy)-1,1'-biphenyl-4-yl)methyl)oxy)phenyl)propanoic acid or (3S)-3-cyclopropyl-3-(3-(((2-((1S)-2,2-dimethylcyclohexyl)-2'-fluoro-5'-(methyloxy)-1,1'-biphenyl-4-yl)methyl)oxy)phenyl)propanoic acid or (3R)-3-cyclopropyl-3-(3-(((2-((1R)-2,2-dimethylcyclohexyl)-2'-fluoro-5'-(methyloxy)-1,1'-biphenyl-4-yl)methyl)oxy)phenyl)propanoic acid or (3R)-3-cyclopropyl-3-(3-(((2-((1S)-2,2-dimethylcyclohexyl)-2'-fluoro-5'-(methyloxy)-1,1'-biphenyl-4-yl)methyl)oxy)phenyl)propanoic acid 66.22. The alkylation and hydrolysis were conducted in an analogous manner to Example 66.6 (using peak two from the chiral separation of 66.21G on the OD-column, described herein) to yield 66.22 (0.0151 g, 39% yield over two steps). MS ESI (neg.) m/e: 529.3 $(M-H)^+$.

298

Example 66.23

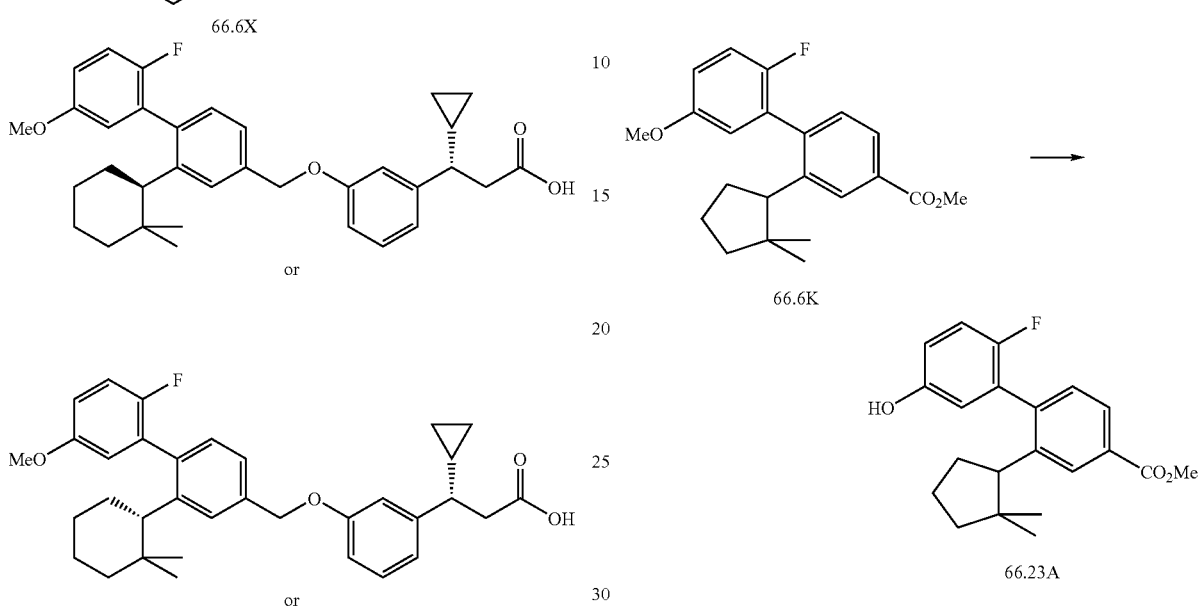

Methyl 2-(2,2-dimethylcyclopentyl)-2'-fluoro-5'-hydroxy-1,1'-biphenyl-4-carboxylate (66.23A). To a stirred solution of 66.6K (0.400 g, 1.12 mmol) in DCM (10.00 mL) at 0° C. was added boron tribromide (1.0M in DCM) (4.49 mL, 4.49 mmol). The reaction was stirred for one hour at 0° C. Water was then added, and the mixture was extracted three times with EtOAc. After drying over anhydrous magnesium sulfate and filtering, the organic solvent was removed under reduced pressure and the desired product was isolated. The initial product was dissolved in a 1/1 mixture of THF/ethanol and to this was added 1N NaOH (aq), the resulting solution was stirred for 16 hours, after which it was concentrated in vacuo. The reaction was acidified with 1N HCl and the resulting solution was extracted three times with EtOAc. After drying over anhydrous magnesium sulfate and filtering, the organic solvent was removed under reduced pressure. The resulting product was dissolved in MeOH and a drop of sulfuric acid was added. The mixture was heated at 70° C. for 16 hours. The reaction mixture was then concentrated in vacuo. The product was then purified on silica gel (0-20% EtOAc in hexanes) to yield 66.23A as a colorless oil (0.250 g, 65% yield).

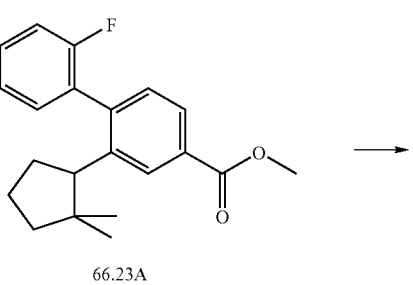

66.23A

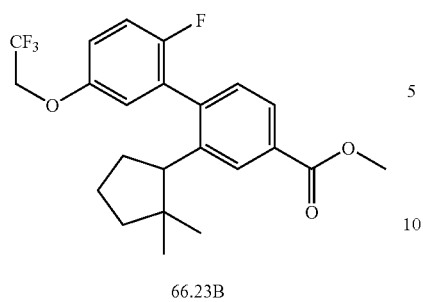

66.23B

Methyl 2-(2,2-dimethylcyclopentyl)-2'-fluoro-5'-((2,2,2-trifluoroethyl)oxy)-1,1'-biphenyl-4-carboxylate (66.23B). To a flask containing 66.23A (0.100 g, 0.29 mmol) and cesium carbonate (0.29 g, 0.88 mmol) in DMF (2 mL) was added 1,1,1-trifluoro-2-iodoethane (0.12 g, 0.58 mmol) (commercially available from Aldrich), and stirring was continued for 5 hours. The reaction was diluted with water and extracted three times with EtOAc. After drying over anhydrous magnesium sulfate and filtering, the organic solvent was removed under reduced pressure and the product was then purified on silica gel (0-10% EtOAc in hexanes) to yield 66.23B as a colorless oil (0.113 g, 91% yield).

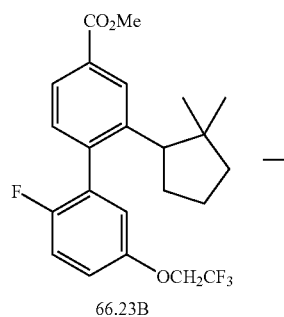

66.23B

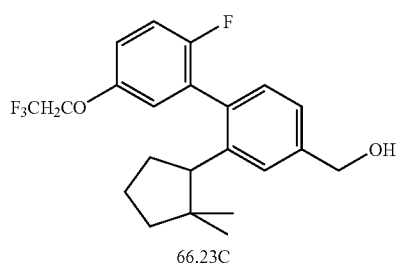

66.23C

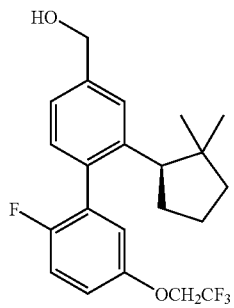

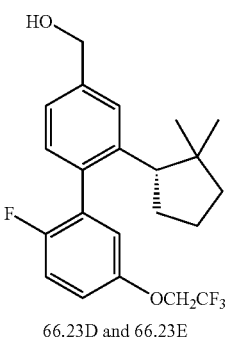

66.23D and 66.23E (2-((1R)-2,2-Dimethylcyclopentyl)-2'-fluoro-5'-((2,2,2-trifluoroethyl)oxy)-1,1'-biphenyl-4-yl)methanol and (2-((1S)-2,2-dimethylcyclopentyl)-2'-fluoro-5'-((2,2,2-trifluoroethyl)oxy)-1,1'-biphenyl-4-yl)methanol (66.23D and 66.23E). To a stirred solution of 66.23B (0.113 g, 0.3 mmol) in THF (5 mL) at 0° C. was added LAH in THF (0.5 mL, 0.5 mmol, 1.0M). The mixture was stirred for one hour and then 1N NaOH(aq) was added to quench the reaction. The reaction mixture was extracted three times with EtOAc. After drying over anhydrous magnesium sulfate and filtering, the organic solvent was removed under reduced pressure and the product was then purified on silica gel (0-20% EtOAc in hexanes) to yield 66.23C as a colorless oil (0.075 g, 71% yield). Chiral separation of 66.23C was accomplished on Chiracel-OD (3% IPA in hexane) to provide 66.23D (peak one) and 66.23E (peak two). Both enantiomers were used to synthesize example compounds, and both enantiomers gave active example compounds. However, the enantiomer corresponding to peak 2 provided the most active example compounds.[1]

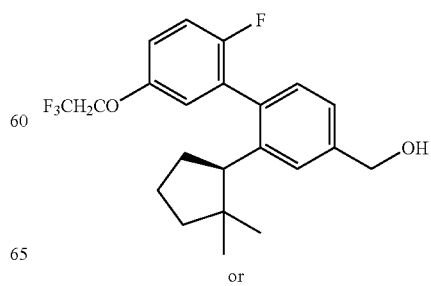

66.23C or

-continued

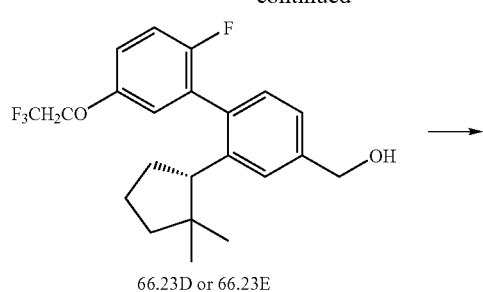
66.23D or 66.23E

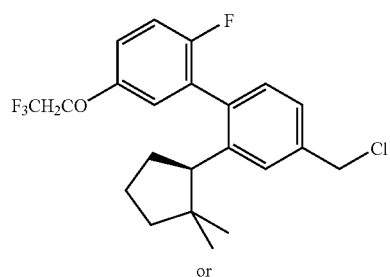
or

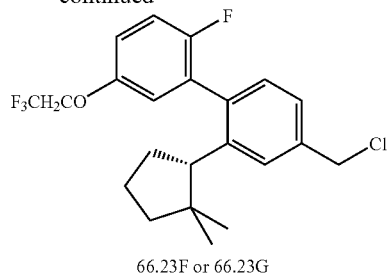
66.23F or 66.23G 4-(Chloromethyl)-2-((1R)-2,2-dimethylcyclopentyl)-2'-fluoro-5'-((2,2,2-trifluoroethyl)oxy)-1,1'-biphenyl or 4-(chloromethyl)-2-((1S)-2,2-dimethylcyclopentyl)-2'-fluoro-5'-((2,2,2-trifluoroethyl)oxy)-1,1'-biphenyl (66.23F or 66.23G). To a stirred solution of 66.23D or 66.23E (0.022 g, 0.055 mmol) in DCM (2.00 mL) at 23° C. was added DMF (0.00043 mL) followed by thionyl chloride (0.0081 mL, 0.11 mmol). The reaction was stirred for two hours and then the reaction mixture was concentrated in vacuo. The product was then purified on silica gel (0-10% EtOAc in hexanes) to yield 66.23F or 66.23G as a colorless oil (0.019 g, 83% yield).

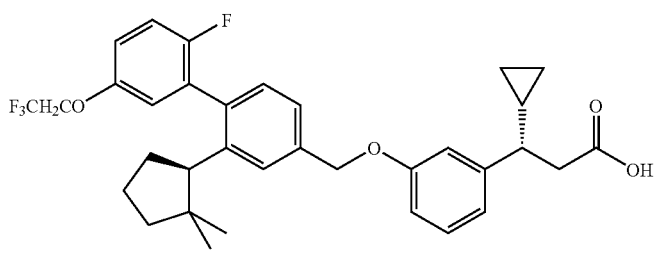
or

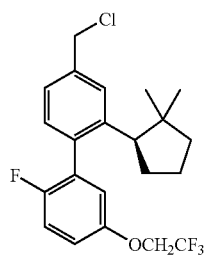
or

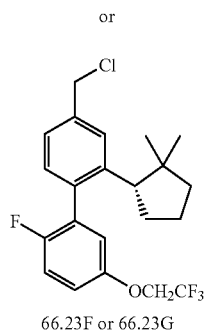
66.23F or 66.23G

+

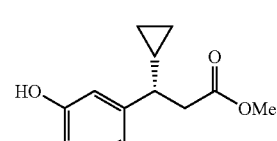
or

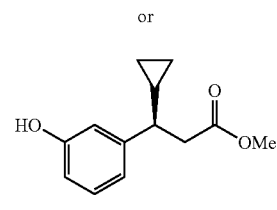
66.6X

→

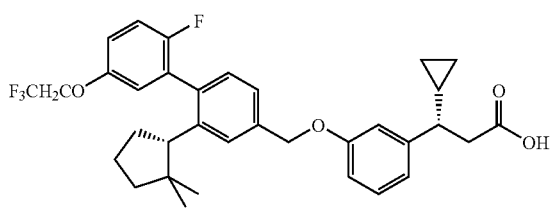
or

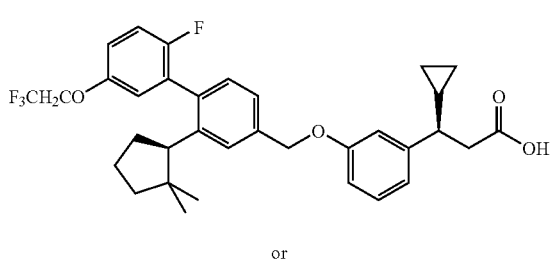
or

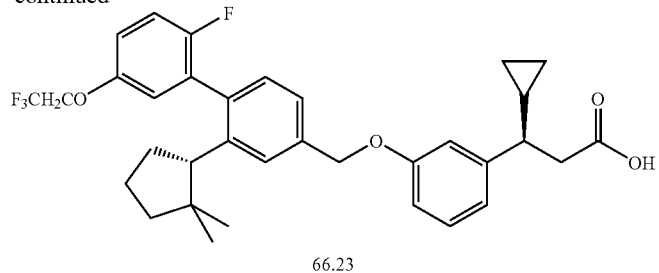

66.23

(3S)-3-Cyclopropyl-3-(3-(((2-((1R)-2,2-dimethylcyclopentyl)-2'-fluoro-5'-((2,2,2-trifluoroethyl)oxy)-1,1'-biphenyl-4-yl)methyl)oxy)phenyl)propanoic acid or (3S)-3-cyclopropyl-3-(3-(((2-((1S)-2,2-dimethylcyclopentyl)-2'-fluoro-5'-((2,2,2-trifluoroethyl)oxy)-1,1'-biphenyl-4-yl)methyl)oxy)phenyl)propanoic acid or (3R)-3-cyclopropyl-3-(3-(((2-((1R)-2,2-dimethylcyclopentyl)-2'-fluoro-5'-((2,2,2-trifluoroethyl)oxy)-1,1'-biphenyl-4-yl)methyl)oxy)phenyl)propanoic acid or (3R)-3-cyclopropyl-3-(3-(((2-((1S)-2,2-dimethylcyclopentyl)-2'-fluoro-5'-((2,2,2-trifluoroethyl) oxy)-1,1'-biphenyl-4-yl)methyl)oxy)phenyl)propanoic acid (66.23H or 66.23I). The alkylation and hydrolysis were conducted in an analogous manner to Example 66.6 (using the compound derived from peak two from the chiral separation of 66.23C on the OD-column, described herein) to yield 66.23 (0.011 g, 41% yield over two steps). MS ESI (neg.) m/e: 583.3 (M–H)+.

Example 66.24

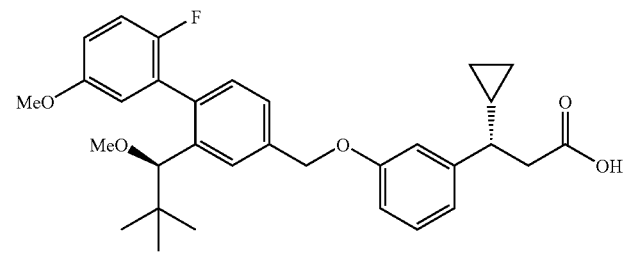

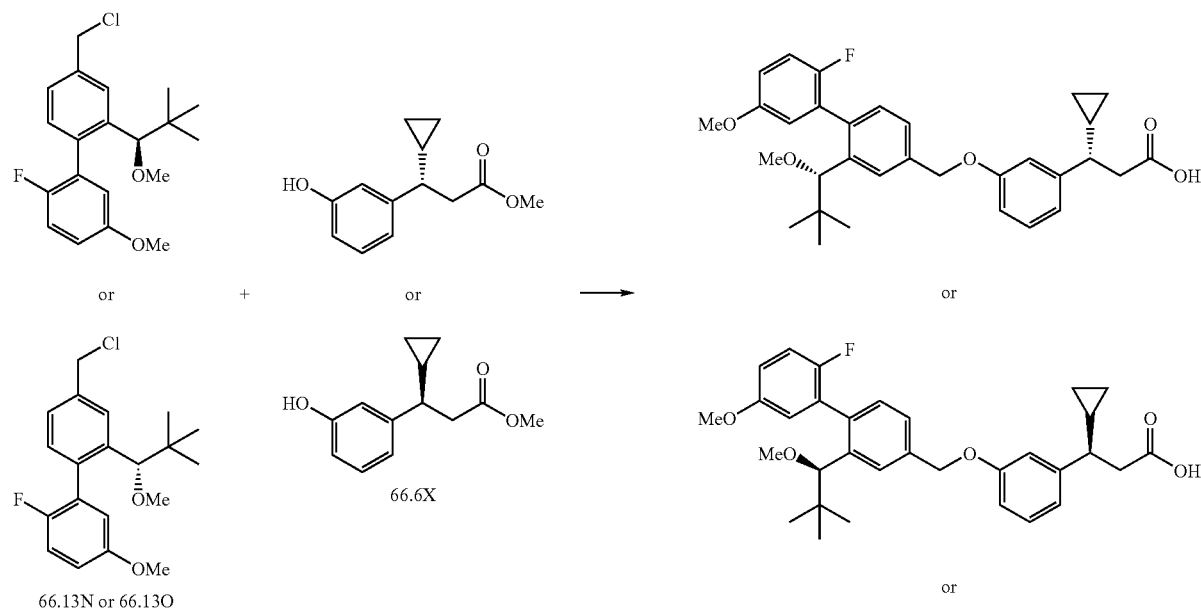

66.13N or 66.13O 66.6X

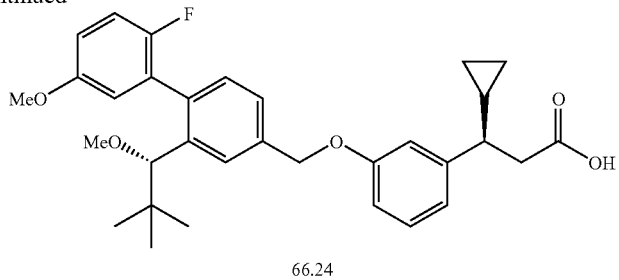

66.24

(3S)-3-Cyclopropyl-3-(3-(((2-((1R)-2,2-dimethyl-1-(methyloxy)propyl)-2'-fluoro-5'-(methyloxy)-1,1'-biphenyl-4-yl)methyl)oxy)phenyl)propanoic acid or (3S)-3-cyclopropyl-3-(3-(((2-((1S)-2,2-dimethyl-1-(methyloxy)propyl)-2'-fluoro-5'-(methyloxy)-1,1'-biphenyl-4-yl)methyl)oxy)phenyl)propanoic acid or (3R)-3-cyclopropyl-3-(3-(((2-((1R)-2,2-dimethyl-1-(methyloxy)propyl)-2'-fluoro-5'-(methyloxy)-1,1'-biphenyl-4-yl)methyl)oxy)phenyl)propanoic acid or (3R)-3-cyclopropyl-3-(3-(((2-((1S)-2,2-dimethyl-1-(methyloxy)propyl)-2'-fluoro-5'-(methyloxy)-1,1'-biphenyl-4-yl)methyl)oxy)phenyl)propanoic acid (66.24). The alkylation and hydrolysis were conducted in an analogous manner to Example 66.6 (using the chloromethyl compound derived from peak one from the chiral separation of 66.13G on the OD-column, described herein) to yield 66.24 (0.0332 g, 70% yield). MS ESI (neg.) m/e: 519.2 (M−H)+.

Example 66.25

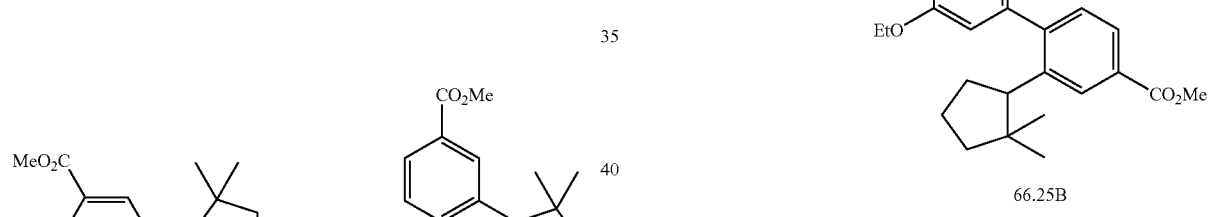

Methyl 2-(5,5-dimethyl-1-cyclopenten-1-yl)-5'-(ethyloxy)-2'-fluoro-1,1'-biphenyl-4-carboxylate (66.25A). To a stirred solution of methyl 3-(5,5-dimethylcyclopent-1-enyl)-4-(trifluoromethylsulfonyloxy)benzoate 66.6I (0.400 g, 1.1 mmol) in DMF (4.00 mL) at 23° C. was added 5-ethoxy-2-fluorophenylboronic acid (0.29 g, 1.6 mmol, commercially available from Aldrich), potassium carbonate (0.44 g, 3.2 mmol), and then tetrakis(triphenylphosphine)palladium (0.12 g, 0.11 mmol). The mixture was heated to 90° C. and stirred for 21 hours. The mixture was then cooled to room temperature, diluted with brine, and extracted three times with EtOAc. After drying over anhydrous magnesium sulfate and filtering, the organic solvent was removed under reduced pressure and the product was then purified on silica gel (0-10% EtOAc in hexanes) to yield 66.25A as a colorless oil (0.350 g, 90% yield).

Methyl 2-(2,2-dimethylcyclopentyl)-5'-(ethyloxy)-2'-fluoro-1,1'-biphenyl-4-carboxylate (66.25B). To a stirred solution of 66.25A (0.400 g, 1.09 mmol) in MeOH (10.00 mL, 1.09 mmol) at 23° C. was added palladium on carbon (0.116 g, 1.09 mmol). The reaction was placed under an atmosphere of hydrogen and stirred for 23 hours. The mixture was then filtered and concentrated in vacuo. The initial product was then purified on silica gel (0-20% EtOAc in hexanes) to yield 66.25B as a colorless oil (0.400 g, 99.5% yield).

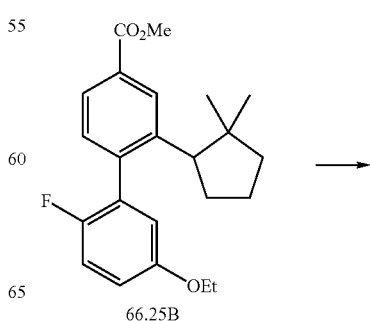

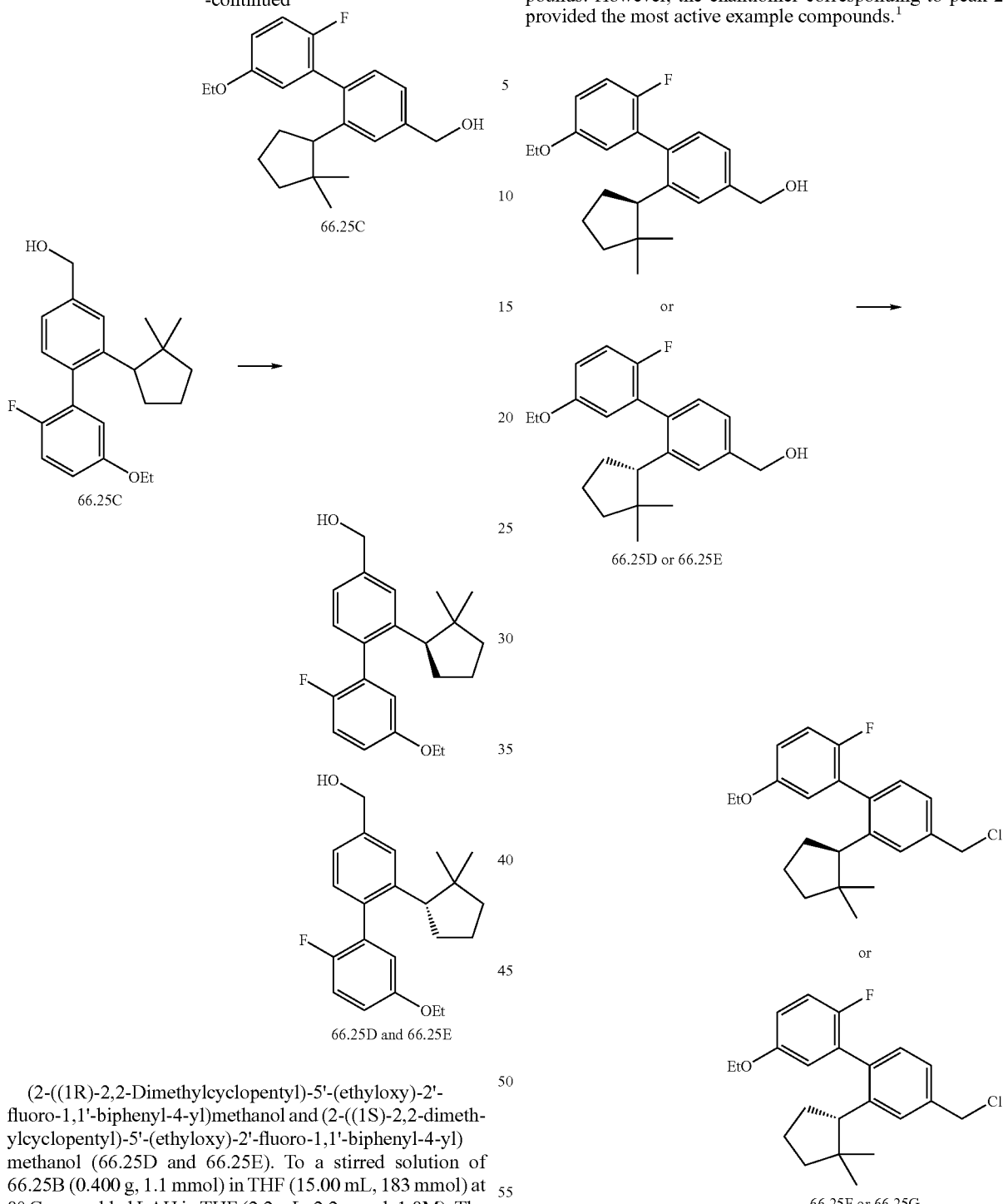

66.25C 66.25C 66.25D and 66.25E (2-((1R)-2,2-Dimethylcyclopentyl)-5'-(ethyloxy)-2'-fluoro-1,1'-biphenyl-4-yl)methanol and (2-((1S)-2,2-dimethylcyclopentyl)-5'-(ethyloxy)-2'-fluoro-1,1'-biphenyl-4-yl)methanol (66.25D and 66.25E). To a stirred solution of 66.25B (0.400 g, 1.1 mmol) in THF (15.00 mL, 183 mmol) at 0° C. was added LAH in THF (2.2 mL, 2.2 mmol, 1.0M). The mixture was stirred for one hour and then 1N NaOH(aq) was added to quench the reaction. The reaction mixture was extracted three times with EtOAc. After drying over anhydrous magnesium sulfate and filtering, the organic solvent was removed under reduced pressure and the product was then purified on silica gel (0-20% EtOAc in hexanes) to yield 66.25C as a colorless oil (0.320 g, 87% yield). Chiral separation of 66.25C was accomplished on Chiracel-OD (3% IPA in hexane) to provide 66.25D (peak one) and 66.25E (peak two). Both enantiomers were used to synthesize example compounds, and both enantiomers gave active example compounds. However, the enantiomer corresponding to peak 2 provided the most active example compounds.[1]

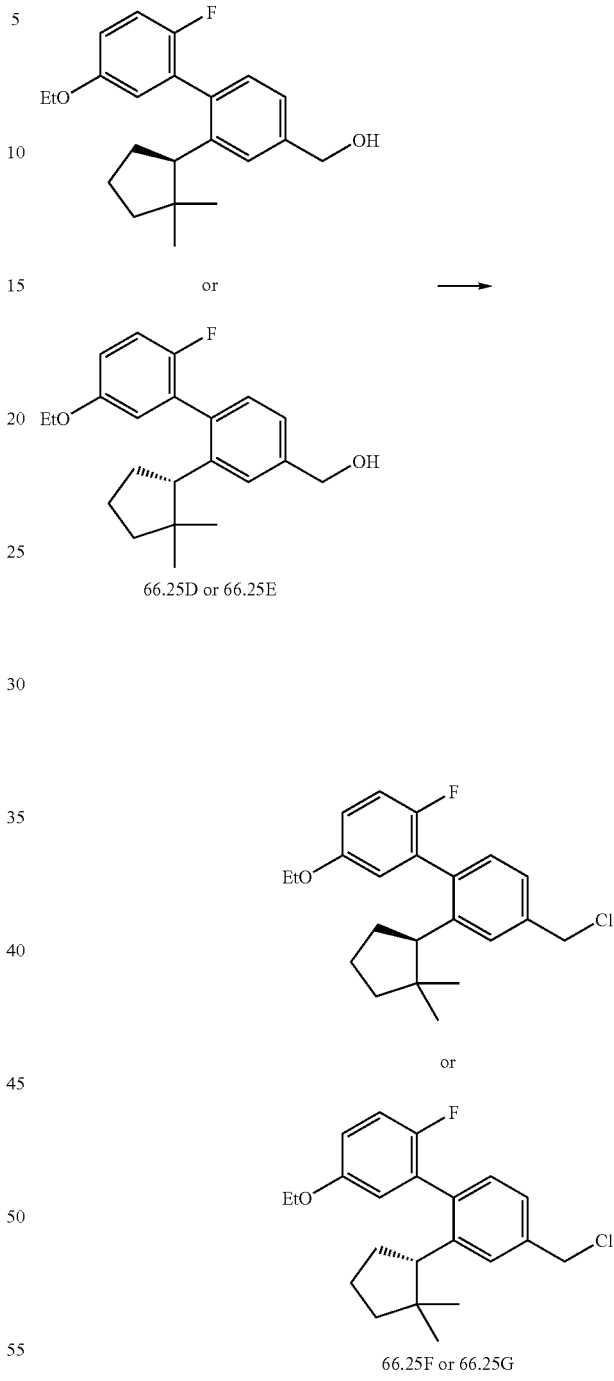

66.25D or 66.25E 66.25F or 66.25G 4-(Chloromethyl)-2-((1R)-2,2-dimethylcyclopentyl)-5'-(ethyloxy)-2'-fluoro-1,1'-biphenyl or 4-(chloromethyl)-2-((1S)-2,2-dimethylcyclopentyl)-5'-(ethyloxy)-2'-fluoro-1,1'-biphenyl (66.25F or 66.25G. To a stirred solution of 66.25C or 66.25D (0.147 g, 0.43 mmol) in DCM (2.00 mL) at 23° C. was added DMF (0.0033 mL) followed by thionyl chloride (0.063 mL, 0.86 mmol). The reaction was then stirred for 4 hours and then concentrated in vacuo. The initial product was then purified on silica gel (0-10% EtOAc in hexanes) to yield 66.25F or 66.25G as a colorless oil (0.120 g, 77% yield).

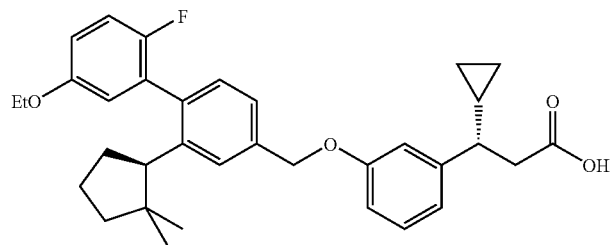

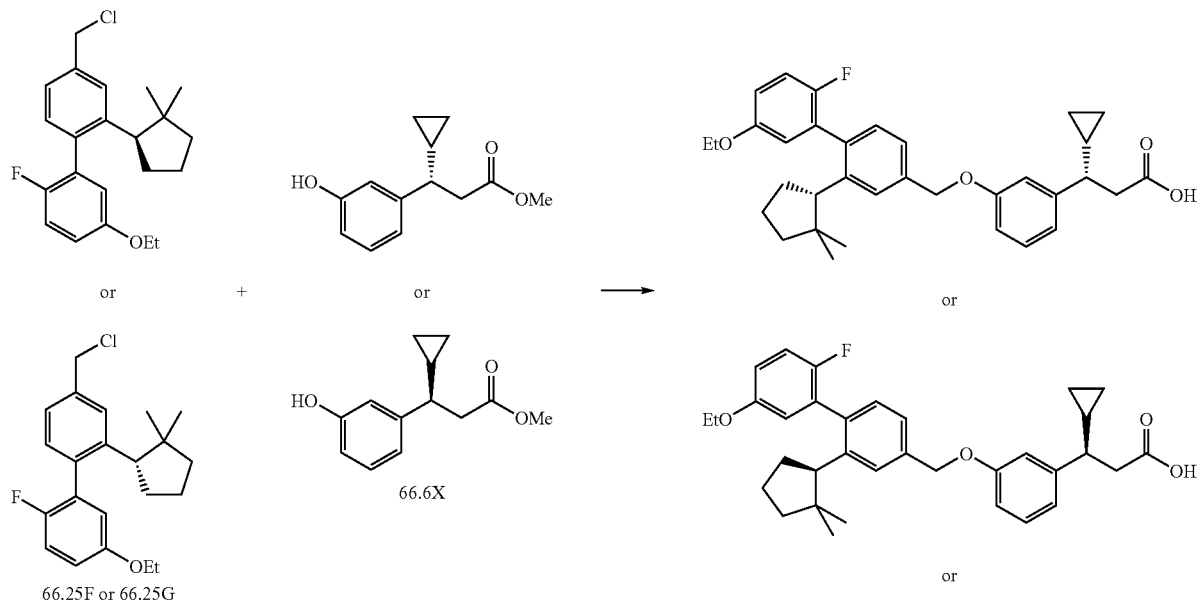

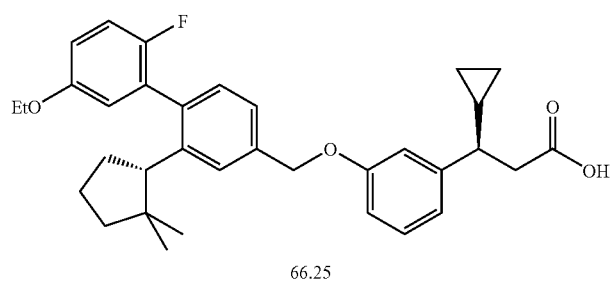

(3S)-3-Cyclopropyl-3-(3-(((2-((1R)-2,2-dimethylcyclopentyl)-5'-(ethyloxy)-2'-fluoro-1,1'-biphenyl-4-yl)methyl)oxy)phenyl)propanoic acid or (3S)-3-cyclopropyl-3-(3-(((2-((1S)-2,2-dimethylcyclopentyl)-5'-(ethyloxy)-2'-fluoro-1,1'-biphenyl-4-yl)methyl)oxy)phenyl)propanoic acid or (3R)-3-cyclopropyl-3-(3-(((2-((1R)-2,2-dimethylcyclopentyl)-5'-(ethyloxy)-2'-fluoro-1,1'-biphenyl-4-yl)methyl)oxy)phenyl) propanoic acid or (3R)-3-cyclopropyl-3-(3-(((2-((1S)-2,2-dimethylcyclopentyl)-5'-(ethyloxy)-2'-fluoro-1,1'-biphenyl-4-yl)methyl)oxy)phenyl)propanoic acid (66.25). The alkylation and hydrolysis were conducted in an analogous manner to Example 66.6 (using the chloromethyl compound derived from peak one from the chiral separation of 66.25C on the OD-column) to yield 66.25 (0.0337 g, 70% yield over two steps). MS ESI (neg.) m/e: 529.3 (M–H)$^+$.

Example 66.26
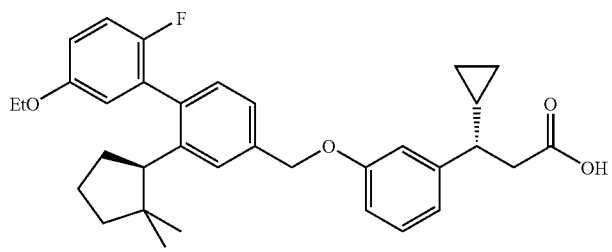
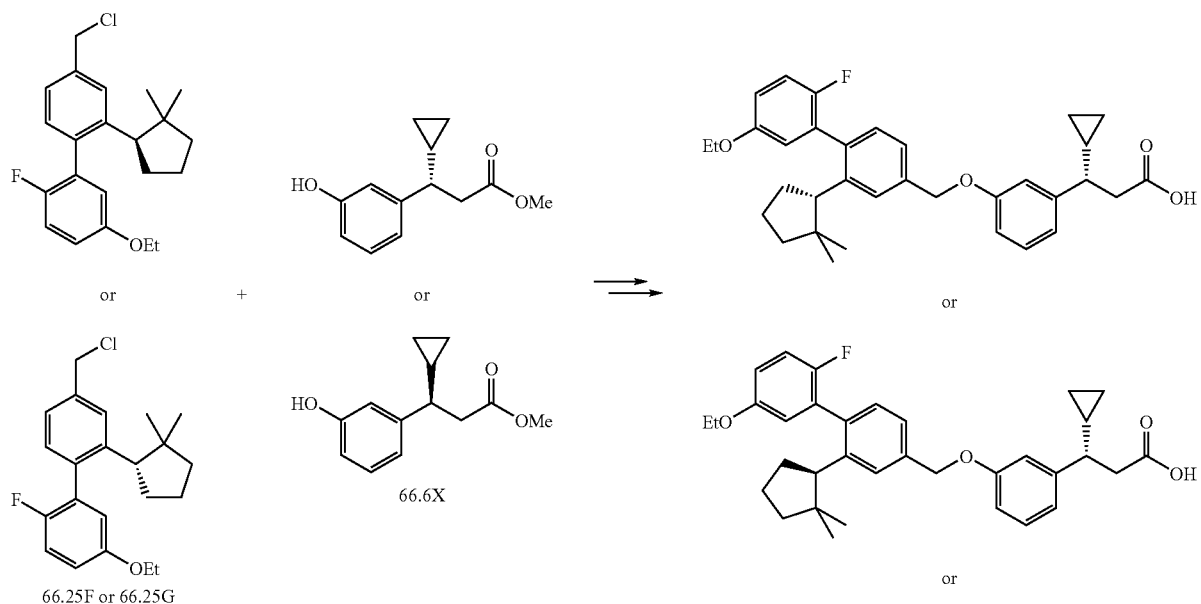
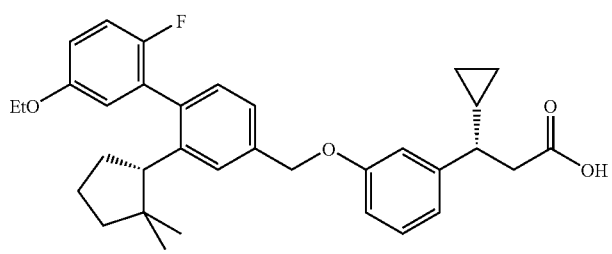
(3S)-3-Cyclopropyl-3-(3-(((2-((1R)-2,2-dimethylcyclopentyl)-5'-(ethyloxy)-2'-fluoro-1,1'-biphenyl-4-yl)methyl)oxy)phenyl)propanoic acid or (3S)-3-cyclopropyl-3-(3-(((2-((1S)-2,2-dimethylcyclopentyl)-5'-(ethyloxy)-2'-fluoro-1,1'-biphenyl-4-yl)methyl)oxy)phenyl)propanoic acid or (3R)-3-cyclopropyl-3-(3-(((2-((1R)-2,2-dimethylcyclopentyl)-5'-(ethyloxy)-2'-fluoro-1,1'-biphenyl-4-yl)methyl)oxy)phenyl)propanoic acid or (3R)-3-cyclopropyl-3-(3-(((2-((1S)-2,2- dimethylcyclopentyl)-5'-(ethyloxy)-2'-fluoro-1,1'-biphenyl-4-yl)methyl)oxy)phenyl)propanoic acid (66.26). The alkylation and hydrolysis were conducted in an analogous manner to Example 66.6 (using the chloromethyl compound derived from peak two from the chiral separation of 66.25C on the OD-column, described herein) to yield 66.26 (0.0339 g, 71% yield over two steps). MS ESI (neg.) m/e: 529.3 (M−H)+.

Example 66.27 from peak two from chiral separation of 66.13G) (0.110 g, 0.25 mmol) in DMF (2.00 mL) at 23° C. was added iodoethane (0.048 g, 0.31 mmol), followed by sodium hydride (0.0073 g, 0.31 mmol). The mixture was stirred at 60° C. for 21 hours and then cooled to room temperature. The reaction was diluted with brine and extracted three times with EtOAc. After drying over anhydrous magnesium sulfate and filtering, the organic solvent was removed under reduced pressure and the product was then purified on silica gel (0-10% EtOAc in hexanes) to yield 66.27A or 66.27B as a colorless oil (0.065 g, 55% yield).

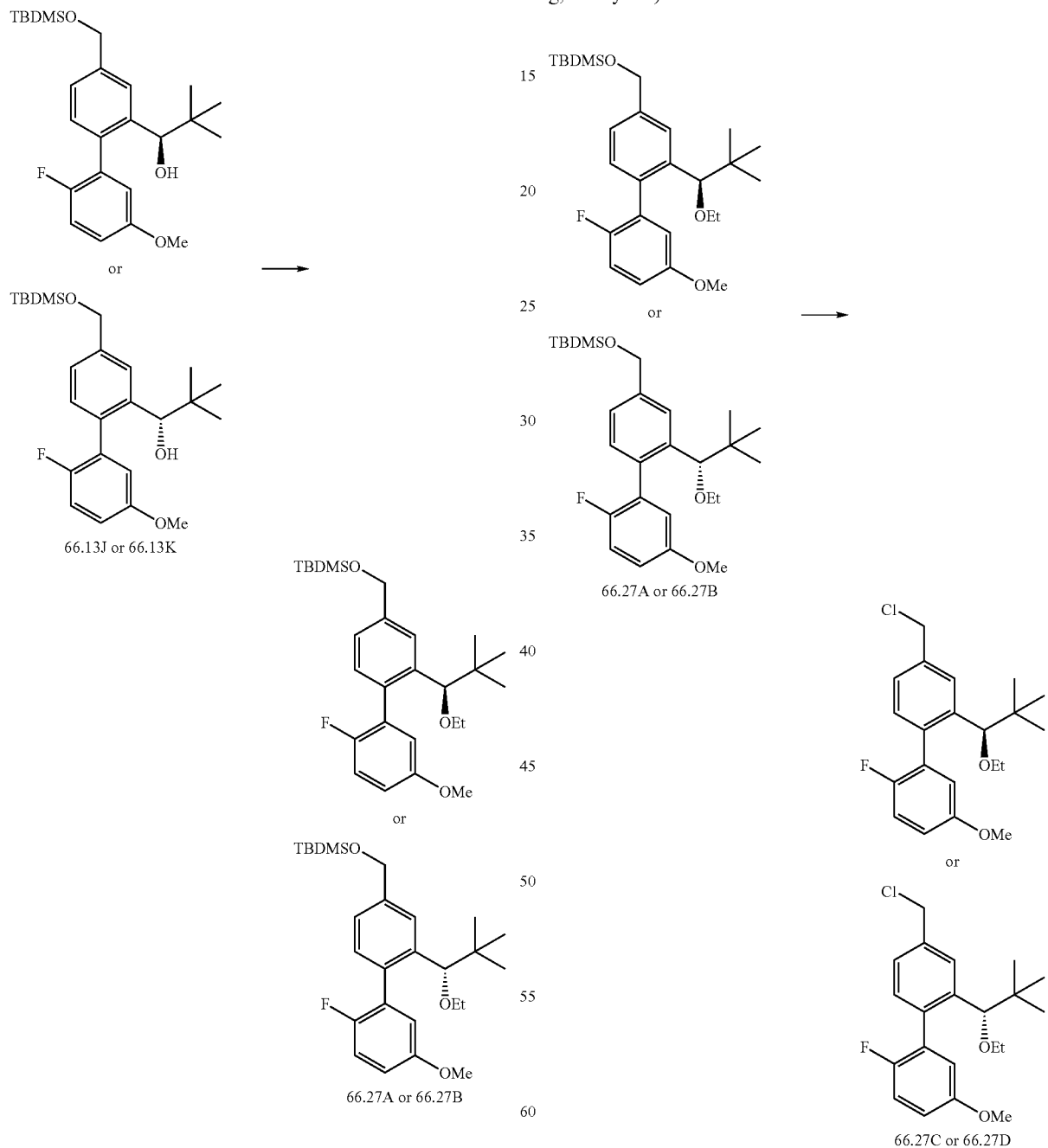

(1,1-Dimethylethyl)(((2-((1R)-1-(ethyloxy)-2,2-dimethylpropyl)-2'-fluoro-5'-(methyloxy)-1,1'-biphenyl-4-yl)methyl)oxy)dimethylsilane or (1,1-dimethylethyl)(((2-((1S)-1-(ethyloxy)-2,2-dimethylpropyl)-2'-fluoro-5'-(methyloxy)-1,1'-biphenyl-4-yl)methyl)oxy)dimethylsilane (66.27A or 66.27B). To a stirred solution of 66.13J or 66.13K (derived 4-(Chloromethyl)-2-((1R)-1-(ethyloxy)-2,2-dimethylpropyl)-2'-fluoro-5'-(methyloxy)-1,1'-biphenyl or 4-(chloromethyl)-2-((1S)-1-(ethyloxy)-2,2-dimethylpropyl)-2'-fluoro-5'-(methyloxy)-1,1'-biphenyl 66.27C or 66.27D). To a stirred solution of 66.27A or 66.27B (0.065 g, 0.1 mmol) in DCM (2.00 mL) at 23° C. was added DMF (0.001 mL) followed by thionyl chloride (0.02 mL, 0.3 mmol). The mixture was stirred for 2 hours and then concentrated in vacuo. The product was then purified on silica gel (0-10% EtOAc in hexanes) to yield 66.27C or 66.27D as a colorless oil (0.04 g, 78% yield).

yl)methyl)oxy)phenyl)propanoic acid or (3S)-3-cyclopropyl-3-(3-(((2-((1S)-1-(ethyloxy)-2,2-dimethylpropyl)-2'-fluoro-5'-(methyloxy)-1,1'-biphenyl-4-yl)methyl)oxy) phenyl)propanoic acid or (3R)-3-cyclopropyl-3-(3-(((2-((1R)-1-(ethyloxy)-2,2-dimethylpropyl)-2'-fluoro-5'-(methyloxy)-1,1'-biphenyl-4-yl)methyl)oxy)phenyl) propanoic acid or (3R)-3-cyclopropyl-3-(3-(((2-((1S)-1-

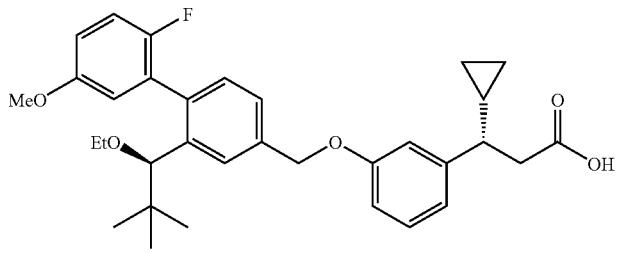

or

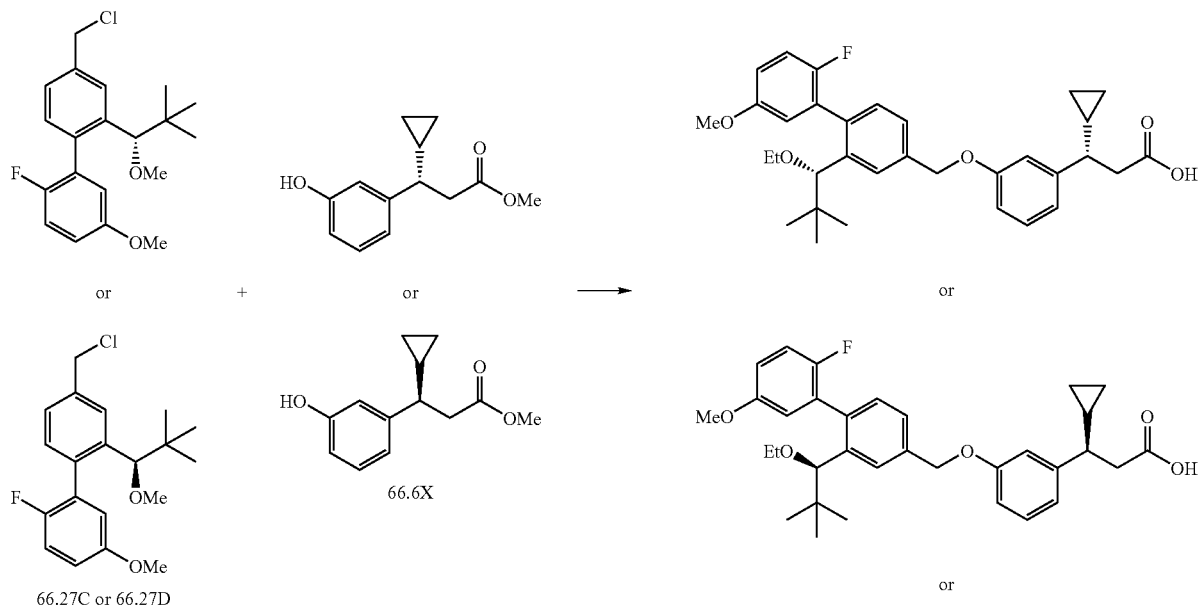

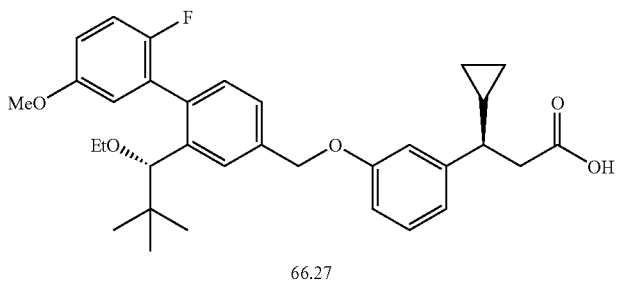

66.27

(3S)-3-Cyclopropyl-3-(3-(((2-((1R)-1-(ethyloxy)-2,2-dimethylpropyl)-2'-fluoro-5'-(methyloxy)-1,1'-biphenyl-4-

(ethyloxy)-2,2-dimethylpropyl)-2'-fluoro-5'-(methyloxy)-1, 1'-biphenyl-4-yl)methyl)oxy)phenyl)propanoic acid (66.27).

The alkylation and hydrolysis were conducted in an analogous manner to Example 66.6 (using 66.6X and the chloromethyl compound derived from peak two from the chiral separation of 66.13G from the OD-column) to yield 66.27 (0.0418 g, 69% yield over two steps). MS ESI (neg.) m/e: 529.3 (M−H)+.

Example 66.28

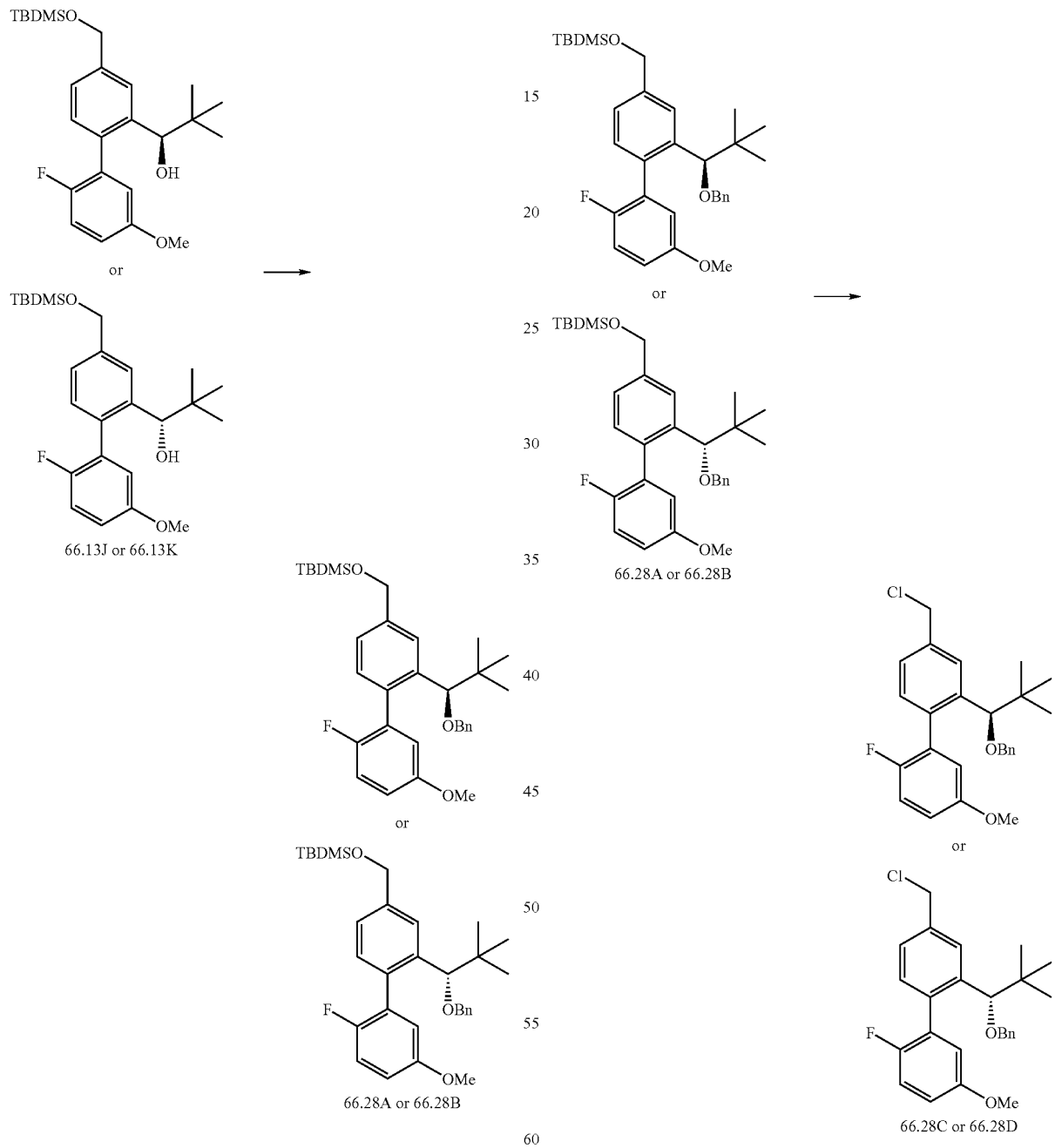

(1,1-Dimethylethyl)(((2-((1R)-2,2-dimethyl-1-((phenylmethyl)oxy)propyl)-2'-fluoro-5'-(methyloxy)-1,1'-biphenyl-4-yl)methyl)oxy)dimethylsilane or (1,1-dimethylethyl)(((2-((1S)-2,2-dimethyl-1-((phenylmethyl)oxy)propyl)-2'-fluoro-5'-(methyloxy)-1,1'-biphenyl-4-yl)methyl)oxy)dimethylsilane (66.28A or 66.28B). To a stirred solution of 66.13J or 66.13K (derived from peak two from chiral separation of 66.13G) (0.110 g, 0.25 mmol) in DMF (2.00 mL) at 23° C. was added 1-(bromomethyl)benzene (0.052 g, 0.31 mmol), followed by sodium hydride (0.0073 g, 0.31 mmol). The reaction was stirred at 60° C. for 26 hours. The reaction was then cooled to room temperature, diluted with water, and extracted three times with EtOAc. After drying over anhydrous magnesium sulfate and filtering, the organic solvent was removed under reduced pressure and the product was then purified on silica gel (0-10% EtOAc in hexanes) to yield 66.28A or 66.28B as a colorless oil (0.132 g, 99% yield).

4-(Chloromethyl)-2-((1R)-2,2-dimethyl-1-((phenylmethyl)oxy)propyl)-2'-fluoro-5'-(methyloxy)-1,1'-biphenyl or 4-(chloromethyl)-2-((1S)-2,2-dimethyl-1-((phenylmethyl)oxy)propyl)-2'-fluoro-5'-(methyloxy)-1,1'-biphenyl (66.28C or 66.28D). To a stirred solution of 66.28A or 66.28B (0.132 g, 0.3 mmol) in DCM (2.00 mL) at 23° C. was added DMF (0.002 mL) followed by thionyl chloride (0.04 mL, 0.5 mmol). The reaction was stirred for two hours and then the reaction was concentrated in vacuo. The initial product was purified on silica gel (0-10% EtOAc in hexanes) to yield 66.28C or 66.28D as a colorless oil (0.08 g, 74% yield).

biphenyl-4-yl)methyl)oxy)phenyl)propanoic acid or (3S)-3-cyclopropyl-3-(3-(((2-((1S)-2,2-dimethyl-1-((phenylmethyl)oxy)propyl)-2'-fluoro-5'-(methyloxy)-1,1'-biphenyl-4-yl)methyl)oxy)phenyl)propanoic acid or (3R)-3-cyclopropyl-3-(3-(((2-((1R)-2,2-dimethyl-1-

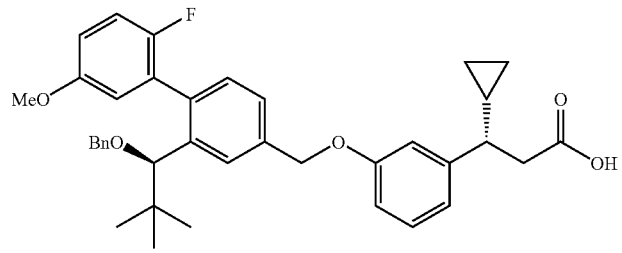

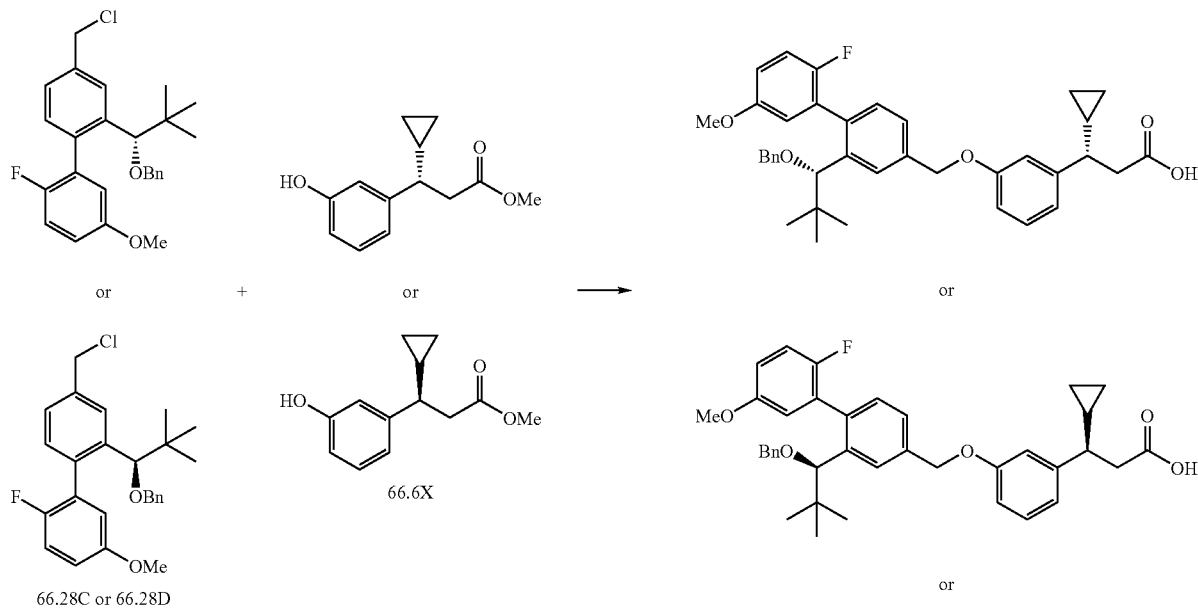

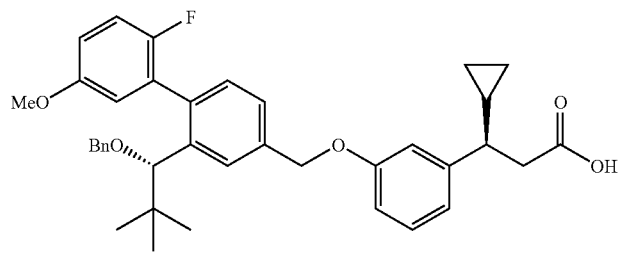

(3S)-3-Cyclopropyl-3-(3-(((2-((1R)-2,2-dimethyl-1-((phenylmethyl)oxy)propyl)-2'-fluoro-5'-(methyloxy)-1,1'-

((phenylmethyl)oxy)propyl)-2'-fluoro-5'-(methyloxy)-1,1'-biphenyl-4-yl)methyl)oxy)phenyl)propanoic acid or (3R)-3- cyclopropyl-3-(3-(((2-((1S)-2,2-dimethyl-1-((phenylmethyl)oxy)propyl)-2'-fluoro-5'-(methyloxy)-1,1'-biphenyl-4-yl)methyl)oxy)phenyl)propanoic acid (66.28). The alkylation and hydrolysis were conducted in an analogous manner to Example 66.6 (using 66.6X and the chloromethyl compound derived from peak two from chiral separation of 66.13G from the OD-column, described herein) to yield 66.28 (0.0297 g, 44% yield over two steps). MS ESI (neg.) m/e: 595.3 (M–H)+.

Example 66.29

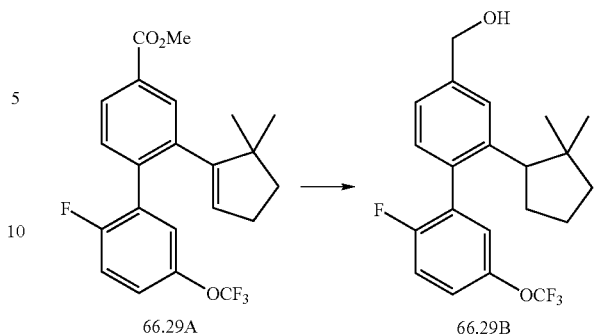

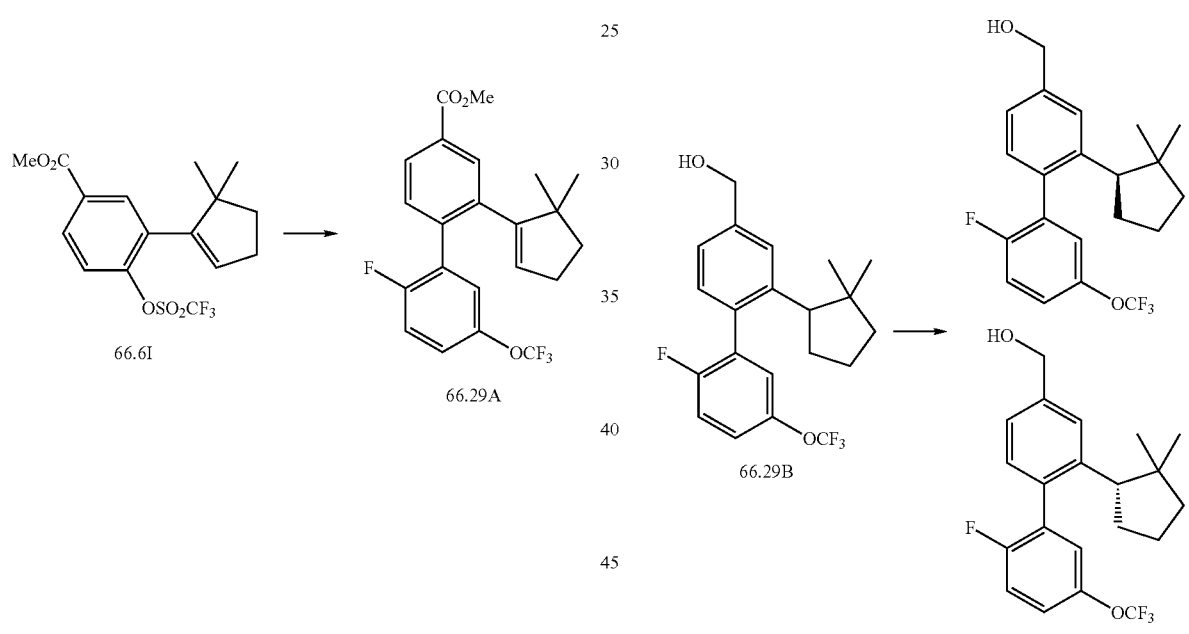

Methyl 2-(5,5-dimethyl-1-cyclopenten-1-yl)-2'-fluoro-5'-((trifluoromethyl)oxy)-1,1'-biphenyl-4-carboxylate 66.29A. To a stirred solution of methyl 3-(5,5-dimethylcyclopent-1-enyl)-4-(trifluoromethylsulfonyloxy)benzoate 66.6I (0.400 g, 1.1 mmol) in DMF (4.00 mL) at 23° C. was added 2-fluoro-5-(trifluoromethoxy)phenylboronic acid (0.36 g, 1.6 mmol, commercially available from Aldrich), potassium carbonate (0.44 g, 3.2 mmol), and then tetrakis(triphenylphosphine)palladium (0.12 g, 0.11 mmol). The mixture was heated to 90° C. and stirred for 23 hours. The reaction was then cooled to room temperature, diluted with water, and extracted three times with EtOAc. After drying over anhydrous magnesium sulfate and filtering, the organic solvent was removed under reduced pressure and the product was then purified on silica gel (0-10% EtOAc in hexanes) to yield 66.29A as a colorless oil (0.400 g, 93% yield).

(2-((1R)-2,2-Dimethylcyclopentyl)-2'-fluoro-5'-((trifluoromethyl)oxy)-1,1'-biphenyl-4-yl)methanol and (2-((1S)-2,2-dimethylcyclopentyl)-2'-fluoro-5'-((trifluoromethyl)oxy)-1,1'-biphenyl-4-yl)methanol (66.29C and 66.29D). To a stirred solution of 66.29A (0.325 g, 1.09 mmol) in MeOH (10.00 mL) at 23° C. was added palladium on carbon (0.116 g, 1.09 mmol). The reaction was placed under an atmosphere of hydrogen and stirred for 23 hours. The reaction mixture was then filtered and concentrated in vacuo. The product thus obtained was used without further purification. To a stirred solution of the product (0.325 g, 0.79 mmol) in THF (15.00 mL, 183 mmol) at 0° C. was added LAH in THF (1.6 mL, 1.6 mmol, 1.0M) and the mixture was stirred for two hours. 1N NaOH(aq) was added to quench the reaction, and the quenched mixture was extracted three times with EtOAc. After drying over anhydrous magnesium sulfate and filtering, the organic solvent was removed under reduced pressure and the product was then purified on silica gel (0-20% EtOAc in hexanes) to yield 66.29B as a colorless oil (0.270 g, 89% yield). Chiral separation of 66.29B was accomplished on Chiracel-OD (3% IPA in hexane) to provide 66.29C and 66.29D. Both enantiomers were used to synthesize example compounds, and both enantiomers gave active example compounds. However, the enantiomer corresponding to peak 2 provided the most active example compounds.[1]

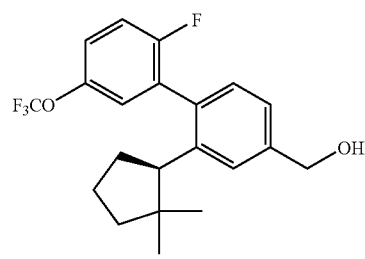

or

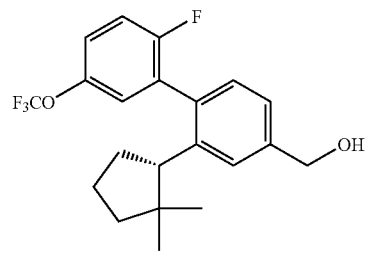

66.29C or 66.29D

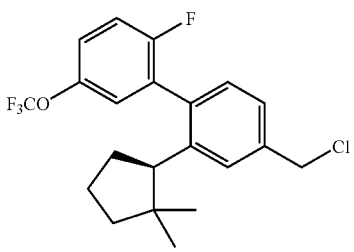

or

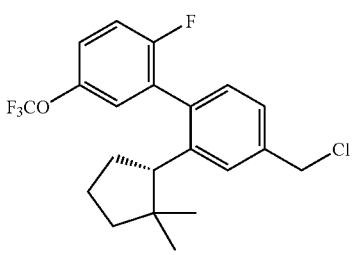

66.29E or 66.29F 4-(Chloromethyl)-2-((1R)-2,2-dimethylcyclopentyl)-2'-fluoro-5'-((trifluoromethyl)oxy)-1,1'-biphenyl or 4-(chloromethyl)-2-((1S)-2,2-dimethylcyclopentyl)-2'-fluoro-5'-((trifluoromethyl)oxy)-1,1'-biphenyl (66.29E or 66.29F). To a stirred solution of 66.29C or 66.29D (0.086 g, 0.22 mmol) in DCM (2.00 mL) at 23° C. was added DMF (0.0017 mL) followed by thionyl chloride (0.033 mL, 0.45 mmol). The reaction was stirred for 2 hours and then concentrated in vacuo. The product was then purified on silica gel (0-10% EtOAc in hexanes) to yield 66.29E or 66.29F as a colorless oil (0.085 g, 94% yield).

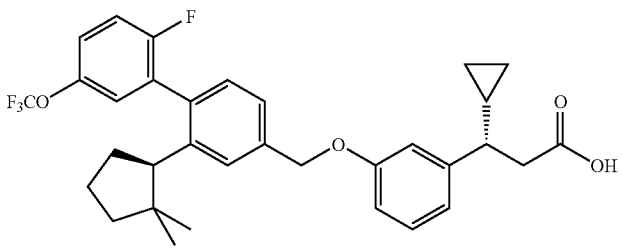

or

-continued

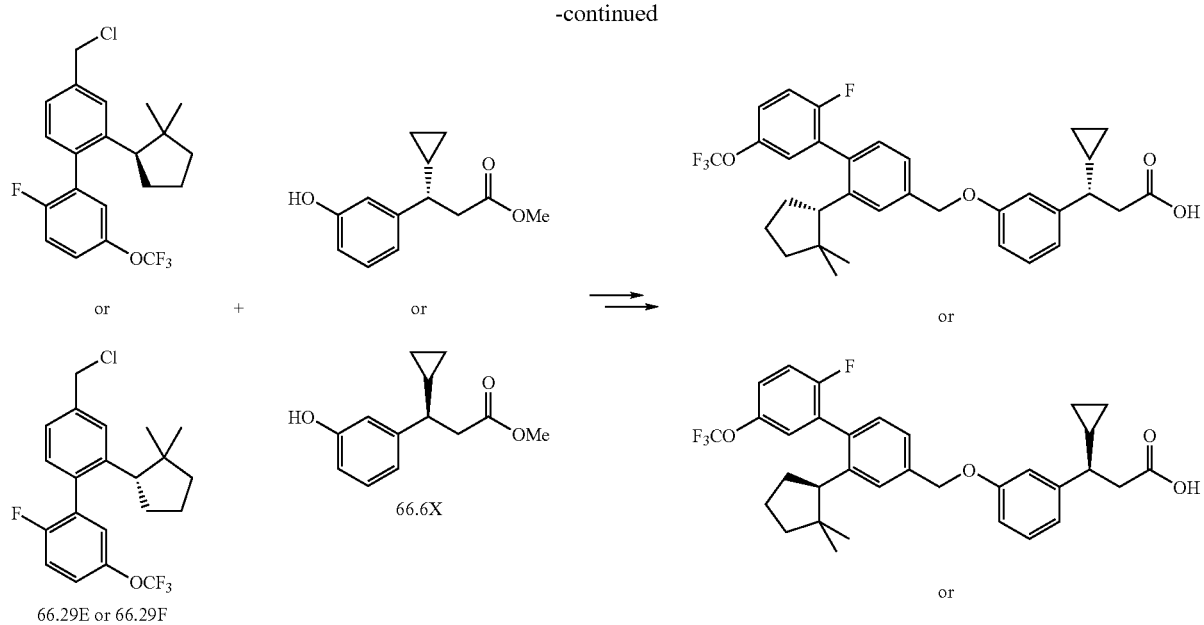

(3S)-3-Cyclopropyl-3-(3-(((2-((1R)-2,2-dimethylcyclopentyl)-2'-fluoro-5'-((trifluoromethyl)oxy)-1,1'-biphenyl-4-yl)methyl)oxy)phenyl)propanoic acid or (3S)-3-cyclopropyl-3-(3-(((2-((1S)-2,2-dimethylcyclopentyl)-2'-fluoro-5'-((trifluoromethyl)oxy)-1,1'-biphenyl-4-yl)methyl)oxy)phenyl)propanoic acid or (3R)-3-cyclopropyl-3-(3-(((2-((1R)-2,2-dimethylcyclopentyl)-2'-fluoro-5'-((trifluoromethyl)oxy)-1,1'-biphenyl-4-yl)methyl)oxy)phenyl)propanoic acid or (3R)-3-cyclopropyl-3-(3-(((2-((1S)-2,2-dimethylcyclopentyl)-2'-fluoro-5'-((trifluoromethyl)oxy)-1,1'-biphenyl-4-yl)methyl)oxy)phenyl)propanoic acid (66.29). The alkylation and hydrolysis were conducted in an analogous manner to Example 66.6 (using 66.6X and the chloromethyl compound derived from peak two from the chiral separation of 66.29B from the OD-column, described herein) to yield 66.29 (0.0483 g, 75% yield over two steps). MS ESI (neg.) m/e: 569.2 (M−H)+.

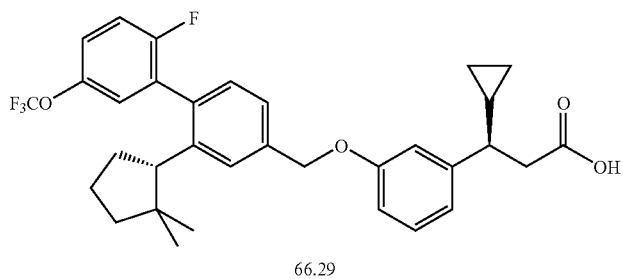

Example 66.30

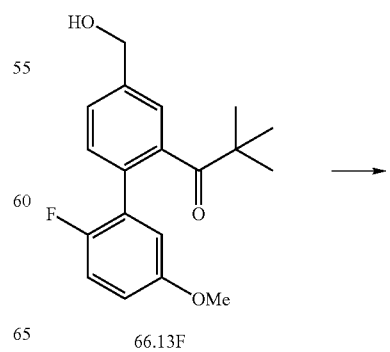

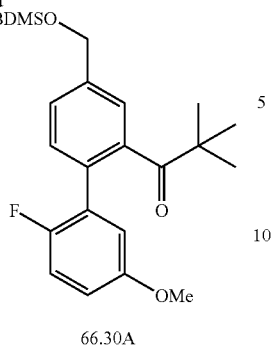

66.30A

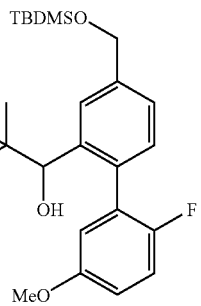

66.30B 1-(4-((((1,1-Dimethylethyl)(dimethyl)silyl)oxy)methyl)-2'-fluoro-5'-(methyloxy)-1,1'-biphenyl-2-yl)-2,2-dimethyl-1-propanone (66.30A). To a stirred solution of 66.13F (1.00 g, 3 mmol) in DCM (10.00 mL) at 23° C. was added tert-butyldimethylsilyl chloride (0.6 mL, 4 mmol), followed by TEA (0.5 mL, 4 mmol) and DMAP (0.04 g, 0.3 mmol). The reaction was stirred for 16 hours and then the reaction was concentrated in vacuo. The product was purified on silica gel (0-10% EtOAc in hexanes) to yield 66.30A as a colorless oil (1.30 g, 96% yield).

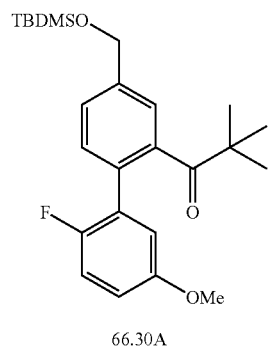

66.30A

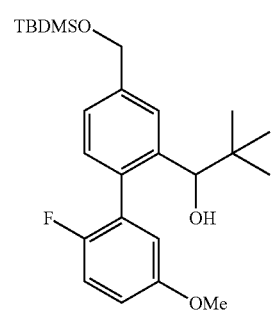

66.30B 1-(4-((((1,1-Dimethylethyl)(dimethyl)silyl)oxy)methyl)-2'-fluoro-5'-(methyloxy)-1,1'-biphenyl-2-yl)-2,2-dimethyl-1-propanol (66.30B). To a stirred solution of 66.30A (0.500 g, 1.2 mmol) in THF (15.00 mL, 183 mmol) at 0° C. was added LAH in THF (2.3 mL, 2.3 mmol, 1.0M). The reaction was stirred for two hours. 1N NaOH(aq) was added to quench the reaction mixture, and the reaction was then extracted three times with EtOAc. After drying over anhydrous magnesium sulfate and filtering, the organic solvent was removed under reduced pressure and the product was then purified on silica gel (0-10% EtOAc in hexanes) to yield 66.30B as a colorless oil (0.400 g, 80% yield).

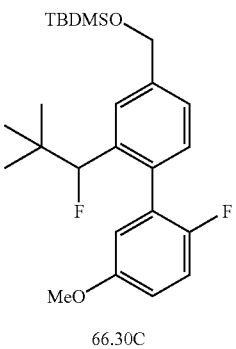

66.30C (1,1-Dimethylethyl)(((2'-fluoro-2-(1-fluoro-2,2-dimethylpropyl)-5'-(methyloxy)-1,1'-biphenyl-4-yl)methyl)oxy)dimethylsilane (66.30C). To a solution of 66.30B (0.400 g, 0.925 mmol) in toluene (10 mL) at −78° C. was added DAST (0.209 g, 1.29 mmol) dropwise. The reaction was stirred at −78° C. for 30 minutes and then warmed to 23° C. and stirred for an additional 2 hours. Water was added to quench the reaction mixture. The reaction was then extracted three times with EtOAc. After drying over anhydrous magnesium sulfate and filtering, the organic solvent was removed under reduced pressure and the product was then purified on silica gel (0-10% EtOAc in hexanes) to yield 66.30C as a colorless oil (0.400 g, 99% yield).

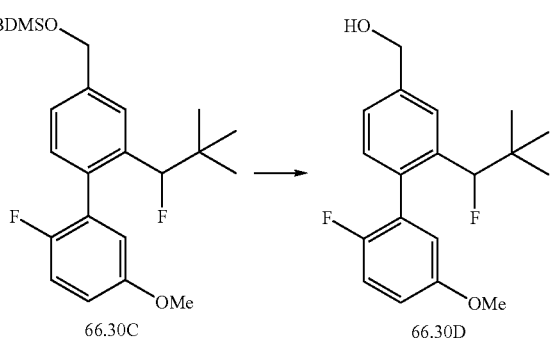

66.30C      66.30D

-continued

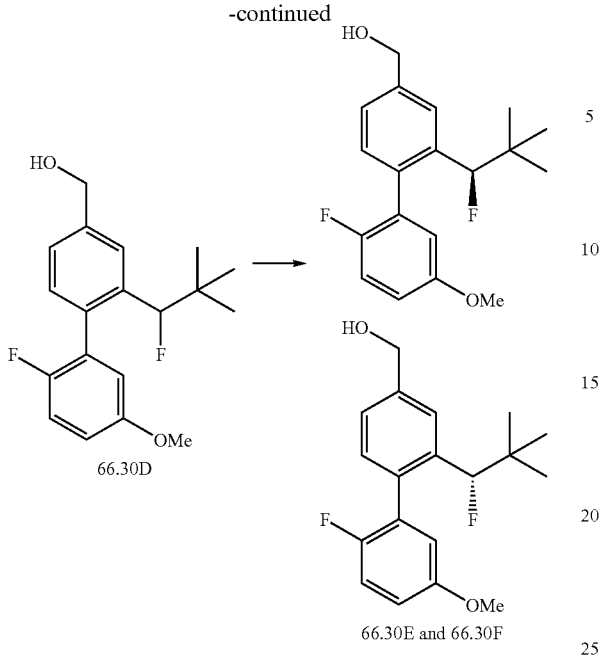

66.30D 66.30E and 66.30F (2'-Fluoro-2-((1R)-1-fluoro-2,2-dimethylpropyl)-5'-(methyloxy)-1,1'-biphenyl-4-yl)methanol and (2'-fluoro-2-((1S)-1-fluoro-2,2-dimethylpropyl)-5'-(methyloxy)-1,1'-biphenyl-4-yl)methanol (66.30E and 66.30F). To a stirred solution of 66.30C (0.400 g, 0.920 mmol) in MeOH (10.00 mL) at 23° C. was added PPTS (0.0231 g, 0.0920 mmol). The reaction was stirred for 19 hours and then concentrated in vacuo to give a clear oil. The product was then purified on silica gel (0-20% EtOAc in hexanes) to yield 66.30D as a colorless oil (0.272 g, 92% yield). Chiral separation of 66.30D was accomplished on Chiracel-OD (3% IPA in hexane) to provide 66.30E and 66.30F. Both enantiomers were used to synthesize example compounds, and both enantiomers gave active example compounds. However, the enantiomer corresponding to peak 2 provided the most active example compounds.

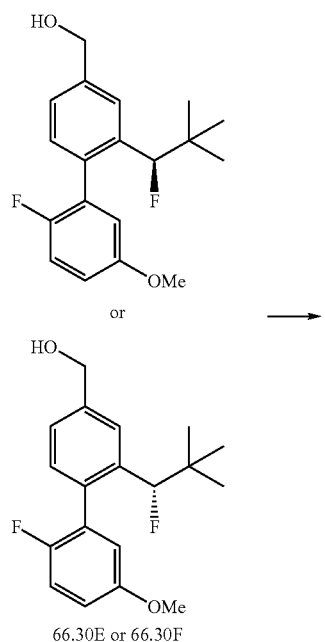

66.30E or 66.30F

-continued

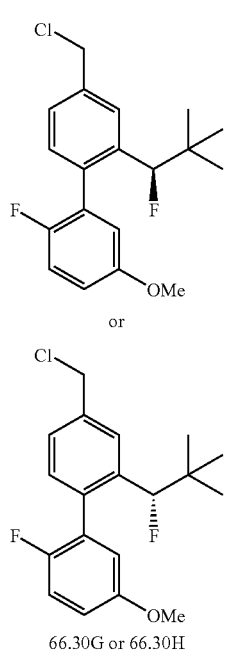

66.30G or 66.30H 4-(Chloromethyl)-2'-fluoro-2-((1R)-1-fluoro-2,2-dimethylpropyl)-5'-(methyloxy)-1,1'-biphenyl or 4-(chloromethyl)-2'-fluoro-2-((1R)-1-fluoro-2,2-dimethylpropyl)-5'-(methyloxy)-1,1'-biphenyl (66.30G or 66.30H). To a stirred solution of 66.30E or 66.30F (0.102 g, 0.3 mmol) in DCM (2.00 mL) at 23° C. was added DMF (0.002 mL) followed by thionyl chloride (0.05 mL, 0.6 mmol). The reaction was stirred for 1.5 hours. The reaction was concentrated in vacuo. The product was then purified on silica gel (0-10% EtOAc in hexanes) to yield 66.30G or 66.30H as a colorless oil (0.09 g, 83% yield).

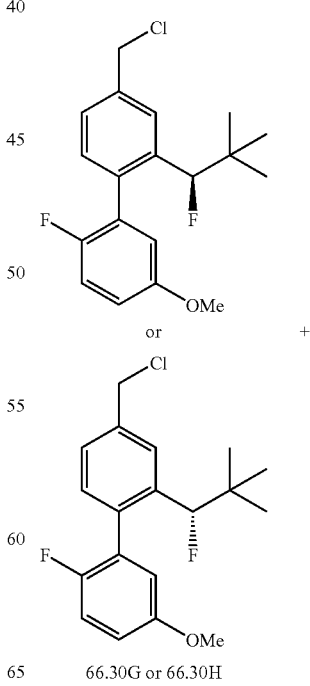

66.30G or 66.30H

331

-continued

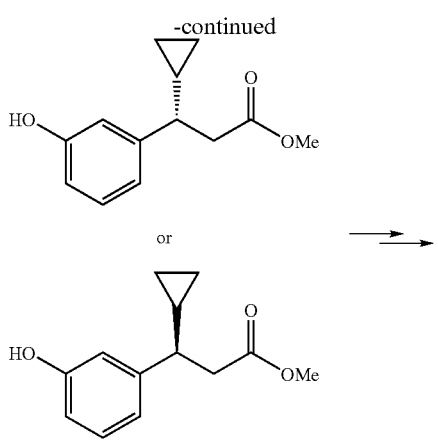

66.6X

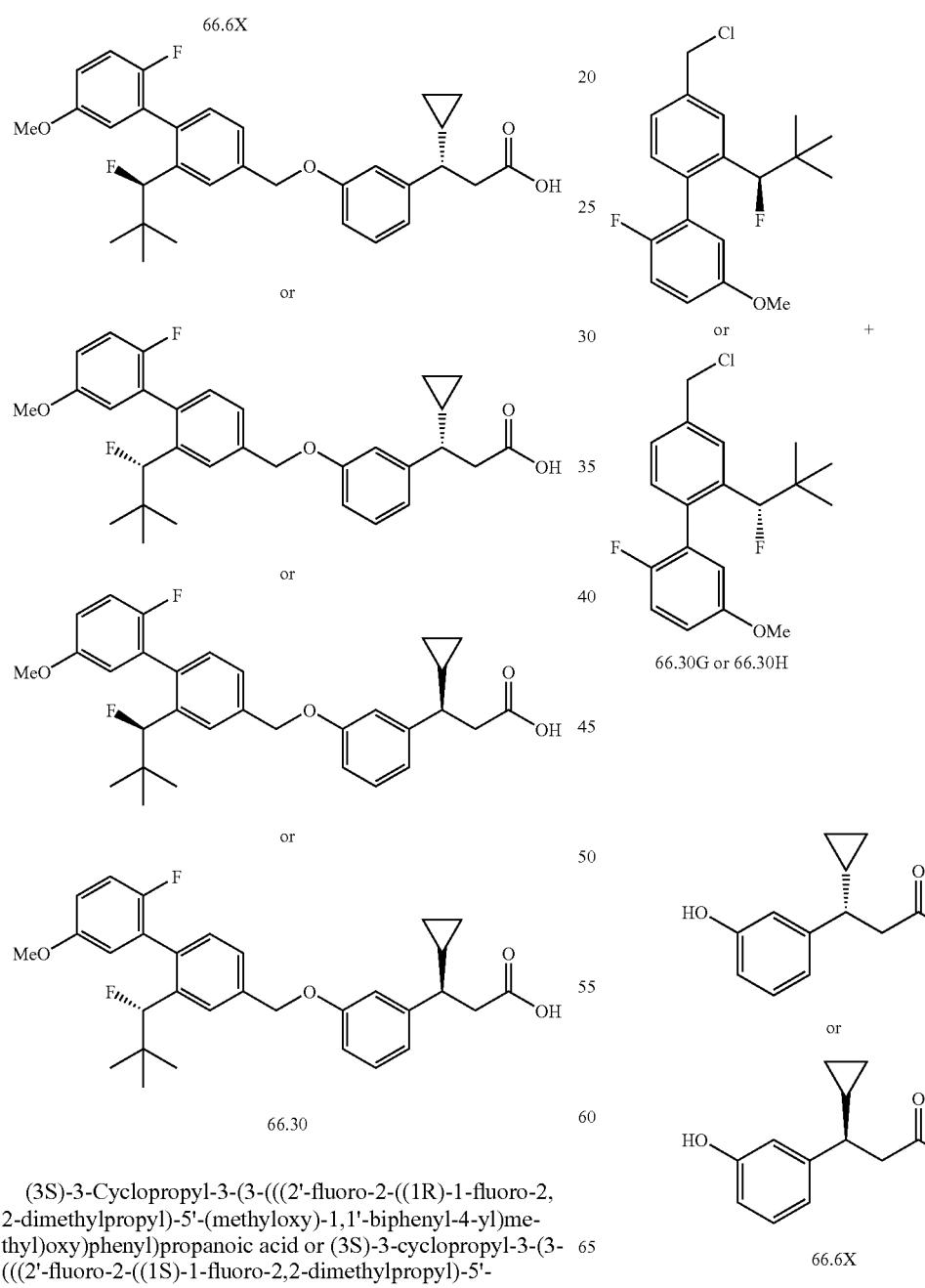

66.30

(3S)-3-Cyclopropyl-3-(3-(((2'-fluoro-2-((1R)-1-fluoro-2,2-dimethylpropyl)-5'-(methyloxy)-1,1'-biphenyl-4-yl)methyl)oxy)phenyl)propanoic acid or (3S)-3-cyclopropyl-3-(3-(((2'-fluoro-2-((1S)-1-fluoro-2,2-dimethylpropyl)-5'-(methyloxy)-1,1'-biphenyl-4-yl)methyl)oxy)phenyl)

332 propanoic acid or (3R)-3-cyclopropyl-3-(3-(((2'-fluoro-2-((1R)-1-fluoro-2,2-dimethylpropyl)-5'-(methyloxy)-1,1'-biphenyl-4-yl)methyl)oxy)phenyl)propanoic acid or (3R)-3-cyclopropyl-3-(3-(((2'-fluoro-2-((1S)-1-fluoro-2,2-dimethylpropyl)-5'-(methyloxy)-1,1'-biphenyl-4-yl)methyl)oxy)phenyl)propanoic acid (66.30). The alkylation and hydrolysis were conducted in an analogous manner to Example 66.6 (using 66.6X and the chloromethyl compound derived from peak one from chiral separation of 66.30D from the OD-column, described herein) to yield 66.30 (0.0467 g, 80% yield over two steps). MS ESI (neg.) m/e: 507.2 (M–H)$^+$.

Example 66.31

-continued

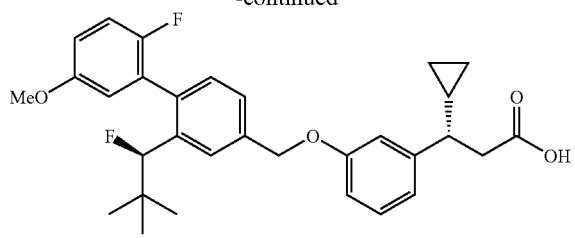

or

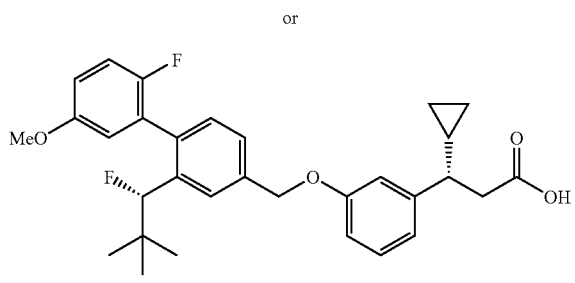

or

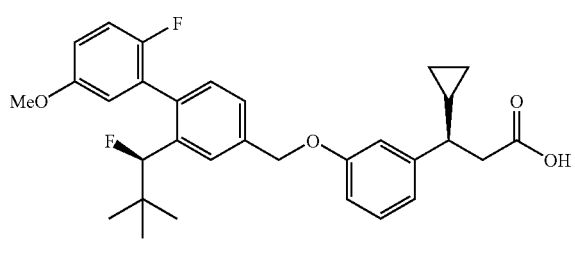

or

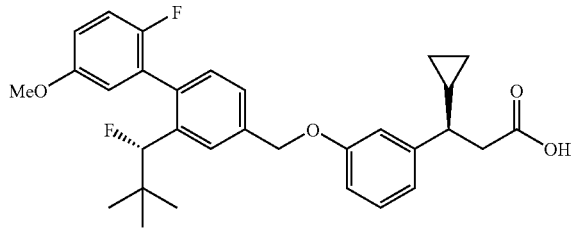

66.31

(3S)-3-Cyclopropyl-3-(3-(((2'-fluoro-2-((1R)-1-fluoro-2,2-dimethylpropyl)-5'-(methyloxy)-1,1'-biphenyl-4-yl)methyl)oxy)phenyl)propanoic acid or (3S)-3-cyclopropyl-3-(3-(((2'-fluoro-2-((1S)-1-fluoro-2,2-dimethylpropyl)-5'-(methyloxy)-1,1'-biphenyl-4-yl)methyl)oxy)phenyl)propanoic acid or (3R)-3-cyclopropyl-3-(3-(((2'-fluoro-2-((1R)-1-fluoro-2,2-dimethylpropyl)-5'-(methyloxy)-1,1'-biphenyl-4-yl)methyl)oxy)phenyl)propanoic acid or (3R)-3-cyclopropyl-3-(3-(((2'-fluoro-2-((1S)-1-fluoro-2,2-dimethylpropyl)-5'-(methyloxy)-1,1'-biphenyl-4-yl)methyl)oxy)phenyl)propanoic acid (66.31). The alkylation and hydrolysis were conducted in an analogous manner to Example 66.6 (using 66.6X and the chloromethyl compound derived from peak two from the chiral separation of 66.30D from the OD-column, described herein) to yield 66.31 (0.059 g, 85% yield over two steps). MS ESI (neg.) m/e: 507.2 (M−H)+.

Example 66.32

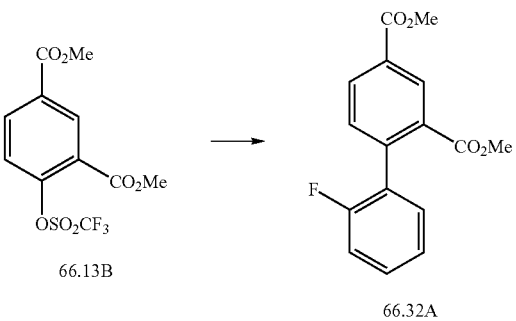

Dimethyl 2'-fluoro-1,1'-biphenyl-2,4-dicarboxylate (66.32A). To a stirred solution of dimethyl 4-(trifluoromethylsulfonyloxy)isophthalate 66.13B (1.60 g, 4.7 mmol) in DMF (9.4 mL, 4.7 mmol) at 23° C. was added 2-fluorophenylboronic acid (0.98 g, 7.0 mmol, commercially available from Aldrich), potassium carbonate (1.9 g, 14 mmol), and then tetrakis(triphenylphosphine)palladium (0.54 g, 0.47 mmol). The reaction mixture was heated to 90° C. and the reaction was stirred for 22 hours. The reaction was then cooled to room temperature, diluted with water, and extracted three times with EtOAc. After drying over anhydrous magnesium sulfate and filtering, the organic solvent was removed under reduced pressure and the product was then purified on silica gel (0-10% EtOAc in hexanes) to yield 66.32A as a colorless oil (1.10 g, 82% yield).

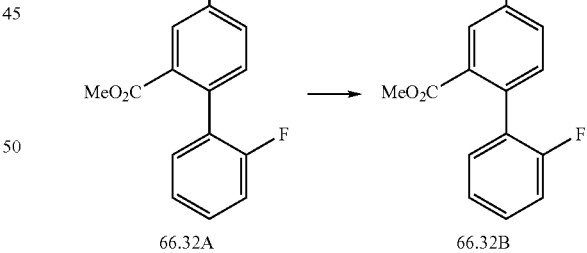

2'-Fluoro-2-((methyloxy)carbonyl)-1,1'-biphenyl-4-carboxylic acid (66.32B). To a stirred solution of 66.32A (1.00 g, 3.5 mmol) in THF (70.0 mL) and MeOH (70.0 mL) at 0° C. was slowly added potassium hydroxide (1.9 mL, 3.8 mmol) to maintain the temperature below 6° C. The reaction mixture was allowed to warm to room temperature and stirred for 48 hours. The reaction mixture was then concentrated in vacuo, acidified with 1N HCl, and extracted three times with EtOAc. After drying over anhydrous magnesium sulfate and filtering, the organic solvent was removed under reduced pressure and to give a white solid 66.32B (0.90 g, 95% yield).

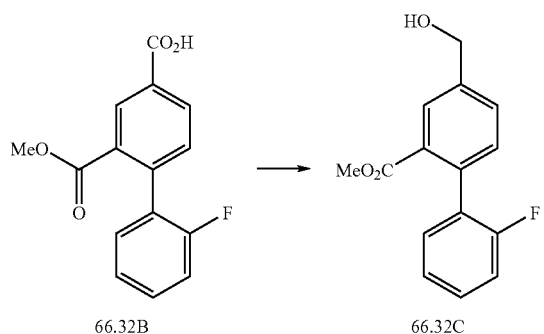

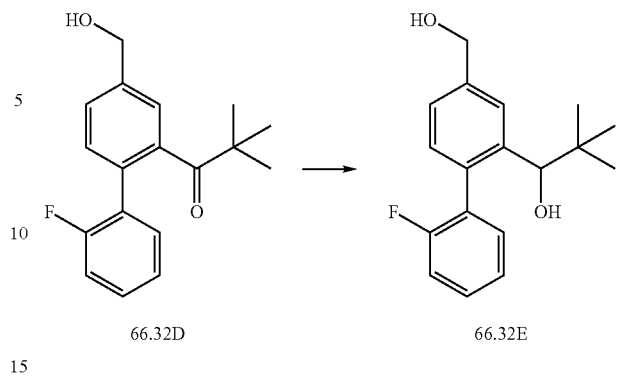

Methyl 2'-fluoro-4-(hydroxymethyl)-1,1'-biphenyl-2-carboxylate (66.32C). To a stirred solution of 66.32B (0.90 g, 3 mmol) in THF (33 mL) at 0° C. was added borane-THF complex (7 mL, 7 mmol, 1.0M). The reaction was allowed to warm to 23° C. and stirred for 7 hours. The reaction mixture was then concentrated in vacuo. The reaction was diluted with 1N HCl and extracted three times with EtOAc. After drying over anhydrous magnesium sulfate and filtering, the organic solvent was removed under reduced pressure and the product was then purified on silica gel (0-40% EtOAc in hexanes) to yield 66.32C as a colorless solid (0.850 g, 100% yield).

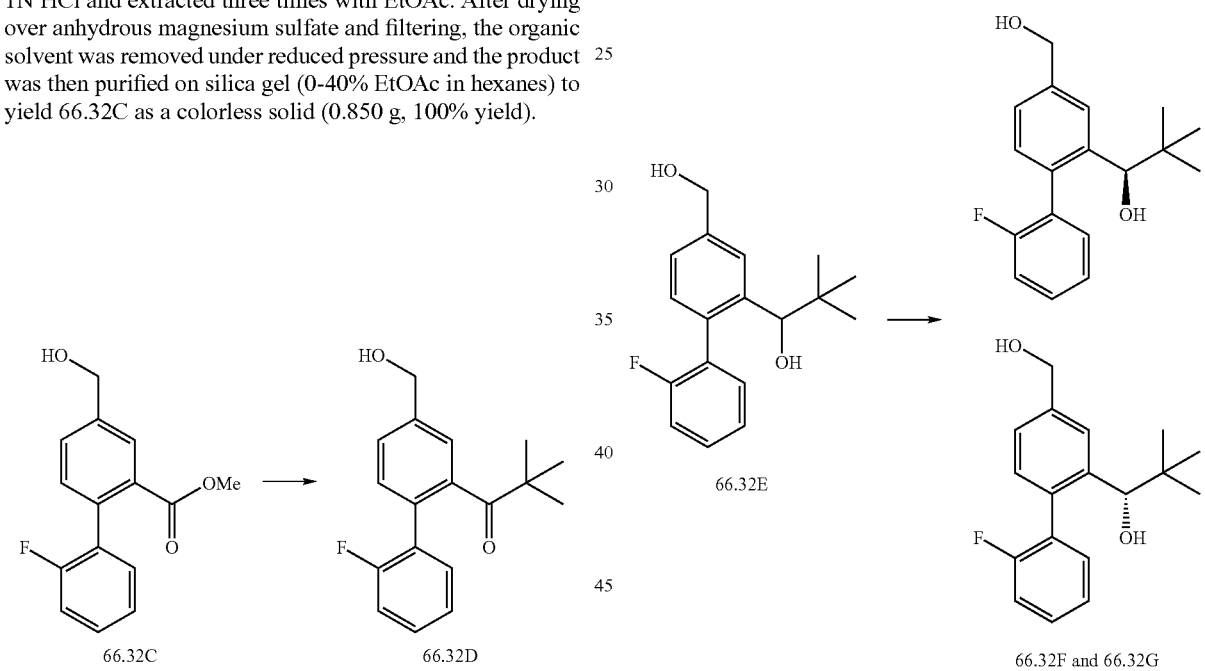

1-(2'-Fluoro-4-(hydroxymethyl)-1,1'-biphenyl-2-yl)-2,2-dimethyl-1-propanone (66.32D). To a stirred solution of 66.32C (0.850 g, 3 mmol) in THF (33 mL) at −78° C. was added tert-butyllithium (6 mL, 10 mmol, 1.7M). The reaction was stirred for 5 hours and then a saturated solution of ammonium chloride was added and the mixture was extracted three times with EtOAc. After drying over anhydrous magnesium sulfate and filtering, the organic solvent was removed under reduced pressure and the product was then purified on silica gel (0-40% EtOAc in hexanes) to yield 66.32D as a colorless oil (0.670 g, 72% yield).

(1R)-1-(2'-Fluoro-4-(hydroxymethyl)-1,1'-biphenyl-2-yl)-2,2-dimethyl-1-propanol and (1S)-1-(2'-fluoro-4-(hydroxymethyl)-1,1'-biphenyl-2-yl)-2,2-dimethyl-1-propanol (66.32 F and 66.32G). To a stirred solution of 66.32D (0.670 g, 2 mmol) in THF (6 mL) at 0° C. was added LAH in THF (5 mL, 5 mmol, 1.0M). The reaction was stirred for 1.5 hours and then 1N NaOH(aq) was added to quench the reaction mixture. The reaction was then extracted three times with EtOAc. After drying over anhydrous magnesium sulfate and filtering, the organic solvent was removed under reduced pressure and the product was purified on silica gel (0-20% EtOAc in hexanes) to yield 66.32E as a colorless oil (0.450 g, 67% yield). Chiral separation of 66.32E was accomplished on Chiracel-OD (3% IPA in hexane) to provide 66.32F and 66.32G. Both enantiomers were used to synthesize example compounds, and both enantiomers gave active example compounds. However, the enantiomer corresponding to peak 2 provided the most active example compounds.

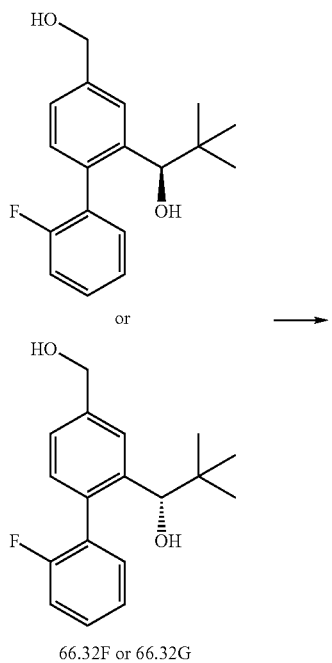

66.32F or 66.32G

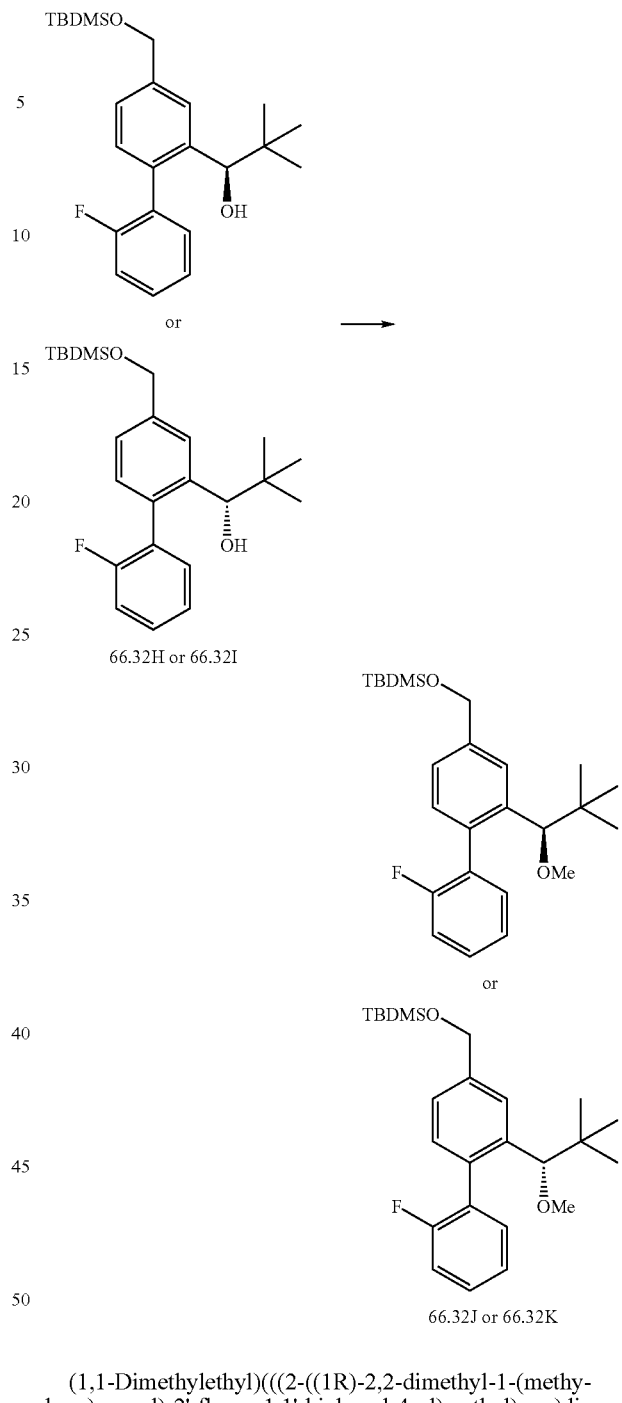

(1R)-1-(4-(((((1,1-Dimethylethyl)(dimethyl)silyl)oxy)methyl)-2'-fluoro-1,1'-biphenyl-2-yl)-2,2-dimethyl-1-propanol or (1S)-1-(4-(((((1,1-dimethylethyl)(dimethyl)silyl)oxy)methyl)-2'-fluoro-1,1'-biphenyl-2-yl)-2,2-dimethyl-1-propanol (66.32H or 66.32I). To a stirred solution of 66.32F or 66.32G (0.200 g, 0.7 mmol) in DCM (10.00 mL) at 23° C. was added tert-butyldimethylsilyl chloride (0.1 mL, 0.8 mmol), followed by TEA (0.1 mL, 0.8 mmol) and DMAP (0.008 g, 0.07 mmol). The reaction was stirred for 14 hours and then concentrated in vacuo. The product was then purified on silica gel (0-10% EtOAc in hexanes) to yield 66.32H or 66.32I as a colorless oil (0.250 g, 90% yield).

(1,1-Dimethylethyl)(((2-((1R)-2,2-dimethyl-1-(methyloxy)propyl)-2'-fluoro-1,1'-biphenyl-4-yl)methyl)oxy)dimethylsilane or (1,1-dimethylethyl)(((2-((1S)-2,2-dimethyl-1-(methyloxy)propyl)-2'-fluoro-1,1'-biphenyl-4-yl)methyl)oxy)dimethylsilane (66.32J 66.32K). To a stirred solution of 66.32H or 66.32I (0.060 g, 0.15 mmol) in DMF (2.00 mL) at 23° C. was added iodomethane (0.025 g, 0.18 mmol), followed by sodium hydride (0.0043 g, 0.18 mmol). The reaction was stirred at 60° C. for 19 hours, diluted with water, and the mixture was extracted three times with EtOAc. After drying over anhydrous magnesium sulfate and filtering, the organic solvent was removed under reduced pressure and the product was then purified on silica gel (0-5% EtOAc in hexanes) to yield 66.32J or 66.32K as a colorless oil (0.062 g, 100% yield).

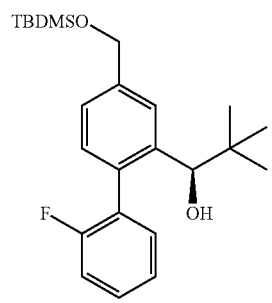

or

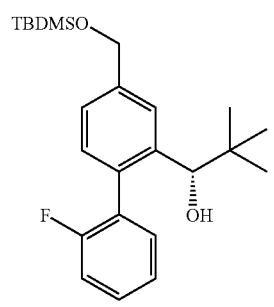

66.32J or 66.32K


or +

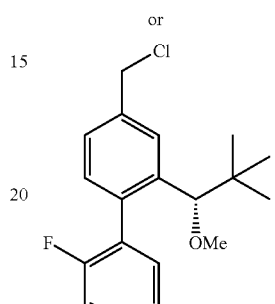

66.32L or 66.32M

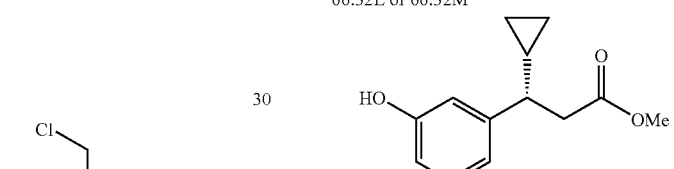

66.32L or 66.32M 4-(Chloromethyl)-2-((1R)-2,2-dimethyl-1-(methyloxy) propyl)-2'-fluoro-1,1'-biphenyl or 4-(chloromethyl)-2-((1S)-2,2-dimethyl-1-(methyloxy)propyl)-2'-fluoro-1,1'-biphenyl (66.32L 66.32M). To a stirred solution of 66.32J or 66.32K (0.071 g, 0.17 mmol) in DCM (1.7 mL) and DMF (0.013 mL) at 0° C. was added thionyl chloride (0.025 mL, 0.34 mmol). The reaction was stirred at room temperature for 1.5 hours and then concentrated in vacuo. The product was then purified on silica gel (0-5% EtOAc in hexanes) to yield 66.32L or 66.32M as a colorless oil (0.036 g, 66% yield).

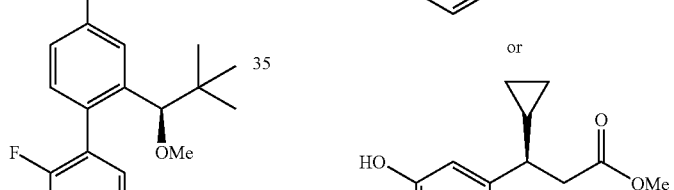

or

66.6X

or

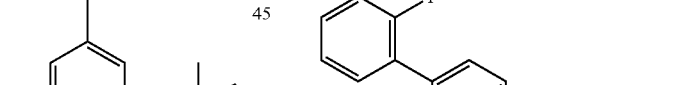

-continued

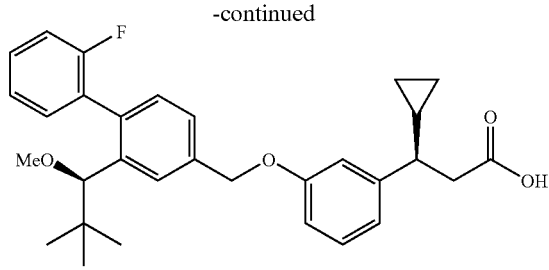

or

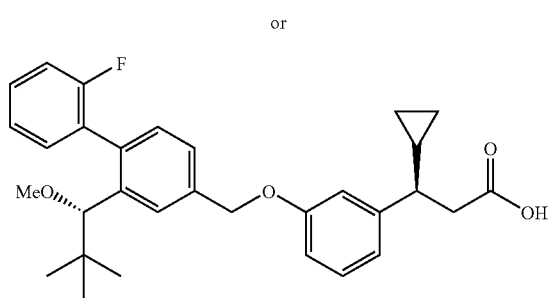

66.32

(3S)-3-Cyclopropyl-3-(3-(((2-((1R)-2,2-dimethyl-1-(methyloxy)propyl)-2'-fluoro-1,1'-biphenyl-4-yl)methyl)oxy)phenyl)propanoic acid or (3S)-3-cyclopropyl-3-(3-(((2-((1S)-2,2-dimethyl-1-(methyloxy)propyl)-2'-fluoro-1,1'-biphenyl-4-yl)methyl)oxy)phenyl)propanoic acid or (3R)-3-cyclopropyl-3-(3-(((2-((1R)-2,2-dimethyl-1-(methyloxy)propyl)-2'-fluoro-1,1'-biphenyl-4-yl)methyl)oxy)phenyl)propanoic acid or (3R)-3-cyclopropyl-3-(3-(((2-((1S)-2,2-dimethyl-1-(methyloxy)propyl)-2'-fluoro-1,1'-biphenyl-4-yl)methyl)oxy)phenyl)propanoic acid 66.32. The alkylation and hydrolysis were conducted in an analogous manner to Example 66.6 (using 66.6X and the chloromethyl compound derived from peak one from chiral separation of 66.32E from the OD-column) to yield 66.32 (0.024 g, 43% yield over two steps). MS ESI (neg.) m/e: 489.2 (M−H)+.

Example 66.33

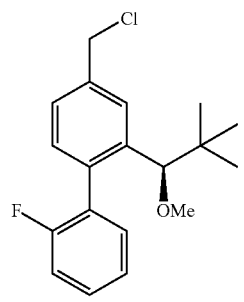

or


66.32L or 66.32M

-continued

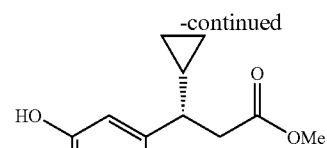

or

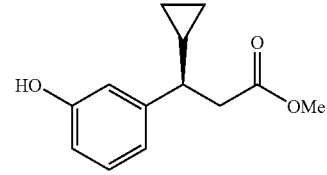

66.6X

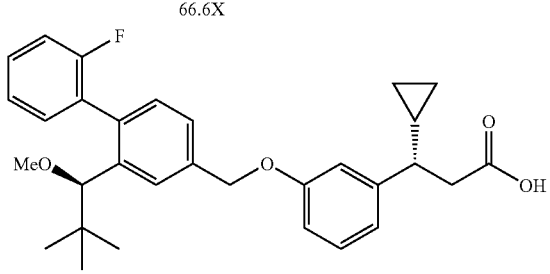

or

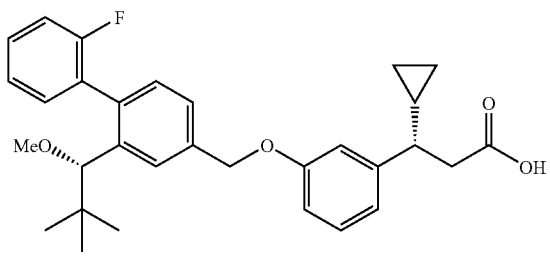

or

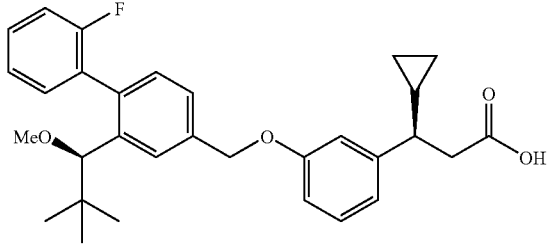

or

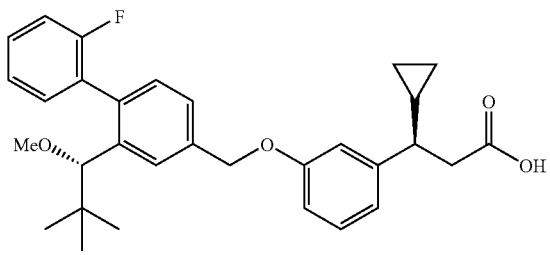

66.33

(3S)-3-Cyclopropyl-3-(3-(((2-((1R)-2,2-dimethyl-1-(methyloxy)propyl)-2'-fluoro-1,1'-biphenyl-4-yl)methyl)oxy)

phenyl)propanoic acid or (3S)-3-cyclopropyl-3-(3-(((2-((1S)-2,2-dimethyl-1-(methyloxy)propyl)-2'-fluoro-1,1'-biphenyl-4-yl)methyl)oxy)phenyl)propanoic acid or (3R)-3-cyclopropyl-3-(3-(((2-((1R)-2,2-dimethyl-1-(methyloxy)propyl)-2'-fluoro-1,1'-biphenyl-4-yl)methyl)oxy)phenyl)propanoic acid or (3R)-3-cyclopropyl-3-(3-(((2-((1S)-2,2-dimethyl-1-(methyloxy)propyl)-2'-fluoro-1,1'-biphenyl-4-yl)methyl)oxy)phenyl)propanoic acid (66.33). The alkylation and hydrolysis were conducted in an analogous manner to Example 66.6 (using 66.6X and the chloromethyl compound derived from peak two from chiral separation of 66.32E from the OD-column, described herein) to yield 66.33 (0.026 g, 48% yield over two steps). MS ESI (neg.) m/e: 489.2 (M−H)+.

Example 66.34

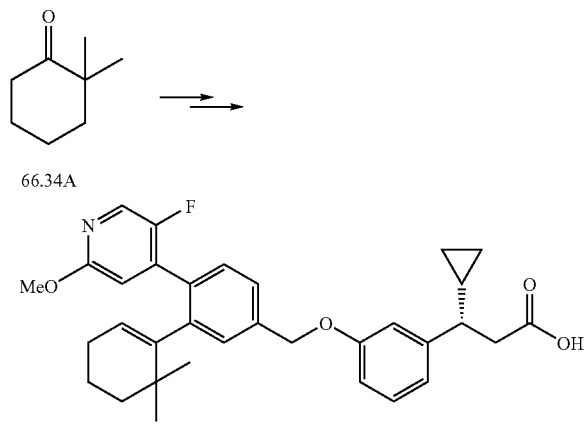

66.34A or

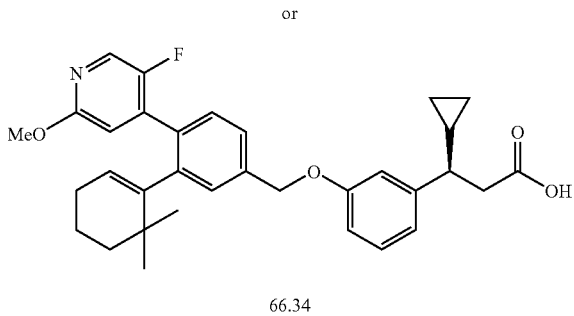

66.34

(3S)-3-Cyclopropyl-3-(3-(((3-(6,6-dimethyl-1-cyclohexen-1-yl)-4-(5-fluoro-2-(methyloxy)-4-pyridinyl)phenyl)methyl)oxy)phenyl)propanoic acid or (3S)-3-Cyclopropyl-3-(3-(((3-(6,6-dimethyl-1-cyclohexen-1-yl)-4-(5-fluoro-2-(methyloxy)-4-pyridinyl)phenyl)methyl)oxy)phenyl)propanoic acid (66.34). This compound was prepared using a method analogous to that described for 66.12 starting from 2,2-dimethylcyclohexanone 66.34A which is commercially available from Carbocore. MS ESI (neg.) m/e: 528.3 (M−H)+.

(3S)-3-Cyclopropyl-3-(3-(((3-(6,6-dimethyl-1-cyclohexen-1-yl)-4-(5-fluoro-2-oxo-1,2-dihydro-4-pyridinyl)phenyl)methyl)oxy)phenyl)propanoic acid or (3R)-3-cyclopropyl-3-(3-(((3-(6,6-dimethyl-1-cyclohexen-1-yl)-4-(5-fluoro-2-oxo-1,2-dihydro-4-pyridinyl)phenyl)methyl)oxy)phenyl)propanoic acid (66.35). To a reaction vessel containing 66.34 (26 mg, 0.049 mmol) was added 1.1 mL dioxane and 0.2 mL concentrated HCl. The reaction was heated at 60° C. for 16 hours, neutralized with NaHCO3, and extracted with EtOAc. Purification by silica gel column chromatography with MeOH/DCM afforded 10 mg of 66.35. MS ESI (pos.) m/e: 516.3 (M+H)+.

(3S)-3-Cyclopropyl-3-(3-(((3-((1S)-2,2-dimethylcyclopentyl)-4-(5-fluoro-2-(methyloxy)-4-pyridinyl)phenyl)methyl)oxy)phenyl)propanoic acid or (3S)-3-cyclopropyl-3-(3-(((3-((1R)-2,2-dimethylcyclopentyl)-4-(5-fluoro-2-(methyloxy)-4-pyridinyl)phenyl)methyl)oxy)phenyl)propanoic acid or (3R)-3-cyclopropyl-3-(3-(((3-((1S)-2,2-dimethylcyclopentyl)-4-(5-fluoro-2-(methyloxy)-4-pyridinyl)phenyl)methyl)oxy)phenyl)propanoic acid or (3R)-3-cyclopropyl-3-(3-(((3-((1R)-2,2-dimethylcyclopentyl)-4-(5-fluoro-2-(methyloxy)-4-pyridinyl)phenyl)methyl)oxy)phenyl)propanoic acid (66.36). The title compound was prepared in similar method as 66.6 through the hydrogenation of intermediate 66.12C. The detailed synthesis of the chloromethyl half is described in 83.4C. MS ESI (neg.) m/e: 516.3 (M−H)+.

(3S)-3-Cyclopropyl-3-(3-(((3-((1R)-2,2-dimethylcyclopentyl)-4-(5-fluoro-2-(methyloxy)-4-pyridinyl)phenyl)methyl)oxy)phenyl)propanoic acid or (3S)-3-cyclopropyl-3-(3-(((3-((1S)-2,2-dimethylcyclopentyl)-4-(5-fluoro-2-(methyloxy)-4-pyridinyl)phenyl)methyl)oxy)phenyl)propanoic acid or (3R)-3-cyclopropyl-3-(3-(((3-((1R)-2,2-dimethylcyclopentyl)-4-(5-fluoro-2-(methyloxy)-4-pyridinyl)phenyl)methyl)oxy)phenyl)propanoic acid or (3R)-3-cyclopropyl-3-(3-(((3-((1S)-2,2-dimethylcyclopentyl)-4-(5-fluoro-2-(methyloxy)-4-pyridinyl)phenyl)methyl)oxy)phenyl)propanoic acid (66.37). This compound was prepared in similar method as 66.6 through the hydrogenation of intermediate 66.12C. The detailed synthesis of the chloromethyl half is described in 83.5. MS ESI (neg.) m/e: 516.3 (M−H)+.

Example 66.38

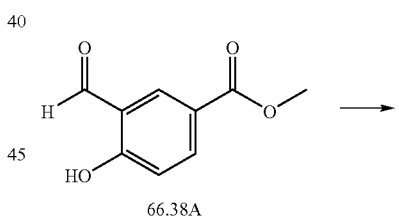

66.38A

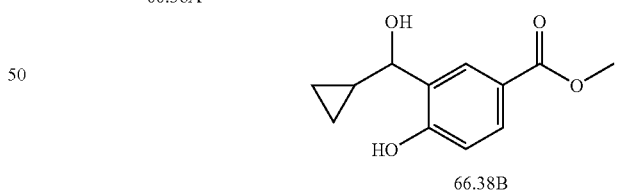

66.38B

Methyl 3-(cyclopropyl(hydroxy)methyl)-4-hydroxybenzoate (66.38B). In an ice-bath, methyl 3-formyl-4-hydroxybenzoate 66.38A (900 mg, 5 mmol) (commercially available from Aldrich) was dissolved in 5 mL THF. Then cyclopropylmagnesium bromide, 0.5 m in THF (22000 μL, 11 mmol) (commercially available from Aldrich) was added slowly. The reaction was raised to room temperature immediately and stirred at room temperature for 2 hours. After quenching with 1N HCl 11 mL, the reaction was extracted with EtOAc and dried. Silica gel chromatography afforded 950 mg of the product 66.38B (85%).

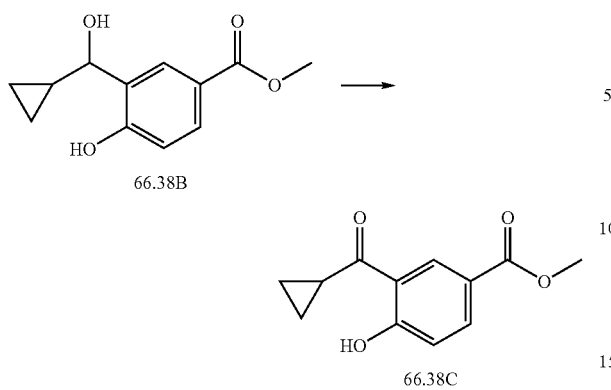

Methyl 3-(cyclopropanecarbonyl)-4-hydroxybenzoate (66.38C). To a flask with methyl 3-(cyclopropyl(hydroxy)methyl)-4-hydroxybenzoate (66.38B) (845 mg, 0.38 mmol) was added manganese (IV) oxide (1.65 g, 1.9 mmol). Then dioxane 3.5 mL was added and the reaction was heated at reflux for 4 hours. The reaction was filtered and concentrated and silica gel chromatography afforded 693 mg of 66.38C (83%).

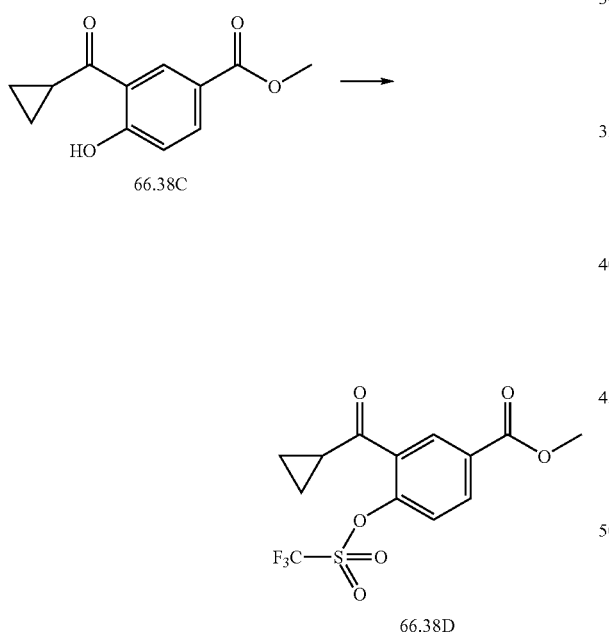

Methyl 3-(cyclopropanecarbonyl)-4-(trifluoromethylsulfonyloxy)benzoate (66.38D). To a flask with methyl 3-(cyclopropanecarbonyl)-4-hydroxybenzoate 66.38C (693 mg, 3.1 mmol) was added DMAP (38 mg, 0.31 mmol), and the mixture was flushed with nitrogen. DCM was then added followed by TEA (0.88 mL, 6.3 mmol). After stirring at room temperature for 20 minutes, PhN(Tf)2 (1.2 g, 3.5 mmol) was added. The reaction gradually turned red and was stirred for another hour. The mixture was concentrated and purified by silica gel chromatography to afford 1.077 g of 66.38D as a colorless oil (97%).

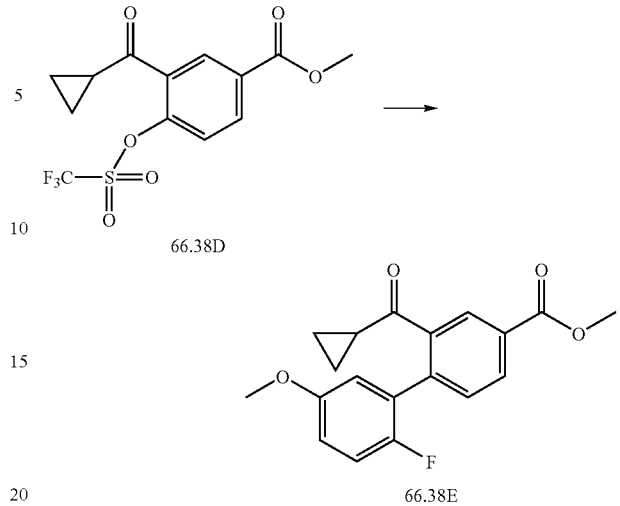

Methyl 3-(cyclopropanecarbonyl)-4-(2-fluoro-5-methoxyphenyl))benzoate (66.38E). Methyl 3-(cyclopropanecarbonyl)-4-(trifluoromethylsulfonyloxy)benzoate (66.38D) (1.077 g, 3.1 mmol) was dried under vacuum. To a second flask was added 2-fluoro-5-methoxyphenylboronic acid (1.5 g, 8.9 mmol) (commercially available from Aldrich), cesium carbonate (3.5 g, 11 mmol), and tetrakis(triphenylphosphine) Palladium (0) (0.35 g, 0.31 mmol). Both flasks were flushed with nitrogen followed by vacuum. Degassed DME was then added to the flask with 66.38D (3 mL). Another 17 mL DME was added to the flask with the palladium catalyst followed by the DME solution of 66.38D. The resulting slurry was stirred overnight in a 95° C. oil-bath. The reaction was filtered, concentrated, and purified by silica gel chromatography to afford 0.94 g of the desired product 66.38E (94%).

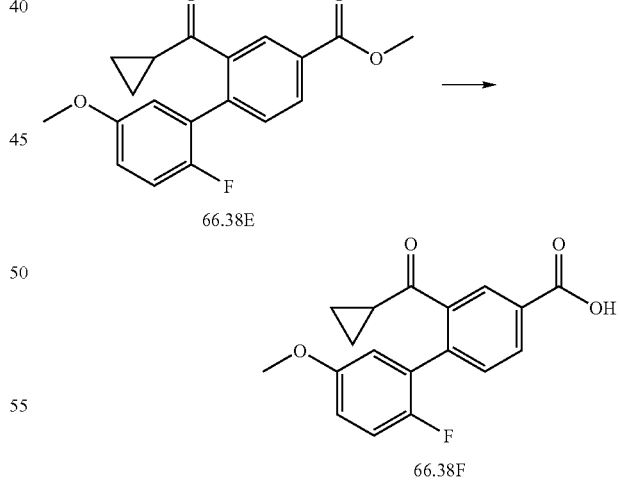

3-(Cyclopropanecarbonyl)-4-(2-fluoro-5-methoxyphenyl))benzoic acid (66.38F). To a flask with methyl 3-(cyclopropanecarbonyl)-4-(2-fluoro-5-methoxyphenyl))benzoate (66.38E) (523 mg, 1593 μmol) was added 9.6 mL of MeOH and 1N NaOH (3186 μL, 3186 μmol). The reaction was heated to 55 C for 2 hours. The mixture was then acidified with 1N HCl, concentrated, and extracted with EtOAc. Removal of the solvent afforded 500 mg of 66.38F (100%).

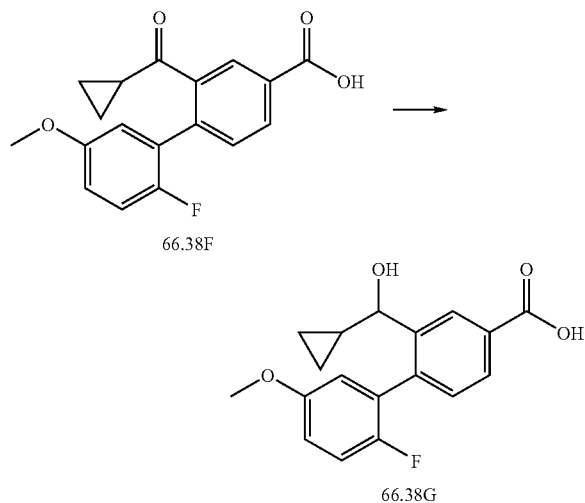

66.38F

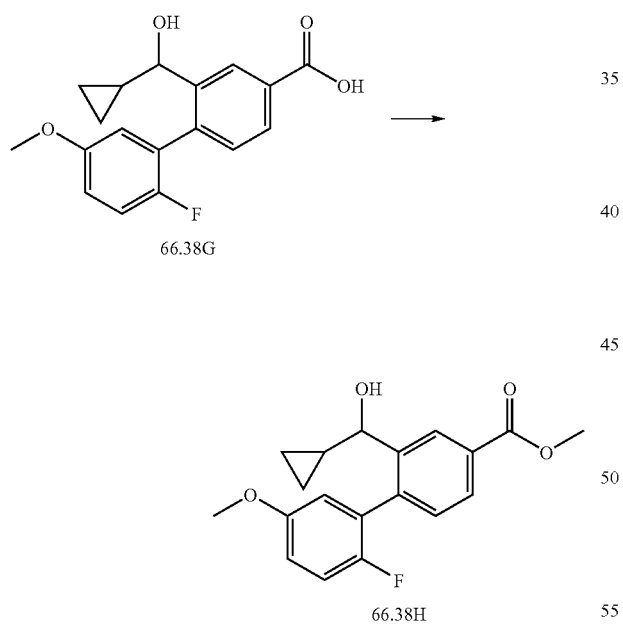

66.38G 66.38G 66.38H 3-(Cyclopropyl(hydroxy)methyl)-4-(2-fluoro-5-methoxyphenyl))benzoic acid (66.38G). To a flask with 3-(cyclopropanecarbonyl)-4-(2-fluoro-5-methoxyphenyl))benzoic acid (66.38F) (500 mg, 1591 μmol) was added anhydrous EtOH 10 mL, followed by addition of sodium borohydride (361 mg, 0.95 mmol). The reaction mixture was stirred overnight, quenched with water, and extracted with EtOAc. Removal of solvent gave 503 mg of 66.38G in racemic form.

Methyl 3-(cyclopropyl(hydroxy)methyl)-4-(2-fluoro-5-methoxyphenyl))benzoate (66.38H). To a flask with 3-(cyclopropyl(hydroxy)methyl)-4-(2-fluoro-5-methoxyphenyl))benzoic acid (66.38G), (503 mg, 1.6 mmol) was added 10 mL DCM and 2 mL MeOH. TMS diazomethane (795 μL, 1590 μmol) in ether was then added, and the reaction was stirred at room temperature for 1 hour, and then quenched with a acetic acid. Water was added, and the reaction was extracted with EtOAc. Purification by silica gel chromatography afforded 484 mg of 66.38H (92%) in racemic form.

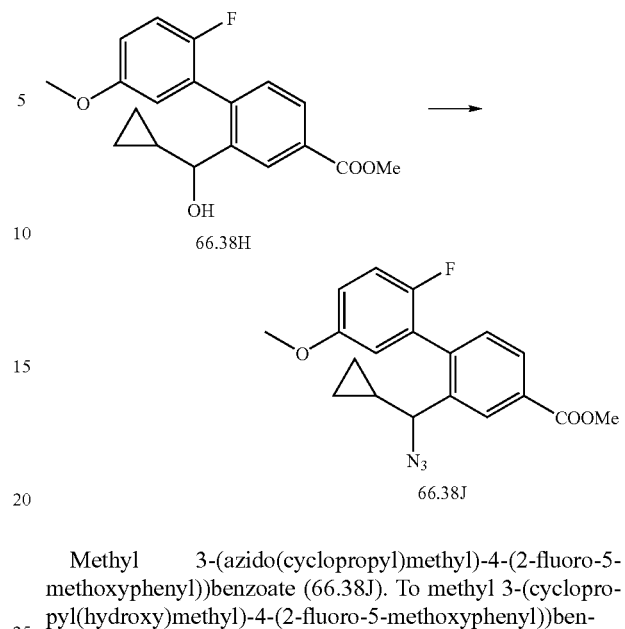

66.38H 66.38J

Methyl 3-(azido(cyclopropyl)methyl)-4-(2-fluoro-5-methoxyphenyl))benzoate (66.38J). To methyl 3-(cyclopropyl(hydroxy)methyl)-4-(2-fluoro-5-methoxyphenyl))benzoate (66.38H) (235 mg, 711 μmol) was added DMF 4 mL, then 1,8-diazabicyclo[5.4.0]undec-7-ene (160 μL, 1067 μmol), and diphenylphosphoryl azide (231 μL, 1067 μmol). The mixture was heated to 80° C. After 3 hours, 1.5 equivalents more of each of the 1,8-diazabicyclo[5.4.0]undec-7-ene and diphenylphosphoryl azide were added. The reaction was heated for two more hours and water was then added followed by EtOAc extraction. Purification by silica gel chromatography afforded 260 mg of 66.38J mixed with a non-polar side product. The product thus obtained was carried to the next step without further purification.

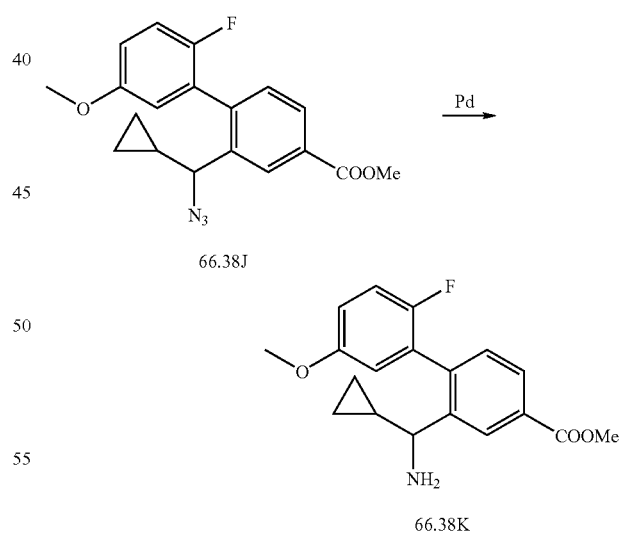

66.38J 66.38K

Methyl 3-(amino(cyclopropyl)methyl)-4-(2-fluoro-5-methoxyphenyl))benzoate (66.38K). To a flask with methyl 3-(azido(cyclopropyl)methyl)-4-(2-fluoro-5-methoxyphenyl))benzoate (66.38J) (260 mg, 732 μmol) was added 10% Pd/C (78 mg, 732 μmol), and then 6 mL of MeOH was added. The reaction was purged with hydrogen and stirred under a hydrogen balloon for about 6 hours. The reaction was filtered through a pad of Celite filter aid, concentrated, and purified by silica gel chromatography to afford 76 mg of the desired product 66.38K (32% for 2 steps).

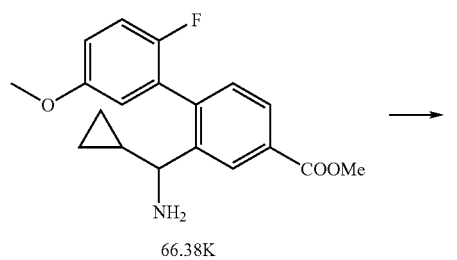

66.38K

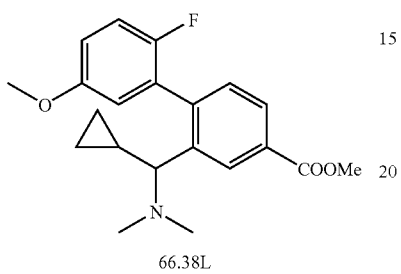

66.38L

Methyl 3-(cyclopropyl(dimethylamino)methyl)-4-(2-fluoro-5-methoxyphenyl)benzoate (66.38L). To a flask with methyl 3-(amino(cyclopropyl)methyl)-4-(2-fluoro-5-methoxyphenyl))benzoate (66.38K) (76 mg, 231 μmol) were added 2 mL DCM, formaldehyde (70 μL, 923 μmol), and acetic acid (26 μL, 461 μmol). Sodium triacetoxyborohydride (245 mg, 1154 μmol) was then added to the reaction mixture. The reaction was stirred for 1.5 hours and worked up with water and EtOAc. Silica gel chromatography afforded 35 mg of 66.38L (43%).

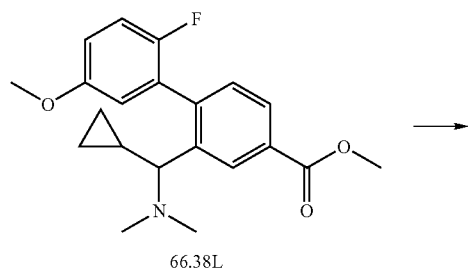

66.38L

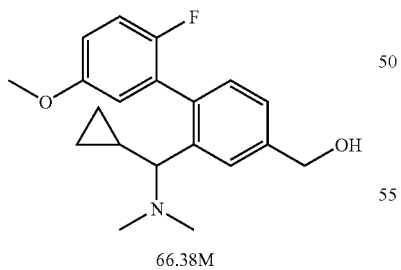

66.38M (3-(Cyclopropyl(dimethylamino)methyl))-4-(2-fluoro-5-methoxyphenyl)phenyl)methanol (66.38M). To a flask with methyl 3-(amino(cyclopropyl)methyl)-4-(2-fluoro-5-methoxyphenyl))benzoate (66.38K) (35 mg, 98 μmol) was added THF (1.5 mL). The mixture was cooled to 0° C. and then 1M LAH (196 μL, 196 μmol, 1M solution in THF) was added. The temperature was slowly raised to room temperature over 1 hour. Water and a small amount of Rochelle's salt solution were added to quench the reaction and it was then extracted with EtOAc. Silica gel chromatography afforded 26 mg of 66.38M (81%).

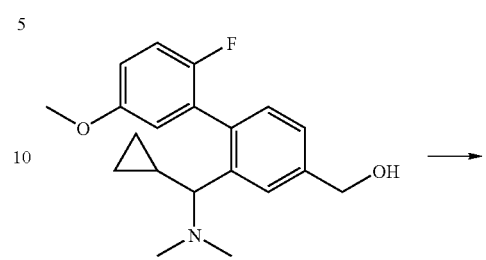

66.38M

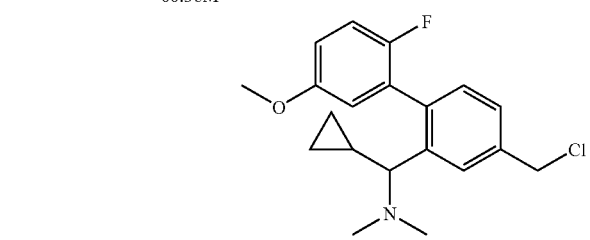

66.38N (5-(Chloromethyl)-2-(2-fluoro-5-methoxyphenyl)phenyl)(cyclopropyl)-N,N-dimethylmethanamine (66.38N). To a flask with (3-(cyclopropyl(dimethylamino)methyl))-4-(2-fluoro-5-methoxyphenyl)phenyl)methanol (66.38M) (26 mg, 79 μmol) was added DCM. The mixture was cooled in an ice-bath and then thionyl chloride (12 μL, 158 μmol) and DMF (6 μL, 79 μmol) were added. The reaction was stirred at room temperature for 1 hour, and then it was concentrated and purified by silica gel chromatography to afford 28 mg of 66.38N (102%).

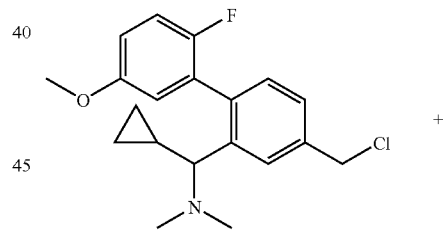

66.38N

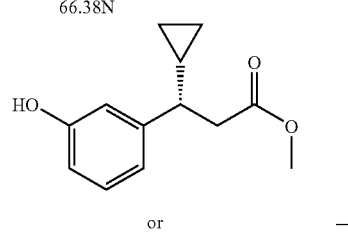

8.4

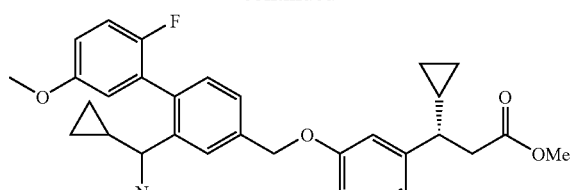

or

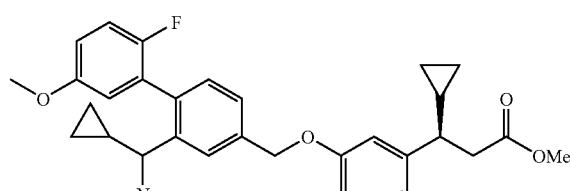

66.38O (3S)-Methyl 3-cyclopropyl-3-(3-(((2-(cyclopropyl(dimethylamino)methyl)-2'-fluoro-5'-(methyloxy)-1,1'-biphenyl-4-yl)methyl)oxy)phenyl)propanoate or (3R)-methyl 3-cyclopropyl-3-(3-(((2-(cyclopropyl(dimethylamino)methyl)-2'-fluoro-5'-(methyloxy)-1,1'-biphenyl-4-yl)methyl)oxy)phenyl)propanoate (66.38O). To a flask with 66.38N (28 mg, 80 μmol), was added 8.4 (21 mg, 97 μmol), and cesium carbonate (39 mg, 121 μmol). DMF (1.2 mL) was then added to the mixture. The reaction was stirred for 16 hours and worked up with water and EtOAc. Silica gel chromatography afforded 43 mg of 66.38O (100%).

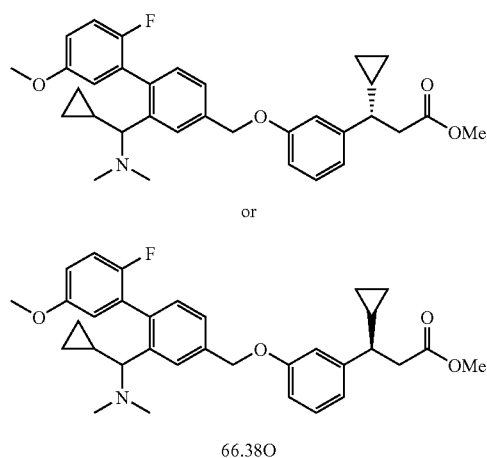

66.38O

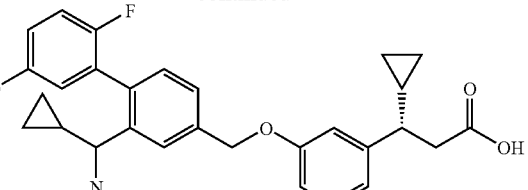

or

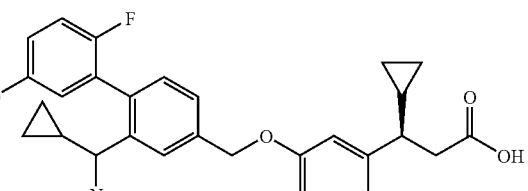

66.38

(3S)-3-Cyclopropyl-3-(3-(((2-(cyclopropyl(dimethylamino)methyl)-2'-fluoro-5'-(methyloxy)-1,1'-biphenyl-4-yl)methyl)oxy)phenyl)propanoic acid or (3R)-3-cyclopropyl-3-(3-(((2-(cyclopropyl(dimethylamino)methyl)-2'-fluoro-5'-(methyloxy)-1,1'-biphenyl-4-yl)methyl)oxy)phenyl)propanoic acid (66.38). To a flask with 66.38O (43 mg) was added 1 mL THF (0.5 mL), MeOH (0.5 mL) and LiOH. The reaction was stirred overnight, neutralized with 1N HCl, and extracted with EtOAc. The reaction was purified by silica gel chromatography to afford 8 mg of 66.38 (19%) as 1:1 ratio of diastereomers. MS ESI (pos.) m/e: 518.2 (M+H)⁺.

Example 66.40

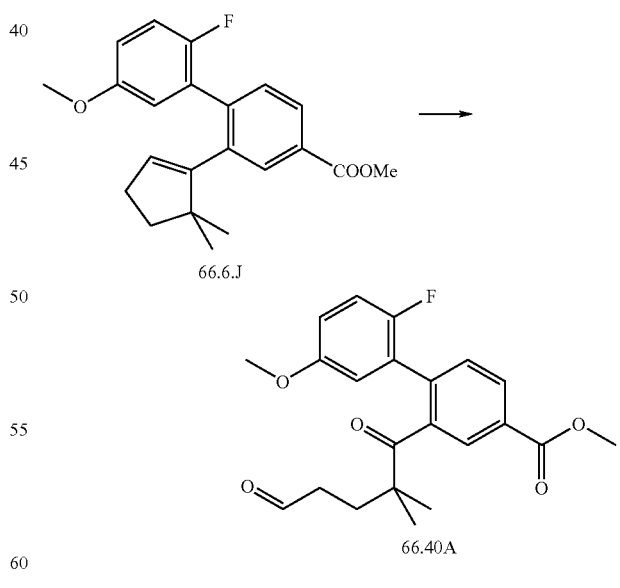

2'-Fluoro-5'-methoxy-2-(5-oxo-pentanoyl)-biphenyl-4-carboxylic acid methyl ester (66.40A). To a solution of 2-(5,5-Dimethyl-cyclopent-1-enyl)-2'-fluoro-5'-methoxy-biphenyl-4-carboxylic acid methyl ester 66.6J (0.10 g, 0.28 mmol) in a mixed solvent of MeOH and DCM (3/1) at −78° C., was slowly bubbled O₃ for 5 minutes. Dimethylsulfane (0.052 g, 0.84 mmol) was added to the solution, and the resulting mixture was warmed to room temperature and stirred for 16 hours. The solvent was evaporated, and the residue was purified by silica gel chromatography (eluent was EtOAc and hexane) to give 66.40A. $^1$H NMR (CDCl$_3$) δ ppm 1.01 (s, 6H), 1.77 (t, J=8.0 Hz, 2H), 2.21 (t, J=8.0 Hz, 2H), 3.79 (s, 3H), 3.98 (s, 3H), 6.79 (m, 1H), 6.90 (m, 1H), 7.07 (t, J=8.0 Hz, 1H), 7.51 (d, J=8.0 Hz, 1H), 7.94 (s, 1H), 8.12 (d, J=8.0 Hz, 1H), 9.67 (s, 1H).

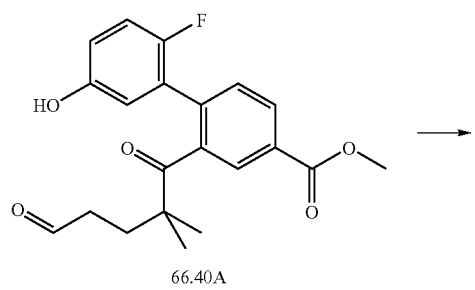

66.40A

2'-Fluoro-5'-methoxy-2-(1,3,3-trimethyl-piperidin-2-yl)-biphenyl-4-carboxylic acid methyl ester (66.40B). To a solution of 66.40B (45 mg, 116 µmol) in EtOH, was added methylamine (33% wt solution in absolute EtOH) (146 µL, 1165 µmol) and acetic acid (70 mg, 1165 µmol). The resulting mixture was stirred at room temperature for 10 minutes and then sodium cyanoborohydride (15 µL, 291 µmol) was added. The mixture was stirred at room temperature for 2 hours and then heated at reflux for 16 hours. Solvent was removed, and the reaction mixture was diluted with EtOAc. The organic phase was washed carefully with saturated aqueous NaHCO$_3$, once with brine, and then dried over anhydrous sodium sulfate. After filtration, the organic solvent was removed in vacuo to yield 66.40B (36 mg) which was used without purification.

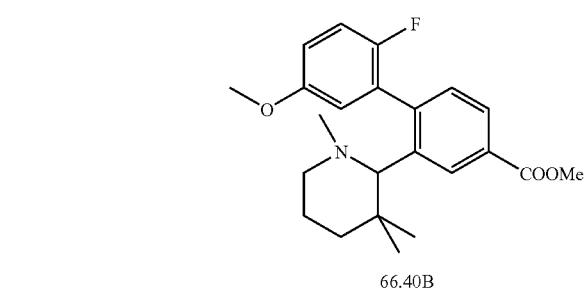

66.40B

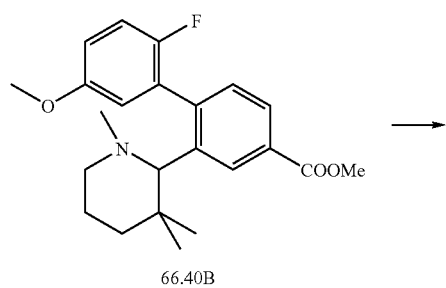

66.40B

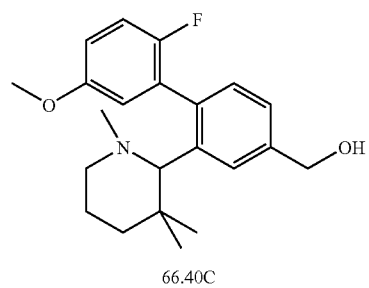

66.40C

[2'-Fluoro-5'-methoxy-2-(1,3,3-trimethyl-piperidin-2-yl)-biphenyl-4-yl]-methanol (66.40C) Compound 66.40C was synthesized by a method analogous to the method used for synthesizing compound 8.9 from 8.8. MS ESI m/e: 358.2 (M+H)$^+$.

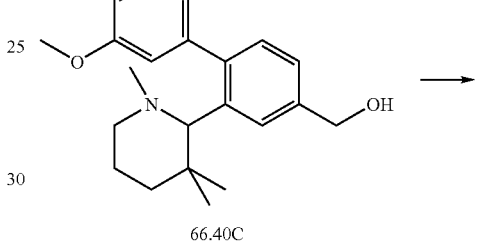

66.40C

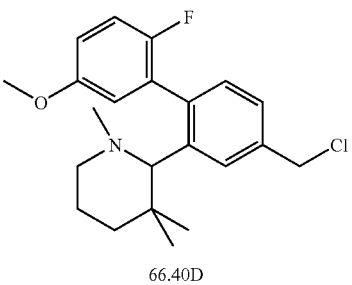

66.40D 2-(4-Chloromethyl-2'-fluoro-5'-methoxy-biphenyl-2-yl)-1,3,3-trimethyl-piperidine (66.40D) Compound 66.40D was synthesized by a method analogous to the method used to prepare compound 8.10 from 8.9. MS ESI m/e: 376.2 (M+H)$^+$.

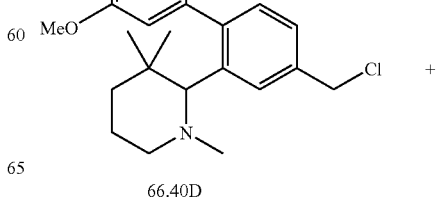

66.40D

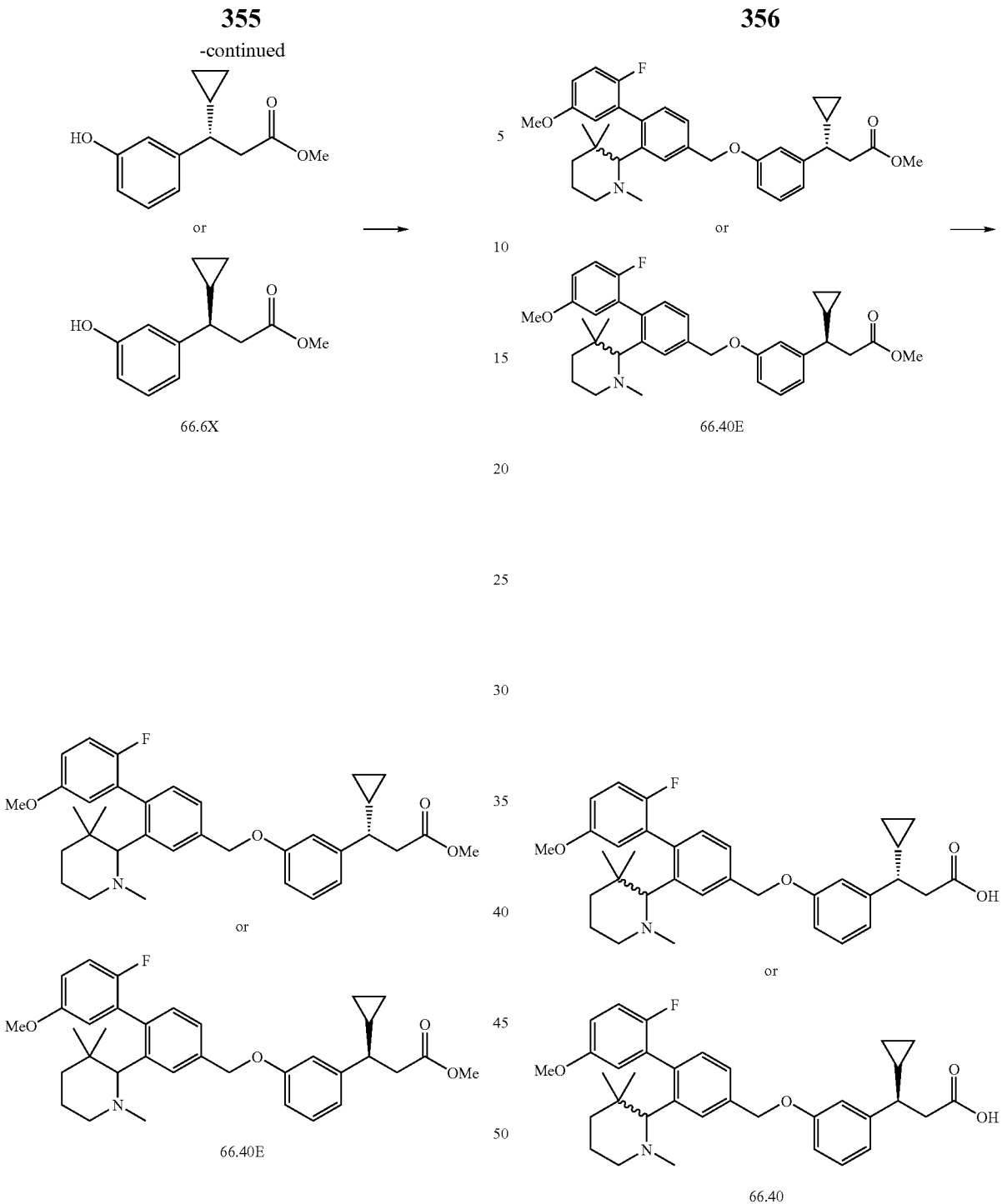

(S)-3-Cyclopropyl-3-{3-[2'-fluoro-5'-methoxy-2-(1,3,3-trimethyl-piperidin-2-yl)-biphenyl-4-ylmethoxy]-phenyl}-propionic acid methyl ester or (R)-3-Cyclopropyl-3-{3-[2'-fluoro-5'-methoxy-2-(1,3,3-trimethyl-piperidin-2-yl)-biphenyl-4-ylmethoxy]-phenyl}-propionic acid methyl ester (66.40E). Compound 66.40E was synthesized using a method analogous to the method used for compound to prepare compound 66.13P from 66.40E and 66.6X. MS ESI m/e: 560.3 (M+H)⁺.

(S)-3-Cyclopropyl-3-{3-[2'-fluoro-5'-methoxy-2-(1,3,3-trimethyl-piperidin-2-yl)-biphenyl-4-ylmethoxy]-phenyl}-propionic acid or (R)-3-cyclopropyl-3-{3-[2'-fluoro-5'-methoxy-2-(1,3,3-trimethyl-piperidin-2-yl)-biphenyl-4-ylmethoxy]-phenyl}-propionic acid (66.40). Compound 66.40 was synthesized by a method analogous to the method used to prepare compound 66.13 from 66.13P. MS ESI m/e: 546.3 (M+H)⁺. ¹H NMR (400 MHz, CDCl₃) δ ppm 7.65 (m, 1H), 7.53 (m, 1H), 7.38 (m 1H), 7.20 (m, 2H), 7.05 (m 1H) 6.80-6.89 (m, 4H), 5.26 (s, 2H), 4.14 (s, 0.3H) 3.91 (s, 0.7H), 3.84 (s, 1.2H), 3.79 (s, (s, 1.8H), 3.65 (m, 1H), 3.15 (m, 1H), 2.74 (m, 2H), 2.69 (d, J=4 Hz, 2.3H), 2.65 (s, 0.7H), 2.30 (m, 1H), 2.03 (m, 1H), 1.82 (m, 1H), 1.60 (m, 1H), 1.42 (m, 1H), 1.02 (m, 1H), 0.96 (d, J=4 Hz, 3H), 0.55 (m, 4H), 0.37 (m, 1H), 0.27 (m, 1H), 0.09 (m, 1H).

Example 66.41

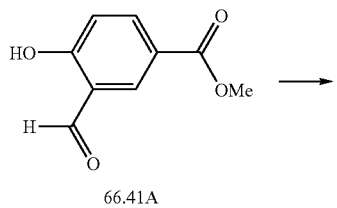

66.41A

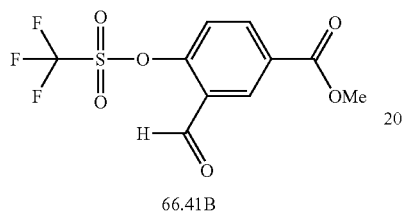

66.41B

Methyl 3-formyl-4-(trifluoromethylsulfonyloxy)benzoate (66.41B). Compound 66.41B was synthesized from methyl 3-formyl-4-hydroxybenzoate 66.41A (commercially available from Aldrich) using a method analogous to the method used to prepare compound 66.6I from 66.6H. MS ESI m/e: 313.2 (M+H)$^+$.

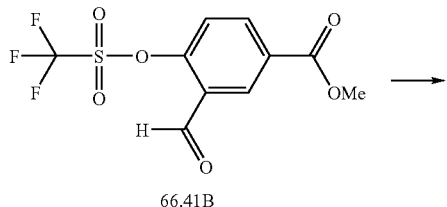

66.41B

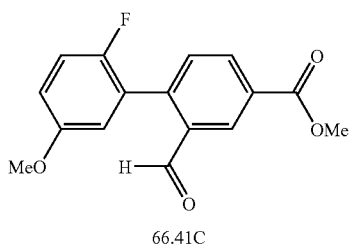

66.41C

2'-Fluoro-2-formyl-5'-methoxy-biphenyl-4-carboxylic acid methyl ester (66.41C). To a round bottle flask, was added methyl 3-formyl-4-(trifluoromethylsulfonyloxy)benzoate (6300 mg, 20 mmol), 2-fluoro-5-methoxyphenylboronic acid (10 g, 61 mmol) (commercially available from Aldrich), potassium phosphate tribasic (6.6 mL, 81 mmol) (granular) and tetrakis(triphenylphosphine)palladium (2.3 g, 2.0 mmol). The flask was flushed with nitrogen, DME was added, and the mixture was heated at 90° C. for 6 hours. The reaction mixture was diluted with EtOAc and water. The organic phase was washed with water and brine and then dried over anhydrous sodium sulfate. After filtration, the organic solvent was removed in vacuo to give a residue which was purified by chromatography to give the product as a yellow solid (5.80 g, 100%). MS ESI m/e: 289.2 (M+H)$^+$.

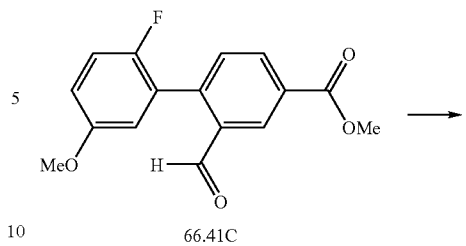

66.41C

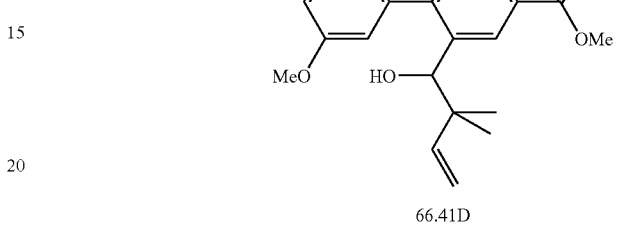

66.41D

2'-Fluoro-2-(1-hydroxy-2,2-dimethyl-but-3-enyl)-5'-methoxy-biphenyl-4-carboxylic acid methyl ester (66.41D). To a mixed solution of sodium iodide (2080 mg, 13876 µmol), indium (2000 mg, 6938 µmol) and 1-bromo-3-methylbut-2-ene (1616 µL, 13876 µmol) in DMF (30 mL), was added 66.41C (1593 mg, 13876 µmol). The mixture was stirred at room temperature for 1 hour, and then was diluted with EtOAc and water. The organic phase was washed with water and brine and then dried over anhydrous sodium sulfate. After filtration, the organic solvent was removed in vacuo to give a residue which was purified by chromatography to give the product as an oil (2.30 g, 92%). MS ESI m/e: 376.1 (M+18)$^+$.

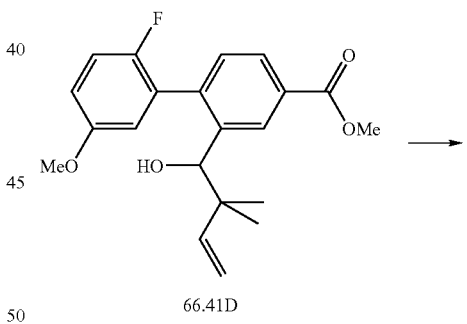

66.41D 66.41E

2'-Fluoro-5'-methoxy-2-(1-methoxy-2,2-dimethyl-but-3-enyl)-biphenyl-4-carboxylic acid methyl ester (66.41E). To a solution of 66.41D (1530 mg, 4269 µmol) in DMF (40 mL), was added sodium hydride (60% in oil) (213 µL, 8538 µmol).

The mixture was stirred at room temperature for 10 minutes and then methyl iodide (530 µL, 8538 µmol) was added in one portion and the mixture was stirred at room temperature for 30 minutes. Water was added and the mixture was, extracted with EtOAc. The organic phase was washed with water and brine and then dried over anhydrous sodium sulfate. After filtration, the organic solvent was removed in vacuo to give the product as a residue which was purified by chromatography to give the product as an oil (0.75 g, 47%). MS ESI m/e: 373.2 (M+18)$^+$.

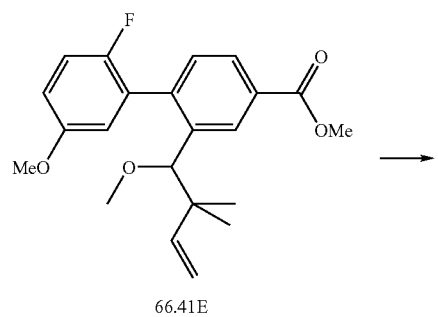

66.41E

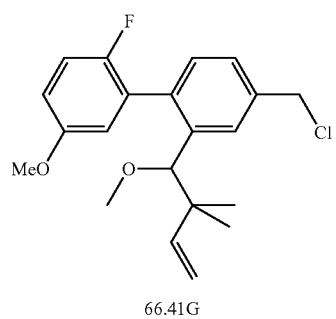

66.41G

4-Chloromethyl-2'-fluoro-5'-methoxy-2-(1-methoxy-2,2-dimethyl-but-3-enyl)-biphenyl (66.41G). Compound 66.41G was synthesized by a method analogous to the method used to prepare compound 8.10 from 8.9. MS ESI m/e: 363.2 (M+H)$^+$.

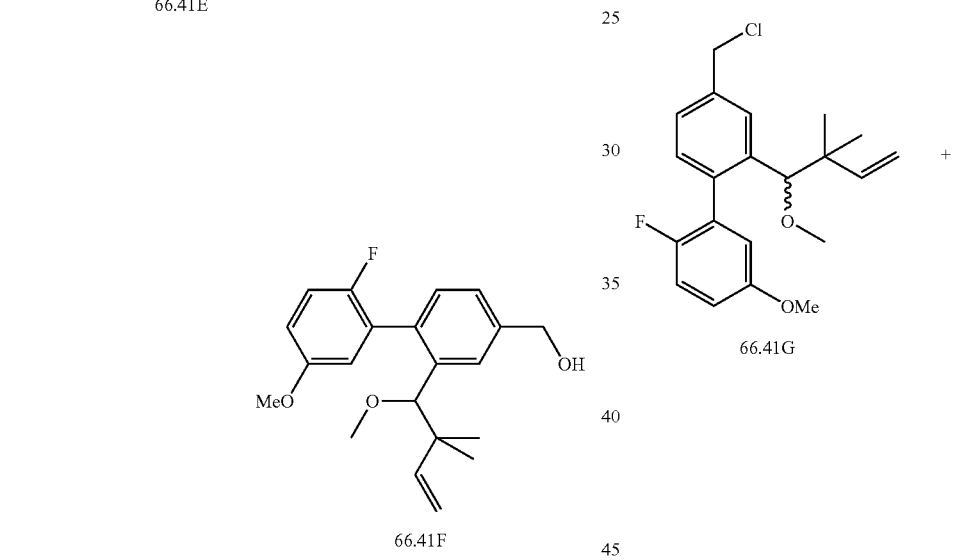

66.41F

[2'-Fluoro-5'-methoxy-2-(1-methoxy-2,2-dimethyl-but-3-enyl)-biphenyl-4-yl]-methanol (66.41F). Compound 66.41F was synthesized from 66.41E by a method analogous to that used to prepare compound 8.9 from 8.8. MS ESI m/e: 345.2 (M+H)$^+$.

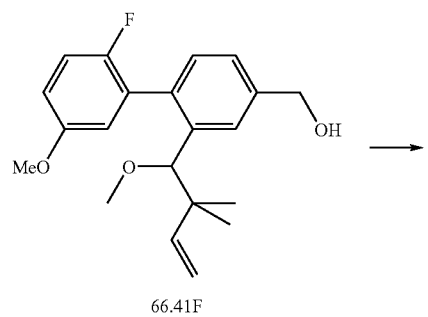

66.41F

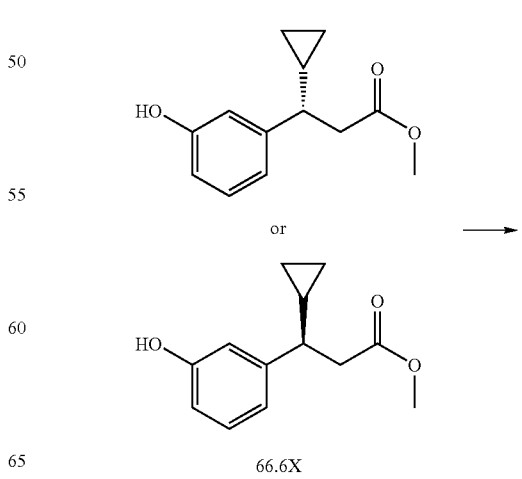

66.6X

-continued

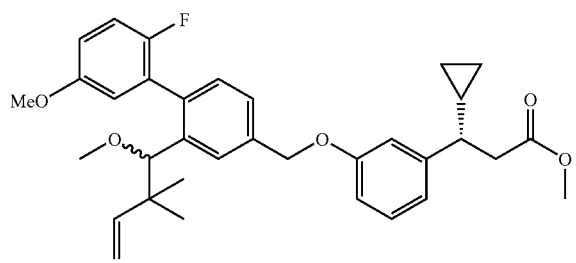

or

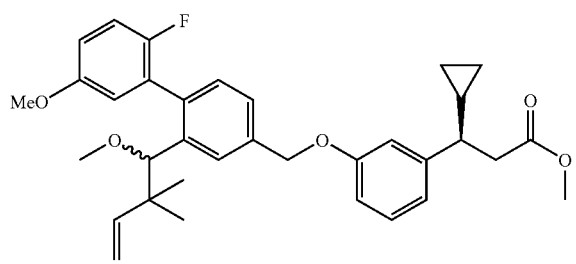

66.41H (R)-3-{3-[2'-Fluoro-5'-methoxy-2-(1-methoxy-2,2-dimethyl-but-3-enyl)-biphenyl-4-ylmethoxy]-phenyl}-pentanoic acid methyl ester or (S)-3-{3-[2'-fluoro-5'-methoxy-2-(1-methoxy-2,2-dimethyl-but-3-enyl)-biphenyl-4-ylmethoxy]-phenyl}-pentanoic acid methyl ester (66.41H). Compound 66.41H was synthesized from 66.41G and 66.6X using a method analogous to the method used to prepare compound 66.13P. MS ESI m/e: 547.3 (M+H)⁺.

-continued

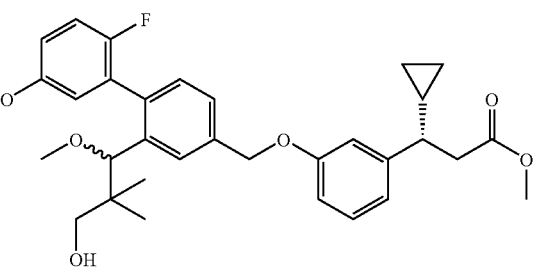

or

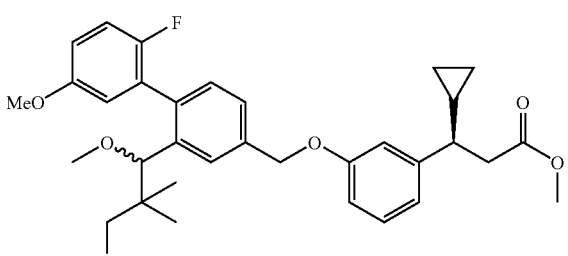

66.41I (S)-3-Cyclopropyl-3-{3-[2'-fluoro-2-(3-hydroxy-1-methoxy-2,2-dimethyl-propyl)-5'-methoxy-biphenyl-4-ylmethoxy]-phenyl}-propionic acid methyl ester or (R)-3-cyclopropyl-3-{3-[2'-fluoro-2-(3-hydroxy-1-methoxy-2,2-dimethyl-propyl)-5'-methoxy-biphenyl-4-ylmethoxy]-phenyl}-propionic acid methyl ester (66.41I). Into a solution of 66.41H (303 mg, 554 μmol) at −78° C. in DCM/methanol (1 mL/5 mL), was bubbled with O₃ for 3 minutes and then sodium borohydride (195 μL, 5543 μmol) was added. The mixture was stirred at room temperature for 16 hours and then solvent was removed and the reaction mixture was diluted with EtOAc. The organic phase was washed carefully with saturated aqueous NaHCO₃, once with brine, and then dried over anhydrous sodium sulfate. After filtration, the organic solvent was removed in vacuo to yield 66.41I that was used without purification. MS ESI m/e: 551.3 (M+H)⁺.

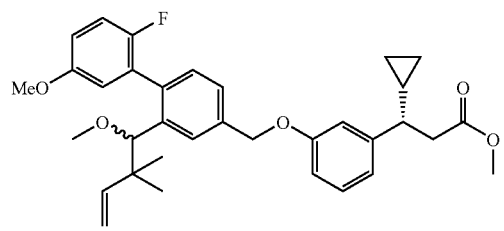

or

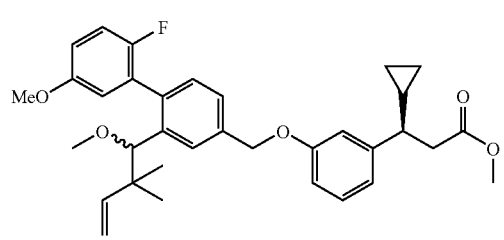

66.41H

⟶

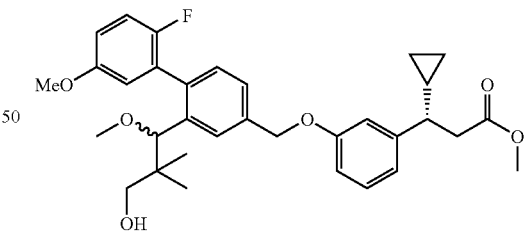

or

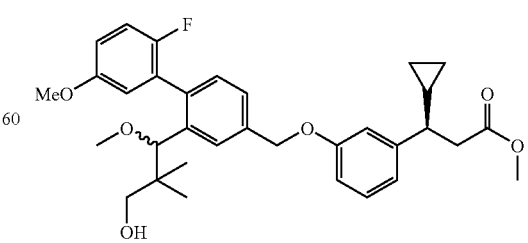

66.41I

⟶

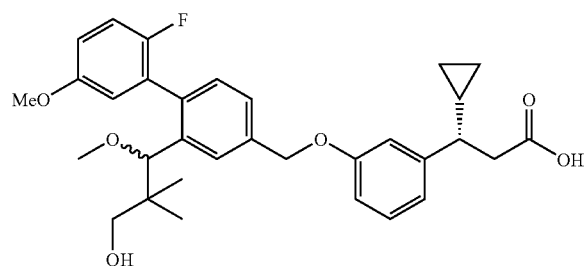

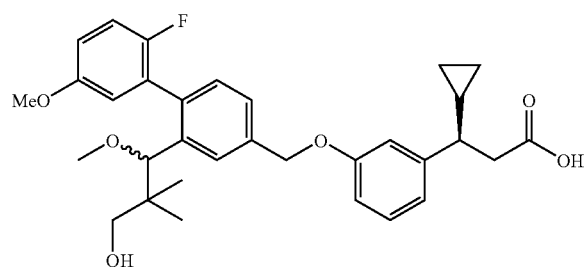

66.41

(S)-3-Cyclopropyl-3-{3-[2'-fluoro-2-(3-hydroxy-1-methoxy-2,2-dimethyl-propyl)-5'-methoxy-biphenyl-4-ylmethoxy]-phenyl}-propionic acid or (R)-3-cyclopropyl-3-{3-[2'-fluoro-2-(3-hydroxy-1-methoxy-2,2-dimethyl-propyl)-5'-methoxy-biphenyl-4-ylmethoxy]-phenyl}-propionic acid (66.41). Compound 66.41 was synthesized by a method analogous to the method used to prepare compound 66.13 from 66.13P. MS ESI m/e: 537.3 (M+H)+. $^1$H NMR (400 MHz, CDCl$_3$) δ ppm 7.55 (m, 1H), 7.45 (m, 1H), 7.21 (m, 2H), 7.01 (m, 1H), 6.94 (m 3H) 6.79 (m, 1H), 6.71 (m, 1H), 5.18 (s, 2H), 4.47 (s, 0.4H) 4.26 (s, 0.6H), 3.79 (s, 3H), 3.25 (m, 5H), 2.77 (m, 2H), 2.37 (m, 1H), 1.03 (m, 1H), 0.61 (m, 7H), 0.43 (m, 1H), 0.29 (m, 1H), 0.19 (m, 1H).

Example 66.42

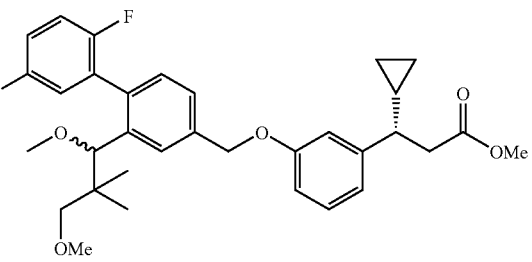

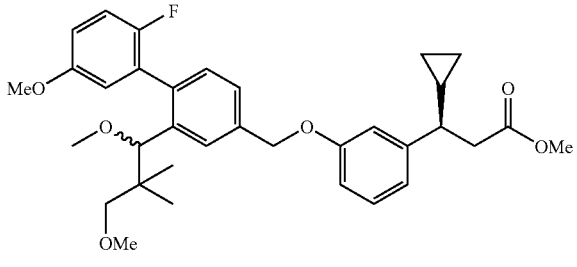

66.42A (S)-3-Cyclopropyl-3-{3-[2-(1,3-dimethoxy-2,2-dimethyl-propyl)-2'-fluoro-5'-methoxy-biphenyl-4-ylmethoxy]-phenyl}-propionic acid methyl ester or (R)-3-cyclopropyl-3-{3-[2-(1,3-dimethoxy-2,2-dimethyl-propyl)-2'-fluoro-5'-methoxy-biphenyl-4-ylmethoxy]-phenyl}-propionic acid methyl ester (66.42A). Compound 66.42A was synthesized by a method analogous to the method used to prepare compound 66.41E from 66.41D. MS ESI m/e: 565.3 (M+H)+.

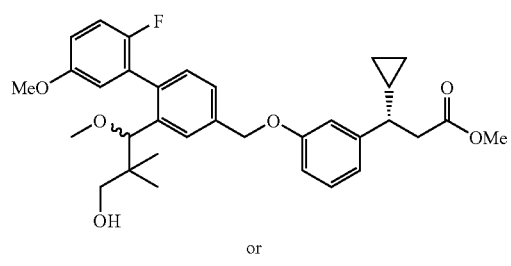

66.41I

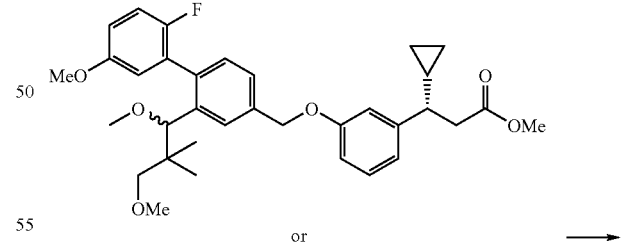

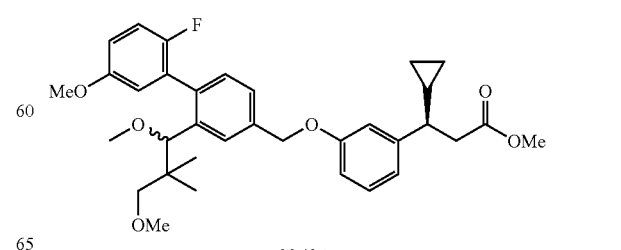

66.42A

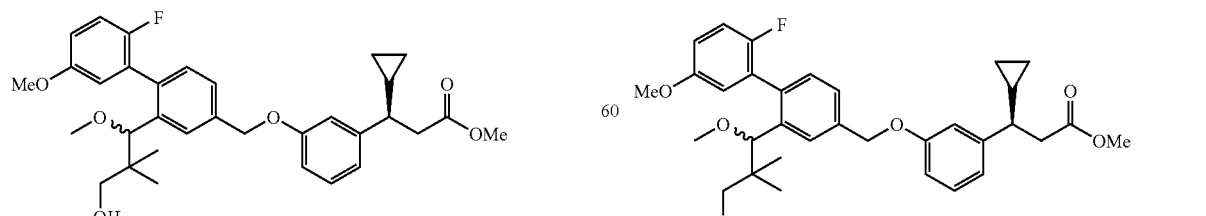

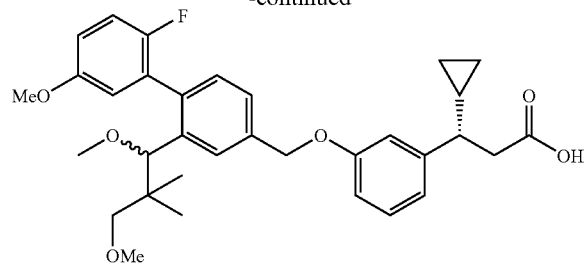

or

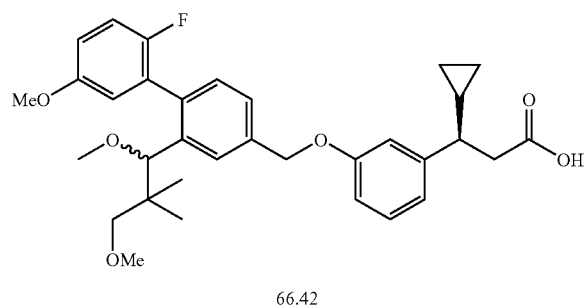

66.42

(S)-3-Cyclopropyl-3-{3-[2-(1,3-dimethoxy-2,2-dimethyl-propyl)-2'-fluoro-5'-methoxy-biphenyl-4-ylmethoxy]-phenyl}-propionic acid or (S)-3-Cyclopropyl-3-{3-[2-(1,3-dimethoxy-2,2-dimethyl-propyl)-2'-fluoro-5'-methoxy-biphenyl-4-ylmethoxy]-phenyl}-propionic acid (66.42). Compound 66.42 was synthesized using a method analogous to that used to prepare compound 66.13 from 66.13P. MS ESI m/e: 551.3 (M+H)+. $^1$H NMR (400 MHz, CDCl$_3$) δ ppm 7.57 (m, 1H), 7.42 (m, 1H), 7.20 (m, 2H), 7.01 (m, 1H), 6.86 (m, 4H), 6.74 (m 1H), 5.15 (s, 2H), 4.41 (s, 0.3H) 4.19 (s, 0.7H), 3.78 (s, 3H), 3.19 (m, 7H), 2.96 (m, 1H), 2.78 (m, 2H), 2.36 (m, 1H), 1.01 (m, 1H), 0.74 (s, 3H), 0.56 (m, 4H), 0.41 (m, 1H), 0.28 (m, 1H), 0.17 (m, 1H).

Example 66.43

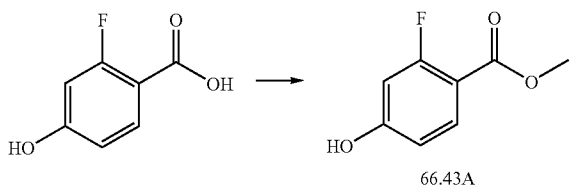

Methyl 2-fluoro-4-hydroxybenzoate (66.43A). To a round bottom containing 2-fluoro-4-hydroxybenzoic acid (5.34 g, 34.19 mmol) (commercially available from Matrix Scientific and TCI America) was added a cold solution of MeOH (50 mL) and sulfuric acid (2.0 mL). The mixture was heated to 80° C. and monitored with TLC. After 20.5 hours, the solvent was removed, and the mixture was diluted with diethyl ether. The organic phase was washed carefully two times with saturated. aqueous NaHCO$_3$, once with brine, and then dried over anhydrous sodium sulfate. After filtration, the organic solvent was removed in vacuo to yield 66.43A as a white solid (5.82, 85% yield). $^1$H NMR (400 MHz, DMSO-d$_6$) δ ppm 10.79 (1H, s), 7.75 (1H, t, J=8.8 Hz), 6.69 (1H, dd, J=8.6, 2.3 Hz), 6.62 (1H, dd, J=13.1, 2.2 Hz), 3.78 (3H, s).

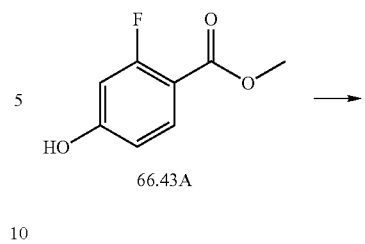

Methyl 5-bromo-2-fluoro-4-hydroxybenzoate (66.43B). To a solution of 66.43A (2.03 g, 11.9 mmol) in acetic acid (65 mL) was added a pre-mixed solution of bromine (0.67 mL, 13.1 mmol) in acetic acid (10 mL). The mixture was stirred at 45° C. and monitored with TLC and LC-MS. After 18 hours, the reaction mixture was concentrated under reduced pressure. Brine was added to the residue, and the mixture was extracted three times with EtOAc. The combined organic layers were dried over anhydrous magnesium sulfate, filtered and concentrated to provide 66.43B as a white solid (2.12 g, 71% yield). $^1$H NMR (400 MHz, CDCl$_3$) δ ppm 8.13 (1H, d, J=7.4 Hz), 6.82 (1H, d, J=11.3 Hz), 6.04 (1H, s), 3.92 (3H, s).

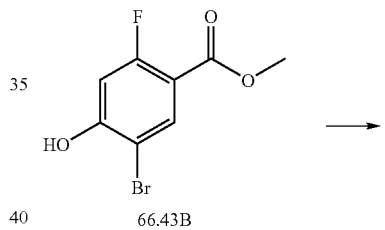

Methyl 5-bromo-2-fluoro-4-(tetrahydro-2H-pyran-2-yloxy)benzoate (66.43C). To a round bottom containing 66.43B (13.15 g, 52.8 mmol) in dry DCM (90 mL) was added 3,4-dihydro-2H-pyran (10 mL, 110 mmol) followed by PPTS (0.13 g, 0.53 mmol). The reaction mixture was heated to a gentle reflux (50° C.) and monitored with TLC and LC-MS. After 24 hours, the reaction was concentrated under reduced pressure and then diluted with MeOH. After concentration, the residue was heated in a round bottom flask containing MeOH on the rotary evaporator (without vacuum.) at 40° C. After about 30 minutes, the solution was concentrated to a volume of about 5 mL. After cooling to room temperature, the white solid was filtered and rinsed once with MeOH to yield 66.43C (13.35 g, 76% yield). $^1$H NMR (400 MHz, CDCl$_3$) δ ppm 8.25 (1H, m), 6.96 (1H, d, J=12.5 Hz), 5.56 (1H, m), 3.91 (3H, s), 3.79 (1H, td, J=11.1, 2.5 Hz), 3.65 (1H, d, J=10.6 Hz), 2.23 (2H, m), 1.96 (3H, m), 1.68 (1H, m).

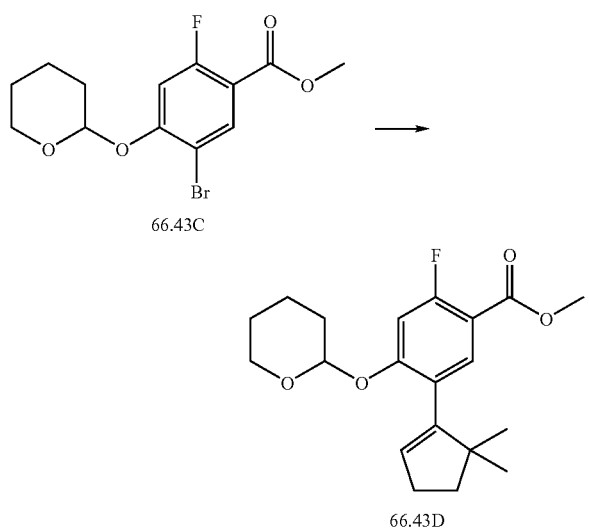

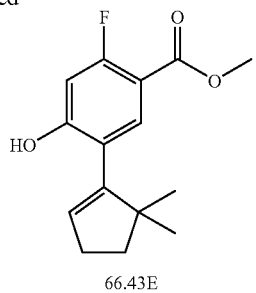

Methyl 5-(5,5-dimethylcyclopent-1-enyl)-2-fluoro-4-hydroxybenzoate (66.43E). To a stirred mixture of 66.43D (5.65 g, 16.2 mmol) in MeOH (60 mL) was added PPTS (0.42 g, 1.69 mmol). The mixture was heated to 50° C. and monitored with TLC and LCMS. After 19 hours, the organic solvent was removed under reduced pressure, and the residue was then purified on silica gel (0-15% EtOAc in hexanes) to yield 66.43E as a white solid (3.47 g, 81% yield). $^1$H NMR (500 MHz, CDCl$_3$) δ ppm 7.69 (1H, d, J=8.3 Hz), 6.71 (1H, d, J=12.0 Hz), 5.93 (1H, d, J=1.7 Hz), 5.80 (1H, t, J=2.4 Hz), 3.90 (3H, s), 2.54 (2H, m), 1.93 (2H, t, J=7.1 Hz), 1.11 (6H, s).

Methyl 5-(5,5-dimethylcyclopent-1-enyl)-2-fluoro-4-(tetrahydro-2H-pyran-2-yloxy)benzoate (66.43D). A stirred mixture of 66.43 C (10.33 g, 31.0 mmol), ground S-Phos (2.55 g, 6.21 mmol), palladium acetate (0.70 g, 3.11 mmol), and potassium phosphate, tribasic (16.49 g, 77.7 mmol) in DMF (75 mL) and water (4 mL) was purged with argon and placed under vacuum and the process repeated three times. Before heating, 2-(5,5-dimethylcyclopent-1-enyl)-4,4,5,5-tetramethyl-1,3,2-dioxaborolane (66.6 C) (8.96 g, 40.4 mmol) was added via syringe. The mixture was then heated at 75° C. After 21 hours, the reaction was cooled to room temperature, diluted with water, and extracted three times with EtOAc. The organic layers were combined and washed twice with brine. After drying over anhydrous sodium sulfate and filtration, the organic solvent was removed under reduced pressure. The residue was purified by silica gel flash chromatography (0-10% EtOAc/hexane) to yield 66.43D (5.65 g, 52% yield).

$^1$H NMR (400 MHz, CDCl$_3$) δ ppm 7.63 (1H, d, J=8.6 Hz), 6.93 (1H, d, J=13.3 Hz), 5.55 (1H, t, J=2.3 Hz), 5.43 (1H, t, J=2.7 Hz), 3.90 (3H, s), 3.82 (1H, m), 3.67 (1H, m), 2.41 (2H, td, J=7.0, 2.3 Hz), 1.97 (5H, m), 1.79 (3H, m), 1.07 (6H, d, J=13.7 Hz).

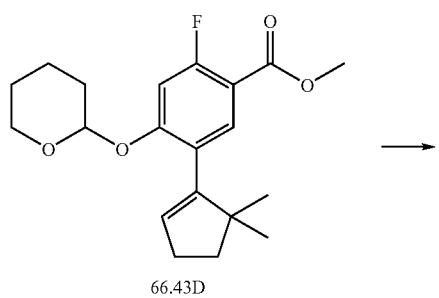

Methyl 5-(5,5-dimethylcyclopent-1-enyl)-2-fluoro-4-(trifluoromethylsulfonyloxy)benzoate (66.43F). To a stirred solution of 66.43E (0.80 g, 3.02 mmol) in dry DCM (15 mL) was added TEA (1.0 mL, 7.19 mmol) and 4-dimethylaminopyridine (38.1 mg, 0.312 mmol). After about 20 minutes, N-phenyl-bis(trifluoromethanesulfonimide) (1.30 g, 3.64 mmol) was added in portions. Upon complete addition, the solution was stirred at room temperature and monitored with TLC and LC-MS. After 19 hours, the organic solvent was removed under reduced pressure and the resulting residue was purified with silica gel chromatography using 0-10% EtOAc in hexanes to yield 66.43F as a colorless oil (1.05 g, 88% yield). $^1$H NMR (400 MHz, CDCl$_3$) δ ppm 7.84 (1H, d, J=7.8 Hz), 7.13 (1H, d, J=10.2 Hz), 5.79 (1H, t, J=2.3 Hz), 3.96 (3H, s), 2.47 (2H, td, J=7.0, 2.3 Hz), 1.91 (2H, t, J=7.0 Hz), 1.08 (6H, s).

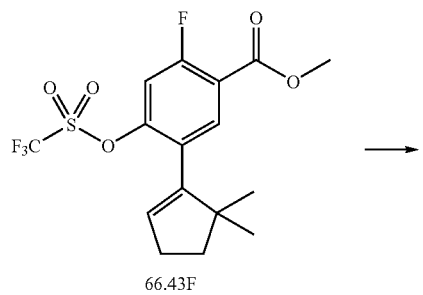

66.43F

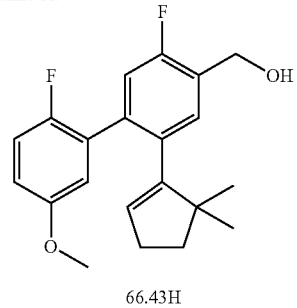

66.43H (2-(5,5-Dimethyl-1-cyclopenten-1-yl)-2',5-difluoro-5'-(methyloxy)-1,1'-biphenyl-4-yl)methanol (66.43H). To a cooled solution of 66.43G (0.92 g, 2.47 mmol) in dry THF (15 mL) at 0° C. was added LAH (1.0 M in THF) (5.0 mL, 5.0 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by flash chromatography (silica gel 60, eluted with 0%-50% EtOAc in hexanes). Fractions containing the desired product were combined and concentrated to provide 66.43H as a colorless oil (0.70 g, 82% yield). $^1$H NMR (500 MHz, CDCl$_3$) δ ppm 7.30 (1H, m), 7.05 (1H, dd, J=10.6, 1.1 Hz), 6.97 (1H, t, J=8.9 Hz), 6.83 (2H, m), 5.52 (1H, td, J=2.4, 0.9 Hz), 4.81 (2H, s), 3.76 (3H, s), 2.25 (2H, td, J=7.1, 2.4 Hz), 1.76 (1H, br. s.), 1.69 (2H, m), 0.85 (6H, s).

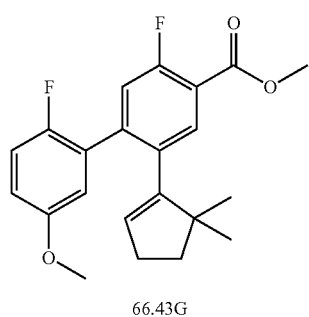

66.43G

Methyl 2-(5,5-dimethyl-1-cyclopenten-1-yl)-2',5-difluoro-5'-(methyloxy)-1,1'-biphenyl-4-carboxylate (66.43G). To a stirred solution of 66.43F (1.05 g, 2.65 mmol) in DMF (5 mL) at 23° C. was added 2-fluoro-5-methoxyphenylboronic acid (0.90 g, 5.32 mmol) (commercially available from Aldrich) and potassium carbonate (1.10 g, 7.96 mmol) followed by tetrakis(triphenylphosphine)palladium (0.31 g, 0.27 mmol). The mixture was heated to 90° C. After 17 hours, the mixture was cooled to room temperature and then diluted with water. After extracting three times with EtOAc, the mixture was concentrated in vacuo and then purified on silica gel (0%-10% EtOAc/hexane) to give 66.43G as a clear oil that was used without further purification (0.92 g, 93% yield). $^1$H NMR (400 MHz, CDCl$_3$) δ ppm 7.79 (1H, d, J=7.4 Hz), 7.13 (1H, d, J=11.3 Hz), 6.99 (1H, t, J=9.0 Hz), 6.84 (1H, dt, J=8.7, 3.7 Hz), 6.78 (1H, dd, J=5.9, 3.1 Hz), 5.55 (1H, s), 3.96 (3H, s), 3.79 (3H, s), 2.27 (2H, td, J=7.1, 2.5 Hz), 1.67 (2H, t, J=7.0 Hz), 0.84 (6H, s).

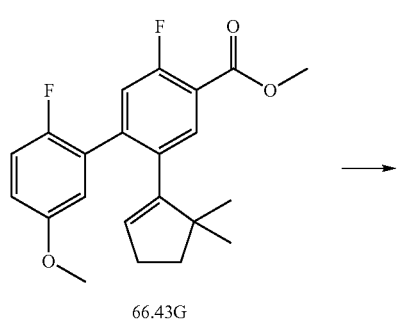

66.43G

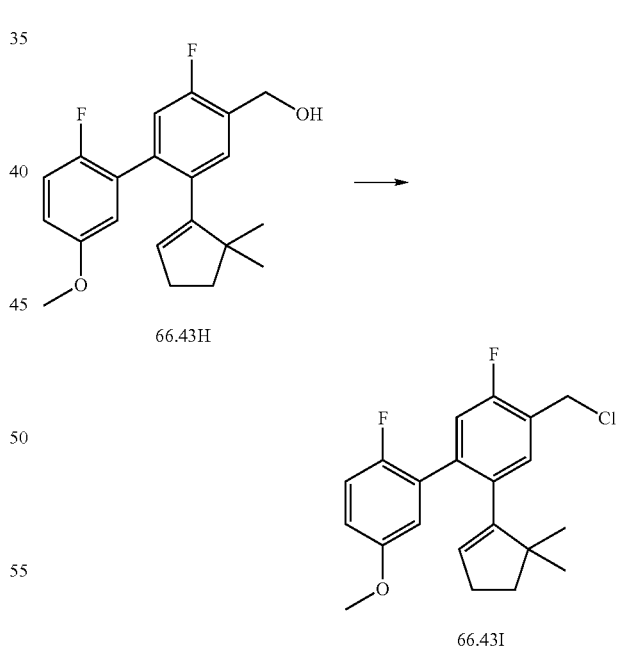

66.43H 66.43I 4-(Chloromethyl)-2-(5,5-dimethyl-1-cyclopenten-1-yl)-2',5-difluoro-5'-(methyloxy)-1,1'-biphenyl (66.43I). To a solution of 66.43H (0.17 g, 0.48 mmol) in dry DCM (2.0 mL) and dry DMF (0.020 mL) was added thionyl chloride (0.080 mL, 1.1 mmol) dropwise at 0° C. The resulting solution was warmed to room temperature and monitored with TLC and LCMS. After 45 minutes, the reaction was concentrated and then purified by silica gel flash chromatography (0-5%

EtOAc/hexane) to afford 66.43I as a colorless oil (0.16 g, 93% yield). ¹H NMR (400 MHz, CDCl₃) δ ppm 7.29 (1H, d, J=7.8 Hz), 7.08 (1H, d, J=10.2 Hz), 6.98 (1H, t, J=9.0 Hz), 6.85 (2H, m), 5.56 (1H, s), 4.69 (2H, s), 3.77 (3H, s), 2.27 (2H, td, J=7.0, 2.7 Hz), 1.68 (2H, t, J=7.0 Hz), 0.86 (6H, s).

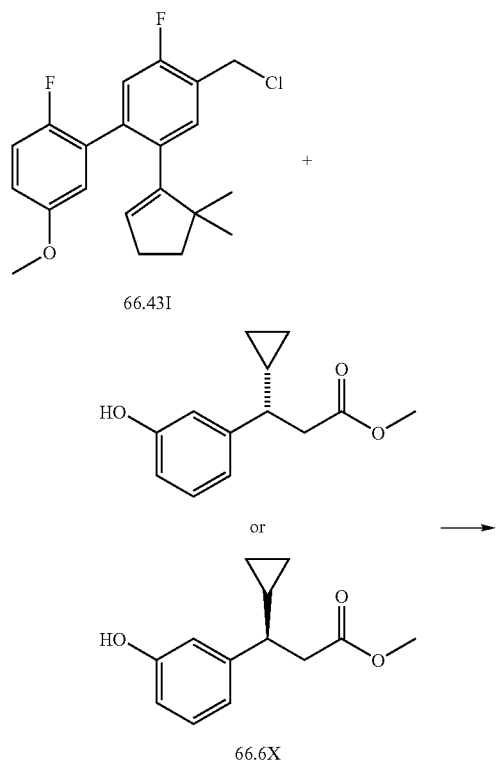

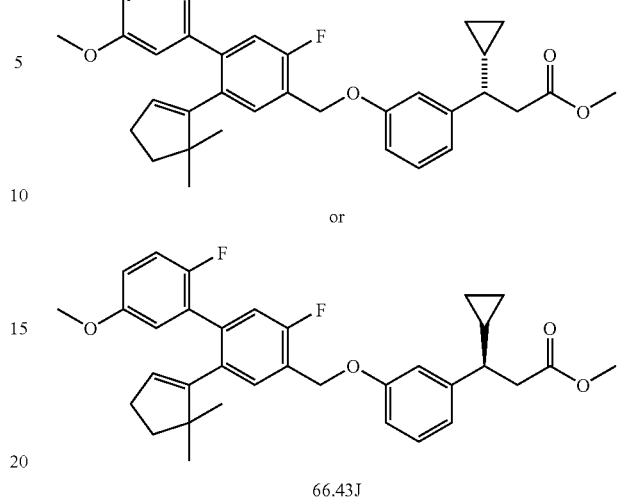

Methyl (3S)-3-cyclopropyl-3-(3-(((2-(5,5-dimethyl-1-cyclopenten-1-yl)-2',5-difluoro-5'-(methyloxy)-1,1'-biphenyl-4-yl)methyl)oxy)phenyl)propanoate or methyl (3R)-3-cyclopropyl-3-(3-(((2-(5,5-dimethyl-1-cyclopenten-1-yl)-2',5-difluoro-5'-(methyloxy)-1,1'-biphenyl-4-yl)methyl)oxy) phenyl)propanoate (66.43J). To a vial containing 66.6X (23.3 mg, 0.11 mmol) in 1.0 mL dry DMF was added cesium carbonate (42.0 mg, 0.13 mmol). The mixture was stirred at room temperature for 10 minutes and then 66.43I (42.4 mg, 0.12 mmol) was added. After 22 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-10% EtOAc/hexane) to afford 66.43J as a colorless oil (50.6 mg, 88% yield). MS ESI (pos.) m/e: 568.9 (M+H₂O)⁺.

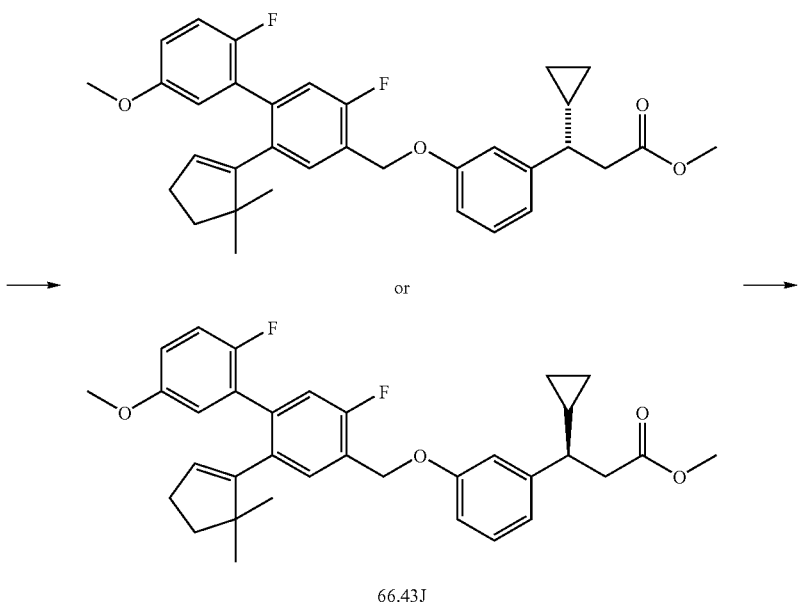

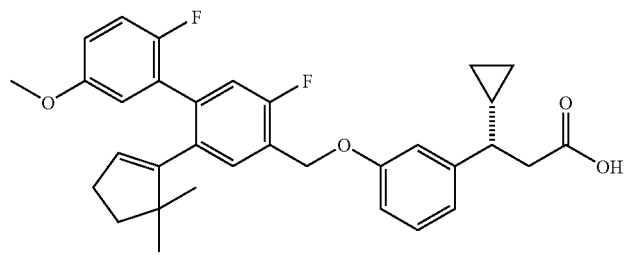

or


66.43

(3S)-3-Cyclopropyl-3-(3-(((2-(5,5-dimethyl-1-cyclopenten-1-yl)-2',5-difluoro-5'-(methyloxy)-1,1'-biphenyl-4-yl)methyl)oxy)phenyl)propanoic acid or (3R)-3-cyclopropyl-3-(3-(((2-(5,5-dimethyl-1-cyclopenten-1-yl)-2',5-difluoro-5'-(methyloxy)-1,1'-biphenyl-4-yl)methyl)oxy)phenyl)propanoic acid (66.43). A pre-mixed solution of 2M NaOH (0.50 mL, 1.00 mmol), MeOH (1.00 mL), and THF (1.00 mL) was added to a vial containing 66.43J (50.6 mg, 0.0926 mmol). This solution was stirred at room temperature and monitored with TLC and LC-MS. After 24 hours, the mixture was diluted with water and acidified with 1M aqueous HCl solution and then extracted five times with EtOAc. The organic phase was dried over anhydrous magnesium sulfate, filtered, and concentrated. The residue was purified by silica gel flash chromatography (0-40% EtOAc/hexane) to afford 66.43 as a colorless oil (37.2 mg, 76% yield). $^1$H NMR (400 MHz, CDCl$_3$) δ ppm 7.40 (1H, d, J=7.4 Hz), 7.30 (1H, d, J=7.0 Hz), 7.12 (1H, d, J=10.2 Hz), 7.01 (1H, t, J=8.8 Hz), 6.96 (3H, m), 2H, m), 5.55 (1H, s), 5.20 (2H, s), 3.80 (3H, s), 2.83 (2H, ddd, J=20.0, 15.3, 7.4 Hz), 2.46 (1H, m), 2.28 (2H, td, J=6.9, 2.2 Hz), 1.69 (2H, t, J=7.0 Hz), 1.12 (1H, m), 0.85 (6H, s), 0.69 (1H, m), 0.51 (1H, m), 0.34 (1H, dq, J=9.7, 4.8 Hz), 0.20 (1H, dq, J=9.6, 4.9 Hz). MS ESI (neg.) m/e: 531.0 (M−H)$^+$.

Example 66.44

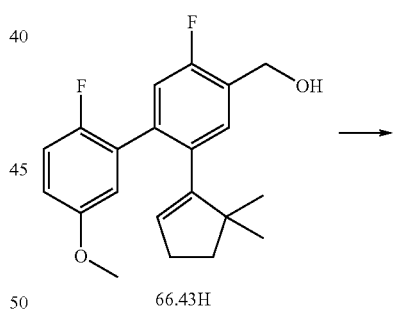

66.43H

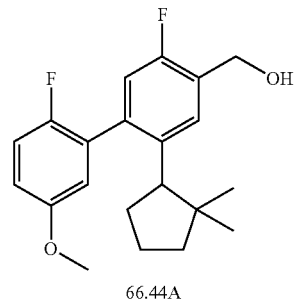

66.44A

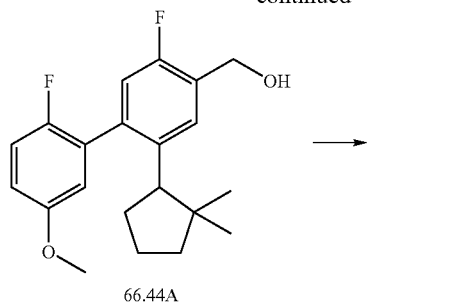

66.44A

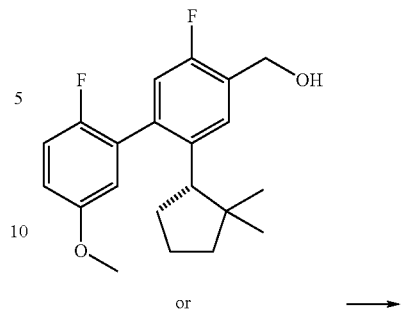

66.44B or

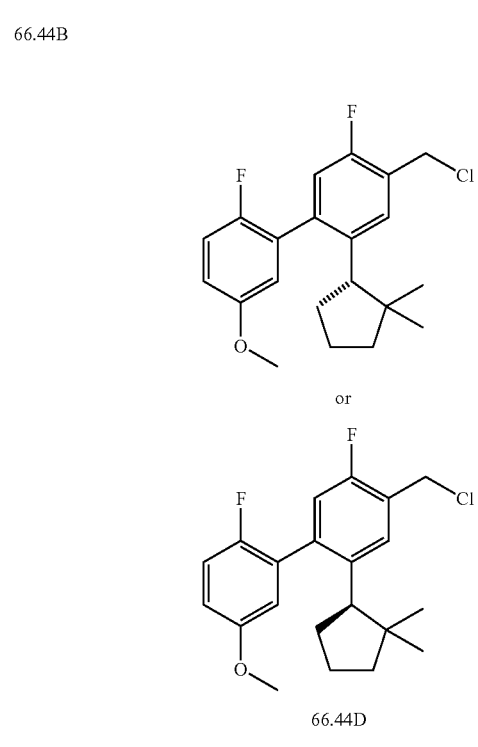

66.44B and 66.44C (2-(2,2-Dimethylcyclopentyl)-2',5-difluoro-5'-(methyloxy)-1,1'-biphenyl-4-yl)methanol (66.44A). To a dry flask containing 66.43H (0.70 g, 2.03 mmol) in dry MeOH (5 mL) and EtOAc (3 mL) was added palladium, 10 wt. % on activated carbon (77.2 mg). After purging, the mixture was stirred under an atmosphere of hydrogen at room temperature. After 4.5 hours, the mixture was filtered through Celite. After concentration, the residue was identified as 66.44A as a mixture of enantiomers and rotamers (0.31 g, 45% yield). Chiral separation of 66.44A was accomplished on Chiracel-OJ (2% IPA in hexane) to provide 66.44B (peak 1) and 66.44C (peak 2). Both enantiomers were used to synthesize example compounds, and both enantiomers gave active compounds.

4-(Chloromethyl)-2-((1S)-2,2-dimethylcyclopentyl)-2',5-difluoro-5'-(methyloxy)-1,1'-biphenyl or 4-(chloromethyl)-2-((1R)-2,2-dimethylcyclopentyl)-2',5-difluoro-5'-(methyloxy)-1,1'-biphenyl (66.44D). To a solution of 66.44B (0.71 g, 2.05 mmol) in dry DCM (23 mL) and dry DMF (0.18 mL) was added thionyl chloride (0.3 mL, 4.1 mmol) dropwise at 0° C. The resulting solution was warmed to room temperature and monitored with TLC and LCMS. After 45 minutes, the reaction was concentrated and then purified by silica gel flash chromatography (0-5% EtOAc/hexane) to yield 66.44D as a colorless oil (0.73 g, 97% yield). $^1$H NMR (400 MHz, CDCl$_3$) δ ppm 7.46 (1H, m), 7.11 (3H, m), 6.75 (1H, m), 4.78 (2H, m), 3.80 (3H, s), 2.91 (1H, m), 2.20 (2H, m), 1.87 (2H, m), 1.59 (1H, m), 1.43 (1H, m), 0.77 (3H, m), 0.64 (3H, m).

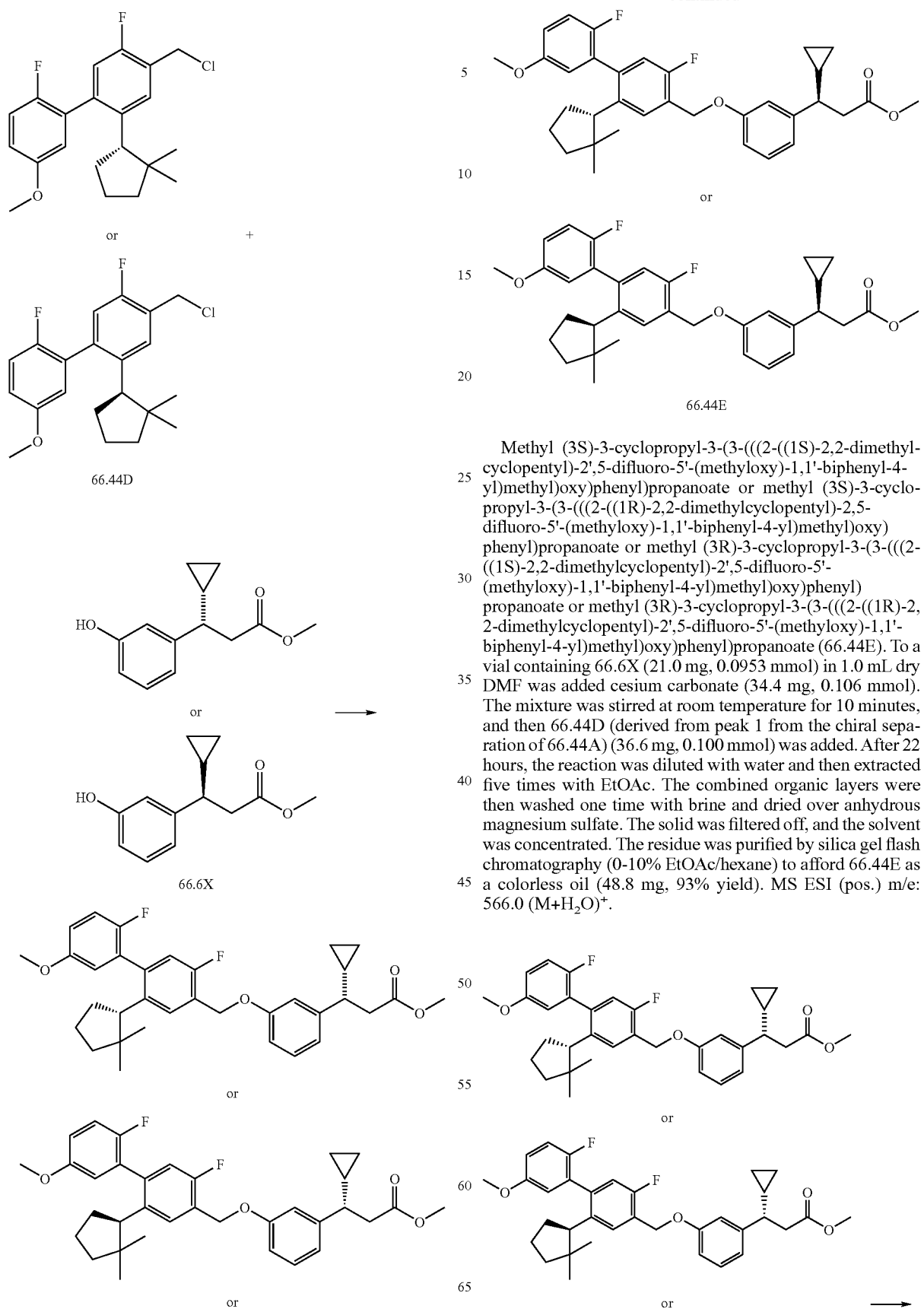

Methyl (3S)-3-cyclopropyl-3-(3-(((2-((1S)-2,2-dimethylcyclopentyl)-2',5-difluoro-5'-(methyloxy)-1,1'-biphenyl-4-yl)methyl)oxy)phenyl)propanoate or methyl (3S)-3-cyclopropyl-3-(3-(((2-((1R)-2,2-dimethylcyclopentyl)-2,5-difluoro-5'-(methyloxy)-1,1'-biphenyl-4-yl)methyl)oxy)phenyl)propanoate or methyl (3R)-3-cyclopropyl-3-(3-(((2-((1S)-2,2-dimethylcyclopentyl)-2',5-difluoro-5'-(methyloxy)-1,1'-biphenyl-4-yl)methyl)oxy)phenyl)propanoate or methyl (3R)-3-cyclopropyl-3-(3-(((2-((1R)-2,2-dimethylcyclopentyl)-2',5-difluoro-5'-(methyloxy)-1,1'-biphenyl-4-yl)methyl)oxy)phenyl)propanoate (66.44E). To a vial containing 66.6X (21.0 mg, 0.0953 mmol) in 1.0 mL dry DMF was added cesium carbonate (34.4 mg, 0.106 mmol). The mixture was stirred at room temperature for 10 minutes, and then 66.44D (derived from peak 1 from the chiral separation of 66.44A) (36.6 mg, 0.100 mmol) was added. After 22 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-10% EtOAc/hexane) to afford 66.44E as a colorless oil (48.8 mg, 93% yield). MS ESI (pos.) m/e: 566.0 (M+H$_2$O)$^+$.

-continued

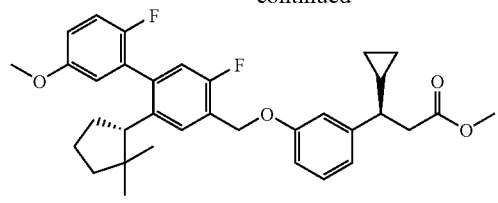

or

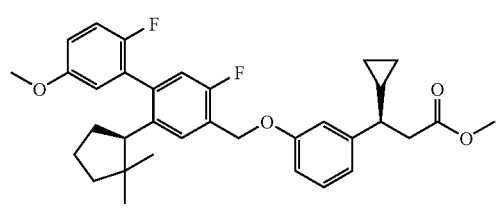

66.44E

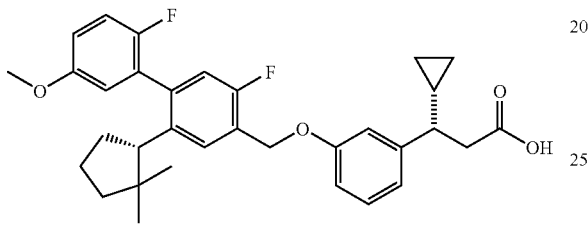

or

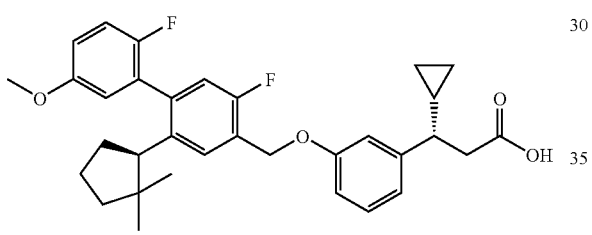

or


or


66.44

(3S)-3-Cyclopropyl-3-(3-(((2-((1S)-2,2-dimethylcyclopentyl)-2',5-difluoro-5'-(methyloxy)-1,1'-biphenyl-4-yl)methyl)oxy)phenyl)propanoic acid or (3S)-3-cyclopropyl-3-(3-(((2-((1R)-2,2-dimethylcyclopentyl)-2',5-difluoro-5'-(methyloxy)-1,1'-biphenyl-4-yl)methyl)oxy)phenyl)propanoic acid or (3R)-3-cyclopropyl-3-(3-(((2-((1S)-2,2-dimethylcyclopentyl)-2',5-difluoro-5'-(methyloxy)-1,1'-biphenyl-4-yl)methyl)oxy)phenyl)propanoic acid or (3R)-3-cyclopropyl-3-(3-(((2-((1R)-2,2-dimethylcyclopentyl)-2',5-difluoro-5'-(methyloxy)-1,1'-biphenyl-4-yl)methyl)oxy) phenyl)propanoic acid (66.44). A pre-mixed solution of 2M NaOH (0.50 mL, 1.00 mmol), MeOH (1.00 mL), and THF (1.00 mL) was added to a vial containing 66.44E (48.8 mg, 0.0889 mmol). The resulting solution was stirred at room temperature and monitored with TLC and LC-MS. After 24 hours, the mixture was diluted with water and acidified with 1M aqueous HCl solution. The resulting mixture was then extracted five times with EtOAc. The combined organic layers were dried over anhydrous magnesium sulfate, filtered, and concentrated. The residue was purified by silica gel flash chromatography (0-30% EtOAc/hexane) to afford 66.44 as a colorless oil (37.4 mg, 79% yield). MS ESI (neg.) m/e: 532.9 $(M-H)^+$.

Asymmetric Synthesis of 66.44B or 66.44C

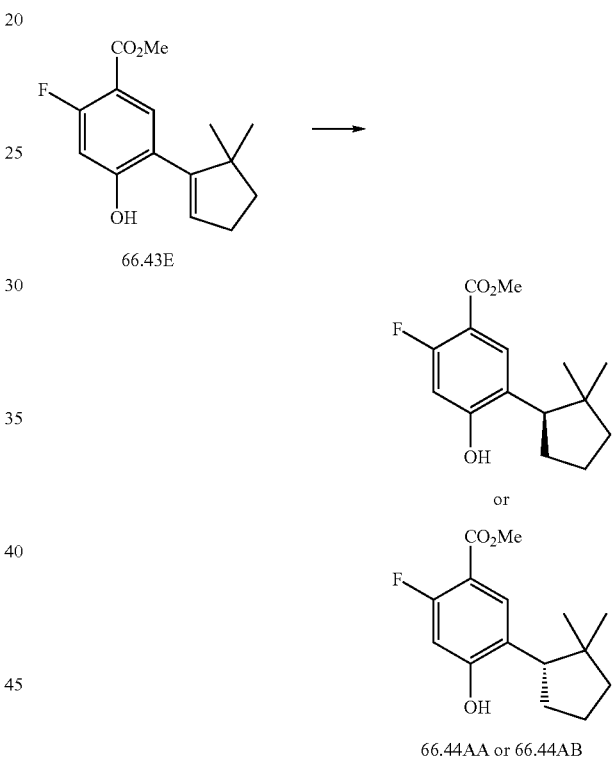

(R)-Methyl 5-(2,2-dimethylcyclopentyl)-2-fluoro-4-hydroxybenzoate or (S)-methyl 5-(2,2-dimethylcyclopentyl)-2-fluoro-4-hydroxybenzoate (66.44AA or 66.44AB). A mixture of $Rh(COD)_2BF_4$ (Stem Chemical) 35138-22-8, 36.95 mg, 0.091 mmol) and (R)-1-[(S)-2-(R)-(Ditertbutylphosphino)ferrocenyl]ethyl-bis-(3,5-bistrifluoromethylphenyl) phosphine (Solvias, SL-J210-1, 81.5 mg, 0.100 mmol), was stirred in THF (75 mL) under $N_2$ for 60 minutes and a dark red solution formed. To the resulting solution was added 66.43E (8.2 g, 45.4 mmol) and TEA (10 mol %, 0.63 mL, 4.54 mmol). The resulting solution was filled with $H_2$ (200 psi) three times and stirred at room temperature under 200 psi $H_2$ for 2 hours. The resulting mixture was passed through a short plug of silica gel, eluting with 1:1 hexane/EtOAc and then concentrated affording the desired product as a white solid (83% yield (6.8 g), 99.3% ee). The other enantiomer may be obtained as the majority product using the enantiomer of the ferrocenyl compound.

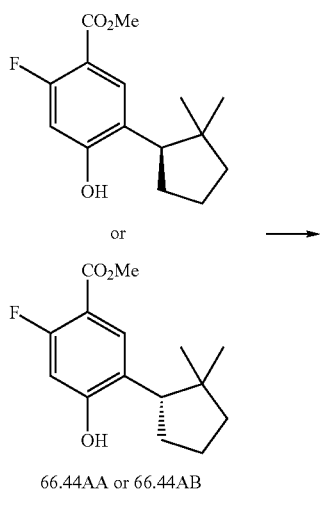

66.44AA or 66.44AB

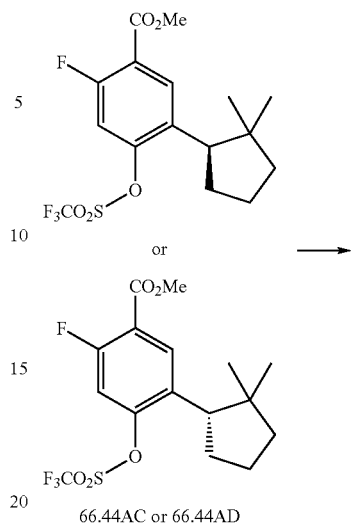

66.44AC or 66.44AD

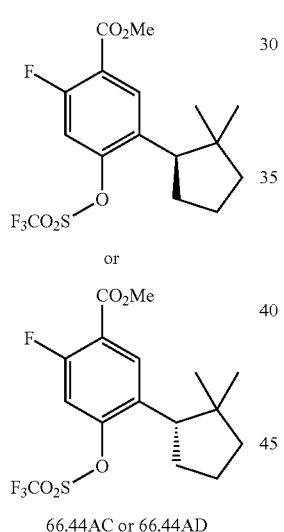

66.44AC or 66.44AD

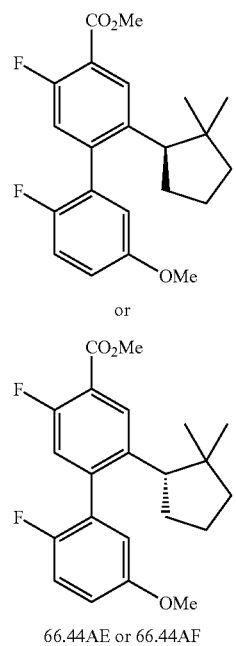

66.44AE or 66.44AF (R)-Methyl 5-(2,2-dimethylcyclopentyl)-2-fluoro-4-(trifluoromethylsulfonyloxy)benzoate or (S)-methyl 5-(2,2-dimethylcyclopentyl)-2-fluoro-4-(trifluoromethylsulfonyloxy)benzoate (66.44AC or 66.44AD). To a stirred solution of 66.44AA or 66.44AB (4.02 g, 15.1 mmol) in dry DCM (50 mL) was added TEA (4.2 mL, 30.2 mmol) and DMAP (0.19 g, 1.52 mmol). After 20 minutes, N-phenyl-bis(trifluoromethanesulfonimide) (5.94 g, 16.6 mmol) was added in portions. Upon complete addition, the solution was stirred at room temperature and monitored with TLC and LC-MS. After 4 hours, the mixture was washed twice with brine, dried over anhydrous magnesium sulfate. After filtration and concentration, the residue was purified with silica gel chromatography (0-10% EtOAc in hexanes) to yield 66.44AC or 66.44AD as a colorless oil (5.51 g, 92%). $^1$H NMR (500 MHz, CDCl$_3$) δ ppm 7.97 (1H, d, J=7.8 Hz), 7.14 (1H, d, J=10.0 Hz), 3.96 (3H, s), 3.13 (1H, dd, J=10.1, 8.2 Hz), 2.14 (2H, m), 1.96 (2H, m), 1.70 (2H, m), 1.00 (3H, s), 0.69 (3H, s).

Methyl 2-((1R)-2,2-dimethylcyclopentyl)-2',5-difluoro-5'-(methyloxy)-1,1'-biphenyl-4-carboxylate or methyl 2-((1S)-2,2-dimethylcyclopentyl)-2',5-difluoro-5'-(methyloxy)-1,1'-biphenyl-4-carboxylate (66.44AE or 66.44AF). To a stirred solution of 66.44AC or 66.44AD (5.51 g, 13.8 mmol) in DMF (25 mL) at 23° C. was added 2-fluoro-5-methoxyphenylboronic acid (4.71 g, 27.7 mmol) (commercially available from Aldrich and potassium carbonate (5.74 g, 41.6 mmol) followed by tetrakis(triphenylphosphine)palladium (1.60 g, 1.39 mmol). The mixture was heated to 90° C. After 3.5 hours, the mixture was cooled to room temperature and then diluted with water. After extracting three times with EtOAc, the mixture was concentrated in vacuo and then purified on silica gel (0%-10% EtOAc/hexane) to yield 66.44AE or 66.44AF as an oil that solidified (5.11 g, 99%).

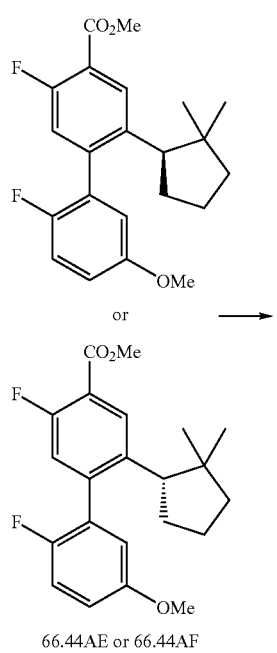

66.44AE or 66.44AF

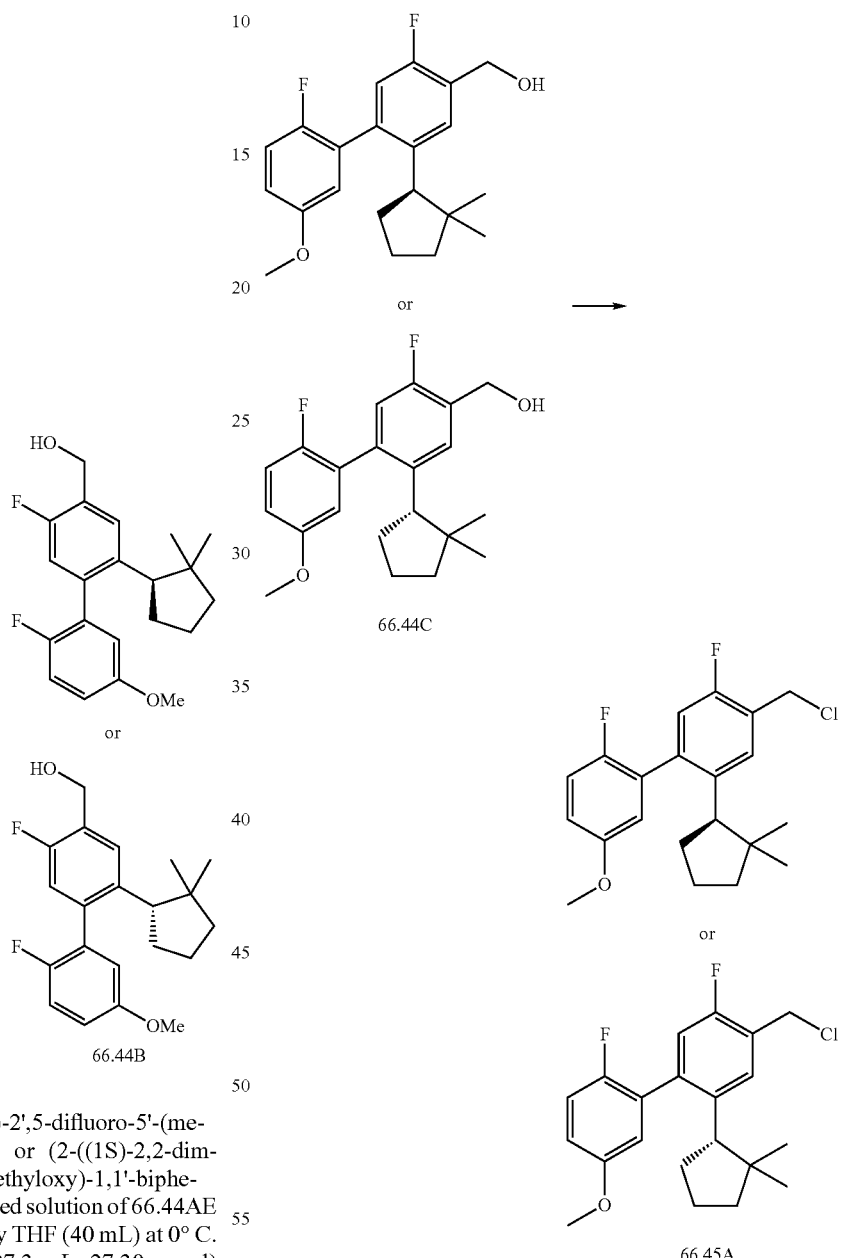

ppm 7.50 (1H, m), 7.11 (3H, m), 6.85 (1H, m), 4.81 (2H, s), 3.80 (3H, s), 2.92 (1H, m), 2.19 (2H, m), 1.83 (1H, m), 1.72 (1H, m), 1.59 (2H, m), 1.42 (1H, m), 0.82 (3H, m), 0.65 (3H, m).

Example 66.45

(2-((1R)-2,2-Dimethylcyclopentyl)-2',5-difluoro-5'-(methyloxy)-1,1'-biphenyl-4-yl)methanol or (2-((1S)-2,2-dimethylcyclopentyl)-2',5-difluoro-5'-(methyloxy)-1,1'-biphenyl-4-yl)methanol (66.44B). To a cooled solution of 66.44AE or 66.44AF (5.11 g, 13.6 mmol) in dry THF (40 mL) at 0° C. was added LAH, (1.0 M in THF) (27.3 mL, 27.30 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by silica gel chromatography (0-25% EtOAc in hexanes) to yield 66.44B (this enantiomer corresponds to peak one from the chiral separation of 66.44A on the OJ column) as a colorless oil (3.94 g, 83%). $^1$H NMR (400 MHz, CDCl$_3$) δ

4-(Chloromethyl)-2-((1R)-2,2-dimethylcyclopentyl)-2',5-difluoro-5'-(methyloxy)-1,1'-biphenyl or 4-(chloromethyl)-2-((1S)-2,2-dimethylcyclopentyl)-2',5-difluoro-5'-(methyloxy)-1,1'-biphenyl (66.45A). To a solution of 66.44C (40.0 mg, 0.12 mmol) in dry DCM (2.0 mL) and dry DMF (0.010 mL) was added thionyl chloride (0.020 mL, 0.27 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford 66.45A as a colorless oil (39.9 mg, 95% yield). ¹H NMR (400 MHz, CDCl₃) δ ppm 7.46 (1H, m), 7.11 (3H, m), 6.75 (1H, m), 4.78 (2H, m), 3.80 (3H, s), 2.91 (1H, m), 2.20 (2H, m), 1.87 (2H, m), 1.59 (1H, m), 1.43 (1H, m), 0.77 (3H, m), 0.64 (3H, m).

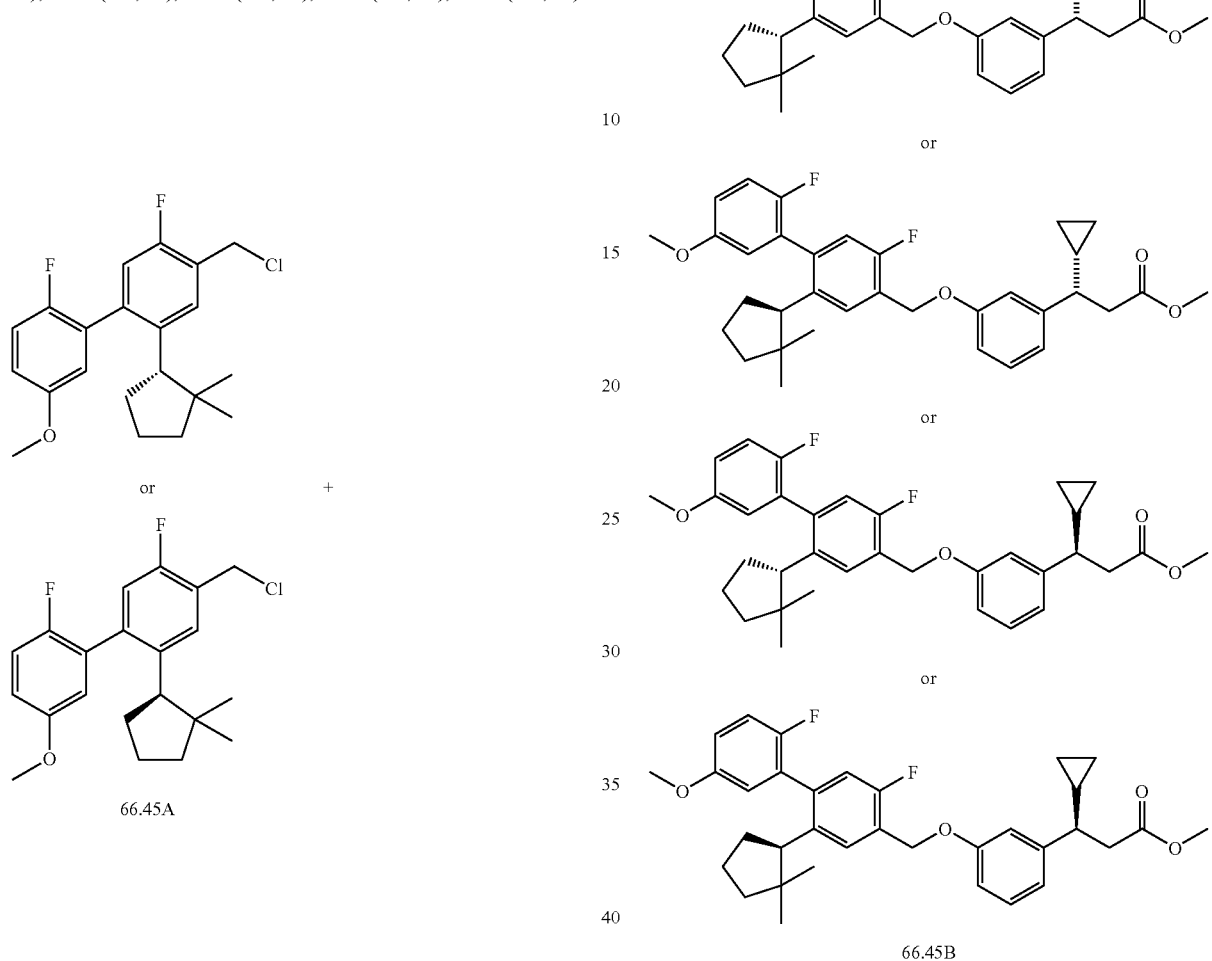

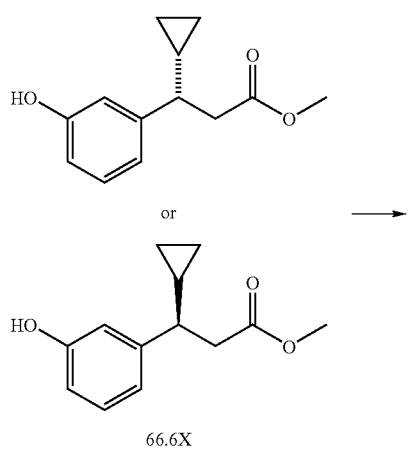

Methyl (3S)-3-cyclopropyl-3-(3-(((2-((1R)-2,2-dimethyl-cyclopentyl)-2',5-difluoro-5'-(methyloxy)-1,1'-biphenyl-4-yl)methyl)oxy)phenyl)propanoate or methyl (3S)-3-cyclopropyl-3-(3-(((2-((1S)-2,2-dimethylcyclopentyl)-2',5-difluoro-5'-(methyloxy)-1,1'-biphenyl-4-yl)methyl)oxy)phenyl)propanoate or methyl (3R)-3-cyclopropyl-3-(3-(((2-((1R)-2,2-dimethylcyclopentyl)-2',5-difluoro-5'-(methyloxy)-1,1'-biphenyl-4-yl)methyl)oxy)phenyl)propanoate or methyl (3R)-3-cyclopropyl-3-(3-(((2-((1S)-2,2-dimethylcyclopentyl)-2',5-difluoro-5'-(methyloxy)-1,1'-biphenyl-4-yl)methyl)oxy)phenyl)propanoate (66.45B). To a vial containing 66.6X (23.1 mg, 0.105 mmol) in 1.0 mL dry DMF was added cesium carbonate (38.7 mg, 0.119 mmol). The mixture was stirred at room temperature for 10 minutes and then 66.45A (39.9 g, 0.109 mmol) was added. After 22 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-20% EtOAc/hexane) to afford 66.45B as a colorless oil (57.5 mg, 96% yield). MS ESI (pos.) m/e: 566.0 (M+H₂O)⁺.

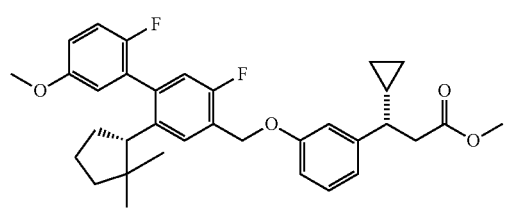

or

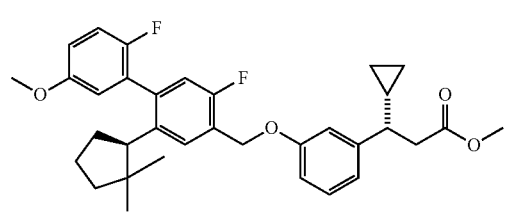

or

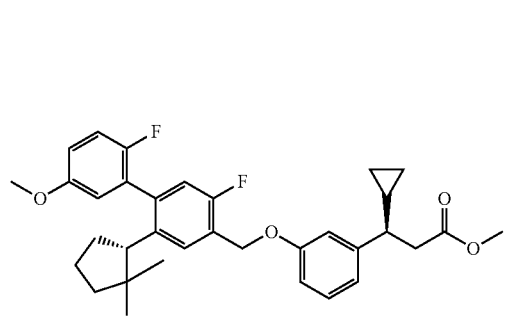

66.45 B or

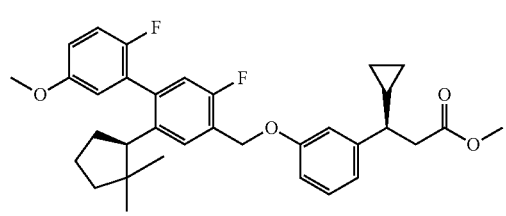

or

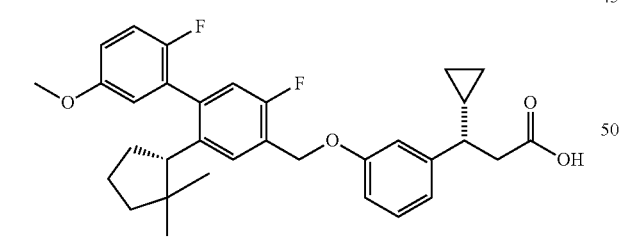

or

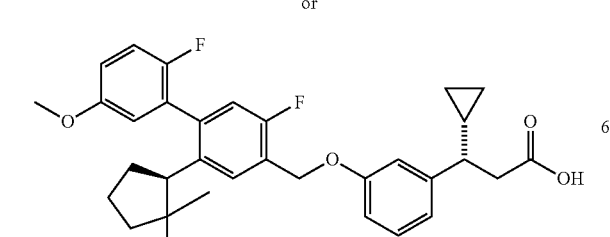

or

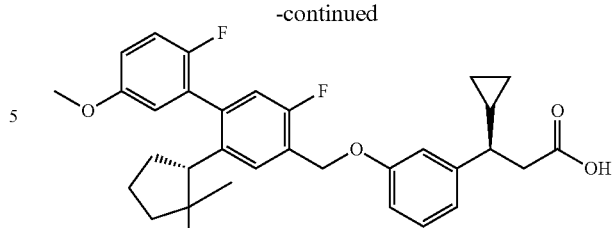

or

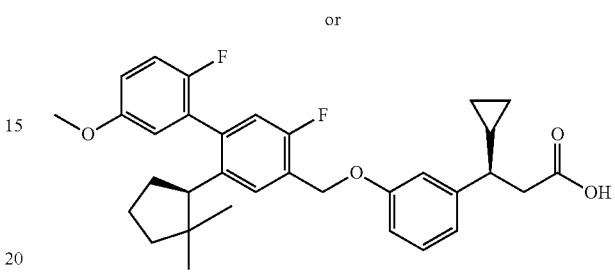

66.45

(3S)-3-Cyclopropyl-3-(3-(((2-((1R)-2,2-dimethylcyclopentyl)-2',5-difluoro-5'-(methyloxy)-1,1'-biphenyl-4-yl)methyl)oxy)phenyl)propanoic acid or (3S)-3-cyclopropyl-3-(3-(((2-((1S)-2,2-dimethylcyclopentyl)-2',5-difluoro-5'-(methyloxy)-1,1'-biphenyl-4-yl)methyl)oxy)phenyl)propanoic acid or (3R)-3-cyclopropyl-3-(3-(((2-((1R)-2,2-dimethylcyclopentyl)-2',5-difluoro-5'-(methyloxy)-1,1'-biphenyl-4-yl)methyl)oxy)phenyl)propanoic acid or (3R)-3-cyclopropyl-3-(3-(((2-((1S)-2,2-dimethylcyclopentyl)-2',5-difluoro-5'-(methyloxy)-1,1'-biphenyl-4-yl)methyl)oxy)phenyl)propanoic acid (66.45). A pre-mixed solution of 2M NaOH (0.50 mL, 1.00 mmol), MeOH (1.00 mL), and THF (1.00 mL) was added to a vial containing 66.45B (55.3 mg, 0.101 mmol). The resulting solution was stirred at room temperature and monitored by TLC and LC-MS. After 24 hours, the mixture was diluted with water and acidified with 1M aqueous HCl solution. The mixture was then extracted five times with EtOAc. The combined organic layers were dried over anhydrous magnesium sulfate, filtered, and concentrated. The residue was purified by silica gel flash chromatography (0-30% EtOAc/hexane) to afford 66.45 as a colorless oil (53.9 mg, 71% yield). MS ESI (neg.) m/e: 532.9 (M−H)⁺.

Example 66.46

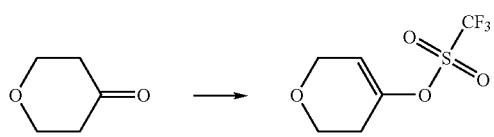

66.46A 3,6-Dihydro-2H-pyran-4-yl trifluoromethanesulfonate (66.46A). To a −78° C. solution of tetrahydropyran-4-one (2.0 mL, 21.65 mmol) (commercially available from Aldrich) in dry THF (47.0 mL) was added LDA (2.0 M in heptane/THF/ethylbenzene) (12.5 mL, 25.00 mmol) dropwise under nitrogen. Stirring was continued for 45 minutes at the same temperature to afford a cloudy yellow mixture, to which a solution of N-phenyl-bis(trifluoromethanesulfonimide) (8.5 g, 23.83 mmol) in dry THF (24.00 mL) was added dropwise via syringe. The cooling bath was removed, and the mixture was stirred at room temperature. After 3 hours, the mixture was concentrated and then diluted with water. After extracting three times with hexanes, the combined organic layers were washed brine. After drying over anhydrous magnesium sulfate and subsequent filtration, the solvent was removed under reduced pressure. The residue was then purified by flash chromatography (SiO$_2$ gel 60, eluted with 0%-5% EtOAc in hexanes). Fractions containing the desired product were combined and concentrated to afford 66.46A as a colorless oil (1.89 g, 38% yield). $^1$H NMR (400 MHz, CDCl$_3$) δ ppm 5.82 (1H, tt, J=2.9, 1.4 Hz), 4.26 (2H, q, J=2.7 Hz), 3.91 (2H, m), 2.49 (2H, m).

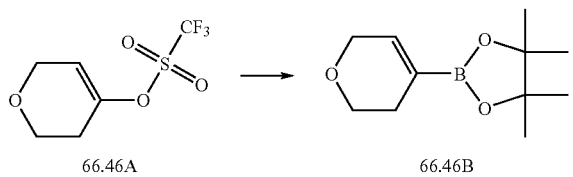

66.46A           66.46B 4-(4,4,5,5-Tetramethyl-1,3,2-dioxaborolan-2-yl)-3,6-dihydro-2H-pyran (66.46 B). A mixture of triphenylphosphine (0.21 g, 0.82 mmol), potassium phenolate (1.50 g, 11.38 mmol), bis(pinacolato)diboron (2.06 g, 8.1 mmol), and 66.46A (1.88 g, 8.1 mmol) in dry toluene (35.00 mL) was degassed by flushing with nitrogen. Dichlorobis(triphenylphosphine)palladium (II) (0.2855 g, 0.4068 mmol) was then added. The mixture was degassed with nitrogen again and then heated to 50° C. After 5 hours, the reaction was cooled to room temperature and then filtered. After concentration, the residue was purified on silica gel using 0-5% EtOAc in hexanes to afford 66.46B as a colorless oil contaminated with triphenylphosphine oxide (1.40 g, 82% yield). 66.46B was used without further purification.

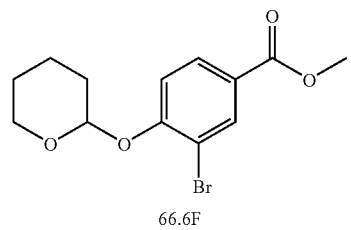

66.6F

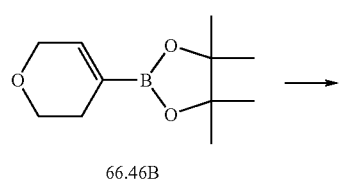

66.46B

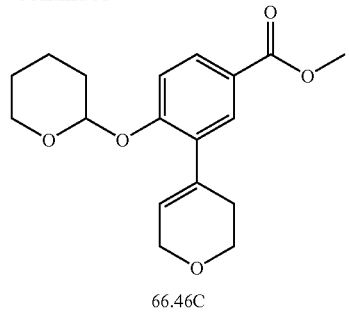

66.46C

Methyl 3-(3,6-dihydro-2H-pyran-4-yl)-4-(tetrahydro-2H-pyran-2-yloxy)benzoate (66.46C). A stirred mixture of 66.6 F (1.40 g, 4.45 mmol), ground S-Phos (0.38 g, 0.920 mmol), palladium acetate (0.11 g, 0.475 mmol), 66.46B (1.40 g, 6.65 mmol), and potassium phosphate tribasic (2.48 g, 11.7 mmol) in DMF (10.0 mL) and water (0.5 mL) was purged three times with argon. The mixture was heated to 75° C. and monitored with LC-MS. After 21 hours, the reaction was cooled to room temperature and then diluted with water and extracted three times with EtOAc. The organic layers were combined and washed twice with brine. After drying over anhydrous sodium sulfate and filtration, the organic solvent was removed under reduced pressure. The residue was purified on silica gel using 0-20% EtOAc in hexanes to afford 66.46C as a colorless oil (0.73 g, 52% yield). MS ESI (pos.) m/e: 340.9 (M+Na)$^+$.

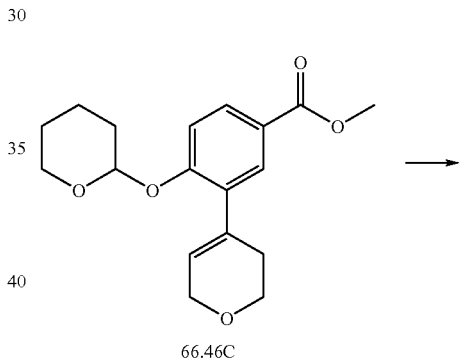

66.46C

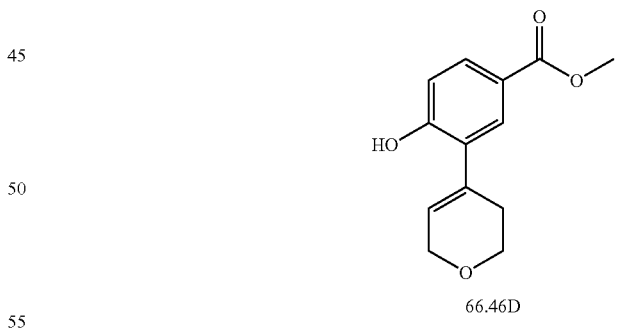

66.46D

Methyl 3-(3,6-dihydro-2H-pyran-4-yl)-4-hydroxybenzoate (66.46D). To a stirred mixture of 66.46C (0.73 g, 2.30 mmol) in MeOH (10 mL) was added PPTS (58.8 mg, 0.234 mmol). The mixture was heated to 45° C. and monitored with TLC and LCMS. After 19 hours, the organic solvent was removed under reduced pressure and the residue was purified on silica gel (0-25% EtOAc in hexanes) to afford 66.46D (361 mg, 67% yield). $^1$H NMR (400 MHz, CDCl$_3$) δ ppm 7.87 (2H, td, J=8.7, 2.2 Hz), 6.95 (1H, d, J=8.6 Hz), 6.00 (1H, m), 5.94 (1H, s), 4.34 (2H, q, J=2.7 Hz), 3.97 (2H, t, J=5.5 Hz), 3.89 (3H, s), 2.47 (2H, ddd, J=9.8, 5.5, 2.7 Hz).

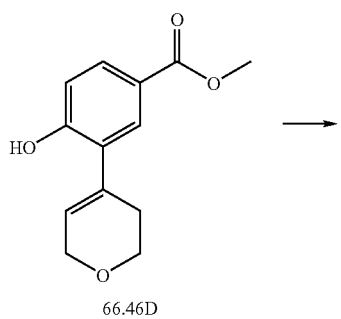

66.46D

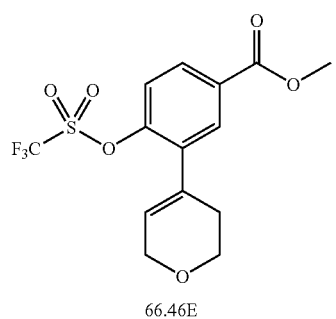

66.46E

Methyl 3-(3,6-dihydro-2H-pyran-4-yl)-4-(((trifluoromethyl)sulfonyl)oxy)benzoate (66.46E). To a stirred solution of 66.46D (361 mg, 1.54 mmol) in dry DCM (10 mL) was added TEA (0.42 mL, 3.02 mmol) and 4-dimethylaminopyridine (19.0 mg, 0.156 mmol). After about 20 minutes, N-phenyl-bis(trifluoromethanesulfonimide) (661.2 mg, 1.85 mmol) was added in portions. Upon complete addition, the solution was stirred at room temperature and monitored with TLC and LC-MS. After 3 hours, the reaction was diluted with brine and extracted three times with DCM. After drying over anhydrous magnesium sulfate and filtration, the organic solvent was removed under reduced pressure, and the residue was purified on silica gel (0-50% EtOAc in hexanes) to afford 66.46E (555 mg, 98% yield). MS ESI (pos.) m/e: 383.8 (M+H$_2$O)$^+$.

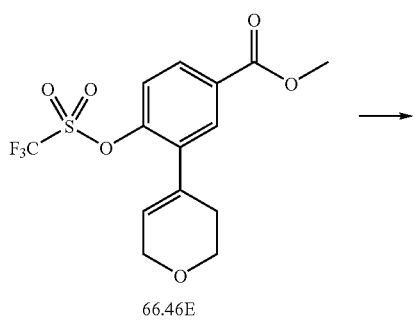

66.46E

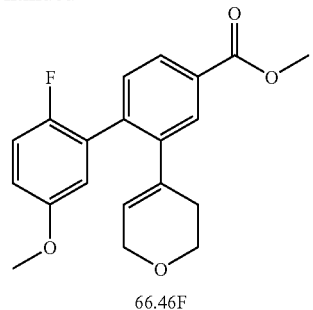

66.46F

Methyl 2-(3,6-dihydro-2H-pyran-4-yl)-2'-fluoro-5'-(methyloxy)-1,1'-biphenyl-4-carboxylate (66.46F). To a stirred solution of 66.46E (555 mg, 1.52 mmol) in DMF (10 mL) at 23° C. was added 2-fluoro-5-methoxyphenylboronic acid (512.3 mg, 3.0 mmol) (commercially available from Aldrich) and potassium carbonate (630.1 mg, 4.56 mmol) followed by tetrakis(triphenylphosphine)palladium(0) (176.8 mg, 0.15 mmol). The mixture was heated to 90° C. After 18 hours, LCMS showed the reaction was complete. The mixture was cooled to room temperature and diluted with water. After extracting three times with EtOAc, the mixture was concentrated in vacuo, and the residue was purified on silica gel (0-50% EtOAc in hexanes) to afford 66.46F (452.7 mg, 87% yield). MS ESI (pos.) m/e: 343.0 (M+H)$^+$.

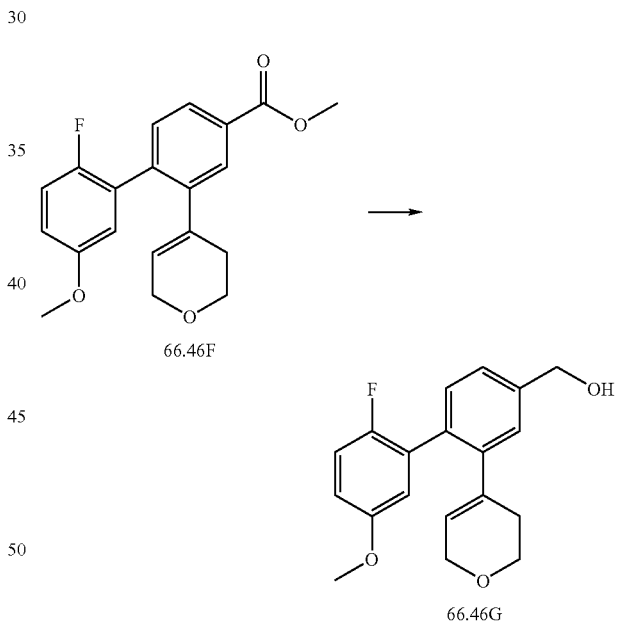

66.46F 66.46G (2-(3,6-Dihydro-2H-pyran-4-yl)-2'-fluoro-5'-(methyloxy)-1,1'-biphenyl-4-yl)methanol (66.46G). To a cooled solution of 66.46F (452.7 mg, 1.3 mmol) in dry THF (10 mL) at 0° C. was added LAH (1.0 M in THF) (2.7 mL, 2.7 mmol) dropwise. Upon complete addition, the reaction was maintained at 0° C. and was monitored by TLC and LCMS. After 45 minutes, 1N NaOH was added to quench the reaction. The resulting solution was extracted three times with EtOAc. After drying over anhydrous magnesium sulfate, filtration, and concentration, the residue was purified by flash chromatography (silica gel 60, eluted with 0%-50% EtOAc in hexanes). Fractions containing the desired product were combined and concentrated to provide 66.46G as a colorless oil (330.4 mg, 80%). $^1$H NMR (400 MHz, CDCl$_3$) δ ppm 7.33 (3H, m), 7.03 (1H, m), 6.84 (2H, m), 5.51 (1H, s), 4.69 (2H, s), 4.08 (2H, q, J=2.5 Hz), 3.77 (3H, s), 3.67 (2H, t, J=5.3 Hz), 3.00 (1H, s), 2.13 (2H, m).

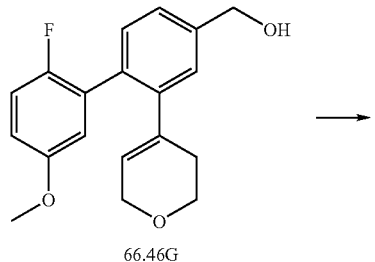

66.46G

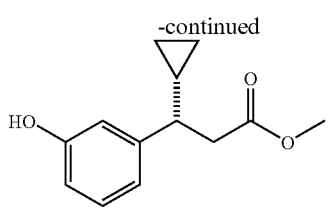

66.6X or

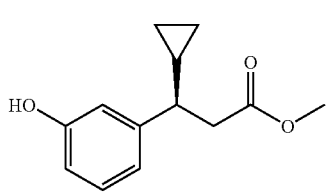

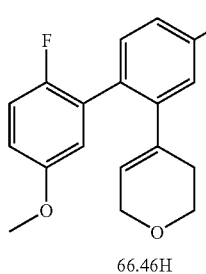

66.46H 4-(4-(Chloromethyl)-2'-fluoro-5'-(methyloxy)-1,1'-biphenyl-2-yl)-3,6-dihydro-2H-pyran (66.46H). To a solution of 66.46G (39.3 mg, 0.13 mmol) in dry DCM (1.0 mL) and dry DMF (0.010 mL) was added thionyl chloride (0.020 mL, 0.27 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford 66.46H (39.5 mg, 95% yield). $^1$H NMR (400 MHz, CDCl$_3$) δ ppm 7.39 (3H, m), 7.02 (1H, t, J=8.8 Hz), 6.85 (2H, m), 5.57 (1H, s), 4.64 (2H, s), 4.13 (2H, q, J=2.7 Hz), 3.80 (3H, s), 3.70 (2H, t, J=5.3 Hz), 2.14 (2H, dd, J=4.5, 2.5 Hz).

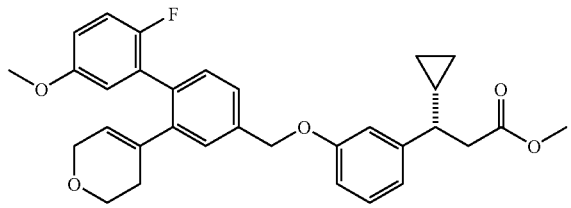

or 66.46I

Methyl (3S)-3-cyclopropyl-3-(3-(((2-(3,6-dihydro-2H-pyran-4-yl)-2'-fluoro-5'-(methyloxy)-1,1'-biphenyl-4-yl)methyl)oxy)phenyl)propanoate or methyl (3R)-3-cyclopropyl-3-(3-(((2-(3,6-dihydro-2H-pyran-4-yl)-2'-fluoro-5'-(methyloxy)-1,1'-biphenyl-4-yl)methyl)oxy)phenyl) propanoate (66.46I). To a vial containing 66.6X (21.5 mg, 0.0976 mmol) in 1.0 mL dry DMF was added cesium carbonate (31.8 mg, 0.0976 mmol). The mixture was stirred at room temperature for 10 minutes and then 66.46H (39.5 g, 0.119 mmol) was added. After 22 hours, the reaction was diluted with water and then extracted five times with EtOAc. The combined organic layers were washed one time with brine and dried over anhydrous magnesium sulfate. The solid was filtered away, and the solvent was concentrated. The residue was purified by silica gel flash chromatography (0-10% EtOAc/hexane) to afford 66.46I as a colorless oil (38.9 mg, 77% yield). MS ESI (pos.) m/e: 534.0 (M+H$_2$O)$^+$.

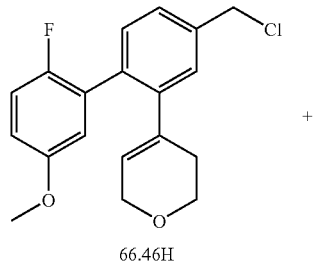

66.46H

+

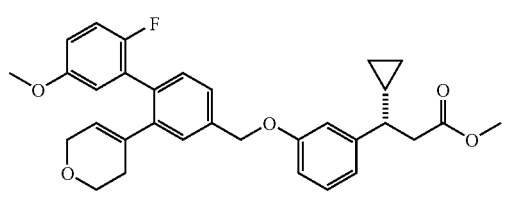

or

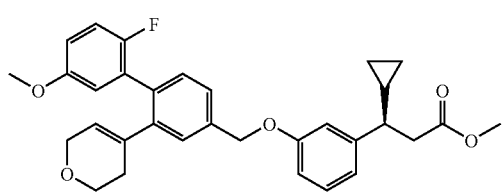

66.46I

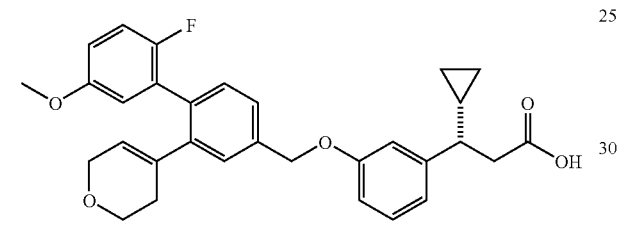

or

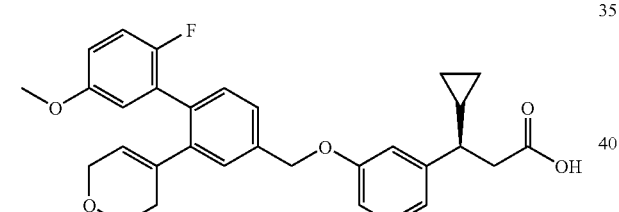

66.46

(3S)-3-Cyclopropyl-3-(3-(((2-(3,6-dihydro-2H-pyran-4-yl)-2'-fluoro-5'-(methyloxy)-1,1'-biphenyl-4-yl)methyl)oxy)phenyl)propanoic acid or (3R)-3-cyclopropyl-3-(3-(((2-(3,6-dihydro-2H-pyran-4-yl)-2'-fluoro-5'-(methyloxy)-1,1'-biphenyl-4-yl)methyl)oxy)phenyl)propanoic acid (66.46). A pre-mixed solution of 2M NaOH (0.5 mL, 1.00 mmol), MeOH (1.0 mL), and THF (1.0 mL) was added to a vial containing 66.46I (38.9 mg, 0.0753 mmol). The mixture was stirred at room temperature and monitored with TLC and LC-MS. After 24 hours, the mixture was diluted with water and acidified with 1M aqueous HCl and then was extracted five times with EtOAc. The organic phase was dried over anhydrous magnesium sulfate, filtered, and concentrated. The residue was purified by silica gel flash chromatography (0-40% EtOAc/hexane) to afford 66.46 as a colorless oil (30.2 mg, 80% yield). $^1$H NMR (400 MHz, CDCl$_3$) δ ppm 7.44 (3H, m), 7.26 (1H, t, J=7.8 Hz), 7.06 (1H, m), 6.92 (5H, m), 5.56 (1H, s), 5.10 (2H, s), 4.16 (2H, m), 3.80 (3H, s), 3.71 (2H, t, J=5.3 Hz), 2.79 (2H, ddd, J=20.0, 15.3, 7.4 Hz), 2.42 (1H, m), 2.16 (2H, d, J=2.0 Hz), 1.08 (1H, m, J=17.7, 7.9, 5.1, 4.9 Hz), 0.64 (1H, m), 0.44 (1H, tt, J=8.8, 4.7 Hz), 0.34 (1H, m), 0.21 (1H, m). MS ESI (neg.) m/e: 501.0 (M–H)$^+$.

Example 66.47

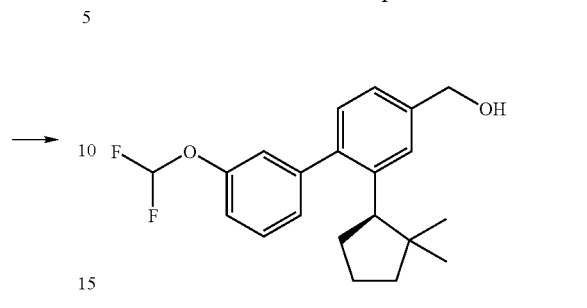

4-(Chloromethyl)-3'-((difluoromethyl)oxy)-2-((1R)-2,2-dimethylcyclopentyl)-1,1'-biphenyl or (chloromethyl)-3'-((difluoromethyl)oxy)-2-((1S)-2,2-dimethylcyclopentyl)-1,1'-biphenyl (66.47A). To a solution of 66.11I (110.3 mg, 0.318 mmol) in dry DCM (4.0 mL) and dry DMF (0.03 mL) was added thionyl chloride (0.06 mL, 0.823 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford 66.47A as a colorless oil (106.1 mg, 91% yield). $^1$H NMR (400 MHz, CDCl$_3$) δ ppm 7.42 (2H, m), 7.25 (1H, d, J=2.0 Hz), 7.20 (1H, m), 7.11 (2H, dd, J=7.8, 2.0 Hz), 7.03 (1H, s), 6.54 (1H, t, J=74 Hz), 4.71 (2H, m), 3.04 (1H, dd, J=10.4, 8.4 Hz), 2.14 (2H, m), 1.88 (1H, m), 1.74 (1H, m), 1.54 (2H, ddd, J=12.6, 8.1, 4.7 Hz), 1.41 (1H, m), 0.73 (3H, s), 0.56 (3H, s).

397

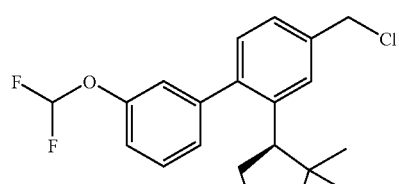

or +

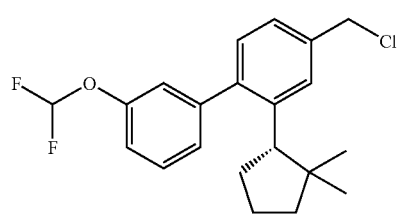

66.47A

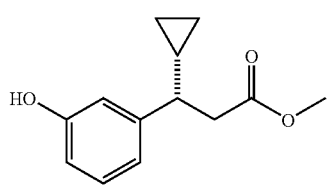

or

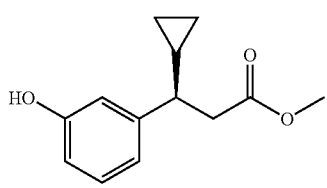

66.6X

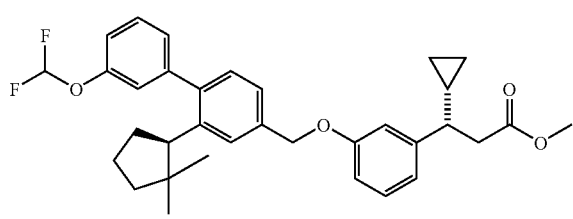

or

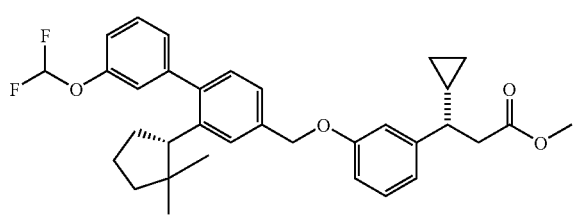

or

398
-continued

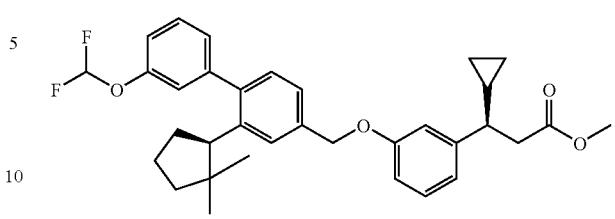

or

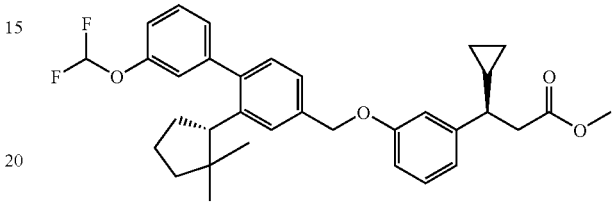

66.47B

Methyl (3S)-3-cyclopropyl-3-(3-(((3'-((difluoromethyl) oxy)-2-((1R)-2,2-dimethylcyclopentyl)-1,1'-biphenyl-4-yl) methyl)oxy)phenyl)propanoate or methyl (3S)-3-cyclopropyl-3-(3-(((3'-((difluoromethyl)oxy)-2-((1S)-2,2-dimethylcyclopentyl)-1,1'-biphenyl-4-yl)methyl)oxy) phenyl)propanoate or methyl (3R)-3-cyclopropyl-3-(3-(((3'-((difluoromethyl)oxy)-2-((1R)-2,2-dimethylcyclopentyl)-1, 1'-biphenyl-4-yl)methyl)oxy)phenyl)propanoate or methyl (3R)-3-cyclopropyl-3-(3-(((3'-((difluoromethyl)oxy)-2-((1S)-2,2-dimethylcyclopentyl)-1,1'-biphenyl-4-yl)methyl) oxy)phenyl)propanoate (66.47B). To a vial containing 66.6X (16.4 mg, 0.0745 mmol) in 1.0 mL dry DMF was added cesium carbonate (30.1 mg, 0.0924 mmol). The mixture was stirred at room temperature for 10 minutes and then 66.47A (30.2 mg, 0.0828 mmol) was added. After 22 hours, the reaction was diluted with water and then it was extracted five times with EtOAc. The combined organic layers were then washed one time with brine and dried over anhydrous magnesium sulfate. The solid was filtered off, and the solvent was concentrated. The residue was purified by silica gel flash chromatography (0-10% EtOAc/hexane) to afford 66.47B as a colorless oil (37.3 mg, 91% yield). MS ESI (pos.) m/e: 566.0 $(M+H_2O)^+$.

399
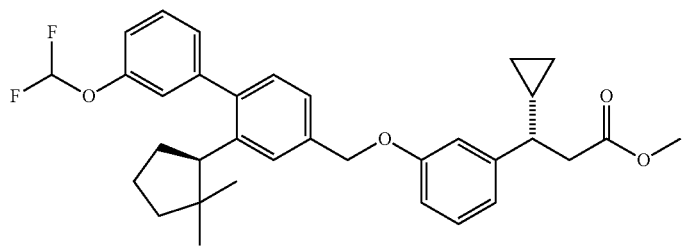
or
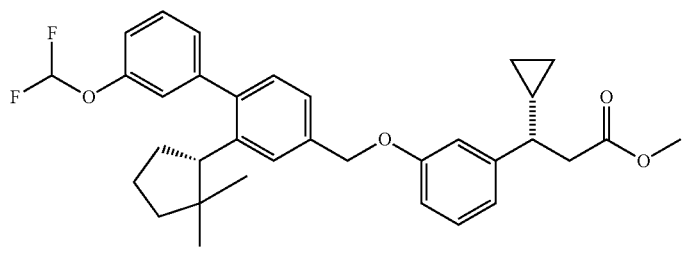
or
400
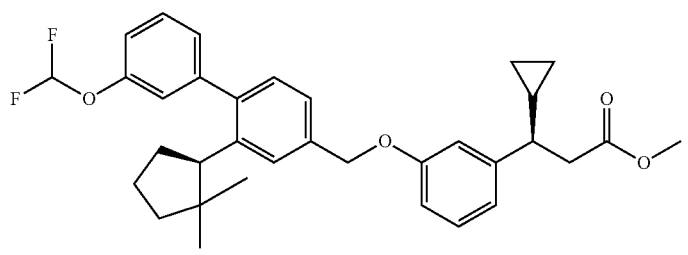
or
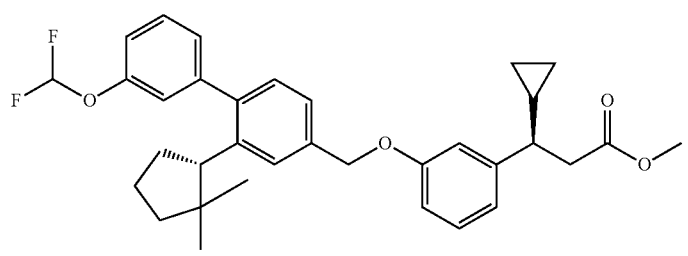
66.47B

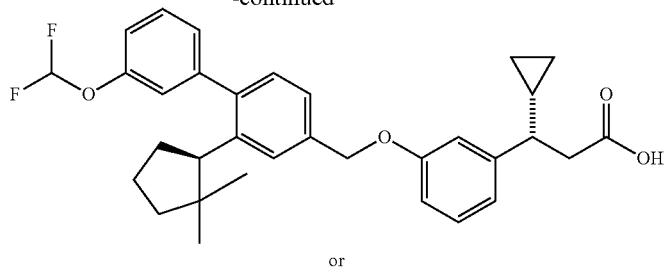

or

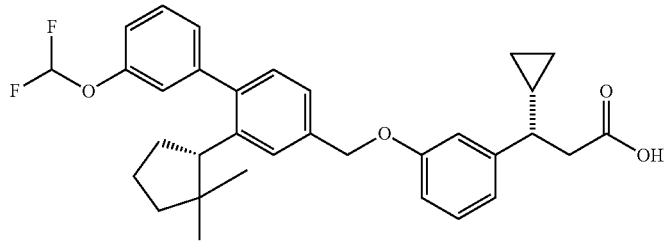

or

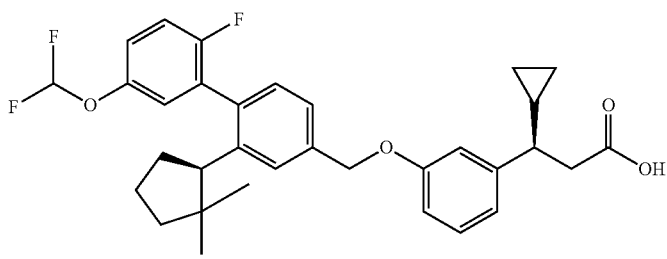

or

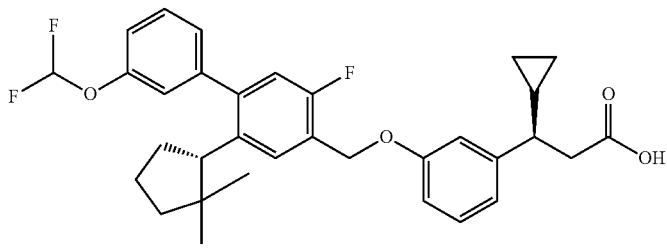

66.47

(3S)-3-Cyclopropyl-3-(3-(((3'-((difluoromethyl)oxy)-2-((1R)-2,2-dimethylcyclopentyl)-1,1'-biphenyl-4-yl)methyl)oxy)phenyl)propanoic acid or (3S)-3-cyclopropyl-3-(3-(((3'-((difluoromethyl)oxy)-2-((1S)-2,2-dimethylcyclopentyl)-1,1'-biphenyl-4-yl)methyl)oxy)phenyl)propanoic acid or (3R)-3-cyclopropyl-3-(3-(((3'-((difluoromethyl)oxy)-2-((1R)-2,2-dimethylcyclopentyl)-1,1'-biphenyl-4-yl)methyl)oxy)phenyl)propanoic acid or (3R)-3-cyclopropyl-3-(3-(((3'-((difluoromethyl)oxy)-2-((1S)-2,2-dimethylcyclopentyl)-1,1'-biphenyl-4-yl)methyl)oxy)phenyl)propanoic acid (66.47). A pre-mixed solution of 2M NaOH (0.30 mL), THF (0.50 mL), and MeOH (0.50 mL) was added to a vial containing 66.47B (37.3 mg, 0.068 m0 mmol). The resulting solution was stirred at room temperature and monitored with TLC and LC-MS. After 24 hours, the mixture was diluted with water and acidified with 1M aqueous. HCl solution. The mixture was then extracted five times with EtOAc. The combined organic layers were dried over anhydrous magnesium sulfate, filtered, and concentrated. The residue was purified by silica gel flash chromatography (0-40% EtOAc/hexane) to afford 66.47 as a colorless oil (25.8 mg, 71% yield). $^1$H NMR (400 MHz, CDCl$_3$) δ ppm 7.45 (2H, m), 7.31 (1H, dd, J=7.8, 2.0 Hz), 7.28 (3H, m), 7.14 (2H, m), 7.04 (1H, d, J=1.6 Hz), 6.92 (3H, m), 6.54 (1H, t, J=78 Hz), 5.10 (2H, s), 3.05 (1H, dd, J=10.4, 8.4 Hz), 2.87 (2H, m), 2.44 (1H, m), 2.13 (2H, m), 1.87 (1H, m), 1.72 (1H, m), 1.52 (1H, ddd, J=12.7, 8.2, 4.9 Hz), 1.41 (1H, m), 1.10 (1H, m), 0.74 (3H, m), 0.65 (4H, m), 0.49 (1H, m), 0.30 (1H, dq, J=9.6, 4.8 Hz), 0.22 (1H, m). MS ESI (neg.) m/e: 532.9 (M−H)⁺.

Example 66.48

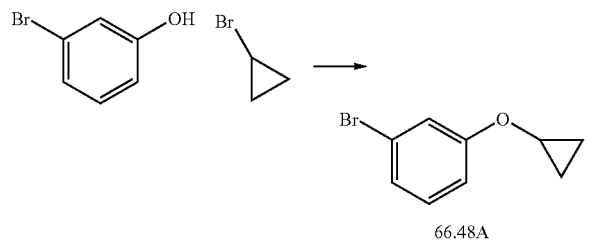

3-Bromophenyl cyclopropyl ether (66.48 A). To a solution of 3-bromophenol (0.57 g, 3.29 mmol) (commercially available from Aldrich) in dry DMF (5.0 mL) was added cyclopropyl bromide (0.53 mL, 6.62 mmol) (commercially available from Aldrich), sodium iodide (50.1 mg, 0.334 mmol), and cesium carbonate (3.2 g, 9.86 mmol). The reaction mixture was heated in a pressure tube to 150° C. After 19 hours, the reaction was cooled to room temperature then diluted with EtOAc, washed with water, and extracted three times with EtOAc. The combined organic layers were dried over sodium sulfate, filtered, and concentrated. The residue was purified by silica gel flash chromatography (0-5% EtOAc/hexane) to afford 66.48A as a colorless oil (144 mg, 21% yield). ¹H NMR (400 MHz, CDCl₃) δ ppm 7.29 (1H, m), 7.19 (2H, m), 6.99 (1H, d, J=7.8 Hz), 3.74 (1H, ddd, J=8.9, 5.8, 3.3 Hz), 0.81 (4H, ddd, J=11.2, 9.0, 8.8 Hz.).

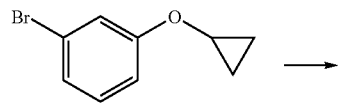

2-(3-(Cyclopropyloxy)phenyl)-4,4,5,5-tetramethyl-1,3,2-dioxaborolane (66.48B). A stirred mixture of 66.48A (0.144 g, 0.676 mmol), bis(pinacolato)diboron (0.189 g, 0.745 mmol), potassium acetate (0.2007 g, 2.04 mmol), and dichloro[1,1'-bis(diphenylphosphino)ferrocene]palladium (II) DCM adduct (25.3 mg, 0.0346 mmol) in dry 1,4-dioxane (3.0 mL) was purged three times with argon and placed under vacuum three times. The mixture was heated to 100° C., and monitored with LC-MS and TLC. After 21 hours, the reaction was cooled to room temperature and filtered through Celite. The organic solvent was removed under reduced pressure. The residue was purified by silica gel flash chromatography (0-10% EtOAc/hexane) to afford 66.48B as a colorless oil (72 mg, 41% yield). ¹H NMR (400 MHz, CDCl₃) δ ppm 7.51 (1H, d, J=2.7 Hz), 7.44 (1H, d, J=7.0 Hz), 7.34 (1H, m), 7.14 (1H, dd, J=7.6, 2.2 Hz), 3.80 (1H, ddd, J=8.8, 5.9, 3.3 Hz), 1.36 (12H, s), 0.82 (4H, m).

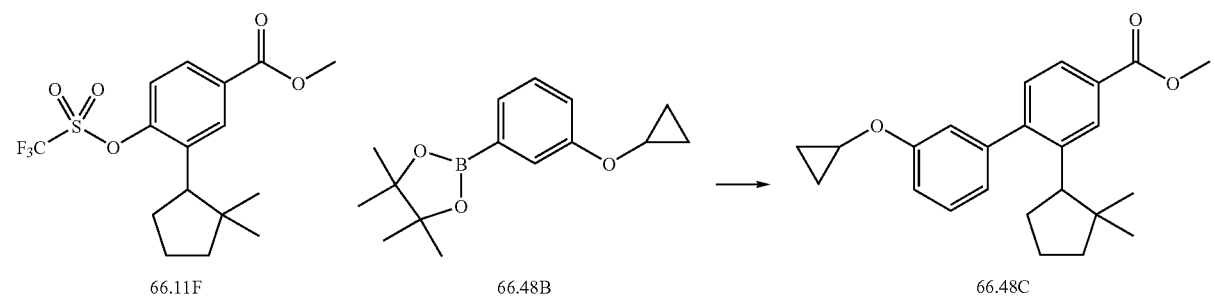

Methyl 3'-(cyclopropyloxy)-2-(2,2-dimethylcyclopentyl)-1,1'-biphenyl-4-carboxylate (66.48C.) To a stirred solution of 66.11F (438.2 mg, 1.15 mmol) in dry DMF (5.0 mL) at 23° C. was added potassium carbonate (480.3 mg, 3.47 mmol) followed by tetrakis(triphenylphosphine)palladium (140.2 mg, 0.121 mmol). The mixture was purged three times with argon and placed under vacuum three times. Before heating, 66.48B (523.1 mg, 2.01 mmol) was added via syringe and then the mixture was heated to 90° C. After 19 hours, LCMS showed reaction was complete. The mixture was cooled to room temperature and then diluted with water. After extracting three times with EtOAc, the mixture was concentrated in vacuo and then purified on silica gel (0%-10% EtOAc/hexane) to afford 66.48C as a colorless oil that was used without further purification (411.5 mg, 98% yield). MS ESI (pos.) m/e: 365.0 (M+H)⁺.

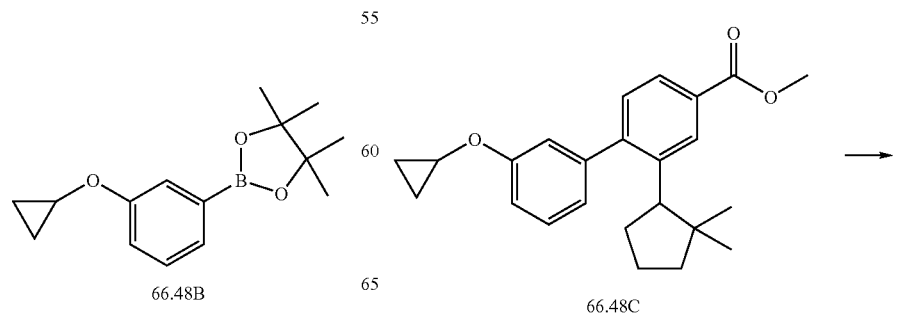

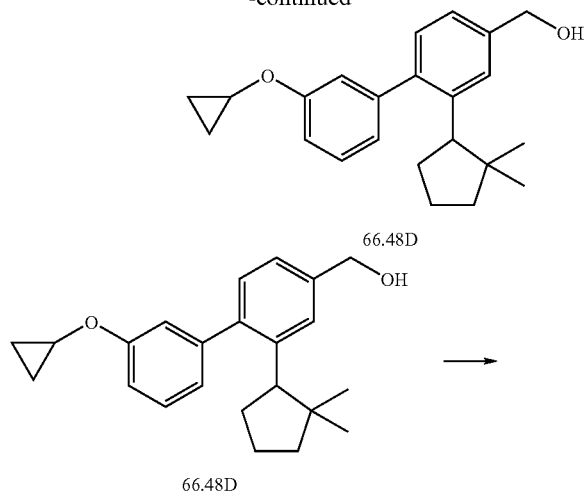

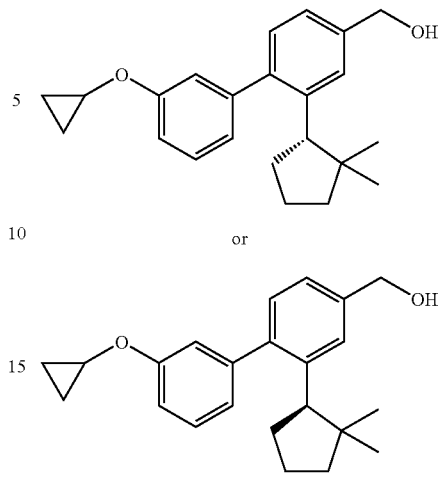

(3'-(Cyclopropyloxy)-2-(2,2-dimethylcyclopentyl)-1,1'-biphenyl-4-yl)methanol (66.48D). To a cooled solution of 66.48C (0.4115 g, 1.129 mmol) in dry THF (10 mL) at 0° C. was added LAH (1.0M in THF) (2.30 mL, 2.3 mmol) dropwise. Upon complete addition, the reaction was maintained at 0° C. and was monitored by TLC and LCMS. After 45 minutes, 1N NaOH was added to quench the reaction. The resulting mixture was extracted three times with EtOAc. After drying over anhydrous magnesium sulfate, filtration, and concentration, the residue was purified by flash chromatography (SiO₂ gel 60, eluted with 0%-50% EtOAc in hexanes). Fractions containing the desired product were combined and concentrated to a colorless oil as 66.48D (317.1 mg, 83% yield). MS ESI (pos.) m/e: 319.0 (M–H₂O)⁺. Chiral separation of 66.48D was accomplished on Chiracel-OD (3% IPA in hexane) to provide 66.48E (peak 1) and 66.48F (peak 2). Both enantiomers were used to synthesize example compounds, and both enantiomers gave active compounds.

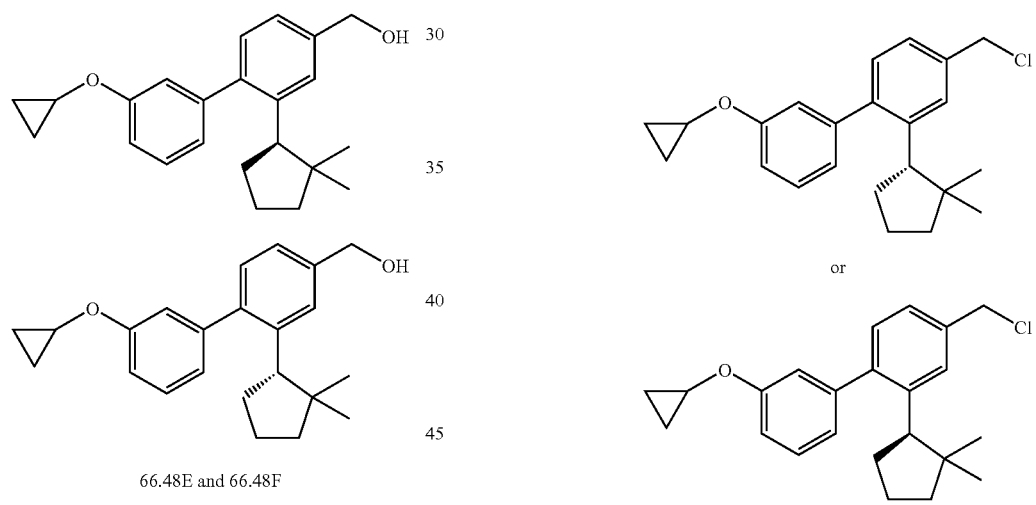

4-(Chloromethyl)-3'-(cyclopropyloxy)-2-((1S)-2,2-dimethylcyclopentyl)-1,1'-biphenyl or 4-(chloromethyl)-3'-(cyclopropyloxy)-2-((1R)-2,2-dimethylcyclopentyl)-1,1'-biphenyl (66.48G). To a solution of 66.48F (0.1335 g, 0.397 mmol) in dry DCM (4 mL) and dry DMF (0.03 mL) was added thionyl chloride (0.07 mL, 0.96 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford 66.48G as a colorless oil (118.3 mg, 84% yield). $^1$H NMR (400 MHz, CDCl₃) δ ppm 7.39 (1H, d, J=1.6 Hz), 7.34 ( ), 3.78 (1H, m), 3.15 (1H, dd, J=10.4, 3H, m), 7.01 (1H, dd, J=7.8, 3.1 Hz), 6.98 (1H, m), 6.85 (1H, d, J=7.4 Hz), 4.69 (2H, m 8.4 Hz), 2.13 (2H, m), 1.88 (1H, m), 1.72 (1H, m), 1.59 (1H, m), 1.41 (1H, m), 0.82 (6H, m), 0.58 (3H, s).

407

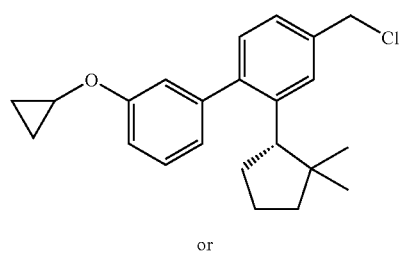

or

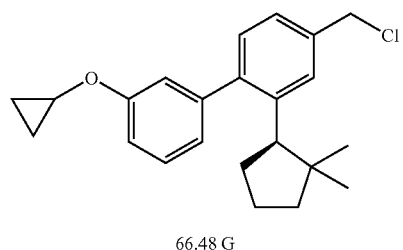

66.48 G

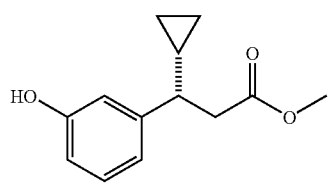

or

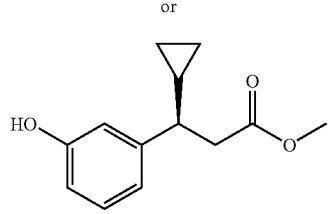

66.6X

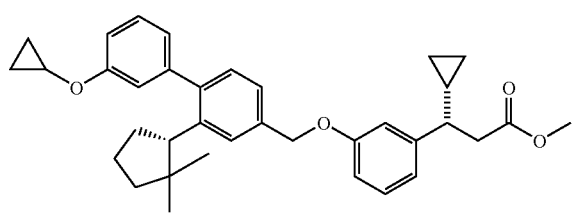

or

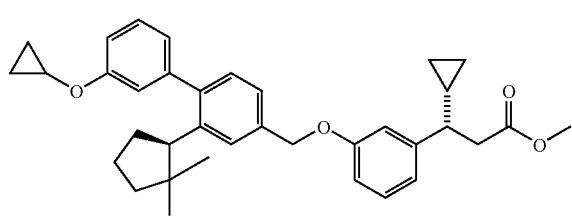

or

408
-continued

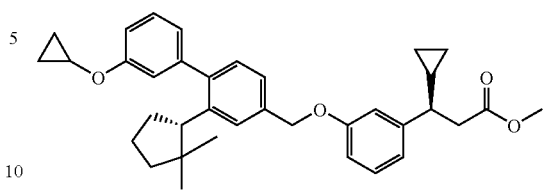

or

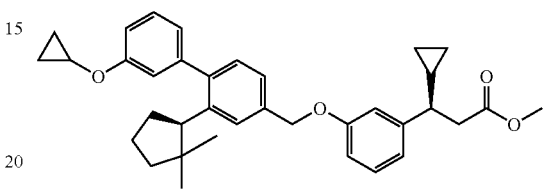

66.48H

Methyl (3S)-3-cyclopropyl-3-(3-(((3'-(cyclopropyloxy)-2-((1S)-2,2-dimethylcyclopentyl)-1,1'-biphenyl-4-yl)methyl)oxy)phenyl)propanoate or methyl (3S)-3-cyclopropyl-3-(3-(((3'-(cyclopropyloxy)-2-((1R)-2,2-dimethylcyclopentyl)-1,1'-biphenyl-4-yl)methyl)oxy)phenyl)propanoate or methyl (3R)-3-cyclopropyl-3-(3-(((3'-(cyclopropyloxy)-2-((1S)-2,2-dimethylcyclopentyl)-1,1'-biphenyl-4-yl)methyl)oxy)phenyl)propanoate or methyl (3R)-3-cyclopropyl-3-(3-(((3'-(cyclopropyloxy)-2-((1R)-2,2-dimethylcyclopentyl)-1,1'-biphenyl-4-yl)methyl)oxy)phenyl)propanoate (66.48H). To a vial containing 66.6X (0.0202 g, 0.0917 mmol) in 1.0 mL dry DMF was added cesium carbonate (0.0389 g, 0.119 mmol). The mixture was stirred at room temperature for 10 minutes and then 66.48G (0.0374 g, 0.105 mmol) was added. After 22 hours, the reaction was diluted with water and then was extracted five times with EtOAc. The combined organic layers were then washed one time with brine and dried over anhydrous magnesium sulfate. The solid was filtered off, and the solvent was concentrated. The residue was purified by silica gel flash chromatography (0-10% EtOAc/hexane) to afford 66.48H as a colorless oil (21.8 mg, 44% yield).

409
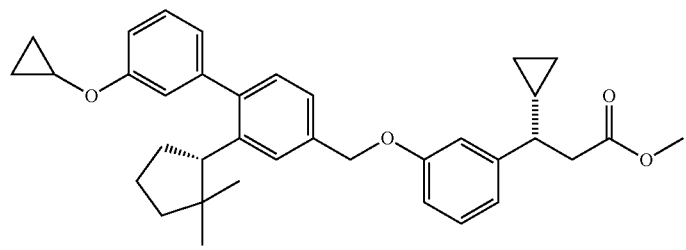
or
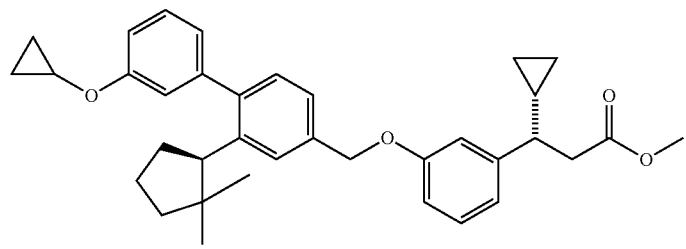
or
→
410
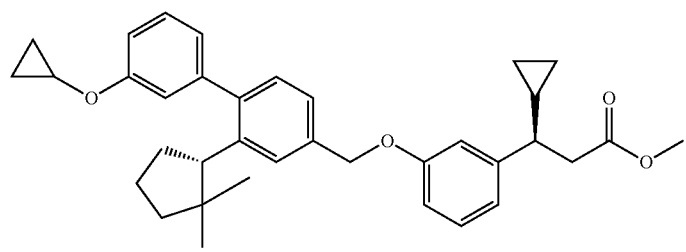
or
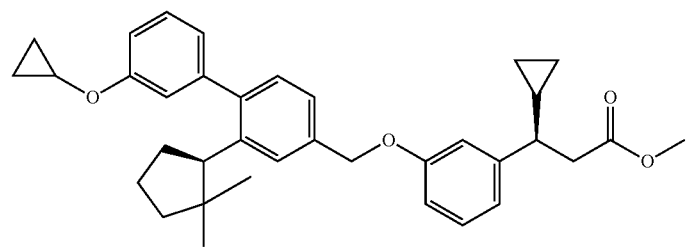
66.48H

-continued


or

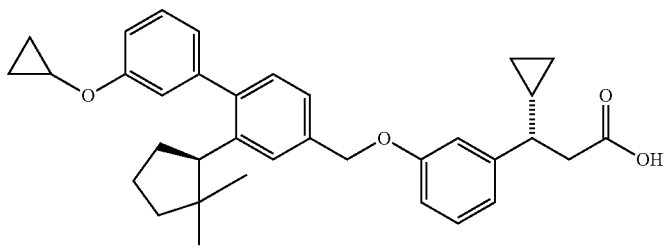

or

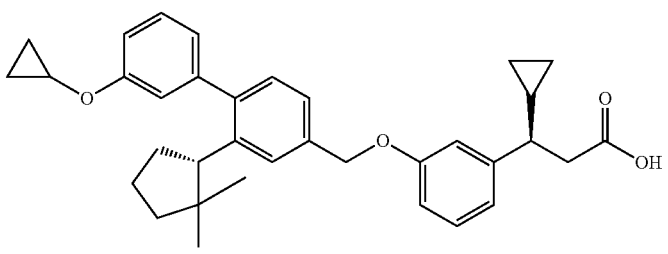

or

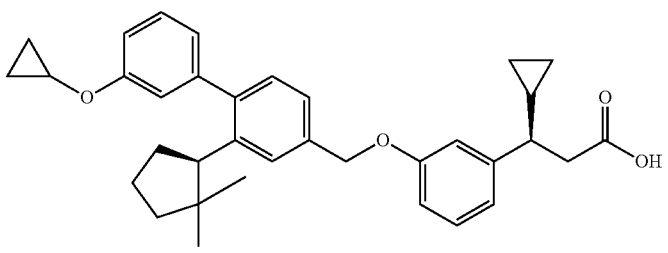

66.48

(3S)-3-Cyclopropyl-3-(3-(((3'-(cyclopropyloxy)-2-((1S)-2,2-dimethylcyclopentyl)-1,1'-biphenyl-4-yl)methyl)oxy)phenyl)propanoic acid or (3S)-3-cyclopropyl-3-(3-(((3'-(cyclopropyloxy)-2-((1R)-2,2-dimethylcyclopentyl)-1,1'-biphenyl-4-yl)methyl)oxy)phenyl)propanoic acid or (3R)-3-cyclopropyl-3-(3-(((3'-(cyclopropyloxy)-2-((1S)-2,2-dimethylcyclopentyl)-1,1'-biphenyl-4-yl)methyl)oxy)phenyl)propanoic acid or (3R)-3-cyclopropyl-3-(3-(((3'-(cyclopropyloxy)-2-((1R)-2,2-dimethylcyclopentyl)-1,1'-biphenyl-4-yl)methyl)oxy)phenyl)propanoic acid (66.48). A pre-mixed solution of 2M NaOH (0.3 mL), THF (0.5 mL), and MeOH (0.5 mL) was added to a vial containing 66.48H (0.0218 g, 0.0405 mmol). The mixture was stirred at room temperature and monitored with TLC and LC-MS. After 24 hours, the mixture was diluted with water and acidified with 1M aqueous HCl. The mixture was then extracted five times with EtOAc. The organic phase was dried over anhydrous magnesium sulfate, filtered, and concentrated. The residue was purified by silica gel flash chromatography (0-40% EtOAc/hexane) to afford 66.48 as a colorless oil (13.9 mg, 65% yield). $^1$H NMR (400 MHz, CDCl$_3$) δ ppm 7.42 (1H, d, J=1.6 Hz), 7.34 (5H, m), 7.03 (2H, m), 6.93 (4H, m), 5.09 (2H, s), 3.79 (1H, m), 3.15 (1H, dd, J=10.4, 8.4 Hz), 2.86 (2H, m), 2.43 (1H, m), 2.12 (2H, m), 1.86 (1H, m), 1.72 (1H, m), 1.51 (1H, ddd, J=12.7, 8.0, 5.1 Hz), 1.40 (1H, m), 1.10 (1H, m), 0.84 (4H, m), 0.74 (3H, m), 0.64 (4H, m), 0.49 (1H, m), 0.36 (1H, m), 0.22 (1H, m). MS ESI (neg.) m/e: 523.0 (M–H)+.

Example 66.49

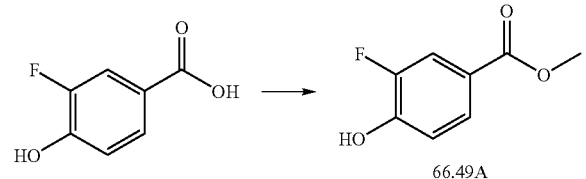

66.49A

Methyl 3-fluoro-4-hydroxybenzoate (66.49A). To a round bottom flask containing 3-fluoro-4-hydroxybenzoic acid (5.03 g, 32.22 mmol) (commercially available from Aldrich) was added a cold solution of MeOH (50.0 mL) and sulfuric acid (2.0 mL). The mixture was heated to 80° C. and monitored with TLC. After 20.5 hours, the solvent was removed and the mixture was diluted with diethyl ether. The organic phase was washed carefully twice with saturated aqueous NaHCO3 and once with brine. The organic phase was then dried over anhydrous sodium sulfate. After filtration, the organic solvent was removed in vacuo to afford 66.49A as a white solid (4.79 g, 87% yield). $^1$H NMR (400 MHz, CDCl3) δ ppm 7.81 (2H, m), 7.06 (1H, t, J=8.4 Hz), 5.62 (1H, d, J=4.3 Hz), 3.91 (3H, s).

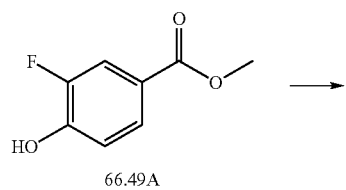

66.49A

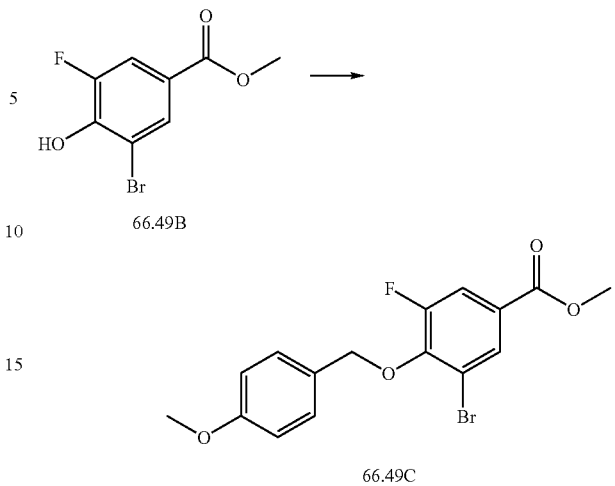

66.49B 66.49C

Methyl 3-bromo-5-fluoro-4-hydroxybenzoate (66.49B). Bromine (1.60 mL, 31.1 mmol) was added dropwise with stirring over 30 minutes to an ice-cooled solution of 66.49A (4.79 g, 28.1 mmol) in a 1:1 mixture of DCM (20 mL) and acetic acid (20 mL). Upon complete addition, the reaction mixture was allowed to warm to room temperature and monitored with TLC and LC-MS. After stirring at room temperature for 40 hours, the mixture was diluted with EtOAc, and then the resulting solution was washed twice with aqueous saturated Na2SO3, once with water, and once with brine. After drying over anhydrous magnesium sulfate, filtration, and concentration, the white solid 66.49B was obtained 6.69 g, 95% yield). $^1$H NMR (400 MHz, CDCl3) δ ppm 8.05 (1H, m), 7.75 (1H, dd, J=10.6, 2.0 Hz), 6.12 (1H, s), 3.94 (3H, s).

Methyl 3-bromo-5-fluoro-4-(((4-(methyloxy)phenyl)methyl)oxy)benzoate (66.49C). To a vial containing 66.49B (0.64 g, 2.58 mmol) in 5.0 mL dry DMF was added cesium carbonate (1.10 g, 3.36 mmol). The mixture was stirred at room temperature for 10 minutes and then 4-methoxybenzyl bromide (0.45 mL, 3.1 mmol) was added. After 4 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-40% EtOAc/hexane) to afford 66.49 C as a white solid (679.1 mg, 71% yield). $^1$H NMR (400 MHz, CDCl3) δ ppm 8.02 (1H, t, J=2.0 Hz), 7.72 (1H, dd, J=11.5, 2.2 Hz), 7.42 (2H, m, J=8.6 Hz), 6.90 (2H, m), 5.20 (2H, s), 3.91 (3H, s), 3.82 (3H, s).

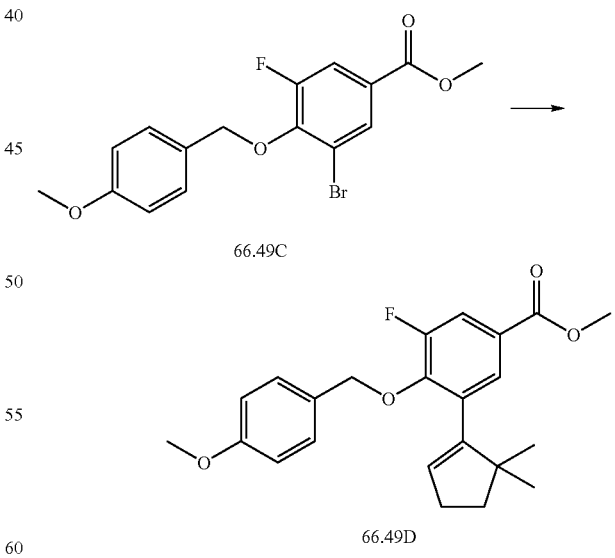

66.49C 66.49D

Methyl 3-(5,5-dimethyl-1-cyclopenten-1-yl)-5-fluoro-4-(((4-(methyloxy)phenyl)methyl)oxy)benzoate (66.49D). A stirred mixture of 66.49C (1.63 g, 4.420 mmol), ground S-Phos (0.36 g, 0.88 mmol), palladium acetate (0.10 g, 0.45 mmol), and potassium phosphate tribasic (2.35 g, 11.06 mmol) in DMF (13 mL) and water (0.4 mL) was purged with argon and placed under vacuum and the process repeated three times. Before heating, 2-(5,5-dimethylcyclopent-1-enyl)-4,4,5,5-tetramethyl-1,3,2-dioxaborolane (66.6C) (1.47 g, 6.63 mmol) was added via syringe and then the mixture was heated to 75° C. After 18 hours, the reaction was cooled to room temperature, diluted with water, and extracted three times with EtOAc. The organic layers were combined and washed twice with brine. After drying over anhydrous sodium sulfate and filtration, the organic solvent was removed under reduced pressure. The residue was purified on a 40 g column of silica gel (0-10% EtOAc in hexanes) to afford 66.49D as a white solid (1.12 g, 66% yield). $^1$H NMR (400 MHz, CDCl$_3$) δ ppm 7.69 (1H, dd, J=11.7, 2.3 Hz), 7.57 (1H, dd, J=2.0, 1.2 Hz), 7.31 (2H, m), 6.88 (2H, m), 5.56 (1H, t, J=2.5 Hz), 5.01 (2H, s), 3.91 (3H, s), 3.82 (3H, s), 2.42 (2H, td, J=7.0, 2.7 Hz), 1.86 (2H, t, J=7.2 Hz), 1.06 (6H, s).

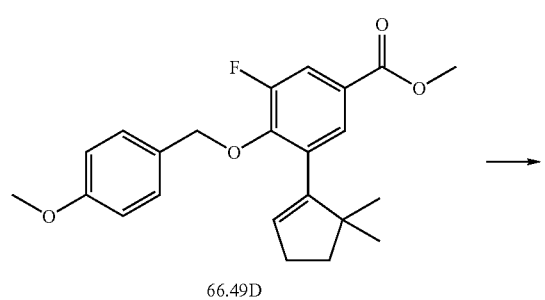

66.49D

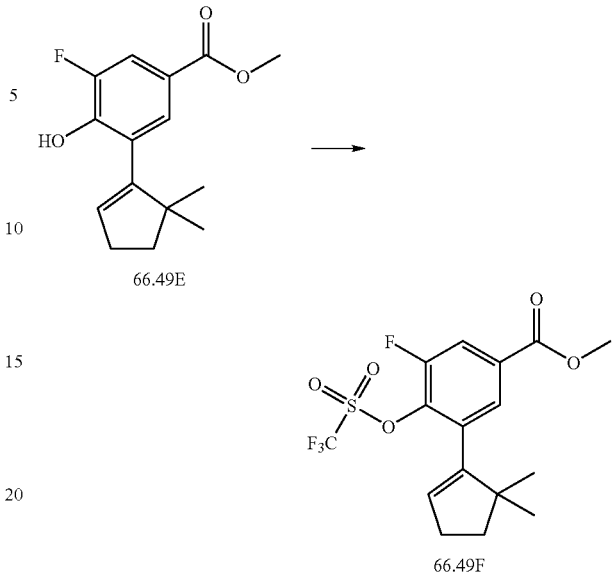

66.49E 66.49F

Methyl 3-(5,5-dimethyl-1-cyclopenten-1-yl)-5-fluoro-4-(((trifluoromethyl)sulfonyl)oxy)benzoate (66.49F). To a stirred solution of 66.49E (0.7326 g, 2.77 mmol) in dry DCM (15 mL) was added TEA (0.78 mL, 5.60 mmol) and 4-(dimethylamino)pyridine (0.0354 g, 0.29 mmol). After about 20 minutes, N-phenyl-bis(trifluoromethanesulfonimide) (1.20 g, 3.36 mmol) was added in portions. Upon complete addition, the solution was stirred at room temperature and monitored with TLC and LC-MS. After 19 hours, the organic solvent was removed under reduced pressure and the product thus obtained was then purified with silica gel chromatography using 0-10% EtOAc in hexanes to afford 66.49 F as a colorless oil (946.4 mg, 86% yield). $^1$H NMR (400 MHz, CDCl$_3$) δ ppm 7.82 (1H, dd, J=9.9, 2.1 Hz), 7.75 (1H, m), 5.87 (1H, t, J=2.4 Hz), 3.95 (3H, s), 2.49 (2H, td, J=7.1, 2.4 Hz), 1.92 (2H, t, J=7.0 Hz), 1.11 (6H, s).

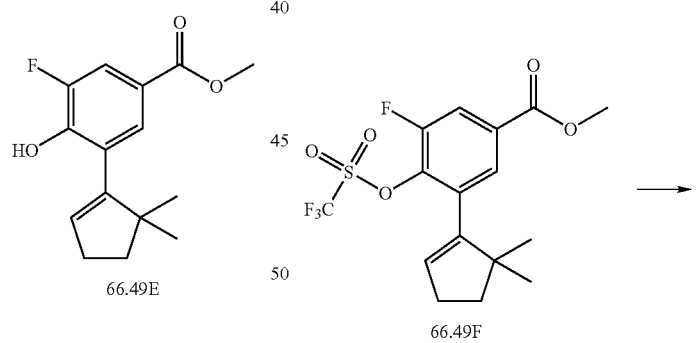

66.49E 66.49F

Methyl 3-(5,5-dimethyl-1-cyclopenten-1-yl)-5-fluoro-4-hydroxybenzoate (66.49E). To a flask containing 66.49D (1.12 g, 2.93 mmol) was added a premixed solution of DCM (14 mL) and TFA (1 mL). The mixture was stirred at room temperature and monitored with TLC and LC-MS. After 1 hour, the reaction was diluted with DCM and then washed once with saturated aqueous sodium bicarbonate solution and brine. After washing, the organic layer was dried over anhydrous sodium sulfate, filtered, and concentrated in vacuo. The residue was purified by flash chromatography (SiO$_2$ gel 60, eluted with 0%-50% EtOAc in hexanes). Fractions containing the desired product were combined and concentrated to provide a colorless oil that solidified as 66.49E and which was used without further purification (732.6 mg, 95% yield).

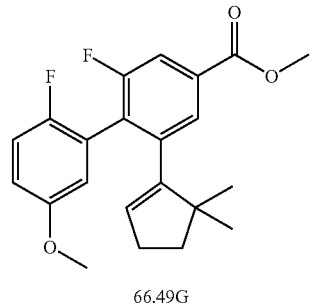

66.49G

Methyl 2-(5,5-dimethyl-1-cyclopenten-1-yl)-2',6-difluoro-5'-(methyloxy)-1,1'-biphenyl-4-carboxylate (66.49 G). A stirred mixture of 66.49 F (0.9464 g, 2.39 mmol), ground S-Phos (0.1977 g, 0.482 mmol), palladium acetate (0.0555 g, 0.247 mmol), 2-fluoro-5-methoxyphenylboronic acid (0.8114 g, 4.77 mmol) (commercially available from Aldrich), and potassium phosphate tribasic (1.2888 g, 6.072 mmol) in dry DMF (7.000 mL) was purged with argon and placed under vacuum and the process repeated three times. The mixture was then heated to 75° C. and the reaction was stirred for 21 hours. The reaction was then cooled to room temperature, diluted with water and extracted three times with EtOAc. The organic layers were combined and washed twice with brine. After drying over anhydrous sodium sulfate and filtration, the organic solvent was removed under reduced pressure. The residue was purified on an 80 g column of silica gel (0-20% EtOAc in hexanes) to afford 66.49G as a colorless oil that was used without further purification (850.5 mg, 95% yield). MS ESI (pos.) m/e: 373.0 (M+H)$^+$.

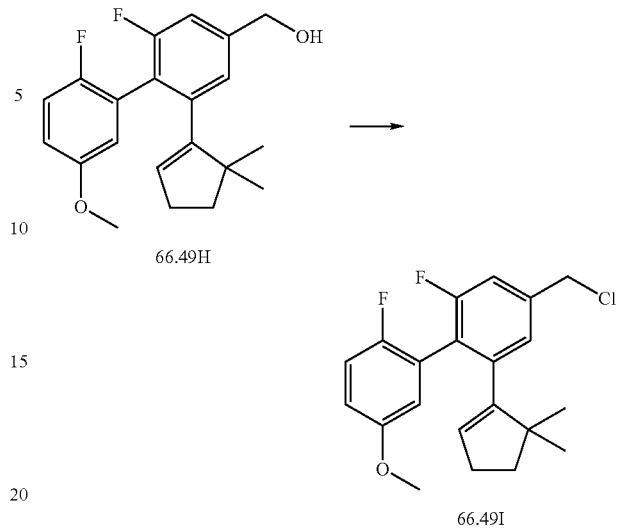

66.49H 66.49I 4-(Chloromethyl)-2-(5,5-dimethyl-1-cyclopenten-1-yl)-2',6-difluoro-5'-(methyloxy)-1,1'-biphenyl (66.49I). To a solution of 66.49H (0.1149 g, 0.334 mmol) in dry DCM (4 mL) and dry DMF (0.03 mL) was added thionyl chloride (0.05 mL, 0.685 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford 66.49I as a colorless oil (35.6 mg, 29% yield). $^1$H NMR (400 MHz, CDCl$_3$) δ ppm 7.14 (1H, dd, J=9.4, 1.6 Hz), 7.06 (1H, s), 7.00 (1H, t, J=9.0 Hz), 6.85 (1H, dt, J=9.0, 3.7 Hz), 6.74 (1H, dd, J=5.5, 3.1 Hz), 5.53 (1H, t, J=2.3 Hz), 4.61 (2H, s), 3.76 (3H, s), 2.25 (2H, td, J=7.1, 2.5 Hz), 1.73 (2H, m), 0.97 (3H, s), 0.78 (3H, s).

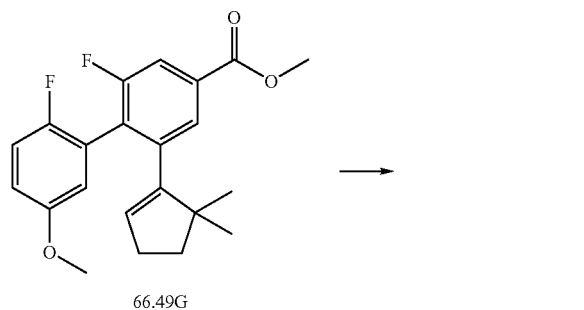

66.49G

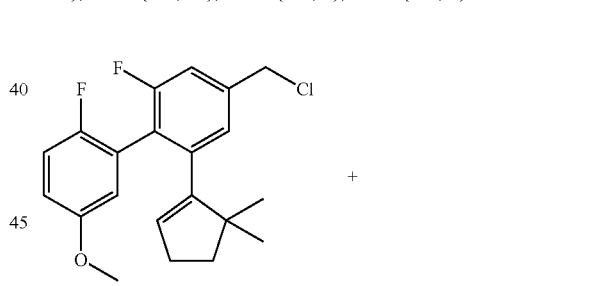

66.49H 66.49I (2-(5,5-Dimethyl-1-cyclopenten-1-yl)-2',6-difluoro-5'-(methyloxy)-1,1'-biphenyl-4-yl)methanol (66.49H). To a cooled solution of 66.49 G (0.1435 g, 0.385 mmol) in dry THF (9 mL) at 0° C. was added LAH (1.0 M in THF) (0.8 mL, 0.80 mmol) dropwise. Upon complete addition, the reaction was maintained at 0° C. and was monitored by TLC and LCMS. After 45 minutes, 1N NaOH was added to quench the reaction (gas evolution occurred), and the resulting solution was extracted three times with EtOAc. After drying over anhydrous magnesium sulfate, filtration, and concentration, the residue was purified by flash chromatography (SiO$_2$ gel 60, eluted with 0%-50% EtOAc in hexanes). Fractions containing the desired product were combined and concentrated to provide 66.49H as a colorless oil (114.9 mg, 87% yield). $^1$H NMR (400 MHz, CDCl$_3$) δ ppm 7.12 (1H, dd, J=9.8, 1.6 Hz), 7.04 (2H, m), 6.84 (1H, dt, J=9.0, 3.5 Hz), 6.74 (1H, dd, J=5.5, 3.1 Hz), 5.50 (1H, t, J=2.3 Hz), 4.74 (2H, s), 3.76 (3H, s), 2.24 (2H, td, J=7.0, 2.3 Hz), 1.75 (5H, m), 0.97 (3H, s), 0.78 (3H, s).

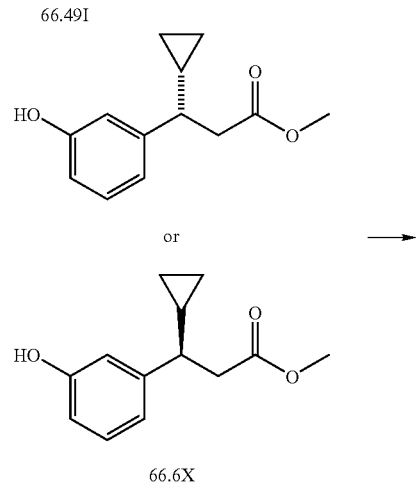

66.6X

-continued

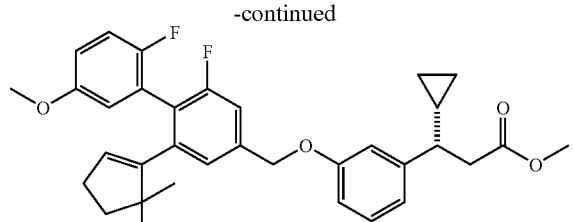

or

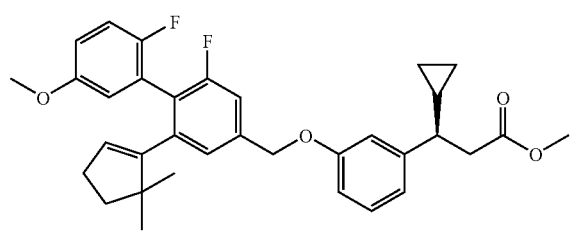

66.49J

Methyl (3S)-3-cyclopropyl-3-(3-(((2-(5,5-dimethyl-1-cyclopenten-1-yl)-2',6-difluoro-5'-(methyloxy)-1,1'-biphenyl-4-yl)methyl)oxy)phenyl)propanoate or methyl (3R)-3-cyclopropyl-3-(3-(((2-(5,5-dimethyl-1-cyclopenten-1-yl)-2',6-difluoro-5'-(methyloxy)-1,1'-biphenyl-4-yl)methyl)oxy) phenyl)propanoate (66.49 J). To a vial containing 66.6X (0.0191 g, 0.0867 mmol) in 1.00 mL dry DMF was added cesium carbonate (0.0363 g, 0.111 mmol). The mixture was stirred at room temperature for 10 minutes and then 66.49I (0.0356 g, 0.0981 mmol) was added. After 22 hours, the reaction was diluted with water and then extracted five times with EtOAc. The organic layers were combined and then washed one time with brine and dried over anhydrous magnesium sulfate. The solid was filtered off, and the mixture was concentrated. The residue was purified by silica gel flash chromatography (0-50% EtOAc/hexane) to afford 66.49J as a colorless oil (43.2 mg, 91% yield). $^1$H NMR (400 MHz, CDCl$_3$) δ ppm 7.29 (2H, m), 7.10 (1H, s), 6.99 (1H, t, J=8.8 Hz), 6.92 (4H, m), 6.75 (1H, dd, J=5.5, 3.1 Hz), 5.52 (1H, t, J=2.3 Hz), 5.09 (2H, s), 3.76 (3H, s), 3.62 (3H, s), 2.83 (2H, m), 2.43 (1H, m), 2.25 (2H, td, J=7.0, 2.3 Hz), 1.74 (2H, m), 1.09 (4H, m), 0.78 (3H, s), 0.64 (1H, m), 0.49 (1H, m), 0.28 (1H, dq, J=9.7, 4.8 Hz), 0.20 (1H, m).

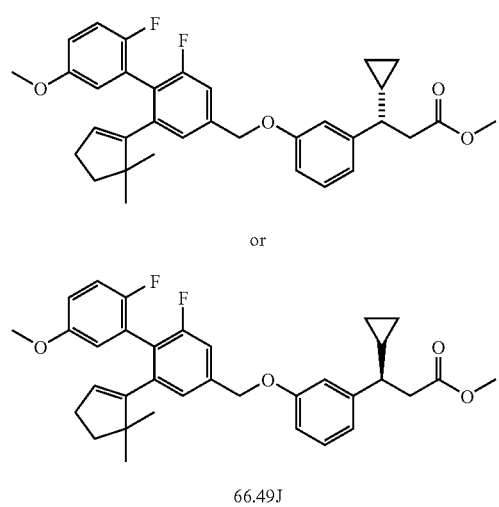

66.49J

-continued

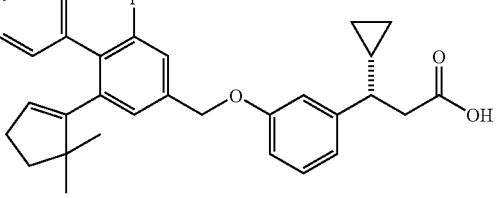

or

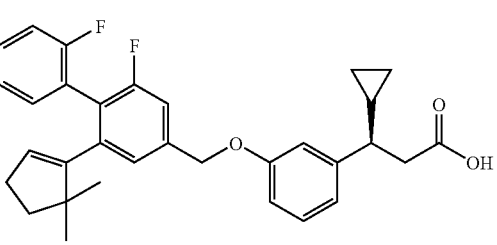

66.49

(3S)-3-Cyclopropyl-3-(3-(((2-(5,5-dimethyl-1-cyclopenten-1-yl)-2',6-difluoro-5'-(methyloxy)-1,1'-biphenyl-4-yl)methyl)oxy)phenyl)propanoic acid or (3R)-3-cyclopropyl-3-(3-(((2-(5,5-dimethyl-1-cyclopenten-1-yl)-2',6-difluoro-5'-(methyloxy)-1,1'-biphenyl-4-yl)methyl)oxy) phenyl)propanoic acid (66.49). A pre-mixed solution of 2M NaOH (0.5 mL, 1.00 mmol), MeOH (1.5 mL), and THF (1.5 mL) was added to a vial containing 66.49J (0.0432 g, 0.0790 mmol). The resulting solution was stirred at room temperature and monitored with TLC and LC-MS. After 24 hours, the mixture was diluted with water and acidified with 1M aqueous HCl solution and then extracted five times with EtOAc. The organic phase was dried over anhydrous magnesium sulfate and then was filtered and concentrated. The residue was purified by silica gel flash chromatography (0-40% EtOAc/hexane) to afford 66.49 as a colorless oil (36.1 mg, 86% yield). $^1$H NMR (400 MHz, CDCl$_3$) δ ppm 7.29 (3H, m), 7.09 (1H, d, J=1.2 Hz), 6.99 (1H, t, J=8.8 Hz), 6.91 (4H, m), 6.75 (1H, dd, J=5.9, 3.1 Hz), 5.52 (1H, t, J=2.2 Hz), 5.09 (2H, s), 2.86 (2H, m), 2.42 (1H, m), 2.24 (2H, td, J=7.0, 2.3 Hz), 1.74 (2H, m), 1.08 (4H, m), 0.77 (3H, s), 0.66 (1H, m), 0.44 (1H, tt, J=8.9, 4.6 Hz), 0.30 (1H, dq, J=9.6, 4.8 Hz), 0.22 (1H, m). MS ESI (neg.) m/e: 531.0 (M−H)$^+$.

Example 66.50

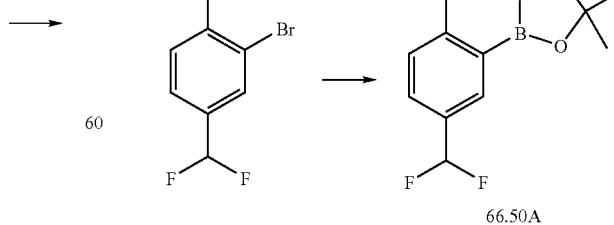

66.50A 2-(5-(Difluoromethyl)-2-fluorophenyl)-4,4,5,5-tetramethyl-1,3,2-dioxaborolane (66.50A). A stirred mixture of 1-bromo-5-difluoromethyl-2-fluorobenzene (commercially available from Oakwood Products, Inc.) (2.0231 g, 8.991 mmol), bis(pinacolato)diboron (2.5123 g, 9.893 mmol), dichloro[1,1'-bis(diphenylphosphino)ferrocene]palladium (II) DCM adduct (0.3688 g, 0.4516 mmol), and potassium acetate (2.6504 g, 27.01 mmol) in dry 1,4-dioxane (35 mL) was purged with argon and placed under vacuum and the purging vacuum process repeated three times. The mixture was heated to 90° C. and monitored with LC-MS and TLC. After 18 hours, the reaction was cooled to room temperature and then filtered through Celite. The organic solvent was removed under reduced pressure, and the residue was purified on a 40 g column of silica gel (0-10% EtOAc in hexanes) to afford 66.50A as a colorless oil that was used without further purification (1.6019 g, 65% yield). $^1$H NMR (400 MHz, CDCl$_3$) δ ppm 7.89 (1H, td, J=2.7, 1.2 Hz), 7.63 (1H, m), 7.09 (1H, t, J=8.6 Hz), 6.62 (1H, t), 1.35 (12H, s).

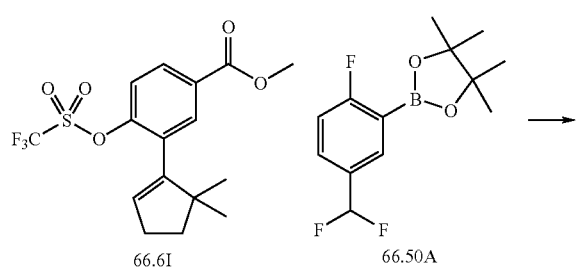

66.6I        66.50A

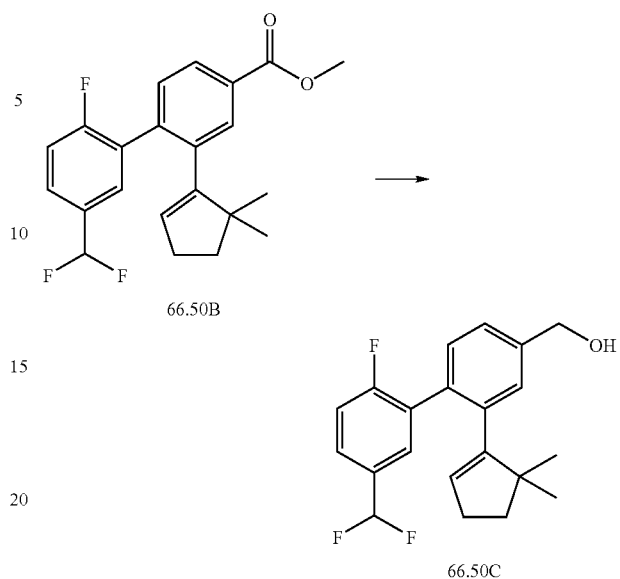

66.50B

Methyl 5'-(difluoromethyl)-2-(5,5-dimethyl-1-cyclopenten-1-yl)-2'-fluoro-1,1'-biphenyl-4-carboxylate (66.50B). To a stirred solution of 66.6I (1.1209 g, 2.962 mmol) in dry DMF (10 mL) at 23° C. was added potassium carbonate (1.2262 g, 8.872 mmol) and then tetrakis(triphenylphosphine)palladium (0.3408 g, 0.2949 mmol). The mixture was purged with argon and placed under vacuum and the purging and vacuum process repeated three times. Before heating, 66.50A (1.6019 g, 5.888 mmol) was added via syringe and then the mixture was heated to 90° C. After 19 hours, LC-MS showed that the reaction was complete. The mixture was cooled to room temperature and then diluted with water. After extracting three times with EtOAc, the mixture was concentrated in vacuo and then purified on silica gel (0%-10% EtOAc/hexane) to afford 66.50B as a clear oil (994.4 mg, 90% yield). $^1$H NMR (400 MHz, CDCl$_3$) δ ppm 8.00 (1H, dd, J=8.0, 1.8 Hz), 7.94 (1H, d, J=1.6 Hz), 7.50 (3H, m), 7.16 (1H, t, J=9.0 Hz), 6.63 (1H, t), 5.53 (1H, s), 3.96 (3H, s), 2.25 (2H, td, J=7.0, 2.3 Hz), 1.65 (2H, t, J=7.0 Hz), 0.85 (6H, s).

(5'-(Difluoromethyl)-2-(5,5-dimethyl-1-cyclopenten-1-yl)-2'-fluoro-1,1'-biphenyl-4-yl)methanol (66.50C). To a cooled solution of 66.50B (0.2349 g, 0.6274 mmol) in dry THF (5 mL) at 0° C. was added LAH (1.0 M in THF) (1.3 mL, 1.3 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was then purified by flash chromatography (SiO$_2$ gel 60, eluted with 0%-50% EtOAc in hexanes). Fractions containing the desired product were combined and concentrated to a colorless oil as 66.50C (166.6 mg, 77% yield). $^1$H NMR (400 MHz, CDCl$_3$) δ ppm 7.47 (2H, m), 7.38 (2H, m), 7.14 (1H, t, J=9.0 Hz), 6.62 (1H, t), 5.50 (1H, td, J=2.4, 1.0 Hz), 4.76 (2H, s), 2.23 (2H, td, J=7.0, 2.3 Hz), 1.74 (3H, m), 0.85 (6H, s).

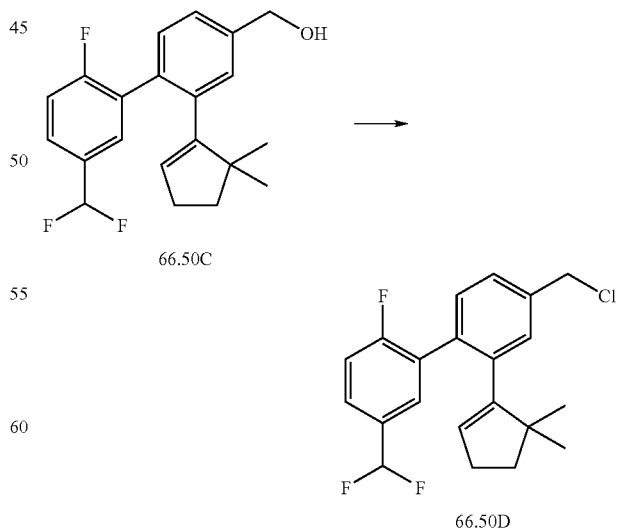

4-(Chloromethyl)-5'-(difluoromethyl)-2-(5,5-dimethyl-1-cyclopenten-1-yl)-2'-fluoro-1,1'-biphenyl (66.50D). To a solution of 66.50C (0.1666 g, 0.481 mmol) in dry DCM (3 mL) and dry DMF (0.06 mL) was added thionyl chloride (0.07 mL, 0.96 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford 66.50D (172.1 mg, 98% yield). $^1$H NMR (500 MHz, CDCl$_3$) δ ppm 7.46 (2H, m), 7.39 (1H, m), 7.33 (1H, m), 7.28 (1H, d, J=1.7 Hz), 7.17 (1H, m), 6.62 (1H, t), 5.51 (1H, td, J=2.3, 1.0 Hz), 4.64 (2H, s), 2.24 (2H, td, J=7.1, 2.4 Hz), 1.68 (2H, m), 0.85 (6H, s).

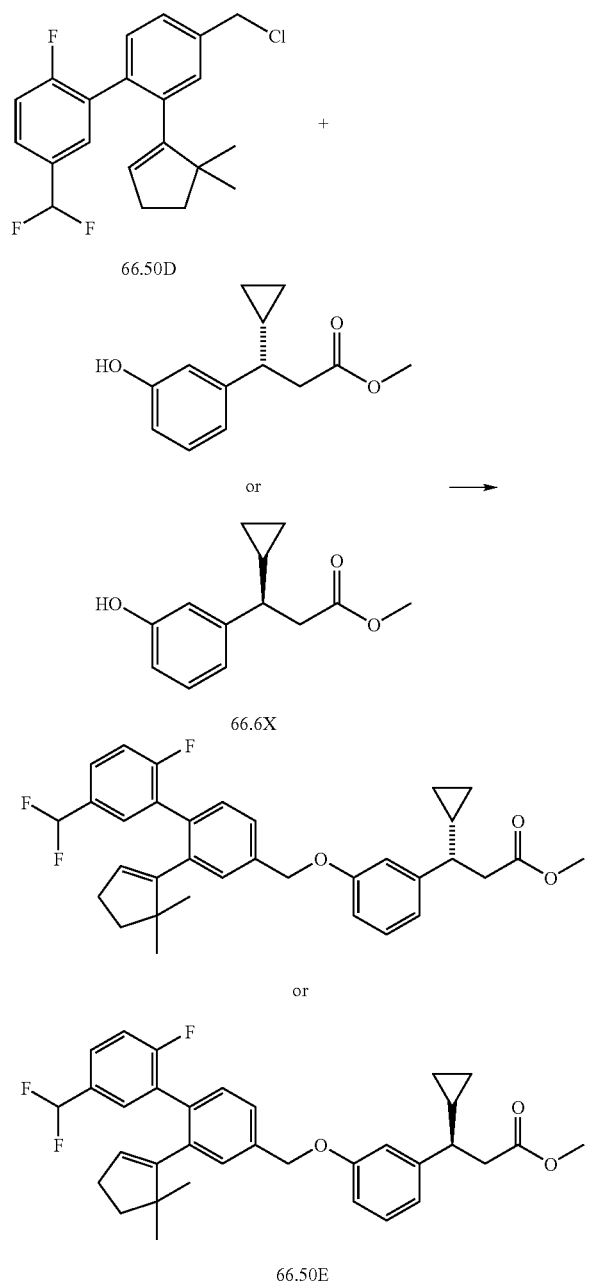

cyclopenten-1-yl)-2'-fluoro-1,1'-biphenyl-4-yl)methyl)oxy) phenyl)propanoate (66.50E). To a vial containing 66.6X (0.0321 g, 0.146 mmol) in 1.00 mL dry DMF was added cesium carbonate (0.0577 g, 0.177 mmol). The mixture was stirred at room temperature for 10 minutes and then 66.50D (0.0604 g, 0.166 mmol) was added. After 22 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-5% EtOAc/hexane) to afford 66.50E (60.8 mg, 76% yield). MS ESI (pos.) m/e: 566.0 (M+H$_2$O)$^+$.

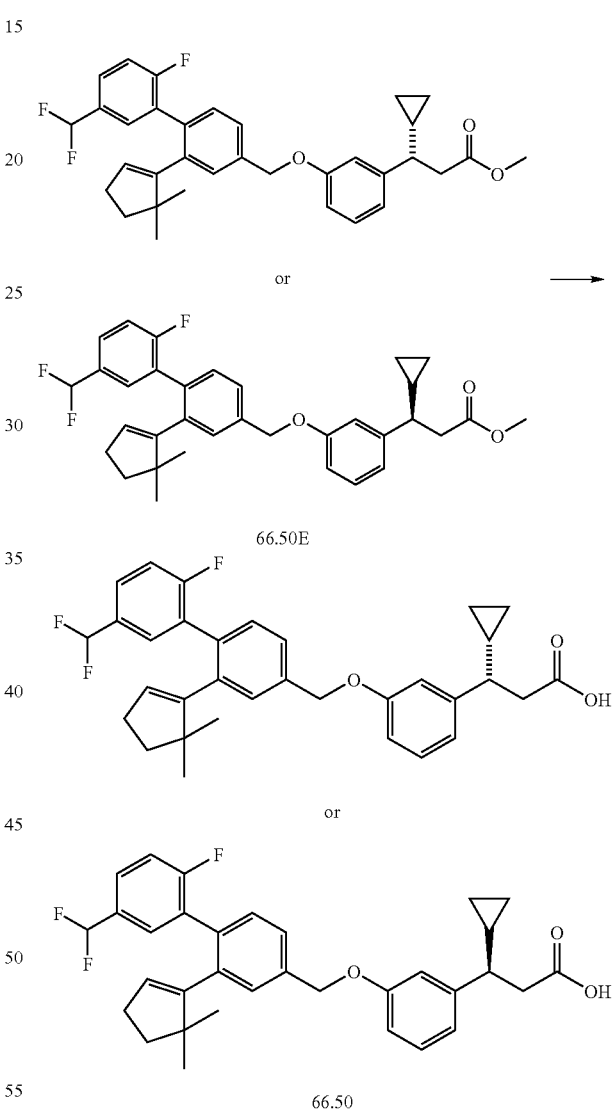

Methyl (3S)-3-cyclopropyl-3-(3-(((5'-(difluoromethyl)-2-(5,5-dimethyl-1-cyclopenten-1-yl)-2'-fluoro-1,1'-biphenyl-4-yl)methyl)oxy)phenyl)propanoate or methyl (3R)-3-cyclopropyl-3-(3-(((5'-(difluoromethyl)-2-(5,5-dimethyl-1-cyclopenten-1-yl)-2'-fluoro-1,1'-biphenyl-4-yl)methyl)oxy) phenyl)propanoate (66.50E).

(3S)-3-Cyclopropyl-3-(3-(((5'-(difluoromethyl)-2-(5,5-dimethyl-1-cyclopenten-1-yl)-2'-fluoro-1,1'-biphenyl-4-yl) methyl)oxy)phenyl)propanoic acid or (3R)-3-cyclopropyl-3-(3-(((5'-(difluoromethyl)-2-(5,5-dimethyl-1-cyclopenten-1-yl)-2'-fluoro-1,1'-biphenyl-4-yl)methyl)oxy)phenyl) propanoic acid (66.50). A pre-mixed solution of 2M NaOH (0.5 mL, 1.00 mmol), MeOH (1 mL), and THF (1 mL) was added to a vial containing 66.50E (0.0608 g, 0.111 mmol). The resulting solution was stirred at room temperature and monitored with TLC and LC-MS. After 24 hours, the mixture was diluted with water, acidified with 1M aqueous HCl, and then extracted five times with EtOAc. The combined organic layers were dried over anhydrous magnesium sulfate and then filtered and concentrated. The residue was purified by silica gel flash chromatography (0-40% EtOAc/hexane) to afford 66.50 as a colorless oil (47.8 mg, 81% yield). $^1$H NMR (400 MHz, CDCl$_3$) δ ppm 7.49 (3H, m), 7.37 (2H, m), 7.25 (1H, t, J=7.8 Hz), 7.15 (1H, t, J=8.8 Hz), 6.94 (3H, m), 6.77 (1H, t), 5.51 (1H, m), 5.12 (2H, s), 2.87 (2H, m), 2.44 (1H, m), 2.24 (2H, td, J=7.0, 2.3 Hz), 1.64 (2H, t, J=7.0 Hz), 1.10 (1H, m), 0.84 (6H, s), 0.65 (1H, m), 0.49 (1H, m), 0.31 (1H, dq, J=9.6, 4.8 Hz), 0.17 (1H, dq, J=9.7, 5.0 Hz). MS ESI (neg.) m/e: 532.9 (M−H)$^+$.

Example 66.51

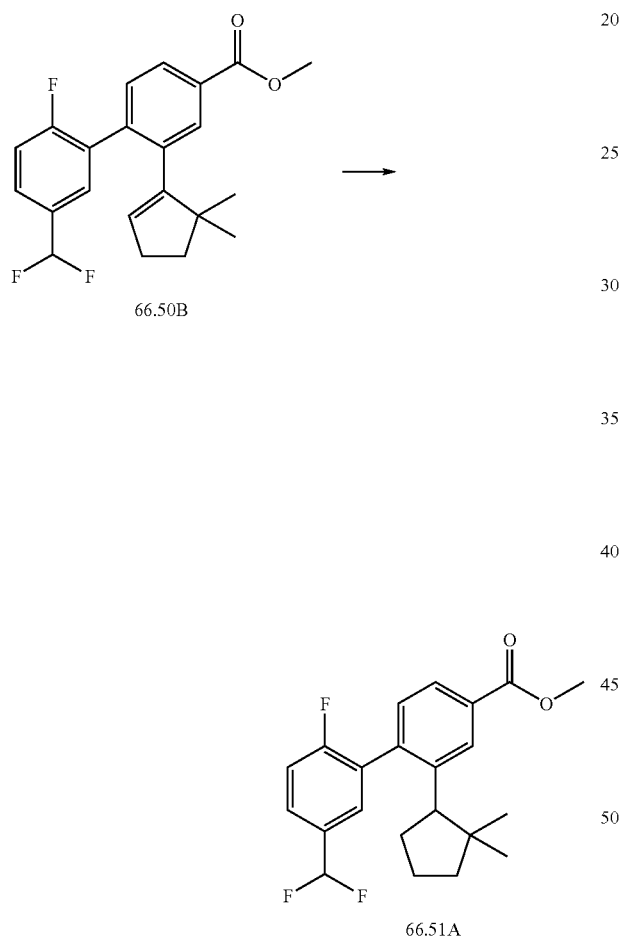

66.50B 66.51A

Methyl 5'-(difluoromethyl)-2-(2,2-dimethylcyclopentyl)-2'-fluoro-1,1'-biphenyl-4-carboxylate (66.51A). To a dry flask containing 66.50B (0.8621 g, 2.303 mmol) in dry MeOH (10 mL) and EtOAc (2 mL) was added palladium (10% wt. on activated carbon) (0.2455 g, 0.2307 mmol). After purging, the mixture was stirred under an atmosphere of hydrogen at room temperature. The reaction was monitored with TLC and LC-MS. After 22.5 hours, the reaction was filtered through Celite. After concentration, the residue was identified as 66.51A and was used without purification (863 mg, 99% yield). MS ESI (pos.) m/e: 376.9 (M+H)$^+$.

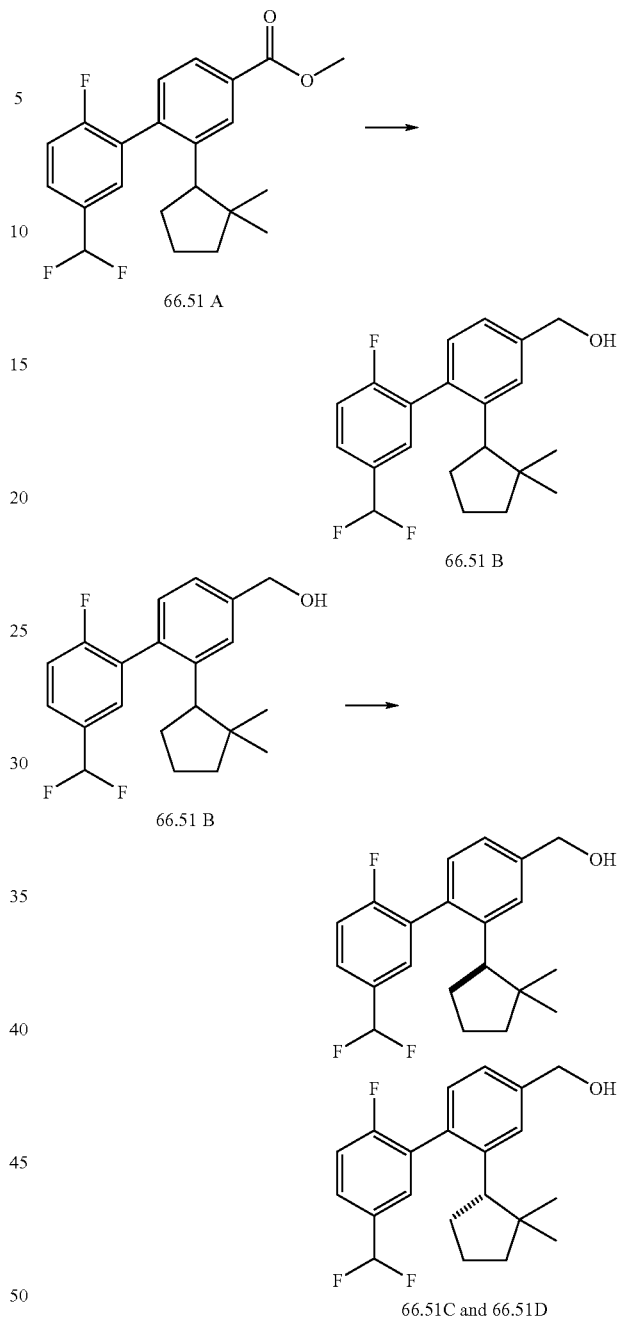

66.51 A 66.51 B 66.51 B 66.51C and 66.51D (5'-(Difluoromethyl)-2-(2,2-dimethylcyclopentyl)-2'-fluoro-1,1'-biphenyl-4-yl)methanol (66.51B). To a cooled solution of 66.51A (0.8631 g, 2.293 mmol) in dry THF (15.4 mL) at 0° C. was added LAH (1.0 M in THF) (4.6 mL, 4.6 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was then purified by flash chromatography (SiO$_2$ gel 60, eluted with 0%-100% EtOAc in hexanes). Fractions containing the desired product were combined and concentrated to a colorless oil as 66.51B (617.1 mg, 77% yield). MS ESI (pos.) m/e: 331.0 (M−H$_2$O)$^+$. Chiral separation of 66.51B was accomplished on a Chiracel-OD column (4% IPA in hexane) to provide 66.51C (peak 1) and 66.51D (peak 2). Both enantiomers were used to synthesize example compounds, and both enantiomers gave active compounds.

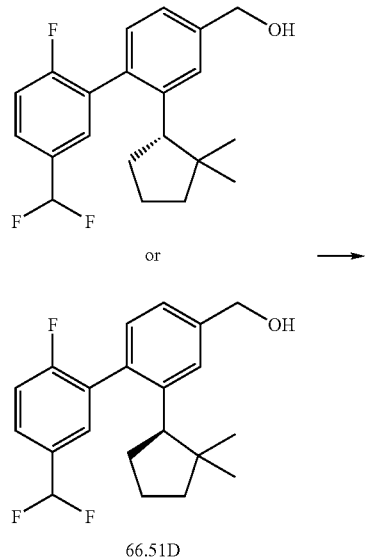

66.51D

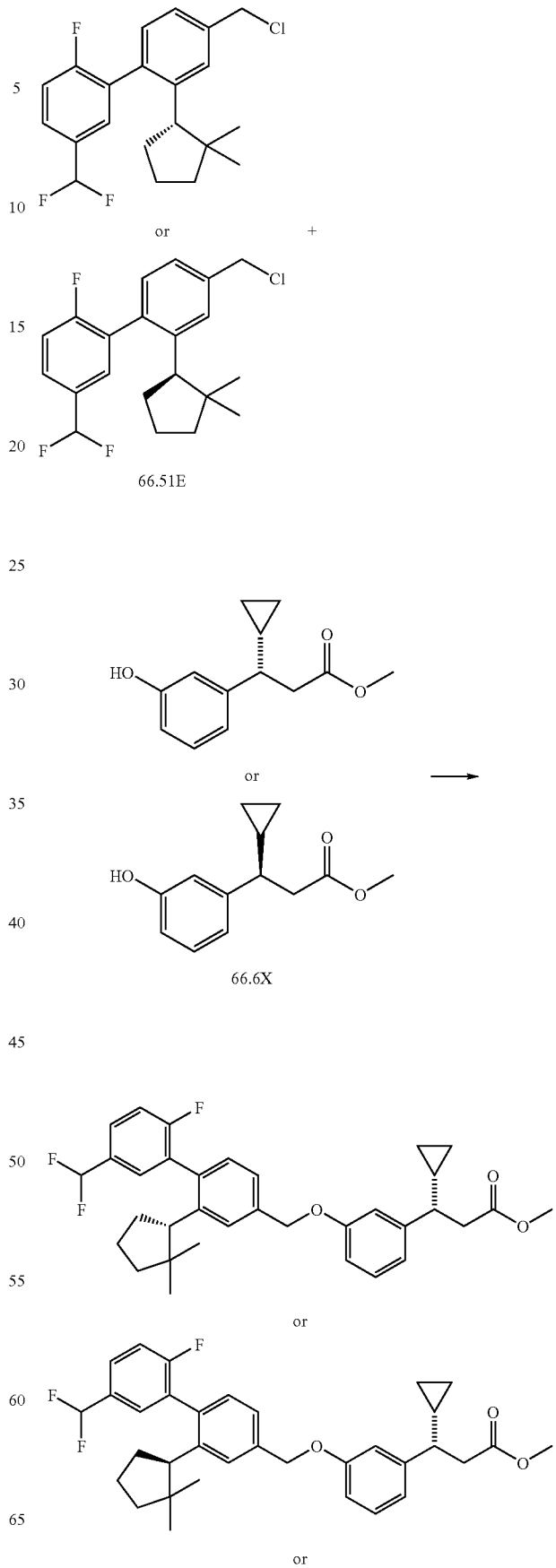

66.51E 4-(Chloromethyl)-5'-(difluoromethyl)-2-((1S)-2,2-dimethylcyclopentyl)-2'-fluoro-1,1'-biphenyl or 4-(chloromethyl)-5'-(difluoromethyl)-2-((1R)-2,2-dimethylcyclopentyl)-2'-fluoro-1,1'-biphenyl (66.51E). To a solution of 66.51D (0.2882 g, 0.827 mmol) in dry DCM (10.5 mL) and dry DMF (0.08 mL) was added thionyl chloride (0.12 mL, 1.65 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford 66.51E (272.1 mg, 90% yield).

-continued

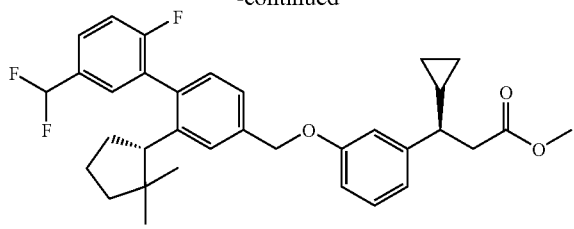

or

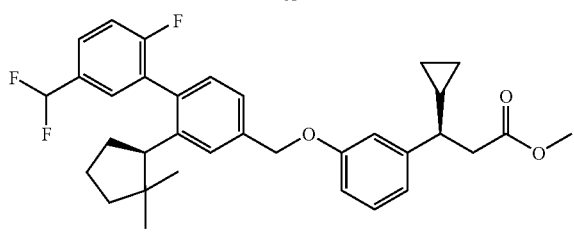

66.51F

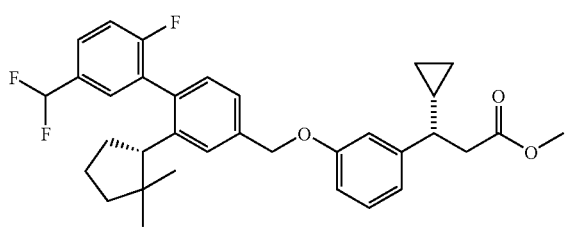

or

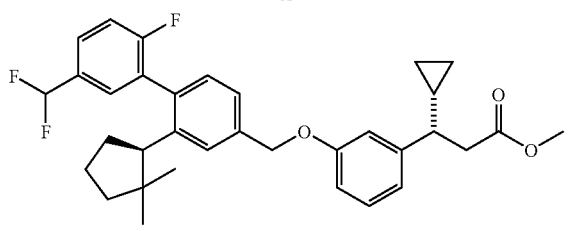

or

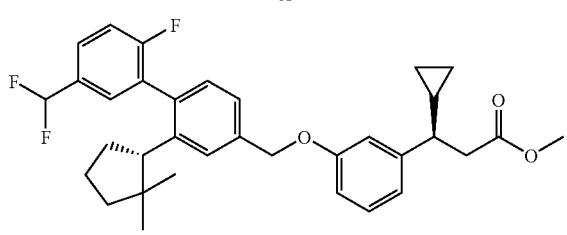

or

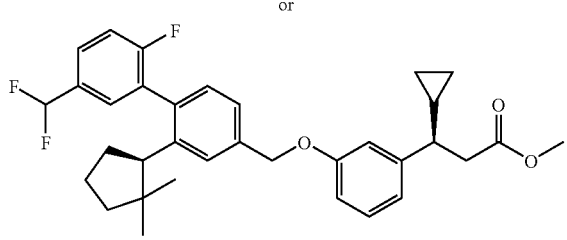

66.51F

Methyl (3S)-3-cyclopropyl-3-(3-(((5'-(difluoromethyl)-2-((1S)-2,2-dimethylcyclopentyl)-2'-fluoro-1,1'-biphenyl-4-yl)methyl)oxy)phenyl)propanoate or methyl (3S)-3-cyclopropyl-3-(3-(((5'-(difluoromethyl)-2-((1R)-2,2-dimethylcyclopentyl)-2'-fluoro-1,1'-biphenyl-4-yl)methyl)oxy)phenyl)propanoate or methyl (3R)-3-cyclopropyl-3-(3-(((5'-(difluoromethyl)-2-((1S)-2,2-dimethylcyclopentyl)-2'-fluoro-1,1'-biphenyl-4-yl)methyl)oxy)phenyl)propanoate or methyl (3R)-3-cyclopropyl-3-(3-(((5'-(difluoromethyl)-2-((1R)-2,2-dimethylcyclopentyl)-2'-fluoro-1,1'-biphenyl-4-yl)methyl)oxy)phenyl)propanoate (66.51F). To a vial containing 66.6X (0.0338 g, 0.153 mmol) in 1.00 mL dry DMF was added cesium carbonate (0.0689 g, 0.211 mmol). The mixture was stirred at room temperature for 10 minutes and then 66.51E (0.0622 g, 0.170 mmol) was added. After 22 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-5% EtOAc/hexane) to afford 66.51F (64.9 mg, 77% yield). MS ESI (pos.) m/e: 568.0 (M+H$_2$O)$^+$.

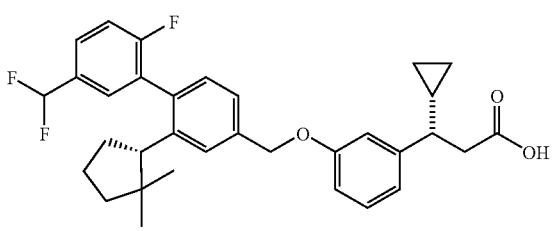

or

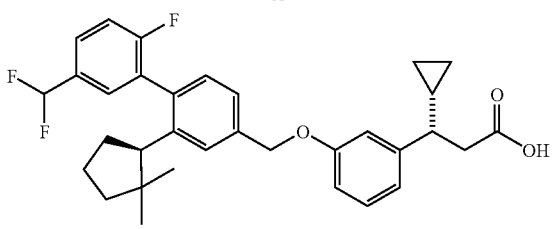

or

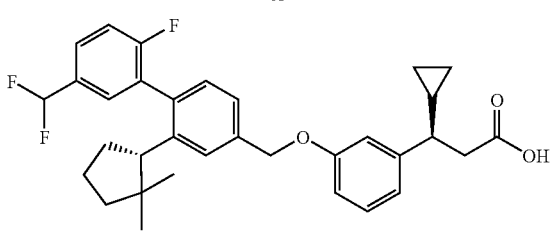

or

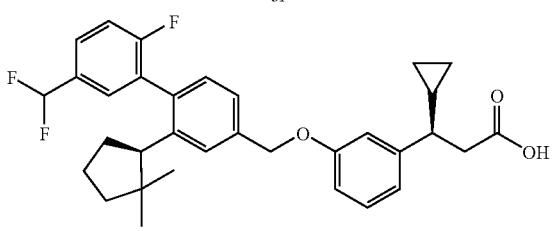

66.51

(3S)-3-Cyclopropyl-3-(3-(((5'-(difluoromethyl)-2-((1S)-2,2-dimethylcyclopentyl)-2'-fluoro-1,1'-biphenyl-4-yl)methyl)oxy)phenyl)propanoic acid or (3S)-3-cyclopropyl-3-(3-(((5'-(difluoromethyl)-2-((1R)-2,2-dimethylcyclopentyl)-2'-fluoro-1,1'-biphenyl-4-yl)methyl)oxy)phenyl)propanoic acid or (3R)-3-cyclopropyl-3-(3-(((5'-(difluoromethyl)-2-((1S)-2,2-dimethylcyclopentyl)-2'-fluoro-1,1'-biphenyl-4-yl)methyl)oxy)phenyl)propanoic acid or (3R)-3-cyclopropyl-3-(3-(((5'-(difluoromethyl)-2-((1R)-2,2-dimethylcyclopentyl)-2'-fluoro-1,1'-biphenyl-4-yl)methyl)oxy)phenyl)propanoic acid (66.51). A pre-mixed solution of 2M NaOH (0.5 mL, 1.00 mmol), THF (1 mL), and MeOH (1 mL) was added to a vial containing 66.51F (0.0649 g, 0.118 mmol). The resulting solution was stirred at room temperature and monitored with TLC and LC-MS. After 24 hours, the mixture was diluted with water, acidified with 1M aqueous HCl, and then extracted five times with EtOAc. The combined organic layers were dried over anhydrous magnesium sulfate and then filtered and concentrated. The residue was purified with reverse phase HPLC using 30-90% Solvent B (0.1% TFA in acetonitrile) to afford 66.51 (36.9 mg, 58% yield). $^1$H NMR (400 MHz, CDCl$_3$) δ ppm 7.55 (4H, m), 7.29 (3H, m), 6.91 (3H, m), 6.53 (1H, t), 5.12 (2H, m), 2.90 (3H, m), 2.37 (1H, dt, J=9.5, 7.6 Hz), 2.22 (2H, m), 1.85 (1H, m), 1.72 (1H, m), 1.58 (1H, m), 1.42 (1H, m), 1.13 (1H, m), 0.76 (3H, m), 0.65 (2H, m), 0.51 (2H, m), 0.49 (1H, m), 0.37 (1H, m), 0.22 (1H, m). MS ESI (neg.) m/e: 535.0 (M−H)$^+$.

Example 66.52

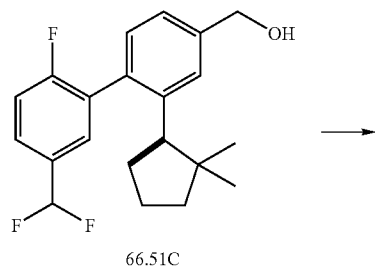

66.51C

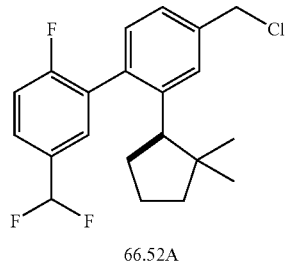

66.52A 4-(Chloromethyl)-5'-(difluoromethyl)-2-((1R)-2,2-dimethylcyclopentyl)-2'-fluoro-1,1'-biphenyl (66.52A). To a solution of 66.51C (0.2798 g, 0.803 mmol) in dry DCM (10 mL) and dry DMF (0.076 mL) was added thionyl chloride (0.12 mL, 1.65 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford 66.52A (282.5 mg, 96% yield).

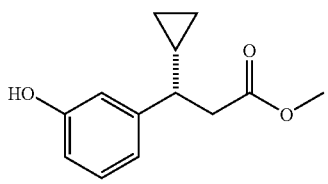

or +

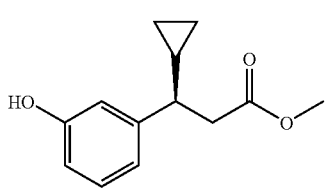

66.52A

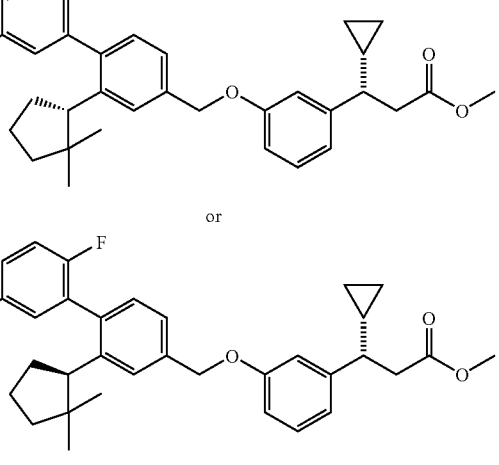

66.6X or

433

-continued


or

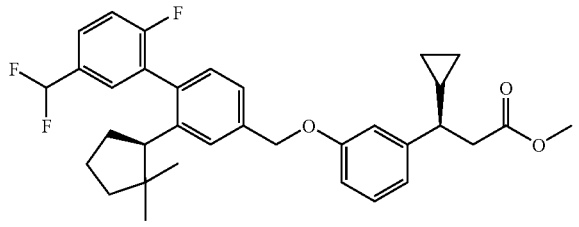

66.52B

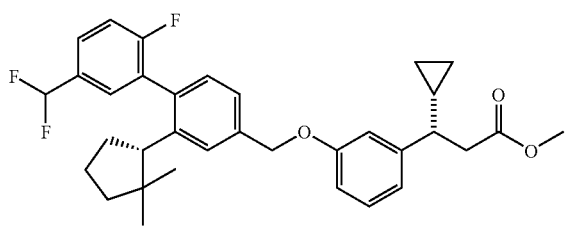

or

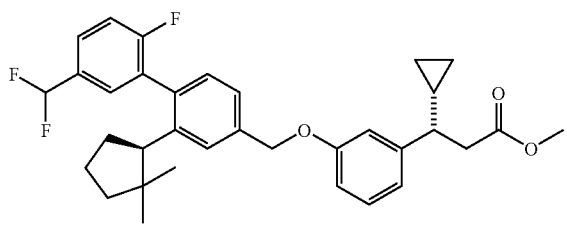

or

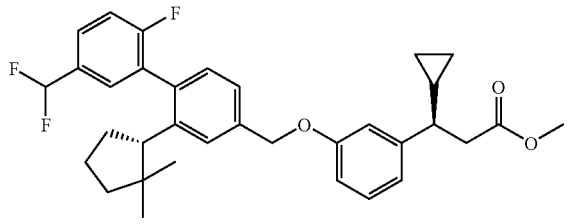

or

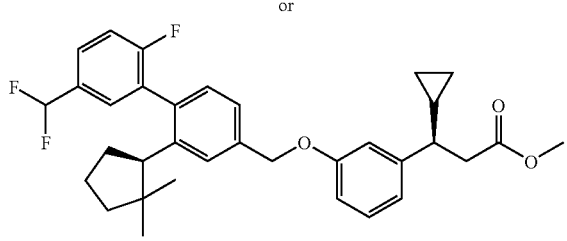

66.52B

434

Methyl (3S)-3-cyclopropyl-3-(3-(((5'-(difluoromethyl)-2-((1R)-2,2-dimethylcyclopentyl)-2'-fluoro-1,1'-biphenyl-4-yl)methyl)oxy)phenyl)propanoate or methyl (3S)-3-cyclopropyl-3-(3-(((5'-(difluoromethyl)-2-((1S)-2,2-dimethylcyclopentyl)-2'-fluoro-1,1'-biphenyl-4-yl)methyl)oxy)phenyl)propanoate or methyl (3R)-3-cyclopropyl-3-(3-(((5'-(difluoromethyl)-2-((1R)-2,2-dimethylcyclopentyl)-2'-fluoro-1,1'-biphenyl-4-yl)methyl)oxy)phenyl)propanoate or methyl (3R)-3-cyclopropyl-3-(3-(((5'-(difluoromethyl)-2-((1S)-2,2-dimethylcyclopentyl)-2'-fluoro-1,1'-biphenyl-4-yl)methyl)oxy)phenyl)propanoate (66.52B). To a vial containing 66.6X (0.0258 g, 0.117 mmol) in 1.00 mL dry DMF was added cesium carbonate (0.0466 g, 0.143 mmol). The mixture was stirred at room temperature for 10 minutes and then 66.52A (0.0478 g, 0.130 mmol) was added. After 22 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-5% EtOAc/hexane) to afford 66.52B (57.6 mg, 89% yield). MS ESI (pos.) m/e: 568.3 $(M+H_2O)^+$.

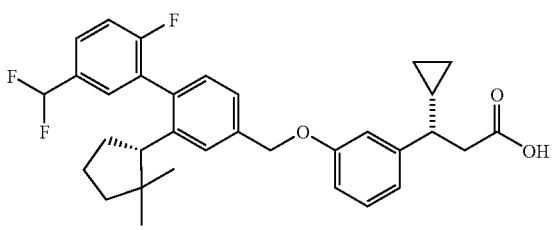

or

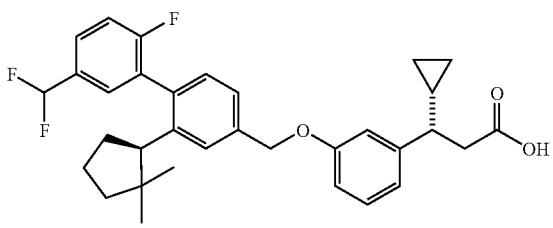

or

→

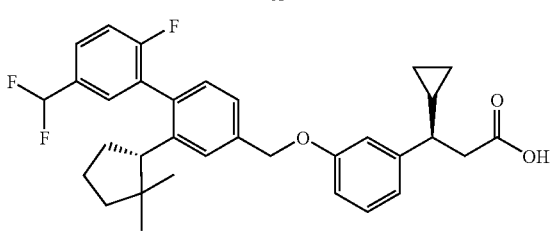

or

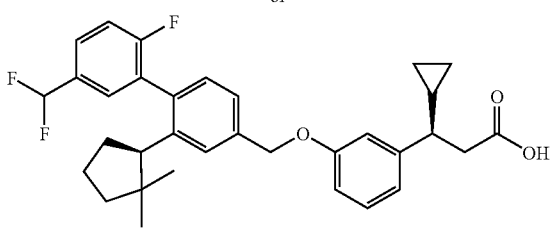

66.52

(3S)-3-Cyclopropyl-3-(3-(((5'-(difluoromethyl)-2-((1R)-2,2-dimethylcyclopentyl)-2'-fluoro-1,1'-biphenyl-4-yl)methyl)oxy)phenyl)propanoic acid or (3S)-3-cyclopropyl-3-(3-(((5'-(difluoromethyl)-2-((1S)-2,2-dimethylcyclopentyl)-2'-fluoro-1,1'-biphenyl-4-yl)methyl)oxy)phenyl)propanoic acid or (3R)-3-cyclopropyl-3-(3-(((5'-(difluoromethyl)-2-((1R)-2,2-dimethylcyclopentyl)-2'-fluoro-1,1'-biphenyl-4-yl)methyl)oxy)phenyl)propanoic acid or (3R)-3-cyclopropyl-3-(3-(((5'-(difluoromethyl)-2-((1S)-2,2-dimethylcyclopentyl)-2'-fluoro-1,1'-biphenyl-4-yl)methyl)oxy)phenyl)propanoic acid (66.52). A pre-mixed solution of 2M NaOH (0.5 mL, 1.00 mmol), THF (1 mL), and MeOH (1 mL) was added to a vial containing 66.52B (0.0576 g, 0.105 mmol). The mixture was stirred at room temperature and monitored with TLC and LC-MS. After 24 hours, the mixture was diluted with water, acidified with 1M aqueous HCl, and then extracted five times with EtOAc. The combined organic layers were then dried over anhydrous magnesium sulfate and then filtered and concentrated. The residue was purified with reverse phase HPLC using 30-90% Solvent B (0.1% TFA in acetonitrile) to afford 66.52 (29.3 mg, 52% yield). $^1$H NMR (400 MHz, CDCl$_3$) δ ppm 7.39 (4H, m), 7.13 (3H, m), 6.74 (3H, m), 6.64 (1H, t), 4.98 (2H, m), 2.72 (3H, m), 2.27 (1H, m), 2.07 (2H, m), 1.69 (1H, m), 1.56 (1H, m), 1.40 (1H, m), 1.26 (1H, m), 0.94 (1H, m), 0.56 (3H, m), 0.48 (2H, m), 0.34 (2H, m), 0.32 (1H, m), 0.18 (1H, m), −0.01 (1H, dq, J=9.7, 5.0 Hz). MS ESI (neg.) m/e: 535.0 (M−H)$^+$.

Example 66.53

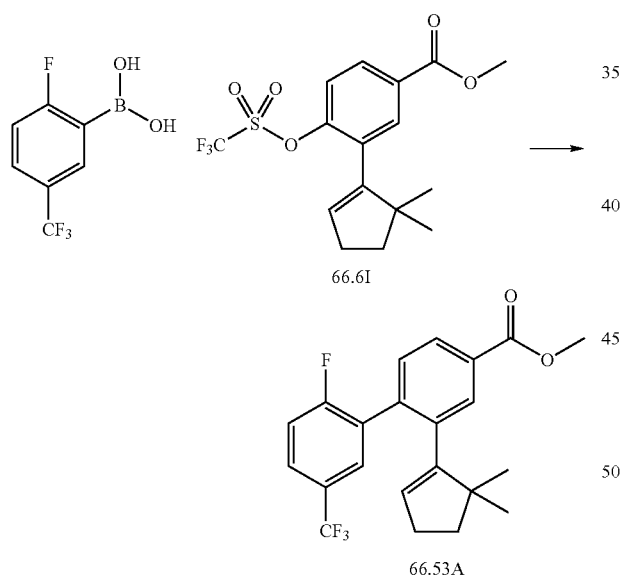

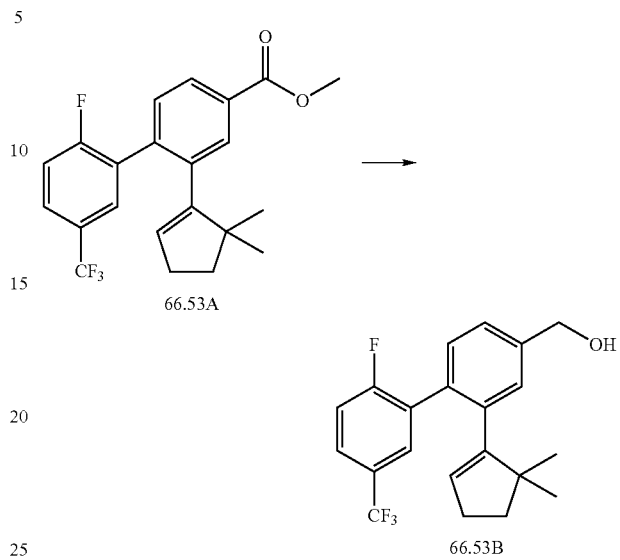

Methyl 2-(5,5-dimethyl-1-cyclopenten-1-yl)-2'-fluoro-5'-(trifluoromethyl)-1,1'-biphenyl-4-carboxylate (66.53A). To a stirred solution of 66.61 (0.7595 g, 2.007 mmol) in DMF (5 mL) at 23° C. was added 2-fluoro-5-(trifluoromethyl)phenylboronic acid (commercially available from Aldrich Chemical Company, Inc.) (0.8352 g, 4.017 mmol) and potassium carbonate (0.8357 g, 6.047 mmol) followed by tetrakis(triphenylphosphine)palladium (0.2364 g, 0.2046 mmol). The mixture was heated to 90° C. After 17 hours, LCMS-showed that the reaction was complete. The mixture was cooled to room temperature and then diluted with water. After extracting three times with EtOAc, the mixture was concentrated in vacuo and then purified on silica gel (0%-10% EtOAc/hexane) to afford 66.53A as a clear oil that was used without further purification (414.2 mg, 53% yield).

(2-(5,5-Dimethyl-1-cyclopenten-1-yl)-2'-fluoro-5'-(trifluoromethyl)-1,1'-biphenyl-4-yl)methanol (66.53B). To a cooled solution of 66.53A (0.4142 g, 1.056 mmol) in dry THF (7.8 mL) at 0° C. was added LAH (1.0 M in THF) (2.2 mL, 2.200 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by flash chromatography (SiO$_2$ gel 60, eluted with 0%-100% EtOAc in hexanes). Fractions containing the desired product were combined and concentrated to afford 66.53B as a colorless oil (257.4 mg, 67% yield). $^1$H NMR (400 MHz, CDCl$_3$) δ ppm 7.61 (2H, m), 7.40 (2H, m), 7.17 (1H, t, J=8.8 Hz), 5.52 (1H, m), 4.77 (2H, s), 2.24 (2H, td, J=7.0, 2.3 Hz), 1.71 (3H, m), 0.84 (6H, s).

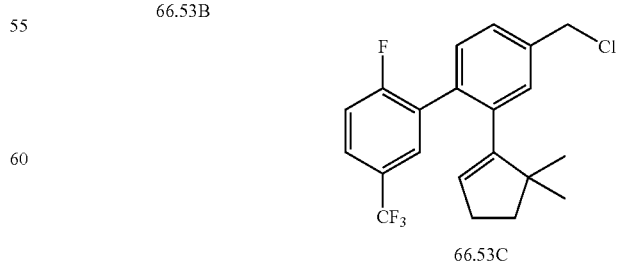

4-(Chloromethyl)-2-(5,5-dimethyl-1-cyclopenten-1-yl)-2'-fluoro-5'-(trifluoromethyl)-1,1'-biphenyl (66.53C). To a solution of 66.53B (0.2574 g, 0.706 mmol) in dry DCM (10 mL) and dry DMF (0.07 mL) was added thionyl chloride (0.11 mL, 1.51 mmol) at 0° C. The resulting solution was warmed to room temperature and monitored with TLC and LCMS. After 45 minutes, the reaction was concentrated and then purified by silica gel flash chromatography (0-5% EtOAc/hexane) to afford 66.53C (242.8 mg, 90% yield). ¹H NMR (400 MHz, CDCl₃) δ ppm 7.60 (2H, m), 7.40 (1H, m), 7.35 (2H, m), 7.21 (1H, m), 5.52 (1H, td, J=2.4, 0.9 Hz), 4.66 (2H, m), 2.24 (2H, td, J=7.0, 2.3 Hz), 1.68 (2H, m), 0.84 (6H, s).

(0.0358 g, 0.163 mmol) in 1.00 mL dry DMF was added cesium carbonate (0.0674 g, 0.207 mmol). The mixture was stirred at room temperature for 10 minutes and then 66.53C (0.0699 g, 0.183 mmol) was added. After 22 hours, the reaction was diluted with water and then extracted five times with EtOAc. The organic extraction was then washed one time with brine and dried over anhydrous magnesium sulfate. The solid was filtered off, and the solvent was concentrated. The residue was purified by silica gel flash chromatography (0-10% EtOAc/hexane) to afford 66.53D (64.2 mg, 70% yield). ¹H NMR (400 MHz, CDCl₃) δ ppm 7.62 (2H, m), 7.46 (1H, m), 7.35 (2H, dd, J=10.8, 1.4 Hz), 7.29 (1H, m), 7.17 (1H, t, J=8.8 Hz), 6.93 (3H, m), 5.51 (1H, t, J=2.0 Hz), 5.11 (2H, s), 3.62 (2H, s), 2.82 (2H, m), 2.44 (1H, m), 2.24 (2H, td, J=7.0, 2.7 Hz), 1.64 (2H, t, J=7.0 Hz), 1.33 (4H, m), 0.93 (6H, m), 0.65 (1H, m), 0.48 (1H, m), 0.27 (1H, dq, J=9.4, 4.8 Hz), 0.21 (1H, m).

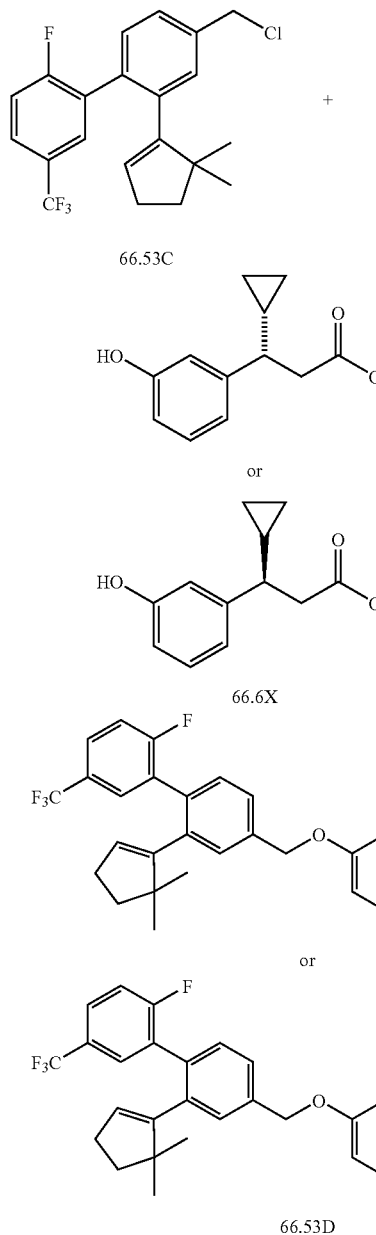

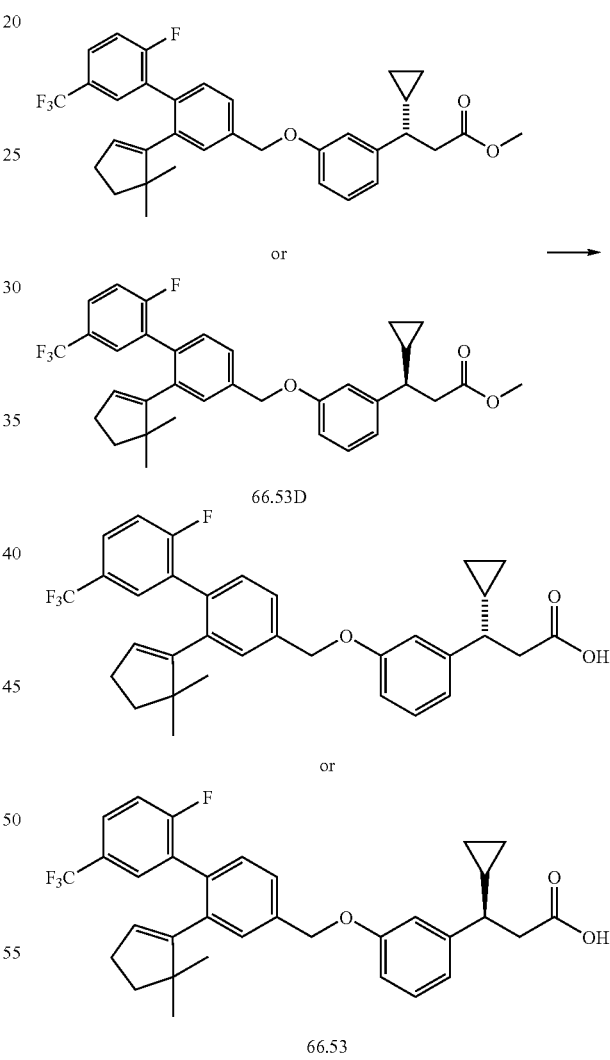

Methyl (3S)-3-cyclopropyl-3-(3-(((2-(5,5-dimethyl-1-cyclopenten-1-yl)-2'-fluoro-5'-(trifluoromethyl)-1,1'-biphenyl-4-yl)methyl)oxy)phenyl)propanoate or methyl (3R)-3-cyclopropyl-3-(3-(((2-(5,5-dimethyl-1-cyclopenten-1-yl)-2'-fluoro-5'-(trifluoromethyl)-1,1'-biphenyl-4-yl)methyl)oxy)phenyl)propanoate (66.53D). To a vial containing 66.6X (3S)-3-Cyclopropyl-3-(3-(((2-(5,5-dimethyl-1-cyclopenten-1-yl)-2'-fluoro-5'-(trifluoromethyl)-1,1'-biphenyl-4-yl)methyl)oxy)phenyl)propanoic acid or (3R)-3-cyclopropyl-3-(3-(((2-(5,5-dimethyl-1-cyclopenten-1-yl)-2'-fluoro-5'-(trifluoromethyl)-1,1'-biphenyl-4-yl)methyl)oxy)phenyl)propanoic acid (66.53). A pre-mixed solution of 2M NaOH (0.5 mL, 1.00 mmol), MeOH (1 mL), and THF (1 mL) was added to a vial containing 66.53D (0.0642 g, 0.113 mmol). This solution was stirred at room temperature and monitored with TLC and LC-MS. After 24 hours, the mixture was diluted with water, acidified with 1M aqueous HCl, and then extracted five times with EtOAc. The combined organic layers were dried over anhydrous magnesium sulfate and then were filtered and concentrated. The residue was purified with reverse phase HPLC using 30-90% Solvent B (0.1% TFA in ACN) to afford 66.53 (46.3 mg, 74% yield). $^{1}$H NMR (500 MHz, CDCl$_3$) δ ppm 7.61 (2H, m), 7.43 (1H, dd, J=7.8, 1.7 Hz), 7.37 (2H, m), 7.28 (3H, m), 7.17 (1H, t, J=8.8 Hz), 6.92 (3H, m), 5.50 (1H, m), 5.11 (2H, s), 2.86 (2H, m), 2.42 (1H, m), 2.23 (2H, td, J=7.0, 2.3 Hz), 1.63 (2H, t, J=7.0 Hz), 1.08 (1H, m), 0.82 (6H, s), 0.65 (1H, m), 0.48 (1H, m), 0.30 (1H, dq, J=9.6, 4.9 Hz), 0.17 (1H, dddd, J=9.7, 5.1, 5.0, 4.9 Hz). MS ESI (neg.) m/e: 550.9 (M−H)$^{+}$.

Example 66.54 and 66.55 blue color did not change. Nitrogen was then bubbled into the solution for 10 minutes. NaBH$_4$ (25.8 mg, 0.681 mmol) was added, and the mixture was warmed to room temperature and stirred for 16 hours. Additional NaBH$_4$ (25.8 mg, 0.681 mmol) was added to the reaction, and LC-MS indicated that the reaction was complete. The solvent was removed and the residue was diluted with EtOAc and washed with saturated NaHCO$_3$, water, and brine. The organic layer was then dried, evaporated, and the product was used in the next step without further purification. $^{1}$H NMR (500 MHz, CDCl$_3$) δ ppm 7.35 (1H, d, J=1.5 Hz), 7.27 (1H, dd, J=7.9, 1.8 Hz), 7.09-7.18 (2H, m), 6.88 (1H, t, J=9.0 Hz), 6.56-6.78 (5H, m), 4.97 (2H, s), 3.56-3.73 (3H, m), 3.46 (3H, s), 3.46 (1H, d, J=6.8 Hz), 2.50-2.69 (2H, m), 2.21 (1H, m), 1.32 (2H, br. s.), 1.33 (1H, dd, J=7.6, 5.1 Hz), 1.08-1.27 (2H, m), 0.69-0.91 (7H, m), 0.36-0.59 (1H, m), 0.22-0.34 (1H, m), 0.11 (1H, dt, J=9.7, 4.8 Hz), −0.09-0.05 (1H, m).

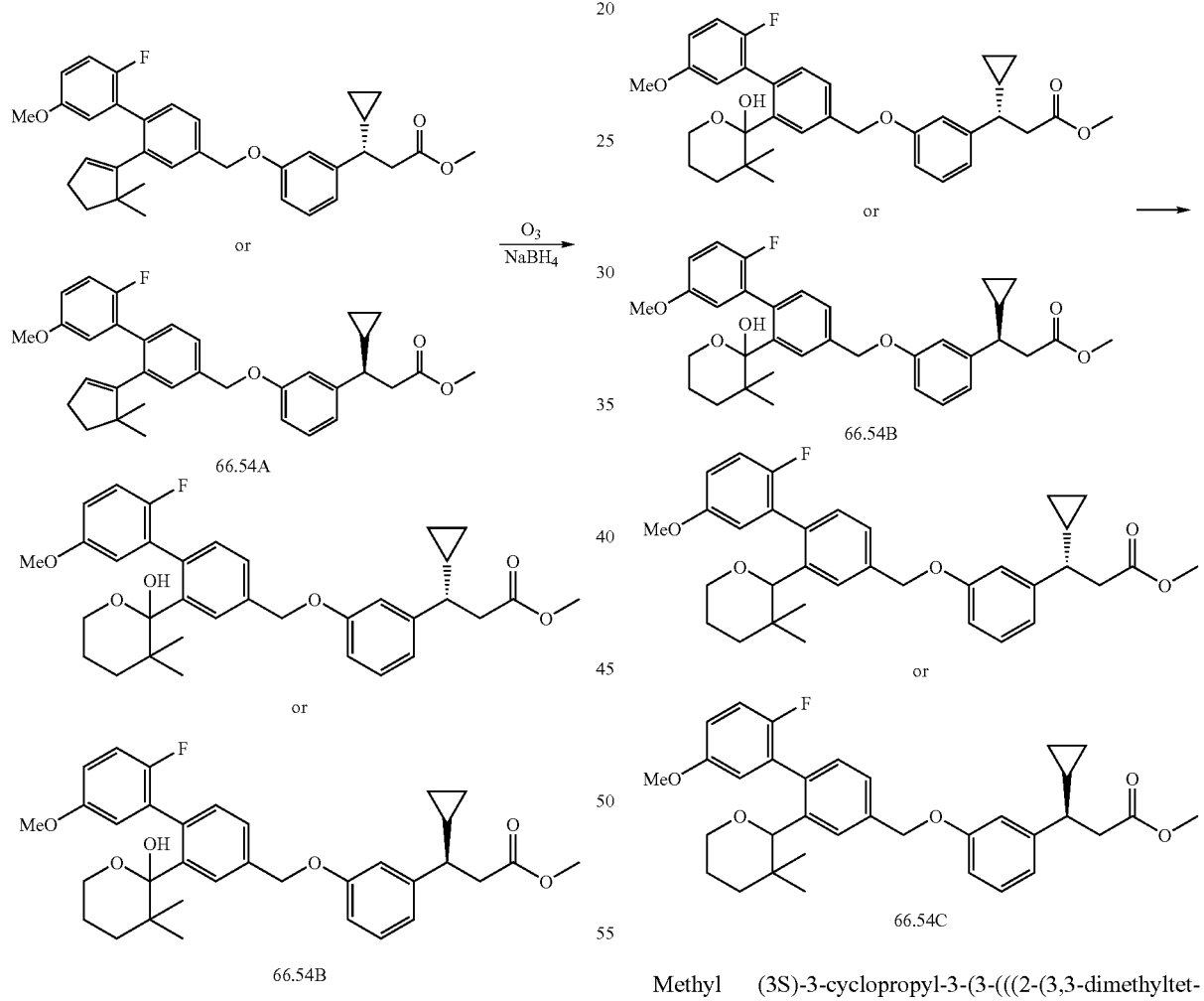

Methyl (3S)-3-cyclopropyl-3-(3-(((2'-fluoro-2-(2-hydroxy-3,3-dimethyltetrahydro-2H-pyran-2-yl)-5'-(methyloxy)-1,1'-biphenyl-4-yl)methyl)oxy)phenyl)propanoate or methyl (3R)-3-cyclopropyl-3-(3-(((2'-fluoro-2-(2-hydroxy-3,3-dimethyltetrahydro-2H-pyran-2-yl)-5'-(methyloxy)-1,1'-biphenyl-4-yl)methyl)oxy)phenyl)propanoate (66.54B). To a solution of 66.54A (see Example 14) (120 mg, 0.227 mmol) in DCM/MeOH (1.5 mL/10 mL) at −78° C., was bubbled O$_3$ (109 mg, 2.27 mmol) for 10 minutes until the deep Methyl (3S)-3-cyclopropyl-3-(3-(((2-(3,3-dimethyltetrahydro-2H-pyran-2-yl)-2'-fluoro-5'-(methyloxy)-1,1'-biphenyl-4-yl)methyl)oxy)phenyl)propanoate or methyl (3R)-3-cyclopropyl-3-(3-(((2-(3,3-dimethyltetrahydro-2H-pyran-2-yl)-2'-fluoro-5'-(methyloxy)-1,1'-biphenyl-4-yl)methyl)oxy)phenyl)propanoate (66.54C). To a solution 66.54B (128 mg, 0.227 mmol) in 15 mL DCM at −78° C. was added TFA (169 µL, 2.275 mmol). The resulting mixture was stirred for 15 minutes and then triethylsilane (363 µL, 2.275 mmol) was added. The mixture was slowly returned to room temperature over 1 hour. The product was chromatographed on silica gel (hexane:EtOAc 5:1 Rf=0.2) to give product. $^1$H NMR (400 MHz, CDCl$_3$) δ ppm 7.47 (1H, dd, J=14.1, 2.0 Hz), 7.26 (1H, ddd, J=12.7, 8.0, 2.3 Hz), 6.97-7.17 (2H, m), 6.80-6.97 (1H, m), 6.48-6.78 (5H, m), 4.95 (2H, s), 3.99-4.07 (1H, m), 3.64 (3H, d, J=3.1 Hz), 3.46 (3H, s), 3.30-3.35 (1H, dd, J=11.5, 2.5 Hz), 2.52-2.71 (2H, m), 2.20 (1H, ddd, J=10.0, 7.6, 7.4 Hz), 1.05-1.34 (4H, m), 0.66-0.94 (4H, m), 0.41 (1H, m), 0.34-0.59 (1H, m), 0.23-0.26 (1H, m), 0.17-0.23 (3H, m), 0.05-0.15 (1H, m), −0.01-0.08 (1H, m). Mass Spectrum (ESI) m/e=564.0.0 [M+18].

2H-pyran-2-yl)-2'-fluoro-5'-(methyloxy)-1,1'-biphenyl-4-yl)methyl)oxy)phenyl)propanoate; or methyl (3R)-3-cyclopropyl-3-(3-(((2-((2S)-3,3-dimethyltetrahydro-2H-pyran-2-yl)-2'-fluoro-5'-(methyloxy)-1,1'-biphenyl-4-yl)methyl)oxy)phenyl)propanoate and methyl (3R)-3-cyclopropyl-3-(3-(((2-((2R)-3,3-dimethyltetrahydro-2H-pyran-2-yl)-2'-fluoro-5'-(methyloxy)-1,1'-biphenyl-4-yl)methyl)oxy)phenyl)propanoate (66.54D and 66.55D). Compounds 66.54D and 66.55D were separated by chiral HPLC using an

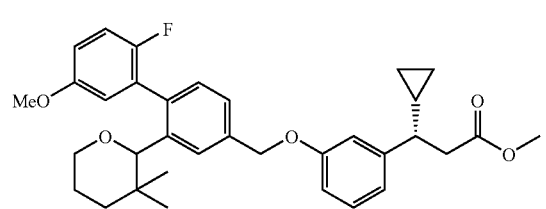

or

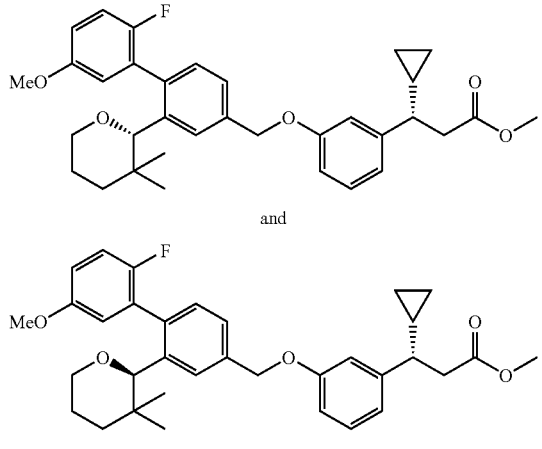

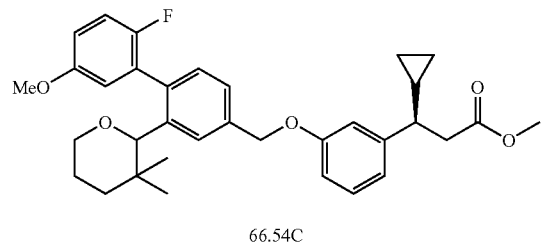

66.54C

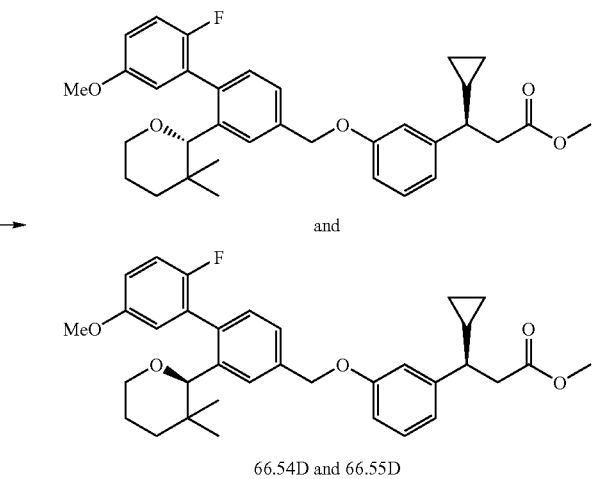

66.54D and 66.55D

Methyl (3S)-3-cyclopropyl-3-(3-(((2-((2S)-3,3-dimethyltetrahydro-2H-pyran-2-yl)-2'-fluoro-5'-(methyloxy)-1,1'-biphenyl-4-yl)methyl)oxy)phenyl)propanoate and methyl (3S)-3-cyclopropyl-3-(3-(((2-((2R)-3,3-dimethyltetrahydro- OD-H column with isocratic 4% isopropanol in hexane. The first eluted enantiomer was 66.54D. Mass Spectrum (ESI) m/e=564.0.0 [M+18]. The second eluted enantiomer was 66.55D.

443

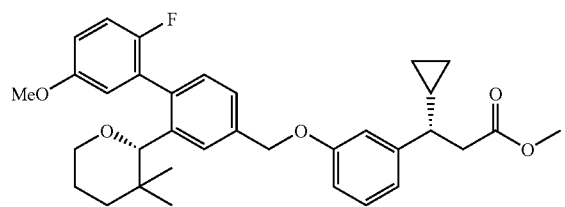

or

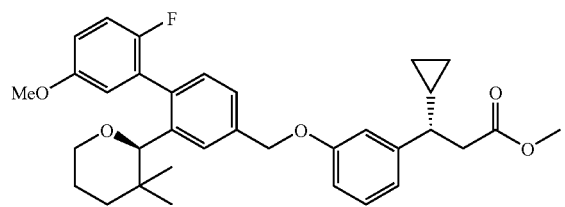

or

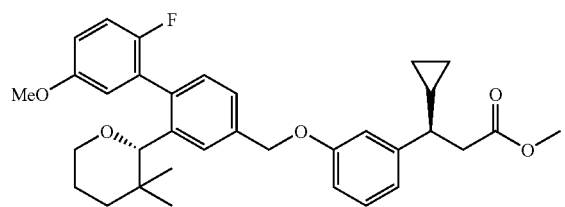

or

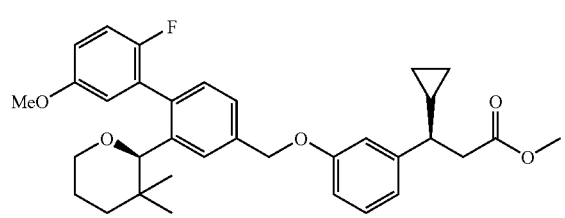

66.54D
66.55D

444

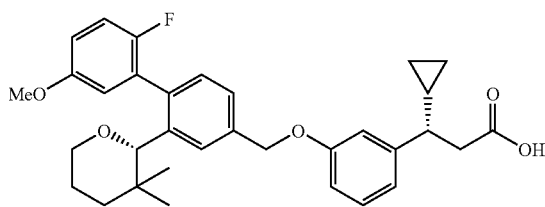

or

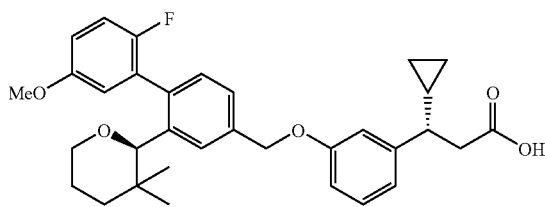

or

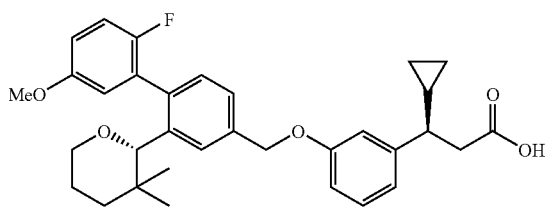

or

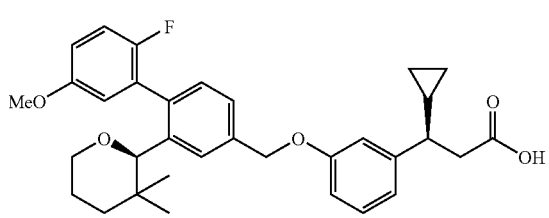

66.54
66.55

(3S)-3-Cyclopropyl-3-(3-(((2-((2S)-3,3-dimethyltetrahydro-2H-pyran-2-yl)-2'-fluoro-5'-(methyloxy)-1,1'-biphenyl-4-yl)methyl)oxy)phenyl)propanoic acid and (3S)-3-cyclopropyl-3-(3-(((2-((2R)-3,3-dimethyltetrahydro-2H-pyran-2-yl)-2'-fluoro-5'-(methyloxy)-1,1'-biphenyl-4-yl)methyl)oxy)phenyl)propanoic acid; or (3R)-3-cyclopropyl-3-(3-(((2-((2S)-3,3-dimethyltetrahydro-2H-pyran-2-yl)-2'-fluoro-5'-(methyloxy)-1,1'-biphenyl-4-yl)methyl)oxy)phenyl)propanoic acid and (3R)-3-cyclopropyl-3-(3-(((2-((2R)-3,3-dimethyltetrahydro-2H-pyran-2-yl)-2'-fluoro-5'-(methyloxy)-1,1'-biphenyl-4-yl)methyl)oxy)phenyl)propanoic acid (66.54 and 66.55). The mixture of 66.54D (35 mg, 0.064 mmol), LiOH, monohydrate (8.9 μL, 0.32 mmol) in the mixture solvent (THF:MeOH:H$_2$O=2:2:1) was stirred for 2 hours. The resulting product was purified by HPLC to give 66.54. Mass Spectrum (ESI) m/e=533.2 [M+1]. $^1$H NMR (400 MHz, CDCl$_3$) δ ppm 7.40 (1H, dd, J=7.6, 1.8 Hz), 7.23 (1H, ddd, J=12.7, 8.0, 2.0 Hz), 7.00-7.13 (2H, m), 6.84-6.93 (1H, m), 6.58-6.75 (5H, m), 4.94-5.03 (2H, m), 4.30 (1H, s), 3.97-4.10 (1H, m), 3.63 (3H, d, J=5.5 Hz), 3.24-3.38 (1H, m), 2.49-2.66 (2H, m), 2.11 (1H, ddd, J=8.8, 7.8, 1.4 Hz), 1.70-1.85 (1H, m), 1.06-1.34 (3H, m), 0.84-0.95 (1H, m, J=8.9, 8.9, 4.3, 4.1 Hz), 0.74 (3H, d, J=2.7 Hz), 0.42 (1H, tt, J=8.8, 4.7 Hz), 0.16-0.33 (4H, m), 0.06-0.15 (1H, m, J=9.5, 5.1, 4.8, 4.8 Hz), −0.04-0.04 (1H, m). Example 66.55 was synthesized using 66.55D in place of 66.54D. Mass Spectrum (ESI) m/e=533.2 [M+1].

Example 66.56

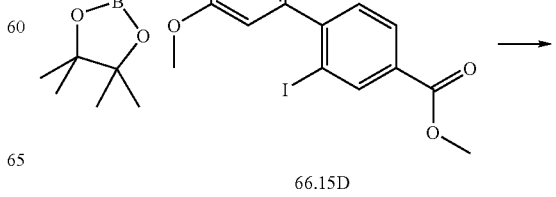

66.15D

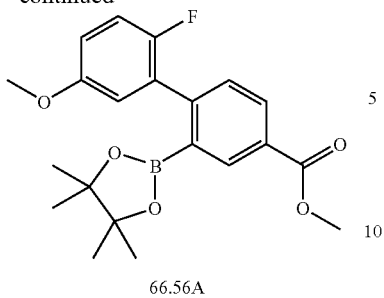

66.56A

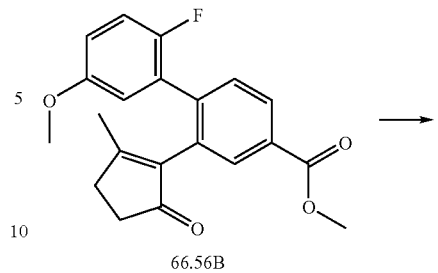

66.56B

Methyl 2'-fluoro-5'-(methyloxy)-2-(4,4,5,5-tetramethyl-1,3,2-dioxaborolan-2-yl)-1,1'-biphenyl-4-carboxylate (66.56A). A screw-cap vial was charged with 66.15D (2.08 g, 5.39 mmol), 1,4-dioxane (20 mL), and dichloro[1,1'-bis(diphenylphosphino)ferrocene]palladium(II) DCM adduct (available from Strem) (0.220 g, 0.269 mmol). The suspension was sparged with $N_2$, and to it were added TEA (2.25 mL, 16.2 mmol) and 4,4,5,5-tetramethyl-1,3,2-dioxaborolane (available from Aldrich) (1.17 mL, 8.08 mmol). The resulting mixture was stirred overnight at 100° C. (sealed vial), cooled to room temperature, diluted with water, and extracted with EtOAc. The combined organic layers were washed with water, 1 N HCl, and brine, dried ($MgSO_4$), and concentrated. The crude product was twice purified by silica gel flash chromatography (0-15% EtOAc/hexane) to afford 66.56A (1.09 g, 52% yield) as a crystalline white solid.

Methyl 2'-fluoro-2-(2-methyl-5-oxocyclopentyl)-5'-(methyloxy)-1,1'-biphenyl-4-carboxylate (66.56C). A pressure tube was charged with 66.56B (0.72 g, 2.0 mmol), EtOAc (20 mL), and Pd/C (10 wt. %) (0.22 g, 0.20 mmol). The tube was purged three times with $H_2$ at 45 psi and sealed, and the contents were stirred for 48 hours. The mixture was filtered through silica gel (EtOAc) and concentrated. The crude product was purified by silica gel flash chromatography (0-20% EtOAc/hexane) to afford 66.56C (mixture of diastereomers) (0.63 g, 87% yield) as a colorless oil.

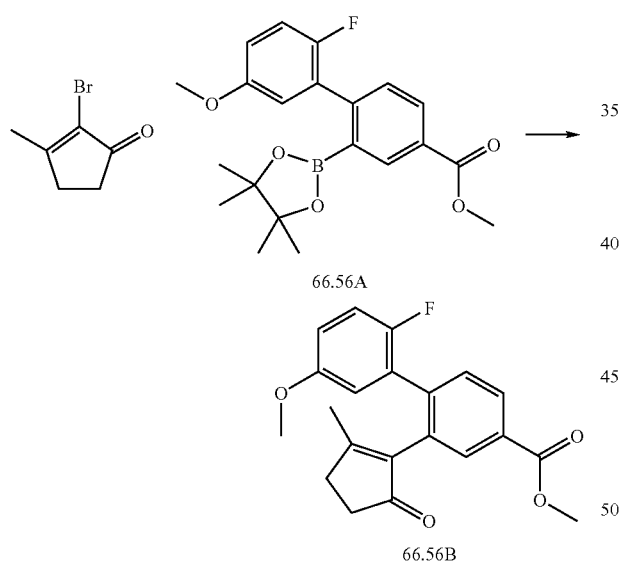

66.56A 66.56B

Methyl 2'-fluoro-2-(2-methyl-5-oxo-1-cyclopenten-1-yl)-5'-(methyloxy)-1,1'-biphenyl-4-carboxylate (66.56B). A screw-cap vial was charged with 2-bromo-3-methyl-2-cyclopenten-1-one (available from Aldrich) (0.68 g, 3.9 mmol), 66.56A (1.00 g, 2.6 mmol), potassium phosphate (1.6 g, 7.8 mmol), 2-dicyclohexylphosphino-2',6'-dimethoxybiphenyl (available from Aldrich) (0.33 g, 0.80 mmol), palladium(II) acetate (available from Aldrich) (0.058 g, 0.26 mmol), degassed THF (17 mL), and water (0.23 mL, 13 mmol). The mixture was purged three times with $N_2$, stirred for 48 hours at room temperature under $N_2$, filtered through silica gel (EtOAc), and concentrated. Trituration of the crude residue with ether afforded 66.56B (0.72 g, 78% yield) as a pale yellow solid.

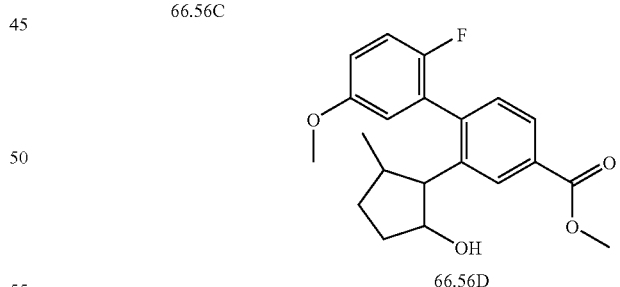

66.56C 66.56D

Methyl 2'-fluoro-2-(2-hydroxy-5-methylcyclopentyl)-5'-(methyloxy)-1,1'-biphenyl-4-carboxylate (66.56D). A 100 mL round bottom flask was charged with 66.56C (mixture of diastereomers) (0.59 g, 1.7 mmol) and 1:1 THF/MeOH (15 mL). To the solution was added sodium borohydride (0.063 g, 1.7 mmol) in one portion at room temperature. The mixture was stirred for 1 hour, quenched with 1 N HCl, and extracted with ether. The combined organic layers were dried ($MgSO_4$) and concentrated to afford 66.56D (mixture of diastereomers) as a colorless oil. The product thus obtained was used without further purification.

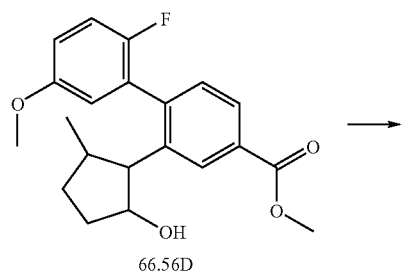

66.56D

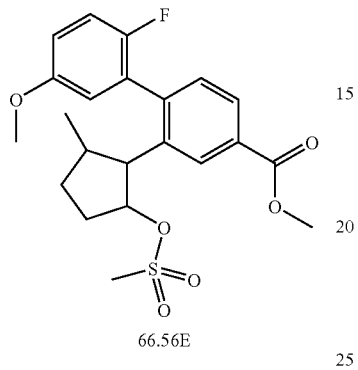

66.56E

Methyl 2'-fluoro-2-(2-methyl-5-((methylsulfonyl)oxy)cyclopentyl)-5'-(methyloxy)-1,1'-biphenyl-4-carboxylate (66.56E). A 250 mL round bottom flask was charged with 66.56D (mixture of diastereomers) (0.61 g, 1.7 mmol), DCM (10 mL), and TEA (0.28 mL, 2.0 mmol) and cooled to 0° C. To the cold solution was added methanesulfonyl chloride (available from Aldrich) (0.16 mL, 2.0 mmol) dropwise. The cooling bath was removed, and the mixture was stirred for 1 hour at ambient temperature. The mixture was diluted with EtOAc, washed with water and brine, dried (MgSO$_4$), and concentrated. The crude product was purified by silica gel flash chromatography (0-40% EtOAc/hexane) to afford 66.56E (mixture of diastereomers) (0.69 g, 93% yield) as a colorless oil.

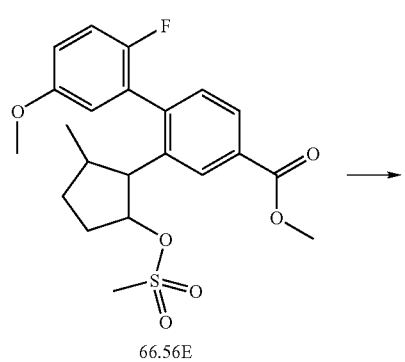

66.56E

Methyl 2'-fluoro-2-(5-methyl-2-cyclopenten-1-yl)-5'-(methyloxy)-1,1'-biphenyl-4-carboxylate (66.56F). A 200 mL round bottom flask was charged with 66.56E (mixture of diastereomers) (0.59 g, 1.4 mmol), toluene (10 mL), and DBU (2.0 mL, 14 mmol). The resulting solution was stirred for 16 hours at 95° C., cooled to room temperature, and quenched with 1 N HCl. The mixture was diluted with EtOAc, washed with water and brine, dried (MgSO$_4$), and concentrated. The initial product was purified by silica gel flash chromatography (0-10% EtOAc/hexane) to afford 66.56F (mixture of diastereomers) (0.31 g, 67% yield) as a colorless oil.

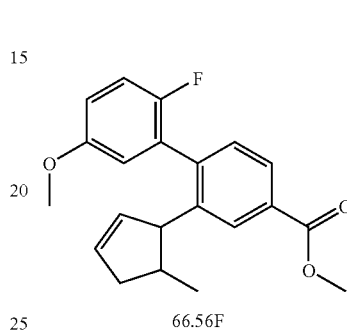

66.56F

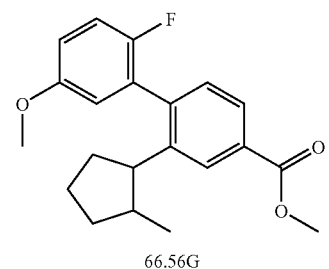

66.56G

Methyl 2'-fluoro-2-(2-methylcyclopentyl)-5'-(methyloxy)-1,1'-biphenyl-4-carboxylate (66.56G). A 100 mL round bottom flask was charged with 66.56F (mixture of diastereomers) (0.31 g, 0.91 mmol), EtOAc (10 mL), and Pd/C (10 wt. %) (0.097 g, 0.091 mmol). The mixture was purged three times with H$_2$, stirred overnight under a H$_2$ balloon, filtered through silica gel (EtOAc), and concentrated to afford 66.56G (mixture of diastereomers) (0.31 g, 99% yield) as a colorless oil.

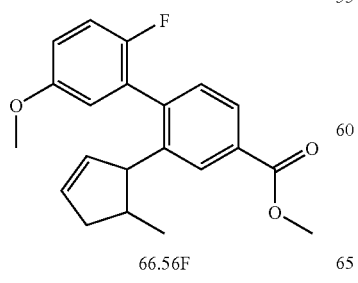

66.56F

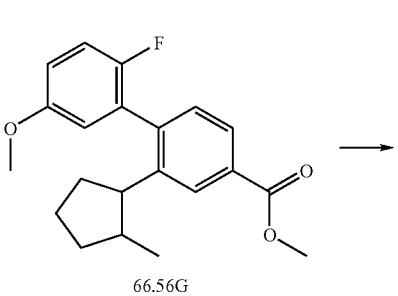

66.56G

-continued

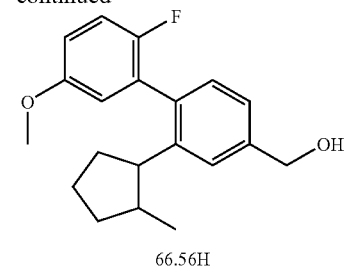

66.56H (2'-Fluoro-2-(2-methylcyclopentyl)-5'-(methyloxy)-1,1'-biphenyl-4-yl)methanol (66.56H). A 200 mL round bottom flask was charged with 66.56G (0.31 g, 0.91 mmol) and THF (10 mL). To the solution was added LAH (1.0 M in THF) (0.91 mL, 0.91 mmol) dropwise at room temperature. The resulting solution was stirred for 15 minutes, quenched with saturated aqueous Rochelle salt, and extracted with ether. The combined organic layers were dried (MgSO₄) and concentrated. The initial product was purified by silica gel flash chromatography (0-30% EtOAc/hexane) to afford 66.56H (mixture of diastereomers) (0.27 g, 95% yield) as a colorless oil.

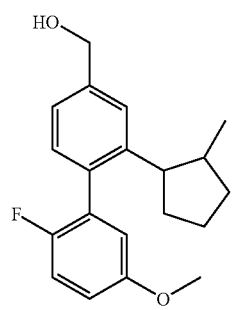

66.56H

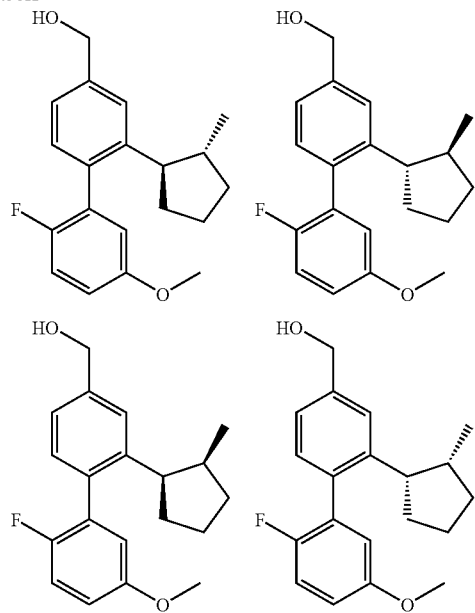

66.56I and 66.56J and 66.56K and 66.56L (2'-Fluoro-2-((1R,2R)-2-methylcyclopentyl)-5'-(methyloxy)-1,1'-biphenyl-4-yl)methanol and (2'-fluoro-2-((1R,2S)-2-methylcyclopentyl)-5'-(methyloxy)-1,1'-biphenyl-4-yl)methanol and (2'-fluoro-2-((1S,2S)-2-methylcyclopentyl)-5'-(methyloxy)-1,1'-biphenyl-4-yl)methanol and (2'-fluoro-2-((1S,2R)-2-methylcyclopentyl)-5'-(methyloxy)-1,1'-biphenyl-4-yl)methanol (66.56I, 66.56J, 66.56K, and 66.56L). 66.56H (0.27 g, 0.86 mmol) was resolved by chiral HPLC (Chiralcel OD column, 2% IPA/hexane, detection at 220 nm) to afford (in order of elution) an epimeric mixture of 66.56I and 66.56J, 66.56K (0.11 g, 41% yield), and 66.56L (0.030 g, 11% yield) as colorless oils. The epimeric mixture of 66.56I and 66.56J was resolved by chiral HPLC (Chiralpak AD column, 2% IPA/hexane, detection at 220 nm) to afford (in order of elution) 66.56I (0.11 g, 41% yield) and 66.56J (0.028 g, 10% yield) as colorless oils.

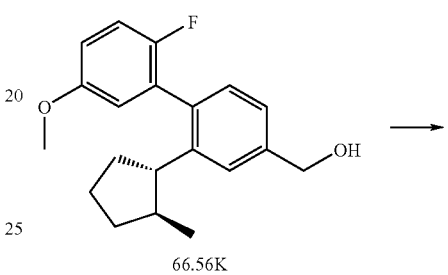

66.56K

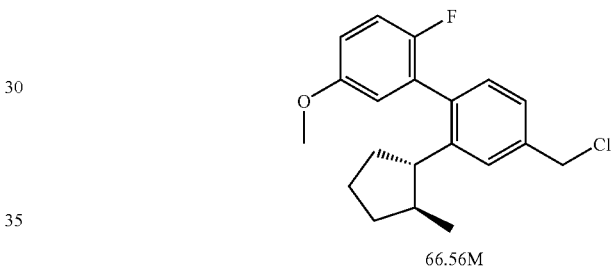

66.56M

Only one of the stereoisomers is shown above, but it could be any of the four.

4-(Chloromethyl)-2'-fluoro-2-((1S,2S)-2-methylcyclopentyl)-5'-(methyloxy)-1,1'-biphenyl or 4-(chloromethyl)-2'-fluoro-2-((1R,2R)-2-methylcyclopentyl)-5'-(methyloxy)-1,1'-biphenyl or 4-(chloromethyl)-2'-fluoro-2-((1R,2S)-2-methylcyclopentyl)-5'-(methyloxy)-1,1'-biphenyl or 4-(chloromethyl)-2'-fluoro-2-((1S,2R)-2-methylcyclopentyl)-5'-(methyloxy)-1,1'-biphenyl (66.56M). A 25 mL conical flask was charged with 66.56K (0.12 g, 0.38 mmol) and DCM (3 mL). To the solution were added thionyl chloride (available from Aldrich) (0.056 mL, 0.76 mmol) and catalytic DMF (one drop). The resulting solution was stirred overnight at room temperature and concentrated. The crude product was purified by silica gel flash chromatography (0-5% EtOAc/hexane) to afford 66.56M (0.093 g, 73%) as a colorless oil.

(3S)-3-Cyclopropyl-3-(3-(((2'-fluoro-2-((1S,2S)-2-methylcyclopentyl)-5'-(methyloxy)-1,1'-biphenyl-4-yl)methyl)oxy)phenyl)propanoic acid or (3S)-3-Cyclopropyl-3-(3-(((2'-fluoro-2-((1R,2R)-2-methylcyclopentyl)-5'-(methyloxy)-1,1'-biphenyl-4-yl)methyl)oxy)phenyl) propanoic acid or (3S)-3-Cyclopropyl-3-(3-(((2'-fluoro-2-((1R,2S)-2-methylcyclopentyl)-5'-(methyloxy)-1,1'-biphenyl-4-yl)methyl)oxy)phenyl)propanoic acid or (3S)-3-Cyclopropyl-3-(3-(((2'-fluoro-2-((1S,2R)-2-methylcyclopentyl)-5'-(methyloxy)-1,1'-biphenyl-4-yl) methyl)oxy)phenyl)propanoic acid or (3R)-3-Cyclopropyl-3-(3-(((2'-fluoro-2-((1S,2S)-2-methylcyclopentyl)-5'-(methyloxy)-1,1'-biphenyl-4-yl)methyl)oxy)phenyl)

propanoic acid or (3R)-3-Cyclopropyl-3-(3-(((2'-fluoro-2-((1R,2R)-2-methylcyclopentyl)-5'-(methyloxy)-1,1'-biphenyl-4-yl)methyl)oxy)phenyl)propanoic acid or (3R)-3-Cyclopropyl-3-(3-(((2'-fluoro-2-((1R,2S)-2-methylcyclopentyl)-5'-(methyloxy)-1,1'-biphenyl-4-yl)methyl)oxy)phenyl)propanoic acid or (3R)-3-Cyclopropyl-3-(3-(((2'-fluoro-2-((1S,2R)-2-methylcyclopentyl)-5'-(methyloxy)-1,1'-biphenyl-4-yl)methyl)oxy)phenyl)propanoic acid (66.56). 66.56 was prepared from 66.56M and 8.4 according to the analogous methods described in Example 7. MS ESI (pos.) m/e: 503.2 (M+H)$^+$, 520.3 (M+H$_2$O)$^+$, 525.3 (M+Na)$^+$.

Example 66.57

Diastereomer of 66.56 (66.57). Example 66.57 was prepared from the chloromethyl compound derived from 66.56L and 8.4 according to the analogous methods described in Example 66.56. MS ESI (pos.) m/e: 503.2 (M+H)$^+$, 520.3 (M+H$_2$O)$^+$, 525.3 (M+Na)$^+$.

Example 66.58

Diastereomer of 66.56 and 66.57 (66.58). Example 66.58 was prepared from the chloromethyl compound derived from 66.56I and 8.4 according to the analogous methods described in Example 66.56. MS ESI (pos.) m/e: 503.2 (M+H)$^+$, 520.3 (M+H$_2$O)$^+$, 525.3 (M+Na)$^+$.

Example 66.59

Diastereomer of 66.56, 66.57, and 66.58 (66.59). Example 66.59 was prepared from the chloromethyl compound derived from 66.56J and 8.4 according to the analogous methods described in Example 66.56. MS ESI (pos.) m/e: 503.2 (M+H)$^+$, 520.3 (M+H$_2$O)$^+$, 525.3 (M+Na)$^+$.

Example 66.60

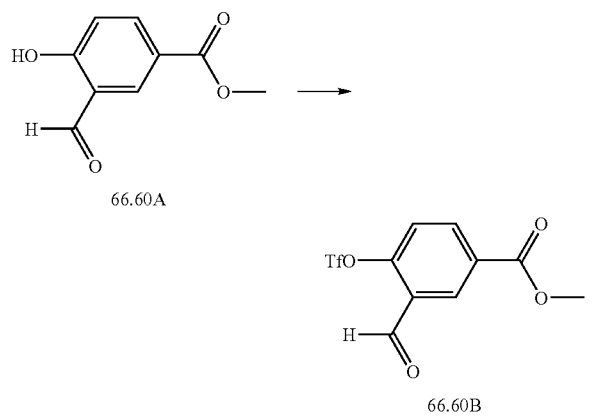

Methyl 3-formyl-4-(trifluoromethylsulfonyloxy)benzoate (66.60B). TEA (6.81 mL, 48.8 mmol), and N,N-dimethylpyridin-4-amine (0.298 g, 2.44 mmol) were added to a solution of methyl 3-formyl-4-hydroxybenzoate (commercially available from Aldrich) (4.40 g, 24.4 mmol) in DCM (26 mL). The resulting mixture was stirred at room temperature for 20 minutes and then N-phenyltrifluoromethanesulfonimide (9.60 g, 26.9 mmol) was added in one portion. The mixture was then stirred at room temperature for 30 minutes. After removing solvent, the residue was purified by flash chromatography (silica gel, 1:1 EtOAc/hexane) and gave 66.60B, a colorless oil, in 99% yield (7.57 g).

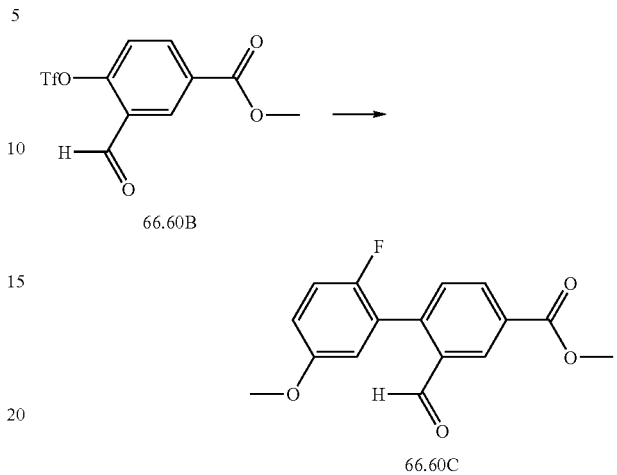

Methyl 2'-fluoro-2-formyl-5'-(methyloxy)-1,1'-biphenyl-4-carboxylate (66.60C). A mixture of methyl 3-formyl-4-(trifluoromethyl-sulfonyloxy)benzoate (66.60B) (7.57 g, 24.2 mmol), 2-fluoro-5-methoxy-phenylboronic acid (commercially available from Aldrich) (12.4 g, 72.7 mmol), cesium carbonate (27.6 g, 84.9 mmol), and tetrakis(triphenylphosphine) palladium (2.80 g, 2.42 mmol) in 1,2-dimethoxyethane (DME) (75 mL) was degassed with N$_2$ at room temperature The mixture was heated at 95° C. for 9 hours. After removing solvent, the residue was purified by flash chromatography (silica gel, 1:19 EtOAc/hexane) and gave 66.60C, a white solid, in 56% yield (2.9 g). $^1$H NMR (400 MHz, DMSO-d6) δ ppm 9.88 (dd, J=4 Hz, 1H), 8.45 (s, 1H), 8.28 (m, 1H), 7.69 (d, j=8 Hz, 1H), 7.29 (t, J=9 HZ, 1H), 7.08 (m, 2H), 3.92 (s, 3H), 3.79 (s, 3H).

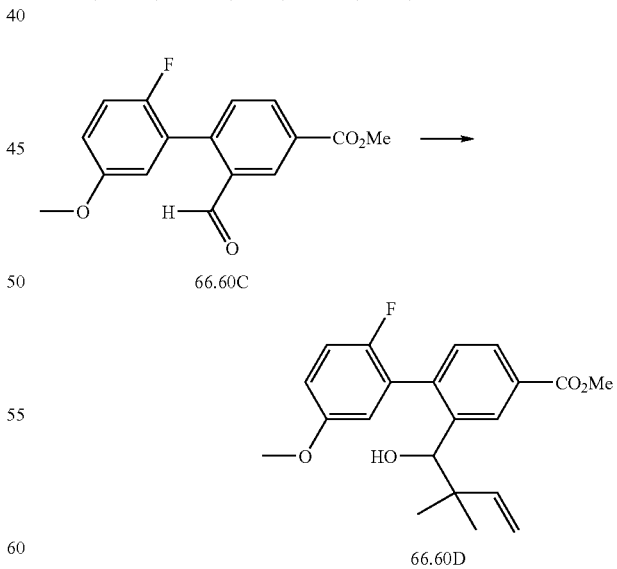

Methyl 2'-fluoro-2-(1-hydroxy-2,2-dimethyl-3-butenyl)-5'-(methyloxy)-1,1'-biphenyl-4-carboxylate (66.60D). To a mixture of 66.60C (0.38 g, 1.3 mmol), 1-bromo-3-methylbut-2-ene (commercially available from Aldrich) (0.31 mL, 2.6 mmol) and sodium iodide (0.40 g, 2.6 mmol) in DMF (8 mL), was added indium (0.30 g, 2.6 mmol). The resulting mixture was stirred at room temperature for 1 hour and then additional 1-bromo-3-methylbut-2-ene (100 mg) and indium (100 mg) were added and the mixture was stirred at room temperature for one more hour. The reaction was quenched with water (20 mL) and extracted with EtOAc (200 mL). The organic phase was washed with brine, dried over anhydrous sodium sulfate, and filtered. After removing solvent, the residue was purified by flash chromatography (silica gel, 1:4 EtOAc/hexane) and gave product (66.60D), in 94% yield.

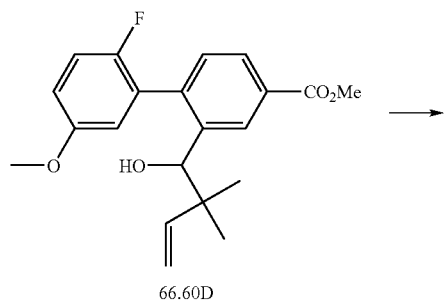

66.60D

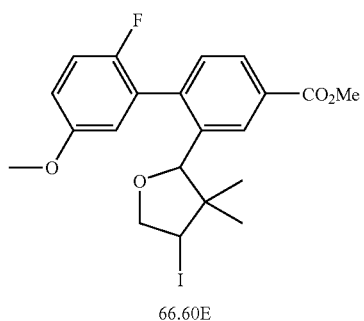

66.60E

Methyl 2'-fluoro-2-(3-iodo-2,2-dimethylcyclopentyl)-5'-(methyloxy)-1,1'-biphenyl-4-carboxylate (66.60E). To a mixture of NaHCO₃ (0.035 g, 0.42 mmol) and 66.60D (0.050 g, 0.14 mmol) in ACN (2 mL), was added iodine (0.12 g, 0.49 mmol). The mixture was then stirred at room temperature for 16 hours. Next, the mixture was poured into a 0.2 M solution of Na₂S₂O₃ and extracted with EtOAc. The organic phase was dried over anhydrous Na₂SO₄ and filtered. After removing solvent, the residue was purified by flash chromatography (silica gel, 1:19 EtOAc/hexane) and gave product 66.60E, a white solid, in 84% yield.

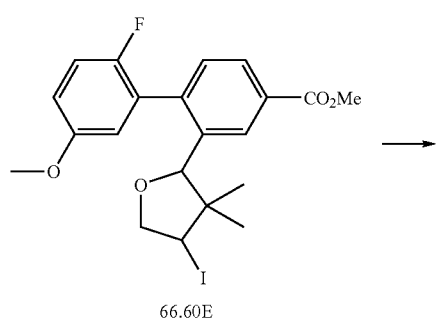

66.60E

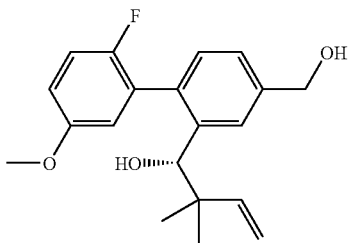

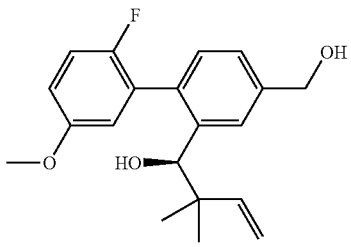

66.60F and 66.60G (1S)-1-(2'-Fluoro-4-(hydroxymethyl)-5'-(methyloxy)-1,1'-biphenyl-2-yl)-2,2-dimethyl-3-buten-1-ol (66.60F) and (1R)-1-(2'-fluoro-4-(hydroxymethyl)-5'-(methyloxy)-1,1'-biphenyl-2-yl)-2,2-dimethyl-3-buten-1-ol (66.60G). To a mixture of 66.60E (0.460 g, 0.950 mmol) in THF (12 mL), was added LAH (0.108 g, 2.85 mmol), and the mixture was stirred at room temperature for 45 minutes. The reaction mixture was then poured into water and extracted with EtOAc. The organic phase was dried over anhydrous Na₂SO₄ and filtered. After removing solvent, the residue was purified by flash chromatography (silica gel, 1:2 EtOAc/hexane) and gave racemic product, which was separated by chiral chromatography (column: OD-H; solvent: 6% i-PrOH/hexane) to yield 66.60F (72 mg) (retention time=12.9 min) and 66.60G (74 mg) (retention time=18.2 min).

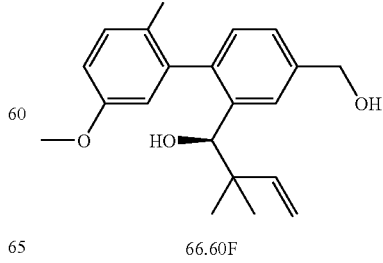

66.60F

-continued

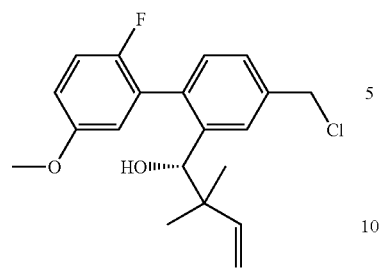

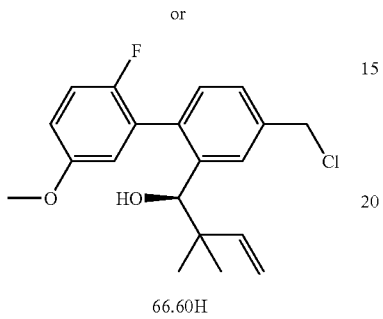

66.60H (1S)-1-(4-(Chloromethyl)-2'-fluoro-5'-(methyloxy)-1,1'-biphenyl-2-yl)-2,2-dimethyl-3-buten-1-ol or (1R)-1-(4-(chloromethyl)-2'-fluoro-5'-(methyloxy)-1,1'-biphenyl-2-yl)-2,2-dimethyl-3-buten-1-ol (66.60H). Thionyl chloride (0.27 g, 2.2 mmol) was added to a solution of 66.60F (0.074 g, 0.22 mmol) in DCM (2 mL), and the mixture was stirred at room temperature for 40 minutes. After removing solvent, 66.60H was obtained.

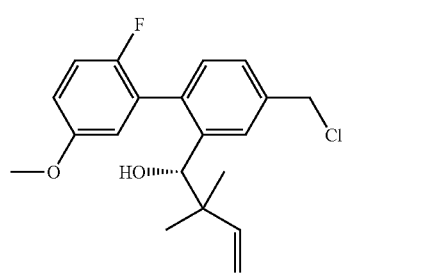

or

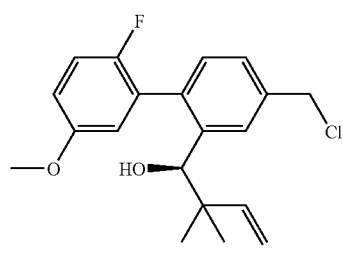

66.60H

-continued

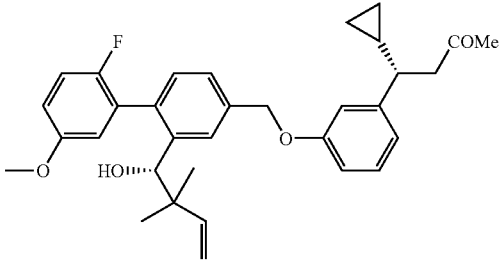

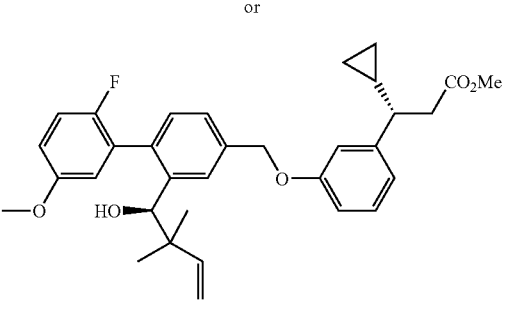

or

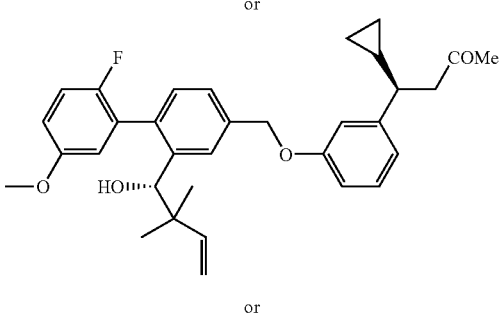

or

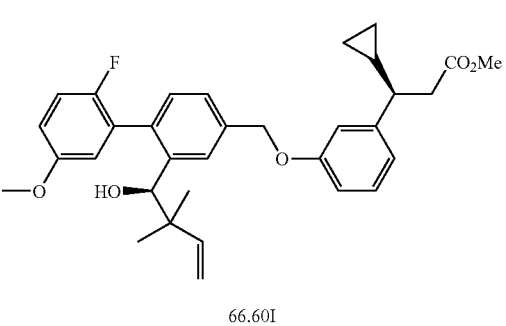

66.60I (3S)-3-Cyclopropyl-3-(3-(((2'-fluoro-2-((1S)-1-hydroxy-2,2-dimethyl-3-butenyl)-5'-(methyloxy)-1,1'-biphenyl-4-yl)methyl)oxy)phenyl) propanoic acid methyl ester or (3S)-3-cyclopropyl-3-(3-(((2'-fluoro-2-((1R)-1-hydroxy-2,2-dimethyl-3-butenyl)-5'-(methyloxy)-1,1'-biphenyl-4-yl)methyl)oxy)phenyl) propanoic acid methyl ester or (3R)-3-cyclopropyl-3-(3-(((2'-fluoro-2-((1S)-1-hydroxy-2,2-dimethyl-3-butenyl)-5'-(methyloxy)-1,1'-biphenyl-4-yl)methyl)oxy)phenyl) propanoic acid methyl ester or (3R)-3-cyclopropyl-3-(3-(((2'-fluoro-2-((1R)-1-hydroxy-2,2-dimethyl-3-butenyl)-5'-(methyloxy)-1,1'-biphenyl-4-yl)methyl)oxy)phenyl) propanoic acid methyl ester (66.60I). A mixture of 8.4 (0.019 g, 0.087 mmol), 66.60H (0.019 g, 0.054 mmol) and $Cs_2CO_3$ (0.035 g, 0.11 mmol) in DMF (1.5 mL) was stirred at room temperature overnight. After removing solvent, the residue was purified by flash chromatography (silica gel, 1:6 EtOAc/hexane) and gave 66.60I (30 mg).

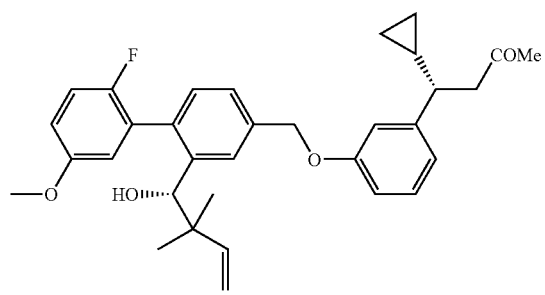

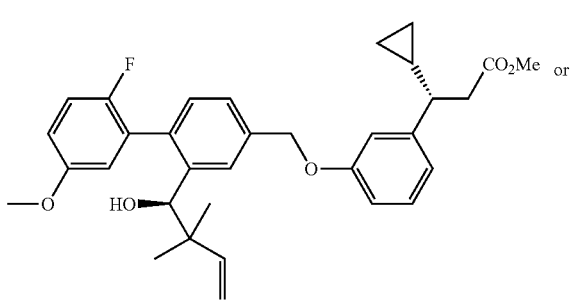

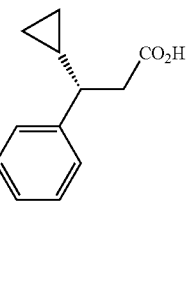

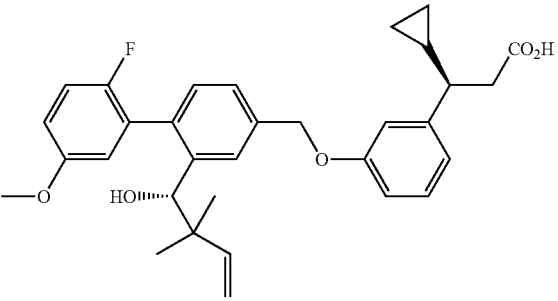

66.60

(3S)-3-Cyclopropyl-3-(3-(((2'-fluoro-2-((1S)-1-hydroxy-2,2-dimethyl-3-butenyl)-5'-(methyloxy)-1,1'-biphenyl-4-yl)methyl)oxy)phenyl) propanoic acid or (3S)-3-cyclopropyl-3-(3-(((2'-fluoro-2-((1R)-1-hydroxy-2,2-dimethyl-3-butenyl)-5'-(methyloxy)-1,1'-biphenyl-4-yl)methyl)oxy)phenyl) propanoic acid or (3R)-3-cyclopropyl-3-(3-(((2'-fluoro-2-((1S)-1-hydroxy-2,2-dimethyl-3-butenyl)-5'-(methyloxy)-1,1'-biphenyl-4-yl)methyl)oxy)phenyl) propanoic acid or (3R)-3-cyclopropyl-3-(3-(((2'-fluoro-2-((1R)-1-hydroxy-2,2-dimethyl-3-butenyl)-5'-(methyloxy)-1,1'-biphenyl-4-yl)methyl)oxy)phenyl) propanoic acid (66.60). A mixture of 60.60I (0.030 g, 0.056 mmol), NaOH(aq, 10%) (0.6 mL) and EtOH (2 mL) was stirred at room temperature for 16 hours. The product was purified by reverse-phase HPLC and 66.60 (7 mg) was obtained. MS ESI (neg.) m/e: 517 (M–H)$^+$. $^1$H NMR (400 MHz, CDCl$_3$) δ ppm 7.64 (d, 1H), 7.42 (m, 1H), 7.18-7.23 (m, 2H), 7.03 (m, 1H), 6.76 (m, 1H), 5.78 (m, 1H), 5.16 (s, 2H), 5.03 (m, 2H), 3.81 (m, 3H), 2.64-2.83 (m, 2H), 2.34 (m, 1H), 1.27 (m, 1H), 1.05 (m, 1H), 0.84 (s, 3H), 0.79 (s, 3H), 0.59 (m, 1H), 0.46 (m, 1H), 0.29 (m, 1H), 0.17 (m, 1H).

(3S)-3-Cyclopropyl-3-(3-(((2'-fluoro-2-((1S)-1-hydroxy-2,2-dimethyl-3-butenyl)-5'-(methyloxy)-1,1'-biphenyl-4-yl)methyl)oxy)phenyl) propanoic acid or (3S)-3-cyclopropyl-3-(3-(((2'-fluoro-2-((1R)-1-hydroxy-2,2-dimethyl-3-butenyl)-5'-(methyloxy)-1,1'-biphenyl-4-yl)methyl)oxy)phenyl) propanoic acid or (3R)-3-cyclopropyl-3-(3-(((2'-fluoro-2-

((1S)-1-hydroxy-2,2-dimethyl-3-butenyl)-5'-(methyloxy)-1,1'-biphenyl-4-yl)methyl)oxy)phenyl) propanoic acid or (3R)-3-cyclopropyl-3-(3-(((2'-fluoro-2-((1R)-1-hydroxy-2,2-dimethyl-3-butenyl)-5'-(methyloxy)-1,1'-biphenyl-4-yl)methyl)oxy)phenyl) propanoic acid (66.61). Example 66.61 was prepared from 66.60H and 8.4 using the alkylation and hydrolysis conditions described with respect to 60.60I. The product was purified by reverse-phase HPLC and 66.61 (6 mg) was obtained. MS ESI (neg.) m/e: 517 (M–H)⁺. ¹H NMR (400 MHz, CD₃OD) δ ppm 7.40 (d, 1H), 7.33 (m, 1H), 7.10-7.40 (m, 3H), 6.79-6.89 (m, 5H), 5.76 (m, 1H), 5.14 (s, 2H), 4.74 (m, 2H), 3.79 (s, 3H), 2.64-2.77 (m, 2H), 2.32 (m, 1H), 1.03 (m, 1H), 0.82 (s, 3H), 0.72 (s, 3H), 0.57 (m, 1H), 0.38 (m, 1H), 0.28 (m, 1H), 0.11 (m, 1H).

Example 66.62

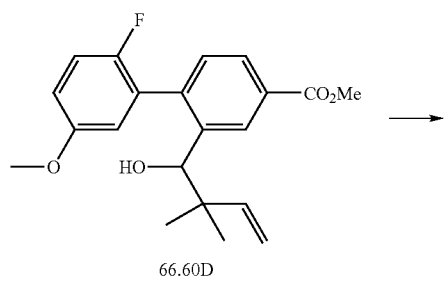

66.60D

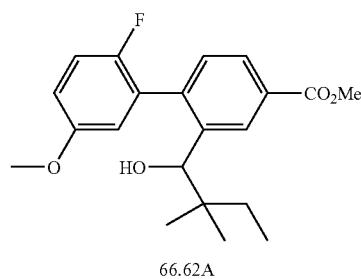

66.62A

Methyl 2'-fluoro-2-(1-hydroxy-2,2-dimethylbutyl)-5'-(methyloxy)-1,1'-biphenyl-4-carboxylate (66.62A). To a solution of 66.60D (0.453 g, 1.26 mmol) in MeOH (10 mL) (degassed by N₂), was added palladium on carbon (0.135 g, 1.26 mmol). The resulting mixture was stirred at room temperature under H₂ for 18 hrs. The reaction mixture was then filtered through silica gel. After removing solvent, 66.62A (394 mg) was obtained as a colorless oil.

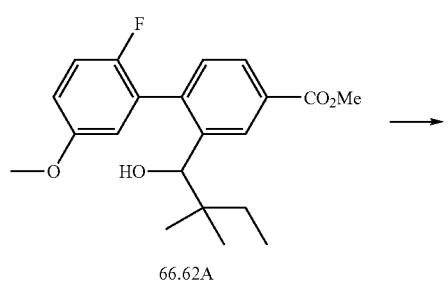

66.62A

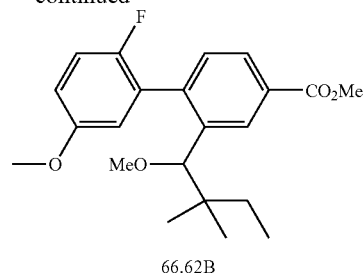

66.62B

Methyl 2-(2,2-dimethyl-1-(methyloxy)butyl)-2'-fluoro-5'-(methyloxy)-1,1'-biphenyl-4-carboxylate (66.62B). To a solution of 66.62A (0.39 g, 1.1 mmol) in DMF (5 mL), was added NaH (0.034 g, 1.4 mmol). The mixture was stirred at room temperature for 10 minutes and then iodomethane (0.20 mL, 3.2 mmol) was added. The mixture was stirred at room temperature for 60 minutes and then it was diluted with EtOAc, washed with water and brine, and dried over anhydrous Na₂SO₄. After removing solvent, the residue was purified by flash chromatography (silica gel, 1:9 EtOAc/hexane) and gave 66.62B, colorless oil, in 64% yield (260 mg).

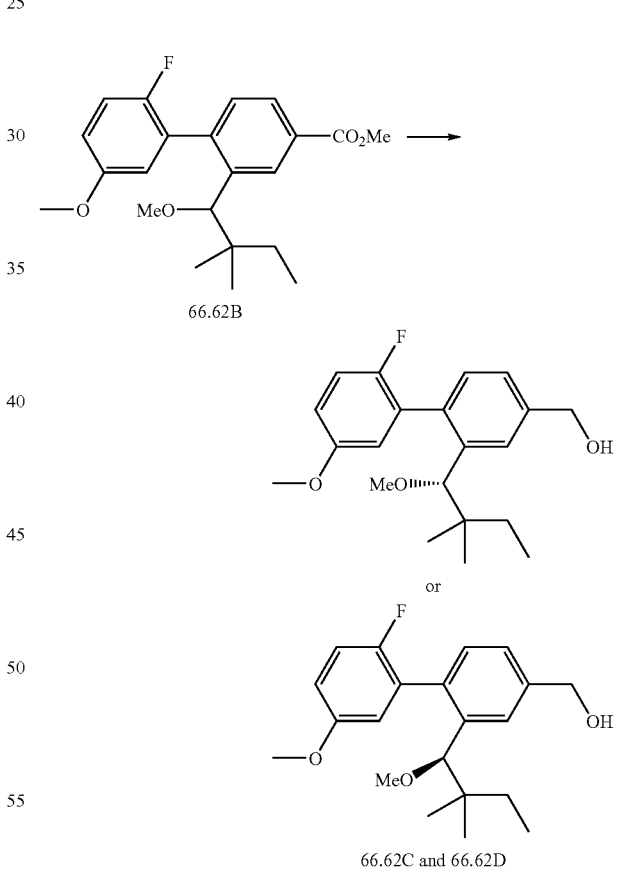

66.62C and 66.62D (2-((1S)-2,2-Dimethyl-1-(methyloxy)butyl)-2'-fluoro-5'-(methyloxy)-1,1'-biphenyl-4-yl)methanol and (2-((1R)-2,2-dimethyl-1-(methyloxy)butyl)-2'-fluoro-5'-(methyloxy)-1,1'-biphenyl-4-yl)methanol (66.62C and 66.62D). To a solution of 66.62B (0.26 g, 0.69 mmol) in THF (4 mL), was added LAH (0.026 g, 0.69 mmol). The resulting mixture was stirred at room temperature for 10 minutes and then was poured into to water and extracted with EtOAc. The combined organic layers were dried over anhydrous Na₂SO₄. After removing solvent, the residue was purified by flash chromatography (silica gel, 1:6 EtOAc/hexane) and gave racemic product (157 mg) as a colorless oil, which was separated by chiral chromatography (column: OD; solvent: 6% i-PrOH/hexane) to yield 66.62C (68 mg) (retention time=11.8 min) and 66.62D (70 mg) (retention time=15.1 min).

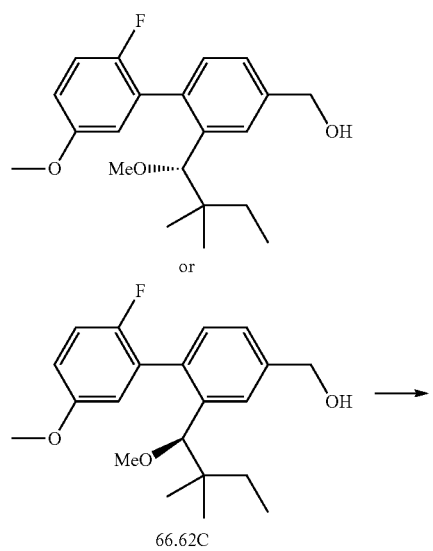

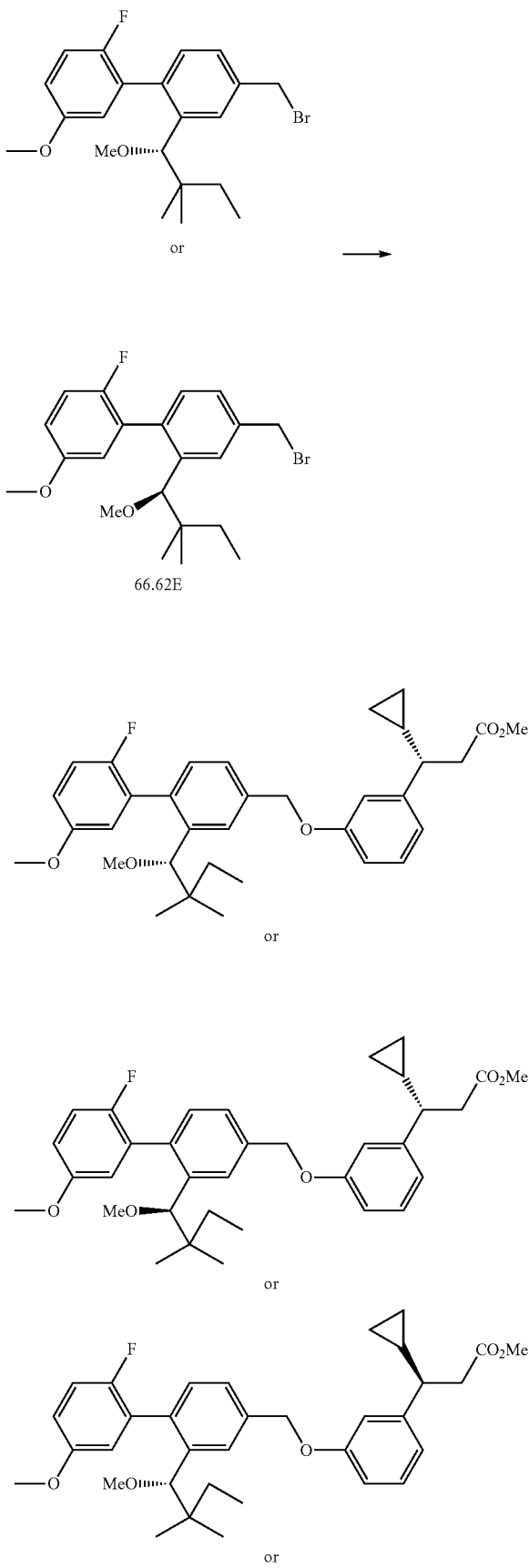

4-(Bromomethyl)-2-((1S)-2,2-dimethyl-1-(methyloxy) butyl)-2'-fluoro-5'-(methyloxy)-1,1'-biphenyl or 4-(bromomethyl)-2-((1R)-2,2-dimethyl-1-(methyloxy)butyl)-2'-fluoro-5'-(methyloxy)-1,1'-biphenyl (66.62E). To a solution of 66.62C (0.070 g, 0.20 mmol) in THF (2 mL), was added triphenylphosphine (0.11 g, 0.40 mmol) and 1-bromopyrrolidine-2,5-dione (0.072 g, 0.40 mmol). The resulting mixture was stirred at room temperature for 10 minutes. After removing solvent, the residue was purified by flash chromatography (silica gel, 1:6 EtOAc/hexane) and gave 66.62E (73 mg).

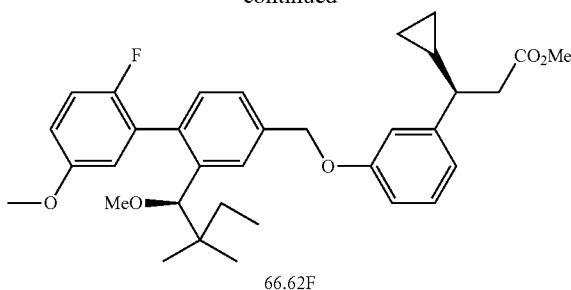

66.62F

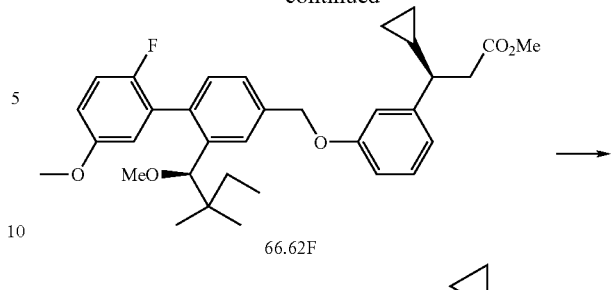

66.62F

Methyl (3S)-3-cyclopropyl-3-(3-(((2-((1S)-2,2-dimethyl-1-(methyloxy)butyl)-2'-fluoro-5'-(methyloxy)-1,1'-biphenyl-4-yl)methyl)oxy)phenyl)propanoate or methyl (3S)-3-cyclopropyl-3-(3-(((2-((1R)-2,2-dimethyl-1-(methyloxy)butyl)-2'-fluoro-5'-(methyloxy)-1,1'-biphenyl-4-yl)methyl)oxy)phenyl)propanoate or methyl (3R)-3-cyclopropyl-3-(3-(((2-((1R)-2,2-dimethyl-1-(methyloxy)butyl)-2'-fluoro-5'-(methyloxy)-1,1'-biphenyl-4-yl)methyl)oxy)phenyl)propanoate or methyl (3R)-3-cyclopropyl-3-(3-(((2-((1R)-2,2-dimethyl-1-(methyloxy)butyl)-2'-fluoro-5'-(methyloxy)-1,1'-biphenyl-4-yl)methyl)oxy)phenyl)propanoate (66.62F). A mixture of 8.4 (0.018 g, 0.082 mmol), 66.62E (0.024 g, 0.059 mmol) and Cs$_2$CO$_3$ (0.038 g, 0.12 mmol) in DMF (2 mL) were stirred at room temperature for 2 hours. After removing solvent, the residue was purified by flash chromatography (silica gel, 1:6 EtOAc/hexane) and gave 66.62F (25 mg).

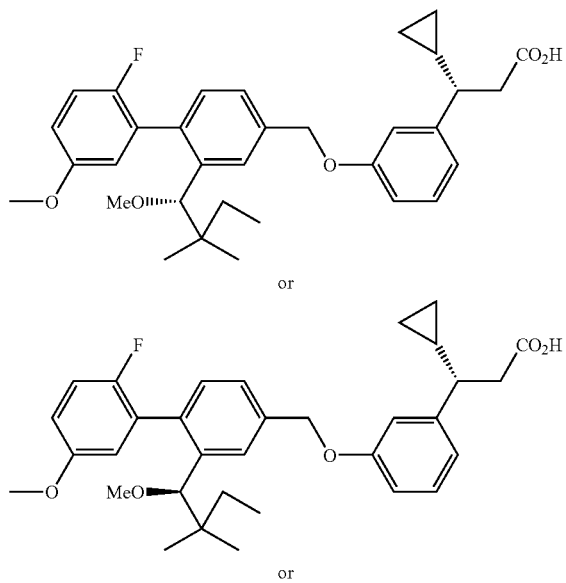

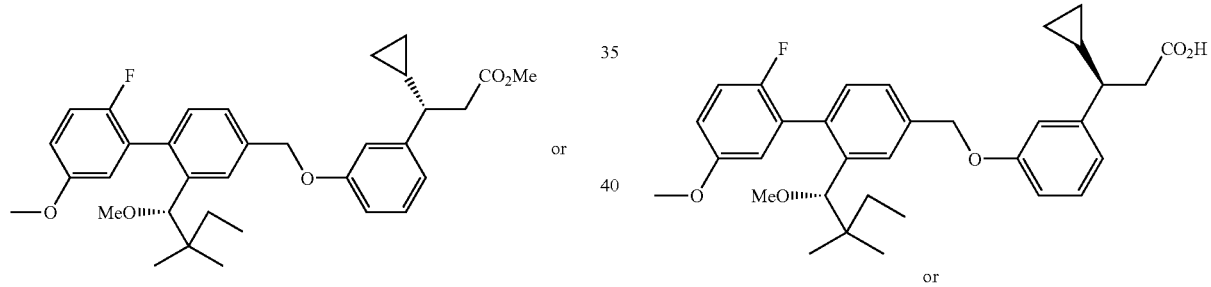

or

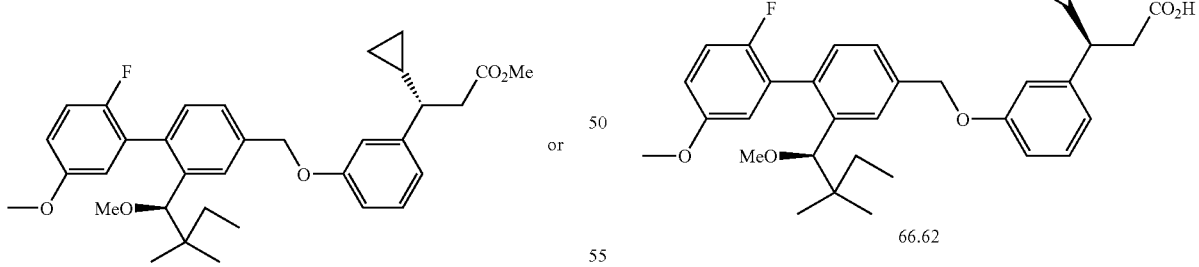

or

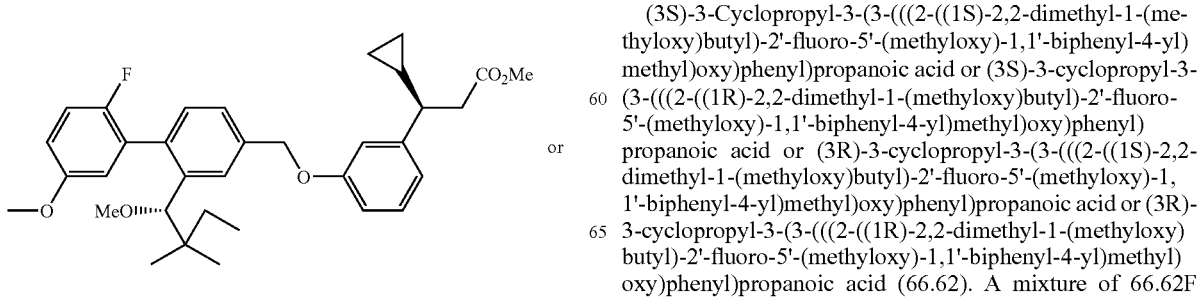

or 66.62

(3S)-3-Cyclopropyl-3-(3-(((2-((1S)-2,2-dimethyl-1-(methyloxy)butyl)-2'-fluoro-5'-(methyloxy)-1,1'-biphenyl-4-yl)methyl)oxy)phenyl)propanoic acid or (3S)-3-cyclopropyl-3-(3-(((2-((1R)-2,2-dimethyl-1-(methyloxy)butyl)-2'-fluoro-5'-(methyloxy)-1,1'-biphenyl-4-yl)methyl)oxy)phenyl)propanoic acid or (3R)-3-cyclopropyl-3-(3-(((2-((1S)-2,2-dimethyl-1-(methyloxy)butyl)-2'-fluoro-5'-(methyloxy)-1,1'-biphenyl-4-yl)methyl)oxy)phenyl)propanoic acid or (3R)-3-cyclopropyl-3-(3-(((2-((1R)-2,2-dimethyl-1-(methyloxy)butyl)-2'-fluoro-5'-(methyloxy)-1,1'-biphenyl-4-yl)methyl)oxy)phenyl)propanoic acid (66.62). A mixture of 66.62F (0.025 g, 0.044 mmol), NaOH(aq, 10%) (1 mL) and EtOH (3 mL) was stirred at room temperature for 2.5 hours. After removing solvent, the mixture was acidified with 1N HCl to pH 3-5 and extracted with EtOAc (120 mL). The organic phase was washed with brine and dried over anhydrous sodium sulfate. After filtering and removing solvent, the residue was purified by flash chromatography (silica gel, 1:6 MeOH/DCM) and gave 66.62 (6.4 mg). MS ESI (neg.) m/e: 533 (M–H)+. 1H NMR (400 MHz, CDCl3) δ ppm 7.57 (m, 1H), 7.43 (m, 1H), 7.08-7.23 (m, 2H), 7.05 (m, 1H), 6.84-6.90 (m, 4H), 6.75 (m, 1H), 5.16 (s, 2H), 4.06-4.29 (m, 1H), 3.80 (s, 3H), 3.23-3.29 (m, 3H), 2.78-2.80 (m, 2H), 2.37 (m, 1H), 1.27 (m, 2H), 1.07 (m, 2H), 1.03 (m, 1H), 0.71 (s, 3H), 0.60 (m, 3H), 0.49 (m, 3H), 0.44 (m, 1H), 0.30 (m, 1H), 0.18 (m, 1H).

Example 66.63

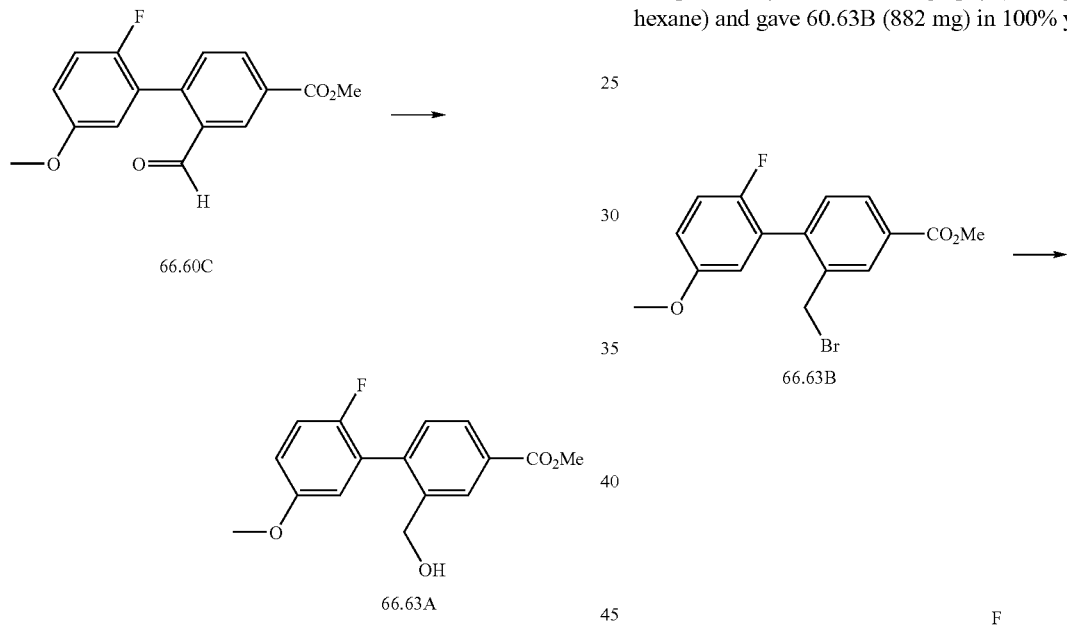

Methyl 2'-fluoro-2-(hydroxymethyl)-5'-(methyloxy)-1,1'-biphenyl-4-carboxylate (66.63A). Sodium tetrahydroborate (available from Aldrich) (0.656 g, 17.3 mmol) was added portion by portion slowly to 66.60C (1.00 g, 3.47 mmol) in MeOH (20 mL). The resulting mixture was stirred at room temperature for 25 minutes. After removing solvent, the residue was purified by flash chromatography (silica gel, 1:2 EtOAc/hexane) and gave 60.63A (725 mg) in 72% yield.

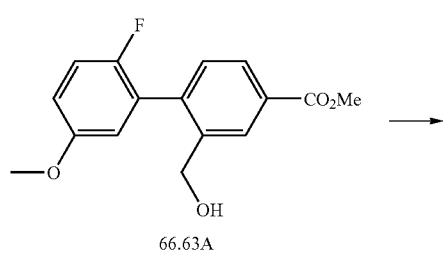

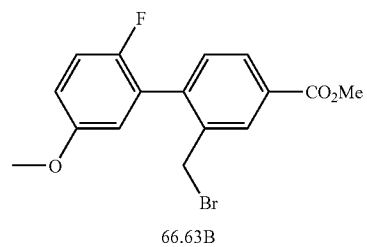

Methyl 2-(bromomethyl)-2'-fluoro-5'-(methyloxy)-1,1'-biphenyl-4-carboxylate (66.63B). To a solution of 66.63A (0.725 g, 2.50 mmol) and triphenylphosphine (2.62 g, 9.99 mmol) in THF (20 mL) was added portion by portion 1-bromopyrrolidine-2,5-dione (available from Aldrich) (1.78 g, 9.99 mmol). The resulting mixture was stirred at room temperature for 20 minutes. After removing solvent, the residue was purified by flash chromatography (silica gel, 1:9 EtOAc/hexane) and gave 60.63B (882 mg) in 100% yield.

2-(((1,1-Dimethylethyl)oxy)methyl)-2'-fluoro-5'-(methyloxy)-1,1'-biphenyl-4-carboxylic acid (66.63C). A mixture of 66.63B (0.245 g, 0.69 mmol) and sodium 2-methylpropan-2-olate (0.20 g, 2.1 mmol) in DMF (6 mL) was stirred at room temperature for 28 minutes. The mixture was acidified with 1N HCl to pH 3-4 and then was extracted with EtOAc (100 mL). The organic phase was washed with brine and dried over anhydrous Na2SO4. After removing solvent, the residue was purified by flash chromatography (silica gel, 1:4 EtOAc/hexane) and gave 60.63B (49 mg) in 20% yield.

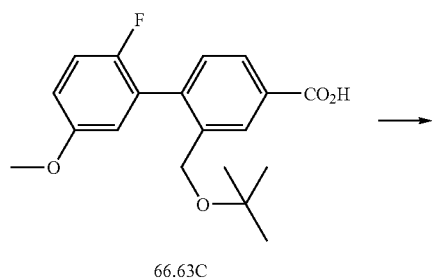

66.63C

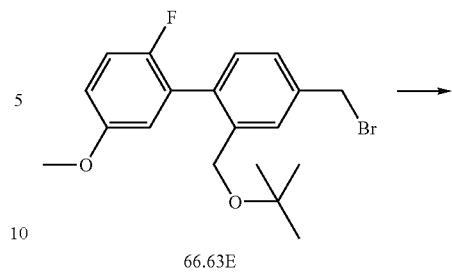

66.63E

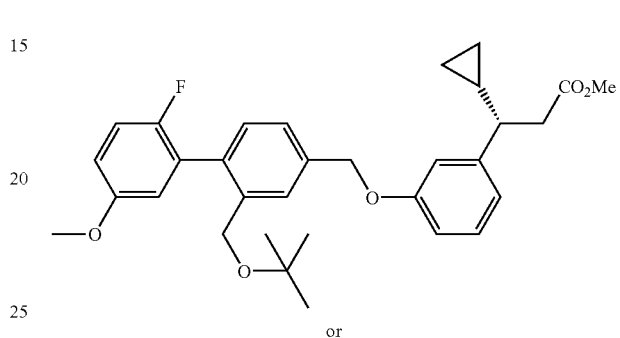

or (2-(((1,1-Dimethylethyl)oxy)methyl)-2'-fluoro-5'-(methyloxy)-1,1'-biphenyl-4-yl)methanol (66.63D). LAH (0.15 mL, 0.15 mmol) was added to a solution of 66.63C (0.049 g, 0.15 mmol) in THF (2 mL). The resulting mixture was stirred at room temperature for 10 minutes and then was poured slowly into brine (5 mL). The mixture was extracted with EtOAc (2×50 mL). The organic phase was dried over anhydrous sodium sulfate. After filtering and removing solvent, the residue was purified by flash chromatography (silica gel, 1:2 EtOAc/hexane) and gave 60.63D (6 mg).

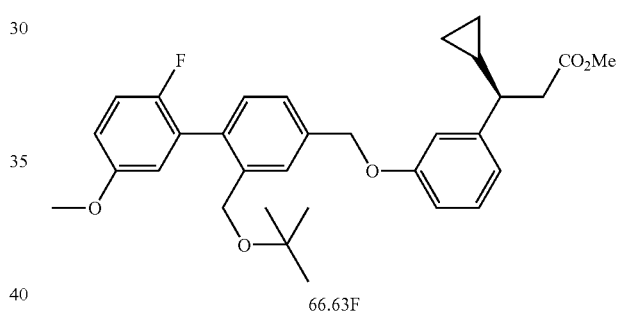

66.63F

Methyl (3S)-3-cyclopropyl-3-(3-(((2-(((1,1-dimethylethyl)oxy)methyl)-2'-fluoro-5'-(methyloxy)-1,1'-biphenyl-4-yl)methyl)oxy)phenyl)propanoate or methyl (3R)-3-cyclopropyl-3-(3-(((2-(((1,1-dimethylethyl)oxy)methyl)-2'-fluoro-5'-(methyloxy)-1,1'-biphenyl-4-yl)methyl)oxy)phenyl)propanoate (66.63F). A mixture of 8.4 (0.0046 g, 0.021 mmol), 66.63E (0.0061 g, 0.016 mmol) and Cs$_2$CO$_3$ (0.010 g, 0.032 mmol) in DMF (1 mL) was stirred at room temperature for 3 hours. After removing solvent, the residue was purified by flash chromatography (silica gel, 1:4 EtOAc/hexane) and gave 60.63F (6 mg).

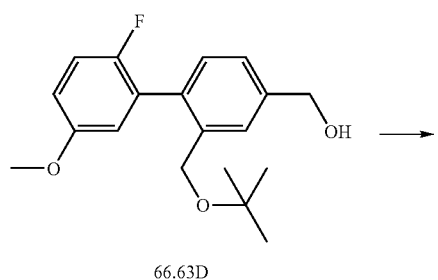

66.63D

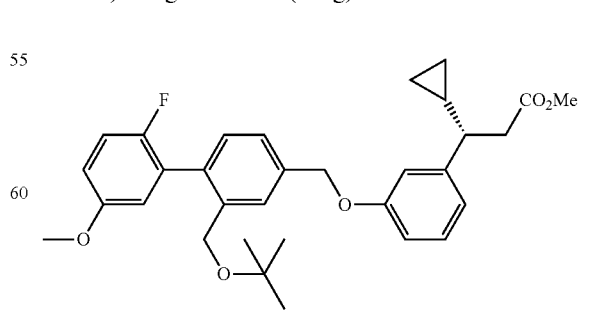

or 4-(Bromomethyl)-2-(((1,1-dimethylethyl)oxy)methyl)-2'-fluoro-5'-(methyloxy)-1,1'-biphenyl (66.63E). Bromomethyl compound 66.63E was prepared using an analogous procedure to that set forth for the synthesis of 66.63B.

-continued

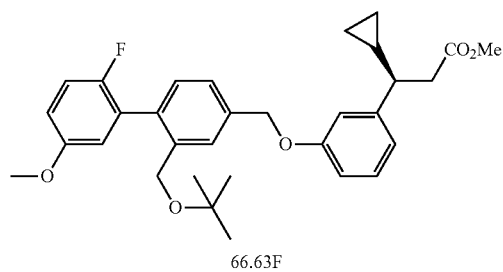

66.63F

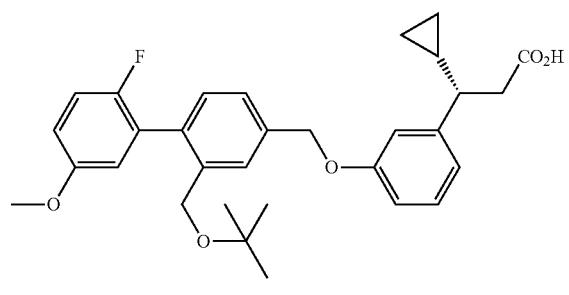

or

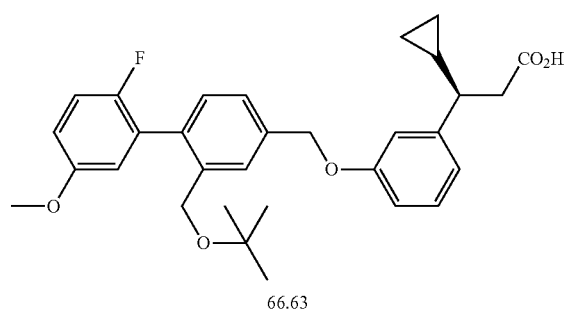

66.63

(3S)-3-Cyclopropyl-3-(3-(((2-(((1,1-dimethylethyl)oxy)methyl)-2'-fluoro-5'-(methyloxy)-1,1'-biphenyl-4-yl)methyl)oxy)phenyl)propanoic acid or (3R)-3-cyclopropyl-3-(3-(((2-(((1,1-dimethylethyl)oxy)methyl)-2'-fluoro-5'-(methyloxy)-1,1'-biphenyl-4-yl)methyl)oxy)phenyl)propanoic acid (66.63). 66.63F was converted to 66.63 using a procedure analogous to that used in 66.62. MS ESI (neg.) m/e: 505 (M−H)+. 1H NMR (400 MHz, CDCl3) δ ppm 7.53 (s, 1H), 7.40 (d, 1H), 7.23-7.24 (m, 2H), 7.03 (m, 1H), 6.84-6.92 (m, 4H), 6.79 (m, 1H), 5.18 (m, 2H), 4.33 (m, 2H), 3.79 (s, 3H), 2.73 (m, 1H), 2.60 (m, 1H), 2.31 (m, 1H), 1.20 (m, 1H), 1.10 (s, 9H), 0.90 (m, 1H), 0.60 (m, 1H), 0.49 (m, 1H), 0.34 (m, 1H), 0.20 (m, 1H).

Example 66.64

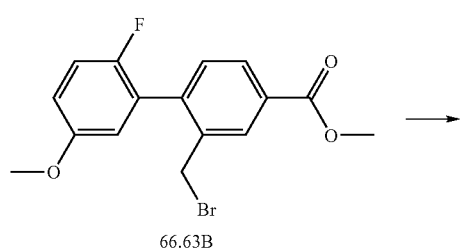

66.63B

-continued

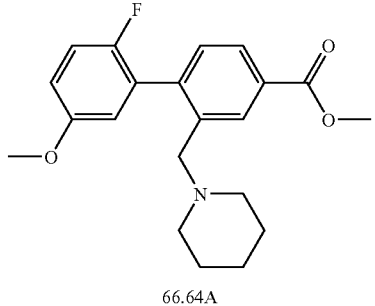

66.64A

Methyl 2'-fluoro-5'-(methyloxy)-2-(1-piperidinylmethyl)-1,1'-biphenyl-4-carboxylate (66.64A). Piperidine (commercially available from Aldrich) (0.038 g, 0.44 mmol) was added to a solution of 66.63B (0.13 g, 0.37 mmol) in DMSO (3 mL). Cs2CO3 (0.18 g, 0.55 mmol) was then added to the reaction and it was stirred at room temperature for 1 hour. EtOAc (100 mL) was added and the organic phase was washed with water and brine and dried over anhydrous sodium sulfate. After removing solvent, the residue was purified by flash chromatography (silica gel, 1:1 EtOAc/DCM) and gave 66.64A (100 mg) in 76% yield. MS ESI (pos.) m/e: 358 (M+H)+.

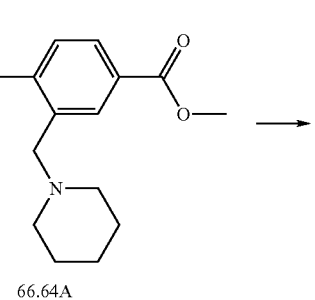

66.64A

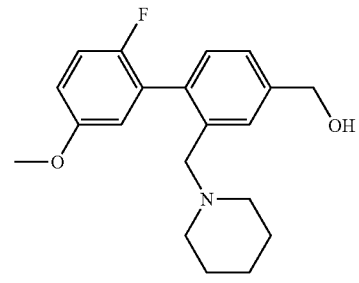

66.64B (2'-Fluoro-5'-(methyloxy)-2-(1-piperidinylmethyl)-1,1'-biphenyl-4-yl)methanol (66.64B). LAH (1.0 M solution in THF) (0.55 mL, 0.55 mmol) was added to a solution of 66.64A (0.098 g, 0.27 mmol) in THF (5 mL). The resulting mixture was stirred at room temperature for 1 hour and then it was diluted with EtOAc, washed with water and brine, and dried over anhydrous Na2SO4. After removing solvent, 66.64B was obtained as a colorless oil in 100% yield.

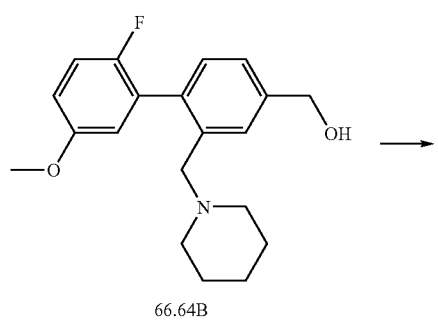

66.64B

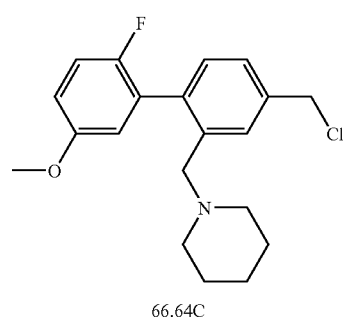

66.64C 1-((4-(Chloromethyl)-2'-fluoro-5'-(methyloxy)-1,1'-biphenyl-2-yl)methyl)piperidine (66.64C). Thionyl chloride (0.066 g, 0.56 mmol) was added to a solution of 66.64B (0.023 g, 0.070 mmol) in DCM (1 mL). The resulting mixture was stirred at room temperature for 2 hours. After removing solvent, 66.64C was obtained in 100% yield.

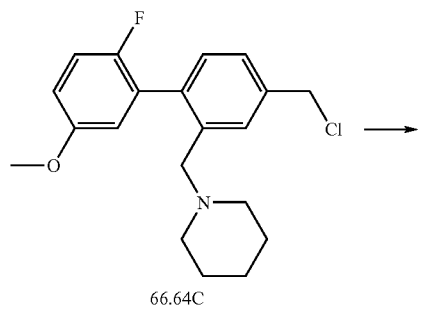

66.64C

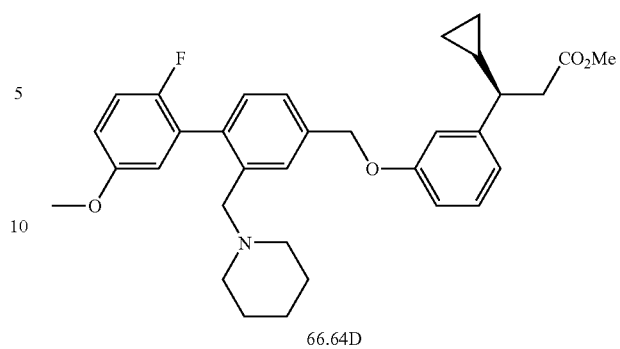

66.64D

Methyl (3S)-3-cyclopropyl-3-(3-(((2'-fluoro-5'-(methyloxy)-2-(1-piperidinylmethyl)-1,1'-biphenyl-4-yl)methyl)oxy)phenyl)propanoate or methyl (3R)-3-cyclopropyl-3-(3-(((2'-fluoro-5'-(methyloxy)-2-(1-piperidinylmethyl)-1,1'-biphenyl-4-yl)methyl)oxy)phenyl)propanoate (66.64D). Compound 66.64D was prepared using a procedure similar to that used to prepare 66.63F.

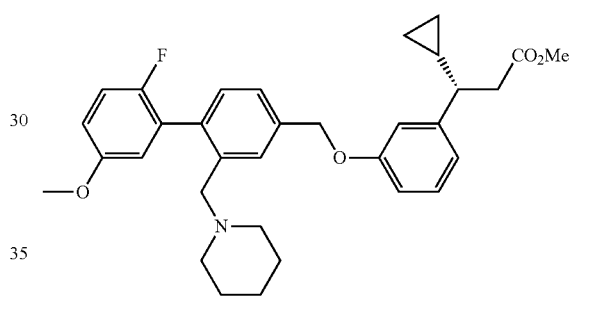

or

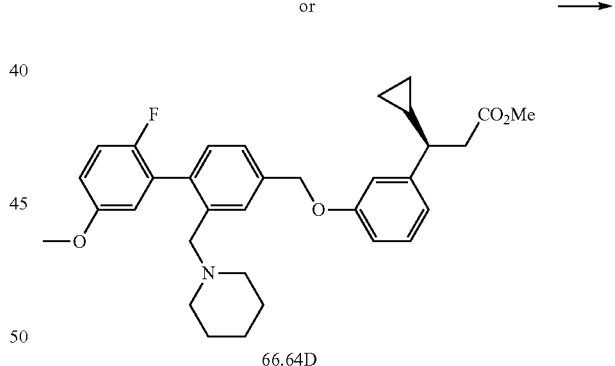

66.64D

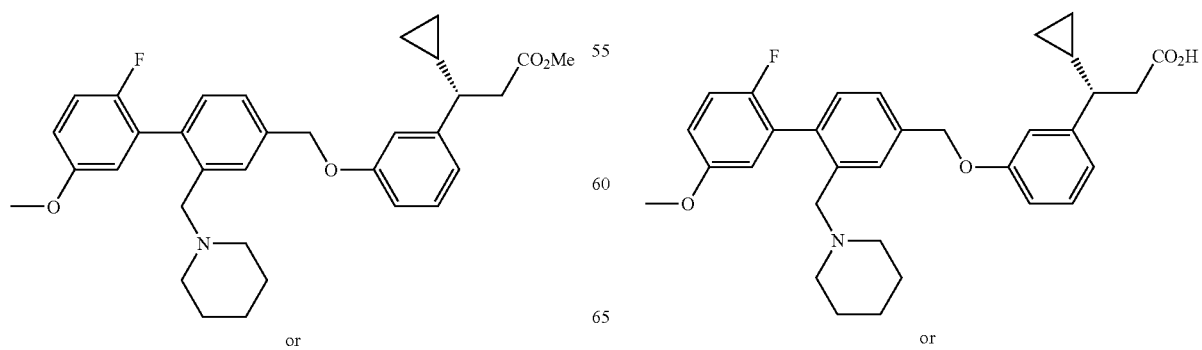

or

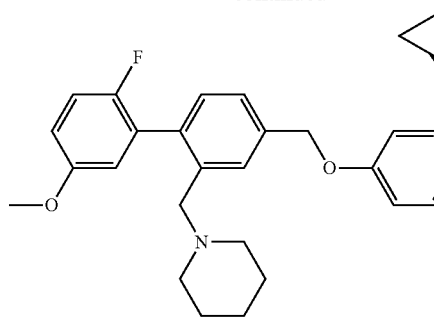

66.64

(3S)-3-Cyclopropyl-3-(3-(((2'-fluoro-5'-(methyloxy)-2-(1-piperidinylmethyl)-1,1'-biphenyl-4-yl)methyl)oxy)phenyl)propanoic acid or (3R)-3-cyclopropyl-3-(3-(((2'-fluoro-5'-(methyloxy)-2-(1-piperidinylmethyl)-1,1'-biphenyl-4-yl)methyl)oxy)phenyl)propanoic acid (66.64). A mixture of 66.64D (0.039 g, 0.073 mmol), NaOH (aq, 10%) (0.6 mL) and EtOH (2 mL) was stirred at room temperature overnight. The resulting product was purified by reverse phase HPLC. After removing solvent, 66.64 (TFA salt), was obtained (26 mg). MS ESI (neg.) m/e: 516 (M–H)+. $^1$H NMR (400 MHz, DMSO-$d_6$) δ ppm 9.20 (m, 1H), 7.87 (s, 1H), 7.64 (d, 1H), 7.40 (d, 1H), 7.21-7.31 (m, 2H), 7.07 (m, 1H), 6.86-6.96 (m, 4H), 5.19 (s, 2H), 4.04-4.40 (m, 2H), 3.10-3.31 (m, 2H), 2.66 (m, 3H), 1.62 (m, 5H), 1.25 (m, 1H), 1.00 (m, 1H), 0.50 (m, 1H), 0.24-0.29 (m, 1H), 0.10 (m, 1H).

Example 66.65

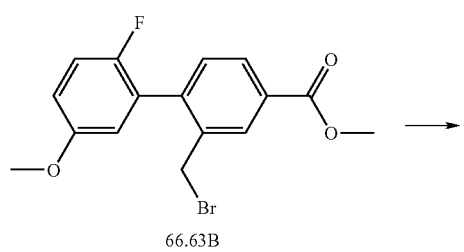

66.63B

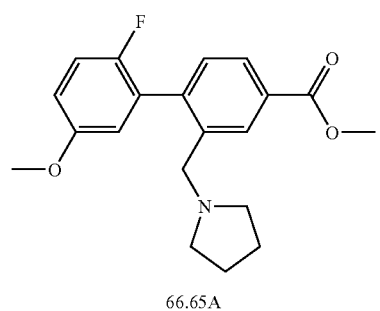

66.65A

Methyl 2'-fluoro-5'-(methyloxy)-2-(1-pyrrolidinylmethyl)-1,1'-biphenyl-4-carboxylate (66.65A). Compound 66.65A was synthesized using a procedure analogous to that used for 66.64A using pyrrolidine in place of piperidine. MS ESI (pos.) m/e: 344 (M+H)+.

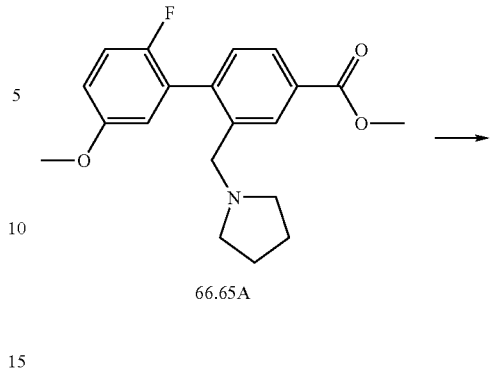

66.65A

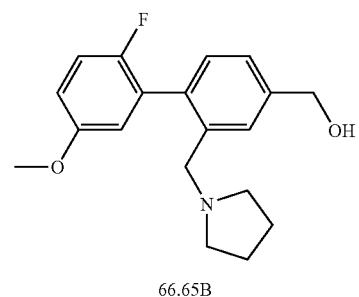

66.65B (2'-Fluoro-5'-(methyloxy)-2-(1-pyrrolidinylmethyl)-1,1'-biphenyl-4-yl)methanol (66.65B). Compound 66.65B was synthesized using a procedure analogous to that used for 66.64B.

66.65B

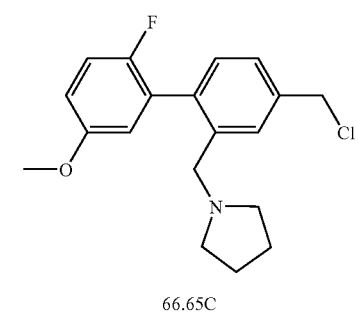

66.65C 1-((4-(Chloromethyl)-2'-fluoro-5'-(methyloxy)-1,1'-biphenyl-2-yl)methyl)pyrrolidine (66.65C). Compound 66.65C was synthesized using a procedure analogous to that used for 66.64C.

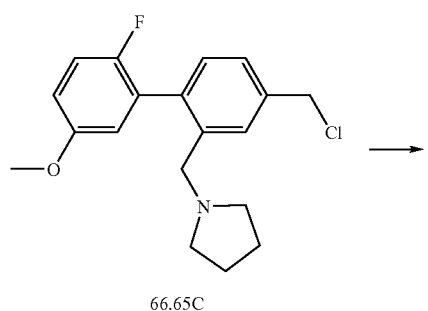

66.65C

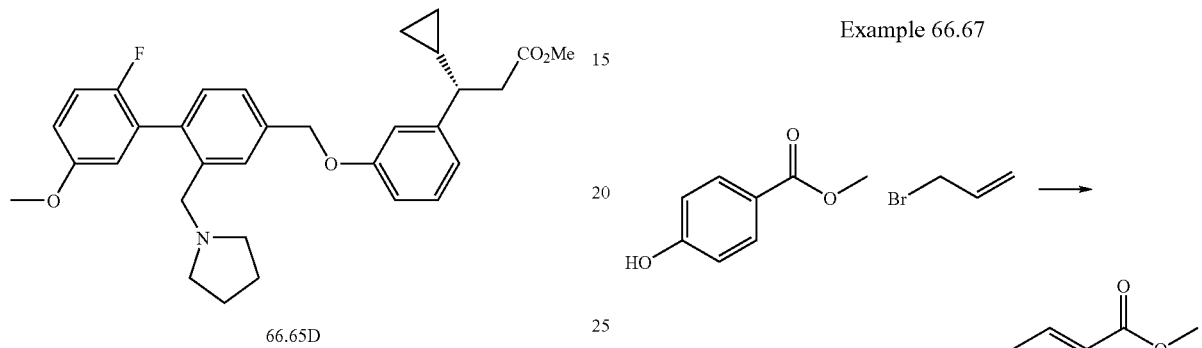

66.65D

Methyl (3S)-3-cyclopropyl-3-(3-(((2'-fluoro-5'-(methyloxy)-2-(1-pyrrolidinylmethyl)-1,1'-biphenyl-4-yl)methyl)oxy)phenyl)propanoate or methyl (3R)-3-cyclopropyl-3-(3-(((2'-fluoro-5'-(methyloxy)-2-(1-pyrrolidinylmethyl)-1,1'-biphenyl-4-yl)methyl)oxy)phenyl)propanoate (66.65D). Compound 66.65D was synthesized using a procedure analogous to that used for 66.64D.

(3S)-3-Cyclopropyl-3-(3-(((2'-fluoro-5'-(methyloxy)-2-(1-pyrrolidinylmethyl)-1,1'-biphenyl-4-yl)methyl)oxy)phenyl)propanoic acid or (3R)-3-cyclopropyl-3-(3-(((2'-fluoro-5'-(methyloxy)-2-(1-pyrrolidinylmethyl)-1,1'-biphenyl-4-yl)methyl)oxy)phenyl)propanoic acid (66.65). Example 66.65 was synthesized using a procedure analogous to that used for 66.64. After removing solvent, 41 mg of 66.65 (TFA salt) was obtained. MS ESI (neg.) m/e: 502 (M−H)+. 1H NMR (400 MHz, DMSO-d6) δ ppm 9.68 (m, 1H), 7.83 (s, 1H), 7.60 (m, 1H), 7.39 (m, 1H), 7.21-7.30 (m, 2H), 7.07 (m, 1H), 6.86-6.96 (m, 4H), 5.17 (s, 2H), 4.04-4.40 (m, 2H), 3.34 (m, 2H), 2.59-2.70 (m, 4H), 2.27 (m, 1H), 1.79 (m, 4H), 1.00 (m, 1H), 0.50 (m, 1H), 0.24 (m, 2H), 0.10 (m, 1H).

(3S)-3-(3-(3-(5,5-Dimethylcyclopent-1-enyl)-4-(2-methoxypyridin-4-yl)benzyloxy)phenyl)-3-cyclopropylpropanoic acid or (3R)-3-(3-(5,5-dimethylcyclopent-1-enyl)-4-(2-methoxypyridin-4-yl)benzyloxy)phenyl)-3-cyclopropylpropanoic acid (66.66). This compound was prepared using the same method described for 66.12 using 2-methoxypyridin-4-ylboronic acid (commercially available from Asymchem) as the Suzuki coupling reagent. MS ESI (pos.) m/e: 498.2 (M+H)+.

Example 66.67

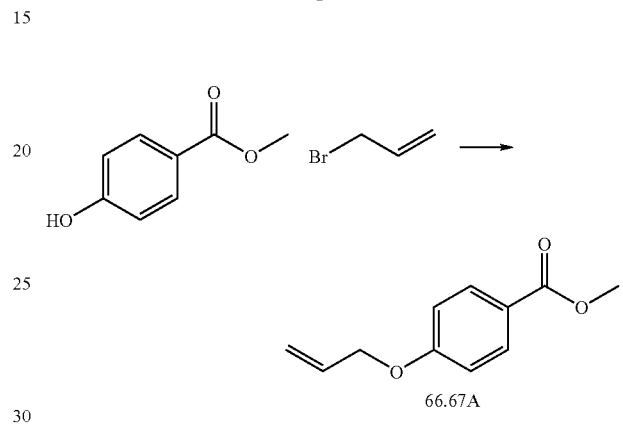

66.67A

Methyl 4-(allyloxy)benzoate (66.67A). The reaction mixture of 4-hydroxybenzoic acid, methyl ester (20.0 g, 131.0 mmol), allyl bromide (17.0 g, 138.0 mmol) and potassium carbonate (45.0 g, 329.0 mmol) in DMSO (30.0 mL) was stirred at room temperature for 8 hours. EtOAc (150 mL) was added, and the organic phase was washed with water (30×3 mL). The organic layer was dried over MgSO4. The solvent was removed. The product thus obtained was of sufficient quality for use in the next step without further purification, (25.0 g, yield 99%). 1H NMR (400 MHz, CDCl3) δ ppm 7.91 (2H, m), 6.86 (2H, m), 5.98 (1H, dt, J=17.2, 5.3 Hz), 5.35 (1H, dd, J=17.2, 1.6 Hz), 5.24 (1H, dd, J=10.6, 1.6 Hz), 4.52 (2H, d, J=5.5 Hz), 3.81 (3H, s).

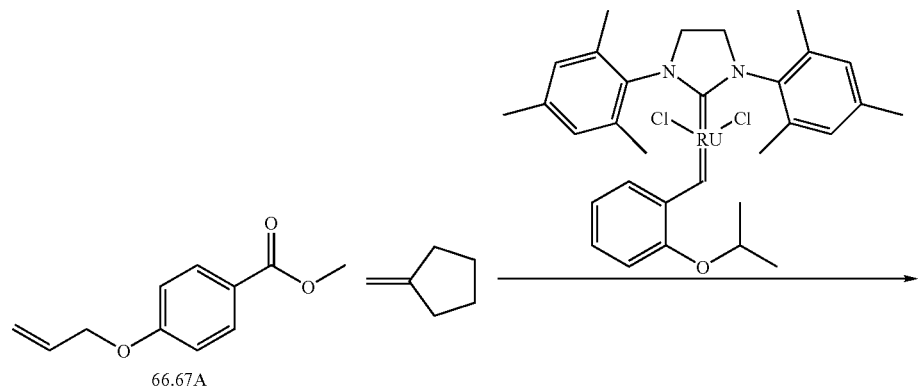

66.67A

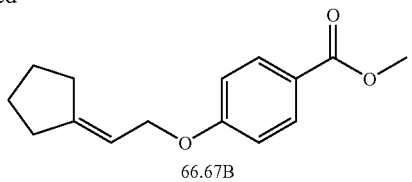

66.67B

Methyl 4-(2-cyclopentylideneethoxy)benzoate (66.67B). To a solution of methyl 4-(allyloxy)benzoate 66.67A (3.00 g, 16.0 mmol) and methylenecyclopentane (1.9 g, 23.0 mmol) in DCM (5.0 mL) was added Hoveyda Grubbs reagent (0.39 g, 0.62 mmol) at room temperature. The resulting reaction mixture was degassed three times and stirred at 55° C. under nitrogen overnight. The reaction mixture was purified by Combi Flash silica gel chromatography (hexane/EtOAc 95/5) to give the compound 66.67B, (2.60 g, yield 68%). $^1$H NMR (500 MHz, CDCl$_3$) δ ppm 7.82-7.93 (2H, m), 6.80-6.88 (2H, m), 5.44-5.56 (1H, m), 4.47 (2H, d, J=6.6 Hz), 3.80 (3H, s), 2.20-2.31 (4H, m), 1.50-1.71 (4H, m).

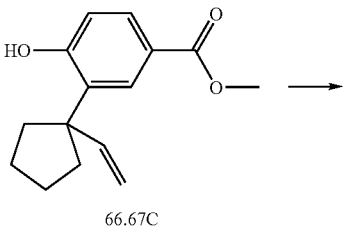

66.67C

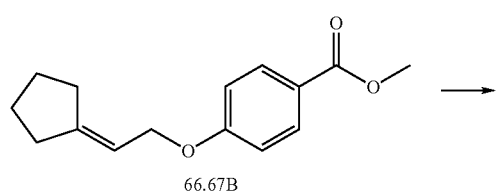

66.67B

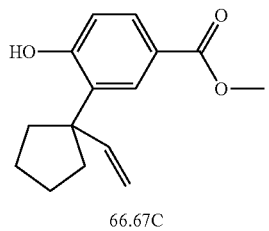

66.67C

Methyl 4-hydroxy-3-(1-vinylcyclopentyl)benzoate (66.67C). A mixture of methyl 4-(2-cyclopentylideneethoxy) benzoate 66.67B (0.50 g, 2.0 mmol), N,N-diethylaniline (3.2 mL, 20 mmol) and N,O-bis(trimethylsilyl)acetamide (2.5 mL, 10 mmol) in a 20 mL seal tube was heated at 240° C. for 48 hours. The reaction was then cooled to room temperature, ether (60 mL) was added, and the mixture was washed with HCl (3N, 20 mL). The organic layer was separated and the solvent was removed. The residue was dissolved in MeOH (10 mL) and HCl (3N, 2 mL) and stirred at room temperature for 30 minutes. Ether (80 mL) was added, and the mixture was washed with NaHCO$_3$ (30 mL) and brine (15 mL). The organic layer was dried over MgSO$_4$. After filtering, the solvent was removed. The residue was purified by Combi Flash silica gel column, eluting with hexane/EtOAc (95/5) to give the compound 66.67C, (0.15 g, yield 30%). $^1$H NMR (500 MHz, CDCl$_3$) δ ppm 7.90 (1H, d, J=2.2 Hz), 7.80 (1H, dd, J=8.3, 2.0 Hz), 6.81 (1H, d, J=8.3 Hz), 5.99 (1H, dd, J=17.6, 10.5 Hz), 5.77 (1H, s), 5.18 (1H, dd, J=10.5, 1.0 Hz), 5.08 (1H, d, J=17.6 Hz), 3.82 (3H, s), 1.89-2.03 (4H, m), 1.56-1.78 (4H, m). MS ESI (neg.) m/e: 245.1 (M−H)$^+$.

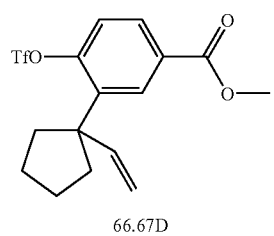

66.67D

Methyl 4-(trifluoromethylsulfonyloxy)-3-(1-vinylcyclopentyl)benzoate (66.67D). To a solution of methyl 4-hydroxy-3-(1-vinylcyclopentyl)benzoate 66.67C (0.19 g, 0.77 mmol) and a catalytic amount of DMAP in pyridine (1.5 mL) was slowly added trifluoromethanesulfonic anhydride (0.17 mL, 1.0 mmol) at 0° C. After addition, the reaction mixture was stirred at ambient temperature for 16 hours. EtOAc (70 mL) was added, and the mixture was washed with citric acid (15.0 mL, 1 M in water) and brine (20.0 mL), and then dried with magnesium sulfate. After filtration, the solvent was removed. The desired product 66.67 D was sufficient for use in the next step. $^1$H NMR (400 MHz, CDCl$_3$) δ ppm 8.06 (1H, d, J=2.3 Hz), 7.87 (1H, dd, J=8.6, 2.0 Hz), 7.16 (1H, s), 5.85 (1H, dd, J=17.2, 10.6 Hz), 4.95 (1H, d, J=10.6 Hz), 4.72 (1H, d, J=17.2 Hz), 3.83 (3H, s), 2.12-2.28 (2H, m), 1.74-1.94 (2H, m), 1.66 (4H, m).

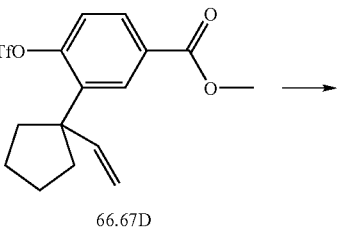

66.67D

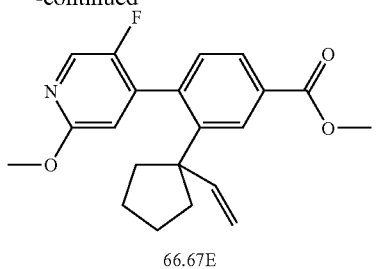

66.67E

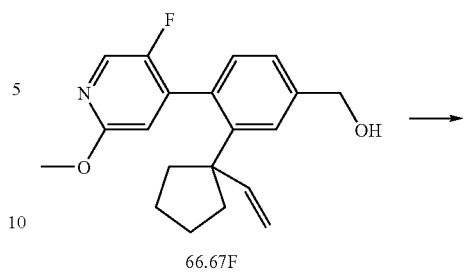

66.67F

Methyl 4-(5-fluoro-2-methoxypyridin-4-yl)-3-(1-vinylcyclopentyl)benzoate (66.67E). A mixture of methyl 4-(trifluoromethylsulfonyloxy)-3-(1-vinylcyclopentyl)benzoate 66.67 D (0.29 g, 0.8 mmol), 5-fluoro-2-methoxypyridin-4-ylboronic acid (0.2 g, 1.0 mmol) (commercially available from Asymchem), potassium phosphate (0.5 g, 2.0 mmol), S-phos (0.06 g, 0.2 mmol) and palladium acetate (0.02 g, 0.08 mmol) in DMF (1.5 mL) was purged with nitrogen three times. The resulting mixture was heated at 90° C. for 2 hours. The reaction mixture was purified by Combi Flash silica gel, eluting with hexane/EtOAc (9/1) to give 66.67 E. $^1$H NMR (500 MHz, CDCl$_3$) δ ppm 8.20 (1H, d, J=1.7 Hz), 8.00 (1H, s), 7.91 (1H, dd, J=7.8, 1.7 Hz), 7.10 (1H, d, J=8.1 Hz), 6.63 (1H, d, J=4.9 Hz), 5.87 (1H, dd, J=17.4, 10.5 Hz), 4.97 (1H, d, J=10.5 Hz), 4.69 (1H, d, J=17.4 Hz), 3.98 (3H, s), 3.85 (3H, s), 2.00-2.20 (1H, m), 1.80-1.96 (1H, m), 1.51-1.75 (6H, m). MS ESI (pos.) m/e: 355.9 (M+H)$^+$.

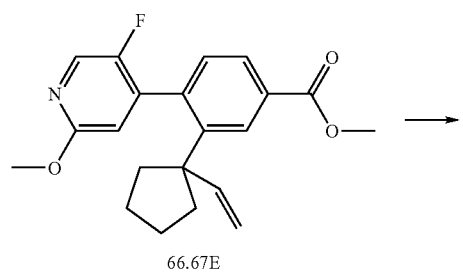

66.67E

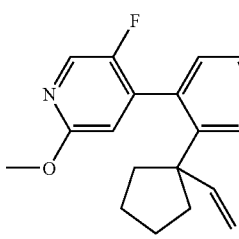

66.67F (4-(5-Fluoro-2-methoxypyridin-4-yl)-3-(1-vinylcyclopentyl)phenyl)methanol (66.67F). To a solution of methyl 4-(5-fluoro-2-methoxypyridin-4-yl)-3-(1-vinylcyclopentyl)benzoate 66.67E (51.0 mg, 143 μmol) in THF (2.0 mL) was slowly added LAH, (1.0M solution in diethyl ether) (0.30 mL, 287 μmol) at room temperature. The resulting mixture was stirred at 50° C. for 1 hour. Standard work up conditions were employed and the solvent was removed. The desired product was used in the next step without further purification. MS ESI (pos.) m/e: 328.2 (M+H)$^+$.

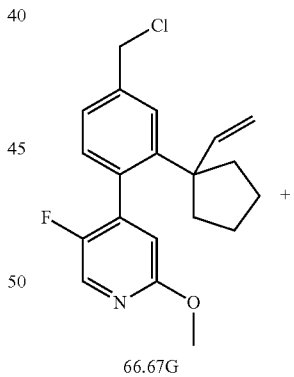

66.67G 4-(4-(Chloromethyl)-2-(1-vinylcyclopentyl)phenyl)-5-fluoro-2-methoxypyridine (66.67G). To a solution of (4-(5-fluoro-2-methoxypyridin-4-yl)-3-(1-vinylcyclopentyl)phenyl)methanol 66.67F (47.0 mg, 144 μmol) in DMF (0.01 mL) and DCM (4.0 mL) was slowly added thionyl chloride (14.7 μL, 201 μmol) at 0° C. After addition, the resulting mixture was stirred at room temperature for 1 hour. The solvent was removed, and the desired product was used directly in the next step. $^1$H NMR (400 MHz, CDCl$_3$) δ ppm 8.01-8.11 (1H, m), 7.98 (1H, m), 7.47 (1H, s), 6.94 (1H, d, J=7.8 Hz), 6.69-6.82 (1H, m), 5.80 (1H, dd, J=17.2, 10.6 Hz), 4.89 (1H, d, J=10.2 Hz), 4.52-4.69 (3H, m), 3.89 (3H, s), 1.68-1.84 (4H, m), 1.49-1.67 (4H, m).

66.67G

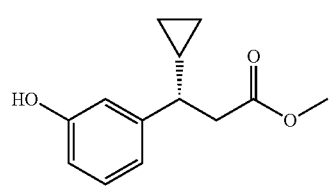

or

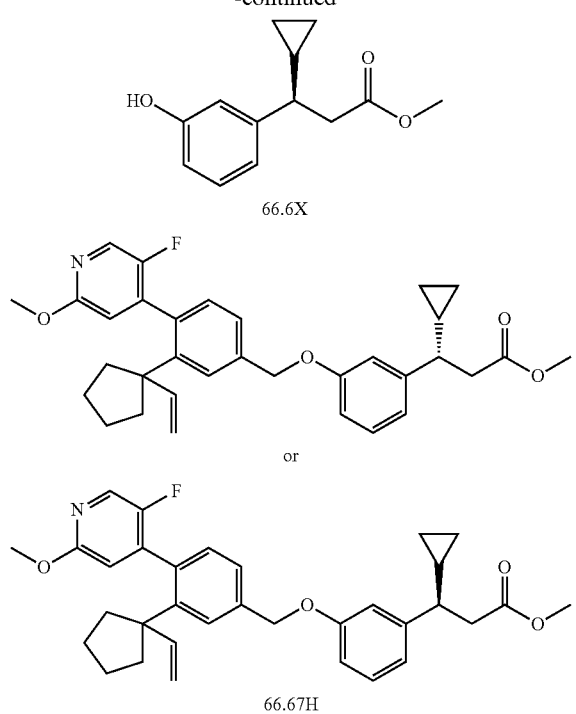

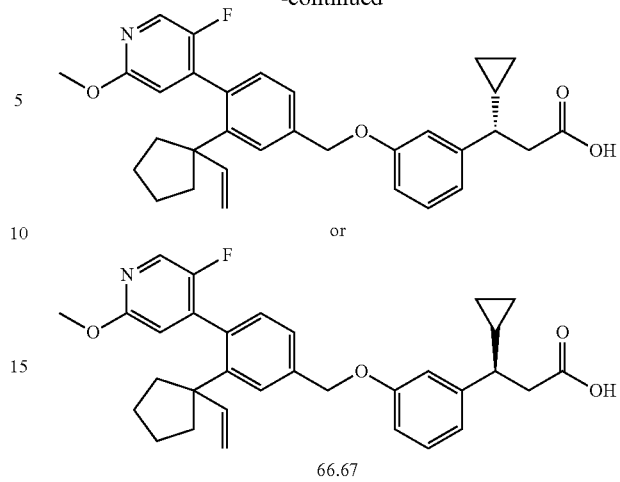

(3S)-Methyl 3-(3-(4-(5-fluoro-2-methoxypyridin-4-yl)-3-(1-vinylcyclopentyl)benzyloxy)phenyl)-3-cyclopropylpropanoate or (3R)-methyl 3-(3-(4-(5-fluoro-2-methoxypyridin-4-yl)-3-(1-vinylcyclopentyl)benzyloxy)phenyl)-3-cyclopropylpropanoate (66.67H). The reaction mixture of 66.67G (24.0 mg, 69.4 µmol), 66.6X (15.3 mg, 69.4 µmol) and cesium carbonate (Cabot high purity grade) (33.9 mg, 104 µmol) in DMSO (1.5 mL) was stirred at room temperature for 16 hours. LCMS indicated that the reaction was complete. EtOAc (50 mL) was added, and the mixture was washed with brine (15×2 mL) and then dried over MgSO$_4$. After filtration, the solvent was removed. The product thus obtained was used in the next step without further purification. MS ESI (pos.) m/e: 530.2 (M+H)$^+$.

(3S)-3-(3-(4-(5-Fluoro-2-methoxypyridin-4-yl)-3-(1-vinylcyclopentyl)benzyloxy)phenyl)-3-cyclopropylpropanoic acid or (3R)-3-(3-(4-(5-fluoro-2-methoxypyridin-4-yl)-3-(1-vinylcyclopentyl) benzyloxy)phenyl)-3-cyclopropylpropanoic acid (66.67). A reaction mixture of 66.67H (36.8 mg, 69 µmol) and LiOH (3.33 mmol in water, 0.2 mL, 695 µmol) in MeOH (1.0 mL) was stirred at room temperature for 16 hours. LCMS indicated that the reaction was complete. The reaction mixture was brought to a pH of 6 with HCl (3.0 N in water) and purified by preparative HPLC (reversed phase) to give the product 66.67. $^1$H NMR (400 MHz, CD$_3$CN) δ ppm 7.87 (1H, s), 7.50 (1H, d, J=1.6 Hz), 7.23 (1H, dd, J=7.8, 1.6 Hz), 7.04-7.17 (1H, m), 6.88-6.96 (1H, m), 6.68-6.83 (3H, m), 6.46-6.60 (1H, m), 5.74 (1H, dd, J=17.2, 10.6 Hz), 5.01 (2H, s), 4.79 (1H, d, J=10.6 Hz), 4.57 (1H, d, J=17.2 Hz), 3.75 (3H, s), 2.51-2.70 (2H, m), 2.14 (1H, td, J=9.2, 6.3 Hz), 1.85-2.01 (1H, m), 1.59-1.74 (1H, m), 1.33-1.59 (6H, m), 0.81-0.96 (1H, m), 0.35-0.49 (1H, m), 0.08-0.27 (2H, m, J=12.2, 12.2, 8.5, 3.9 Hz), 0.00 (1H, ddd, J=9.5, 4.6, 4.3 Hz). MS ESI (neg.) m/e: 514.3 (M–H)$^+$.

Example 66.68

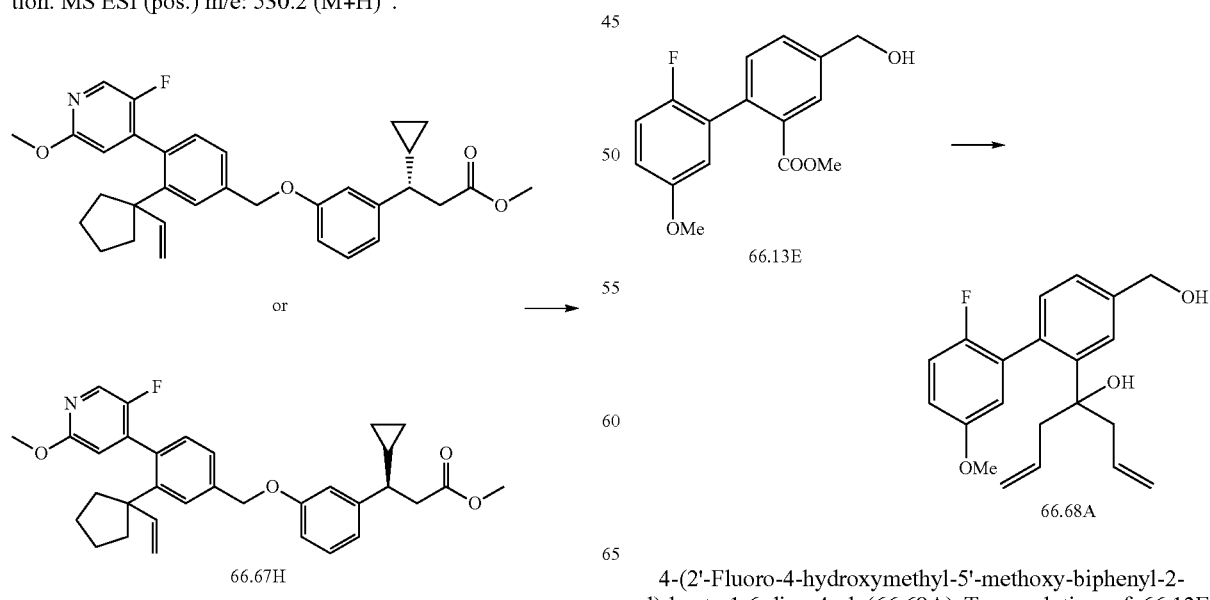

4-(2'-Fluoro-4-hydroxymethyl-5'-methoxy-biphenyl-2-yl)-hepta-1,6-dien-4-ol (66.68A) To a solution of 66.13E (712 mg, 2453 μmol) in benzene, was added allylmagnesium bromide (24528 μL, 24528 μmol) in ether. The mixture was stirred at room temperature for 1 hour and then quenched with saturated NH₄Cl. EtOAc was added, and the organic layer was washed with water and brine. The organic layer was then dried and concentrated to give a residue which was purified by flash column to give the product as an oil (670 mg, 80%).

was added (under a nitrogen atmosphere) Grubbs reagent in 20 mL of DCM by syringe. The resulting mixture was stirred at room temperature for 2 hours. Solvent was then removed in vacuo to give a residue which was purified by Combiflash chromatography to give the product as an oil (110 mg, 45%). MS ESI m/e: 429.3 (M+H)⁺.

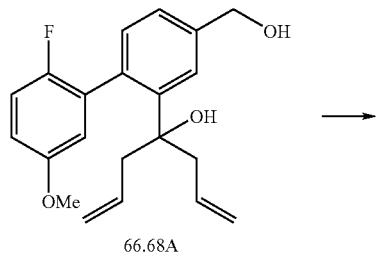

66.68A

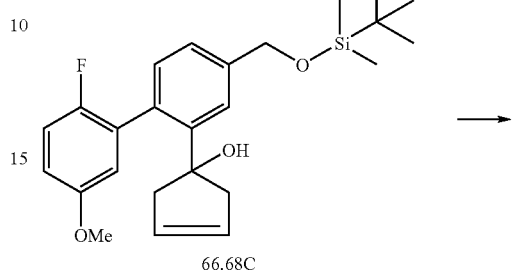

66.68C

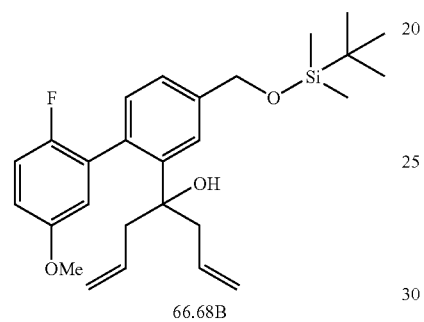

66.68B

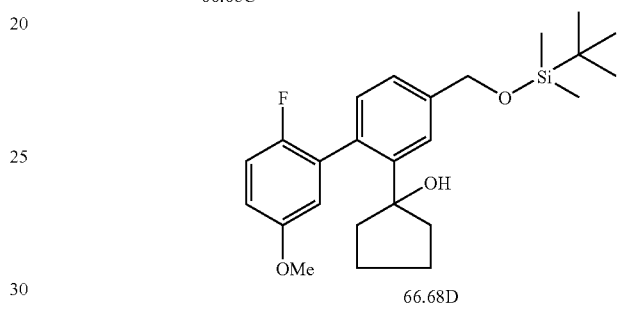

66.68D

4-[4-(tert-Butyl-dimethyl-silanyloxymethyl)-2'-fluoro-5'-methoxy-biphenyl-2-yl]-hepta-1,6-dien-4-ol (66.68B) Compound 66.68B was synthesized from 66.68A using a method analogous to the method used to prepare compound 66.13J from 66.13H. MS ESI m/e: 457.3 (M+1)⁺.

1-[4-(tert-Butyl-dimethyl-silanyloxymethyl)-2'-fluoro-5'-methoxy-biphenyl-2-yl]-cyclopentanol (66.68D) To a solution of 66.68C (100 mg, 212 μmol) in EtOAc, was added 10% PtO₂/C (50 mg). The mixture was then stirred under a hydrogen atmosphere for 0.5 hours, the solid was filtered away, and the filtrate was concentrated to give the product as an oil which was used in the next step.

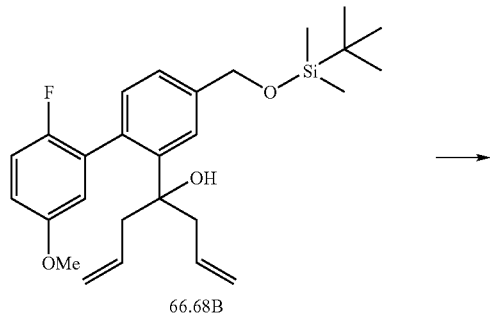

66.68B

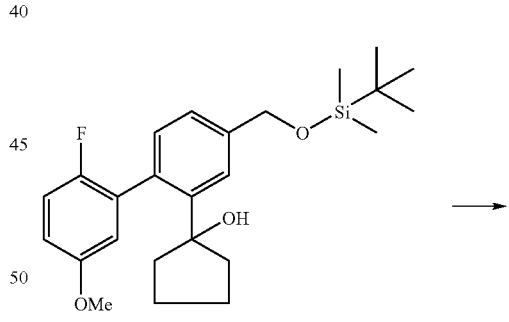

66.68D

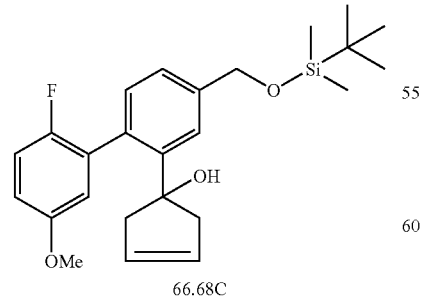

66.68C

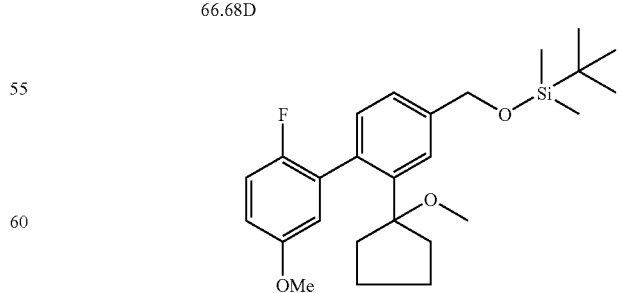

66.68E

1-[4-(tert-Butyl-dimethyl-silanyloxymethyl)-2'-fluoro-5'-methoxy-biphenyl-2-yl]-cyclopent-3-enol (66.68C). To a solution of 66.68B (259 mg, 567 μmol) in 20 mL of DCM, tert-Butyl-[2'-fluoro-5'-methoxy-2-(1-methoxy-cyclopentyl)-biphenyl-4-ylmethoxy]-dimethyl-silane (66.68E) Compound 66.68E was synthesized from 66.68D using a method analogous to the method used to prepare compound 66.41E from 66.41D. MS ESI m/e: 445.3 (M+H)+.

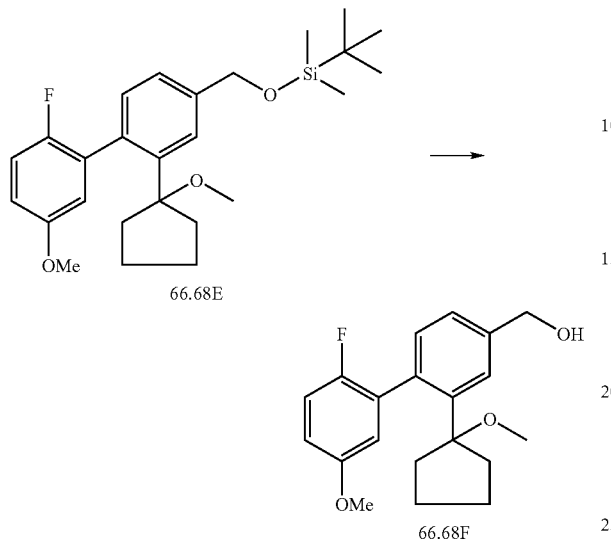

[2'-Fluoro-5'-methoxy-2-(1-methoxy-cyclopentyl)-biphenyl-4-yl]-methanol (66.68F). To a solution of 66.68E (66 mg, 168 μmol) in MeOH, was added PPTS (11 mg, 45 μmol), and the mixture was stirred for 16 hours. Solvent was then removed in vacuo to give a residue which was purified by Combiflash chromatography to give the product as an oil (30 mg, 61%). MS ESI m/e: 331.2 (M+H)+.

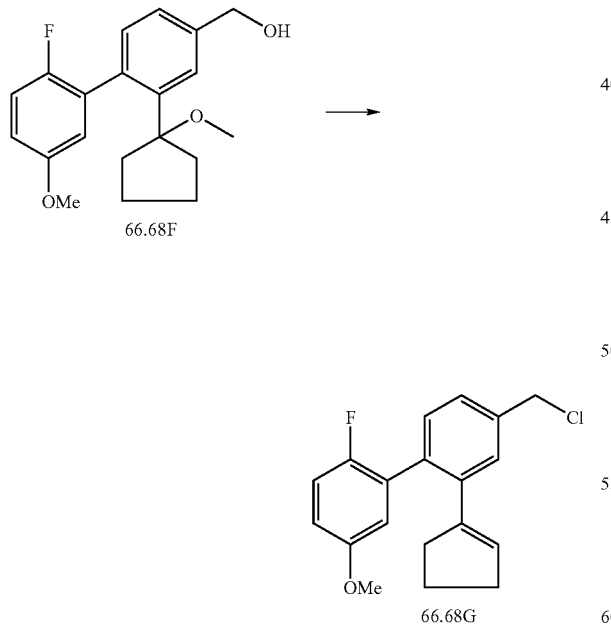

4-Chloromethyl-2-cyclopent-1-enyl-2'-fluoro-5'-methoxy-biphenyl (66.68G). Compound 66.68G was synthesized from 66.68F using a method analogous to the method used to prepare compound 66.12D from 66.12C. MS ESI m/e: 317.1 (M+1)+.

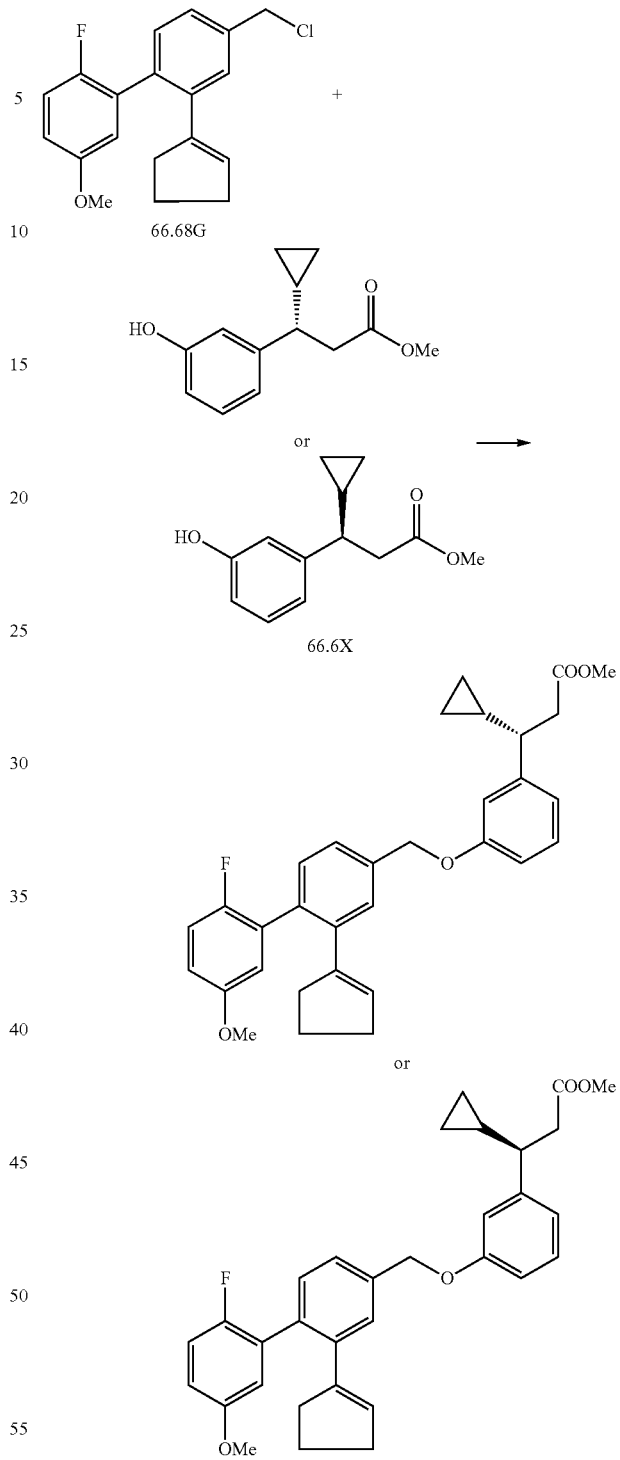

(S)-3-[3-(2-Cyclopent-1-enyl-2'-fluoro-5'-methoxy-biphenyl-4-ylmethoxy)-phenyl]-3-cyclopropyl-propionic acid methyl ester or (R)-3-[3-(2-cyclopent-1-enyl-2'-fluoro-5'-methoxy-biphenyl-4-ylmethoxy)-phenyl]-3-cyclopropyl-propionic acid methyl ester (66.68H). Compound 66.68H was synthesized from 66.68G and 66.6X using a method analogous to the method used to prepare compound 66.13P. MS ESI m/e: 501.3 (M+H)+.

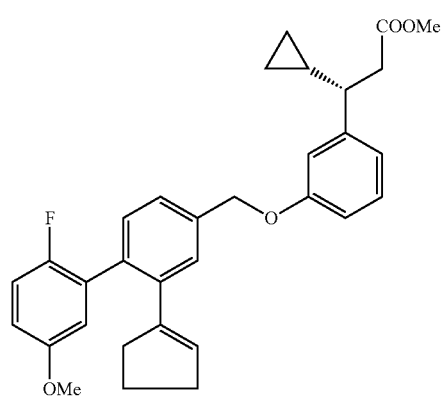

or

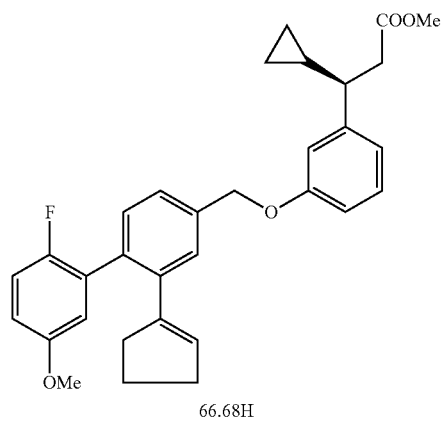

66.68H

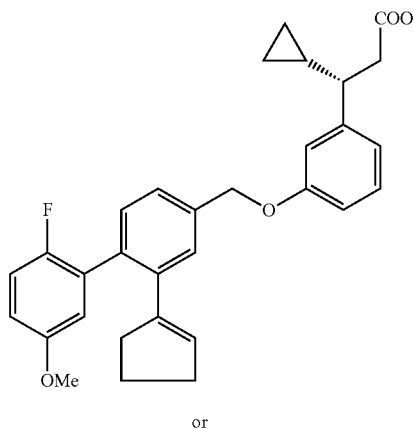

or

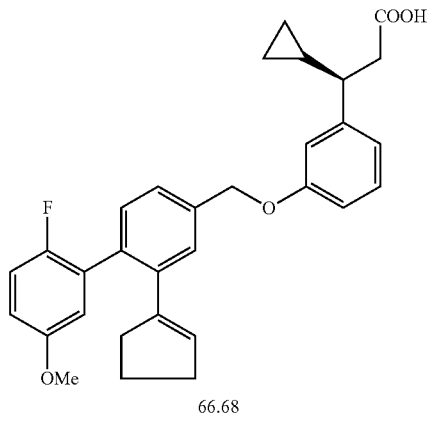

66.68

(S)-3-[3-(2-Cyclopent-1-enyl-2'-fluoro-5'-methoxy-biphenyl-4-ylmethoxy)-phenyl]-3-cyclopropyl-propionic acid or (R)-3-[3-(2-cyclopent-1-enyl-2'-fluoro-5'-methoxy-biphenyl-4-ylmethoxy)-phenyl]-3-cyclopropyl-propionic acid (66.68). Compound 66.68 was synthesized from 66.68H by a method analogous to that used to prepare compound 66.13 from 66.13P. MS ESI m/e: 487.2 (M+1)$^+$. $^1$H NMR (400 MHz, CDCl$_3$) δ ppm 7.44 (m, 1H), 7.37 (m, 1H), 7.29 (m, 1H), 7.24 (m, 1H), 6.99 (m, 1H), 6.79-6.89 (m, 5H), 5.52 (m, 1H), 5.07 (s, 2H), 3.78 (s, 3H), 2.78 (m, 2H), 2.36 (m, 4H), 1.85 (m, 2H), 1.27 (m, 1H), 1.03 (m, 1H), 0.58 (m, 1H), 0.43 (m, 1H), 0.28 (m, 1H), 0.17 (m, 1H).

Example 66.69

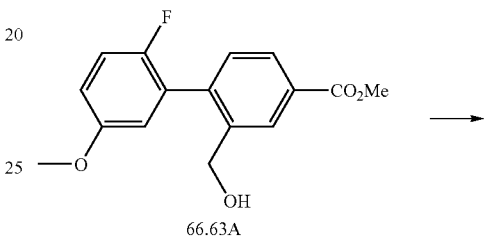

66.63A

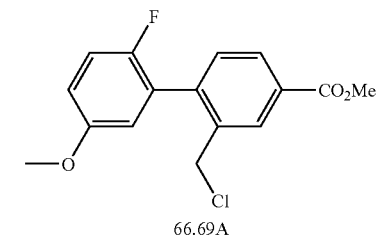

66.69A

Methyl 2-(chloromethyl)-2'-fluoro-5'-(methyloxy)-1,1'-biphenyl-4-carboxylate (66.69A). Thionyl chloride (available from Aldrich) (4.46 g, 37.5 mmol) was added to a solution or 66.63A in DCM (6 mL). The reaction mixture was stirred at room temperature for 2 hours and then at 50° C. for 3 hours. After removing solvent, the residue was purified by flash chromatography (silica gel, 1:9 EtOAc/hexane) and gave 66.69A (386 mg) as a colorless oil.

66.69A

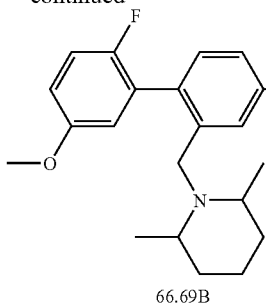

66.69B

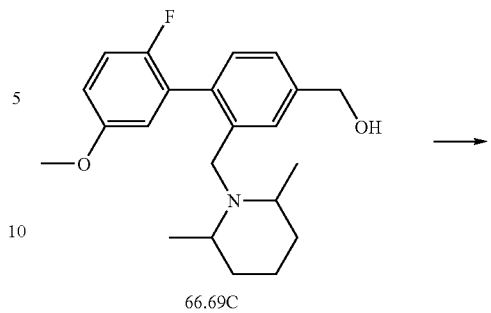

66.69C

Methyl 2-((2,6-dimethyl-1-piperidinyl)methyl)-2'-fluoro-5'-(methyloxy)-1,1'-biphenyl-4-carboxylate (66.69B). A mixture of 66.69A (0.094 g, 0.30 mmol), 2,6-dimethylpiperidine (0.069 g, 0.61 mmol) (commercially available from Aldrich) and cesium carbonate (0.20 g, 0.61 mmol) in DMSO (4 mL) was stirred at 70° C. for 24 hours. The product was purified by reverse phase HPLC to give 66.69B in 30% yield.

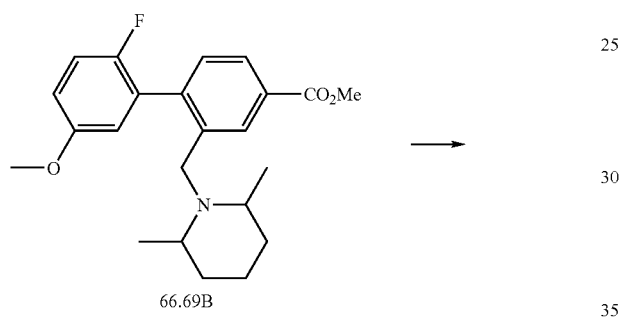

66.69B

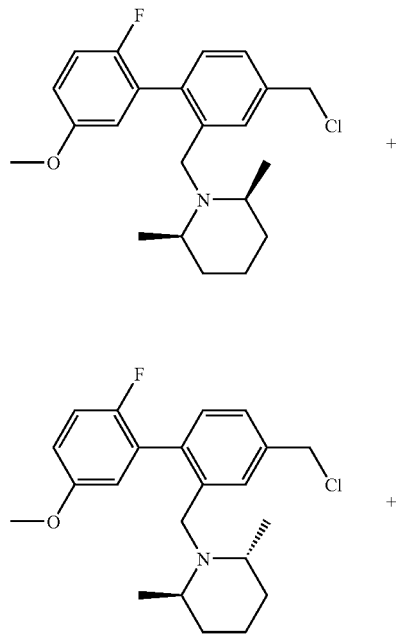

66.69D and 66.69E

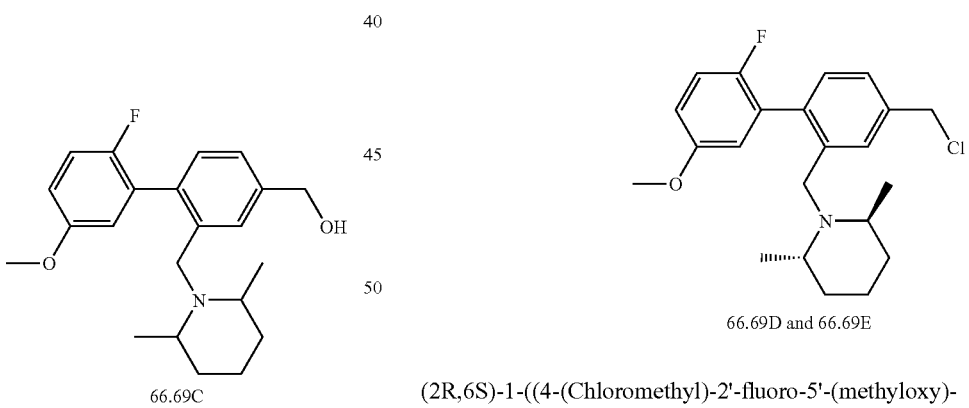

66.69C (2-((2,6-Dimethyl-1-piperidinyl)methyl)-2'-fluoro-5'-(methyloxy)-1,1'-biphenyl-4-yl)methanol (66.69C). LAH (1.0 M solution in THF) (0.088 mL, 0.088 mmol) was added slowly to a solution of 66.69B (0.034 g, 0.088 mmol) in THF (1 mL). The resulting mixture was stirred at room temperature for 25 minutes and then was poured into brine (2 mL) and extracted with EtOAc (3×30 mL). The combined organic layers were dried over anhydrous sodium sulfate. After removing solvent, the residue was purified by flash chromatography (silica gel, 1:1 EtOAc/hexane) and gave 66.69C (22 mg) as a colorless oil.

(2R,6S)-1-((4-(Chloromethyl)-2'-fluoro-5'-(methyloxy)-1,1'-biphenyl-2-yl)methyl)-2,6-dimethylpiperidine and (2S,6S)-1-((4-(chloromethyl)-2'-fluoro-5'-(methyloxy)-1,1'-biphenyl-2-yl)methyl)-2,6-dimethylpiperidine and (2R,6R)-1-((4-(chloromethyl)-2'-fluoro-5'-(methyloxy)-1,1'-biphenyl-2-yl)methyl)-2,6-dimethylpiperidine (66.69D). Thionyl chloride (available from Aldrich) (0.11 mL, 1.5 mmol) was added to a solution of 66.69C (0.022 g, 0.062 mmol) in DCM (0.2 mL) and it was stirred at room temperature for 4 hours. The product was purified by reverse phase HPLC to give 66.69D (6 mg) and 66.69E (8 mg). One of these included the racemic mixture of the trans R,R and S,S compounds and the other was the R,S cis compound. The configuration of cis- and trans-2,6-dimethylpiperidine was not confirmed.

491

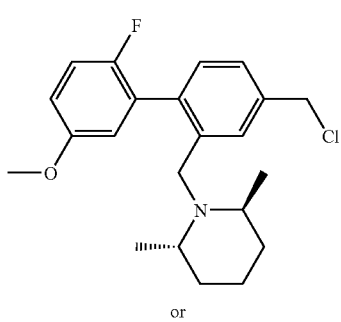

or

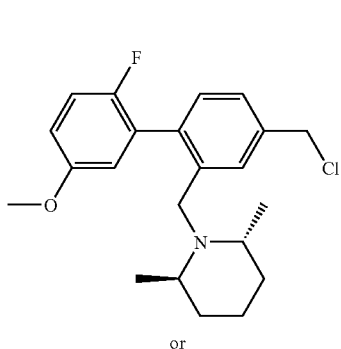

or

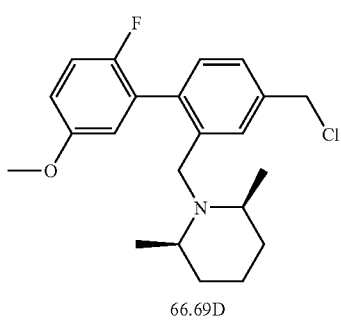

66.69D

492

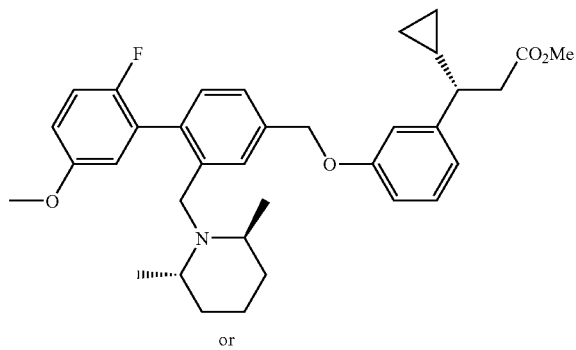

or

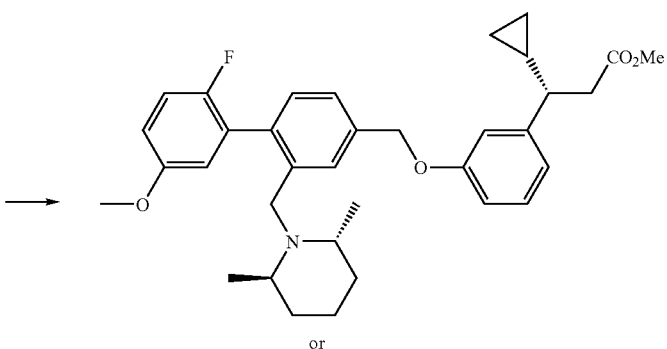

or

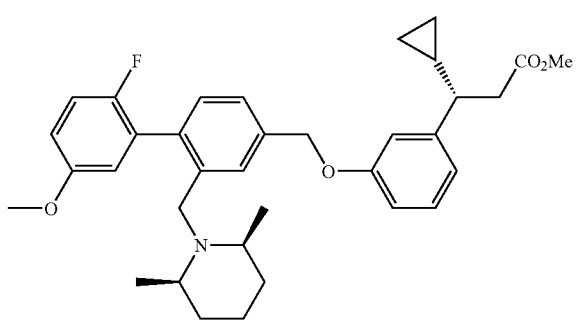

or the compounds from the R cyclopropyl compound
66.69F

Methyl (3S)-3-cyclopropyl-3-(3-(((2-(((2R,6S)-2,6-dimethyl-1-piperidinyl)methyl)-2'-fluoro-5'-(methyloxy)-1,1'-biphenyl-4-yl)methyl)oxy)phenyl)propanoate or methyl (3S)-3-cyclopropyl-3-(3-(((2-(((2R,6R)-2,6-dimethyl-1-piperidinyl)methyl)-2'-fluoro-5'-(methyloxy)-1,1'-biphenyl-4-yl)methyl)oxy)phenyl)propanoate and methyl (3S)-3-cyclopropyl-3-(3-(((2-(((2S,6S)-2,6-dimethyl-1-piperidinyl)methyl)-2'-fluoro-5'-(methyloxy)-1,1'-biphenyl-4-yl)methyl)oxy)phenyl)propanoate; or methyl (3R)-3-cyclopropyl-3-(3-(((2-(((2R,6S)-2,6-dimethyl-1-piperidinyl) methyl)-2'-fluoro-5'-(methyloxy)-1,1'-biphenyl-4-yl)methyl)oxy)phenyl)propanoate or methyl (3R)-3-cyclopropyl-3-(3-(((2-(((2R,6R)-2,6-dimethyl-1-piperidinyl)methyl)-2'-fluoro-5'-(methyloxy)-1,1'-biphenyl-4-yl)methyl)oxy)phenyl)propanoate and methyl (3R)-3-cyclopropyl-3-(3-(((2-(((2S,6S)-2,6-dimethyl-1-piperidinyl)methyl)-2'-fluoro-5'-(methyloxy)-1,1'-biphenyl-4-yl) methyl)oxy)phenyl)propanoate (66.69F). The title ester compound was synthesized from 66.69D using the same procedure used to prepare 66.62F.

493

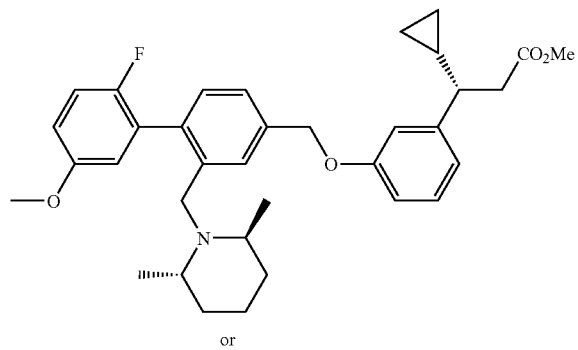

or

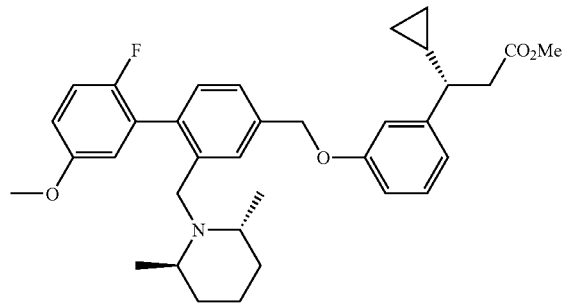

or

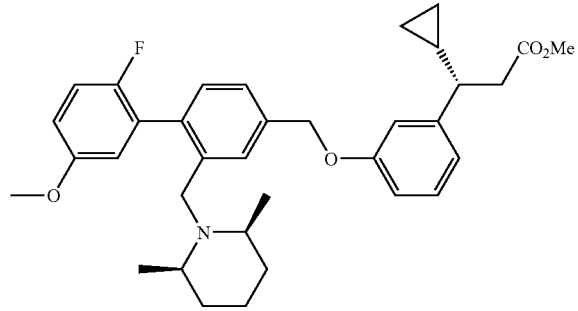

or the compounds with the R cyclopropyl head
66.69F

494

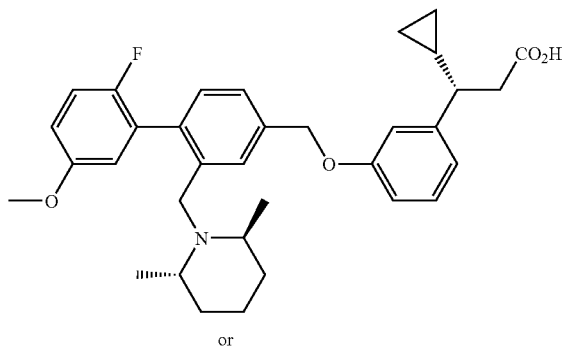

or

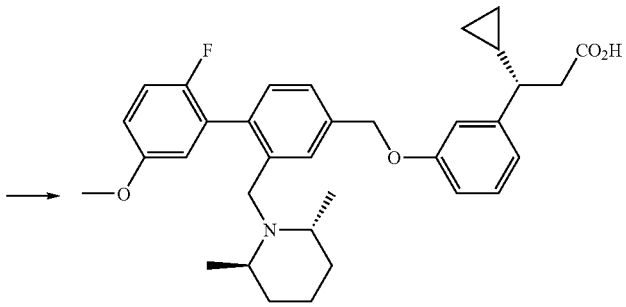

or

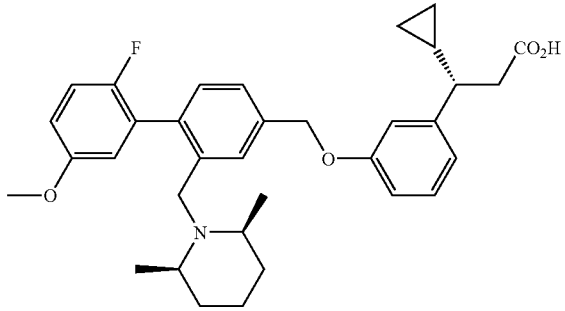

or the compounds with the R cyclopropyl head
66.69

(3S)-3-Cyclopropyl-3-(3-(((2-(((2R,6S)-2,6-dimethyl-1-piperidinyl)methyl)-2'-fluoro-5'-(methyloxy)-1,1'-biphenyl-4-yl)methyl)oxy)phenyl)propanoic acid or (3S)-3-cyclopropyl-3-(3-(((2-(((2R,6R)-2,6-dimethyl-1-piperidinyl)methyl)-2'-fluoro-5'-(methyloxy)-1,1'-biphenyl-4-yl)methyl)oxy)phenyl)propanoic acid and (3S)-3-cyclopropyl-3-(3-(((2-(((2S,6S)-2,6-dimethyl-1-piperidinyl) methyl)-2'-fluoro-5'-(methyloxy)-1,1'-biphenyl-4-yl)methyl)oxy) phenyl)propanoic acid; or (3R)-3-cyclopropyl-3-(3-(((2-(((2R,6S)-2,6-dimethyl-1-piperidinyl)methyl)-2'-fluoro-5'-(methyloxy)-1,1'-biphenyl-4-yl)methyl)oxy)phenyl) propanoic acid or (3R)-3-cyclopropyl-3-(3-(((2-(((2R,6R)-2,6-dimethyl-1-piperidinyl)methyl)-2'-fluoro-5'-(methyloxy)-1,1'-biphenyl-4-yl)methyl)oxy)phenyl)propanoic acid and (3R)-3-cyclopropyl-3-(3-(((2-(((2S,6S)-2,6-dimethyl-1-piperidinyl) methyl)-2'-fluoro-5'-(methyloxy)-1,1'-biphenyl-4-yl)methyl)oxy)phenyl)propanoic acid (66.69). Example 66.69 was prepared from 66.69F using a procedure similar to that used to prepare 66.65. After removing solvent, 4 mg of 66.69 (TFA salt) was obtained. MS ESI (neg.) m/e: 544 (M–H)$^+$. $^1$H NMR (400 MHz, CDCl$_3$) δ ppm 9.54 (m, 1H), 7.73-7.77 (m, 1H), 7.57-7.59 (m, 1H), 7.34-7.39 (m, 1H), 7.10-7.24 (m, 2H), 6.88-6.90 (m, 3H), 6.78-6.80 (m, 2H), 5.22 (s, 2H), 4.30-4.60 (m, 1H), 4.11-4.16 (m, 1H), 3.97 (m, 1H), 3.66 (m, 1H), 2.66-2.83 (m, 3H), 2.33 (m, 1H), 1.69 (m, 2H), 1.55 (m, 2H), 1.25-1.34 (m, 6H), 1.01-1.13 (m, 2H), 0.77-0.86 (m, 1H), 0.60 (m, 1H), 0.45 (m, 1H), 0.29 (m, 1H), 0.18 (m, 1H).

Methyl (3S)-3-cyclopropyl-3-(3-(((2-(((2R,6S)-2,6-dimethyl-1-piperidinyl)methyl)-2'-fluoro-5'-(methyloxy)-1,1'-biphenyl-4-yl)methyl)oxy)phenyl)propanoate or methyl (3S)-3-cyclopropyl-3-(3-(((2-(((2R,6R)-2,6-dimethyl-1-piperidinyl)methyl)-2'-fluoro-5'-(methyloxy)-1,1'-biphenyl-4-yl)methyl)oxy)phenyl)propanoate and methyl (3S)-3-cyclopropyl-3-(3-(((2-(((2S,6S)-2,6-dimethyl-1-piperidinyl) methyl)-2'-fluoro-5'-(methyloxy)-1,1'-biphenyl-4-yl)methyl)oxy)phenyl)propanoate; or methyl (3R)-3-cyclopropyl-3-(3-(((2-(((2R,6S)-2,6-dimethyl-1-piperidinyl)methyl)-2'-fluoro-5'-(methyloxy)-1,1'-biphenyl-4-yl)methyl)oxy)phenyl)propanoate or methyl (3R)-3-cyclopropyl-3-(3-(((2-(((2R,6R)-2,6-dimethyl-1-piperidinyl)methyl)-2'-fluoro-5'-(methyloxy)-1,1'-biphenyl-4-yl)methyl)oxy)phenyl)propanoate and methyl (3R)-3-cyclopropyl-3-(3-(((2-(((2S,6S)-2,6-dimethyl-1-piperidinyl) methyl)-2'-fluoro-5'-(methyloxy)-1,1'-biphenyl-4-yl) methyl)oxy)phenyl)propanoate (66.70A). The methyl ester 66.70A was obtained from 66.69E using the same procedure described above with respect to 66.69.

(3S)-3-Cyclopropyl-3-(3-(((2-(((2R,6S)-2,6-dimethyl-1-piperidinyl)methyl)-2'-fluoro-5'-(methyloxy)-1,1'-biphenyl-4-yl)methyl)oxy)phenyl)propanoic acid or (3S)-3-cyclopropyl-3-(3-(((2-(((2R,6R)-2,6-dimethyl-1-piperidinyl)methyl)-2'-fluoro-5'-(methyloxy)-1,1'-biphenyl-4-yl)methyl)oxy)phenyl)propanoic acid and (3S)-3-cyclopropyl-3-(3-(((2-(((2S,6S)-2,6-dimethyl-1-piperidinyl)methyl)-2'-fluoro-5'-(methyloxy)-1,1'-biphenyl-4-yl)methyl)oxy)phenyl)propanoic acid; or (3R)-3-cyclopropyl-3-(3-(((2-(((2R,6S)-2,6-dimethyl-1-piperidinyl)methyl)-2'-fluoro-5'-(methyloxy)-1,1'-biphenyl-4-yl)methyl)oxy)phenyl)propanoic acid or (3R)-3-cyclopropyl-3-(3-(((2-(((2R,6R)-2,6-dimethyl-1-piperidinyl)methyl)-2'-fluoro-5'-(methyloxy)-1,1'-biphenyl-4-yl)methyl)oxy)phenyl)propanoic acid and (3R)-3-cyclopropyl-3-(3-(((2-(((2S,6S)-2,6-dimethyl-1-piperidinyl)methyl)-2'-fluoro-5'-(methyloxy)-1,1'-biphenyl-4-yl)methyl)oxy)phenyl)propanoic acid (66.70). Example 66.70 was prepared from 66.70A using a procedure similar to that used to prepare 66.65. After removing solvent, 3.6 mg of 66.70 (TFA salt) was obtained. MS ESI (neg.) m/e: 544 (M−H)$^+$. $^1$H NMR (400 MHz, CDCl$_3$) δ ppm 9.50 (m, 1H), 7.73-7.77 (m, 1H), 7.57-7.59 (m, 1H), 7.36-7.39 (m, 1H), 7.13-7.24 (m, 2H), 6.88-6.90 (m, 3H), 6.78-6.88 (m, 2H), 5.22 (s, 2H), 4.30-4.60 (m, 1H), 4.13-4.14 (m, 1H), 3.97 (m, 1H), 3.67 (m, 1H), 2.66-2.85 (m, 3H), 2.33 (m, 1H), 1.72 (m, 2H), 1.55 (m, 2H), 1.25-1.33 (m, 6H), 1.01-1.13 (m, 2H), 0.77-0.86 (m, 1H), 0.60 (m, 1H), 0.45 (m, 1H), 0.29 (m, 1H), 0.18 (m, 1H).

Example 66.71

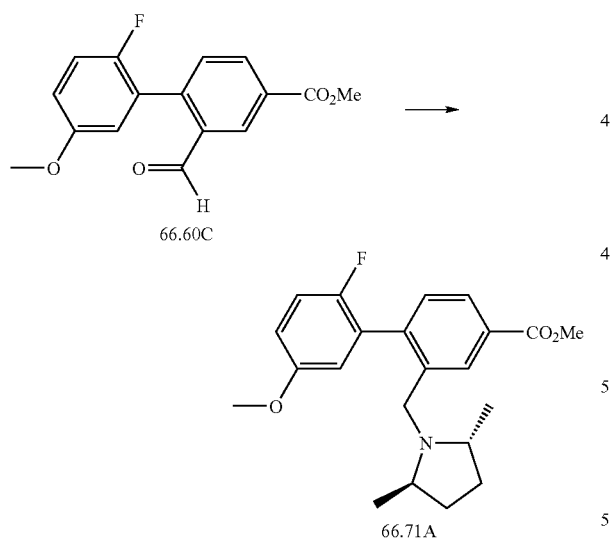

Methyl 2-(((2R,5R)-2,5-dimethyl-1-pyrrolidinyl)methyl)-2'-fluoro-5'-(methyloxy)-1,1'-biphenyl-4-carboxylate (66.71A). Sodium cyanoborohydride (0.071 g, 1.1 mmol) was added to a solution of 66.60C (0.180 g, 0.62 mmol) and (2R,5R)-2,5-dimethylpyrrolidine (available from Aldrich) (0.073 g, 0.74 mmol) in MeOH (3 mL). The reaction was stirred at 110° C. for 30 minutes and then was diluted with EtOAc (100 mL). The mixture was washed with an aqueous Na$_2$CO$_3$ solution and brine, and dried over anhydrous sodium sulfate. After filtration, solvent was removed, and the residue was purified by flash chromatography (silica gel, 1:6 EtOAc/hexane) and gave 66.71A (32 mg).

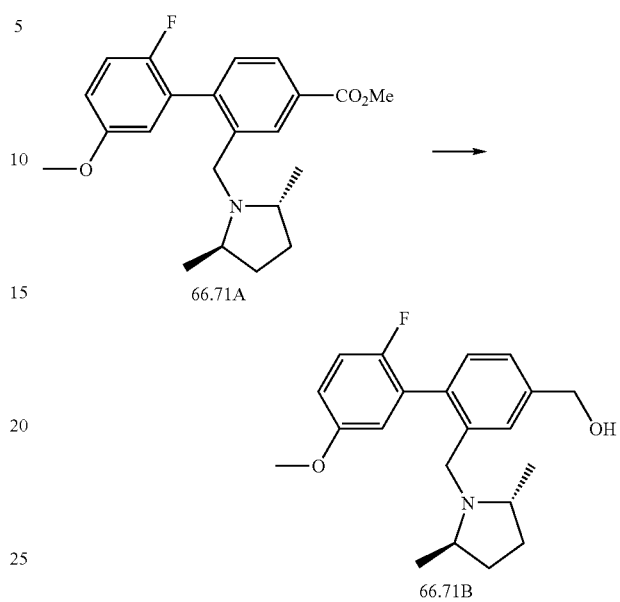

(2-(((2R,5R)-2,5-Dimethyl-1-pyrrolidinyl)methyl)-2'-fluoro-5'-(methyloxy)-1,1'-biphenyl-4-yl)methanol (66.71B). LAH (1.0 M solution in THF) (0.086 mL, 0.086 mmol) was added slowly to a solution of 66.71A (0.032 g, 0.086 mmol) in THF (1.5 mL) and the mixture was stirred at room temperature for 33 minutes. The mixture was poured into brine (2 mL) and extracted with EtOAc (3×30 mL). The combined organic phase was dried over anhydrous sodium sulfate and filtered. After removing solvent, 66.71B (29 mg) was obtained.

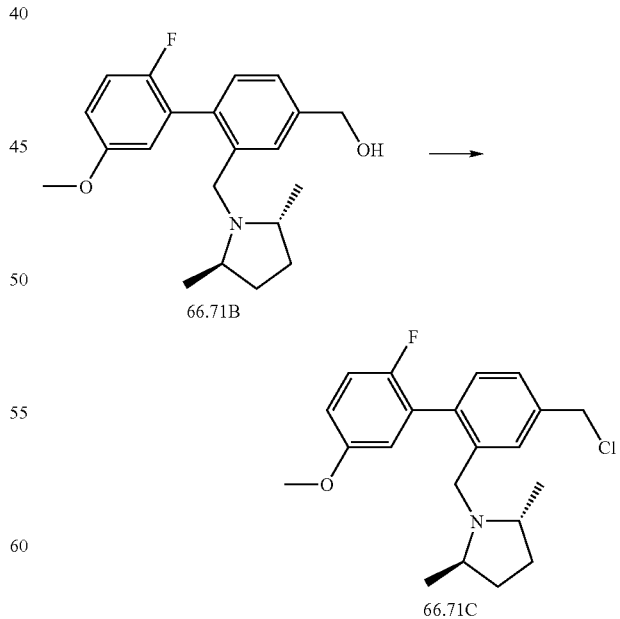

(2R,5R)-1-((4-(Chloromethyl)-2'-fluoro-5'-(methyloxy)-1,1'-biphenyl-2-yl)methyl)-2,5-dimethylpyrrolidine (66.71C). Thionyl chloride (0.25 g, 2.1 mmol) was added to a solution of 66.71B (0.029 g, 0.084 mmol) in DCM (0.7 mL) and the mixture was stirred at room temperature for 1 hour. After removing solvent, 66.71C (28 mg) was obtained.

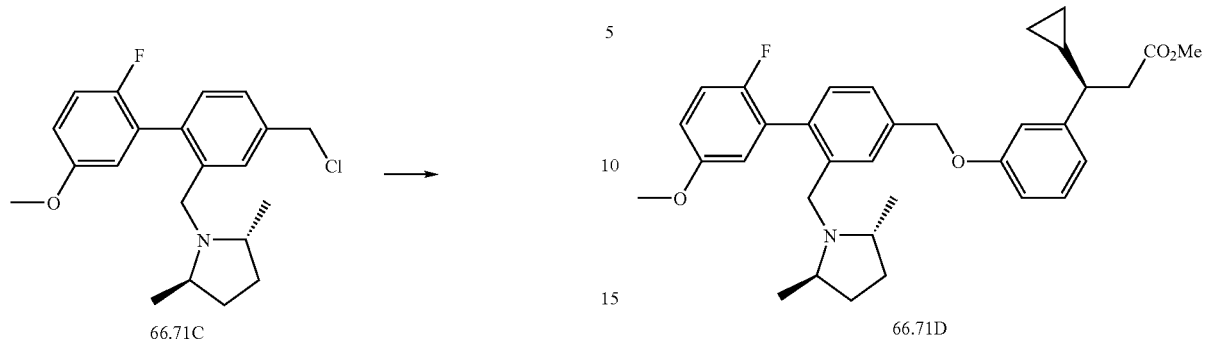

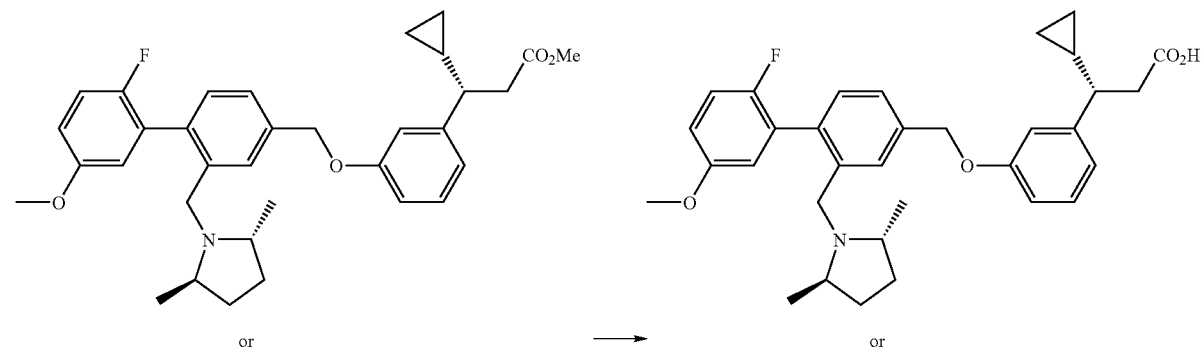

Methyl (3S)-3-cyclopropyl-3-(3-(((2-(((2R,5R)-2,5-dimethyl-1-pyrrolidinyl)methyl)-2'-fluoro-5'-(methyloxy)-1,1'-biphenyl-4-yl)methyl)oxy)phenyl)propanoate or methyl (3R)-3-cyclopropyl-3-(3-(((2-(((2R,5R)-2,5-dimethyl-1-pyrrolidinyl)methyl)-2'-fluoro-5'-(methyloxy)-1,1'-biphenyl-4-yl)methyl)oxy)phenyl)propanoate (66.71D). The title compound was prepared from 66.71C and 66.6X using a procedure similar to that described for 66.62F.

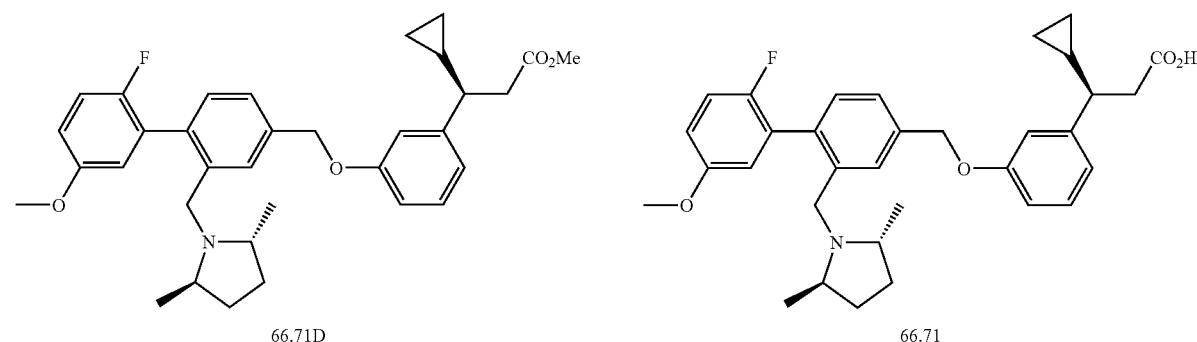

(3S)-3-Cyclopropyl-3-(3-(((2-(((2R,5R)-2,5-dimethyl-1-pyrrolidinyl)methyl)-2'-fluoro-5'-(methyloxy)-1,1'-biphenyl-4-yl)methyl)oxy)phenyl)propanoic acid or (3R)-3-cyclopropyl-3-(3-(((2-(((2R,5R)-2,5-dimethyl-1-pyrrolidinyl)methyl)-2'-fluoro-5'-(methyloxy)-1,1'-biphenyl-4-yl)methyl)oxy)phenyl)propanoic acid (66.71). Example 66.71 was prepared from 66.71D using a procedure analogous to that used to prepare 66.65. After removing solvent, 15 mg of 66.71 (TFA salt) was obtained. MS ESI (neg.) m/e: 530 (M–H)+. 1H NMR (400 MHz, DMSO-d6) δ ppm 9.55 (m 1H), 7.87 (m, 1H), 7.62-7.64 (m, 1H), 7.41-7.43 (m, 1H), 7.31 (m, 1H), 7.22 (m, 1H), 7.08 (m, 1H), 6.93 (m, 2H), 6.87 (m, 2H), 5.19 (s, 2H), 4.10-4.40 (m, 1H), 3.78 (s, 3H), 3.60-3.80 (m, 1H), 2.65 (m, 1H), 2.27 (m, 1H), 2.08 (m, 1H), 1.56 (m, 2H), 1.26 (m, 1H), 1.14 (m, 1H), 0.85-1.05 (m, 3H), 0.85 (m, 1H), 0.49 (m, 1H), 0.20-0.30 (m, 2H), 0.11 (m, 1H).

(3S)-3-(3-(((2-(1-Azepanylmethyl)-2'-fluoro-5'-(methyloxy)-1,1'-biphenyl-4-yl)methyl)oxy)phenyl)-3-cyclopropylpropanoic acid or (3R)-3-(3-(((2-(1-azepanylmethyl)-2'-fluoro-5'-(methyloxy)-1,1'-biphenyl-4-yl)methyl)oxy)phenyl)-3-cyclopropylpropanoic acid (66.73). The title compound was synthesized using a procedure analogous to that described in 66.64 starting using azepane (commercially available from Aldrich) in place of piperidine. After removing solvent, 66.73 (26 mg) was obtained as the TFA salt. MS ESI (neg.) m/e: 530 (M–H)+. 1H NMR (400 MHz, DMSO-d6) δ ppm 9.37 (m, 1H), 7.91 (m, 1H), 7.63-7.65 (m, 1H), 7.41-7.43 (m, 1H), 7.22-7.33 (m, 1H), 7.06-7.10 (m, 1H), 6.88-6.98 (m, 4H), 5.18 (s, 2H), 4.05-4.20 (m, 1H), 3.79 (s, 3H), 2.90-3.17 (m, 4H), 2.67 (m, 2H), 2.30 (m, 1H), 1.49 (m, 8H), 1.00 (m, 1H), 0.52 (m, 1H), 0.26 (m, 2H), 0.11 (m, 1H).

Example 66.74

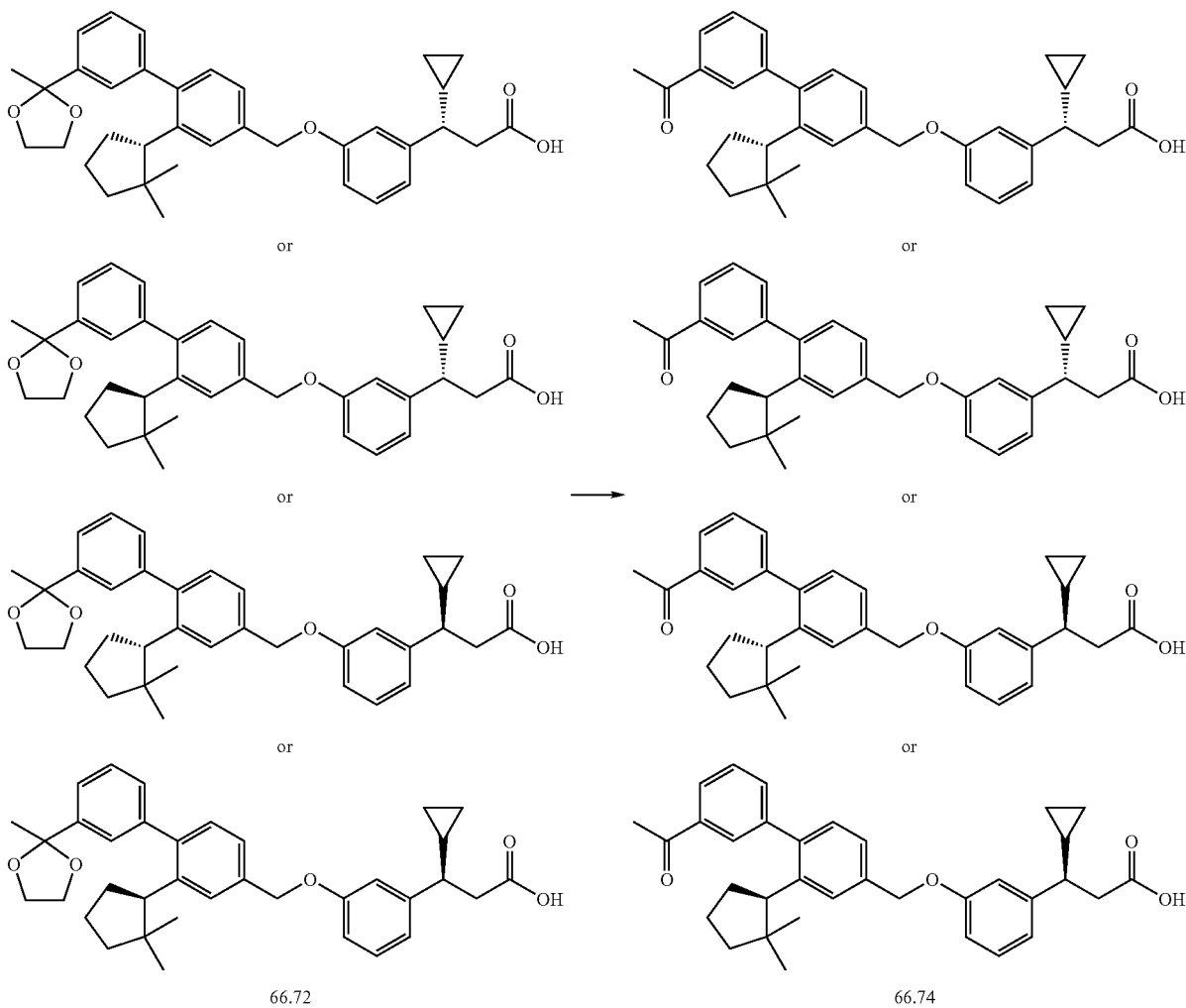

66.72

66.74

(S)-3-(3-((S)-3-((S)-2,2-Dimethylcyclopentyl)-4-(3-(2-methyl-1,3-dioxolan-2-yl)phenyl)benzyloxy)phenyl)-3-cyclopropylpropanoic acid or stereoisomer thereof (66.72). This compound was prepared as the same method described for 66.6 using 66.6X and 3-(2-methyl-1,3-dioxolan-2-yl)phenylboronic acid as the Suzuki coupling reagent to form the biphenyl reagent. MS ESI (neg.) m/e: 553.3 (M–H)+.

(S)-3-(3-((S)-3-((S)-2,2-Dimethylcyclopentyl)-4-(3-acetylphenyl)benzyloxy)phenyl)-3-cyclopropylpropanoic acid or stereoisomer thereof (66.74). To a flask with 66.72 (39 mg, 70 μmol) was added PPTS (5.3 mg, 21 μmol), 2 mL acetone, 0.1 mL water. The reaction was heated to reflux. After about 3 hours, the reaction had a little starting material left and was stored in refrigerator for 48 hours. A little more PPTS was added, and the reaction was heated for two more hours. The reaction was then concentrated, diluted with EtOAc and washed with NaHCO₃ and brine. Silica gel chromatography afforded 28 mg of 66.74 (78%). MS ESI (neg.) m/e: 509.0 (M−H)⁺.

(3S)-3-Cyclopropyl-3-(3-(((2'-fluoro-5'-(methyloxy)-2-(((2S)-2-methyl-1-piperidinyl)methyl)-1,1'-biphenyl-4-yl)methyl)oxy)phenyl)propanoic acid or (3R)-3-cyclopropyl-3-(3-(((2'-fluoro-5'-(methyloxy)-2-(((2S)-2-methyl-1-piperidinyl)methyl)-1,1'-biphenyl-4-yl)methyl)oxy)phenyl)propanoic acid (66.75). The title compound was synthesized using a procedure analogous to that described in 66.64 starting using (S)-2-methylpiperidine (commercially available from Aldrich) in place of piperidine. After removing solvent, 66.75 (5 mg) was obtained as the TFA salt. MS ESI (neg.) m/e: 530 (M−H)⁺. ¹H NMR (400 MHz, CDCl₃) δ ppm 10.60 (m, 1H), 7.74 (m, 1H), 7.57 (d, 1H), 7.34 (m, 1H), 7.10-7.17 (m, 2H), 6.85-7.00 (m, 3H), 6.60-6.80 (m, 2H), 5.23 (m, 2H), 4.70 (m, 1H), 4.10-3.20 (m, 1H), 3.81 (m, 3H), 3.05 (m, 1H), 2.60-2.90 (m, 3H), 2.35 (m, 1H), 1.90-2.06 (m, 1H), 1.65-1.80 (m, 1H), 1.40-1.55 (1H), 1.27 (m, 3H), 0.90-1.20 (m, 2H), 0.60 (m, 1H), 0.47 (m, 1H), 0.30 (m, 1H), 0.19 (m, 1H).

Example 66.76

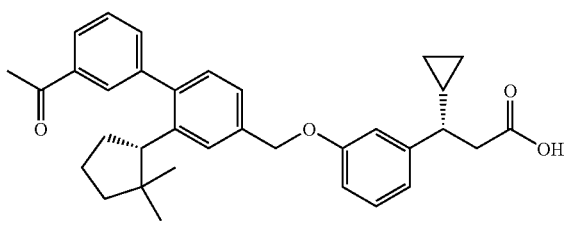

or

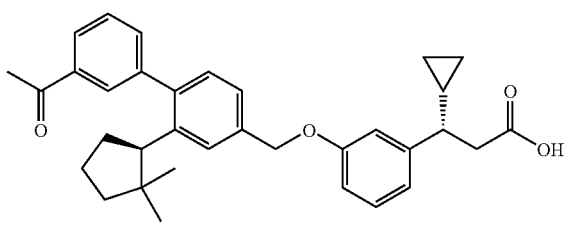

or

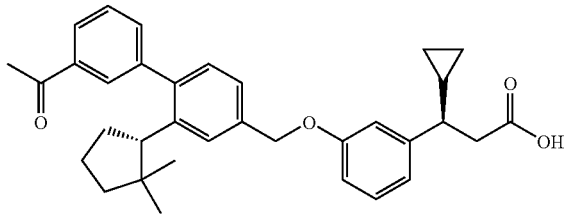

or

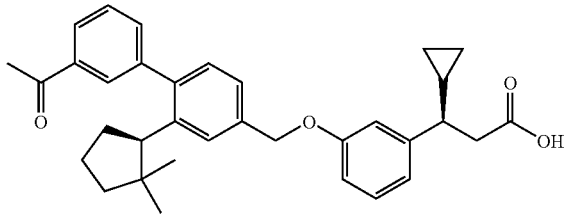

66.74

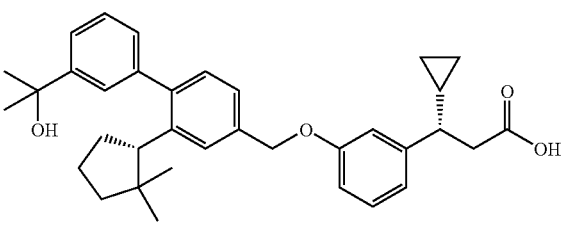

or

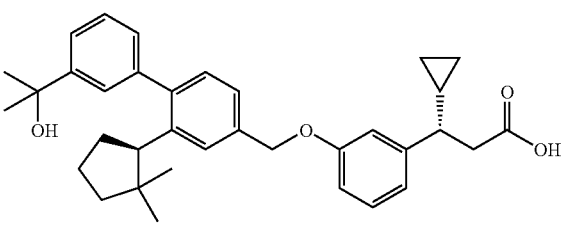

or

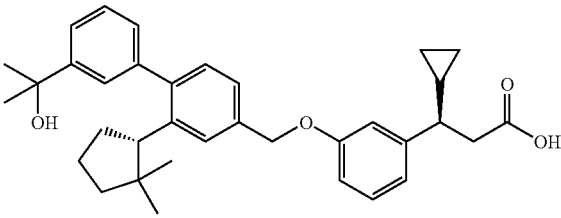

or

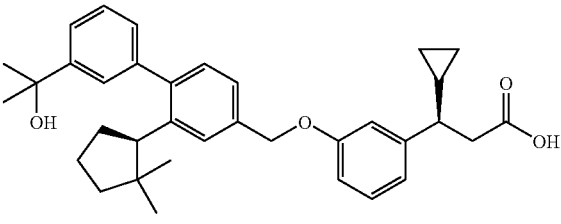

66.76

(S)-3-(3-((S)-3-((S)-2,2-dimethylcyclopentyl)-4-(3-(2-hydroxypropan-2-yl)phenyl)benzyloxy)phenyl)-3-cyclopropylpropanoic acid or stereoisomer thereof (66.76). Example 66.74 (26.5 mg, 52 µmol) was azeotroped with toluene. Anhydrous THF was added, and the reaction was cooled in an ice-bath. Methylmagnesium bromide (3.0 M in diethyl ether) (52 µL, 156 µmol) was added, and the reaction was stirred at room temperature for 1.5 hours and then quenched with NH₄Cl. Purification with silica gel chromatography afforded 14 mg of product 66.76 (51%). MS ESI (neg.) m/e: 525.1 (M−H)⁺.

Example 66.77

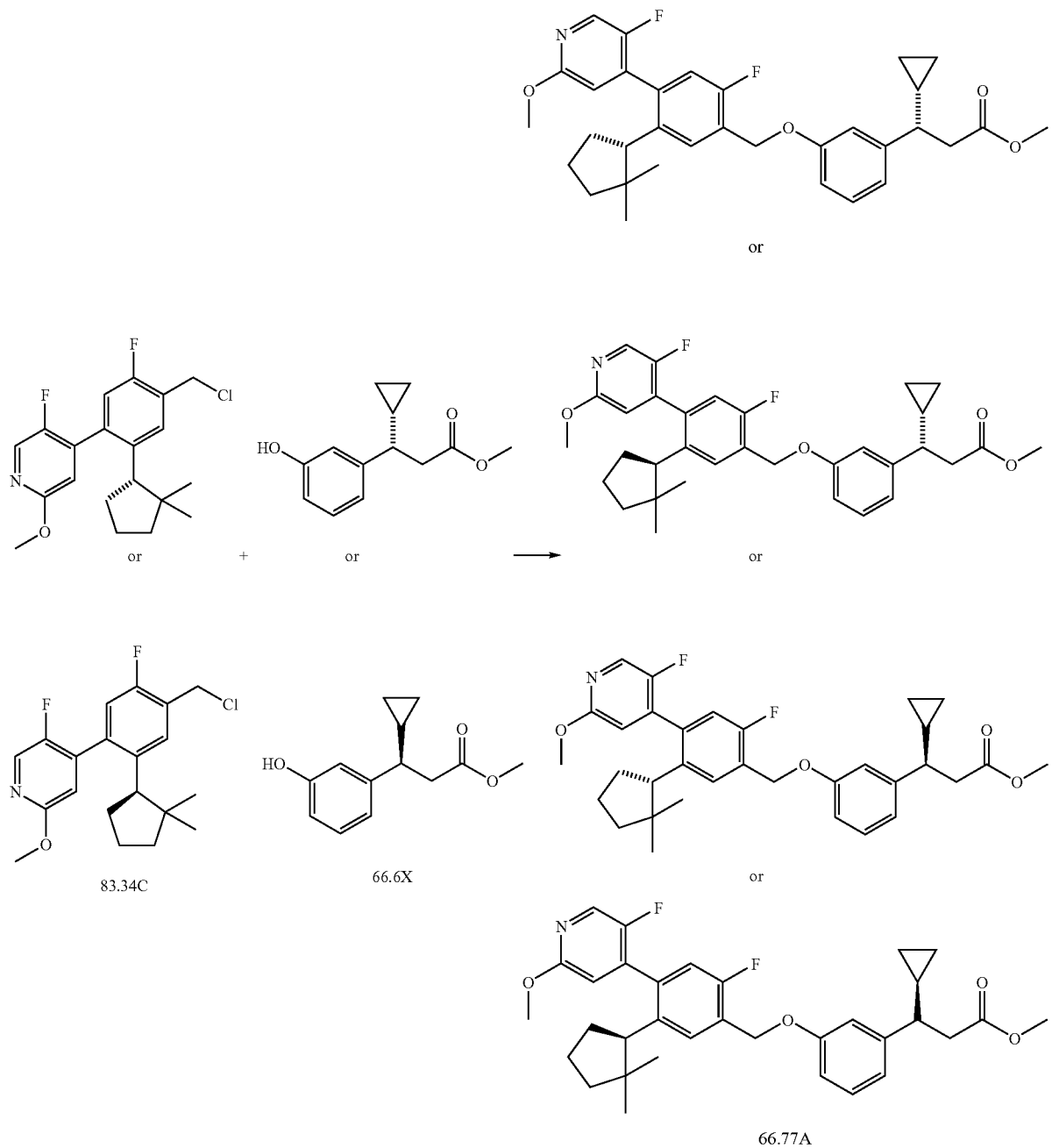

Methyl (3S)-3-cyclopropyl-3-(3-(((5-((1S)-2,2-dimethyl-cyclopentyl)-2-fluoro-4-(5-fluoro-2-(methyloxy)-4-pyridinyl)phenyl)methyl)oxy)phenyl)propanoate or methyl (3S)-3-cyclopropyl-3-(3-(((5-((1R)-2,2-dimethylcyclopentyl)-2-fluoro-4-(5-fluoro-2-(methyloxy)-4-pyridinyl)phenyl)methyl)oxy)phenyl)propanoate or methyl (3R)-3-cyclopropyl-3-(3-(((5-((1S)-2,2-dimethylcyclopentyl)-2-fluoro-4-(5-fluoro-2-(methyloxy)-4-pyridinyl)phenyl)methyl)oxy)phenyl)propanoate or methyl (3R)-3-cyclopropyl-3-(3-(((5-((1R)-2,2-dimethylcyclopentyl)-2-fluoro-4-(5-fluoro-2-(methyloxy)-4-pyridinyl)phenyl)methyl)oxy)phenyl)propanoate (66.77A). To a vial containing 66.6X (0.0251 g, 0.114 mmol) in 1.50 mL dry DMF was added cesium carbonate (0.0447 g, 0.137 mmol). The mixture was stirred at room temperature for 10 minutes, and then 83.34C (0.0447 g, 0.122 mmol) was added. After 22 hours, the reaction was diluted with water and then the mixture was extracted five times with EtOAc. The combined organic layers were then washed one time with brine and dried over anhydrous magnesium sulfate. The solid was filtered off, and the solvent was concentrated. The residue was purified by silica gel flash chromatography (0-30% EtOAc/hexane) to afford 66.77 A (53.6 mg, 86% yield). MS ESI (pos.) m/e: 550.3 (M+H)$^+$.

505

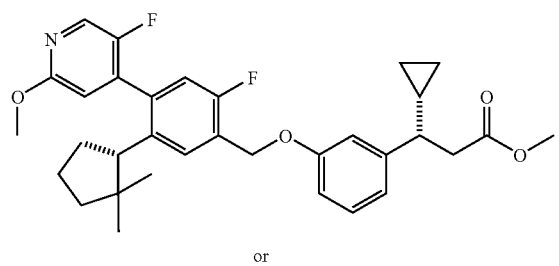

or

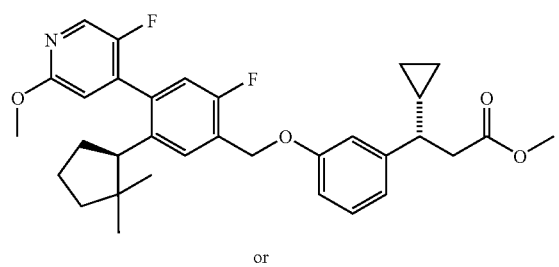

or

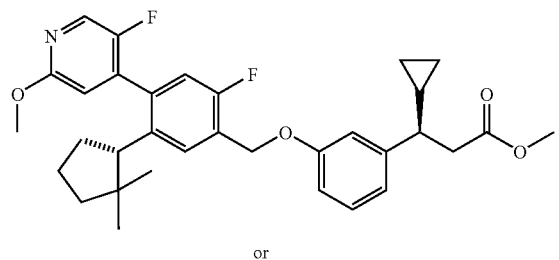

or

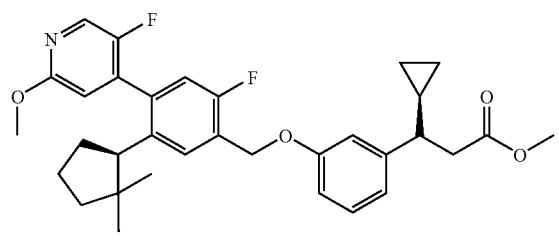

66.77A (3S)-3-Cyclopropyl-3-(3-(((5-((1S)-2,2-dimethylcyclopentyl)-2-fluoro-4-(5-fluoro-2-(methyloxy)-4-pyridinyl)phenyl)methyl)oxy)phenyl)propanoic acid or (3S)-3-cyclopropyl-3-(3-(((5-((1R)-2,2-dimethylcyclopentyl)-2-fluoro-4-(5-fluoro-2-(methyloxy)-4-pyridinyl)phenyl)methyl)oxy)phenyl)propanoic acid or (3R)-3-cyclopropyl-3-(3-(((5-((1S)-2,2-dimethylcyclopentyl)-2-fluoro-4-(5-fluoro-2-(methyloxy)-4-pyridinyl)phenyl)methyl)oxy)phenyl)propanoic acid or (3R)-3-cyclopropyl-3-(3-(((5-((1R)-2,2-dimethylcyclopentyl)-2-fluoro-4-(5-fluoro-2-(methyloxy)-4-pyridinyl)phenyl)methyl)oxy)phenyl)propanoic acid (66.90). A pre-mixed solution of 2 M NaOH (0.5 mL, 1.00 mmol), MeOH (1 mL), and THF (1 mL) was added to a vial containing 66.77A (0.0536 g, 0.0975 mmol). The resulting

506

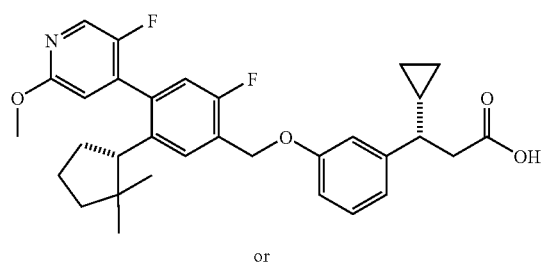

or

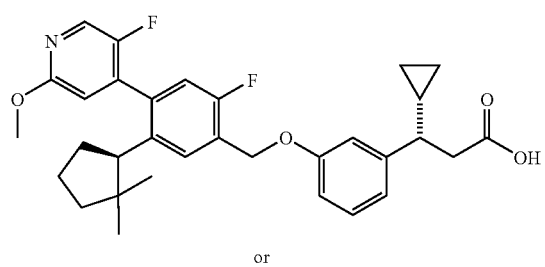

or

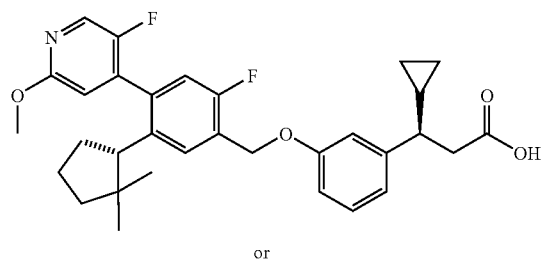

or

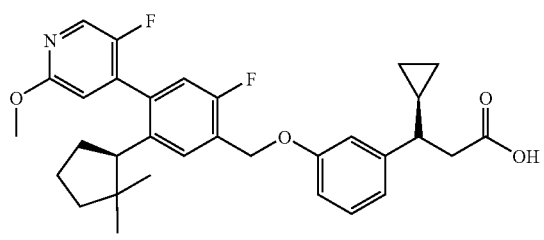

66.77 mixture was stirred at room temperature and monitored with TLC and LC-MS. After 24 hours, the mixture was diluted with water and acidified with 1M aqueous HCl solution and then extracted five times with EtOAc. The organic phase was dried over anhydrous magnesium sulfate, filtered, and concentrated. The residue was purified by silica gel flash chromatography (0-30% EtOAc/hexane) to afford 66.77 (41.2 mg, 79% yield). MS ESI (pos.) m/e: 536.2 (M+H)$^+$. MS ESI (neg.) m/e: 534.1 (M−H)$^+$.

Example 67

The following compounds were prepared from 43.6 and the appropriate halomethyl or hydroxymethyl compound according to the methods described herein. Each of the compounds in the following table were prepared using the same enantiomer of the phenol.
TABLE 7
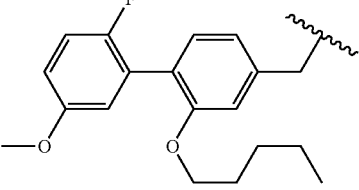
or
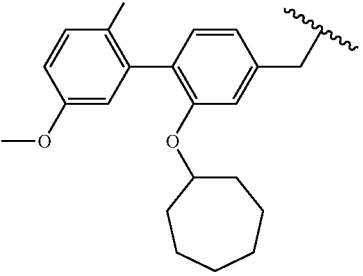
| Compound | TG |
|---|---|
| 67.1 | 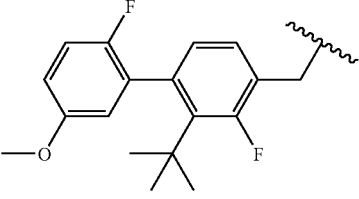 |
| 67.2 | 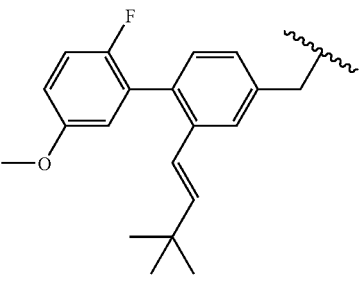 |
| 67.3 | 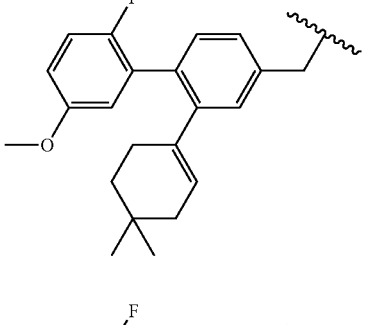 |
| 67.4 | 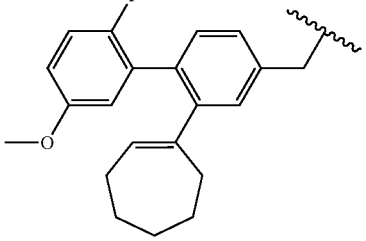 |
TABLE 7-continued
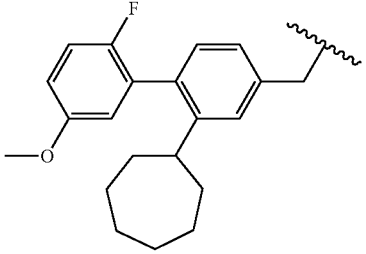
or
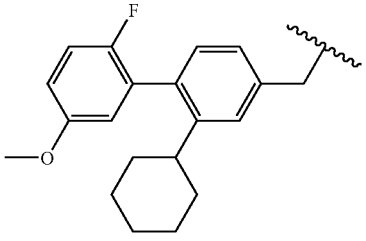
| Compound | TG |
|---|---|
| 67.5 | 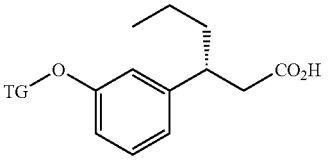 |
| 67.6 | 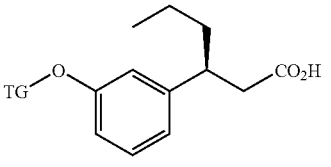 |
| 67.7 | 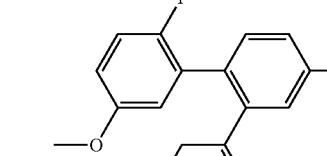 |
| 67.8 | 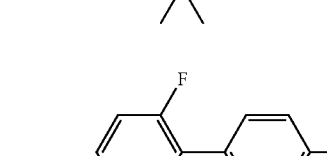 |

TABLE 7-continued

| Compound | TG |
|---|---|
| 67.9 | 2-fluoro-5-methoxy-2'-(trans-2-cyclopropylvinyl)biphenyl-4-ylmethyl |
| 67.10 | 2-fluoro-5-methoxy-2'-cyclopentylbiphenyl-4-ylmethyl |
| 67.11 | 2-fluoro-5-methoxy-2'-(2,2-dimethylcyclopentyl)biphenyl-4-ylmethyl |
| 67.12 | 3'-methoxy-2-(2,2-dimethylcyclopent-1-en-1-yl)biphenyl-4-ylmethyl |
| 67.13 | 3'-methoxy-2-butoxybiphenyl-4-ylmethyl |
| 67.14 | 2-fluoro-5-methoxy-2'-(tetrahydro-2H-pyran-2-yloxy)biphenyl-4-ylmethyl |
| 67.15 | 2-fluoro-5-methoxy-2'-pentyloxybiphenyl-4-ylmethyl |
| 67.16 | 2-fluoro-5-methoxy-2'-(3-methylbutoxy)biphenyl-4-ylmethyl |
| 67.17 | 2-fluoro-5-methoxy-2'-(cyclohexylmethoxy)biphenyl-4-ylmethyl |

(Structures depict TG-O-aryl-CH(propyl)-CH2-CO2H scaffolds with various TG substituents as shown in tables 67.9–67.17.)

TABLE 7-continued

| Compound | TG |
|---|---|
| 67.18 | 2'-tert-butyl-2-fluoro-biphenyl-4-ylmethyl group |
| 67.19 | 4-(6-methoxypyridin-3-yl)-3-tert-butyl-benzyl group |
| 67.20 | 2'-fluoro-5-methoxy-6-piperidin-1-yl-biphenyl-3-ylmethyl group |
| 67.21 | 2',5-difluoro-5'-methoxy-6-(5,5-dimethylcyclopent-1-enyl)-biphenyl-3-ylmethyl group |
| 67.22 | 4-(6-methoxypyridin-2-yl)-benzyl group |

TABLE 7-continued

| Compound | TG |
|---|---|
| 67.23 | 2'-(ethoxymethyl)-2-fluoro-5'-methoxy-biphenyl-4-ylmethyl group |
| 67.24 | 2'-[(S)-1-hydroxy-2,2-dimethyl-but-3-enyl]-2-fluoro-5'-methoxy-biphenyl-4-ylmethyl group (or R) |
| 67.25 | 2'-[(S)-1-hydroxy-2,2-dimethyl-but-3-enyl]-2-fluoro-5'-methoxy-biphenyl-4-ylmethyl group (or) |

TABLE 7-continued

| Compound | TG |
|---|---|
| 67.26 | (structure: 2'-fluoro-5'-methoxy-biphenyl with HO-CH(C(CH3)2-CH=CH2)- substituent) but not the same one as 67.24 |
| 67.27 | (structure: 2'-fluoro-5'-methoxy-biphenyl with MeO-CH(C(CH3)(Et))- substituent, or enantiomer) |

TABLE 7-continued

| Compound | TG |
|---|---|
| 67.28 | (structure: 2'-fluoro-5'-methoxy-biphenyl with -CH2-O-CH2-pyrrolidine substituent) |

(3R)-3-(3-(((2'-Fluoro-5'-(methyloxy)-2-(pentyloxy)-1,1'-biphenyl-4-yl)methyl)oxy)phenyl)hexanoic acid or (3S)-3-(3-(((2∝-fluoro-5'-(methyloxy)-2-(pentyloxy)-1,1'-biphenyl-4-yl)methyl)oxy)phenyl)hexanoic acid (67.1). MS ESI (neg.) m/e: 507.2 (M–H).

(3R)-3-(3-(((2-(Cycloheptyloxy)-2'-fluoro-5'-(methyloxy)-1,1'-biphenyl-4-yl)methyl)oxy)phenyl)hexanoic acid or (3S)-3-(3-(((2-(cycloheptyloxy)-2'-fluoro-5'-(methyloxy)-1,1'-biphenyl-4-yl)methyl)oxy)phenyl)hexanoic acid (67.2). $^1$H NMR (500 MHz, CDCl$_3$) δ ppm 7.30 (1H, d, J=7.6 Hz), 7.23 (1H, t, J=7.8 Hz), 7.00-7.06 (3H, m), 6.81-6.90 (5H, m), 5.07 (2H, s), 4.42 (1H, dt, J=7.8, 3.8 Hz), 3.80 (3H, s), 3.05-3.11 (1H, m), 2.63 (2H, dd, J=7.3, 5.6 Hz), 1.87-1.93 (2H, m), 1.67-1.75 (2H, m), 1.56-1.65 (4H, m), 1.49-1.53 (4H, m), 1.34-1.41 (2H, m), 1.15-1.24 (2H, m), 0.84-0.88 (3H, t, J=7.3 Hz).

(3R)-3-(3-(((2-(1,1-Dimethylethyl)-2',3-difluoro-5'-(methyloxy)-1,1'-biphenyl-4-yl)methyl)oxy)phenyl)hexanoic acid or (3S)-3-(3-(((2-(1,1-dimethylethyl)-2',3-difluoro-5'-(methyloxy)-1,1'-biphenyl-4-yl)methyl)oxy)phenyl)hexanoic acid (67.3). MS ESI (neg.) m/e: 991.5 (2M–H)$^+$, 495.2 (M–H)$^+$.

(3R)-3-(3-(((2-((1E)-3,3-Dimethyl-1-butenyl)-2'-fluoro-5'-(methyloxy)-1,1'-biphenyl-4-yl)methyl)oxy)phenyl)hexanoic acid or (3S)-3-(3-(((2-((1E)-3,3-dimethyl-1-butenyl)-2'-fluoro-5'-(methyloxy)-1,1'-biphenyl-4-yl)methyl)oxy)phenyl)hexanoic acid (67.4). MS ESI (neg.) m/e: 503.2 (M–H)$^+$.

(3R)-3-(3-(((2-(4,4-Dimethyl-1-cyclohexen-1-yl)-2'-fluoro-5'-(methyloxy)-1,1'-biphenyl-4-yl)methyl)oxy)phenyl)hexanoic acid or (3S)-3-(3-(((2-(4,4-dimethyl-1-cyclohexen-1-yl)-2'-fluoro-5'-(methyloxy)-1,1'-biphenyl-4-yl)methyl)oxy)phenyl)hexanoic acid (67.5). MS ESI (neg.) m/e: 529.3 (M–H)$^+$.

(3R)-3-(3-(((2-(1-Cyclohepten-1-yl)-2'-fluoro-5'-(methyloxy)-1,1'-biphenyl-4-yl)methyl)oxy)phenyl)hexanoic acid or (3S)-3-(3-(((2-(1-cyclohepten-1-yl)-2'-fluoro-5'-(methyloxy)-1,1'-biphenyl-4-yl)methyl)oxy)phenyl)hexanoic acid (67.6). MS ESI (neg.) m/e: 515.2 (M–H)⁺.

(3R)-3-(3-(((2-Cycloheptyl-2'-fluoro-5'-(methyloxy)-1,1'-biphenyl-4-yl)methyl)oxy)phenyl)hexanoic acid or (3S)-3-(3-(((2-cycloheptyl-2'-fluoro-5'-(methyloxy)-1,1'-biphenyl-4-yl)methyl)oxy)phenyl)hexanoic acid (67.7). MS ESI (neg.) m/e: 517.3 (M–H)⁺.

(3R)-3-(3-(((2-Cyclohexyl-2'-fluoro-5'-(methyloxy)-1,1'-biphenyl-4-yl)methyl)oxy)phenyl)hexanoic acid or (3S)-3-(3-(((2-cyclohexyl-2'-fluoro-5'-(methyloxy)-1,1'-biphenyl-4-yl)methyl)oxy)phenyl)hexanoic acid (67.8). MS ESI (neg.) m/e: 503.2 (M–H)⁺.

(3R)-3-(3-(((2-((E)-2-Cyclopropylethenyl)-2'-fluoro-5'-(methyloxy)-1,1'-biphenyl-4-yl)methyl)oxy)phenyl)hexanoic acid or (3S)-3-(3-(((2-((E)-cyclopropylethenyl)-2'-fluoro-5'-(methyloxy)-1,1'-biphenyl-4-yl)methyl)oxy)phenyl)hexanoic acid (67.9). MS ESI (neg.) m/e: 975.4 (2M–H)⁺, 487.2 (M–H)⁺.

(3R)-3-(3-(((2-Cyclopentyl-2'-fluoro-5'-(methyloxy)-1,1'-biphenyl-4-yl)methyl)oxy)p acid or (3S)-3-(3-(((2-cyclopentyl-2'-fluoro-5'-(methyloxy)-1,1'-biphenyl-4-yl)methyl)oxy)phenyl)hexanoic acid (67.10). MS ESI (neg.) m/e: 979.5 (2M–H)⁺, 489.2 (M–H)⁺.

(3R)-3-(3-(((2-(2,2-Dimethylcyclopentyl)-2'-fluoro-5'-(methyloxy)-1,1'-biphenyl-4-yl)methyl)oxy)phenyl)hexanoic acid or (3S)-3-(3-(((2-(2,2-dimethylcyclopentyl)-2'-fluoro-5'-(methyloxy)-1,1'-biphenyl-4-yl)methyl)oxy)phenyl)hexanoic acid (67.11). MS ESI (neg.) m/e: 497.4 (M–H).

(3R)-3-(3-(((2-(5,5-Dimethyl-1-cyclopenten-1-yl)-3'-(methyloxy)-1,1'-biphenyl-4-yl)methyl)oxy)phenyl)hexanoic acid or (3S)-3-(3-(((2-(5,5-dimethyl-1-cyclopenten-1-yl)-3'-(methyloxy)-1,1'-biphenyl-4-yl)methyl)oxy)phenyl)hexanoic acid (67.12). MS ESI (neg.) m/e: 497.4 (M–H).

(3R)-3-(3-(((2-(Butyloxy)-3'-(methyloxy)-1,1'-biphenyl-4-yl)methyl)oxy)phenyl)hexanoic acid or (3S)-3-(3-(((2-(butyloxy)-3'-(methyloxy)-1,1'-biphenyl-4-yl)methyl)oxy)phenyl)hexanoic acid (67.13). ¹H NMR (400 MHz, CDCl₃) δ ppm 7.35 (d, 1H), 7.31 (t, 1H), 7.23 (t, 1H), 7.13 (m, 2H), 7.07 (m, 2H), 6.87 (m, 3H), 6.81 (bd, 1H), 5.06 (s, 2H), 3.99 (t, 2H), 3.84 (s, 3H), 3.08 (m, 1H), 2.63 (m, 2H), 1.71 (m, 2H), 1.60 (m, 2H), 1.43 (m, 2H), 1.18 (m, 2H), 0.92 (t, 3H), 0.85 (t, 3H).

Example 67.14

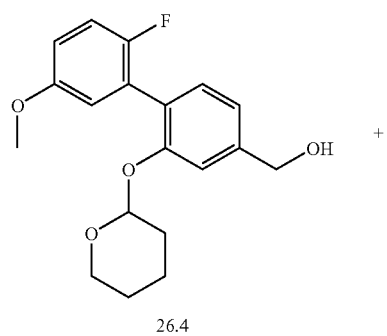

26.4

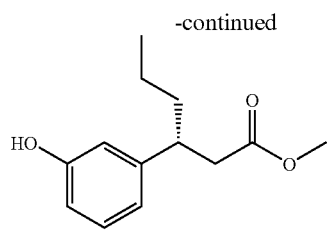

43.6 or

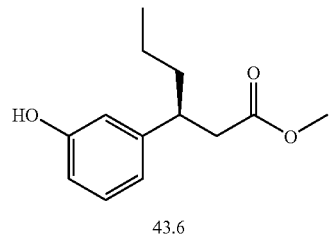

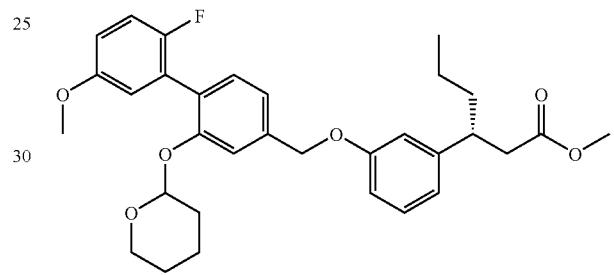

or

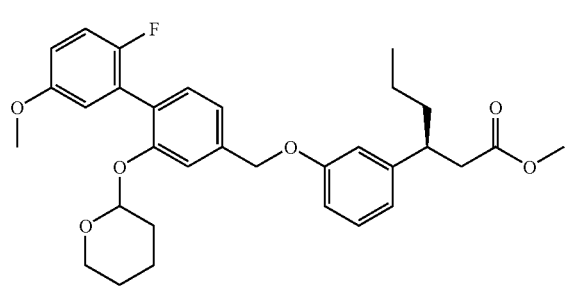

67.14A

Methyl (3R)-3-(3-(((2'-fluoro-5'-(methyloxy)-2-(tetrahydro-2H-pyran-2-yloxy)-1,1'-biphenyl-4-yl)methyl)oxy)phenyl)hexanoate or methyl (3S)-3-(3-(((2'-fluoro-5'-(methyloxy)-2-(tetrahydro-2H-pyran-2-yloxy)-1,1'-biphenyl-4-yl)methyl)oxy)phenyl)hexanoate (67.14A). To flask containing 43.6 (300.0 mg, 1350 µmol), 26.4 (583.2 mg, 1755 µmol), and polymer supported triphenylphosphine (674.8 mg, 2024 µmol) in DCM (6 mL) was added diethyl azodicarboxylate (318.8 µL, 2024 µmol) at 0° C. The mixture was then allowed to warm to room temperature and stirred for 1 hour. The reaction was concentrated and then purified by silica chromatography (0 to 20% EtOAc/Hexanes) to provide 67.14A (311.7 mg, 43.04% yield).

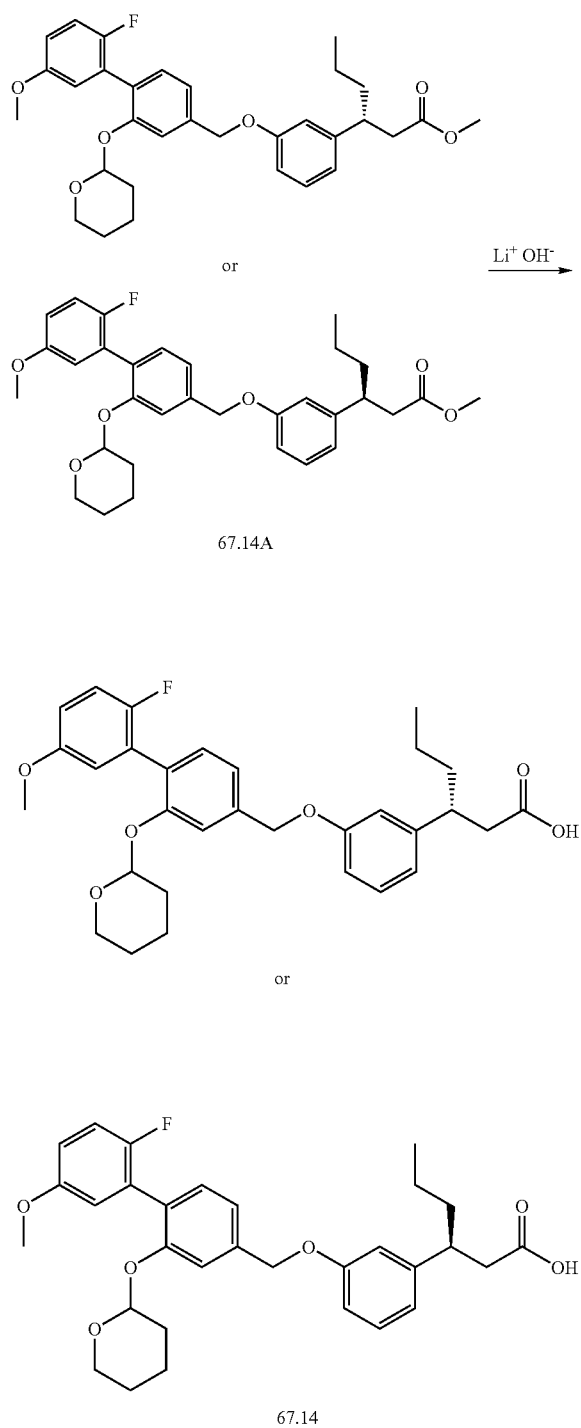

67.14A 67.14

(3R)-3-(3-(((2'-Fluoro-5'-(methyloxy)-2-(tetrahydro-2H-pyran-2-yloxy)-1,1'-biphenyl-4-yl)methyl)oxy)phenyl)hexanoic acid or (3S)-3-(3-(((2'-fluoro-5'-(methyloxy)-2-(tetrahydro-2H-pyran-2-yloxy)-1,1'-biphenyl-4-yl)methyl)oxy)phenyl)hexanoic acid (67.14). To a solution of 67.14A (15.0 mg, 28 µmol) in THF/MeOH (2/1) (1.5 mL) was added LiOH (0.500 mL, 500 µmol). The resulting mixture was stirred overnight at 23° C., quenched with excess 1N HCl, and extracted with EtOAc. The combined organic layers were dried over Na$_2$SO$_4$ and concentrated. The residue was purified by chromatography (0 to 40% EtOAc/hexanes) to afford a 67.14 (9.6 mg, 66% yield): MS ESI (neg.) m/e: 521.2 (M–H).

Example 67.15

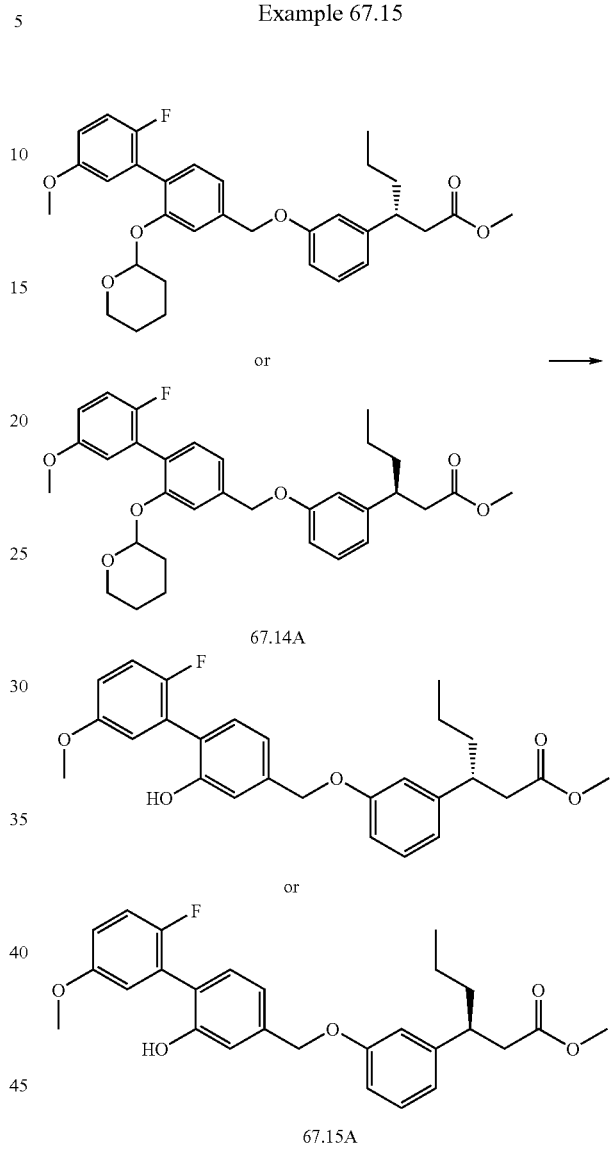

67.14A 67.15A

Methyl (3R)-3-(3-(((2'-fluoro-2-hydroxy-5'-(methyloxy)-1,1'-biphenyl-4-yl)methyl)oxy)phenyl)hexanoate or methyl (3S)-3-(3-(((2'-fluoro-2-hydroxy-5'-(methyloxy)-1,1'-biphenyl-4-yl)methyl)oxy)phenyl)hexanoate (67.15A). To a solution of 67.14A (295 mg, 550 µmol) in MeOH (2.5 mL) was added PPTS (13.8 mg, 55.0 µmol) at room temperature. The mixture was heated overnight, cooled to room temperature, diluted with EtOAc, washed with water and brine, dried (MgSO$_4$), and concentrated. The crude product was purified by silica gel flash chromatography (0-25% EtOAc/hexane) to afford 67.15A (132.5 mg, 53.3% yield) as a colorless oil.

(3R)-3-(3-(((2'-Fluoro-2-(hexyloxy)-5'-(methyloxy)-1,1'-biphenyl-4-yl)methyl)oxy)phenyl)hexanoic acid or (3S)-3-(3-(((2'-fluoro-2-(hexyloxy)-5'-(methyloxy)-1,1'-biphenyl-4-yl)methyl)oxy)phenyl)hexanoic acid (67.15). Example 67.15 was synthesized from 67.15A by a method analogous to that used to prepare compound 27 using 1-bromohexane which is available from Aldrich. MS ESI (neg.) m/e: 521.2 (M–H).

(3R)-3-(3-(((2'-Fluoro-5'-(methyloxy)-2-((4-methylpentyl)oxy)-1,1'-biphenyl-4-yl)methyl)oxy)phenyl)hexanoic acid or (3S)-3-(3-(((2'-fluoro-5'-(methyloxy)-2-((4-methylpentyl)oxy)-1,1'-biphenyl-4-yl)methyl)oxy)phenyl)hexanoic acid (67.16). Example 67.16 was synthesized from 67.15A by a method analogous to that used to prepare compound 27 using 1-bromo-4-methylpentane which is commercially available from Aldrich. $^1$H NMR (500 MHz, CDCl$_3$) δ ppm 7.30 (1H, d, J=8.1 Hz), 7.24 (1H, t, J=7.8 Hz), 6.97-7.10 (3H, m), 6.79-6.92 (5H, m), 5.07 (2H, s), 3.97 (2H, t, J=6.5 Hz), 3.80 (3H, s), 3.05-3.12 (1H, m), 2.58-2.69 (2H, m), 1.47-1.71 (5H, m), 1.12-1.33 (4H, m), 0.76-0.91 (9H, m).

(3R)-3-(3-(((2-((Cyclohexylmethyl)oxy)-2'-fluoro-5'-(methyloxy)-1,1'-biphenyl-4-yl)methyl)oxy)phenyl)hexanoic acid or (3S)-3-(3-(((2-((cyclohexylmethyl)oxy)-2'-fluoro-5'-(methyloxy)-1,1'-biphenyl-4-yl)methyl)oxy)phenyl)hexanoic acid (67.17). Example 67.17 was synthesized from 67.15A by a method analogous to that used to prepare compound 27 using cyclohexylmethyl bromide which is commercially available from Alfa Aesar. $^1$H NMR (500 MHz, CDCl$_3$) δ ppm 7.31 (1H, d, J=7.2 Hz), 7.21-7.28 (1H, m), 7.01-7.10 (3H, m), 6.81-6.92 (5H, m), 5.08 (2H, s), 3.82 (3H, s), 3.79 (2H, d, J=5.9 Hz), 3.06-3.14 (1H, m), 2.65 (2H, dd, J=7.4, 3.3 Hz), 1.55-1.78 (8H, m), 1.08-1.32 (5H, m), 0.93-1.05 (2H, m), 0.84-0.90 (3H, m).

Example 67.18

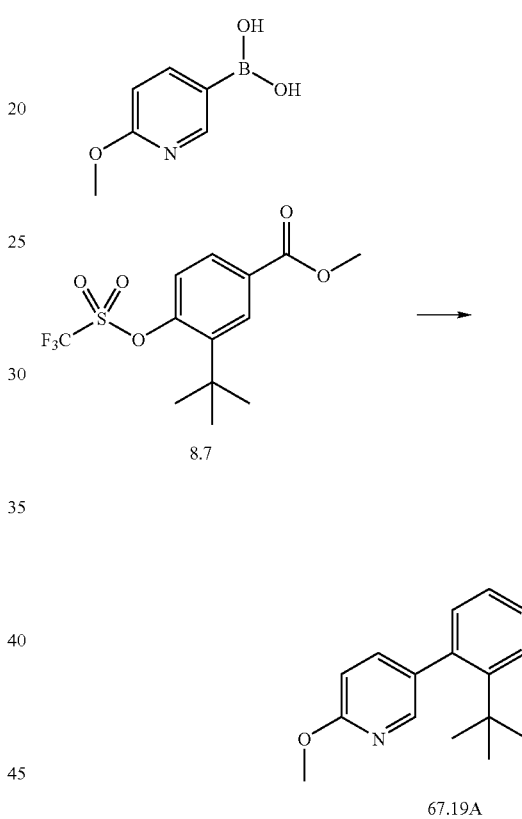

4-(Chloromethyl)-2-(1,1-dimethylethyl)-2'-fluoro-1,1'-biphenyl (67.18A). The formation of chloromethyl compound 67.18A was conducted in an analogous manner to Example 8.7-8.10, described herein using 2-fluorobenzeneboronic acid (commercially available from Aldrich) to yield 67.18A as a colorless oil (532.3 mg, 80% yield). $^1$H NMR (400 MHz, DMSO-d$_6$) δ ppm 7.63 (1H, d, J=1.6 Hz), 7.48 (1H, m), 7.35 (4H, m), 6.97 (1H, d, J=7.8 Hz), 4.83 (2H, s), 1.16 (9H, s).

(3R)-3-(3-(((2-(1,1-Dimethylethyl)-2'-fluoro-1,1'-biphenyl-4-yl)methyl)oxy)phenyl)hexanoic acid or (3S)-3-(3-(((2-(1,1-dimethylethyl)-2'-fluoro-1,1'-biphenyl-4-yl)methyl) oxy)phenyl)hexanoic acid (67.18). The alkylation and hydrolysis were conducted in an analogous manner to Example 66.6 (using 67.18A and 43.6 (derived from peak one from the chiral separation of 43.4 from the OD-column), described herein) to yield 67.18 (41.8 mg, 82% yield). $^1$H NMR (400 MHz, CDCl$_3$) δ ppm 7.64 (1H, d, J=1.6 Hz), 7.37 (2H, m), 7.29 (2H, m), 7.18 (2H, m), 7.09 (1H, m), 6.92 (3H, m), 5.10 (2H, s), 3.15 (1H, m), 2.65 (2H, ddd, J=17.6, 15.7, 7.4 Hz), 1.69 (2H, m), 1.29 (12H, m), 0.88 (3H, t, J=7.4 Hz). MS ESI (neg.) m/e: 447.1 (M–H)$^+$.

Example 67.19

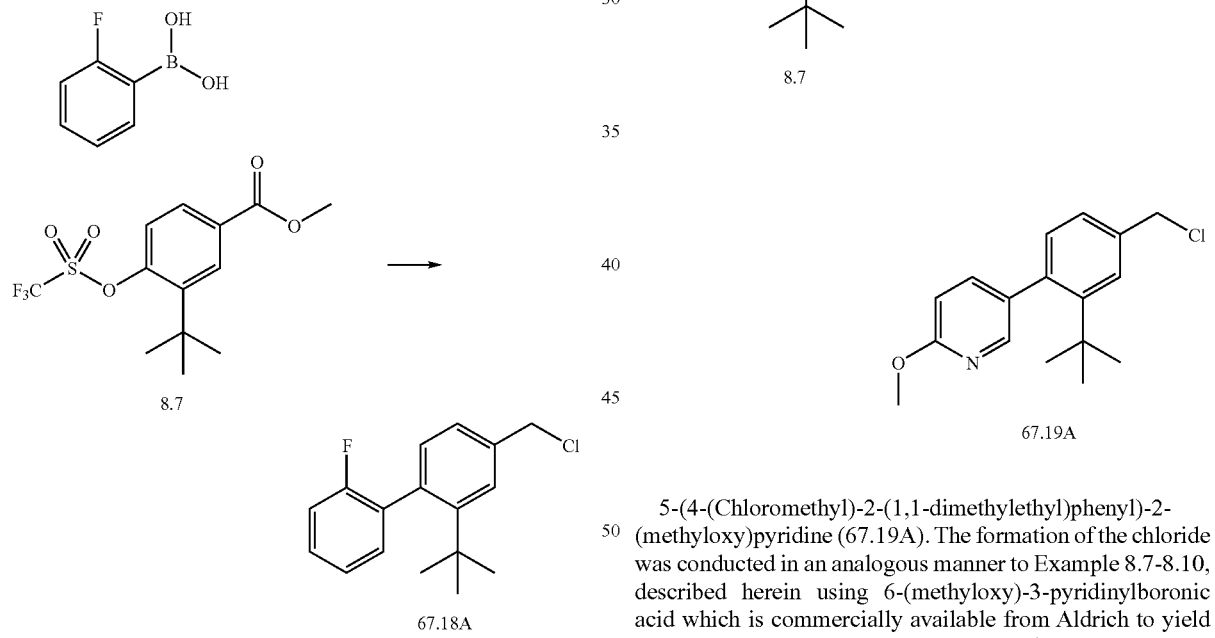

5-(4-(Chloromethyl)-2-(1,1-dimethylethyl)phenyl)-2-(methyloxy)pyridine (67.19A). The formation of the chloride was conducted in an analogous manner to Example 8.7-8.10, described herein using 6-(methyloxy)-3-pyridinylboronic acid which is commercially available from Aldrich to yield 67.19A MS ESI (pos.) m/e: 290.2 (M+H)$^+$.

(3R)-3-(3-(((3-(1,1-Dimethylethyl)-4-(6-(methyloxy)-3-pyridinyl)phenyl)methyl)oxy)phenyl)hexanoic acid or (3S)-3-(3-(((3-(1,1-dimethylethyl)-4-(6-(methyloxy)-3-pyridinyl)phenyl)methyl)oxy)phenyl)hexanoic acid (67.19). The alkylation and hydrolysis were conducted in an analogous manner to Example 66.6 (using 67.19A and 43.6 (derived from peak one from the chiral separation of 43.4 from the OD-column), described herein) to yield 67.19. $^1$H NMR (400 MHz, CDCl$_3$) δ ppm 8.08 (1H, d, J=2.3 Hz), 7.61 (1H, d, J=1.6 Hz), 7.50 (1H, dd, J=8.4, 2.5 Hz), 7.32 (2H, m), 7.04 (1H, d, J=7.8 Hz), 6.90 (3H, m), 6.78 (1H, d, J=8.6 Hz), 5.09 (2H, s), 4.01 (3H, s), 3.15 (1H, m), 2.65 (2H, ddd, J=17.6, 15.7, 7.4 Hz), 1.69 (2H, m), 1.28 (11H, m), 0.87 (3H, t, J=7.4 Hz). MS ESI (neg.) m/e: 460.1 (M−H)+.

Example 67.20

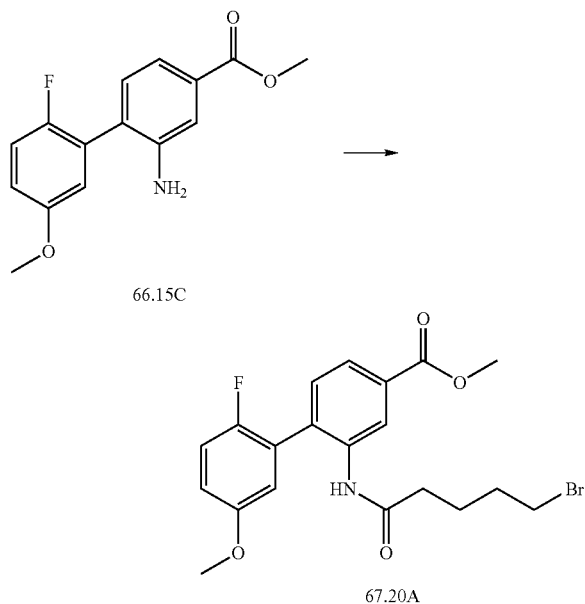

Methyl 2-((5-bromopentanoyl)amino)-2'-fluoro-5'-(methyloxy)-1,1'-biphenyl-4-carboxylate (67.20 C). To a dry round bottom flask containing 66.15C (0.7779 g, 2.83 mmol) was added dry chloroform (8 mL) at 0° C. After five minutes, 5-bromovaleryl chloride (0.5 mL, 3.73 mmol) (commercially available from Aldrich) was added followed by dropwise addition of dry pyridine (0.31 mL, 3.80 mmol). The reaction mixture was allowed to warm to room temperature and monitored with TLC and LC-MS. After 3 hours, the reaction was diluted with DCM and washed twice with saturated aqueous sodium bicarbonate solution, twice with water, and once with brine. The organic layer was dried over anhydrous sodium sulfate then filtered and concentrated. The residue was purified by recrystallization from isopropanol to afford 67.20A as an off white solid (726.2 mg, 59% yield). 1H NMR (400 MHz, CDCl3) δ ppm 8.78 (1H, s), 7.91 (1H, d, J=7.8 Hz), 7.36 (1H, d, J=7.8 Hz), 7.15 (1H, t, J=9.2 Hz), 7.08 (1H, s), 6.97 (1H, dt, J=9.0, 3.7 Hz), 6.81 (1H, dd, J=5.9, 3.1 Hz), 3.94 (3H, s), 3.83 (3H, s), 3.39 (2H, t, J=6.3 Hz), 2.28 (2H, t, J=7.0 Hz), 1.89 (2H, m), 1.82 (2H, m).

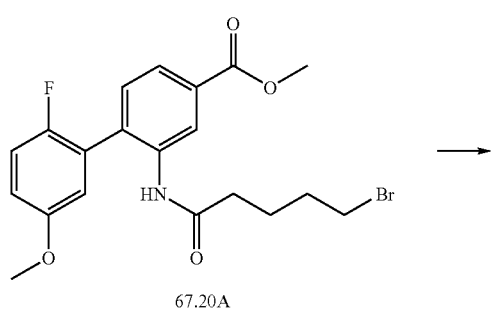

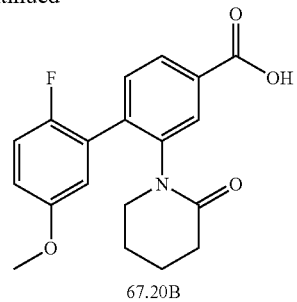

2'-Fluoro-5'-(methyloxy)-2-(2-oxo-1-piperidinyl)-1,1'-biphenyl-4-carboxylic acid (67.20B). To a dry vial containing 67.20A (0.5858 g, 1.337 mmol) was added dry DMF (25 mL). The mixture was stirred at 0° C. for about 15 minutes, then potassium tert-butoxide (0.3766 g, 3.356 mmol) was carefully added in portions. The mixture was heated to 145° C. and monitored with TLC and LC-MS. After 2.5 hours, the reaction was cooled to room temperature and then carefully quenched with 2 M aqueous citric acid solution. After extracting three times with DCM, the organic layer was dried over anhydrous magnesium sulfate, filtered and concentrated. The residue was purified with silica gel flash chromatography (0-25% MeOH in DCM) to afford 67.20B as an oil (440.1 mg, 96% yield). MS ESI (neg.) m/e: 342.0 (M−H)+.

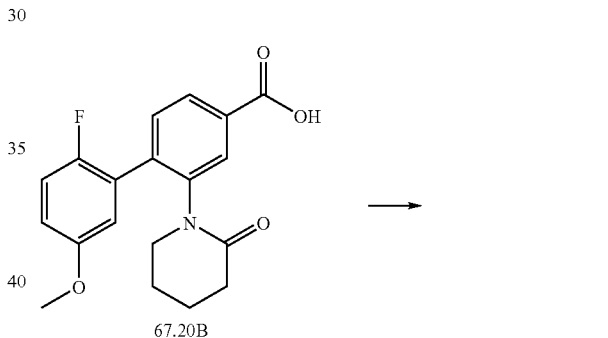

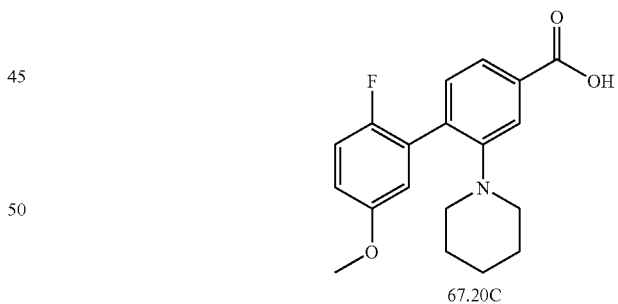

2'-Fluoro-5'-(methyloxy)-2-(1-piperidinyl)-1,1'-biphenyl-4-carboxylic acid (67.20C). To a cooled solution of 67.20B (0.4401 g, 1.282 mmol) in dry THF (8 mL) at 0° C. was added borane THF complex, 1.0 M in THF (2.5 mL, 2.5 mmol) dropwise. Upon complete addition, the reaction was maintained at 0° C. and monitored by TLC and LCMS. After 3 hours, water was added to quench the reaction, and the resulting solution was extracted three times with EtOAc. The organic extractions were combined and washed successively with saturated aqueous sodium bicarbonate, water, and then brine. After drying over anhydrous magnesium sulfate, filtration, and concentration, the residue was purified with silica gel flash chromatography (0-25% MeOH in DCM) to afford 67.20C as an oil (292.9 mg, 69% yield). $^1$H NMR (400 MHz, CDCl$_3$) δ ppm 7.85 (2H, m), 7.36 (1H, d, J=7.8 Hz), 7.11 (2H, m), 6.86 (1H, dt, J=8.9, 3.6 Hz), 3.83 (3H, s), 2.85 (4H, m), 1.46 (6H, m).

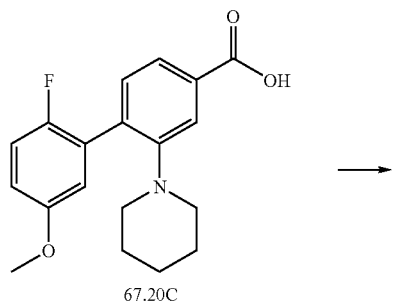

(2'-Fluoro-5'-(methyloxy)-2-(1-piperidinyl)-1,1'-biphenyl-4-yl)methanol (67.20D). To a cooled solution of 67.20C (0.2929 g, 0.8893 mmol) in dry THF (10 mL) at 0° C. was added LAH (1M in THF) (1.8 mL, 1.8 mmol). Upon complete addition, the reaction was maintained at 0° C. and was monitored by TLC and LCMS. After 2 hours, 1N NaOH was added to quench the reaction (gas evolution occurred). The resulting solution was extracted three times with EtOAc. After drying over anhydrous magnesium sulfate, filtration, and concentration, the residue was purified by flash chromatography (SiO$_2$ gel 60, eluted with 0%-50% EtOAc in hexanes). Fractions containing the desired product were combined and concentrated to afford 67.20D as a colorless oil (231.8 mg, 83% yield). $^1$H NMR (400 MHz, CDCl$_3$) δ ppm 7.25 (1H, d, J=9.0 Hz), 7.11 (4H, m), 6.82 (1H, dt, J=9.0, 3.5 Hz), 4.71 (2H, d, J=5.5 Hz), 3.81 (3H, s), 2.81 (4H, m), 1.69 (1H, s), 1.43 (6H, m).

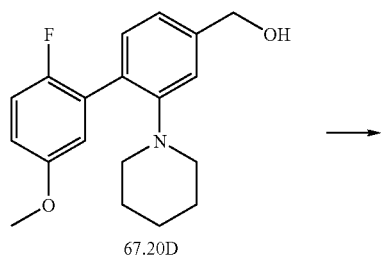

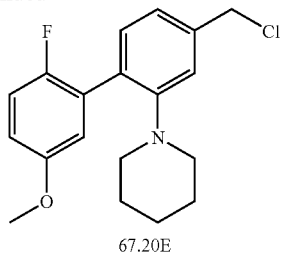

1-(4-(Chloromethyl)-2'-fluoro-5'-(methyloxy)-1,1'-biphenyl-2-yl)piperidine (67.20E). To a solution of 67.20D (0.2318 g, 0.73 mmol) in dry DMF (0.03 mL) and dry DCM (3 mL) was added thionyl chloride (0.13 mL, 1.8 mmol) at 0° C. The resulting solution was warmed to room temperature and monitored with TLC and LCMS. After 45 minutes, the reaction was diluted with DCM and then washed once with saturated aqueous sodium bicarbonate and once with brine. After drying over anhydrous magnesium sulfate, filtering, and removing the solvent under reduced pressure, the residue was purified by silica gel flash chromatography (0-5% EtOAc/hexane) to afford 67.20E (86.3 mg, 35% yield). $^1$H NMR (400 MHz, CDCl$_3$) δ ppm 7.16 (1H, m), 7.00 (4H, m), 6.72 (1H, dt, J=9.0, 3.5 Hz), 4.50 (2H, s), 3.71 (3H, s), 2.71 (4H, m), 1.34 (6H, m).

(3R)-3-(3-(((2'-Fluoro-5'-(methyloxy)-2-(1-piperidinyl)-1,1'-biphenyl-4-yl)methyl)oxy)phenyl)hexanoic acid or (3S)-3-(3-(((2'-fluoro-5'-(methyloxy)-2-(1-piperidinyl)-1,1'-biphenyl-4-yl)methyl)oxy)phenyl)hexanoic acid (67.20). The alkylation and hydrolysis were conducted in an analogous manner to Example 66.6 (using 67.20E and 43.6 (derived from peak one from the chiral separation of 43.4 from the OD-column), described herein) to yield 67.19 (37.2 mg, 72% yield). $^1$H NMR (400 MHz, CDCl$_3$) δ ppm 7.19 (2H, m), 7.07 (4H, m), 6.80 (4H, m), 4.95 (2H, s), 3.72 (3H, s), 3.04 (1H, m), 2.72 (4H, m), 2.55 (2H, m), 1.59 (2H, m), 1.34 (6H, m), 1.15 (2H, m), 0.77 (3H, t, J=7.2 Hz). MS ESI (pos.) m/e: 506.0 (M+H)$^+$.

(3R)-3-(3-(((2-(5,5-dimethyl-1-cyclopenten-1-yl)-2',5-difluoro-5'-(methyloxy)-1,1'-biphenyl-4-yl)methyl)oxy)phenyl)hexanoic acid (67.21). The alkylation and hydrolysis were conducted in an analogous manner to Example 66.6 (using 43.6 (derived from peak one from the chiral separation of 43.4 from the OD-column) and 66.43I, described herein) to yield 67.21 (29.2 mg, 72% yield). $^1$H NMR (400 MHz, CDCl$_3$) δ ppm 7.35 (1H, d, J=7.4 Hz), 7.24 (1H, t, J=8.0 Hz), 7.08 (1H, d, J=10.6 Hz), 6.98 (1H, t, J=9.0 Hz), 6.89 (5H, m), 5.51 (1H, m), 5.16 (2H, s), 3.76 (3H, s), 3.13 (1H, m), 2.64 (2H, ddd, J=18.0, 15.7, 7.4 Hz), 2.24 (2H, td, J=7.0, 2.3 Hz), 1.68 (4H, m), 1.24 (2H, m), 0.90 (9H, m). MS ESI (neg.) m/e: 532.9 (M−H)$^+$.

(3R)-3-(3-(((4-(6-(Methyloxy)-2-pyridinyl)phenyl)methyl)oxy)phenyl)hexanoic acid or (3S)-3-(3-(((4-(6-(methyloxy)-2-pyridinyl)phenyl)methyl)oxy)phenyl)hexanoic acid (67.22). MS ESI (pos.) m/e: 462.3 (M+H)$^+$.

Example 67.23

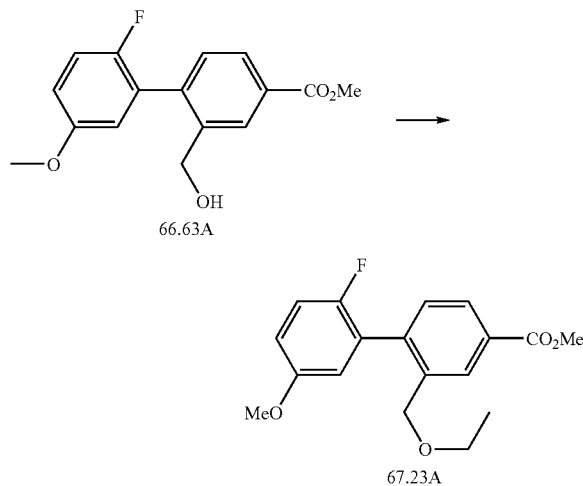

Methyl 2-((ethyloxy)methyl)-2'-fluoro-5'-(methyloxy)-1,1'-biphenyl-4-carboxylate (67.23A). To a solution of 66.63A (0.200 g, 0.689 mmol) in DMF (5 mL), was added NaH (0.0198 g, 0.827 mmol). The reaction was stirred at room temperature for 10 minutes. Ethyl iodide was then added and the reaction was stirred at room temperatures for 1 hour. The mixture was diluted with EtOAc, washed with water and brine, and dried over anhydrous Na$_2$SO$_4$. After removing solvent, the residue was purified by flash chromatography (silica gel, 1:1 EtOAc/hexane) and gave 67.23A in 79% yield. MS ESI (pos.) m/e: 336 (M+18)$^+$.

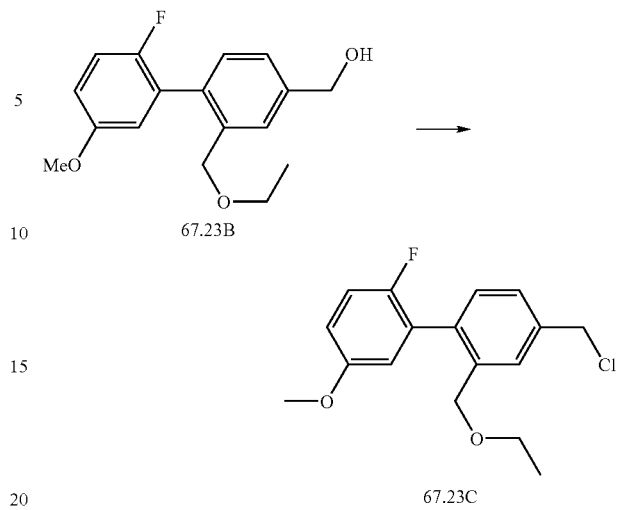

(2-((Ethyloxy)methyl)-2'-fluoro-5'-(methyloxy)-1,1'-biphenyl-4-yl)methanol (67.23B). Example 67.23A was reduced using LAH using a procedure analogous to that of Example 66.6 to yield 67.23B.

4-(Chloromethyl)-2-((ethyloxy)methyl)-2'-fluoro-1'-(methyloxy)-1,1'-biphenyl (67.23C). Compound 67.23B was converted to the chloromethyl compound using a procedure analogous to that described in Example 66.6.

(3R)-3-(3-(((2-((Ethyloxy)methyl)-2'-fluoro-5'-(methyloxy)-1,1'-biphenyl-4-yl)methyl)oxy)phenyl)hexanoic acid or (3S)-3-(3-(((2-((ethyloxy)methyl)-2'-fluoro-5'-(methyloxy)-1,1'-biphenyl-4-yl)methyl)oxy)phenyl)hexanoic acid (67.23). The alkylation and hydrolysis were conducted in an analogous manner to Example 66.6 (using 43.6 (derived from peak one from the chiral separation of 43.4 from the OD-column) and 67.23C, described herein) to yield 67.23. MS ESI (neg.) m/e: 479 (M−H)$^+$. $^1$H NMR (400 MHz, DMSO-d6) δ ppm 7.59 (m, 1H), 7.43-7.45 (m, 1H), 7.17-7.27 (m, 3H), 6.95-6.99 (m, 1H), 6.83-6.87 (m, 3H), 6.79 (m, 1H), 5.13 (s, 2H), 4.28 (s, 2H), 3.75 (s, 3H), 3.34 (m, 2H), 2.95 (m, 1H), 2.43-2.57 (m, 2H), 1.51 (m, 2H), 1.13 (m, 2H), 1.03 (t, 3H), 0.78 (t, 3H).

Example 67.24

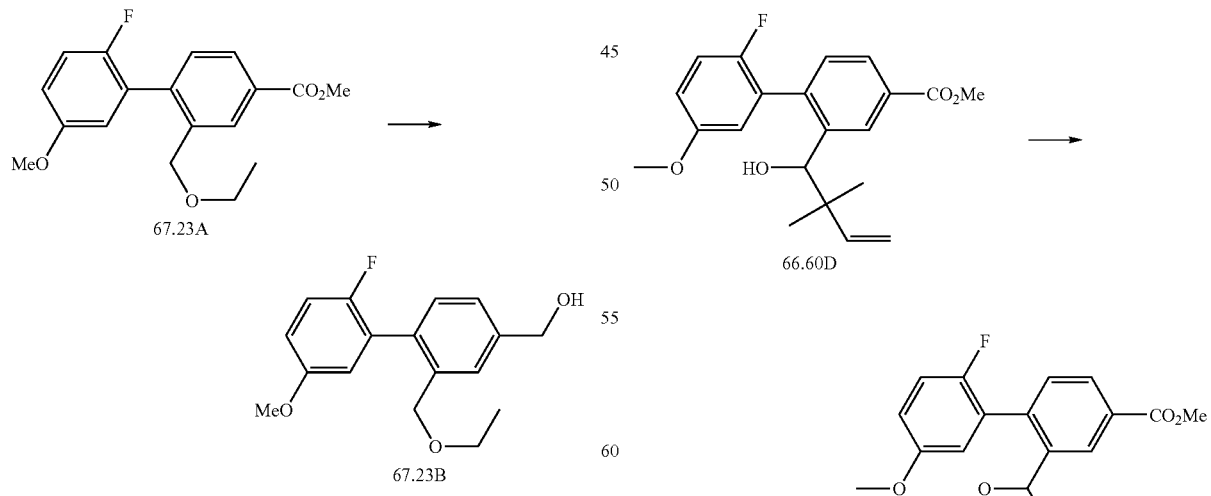

Methyl 2-(2,2-dimethyl-1-(methyloxy)-3-butenyl)-2'-fluoro-5'-(methyloxy)-1,1'-biphenyl-4-carboxylate (67.24). Compound 66.60D was alkylated using a procedure similar to that described in 66.62B to provide compound 67.24A.

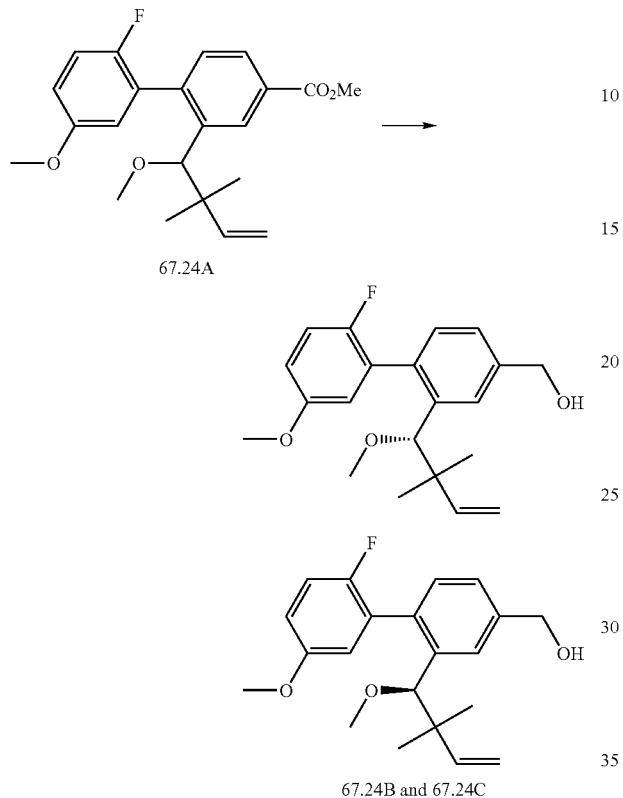

(2-((1S)-2,2-Dimethyl-1-(methyloxy)-3-butenyl)-2'-fluoro-5'-(methyloxy)-1,1'-biphenyl-4-yl)methanol and (2-((1R)-2,2-dimethyl-1-(methyloxy)-3-butenyl)-2'-fluoro-5'-(methyloxy)-1,1'-biphenyl-4-yl)methanol (67.24B and 67.24C). To a solution of 67.24A (0.187 g, 0.52 mmol) in THF (10 mL), was added dropwise LAH (0.020 g, 0.52 mmol). The reaction was then stirred at room temperature for 10 minutes and then was carefully poured into water and extracted with EtOAc. The organic phase was dried over anhydrous $Na_2SO_4$. After removing solvent, the residue was purified by flash chromatography (silica gel, 1:2 EtOAc/hexane) and gave the racemic product (168 mg) as a colorless oil, which was separated by chiral chromatography (column: OD; solvent: 3% i-PrOH/hexane) to yield 66.24B (70 mg, first peak) and 66.24C (85 mg, second peak).

(3R)-3-(3-(((2-((1S)-2,2-Dimethyl-1-(methyloxy)-3-butenyl)-2'-fluoro-5'-(methyloxy)-1,1'-biphenyl-4-yl)methyl)oxy)phenyl)hexanoic acid or (3R)-3-(3-(((2-((1R)-2,2-dimethyl-1-(methyloxy)-3-butenyl)-2'-fluoro-5'-(methyloxy)-1,1'-biphenyl-4-yl)methyl)oxy)phenyl) hexanoic acid or (3S)-3-(3-(((2-((1S)-2,2-Dimethyl-1-(methyloxy)-3-butenyl)-2'-fluoro-5'-(methyloxy)-1,1'-biphenyl-4-yl)methyl)oxy)phenyl)hexanoic acid or (3S)-3-(3-(((2-((1R)-2,2-dimethyl-1-(methyloxy)-3-butenyl)-2'-fluoro-5'-(methyloxy)-1,1'-biphenyl-4-yl)methyl)oxy) phenyl)hexanoic acid (67.24). The alkylation and hydrolysis were conducted in an analogous manner to Example 66.6 (using 43.6 (derived from peak one from the chiral separation of 43.4 from the OD-column) and 66.24B (derived from peak one from the chiral separation of the reduction product of 67.24A) to yield 67.24. MS ESI (neg.) m/e: 533 $(M-H)^+$. $^1H$ NMR (400 MHz, $CDCl_3$) δ ppm 7.53 (m, 1H), 7.42-7.45 (m, 1H), 7.17-7.23 (m, 2H), 7.01-7.07 (m, 1H), 6.80-6.89 (m, 4H), 6.73-6.75 (m, 1H), 6.39 (m, 2H), 5.75 (m, 1H), 5.14 (m, 2H), 3.81 (m, 2H), 3.07 (m, 3H), 3.09 (m, 1H), 2.13 (m, 2H), 1.62 (m, 2H), 1.29 (m, 6H), 1.21 (m, 2H), 0.87 (m, 3H).

Example 67.25

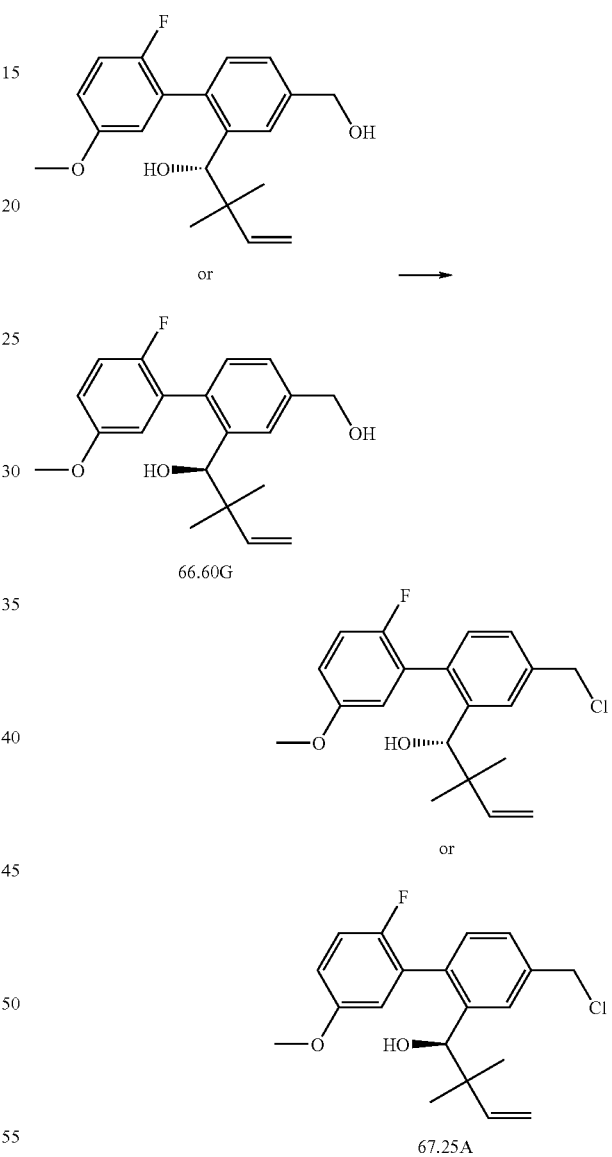

(1S)-1-(4-(Chloromethyl)-2'-fluoro-5'-(methyloxy)-1,1'-biphenyl-2-yl)-2,2-dimethyl-3-buten-1-ol or (1R)-1-(4-(chloromethyl)-2'-fluoro-5'-(methyloxy)-1,1'-biphenyl-2-yl)-2,2-dimethyl-3-buten-1-ol (67.25A). Hydroxymethyl compound 66.60G was chlorinated using a procedure analogous to that used to prepare Example 66.60H, (using peak two from the chiral separation of the reduction product of 66.60E from the OD-column, described herein) to yield 67.25A.

(3R)-3-(3-(((2'-Fluoro-2-((1S)-1-hydroxy-2,2-dimethyl-3-butenyl)-5'-(methyloxy)-1,1'-biphenyl-4-yl)methyl)oxy)

phenyl)hexanoic acid or (3R)-3-(3-(((2'-fluoro-2-((1R)-1-hydroxy-2,2-dimethyl-3-butenyl)-5'-(methyloxy)-1,1'-biphenyl-4-yl)methyl)oxy)phenyl)hexanoic acid 67.25). The alkylation and hydrolysis were conducted in an analogous manner to Example 66.6 (using 43.6 (derived from peak one from the chiral separation of 43.4 from the OD-column) and 67.25A (derived from peak two from the chiral separation of the reduction product of 66.60E) to yield 67.25. MS ESI (neg.) m/e: 519 (M−H). $^1$H NMR (400 MHz, CD$_3$OD) δ ppm 7.69 (d, 1H), 7.39 (m, 1H), 7.05-7.25 (m, 3H), 6.94 (m, 1H), 6.79-6.84 (m, 4H), 5.78 (m, 1H), 5.14 (m, 2H), 4.71 (m, 2H), 3.79 (s, 3H), 3.03 (m, 1H), 2.52-2.58 (m, 2H), 1.59 (m, 2H), 1.16 (m, 2H), 0.82 (m, 6H), 0.72 (s, 3H).

(3R)-3-(3-(((2-((1S)-2,2-Dimethyl-1-(methyloxy)butyl)-2'-fluoro-5'-(methyloxy)-1,1'-biphenyl-4-yl)methyl)oxy)phenyl)hexanoic acid or (3R)-3-(3-(((2-((1R)-2,2-dimethyl-1-(methyloxy)butyl)-2'-fluoro-5'-(methyloxy)-1,1'-biphenyl-4-yl)methyl)oxy)phenyl)hexanoic acid or (3S)-3-(3-(((2-((1S)-2,2-dimethyl-1-(methyloxy)butyl)-2'-fluoro-5'-(methyloxy)-1,1'-biphenyl-4-yl)methyl)oxy)phenyl)hexanoic acid or (3S)-3-(3-(((2-((1R)-2,2-dimethyl-1-(methyloxy)butyl)-2'-fluoro-5'-(methyloxy)-1,1'-biphenyl-4-yl)methyl)oxy)phenyl)hexanoic acid (67.26). The alkylation and hydrolysis were conducted in an analogous manner to Example 66.6 (using 43.6 (derived from peak one from the chiral separation of 43.4 from the OD-column), also using the chloride derived from peak one from the chiral separation of the reduction product of 66.60E, described herein) to yield 67.26. MS ESI (neg.) m/e: 536 (M−H). $^1$H NMR (400 MHz, CD$_3$OD) δ ppm 7.58 (m, 1H), 7.45 (m, 1H), 7.22 (m, 2H), 6.82-6.88 (m, 4H), 6.74 (m, 1H), 5.15 (s, 2H), 4.05-4.30 (m, 1H), 3.23-3.29 (m, 3H), 3.08 (m, 1H), 2.61-2.65 (m, 2H), 1.62 (m, 2H), 1.10-1.27 (m, 4H), 0.86 (t, 3H), 0.72 (s, 3H), 0.61 (m, 3H), 0.49 (m, 3H).

Example 67.27

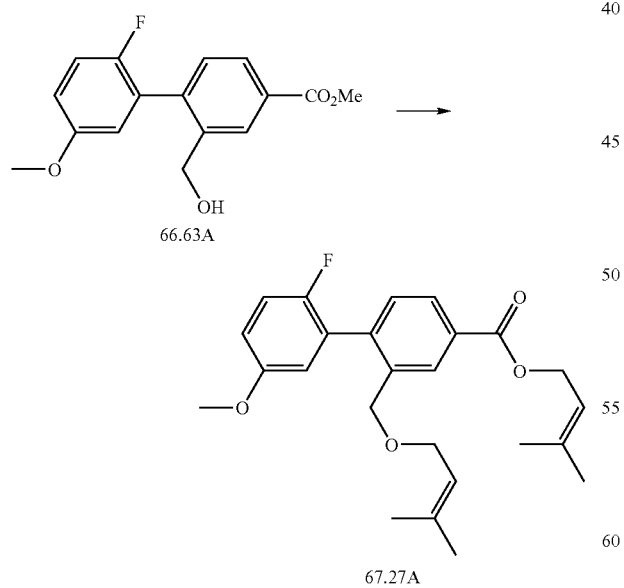

3-Methyl-2-butenyl 2'-fluoro-2-(((3-methyl-2-butenyl)oxy)methyl)-5'-(methyloxy)-1,1'-biphenyl-4-carboxylate (67.27A). To a solution of 66.63A (0.322 mmol) in DMF (4 mL), was added NaH (0.0100 g, 0.419 mmol). The resulting mixture was stirred at room temperature for 10 minutes. 1-Bromo-3-methylbut-2-ene (0.240 g, 1.61 mmol) (commercially available from Aldrich) was added and the mixture was stirred at room temperature for 2 hours. After removing solvent, the residue was purified by flash chromatography (silica gel, 1:6 EtOAc/hexane) and gave 67.27A as a colorless oil, in 77% yield. MS ESI (pos.) m/e: 430 (M+18)$^+$.

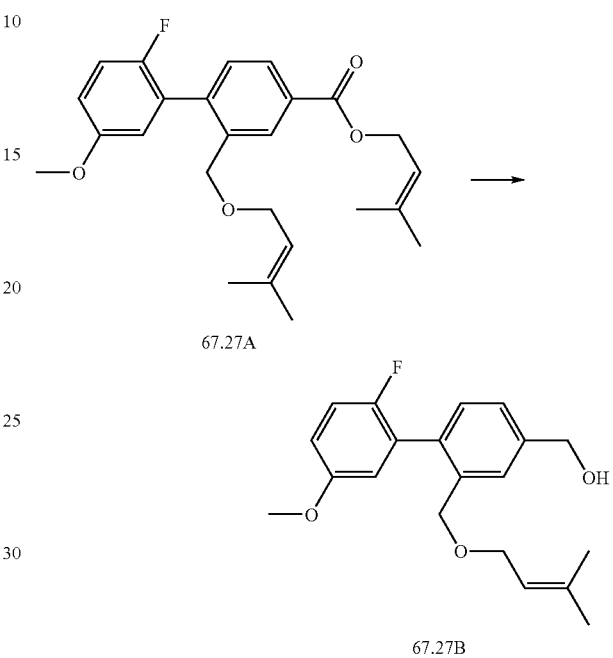

(2'-Fluoro-2-(((3-methyl-2-butenyl)oxy)methyl)-5'-(methyloxy)-1,1'-biphenyl-4-yl)methanol (67.27B). The conversion of ester 67.27A to hydroxymethyl compound 67.27B was conducted using a procedure analogous to that described in Example 66.63D.

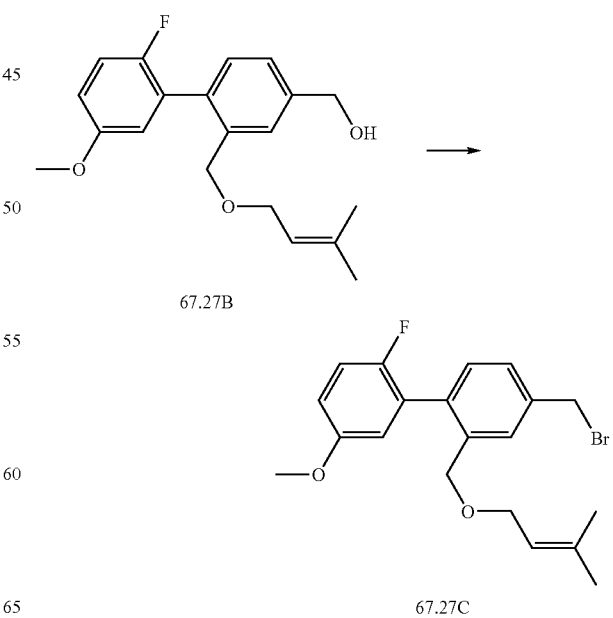

4-(Bromomethyl)-2'-fluoro-2-(((3-methyl-2-butenyl)oxy)methyl)-5'-(methyloxy)-1,1'-biphenyl (67.27C). Hydroxymethyl compound 67.2B was converted to bromomethyl 67.27C using a procedure analogous to that of Example 66.62E.

(3R)-3-(3-(((2'-Fluoro-2-(((3-methyl-2-butenyl)oxy)methyl)-5'-(methyloxy)-1,1'-biphenyl-4-yl)methyl)oxy)phenyl)hexanoic acid or (3S)-3-(3-(((2'-fluoro-2-(((3-methyl-2-butenyl)oxy)methyl)-5'-(methyloxy)-1,1'-biphenyl-4-yl)methyl)oxy)phenyl)hexanoic acid (67.27). The alkylation and hydrolysis were conducted in an analogous manner to Example 66.6 (using 43.6 (derived from peak one from the chiral separation of 43.4 from the OD-column) and 67.27C) to yield 67.27. MS ESI (neg.) m/e: 519 (M−H). $^1$H NMR (400 MHz, CDCl$_3$) δ ppm 7.59 (m, 1H), 7.42 (m, 1H), 7.21-7.29 (m, 2H), 7.02-7.07 (m, 1H), 6.80-6.87 (m, 5H), 5.23 (m, 1H), 5.15 (s, 2H), 4.37 (s, 2H), 3.92 (d, 3H), 3.06 (m, 1H), 2.52-2.65 (m, 2H), 1.70 (m, 3H), 1.62 (m, 2H), 1.58 (s, 3H), 1.21 (m, 2H), 0.87 (t, 3H).

(3R)-3-(3-(((2'-Fluoro-5'-(methyloxy)-2-(1-pyrrolidinylmethyl)-1,1'-biphenyl-4-yl)methyl)oxy)phenyl)hexanoic acid or (3S)-3-(3-(((2'-fluoro-5'-(methyloxy)-2-(1-pyrrolidinylmethyl)-1,1'-biphenyl-4-yl)methyl)oxy)phenyl)hexanoic acid (67.28). The alkylation and hydrolysis were conducted in an analogous manner to Example 66.6 (using 43.6 (derived from peak one from the chiral separation of 43.4 from the OD-column) and 66.65C) to yield 67.28. After removing solvent, 67.28 (TFA salt), 28 mg, was obtained. MS ESI (neg.) m/e: 504 (M−H)$^+$. $^1$H NMR (400 MHz, DMSO-d$_6$) δ ppm 9.70 (m, 1H), 7.84 (s, 1H), 7.60 (m, 1H), 7.39 (m, 1H), 7.21-7.30 (m, 2H), 7.05-7.07 (m, 1H), 6.3-6.95 (m, 1H), 6.88 (m, 2H), 6.83 (m, 1H), 5.17 (s, 2H), 4.10-4.40 (m, 2H), 3.79 (s, 3H), 3.40-3.60 (m, 4H), 2.97 (m, 1H), 2.42-2.55 (m, 2H), 1.80 (m, 4H), 1.51 (m, 2H), 1.06 (m, 2H), 0.80 (t, 3H).

Example 68

Synthesis of methyl (3R)-6,6,6-trifluoro-3-(3-hydroxyphenyl)hexanoate (68)

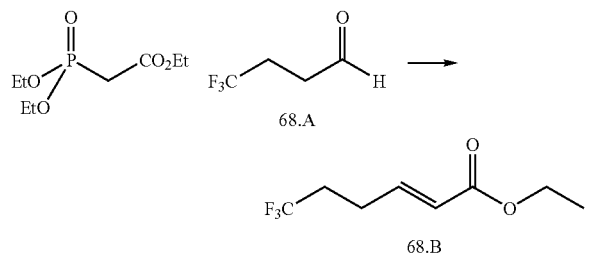

(E)-Ethyl 6,6,6-trifluorohex-2-enoate (68.B). To a suspension of lithium chloride (0.504 g, 11.9 mmol) in MeCN (20 mL) were added ethyl 2-(diethoxyphosphoryl)acetate (available from Aldrich) (1.91 mL, 9.52 mmol) and DBU (1.42 mL, 9.52 mmol) at room temperature. The mixture was cooled to 0° C., and 4,4,4-trifluorobutanal (available from Matrix Scientific) (1.00 g, 7.93 mmol) was added dropwise. The resulting mixture was warmed to room temperature and stirred overnight. The mixture was partitioned between water and EtOAc. The layers were separated, and the aqueous phase was extracted with additional EtOAc. The combined organic layers were washed with water and brine, dried (MgSO$_4$), and concentrated. The residue was purified by silica gel flash chromatography (0-10% EtOAc/hexane) to afford (E)-ethyl 6,6,6-trifluorohex-2-enoate 68.B (6:1 E/Z) as a colorless liquid (1.13 g, 73%).

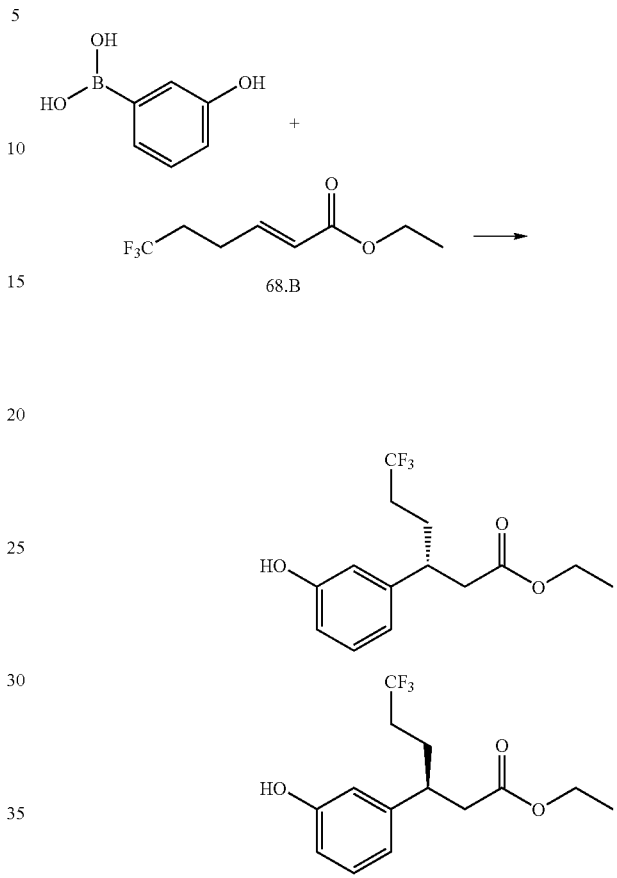

Methyl (3R)-6,6,6-trifluoro-3-(3-hydroxyphenyl)hexanoate or methyl (3S)-6,6,6-trifluoro-3-(3-hydroxyphenyl)hexanoate (68). A mixture of 3-hydroxyphenylboronic acid (available from Aldrich) (1.8 g, 13 mmol) and hydroxy[(S)-BINAP]-rhodium(I) dimer (0.19 g, 0.13 mmol) in 1,4-dioxane (10 mL, 2.5 mmol) was sparged with N$_2$. To the mixture were added water (1.0 mL, 2.5 mmol) and (E)-ethyl 6,6,6-trifluorohex-2-enoate 68.B (0.56 mL, 2.5 mmol). The resulting red-brown solution was warmed to 45° C. and stirred for 3 hours (sealed vial). The mixture was cooled to room temperature, diluted with EtOAc, washed with saturated aqueous NaHCO$_3$ and brine, dried (MgSO$_4$), and concentrated. The residue was purified by silica gel flash chromatography (0-25% EtOAc/hexane) to afford (R)-ethyl 6,6,6-trifluoro-3-(3-hydroxyphenyl)hexanoate and (S)-ethyl 6,6,6-trifluoro-3-(3-hydroxyphenyl)hexanoate 68 as a pale yellow oil (84% e.e.). The enantiomerically enriched mixture was further purified by chiral HPLC (Chiralcel OD, 3% i-PrOH/hexane, 220 nm) to afford 68 as a colorless oil (0.65 g, >99% e.e.). The R enantiomer is believed to be the major product used in the following steps.

The following compounds were prepared from 68 and the appropriate halomethyl or hydroxymethyl compound according to the methods described herein. Both of the compounds in the following table were prepared using the same enantiomer of the phenol.

TABLE 8

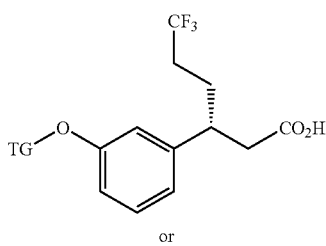

Compound     TG 68.1

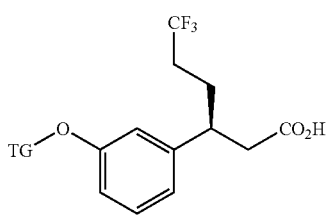

68.2

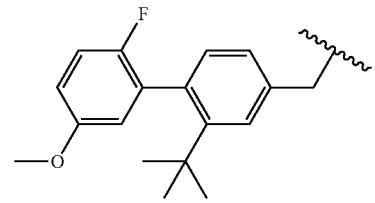

(3R)-3-(3-(((2-(1,1-Dimethylethyl)-2'-fluoro-5'-(methyloxy)-1,1'-biphenyl-4-yl)methyl)oxy)phenyl)-6,6,6-trifluorohexanoic acid or (3S)-3-(3-(((2-(1,1-dimethylethyl)-2'-fluoro-5'-(methyloxy)-1,1'-biphenyl-4-yl)methyl)oxy)phenyl)-6,6,6-trifluorohexanoic acid (68.1). $^1$H NMR (400 MHz, CDCl$_3$) δ ppm 7.60 (d, 1H), 7.28 (m, 2H), 7.05 (d, 1H), 6.99 (t, 1H), 6.91 (dd, 1H), 6.84 (m, 2H), 6.80 (bd, 1H), 6.77 (dd, 1H), 5.07 (s, 2H), 3.78 (s, 3H), 3.10 (m, 1H), 2.67 (m, 2H), 1.91 (m, 4H), 1.23 (s, 9H).

(3R)-3-(3-(((2-(Butyloxy)-2'-fluoro-5'-(methyloxy)-1,1'-biphenyl-4-yl)methyl)oxy)phenyl)-6,6,6-trifluorohexanoic acid or (3S)-3-(3-(((2-(butyloxy)-2'-fluoro-5'-(methyloxy)-1,1'-biphenyl-4-yl)methyl)oxy)phenyl)-6,6,6-trifluorohexanoic acid (68.2). $^1$H NMR (400 MHz, CDCl$_3$) δ ppm 7.29 (d, 1H), 7.26 (t, 1H), 7.06 (m, 2H), 7.02 (t, 1H), 6.89 (m, 2H), 6.82 (m, 3H), 5.07 (s, 2H), 3.99 (t, 2H), 3.79 (s, 3H), 3.09 (m, 1H), 2.67 (m, 2H), 1.91 (m, 4H), 1.66 (m, 2H), 1.37 (m, 2H), 0.88 (t, 3H).

Example 69

Synthesis of (R)-ethyl 4-cyclopropyl-3-(3-hydroxyphenyl)butanoate or (S)-ethyl 4-cyclopropyl-3-(3-hydroxyphenyl)butanoate (69)

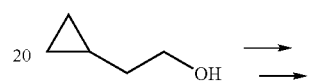

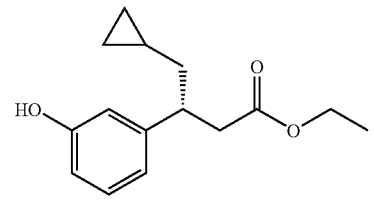

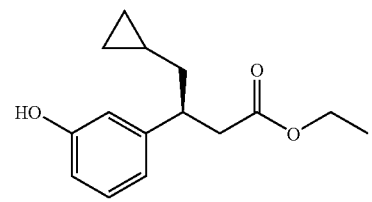

69

(R)-Ethyl 4-cyclopropyl-3-(3-hydroxyphenyl)butanoate and (S)-Ethyl 4-cyclopropyl-3-(3-hydroxyphenyl)butanoate (69). Compound 69 (99% e.e.) was prepared from 2-cyclopropylethanol (commercially available from Alfa Aesar) according to the analogous methods described in Example 70. The final chiral resolution was achieved by chiral HPLC (Chiralcel OD column, 3% IPA/hexane, detection at 220 nm) to afford 69 as the first of two eluted peaks. This is believed to be the R enantiomer.

The following compounds were prepared from 69 and the appropriate halomethyl or hydroxymethyl compound according to the methods described herein. Each of the compounds in the following table were prepared using the same enantiomer of the phenol.

TABLE 9
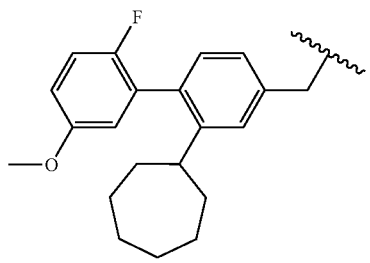
or
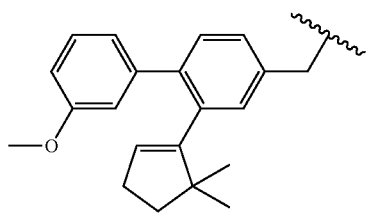
| Compound | TG |
|---|---|
| 69.1 | 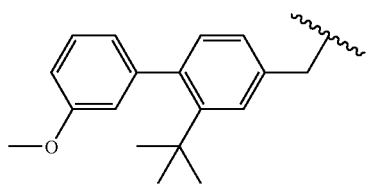 |
| 69.2 | 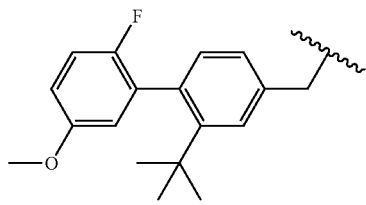 |
| 69.3 | 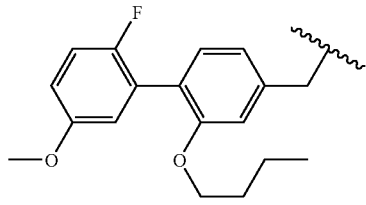 |
| 69.4 | 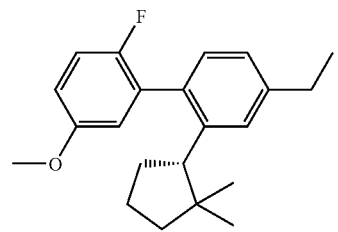 |
| 69.5 | 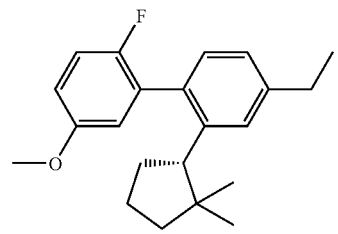 |
TABLE 9-continued
| | |
|---|---|
| 69.6 | 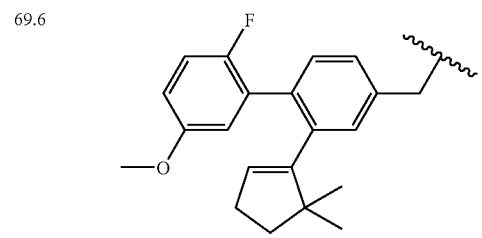 |
| 69.7 | 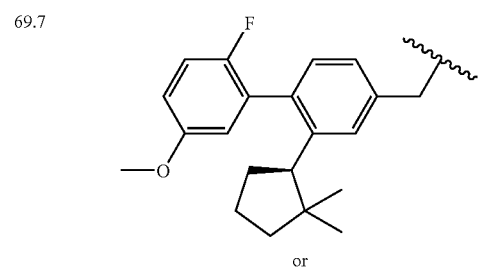 |
or
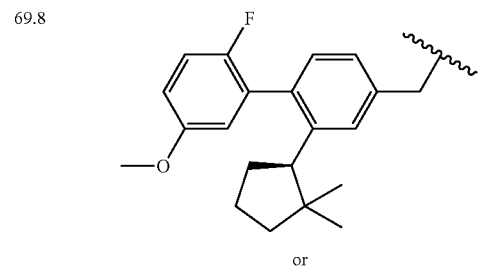
| 69.8 | 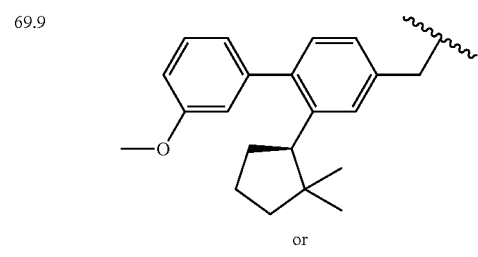 |
or
but not the same one as 69.7
| 69.9 | |
or TABLE 9-continued
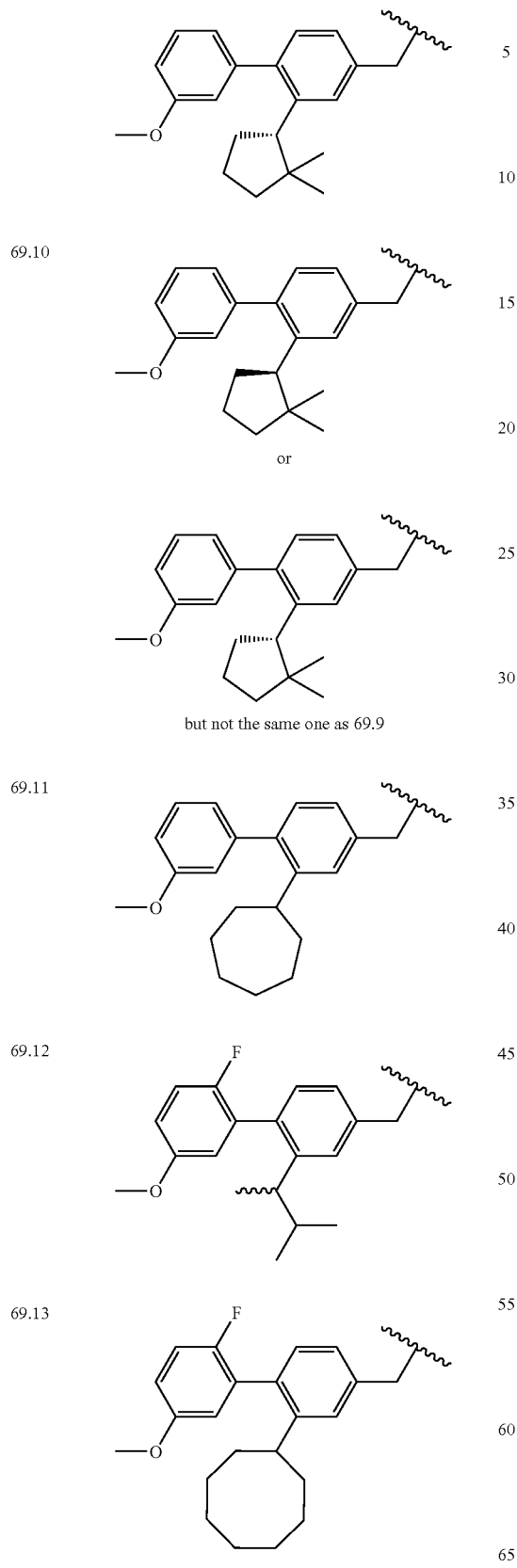
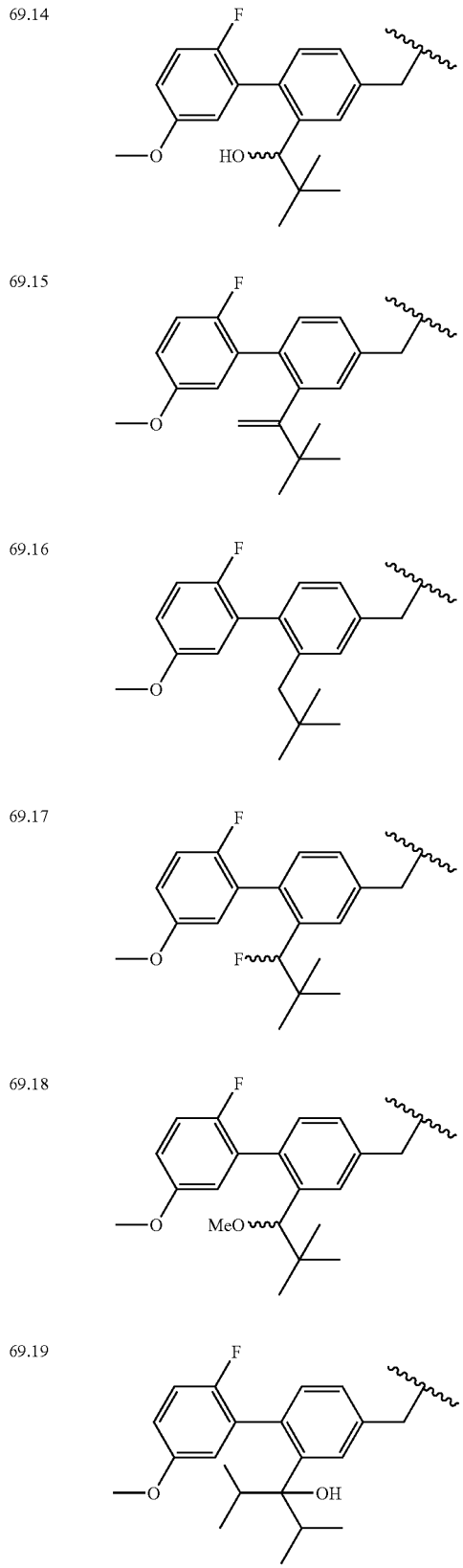

TABLE 9-continued
69.20 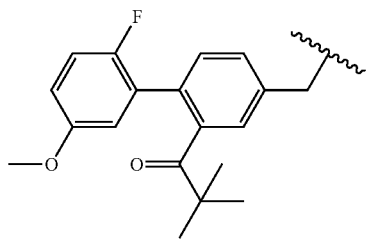
69.21 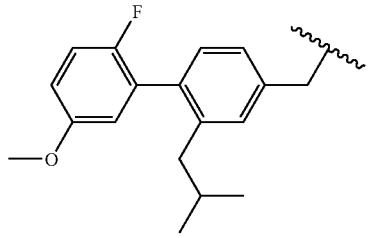
69.22 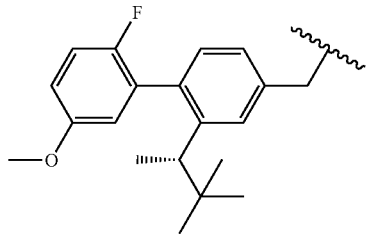
or

69.23 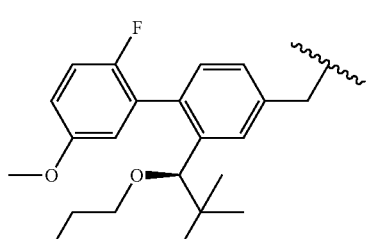
or
TABLE 9-continued
69.24 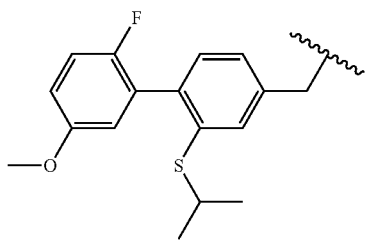
69.25 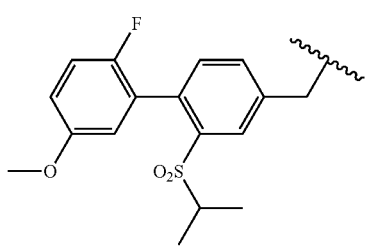
69.26 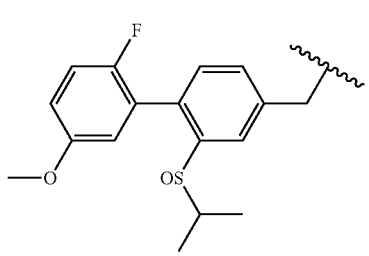
69.27 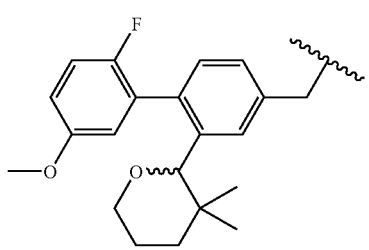
69.28 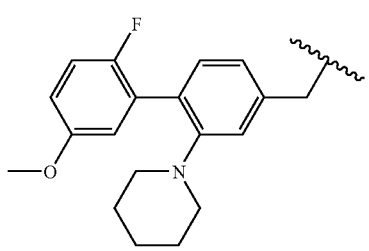
69.29 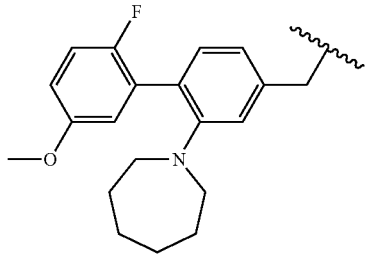

TABLE 9-continued
69.30 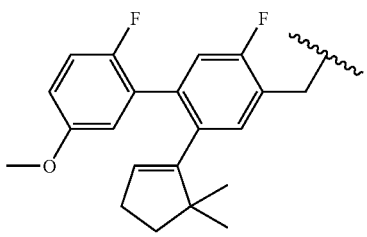
69.31 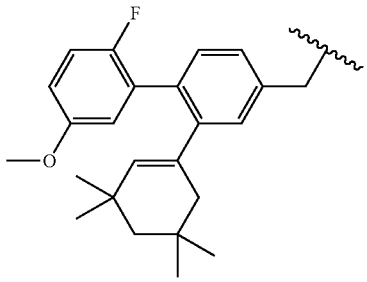
69.32 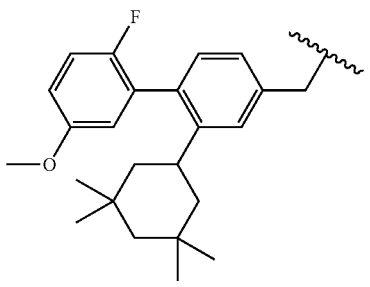
69.33 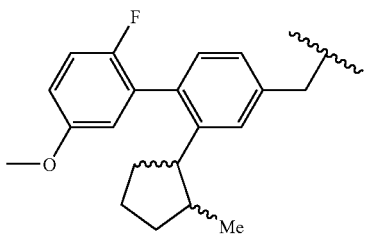
69.34 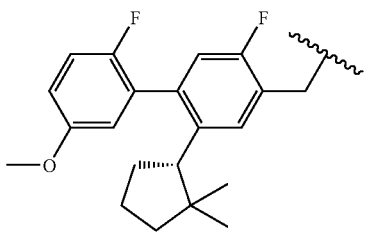
or
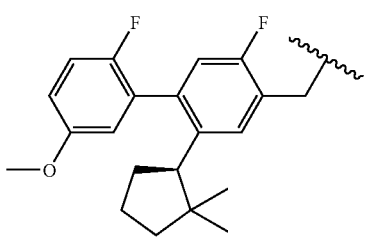
TABLE 9-continued
69.35 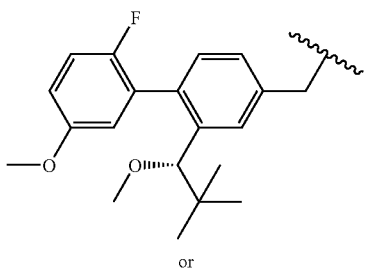
or
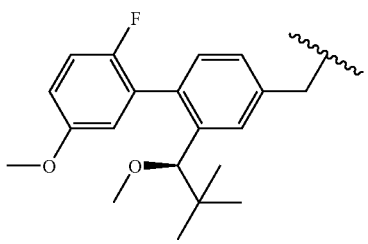
69.36 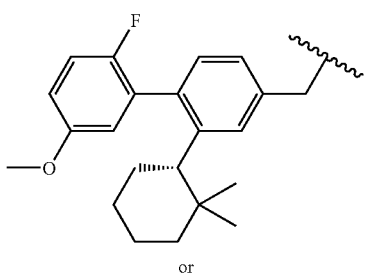
or
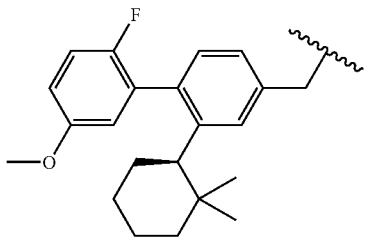
69.37 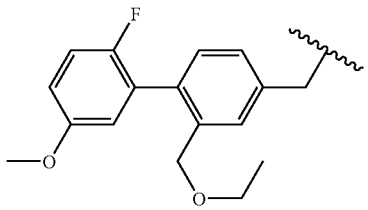
69.38 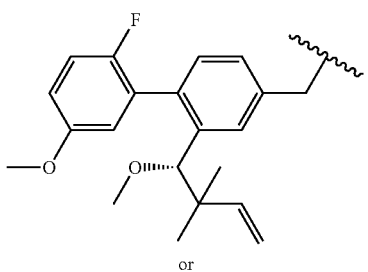
or TABLE 9-continued
69.39
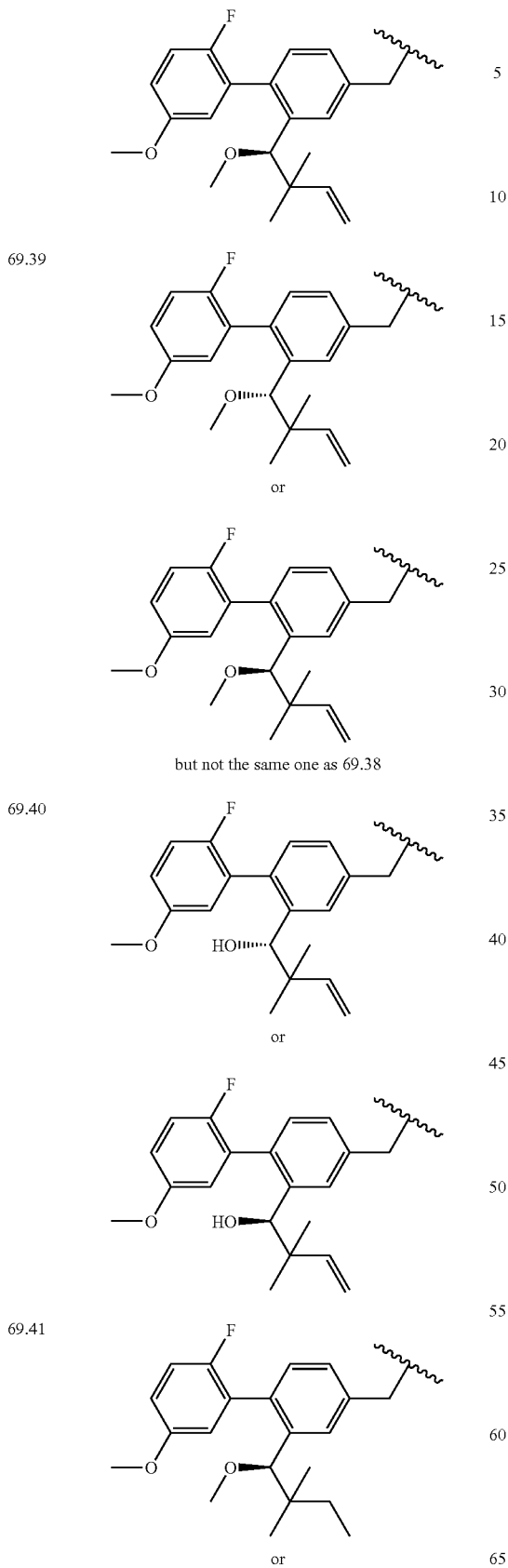
but not the same one as 69.38
69.40
69.41
TABLE 9-continued
69.42
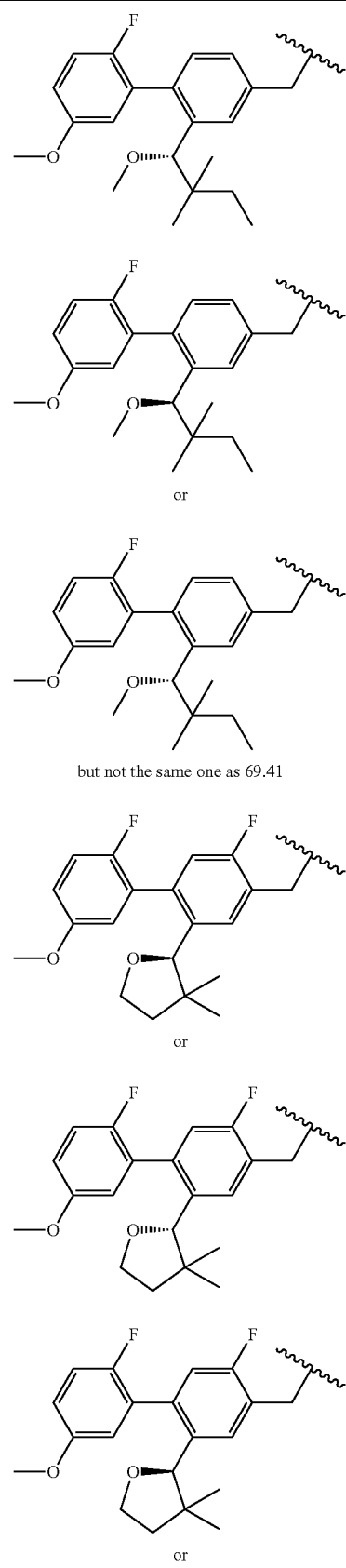
but not the same one as 69.41
69.43
69.44

TABLE 9-continued

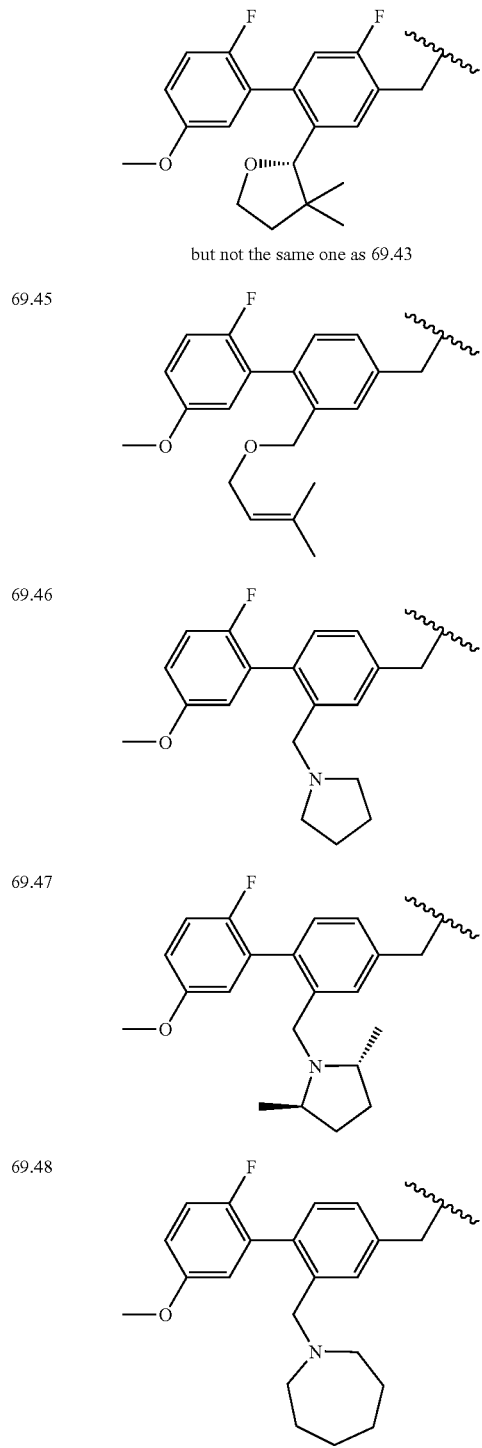

| | |
|---|---|
| 69.45 | but not the same one as 69.43 |
| 69.46 | |
| 69.47 | |
| 69.48 | |

(3R)-3-(3-(((2-Cycloheptyl-2'-fluoro-5'-(methyloxy)-1,1'-biphenyl-4-yl)methyl)oxy)phenyl)-4-cyclopropylbutanoic acid or (3S)-3-(3-(((2-cycloheptyl-2'-fluoro-5'-(methyloxy)-1,1'-biphenyl-4-yl)methyl)oxy)phenyl)-4-cyclopropylbutanoic acid (69.1). MS ESI (neg.) m/e: 529.3 (M–H)⁺.

(3R)-4-Cyclopropyl-3-(3-(((2-(5,5-dimethyl-1-cyclopenten-1-yl)-3'-(methyloxy)-1,1'-biphenyl-4-yl)methyl)oxy)phenyl)butanoic acid or (3S)-4-cyclopropyl-3-(3-(((2-(5,5-dimethyl-1-cyclopenten-1-yl)-3'-(methyloxy)-1,1'-biphenyl-4-yl)methyl)oxy)phenyl)butanoic acid (69.2). MS ESI (neg.) m/e: 509.2 (M–H)⁺.

(3R)-4-Cyclopropyl-3-(3-(((2-(1,1-dimethylethyl)-3'-(methyloxy)-1,1'-biphenyl-4-yl)methyl)oxy)phenyl)butanoic acid or (3S)-4-cyclopropyl-3-(3-(((2-(1,1-dimethylethyl)-3'-(methyloxy)-1,1'-biphenyl-4-yl)methyl)oxy)phenyl)butanoic acid (69.3). (MS ESI (neg.) m/e: 471.3 (M–H). ¹H NMR (400 MHz) (CDCl₃) δ ppm 7.55 (1H, d, J=1.6 Hz), 7.25 (3H, m), 7.02 (1H, d, J=7.4 Hz), 6.85 (5H, dt, J=5.5, 2.7 Hz), 6.81 (1H, s), 5.04 (2H, s), 3.78 (3H, s), 3.23 (1H, m), 2.75 (1H, m), 2.66 (1H, m), 1.68 (1H, ddd, J=13.9, 8.4, 5.9 Hz), 1.37 (1H, m), 1.20 (9H, s), 0.55 (1H, m), 0.39 (2H, m), 0.04 (2H, m).

(3R)-4-Cyclopropyl-3-(3-(((2-(1,1-dimethylethyl)-2'-fluoro-5'-(methyloxy)-1,1'-biphenyl-4-yl)methyl)oxy)phenyl)butanoic acid or (3S)-4-cyclopropyl-3-(3-(((2-(1,1-dimethylethyl)-2'-fluoro-5'-(methyloxy)-1,1'-biphenyl-4-yl)methyl)oxy)phenyl)butanoic acid (69.4). ¹H NMR (400 MHz, CDCl₃) δ ppm 7.60 (dd, 1H), 7.29 (dd, 1H), 7.24 (t, 1H), 7.04 (d, 1H), 6.99 (t, 1H), 6.86 (m, 4H), 6.77 (dd, 1H), 5.07 (s, 2H), 3.78 (s, 3H), 3.21 (m, 1H), 2.75 (dd, 1H), 2.64 (dd, 1H), 1.71 (m, 1H), 1.34 (m, 1H), 1.23 (s, 9H), 0.52 (m, 1H), 0.36 (m, 2H), 0.00 (m, 2H).

(3R)-3-(3-(((2-(Butyloxy)-2'-fluoro-5'-(methyloxy)-1,1'-biphenyl-4-yl)methyl)oxy)phenyl)-4-cyclopropylbutanoic acid or (3S)-3-(3-(((2-(butyloxy)-2'-fluoro-5'-(methyloxy)-1,1'-biphenyl-4-yl)methyl)oxy)phenyl)-4-cyclopropylbutanoic acid (69.5). ¹H NMR (400 MHz, CDCl₃) δ ppm 7.28 (d, 1H), 7.23 (t, 1H), 7.06 (m, 2H), 7.02 (t, 1H), 6.85 (m, 5H), 5.07 (s, 2H), 3.98 (t, 2H), 3.79 (s, 3H), 3.21 (m, 1H), 2.75 (dd, 1H), 2.64 (dd, 1H), 1.70 (m, 1H), 1.66 (m, 2H), 1.36 (m, 3H), 0.88 (t, 3H), 0.52 (m, 1H), 0.36 (m, 2H), 0.00 (m, 2H).

(3R)-4-Cyclopropyl-3-(3-(((2-(5,5-dimethyl-1-cyclopenten-1-yl)-2'-fluoro-5'-(methyloxy)-1,1'-biphenyl-4-yl)methyl)oxy)phenyl)butanoic acid or (3S)-4-cyclopropyl-3-(3-(((2-(5,5-dimethyl-1-cyclopenten-1-yl)-2'-fluoro-5'-(methyloxy)-1,1'-biphenyl-4-yl)methyl)oxy)phenyl)butanoic acid (69.6). MS ESI (pos.) m/e: 546.3 (M+H₂O)⁺.

(3R)-4-Cyclopropyl-3-(3-(((2-((1R)-2,2-dimethylcyclopentyl)-2'-fluoro-5'-(methyloxy)-1,1'-biphenyl-4-yl)methyl)oxy)phenyl)butanoic acid or (3R)-4-cyclopropyl-3-(3-(((2-((1S)-2,2-dimethylcyclopentyl)-2'-fluoro-5'-(methyloxy)-1,1'-biphenyl-4-yl)methyl)oxy)phenyl)butanoic acid or (3S)-4-cyclopropyl-3-(3-(((2-((1R)-2,2-dimethylcyclopentyl)-2'-fluoro-5'-(methyloxy)-1,1'-biphenyl-4-yl)methyl)oxy)phenyl)butanoic acid or (3S)-4-cyclopropyl-3-(3-(((2-((1S)-2,2-dimethylcyclopentyl)-2'-fluoro-5'-(methyloxy)-1,1'-biphenyl-4-yl)methyl)oxy)phenyl)butanoic acid (69.7). MS ESI (neg.) m/e: 529.3 (M–H)⁺.

(3R)-4-Cyclopropyl-3-(3-(((2-((1S)-2,2-dimethylcyclopentyl)-2'-fluoro-5'-(methyloxy)-1,1'-biphenyl-4-yl)methyl)oxy)phenyl)butanoic acid or (3R)-4-cyclopropyl-3-(3-(((2-((1R)-2,2-dimethylcyclopentyl)-2'-fluoro-5'-(methyloxy)-1,1'-biphenyl-4-yl)methyl)oxy)phenyl)butanoic acid or (3S)-4-cyclopropyl-3-(3-(((2-((1S)-2,2-dimethylcyclopentyl)-2'-fluoro-5'-(methyloxy)-1,1'-biphenyl-4-yl)methyl)oxy)phenyl)butanoic acid or (3S)-4-cyclopropyl-3-(3-(((2-((1R)-2,2-dimethylcyclopentyl)-2'-fluoro-5'-(methyloxy)-1,1'-biphenyl-4-yl)methyl)oxy)phenyl)butanoic acid (69.8). MS ESI (neg.) m/e: 529.3 (M–H)⁺.

(3R)-4-Cyclopropyl-3-(3-(((2-((1R)-2,2-dimethylcyclopentyl)-3'-(methyloxy)-1,1'-biphenyl-4-yl)methyl)oxy)phenyl)butanoic acid or (3R)-4-cyclopropyl-3-(3-(((2-((1S)-2,2-dimethylcyclopentyl)-3'-(methyloxy)-1,1'-biphenyl-4-yl)methyl)oxy)phenyl)butanoic acid or (3S)-4-cyclopropyl-3-(3-(((2-((1R)-2,2-dimethylcyclopentyl)-3'-(methyloxy)-1,1'- biphenyl-4-yl)methyl)oxy)phenyl)butanoic acid or (3S)-4-cyclopropyl-3-(3-(((2-((1S)-2,2-dimethylcyclopentyl)-3'-(methyloxy)-1,1'-biphenyl-4-yl)methyl)oxy)phenyl)butanoic acid (69.9). MS ESI (neg.) m/e: 511.3 (M−H)⁺.

(3R)-4-Cyclopropyl-3-(3-(((2-((1S)-2,2-dimethylcyclopentyl)-3'-(methyloxy)-1,1'-biphenyl-4-yl)methyl)oxy)phenyl)butanoic acid or (3R)-4-cyclopropyl-3-(3-(((2-((1R)-2,2-dimethylcyclopentyl)-3'-(methyloxy)-1,1'-biphenyl-4-yl)methyl)oxy)phenyl)butanoic acid or (3S)-4-cyclopropyl-3-(3-(((2-((1S)-2,2-dimethylcyclopentyl)-3'-(methyloxy)-1,1'-biphenyl-4-yl)methyl)oxy)phenyl)butanoic acid or (3S)-4-cyclopropyl-3-(3-(((2-((1R)-2,2-dimethylcyclopentyl)-3'-(methyloxy)-1,1'-biphenyl-4-yl)methyl)oxy)phenyl)butanoic acid (69.10). MS ESI (neg.) m/e: 511.3 (M−H)⁺.

(3R)-3-(3-(((2-Cycloheptyl-3'-(methyloxy)-1,1'-biphenyl-4-yl)methyl)oxy)phenyl)-4-cyclopropylbutanoic acid or (3S)-3-(3-(((2-cycloheptyl-3'-(methyloxy)-1,1'-biphenyl-4-yl)methyl)oxy)phenyl)-4-cyclopropylbutanoic acid (69.11). MS ESI (neg.) m/e: 511.3 (M−H)⁺.

Example 69.12

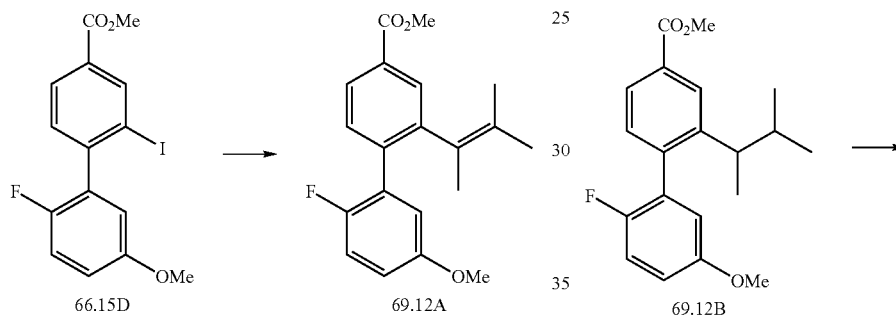

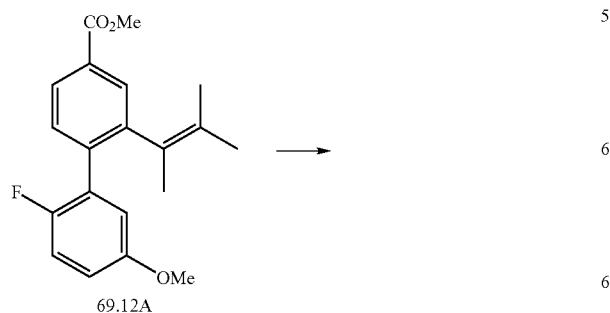

Methyl 2-(1,2-dimethyl-1-propenyl)-2'-fluoro-5'-(methyloxy)-1,1'-biphenyl-4-carboxylate (69.12A). To a stirred solution of 66.15D (0.231 g, 0.60 mmol) in DMF (4.00 mL) at 23° C. was added 3-methylbut-2-en-2-ylboronic acid (0.14 g, 1.2 mmol, commercially available from Aldrich), and potassium carbonate (0.25 g, 1.8 mmol). Tetrakis(triphenylphosphine)palladium (0.069 g, 0.060 mmol) was then added to the reaction. The mixture was heated to 90° C. and stirring was continued for 18 hours. The reaction was then cooled to room temperature, diluted with water and extracted three times with EtOAc. After drying over anhydrous magnesium sulfate and filtering, the organic solvent was removed under reduced pressure and the product was then purified on silica gel (0-10% EtOAc in hexanes) to yield 69.12A as a colorless oil (0.100 g, 51% yield).

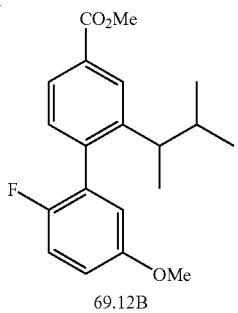

Methyl 2-(1,2-dimethylpropyl)-2'-fluoro-5'-(methyloxy)-1,1'-biphenyl-4-carboxylate (69.12B). To a stirred solution of 69.12A (0.050 g, 0.2 mmol) in EtOAc (3 mL) at 23° C. was added palladium on carbon (0.02 g, 0.2 mmol). The reaction was placed under an atmosphere of hydrogen and stirred for four hours. The reaction was then filtered and concentrated in vacuo. The purity of 69.12B was deemed sufficient such that it was used directly in the next reaction.

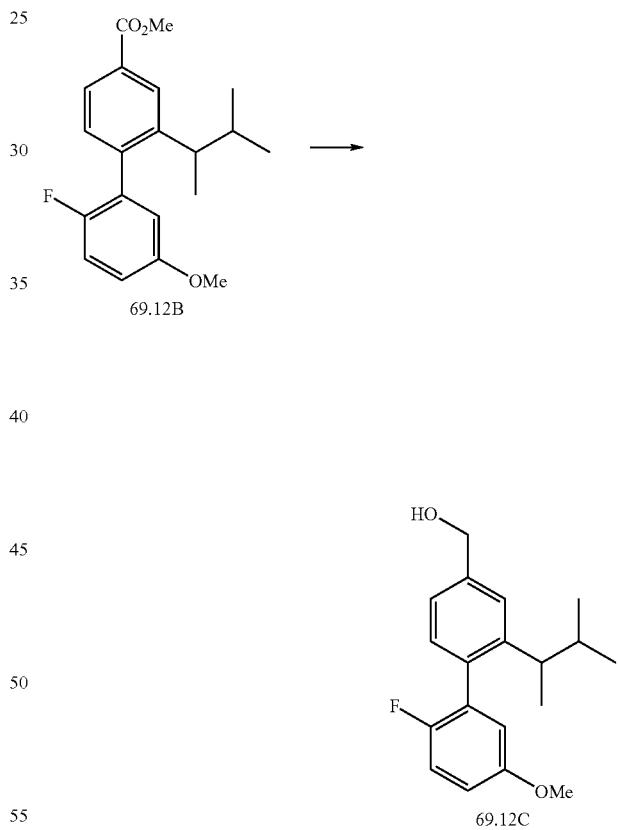

(2-(1,2-Dimethylpropyl)-2'-fluoro-5'-(methyloxy)-1,1'-biphenyl-4-yl)methanol (69.12C). To a stirred solution of 69.12B (0.050 g, 0.2 mmol) in THF (3 mL) at 0° C. was added LAH (0.3 mL, 0.3 mmol, 1.0M). The reaction was stirred for one hour and then 1N NaOH(aq) was added to the mixture. The reaction was extracted three times with EtOAc. After drying over anhydrous magnesium sulfate and filtering, the organic solvent was removed under reduced pressure and the product was purified on silica gel (0-20% EtOAc in hexanes) to yield 69.12C as a colorless oil (0.011 g, 24% yield).

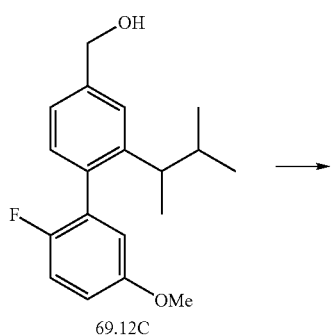

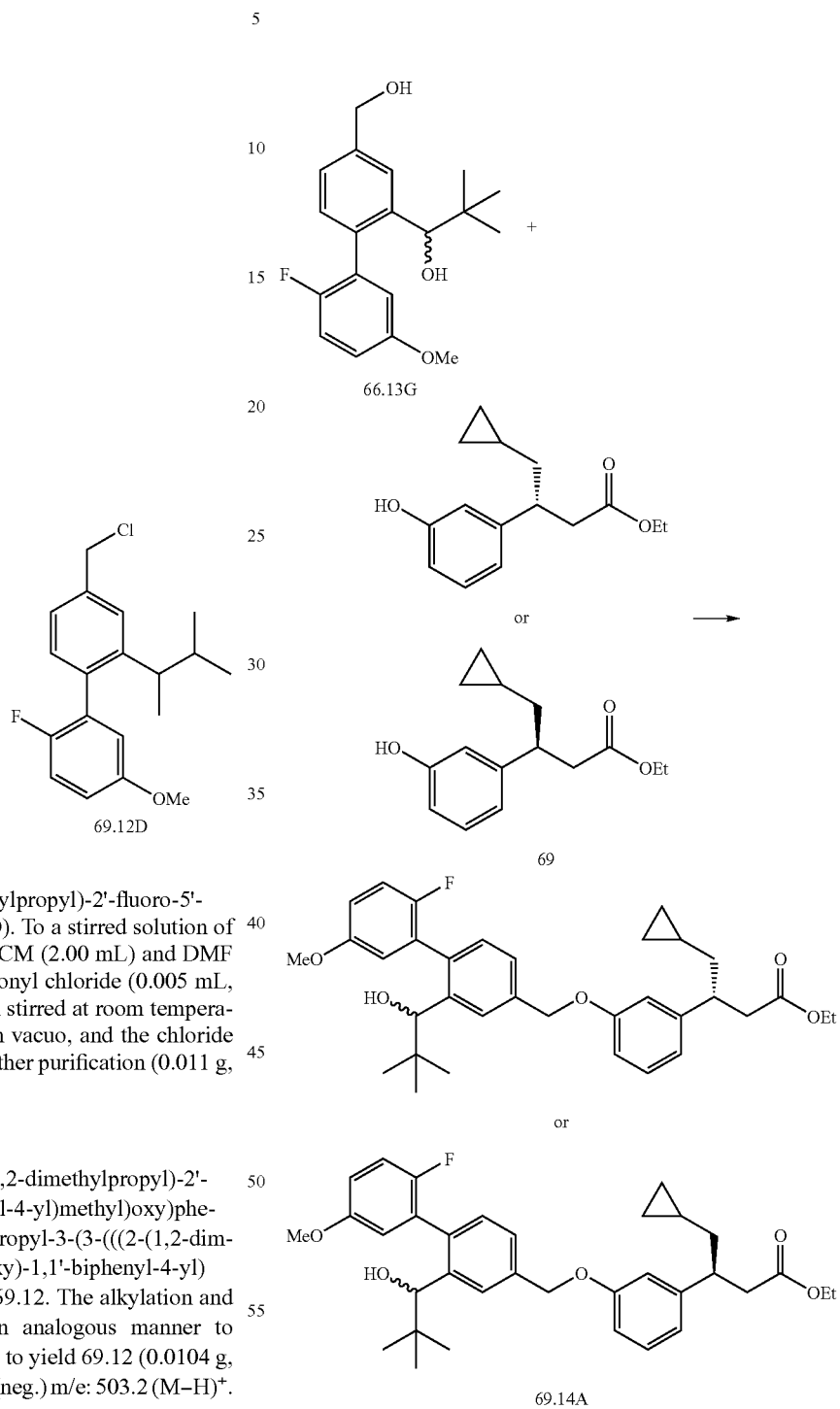

4-(Chloromethyl)-2-(1,2-dimethylpropyl)-2'-fluoro-5'-(methyloxy)-1,1'-biphenyl (69.12D). To a stirred solution of 69.12C (0.011 g, 0.04 mmol) in DCM (2.00 mL) and DMF (0.003 mL) at 0° C. was added thionyl chloride (0.005 mL, 0.07 mmol). The reaction was then stirred at room temperature for two hours, concentrated in vacuo, and the chloride 69.12D was used crude without further purification (0.011 g, 94% yield).

(3R)-4-Cyclopropyl-3-(3-(((2-(1,2-dimethylpropyl)-2'-fluoro-5'-(methyloxy)-1,1'-biphenyl-4-yl)methyl)oxy)phenyl)butanoic acid or (3S)-4-cyclopropyl-3-(3-(((2-(1,2-dimethylpropyl)-2'-fluoro-5'-(methyloxy)-1,1'-biphenyl-4-yl)methyl)oxy)phenyl)butanoic acid 69.12. The alkylation and hydrolysis were conducted in an analogous manner to Example 66.6 using 69.12D and 69 to yield 69.12 (0.0104 g, 52% yield over two steps). MS ESI (neg.) m/e: 503.2 (M–H)⁺.

(3R)-3-(3-(((2-Cyclooctyl-2'-fluoro-5'-(methyloxy)-1,1'-biphenyl-4-yl)methyl)oxy)phenyl)-4-cyclopropylbutanoic acid or (3S)-3-(3-(((2-cyclooctyl-2'-fluoro-5'-(methyloxy)-1,1'-biphenyl-4-yl)methyl)oxy)phenyl)-4-cyclopropylbutanoic acid (69.13). The alkylation and hydrolysis were conducted in an analogous manner to Example 66.6 using 66.16G and 69 to yield 69.13 (0.021 g, 63% yield over two steps). MS ESI (neg.) m/e: 543.2 (M–H)⁺.

Example 69.14

Ethyl (3R)-4-cyclopropyl-3-(3-(((2'-fluoro-2-(1-hydroxy-2,2-dimethylpropyl)-5'-(methyloxy)-1,1'-biphenyl-4-yl)methyl)oxy)phenyl)butanoate or ethyl (3S)-4-cyclopropyl-3-(3-(((2'-fluoro-2-(1-hydroxy-2,2-dimethylpropyl)-5'-(methyloxy)-1,1'-biphenyl-4-yl)methyl)oxy)phenyl)butanoate (69.14A). To a stirred solution of 69 (0.078 g, 0.31 mmol) in THF (2.00 mL, 24 mmol) at 23° C. was added 66.13G (0.050 g, 0.16 mmol) followed by triphenylphosphine (0.082 g, 0.31 mmol) and diethyl azodicarboxylate (0.049 mL, 0.31 mmol). The reaction was then stirred for 23 hours, diluted with water, and extracted three times with EtOAc. After drying over anhydrous magnesium sulfate and filtering, the organic solvent was removed under reduced pressure and the product was then purified on silica gel (0-20% EtOAc in hexanes) to yield 69.14A as a colorless oil (0.045 g, 52% yield).

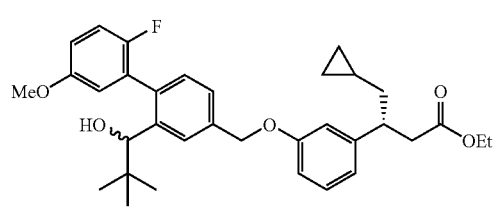

or

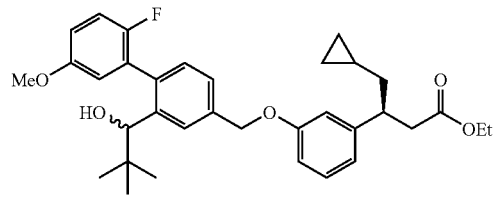

69.14A

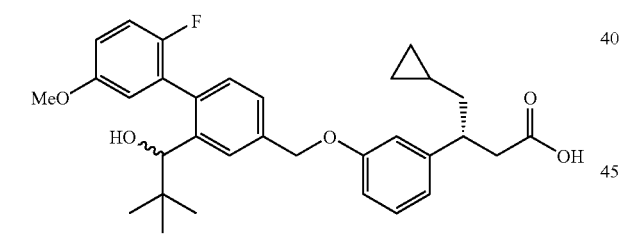

or

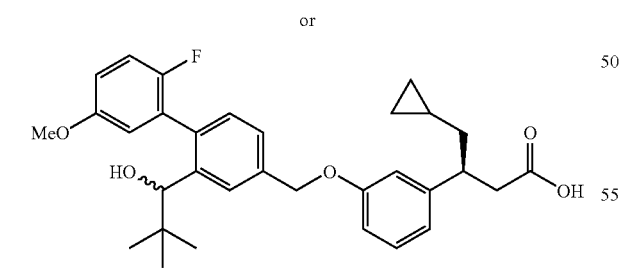

69.14

(3R)-4-Cyclopropyl-3-(3-(((2'-fluoro-2-(1-hydroxy-2,2-dimethylpropyl)-5'-(methyloxy)-1,1'-biphenyl-4-yl)methyl)oxy)phenyl)butanoic acid or (3S)-4-cyclopropyl-3-(3-(((2'-fluoro-2-(1-hydroxy-2,2-dimethylpropyl)-5'-(methyloxy)-1,1'-biphenyl-4-yl)methyl)oxy)phenyl)butanoic acid (69.14). The hydrolysis was conducted in an analogous manner to Example 66.6 using 69.14A to yield 69.14 (0.014 g, 98% yield). MS ESI (neg.) m/e: 519.2 (M–H)$^+$.

Example 69.15

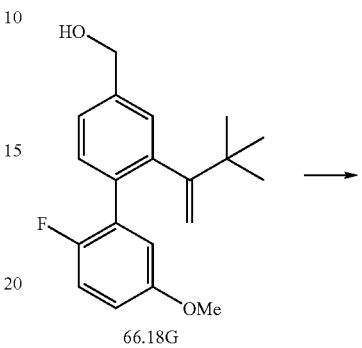

66.18G

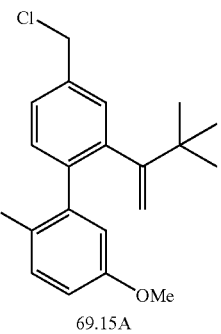

69.15A 4-(Chloromethyl)-2-(1(1,1-dimethylethyl)ethenyl)-2'-fluoro-5'-(methyloxy)-1,1'-biphenyl (69.15A). To a stirred solution of 66.18F (0.050 g, 0.16 mmol) in DCM (2.00 mL) at 0 C was added DMF (0.0012 mL), followed by thionyl chloride (0.023 mL, 0.32 mmol). The reaction was then stirred for 1.5 hours and then concentrated in vacuo. The product was purified on silica gel (0-10% EtOAc in hexanes) to yield 69.15A as a colorless oil (0.050 g, 94% yield).

(3R)-4-Cyclopropyl-3-(3-(((2-(1-(1,1-dimethylethyl)ethenyl)-2'-fluoro-5'-(methyloxy)-1,1'-biphenyl-4-yl)methyl)oxy)phenyl)butanoic acid or (3S)-4-cyclopropyl-3-(3-(((2-(1-(1,1-dimethylethyl)ethenyl)-2'-fluoro-5'-(methyloxy)-1,1'-biphenyl-4-yl)methyl)oxy)phenyl)butanoic acid (69.15). The alkylation and hydrolysis were conducted in an analogous manner to Example 66.6 using 69.15A and 69 to yield 69.15 (0.0342 g, 90% yield over two steps). MS ESI (neg.) m/e: 515.2 (M−H)⁺.

Example 69.16

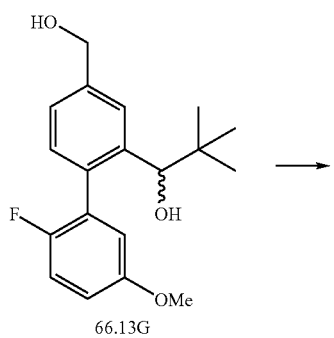
66.13G

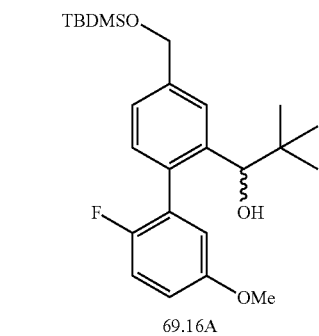
69.16A 1-(4-((((1,1-Dimethylethyl)(dimethyl)silyl)oxy)methyl)-2'-fluoro-5'-(methyloxy)-1,1'-biphenyl-2-yl)-2,2-dimethyl-1-propanol (69.16A). To a stirred solution of 66.13G (0.500 g, 2 mmol) in DCM (10.00 mL) at 23° C. was added tert-butyldimethylsilyl chloride (0.3 mL, 2 mmol), followed by TEA (0.3 mL, 2 mmol) and DMAP (0.02 g, 0.2 mmol). The reaction was then stirred for 16 hours and concentrated in vacuo. The product was purified on silica gel (0-10% EtOAc in hexanes) to yield 69.16A as a colorless oil (0.655 g, 96% yield).

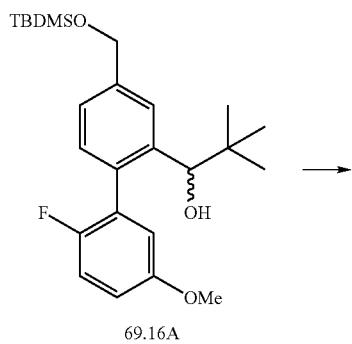
69.16A

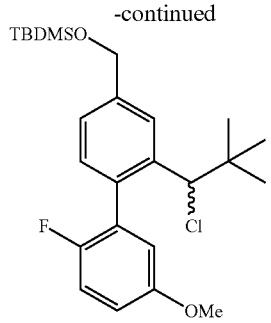
69.16B

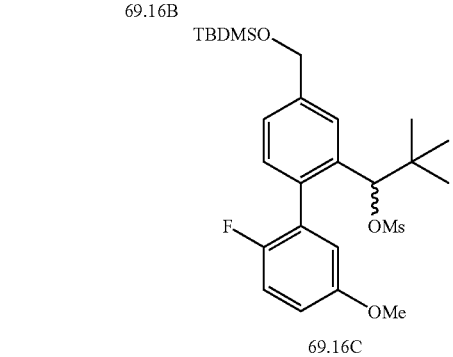
69.16C (((2-(1-Chloro-2,2-dimethylpropyl)-2'-fluoro-5'-(methyloxy)-1,1'-biphenyl-4-yl)methyl)oxy)(1,1-dimethylethyl)dimethylsilane (69.16B). To a stirred solution of 69.16A (0.200 g, 0.46 mmol) in DCM (5.00 mL) at 0° C. was added TEA (0.077 mL, 0.55 mmol), followed by methanesulfonyl chloride (0.043 mL, 0.55 mmol). The reaction was then stirred for 22 hours, diluted with water, and extracted three times with EtOAc. After drying over anhydrous magnesium sulfate and filtering, the organic solvent was removed under reduced pressure and the product was purified on silica gel (0-10% EtOAc in hexanes) to yield 69.16B as a colorless oil (0.090 g, 43% yield) and a further product 69.16C as a clear oil (0.050 g, 21% yield).

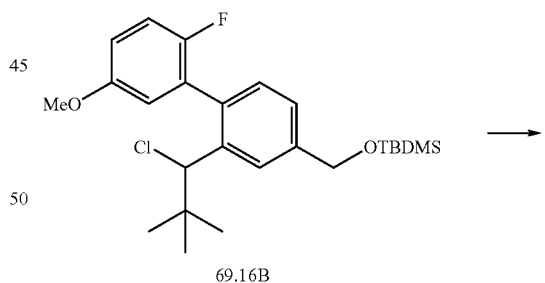
69.16B

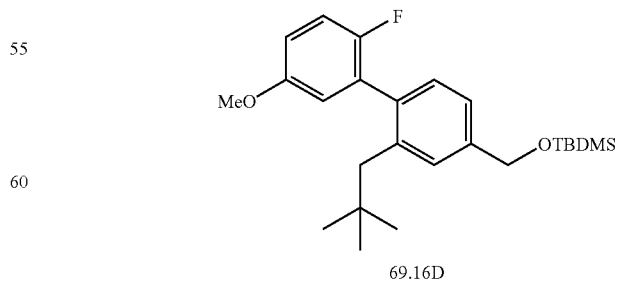
69.16D (1,1-Dimethylethyl)(((2-(2,2-dimethylpropyl)-2'-fluoro-5'-(methyloxy)-1,1'-biphenyl-4-yl)methyl)oxy)dimethylsilane (69.16D). To a stirred solution of 69.16B (0.015 g, 0.033 mmol) in toluene (2.00 mL) at 23° C. was added AIBN (0.00055 g, 0.0033 mmol) followed by tri-n-butyltin hydride (0.048 g, 0.17 mmol). The reaction was stirred at 100° C. for two hours. After which, the reaction was cooled to room temperature and concentrated in vacuo. The product was then purified on silica gel (0-10% EtOAc in hexanes) to yield 69.16D as a colorless oil (0.013 g, 94% yield).

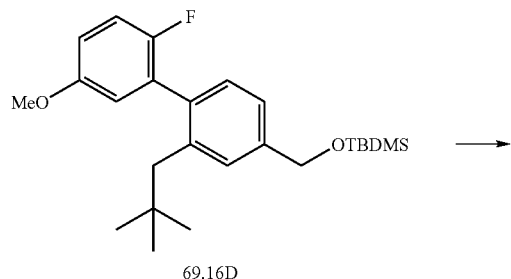

69.16D

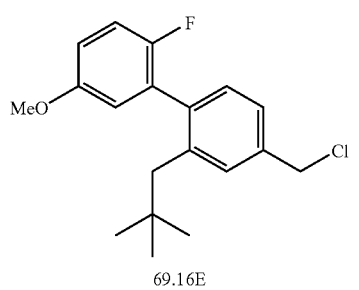

69.16E 4-(Chloromethyl)-2-(2,2-dimethylpropyl)-2'-fluoro-5'-(methyloxy)-1,1'-biphenyl (69.16E). The chlorination was conducted in an analogous manner to that employed in Example 66.6 using 69.16D (described here within) to yield chloride 69.16E.

(3R)-4-Cyclopropyl-3-(3-(((2-(2,2-dimethylpropyl)-2'-fluoro-5'-(methyloxy)-1,1'-biphenyl-4-yl)methyl)oxy)phenyl)butanoic acid or (3S)-4-cyclopropyl-3-(3-(((2-(2,2-dimethylpropyl)-2'-fluoro-5'-(methyloxy)-1,1'-biphenyl-4-yl)methyl)oxy)phenyl)butanoic acid (69.16). The alkylation and hydrolysis were conducted in an analogous manner to Example 66.6 using 69.16E and 69 to yield 69.16 (0.0286 g, 70% yield over two steps). MS ESI (neg.) m/e: 503.2 (M–H)⁺.

Example 69.17

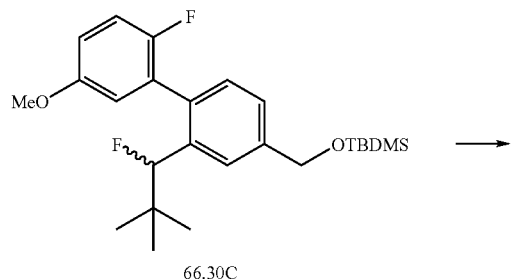

66.30C

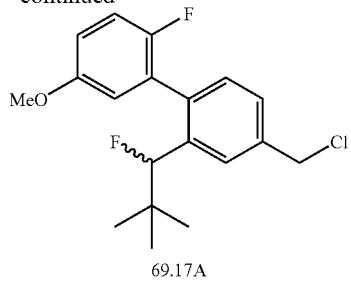

69.17A 4-(Chloromethyl)-2'-fluoro-2-(1-fluoro-2,2-dimethylpropyl)-5'-(methyloxy)-1,1'-biphenyl (69.17A). The chlorination of Example 66.30C was conducted in an analogous manner to that employed in Example 66.6 using 66.30C to yield chloride 69.17A.

(3R)-4-cyclopropyl-3-(3-(((2'-fluoro-2-(1-fluoro-2,2-dimethylpropyl)-5'-(methyloxy)-1,1'-biphenyl-4-yl)methyl)oxy)phenyl)butanoic acid or (3S)-4-cyclopropyl-3-(3-(((2'-fluoro-2-(1-fluoro-2,2-dimethylpropyl)-5'-(methyloxy)-1,1'-biphenyl-4-yl)methyl)oxy)phenyl)butanoic acid (69.17). The alkylation and hydrolysis were conducted in an analogous manner to Example 66.6 using 69.17A and 69 to yield 69.17 (0.0294 g, 70% yield over two steps). MS ESI (neg.) m/e: 521.2 (M–H)⁺.

Example 69.18

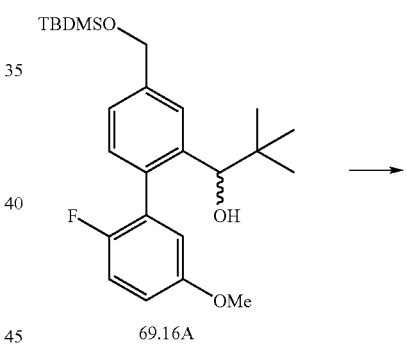

69.16A

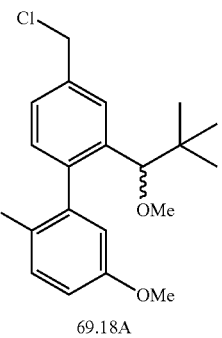

69.18A 4-(Chloromethyl)-2-(2,2-dimethyl-1-(methyloxy)propyl)-2'-fluoro-5'-(methyloxy)-1,1'-biphenyl (69.18B). The alkylation and chlorination were conducted in an analogous manner to that employed in Example 66.13 using 69.16A to yield chloride 69.18A.

(3R)-4-Cyclopropyl-3-(3-(((2-(2,2-dimethyl-1-(methyloxy)propyl)-2'-fluoro-5'-(methyloxy)-1,1'-biphenyl-4-yl)methyl)oxy)phenyl)butanoic acid or (3S)-4-cyclopropyl-3-

(3-(((2-(2,2-dimethyl-1-(methyloxy)propyl)-2'-fluoro-5'-(methyloxy)-1,1'-biphenyl-4-yl)methyl)oxy)phenyl) butanoic acid (69.18). The alkylation and hydrolysis were conducted in an analogous manner to Example 66.6 using 69.18A and 69 to yield 69.18 (0.0297 g, 69% yield over two steps). MS ESI (neg.) m/e: 533.2 (M–H)+.

Example 69.19

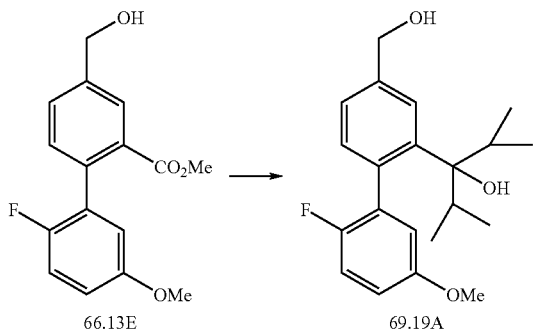

66.13E → 69.19A 3-(2'-Fluoro-4-(hydroxymethyl)-5'-(methyloxy)-1,1'-biphenyl-2-yl)-2,4-dimethyl-3-pentanol (69.19A). To a stirred solution of 66.13E (0.500 g, 1.7 mmol) in THF (17 mL, 1.7 mmol) at –78° C. was added isopropyllithium (8.6 mL, 6.0 mmol). The reaction was allowed to warm to room temperature and stirred for 22 hours. The reaction was then diluted with a saturated solution of ammonium chloride and extracted three times with EtOAc. After drying over anhydrous magnesium sulfate and filtering, the organic solvent was removed under reduced pressure and the product was then purified on silica gel (0-20% EtOAc in hexanes) to yield 69.19A as a yellow oil (0.450 g, 75% yield).

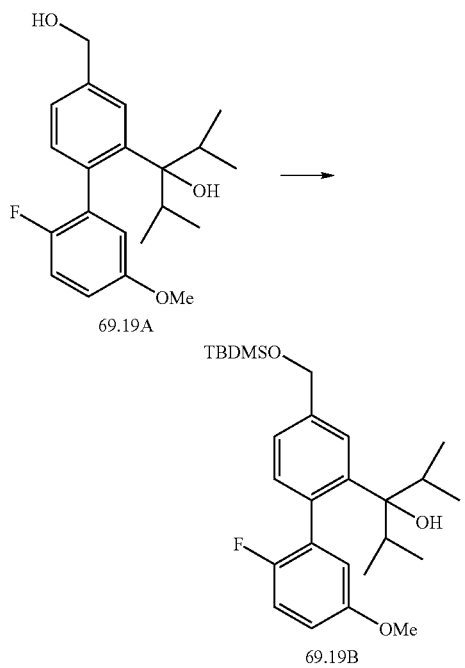

69.19A → 69.19B 3-(4-((((1,1-Dimethylethyl)(dimethyl)silyl)oxy)methyl)-2'-fluoro-5'-(methyloxy)-1,1'-biphenyl-2-yl)-2,4-dimethyl-3-pentanol (69.19B). To a stirred solution of 66.19A (0.500 g, 1 mmol) in DCM (10.00 mL) at 23° C. was added tert-butyldimethylsilyl chloride (0.3 mL, 2 mmol), followed by TEA (0.2 mL, 2 mmol) and DMAP (0.02 g, 0.1 mmol). The reaction was then stirred for 2.5 hours and then concentrated in vacuo. The product was purified on silica gel (0-10% EtOAc in hexanes) to yield 69.19B as a colorless oil (0.600 g, 90% yield).

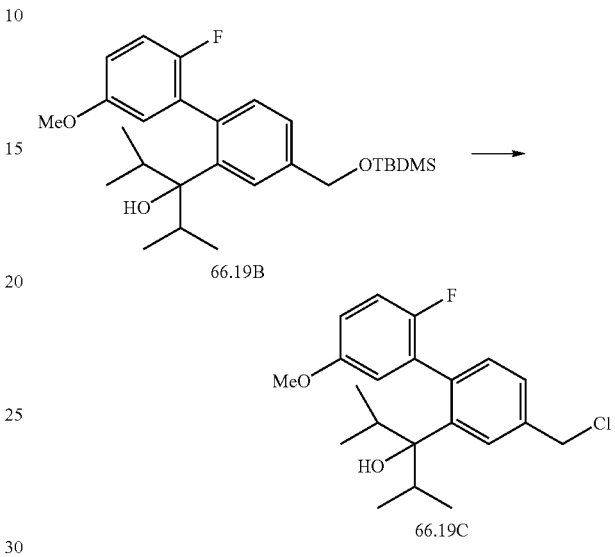

66.19B → 66.19C 3-(4-(Chloromethyl)-2'-fluoro-5'-(methyloxy)-1,1'-biphenyl-2-yl)-2,4-dimethyl-3-pentanol (69.19C). To a stirred solution of 69.19B (0.050 g, 0.1 mmol) in DCM (2.00 mL) at 23° C. was added DMF (0.0008 mL) followed by thionyl chloride (0.01 mL, 0.2 mmol). The reaction was then stirred for 1.5 hours and then concentrated in vacuo. The product was purified on silica gel (0-10% EtOAc in hexanes) to yield 69.19C as a colorless oil (0.04 g, 100% yield).

(3R)-4-Cyclopropyl-3-(3-(((2'-fluoro-2-(1-hydroxy-2-methyl-1-(1-methylethyl)propyl)-5'-(methyloxy)-1,1'-biphenyl-4-yl)methyl)oxy)phenyl)butanoic acid or (3S)-4-cyclopropyl-3-(3-(((2'-fluoro-2-(1-hydroxy-2-methyl-1-(1-methylethyl)propyl)-5'-(methyloxy)-1,1'-biphenyl-4-yl) methyl)oxy)phenyl)butanoic acid (69.19). The alkylation and hydrolysis were conducted in an analogous manner to Example 66.6 using 69.19C and 69 to yield 69.19 (0.0236 g, 71% yield over two steps). MS ESI (neg.) m/e: 547.3 (M–H)+.

(3R)-4-Cyclopropyl-3-(3-(((2-(2,2-dimethylpropanoyl)-2'-fluoro-5'-(methyloxy)-1,1'-biphenyl-4-yl)methyl)oxy) phenyl)butanoic acid or (3S)-4-cyclopropyl-3-(3-(((2-(2,2-dimethylpropanoyl)-2'-fluoro-5'-(methyloxy)-1,1'-biphenyl-4-yl)methyl)oxy)phenyl)butanoic acid (69.20). The Mitsunobu reaction and hydrolysis were conducted in an analogous manner to Example 26.5 (Mitsunobu) and 66.6 (hydrolysis) using 66.13F and 69 to yield 69.20. MS ESI (neg.) m/e: 517.3 (M–H)+.

(3R)-4-Cyclopropyl-3-(3-(((2'-fluoro-5'-(methyloxy)-2-(2-methylpropyl)-1,1'-biphenyl-4-yl)methyl)oxy)phenyl) butanoic acid or (3S)-4-cyclopropyl-3-(3-(((2'-fluoro-5'-(methyloxy)-2-(2-methylpropyl)-1,1'-biphenyl-4-yl)methyl) oxy)phenyl)butanoic acid (69.21). The alkylation and hydrolysis were conducted in an analogous manner to Example 66.6 using 66.20G and 69 to yield 69.21 (0.0405 g, 100% yield). MS ESI (neg.) m/e: 489.2 (M–H)+.

(3R)-4-Cyclopropyl-3-(3-(((2'-fluoro-5'-(methyloxy)-2-((1R)-1,2,2-trimethylpropyl)-1,1'-biphenyl-4-yl)methyl)

oxy)phenyl)butanoic acid or (3R)-4-cyclopropyl-3-(3-(((2'-fluoro-5'-(methyloxy)-2-((1S)-1,2,2-trimethylpropyl)-1,1'-biphenyl-4-yl)methyl)oxy)phenyl)butanoic acid or (3S)-4-cyclopropyl-3-(3-(((2'-fluoro-5'-(methyloxy)-2-((1R)-1,2,2-trimethylpropyl)-1,1'-biphenyl-4-yl)methyl)oxy)phenyl)butanoic acid or (3S)-4-cyclopropyl-3-(3-(((2'-fluoro-5'-(methyloxy)-2-((1S)-1,2,2-trimethylpropyl)-1,1'-biphenyl-4-yl)methyl)oxy)phenyl)butanoic acid (69.22). The alkylation and hydrolysis were conducted in an analogous manner to Example 66.6 using 69 and 66.18M or 66.18N (derived from peak two of the chiral separation of 66.18J on the OD-column, described herein) to yield 69.22 (0.0315 g, 75% yield over the two steps). MS ESI (neg.) m/e: 517.3 (M–H)$^+$.

Example 69.23

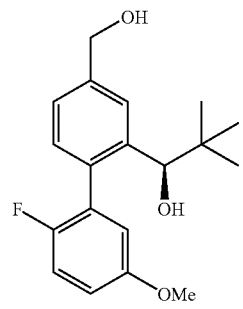

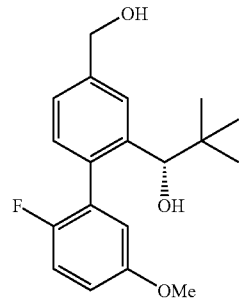

66.13H or 66.13I

+

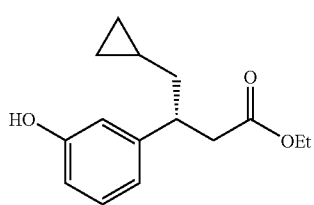

or

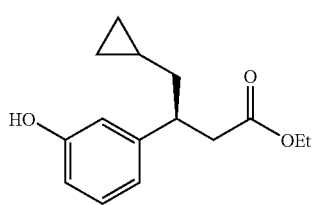

69

→

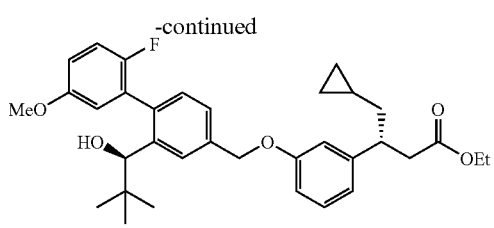

or

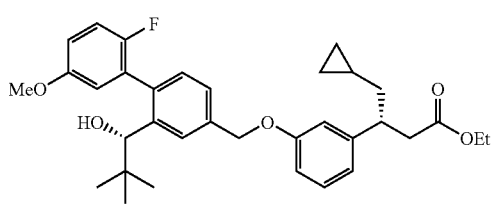

or

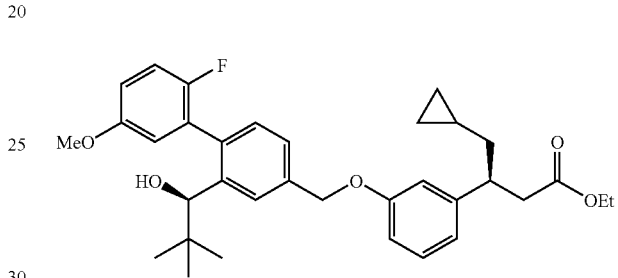

or

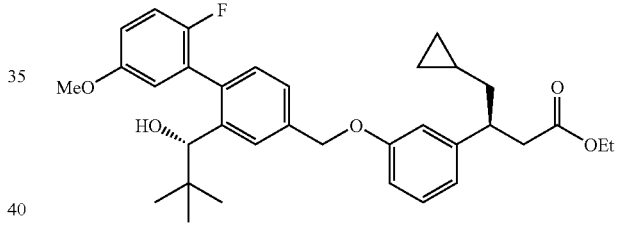

69.23A

Ethyl (3R)-4-cyclopropyl-3-(3-(((2'-fluoro-2-((1R)-1-hydroxy-2,2-dimethylpropyl)-5'-(methyloxy)-1,1'-biphenyl-4-yl)methyl)oxy)phenyl)butanoate or ethyl (3R)-4-cyclopropyl-3-(3-(((2'-fluoro-2-((1S)-1-hydroxy-2,2-dimethylpropyl)-5'-(methyloxy)-1,1'-biphenyl-4-yl)methyl)oxy)phenyl)butanoate or ethyl (3S)-4-cyclopropyl-3-(3-(((2'-fluoro-2-((1R)-1-hydroxy-2,2-dimethylpropyl)-5'-(methyloxy)-1,1'-biphenyl-4-yl)methyl)oxy)phenyl)butanoate or ethyl (3S)-4-cyclopropyl-3-(3-(((2'-fluoro-2-((1S)-1-hydroxy-2,2-dimethylpropyl)-5'-(methyloxy)-1,1'-biphenyl-4-yl)methyl)oxy)phenyl)butanoate (69.23A). To a stirred solution of 69 (0.500 g, 2.0 mmol) in THF (20.00 mL, 244 mmol) at 23° C. was added 66.13H or 66.13I (0.64 g, 2.0 mmol, peak two from the chiral separation of 66.13G) followed by triphenylphosphine (0.79 g, 3.0 mmol), and then by dropwise addition of DEAD (0.48 mL, 3.0 mmol) over two hours. The reaction was then stirred for 21 hours. The reaction was then diluted with water and extracted three times with EtOAc. After drying over anhydrous magnesium sulfate and filtering, the organic solvent was removed under reduced pressure and the product was then purified on silica gel (0-20% EtOAc in hexanes) to yield 69.23A as a colorless oil (1.00 g, 91% yield).

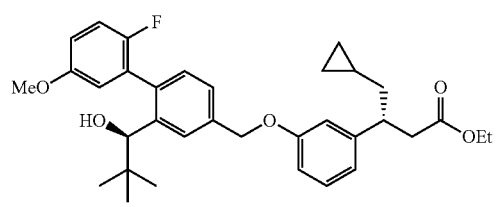

or

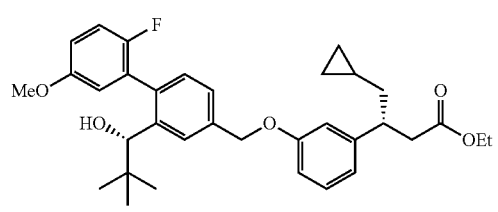

or

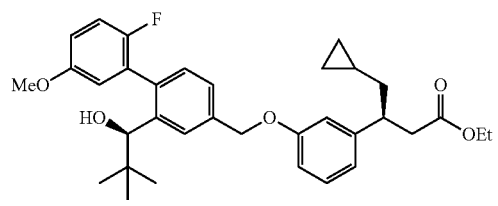

or

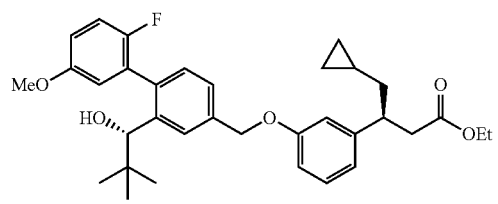

69.23A

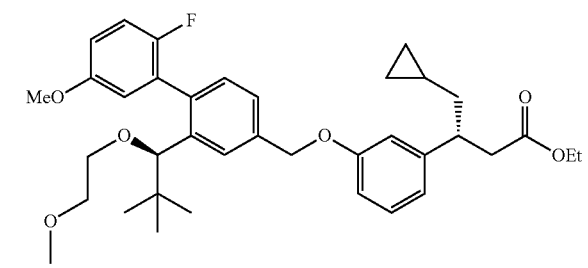

or

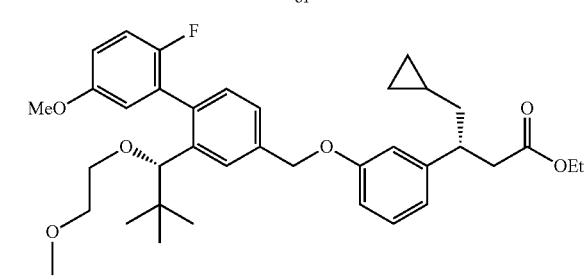

or

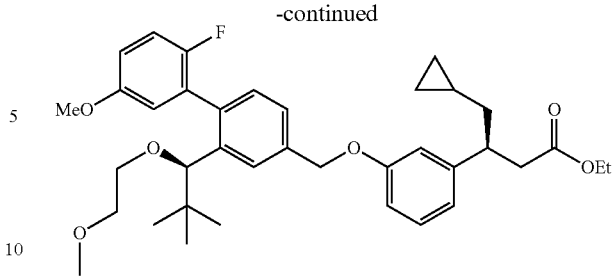

or

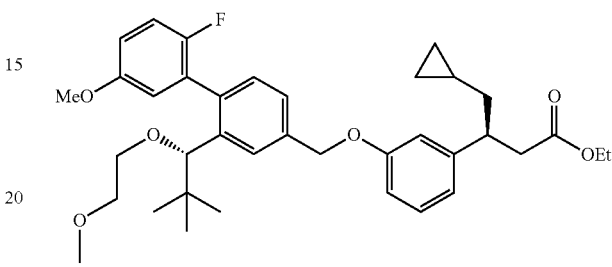

69.23B

Ethyl (3R)-4-cyclopropyl-3-(3-(((2-((1R)-2,2-dimethyl-1-((2-(methyloxy)ethyl)oxy)propyl)-2'-fluoro-5'-(methyloxy)-1,1'-biphenyl-4-yl)methyl)oxy)phenyl)butanoate or ethyl (3R)-4-cyclopropyl-3-(3-(((2-((1S)-2,2-dimethyl-1-((2-(methyloxy)ethyl)oxy)propyl)-2'-fluoro-5'-(methyloxy)-1,1'-biphenyl-4-yl)methyl)oxy)phenyl)butanoate or ethyl (3S)-4-cyclopropyl-3-(3-(((2-((1R)-2,2-dimethyl-1-((2-(methyloxy)ethyl)oxy)propyl)-2'-fluoro-5'-(methyloxy)-1,1'-biphenyl-4-yl)methyl)oxy)phenyl)butanoate or ethyl (3S)-4-cyclopropyl-3-(3-(((2-((1S)-2,2-dimethyl-1-((2-(methyloxy)ethyl)oxy)propyl)-2'-fluoro-5'-(methyloxy)-1,1'-biphenyl-4-yl)methyl)oxy)phenyl)butanoate (69.23B). To a stirred solution of 69.23A (0.050 g, 0.091 mmol) in DMF (2.00 mL) at 23° C. was added 1-bromo-2-methoxyethane (0.019 g, 0.14 mmol) (commercially available from Aldrich) followed by sodium hydride (0.0026 g, 0.11 mmol). The reaction was stirred at 60° C. for 21 hours, diluted with water and extracted three times with EtOAc. After drying over anhydrous magnesium sulfate and filtering, the organic solvent was removed under reduced pressure and the product was then purified on silica gel (0-5% EtOAc in hexanes) to yield 69.23B as a colorless oil (0.018 g, 33% yield)

(3R)-4-Cyclopropyl-3-(3-(((2-((1R)-2,2-dimethyl-1-((2-(methyloxy)ethyl)oxy)propyl)-2'-fluoro-5'-(methyloxy)-1,1'-biphenyl-4-yl)methyl)oxy)phenyl)butanoic acid or (3R)-4-cyclopropyl-3-(3-(((2-((1S)-2,2-dimethyl-1-((2-(methyloxy)ethyl)oxy)propyl)-2'-fluoro-5'-(methyloxy)-1,1'-biphenyl-4-yl)methyl)oxy)phenyl)butanoic acid or (3S)-4-cyclopropyl-3-(3-(((2-((1R)-2,2-dimethyl-1-((2-(methyloxy)ethyl)oxy)propyl)-2'-fluoro-5'-(methyloxy)-1,1'-biphenyl-4-yl)methyl)oxy)phenyl)butanoic acid or (3S)-4-cyclopropyl-3-(3-(((2-((1S)-2,2-dimethyl-1-((2-(methyloxy)ethyl)oxy)propyl)-2'-fluoro-5'-(methyloxy)-1,1'-biphenyl-4-yl)methyl)oxy)phenyl)butanoic acid (69.23). The hydrolysis of 69.23B was conducted in an analogous manner to Example 66.6 to yield 69.23 (0.0072 g, 42% yield). MS ESI (neg.) m/e: 577.3 (M−H)+.

Example 69.24

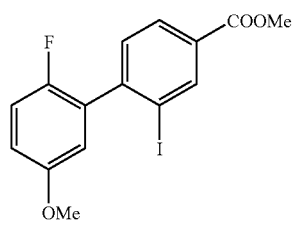

66.15D

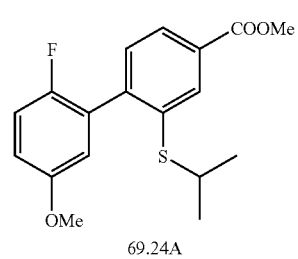

69.24A

2'-Fluoro-2-isopropylsulfanyl-5'-methoxy-biphenyl-4-carboxylic acid methyl ester (69.24A). A tube was charged with 66.15D (213 mg, 552 µmol), N-ethyl-N-isopropylpropan-2-amine (143 mg, 1103 µmol) and toluene, evacuated and back-filled with nitrogen three times. Pd$_2$(dba)$_3$, 4,5-bis(diphenylphosphino)-9,9-dimethyl-9H-xanthene (31.9 mg, 55.2 µmol) and propane-2-thiol (63.0 mg, 827 µmol) were added to the mixture and then the mixture was degassed three times. The suspension was refluxed overnight, filtered, and concentrated to give a residue which was purified by silica gel chromatography to give 69.24A as a pale yellow solid (164 mg, 89%). MS ESI m/e: 335.2 (M+1)+.

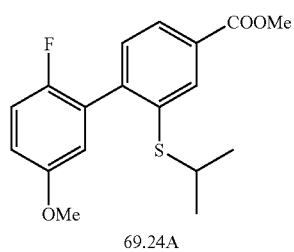

69.24A

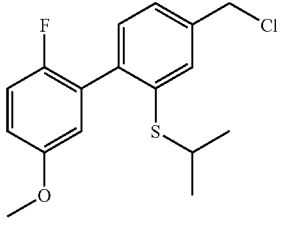

69.24B

4-Chloromethyl-2'-fluoro-2-isopropylsulfanyl-5'-methoxy-biphenyl (69.24B). The reduction and chlorination of 69.24A was conducted in an analogous manner to that used to synthesize 8.10. MS ESI m/e: 325.10 (M+H)+.

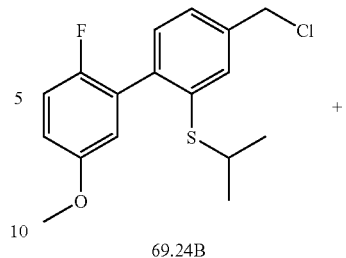

69.24B

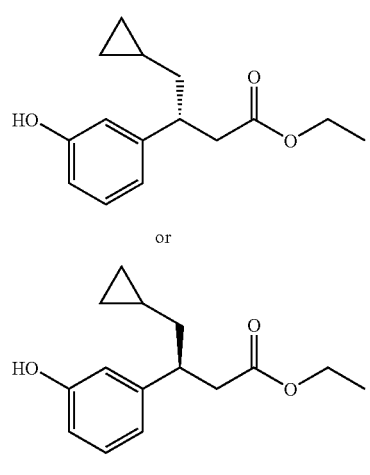

69

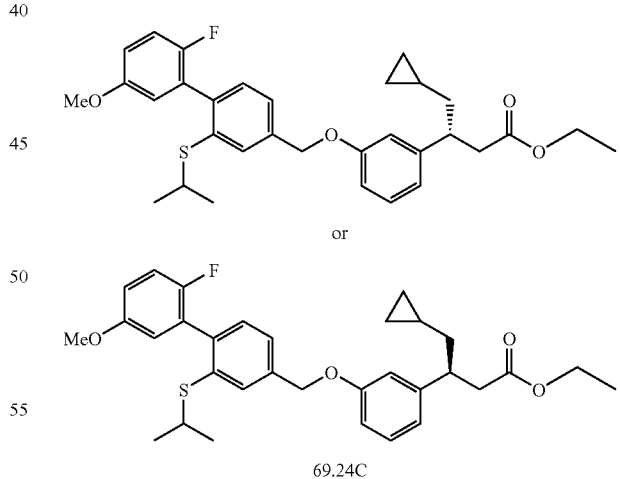

69.24C (R)-4-Cyclopropyl-3-[3-(2'-fluoro-2-isopropylsulfanyl-5'-methoxy-biphenyl-4-ylmethoxy)-phenyl]-butyric acid ethyl ester or (S)-4-cyclopropyl-3-[3-(2'-fluoro-2-isopropylsulfanyl-5'-methoxy-biphenyl-4-ylmethoxy)-phenyl]-butyric acid ethyl ester (69.24C) Compound 69.24C was synthesized by a method analogous to the method used for preparation of compound 66.13P from 69.24F and 69. MS ESI m/e: 537.3 (M+H)+.

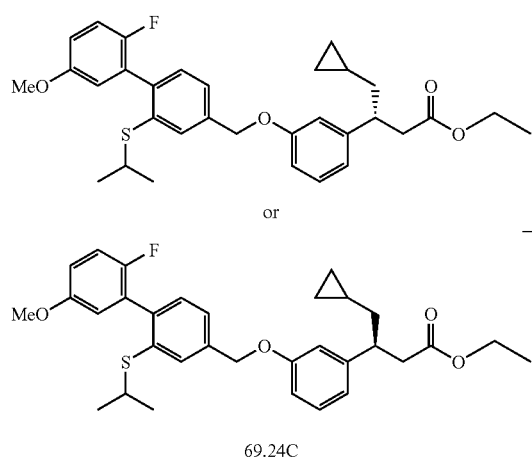

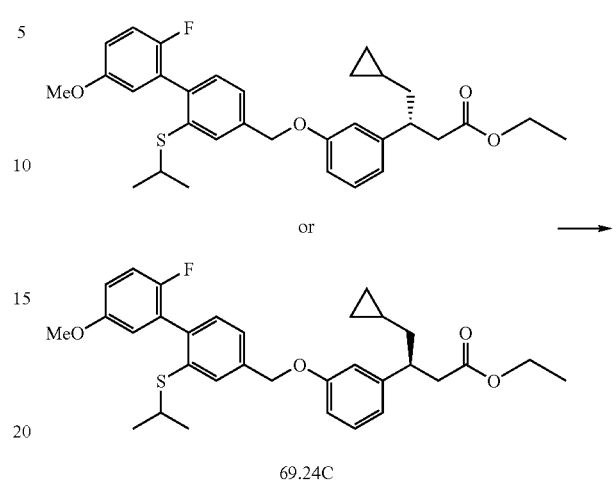

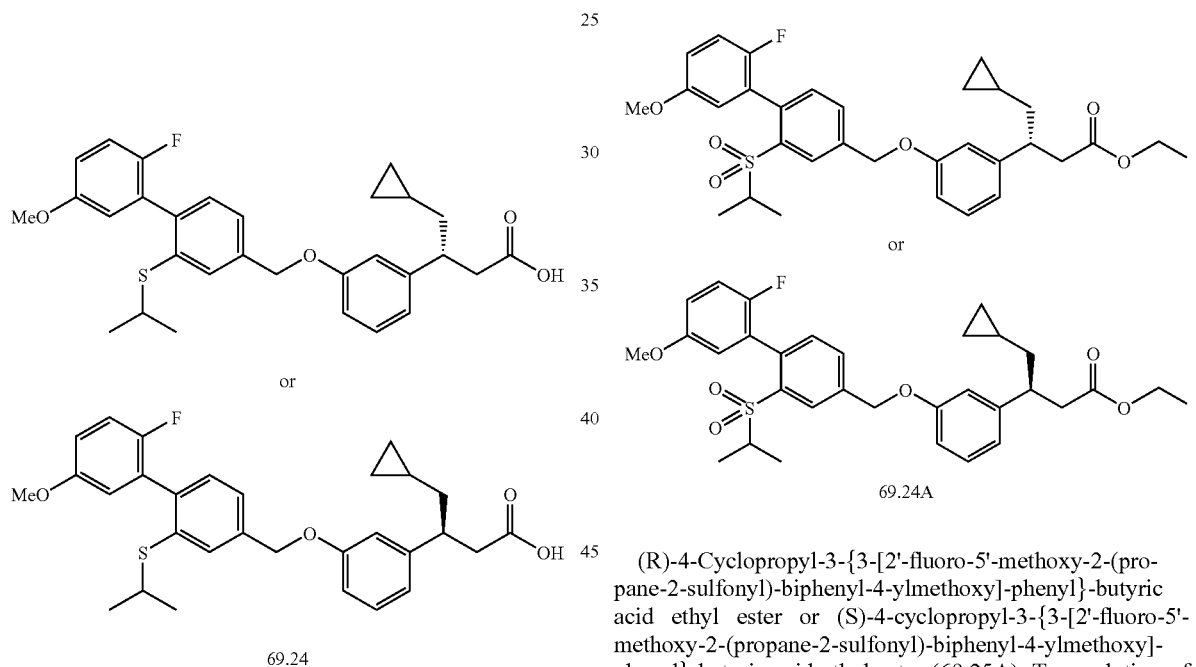

(R)-4-Cyclopropyl-3-[3-(2'-fluoro-2-isopropylsulfanyl-5'-methoxy-biphenyl-4-ylmethoxy)-phenyl]-butyric acid or (S)-4-cyclopropyl-3-[3-(2'-fluoro-2-isopropylsulfanyl-5'-methoxy-biphenyl-4-ylmethoxy)-phenyl]-butyric acid (69.24). Compound 69.24 was synthesized by a method analogous to the method used for compound 66.13 from 69.24C. MS ESI m/e: 526.2 (M+18). $^1$H NMR (400 MHz, CDCl$_3$) δ ppm 7.52 (s, 1H), 7.29 (m, 1H), 7.24 (d, J=8 Hz, 1H), 7.20 (t, J=8 Hz, 1H), 7.01 (t, J=8 Hz, 1H) 6.83 (m, 4H), 6.76 (m, 1H), 5.06 (s, 2H), 3.77 (s, 3H), 3.20 (m, 2H), 2.72 (m, 1H), 2.65 (m, 1H), 1.67 (m, 1H), 1.32 (m, 1H), 1.15 (d, J=8 Hz, 6H), 0.49 (m, 1H), 0.34 (m, 2H), 0.04 (m, 2H).

Example 69.25

(R)-4-Cyclopropyl-3-{3-[2'-fluoro-5'-methoxy-2-(propane-2-sulfonyl)-biphenyl-4-ylmethoxy]-phenyl}-butyric acid ethyl ester or (S)-4-cyclopropyl-3-{3-[2'-fluoro-5'-methoxy-2-(propane-2-sulfonyl)-biphenyl-4-ylmethoxy]-phenyl}-butyric acid ethyl ester (69.25A). To a solution of 69.24C (70 mg, 130 μmol) in DCM, was added 3-chloroperoxybenzoic acid (45 mg, 261 μmol) in one portion. The resulting mixture was stirred overnight and diluted with EtOAc. The organic phase was washed with saturated NaHCO$_3$, water and brine, and dried over sodium sulfate. Solvent was removed in vacuo to give a residue which was purified by chromatography to give the product as an oil (60 mg, 81%).

(R)-4-Cyclopropyl-3-{3-[2'-fluoro-5'-methoxy-2-(propane-2-sulfonyl)-biphenyl-4-ylmethoxy]-phenyl}-butyric acid or (S)-4-cyclopropyl-3-{3-[2'-fluoro-5'-methoxy-2-(propane-2-sulfonyl)-biphenyl-4-ylmethoxy]-phenyl}-butyric acid (69.25). Compound 69.25A was hydrolyzed by a method analogous to the method used for compound 66.13 using 69.25A. MS ESI m/e: 558.30 (M+18)$^+$. $^1$H NMR (400 MHz, CDCl$_3$) δ ppm 8.18 (s, 1H), 7.71 (d, J=8 Hz, 1H), 7.36 (d, J=8 Hz, 1H), 7.20 (t, J=8 Hz, 1H), 7.01 (m, 1H), 6.78-6.90 (m, 5H), 5.15 (s, 2H), 3.76 (s, 3H), 3.17 (m, 1H), 2.83 (m, 1H), 2.72 (m, 1H), 2.63 (m, 1H), 1.67 (m, 1H), 1.34 (m, 1H), 1.19 (d, J=8 Hz, 3H), 1.05 (d, J=8 Hz, 3H), 0.37 (m, 1H), 0.34 (m, 2H), 0.04 (m, 2H).

Example 69.26

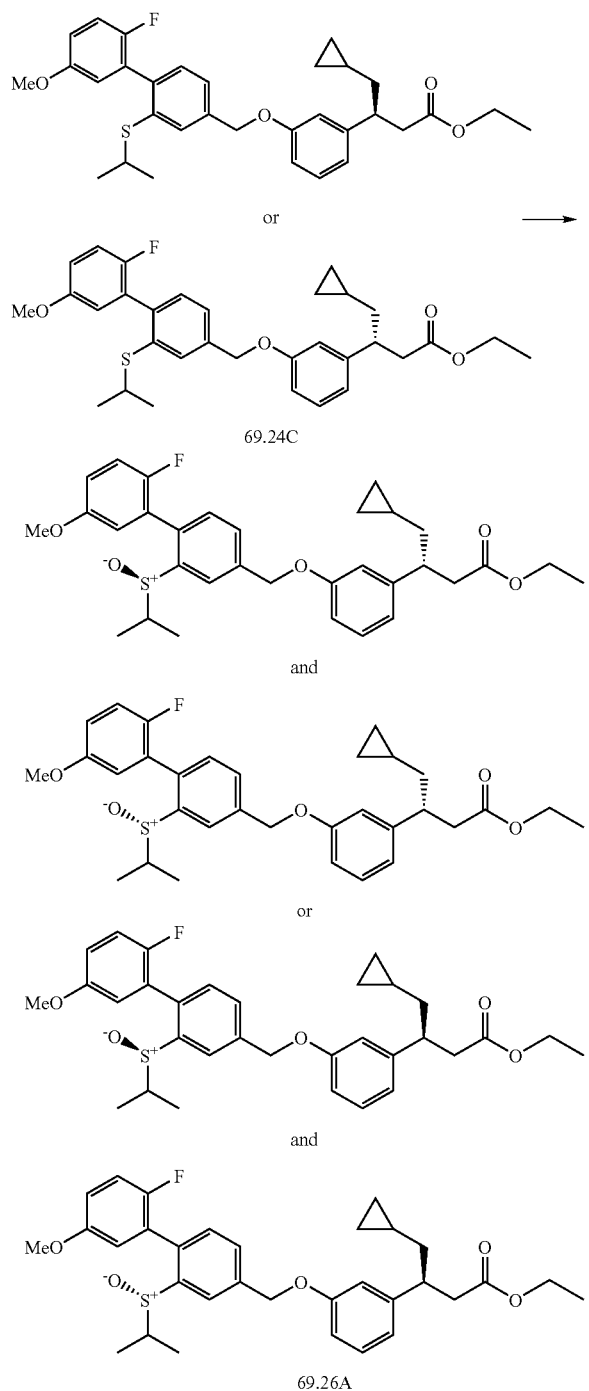

(R)-4-Cyclopropyl-3-{3-[2'-fluoro-5'-methoxy-2-(propane-2-sulfinyl)-biphenyl-4-ylmethoxy]-phenyl}-butyric acid ethyl ester or (S)-4-Cyclopropyl-3-{3-[2'-fluoro-5'-methoxy-2-(propane-2-sulfinyl)-biphenyl-4-ylmethoxy]-phenyl}-butyric acid ethyl ester (69.26A). To a solution of 69.24C (63.6 mg, 119 μmol) in DCM (5 mL) at 0° C., was added 3-chloroperoxybenzoic acid (20.4 mg, 119 μmol) in one portion. The mixture was stirred at room temperature overnight and then diluted with EtOAc. The organic layer was washed with saturated NaHCO₃, water and brine, and dried over sodium sulfate. After filtration, solvent was removed in vacuo to give a residue which was purified by chromatography to give an oil (48 mg, 73%).

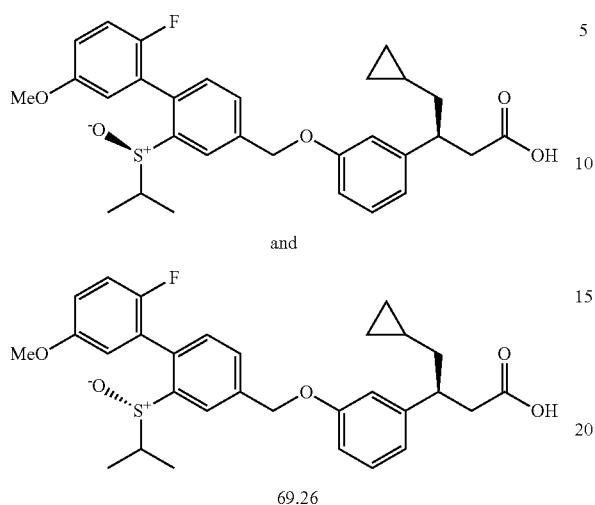

69.26

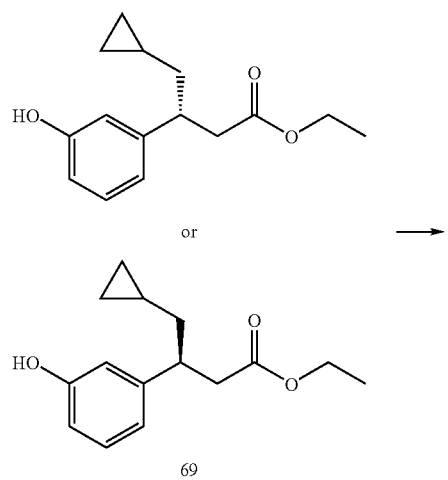

69

(R)-4-Cyclopropyl-3-{3-[2'-fluoro-5'-methoxy-2-(propane-2-sulfinyl)-biphenyl-4-ylmethoxy]-phenyl}-butyric acid or (S)-4-cyclopropyl-3-{3-[2'-fluoro-5'-methoxy-2-(propane-2-sulfinyl)-biphenyl-4-ylmethoxy]-phenyl}-butyric acid (69.26). Compound 69.26 was prepared by a method analogous to the method used to synthesize compound 66.13 using 69.26A. MS ESI m/e: 525.2 (M+18)$^+$. $^1$H NMR (400 MHz, CDCl$_3$) δ ppm 7.94 (d, J=8 Hz, 1H), 7.61 (m, 1H), 7.35 (t, J=8 Hz, 1H), 7.18 (dt, J=8 Hz, J=12 Hz, 1H), 7.07 (dt, J=4 Hz, J=8 Hz, 1H), 6.88 (m, 5H), 5.26 (s, 2H), 3.78 (s, 1.5H), 3.79 (s, 1.5H), 3.17 (m, 1H), 2.74 (m, 1H), 2.57 (m, 2H), 1.75 (m, 1H), 1.37 (m, 1H), 1.03 (d, J=8 Hz, 3H), 0.94 (dd, J=4 Hz, J=8 Hz, 3H), 0.56 (m, 1H), 0.38 (m, 2H), 0.04 (m, 2H).

Example of 69.27

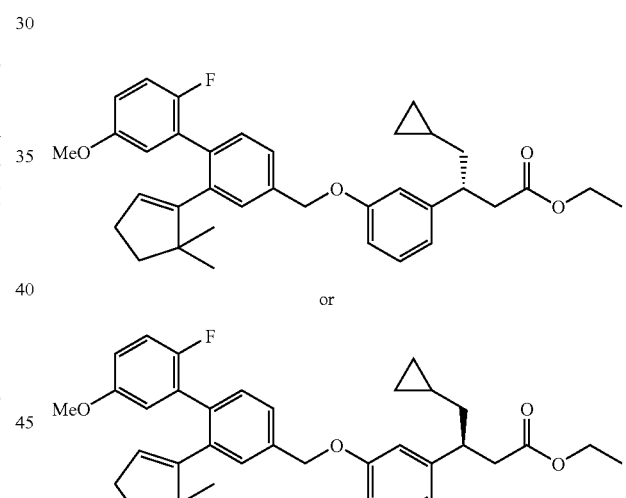

69.27A

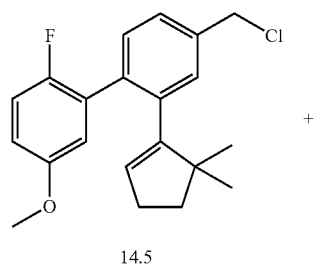

14.5

+

(R)-4-Cyclopropyl-3-{3-[2-(5,5-dimethyl-cyclopent-1-enyl)-2'-fluoro-5'-methoxy-biphenyl-4-ylmethoxy]-phenyl}-butyric acid ethyl ester or (S)-4-cyclopropyl-3-{3-[2-(5,5-dimethyl-cyclopent-1-enyl)-2'-fluoro-5'-methoxy-biphenyl-4-ylmethoxy]-phenyl}-butyric acid ethyl ester (69.27A). Compound 69.27A was synthesized by a method analogous to the method used in the synthesis of 66.13P using 14.5 and 69. MS ESI m/e: 557.3 (M+H)$^+$.

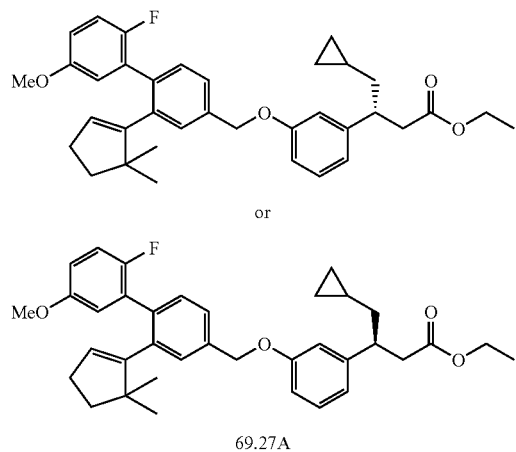

69.27A

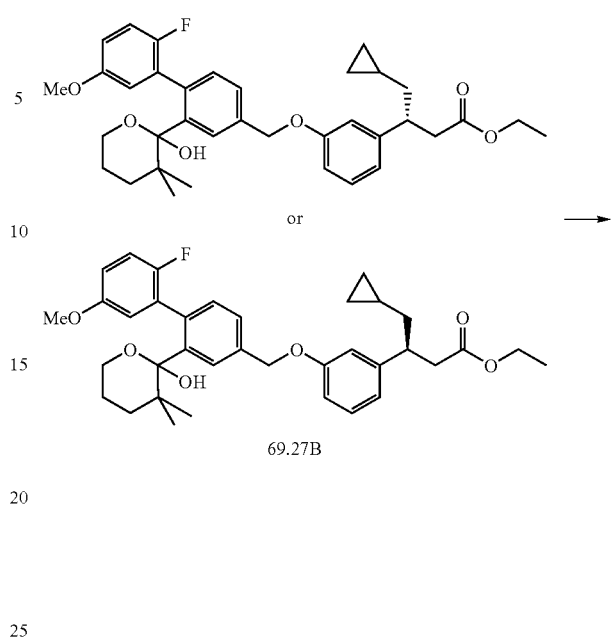

69.27B

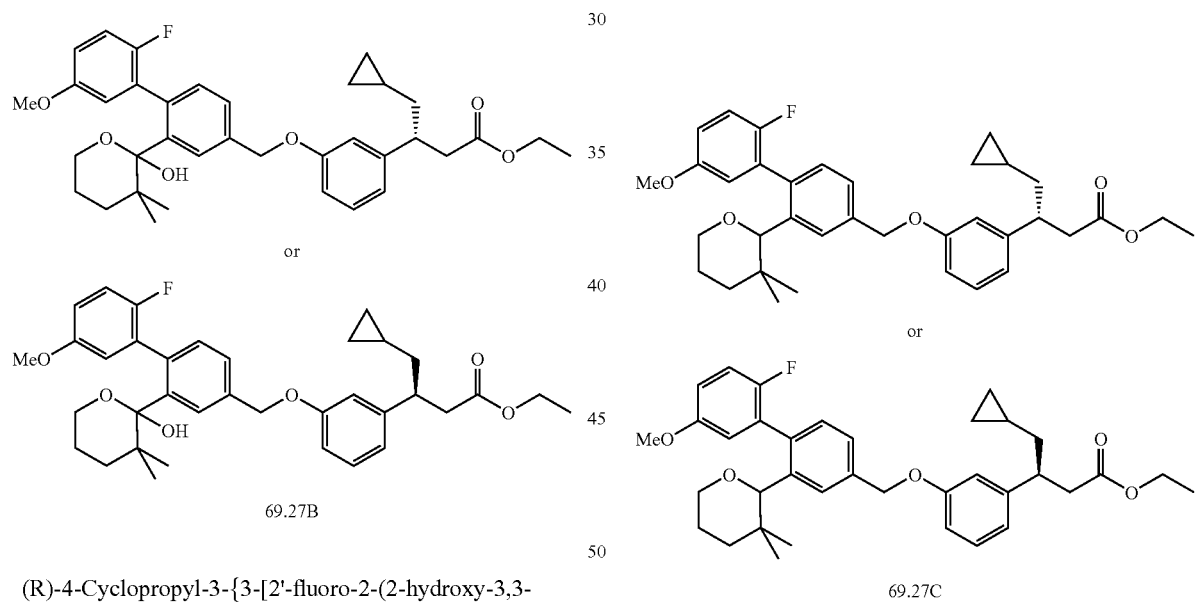

69.27B 69.27C (R)-4-Cyclopropyl-3-{3-[2'-fluoro-2-(2-hydroxy-3,3-dimethyl-tetrahydro-pyran-2-yl)-5'-methoxy-biphenyl-4-yl-methoxy]-phenyl}-butyric acid ethyl ester or (S)-4-cyclopropyl-3-{3-[2'-fluoro-2-(2-hydroxy-3,3-dimethyl-tetrahydro-pyran-2-yl)-5'-methoxy-biphenyl-4-ylmethoxy]-phenyl}-butyric acid ethyl ester (69.27B) To a solution of 69.27A (40 mg, 72 μmol) in a mixed solvent of DCM (0.5 mL) and MeOH (3 mL) at −78° C., was bubbled 03 for 10 minutes. Nitrogen was then bubbled into the solution for 10 minutes. Sodium borohydride (8.2 mg, 216 μmol) was added, and the solution was warmed to room temperature overnight. Solvent was evaporated, the residue was diluted with EtOAc, the organic layer was washed with saturated NaHCO$_3$, water, and brine. The organic layer was then dried, filtered, evaporated in vacuo to yield 69.27B (36 mg) which was used without purification. MS ESI m/e: 608.3 (M+18)$^+$.

(R)-4-Cyclopropyl-3-{3-[2-(3,3-dimethyl-tetrahydro-pyran-2-yl)-2'-fluoro-5'-methoxy-biphenyl-4-ylmethoxy]-phenyl}-butyric acid ethyl ester or (S)-4-cyclopropyl-3-{3-[2-(3,3-dimethyl-tetrahydro-pyran-2-yl)-2'-fluoro-5'-methoxy-biphenyl-4-ylmethoxy]-phenyl}-butyric acid ethyl ester (69.27C). To a solution of 66.27B (30 mg, 51 μmol) in DCM (3 mL) at −78° C., was added 2,2,2-trifluoroacetic acid (TFA) (58 mg, 508 μmol). The mixture was stirred for 15 minutes and then triethylsilane (59 mg, 508 μmol) was added and the mixture was slowly returned to room temperature over 1 hour. The solvent was removed in vacuo to give a residue which was purified by silica gel chromatography to give an oil (20 mg, 69%). MS ESI m/e: 575.3 (M+H)$^+$.

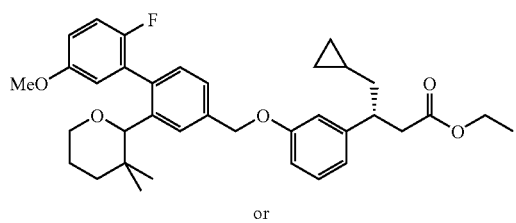

or

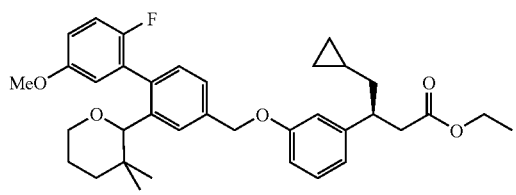

69.27C

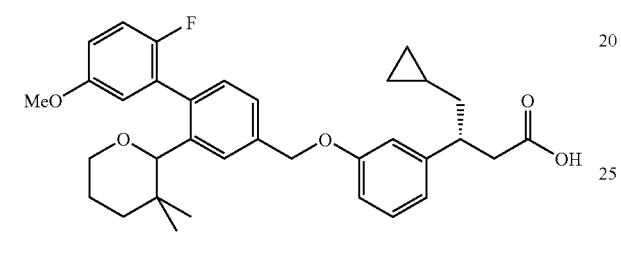

or

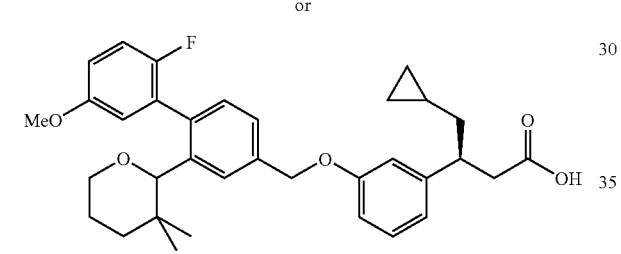

69.27

(R)-4-Cyclopropyl-3-{3-[2-(3,3-dimethyl-tetrahydro-pyran-2-yl)-2'-fluoro-5'-methoxy-biphenyl-4-ylmethoxy]-phenyl}-butyric acid or (S)-4-cyclopropyl-3-{3-[2-(3,3-dimethyl-tetrahydro-pyran-2-yl)-2'-fluoro-5'-methoxy-biphenyl-4-ylmethoxy]-phenyl}-butyric acid (69.27). Compound 69.27 was synthesized from 69.27C by a method analogous to the method used to prepare compound 66.13 from 66.13P. MS ESI m/e: 564.3 (M+18))⁺. ¹H NMR (400 MHz, CDCl₃) δ ppm 7.54 (m, 1H), 7.38 (m, 1H), 7.17 (m, 2H), 7.01 (m, 1H), 6.78 (m, 5H), 5.12 (m, 2H), 4.43 (m, 1/2H), 4.19 (s, 1/2H), 4.15 (m, 1H), 3.76 (m, 3H), 3.42 (m, 1H), 3.17 (m, 1 H), 2.68 (m, 1H), 2.40-2.56 (m, 1H), 1.89 (m, 1H), 1.69 (m, 1H), 1.32 (m, 4H), 0.87 (m, 3H), 0.51 (m, 1H), 0.35 (m, 5H), 0.03 (m, 2H).

(3R)-4-Cyclopropyl-3-(3-(((2'-fluoro-5'-(methyloxy)-2-(1-piperidinyl)-1,1'-biphenyl-4-yl)methyl)oxy)phenyl)butanoic acid or (3S)-4-cyclopropyl-3-(3-(((2'-fluoro-5'-(methyloxy)-2-(1-piperidinyl)-1,1'-biphenyl-4-yl)methyl)oxy)phenyl)butanoic acid (69.28). Example 69.28 was prepared using an alkylation and hydrolysis which were conducted in an analogous manner to Example 66.6 (using 67.20E and 69, described herein) to yield 67.28 (37.7 mg, 88% yield). ¹H NMR (400 MHz, CDCl₃) δ ppm 7.25 (2H, m), 7.12 (4H, m), 6.87 (4H, m), 5.02 (2H, s), 3.78 (3H, s), 3.24 (1H, m), 2.78 (4H, m), 2.76 (1H, m), 2.66 (1H, m), 1.69 (1H, m), 1.40 (6H, m), 1.32 (1H, ddd, J=13.9, 7.8, 6.1 Hz), 0.54 (1H, m), 0.39 (2H, m), 0.08 (2H, m). MS ESI (pos.) m/e: 518.0 (M+H)⁺.

Example of 69.29

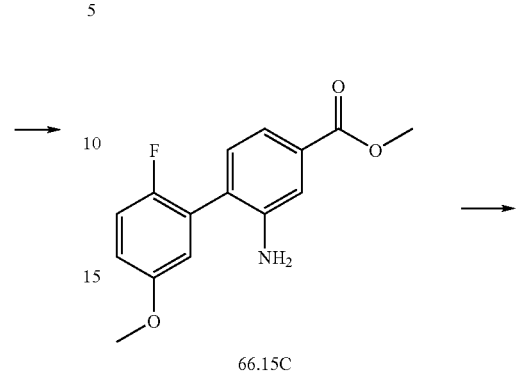

66.15C

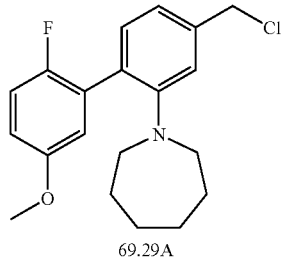

69.29A 1-(4-(Chloromethyl)-2'-fluoro-5'-(methyloxy)-1,1'-biphenyl-2-yl)azepane (69.29A). An acylation, reduction and chlorination strategy was employed similar to that of Example 67.20E (described herein) to yield 67.29A. 6-Commercially available bromohexanoyl chloride (0.9 mL, 6.02 mmol) was used as the acylating reagent. MS ESI (pos.) m/e: 348.0 (M+H)⁺.

(3R)-3-(3-(((2-(1-Azepanyl)-2'-fluoro-5'-(methyloxy)-1,1'-biphenyl-4-yl)methyl)oxy)phenyl)-4-cyclopropylbutanoic acid or (3S)-3-(3-(((2-(1-azepanyl)-2'-fluoro-5'-(methyloxy)-1,1'-biphenyl-4-yl)methyl)oxy)phenyl)-4-cyclopropylbutanoic acid (69.29). The alkylation and hydrolysis were conducted in an analogous manner to Example 66.6 using 67.29A and 69 to yield 69.29. The residue was purified with HPLC using 30-90% solvent B (0.1% TFA in acetonitrile) over 45 minutes to afford 69.29 as a TFA salt (4.0 mg). ¹H NMR (400 MHz, CDCl₃) δ ppm 7.70 (1H, s), 7.51 (1H, d, J=7.8 Hz), 7.31 (1H, d, J=7.8 Hz), 7.22 (1H, t, J=7.8 Hz), 7.11 (1H, t, J=9.0 Hz), 6.97 (1H, ddd, J=8.9, 3.9, 3.6 Hz), 6.89 (3H, m), 6.78 (1H, s), 5.22 (2H, s), 3.82 (3H, m), 3.60 (4H, dd, J=6.5, 3.7 Hz), 3.22 (1H, m), 2.77 (1H, dd, J=15.5, 5.3 Hz), 2.54 (1H, dd, J=15.3, 9.8 Hz), 1.83 (4H, s), 1.71 (1H, ddd, J=13.9, 8.0, 5.9 Hz), 1.61 (4H, s), 1.34 (1H, dt, J=14.2, 7.2 Hz), 0.59 (1H, m), 0.44 (2H, m), 0.05 (1H, td, J=8.9, 4.9 Hz), −0.02 (1H, td, J=8.9, 4.9 Hz). MS ESI (pos.) m/e: 532.0 (M+H)⁺.

(3R)-4-cyclopropyl-3-(3-(((2-(5,5-dimethyl-1-cyclopenten-1-yl)-2',5-difluoro-5'-(methyloxy)-1,1'-biphenyl-4-yl)methyl)oxy)phenyl)butanoic acid or (3S)-4-cyclopropyl-3-(3-(((2-(5,5-dimethyl-1-cyclopenten-1-yl)-2',5-difluoro-5'-(methyloxy)-1,1'-biphenyl-4-yl)methyl)oxy)phenyl)butanoic acid (69.30). The alkylation and hydrolysis were conducted in an analogous manner to Example 66.6 (using 66.43I and 69, described herein) to yield 69.30 (38.9 mg, 78% yield). ¹H NMR (400 MHz, CDCl₃) δ ppm 7.36 (1H, d, J=7.4 Hz), 7.24 (1H, t, J=7.8 Hz), 7.08 (1H, d, J=9.8 Hz), 6.98 (1H, t, J=9.0 Hz), 6.90 (3H, m), 6.84 (2H, m), 5.51 (1H, s), 5.17

(2H, s), 3.76 (3H, s), 3.27 (1H, m), 2.79 (1H, m), 2.69 (1H, m), 2.24 (2H, td, J=7.0, 2.3 Hz), 1.72 (1H, ddd, J=13.9, 8.4, 5.9 Hz), 1.65 (2H, t, J=6.8 Hz), 1.35 (1H, ddd, J=13.9, 7.8, 6.1 Hz), 0.81 (6H, s), 0.57 (1H, m), 0.42 (2H, m), 0.07 (1H, m), −0.01 (1H, m). MS ESI (neg.) m/e: 544.9 (M−H)$^+$.

Example 69.31

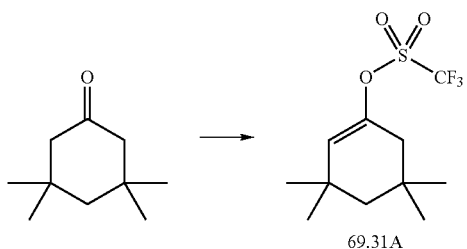

3,3,5,5-Tetramethylcyclohex-1-enyl trifluoromethanesulfonate (69.31A). Compound 69.31A was prepared from 3,3,5,5-tetramethylcyclohexanone (available from Aldrich) according to the analogous method described for the synthesis of A.2.

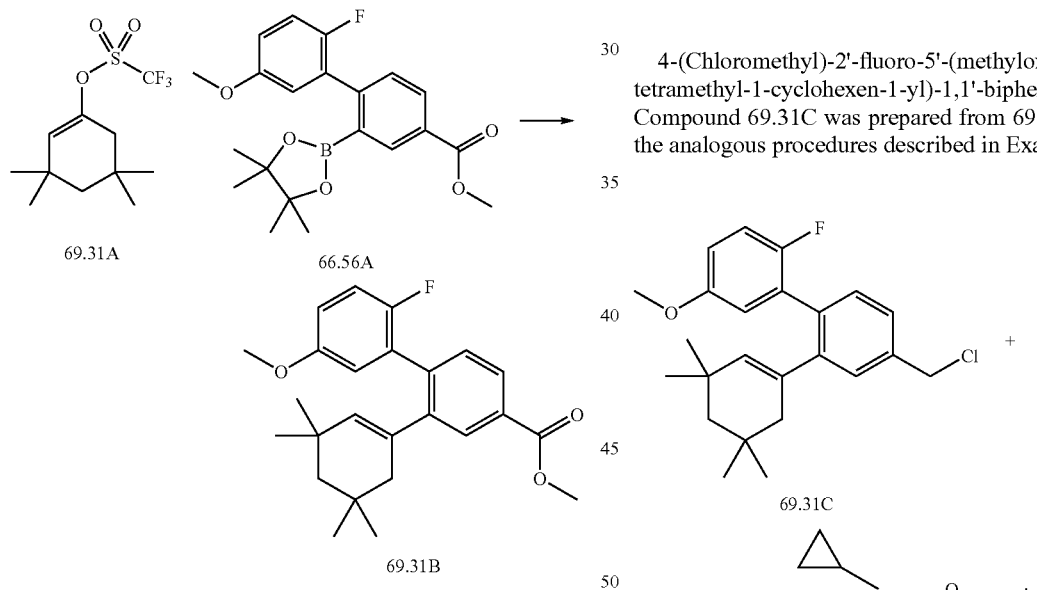

Methyl 2'-fluoro-5'-(methyloxy)-2-(3,3,5,5-tetramethyl-1-cyclohexen-1-yl)-1,1'-biphenyl-4-carboxylate (69.31B). A screw-cap vial was charged with 66.31A (0.556 g, 1.94 mmol), THF (10 mL), 66.56A (0.500 g, 1.29 mmol), potassium phosphate (0.824 g, 3.88 mmol), 2-dicyclohexylphosphino-2',6'-dimethoxybiphenyl (commercially available from Aldrich) (0.165 g, 0.401 mmol), palladium(II) acetate (0.0291 g, 0.129 mmol), and water (0.117 mL, 6.47 mmol). The mixture was purged with argon and stirred for 48 hours at room temperature under an argon balloon. Additional 2-dicyclohexylphosphino-2',6'-dimethoxybiphenyl (0.165 g, 0.401 mmol), palladium(II) acetate (0.0291 g, 0.129 mmol), and 69.31A (0.556 g, 1.94 mmol) were added, and stirring was continued for 16 hours at room temperature under argon. The mixture was filtered through silica gel (EtOAc) and concentrated. The crude product was purified by silica gel flash chromatography (0-5% EtOAc/hexane) to afford 69.31B (0.300 g, 58% yield) as a colorless oil.

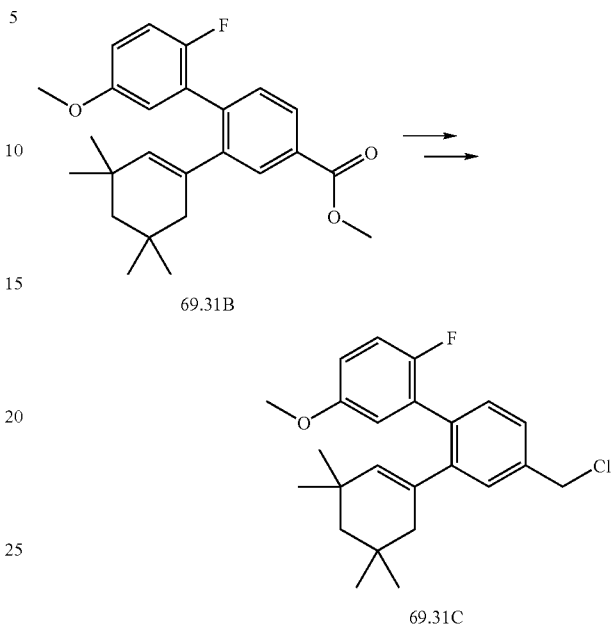

4-(Chloromethyl)-2'-fluoro-5'-(methyloxy)-2-(3,3,5,5-tetramethyl-1-cyclohexen-1-yl)-1,1'-biphenyl (69.31C). Compound 69.31C was prepared from 69.31B according to the analogous procedures described in Example 66.56.

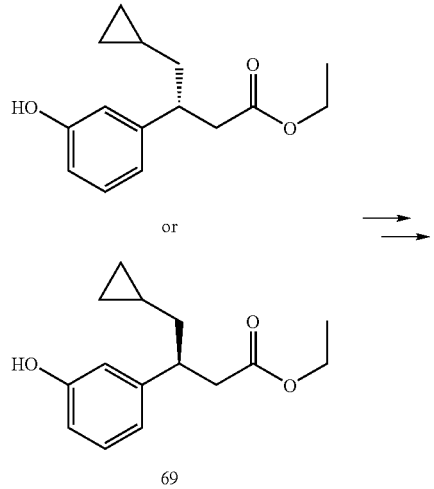

-continued

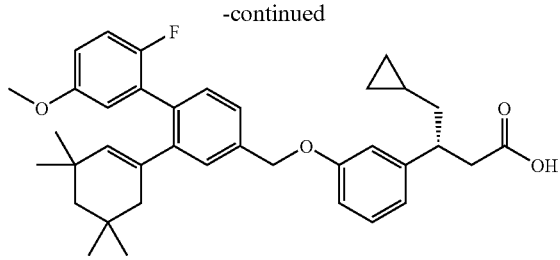

or

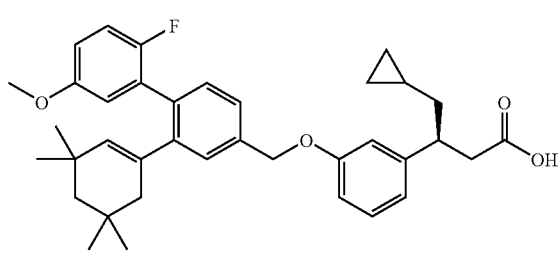

69.31

(3R)-4-Cyclopropyl-3-(3-(((2'-fluoro-5'-(methyloxy)-2-(3,3,5,5-tetramethyl-1-cyclohexen-1-yl)-1,1'-biphenyl-4-yl)methyl)oxy)phenyl)butanoic acid or (3S)-4-cyclopropyl-3-(3-(((2'-fluoro-5'-(methyloxy)-2-(3,3,5,5-tetramethyl-1-cyclohexen-1-yl)-1,1'-biphenyl-4-yl)methyl)oxy)phenyl)butanoic acid (69.31). Example 69.31 was prepared from 69 and 69.31C according to the analogous methods described in Example 7. MS ESI (pos.) m/e: 588.3 (M+H$_2$O)$^+$, 593.3 (M+Na)$^+$.

Example 69.32

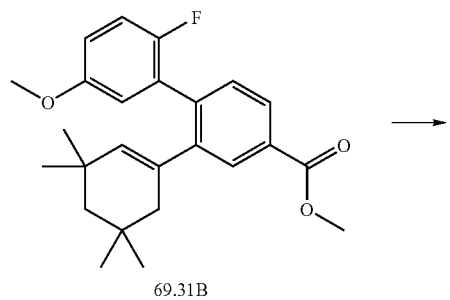

69.31B

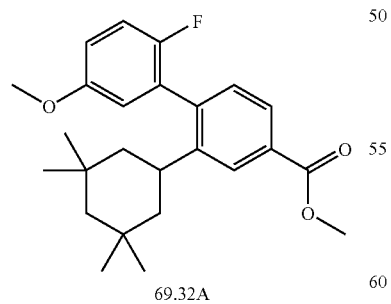

69.32A

Methyl 2'-fluoro-5'-(methyloxy)-2-(3,3,5,5-tetramethylcyclohexyl)-1,1'-biphenyl-4-carboxylate (69.32A). A screw-cap pressure tube was charged with 69.31B (0.22 g, 0.55 mmol), 1:1 EtOAc/MeOH (10 mL), and platinum(IV) oxide (0.025 g, 0.11 mmol). The tube was purged three times with H$_2$ at 50 psi and sealed, and the contents were stirred overnight. The mixture was diluted with EtOAc, filtered through silica gel (EtOAc), and concentrated. The crude product was purified by silica gel flash chromatography (0-8% EtOAc/hexane) to afford 69.32A (0.13 g, 59% yield) as a colorless oil.

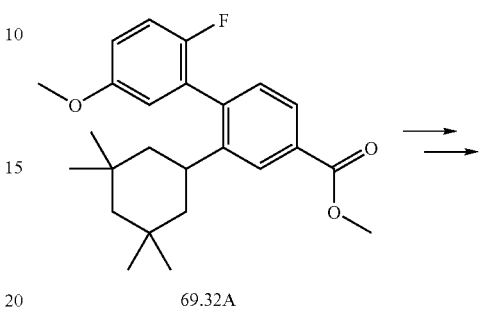

69.32A

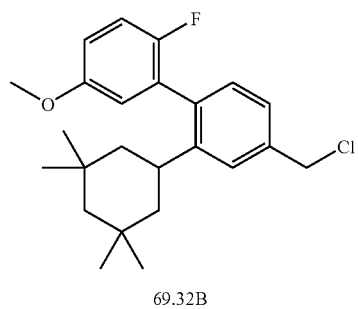

69.32B 4-(Chloromethyl)-2'-fluoro-5'-(methyloxy)-2-(3,3,5,5-tetramethylcyclohexyl)-1,1'-biphenyl (69.32B). Compound 69.32B was prepared from 69.32A according to the analogous methods described in Example 66.56.

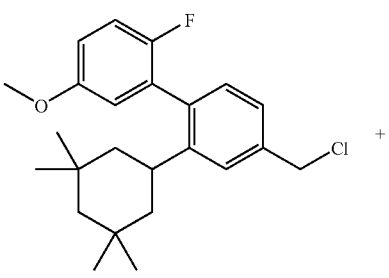

69.32B

-continued

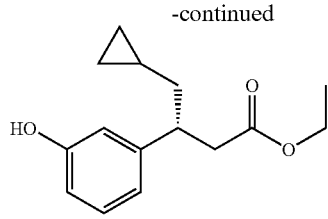

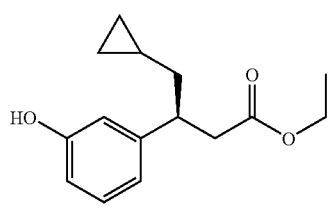

69

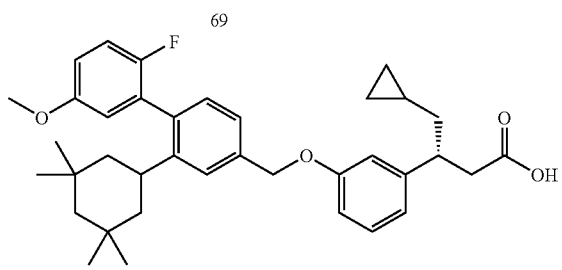

or

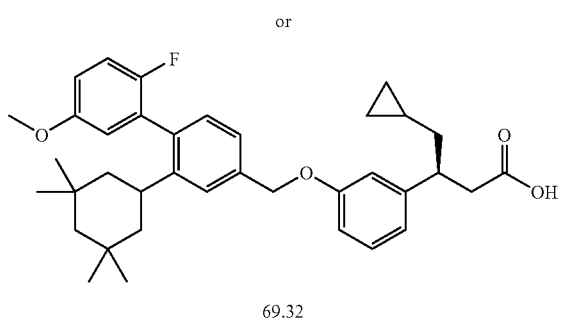

69.32

(3R)-4-Cyclopropyl-3-(3-(((2'-fluoro-5'-(methyloxy)-2-(3,3,5,5-tetramethylcyclohexyl)-1,1'-biphenyl-4-yl)methyl)oxy)phenyl)butanoic acid or (3S)-4-cyclopropyl-3-(3-(((2'-fluoro-5'-(methyloxy)-2-(3,3,5,5-tetramethylcyclohexyl)-1,1'-biphenyl-4-yl)methyl)oxy)phenyl)butanoic acid (69.32). 69.32 was prepared from 69 and 69.32B according to the analogous methods described in Example 7. MS ESI (pos.) m/e: 573.3 (M+H)$^+$, 590.3 (M+H$_2$O)$^+$, 595.3 (M+Na)$^+$.

Example 69.33

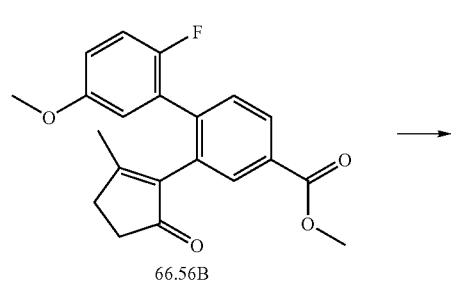

66.56B

-continued

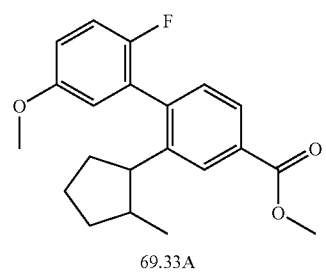

69.33A

Methyl 2'-fluoro-2-(2-methylcyclopentyl)-5'-(methyloxy)-1,1'-biphenyl-4-carboxylate (69.33A). A screw-cap pressure tube was charged with 66.56B (0.31 g, 0.87 mmol), MeOH (10 mL), and platinum(IV) oxide (0.040 g, 0.17 mmol). The tube was purged three times with H$_2$ at 45 psi and sealed, and the contents were stirred overnight. The mixture was diluted with EtOAc, filtered through silica gel (EtOAc), and concentrated. The crude product was purified by silica gel flash chromatography (0-20% EtOAc/hexane) to afford 69.33A (1:1 d.r.) (0.040 g) as a colorless oil.

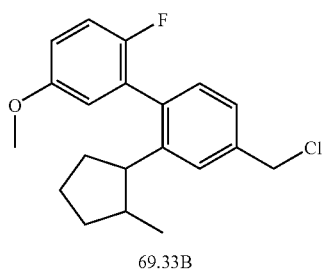

69.33A

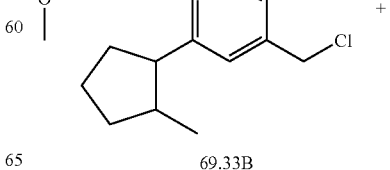

69.33B 4-(Chloromethyl)-2'-fluoro-2-(2-methylcyclopentyl)-5'-(methyloxy)-1,1'-biphenyl (69.33B). 69.33B (1:1 d.r.) was prepared from 66.33A (1:1 d.r.) according to the analogous methods described in Example 66.56.

581
-continued

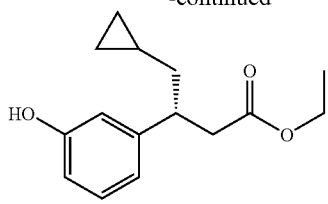

or

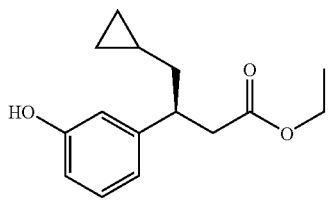

69

→→

582
-continued

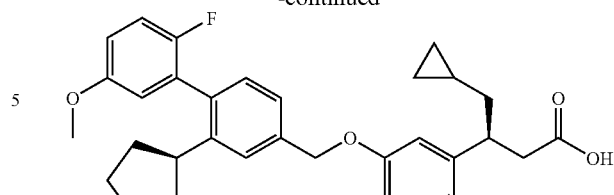

and

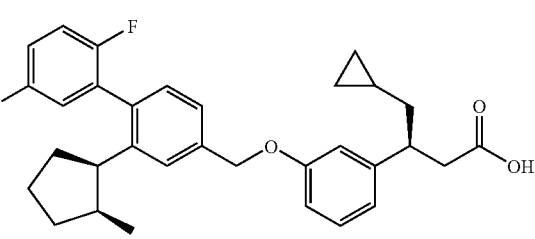

and

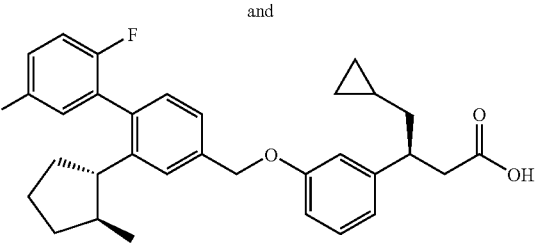

and

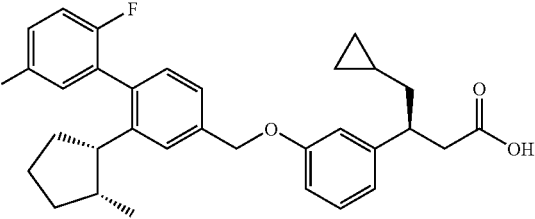

69.33

(3R)-4-Cyclopropyl-3-(3-(((2'-fluoro-2-(2-methylcyclopentyl)-5'-(methyloxy)-1,1'-biphenyl-4-yl)methyl)oxy)phenyl)butanoic acid or (3S)-4-cyclopropyl-3-(3-(((2'-fluoro-2-(2-methylcyclopentyl)-5'-(methyloxy)-1,1'-biphenyl-4-yl)methyl)oxy)phenyl)butanoic acid (69.33). Example 69.33 (1:1:1:1 d.r.) was prepared from 69 and 69.33B (1:1 d.r.) according to the analogous methods described in Example 7. MS ESI (pos.) m/e: 534.2 (M+H$_2$O)$^+$, 539.2 (M+Na)$^+$.

(3R)-4-Cyclopropyl-3-(3-(((2-((1S)-2,2-dimethylcyclopentyl)-2',5-difluoro-5'-(methyloxy)-1,1'-biphenyl-4-yl)methyl)oxy)phenyl)butanoic acid or (3R)-4-cyclopropyl-3-(3-(((2-((1R)-2,2-dimethylcyclopentyl)-2',5-difluoro-5'-(methyloxy)-1,1'-biphenyl-4-yl)methyl)oxy)phenyl)butanoic acid or (3S)-4-cyclopropyl-3-(3-(((2-((1R)-2,2-dimethylcyclopentyl)-2',5-difluoro-5'-(methyloxy)-1,1'-biphenyl-4-yl)methyl)oxy)phenyl)butanoic acid or (3S)-4-Cyclopropyl-3-(3-(((2-((1S)-2,2-dimethylcyclopentyl)-2',5-difluoro-5'-(methyloxy)-1,1'-biphenyl-4-yl)methyl)oxy)phenyl)butanoic acid (69.34). MS ESI (neg.) m/e: 547.3 (M−H)$^+$.

(3R)-4-Cyclopropyl-3-(3-(((2-((1S)-2,2-dimethyl-1-(methyloxy)propyl)-2'-fluoro-5'-(methyloxy)-1,1'-biphenyl-4-yl)methyl)oxy)phenyl)butanoic acid (3R)-4-cyclopropyl-3-(3-(((2-((1R)-2,2-dimethyl-1-(methyloxy)propyl)-2'-fluoro- 5'-(methyloxy)-1,1'-biphenyl-4-yl)methyl)oxy)phenyl) butanoic acid or (3S)-4-cyclopropyl-3-(3-(((2-((1S)-2,2-dimethyl-1-(methyloxy)propyl)-2'-fluoro-5'-(methyloxy)-1,1'-biphenyl-4-yl)methyl)oxy)phenyl)butanoic acid or (3S)-4-cyclopropyl-3-(3-(((2-((1R)-2,2-dimethyl-1-(methyloxy)propyl)-2'-fluoro-5'-(methyloxy)-1,1'-biphenyl-4-yl)methyl)oxy)phenyl)butanoic acid (69.35). MS ESI (neg.) m/e: 533.2 (M−H)⁺.

(3R)-4-Cyclopropyl-3-(3-(((2-((1S)-2,2-dimethylcyclohexyl)-2'-fluoro-5'-(methyloxy)-1,1'-biphenyl-4-yl)methyl)oxy)phenyl)butanoic acid or (3R)-4-cyclopropyl-3-(3-(((2-((1R)-2,2-dimethylcyclohexyl)-2'-fluoro-5'-(methyloxy)-1,1'-biphenyl-4-yl)methyl)oxy)phenyl)butanoic acid or (3S)-4-cyclopropyl-3-(3-(((2-((1S)-2,2-dimethylcyclohexyl)-2'-fluoro-5'-(methyloxy)-1,1'-biphenyl-4-yl)methyl)oxy)phenyl)butanoic acid or (3S)-4-cyclopropyl-3-(3-(((2-((1R)-2,2-dimethylcyclohexyl)-2'-fluoro-5'-(methyloxy)-1,1'-biphenyl-4-yl)methyl)oxy)phenyl)butanoic acid (69.36). MS ESI (neg.) m/e: 543.2 (M−H)⁺.

(3R)-4-Cyclopropyl-3-(3-(((2-((ethyloxy)methyl)-2'-fluoro-5'-(methyloxy)-1,1'-biphenyl-4-yl)methyl)oxy)phenyl)butanoic acid or (3S)-4-cyclopropyl-3-(3-(((2-((ethyloxy)methyl)-2'-fluoro-5'-(methyloxy)-1,1'-biphenyl-4-yl)methyl)oxy)phenyl)butanoic acid (69.37). The alkylation and hydrolysis were conducted in an analogous manner to Example 67.23 using 67.23C and 69 to yield 67.37. MS ESI (neg.) m/e: 491 (M−H)⁺. ¹H NMR (400 MHz, DMSO-d6) δ ppm 7.60 (m, 1H), 7.44-7.46 (m, 1H), 7.18-7.27 (m, 3H), 6.96-7.00 (m, 1H), 6.91 (m, 1H), 6.82-6.87 (m, 3H), 5.15 (s, 2H), 4.29 (s, 2H), 3.76 (s, 3H), 3.36 (m, 2H), 3.07 (m, 1H), 2.65 (m, 1H), 2.48 (m, 1H), 1.55 (m, 2H), 1.33 (m, 1H), 1.04 (t, 3H), 0.45 (m, 1H), 0.27 (m, 2H), 0.02 (m, 1H), −0.09 (m, 1H).

(3R)-4-Cyclopropyl-3-(3-(((2-((1S)-2,2-dimethyl-1-(methyloxy)-3-butenyl)-2'-fluoro-5'-(methyloxy)-1,1'-biphenyl-4-yl)methyl)oxy)phenyl)butanoic acid or (3R)-4-cyclopropyl-3-(3-(((2-((1R)-2,2-dimethyl-1-(methyloxy)-3-butenyl)-2'-fluoro-5'-(methyloxy)-1,1'-biphenyl-4-yl)methyl)oxy)phenyl)butanoic acid or (3S)-4-cyclopropyl-3-(3-(((2-((1S)-2,2-dimethyl-1-(methyloxy)-3-butenyl)-2'-fluoro-5'-(methyloxy)-1,1'-biphenyl-4-yl)methyl)oxy)phenyl)butanoic acid or (3S)-4-cyclopropyl-3-(3-(((2-((1R)-2,2-dimethyl-1-(methyloxy)-3-butenyl)-2'-fluoro-5'-(methyloxy)-1,1'-biphenyl-4-yl)methyl)oxy)phenyl)butanoic acid (69.38). The alkylation and hydrolysis were conducted in an analogous manner to Example 67.24 using peak one from the chiral separation of 67.24A on the OD column and 69 to yield 69.38. MS ESI (neg.) m/e: 545 (M−H)⁺. ¹H NMR (400 MHz, CDCl₃) δ ppm 7.53 (m, 1H), 7.42-7.45 (m, 1H), 7.16-7.24 (m, 2H), 7.01-7.07 (m, 1H), 6.82-6.90 (m, 4H), 6.73-6.75 (m, 1H), 5.70-5.77 (m, 1H), 5.14 (m, 1H), 4.70-4.85 (m, 2H), 4.22 (m, 1H), 3.81 (m, 3H), 3.32 (m, 3H), 2.62-2.79 (m, 3H), 1.70-1.73 (m, 2H), 1.29 (m, 6H), 1.18 (m, 2H), 0.90-0.99 (m, 2H), 0.53 (m, 1H), 0.37 (m, 1H), 0.00-0.10 (m, 2H).

(3R)-4-Cyclopropyl-3-(3-(((2-((1S)-2,2-dimethyl-1-(methyloxy)-3-butenyl)-2'-fluoro-5'-(methyloxy)-1,1'-biphenyl-4-yl)methyl)oxy)phenyl)butanoic acid or (3R)-4-cyclopropyl-3-(3-(((2-((1R)-2,2-dimethyl-1-(methyloxy)-3-butenyl)-2'-fluoro-5'-(methyloxy)-1,1'-biphenyl-4-yl)methyl)oxy)phenyl)butanoic acid or (3S)-4-cyclopropyl-3-(3-(((2-((1S)-2,2-dimethyl-1-(methyloxy)-3-butenyl)-2'-fluoro-5'-(methyloxy)-1,1'-biphenyl-4-yl)methyl)oxy)phenyl)butanoic acid or (3S)-4-cyclopropyl-3-(3-(((2-((1R)-2,2-dimethyl-1-(methyloxy)-3-butenyl)-2'-fluoro-5'-(methyloxy)-1,1'-biphenyl-4-yl)methyl)oxy)phenyl)butanoic acid (69.39). The alkylation and hydrolysis were conducted in an analogous manner to Example 67.24 (using peak two from the chiral separation of 67.24A on the OD column and 69) to yield 69.39. This is a diastereomer of 69.38. MS ESI (neg.) m/e: 545 (M−H)⁺. ¹H NMR (400 MHz, CDCl₃) δppm 7.53 (m, 1H), 7.42-7.45 (m, 1H), 7.16-7.24 (m, 2H), 7.01-7.07 (m, 1H), 6.82-6.90 (m, 4H), 6.73-6.75 (m, 1H), 5.70-5.77 (m, 1H), 5.14 (m, 1H), 4.70-4.85 (m, 2H), 4.22 (m, 1H), 3.81 (m, 3H), 3.32 (m, 3H), 2.62-2.79 (m, 3H), 1.70-1.73 (m, 2H), 1.26 (m, 6H), 1.18 (m, 2H), 0.76-0.90 (m, 2H), 0.53 (m, 1H), 0.37 (m, 1H), 0.10 (m, 2H).

(3R)-4-Cyclopropyl-3-(3-(((2'-fluoro-2-((1S)-1-hydroxy-2,2-dimethyl-3-butenyl)-5'-(methyloxy)-1,1'-biphenyl-4-yl)methyl)oxy)phenyl)butanoic acid or (3R)-4-cyclopropyl-3-(3-(((2-fluoro-2'-((1R)-1-hydroxy-2,2-dimethyl-3-butenyl)-5'-(methyloxy)-1,1'-biphenyl-4-yl)methyl)oxy)phenyl)butanoic acid or (3S)-4-cyclopropyl-3-(3-(((2'-fluoro-2-((1S)-1-hydroxy-2,2-dimethyl-3-butenyl)-5'-(methyloxy)-1,1'-biphenyl-4-yl)methyl)oxy)phenyl)butanoic acid or (3S)-4-cyclopropyl-3-(3-(((2'-fluoro-2-((1R)-1-hydroxy-2,2-dimethyl-3-butenyl)-5'-(methyloxy)-1,1'-biphenyl-4-yl)methyl)oxy)phenyl)butanoic acid (69.40). The alkylation and hydrolysis were conducted in an analogous manner to Example 67.25 (using 67.25A (derived from peak one from the chiral separation of 67.24A) on the OD column and 69) to yield 69.40. MS ESI (neg.) m/e: 531 (M−H). ¹H NMR (400 MHz, CD₃OD) δ ppm 7.66-7.71 (d, 1H), 7.20 (m, 1H), 7.05-7.18 (m, 3H), 6.82-6.95 (m, 5H), 5.78 (m, 1H), 5.14 (m, 2H), 4.71 (m, 2H), 3.79 (s, 3H), 3.13 (m, 1H), 2.52-2.58 (m, 2H), 1.65 (m, 2H), 1.34 (m, 1H), 1.19 (m, 1H), 0.81 (s, 3H), 0.71 (s, 3H), 0.48 (m, 1H), 0.34 (M, 2H), 0.01 (m, 1H), −0.07 (m, 1H).

(3R)-4-Cyclopropyl-3-(3-(((2-((1S)-2,2-dimethyl-1-(methyloxy)butyl)-2'-fluoro-5'-(methyloxy)-1,1'-biphenyl-4-yl)methyl)oxy)phenyl)butanoic acid or (3R)-4-cyclopropyl-3-(3-(((2-((1S)-2,2-dimethyl-1-(methyloxy)butyl)-2'-fluoro-5'-(methyloxy)-1,1'-biphenyl-4-yl)methyl)oxy)phenyl)butanoic acid (69.41). The alkylation and hydrolysis were conducted in an analogous manner to Example 66.62 (using 66.62E (derived from peak two from the chiral separation of 66.62B) on the OD column and 69) to yield 69.41. MS ESI (neg.) m/e: 547 (M−H)⁺. ¹H NMR (400 MHz, CDCl₃) δ ppm 7.58 (m, 1H), 7.42 (m, 1H), 7.20-7.23 (m, 2H), 7.05 (m, 1H), 6.84-6.90 (m, 4H), 6.75 (m, 1H), 5.15 (s, 2H), 4.06-4.29 (m, 1H), 3.80 (s, 3H), 3.23-3.29 (m, 3H), 2.73-2.80 (m, 1H), 2.61-2.67 (m, 2H), 1.72 (m, 1H), 1.35 (m, 2H), 1.07 (m, 1H), 0.80 (m, 1H), 0.72 (s, 3H), 0.61 (m, 3H), 0.49-0.52 (m, 4H), 0.36 (m, 2H), 0.02-0.04 (m, 2H).

(3R)-4-Cyclopropyl-3-(3-(((2-((1S)-2,2-dimethyl-1-(methyloxy)butyl)-2'-fluoro-5'-(methyloxy)-1,1'-biphenyl-4-yl)methyl)oxy)phenyl)butanoic acid or (3R)-4-cyclopropyl-3-(3-(((2-((1R)-2,2-dimethyl-1-(methyloxy)butyl)-2'-fluoro-5'-(methyloxy)-1,1'-biphenyl-4-yl)methyl)oxy)phenyl)butanoic acid or (3S)-4-cyclopropyl-3-(3-(((2-((1S)-2,2-dimethyl-1-(methyloxy)butyl)-2'-fluoro-5'-(methyloxy)-1,1'-biphenyl-4-yl)methyl)oxy)phenyl)butanoic acid or (3S)-4-cyclopropyl-3-(3-(((2-((1R)-2,2-dimethyl-1-(methyloxy)butyl)-2'-fluoro-5'-(methyloxy)-1,1'-biphenyl-4-yl)methyl)oxy)phenyl)butanoic acid (69.42). The alkylation and hydrolysis were conducted in an analogous manner to Example 66.62 (using 66.62E (derived from peak one from the chiral separation of 66.62B) on the OD column and 69) to yield 69.42. MS ESI (neg.) m/e: 547 (M−H)⁺. ¹H NMR (400 MHz, CDCl₃) δ ppm 7.58 (m, 1H), 7.4-27.44 (m, 1H), 7.20-7.23 (m, 2H), 7.18 (m, 1H), 6.83-6.90 (m, 4H), 6.74 (m, 1H), 5.15 (m, 2H), 4.05-4.29 (m, 1H), 3.80 (s, 3H), 3.23-3.28 (m, 3H), 2.64-2.78 (m, 2H), 1.72 (m, 1H), 1.35 (m, 2H), 1.07 (m, 1H), 0.80 (m, 1H), 0.71 (s, 3H), 0.60 (m, 3H), 0.48 (m, 3H), 0.36-0.39 (m, 2H), 0.02-0.04 (m, 2H).

Example 69.43

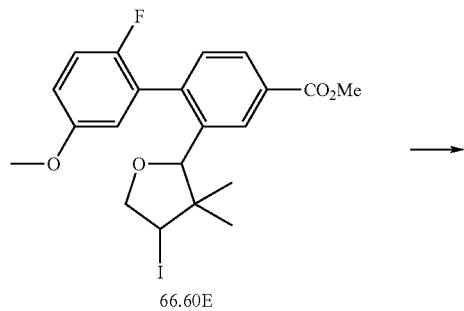

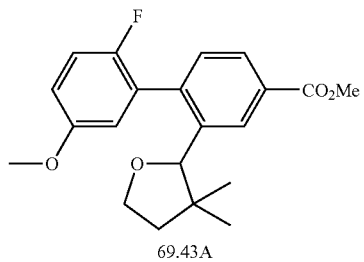

Methyl 2-(3,3-dimethyltetrahydro-2-furanyl)-2'-fluoro-5'-(methyloxy)-1,1'-biphenyl-4-carboxylate (69.43A). To a solution of 66.60E (0.388 g, 0.801 mmol) in MeOH (17 mL) (degassed by $N_2$), was added palladium-carbon (0.0853 g, 0.801 mmol). The resulting mixture was stirred at room temperature under $H_2$ for 23 hours. After removing solvent, the residue was purified by flash chromatography (silica gel, 1:19 EtOAc/hexane) and gave 65 mg of 69.43A. MS ESI (pos.) m/e: 376 (M+18)⁺.

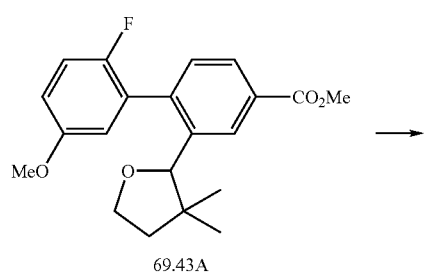

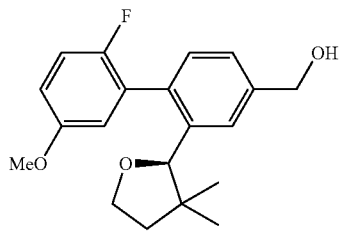

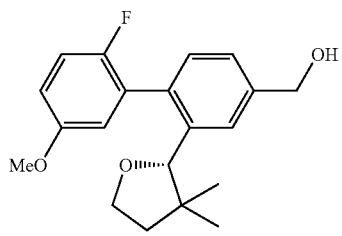

(2-((2S)-3,3-Dimethyltetrahydro-2-furanyl)-2'-fluoro-5'-(methyloxy)-1,1'-biphenyl-4-yl)methanol and (2-((2R)-3,3-dimethyltetrahydro-2-furanyl)-2'-fluoro-5'-(methyloxy)-1,1'-biphenyl-4-yl)methanol (69.43B and 69.43C)). At 0-5° C., LAH, (1.0 M solution in THF) (0.045 mL, 0.045 mmol) was added dropwise to a solution of 69.43A (0.016 g, 0.045 mmol) in THF (1 mL). The resulting mixture was stirred at room temperature for 20 minutes. The reaction mixture was then poured into brine (3 mL) and extracted with EtOAc (2×60 mL). The combined organic phase was dried over anhydrous sodium sulfate. After removing solvent, the residue was purified by flash chromatography (silica gel, 1:4 EtOAc/hexane) and gave 16 mg of racemate, which was further separated by chiral HPLC (column: OD; solvent: 3% i-PrOH/hexane. The first peak (shorter retention time) was 69.43B (5.5 mg) and the second peak (longer retention time) was 69.43C (5.1 mg).

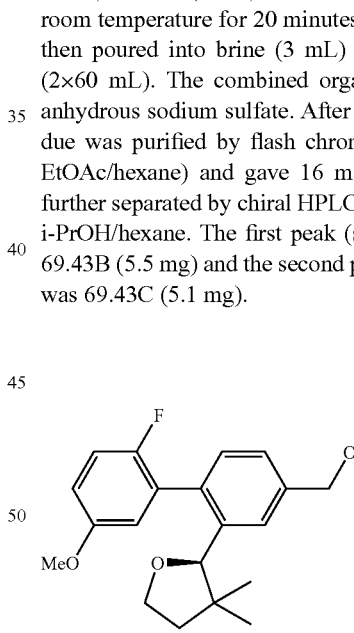

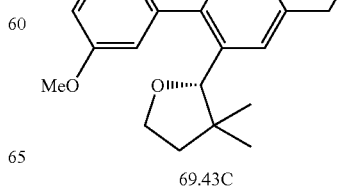

-continued

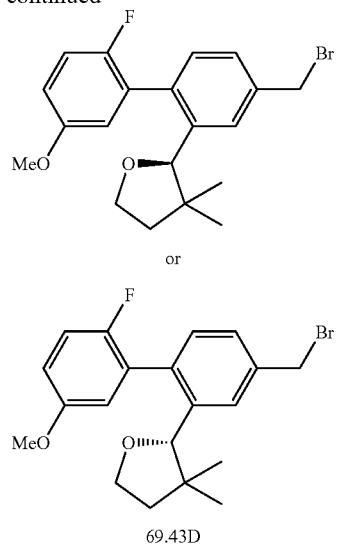

69.43D (2S)-2-(4-(Bromomethyl)-2'-fluoro-5'-(methyloxy)-1,1'-biphenyl-2-yl)-3,3-dimethyltetrahydrofuran or (2R)-2-(4-(bromomethyl)-2'-fluoro-5'-(methyloxy)-1,1'-biphenyl-2-yl)-3,3-dimethyltetrahydrofuran (69.43D). The bromination was conducted in an analogous manner to Example 66.62 to yield 69.43D.

(3R)-4-Cyclopropyl-3-(3-(((2-((2S)-3,3-dimethyltetrahydro-2-furanyl)-2'-fluoro-5'-(methyloxy)-1,1'-biphenyl-4-yl)methyl)oxy)phenyl)butanoic acid or (3R)-4-cyclopropyl-3-(3-(((2-((2R)-3,3-dimethyltetrahydro-2-furanyl)-2'-fluoro-5'-(methyloxy)-1,1'-biphenyl-4-yl)methyl)oxy)phenyl)butanoic acid or (3S)-4-cyclopropyl-3-(3-(((2-((2S)-3,3-dimethyltetrahydro-2-furanyl)-2'-fluoro-5'-(methyloxy)-1,1'-biphenyl-4-yl)methyl)oxy)phenyl)butanoic acid or (3S)-4-cyclopropyl-3-(3-(((2-((2R)-3,3-dimethyltetrahydro-2-furanyl)-2'-fluoro-5'-(methyloxy)-1,1'-biphenyl-4-yl)methyl)oxy)phenyl)butanoic acid (69.43). The alkylation and hydrolysis were conducted in an analogous manner to Example 66.62 (using 69.43D (derived from peak two from the chiral separation of the reduction product of 66.43A) on the OD column and 69) to yield 69.43. MS ESI (neg.) m/e: 531 (M–H)+. $^1$H NMR (400 MHz, CDCl$_3$) δ ppm 7.56 (m, 1H), 7.40 (m, 1H), 7.17 (m, 2H), 7.03 (m, 1H), 6.81-6.83 (m, 5H), 5.20 (m, 2H), 4.71-4.83 (m, 1H), 3.94-4.20 (m, 2H), 3.78 (m, 3H), 3.21 (m, 2H), 2.70 (m, 1H), 2.37 (m, 1H), 1.77 (m, 2H), 1.29 (m, 2H), 0.89 (s, 1H), 0.68 (m, 6H), 0.39-0.41 (m, 2H), 0.08 (m, 2H).

(3R)-4-cyclopropyl-3-(3-(((2-((2S)-3,3-dimethyltetrahydro-2-furanyl)-2'-fluoro-5'-(methyloxy)-1,1'-biphenyl-4-yl)methyl)oxy)phenyl)butanoic acid or (3R)-4-cyclopropyl-3-(3-(((2-((2R)-3,3-dimethyltetrahydro-2-furanyl)-2'-fluoro-5'-(methyloxy)-1,1'-biphenyl-4-yl)methyl)oxy)phenyl)butanoic acid or (3S)-4-cyclopropyl-3-(3-(((2-((2S)-3,3-dimethyltetrahydro-2-furanyl)-2'-fluoro-5'-(methyloxy)-1,1'-biphenyl-4-yl)methyl)oxy)phenyl)butanoic acid or (3S)-4-cyclopropyl-3-(3-(((2-((2R)-3,3-dimethyltetrahydro-2-furanyl)-2'-fluoro-5'-(methyloxy)-1,1'-biphenyl-4-yl)methyl)oxy)phenyl)butanoic acid (69.44). The alkylation and hydrolysis were conducted in an analogous manner to Example 66.62 (using 69.43D (derived from peak one from the chiral separation of the reduction product of 66.43A) on the OD column and 69, described herein) to yield 69.44. MS ESI (neg.) m/e: 531 (M–H)+. $^1$H NMR (400 MHz, CDCl$_3$) δ ppm 7.56 (m, 1H), 7.40 (m, 1H), 7.17 (m, 2H), 7.03 (m, 1H), 6.81-6.83 (m, 5H), 5.18 (m, 2H), 4.71-4.83 (m, 1H), 3.94-4.20 (m, 2H), 3.79 (m, 3H), 3.15 (m, 1H), 2.50-2.70 (m, 2H), 1.77 (m, 2H), 1.29 (m, 2H), 0.89 (m, 1H), 0.68 (m, 6H), 0.51 (m, 1H), 0.40 (m, 2H), 0-0.08 (m, 2H).

(3R)-4-Cyclopropyl-3-(3-(((2'-fluoro-2-(((3-methyl-2-butenyl)oxy)methyl)-5'-(methyloxy)-1,1'-biphenyl-4-yl)methyl)oxy)phenyl)butanoic acid or (3S)-4-cyclopropyl-3-(3-(((2'-fluoro-2-(((3-methyl-2-butenyl)oxy) methyl)-5'-(methyloxy)-1,1'-biphenyl-4-yl)methyl)oxy)phenyl) butanoic acid (69.45). The alkylation and hydrolysis were conducted in an analogous manner to Example 66.62 (using 67.27C and 69, described herein) to yield 69.45. MS ESI (neg.) m/e: 531 (M–H). $^1$H NMR (400 MHz, CDCl$_3$) δ ppm 7.60 (m, 1H), 7.42 (m, 1H), 7.21-7.29 (m, 2H), 7.02-7.07 (m, 1H), 6.82-6.89 (m, 5H), 5.24 (m, 1H), 5.15 (s, 2H), 4.37 (s, 2H), 3.92 (d, 2H), 3.80 (s, 3H), 3.18 (m, 1H), 2.54-2.76 (m, 2H), 1.75 (m, 1H), 1.70 (s, 3H), 1.58 (s, 3H), 1.35 (m, 1H), 0.56 (m, 1H), 0.37 (m, 2H), 0.00 (m, 2H).

(3R)-4-Cyclopropyl-3-(3-(((2'-fluoro-5'-(methyloxy)-2-(1-pyrrolidinylmethyl)-1,1'-biphenyl-4-yl)methyl)oxy)phenyl)butanoic acid or (3S)-4-cyclopropyl-3-(3-(((2'-fluoro-5'-(methyloxy)-2-(1-pyrrolidinylmethyl)-1,1'-biphenyl-4-yl) methyl)oxy)phenyl)butanoic acid (69.46). The alkylation and hydrolysis were conducted in an analogous manner to Example 66.65 using 66.65C and 69 to yield 69.46. MS ESI (neg.) m/e: 516 (M–H)+. $^1$H NMR (400 MHz, DMSO-d$_6$) δ ppm 9.68 (m, 1H), 7.84 (m, 1H), 7.62 (m, 1H), 7.39 (d, 1H), 7.21-7.31 (m, 2H), 7.04-7.07 (m, 1H), 6.86-6.96 (m, 4H), 5.18 (s, 2H), 4.04-4.40 (m, 2H), 3.79 (s, 3H), 3.30 (m, 4H), 3.08 (m, 1H), 2.59-2.70 (m, 2H), 2.64 (m, 1H), 1.80 (m, 4H), 1.57 (m, 1H), 1.34 (m, 1H), 0.45 (m, 1H), 0.28 (m, 2H), 0.02 (m, 1H), –0.80 (m, 1H).

(3R)-4-Cyclopropyl-3-(3-(((2-(((2R,5R)-2,5-dimethyl-1-pyrrolidinyl)methyl)-2'-fluoro-5'-(methyloxy)-1,1'-biphenyl-4-yl)methyl)oxy)phenyl)butanoic acid or (3S)-4-cyclopropyl-3-(3-(((2-(((2R,5R)-2,5-dimethyl-1-pyrrolidinyl)methyl)-2'-fluoro-5'-(methyloxy)-1,1'-biphenyl-4-yl) methyl)oxy)phenyl)butanoic acid (69.47). The alkylation and hydrolysis were conducted in an analogous manner to Example 66.62 (using 66.71C and 69, described herein) to yield 69.47. After removing solvent, 66.69 (TFA salt), 15 mg, was obtained. MS ESI (neg.) m/e: 544 (M–H)+. $^1$H NMR (400 MHz, DMSO-d6) δ ppm 9.55 (M, 1H), 7.87 (m, 1H), 7.61-7.63 (m, 1H), 7.41 (m, 1H), 7.31 (m, 1H), 7.22 (m, 1H), 7.08 (m, 1H), 6.85-6.91 (m, 4H), 5.19 (s, 2H), 4.10-4.40 (m, 1H), 3.78 (s, 3H), 3.08 (m, 1H), 2.64 (m, 1H), 2.08 (m, 1H), 1.56 (m, 3H), 1.35 (m, 3H), 1.00-1.10 (m, 3H), 0.85 (m, 1H), 0.48 (m, 1H), 0.28 (m, 2H), –0.09-0.00 (m, 2H)

(3R)-3-(3-(((2-(1-Azepanylmethyl)-2'-fluoro-5'-(methyloxy)-1,1'-biphenyl-4-yl)methyl)oxy)phenyl)-4-cyclopropylbutanoic acid or (3S)-3-(3-(((2-(1-azepanylmethyl)-2'-fluoro-5'-(methyloxy)-1,1'-biphenyl-4-yl)methyl)oxy) phenyl)-4-cyclopropylbutanoic acid (69.48). The alkylation and hydrolysis were conducted in an analogous manner to Example 66.62 (using 66.73C and 69, described herein) to yield 69.48. After removing solvent, 69.48 (TFA salt), 26 mg, was obtained. MS ESI (neg.) m/e: 544 (M–H)+. $^1$H NMR (400 MHz, DMSO-d6) δ ppm 9.40 (m, 1H), 7.91 (m, 1H), 7.63-7.65 (m, 1H), 7.41 (m, 1H), 7.22-7.33 (m, 1H), 7.06-7.10 (m, 1H), 6.86-6.97 (m, 4H), 5.18 (s, 2H), 4.05-4.20 (m, 1H), 3.79 (s, 3H), 3.09 (m, 2H), 2.90-3.00 (m, 2H), 2.65 (m, 1H), 1.50-1.62 (m, 8H), 1.36 (m, 1H), 0.44 (m, 1H), 0.29 (m, 2H), 0.01 (m, 1H), −0.08 (m, 1H).

Example 70

Synthesis of methyl (3S)-3-cyclobutyl-3-(3-hydroxyphenyl)-propanoate and methyl (3R)-3-cyclobutyl-3-(3-hydroxyphenyl)propanoate (70)

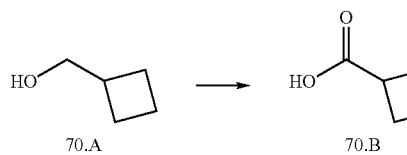

Cyclobutanecarbaldehyde (70.B). To a solution of cyclobutylmethanol (available from Aldrich) (3.29 mL, 34.8 mmol) in 3:1 MeCN/DCM (80 mL) was added TEMPO (0.272 g, 1.74 mmol) and iodobenzene diacetate (11.8 g, 36.6 mmol) as solids. The resulting slurry was stirred overnight at room temperature to afford a homogeneous solution. The reaction mixture was used directly in the next step.

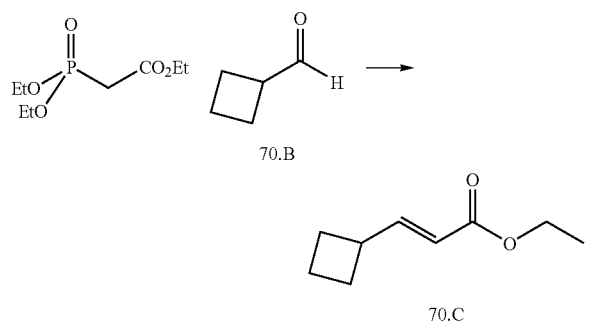

(E)-Ethyl 3-cyclobutylacrylate (70.C). To a suspension of lithium chloride (2.22 g, 52.2 mmol) in MeCN (80 mL) were added ethyl 2-(diethoxyphosphoryl)acetate (available from Aldrich) (8.37 mL, 41.8 mmol) and DBU (16.7 mL, 111 mmol) at room temperature. The mixture was cooled to 0° C., and to it was added cyclobutanecarbaldehyde 70.B (2.93 g, 34.8 mmol) dropwise. The resulting cloudy mixture was warmed to room temperature and stirred overnight. The mixture was partitioned between water and EtOAc. The layers were separated, and the aqueous phase was extracted with additional EtOAc. The combined organic layers were washed with water and brine, dried (MgSO₄), and concentrated. The residue was purified by silica gel flash chromatography (0-10% EtOAc/hexane) to afford (E)-ethyl 3-cyclobutylacrylate 70.C as a colorless liquid (5.00 g, 94%).

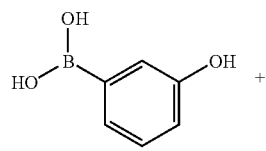

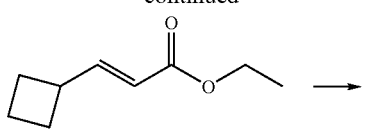

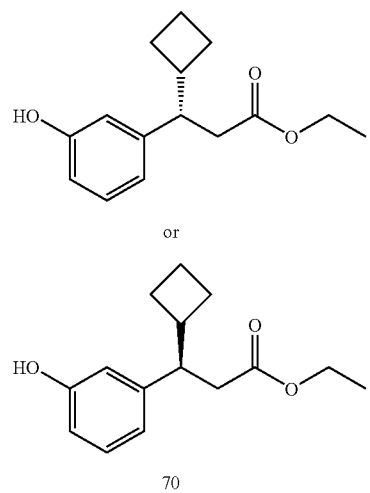

Methyl (3S)-3-cyclobutyl-3-(3-hydroxyphenyl)propanoate or methyl (3R)-3-cyclobutyl-3-(3-hydroxyphenyl) propanoate (70). A mixture of 3-hydroxyphenylboronic acid (available from Aldrich) (2.2 g, 16 mmol) and hydroxy[(S)-BINAP]-rhodium(I) dimer (0.24 g, 0.16 mmol) in 1,4-dioxane (10 mL, 3.2 mmol) was sparged with N₂. To the mixture were added water (1.0 mL, 3.2 mmol) and (E)-ethyl 3-cyclobutylacrylate 70.C (0.56 mL, 3.2 mmol). The resulting red-brown solution was warmed to 45° C. and stirred for 3 hours (sealed vial). The mixture was cooled to room temperature, diluted with EtOAc, washed with saturated aqueous NaHCO₃ and brine, dried (MgSO₄), and concentrated. The crude product was purified by silica gel flash chromatography (0-25% EtOAc/hexane) to afford (S)-ethyl 3-cyclobutyl-3-(3-hydroxyphenyl)propanoate or (R)-ethyl 3-cyclobutyl-3-(3-hydroxyphenyl)propanoate 70 as a pale yellow oil (0.77 g, 96%) (92% e.e.). The enantiomerically enriched mixture was further purified by chiral HPLC (Chiralcel OD, 3% i-PrOH/hexane, 220 nm) to afford 70 as a colorless oil (>99% e.e.).

The following compounds were prepared from 70 and the appropriate halomethyl or hydroxymethyl compound according to the methods described herein. Each of the compounds in the following table were prepared using the same enantiomer of the phenol.

TABLE 10

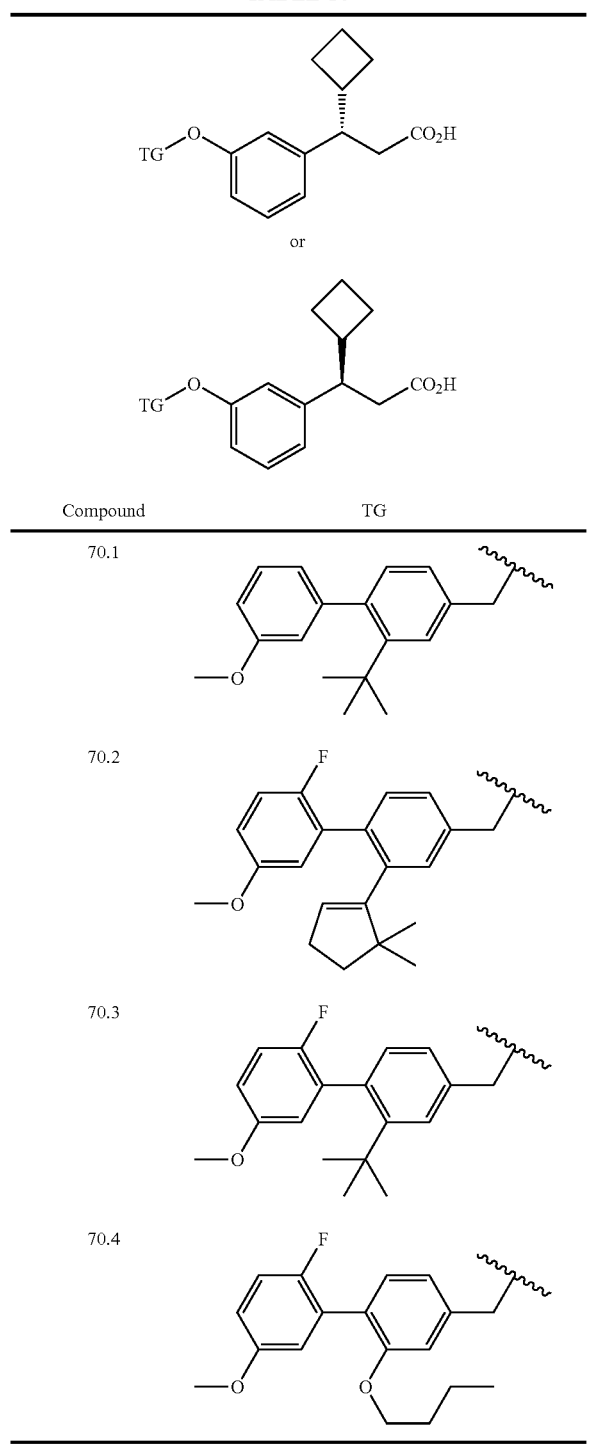

| Compound | TG |
|---|---|
| 70.1 | (3-methoxyphenyl, 2-tert-butyl biphenylmethyl) |
| 70.2 | (2-fluoro-5-methoxyphenyl, 2-(5,5-dimethylcyclopent-1-enyl) biphenylmethyl) |
| 70.3 | (2-fluoro-5-methoxyphenyl, 2-tert-butyl biphenylmethyl) |
| 70.4 | (2-fluoro-5-methoxyphenyl, 2-butyloxy biphenylmethyl) |

(3S)-3-Cyclobutyl-3-(3-(((2-(1,1-dimethylethyl)-3'-(methyloxy)-1,1'-biphenyl-4-yl)methyl)oxy)phenyl)propanoic acid or (3R)-3-cyclobutyl-3-(3-(((2-(1,1-dimethylethyl)-3'-(methyloxy)-1,1'-biphenyl-4-yl)methyl)oxy)phenyl)propanoic acid (70.1). MS ESI (neg.) m/e: 471.3 (M–H). $^1$H NMR (400 MHz) (CDCl$_3$) δ ppm 7.59 (1H, d, J=1.6 Hz), 7.29 (3H, m), 7.07 (1H, d, J=7.8 Hz), 6.91 (5H, m), 6.80 (1H, d, J=7.4 Hz), 5.07 (2H, s), 3.83 (3H, s), 3.02 (1H, td, J=9.8, 5.5 Hz), 2.67 (1H, m), 2.53 (1H, d, J=9.4 Hz), 2.51 (1H, m), 2.14 (1H, m), 1.82 (4H, m), 1.62 (1H, d, J=10.6 Hz), 1.24 (9H, s).

(3S)-3-Cyclobutyl-3-(3-(((2-(5,5-dimethyl-1-cyclopenten-1-yl)-2'-fluoro-5'-(methyloxy)-1,1'-biphenyl-4-yl)methyl)oxy)phenyl)propanoic acid or (3R)-3-cyclobutyl-3-(3-(((2-(5,5-dimethyl-1-cyclopenten-1-yl)-2'-fluoro-5'-(methyloxy)-1,1'-biphenyl-4-yl)methyl)oxy)phenyl)propanoic acid (70.2). $^1$H NMR (400 MHz, CDCl$_3$) δ ppm 7.39 (dd, 1H), 7.33 (d, 1H), 7.28 (d, 1H), 7.20 (t, 1H), 6.95 (t, 1H), 6.84 (dd, 1H), 6.78 (m, 4H), 5.52 (bt, 1H), 5.07 (s, 2H), 3.75 (s, 3H), 3.00 (m, 1H), 2.61 (dd, 1H), 2.48 (m, 2H), 2.24 (dt, 2H), 2.08 (m, 1H), 1.73 (m, 4H), 1.65 (t, 2H), 1.58 (m, 1H), 0.85 (s, 6H).

(3S)-3-Cyclobutyl-3-(3-(((2-(1,1-dimethylethyl)-2'-fluoro-5'-(methyloxy)-1,1'-biphenyl-4-yl)methyl)oxy)phenyl)propanoic acid or (3R)-3-cyclobutyl-3-(3-(((2-(1,1-dimethylethyl)-2'-fluoro-5'-(methyloxy)-1,1'-biphenyl-4-yl)methyl)oxy)phenyl)propanoic acid (70.3). $^1$H NMR (400 MHz, CDCl$_3$) δ ppm 7.60 (d, 1H), 7.28 (dd, 1H), 7.21 (t, 1H), 7.04 (d, 1H), 6.99 (t, 1H), 6.81 (m, 5H), 5.06 (s, 2H), 3.78 (s, 3H), 3.00 (m, 1H), 2.61 (dd, 1H), 2.48 (m, 2H), 2.08 (m, 1H), 1.74 (m, 4H), 1.59 (m, 1H), 1.23 (s, 9H).

(3S)-3-(3-(((2-(Butyloxy)-2'-fluoro-5'-(methyloxy)-1,1'-biphenyl-4-yl)methyl)oxy)phenyl)-3-cyclobutylpropanoic acid or (3R)-3-(3-(((2-(butyloxy)-2'-fluoro-5'-(methyloxy)-1,1'-biphenyl-4-yl)methyl)oxy)phenyl)-3-cyclobutylpropanoic acid (70.4). $^1$H NMR (400 MHz, CDCl$_3$) δ ppm 7.28 (d, 1H), 7.20 (t, 1H), 7.06 (m, 2H), 7.02 (t, 1H), 6.88 (dd, 1H), 6.83 (m, 3H), 6.78 (d, 1H), 5.05 (s, 2H), 3.98 (t, 2H), 3.79 (s, 3H), 3.00 (m, 1H), 2.61 (dd, 1H), 2.48 (m, 2H), 2.08 (m, 1H), 1.74 (m, 4H), 1.66 (m, 2H), 1.59 (m, 1H), 1.37 (m, 2H), 0.88 (t, 3H).

Example 71

Synthesis of methyl (3R)-3-(3-hydroxyphenyl)heptanoate or methyl (3S)-3-(3-hydroxyphenyl)heptanoate (71)

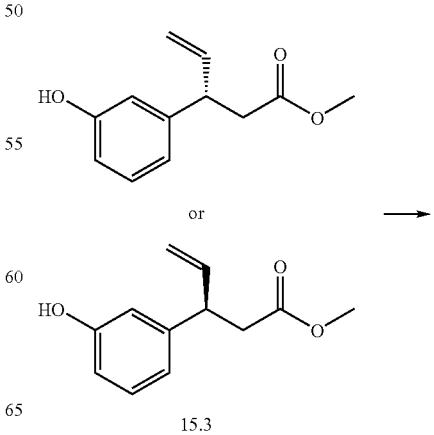

15.3

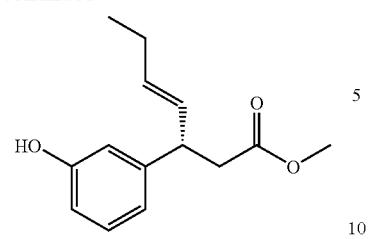

71.A

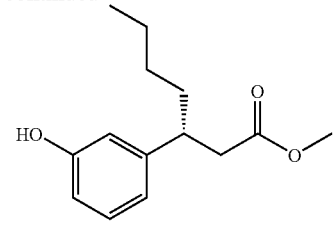

71

(S,E)-Methyl 3-(3-hydroxyphenyl)hept-4-enoate or (R,E)-methyl 3-(3-hydroxyphenyl)hept-4-enoate (71.A). To a solution of 15.3 (0.10 g, 0.48 mmol) in DCM (1 mL) were added (E)-hex-3-ene (available from Aldrich) (0.90 mL, 7.3 mmol) and Grubbs II catalyst (0.021 g, 0.024 mmol). The mixture was stirred overnight at 40° C. (sealed vial), cooled to room temperature, and concentrated. The residue was purified by silica gel flash chromatography (0-25% EtOAc/hexane) to afford 71.A as a pale yellow oil (110 mg, 97%).

Methyl (3R)-3-(3-hdroxyphenyl)heptanoate or methyl (3S-3-(3-hdroxyphenyl)heptanoate). A vial containing a solution of 71.A (91 mg, 388 µmol) in EtOAc (1.5 mL) was purged with $N_2$, and to it was added 10% Pd/C (21 mg, 19 µmol). The vial was then purged with $H_2$ and the contents stirred overnight under a $H_2$ balloon. The black mixture was flushed through a pad of silica gel (EtOAc) and concentrated. The residue was purified by silica gel flash chromatography (0-25% EtOAc/hexane) to afford (R)-methyl 3-(3-hydroxyphenyl)heptanoate or (S-methyl 3-(3-hydroxyphenyl)heptanoate as a colorless oil (81 mg, 88%).

The following compounds were prepared from 71 and the appropriate halomethyl or hydroxymethyl compound according to the methods described herein. Each of the compounds in the following table were prepared using the same enantiomer of the phenol.

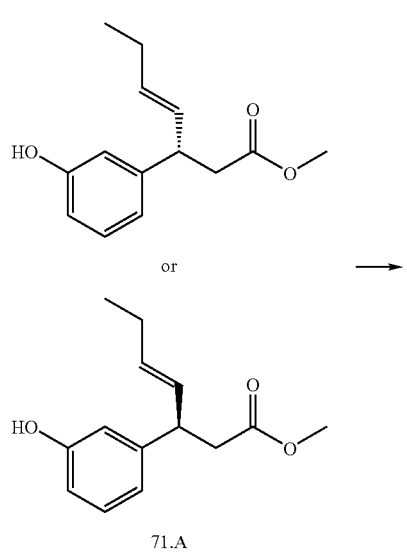

71.A

TABLE 11

| Compound | TG |
|---|---|
| 71.1 | ![structure with F, tert-butyl, and O groups] |

TABLE 11-continued

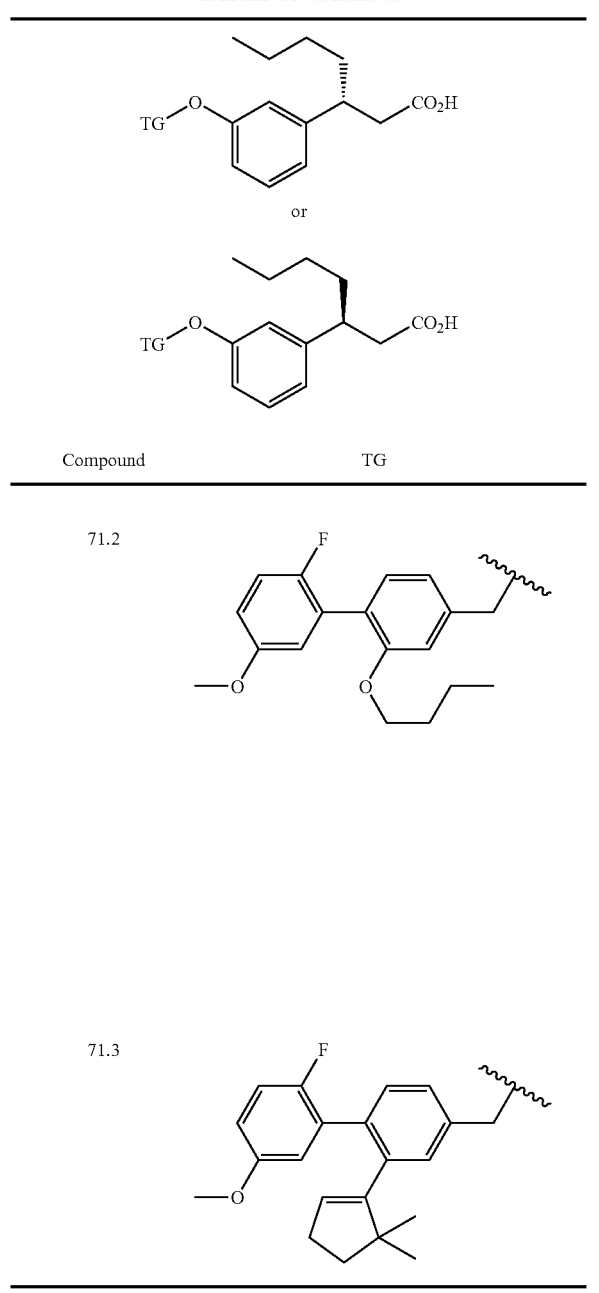

| Compound | TG |
|---|---|
| 71.2 | (structure shown) |
| 71.3 | (structure shown) |

(3R)-3-(3-(((2-(1,1-Dimethylethyl)-2'-fluoro-5'-(methyloxy)-1,1'-biphenyl-4-yl)methyl)oxy)phenyl)heptanoic acid or (3S-3-(3-(((2-(1,1-dimethylethyl)-2'-fluoro-5'-(methyloxy)-1,1'-biphenyl-4-yl)methyl)oxy)phenyl)heptanoic acid.1). MS ESI (pos.) m/e: 493.3 (M+H)$^+$, 510.2 (M+H$_2$O)$^+$, 515.2 (M+Na)$^+$.

(3R)-3-(3-(((2-(Butyloxy)-2'-fluoro-5'-(methyloxy)-1,1'-biphenyl-4-yl)methyl)oxy)phenyl)heptanoic acid or (3S)-3-(3-(((2-(butyloxy)-2'-fluoro-5'-(methyloxy)-1,1'-biphenyl-4-yl)methyl)oxy)phenyl)heptanoic acid (71.2). MS ESI (pos.) m/e: 509.2 (M+H)$^+$, 526.3 (M+H$_2$O)$^+$, 531.2 (M+Na)$^+$, 547.2 (M+K)$^+$.

(3R)-3-(3-(((2-(5,5-Dimethyl-1-cyclopenten-1-yl)-2'-fluoro-5'-(methyloxy)-1,1'-biphenyl-4-yl)methyl)oxy)phenyl)heptanoic acid or (3S)-3-(3-(((2-(5,5-dimethyl-1-cyclo-penten-1-yl)-2'-fluoro-5'-(methyloxy)-1,1'-biphenyl-4-yl)methyl)oxy)phenyl)heptanoic acid (71.3). MS ESI (pos.) m/e: 548.3 (M+H$_2$O)$^+$.

Example 72

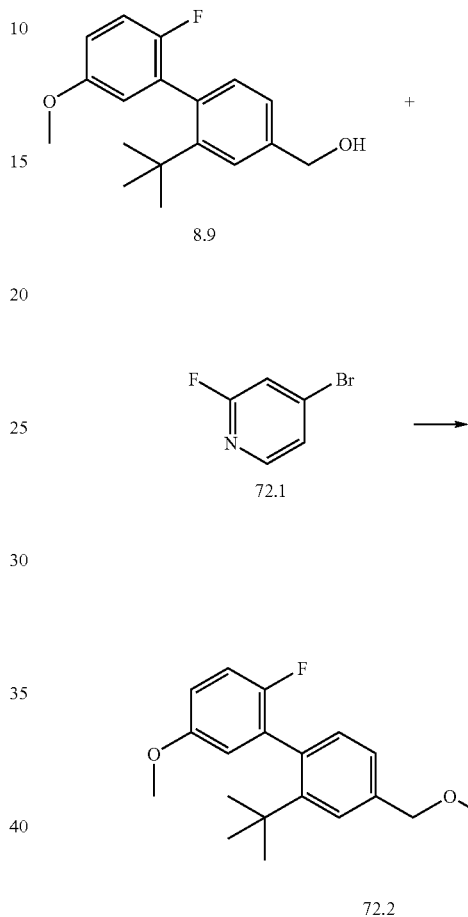

4-Bromo-2-(((2-(1,1-dimethylethyl)-2'-fluoro-5'-(methyloxy)-1,1'-biphenyl-4-yl)methyl)oxy)pyridine (72.2). A dry round bottom flask containing 8.9 (0.0889 g, 0.308 mmol) in dry DMF (1.5 mL) was cooled in an ice bath. After about 10 minutes, sodium hydride (0.0150 g, 0.375 mmol) (60% wt in oil) was added carefully, and the mixture was stirred at 0° C. After 10 minutes, 72.1 (commercially available from Synthonix Corporation) (0.0543 g, 0.308 mmol) was added. The reaction was allowed to stir overnight at room temperature. After 18 hours, the reaction was diluted with water and then extracted five times with EtOAc. The organic extracts were then washed one time with brine and dried over anhydrous MgSO$_4$. The solid was filtered off, and the solvent was concentrated. The residue was purified by flash chromatography (SiO$_2$ gel 60, eluted with 0 to 25% EtOAc in hexanes). Fractions containing the desired product were combined and concentrated to provide 72.2 as a colorless oil (0.0993 g, 73%). $^1$H NMR (400 MHz) (CDCl$_3$) δ ppm 8.07 (1H, m), 7.66 (1H, d, J=1.6 Hz), 7.32 (1H, dd, J=7.8, 1.6 Hz), 7.10 (3H, m), 7.02 (1H, t, J=8.8 Hz), 6.87 (1H, dt, J=8.9, 3.6 Hz), 6.81 (1H, dd, J=5.9, 3.1 Hz), 5.43 (2H, s), 3.80 (3H, s), 1.27 (9H, s).

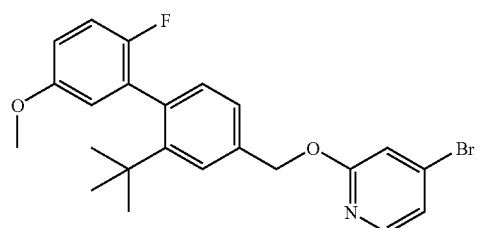

72.2

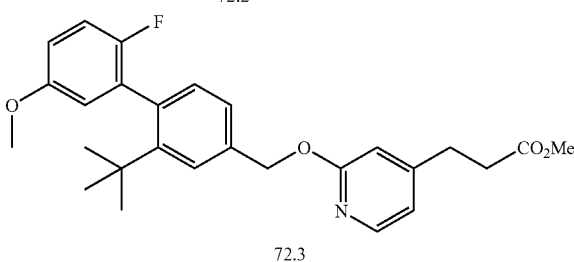

72.3

Methyl 3-(2-(((2-(1,1-dimethylethyl)-2'-fluoro-5'-(methyloxy)-1,1'-biphenyl-4-yl)methyl)oxy)-4-pyridinyl)propanoate (72.3). To a sealed tube containing 72.2 (0.0980 g, 0.22 mmol), bis(dibenzylideneacetone)palladium (0.0068 g, 0.012 mmol), and CTC-Q-Phos (commercially available from Strem Chemicals.) (0.0083 g, 0.0116 mmol) was added dry THF (3.000 mL, 0.22 mmol). After about 5 minutes, 3-ethoxy-3-oxopropylzinc bromide, 0.5M solution in THF (1.000 mL, 0.50 mmol) was added dropwise. After 1 hour, the mixture was heated to 80° C. and monitored with TLC and LC-MS. After 16.5 hours, the reaction was cooled to room temperature and the organic solvent was then removed under reduced pressure. The residue was purified by flash chromatography (SiO$_2$ gel 60, eluted with 0 to 40% EtOAc in hexanes). Fractions containing the desired product were combined and concentrated to a light brown oil (0.0646 g, 63%). $^1$H NMR (400 MHz) (CDCl$_3$) δ ppm 8.11 (1H, d, J=5.3 Hz), 7.65 (1H, d, J=1.6 Hz), 7.32 (1H, dd, J=7.7, 1.7 Hz), 7.07 (2H, m), 6.85 (1H, dt, J=8.9, 3.6 Hz), 6.80 (2H, m), 6.70 (1H, s), 5.41 (2H, s), 4.15 (2H, q, J=7.2 Hz), 3.79 (3H, s), 2.93 (2H, t, J=7.6 Hz), 2.64 (2H, t, J=7.7 Hz), 1.29 (12H, m).

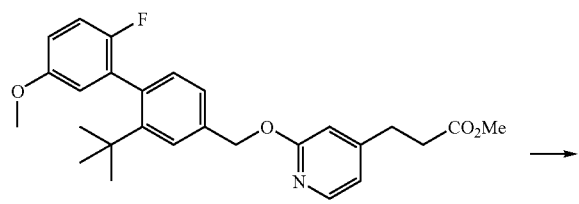

72.3

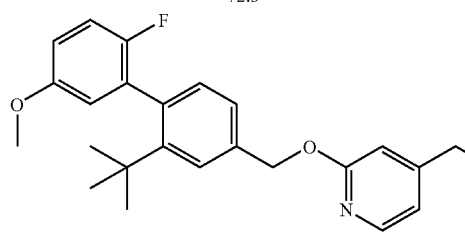

72

3-(2-(((2-(1,1-Dimethylethyl)-2'-fluoro-5'-(methyloxy)-1,1'-biphenyl-4-yl)methyl)oxy)-4-pyridinyl)propanoic acid (72). Ester 72.3 was hydrolyzed by the methods reported in US 2006/0004012 to perform such operations on other compounds. MS ESI (neg.) m/e: 436.1 (M–H). $^1$H NMR (400 MHz) (CDCl$_3$) δ ppm 8.21 (1H, d, J=5.5 Hz), 7.63 (1H, d, J=1.6 Hz), 7.30 (2H, dd, J=7.6, 1.8 Hz), 7.08 (2H, m), 6.91 (1H, m), 6.87 (1H, m), 6.80 (1H, s), 6.77 (1H, dd, J=5.9, 3.1 Hz), 5.40 (2H, s), 3.79 (3H, s), 2.98 (2H, t, J=7.4 Hz), 2.73 (2H, t, J=7.4 Hz), 1.24 (9H, s).

Example 73

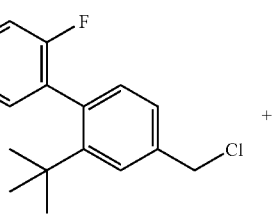

8.10

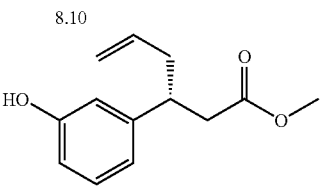

or

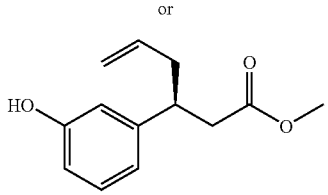

43.5

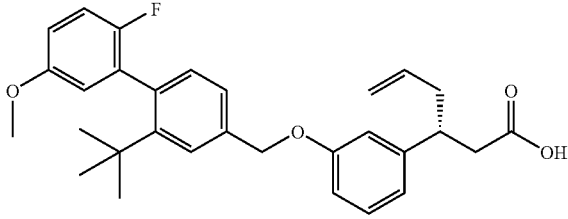

or

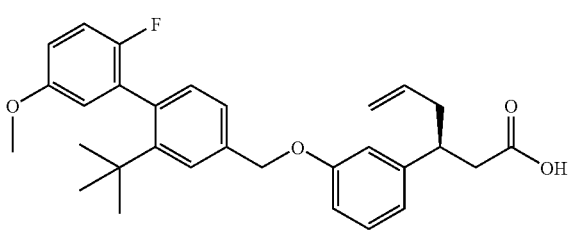

73

(3S)-3-(3-(((2-(1,1-Dimethylethyl)-2'-fluoro-5'-(methyloxy)-1,1'-biphenyl-4-yl)methyl)oxy)phenyl)-5-hexenoic acid or (3R)-3-(3-(((2-(1,1-dimethylethyl)-2'-fluoro-5'-(methyloxy)-1,1'-biphenyl-4-yl)methyl)oxy)phenyl)-5-hexenoic acid (73). Compound 43.5 was coupled with 8.10 and hydrolyzed according to the methods described herein. $^1$H NMR (400 MHz, CDCl$_3$) δ ppm 7.60 (d, 1H), 7.29 (dd, 1H), 7.24 (t, 1H), 7.05 (d, 1H), 6.99 (t, 1H), 6.85 (m, 4H), 6.77 (dd, 1H), 5.65 (m, 1H), 5.07 (s, 2H), 5.00 (m, 2H), 3.78 (s, 3H), 3.19 (m, 1H), 2.72 (dd, 1H), 2.61 (dd, 1H), 2.39 (m, 2H), 1.23 (s, 9H).

Example 74

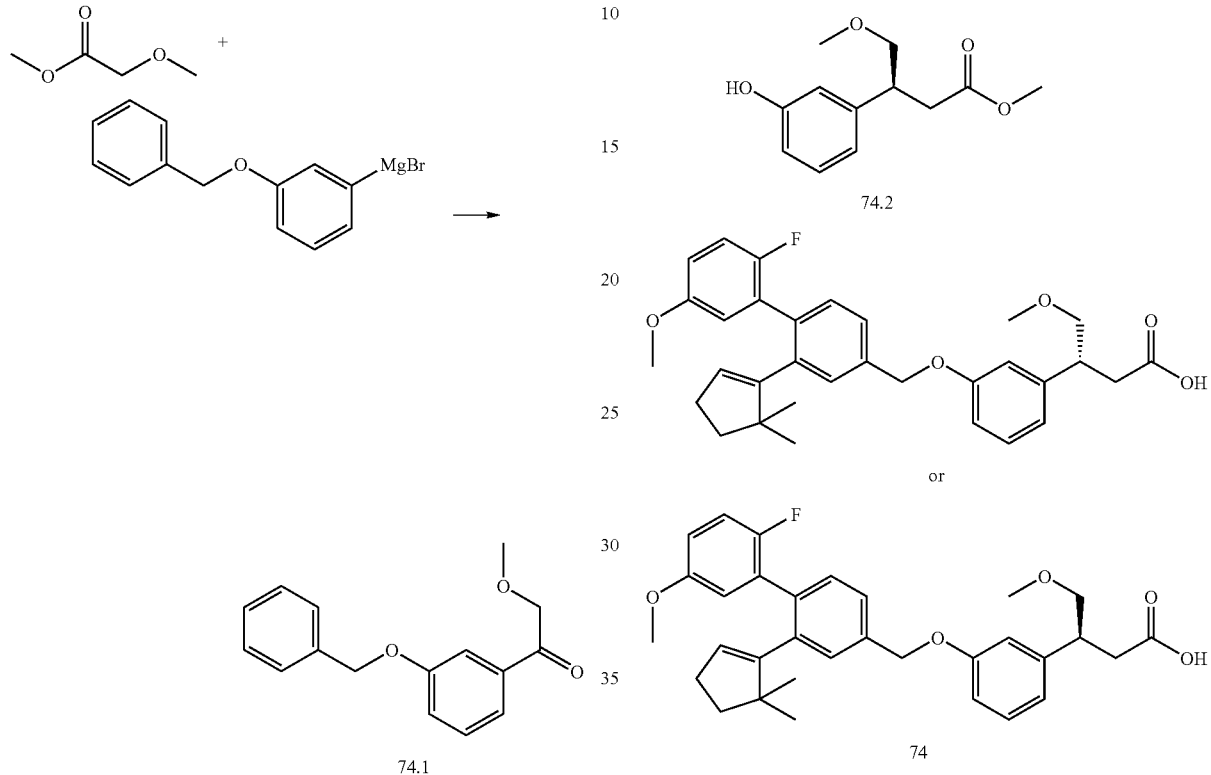

1-(3-(Benzyloxy)phenyl)-2-methoxyethanone (74.1). To a solution of methyl methoxyacetate (available from Aldrich) (0.48 mL, 4.8 mmol) in ether (20.0 mL) was added a 1.0 M solution of (3-(benzyloxy)phenyl)magnesium bromide in THF (available from Aldrich) (5.0 mL, 5.0 mmol) dropwise at −78° C. The mixture was warmed to room temperature overnight, quenched with 1 N HCl, and diluted with EtOAc. The organics were washed with water and brine, dried (MgSO$_4$), and concentrated. The crude product was purified by silica gel flash chromatography (0-20% EtOAc/hexane) to afford 1-(3-(benzyloxy)phenyl)-2-methoxyethanone (0.17 g, 14%) as a pale yellow oil.

(3R)-3-(3-(((2-(5,5-Dimethyl-1-cyclopenten-1-yl)-2'-fluoro-5'-(methyloxy)-1,1'-biphenyl-4-yl)methyl)oxy)phenyl)-4-(methyloxy)butanoic acid or (3S)-3-(3-(((2-(5,5-dimethyl-1-cyclopenten-1-yl)-2'-fluoro-5'-(methyloxy)-1,1'-biphenyl-4-yl)methyl)oxy)phenyl)-4-(methyloxy)butanoic acid (74). Compound 74.2 was obtained from compound 74.1 by a method analogous to that used for the preparation of compound 5.7 as described in Example 5 using a Peterson olefination followed by hydrogenation and final chiral separation. Coupling with 14.5 and hydrolysis was carried out according to the methods described herein. $^1$H NMR (400 MHz, CDCl$_3$) δ ppm 7.39 (dd, 1H), 7.33 (d, 1H), 7.28 (d, 1H), 7.24 (t, 1H), 6.96 (t, 1H), 6.88 (m, 2H), 6.84 (bd, 1H), 6.79 (m, 2H), 5.52 (bt, 1H), 5.08 (s, 2H), 3.75 (s, 3H), 3.56 (dd, 1H), 3.48 (t, 1H), 3.40 (m, 1H), 3.33 (s, 3H), 2.88 (dd, 1H), 2.65 (dd, 1H), 2.24 (dt, 2H), 1.65 (t, 2H), 0.85 (s, 6H).

Example 75

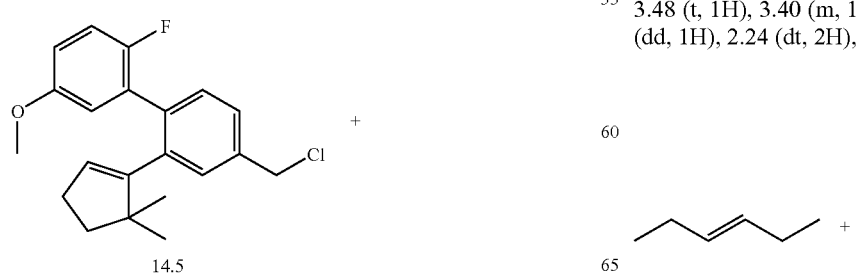

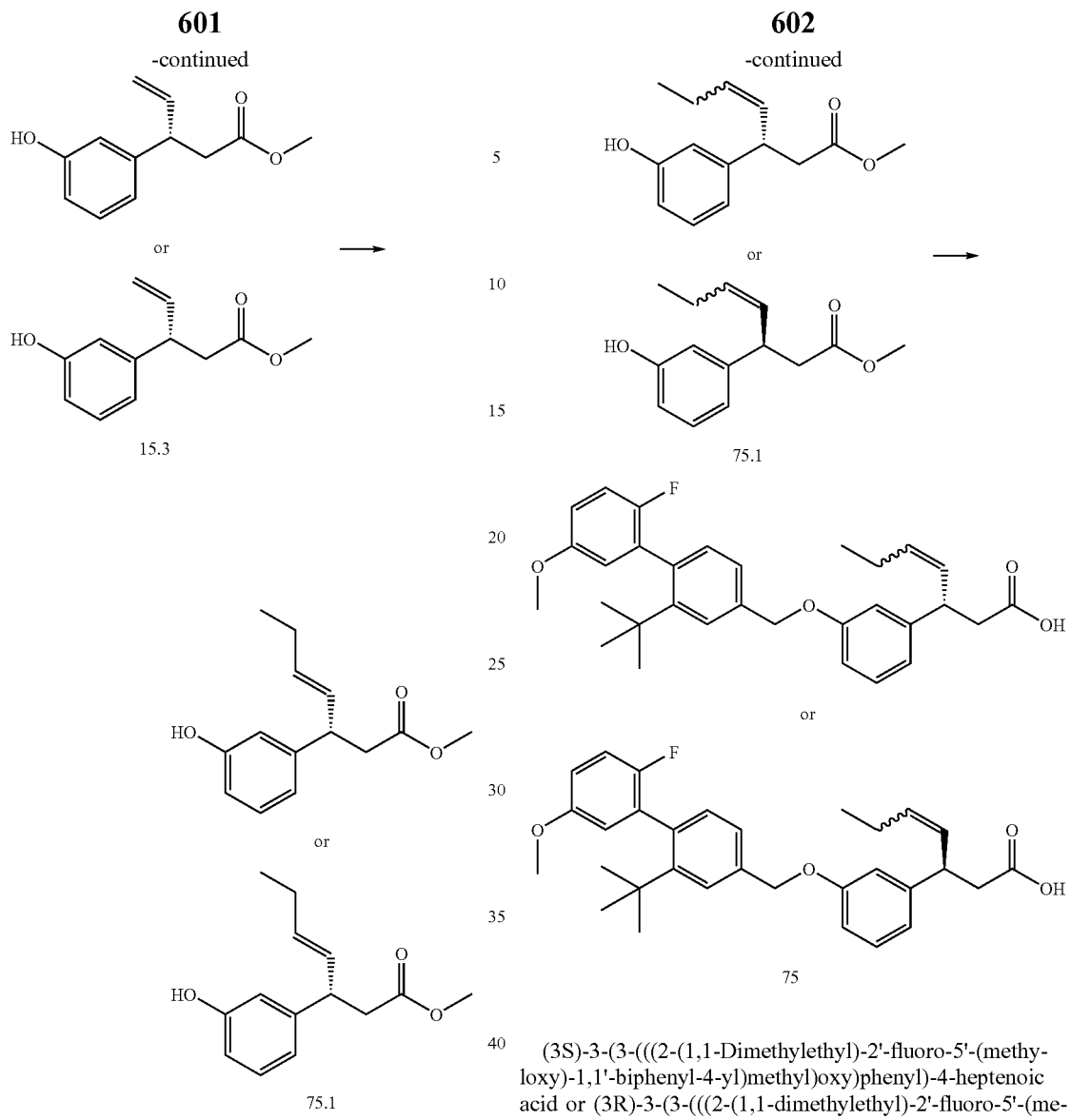

Methyl (3S,4E)-3-(3-hydroxyphenyl)-4-heptenoate or methyl (3R,4E)-3-(3-hydroxyphenyl)-4-heptenoate (75.1). To a solution of 15.3 (0.10 g, 0.48 mmol) in DCM (1 mL), were added (E)-hex-3-ene (available from Aldrich) (0.90 mL, 7.3 mmol) and Grubbs Catalyst $2^{nd}$ Generation (0.021 g, 0.024 mmol). The mixture was stirred overnight at 40° C., cooled to room temperature, and concentrated. The crude product was purified by silica gel flash chromatography (0-25% EtOAc/hexane) to afford 75.1 (0.11 g, 97%) as a pale yellow oil.

(3S)-3-(3-(((2-(1,1-Dimethylethyl)-2'-fluoro-5'-(methyloxy)-1,1'-biphenyl-4-yl)methyl)oxy)phenyl)-4-heptenoic acid or (3R)-3-(3-(((2-(1,1-dimethylethyl)-2'-fluoro-5'-(methyloxy)-1,1'-biphenyl-4-yl)methyl)oxy)phenyl)-4-heptenoic acid (75). Coupling of 75.1 with 8.10 and hydrolysis was carried out according to the methods described herein. MS ESI (pos.) m/e: 491.2 (M+H)$^+$, 508.3 (M+H$_2$O)$^+$, 513.3 (M+Na)$^+$.

Example 76

Synthesis of methyl (3R)-3-(2-fluoro-5-hydroxyphenyl)pentanoate or methyl (3S)-3-(2-fluoro-5-hydroxyphenyl)pentanoate (76)

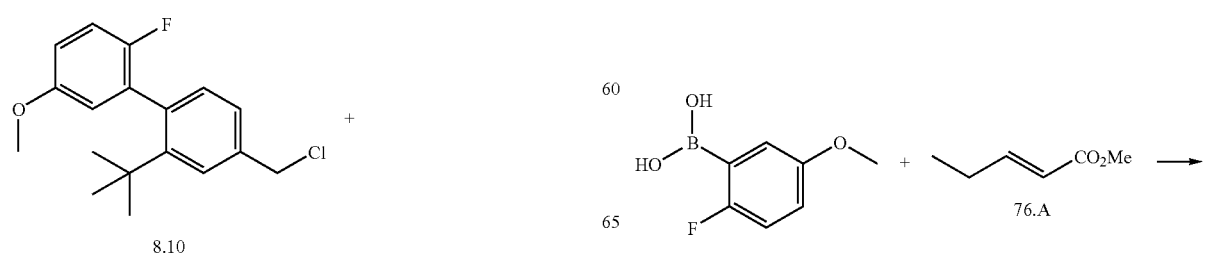

-continued

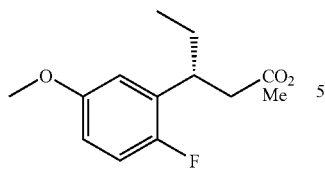

or

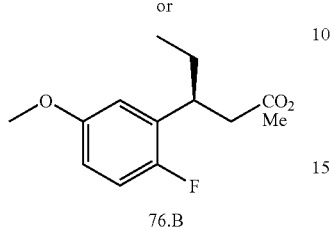

76.B (R)-Methyl 3-(2-fluoro-5-methoxyphenyl)pentanoate or (S)-methyl 3-(2-fluoro-5-methoxyphenyl)pentanoate (76.B). A dioxane/water (10/1 mixture (5.5 mL)) mixture was added to a flask charged with hydroxy[(S)-BINAP]-rhodium(I) dimer (260 mg, 175 µmol) and 2-fluoro-5-methoxyphenyl-boronic acid (commercially available from Aldrich) (3.0 g, 17522 µmol) and (E)-methyl pent-2-enoate (available from Aldrich) (400 mg, 3504 µmol). The mixture was flushed with nitrogen. The resulting mixture was then stirred at 40° C. for 3 hours. After removal of the solvent, the residue was dissolved in EtOAc. The solution was washed with water, brine and dried over anhydrous Na₂SO₄. The crude was purified by silica gel flash chromatography (0 to 15% EtOAc/Hexanes) to provide (R)-methyl 3-(2-fluoro-5-methoxyphenyl)pentanoate or (S)-methyl 3-(2-fluoro-5-methoxyphenyl)pentanoate 76.B (167 mg, 20% yield) as a colorless oil. The product is believed to be the R enantiomer.

-continued

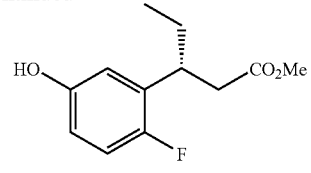

or

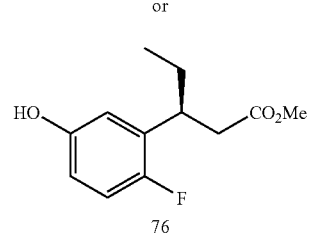

76

Methyl (3R)-3-(2-fluoro-5-hydroxyphenyl)pentanoate or methyl (3S)-3-(2-fluoro-5-hydroxyphenyl)pentanoate (76). To a solution of 76.B (167 mg, 695 µmol) in DCE (5 mL) was added 1,2-ethanedithiol (932 µL, 11121 µmol) followed by anhydrous aluminum chloride (741 mg, 5560 µmol) at 0° C. The reaction mixture was allowed to slowly warm to room temperature over four hours and then quenched with saturated Rochelle's salt solution. The mixture was extracted (2×50 mL) with DCM. The combined organic layers were washed with water (1×40 mL) and brine (1×40 mL) and dried over magnesium sulfate. The filtrate was concentrated, and the residue was purified by chromatography (silica, 0 to 30% EtOAc:hexanes) to give 76 (100 mg, 75%)

The following compounds were prepared from 76 and the appropriate halomethyl or hydroxymethyl compound according to the methods described herein. Each of the compounds in the following table were prepared using the same enantiomer of the phenol.

TABLE 12

| Compound | TG |
|---|---|
| 76.1 | 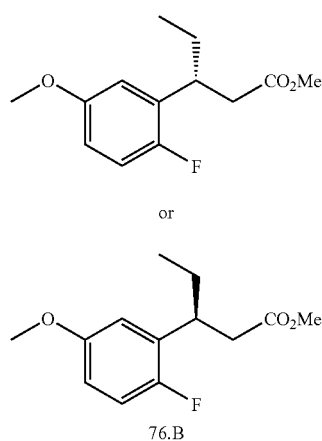 |

TABLE 12-continued

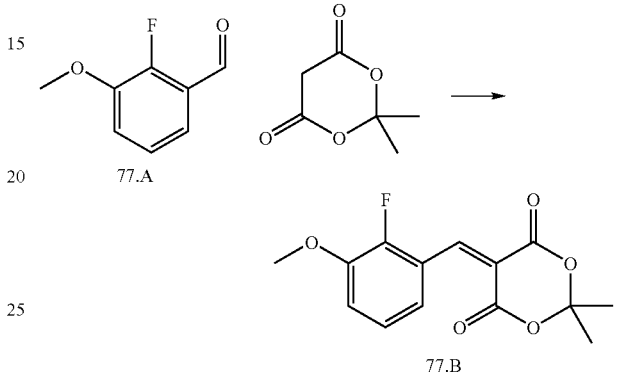

| Compound | TG |
|---|---|
| 76.2 | ![structure] |
| 76.3 | ![structure] |

(3R)-3-(5-(((2-(5,5-Dimethyl-1-cyclopenten-1-yl)-2'-fluoro-5'-(methyloxy)-1,1'-biphenyl-4-yl)methyl)oxy)-2-fluorophenyl)pentanoic acid or (3S)-3-(5-(((2-(5,5-dimethyl-1-cyclopenten-1-yl)-2'-fluoro-5'-(methyloxy)-1,1'-biphenyl-4-yl)methyl)oxy)-2-fluorophenyl)pentanoic acid (76.1). (MS ESI (neg.) m/e: 519.2 (M–H).

(3R)-3-(5-(((2-(1,1-Dimethylethyl)-2'-fluoro-5'-(methyloxy)-1,1'-biphenyl-4-yl)methyl)oxy)-2-fluorophenyl)pentanoic acid or (3S)-3-(5-(((2-(1,1-dimethylethyl)-2'-fluoro-5'-(methyloxy)-1,1'-biphenyl-4-yl)methyl)oxy)-2-fluorophenyl)pentanoic acid (76.2). (MS ESI (neg.) m/e: 481.2 (M–H).

(3R)-3-(5-(((2-((1S)-2,2-Dimethylcyclopentyl)-2'-fluoro-5'-(methyloxy)-1,1'-biphenyl-4-yl)methyl)oxy)-2-fluorophenyl)pentanoic acid or (3R)-3-(5-(((2-((1R)-2,2-dimethylcyclopentyl)-2'-fluoro-5'-(methyloxy)-1,1'-biphenyl-4-yl)methyl)oxy)-2-fluorophenyl)pentanoic acid or (3S)-3-(5-(((2-((1S)-2,2-dimethylcyclopentyl)-2'-fluoro-5'-(methyloxy)-1,1'-biphenyl-4-yl)methyl)oxy)-2-fluorophenyl)pentanoic acid or (3S)-3-(5-(((2-((1R)-2,2-dimethylcyclopentyl)-2'-fluoro-5'-(methyloxy)-1,1'-biphenyl-4-yl)methyl)oxy)-2-fluorophenyl)pentanoic acid (76.3). MS ESI (neg.) m/e: 521.3 (M–H)

Example 77

Synthesis of methyl (3R)-3-(2-fluoro-3-hydroxyphenyl)pentanoate and methyl (3S)-3-(2-fluoro-3-hydroxyphenyl)pentanoate (77.G and 77.H))

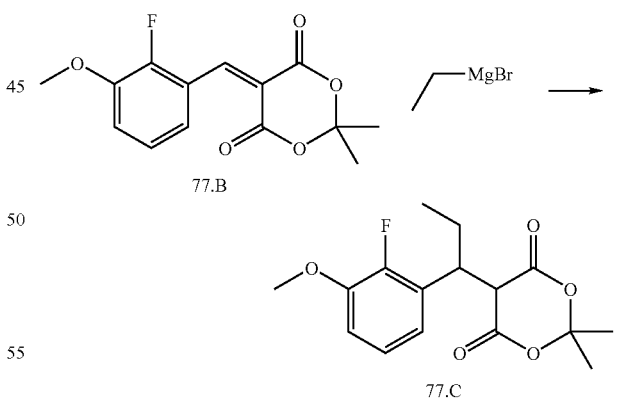

5-(2-Fluoro-3-methoxybenzylidene)-2,2-dimethyl-1,3-dioxane-4,6-dione (77.B). A 500 mL round bottom flask was charged with 2-fluoro-3-methoxybenzaldehyde 77.A (available from Aldrich) (28.6 g, 186 mmol), 2,2-dimethyl-1,3-dioxane-4,6-dione (available from Aldrich) (34.8 g, 241 mmol), and water (350 mL). The heterogeneous mixture was stirred for 2 hours at 90° C. (reflux), cooled to room temperature, and filtered. The resulting off-white solid was triturated with ether to afford 5-(2-fluoro-3-methoxybenzylidene)-2,2-dimethyl-1,3-dioxane-4,6-dione 77.B (30.6 g, 58.8% yield) as a crystalline white powder.

5-(1-(2-Fluoro-3-methoxyphenyl)propyl)-2,2-dimethyl-1,3-dioxane-4,6-dione (77.C). A 500 mL round bottom flask was charged with 5-(2-fluoro-3-methoxybenzylidene)-2,2-dimethyl-1,3-dioxane-4,6-dione 77.B (5.00 g, 17.8 mmol) and THF (100 mL). The resulting slurry was cooled to 0° C., and to it was added ethylmagnesium bromide (available from Aldrich) (3.0 M/ether) (11.9 mL, 35.7 mmol) dropwise over 15 minutes. The cooling bath was removed, and the mixture was stirred for 1 hour at ambient temperature. The reaction was quenched with 1 N HCl and extracted with EtOAc. The combined organic layers were washed with brine, dried (MgSO₄), and concentrated to afford 5-(1-(2-fluoro-3-methoxyphenyl)propyl)-2,2-dimethyl-1,3-dioxane-4,6-dione 77.C (5.17 g, 93.4% yield) as a yellow oil (5.2 g, 93%). The product thus obtained was used without further purification.

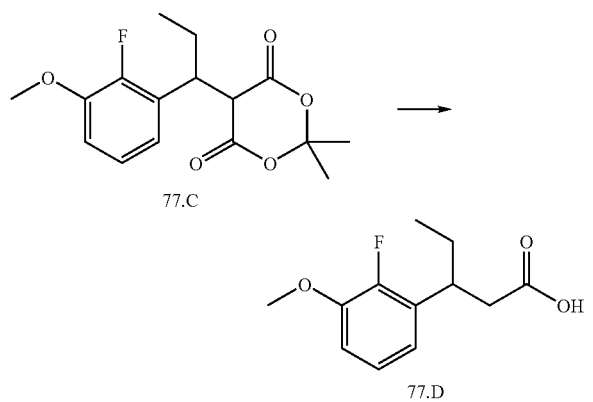

3-(2-Fluoro-3-methoxyphenyl)pentanoic acid (77.D). A 500 mL round bottom flask was charged with 5-(1-(2-fluoro-3-methoxyphenyl)propyl)-2,2-dimethyl-1,3-dioxane-4,6-dione 77.C (5.17 g, 16.7 mmol) and 10:1 DMF/water (80 mL). The pale yellow solution was stirred overnight at 90° C., cooled to room temperature, and diluted with ether. The combined organic layers were washed with water and brine, dried (MgSO₄), and concentrated to afford 3-(2-fluoro-3-methoxyphenyl)pentanoic acid 77.D (3.44 g, 91.3% yield) as a yellow oil. The crude product was used without further purification.

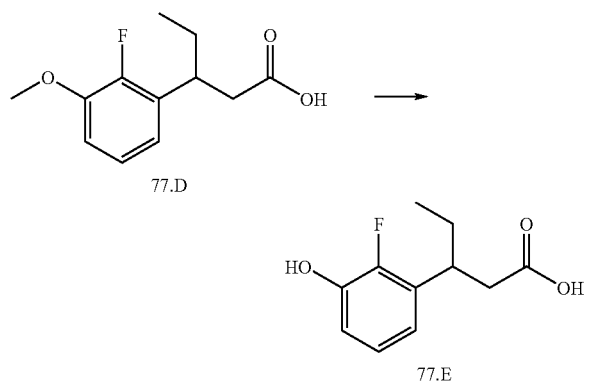

3-(2-Fluoro-3-hydroxyphenyl)pentanoic acid (77.E). A 500 mL round bottom flask was charged with 3-(2-fluoro-3-methoxyphenyl)pentanoic acid 77.D (3.44 g, 15.2 mmol), NMP (30 mL), NaOH (2.74 g, 68.4 mmol), and 1-dodecanethiol (available from Aldrich) (12.8 mL, 53.2 mmol). The mixture was stirred for 5 hours at 125° C. under N₂, cooled to room temperature, and diluted with 1 N HCl and EtOAc. The combined organic layers were washed with water and brine, dried (MgSO₄), and concentrated to afford 3-(2-fluoro-3-hydroxyphenyl)pentanoic acid 77.E as a yellow liquid (3.23 g). The product so obtained was used without further purification.

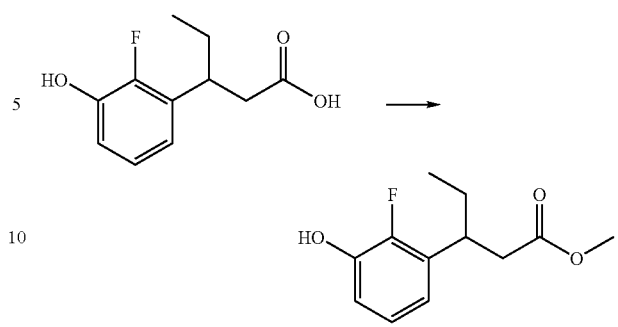

Methyl 3-(2-fluoro-3-hydroxyphenyl)pentanoate (77.F). A 500 mL round bottom flask was charged with 77.E (21.5 g, 101 mmol), MeOH (300 mL), and sulfuric acid (1.08 mL, 20.3 mmol). The solution was stirred for 1 hour at 80° C., cooled to room temperature, and diluted with ether. The organic layers were washed with saturated aqueous NaHCO₃, water, and brine, dried (MgSO₄), and concentrated. The crude product was purified by silica gel flash chromatography (0-30% EtOAc/hexane) to afford 77.F (20.6 g, 90% yield) as a yellow oil.

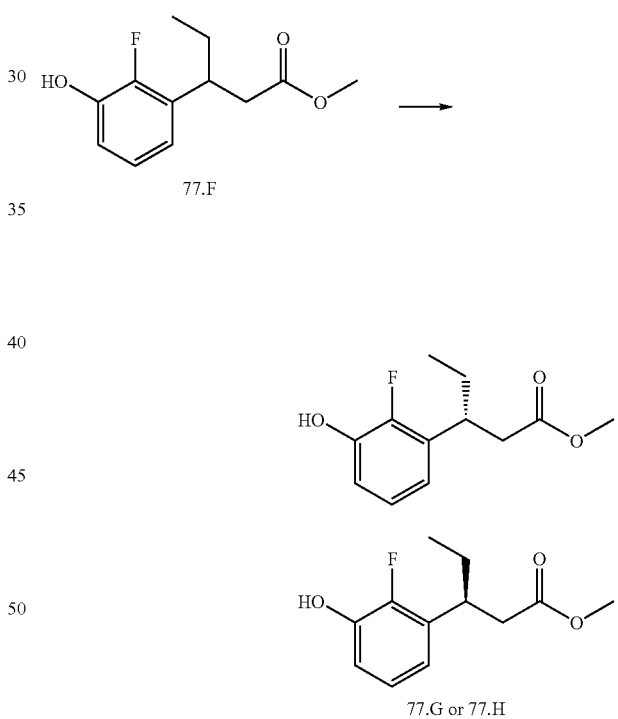

(R)-Methyl 3-(2-fluoro-3-hydroxyphenyl)pentanoate and (S)-methyl 3-(2-fluoro-3-hydroxyphenyl)pentanoate (77.G and 77.H). Racemic 77.F (20 g) was resolved by chiral HPLC (Chiralcel OD column, 3% IPA/hexane, detection at 220 nm) to afford (in order of elution) 77.G (8 g, 80% yield, 99% e.e.) and 77.H (8 g, 80% yield, 99% e.e.) as colorless oils.

The following compounds were prepared from 77.G and the appropriate halomethyl or hydroxymethyl compound according to the methods described herein. Each of the compounds in the following table were prepared using the same enantiomer of the phenol.

TABLE 13

| Compound | TG |
|---|---|
| 77.1 | |
| 77.2 | |
| 77.3 | |
| 77.4 | |

TABLE 13-continued

| Compound | TG |
|---|---|
| 77.5 | |
| 77.6 | |

TABLE 13-continued
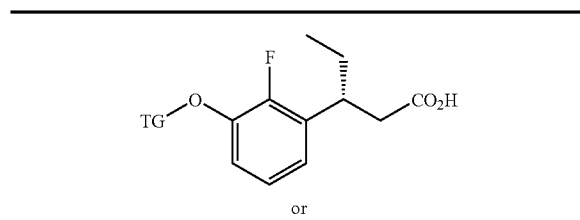
or
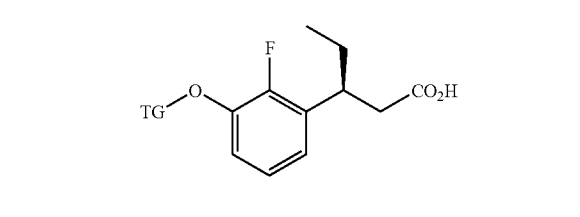
| Compound | TG |
|---|---|
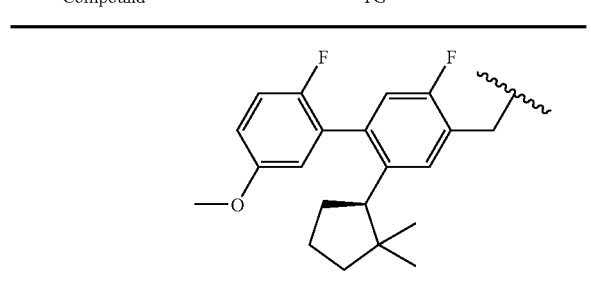
77.7
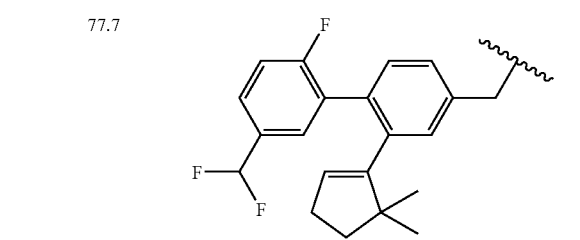
77.8
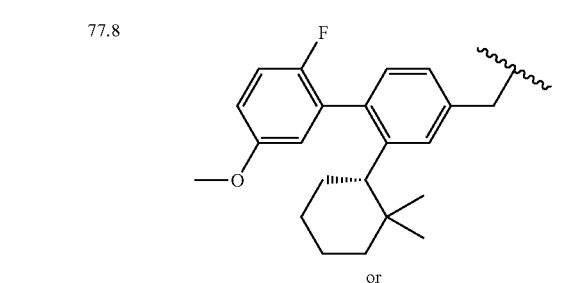
or
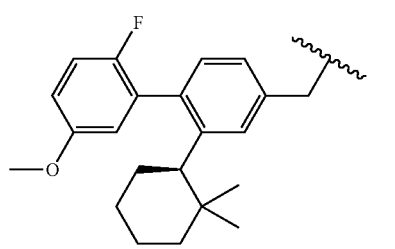
TABLE 13-continued
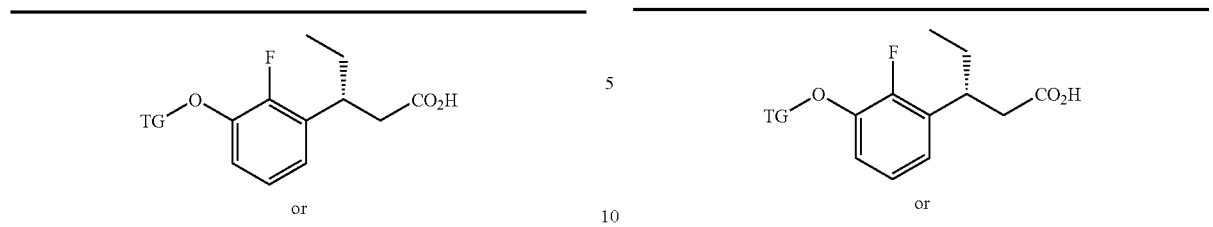
or
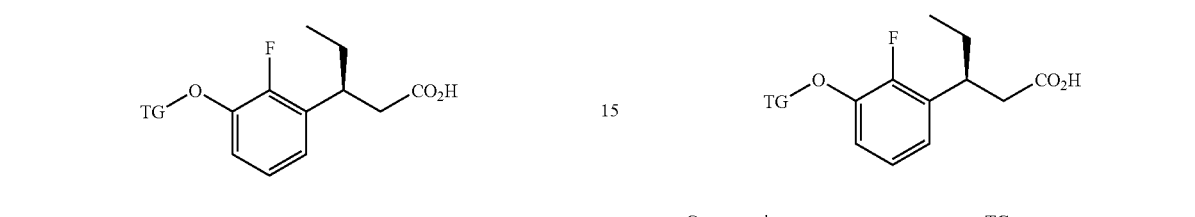
| Compound | TG |
|---|---|
| 77.9 | |
or
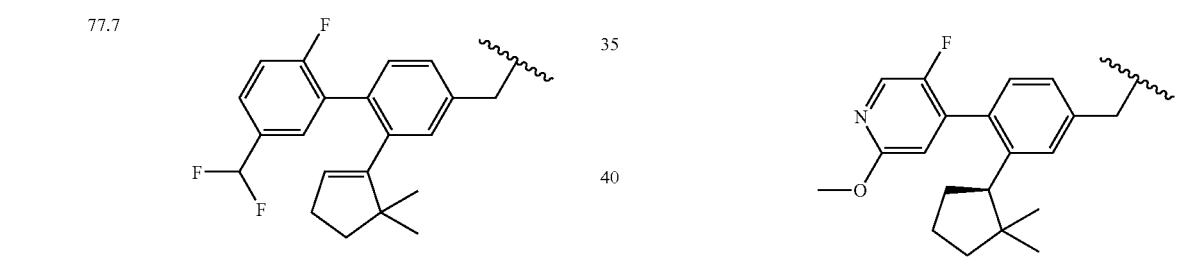
77.10
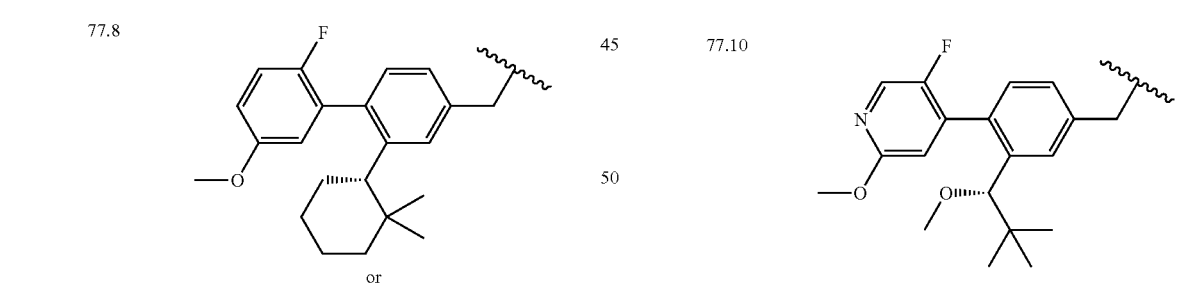
or
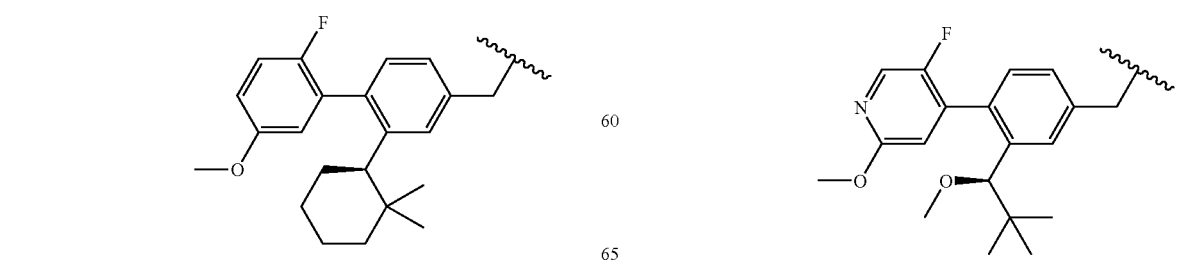

TABLE 13-continued

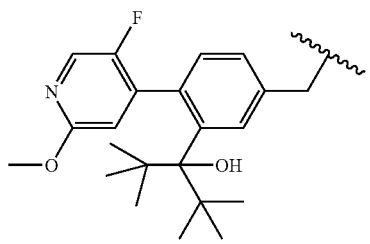

| Compound | TG |
|---|---|
| 77.11 | 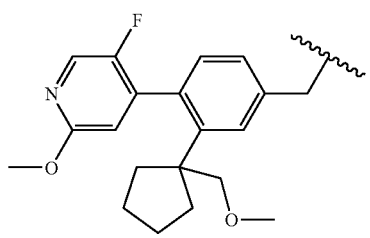 |
| 77.12 | |

(3R)-3-(3-(((2-(5,5-Dimethyl-1-cyclopenten-1-yl)-2'-fluoro-5'-(methyloxy)-1,1'-biphenyl-4-yl)methyl)oxy)-2-fluorophenyl)pentanoic acid or (3S)-3-(3-(((2-(5,5-dimethyl-1-cyclopenten-1-yl)-2'-fluoro-5'-(methyloxy)-1,1'-biphenyl-4-yl)methyl)oxy)-2-fluorophenyl)pentanoic acid (77.1). (MS ESI (neg.) m/e: 519.2 (M−H).

(3R)-3-(3-(((2-(1,1-Dimethylethyl)-2'-fluoro-5'-(methyloxy)-1,1'-biphenyl-4-yl)methyl)oxy)-2-fluorophenyl)pentanoic acid or (3S)-3-(3-(((2-(1,1-dimethylethyl)-2'-fluoro-5'-(methyloxy)-1,1'-biphenyl-4-yl)methyl)oxy)-2-fluorophenyl)pentanoic acid (77.2). (MS ESI (neg.) m/e: 481.2 (M−H).

(R)-3-{3-[2-((S)-2,2-Dimethyl-cyclopentyl)-2'-fluoro-5'-methoxy-biphenyl-4-ylmethoxy]-2-fluoro-phenyl}-pentanoic acid or (S)-3-{3-[2-((S)-2,2-dimethyl-cyclopentyl)-2'-fluoro-5'-methoxy-biphenyl-4-ylmethoxy]-2-fluoro-phenyl}-pentanoic acid or (S)-3-{3-[2-((R)-2,2-dimethyl-cyclopentyl)-2'-fluoro-5'-methoxy-biphenyl-4-ylmethoxy]-2-fluoro-phenyl}-pentanoic acid or (R)-3-{3-[2-((R)-2,2-Dimethyl-cyclopentyl)-2'-fluoro-5'-methoxy-biphenyl-4-ylmethoxy]-2-fluoro-phenyl}-pentanoic acid (77.3). MS ESI (neg.) m/e: 521.2 (M−H).

(3R)-3-(3-(((2-((1S)-2,2-Dimethyl-1-(methyloxy)propyl)-2'-fluoro-5'-(methyloxy)-1,1'-biphenyl-4-yl)methyl)oxy)-2-fluorophenyl)pentanoic acid or (3R)-3-(3-(((2-((1R)-2,2-dimethyl-1-(methyloxy)propyl)-2'-fluoro-5'-(methyloxy)-1,1'-biphenyl-4-yl)methyl)oxy)-2-fluorophenyl)pentanoic acid or (3S)-3-(3-(((2-(1S)-2,2-dimethyl-1-(methyloxy)propyl)-2'-fluoro-5'-(methyloxy)-1,1'-biphenyl-4-yl)methyl)oxy)-2-fluorophenyl)pentanoic acid or (3S)-3-(3-(((2-((1R)-2,2-dimethyl-1-(methyloxy)propyl)-2'-fluoro-5'-(methyloxy)-1,1'-biphenyl-4-yl)methyl)oxy)-2-fluorophenyl)pentanoic acid (77.4). MS ESI (neg.) m/e: 525.3 (M−H).

(3R)-3-(2-Fluoro-3-(((2'-fluoro-5'-(methyloxy)-2-((1S)-1,2,2-trimethylpropyl)-1,1'-biphenyl-4-yl)methyl)oxy)phenyl)pentanoic acid or (3R)-3-(2-fluoro-3-(((2'-fluoro-5'-(methyloxy)-2-((1R)-1,2,2-trimethylpropyl)-1,1'-biphenyl-4-yl)methyl)oxy)phenyl)pentanoic acid or (3S)-3-(2-fluoro-3-(((2'-fluoro-5'-(methyloxy)-2-((1S)-1,2,2-trimethylpropyl)-1,1'-biphenyl-4-yl)methyl)oxy)phenyl)pentanoic acid or (3S)-3-(2-fluoro-3-(((2'-fluoro-5'-(methyloxy)-2-((1R)-1,2,2-trimethylpropyl)-1,1'-biphenyl-4-yl)methyl)oxy)phenyl)pentanoic acid (77.5). MS ESI (neg.) m/e: 509.2 (M−H).

(3R)-3-(3-(((2-((1S)-2,2-Dimethylcyclopentyl)-2',5-difluoro-5'-(methyloxy)-1,1'-biphenyl-4-yl)methyl)oxy)-2-fluorophenyl)pentanoic acid or (3R)-3-(3-(((2-((1R)-2,2-dimethylcyclopentyl)-2',5-difluoro-5'-(methyloxy)-1,1'-biphenyl-4-yl)methyl)oxy)-2-fluorophenyl)pentanoic acid or (3S)-3-(3-(((2-((1S)-2,2-dimethylcyclopentyl)-2',5-difluoro-5'-(methyloxy)-1,1'-biphenyl-4-yl)methyl)oxy)-2-fluorophenyl)pentanoic acid or (3S)-3-(3-(((2-((1R)-2,2-dimethylcyclopentyl)-2',5-difluoro-5'-(methyloxy)-1,1'-biphenyl-4-yl)methyl)oxy)-2-fluorophenyl)pentanoic acid (77.6). The alkylation and hydrolysis were conducted in an analogous manner to Example 66.6 (using 66.44D derived from peak one from the chiral separation of 66.44A from the OJ-column, also using 77.G derived from peak one from the chiral separation of the racemic ester 77.F, described herein) to yield 77.6. MS ESI (neg.) m/e: 538.9 (M−H)+.

Example 77.7

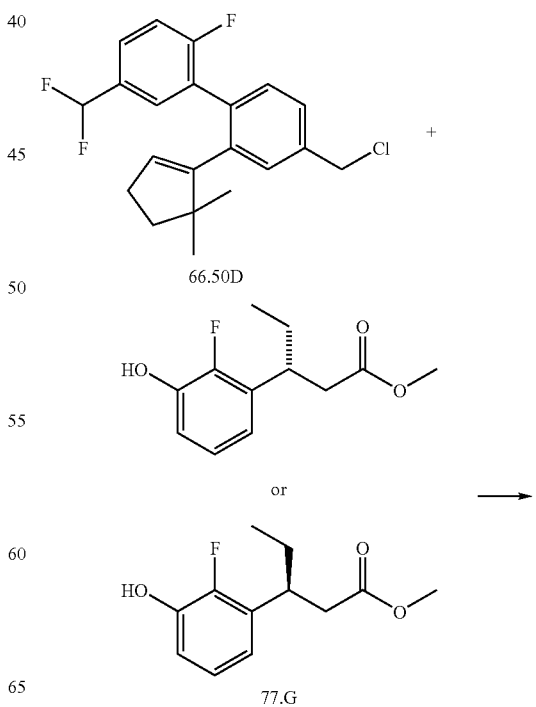

615
-continued

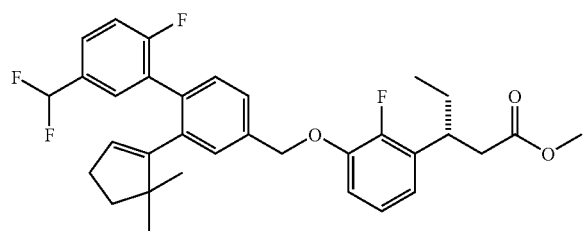

77.7A or

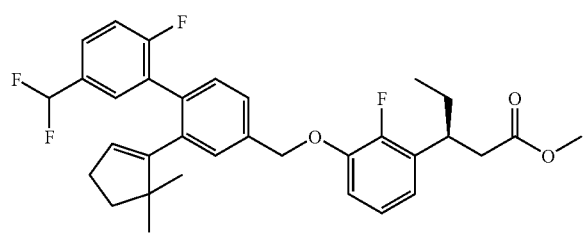

77.7A

616
-continued

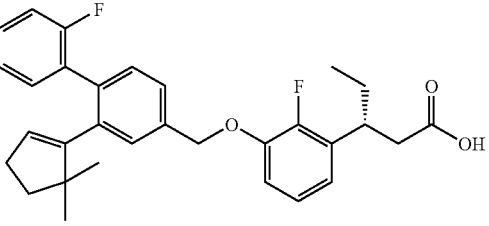

77.7 or

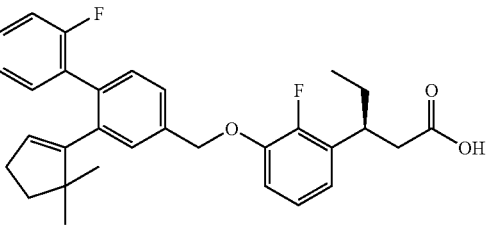

77.7

Methyl (3R)-3-(3-(((5'-(difluoromethyl)-2-(5,5-dimethyl-1-cyclopenten-1-yl)-2'-fluoro-1,1'-biphenyl-4-yl)methyl)oxy)-2-fluorophenyl)pentanoate or methyl (3S)-3-(3-(((5'-(difluoromethyl)-2-(5,5-dimethyl-1-cyclopenten-1-yl)-2'-fluoro-1,1'-biphenyl-4-yl)methyl)oxy)-2-fluorophenyl) pentanoate (77.7A). To a vial containing 77.G (0.0249 g, 0.110 mmol) in 1.00 mL dry DMF was added cesium carbonate (0.0434 g, 0.133 mmol). The mixture was stirred at room temperature for 10 minutes, then 66.50D (0.0444 g, 0.122 mmol) was added. After 22 hours, the reaction was diluted with water and then extracted five times with EtOAc. The organic layers were combined and washed one time with brine and dried over anhydrous magnesium sulfate. The solid was filtered off, and the solvent was removed. The residue was purified by silica gel flash chromatography (0-10% EtOAc/hexane) to afford 77.7A (54.6 mg, 89% yield). MS ESI (pos.) m/e: 571.9 $(M+H_2O)^+$.

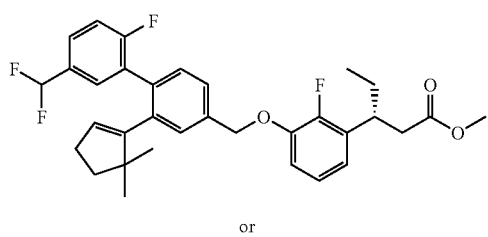

or

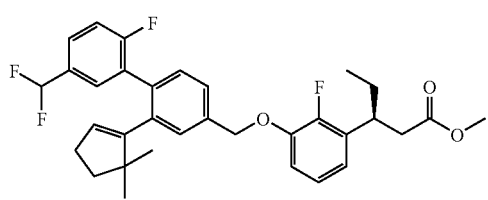

77.7A

⟶

(3R)-3-(3-(((5'-(Difluoromethyl)-2-(5,5-dimethyl-1-cyclopenten-1-yl)-2'-fluoro-1,1'-biphenyl-4-yl)methyl)oxy)-2-fluorophenyl)pentanoic acid or (3S)-3-(3-(((5'-(difluoromethyl)-2-(5,5-dimethyl-1-cyclopenten-1-yl)-2'-fluoro-1,1'-biphenyl-4-yl)methyl)oxy)-2-fluorophenyl)pentanoic acid (77.7). A pre-mixed solution of 2 M NaOH (0.5 mL, 1.00 mmol), THF (1 mL), and MeOH (1 mL) was added to a vial containing 77.7A (0.0546 g, 0.0984 mmol). The mixture was stirred at room temperature and monitored with TLC and LC-MS. After 24 hours, the mixture was diluted with water and acidified with 1M aqueous HCl solution, and then was extracted five times with EtOAc. The organic phase was dried over anhydrous magnesium sulfate, filtered, and concentrated. The residue was purified by silica gel flash chromatography (0-40% EtOAc/hexane) to afford 77.7 (31.3 mg, 59% yield). $^1$H NMR (400 MHz, CDCl$_3$) δ ppm 7.48 (3H, m), 7.37 (2H, m), 7.15 (1H, t, J=9.0 Hz), 7.04 (1H, m), 6.95 (1H, m), 6.83 (1H, m), 6.77 (1H, t), 5.52 (1H, m), 5.18 (2H, s), 3.43 (1H, m), 2.77 (2H, m), 2.23 (2H, td, J=7.0, 2.3 Hz), 1.84 (4H, m), 0.86 (9H, m). MS ESI (neg.) m/e: 538.9 $(M-H)^+$.

(3R)-3-(3-(((2-((1S)-2,2-Dimethylcyclohexyl)-2'-fluoro-5'-(methyloxy)-1,1'-biphenyl-4-yl)methyl)oxy)-2-fluorophenyl)pentanoic acid or (3R)-3-(3-(((2-((1R)-2,2-dimethylcyclohexyl)-2'-fluoro-5'-(methyloxy)-1,1'-biphenyl-4-yl)methyl)oxy)-2-fluorophenyl)pentanoic acid or (3S)-3-(3-(((2-((1S)-2,2-dimethylcyclohexyl)-2'-fluoro-5'-(methyloxy)-1,1'-biphenyl-4-yl)methyl)oxy)-2-fluorophenyl)pentanoic acid or (3S)-3-(3-(((2-((1R)-2,2-dimethylcyclohexyl)-2'-fluoro-5'-(methyloxy)-1,1'-biphenyl-4-yl)methyl)oxy)-2-fluorophenyl)pentanoic acid (77.8). MS ESI (neg.) m/e: 535.3 $(M-H)^+$.

(3R)-3-(3-(((3-((1S)-2,2-Dimethylcyclopentyl)-4-(5-fluoro-2-(methyloxy)-4-pyridinyl)phenyl)methyl)oxy)-2-fluorophenyl)pentanoic acid or (3R)-3-(3-(((3-((1R)-2,2-dimethylcyclopentyl)-4-(5-fluoro-2-(methyloxy)-4-pyridinyl)phenyl)methyl)oxy)-2-fluorophenyl)pentanoic acid or (3S)-3-(3-(((3-((1S)-2,2-dimethylcyclopentyl)-4-(5-fluoro-2-(methyloxy)-4-pyridinyl)phenyl)methyl)oxy)-2-fluorophenyl)pentanoic acid or (3S)-3-(3-(((3-((1R)-2,2-Dimethylcyclopentyl)-4-(5-fluoro-2-(methyloxy)-4-pyridinyl)phenyl)methyl)oxy)-2-fluorophenyl)pentanoic acid (77.9). MS ESI (neg.) m/e: 522.2 $(M-H)^+$.

(3R)-3-(3-(((3-((1S)-2,2-Dimethyl-1-(methyloxy)propyl)-4-(5-fluoro-2-(methyloxy)-4-pyridinyl)phenyl)methyl)oxy)-2-fluorophenyl)pentanoic acid or (3R)-3-(3-(((3-((1R)-2,2-dimethyl-1-(methyloxy)propyl)-4-(5-fluoro-2-(methyloxy)-4-pyridinyl)phenyl)methyl)oxy)-2-fluorophenyl)pentanoic acid or (3S)-3-(3-(((3-((1S)-2,2-dimethyl-1-(methyloxy)propyl)-4-(5-fluoro-2-(methyloxy)-4-pyridinyl)phenyl)methyl)oxy)-2-fluorophenyl)pentanoic acid or (3S)-3-(3-(((3-((1R)-2,2-dimethyl-1-(methyloxy)propyl)-4-(5-fluoro-2-(methyloxy)-4-pyridinyl)phenyl)methyl)oxy)-2-fluorophenyl)pentanoic acid (77.10). (MS ESI) (pos) m/e: 528.3 (M+H).

Example 77.11

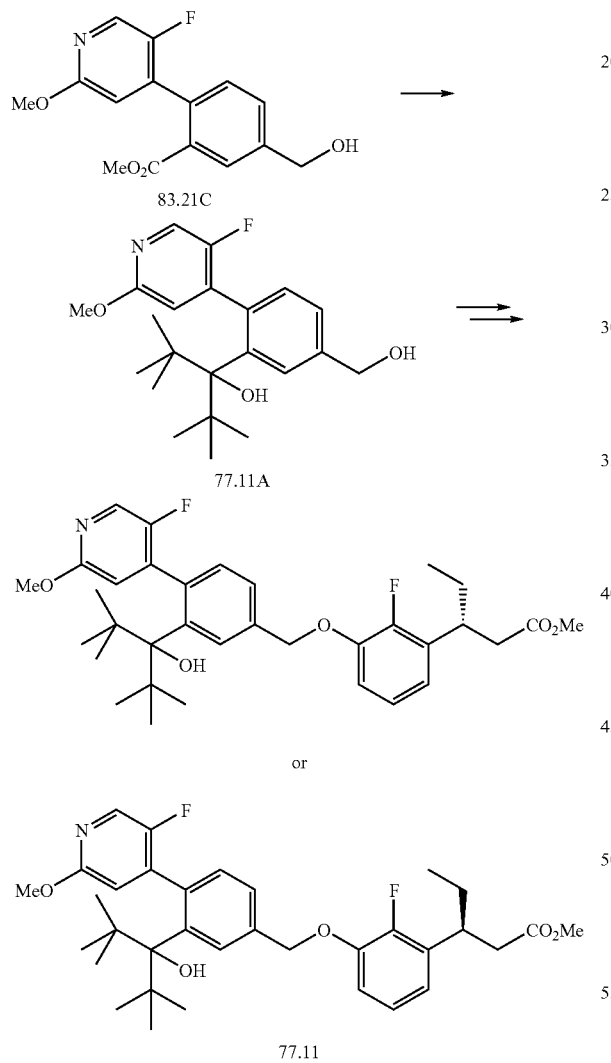

(3R)-3-(3-(4-(5-Fluoro-2-methoxypyridin-4-yl)-3-(3-hydroxy-2,2,4,4-tetramethylpentan-3-yl)benzyloxy)-2-fluorophenyl)pentanoic acid or (3R)-3-(3-(4-(5-fluoro-2-methoxypyridin-4-yl)-3-(3-hydroxy-2,2,4,4-tetramethylpentan-3-yl)benzyloxy)-2-fluorophenyl)pentanoic acid (77.11). To a −78° C. solution of methyl 2-(5-fluoro-2-methoxypyridin-4-yl)-5-(hydroxymethyl)benzoate (83.21 C) (233 mg, 8.0 mol) in THF (60 mL) was added tert-butyllithium (1.70 M, 1.65 mL, 2.80 mmol) dropwise over one hour. After stirring at −78° C. for 40 minutes, the resulting mixture was slowly poured into 4 mL of saturated aqueous ammonium chloride solution. After separation, the aqueous layer was diluted with water (40 mL) and extracted with EtOAc (3×6 mL). The combined organic layers were washed with water (4 mL) and brine (2 mL). After removal of organic solvents under reduced pressure, purification of the residue by flash chromatography on silica gel with 0-75% EtOAc/Hexane for elution gave 77.11A as colorless solid (96 mg, 32%).

The Mitsunobu reaction and hydrolysis were conducted in an analogous manner to Example 69.14 (using 77.11A and using 77.G derived from peak one from the chiral separation of the racemic ester 77.F, described herein) to yield 77.11 (MS ESI (neg.) m/e: 568.3 (M−H).

Example 77.12

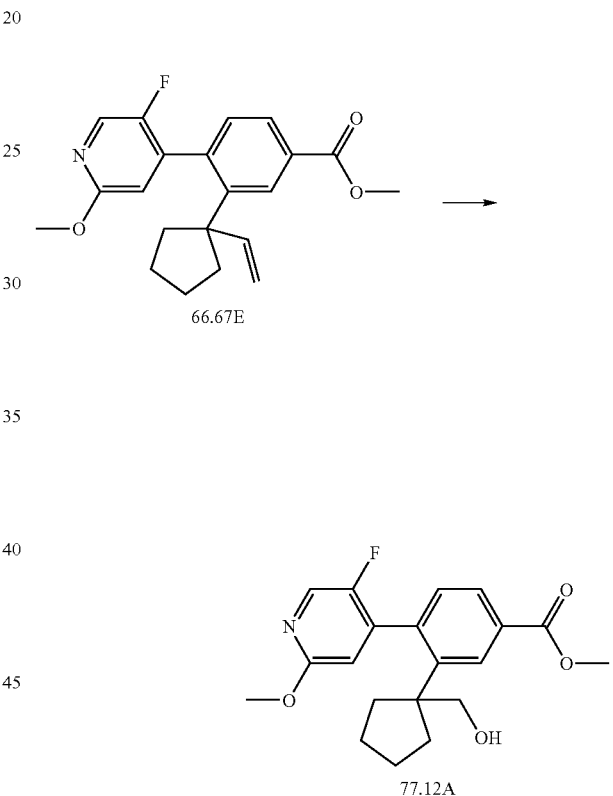

Methyl 4-(5-fluoro-2-methoxypyridin-4-yl)-3-(1-(hydroxymethyl)cyclopentyl)benzoate (77.12A). Ozone gas was passed through a mixture of methyl 4-(5-fluoro-2-methoxypyridin-4-yl)-3-(1-formylcyclopentyl)benzoate (0.13 g, 0.36 mmol) in DCM (6.0 mL) and MeOH (1.5 mL) at −78° C. for 10 minutes. The excess of ozone was purged off by nitrogen, and dimethylsulfide (0.3 mL) was added. The resulting reaction mixture was stirred at room temperature for 30 minutes. Sodium borohydride (0.13 mL, 3.6 mmol) was added, and the mixture was stirred at room temperature for 16 hours. The LCMS results indicated the reaction was completed. EtOAc (50 mL) was added, and the mixture was washed with brine (20×2 mL) and dried over $Na_2SO_4$. The solvent was removed, and the product thus obtained was good enough for use in the next step without further purification. MS ESI (pos.) m/e: 360.2 (M+H)$^+$.

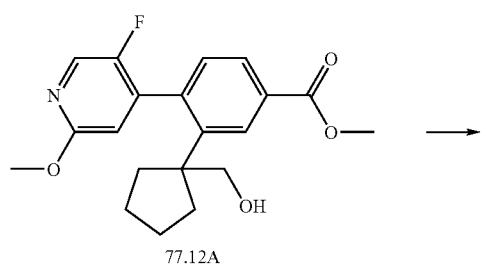

77.12A

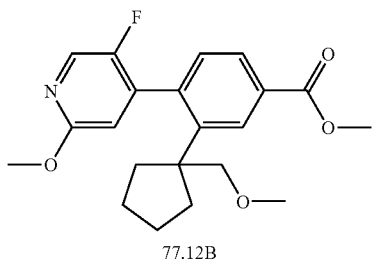

77.12B

Methyl 4-(5-fluoro-2-methoxypyridin-4-yl)-3-(1-(methoxymethyl)cyclopentyl)benzoate (77.12B). To a suspension of sodium hydride (20.0 mg 60% in oil, 522 μmol) in DMF (1.0 mL) was slowly added 77.12A (75.0 mg, 209.0 μmol) at 0° C. The resulting mixture was stirred at room temperature for 30 minutes. Methyl iodide (296.0 mg, 2087 μmol) was then added, and the reaction was stirred for 16 hours at room temperature. EtOAc (60.0 mL) was added, and the mixture was washed with brine (20×2 mL) and dried over MgSO$_4$. The solvent was removed. The product was used in the next step without further purification. MS ESI (pos.) m/e: 374.0 (M+H)$^+$.

77.12B 77.12C 4-(4-(Chloromethyl)-2-(1-(methoxymethyl)cyclopentyl)phenyl)-5-fluoro-2-methoxypyridine (77.12C). The reduction and chlorination of 77.12B to form 77.12C using the procedure described in Example 66.6. MS ESI (pos.) m/e: 364.2 (M+H)$^+$.

(3R)-3-(3-(4-(5-Fluoro-2-methoxypyridin-4-yl)-3-(1-(methoxymethyl)cyclopentyl)benzyloxy)-2-fluorophenyl) pentanoic acid or (3S)-3-(3-(4-(5-fluoro-2-methoxypyridin-4-yl)-3-(1-(methoxymethyl)cyclopentyl)benzyloxy)-2-fluorophenyl)pentanoic acid (77.12). Alkylation and hydrolysis were conducted in an analogous manner to Example 66.6 using 77.12C and 77.G derived from peak one from the chiral separation of the racemic ester 77.F, described herein to yield 77.12. $^1$H NMR (400 MHz, CDCl$_3$) δ ppm 7.94 (1H, s), 7.44 (1H, s), 6.92 (2H, t, J=7.4 Hz), 6.84 (2H, t, J=7.0 Hz), 6.56-6.79 (2H, m), 5.09 (2H, s), 3.88 (3H, s), 3.25-3.36 (1H, m), 3.16-3.25 (1H, m), 3.16 (3H, s), 2.65 (2H, d, J=7.4 Hz), 1.80-1.96 (1H, m), 1.46-1.76 (10H, m), 0.68-0.85 (3H, m). MS ESI (pos.) m/e: 540.3 (M+H)$^+$.

Example 78

Examples 78.1 and 78.2 are prepared and each of the other following compounds were prepared from 17.1 and the appropriate halomethyl or hydroxymethyl compound according to the methods described herein. Examples 78.1 and 78.2 are prepared and each of the other compounds in the following table were prepared using the same enantiomer of the phenol.

TABLE 14

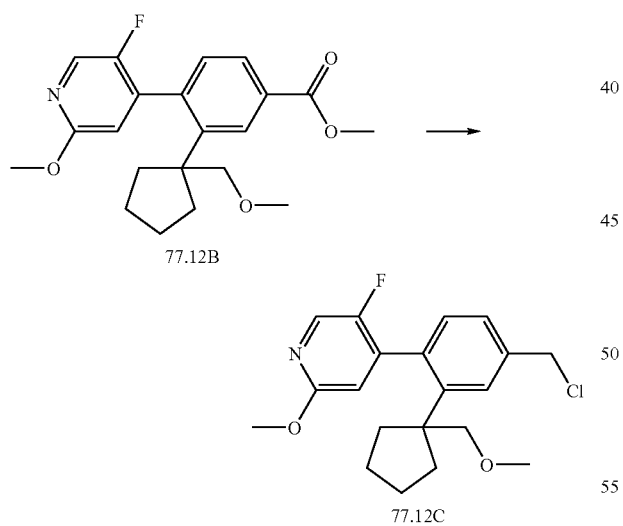

TABLE 14-continued
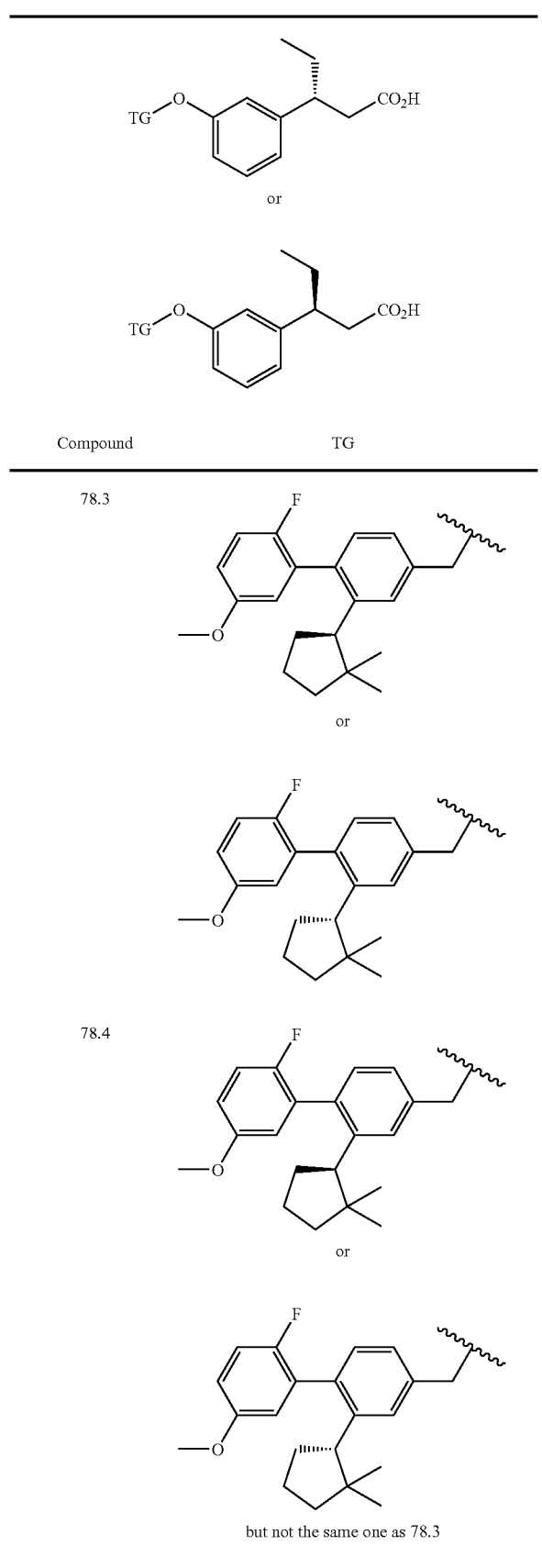
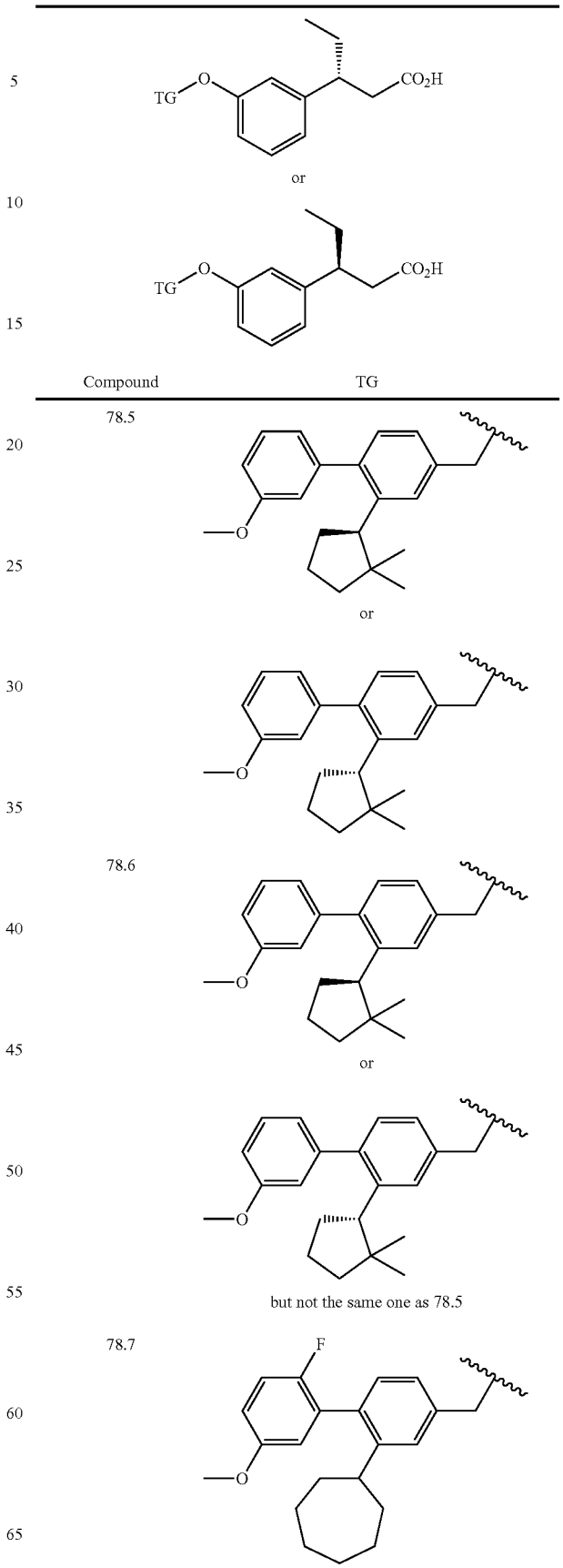

TABLE 14-continued

| Compound | TG |
|---|---|
| 78.8 | 3'-methoxy-2-cycloheptyl-biphenyl-4-ylmethyl |
| 78.9 | 2'-fluoro-5'-chloro-2-(5,5-dimethylcyclopent-1-en-1-yl)biphenyl-4-ylmethyl |
| 78.10 | 2',5-difluoro-5'-methoxy-2-[(1R)-2,2-dimethylcyclopentyl]biphenyl-4-ylmethyl or 2',5-difluoro-5'-methoxy-2-[(1S)-2,2-dimethylcyclopentyl]biphenyl-4-ylmethyl |
| 78.11 | 2'-fluoro-5'-methoxy-2-[(1R)-2,2-dimethylcyclohexyl]biphenyl-4-ylmethyl or 2'-fluoro-5'-methoxy-2-[(1S)-2,2-dimethylcyclohexyl]biphenyl-4-ylmethyl |
| 78.12 | 2'-fluoro-5'-methoxy-2-(ethoxymethyl)biphenyl-4-ylmethyl |
| 78.13 | 2'-fluoro-5'-methoxy-2-[(1R)-1-methoxy-2,2-dimethylbut-3-en-1-yl]biphenyl-4-ylmethyl or |

(Structures shown for compounds with TG group attached to 3-(TG-O)-phenyl-CH(Et)-CH$_2$-CO$_2$H scaffold in both R and S configurations)

TABLE 14-continued

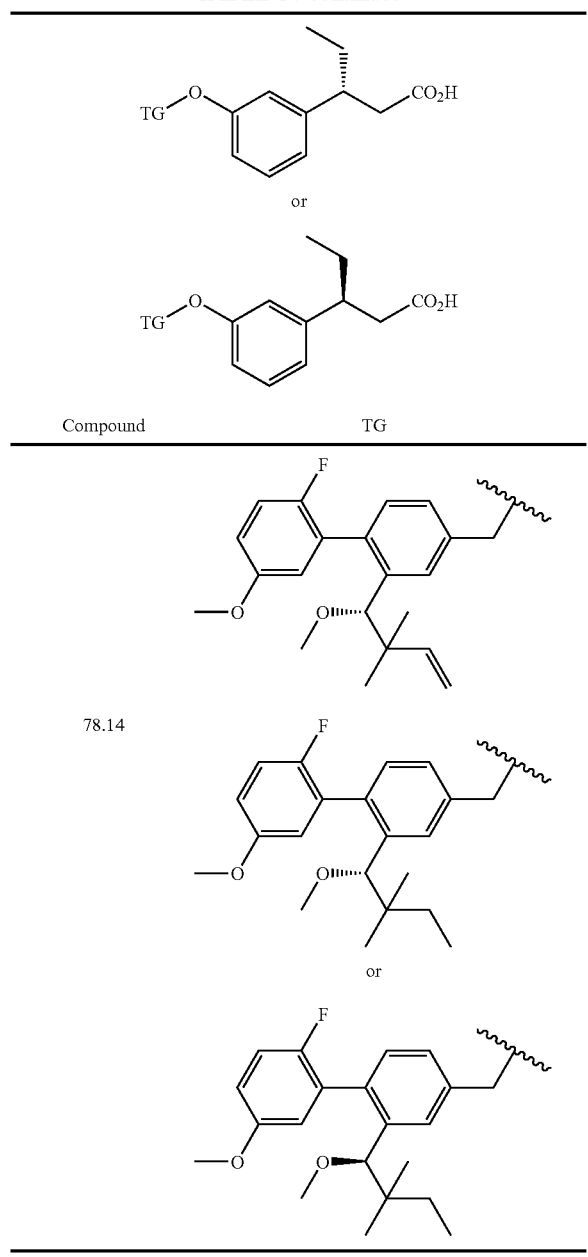

(3R)-3-(3-(((2-(5,5-Dimethyl-1-cyclopenten-1-yl)-3'-(methyloxy)-1,1'-biphenyl-4-yl)methyl)oxy)phenyl)pentanoic acid or (3S)-3-(3-(((2-(5,5-dimethyl-1-cyclopenten-1-yl)-3'-(methyloxy)-1,1'-biphenyl-4-yl)methyl)oxy)phenyl)pentanoic acid (78.1). This compound is prepared from 17.1 and the appropriate halomethyl or hydroxymethyl compound.

(3R)-3-(3-(((2-(2,2-Dimethylcyclopentyl)-3'-(methyloxy)-1,1'-biphenyl-4-yl)methyl)oxy)phenyl)pentanoic acid or (3S)-3-(3-(((2-(2,2-dimethylcyclopentyl)-3'-(methyloxy)-1,1'-biphenyl-4-yl)methyl)oxy)phenyl)pentanoic acid (78.2). This compound is prepared from 17.1 and the appropriate halomethyl or hydroxymethyl compound.

(3R)-3-(3-(((2-((1R)-2,2-Dimethylcyclopentyl)-2'-fluoro-5'-(methyloxy)-1,1'-biphenyl-4-yl)methyl)oxy)phenyl)pentanoic acid or (3R)-3-(3-(((2-((1S)-2,2-dimethylcyclopentyl)-2'-fluoro-5'-(methyloxy)-1,1'-biphenyl-4-yl)methyl)oxy)phenyl)pentanoic acid or (3S)-3-(3-(((2-((1R)-2,2-dimethylcyclopentyl)-2'-fluoro-5'-(methyloxy)-1,1'-biphenyl-4-yl)methyl)oxy)phenyl)pentanoic acid or (3S)-3-(3-(((2-((1S)-2,2-dimethylcyclopentyl)-2'-fluoro-5'-(methyloxy)-1,1'-biphenyl-4-yl)methyl)oxy)phenyl)pentanoic acid (78.3). MS ESI (pos.) m/e: 522.2 (M+H$_2$O)$^+$.

(3R)-3-(3-(((2-((1S)-2,2-Dimethylcyclopentyl)-2'-fluoro-5'-(methyloxy)-1,1'-biphenyl-4-yl)methyl)oxy)phenyl)pentanoic acid or (3R)-3-(3-(((2-((1R)-2,2-dimethylcyclopentyl)-2'-fluoro-5'-(methyloxy)-1,1∝-biphenyl-4-yl)methyl)oxy)phenyl)pentanoic acid or (3S)-3-(3-(((2-((1S)-2,2-dimethylcyclopentyl)-2'-fluoro-5'-(methyloxy)-1,1'-biphenyl-4-yl)methyl)oxy)phenyl)pentanoic acid or (3S)-3-(3-(((2-((1R)-2,2-dimethylcyclopentyl)-2'-fluoro-5'-(methyloxy)-1,1'-biphenyl-4-yl)methyl)oxy)phenyl)pentanoic acid (78.4). MS ESI (pos.) m/e: 522.2 (M+H$_2$O), 527.2 (M+Na)$^+$.

Example 78.5

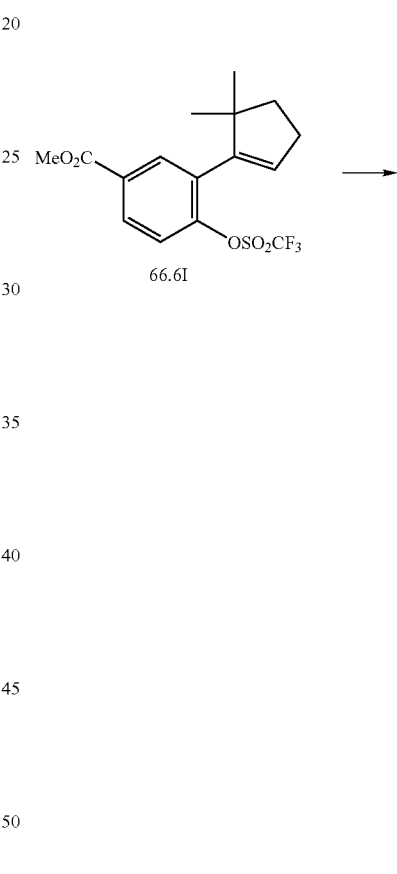

Methyl 2-(5,5-dimethyl-1-cyclopenten-1-yl)-3'-(methyloxy)-1,1'-biphenyl-4-carboxylate (78.5A). To a stirred solution of 66.6I (1.00 g, 2.6 mmol) in DMF (15.00 mL) at 23° C. was added 3-methoxyphenylboronic acid (0.80 g, 5.3 mmol) (commercially available from Aldrich), potassium carbonate (1.1 g, 7.9 mmol), and then tetrakis(triphenylphosphine)palladium (0.31 g, 0.26 mmol). The mixture was heated to 90° C. and stirred for 18 hours. The reaction was then cooled to room temperature, diluted with brine, and extracted three times with EtOAc. After drying over anhydrous magnesium sulfate and filtering, the organic solvent was removed under reduced pressure. The resulting product was then purified on silica gel (0-10% EtOAc in hexanes) to yield 78.5A as a colorless oil (0.80 g, 90% yield).

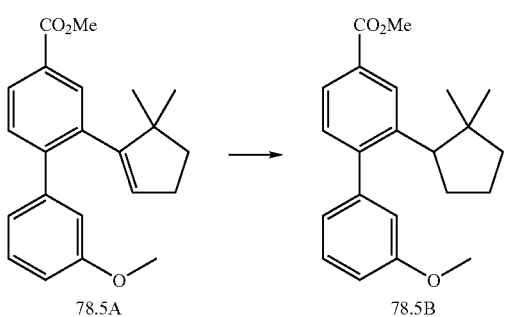

Methyl 2-(2,2-dimethylcyclopentyl)-3'-(methyloxy)-1,1'-biphenyl-4-carboxylate (78.5B). To a stirred solution of 78.5A (0.50 g, 1.5 mmol) in EtOAc (2.00 mL) at 23° C. was added palladium on carbon (0.16 g, 1.5 mmol). The reaction was placed under an atmosphere of hydrogen and stirred for 19 hours. The reaction mixture was then filtered and the filtrate was concentrated in vacuo. The product was purified on silica gel (0-10% EtOAc in hexanes) to yield 78.5B as a colorless oil (0.50 g, 99% yield).

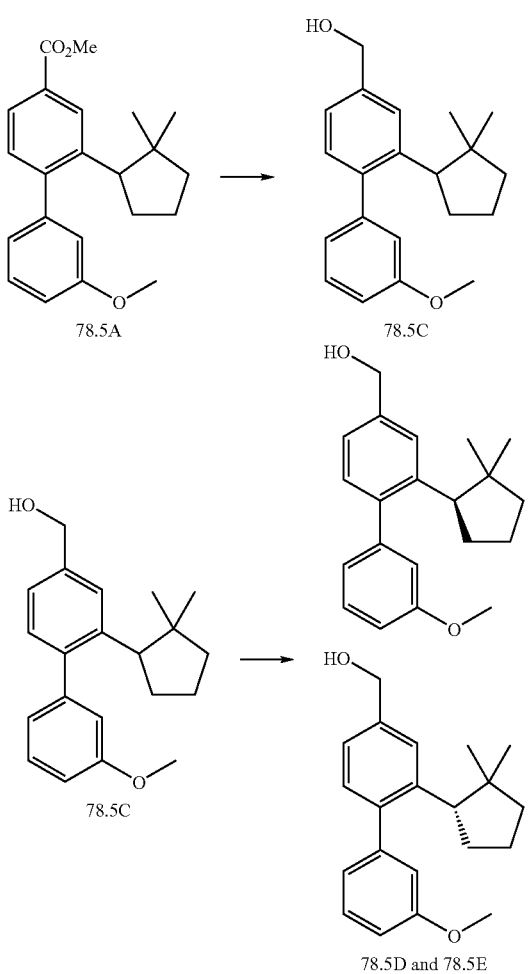

(2-((1R)-2,2-Dimethylcyclopentyl)-3'-(methyloxy)-1,1'-biphenyl-4-yl)methanol and (2-((1S)-2,2-dimethylcyclopentyl)-3'-(methyloxy)-1,1'-biphenyl-4-yl)methanol (78.5D and 78.5E). To a cooled solution of 78.5B (0.500 g, 1.5 mmol) in dry THF (5.00 mL) at 0° C. was added LAH (3.0 mL, 3.0 mmol, 1.0M) dropwise. Upon complete addition, the reaction was maintained at 0° C. for 1.5 hours. 1N NaOH was then added to quench the reaction, and the resulting solution was extracted three times with EtOAc. After drying over anhydrous magnesium sulfate, filtration, and concentration, the product was purified on silica gel (0-20% EtOAc in hexanes) to yield 78.5C as a colorless oil (0.25 g, 55% yield). Chiral separation of 78.5C was accomplished on Chiracel-OD (3% IPA in hexane) to provide 78.5D (peak one) and 78.5E (peak two). Both enantiomers were used to synthesize example compounds, and both enantiomers gave active example compounds. However, the enantiomer corresponding to peak 2 provided the most active example compounds. MS ESI (pos.) m/e: 293.2 (M−OH)$^+$.

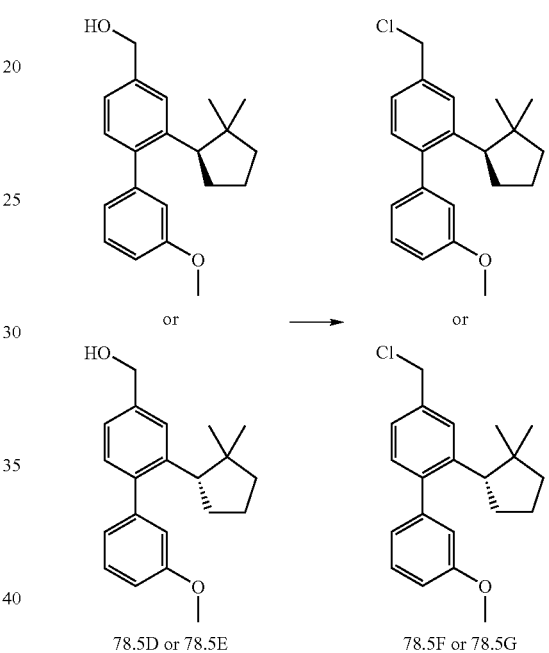

4-(Chloromethyl)-2-((1R)-2,2-dimethylcyclopentyl)-3'-(methyloxy)-1,1'-biphenyl or 4-(chloromethyl)-2-((1S)-2,2-dimethylcyclopentyl)-3∝-(methyloxy)-1,1'-biphenyl (78.F or 78.5G). To a stirred solution of 78.5D or 78.5E (0.116 g, 0.4 mmol) in DCM (4 mL) and DMF (0.03 mL) at 0° C. was added thionyl chloride (0.05 mL, 0.7 mmol). The reaction was then stirred at room temperature for one hour. The reaction mixture was concentrated in vacuo, and the product was purified on silica gel (0-20% EtOAc in hexanes) to yield 78.5F or 78.5G as a colorless oil (0.100 g, 81% yield).

(3R)-3-(3-(((2-((1R)-2,2-Dimethylcyclopentyl)-3'-(methyloxy)-1,1'-biphenyl-4-yl)methyl)oxy)phenyl)pentanoic acid or (3R)-3-(3-(((2-((1S)-2,2-dimethylcyclopentyl)-3'-(methyloxy)-1,1'-biphenyl-4-yl)methyl)oxy)phenyl)pentanoic acid or (3S)-3-(3-(((2-((1R)-2,2-dimethylcyclopentyl)-3'-(methyloxy)-1,1'-biphenyl-4-yl)methyl)oxy)phenyl)pentanoic acid or (3S)-3-(3-(((2-((1S)-2,2-dimethylcyclopentyl)-3'-(methyloxy)-1,1'-biphenyl-4-yl)methyl)oxy)phenyl)pentanoic acid (78.5). The title compound was prepared from chloromethyl compound 78.5F or 78.5G derived from 78.5E (peak two from the separation of the racemic alcohol) using the methods described herein. MS ESI (pos.) m/e: 504.2 (M+H$_2$O)$^+$, 509.2 (M+Na)$^+$.

(3R)-3-(3-(((2-((1S)-2,2-Dimethylcyclopentyl)-3'-(methyloxy)-1,1'-biphenyl-4-yl)methyl)oxy)phenyl)pentanoic acid or (3R)-3-(3-(((2-((1R)-2,2-dimethylcyclopentyl)-3'-(methyloxy)-1,1'-biphenyl-4-yl)methyl)oxy)phenyl)pentanoic acid or (3S)-3-(3-(((2-((1S)-2,2-dimethylcyclopentyl)-3'-(methyloxy)-1,1'-biphenyl-4-yl)methyl)oxy)phenyl)pentanoic acid or (3S)-3-(3-(((2-((1R)-2,2-dimethylcyclopentyl)-3'-(methyloxy)-1,1'-biphenyl-4-yl)methyl)oxy)phenyl)pentanoic acid (78.6). The title compound was prepared from chloromethyl compound 78.5F or 78.5G derived from 78.5D (peak one from the separation of the racemic alcohol) using the methods described herein. MS ESI (pos.) m/e: 504.2 (M+H$_2$O)$^+$, 509.2 (M+Na)$^+$.

Example 78.7

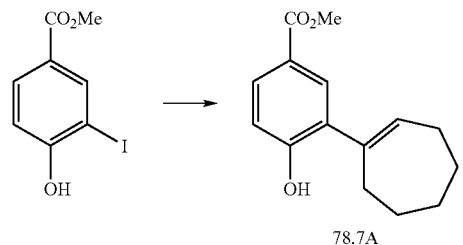

78.7A

Methyl 3-(1-cyclohepten-1-yl)-4-hydroxybenzoate (78.7A). To a stirred solution of methyl 4-hydroxy-3-iodobenzoate (1.4 g, 5.0 mmol) (commercially available from Aldrich) in DMF (15 mL) at 23° C. was added (Z)-cycloheptenylboronic acid (0.74 g, 5.3 mmol, commercially available from Combi-Blocks), potassium carbonate (2.1 g, 15 mmol), followed by tetrakis(triphenylphosphine)palladium (0.58 g, 0.50 mmol). The mixture was heated to 100° C. The reaction was then stirred for 17 hours and then cooled to room temperature. The reaction was diluted with brine and extracted three times with EtOAc. After drying over anhydrous magnesium sulfate and filtering, the organic solvent was removed under reduced pressure and the product was then purified on silica gel (0-20% EtOAc in hexanes) to yield 78.7A as a colorless oil (0.55 g, 44% yield).

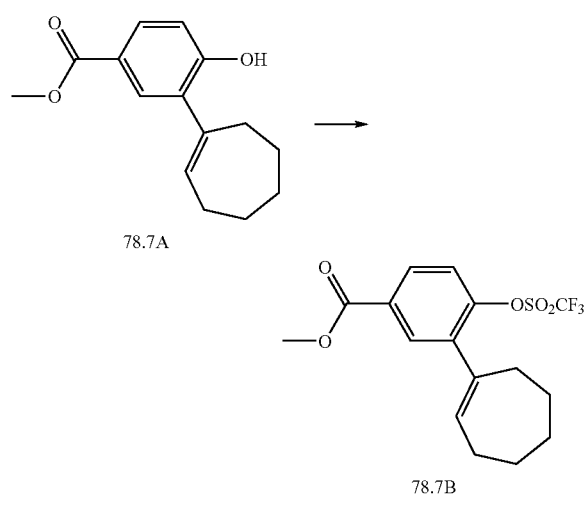

Methyl 3-(1-cyclohepten-1-yl)-4-(((trifluoromethyl)sulfonyl)oxy)benzoate (78.7B). To a stirred solution of methyl 3-(1-cyclohepten-1-yl)-4-hydroxybenzoate 78.7A (0.550 g, 2.23 mmol) in DCM (10.00 mL) at 0 C was added TEA (0.373 mL, 2.68 mmol), and DMAP (catalytic). N-phenyltriflimide (0.878 g, 2.46 mmol), was then added and the reaction mixture was stirred at room temperature for 22 hours. The reaction was then diluted with brine and extracted three times with EtOAc. After drying over anhydrous magnesium sulfate and filtering, the organic solvent was removed under reduced pressure and the product was then purified on silica gel (0-5% EtOAc in hexanes) to yield 78.7B as a colorless oil (0.700 g, 83% yield).

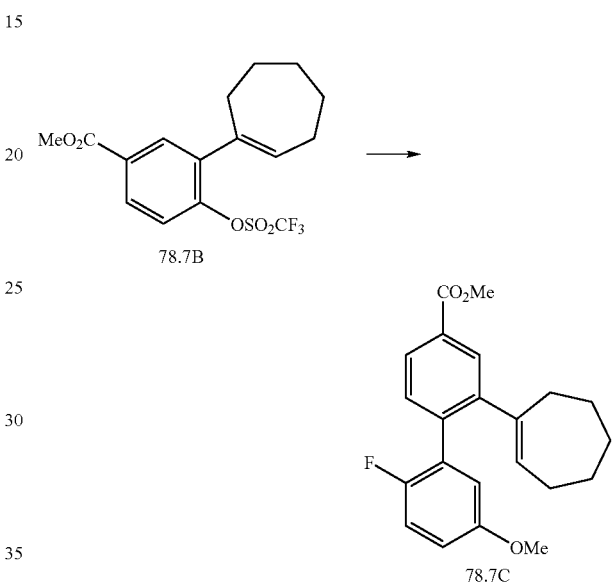

Methyl 2-(1-cyclohepten-1-yl)-2'-fluoro-5'-(methyloxy)-1,1'-biphenyl-4-carboxylaten (78.7C). To a stirred solution of 78.7B (0.350 g, 0.93 mmol) in DMF (5.00 mL) at 23° C. was added 2-fluoro-5-methoxyphenylboronic acid (0.31 g, 1.9 mmol) (commercially available from Aldrich), potassium carbonate (0.38 g, 2.8 mmol), and then tetrakis(triphenylphosphine)palladium (0.11 g, 0.093 mmol). The mixture was heated to 90° C. and stirred for 19 hours. The reaction was then cooled to room temperature, diluted with brine, and extracted three times with EtOAc. After drying over anhydrous magnesium sulfate and filtering, the organic solvent was removed under reduced pressure. The product was then purified on silica gel (0-10% EtOAc in hexanes) to yield 78.7C as a colorless oil (0.262 g, 80% yield).

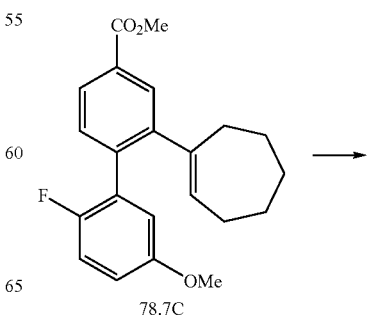

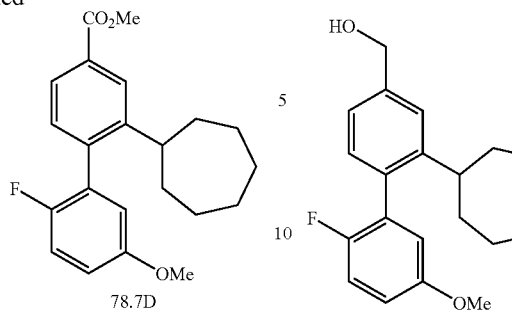

Methyl 2-cycloheptyl-2'-fluoro-5'-(methyloxy)-1,1'-biphenyl-4-carboxylate (78.7D). To a stirred solution of 78.7C (0.262 g, 0.74 mmol) in EtOAc (2.00 mL) at 23° C. was added palladium on carbon (0.079 g, 0.74 mmol). The reaction mixture was placed under an atmosphere of hydrogen and stirred for 3 hours. The reaction mixture was then filtered and concentrated in vacuo to yield 78.7D as a colorless oil (0.260 g, 99% yield).

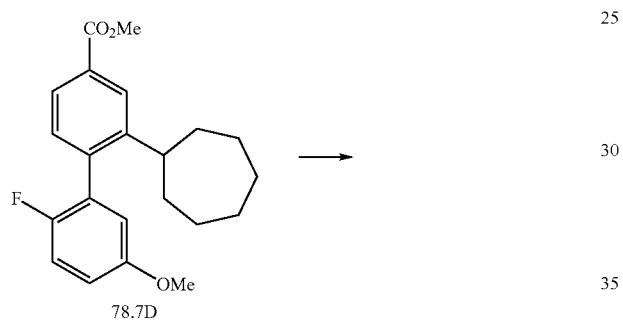

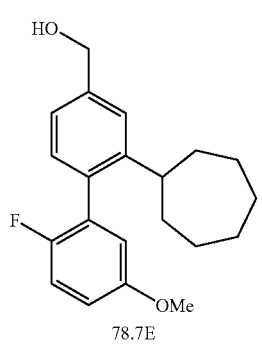

(2-Cycloheptyl-2'-fluoro-5'-(methyloxy)-1,1'-biphenyl-4-yl)methanol (78.7E). To a stirred solution of 78.7D (0.260 g, 0.7 mmol) in THF (7 mL) at 0° C. was added LAH (1 mL, 1 mmol, 1.0M). The reaction was stirred for one hour and then 1N NaOH was added to quench the reaction. The resulting solution was extracted three times with EtOAc. After drying over anhydrous magnesium sulfate and filtering, the organic solvent was removed under reduced pressure and the product was purified on silica gel (0-20% EtOAc in hexanes) to yield 78.7E as a colorless oil (0.192 g, 80% yield). MS ESI (pos.) m/e: 311.2 (M–OH)⁺.

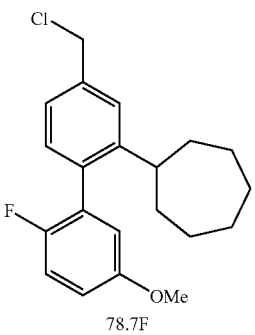

4-(Chloromethyl)-2-cycloheptyl-2'-fluoro-5'-(methyloxy)-1,1'-biphenyl (78.7F). To a stirred solution of 78.7E (0.185 g, 0.6 mmol) in DCM (6 mL) and DMF (0.04 mL) at 0° C. was added thionyl chloride (0.08 mL, 1 mmol). The reaction was stirred at room temperature for one hour and then concentrated in vacuo. The product was purified on silica gel (0-10% EtOAc in hexanes) to yield 78.7F as a colorless oil (0.165 g, 84% yield).

(3R)-3-(3-(((2-Cycloheptyl-2'-fluoro-5'-(methyloxy)-1,1'-biphenyl-4-yl)methyl)oxy)phenyl)pentanoic acid or (3S)-3-(3-(((2-cycloheptyl-2'-fluoro-5'-(methyloxy)-1,1'-biphenyl-4-yl)methyl)oxy)phenyl)pentanoic acid (78.7). The title compound was prepared using 78.7F using the methods described herein. MS ESI (pos.) m/e: 522.2 (M+H₂O)⁺, 527.2 (M+Na)⁺.

Example 78.8

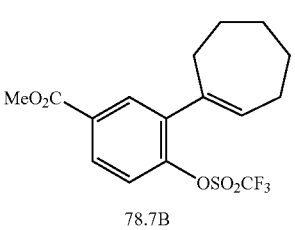
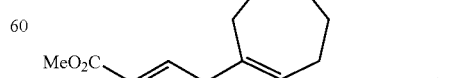

-continued

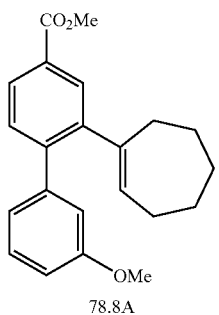
78.8A

Methyl 2-(1-cyclohepten-1-yl)-3'-(methyloxy)-1,1'-biphenyl-4-carboxylate (78.8A). To a stirred solution of 78.8B (0.350 g, 0.93 mmol) in DMF (5.00 mL) at 23° C. was added 3-methoxyphenylboronic acid (0.28 g, 1.9 mmol) (commercially available from Aldrich), potassium carbonate (0.38 g, 2.8 mmol), and then tetrakis(triphenylphosphine)palladium (0.11 g, 0.093 mmol). The mixture was heated to 90° C. and stirred for 18 hours and then cooled to room temperature. The reaction was diluted with brine and extracted three times with EtOAc. After drying over anhydrous magnesium sulfate and filtering, the organic solvent was removed under reduced pressure and the product was then purified on silica gel (0-10% EtOAc in hexanes) to yield 78.8A as a colorless oil (0.291 g, 94% yield).

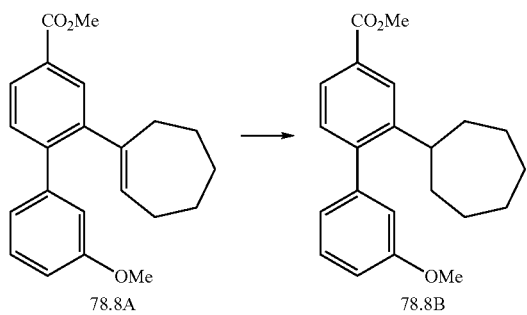

Methyl 2-cycloheptyl-3'-(methyloxy)-1,1'-biphenyl-4-carboxylate (78.8B). To a stirred solution of 78.8A (0.291 g, 0.86 mmol) in EtOAc (2.00 mL) at 23° C. was added palladium on carbon (0.092 g, 0.86 mmol). The reaction was placed under an atmosphere of hydrogen and stirred for four hours. The reaction was then concentrated in vacuo to yield 78.8B (0.290 g, 99% yield).

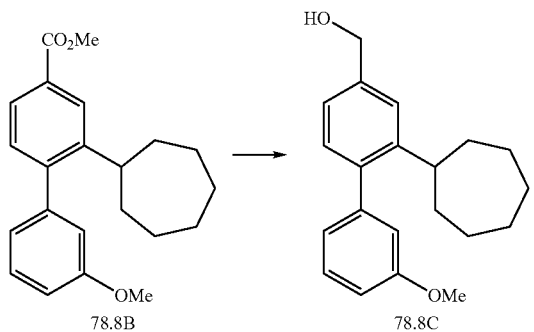

(2-Cycloheptyl-3'-(methyloxy)-1,1'-biphenyl-4-yl)methanol (78.8C). To a stirred solution of 78.8B (0.290 g, 0.86 mmol) in THF (8.6 mL, 0.86 mmol) at 0° C. was added LAH (1.7 mL, 1.7 mmol, 1.0M). The reaction was stirred for one hour and then 1N NaOH was added to quench the reaction. The resulting solution was extracted three times with EtOAc. After drying over anhydrous magnesium sulfate and filtering, the organic solvent was removed under reduced pressure and the product was then purified on silica gel (0-20% EtOAc in hexanes) to yield 78.7C as a colorless oil (0.220 g, 83% yield). MS ESI (pos.) m/e: 293.2 (M−OH)$^+$.

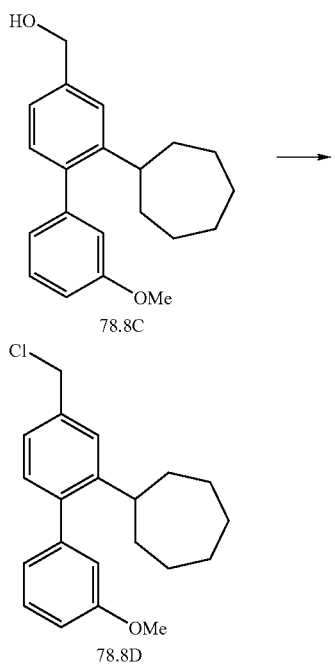

4-(Chloromethyl)-2-cycloheptyl-3'-(methyloxy)-1,1'-biphenyl (78.8D). To a stirred solution of 78.8C (0.212 g, 0.7 mmol) in DCM (7 mL) and DMF (0.05 mL) at 0° C. was added thionyl chloride (0.10 mL, 1 mmol). The reaction was stirred for one hour and then concentrated in vacuo. The product was then purified on silica gel (0-10% EtOAc in hexanes) to yield 78.7D as a colorless oil (0.185 g, 82% yield) (3R)-3-(3-(((2-Cycloheptyl-3'-(methyloxy)-1,1'-biphenyl-4-yl)methyl)oxy)phenyl)pentanoic acid or (3S)-3-(3-(((2-cycloheptyl-3'-(methyloxy)-1,1'-biphenyl-4-yl)methyl)oxy)phenyl)pentanoic acid (78.8). The title compound was prepared from 78.D using the methods described herein. MS ESI (pos.) m/e: 504.2 (M+H$_2$O)$^+$, 509.2 (M+Na)$^+$.

Example 78.9

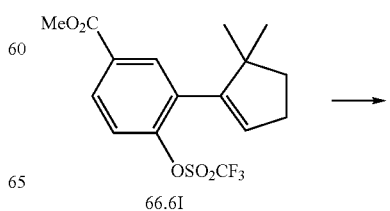
66.6I

-continued

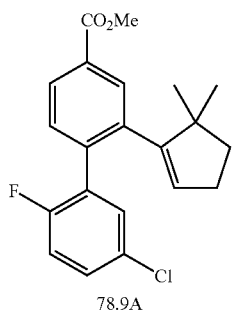
78.9A

Methyl 5'-chloro-2-(5,5-dimethyl-1-cyclopenten-1-yl)-2'-fluoro-1,1'-biphenyl-4-carboxylate (78.9A). To a stirred solution of methyl 3-(5,5-dimethylcyclopent-1-enyl)-4-(trifluoromethylsulfonyloxy)benzoate 66.61 (0.100 g, 0.3 mmol) in DMF (4 mL) at 23° C. was added 5-chloro-2-fluorophenylboronic acid (0.07 g, 0.4 mmol) (commercially available from Aldrich), potassium carbonate (0.1 g, 0.8 mmol), followed by tetrakis(triphenylphosphine)palladium (0.03 g, 0.03 mmol). The mixture was heated to 90° C. and stirring was continued for 23 hours. The reaction was then cooled to room temperature. The reaction was diluted with brine and extracted three times with EtOAc. After drying over anhydrous magnesium sulfate and filtering, the organic solvent was removed under reduced pressure and the product was purified on silica gel (0-10% EtOAc in hexanes) to yield 78.9A as a colorless oil (0.082 g, 86% yield).

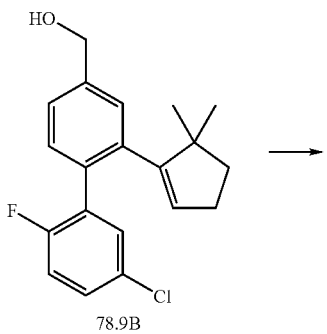
78.9A

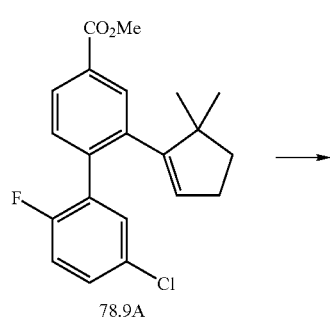
78.9B (5'-Chloro-2-(5,5-dimethyl-1-cyclopenten-1-yl)-2'-fluoro-1,1'-biphenyl-4-yl)methanol (78.9B). To a stirred solution of 78.9A (0.082 g, 0.23 mmol) in THF (5.00 mL) at 0° C. was added LAH (0.46 mL, 0.46 mmol, 1.0M). The reaction was then stirred for 1.5 hours. 1N NaOH(aq) was then added to the quench the reaction. The reaction was extracted three times with EtOAc. After drying over anhydrous magnesium sulfate and filtering, the organic solvent was removed under reduced pressure and the product was purified on silica gel (0-20% EtOAc in hexanes) to yield 78.9B as a colorless oil (0.048 g, 63% yield).

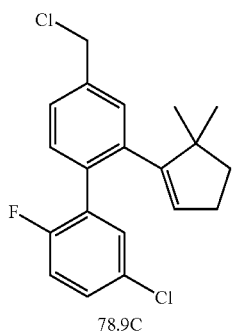
78.9B

5'-Chloro-4-(chloromethyl)-2-(5,5-dimethyl-1-cyclopenten-1-yl)-2'-fluoro-1,1'-biphenyl (78.9C). To a stirred solution of 78.9B (0.048 g, 0.1 mmol) in DCM (2.00 mL) at 23° C. was added DMF (0.001 mL) followed by thionyl chloride (0.02 mL, 0.3 mmol). The reaction was stirred for one hour and then concentrated in vacuo. The product was purified on silica gel (0-10% EtOAc in hexanes) to yield 78.9C as a colorless oil (0.05 g, 99% yield).

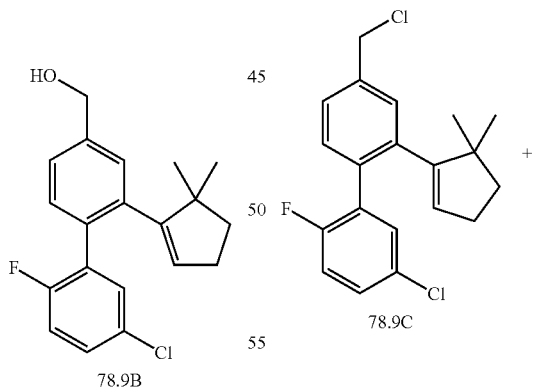
78.9C

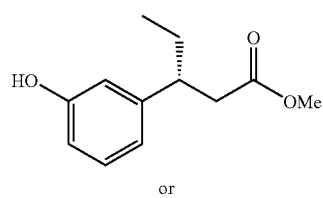
or

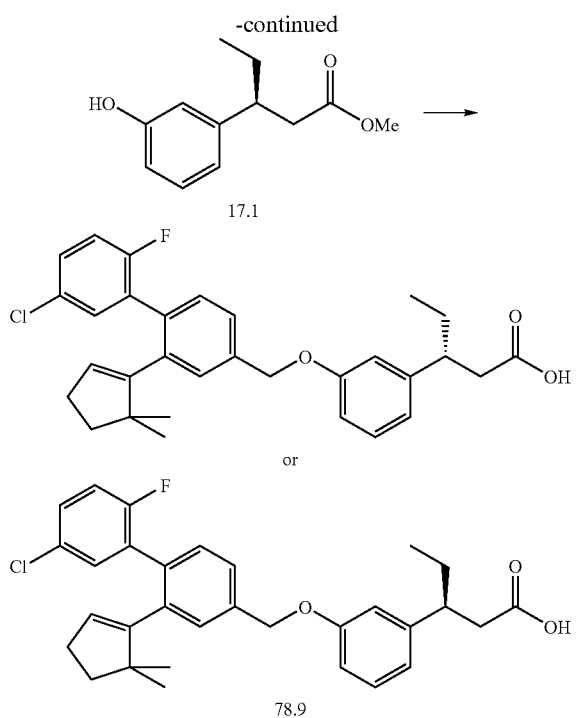

(3R)-3-(3-(((5'-Chloro-2-(5,5-dimethyl-cyclopenten-1-yl)-2'-fluoro-1,1'-biphenyl-4-yl)methyl)oxy)phenyl)pentanoic acid or (3S)-3-(3-(((5'-chloro-2-(5,5-dimethyl-1-cyclopenten-1-yl)-2'-fluoro-1,1'-biphenyl-4-yl)methyl)oxy) phenyl)pentanoic acid 78.9. The alkylation and hydrolysis were conducted in an analogous manner to Example 66.6 (described herein) to yield 78.9 (0.0391 g, 80% yield). MS ESI (neg.) m/e: 505.1 (M–H)⁺.

(3R)-3-(3-(((2-((1S)-2,2-Dimethylcyclopentyl)-2',5-difluoro-5'-(methyloxy)-1,1'-biphenyl-4-yl)methyl)oxy)phenyl)pentanoic acid or (3R)-3-(3-(((2-((1R)-2,2-dimethylcyclopentyl)-2',5-difluoro-5'-(methyloxy)-1,1'-biphenyl-4-yl)methyl)oxy)phenyl)pentanoic acid or (3S)-3-(3-(((2-((1S)-2,2-dimethylcyclopentyl)-2',5-difluoro-5'-(methyloxy)-1,1'-biphenyl-4-yl)methyl)oxy)phenyl)pentanoic acid or (3S)-3-(3-(((2-((1R)-2,2-dimethylcyclopentyl)-2',5-difluoro-5'-(methyloxy)-1,1'-biphenyl-4-yl)methyl)oxy)phenyl) pentanoic acid (78.10). Example 78.10 was prepared using the alkylation and hydrolysis procedure of Example 66.6 using 17.1 and 66.44D derived from peak one from the chiral separation of the racemic alcohol 66.44A on the OJ column, described herein to yield 78.10. MS ESI (neg.) m/e: 520.9 (M–H)⁺.

(3R)-3-(3-(((2-((1S)-2,2-Dimethylcyclohexyl)-2'-fluoro-5'-(methyloxy)-1,1'-biphenyl-4-yl)methyl)oxy)phenyl)pentanoic acid or (3R)-3-(3-(((2-((1R)-2,2-dimethyleyelohexyl)-2'-fluoro-5'-(methyloxy)-1,1'-biphenyl-4-yl)methyl) oxy)phenyl)pentanoic acid or (3S)-3-(3-(((2-((1S)-2,2-dimethylcyclohexyl)-2'-fluoro-5'-(methyloxy)-1,1'-biphenyl-4-yl)methyl)oxy)phenyl)pentanoic acid or (3S)-3-(3-(((2-((1R)-2,2-dimethylcyclohexyl)-2'-fluoro-5'-(methyloxy)-1,1'-biphenyl-4-yl)methyl)oxy)phenyl) pentanoic acid (78.11). MS ESI (neg.) m/e: 517.3 (M–H)⁺.

(3R)-3-(3-(((2-((Ethyloxy)methyl)-2'-fluoro-5'-(methyloxy)-1,1'-biphenyl-4-yl)methyl)oxy)phenyl)pentanoic acid or (3S)-3-(3-(((2-((ethyloxy)methyl)-2'-fluoro-5'-(methyloxy)-1,1'-biphenyl-4-yl)methyl)oxy)phenyl)pentanoic acid (78.12). Example 78.12 was prepared using an alkylation and hydrolysis procedure similar to that in Example 67.23 using 17.1 and 67.23C and also using chloromethyl compound 78.5F or 78.5G derived from 78.5D (peak one from the separation of the racemic alcohol). MS ESI (neg.) m/e: 465 (M–H)⁺. ¹H NMR (400 MHz, DMSO-d6) δ ppm 7.60 (m, 1H), 7.45 (m, 1H), 7.19-7.27 (m, 3H), 6.96 (m, 1H), 6.87 (m, 3H), 6.79 (m, 1H), 5.14 (s, 2H), 4.29 (s, 2H), 3.76 (s, 3H), 3.34 (m, 2H), 2.86 (m, 1H), 2.43-2.57 (m, 2H), 1.64 (m, 2H), 1.51 (m, 2H), 1.04 (t, 3H), 0.70 (t, 3H).

(3R)-3-(3-(((2-((1S)-2,2-Dimethyl-1-(methyloxy)-3-butenyl)-2'-fluoro-5'-(methyloxy)-1,1'-biphenyl-4-yl)methyl)oxy)phenyl)pentanoic acid or (3R)-3-(3-(((2-((1R)-2,2-dimethyl-1-(methyloxy)-3-butenyl)-2'-fluoro-5'-(methyloxy)-1,1'-biphenyl-4-yl)methyl)oxy)phenyl) pentanoic acid or (3S)-3-(3-(((2-((1S)-2,2-dimethyl-1-(methyloxy)-3-butenyl)-2'-fluoro-5'-(methyloxy)-1,1'-biphenyl-4-yl)methyl)oxy)phenyl)pentanoic acid or (3S)-3-(3-(((2-((1R)-2,2-dimethyl-1-(methyloxy)-3-butenyl)-2'-fluoro-5'-(methyloxy)-1,1'-biphenyl-4-yl)methyl)oxy) phenyl)pentanoic acid (78.13). Example 78.13 was prepared using an alkylation and hydrolysis procedure analogous to that used for Example 66.6 (using 17.1, also using 66.24C (derived from peak two from the chiral separation of the reduction product of 67.24A), described herein). MS ESI (neg.) m/e: 519 (M–H)⁺. ¹H NMR (400 MHz, CDCl₃) δ ppm 7.54-7.58 (m, 1H), 7.43-7.45 (m, 1H), 7.22-7.25 (m, 2H), 7.20 (m, 1H), 6.80-6.85 (m, 4H), 6.73-6.75 (m, 1H), 5.75 (m, 1H), 5.14 (m, 2H), 4.71-4.86 (m, 2H), 4.22 (m, 1H), 3.81 (m, 2H), 3.29 (m, 3H), 2.98 (m, 1H), 2.64 (m, 2H), 1.61-1.73 (m, 2H), 1.29 (m, 3H), 0.76-0.84 (m, 9H).

(3R)-3-(3-(((2-((1S)-2,2-Dimethyl-1-(methyloxy)butyl)-2'-fluoro-5'-(methyloxy)-1,1'-biphenyl-4-yl)methyl)oxy) phenyl)pentanoic acid or (3R)-3-(3-(((2-((1R)-2,2-dimethyl-1-(methyloxy)butyl)-2'-fluoro-5'-(methyloxy)-1,1'-biphenyl-4-yl)methyl)oxy)phenyl)pentanoic acid or (3S)-3-(3-(((2-((1S)-2,2-dimethyl-1-(methyloxy)butyl)-2'-fluoro-5'-(methyloxy)-1,1'-biphenyl-4-yl)methyl)oxy)phenyl) pentanoic acid or (3S)-3-(3-(((2-((1R)-2,2-dimethyl-1-(methyloxy)butyl)-2'-fluoro-5'-(methyloxy)-1,1'-biphenyl-4-yl)methyl)oxy)phenyl)pentanoic acid (78.14). Example 78.14 was prepared using an alkylation and hydrolysis procedure analogous to that of Example 66.62 (using 17.1 and using 66.62E (derived from peak one from the chiral separation of the reduction and alkylation product of 66.62B), described herein) MS ESI (neg.) m/e: 521 (M–H)⁺. ¹H NMR (400 MHz, CDCl₃) δ ppm 7.57 (m, 1H), 7.43 (m, 1H), 7.20 (m, 2H), 7.02 (m, 1H), 6.80-6.87 (m, 4H), 6.75 (m, 1H), 5.16 (m, 2H), 4.05-4.29 (m, 1H), 3.80 (s, 3H), 3.23-3.28 (m, 3H), 2.98 (m, 1H), 2.64 (m, 2H), 1.71 (m, 1H), 1.63 (m, 1H), 1.27 (m, 3H), 1.18 (m, 1H), 0.81 (m, 3H), 0.71 (s, 3H), 0.60 (t, 3H), 0.49-0.51 (m, 3H)

Example 79

Examples 79.1 and 79.2 are prepared and each of the other following compounds were prepared from 70 and the appropriate halomethyl or hydroxymethyl compound according to the methods described herein. Examples 79.1 and 79.2 are prepared and each of the other compounds in the following table were prepared using the same enantiomer of the phenol.

TABLE 15
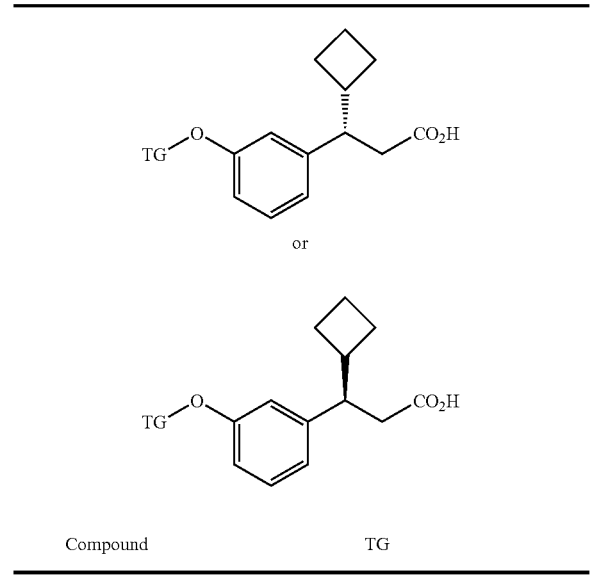
| Compound | TG |
|---|---|
| 79.1 | |
| 79.2 | |
| 79.3 | |
TABLE 15-continued
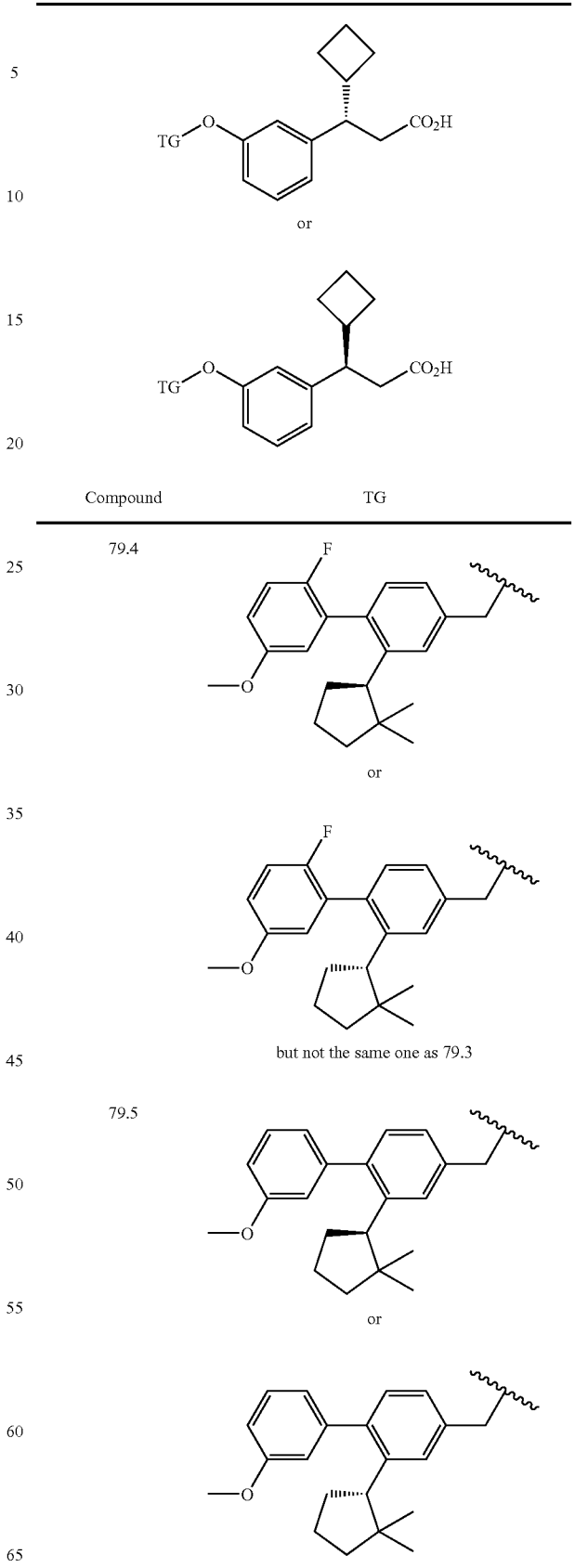
| Compound | TG |
|---|---|
| 79.4 | (but not the same one as 79.3) |
| 79.5 | |

TABLE 15-continued

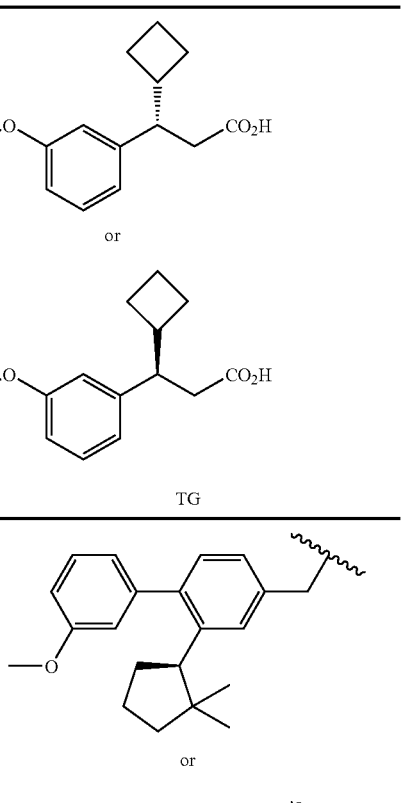

| Compound | TG |
|---|---|
| 79.6 | 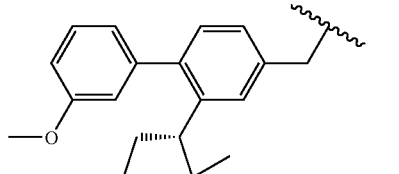 |
| 79.7 | 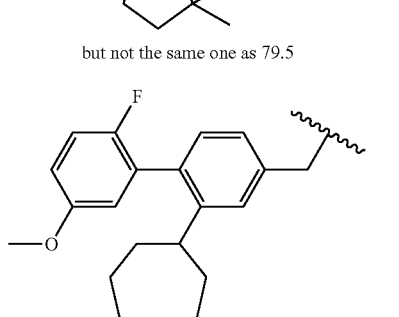 |
| 79.8 | 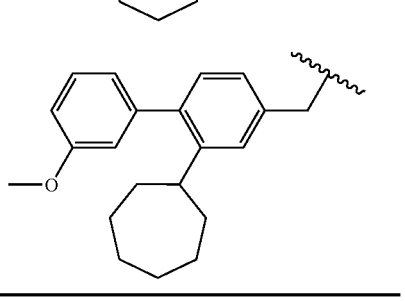 |

(3S)-3-Cyclobutyl-3-(3-(((2-(5,5-dimethyl-1-cyclopenten-1-yl)-3'-(methyloxy)-1,1'-biphenyl-4-yl)methyl)oxy)phenyl)propanoic acid or (3R)-3-cyclobutyl-3-(3-(((2-(5,5-dimethyl-1-cyclopenten-1-yl)-3'-(methyloxy)-1,1'-biphenyl-4-yl)methyl)oxy)phenyl)propanoic acid (79.1). This compound is prepared from 70 and the appropriate halomethyl or hydroxymethyl compound.

(3S)-3-Cyclobutyl-3-(3-(((2-(2,2-dimethylcyclopentyl)-3'-(methyloxy)-1,1'-biphenyl-4-yl)methyl)oxy)phenyl)propanoic acid or (3R)-3-cyclobutyl-3-(3-(((2-(2,2-dimethylcyclopentyl)-3'-(methyloxy)-1,1'-biphenyl-4-yl)methyl)oxy)phenyl)propanoic acid (79.2). This compound is prepared from 70 and the appropriate halomethyl or hydroxymethyl compound.

(3S)-3-Cyclobutyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3S)-3-cyclobutyl-3-(3-(((2-((1S)-2,2-dimethylcyclopentyl)-2'-fluoro-5'-(methyloxy)-1,1'-biphenyl-4-yl)methyl)oxy)phenyl)propanoic acid or (3R)-3-cyclobutyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3R)-3-cyclobutyl-3-(3-(((2-((1S)-2,2-dimethylcyclopentyl)-2'-fluoro-5'-(methyloxy)-1,1'-biphenyl-4-yl)methyl)oxy)phenyl)propanoic acid (79.3). MS ESI (pos.) m/e: 548.3 $(M+H_2O)^+$, 553.3 $(M+Na)^+$.

(3S)-3-Cyclobutyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3S)-3-cyclobutyl-3-(3-(((2-((1S)-2,2-dimethylcyclopentyl)-2'-fluoro-5'-(methyloxy)-1,1'-biphenyl-4-yl)methyl)oxy)phenyl)propanoic acid or (3R)-3-cyclobutyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3R)-3-cyclobutyl-3-(3-(((2-((1S)-2,2-dimethylcyclopentyl)-2'-fluoro-5'-(methyloxy)-1,1'-biphenyl-4-yl)methyl)oxy)phenyl)propanoic acid (79.4). MS ESI (pos.) m/e: 548.3 $(M+H_2O)^+$, 553.3 $(M+Na)^+$.

(3S)-3-Cyclobutyl-3-(3-(((2-((1R)-2,2-dimethylcyclopentyl)-3'-(methyloxy)-1,1'-biphenyl-4-yl)methyl)oxy)phenyl)propanoic acid or (3S)-3-cyclobutyl-3-(3-(((2-((1S)-2,2-dimethylcyclopentyl)-3'-(methyloxy)-1,1'-biphenyl-4-yl)methyl)oxy)phenyl)propanoic acid or (3R)-3-cyclobutyl-3-(3-(((2-((1R)-2,2-dimethylcyclopentyl)-3'-(methyloxy)-1,1'-biphenyl-4-yl)methyl)oxy)phenyl)propanoic acid or (3R)-3-cyclobutyl-3-(3-(((2-((1S)-2,2-dimethylcyclopentyl)-3'-(methyloxy)-1,1'-biphenyl-4-yl)methyl)oxy)phenyl)propanoic acid (79.5). MS ESI (pos.) m/e: 530.3 $(M+H_2O)^+$, 535.3 $(M+Na)^+$.

(3S)-3-Cyclobutyl-3-(3-(((2-((1R)-2,2-dimethylcyclopentyl)-3'-(methyloxy)-1,1'-biphenyl-4-yl)methyl)oxy)phenyl)propanoic acid or (3S)-3-cyclobutyl-3-(3-(((2-((1S)-2,2-dimethylcyclopentyl)-3'-(methyloxy)-1,1'-biphenyl-4-yl)methyl)oxy)phenyl)propanoic acid or (3R)-3-cyclobutyl-3-(3-(((2-((1R)-2,2-dimethylcyclopentyl)-3'-(methyloxy)-1,1'-biphenyl-4-yl)methyl)oxy)phenyl)propanoic acid or (3R)-3-cyclobutyl-3-(3-(((2-((1S)-2,2-dimethylcyclopentyl)-3'-(methyloxy)-1,1'-biphenyl-4-yl)methyl)oxy)phenyl)propanoic acid (79.6). MS ESI (pos.) m/e: 530.3 $(M+H_2O)^+$, 535.3 $(M+Na)^+$.

(3S)-3-(3-(((2-Cycloheptyl-2'-fluoro-5'-(methyloxy)-1,1'-biphenyl-4-yl)methyl)oxy)phenyl)-3-cyclobutylpropanoic acid or (3R)-3-(3-(((2-cycloheptyl-2'-fluoro-5'-(methyloxy)-1,1'-biphenyl-4-yl)methyl)oxy)phenyl)-3-cyclobutylpropanoic acid (79.7). MS ESI (pos.) m/e: 548.3 $(M+H_2O)^+$, 553.3 $(M+Na)^+$.

(3S)-3-(3-(((2-Cycloheptyl-3'-(methyloxy)-1,1'-biphenyl-4-yl)methyl)oxy)phenyl)-3-cyclobutylpropanoic acid or (3R)-3-(3-(((2-cycloheptyl-3'-(methyloxy)-1,1'-biphenyl-4-yl)methyl)oxy)phenyl)-3-cyclobutylpropanoic acid (79.8). MS ESI (pos.) m/e: 530.3 $(M+H_2O)^+$, 535.3 $(M+Na)^+$.

Example 80

Example 80.2 is prepared and each of the other following compounds were prepared from 43.6 and the appropriate halomethyl or hydroxymethyl compound according to the methods described herein. Example 80.2 is prepared and each of the other compounds in the following table were prepared using the same enantiomer of the phenol.
TABLE 16
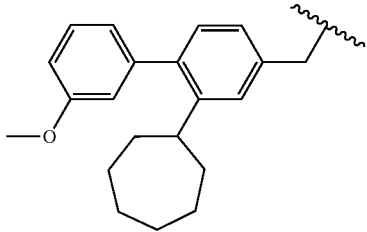
| Compound | TG |
|---|---|
| 80.1 | 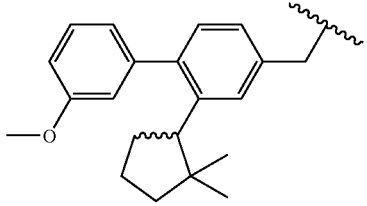 |
| 80.2 | |
| 80.3 | |
TABLE 16-continued
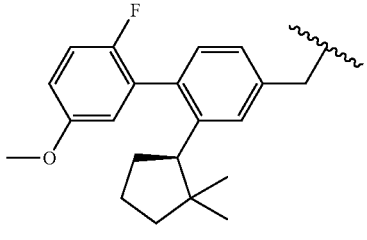
| Compound | TG |
|---|---|
| 80.4 | 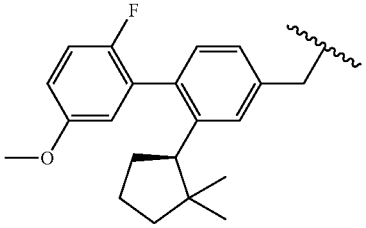 |
but not the same one as 80.3
| 80.5 | 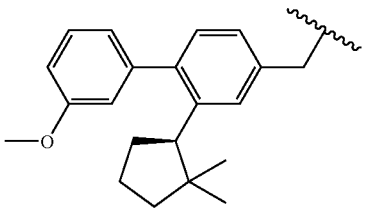 |

TABLE 16-continued

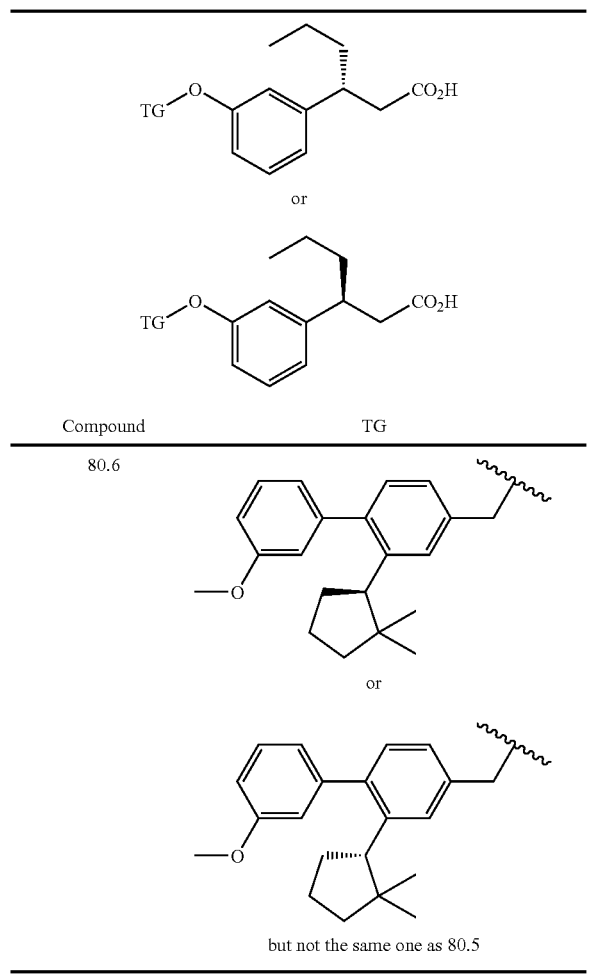

| Compound | TG |
|---|---|
| 80.6 | (shown above) but not the same one as 80.5 |

(3R)-3-(3-(((2-Cycloheptyl-3'-(methyloxy)-1,1'-biphenyl-4-yl)methyl)oxy)phenyl)hexanoic acid or (3S)-3-(3-(((2-cycloheptyl-3'-(methyloxy)-1,1'-biphenyl-4-yl)methyl)oxy)phenyl)hexanoic acid (80.1). MS ESI (pos.) m/e: 518.3 (M+H$_2$O)$^+$, 523.3 (M+Na)$^+$.

(3R)-3-(3-(((2-(2,2-Dimethylcyclopentyl)-3'-(methyloxy)-1,1'-biphenyl-4-yl)methyl)oxy)phenyl)hexanoic acid or (3S)-3-(3-(((2-(2,2-dimethylcyclopentyl)-3'-(methyloxy)-1,1'-biphenyl-4-yl)methyl)oxy)phenyl)hexanoic acid (80.2). This compound is prepared from 43.6 and the appropriate halomethyl or hydroxymethyl compound.

(3R)-3-(3-(((2-((1R)-2,2-Dimethylcyclopentyl)-2'-fluoro-5'-(methyloxy)-1,1'-biphenyl-4-yl)methyl)oxy)phenyl)hexanoic acid or (3R)-3-(3-(((2-((1S)-2,2-dimethylcyclopentyl)-2'-fluoro-5'-(methyloxy)-1,1'-biphenyl-4-yl)methyl)oxy)phenyl)hexanoic acid or (3S)-3-(3-(((2-((1R)-2,2-dimethylcyclopentyl)-2'-fluoro-5'-(methyloxy)-1,1'-biphenyl-4-yl)methyl)oxy)phenyl)hexanoic acid or (3S)-3-(3-(((2-((1S)-2,2-dimethylcyclopentyl)-2'-fluoro-5'-(methyloxy)-1,1'-biphenyl-4-yl)methyl)oxy)phenyl)hexanoic acid (80.3). MS ESI (pos.) m/e: 536.3 (M+H$_2$O)$^+$, 541.3 (M+Na)$^+$.

(3R)-3-(3-(((2-((1S)-2,2-Dimethylcyclopentyl)-2'-fluoro-5'-(methyloxy)-1,1'-biphenyl-4-yl)methyl)oxy)phenyl)hexanoic acid or (3R)-3-(3-(((2-((R)-2,2-dimethylcyclopentyl)-2'-fluoro-5'-(methyloxy)-1,1'-biphenyl-4-yl)methyl)oxy)phenyl)hexanoic acid or (3S)-3-(3-(((2-((1S)-2,2-dimethylcyclopentyl)-2'-fluoro-5'-(methyloxy)-1,1'-biphenyl-4-yl)methyl)oxy)phenyl)hexanoic acid or (3S)-3-(3-(((2-((1R)-2,2-dimethylcyclopentyl)-2'-fluoro-5'-(methyloxy)-1,1'-biphenyl-4-yl)methyl)oxy)phenyl)hexanoic acid (80.4). MS ESI (pos.) m/e: 536.3 (M+H$_2$O)$^+$, 541.3 (M+Na)$^+$.

(3R)-3-(3-(((2-((1R)-2,2-Dimethylcyclopentyl)-3'-(methyloxy)-1,1'-biphenyl-4-yl)methyl)oxy)phenyl)hexanoic acid or (3R)-3-(3-(((2-((1S)-2,2-dimethylcyclopentyl)-3'-(methyloxy)-1,1'-biphenyl-4-yl)methyl)oxy)phenyl)hexanoic acid or (3S)-3-(3-(((2-((1R)-2,2-dimethylcyclopentyl)-3'-(methyloxy)-1,1'-biphenyl-4-yl)methyl)oxy)phenyl)hexanoic acid or (3S)-3-(3-(((2-((1S)-2,2-dimethylcyclopentyl)-3'-(methyloxy)-1,1'-biphenyl-4-yl)methyl)oxy)phenyl)hexanoic acid (80.5). MS ESI (pos.) m/e: 518.3 (M+H$_2$O)$^+$, 523.3 (M+Na)$^+$.

(3R)-3-(3-(((2-((1S)-2,2-Dimethylcyclopentyl)-3'-(methyloxy)-1,1'-biphenyl-4-yl)methyl)oxy)phenyl)hexanoic acid or (3R)-3-(3-(((2-((1R)-2,2-dimethylcyclopentyl)-3'-(methyloxy)-1,1'-biphenyl-4-yl)methyl)oxy)phenyl)hexanoic acid or (3S)-3-(3-(((2-((1S)-2,2-dimethylcyclopentyl)-3'-(methyloxy)-1,1'-biphenyl-4-yl)methyl)oxy)phenyl)hexanoic acid or (3S)-3-(3-(((2-((1R)-2,2-dimethylcyclopentyl)-3'-(methyloxy)-1,1'-biphenyl-4-yl)methyl)oxy)phenyl)hexanoic acid (80.6). MS ESI (pos.) m/e: 518.3 (M+H$_2$O)$^+$, 523.3 (M+Na)$^+$.

Example 81

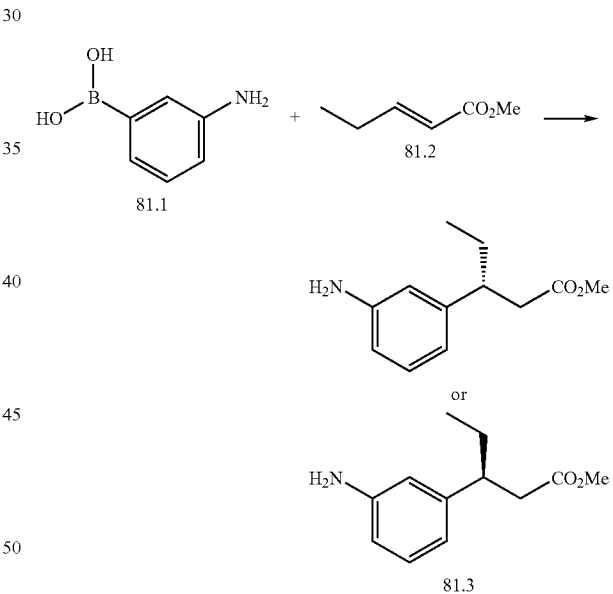

(R)-Methyl 3-(3-aminophenyl)pentanoate or (S)-methyl 3-(3-aminophenyl)pentanoate (81.3). A mixture of dioxane and water (10/1 dioxane/water, 22 mL) was added to a flask charged with hydroxyl[(S)-Binap]-rhodium(I) dimer (260 mg, 175 μmol), and 3-aminophenylboronic acid hydrate (81.1) (available from Aldrich) (3.394 g, 21902 μmol) and flushed with nitrogen and (E)-methyl pent-2-enoate (81.2) (available from Acros) (0.500 g, 4380 μmol). The resulting mixture was then stirred at 40° C. overnight. The reaction was diluted with EtOAc and washed with saturated sodium bicarbonate and brine, and then dried over sodium sulfate, filtered, and concentrated. The crude was purified by combiflash chromatography (0 to 20% EtOAc/Hexanes) to provide (R)-methyl 3-(3-aminophenyl)pentanoate or (S)-methyl 3-(3-aminophenyl)pentanoate (8.3) (400 mg, 44.1% yield). The product is believed to be the R enantiomer.

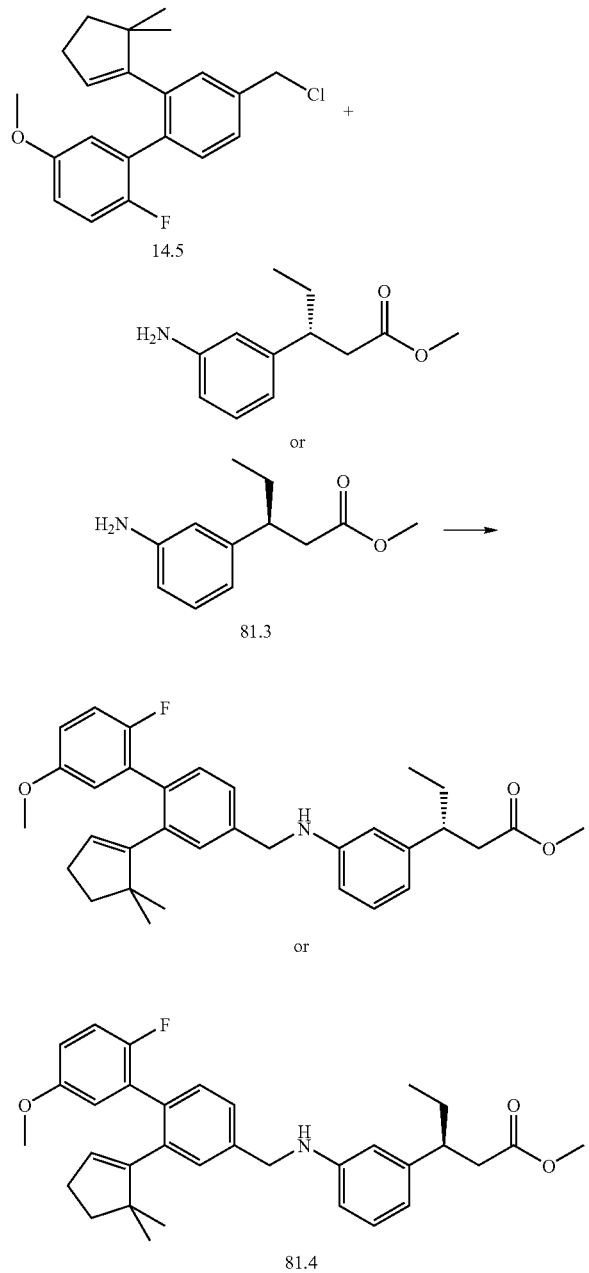

Methyl (3R)-3-(3-(((2-(5,5-dimethyl-1-cyclopenten-1-yl)-2'-fluoro-5'-(methyloxy)-1,1'-biphenyl-4-yl)methyl)amino)phenyl)pentanoate or methyl (3S)-3-(3-(((2-(5,5-dimethyl-1-cyclopenten-1-yl)-2'-fluoro-5'-(methyloxy)-1,1'-biphenyl-4-yl)methyl)amino)phenyl)pentanoate (81.4). To a flask containing 81.3 (20.0 mg, 96 µmol) and cesium carbonate (41 mg, 125 µmol) in DMF (1 mL) was added 14.5 (33 mg, 96 µmol), and the resulting mixture was stirred overnight. The reaction was diluted with water and extracted with EtOAc. The organic layer was washed with brine, dried over Na₂SO₄, filtered, concentrated, and then purified by silica gel chromatography (0 to 20% EtOAc/Hexanes) to provide (81.4) (4.8 mg, 9.6% yield).

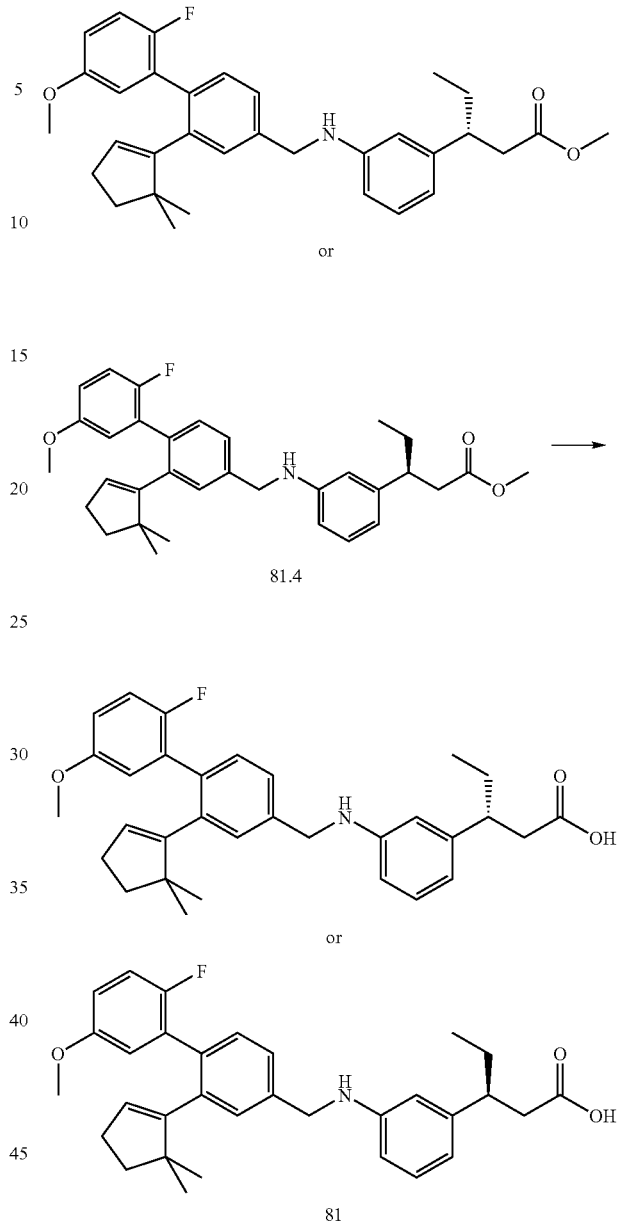

(3R)-3-(3-(((2-(5,5-Dimethyl-1-cyclopenten-1-yl)-2'-fluoro-5'-(methyloxy)-1,1'-biphenyl-4-yl)methyl)amino)phenyl)pentanoic acid or (3S)-3-(3-(((2-(5,5-dimethyl-1-cyclopenten-1-yl)-2'-fluoro-5'-(methyloxy)-1,1'-biphenyl-4-yl)methyl)amino)phenyl)pentanoic acid (81). To a solution of 81.4 (5.0 mg, 9.7 µmol) in THF/MeOH (2/1) (1.5 mL) was added LiOH (0.50 mL, 500 µmol). The resulting mixture was stirred overnight at 23° C., quenched with excess 1N HCl, and extracted with EtOAc. The combined organic layers were dried over Na₂SO₄ and concentrated. The crude residue was purified by combiflash chromatography (0 to 40% EtOAc/hexanes) to afford 81 (2.8 mg, 58% yield). MS ESI (neg.) m/e: 500.2 (M−H)⁺. ¹H NMR (400 MHz, CDCl₃) δ ppm 7.28-7.34 (2H, m), 7.24 (1H, d, J=1.2 Hz), 7.13 (1H, t, J=7.8 Hz), 6.94-6.98 (1H, m), 6.77-6.80 (2H, m), 6.57 (1H, d, J=7.6 Hz), 6.54 (1H, dd, J=8.1, 1.5 Hz), 6.50 (1H, d, J=2.0 Hz), 5.50 (1H, s), 4.36 (2H, s), 3.76 (3H, s), 2.91 (1H, m), 2.62 (2H, dd, J=7.3, 3.4 Hz), 2.24 (2H, td, J=7.1, 2.4 Hz), 1.75-1.55 (5H, m), 0.83 (6H, s), 0.80 (3H, t, J=7.3 Hz).

Example 82

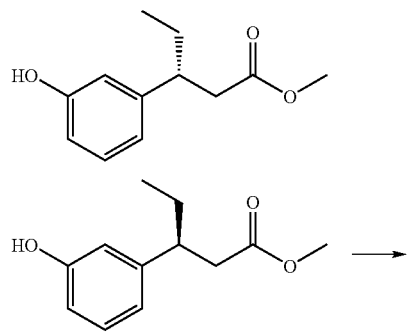

17.1

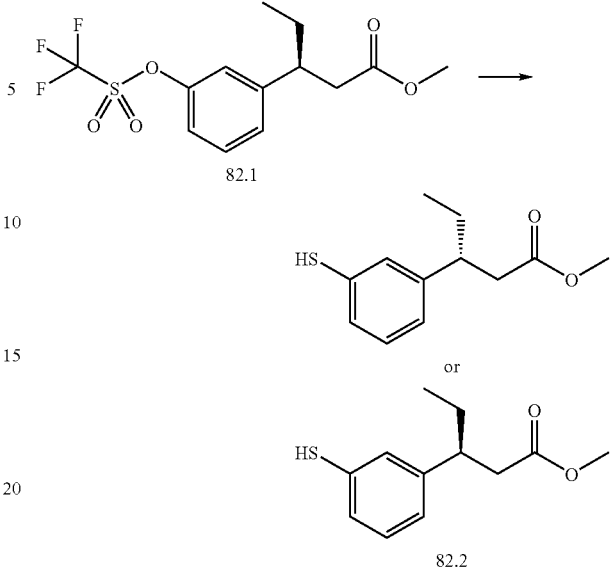

82.1

(R)-Methyl 3-(3-(trifluoromethylsulfonyloxy)-phenyl)pentanoate or (S)-methyl 3-(3-(trifluoromethylsulfonyloxy)-phenyl)pentanoate (82.1). To a stirred solution of 17.1 (280.0 mg, 1345 μmol) in dry DCM (1 mL) was added N,N-dimethylpyridin-4-amine (16.43 mg, 134.5 μmol) and TEA (374.0 μL, 2689 μmol). After about 20 minutes, N-phenyl-bis(trifluoromethanesulfonimide) (576.4 mg, 1613 μmol) was added in portions. Upon complete addition, the solution was stirred at room temperature. After 3 hours, the reaction was diluted with brine and extracted three times with DCM. After drying over anhydrous magnesium sulfate and filtration, the organic solvent was removed under reduced pressure and the residue was then purified with silica gel chromatography on a 12 g column using 0-15% EtOAc in hexanes to yield a colorless oil as (R)-methyl 3-(3-(trifluoromethylsulfonyloxy)phenyl)pentanoate or (S)-methyl 3-(3-(trifluoromethylsulfonyloxy)phenyl)pentanoate 82.1 (311.7 mg, 68.12% yield). The product is believed to be the R enantiomer.

(R)-Methyl 3-(3-(triisopropylsilylthio)phenyl)pentanoate or (S)-methyl 3-(3-(triisopropylsilylthio)phenyl)pentanoate (2.2). A vial was charged with Pd(PPh₃)₄ (13 mg, 11 μmol), cesium carbonate (92 mg, 283 μmol) and 82.1 (74 mg, 217 μmol). The vial was sealed, toluene (3 mL) was added, and the vial was sparged with nitrogen. Tips-thiol (61 μL, 283 μmol) was then added, and the reaction was heated at 100° C. for 16 hours. After cooling to room temperature, tetrabutylammonium fluoride (294 μL, 294 μmol) was added, and the resulting mixture was stirred for two hours. The reaction was concentrated and purified using silica chromatography to provide 82.2 (42.2 mg, 51% yield).

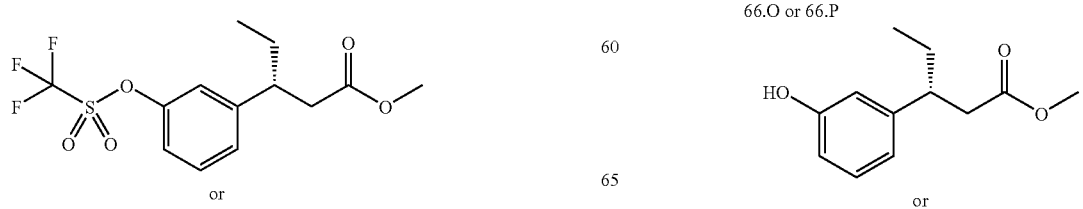

66.O or 66.P

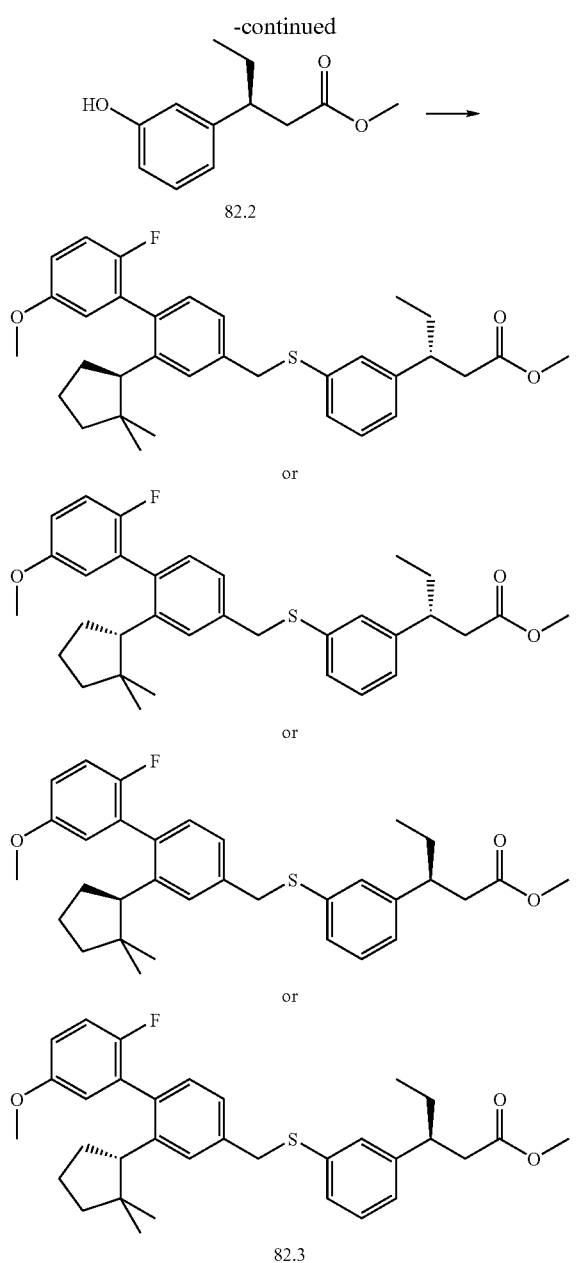

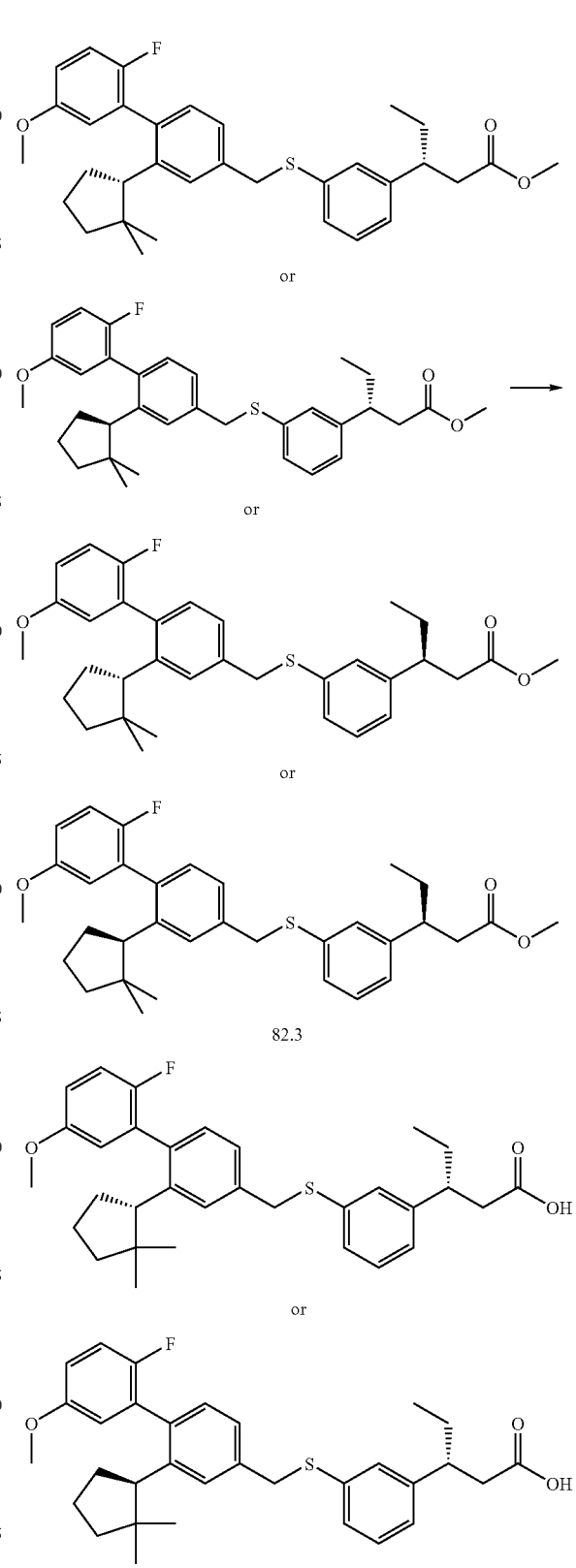

organic layers were washed with brine, dried over Na₂SO₄, filtered, concentrated, and then purified by combiflash chromatography (0 to 20% EtOAc/Hexanes) to provide 82.3 (50.2 mg, 77.2% yield).

Methyl (3R)-3-(3-(((2-((1S)-2,2-dimethylcyclopentyl)-2'-fluoro-5'-(methyloxy)-1,1'-biphenyl-4-yl)methyl)sulfanyl)phenyl)pentanoate or methyl (3R)-3-(3-(((2-((1R)-2,2-dimethylcyclopentyl)-2'-fluoro-5'-(methyloxy)-1,1'-biphenyl-4-yl)methyl)sulfanyl)phenyl)pentanoate or methyl (3S)-3-(3-(((2-((1S)-2,2-dimethylcyclopentyl)-2'-fluoro-5'-(methyloxy)-1,1'-biphenyl-4-yl)methyl)sulfanyl)phenyl)pentanoate or methyl (3S)-3-(3-(((2-((1R)-2,2-dimethylcyclopentyl)-2'-fluoro-5'-(methyloxy)-1,1'-biphenyl-4-yl)methyl)sulfanyl)phenyl)pentanoate (82.3). To a flask containing 82.2 (30.0 mg, 134 μmol) and cesium carbonate (51.5 mg, 158 μmol) in DMF (1 mL) was added 4-(chloromethyl)-2-((1S)-2,2-dimethylcyclopentyl)-2'-fluoro-5'-(methyloxy)-1,1'-biphenyl or 4-(chloromethyl)-2-((1R)-2,2-dimethylcyclopentyl)-2'-fluoro-5'-(methyloxy)-1,1'-biphenyl (66.O or 66.P) (42.2 mg, 122 μmol). The resulting mixture was then stirred overnight. The reaction was next diluted with water and extracted with EtOAc. The combined -continued

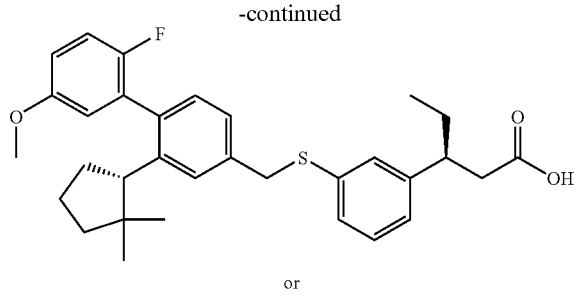

or

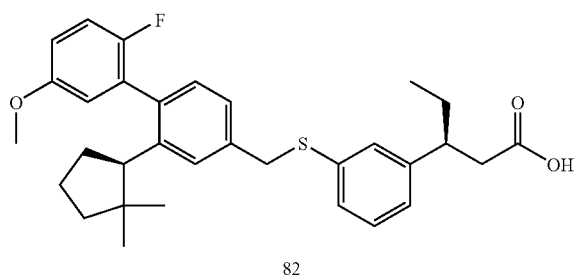

82

(3R)-3-(3-(((2-((1S)-2,2-Dimethylcyclopentyl)-2'-fluoro-5'-(methyloxy)-1,1'-biphenyl-4-yl)methyl)sulfanyl)phenyl)pentanoic acid or (3R)-3-(3-(((2-((1R)-2,2-dimethylcyclopentyl)-2'-fluoro-5'-(methyloxy)-1,1'-biphenyl-4-yl)methyl)sulfanyl)phenyl)pentanoic acid or (3S)-3-(3-(((2-((1S)-2,2-dimethylcyclopentyl)-2'-fluoro-5'-(methyloxy)-11'-biphenyl-4-yl)methyl)sulfanyl)phenyl)pentanoic acid or (3S)-3-(3-(((2-((1R)-2,2-dimethylcyclopentyl)-2'-fluoro-5'-(methyloxy)-1,1'-biphenyl-4-yl)methyl)sulfanyl)phenyl)pentanoic acid (82). To a solution of 82.3 (10.0 mg, 19 µmol) in THF/MeOH (2/1) (1.5 mL) was added LiOH (0.500 mL, 500 µmol). The resulting mixture was stirred overnight at 23° C., quenched with excess 1N HCl, and extracted with EtOAc. The combined organic layers were dried over $Na_2SO_4$ and concentrated. The residue was purified by combiflash chromatography (0 to 40% EtOAc/hexanes) to afford 82 (6.9 mg, 71% yield). MS ESI (neg.) m/e: 519.2 $(M-H)^+$.

Example 83

Synthesis of (S)-methyl 3-cyclopropyl-3-(2-fluoro-3-hydroxyphenyl)propanoate and (R)-methyl 3-cyclopropyl-3-(2-fluoro-3-hydroxyphenyl)propanoate (83.B and 83.C)

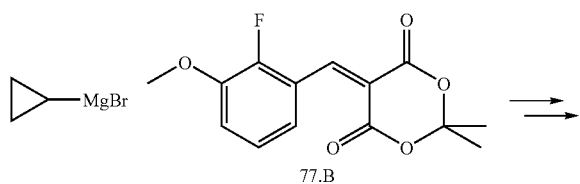

77.B

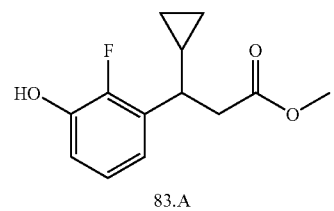

83.A

Methyl 3-cyclopropyl-3-(2-fluoro-3-hydroxyphenyl)propanoate) (83.A). Compound 83.A was prepared from 77.B and cyclopropylmagnesium bromide (0.5 M in THF) (commercially available from Aldrich) according to the analogous methods described in Example 77.

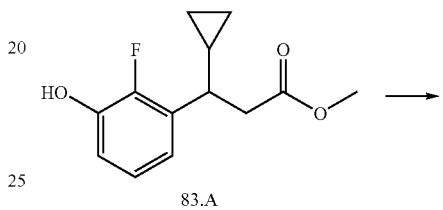

83.A

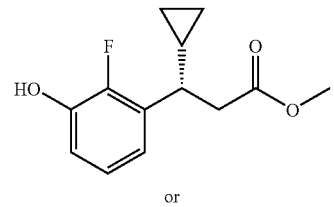

or

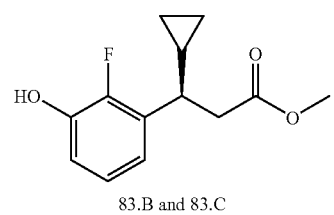

83.B and 83.C (S)-Methyl 3-cyclopropyl-3-(2-fluoro-3-hydroxyphenyl)propanoate and (R)-methyl 3-cyclopropyl-3-(2-fluoro-3-hydroxyphenyl)propanoate (83.B and 83.C). Racemic 83.A (20 g, 84 mmol) was resolved by chiral HPLC (Chiralcel OD column, 3% IPA/hexane, detection at 220 nm) to afford (in order of elution) 83.B (8.8 g, 88% yield, 99% e.e.) and 83.C (8.8 g, 88% yield, 99% e.e.) as white needles. 83.B is believed to be the S enantiomer.

The following compounds were prepared from 83.B and the appropriate halomethyl or hydroxymethyl compound according to the methods described herein. Each of the compounds in the following table were prepared using the same enantiomer of the phenol.

TABLE 17
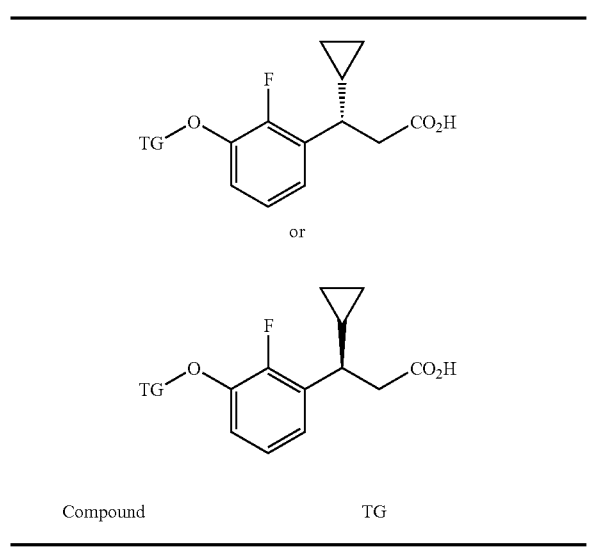
| Compound | TG |
| --- | --- |
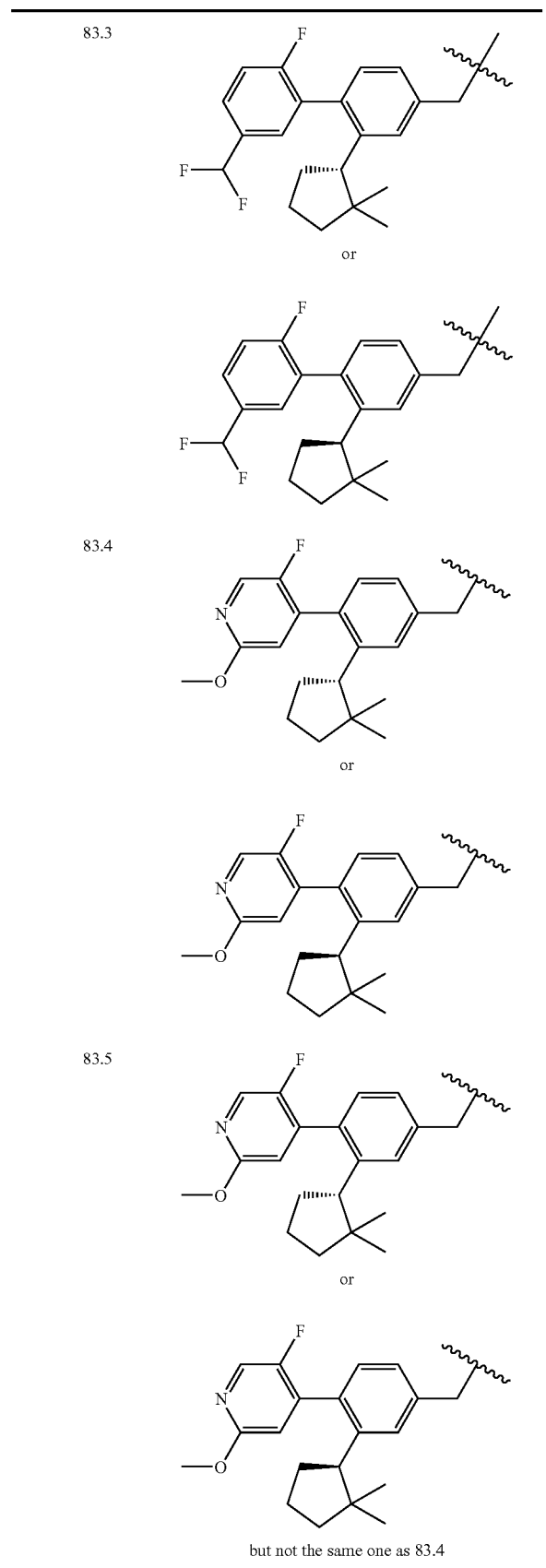
but not the same one as 83.4

TABLE 17-continued
83.6 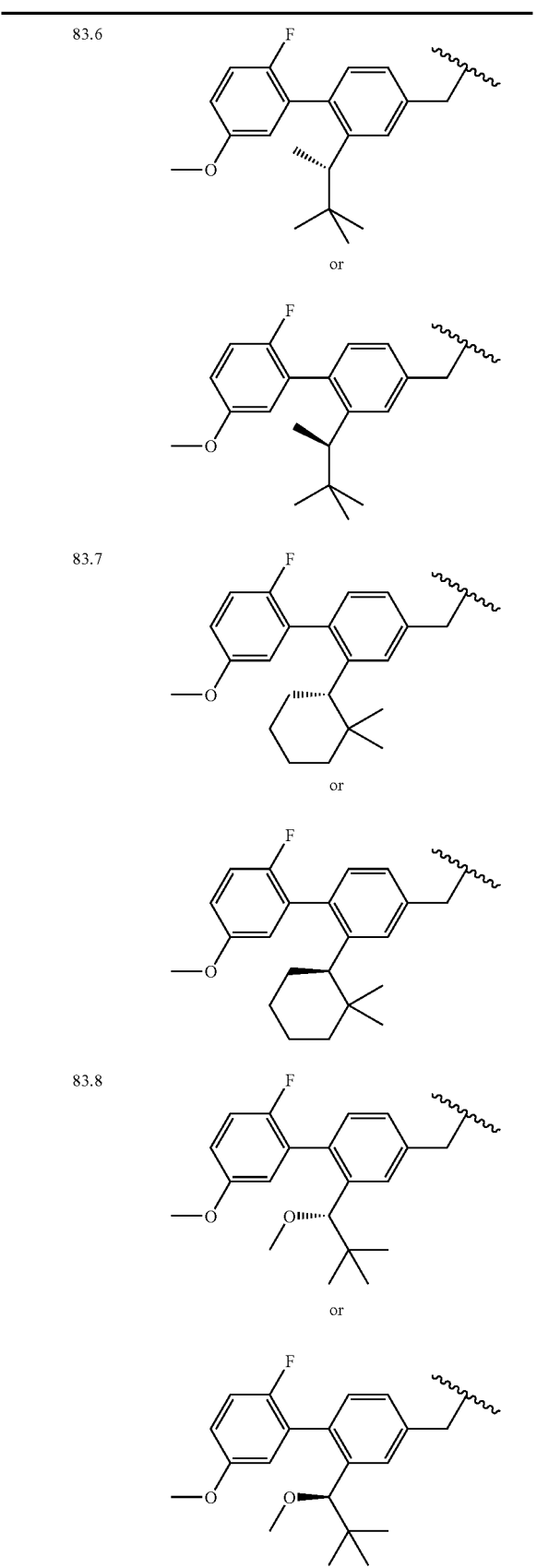
or
83.7
or
83.8
or
TABLE 17-continued
83.9 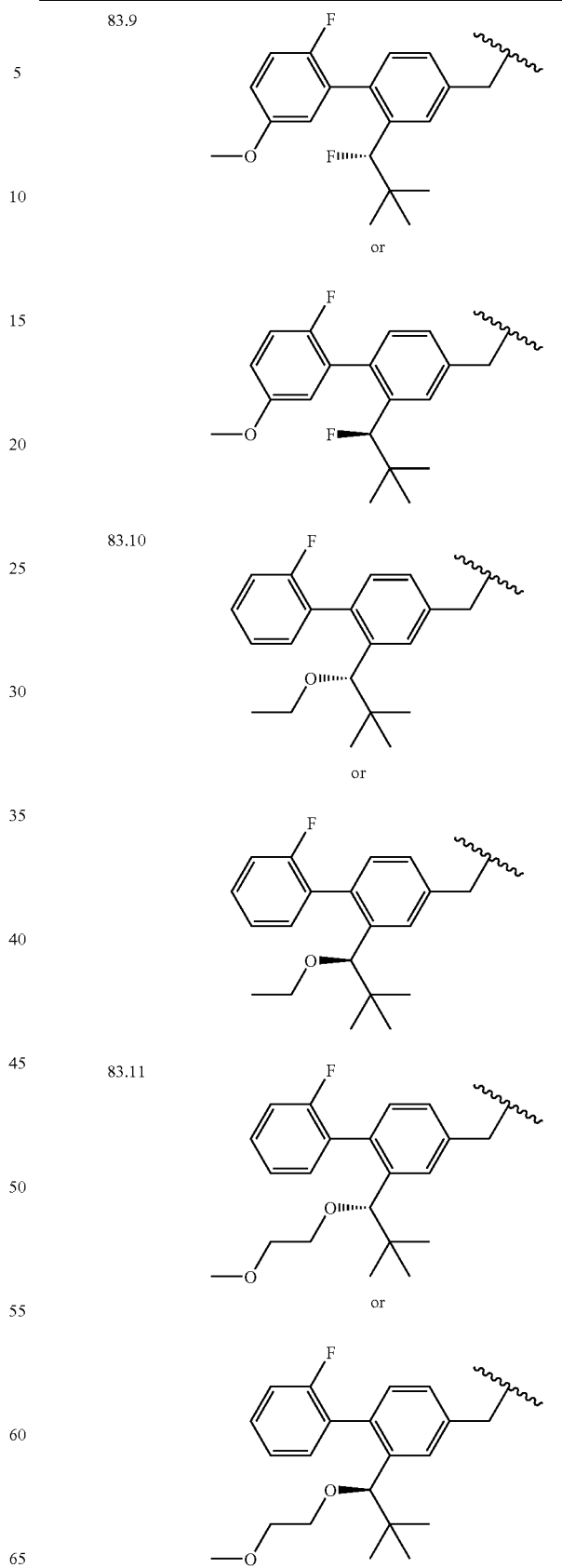
or
83.10
or
83.11
or TABLE 17-continued
83.12 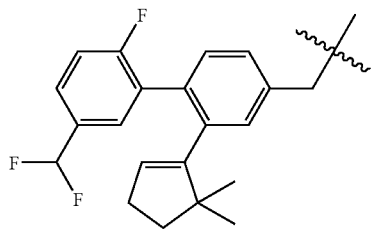
83.13 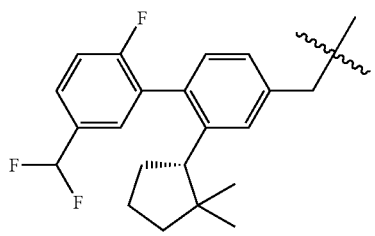
or
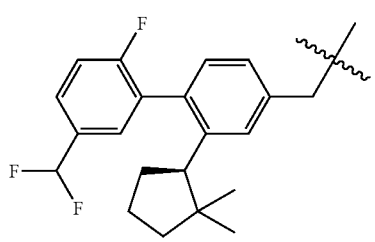
but not the same one as 83.3
83.14 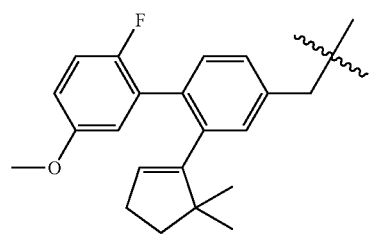
83.15 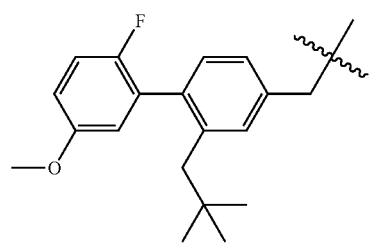
83.16 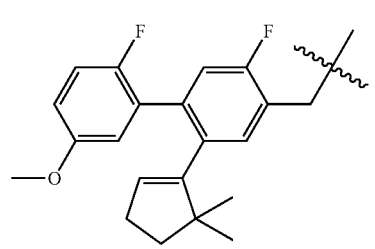
TABLE 17-continued
83.17 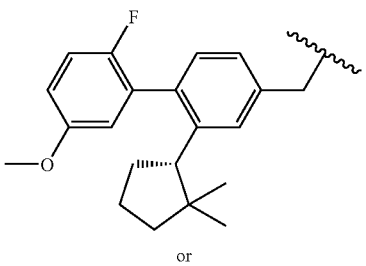
or
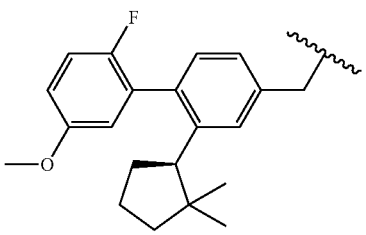
but not the same one as 83.1
83.18 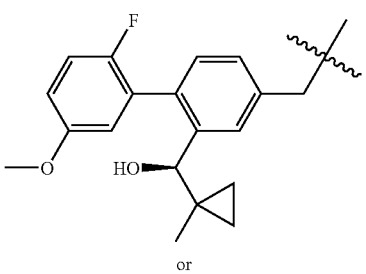
or
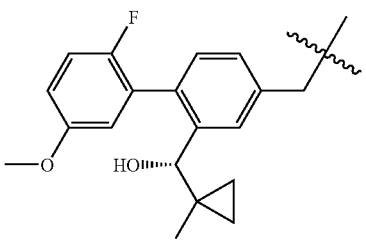
83.19 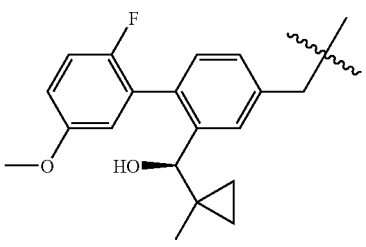
or
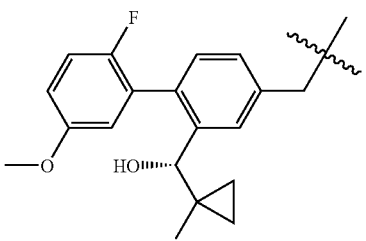
but not the same one as 83.18

TABLE 17-continued
83.20 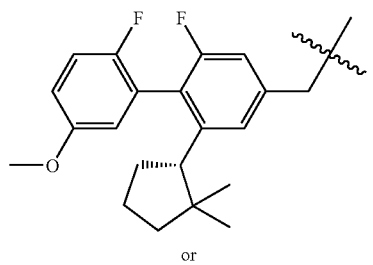
or
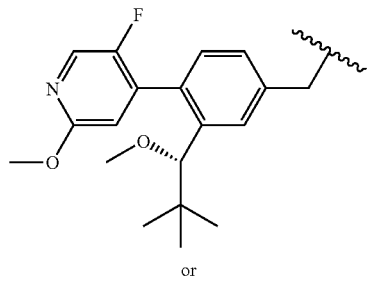
83.21 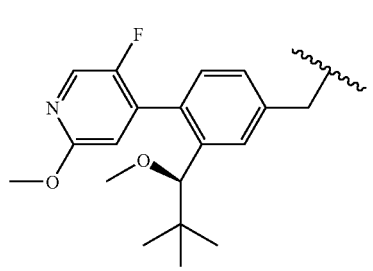
or
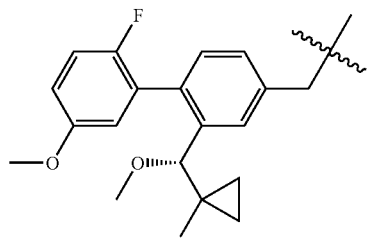
83.22 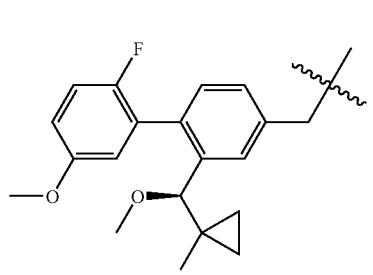
or
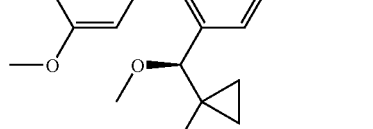
TABLE 17-continued
83.23 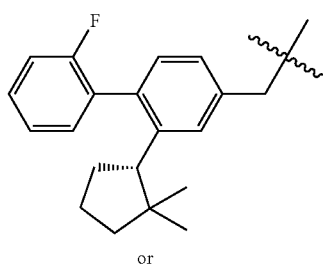
or
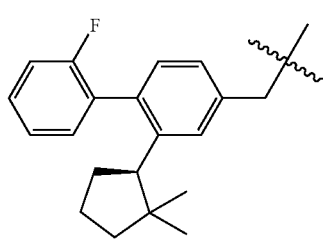
83.24 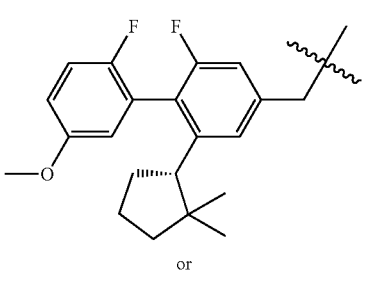
or
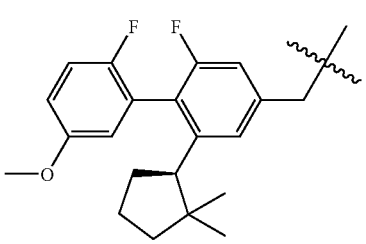
but not the same as 83.20
83.25 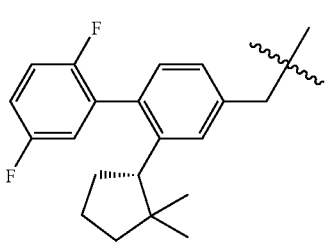
or
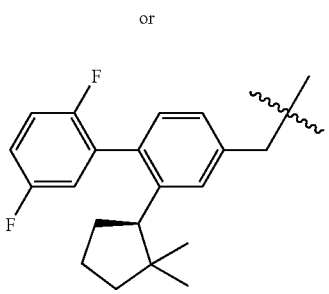

TABLE 17-continued
83.26 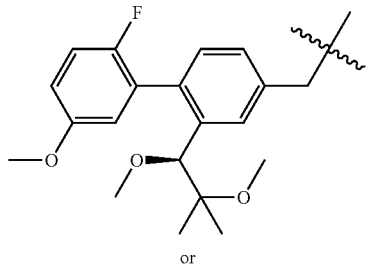
or
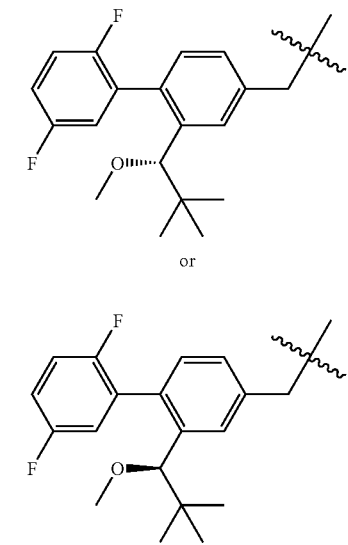
83.27
83.28
TABLE 17-continued
83.29 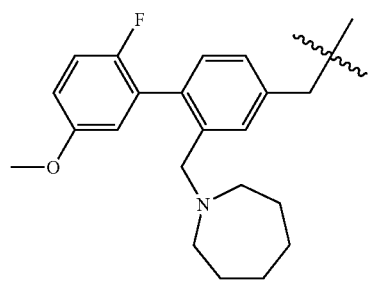
83.30 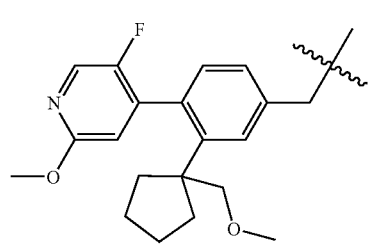
83.31 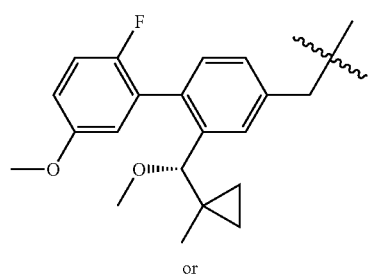
or
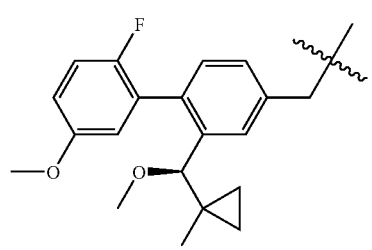
but not the same as 83.22
83.32 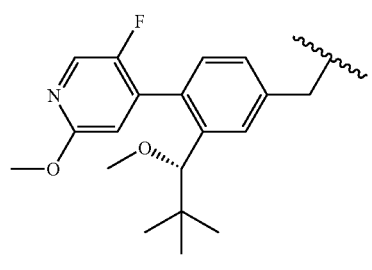
or

TABLE 17-continued

| | |
|---|---|
| 83.33 | 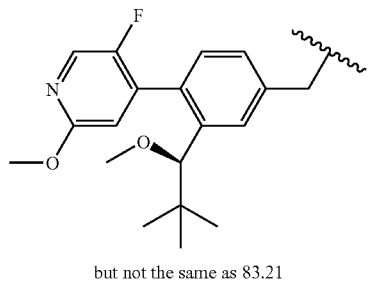<br>but not the same as 83.21 |
| | 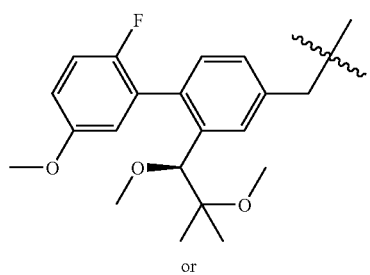<br>or<br>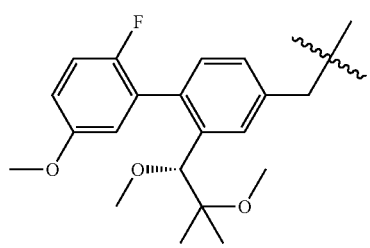<br>but not the same as 83.26 |
| 83.34 | 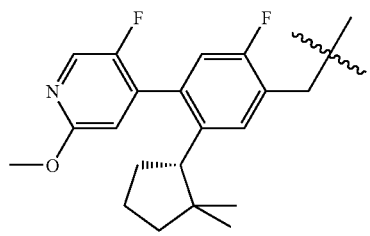<br>or<br>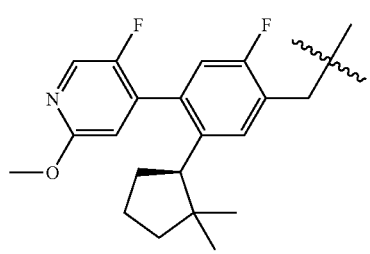 |

(S)-3-Cyclopropyl-3-{3-[2-((S)-2,2-dimethyl-cyclopentyl)-2'-fluoro-5'-methoxy-biphenyl-4-ylmethoxy]-2-fluoro-phenyl}-propionic acid or (S)-3-cyclopropyl-3-{3-[2-((R)-2,2-dimethyl-cyclopentyl)-2'-fluoro-5'-methoxy-biphenyl-4-ylmethoxy]-2-fluoro-phenyl}-propionic acid or (R)-3-cyclopropyl-3-{3-[2-((S)-2,2-dimethyl-cyclopentyl)-2'-fluoro-5'-methoxy-biphenyl-4-ylmethoxy]-2-fluoro-phenyl}-propionic acid or (R)-3-cyclopropyl-3-{3-[2-((R)-2,2-dimethyl-cyclopentyl)-2'-fluoro-5'-methoxy-biphenyl-4-ylmethoxy]-2-fluoro-phenyl}-propionic acid (83.1). MS ESI (neg.) m/e: 533.2 (M−H)+.

Example 83.2

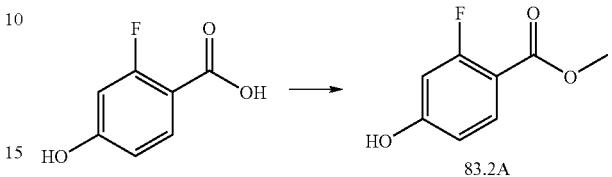

Methyl 2-fluoro-4-hydroxybenzoate (83.2A). To a round bottom flask containing 2-fluoro-4-hydroxybenzoic acid (5.34 g, 34.19 mmol) (commercially available from Matrix Scientific and TCI America) was added a cold solution of MeOH (50 mL) and sulfuric acid (2.0 mL). The mixture was heated to 80° C. and monitored with TLC. After 20.5 hours, the solvent was removed and diluted with diethyl ether. The organic phase was washed carefully two times with saturated aqueous NaHCO$_3$ and once with brine, then dried over anhydrous sodium sulfate. After filtration, the organic solvent was removed in vacuo to yield 83.2A as a white solid (5.82, 85%). $^1$H NMR (400 MHz, DMSO-d$_6$) δ ppm 10.79 (1H, s), 7.75 (1H, t, J=8.8 Hz), 6.69 (1H, dd, J=8.6, 2.3 Hz), 6.62 (1H, dd, J=13.1, 2.2 Hz), 3.78 (3H, s).

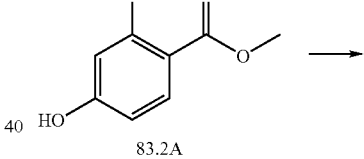

Methyl 5-bromo-2-fluoro-4-hydroxybenzoate (83.2B). To a solution of 83.2A (2.03 g, 11.9 mmol) in acetic acid (65 mL) was added a pre-mixed solution of bromine (0.67 mL, 13.1 mmol) in acetic acid (10 mL). The mixture was stirred at 45° C. and monitored with TLC and LC-MS. After 18 hours, the reaction mixture was concentrated under reduced pressure. Brine was added to the residue, and the mixture was extracted three times with EtOAc. The combined organic layers were dried over anhydrous magnesium sulfate and then filtered and concentrated to provide 83.2B as a white solid (2.12 g, 71%). $^1$H NMR (400 MHz, CDCl$_3$) δ ppm 8.13 (1H, d, J=7.4 Hz), 6.82 (1H, d, J=11.3 Hz), 6.04 (1H, s), 3.92 (3H, s).

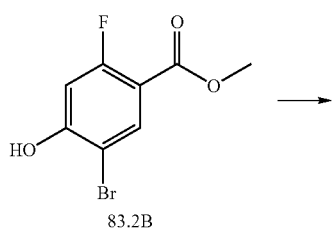

83.2B

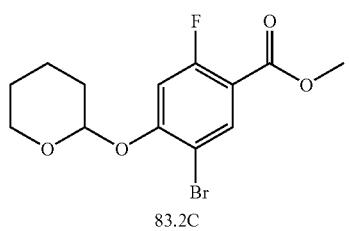

83.2C

Methyl 5-bromo-2-fluoro-4-(tetrahydro-2H-pyran-2-yloxy)benzoate (83.2C). To a round bottom flask containing 83.2B (13.15 g, 52.8 mmol) in dry DCM (90 mL) was added 3,4-dihydro-2H-pyran (10 mL, 110 mmol) followed by PPTS (0.13 g, 0.53 mmol). The reaction mixture was heated to a gentle reflux (50° C.) and monitored with TLC and LC-MS. After 24 hours, the reaction was concentrated under reduced pressure and then diluted with MeOH. After concentration, the residue was heated in a round bottom flask containing MeOH on the rotary evaporator (without vacuum.) to 40° C. After about 30 minutes, the solution was concentrated to a volume of about 5 mL. After cooling to room temperature, the white solid was filtered and rinsed once with MeOH to yield 83.2C (13.35 g, 76%). $^1$H NMR (400 MHz, CDCl$_3$) δ ppm 8.25 (1H, m), 6.96 (1H, d, J=12.5 Hz), 5.56 (1H, m), 3.91 (3H, s), 3.79 (1H, td, J=11.1, 2.5 Hz), 3.65 (1H, d, J=10.6 Hz), 2.23 (2H, m), 1.96 (3H, m), 1.68 (1H, m).

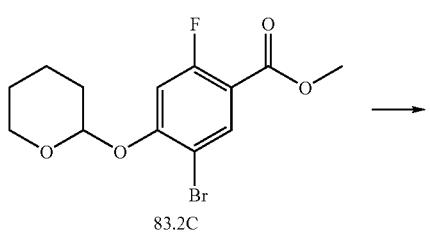

83.2C

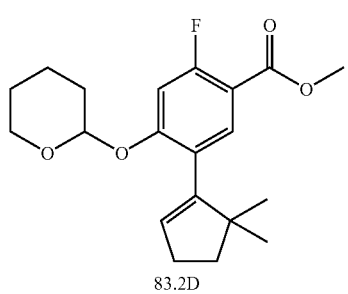

83.2D

Methyl 5-(5,5-dimethylcyclopent-1-enyl)-2-fluoro-4-(tetrahydro-2H-pyran-2-yloxy)benzoate (83.2D). A stirred mixture of 83.2C (10.33 g, 31.0 mmol), ground S-Phos (2.55 g, 6.21 mmol), palladium acetate (0.70 g, 3.11 mmol), and potassium phosphate, tribasic (16.49 g, 77.7 mmol) in DMF (75 mL) and water (4 mL) was purged with argon and placed vacuum and the process was repeated three times. Before heating, 2-(5,5-dimethylcyclopent-1-enyl)-4,4,5,5-tetramethyl-1,3,2-dioxaborolane (66.6° C.) (8.96 g, 40.4 mmol) was added via syringe, and then the mixture was heated to 75° C. After 21 hours, the reaction was cooled to room temperature, diluted with water and extracted three times with EtOAc. The combined organic layers were combined and washed twice with brine. After drying over anhydrous sodium sulfate and filtration, the organic solvent was removed under reduced pressure. The residue was purified by silica gel flash chromatography (0-10% EtOAc/hexane) to yield 83.2D (5.65 g, 52%) $^1$H NMR (400 MHz, CDCl$_3$) δ ppm 7.63 (1H, d, J=8.6 Hz), 6.93 (1H, d, J=13.3 Hz), 5.55 (1H, t, J=2.3 Hz), 5.43 (1H, t, J=2.7 Hz), 3.90 (3H, s), 3.82 (1H, m), 3.67 (1H, m), 2.41 (2H, td, J=7.0, 2.3 Hz), 1.97 (5H, m), 1.79 (3H, m), 1.07 (6H, d, J=13.7 Hz).

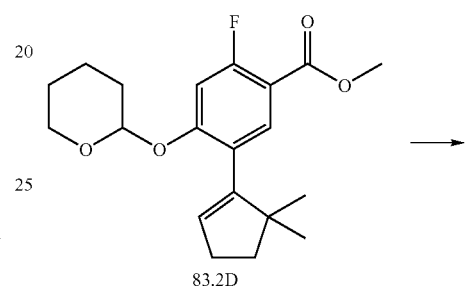

83.2D

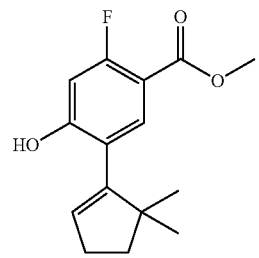

83.2E

Methyl 5-(5,5-dimethylcyclopent-1-enyl)-2-fluoro-4-hydroxybenzoate (83.2 E). To a stirred mixture of 83.2D (5.65 g, 16.2 mmol) in MeOH (60 mL) was added PPTS (0.42 g, 1.69 mmol). The mixture was heated to 50° C. and monitored with TLC and LCMS. After 19 hours, the organic solvent was removed under reduced pressure, then the residue was purified on silica gel (0-15% EtOAc in hexanes) to yield 83.2E as a white solid (3.47 g, 81%). $^1$H NMR (500 MHz, CDCl$_3$) δ ppm 7.69 (1H, d, J=8.3 Hz), 6.71 (1H, d, J=12.0 Hz), 5.93 (1H, d, J=1.7 Hz), 5.80 (1H, t, J=2.4 Hz), 3.90 (3H, s), 2.54 (2H, m), 1.93 (2H, t, J=7.1 Hz), 1.11 (6H, s).

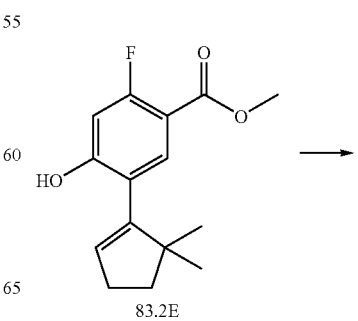

83.2E

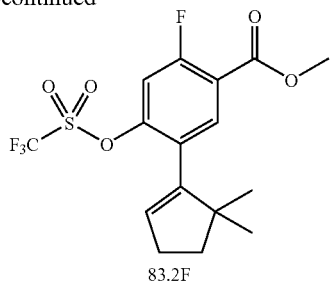

83.2F

Methyl 5-(5,5-dimethylcyclopent-1-enyl)-2-fluoro-4-(trifluoromethylsulfonyloxy)benzoate (83.2F). To a stirred solution of 83.2E (0.80 g, 3.02 mmol) in dry DCM (15 mL) was added TEA (1.0 mL, 7.19 mmol) and 4-dimethylaminopyridine (38.1 mg, 0.312 mmol). After about 20 minutes, N-phenyl-bis(trifluoromethanesulfonimide) (1.30 g, 3.64 mmol) was added in portions. Upon complete addition, the solution was stirred at room temperature and monitored with TLC and LC-MS. After 19 hours, the organic solvent was removed under reduced pressure, and the residue was purified with silica gel chromatography using 0-10% EtOAc in hexanes to yield 83.2F as a colorless oil (1.05 g, 88%). $^1$H NMR (400 MHz, CDCl$_3$) δ ppm 7.84 (1H, d, J=7.8 Hz), 7.13 (1H, d, J=10.2 Hz), 5.79 (1H, t, J=2.3 Hz), 3.96 (3H, s), 2.47 (2H, td, J=7.0, 2.3 Hz), 1.91 (2H, t, J=7.0 Hz), 1.08 (6H, s).

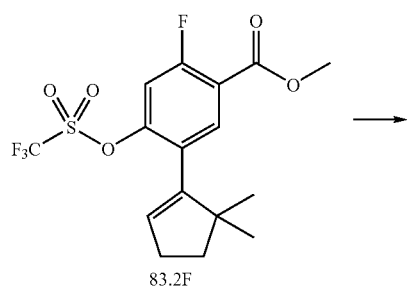

83.2F

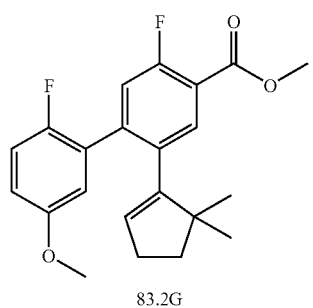

83.2G

Methyl 2-(5,5-dimethyl-1-cyclopenten-1-yl)-2',5-difluoro-5'-(methyloxy)-1,1'-biphenyl-4-carboxylate (83.2G). To a stirred solution of 83.2F (1.05 g, 2.65 mmol) in DMF (5 mL) at 23° C. was added 2-fluoro-5-methoxyphenylboronic acid (0.90 g, 5.32 mmol) (commercially available from Aldrich) and potassium carbonate (1.10 g, 7.96 mmol) followed by tetrakis(triphenylphosphine)palladium (0.31 g, 0.27 mmol). The mixture was heated to 90° C. After 17 hours, the mixture was cooled to room temperature and then diluted with water. After extracting three times with EtOAc, the mixture was concentrated in vacuo and the residue was then purified on silica gel (0%-10% EtOAc/hexane) to give 83.2G as a clear oil that was used without further purification (0.92 g, 93%). $^1$H NMR (400 MHz, CDCl$_3$) δ ppm 7.79 (1H, d, J=7.4 Hz), 7.13 (1H, d, J=11.3 Hz), 6.99 (1H, t, J=9.0 Hz), 6.84 (1H, dt, J=8.7, 3.7 Hz), 6.78 (1H, dd, J=5.9, 3.1 Hz), 5.55 (1H, s), 3.96 (3H, s), 3.79 (3H, s), 2.27 (2H, td, J=7.1, 2.5 Hz), 1.67 (2H, t, J=7.0 Hz), 0.84 (6H, s).

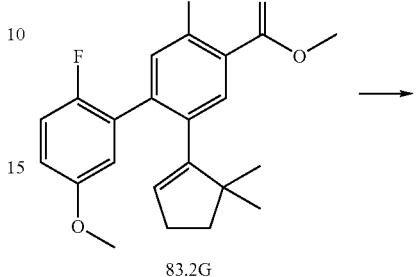

83.2G

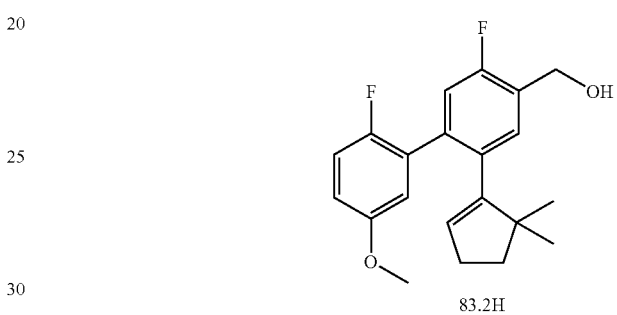

83.2H (2-(5,5-Dimethyl-1-cyclopenten-1-yl)-2',5-difluoro-5'-(methyloxy)-1,1'-biphenyl-4-yl)methanol (83.2H). To a cooled solution of 83.2G (0.92 g, 2.47 mmol) in dry THF (15 mL) at 0° C. was added LAH, 1.0 M in THF (5.0 mL, 5.0 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was then purified by flash chromatography (SiO$_2$ gel 60, eluted with 0%-50% EtOAc in hexanes). Fractions containing the desired product were combined and concentrated to provide 83.2H as a colorless oil (0.70 g, 82%). $^1$H NMR (500 MHz, CDCl$_3$) δ ppm 7.30 (1H, m), 7.05 (1H, dd, J=10.6, 1.1 Hz), 6.97 (1H, t, J=8.9 Hz), 6.83 (2H, m), 5.52 (1H, td, J=2.4, 0.9 Hz), 4.81 (2H, s), 3.76 (3H, s), 2.25 (2H, td, J=7.1, 2.4 Hz), 1.76 (1H, br. s.), 1.69 (2H, m), 0.85 (6H, s).

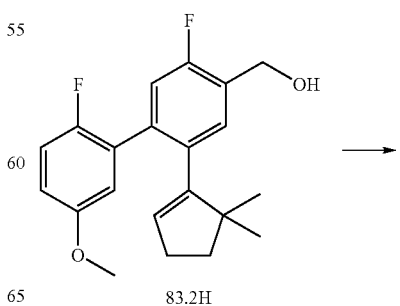

83.2H

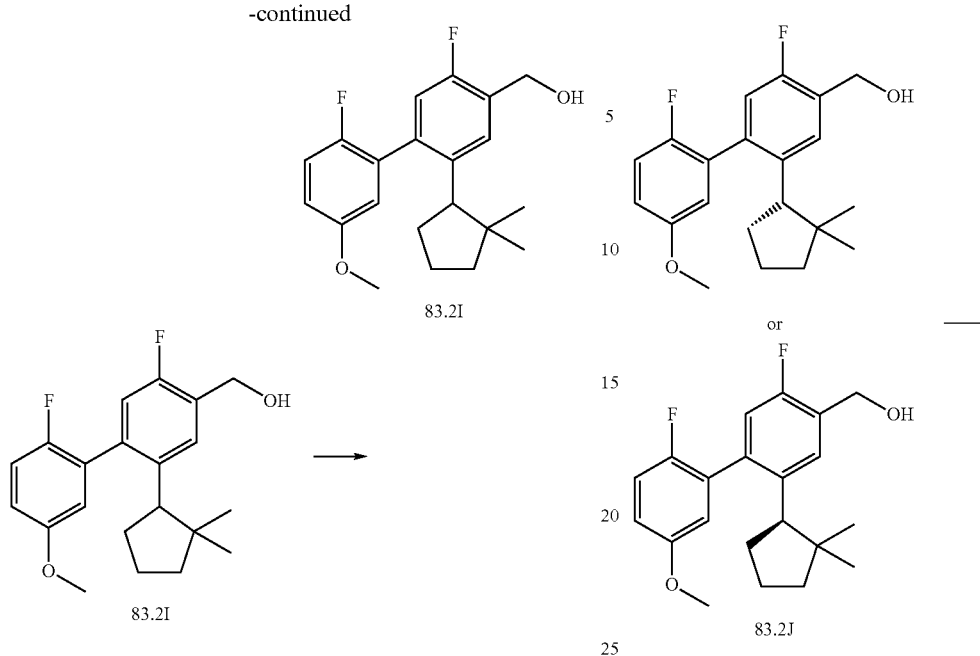

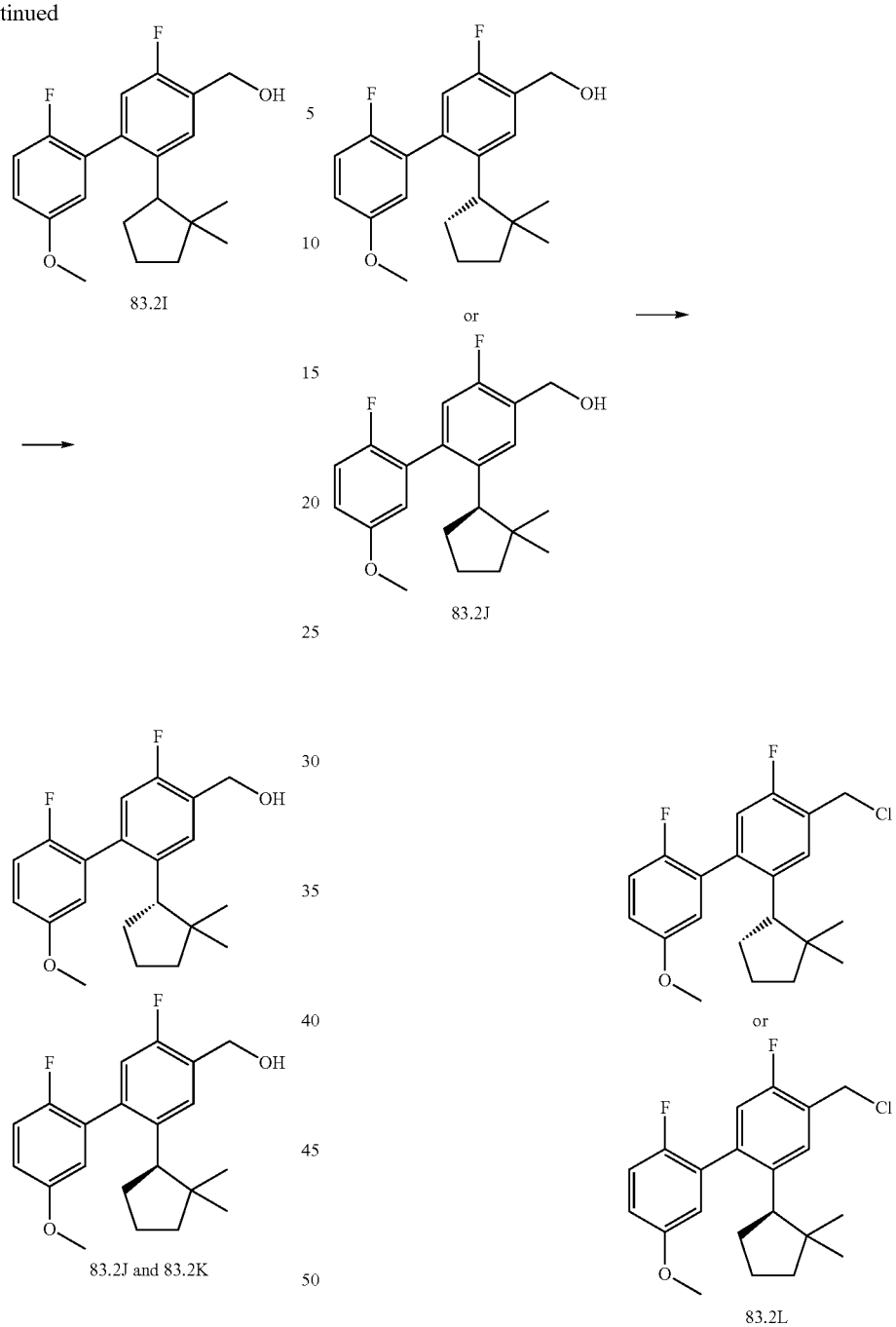

(2-(2,2-Dimethylcyclopentyl)-2',5-difluoro-5'-(methyloxy)-1,1'-biphenyl-4-yl)methanol (83.2I). To a dry flask containing 83.2H (0.70 g, 2.03 mmol) in dry MeOH (5 mL) and EtOAc (3 mL) was added palladium, 10 wt. % on activated carbon (77.2 mg). After purging, the mixture was stirred under an atmosphere of hydrogen at room temperature. After 4.5 hours, the mixture was filtered through Celite. After concentration, the residue was identified as 83.2I as a mixture of enantiomers and rotamers (0.31 g, 45%). Chiral separation of 83.2 I was accomplished on Chiracel-OJ (2% IPA in hexane) to provide 83.2J (peak 1) and 83.2K (peak 2). Both enantiomers were used to synthesize example compounds, and both enantiomers gave active compounds. The enantiomer corresponding to peak 1 provided the more active example compound.

4-(Chloromethyl)-2-((1S)-2,2-dimethylcyclopentyl)-2',5-difluoro-5'-(methyloxy)-1,1'-biphenyl (83.2L). To a solution of 83.2J (0.71 g, 2.05 mmol) in dry DCM (23 mL) and dry DMF (0.18 mL) was added thionyl chloride (0.3 mL, 4.1 mmol) dropwise at 0° C. The resulting solution was warmed to room temperature and monitored with TLC and LCMS. After 45 minutes, the reaction was concentrated then purified by silica gel flash chromatography (0-5% EtOAc/hexane) to yield 83.2L as a colorless oil (0.73 g, 97%). $^1$H NMR (400 MHz, CDCl$_3$) δ ppm 7.46 (1H, m), 7.11 (3H, m), 6.75 (1H, m), 4.78 (2H, m), 3.80 (3H, s), 2.91 (1H, m), 2.20 (2H, m), 1.87 (2H, m), 1.59 (1H, m), 1.43 (1H, m), 0.77 (3H, m), 0.64 (3H, m).

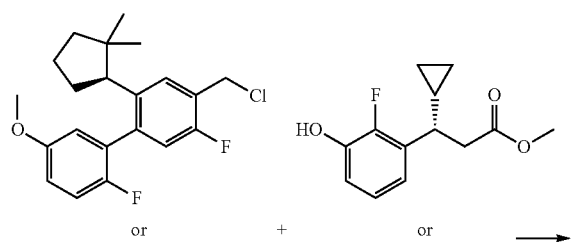
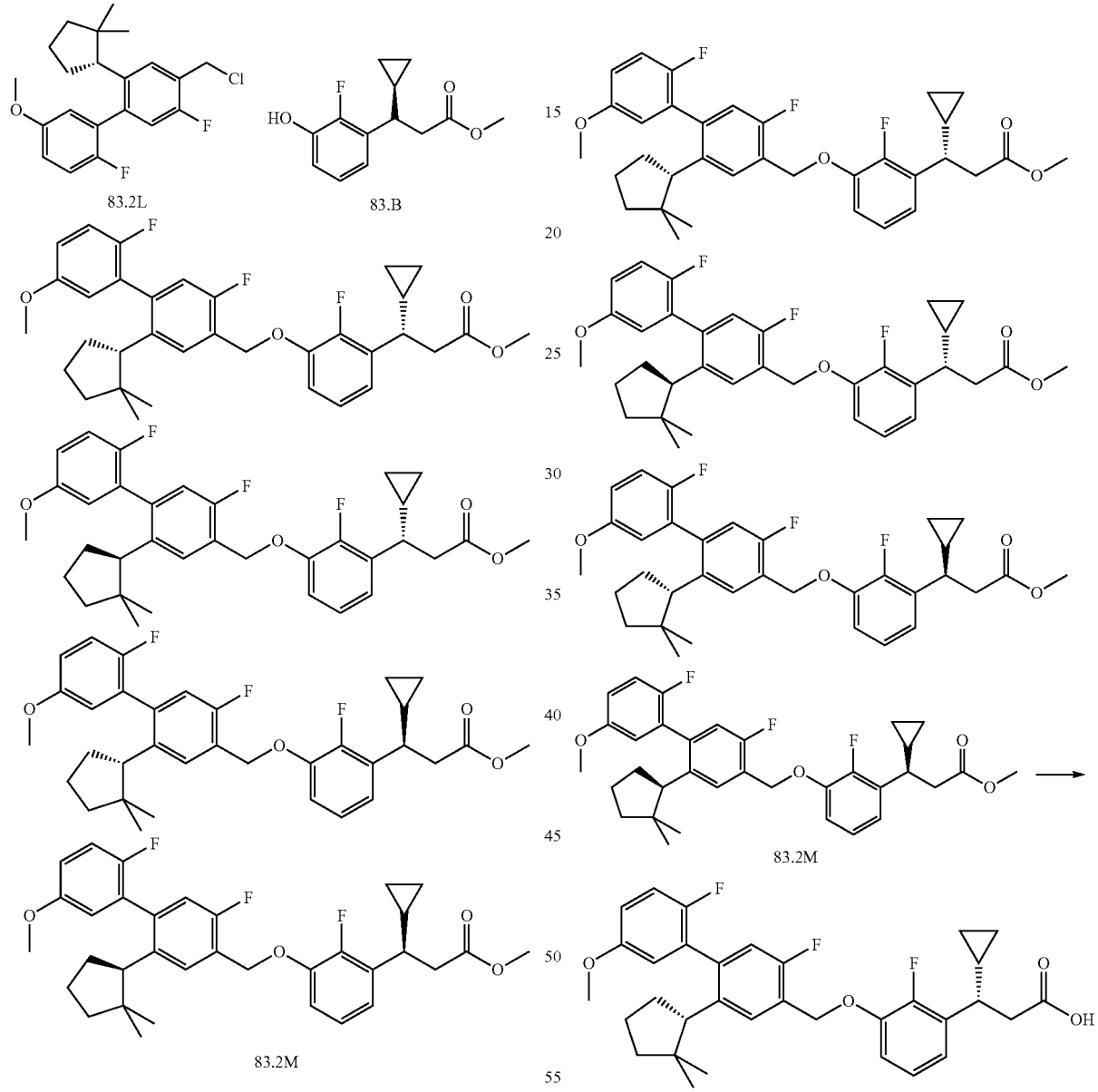

fluorophenyl)propanoate (83.2 M). To a flask containing 83.B (445.9 mg, 1872 μmol) and cesium carbonate (792.7 mg, 2433 μmol) in DMF (10 mL) was added 83.2 L (717.0 mg, 1965 μmol), and the mixture was stirred overnight. The reaction was diluted with water and extracted with EtOAc. The combined organic layers were washed with brine, dried over Na₂SO₄, filtered, concentrated, and then purified by silica gel chromatography (0 to 20% EtOAc/Hexanes) to provide 83.2M (992.3 mg, 93.57% yield).

Methyl (3S)-3-cyclopropyl-3-(3-(((2-((1S)-2,2-dimethylcyclopentyl)-2',5-difluoro-5'-(methyloxy)-1,1'-biphenyl-4-yl)methyl)oxy)-2-fluorophenyl)propanoate or methyl (3S)-3-cyclopropyl-3-(3-(((2-((1R)-2,2-dimethylcyclopentyl)-2',5-difluoro-5'-(methyloxy)-1,1'-biphenyl-4-yl)methyl)oxy)-2-fluorophenyl)propanoate or methyl (3R)-3-cyclopropyl-3-(3-(((2-((1S)-2,2-dimethylcyclopentyl)-2',5-difluoro-5'-(methyloxy)-1,1'-biphenyl-4-yl)methyl)oxy)-2-fluorophenyl)propanoate or methyl (3R)-3-cyclopropyl-3-(3-(((2-((1R)-2,2-dimethylcyclopentyl)-2',5-difluoro-5'-(methyloxy)-1,1'-biphenyl-4-yl)methyl)oxy)-2-

-continued

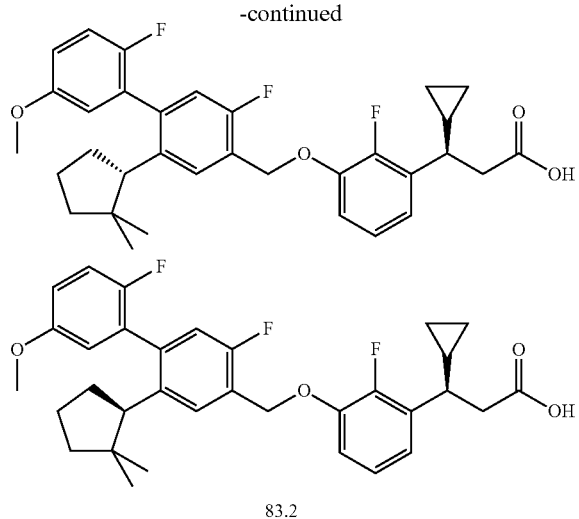

83.2

(S)-3-Cyclopropyl-3-{3-[2-((S)-2,2-dimethyl-cyclopentyl)-5,2'-difluoro-5'-methoxy-biphenyl-4-ylmethoxy]-2-fluoro-phenyl}-propionic acid or (S)-3-cyclopropyl-3-{3-[2-((R)-2,2-dimethyl-cyclopentyl)-5,2'-difluoro-5'-methoxy-biphenyl-4-ylmethoxy]-2-fluoro-phenyl}-propionic acid or (R)-3-cyclopropyl-3-{3-[2-((S)-2,2-dimethyl-cyclopentyl)-5,2'-difluoro-5'-methoxy-biphenyl-4-ylmethoxy]-2-fluoro-phenyl}-propionic acid or (R)-3-cyclopropyl-3-{3-[2-((R)-2,2-dimethyl-cyclopentyl)-5,2'-difluoro-5'-methoxy-biphenyl-4-ylmethoxy]-2-fluoro-phenyl}-propionic acid (83.2). To a solution of 83.2M (992.3 mg, 1.8 mmol) in THF/MeOH (2/1) (15 mL) was added LiOH (5.000 mL, 5.0 mmol). The resulting mixture was stirred overnight at 23° C., quenched with excess 1N HCl, and extracted with EtOAc. The combined organic layers were dried over Na$_2$SO$_4$ and concentrated. The crude residue was purified by silica gel chromatography (5 to 25% EtOAc/hexanes) to afford 83.2 (0.93 g, 96% yield). MS ESI (neg.) m/e: 551.2 (M−H).

Asymmetric synthesis of 83.2J. The following procedures were used to synthesize 83.2J using a highly enantioselective procedure to hydrogenate 83.2E to form 83.2N.

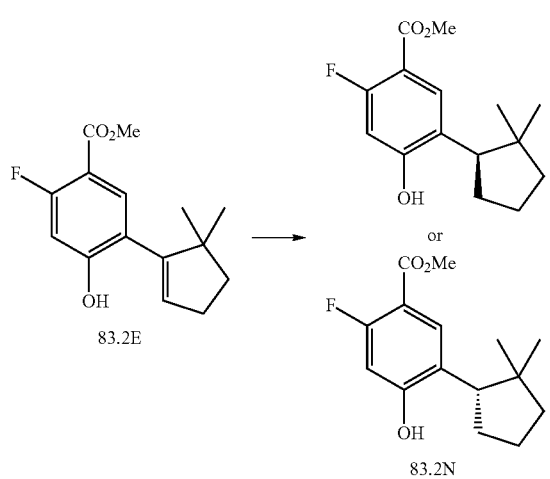

(R)-Methyl 5-(2,2-dimethylcyclopentyl)-2-fluoro-4-hydroxybenzoate or (S)-methyl 5-(2,2-dimethylcyclopentyl)-2-fluoro-4-hydroxybenzoate (83.2N). A mixture of Rh(COD)$_2$BF$_4$ (Stem Chemical, 35138-22-8, 36.95 mg, 0.091 mmol) and (R)-1-[(S)-2-(R)-(Ditertbutylphosphino)ferrocenyl]ethyl-bis-(3,5-bistrifluoromethylphenyl)phosphine (Solvias, SL-J210-1, 81.5 mg, 0.100 mmol) in THF (75 mL) was stirred under N$_2$ for 60 minutes and a dark red solution formed. To the resulting solution was added methyl 5-(5,5-dimethylcyclopent-1-enyl)-2-fluoro-4-hydroxybenzoate 83.2E (8.2 g, 45.4 mmol) and TEA (10 mol %, 0.63 mL, 4.54 mmol). The resulting solution was filled with H$_2$ (200 psi) three times and stirred at room temperature/200 psi for 2 hours. The resulting mixture was passed through a short plug of silica gel, eluting with 1:1 hexane/EtOAc. The mixture was then concentrated affording the desired product as a white solid (83% yield (6.8 g), 99.3% ee).

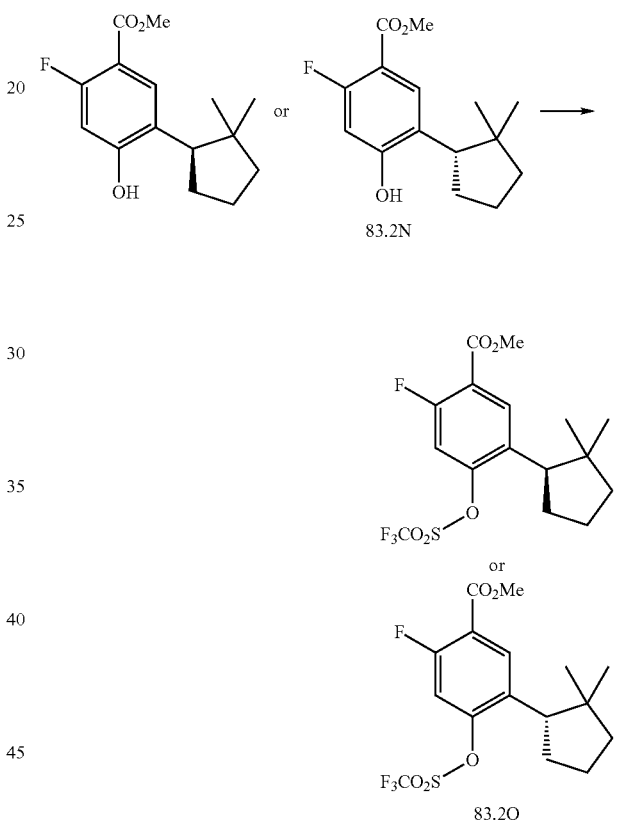

83.2O (R)-Methyl 5-(2,2-dimethylcyclopentyl)-2-fluoro-4-(trifluoromethylsulfonyloxy)benzoate or (S)-methyl 5-(2,2-dimethylcyclopentyl)-2-fluoro-4-(trifluoromethylsulfonyloxy)benzoate (83.2O). To a stirred solution of 83.2N (4.02 g, 15.1 mmol) in dry DCM (50 mL) was added TEA (4.2 mL, 30.2 mmol) and DMAP (0.19 g, 1.52 mmol). After 20 minutes, N-phenyl-bis(trifluoromethanesulfonimide) (5.94 g, 16.6 mmol) was added in portions. Upon complete addition, the solution was stirred at room temperature and monitored with TLC and LC-MS. After 4 hours, the mixture was washed twice with brine and then dried over anhydrous magnesium sulfate. After filtration and concentration, the residue was purified with silica gel chromatography (0-10% EtOAc in hexanes) to yield 83.2O as a colorless oil (5.51, 92%). $^1$H NMR (500 MHz, CDCl$_3$) δ ppm 7.97 (1H, d, J=7.8 Hz), 7.14 (1H, d, J=10.0 Hz), 3.96 (3H, s), 3.13 (1H, dd, J=10.1, 8.2 Hz), 2.14 (2H, m), 1.96 (2H, m), 1.70 (2H, m), 1.00 (3H, s), 0.69 (3H, s).

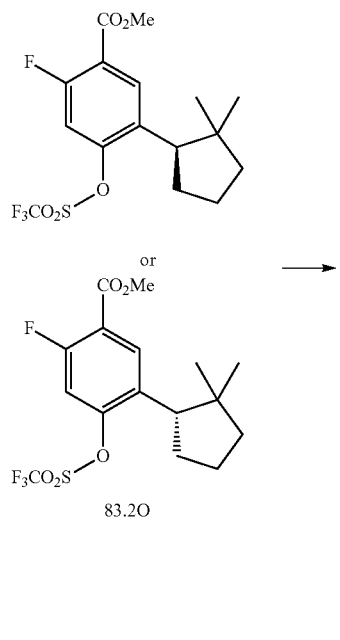

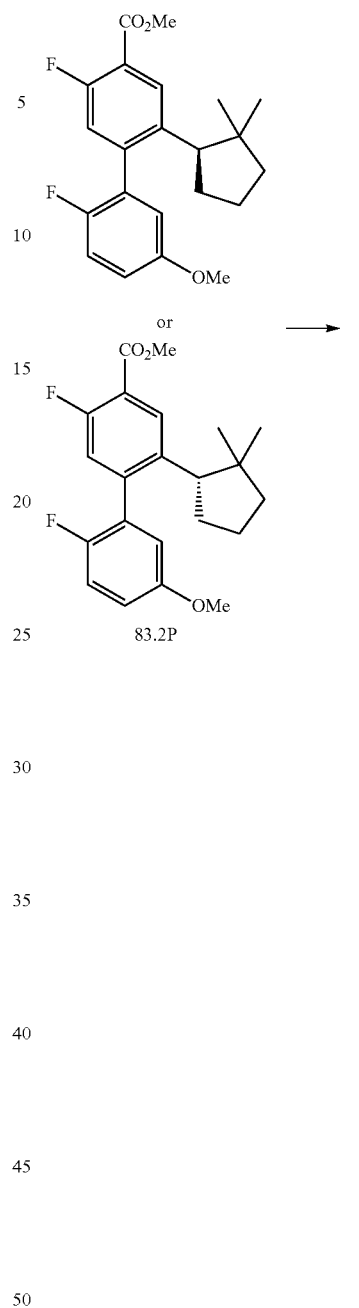

Methyl 2-((1R)-2,2-dimethylcyclopentyl)-2',5-difluoro-5'-(methyloxy)-1,1'-biphenyl-4-carboxylate or methyl 2-((1S)-2,2-dimethylcyclopentyl)-2',5-difluoro-5'-(methyloxy)-1,1'-biphenyl-4-carboxylate (83.2P). To a stirred solution of 83.2O (5.51 g, 13.8 mmol) in DMF (25 mL) at 23° C. was added 2-fluoro-5-methoxyphenylboronic acid (4.71 g, 27.7 mmol) (commercially available from Aldrich) and potassium carbonate (5.74 g, 41.6 mmol) followed by tetrakis(triphenylphosphine)palladium (1.60 g, 1.39 mmol). The mixture was heated to 90° C. After 3.5 hours, the mixture was cooled to room temperature and then diluted with water. After extracting three times with EtOAc, the mixture was concentrated in vacuo and then purified on silica gel (0%-10% EtOAc/hexane) to yield 83.2P as an oil that solidified (5.11 g, 99%).

(2-((1R)-2,2-Dimethylcyclopentyl)-2',5-difluoro-5'-(methyloxy)-1,1'-biphenyl-4-yl)methanol or (2-((1S)-2,2-dimethylcyclopentyl)-2',5-difluoro-5'-(methyloxy)-1,1'-biphenyl-4-yl)methanol (83.2J). To a cooled solution of 83.2P (5.11 g, 13.6 mmol) in dry THF (40 mL) at 0° C. was added LAH (1.0 M in THF) (27.3 mL, 27.30 mmol) dropwise. Upon complete addition, the reaction was maintained at 0° C. and was monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by silica gel chromatography (0-25% EtOAc in hexanes) to yield 83.2J as a colorless oil (3.94 g, 83%). $^1$H NMR (400 MHz, CDCl$_3$) δ ppm 7.50 (1H, m), 7.11 (3H, m), 6.85 (1H, m), 4.81 (2H, s), 3.80 (3H, s), 2.92 (1H, m), 2.19 (2H, m), 1.83 (1H, m), 1.72 (1H, m), 1.59 (2H, m), 1.42 (1H, m), 0.82 (3H, m), 0.65 (3H, m).

Example 83.3

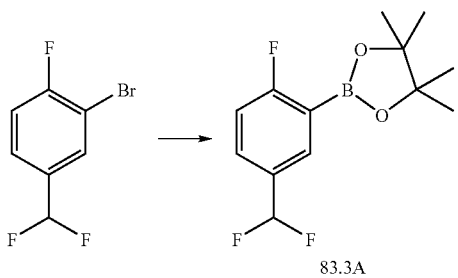

83.3A 2-(5-(Difluoromethyl)-2-fluorophenyl)-4,4,5,5-tetramethyl-1,3,2-dioxaborolane (83.3A). A stirred mixture of 1-bromo-5-difluoromethyl-2-fluorobenzene (available from Oakwood Products, Inc.) (2.02 g, 8.99 mmol), bis(pinacolato)diboron (2.51 g, 9.89 mmol), dichloro[1,1'-bis(diphenylphosphino)ferrocene]palladium (II) DCM adduct (368.8 mg, 0.45 mmol), and potassium acetate (2.65 g, 27.01 mmol) in dry 1,4-dioxane (35 mL) was purged three times with argon and placed under vacuum three times. The mixture was heated to 90° C. and monitored with LC-MS and TLC. After 18 hours, the reaction was cooled to room temperature and then filtered through Celite. The organic solvent was removed under reduced pressure, and the residue was purified by silica gel flash chromatography (0-10% EtOAc/hexane) to yield 83.3A as a colorless oil (1.60 g, 65%). $^1$H NMR (400 MHz, CDCl$_3$) δ ppm 7.89 (1H, td, J=2.7, 1.2 Hz), 7.63 (1H, m), 7.09 (1H, t, J=8.6 Hz), 6.62 (1H, t), 1.35 (12H, s).

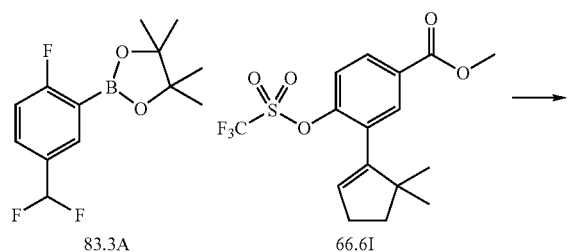

Methyl 5'-(difluoromethyl)-2-(5,5-dimethyl-1-cyclopenten-1-yl)-2'-fluoro-1,1'-biphenyl-4-carboxylate (83.3B). To a stirred solution of 66.6I (1.12 g, 2.96 mmol) in DMF (10 mL) at 23° C. was added potassium carbonate (1.23 g, 8.87 mmol) followed by tetrakis(triphenylphosphine)palladium (0.34 g, 0.29 mmol). The mixture was purged three times with argon and placed under vacuum three times. Before heating, 83.3A (1.60 g, 5.89 mmol) was added via syringe, and then the mixture was heated to 90° C. After 19 hours, the mixture was cooled to room temperature and then diluted with water. After extracting three times with EtOAc, the mixture was concentrated in vacuo and then purified on silica gel (0%-10% EtOAc/hexane) to give 83.3B as a clear oil (0.99, 90%). $^1$H NMR (400 MHz, CDCl$_3$) δ ppm 8.00 (1H, dd, J=8.0, 1.8 Hz), 7.94 (1H, d, J=1.6 Hz), 7.50 (3H, m), 7.16 (1H, t, J=9.0 Hz), 6.63 (1H, t), 5.53 (1H, s), 3.96 (3H, s), 2.25 (2H, td, J=7.0, 2.3 Hz), 1.65 (2H, t, J=7.0 Hz), 0.85 (6H, s).

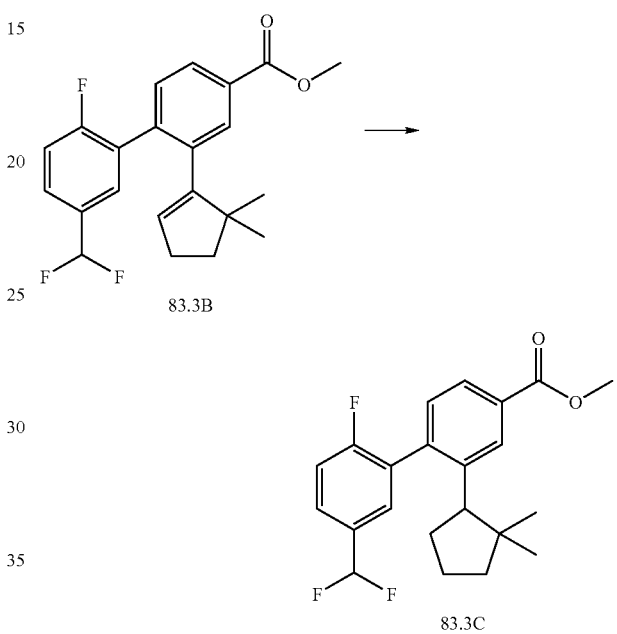

Methyl 5'-(difluoromethyl)-2-(2,2-dimethylcyclopentyl)-2'-fluoro-1,1'-biphenyl-4-carboxylate (83.3C). To a dry flask containing 83.3B (0.86 g, 2.30 mmol) in MeOH (10 mL) and EtOAc (2 mL) was added palladium, 10% wt on activated carbon (0.25 g, 0.23 mmol). After purging, the mixture was stirred under an atmosphere of hydrogen at room temperature. The reaction was monitored with TLC and LC-MS. After 22.5 hours, the reaction was filtered through Celite. After concentration, the residue was identified 83.3C and used without purification (0.86 g, 99%). MS ESI (pos.) m/e: 376.9 (M+H)$^+$.

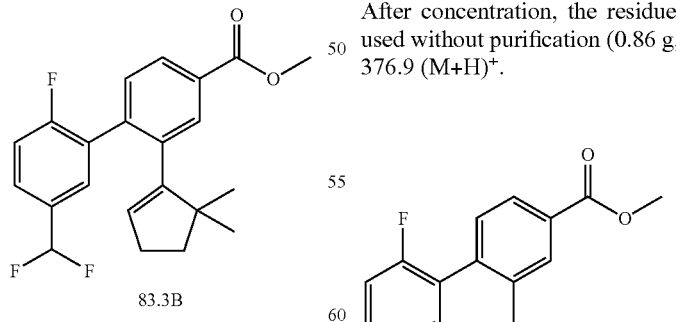

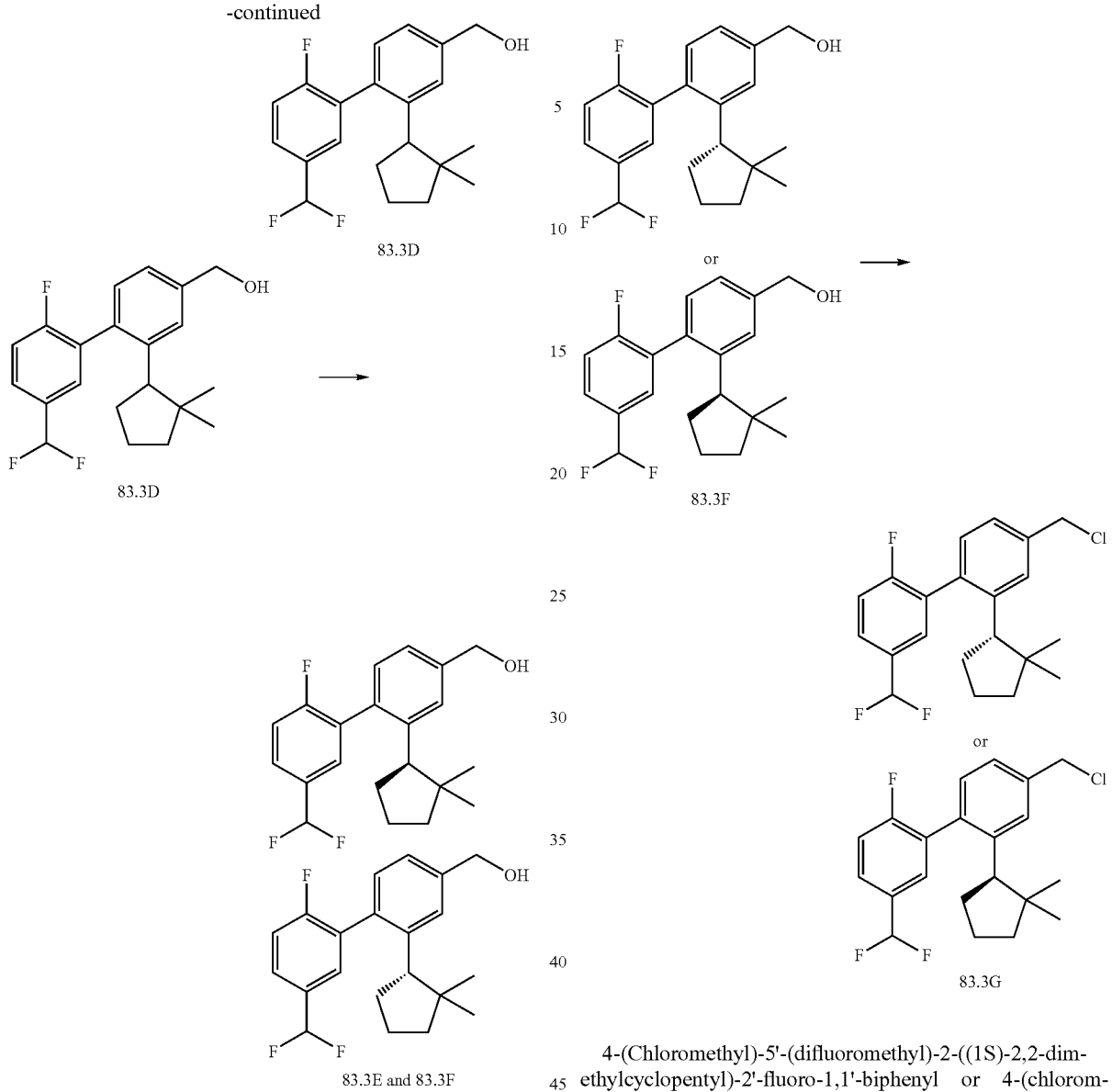

(5'-(Difluoromethyl)-2-(2,2-dimethylcyclopentyl)-2'-fluoro-1,1'-biphenyl-4-yl)methanol (83.3D). To a cooled solution of 83.3C (0.86 g, 2.29 mmol) in dry THF (15 mL) at 0° C. was added LAH, 1.0M in THF (4.6 mL, 4.6 mmol) dropwise. Upon complete addition, the reaction was maintained at 0° C. and monitored by TLC and LCMS. After 45 minutes, 1N NaOH was added to quench the reaction (gas evolution occurred). The resulting solution was extracted three times with EtOAc. After drying over anhydrous magnesium sulfate, filtration, and concentration, the residue was purified by flash chromatography ($SiO_2$ gel 60, eluted with 0%-100% EtOAc in hexanes). Fractions containing the desired product were combined and concentrated to provide 83.3D as a colorless oil (0.62 g, 77%). MS ESI (pos.) m/e: 331.0 $(M-H_2O)^+$. Chiral separation of 83.3D was accomplished on Chiracel-OD (4% EPA in hexane) to provide 83.3E (peak 1) and 83.3F (peak 2). Both enantiomers were used to synthesize example compounds, and both enantiomers gave active compounds. The enantiomer corresponding to peak 2 provided the more active example compound.

4-(Chloromethyl)-5'-(difluoromethyl)-2-((1S)-2,2-dimethylcyclopentyl)-2'-fluoro-1,1'-biphenyl or 4-(chloromethyl)-5'-(difluoromethyl)-2-((1R)-2,2-dimethylcyclopentyl)-2'-fluoro-1,1'-biphenyl (83.3G). To a solution of 83.3F (0.29 g, 0.83 mmol) in dry DCM (10.5 mL) and dry DMF (0.08 mL) was added thionyl chloride (0.12 mL, 1.65 mmol) at 0° C. The resulting solution was warmed to room temperature and monitored with TLC and LCMS. After 45 minutes, the reaction was concentrated then purified by silica gel flash chromatography (0-5% EtOAc/hexane) to yield 83.3G (0.27 g, 90%).

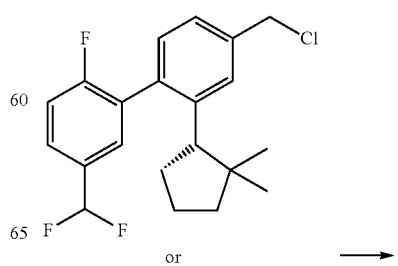

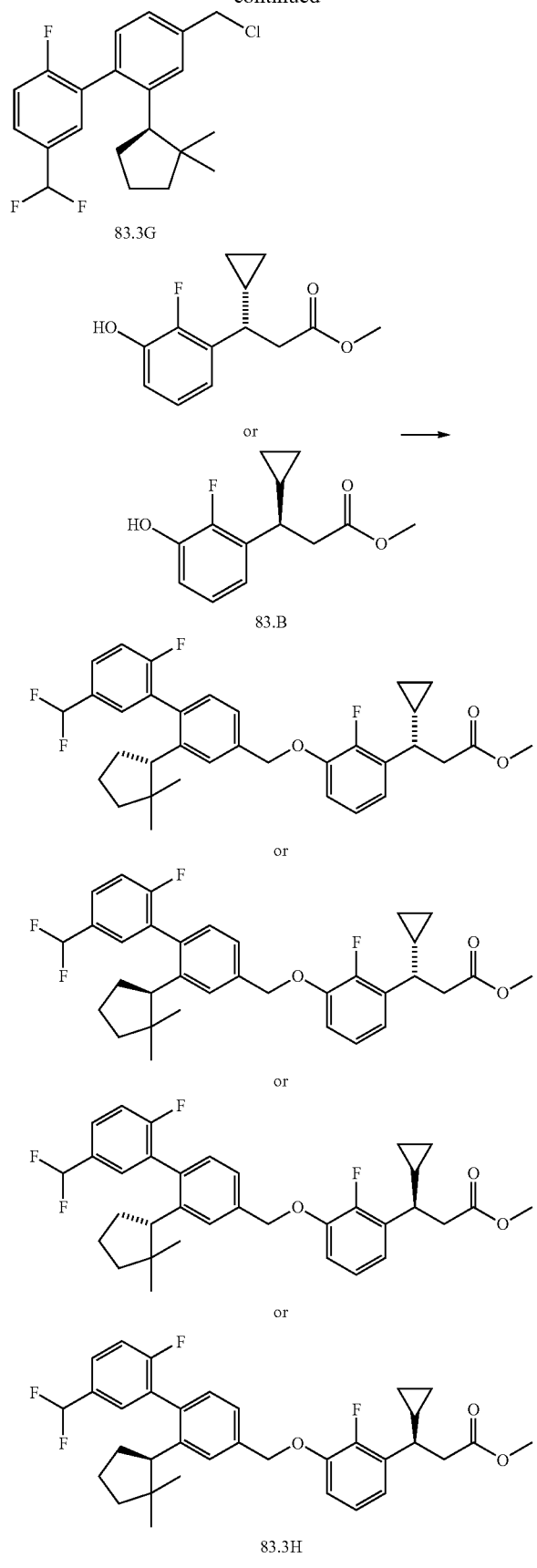

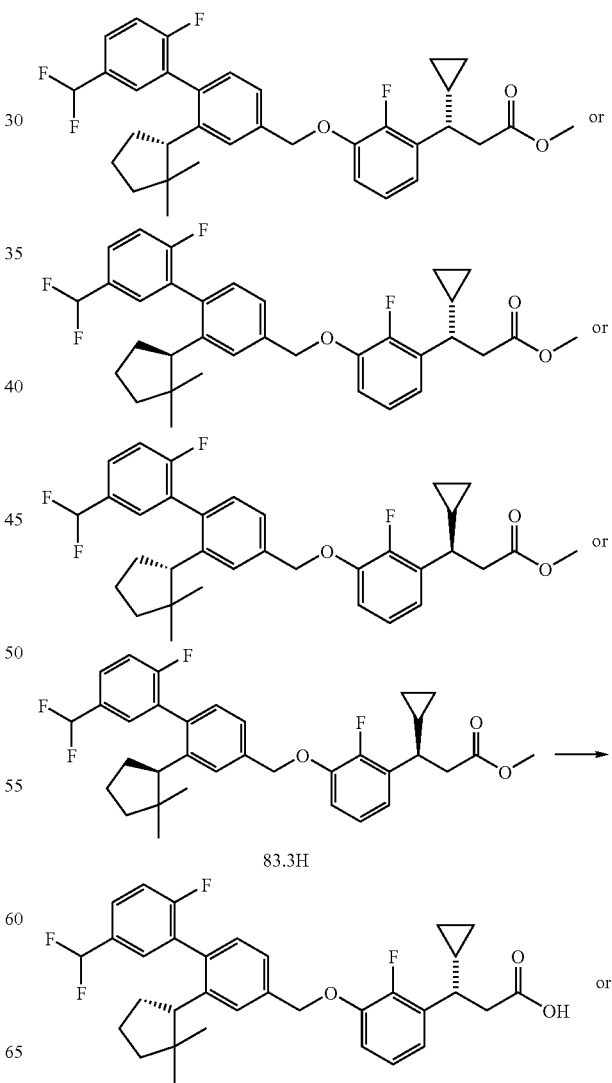

Methyl (3S)-3-cyclopropyl-3-(3-(((5'-(difluoromethyl)-2-((1S)-2,2-dimethylcyclopentyl)-2'-fluoro-1,1'-biphenyl-4-yl)methyl)oxy)-2-fluorophenyl)propanoate or methyl (3S)-3-cyclopropyl-3-(3-(((5'-(difluoromethyl)-2-((1R)-2,2-dimethylcyclopentyl)-2'-fluoro-1,1'-biphenyl-4-yl)methyl)oxy)-2-fluorophenyl)propanoate or methyl (3R)-3-cyclopropyl-3-(3-(((5'-(difluoromethyl)-2-((1S)-2,2-dimethylcyclopentyl)-2'-fluoro-1,1'-biphenyl-4-yl)methyl)oxy)-2-fluorophenyl)propanoate or methyl (3R)-3-cyclopropyl-3-(3-(((5'-(difluoromethyl)-2-((1R)-2,2-dimethylcyclopentyl)-2'-fluoro-1,1'-biphenyl-4-yl)methyl)oxy)-2-fluorophenyl)propanoate (83.3H). To a vial containing 83.B (34.9 mg, 0.146 mmol) in 1.0 mL dry DMF was added cesium carbonate (58.6 mg, 0.180 mmol). The mixture was stirred at room temperature for 10 minutes, and then 83.3G (60.7 mg, 0.165 mmol) was added. After 22 hours, the reaction was diluted with water and then extracted five times with EtOAc. The combined organic layers were then washed with brine and dried over anhydrous magnesium sulfate. The solid was filtered off, and the solvent was concentrated. The residue was purified by silica gel flash chromatography (0-5% EtOAc/hexane) to yield 83.3H (77.7 mg, 93.3%). MS ESI (pos.) m/e: 568.9 (M+H)$^+$.

685

-continued

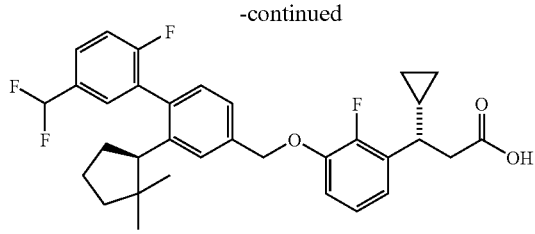

or

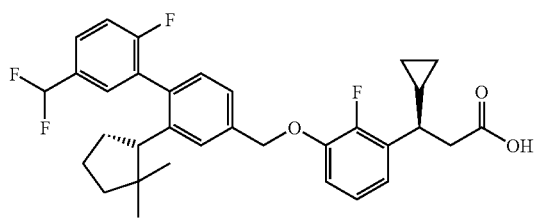

or

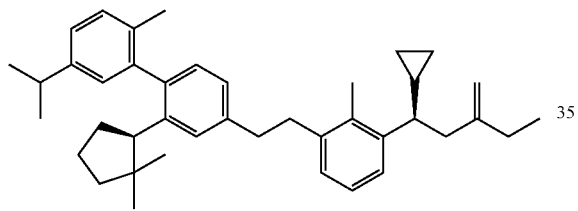

83.3

(3S)-3-Cyclopropyl-3-(3-(((5'-(difluoromethyl)-2-((1S)-2,2-dimethylcyclopentyl)-2'-fluoro-1,1'-biphenyl-4-yl)methyl)oxy)-2-fluorophenyl)propanoic acid or (3S)-3-cyclopropyl-3-(3-(((5'-(difluoromethyl)-2-((1R)-2,2-dimethylcyclopentyl)-2'-fluoro-1,1'-biphenyl-4-yl)methyl)oxy)-2-fluorophenyl)propanoic acid or (3R)-3-cyclopropyl-3-(3-(((5'-(difluoromethyl)-2-((1S)-2,2-dimethylcyclopentyl)-2'-fluoro-1,1'-biphenyl-4-yl)methyl)oxy)-2-fluorophenyl)propanoic acid or (3R)-3-cyclopropyl-3-(3-(((5'-(difluoromethyl)-2-((1R)-2,2-dimethylcyclopentyl)-2'-fluoro-1,1'-biphenyl-4-yl)methyl)oxy)-2-fluorophenyl)propanoic acid (83.3). A pre-mixed solution of 2 M NaOH (0.5 mL, 1.00 mmol), THF (1 mL), and MeOH (1 mL) was added to a vial containing 83.3H (77.7 mg, 0.137 mmol). This solution was stirred at room temperature and monitored with TLC and LC-MS. After 24 hours, the mixture was diluted with water and acidified with 1 M aqueous HCl solution, then extracted five times with EtOAc. The organic phase was dried over anhydrous magnesium sulfate and then filtered and concentrated. The residue was purified with reverse phase HPLC using 30-90% Solvent B to yield 83.3 which was lyophilized (38.2 mg, 50%). $^1$H NMR (400 MHz, CDCl$_3$) δ ppm 7.55 (4H, m), 7.30 (2H, m), 7.04 (1H, m), 6.96 (2H, m), 6.81 (1H, t), 5.18 (2H, m), 2.92 (2H, m), 2.77 (1H, m), 2.24 (2H, m), 1.89 (1H, m), 1.74 (1H, m), 1.56 (1H, m), 1.40 (1H, m), 1.20 (1H, m), 0.72 (4H, m), 0.50 (2H, m), 0.47 (1H, m), 0.34 (1H, dq, J=9.6, 4.8 Hz), 0.25 (1H, m). MS ESI (neg.) m/e: 552.8 (M–H)$^+$.

Example 83.4

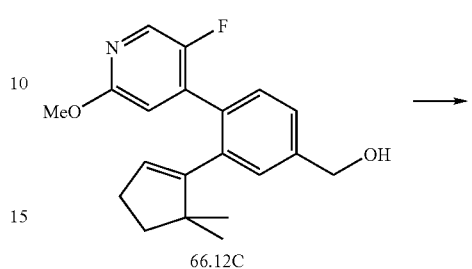

66.12C

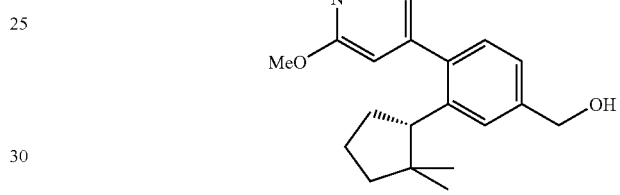

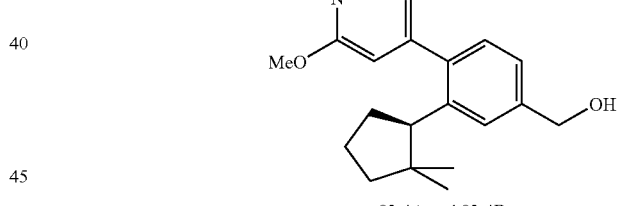

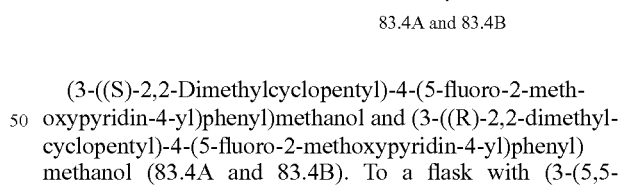

83.4A and 83.4B (3-((S)-2,2-Dimethylcyclopentyl)-4-(5-fluoro-2-methoxypyridin-4-yl)phenyl)methanol and (3-((R)-2,2-dimethylcyclopentyl)-4-(5-fluoro-2-methoxypyridin-4-yl)phenyl)methanol (83.4A and 83.4B). To a flask with (3-(5,5-dimethylcyclopent-1-enyl)-4-(5-fluoro-2-methoxypyridin-4-yl)phenyl)methanol 66.12C (50 mg, 0.153 mmol) was added 10 mg 10% Pd on Carbon, 1.2 mL EtOAc and 1.2 mL MeOH. The flask was purged with hydrogen and then stirred under a hydrogen balloon for 2 hours. LC/MS showed the completion of the reaction. The reaction was filtered through a pad of Celite and rinsed with EtOAc. Two additional reactions were run with the same condition on 70 mg and 81 mg scale. Then the three batches of the reactions (a total of 201 mg of 66.12C) were combined and purified on chiral OD column in four equal portions with 3% IPA/Hexanes to afford 83.4A (54 mg, 98% ee, the later-eluting enantiomer) and 83.4B (78 mg, 100% ee). The mixed fraction was repurified on chiral column to afford an additional 28 mg of 83.4A (>99% ee).

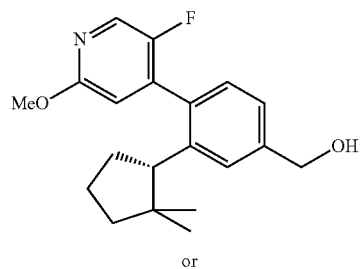
or
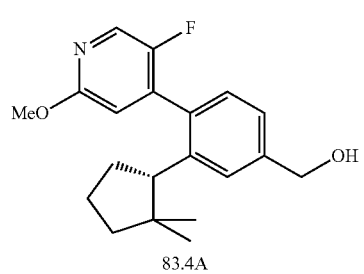
83.4A
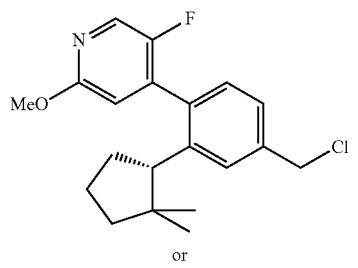
or
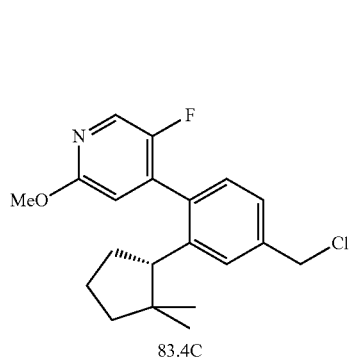
83.4C
4-(4-(Chloromethyl)-2-((S)-2,2-dimethylcyclopentyl)phenyl)-5-fluoro-2-methoxypyridine or 4-(4-(chloromethyl)-2-((R)-2,2-dimethylcyclopentyl)phenyl)-5-fluoro-2-methoxypyridine (83.4C). The same procedure used to prepare 66.12D from 66.12C was applied to make 83.4C from 83.4A (28 mg, >99% ee). Compound 83.4C was obtained as an oil (27 mg, 91%).
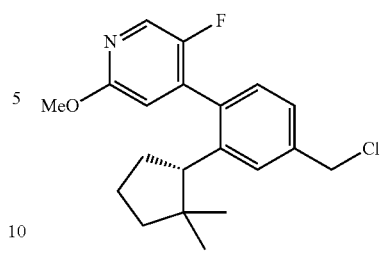
or
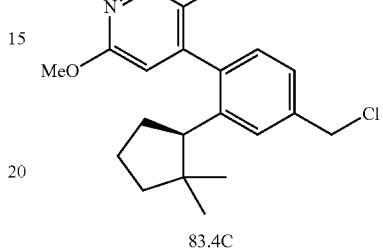
83.4C
+
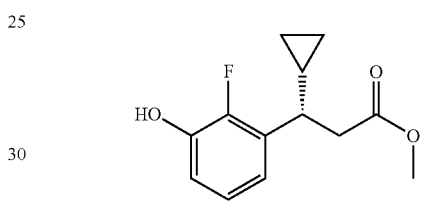
or
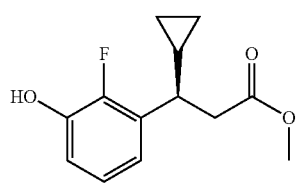
83.B
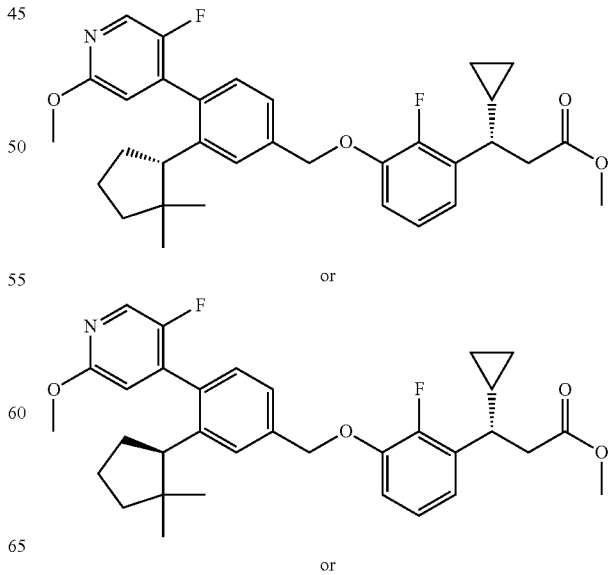
or

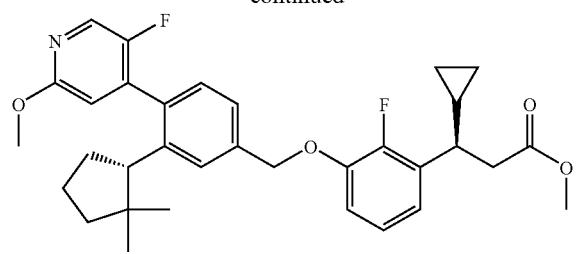

or

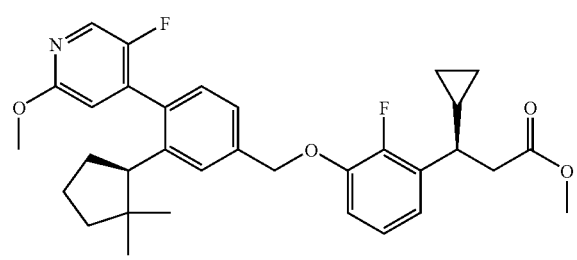

83.4D

Compound 83.4D.

To 83.4C (27 mg, 78 μmol) was added 83.B (25 mg, 105 μmol) and then cesium carbonate (51 mg, 155 μmol). DMF 1.2 mL was added and the reaction was stirred overnight. Water was added and the reaction was extracted with EtOAc. Silica gel chromatography afforded 83.4D 42 mg (98%).

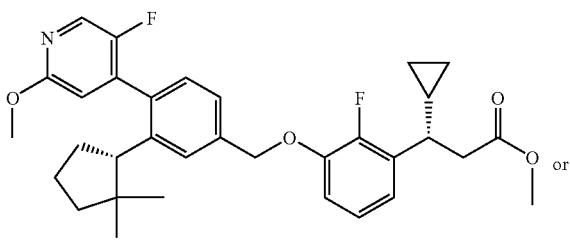

or

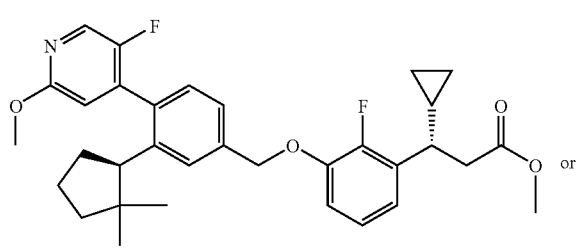

or

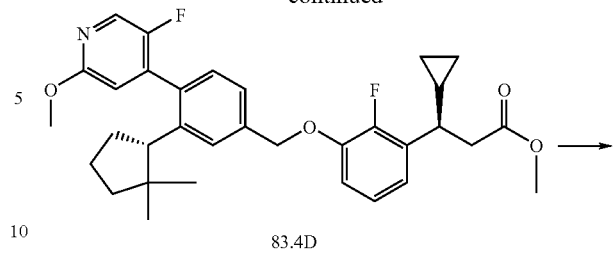

83.4D

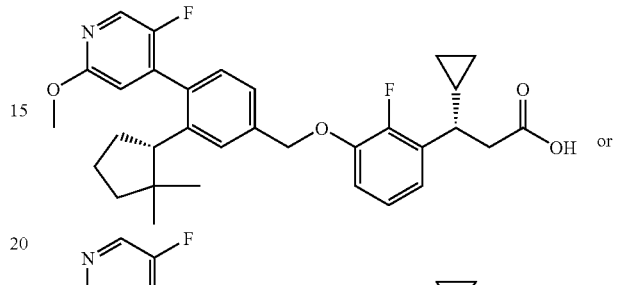

or

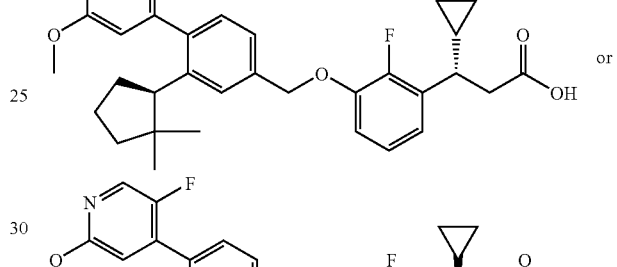

or

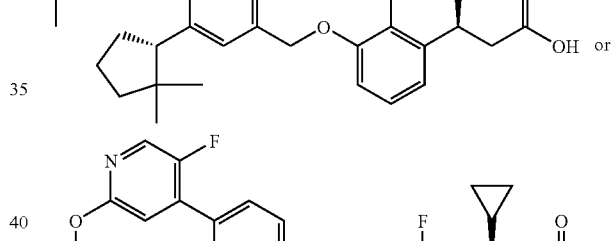

or 83.4

(S)-3-Cyclopropyl-3-{3-[3-((S)-2,2-dimethyl-cyclopentyl)-4-(5-fluoro-2-methoxy-pyridin-4-yl)-benzyloxy]-2-fluoro-phenyl}-propionic acid or (S)-3-cyclopropyl-3-{3-[3-((R)-2,2-dimethyl-cyclopentyl)-4-(5-fluoro-2-methoxy-pyridin-4-yl)-benzyloxy]-2-fluoro-phenyl}-propionic acid or (R)-3-cyclopropyl-3-{3-[3-((S)-2,2-dimethyl-cyclopentyl)-4-(5-fluoro-2-methoxy-pyridin-4-yl)-benzyloxy]-2-fluoro-phenyl}-propionic acid or (R)-3-cyclopropyl-3-{3-[3-((R)-2,2-dimethyl-cyclopentyl)-4-(5-fluoro-2-methoxy-pyridin-4-yl)-benzyloxy]-2-fluoro-phenyl}-propionic acid (83.4). Compound 83.4 was prepared from 42 mg of 83.4D according to the method of preparing 66.12 from 66.12E. Silica gel chromatography afforded 39 mg (95%) of 83.4. MS ESI (neg.) m/e: 534.2 (M−H)+.

(S)-3-Cyclopropyl-3-{3-[3-((R)-2,2-dimethyl-cyclopentyl)-4-(5-fluoro-2-methoxy-pyridin-4-yl)-benzyloxy]-2-fluoro-phenyl}-propionic acid or (S)-3-cyclopropyl-3-{3-[3-((S)-2,2-dimethyl-cyclopentyl)-4-(5-fluoro-2-methoxy-pyridin-4-yl)-benzyloxy]-2-fluoro-phenyl}-propionic acid or (R)-3-cyclopropyl-3-{3-[3-((R)-2,2-dimethyl-cyclopentyl)-4-(5-fluoro-2-methoxy-pyridin-4-yl)-benzyloxy]-2-fluoro-phenyl}-propionic acid or (R)-3-cyclopropyl-3-{3-[3-((S)-2,2-dimethyl-cyclopentyl)-4-(5-fluoro-2-methoxy-pyridin-4-yl)-benzyloxy]-2-fluoro-phenyl}-propionic acid (83.5). Compound 83.5 was prepared using the same method used to prepare compound 83.4 starting from 83.4B (peak one). MS ESI (neg.) m/e: 534.2 (M−H)+.

(3S)-3-Cyclopropyl-3-(2-fluoro-3-(((2'-fluoro-5'-(methyloxy)-2-((1R)-1,2,2-trimethylpropyl)-1,1'-biphenyl-4-yl)methyl)oxy)phenyl)propanoic acid or (3S)-3-cyclopropyl-3-(2-fluoro-3-(((2'-fluoro-5'-(methyloxy)-2-((1S)-1,2,2-trimethylpropyl)-1,1'-biphenyl-4-yl)methyl)oxy)phenyl)propanoic acid or (3R)-3-cyclopropyl-3-(2-fluoro-3-(((2'-fluoro-5'-(methyloxy)-2-((R)-1,2,2-trimethylpropyl)-1,1'-biphenyl-4-yl)methyl)oxy)phenyl)propanoic acid or (3R)-3-cyclopropyl-3-(2-fluoro-3-(((2'-fluoro-5'-(methyloxy)-2-((1S)-1,2,2-trimethylpropyl)-1,1'-biphenyl-4-yl)methyl)oxy)phenyl)propanoic acid (83.6). The alkylation and hydrolysis were conducted in an analogous manner to Example 66.6 (using 66.18M or 66.18N derived from peak two from the chiral separation of 66.18I from the OD-column, described herein) to yield 83.6A or 83.6B (0.0253 g, 63% yield over the two steps). MS ESI (neg.) m/e: 521.2 (M−H)+.

(3S)-3-Cyclopropyl-3-(3-(((2-((1R)-2,2-dimethylcyclohexyl)-2'-fluoro-5'-(methyloxy)-1,1'-biphenyl-4-yl)methyl)oxy)-2-fluorophenyl)propanoic acid or (3S)-3-cyclopropyl-3-(3-(((2-((1S)-2,2-dimethylcyclohexyl)-2'-fluoro-5'-(methyloxy)-1,1'-biphenyl-4-yl)methyl)oxy)-2-fluorophenyl)propanoic acid or (3R)-3-cyclopropyl-3-(3-(((2-((1R)-2,2-dimethylcyclohexyl)-2'-fluoro-5'-(methyloxy)-1,1'-biphenyl-4-yl)methyl)oxy)-2-fluorophenyl)propanoic acid or (3R)-3-cyclopropyl-3-(3-(((2-((1S)-2,2-dimethylcyclohexyl)-2'-fluoro-5'-(methyloxy)-1,1'-biphenyl-4-yl)methyl)oxy)-2-fluorophenyl)propanoic acid (83.7). Example 83.7 was prepared using an alkylation and hydrolysis procedure similar to that used in Example 66.6 (using 83.B and 66.21J or 66.21K derived from peak two from the chiral separation of 66.21G from the OD-column, described herein) to yield 83.7A or 83.7B (0.0358 g, 78% yield over two steps). MS ESI (neg.) m/e: 547.3 (M−H)+.

(3S)-3-Cyclopropyl-3-(3-(((2-((1R)-2,2-dimethyl-1-(methyloxy)propyl)-2'-fluoro-5'-(methyloxy)-1,1'-biphenyl-4-yl)methyl)oxy)-2-fluorophenyl)propanoic acid or (3S)-3-cyclopropyl-3-(3-(((2-((1S)-2,2-dimethyl-1-(methyloxy)propyl)-2'-fluoro-5'-(methyloxy)-1,1'-biphenyl-4-yl)methyl)oxy)-2-fluorophenyl)propanoic acid or (3R)-3-cyclopropyl-3-(3-(((2-((1R)-2,2-dimethyl-1-(methyloxy)propyl)-2'-fluoro-5'-(methyloxy)-1,1'-biphenyl-4-yl)methyl)oxy)-2-fluorophenyl)propanoic acid or (3R)-3-cyclopropyl-3-(3-(((2-((1S)-2,2-dimethyl-1-(methyloxy)propyl)-2'-fluoro-5'-(methyloxy)-1,1'-biphenyl-4-yl)methyl)oxy)-2-fluorophenyl)propanoic acid (83.8). The alkylation and hydrolysis were conducted in an analogous manner to Example 66.6 (using 83.B and 66.13H or 66.13I derived from peak two from the chiral separation of 66.13G from the OD-column, described herein) to yield 83.8A or 83.8B (0.0349 g, 62% yield over two steps). MS ESI (neg.) m/e: 537.3 (M−H)+.

(3S)-3-Cyclopropyl-3-(2-fluoro-3-(((2'-fluoro-2-((1R)-1-fluoro-2,2-dimethylpropyl)-5'-(methyloxy)-1,1'-biphenyl-4-yl)methyl)oxy)phenyl)propanoic acid or (3S)-3-cyclopropyl-3-(2-fluoro-3-(((2'-fluoro-2-((1S)-1-fluoro-2,2-dimethylpropyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((1R)-1-fluoro-2,2-dimethylpropyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((1S)-1-fluoro-2,2-dimethylpropyl)-5'-(methyloxy)-1,1'-biphenyl-4-yl)methyl)oxy)phenyl)propanoic acid (83.9). The alkylation and hydrolysis were conducted in an analogous manner to Example 66.6 (using 83.B and 66.30G or 66.30H derived from peak two from the chiral separation of 66.30D from the OD-column, described herein) to yield 83.8 (0.0256 g, 88% yield). MS ESI (neg.) m/e: 525.3 (M−H)+.

Example 83.10

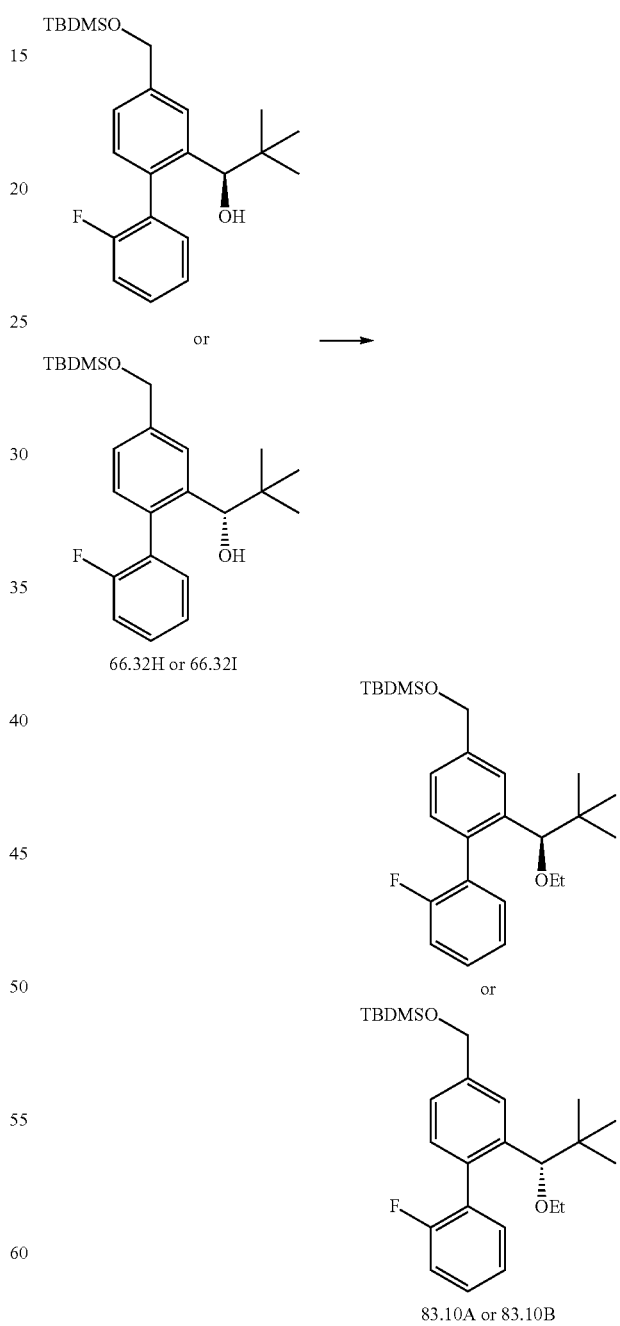

66.32H or 66.32I 83.10A or 83.10B (1,1-Dimethylethyl)(((2-((1R)-1-(ethyloxy)-2,2-dimethylpropyl)-2'-fluoro-1,1'-biphenyl-4-yl)methyl)oxy)dimethylsilane or (1,1-dimethylethyl)(((2-((1S)-1-(ethyloxy)-2,2- dimethylpropyl)-2'-fluoro-1,1'-biphenyl-4-yl)methyl)oxy) dimethylsilane (83.10 A or 83.10B). To a stirred solution of 66.32H or 66.32I (0.05 g, 0.1 mmol) in DMF (1 mL) at 23° C. was added iodoethane (0.02 g, 0.1 mmol), followed by sodium hydride (0.004 g, 0.1 mmol). The reaction was then stirred at 60° C. for 17 hours. Next, the reaction was diluted with water and extracted three times with EtOAc. After drying over anhydrous magnesium sulfate and filtering, the organic solvent was removed under reduced pressure and the product was then purified on silica gel (0-5% EtOAc in hexanes) to yield 83.10A or 83.10B as a colorless oil (0.042 g, 79% yield).

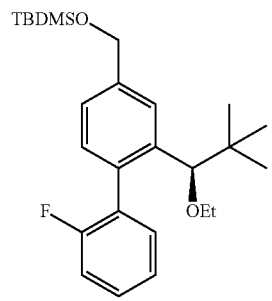

83.10A or 83.10B

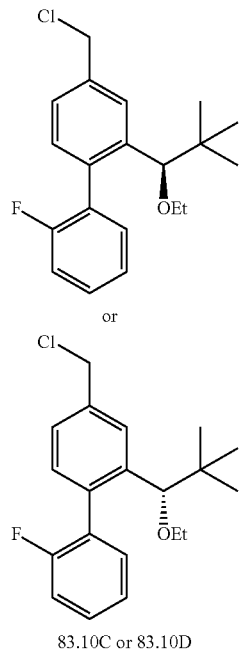

83.10C or 83.10D 4-(Chloromethyl)-2-((1R)-1-(ethyloxy)-2,2-dimethylpropyl)-2'-fluoro-1,1'-biphenyl or 4-(chloromethyl)-2-((1S)-1-(ethyloxy)-2,2-dimethylpropyl)-2'-fluoro-1,1'-biphenyl (83.10C or 83.10D). To a stirred solution of 83.10A or 83.10B (0.042 g, 0.098 mmol) in DCM (0.98 mL, 0.098 mmol) and DMF (0.0076 mL) at 0° C. was added thionyl chloride (0.014 mL, 0.20 mmol). The reaction was stirred at room temperature for one hour. Next, the reaction mixture was concentrated in vacuo. The product was then purified on silica gel (0-5% EtOAc in hexanes) to yield 83.10C or 83.10D as a colorless oil (0.029 g, 89% yield).

(3S)-3-Cyclopropyl-3-(3-(((2-((1R)-1-(ethyloxy)-2,2-dimethylpropyl)-2'-fluoro-1,1'-biphenyl-4-yl)methyl)oxy)-2-fluorophenyl)propanoic acid or (3S)-3-cyclopropyl-3-(3-(((2-((1S)-1-(ethyloxy)-2,2-dimethylpropyl)-2'-fluoro-1,1'-biphenyl-4-yl)methyl)oxy)-2-fluorophenyl)propanoic acid or (3R)-3-cyclopropyl-3-(3-(((2-((1R)-1-(ethyloxy)-2,2-dimethylpropyl)-2'-fluoro-1,1'-biphenyl-4-yl)methyl)oxy)-2-fluorophenyl)propanoic acid or (3R)-3-cyclopropyl-3-(3-(((2-((1S)-1-(ethyloxy)-2,2-dimethylpropyl)-2'-fluoro-1,1'-biphenyl-4-yl)methyl)oxy)-2-fluorophenyl)propanoic acid (83.10). The alkylation and hydrolysis were conducted in an analogous manner to Example 66.6 (using 83.B and 83.10C or 83.10D derived from peak two from the chiral separation of 66.32E from the OD-column, described herein) to yield 83.10 (0.0345 g, 79% yield over two steps). MS ESI (neg.) m/e: 521.2 (M−H)⁺.

Example 83.11

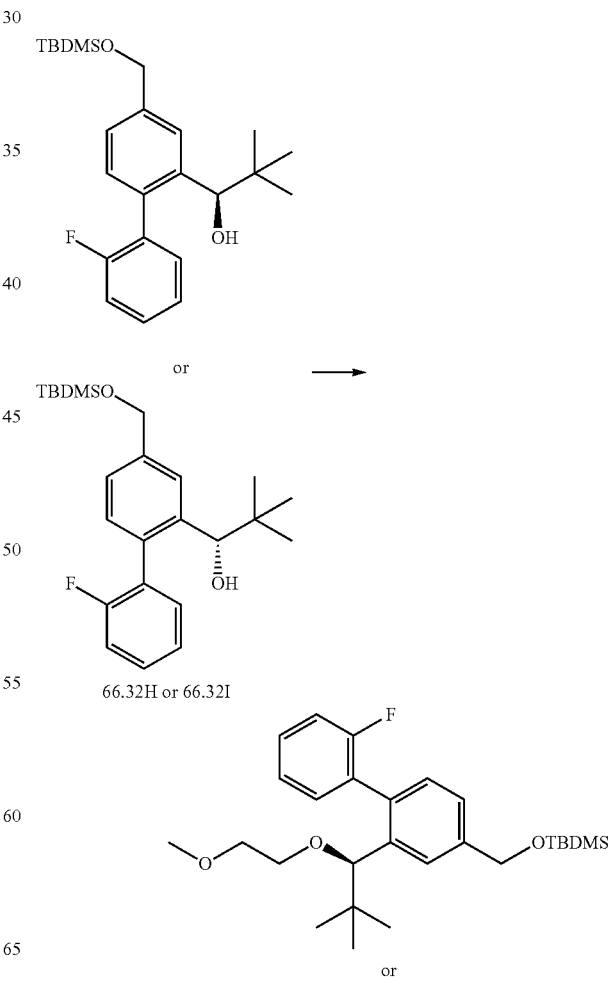

66.32H or 66.32I

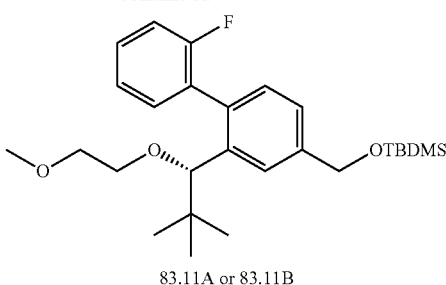

83.11A or 83.11B

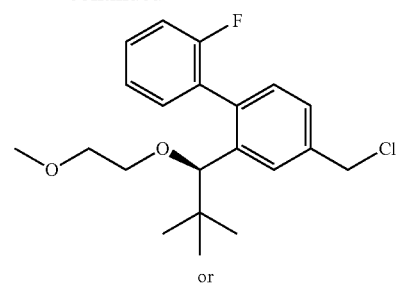

or

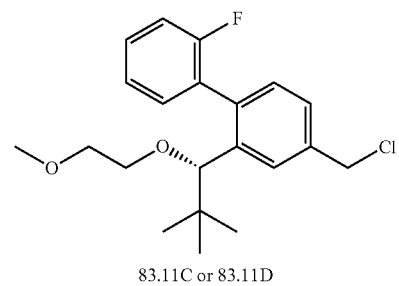

83.11C or 83.11D (1,1-Dimethylethyl)(((2-((1R)-2,2-dimethyl-1-((2-(methyloxy)ethyl)oxy)propyl)-2'-fluoro-1,1'-biphenyl-4-yl)methyl)oxy)dimethylsilane or (1,1-dimethylethyl)(((2-((1S)-2,2-dimethyl-1-((2-(methyloxy)ethyl)oxy)propyl)-2'-fluoro-1,1'-biphenyl-4-yl)methyl)oxy)dimethylsilane (83.11A or 83.11B). To a stirred solution of 66.32H or 66.32I (0.05 g, 0.1 mmol) in DMF (1 mL) at 23° C. was added 1-bromo-2-methoxyethane (0.02 g, 0.1 mmol) (commercially available from Aldrich) followed by sodium hydride (0.004 g, 0.1 mmol). The reaction was stirred at 60° C. for 17 hours. Next, the reaction was diluted with water and extracted three times with EtOAc. After drying over anhydrous magnesium sulfate and filtering, the organic solvent was removed under reduced pressure and the product was then purified on silica gel (0-5% EtOAc in hexanes) to yield 83.11A or 83.11B as a colorless oil (0.046 g, 92%).

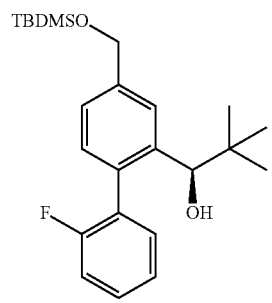

or →

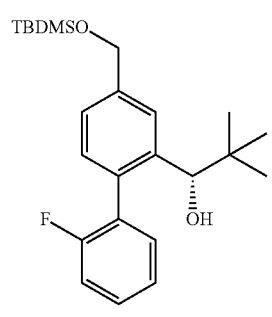

83.11A or 83.11B 4-(Chloromethyl)-2-((1R)-2,2-dimethyl-1-((2-(methyloxy)ethyl)oxy)propyl)-2'-fluoro-1,1'-biphenyl or 4-(chloromethyl)-2-((1S)-2,2-dimethyl-1-((2-(methyloxy)ethyl)oxy)propyl)-2'-fluoro-1,1'-biphenyl (83.11C or 83.11D). To a stirred solution of 83.11A or 83.11B (0.046 g, 0.100 mmol) in DCM (1.00 mL) and DMF (0.0077 mL) at 0° C. was added thionyl chloride (0.015 mL, 0.20 mmol). The reaction was stirred at room temperature for one hour. Next, the reaction was concentrated in vacuo. The product was then purified on silica gel (0-5% EtOAc in hexanes) to yield 83.11C or 83.11D as a colorless oil (0.033 g, 91% yield)

(3S)-3-Cyclopropyl-3-(3-(((2-((1R)-2,2-dimethyl-1-((2-(methyloxy)ethyl)oxy)propyl)-2'-fluoro-1,1'-biphenyl-4-yl)methyl)oxy)-2-fluorophenyl)propanoic acid or (3S)-3-cyclopropyl-3-(3-(((2-((1S)-2,2-dimethyl-1-((2-(methyloxy)ethyl)oxy)propyl)-2'-fluoro-1,1'-biphenyl-4-yl)methyl)oxy)-2-fluorophenyl)propanoic acid or (3R)-3-cyclopropyl-3-(3-(((2-((1R)-2,2-dimethyl-1-((2-(methyloxy)ethyl)oxy)propyl)-2'-fluoro-1,1'-biphenyl-4-yl)methyl)oxy)-2-fluorophenyl)propanoic acid or (3R)-3-cyclopropyl-3-(3-(((2-((1S)-2,2-dimethyl-1-((2-(methyloxy)ethyl)oxy)propyl)-2'-fluoro-1,1'-biphenyl-4-yl)methyl)oxy)-2-fluorophenyl)propanoic acid (83.11). The alkylation and hydrolysis were conducted in an analogous manner to Example 66.6 (using 83.B and 83.11C or 83.11D derived from peak two from the chiral separation of 66.32E from the OD-column, described herein) to yield 83.11E or 83.11F (0.0287 g, 54% yield over two steps). MS ESI (neg.) m/e: 551.2 (M−H)$^+$.

Example 83.12

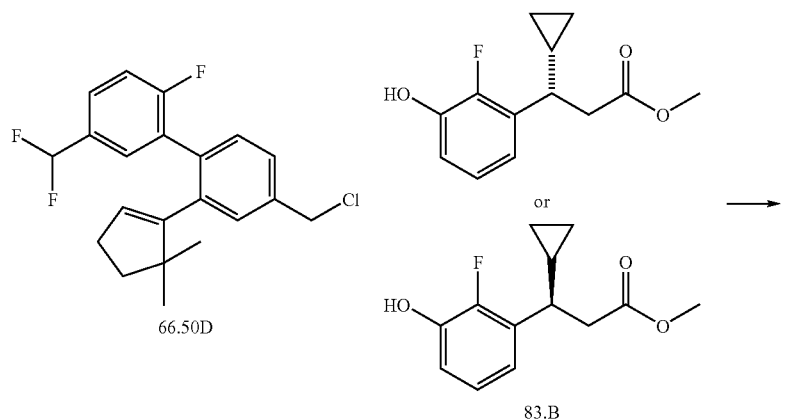

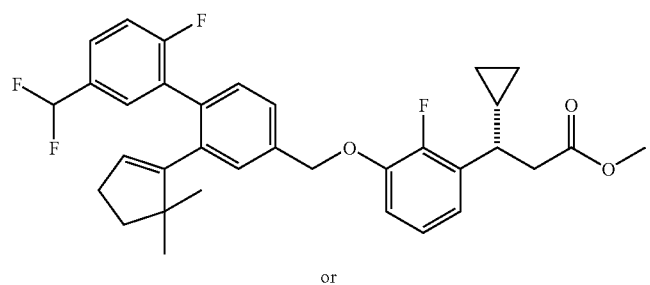

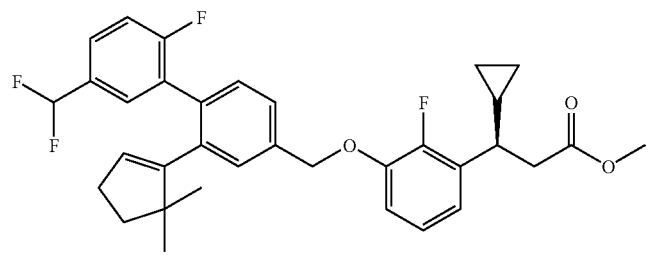

Methyl (3S)-3-cyclopropyl-3-(3-(((5'-(difluoromethyl)-2-(5,5-dimethyl-1-cyclopenten-1-yl)-2'-fluoro-1,1'-biphenyl-4-yl)methyl)oxy)-2-fluorophenyl)propanoate or methyl (3R)-3-cyclopropyl-3-(3-(((5'-(difluoromethyl)-2-(5,5-dimethyl-1-cyclopenten-1-yl)-2'-fluoro-1,1'-biphenyl-4-yl)methyl)oxy)-2-fluorophenyl)propanoate (83.12A). To a vial containing 83.B (0.0322 g, 0.135 mmol) in 1.00 mL dry DMF was added cesium carbonate (0.0568 g, 0.174 mmol). The mixture was stirred at room temperature for 10 minutes, and then 66.50D (0.0551 g, 0.151 mmol) was added. After 22 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-10% EtOAc/hexane) to afford 83.12A (62.5 mg, 82% yield). MS ESI (pos.) m/e: 583.9 (M+H$_2$O)$^+$.

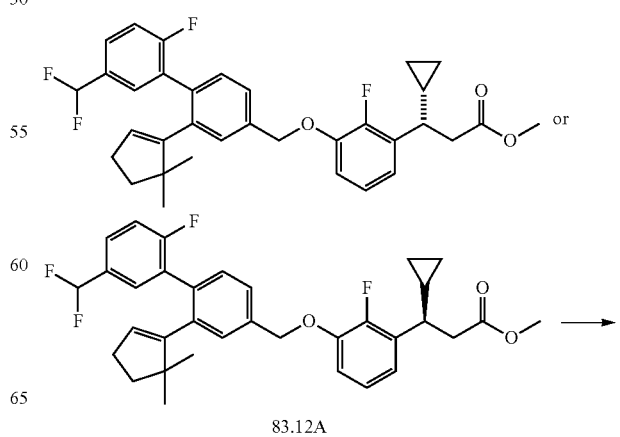

-continued

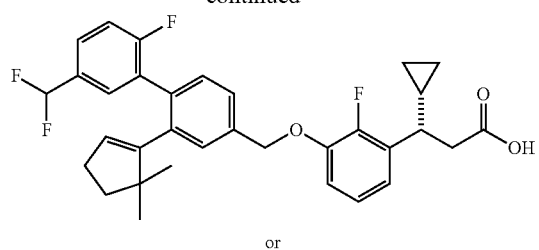

or

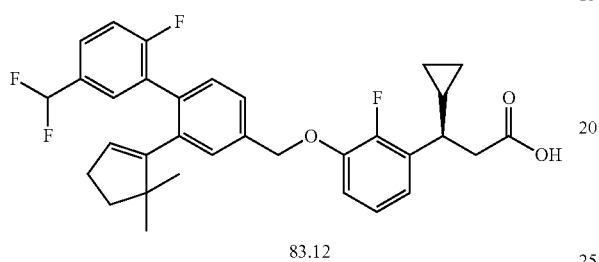

83.12

(3S)-3-Cyclopropyl-3-(3-(((5'-(difluoromethyl)-2-(5,5-dimethyl-1-cyclopenten-1-yl)-2'-fluoro-1,1'-biphenyl-4-yl)methyl)oxy)-2-fluorophenyl)propanoic acid or (3R)-3-cyclopropyl-3-(3-(((5'-(difluoromethyl)-2-(5,5-dimethyl-1-cyclopenten-1-yl)-2'-fluoro-1,1'-biphenyl-4-yl)methyl)oxy)-2-fluorophenyl)propanoic acid (83.12). A pre-mixed solution of 2M NaOH (0.5 mL, 1.00 mmol), THF (1 mL), and MeOH (1 mL) was added to a vial containing 83.12A (0.0625 g, 0.110 mmol). This solution was stirred at room temperature and monitored with TLC and LC-MS. After 24 hours, the mixture was diluted with water and acidified with 1 M aqueous HCl solution, and then extracted five times with EtOAc. The organic phase was dried over anhydrous magnesium sulfate, filtered, and concentrated. The residue was purified by silica gel flash chromatography (0-40% EtOAc/hexane) to afford 83.12 (45.2 mg, 74% yield). $^1$H NMR (400 MHz, CDCl$_3$) δ ppm 7.44 (3H, td, J=6.8, 1.2 Hz), 7.36 (2H, m), 7.14 (1H, t, J=9.0 Hz), 7.05 (1H, m), 6.96 (2H, m), 6.76 (1H, t), 5.50 (1H, s), 5.17 (2H, s), 2.86 (2H, t, J=7.0 Hz), 1.22 (1H, m), 0.84 (6H, s), 0.65 (1H, m), 0.46 (1H, m), 0.33 (1H, dq, J=9.6, 4.8 Hz), 0.20 (1H, dq, J=9.6, 4.9 Hz). MS ESI (neg.) m/e: 550.9 (M−H)$^+$.

Example 83.13

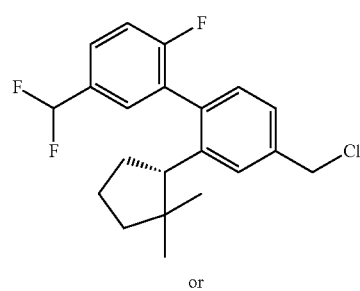

or +

-continued

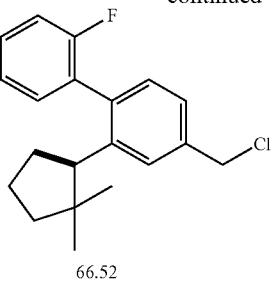

66.52

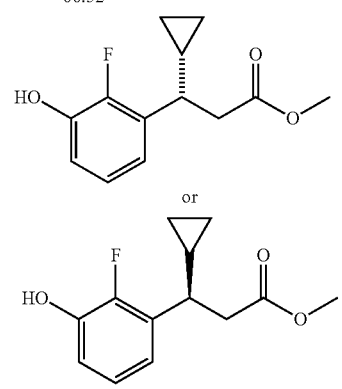

83.B S

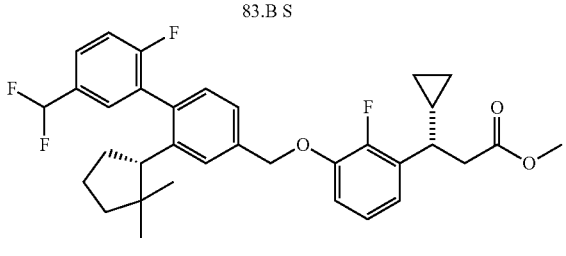

or

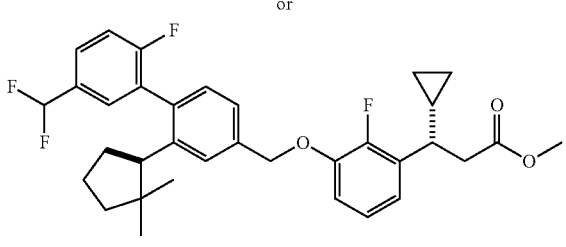

or

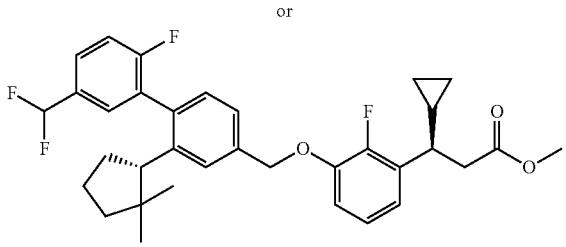

or 83.13 A

Methyl (3S)-3-cyclopropyl-3-(3-(((5'-(difluoromethyl)-2-((1R)-2,2-dimethylcyclopentyl)-2'-fluoro-1,1'-biphenyl-4-yl)methyl)oxy)-2-fluorophenyl)propanoate or methyl (3S)-3-cyclopropyl-3-(3-(((5'-(difluoromethyl)-2-((1S)-2,2-dimethylcyclopentyl)-2'-fluoro-1,1'-biphenyl-4-yl)methyl)oxy)-2-fluorophenyl)propanoate or methyl (3R)-3-cyclopropyl-3-(3-(((5'-(difluoromethyl)-2-((1R)-2,2-dimethylcyclopentyl)-2'-fluoro-1,1'-biphenyl-4-yl)methyl)oxy)-2-fluorophenyl)propanoate or methyl (3R)-3-cyclopropyl-3-(3-(((5'-(difluoromethyl)-2-((1S)-2,2-dimethylcyclopentyl)-2'-fluoro-1,1'-biphenyl-4-yl)methyl)oxy)-2-fluorophenyl)propanoate (83.13 A). To a vial containing 83.B (0.0371 g, 0.156 mmol) in 1.00 mL dry DMF was added cesium carbonate (0.0622 g, 0.191 mmol). The mixture was stirred at room temperature for 10 minutes, and then 66.52A (0.0623 g, 0.170 mmol) was added. After 22 hours, the reaction was diluted with water and then extracted five times with EtOAc. The combined organic layers were then washed one time with brine and dried over anhydrous magnesium sulfate. The solid was filtered off, and the solvent was concentrated. The residue was purified by silica gel flash chromatography (0-10% EtOAc/hexane) to afford 83.13 A (78.5 mg, 89% yield). MS ESI (pos.) m/e: 586.0 (M+H$_2$O)$^+$.

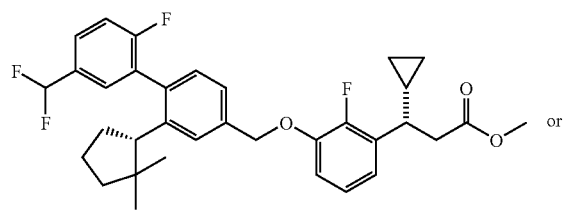

or

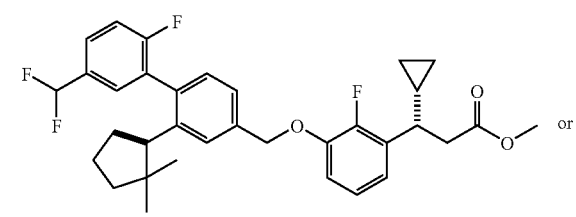

or

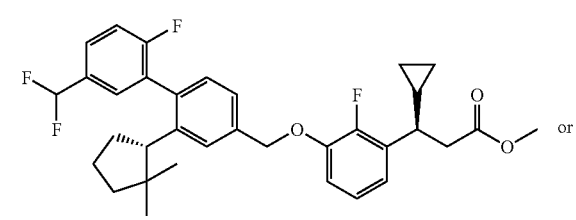

or

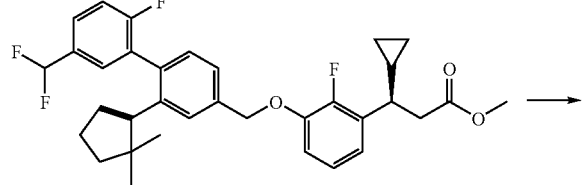

83.13 A

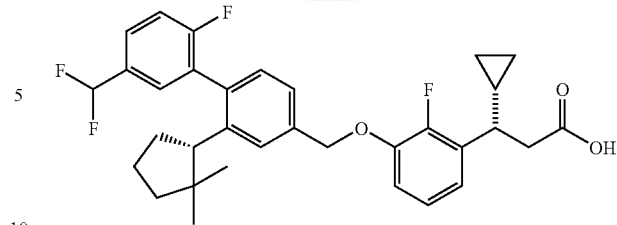

or

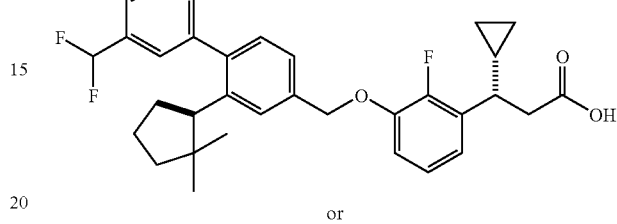

or

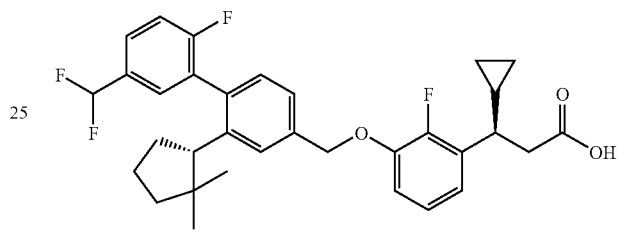

or

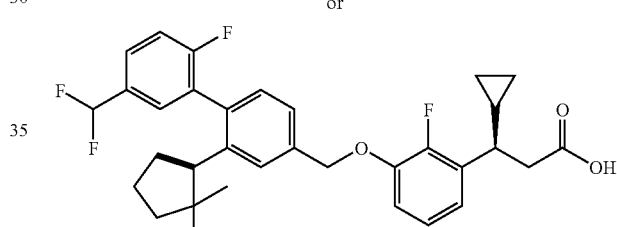

83.13

(3S)-3-Cyclopropyl-3-(3-(((5'-(difluoromethyl)-2-((1R)-2,2-dimethylcyclopentyl)-2'-fluoro-1,1'-biphenyl-4-yl)methyl)oxy)-2-fluorophenyl)propanoic acid or (3S)-3-cyclopropyl-3-(3-(((5'-(difluoromethyl)-2-((1S)-2,2-dimethylcyclopentyl)-2'-fluoro-1,1'-biphenyl-4-yl)methyl)oxy)-2-fluorophenyl)propanoic acid or (3R)-3-cyclopropyl-3-(3-(((5'-(difluoromethyl)-2-((1R)-2,2-dimethylcyclopentyl)-2'-fluoro-1,1'-biphenyl-4-yl)methyl)oxy)-2-fluorophenyl)propanoic acid or (3R)-3-cyclopropyl-3-(3-(((5'-(difluoromethyl)-2-((1S)-2,2-dimethylcyclopentyl)-2'-fluoro-1,1'-biphenyl-4-yl)methyl)oxy)-2-fluorophenyl)propanoic acid (83.13). A pre-mixed solution of 2M NaOH (0.5 mL, 1.00 mmol), THF (1 mL), and MeOH (1 mL) was added to a vial containing 83.13A (0.0785 g, 0.138 mmol). This solution was stirred at room temperature and monitored with TLC and LC-MS. After 24 hours, the mixture was diluted with water and acidified with 1M aqueous HCl solution and then extracted five times with EtOAc. The organic phase was dried over anhydrous magnesium sulfate, filtered and concentrated. The residue was purified with reverse phase HPLC using 30-90% Solvent B (0.1% TFA in acetonitrile) over 45 minutes to afford 83.13 that was lyophilized (39.6 mg, 52% yield). MS ESI (neg.) m/e: 553.0 (M−H)$^+$.

(3S)-3-Cyclopropyl-3-(3-(((2-(5,5-dimethyl-1-cyclopenten-1-yl)-2'-fluoro-5'-(methyloxy)-1,1'-biphenyl-4-yl)

methyl)oxy)-2-fluorophenyl)propanoic acid or (3R)-3-cyclopropyl-3-(3-(((2-(5,5-dimethyl-1-cyclopenten-1-yl)-2'-fluoro-5'-(methyloxy)-1,1'-biphenyl-4-yl)methyl)oxy)-2-fluorophenyl)propanoic acid (83.14). MS ESI (pos.) m/e: 550.3 (M+H$_2$O)$^+$, 555.3 (M+Na)$^+$.

(3S)-3-Cyclopropyl-3-(3-(((2-(2,2-dimethylpropyl)-2'-fluoro-5'-(methyloxy)-1,1'-biphenyl-4-yl)methyl)oxy)-2-fluorophenyl)propanoic acid or (3R)-3-cyclopropyl-3-(3-(((2-(2,2-dimethylpropyl)-2'-fluoro-5'-(methyloxy)-1,1'-biphenyl-4-yl)methyl)oxy)-2-fluorophenyl)propanoic acid (83.15). MS ESI (pos.) m/e: 526.3 (M+H$_2$O)$^+$, 531.2 (M+Na)$^+$.

(3S)-3-Cyclopropyl-3-(3-(((2-(5,5-dimethyl-1-cyclopenten-1-yl)-2',5-difluoro-5'-(methyloxy)-1,1'-biphenyl-4-yl)methyl)oxy)-2-fluorophenyl)propanoic acid or (3R)-3-cyclopropyl-3-(3-(((2-(5,5-dimethyl-1-cyclopenten-1-yl)-2',5-difluoro-5'-(methyloxy)-1,1'-biphenyl-4-yl)methyl)oxy)-2-fluorophenyl)propanoic acid (83.16). MS ESI (pos.) m/e: 568.3 (M+H$_2$O)$^+$, 573.3 (M+Na)$^+$.

(3S)-3-Cyclopropyl-3-(3-(((2-((1R)-2,2-dimethylcyclopentyl)-2'-fluoro-5'-(methyloxy)-1,1'-biphenyl-4-yl)methyl)oxy)-2-fluorophenyl)propanoic acid or (3S)-3-cyclopropyl-3-(3-(((2-((1S)-2,2-dimethylcyclopentyl)-2'-fluoro-5'-(methyloxy)-1,1'-biphenyl-4-yl)methyl)oxy)-2-fluorophenyl)propanoic acid or (3R)-3-cyclopropyl-3-(3-(((2-((1R)-2,2-dimethylcyclopentyl)-2'-fluoro-5'-(methyloxy)-1,1'-biphenyl-4-yl)methyl)oxy)-2-fluorophenyl)propanoic acid or (3R)-3-cyclopropyl-3-(3-(((2-((1S)-2,2-dimethylcyclopentyl)-2'-fluoro-5'-(methyloxy)-1,1'-biphenyl-4-yl)methyl)oxy)-2-fluorophenyl)propanoic acid (83.17). MS ESI (neg.) m/e: 533.2 (M−H)$^+$.

Example 83.18

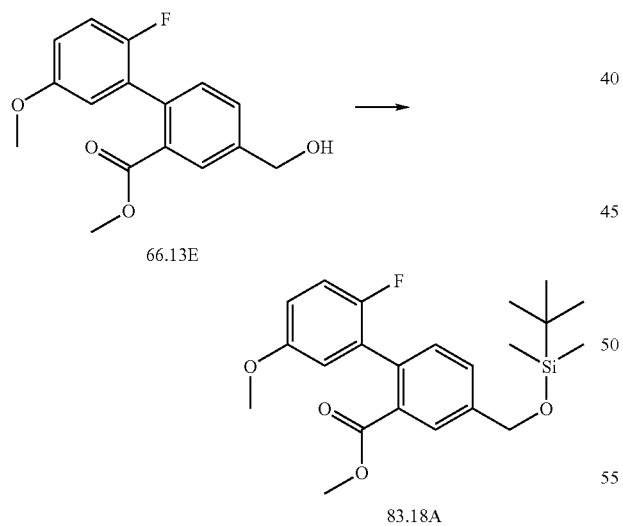

Methyl 4-((((1,1-dimethylethyl)(dimethyl)silyl)oxy)methyl)-2'-fluoro-5'-(methyloxy)-1,1'-biphenyl-2-carboxylate (83.18A). A 50 mL round bottom flask was charged with 66.13E (1.19 g, 4.1 mmol), tert-butyldimethylchlorosilane (commercially available from Aldrich) (0.68 g, 4.5 mmol), DMF (4 mL), and imidazole (0.70 g, 10 mmol). The mixture was stirred overnight at 25° C. and then diluted with hexanes. The organic phase was washed with 1 N HCl, water, and brine, dried (MgSO$_4$), and concentrated to afford 83.18A (1.6 g, 96% yield) as a colorless oil. The product thus obtained was used without further purification.

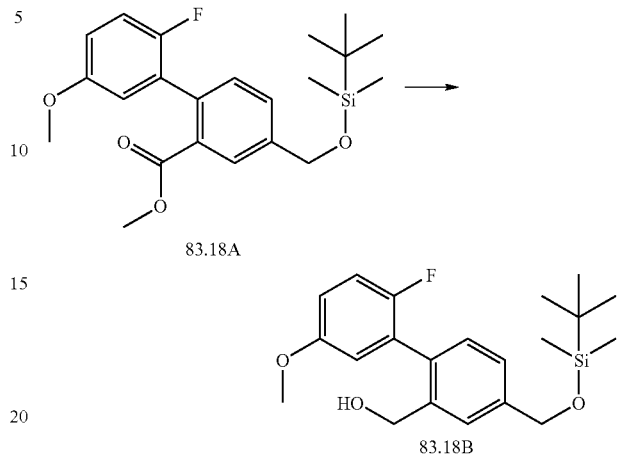

(4-((((1,1-Dimethylethyl)(dimethyl)silyl)oxy)methyl)-2'-fluoro-5'-(methyloxy)-1,1'-biphenyl-2-yl)methanol (83.18B). A 100 mL round bottom flask was charged with 83.18A (0.82 g, 2.0 mmol) and THF (10 mL). To the solution was added LAH (1.0 M in THF) (available from Aldrich) (2.0 mL, 2.0 mmol) dropwise at room temperature. The mixture was stirred for 10 minutes, quenched with aqueous Rochelle salt, and diluted with EtOAc. The organic phase was washed with water and brine, dried (MgSO$_4$), and concentrated. The residue was purified by silica gel flash chromatography (0-25% EtOAc/hexane) to afford 83.18B (0.73 g, 96% yield) as a colorless oil.

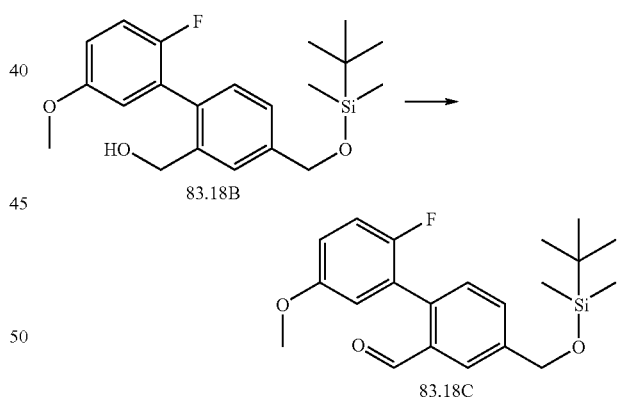

4-((((1,1-Dimethylethyl)(dimethyl)silyl)oxy)methyl)-2'-fluoro-5'-(methyloxy)-1,1'-biphenyl-2-carbaldehyde (83.18C). A 200 mL round bottom flask was charged with 83.18B (1.21 g, 3.21 mmol), DCM (9 mL), iodobenzene diacetate (available from Aldrich) (1.24 g, 3.86 mmol), and TEMPO (available from Aldrich) (0.0502 g, 0.321 mmol). The solution was stirred for 2 hours at room temperature and diluted with EtOAc. The organic phase was washed with saturated aqueous NaHCO$_3$, saturated aqueous Na$_2$S$_2$O$_3$, and brine, dried (MgSO$_4$), and concentrated. The residue was purified by silica gel flash chromatography (0-5% EtOAc/hexane) to afford 83.18C (1.05 g, 87% yield) as a colorless oil.

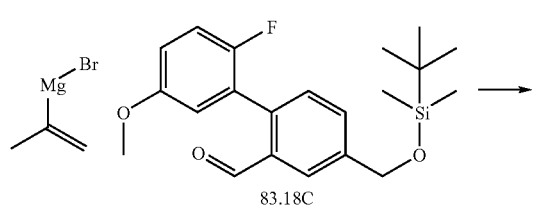

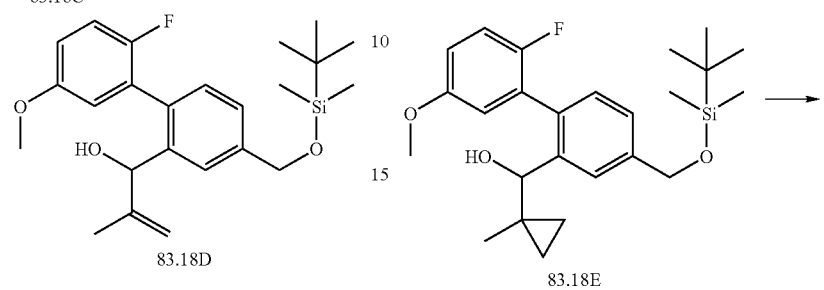

1-(4-((((1,1-Dimethylethyl)(dimethyl)silyl)oxy)methyl)-2'-fluoro-5'-(methyloxy)-1,1'-biphenyl-2-yl)-2-methyl-2-propen-1-ol (83.18D). A 250 mL round bottom flask was charged with 83.18C (1.05 g, 2.80 mmol) and THF (15 mL) and cooled to −78° C. under $N_2$. To the cold solution was added isopropenylmagnesium bromide (0.5 M in THF) (available from Aldrich) (11.2 mL, 5.61 mmol) dropwise. The mixture was stirred for 30 minutes at −78° C. The cooling bath was removed, and the mixture was stirred for 30 minutes at ambient temperature. The reaction was quenched with saturated aqueous $NH_4Cl$ and diluted with EtOAc. The organic phase was washed with water and brine, dried ($MgSO_4$), and concentrated. The residue was purified by silica gel flash chromatography (0-15% EtOAc/hexane) to afford 83.18D (1.05 g, 90% yield) as a colorless oil.

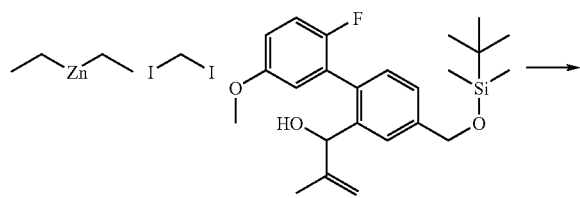

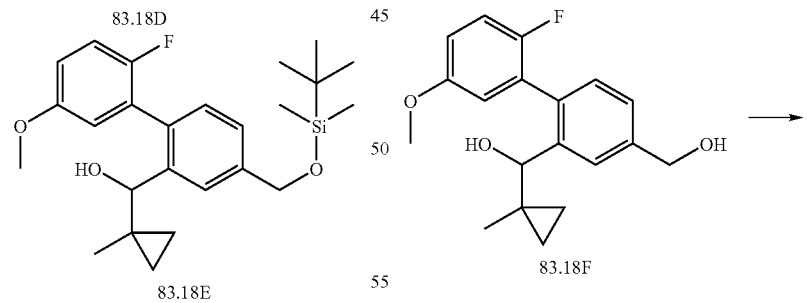

(4-((((1,1-Dimethylethyl)(dimethyl)silyl)oxy)methyl)-2'-fluoro-5'-(methyloxy)-1,1'-biphenyl-2-yl)(1-methylcyclopropyl)methanol (83.18E). A 100 mL round bottom flask was charged with 83.18D (0.92 g, 2.2 mmol), DCM (22 mL), and diiodomethane (available from Aldrich) (0.27 mL, 3.3 mmol) and cooled to 0° C. under $N_2$. To the cold solution was added diethylzinc (1.0 M in heptane) (available from Aldrich) (3.3 mL, 3.3 mmol) at a rapid drip. The colorless mixture was stirred for 5 minutes. The cooling bath was removed, and the mixture was stirred for 2 hours at ambient temperature. The reaction was quenched with saturated aqueous $NH_4Cl$ and diluted with EtOAc. The organic phase was washed with 1 M $Na_2S_2O_3$ and brine, dried ($MgSO_4$), and concentrated. The residue was purified by silica gel flash chromatography (0-15% EtOAc/hexane) to afford 83.18E (0.81 g, 85%) as a colorless oil.

(2'-Fluoro-4-(hydroxymethyl)-5'-(methyloxy)-1,1'-biphenyl-2-yl)(1-methylcyclopropyl)methanol (83.18F). A 200 mL round bottom flask was charged with 83.18E (0.80 g, 1.9 mmol), MeOH (10 mL), and PPTS (0.047 g, 0.19 mmol). The solution was stirred overnight at room temperature and diluted with EtOAc. The organic phase was washed with water and brine, dried ($MgSO_4$), and concentrated. The crude product was purified by silica gel flash chromatography (20-55% EtOAc/hexane) to afford 83.18F (0.52 g, 88%) as a colorless oil.

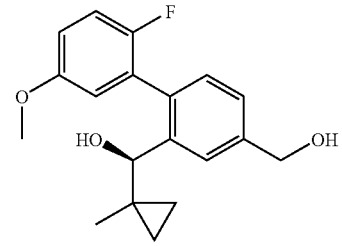

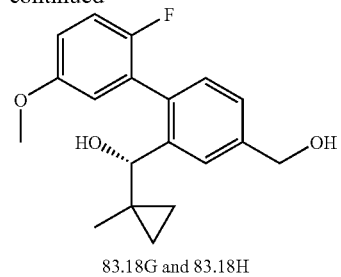

83.18G and 83.18H (R)-(2'-Fluoro-4-(hydroxymethyl)-5'-(methyloxy)-1,1'-biphenyl-2-yl)(1-methylcyclopropyl)methanol and (S)-(2'-fluoro-4-(hydroxymethyl)-5'-(methyloxy)-1,1'-biphenyl-2-yl)(1-methylcyclopropyl)methanol (83.18G and 83.18H). Racemic 83.18F (0.52 g, 1.6 mmol) was resolved by chiral HPLC (Chiralcel OD column, 5% IPA/hexane, detection at 220 nm) to afford (in order of elution) 83.18G (0.23 g, 88% yield, 99% e.e.) and 83.18H (0.23 g, 88% yield, 99% e.e.) as colorless oils.

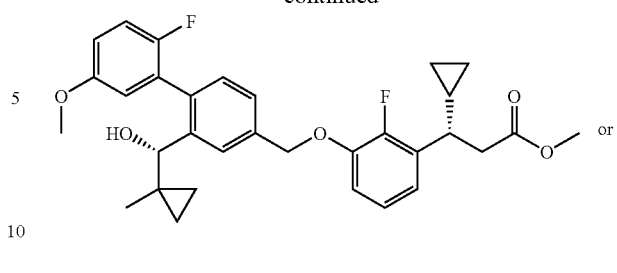

83.18I

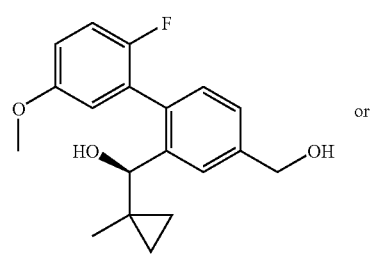

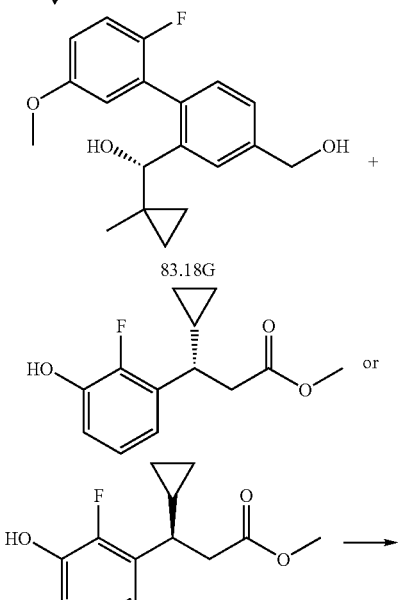

Methyl (3S)-3-cyclopropyl-3-(2-fluoro-3-(((2'-fluoro-2-((R)-hydroxy(1-methylcyclopropyl)methyl)-5'-(methyloxy)-1,1'-biphenyl-4-yl)methyl)oxy)phenyl)propanoate or methyl (3S)-3-cyclopropyl-3-(2-fluoro-3-(((2'-fluoro-2-((S)-hydroxy(1-methylcyclopropyl)methyl)-5'-(methyloxy)-1,1'-biphenyl-4-yl)methyl)oxy)phenyl)propanoate or methyl (3R)-3-cyclopropyl-3-(2-fluoro-3-(((2'-fluoro-2-((R)-hydroxy(1-methylcyclopropyl)methyl)-5'-(methyloxy)-1,1'-biphenyl-4-yl)methyl)oxy)phenyl)propanoate or methyl (3R)-3-cyclopropyl-3-(2-fluoro-3-(((2'-fluoro-2-((S)-hydroxy(1-methylcyclopropyl)methyl)-5'-(methyloxy)-1,1'-biphenyl-4-yl)methyl)oxy)phenyl)propanoate (83.18I). A screw-cap vial was charged with 83.B (0.075 g, 0.31 mmol), 83.18G (0.100 g, 0.31 mmol), triphenylphosphine (0.12 g, 0.47 mmol), and THF (1.8 mL). To the solution was added diethyl azodicarboxylate (0.075 mL, 0.47 mmol) dropwise at room temperature. The mixture was stirred for 1 hour, diluted with brine, and extracted with EtOAc. The combined organic layers were dried (MgSO₄) and concentrated. The residue was purified by silica gel flash chromatography (0-25% EtOAc/hexane) to afford 83.18I (0.122 g, 72% yield) as a colorless oil.

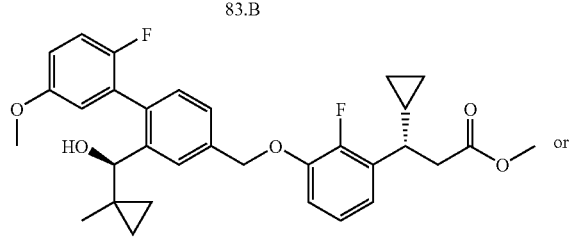

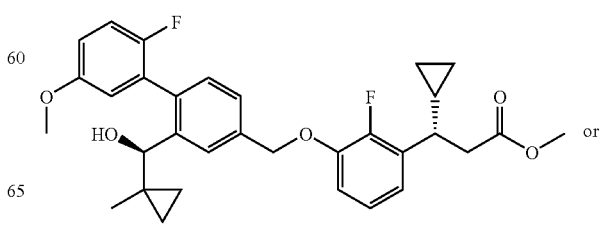

709

-continued

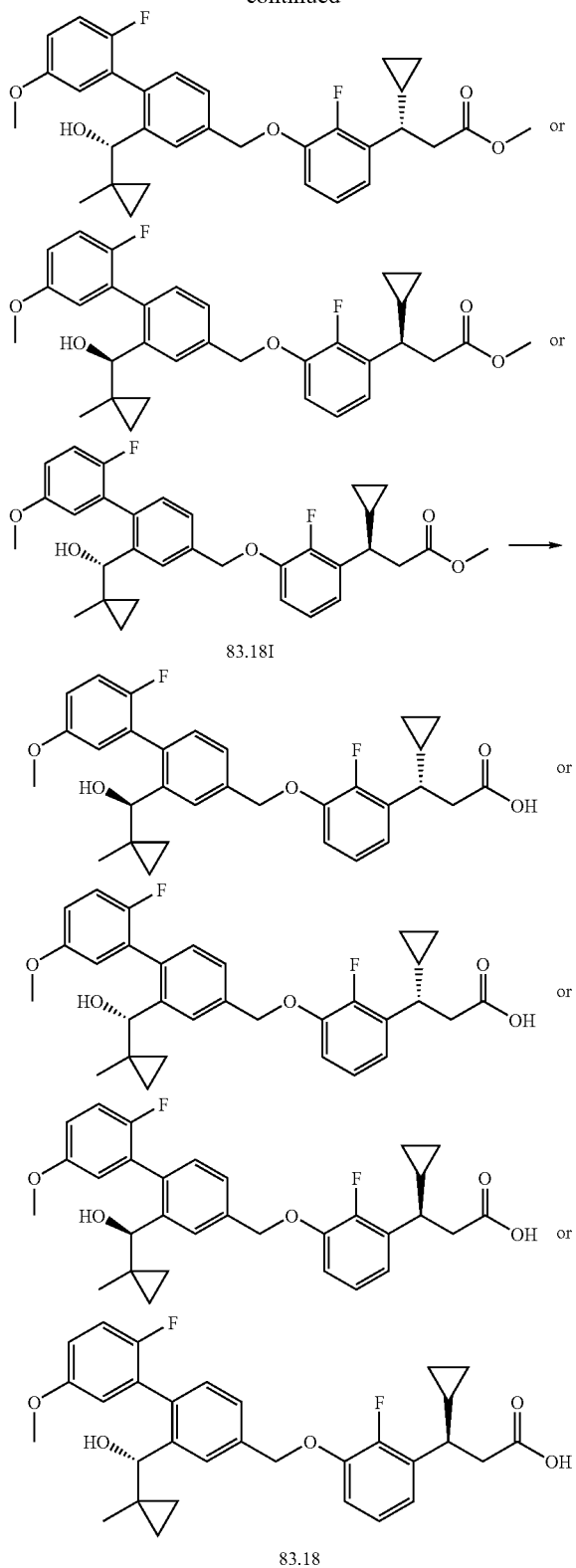

83.18I 83.18

(3S)-3-Cyclopropyl-3-(2-fluoro-3-(((2'-fluoro-2-((1R)-hydroxy(1-methylcyclopropyl)methyl)-5'-(methyloxy)-1,1'-biphenyl-4-yl)methyl)oxy)phenyl)propanoic acid or (3S)-3-cyclopropyl-3-(2-fluoro-3-(((2'-fluoro-2-((1S)-hydroxy(1-methylcyclopropyl)methyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((1R)-hydroxy(1-methylcyclopropyl)methyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((1S)-hydroxy(1-methylcyclopropyl)methyl)-5'-(methyloxy)-1,1'-biphenyl-4-yl)methyl)oxy)phenyl)propanoic acid (83.18). A screw-cap vial was charged with 83.18I (0.021 g, 0.039 mmol), 2:1 THF/MeOH (1.5 mL), and 1 N LiOH (0.50 mL, 0.50 mmol). The mixture was stirred overnight at room temperature, concentrated, quenched with a slight excess of 1 N HCl, and extracted with EtOAc. The combined organic layers were dried (MgSO$_4$) and concentrated. The residue was purified by silica gel flash chromatography (0-40% EtOAc/hexane) to afford 83.18 (0.0184 g, 90% yield) as a white solid. MS ESI (neg.) m/e: 521.2 (M−H)$^+$.

Example 83.19

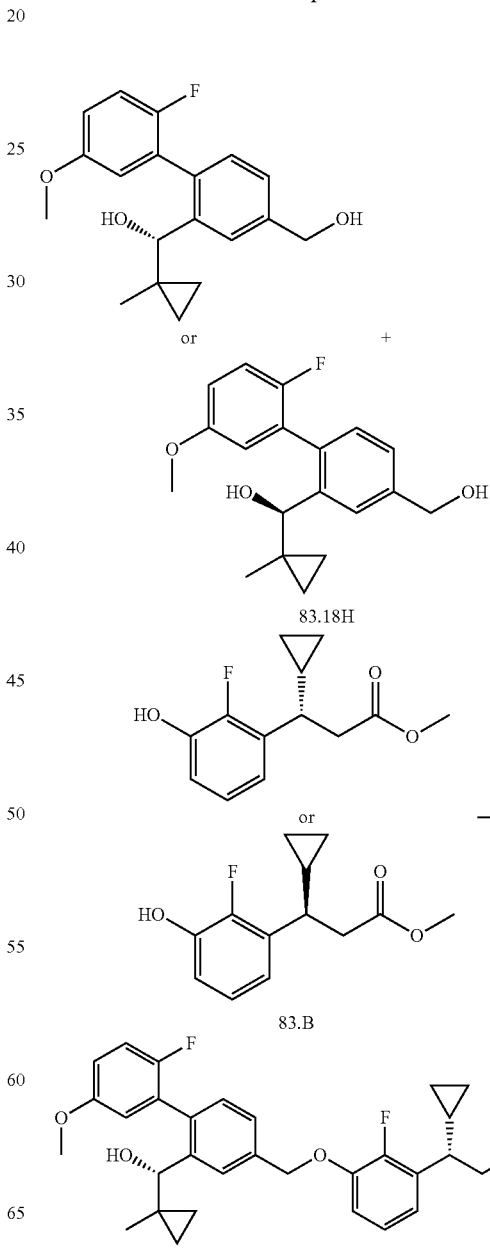

83.18H

83.B

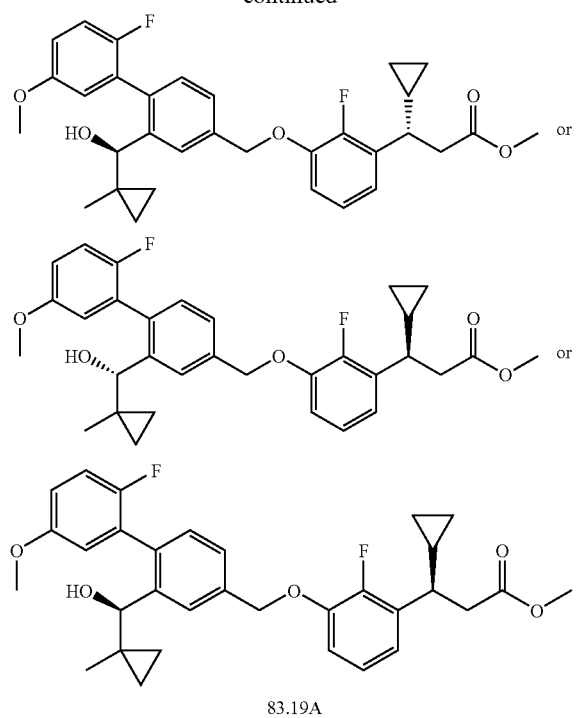

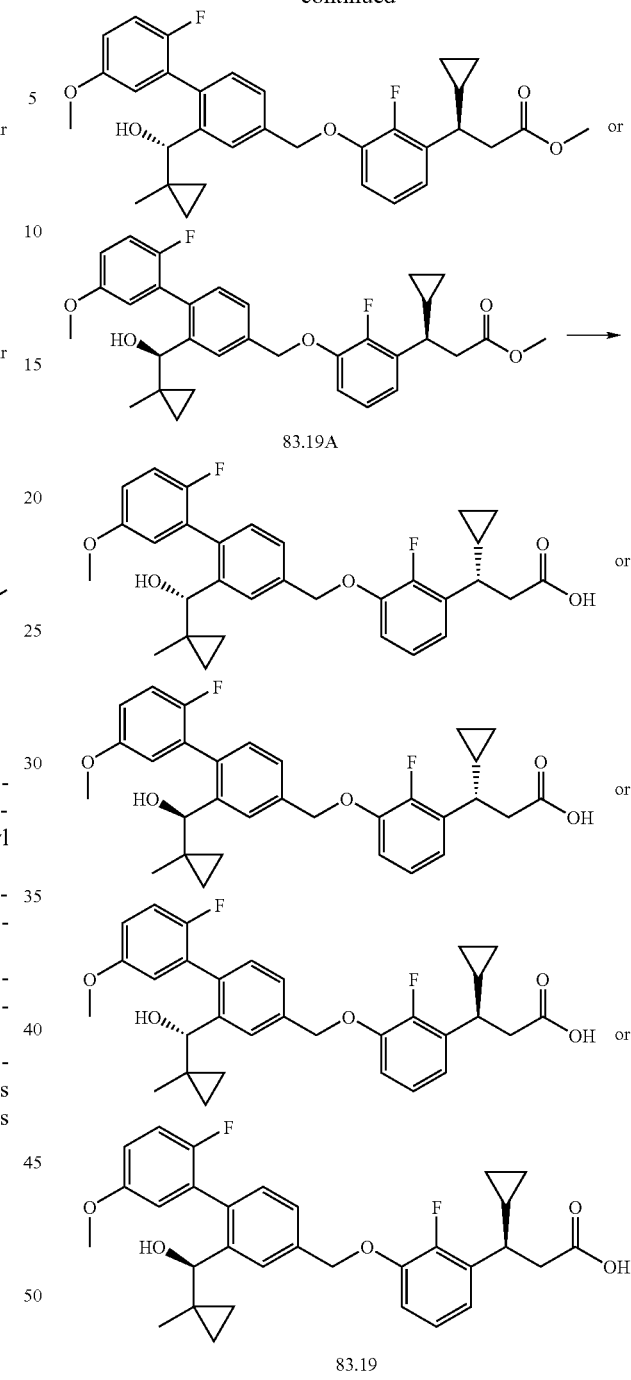

Methyl (3S)-3-cyclopropyl-3-(2-fluoro-3-(((2'-fluoro-2-((S)-hydroxy(1-methylcyclopropyl)methyl)-5'-(methyloxy)-1,1'-biphenyl-4-yl)methyl)oxy)phenyl)propanoate or methyl (3S)-3-cyclopropyl-3-(2-fluoro-3-(((2'-fluoro-2-((R)-hydroxy(1-methylcyclopropyl)methyl)-5'-(methyloxy)-1,1'-biphenyl-4-yl)methyl)oxy)phenyl)propanoate or methyl (3R)-3-cyclopropyl-3-(2-fluoro-3-(((2'-fluoro-2-((S)-hydroxy(1-methylcyclopropyl)methyl)-5'-(methyloxy)-1,1'-biphenyl-4-yl)methyl)oxy)phenyl)propanoate or methyl (3R)-3-cyclopropyl-3-(2-fluoro-3-(((2'-fluoro-2-((R)-hydroxy(1-methylcyclopropyl)methyl)-5'-(methyloxy)-1,1'-biphenyl-4-yl)methyl)oxy)phenyl)propanoate (83.19A). 83.19A was prepared from 83.18H and 83.B according to the analogous method described in Example 83.18.

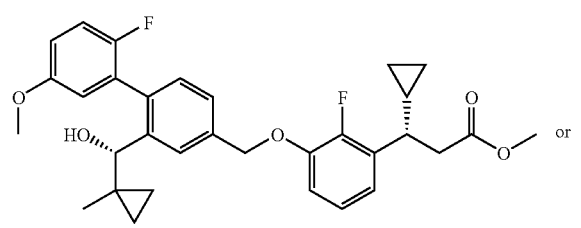

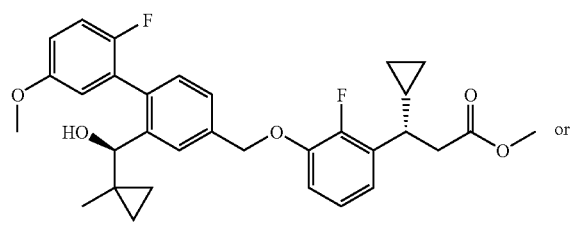

(3S)-3-Cyclopropyl-3-(2-fluoro-3-(((2'-fluoro-2-((1S)-hydroxy(1-methylcyclopropyl)methyl)-5'-(methyloxy)-1,1'-biphenyl-4-yl)methyl)oxy)phenyl)propanoic acid or (3S)-3-cyclopropyl-3-(2-fluoro-3-(((2'-fluoro-2-((1R)-hydroxy(1-methylcyclopropyl)methyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((1S)-hydroxy(1-methylcyclopropyl)methyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((1R)-hydroxy(1-methylcyclopropyl)methyl)-5'-(methyloxy)-1,1'-biphenyl-4-yl)methyl)oxy)phenyl)propanoic acid (83.19). 83.19 was prepared from 83.19A according to the analogous method described in Example 83.18. MS ESI (neg.) m/e: 521.2 (M−H)+.

Example 83.20

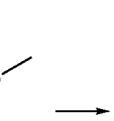

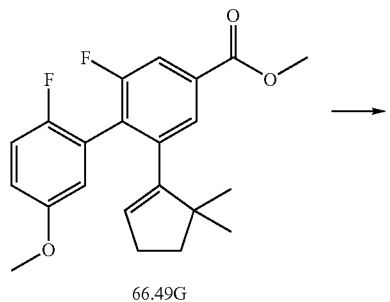
66.49G

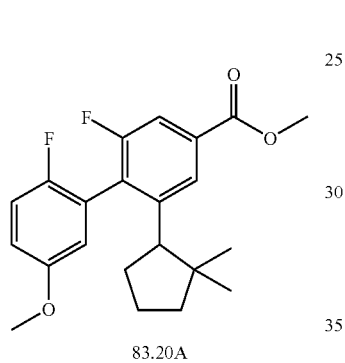
83.20A

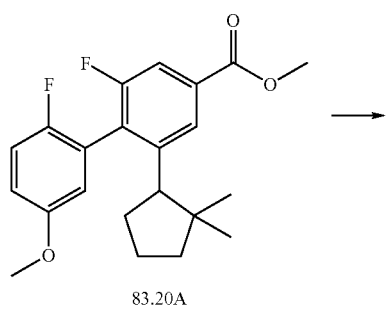
83.20A

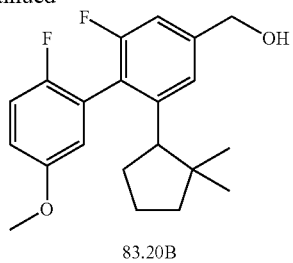
83.20B

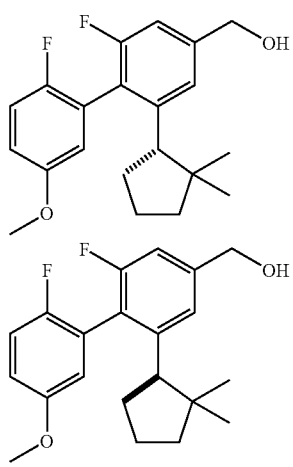
83.20B (top), 83.20C and 83.20 D (bottom)

Methyl 2-(2,2-dimethylcyclopentyl)-2',6-difluoro-5'-(methyloxy)-1,1'-biphenyl-4-carboxylate (83.20A). To a flask containing 66.49 G (0.7168 g, 1.925 mmol) in dry MeOH (8 mL) and EtOAc (5 mL) was added palladium (10 wt. % on activated carbon) (0.2103 g, 0.1976 mmol). After purging, the mixture was stirred under an atmosphere of hydrogen at room temperature. After 18.5 hours, the mixture was filtered through Celite. After concentration, the residue was identified 83.20A (703.6 mg, 98% yield). $^1$H NMR (400 MHz, CDCl$_3$) δ ppm 7.88 (1H, s), 7.65 (1H, dd, J=9.4, 1.6 Hz), 7.13 (2H, m), 6.96 (2H, m), 6.77 (1H, dd, J=5.5, 3.1 Hz), 3.95 (3H, s), 3.80 (3H, s), 2.76 (1H, ddd, J=10.3, 8.3, 1.8 Hz), 2.19 (1H, m), 2.08 (1H, m), 1.91 (1H, m), 1.75 (2H, m), 1.45 (1H, m), 0.78 (3H, s), 0.64 (3H, s).

(2-(2,2-Dimethylcyclopentyl)-2',6-difluoro-5'-(methyloxy)-1,1'-biphenyl-4-yl)methanol (83.20B). To a cooled solution of 83.20A (0.7036 g, 1.879 mmol) in dry THF (15 mL) at 0° C. was added LAH (1.0 M in THF) (4 mL, 4.0 mmol) dropwise. Upon complete addition, the reaction was maintained at 0° C. and was monitored by TLC and LCMS. After 45 minutes, 1N NaOH was added to quench the reaction. Gas evolution occurred. The resulting solution was extracted three times with EtOAc. After drying over anhydrous magnesium sulfate, filtration, and concentration, the residue was purified by flash chromatography (SiO$_2$ gel 60, eluted with 0%-50% EtOAc in hexanes). Fractions containing the desired product were combined and concentrated to provide a colorless oil that solidified as 83.20B (300.5 mg, 46% yield). $^1$H NMR (400 MHz, CDCl$_3$) δ ppm 7.16 (1H, s), 7.10 (2H, m), 6.92 (1H, m), 6.77 (1H, dd, J=5.9, 3.1 Hz), 4.74 (2H, s), 3.81 (3H, m), 2.73 (1H, ddd, J=10.3, 8.3, 1.8 Hz), 2.17 (1H, m), 2.04 (1H, m), 1.87 (1H, m), 1.73 (3H, m), 1.42 (1H, m), 0.78 (3H, s), 0.64 (3H, s). Chiral separation of 83.20B was accomplished on Chiracel-OJ (2% IPA in hexane) to provide 83.20C (peak 1) and 83.20D (peak 2). Both enantiomers were used to synthesize example compounds, and both enantiomers gave active compounds.

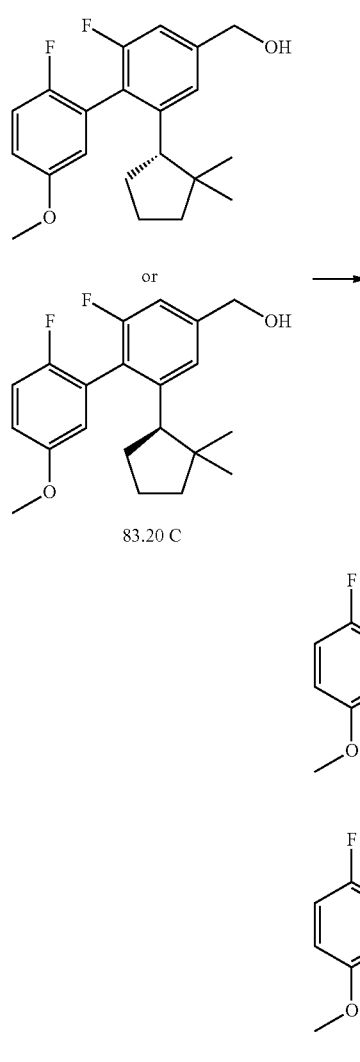

83.20 C or 83.20 E 4-(Chloromethyl)-2-((1S)-2,2-dimethylcyclopentyl)-2',6-difluoro-5'-(methyloxy)-1,1'-biphenyl or 4-(chloromethyl)-2-((1R)-2,2-dimethylcyclopentyl)-2',6-difluoro-5'-(methyloxy)-1,1'-biphenyl (83.20E). To a solution of 83.20C (0.1171 g, 0.338 mmol) in dry DCM (4.5 mL) and dry DMF (0.03 mL) was added thionyl chloride (0.05 mL, 0.685 mmol) at 0° C. The resulting solution was warmed to room temperature and monitored with TLC and LCMS. After 19 hours, the reaction was concentrated and then purified by silica gel flash chromatography (0-5% EtOAc/hexane) to afford 83.20E (99.7 mg, 81% yield). $^1$H NMR (400 MHz, CDCl$_3$) δ ppm 7.18 (1H, d, J=1.6 Hz), 7.13 (2H, m), 6.95 (1H, m), 6.77 (1H, dd, J=5.9, 3.1 Hz), 4.68 (2H, m), 3.84 (3H, m), 2.73 (1H, ddd, J=10.3, 8.3, 1.8 Hz), 2.18 (1H, m), 2.01 (1H, m), 1.88 (1H, m), 1.73 (3H, m), 1.44 (1H, m), 0.78 (3H, s), 0.64 (3H, s).

(3S)-3-Cyclopropyl-3-(3-(((2-((1S)-2,2-dimethylcyclopentyl)-2',6-difluoro-5'-(methyloxy)-1,1'-biphenyl-4-yl)methyl)oxy)-2-fluorophenyl)propanoic acid or (3S)-3-cyclopropyl-3-(3-(((2-((1R)-2,2-dimethylcyclopentyl)-2',6-difluoro-5'-(methyloxy)-1,1'-biphenyl-4-yl)methyl)oxy)-2-fluorophenyl)propanoic acid or (3R)-3-cyclopropyl-3-(3-(((2-((1S)-2,2-dimethylcyclopentyl)-2',6-difluoro-5'-(methyloxy)-1,1'-biphenyl-4-yl)methyl)oxy)-2-fluorophenyl)propanoic acid or (3R)-3-cyclopropyl-3-(3-(((2-((1R)-2,2-dimethylcyclopentyl)-2',6-difluoro-5'-(methyloxy)-1,1'-biphenyl-4-yl)methyl)oxy)-2-fluorophenyl)propanoic acid (83.20). The alkylation and hydrolysis were conducted in an analogous manner to Example 66.6 (using 83.B and 83.20E derived from peak one from the chiral separation of the racemic alcohol 83.20C on the OJ column, described herein) to yield 83.20 (42.5 mg, 92% yield). $^1$H NMR (400 MHz, CDCl$_3$) δ ppm 7.23 (1H, d, J=0.8 Hz), 7.17 (3H, m), 6.94 (3H, m), 6.78 (1H, dd, J=5.9, 3.1 Hz), 5.19 (2H, m), 3.79 (3H, s), 2.86 (2H, d, J=7.4 Hz), 2.79 (2H, m), 2.18 (1H, m), 2.02 (1H, m), 1.86 (1H, m), 1.72 (1H, m), 1.53 (1H, ddd, J=12.7, 8.2, 4.9 Hz), 1.42 (2H, m), 1.20 (1H, m), 0.73 (3H, s), 0.67 (4H, m), 0.48 (1H, m), 0.34 (1H, dq, J=9.6, 4.9 Hz), 0.25 (1H, m). MS ESI (neg.) m/e: 551.2 (M–H)$^+$.

Example 83.21

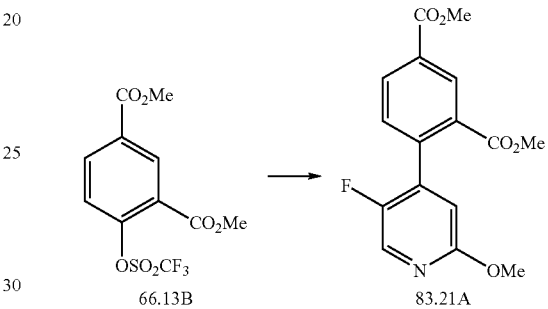

66.13B      83.21A

Dimethyl 4-(5-fluoro-2-(methyloxy)-4-pyridinyl)-1,3-benzenedicarboxylate (83.21A). To a stirred solution of 66.13B (1.00 g, 2.9 mmol) in DMF (12 mL) at 23° C. was added 5-fluoro-2-methoxypyridin-4-ylboronic acid (0.75 g, 4.4 mmol) (commercially available from Asymchem), potassium carbonate (1.2 g, 8.8 mmol), followed by tetrakis(triphenylphosphine)palladium (0.24 g, 0.20 mmol). The mixture was heated to 90° C. The reaction mixture was then stirred for 17 hours and then cooled to room temperature. The reaction was diluted with brine and extracted three times with EtOAc. After drying over anhydrous magnesium sulfate and filtering, the organic solvent was removed under reduced pressure and the product was then purified on silica gel (0-30% EtOAc in hexanes) to yield 83.21A as a colorless solid (0.860 g, 92% yield).

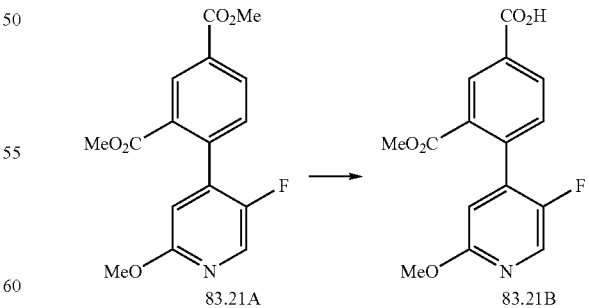

83.21A      83.21B 4-(5-Fluoro-2-(methyloxy)-4-pyridinyl)-3-((methyloxy)carbonyl)benzoic acid (83.21B). To a stirred solution of 83.21A (0.860 g, 2.7 mmol) in THF (7.00 mL) and MeOH (7.00 mL) at 0° C. was added potassium hydroxide (1.5 mL, 3.0 mmol) slowly to maintain the temperature below 6° C.

The reaction mixture was allowed to warm to room temperature and stirred for 17 hours. After which, the reaction was acidified with 1N HCl and extracted three times with EtOAc. After drying over anhydrous magnesium sulfate and filtering, the organic solvent was removed under reduced pressure to yield 83.21B as a colorless solid (0.82 g, 100% yield).

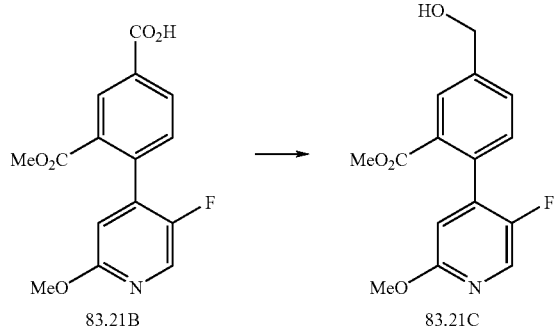

Methyl 2-(5-fluoro-2-(methyloxy)-4-pyridinyl)-5-(hydroxymethyl)benzoate (83.21C). To a stirred solution of 4-(5-fluoro-2-methoxypyridin-4-yl)-3-(methoxycarbonyl)benzoic acid 83.21B (0.416 g, 1 mmol) in THF (14 mL) at 0° C. was added borane-THF (3 mL, 3 mmol, 1.0M). The reaction was warmed to 23° C. and stirred for 46 hours. The reaction was then concentrated in vacuo. The reaction was diluted with 1N HCl and extracted three times with EtOAc. After drying over anhydrous magnesium sulfate and filtering, the organic solvent was removed under reduced pressure and the product was then purified on silica gel (0-40% EtOAc in hexanes) to yield 83.21C as a colorless solid (0.307 g, 77% yield).

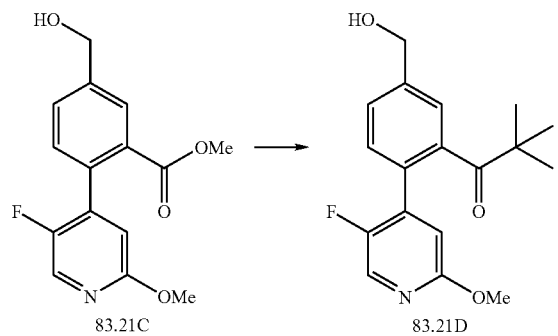

1-(2-(5-Fluoro-2-(methyloxy)-4-pyridinyl)-5-(hydroxymethyl)phenyl)-2,2-dimethyl-1-propanone (83.21D). To a stirred solution of methyl 2-(5-fluoro-2-methoxypyridin-4-yl)-5-(hydroxymethyl)benzoate 83.21C (0.307 g, 1 mmol) in THF (11 mL) at −78° C. was added tert-butyl lithium (2 mL, 3 mmol). The reaction mixture was stirred for one hour and then quenched with a saturated solution of ammonium chloride and extracted three times with EtOAc. After drying over anhydrous magnesium sulfate and filtering, the organic solvent was removed under reduced pressure and the product was then purified on silica gel (0-40% EtOAc in hexanes) to yield 83.21D as a colorless solid (0.28 g, 84% yield).

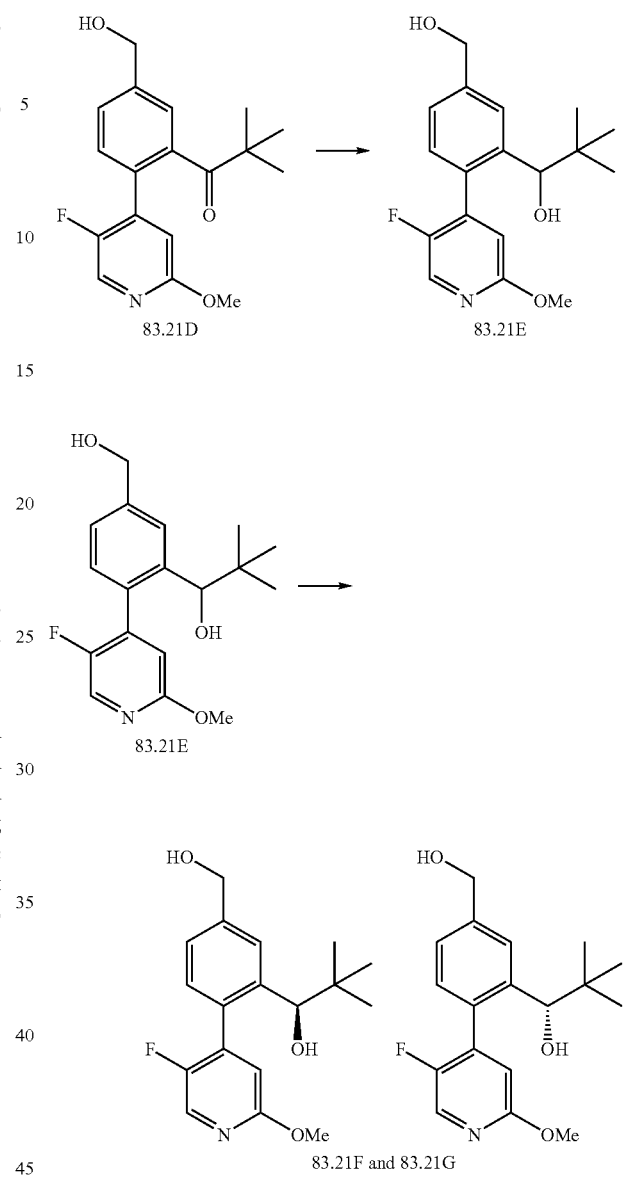

(1R)-1-(2-(5-Fluoro-2-methoxypyridin-4-yl)-5-(hydroxymethyl)phenyl)-2,2-dimethylpropan-1-ol or (1S)-1-(2-(5-fluoro-2-methoxypyridin-4-yl)-5-(hydroxymethyl)phenyl)-2,2-dimethylpropan-1-ol (83.21F or 83.21G). To a stirred solution of 1-(2-(5-fluoro-2-methoxypyridin-4-yl)-5-(hydroxymethyl)phenyl)-2,2-dimethylpropan-1-one 83.21D (0.130 g, 0.4 mmol) in THF (2 mL) at 0° C. was added LAH (0.6 mL, 0.6 mmol, 1.0M). The reaction was stirred for 3 hours. 1N NaOH(aq) was then added to quench the reaction mixture. The reaction was extracted three times with EtOAc. After drying over anhydrous magnesium sulfate and filtering, the organic solvent was removed under reduced pressure and the product was then purified on silica gel (0-20% EtOAc in hexanes) to yield 83.21F and 83.21G as a colorless solid (0.120 g, 92% yield). Chiral separation of 83.21E was accomplished on Chiracel-OD (4% IPA in hexane) to provide 83.21F (peak one-23.87 mins) and 83.21G (peak two-29.04 mins). Both enantiomers were used to synthesize example compounds, and both enantiomers gave active example compounds. However, the enantiomer corresponding to peak 2 provided the most active example compounds.[1]

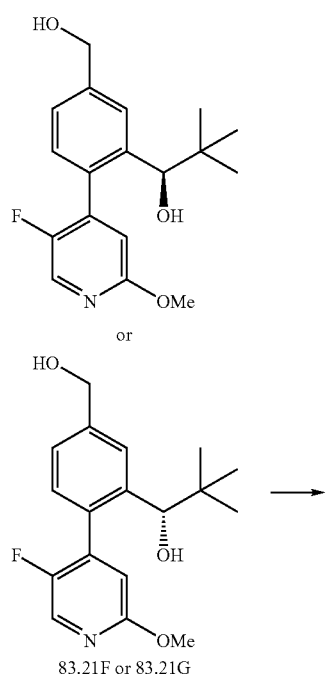

83.21F or 83.21G

→

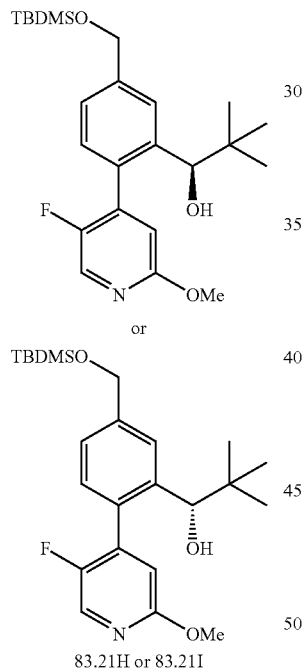

83.21H or 83.21I

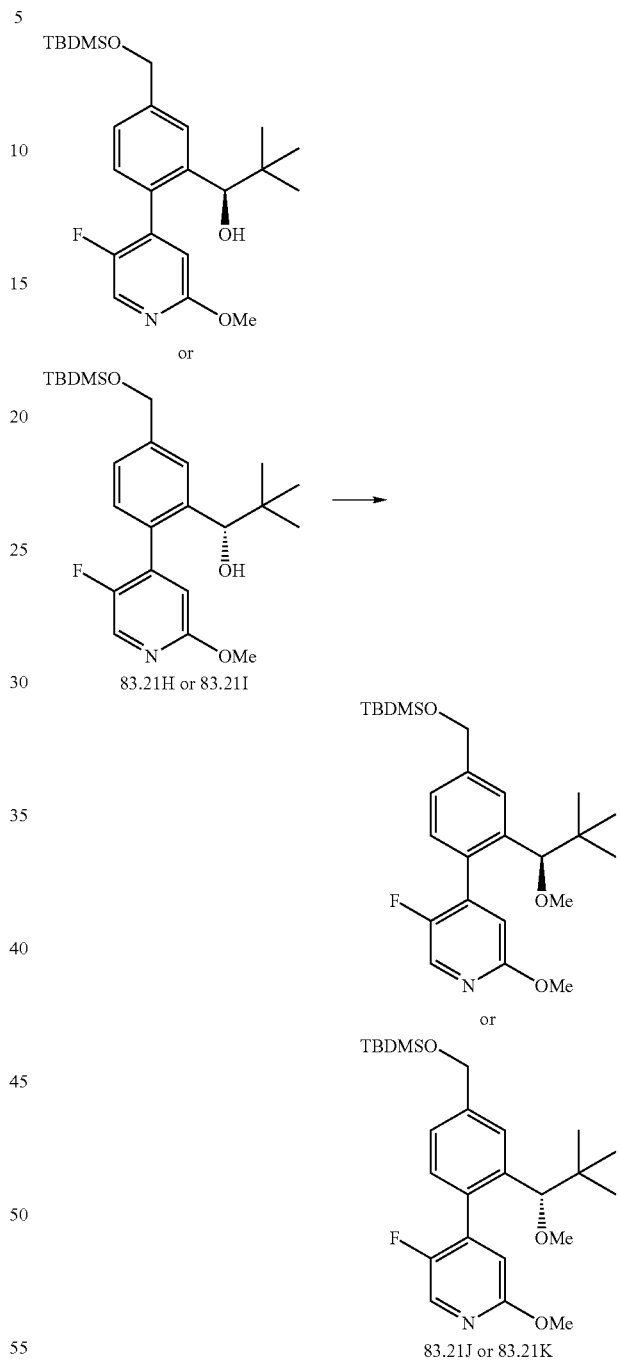

83.21H or 83.21I 83.21J or 83.21K (1R)-1-(5-((((1,1-Dimethylethyl)(dimethyl)silyl)oxy)methyl)-2-(5-fluoro-2-(methyloxy)-4-pyridinyl)phenyl)-2,2-dimethyl-1-propanol or (1S)-1-(5-((((1,1-dimethylethyl)(dimethyl)silyl)oxy)methyl)-2-(5-fluoro-2-(methyloxy)-4-pyridinyl)phenyl)-2,2-dimethyl-1-propanol (83.21H or 83.21I.) To a stirred solution of 83.21F or 83.21G (0.050 g, 0.2 mmol) in DCM (2 mL) at 23° C. was added tert-butyldimethylsilyl chloride (0.03 mL, 0.2 mmol), followed by TEA (0.03 mL, 0.2 mmol) and DMAP (0.002 g, 0.02 mmol). The reaction was then stirred for 24 hours and then concentrated in vacuo. The reaction was extracted three times with EtOAc. After drying over anhydrous magnesium sulfate and filtering, the organic solvent was removed under reduced pressure and the product was then purified on silica gel (0-20% EtOAc in hexanes) to yield 83.21H or 83.21I as a colorless oil (0.062 g, 91% yield).

4-(4-((((1,1-Dimethylethyl)(dimethyl)silyl)oxy)methyl)-2-((1R)-2,2-dimethyl-1-(methyloxy)propyl)phenyl)-5-fluoro-2-(methyloxy)pyridine or 4-(4-((((1,1-dimethylethyl)(dimethyl)silyl)oxy)methyl)-2-((1S)-2,2-dimethyl-1-(methyloxy)propyl)phenyl)-5-fluoro-2-(methyloxy)pyridine (83.21J or 83.21K.) To a stirred solution of 83.21H or 83.21I (0.062 g, 0.14 mmol) in DMF (1.4 mL) at 23° C. was added iodomethane (0.018 mL, 0.29 mmol), followed by sodium hydride (0.0069 g, 0.29 mmol). The reaction was then stirred at 50° C. for 15 hours, diluted with water and extracted three times with EtOAc. After drying over anhydrous magnesium sulfate and filtering, the organic solvent was removed under reduced pressure and the product was then purified on silica gel (0-40% EtOAc in hexanes) to yield 83.21J or 83.21K as a colorless oil (0.047 g, 73% yield).

and concentrated in vacuo. The product was then purified on silica gel (0-10% EtOAc in hexanes) to yield 83.21L or 83.21M as a colorless solid (0.032 g, 87% yield).

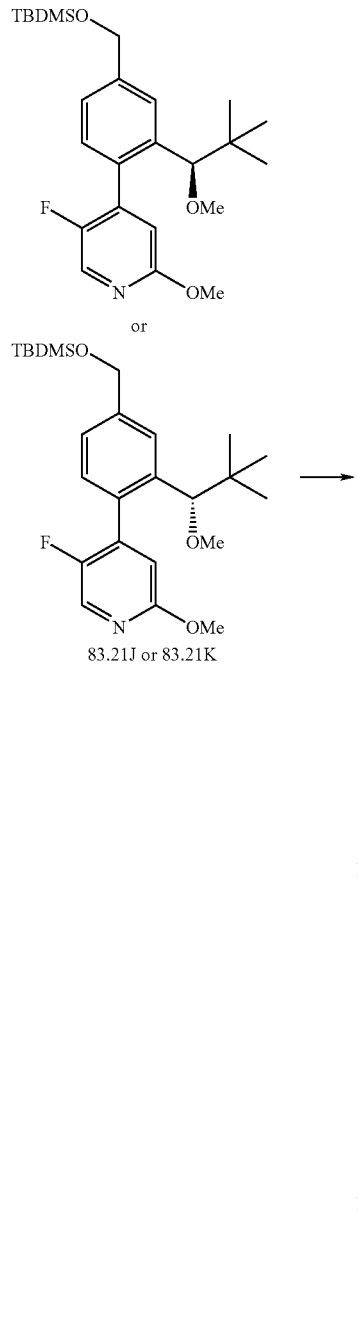

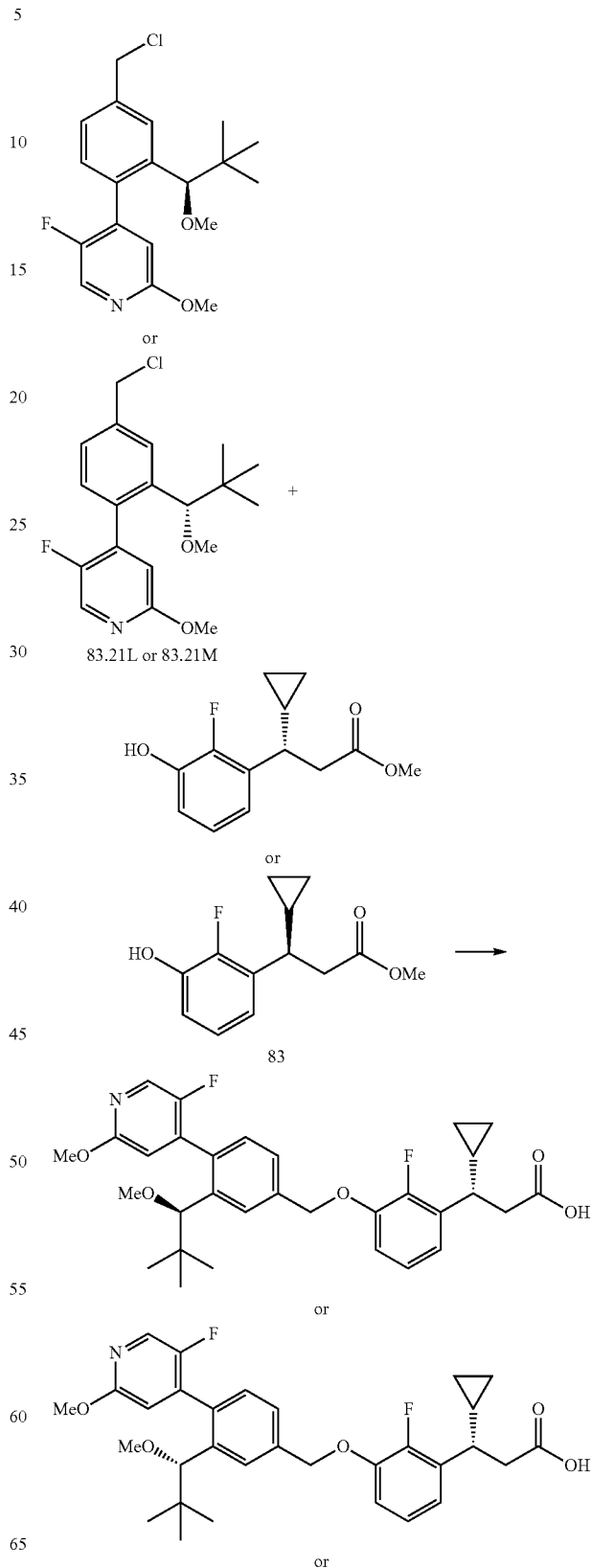

4-(4-(Chloromethyl)-2-((1R)-2,2-dimethyl-1-(methyloxy)propyl)phenyl)-5-fluoro-2-(methyloxy)pyridine or 4-(4-(chloromethyl)-2-((1S)-2,2-dimethyl-1-(methyloxy)propyl)phenyl)-5-fluoro-2-(methyloxy)pyridine (83.21L or 83.21M). To a stirred solution of 83.21J or 83.21K (0.047 g, 0.10 mmol) in DCM (1.0 mL) and DMF (0.0081 mL) at 0° C. was added thionyl chloride (0.015 mL, 0.21 mmol). The reaction was then stirred at room temperature for one hour

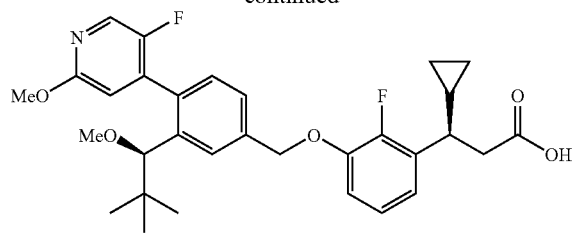

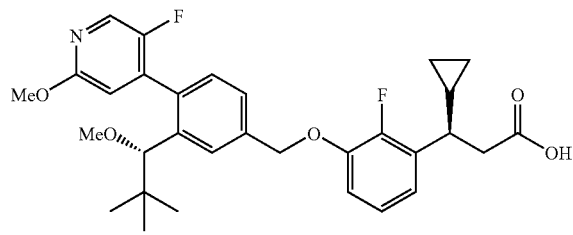

83.21N, 83.21O, 83.21P, or 83.21Q (3S)-3-Cyclopropyl-3-(3-(((3-((1R)-2,2-dimethyl-1-(methyloxy)propyl)-4-(5-fluoro-2-(methyloxy)-4-pyridinyl)phenyl)methyl)oxy)-2-fluorophenyl)propanoic acid or (3S)-3-cyclopropyl-3-(3-(((3-((1S)-2,2-dimethyl-1-(methyloxy)propyl)-4-(5-fluoro-2-(methyloxy)-4-pyridinyl)phenyl)methyl)oxy)-2-fluorophenyl)propanoic acid or (3R)-3-cyclopropyl-3-(3-(((3-((1R)-2,2-dimethyl-1-(methyloxy)propyl)-4-(5-fluoro-2-(methyloxy)-4-pyridinyl)phenyl)methyl)oxy)-2-fluorophenyl)propanoic acid or (3R)-3-cyclopropyl-3-(3-(((3-((1S)-2,2-dimethyl-1-(methyloxy)propyl)-4-(5-fluoro-2-(methyloxy)-4-pyridinyl)phenyl)methyl)oxy)-2-fluorophenyl)propanoic acid (83.21N, 83.21O, 83.21P, or 83.21Q). The alkylation and subsequent hydrolysis were conducted in an analogous manner to Example 66.6 (using the compound obtained from peak two of the chiral separation of 83.21E from the OD-column, described herein) to yield 83.21N or 83.21O (0.0207 g, 40% yield over the two steps). MS ESI (neg.) m/e: 538.3 (M–H)$^+$.

Example 83.22

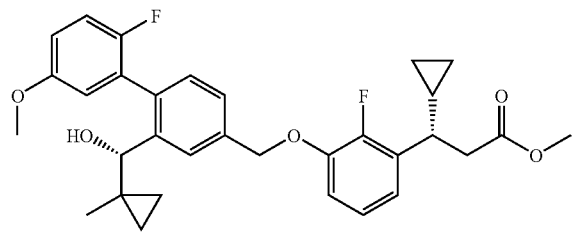

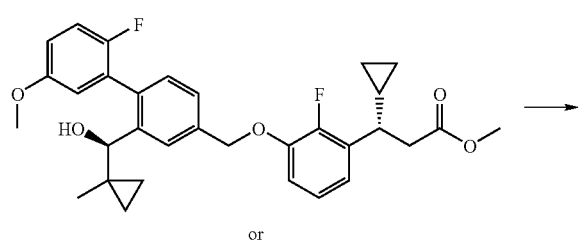

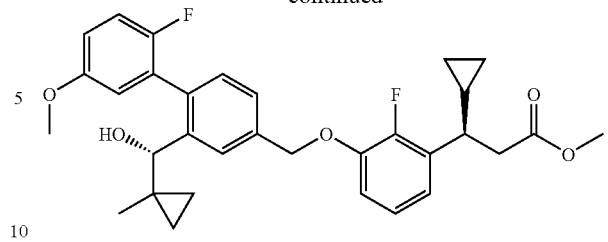

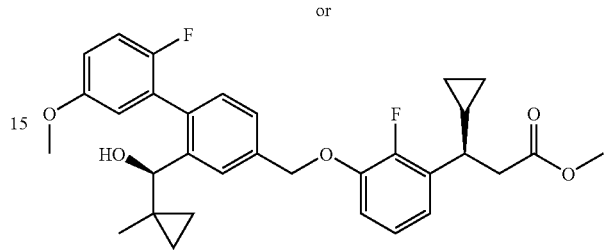

83.19A

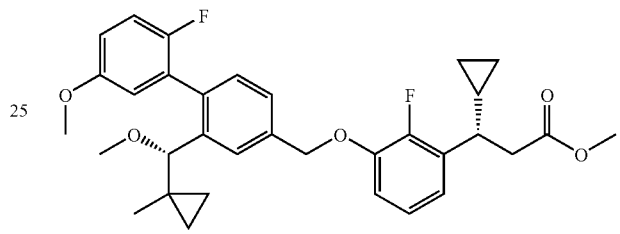

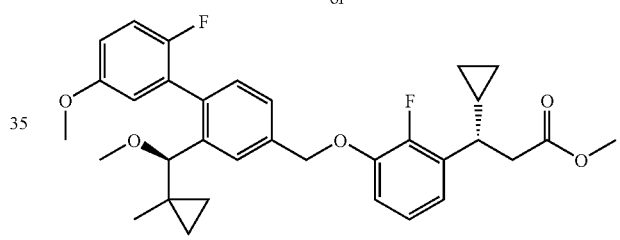

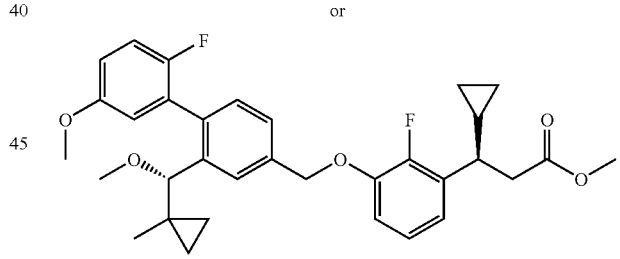

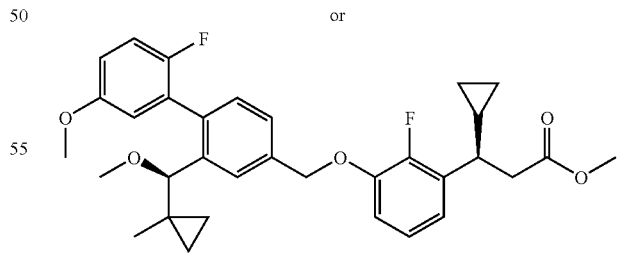

83.22A

Methyl (3S)-3-cyclopropyl-3-(2-fluoro-3-(((2'-fluoro-2-((S)-(1-methylcyclopropyl)(methyloxy)methyl)-5'-(methyloxy)-1,1'-biphenyl-4-yl)methyl)oxy)phenyl)propanoate or methyl (3S)-3-cyclopropyl-3-(2-fluoro-3-(((2'-fluoro-2-((R)-(1-methylcyclopropyl)(methyloxy)methyl)-5'-(methyloxy)-1,1'-biphenyl-4-yl)methyl)oxy)phenyl)propanoate or methyl (3R)-3-cyclopropyl-3-(2-fluoro-3-(((2'-fluoro-2-((S)-(1-methylcyclopropyl)(methyloxy)methyl)-5'-(methyloxy)-1,1'-biphenyl-4-yl)methyl)oxy)phenyl)propanoate or methyl (3R)-3-cyclopropyl-3-(2-fluoro-3-(((2'-fluoro-2-((R)-(1-methylcyclopropyl)(methyloxy)methyl)-5'-(methyloxy)-1,1'-biphenyl-4-yl)methyl)oxy)phenyl)propanoate (83.22A). A screw-cap vial was charged with 83.19A (0.039 g, 0.073 mmol), DMF (0.4 mL), iodomethane (available from Aldrich) (0.0091 mL, 0.15 mmol), and sodium hydride (60% dispersion in mineral oil) (0.0052 g, 0.13 mmol). The mixture was stirred for 1 hour at room temperature, quenched with saturated aqueous NH₄Cl, and extracted with EtOAc. The combined organic layers were dried (MgSO₄) and concentrated. The crude product was purified by silica gel flash chromatography (0-15% EtOAc/hexane) to afford 83.22A (0.0361 g, 90% yield) as a colorless oil.

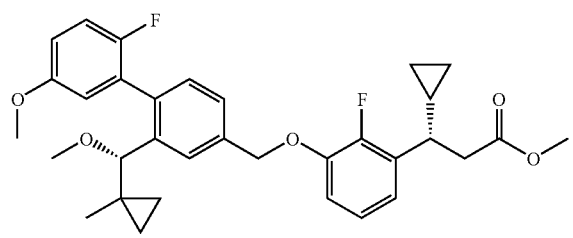

or

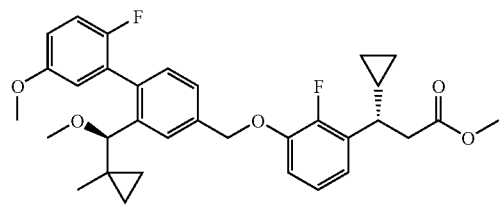

or

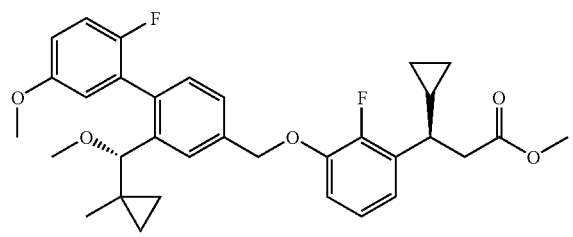

or

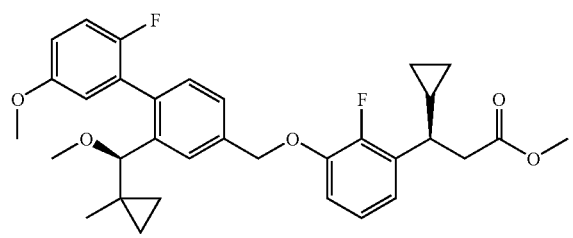

83.22A

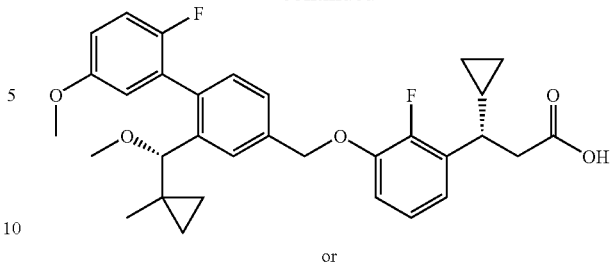

or

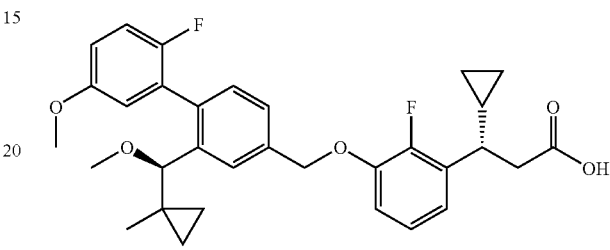

or

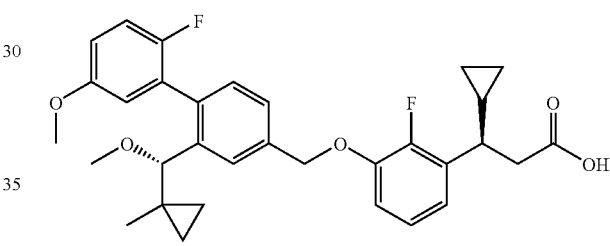

or

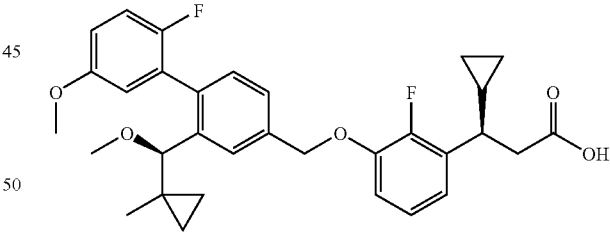

83.22

(3S)-3-Cyclopropyl-3-(2-fluoro-3-(((2'-fluoro-2-((S)-(1-methylcyclopropyl)(methyloxy)methyl)-5'-(methyloxy)-1,1'-biphenyl-4-yl)methyl)oxy)phenyl)propanoic acid or (3S)-3-cyclopropyl-3-(2-fluoro-3-(((2'-fluoro-2-((R)-(1-methylcyclopropyl)(methyloxy)methyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((S)-(1-methylcyclopropyl)(methyloxy)methyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((R)-(1-methylcyclopropyl)(methyloxy)methyl)-5'-(methyloxy)-1,1'-biphenyl-4-yl)methyl)oxy)phenyl)propanoic acid (83.22).

Example 83.22 was prepared from 83.22A according to the analogous method described in Example 83.18. MS ESI (neg.) m/e: 535.2 (M−H)⁺.

Example 83.23

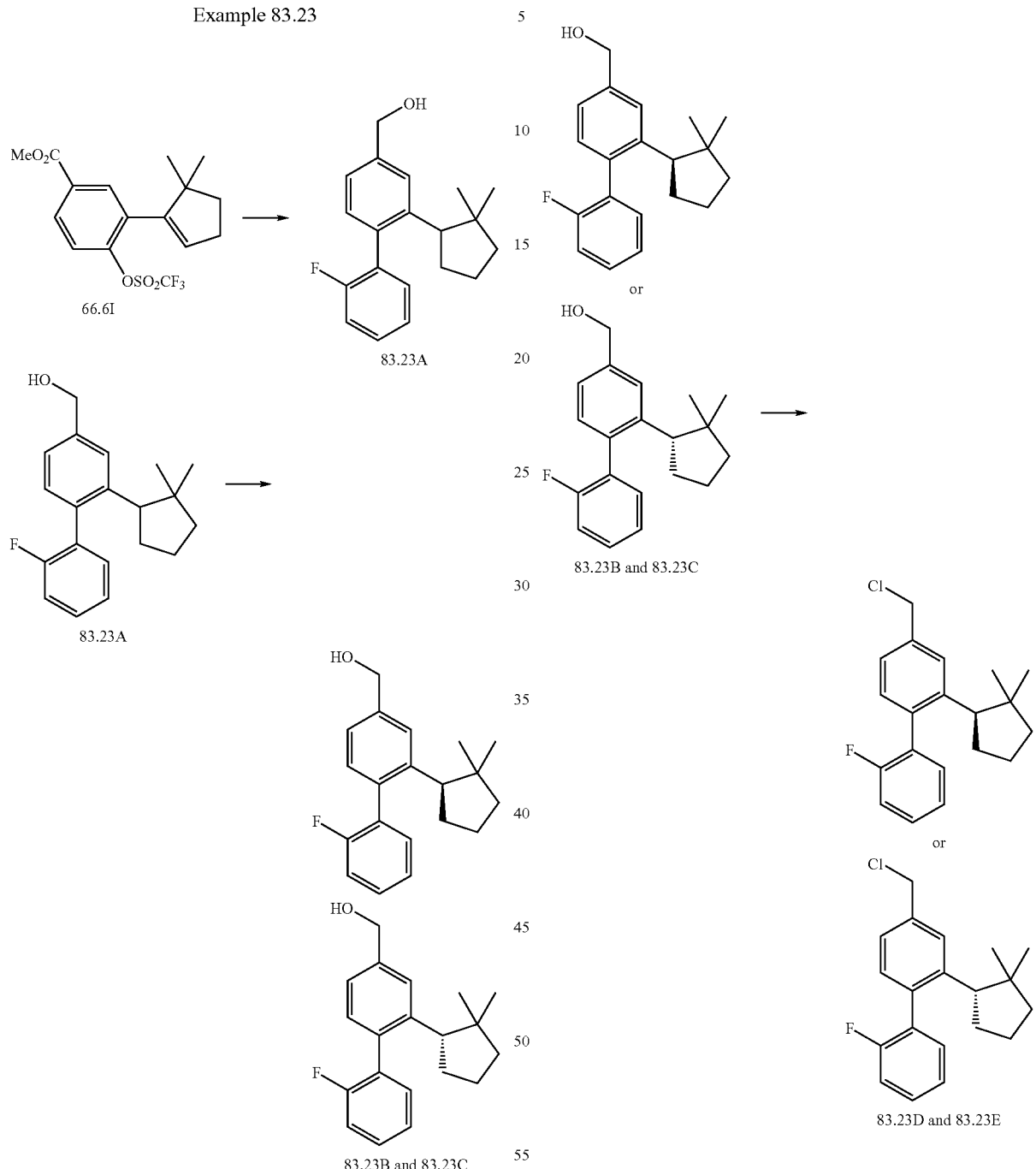

(2-((1R)-2,2-Dimethylcyclopentyl)-2'-fluoro-1,1'-biphenyl-4-yl)methanol and (2-((1S)-2,2-dimethylcyclopentyl)-2'-fluoro-1,1'-biphenyl-4-yl)methanol (83.2B and 83.23C). A Suzuki hydrogenation and reduction strategy was employed similar to that of Example 66.6 using 2-fluorophenylboronic acid (commercially available from Aldrich) to yield alcohol 83.23A. Chiral separation of 83.23A was accomplished on Chiracel-OD (4% IPA in hexane) to provide 83.23B (peak one) and 83.23C (peak two). Both enantiomers were used to synthesize example compounds, and both enantiomers gave active example compounds. However, the enantiomer corresponding to peak 2 provided the most active example compounds.

4-(Chloromethyl)-2-((1R)-2,2-dimethylcyclopentyl)-2'-fluoro-1,1'-biphenyl or 4-(chloromethyl)-2-((1S)-2,2-dimethylcyclopentyl)-2'-fluoro-1,1'-biphenyl (83.23D or 83.23E). To a stirred solution of 83.23B or 83.23C (0.150 g, 0.50 mmol) in DCM (2.5 mL) and DMF (0.0039 mL) at 0° C. was added thionyl chloride (0.073 mL, 1.0 mmol). The reaction was then stirred at room temperature for 1.5 hours. Next, the reaction mixture was concentrated in vacuo. The product was purified on silica gel (0-10% EtOAc in hexanes) to yield 83.23D or 83.23E as a colorless oil (0.140 g, 88% yield).

(3S)-3-Cyclopropyl-3-(3-(((2-((1R)-2,2-dimethylcyclopentyl)-2'-fluoro-1,1'-biphenyl-4-yl)methyl)oxy)-2-fluorophenyl)propanoic acid or (3S)-3-cyclopropyl-3-(3-(((2-((1S)-2,2-dimethylcyclopentyl)-2'-fluoro-1,1'-biphenyl-4-yl)methyl)oxy)-2-fluorophenyl)propanoic acid or (3R)-3-cyclopropyl-3-(3-(((2-((1R)-2,2-dimethylcyclopentyl)-2'-fluoro-1,1'-biphenyl-4-yl)methyl)oxy)-2-fluorophenyl) propanoic acid or (3R)-3-cyclopropyl-3-(3-(((2-((1S)-2,2-dimethylcyclopentyl)-2'-fluoro-1,1'-biphenyl-4-yl)methyl)oxy)-2-fluorophenyl)propanoic acid (83.23). The alkylation and hydrolysis were conducted in an analogous manner to Example 66.6 (using 83.B and 83.23D or 83.23E derived from peak two from the chiral separation of 83.23A from the OD-column, described herein) to yield 83.23 (0.0373 g, 71% yield over the two steps). MS ESI (neg.) m/e: 503.3 (M–H)$^+$.

Example 83.24

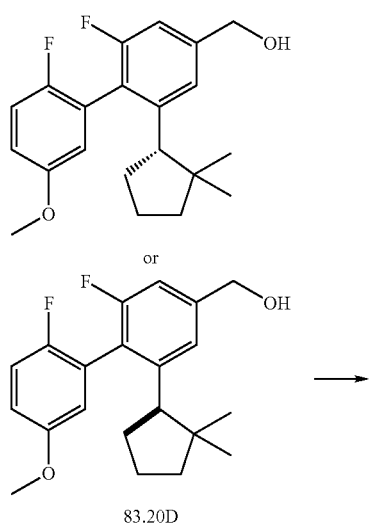

83.20D 4-(Chloromethyl)-2-((1R)-2,2-dimethylcyclopentyl)-2',6-difluoro-5'-(methyloxy)-1,1'-biphenyl or 4-(chloromethyl)-2-((1S)-2,2-dimethylcyclopentyl)-2',6-difluoro-5'-(methyloxy)-1,1'-biphenyl (83.24A). To a solution of 83.20D (0.1492 g, 0.431 mmol) in dry DCM (4.5 mL) and dry DMF (0.035 mL) was added thionyl chloride (0.063 mL, 0.864 mmol) at 0° C. The resulting solution was warmed to room temperature and monitored with TLC and LCMS. After 20 hours, the reaction was concentrated and then purified by silica gel flash chromatography (0-5% EtOAc/hexane) to afford 83.24A which was used without further purification (117.1 mg, 74% yield). 1H NMR (400 MHz, CDCl$_3$) δ ppm 7.18 (1H, d, J=1.6 Hz), 7.13 (2H, m), 6.95 (1H, m), 6.81 (1H, m), 4.68 (2H, m), 3.85 (3H, m), 2.73 (1H, ddd, J=10.3, 8.3, 1.8 Hz), 2.18 (1H, m), 2.01 (1H, m), 1.80 (1H, d, J=4.3 Hz), 1.72 (3H, m), 1.46 (1H, m), 0.78 (3H, s), 0.64 (3H, s).

(3S)-3-Cyclopropyl-3-(3-(((2-((1R)-2,2-dimethylcyclopentyl)-2',6-difluoro-5'-(methyloxy)-1,1'-biphenyl-4-yl)methyl)oxy)-2-fluorophenyl)propanoic acid or (3S)-3-cyclopropyl-3-(3-(((2-((1S)-2,2-dimethylcyclopentyl)-2',6-difluoro-5'-(methyloxy)-1,1'-biphenyl-4-yl)methyl)oxy)-2-fluorophenyl)propanoic acid or (3R)-3-cyclopropyl-3-(3-(((2-((1R)-2,2-dimethylcyclopentyl)-2',6-difluoro-5'-(methyloxy)-1,1'-biphenyl-4-yl)methyl)oxy)-2-fluorophenyl)propanoic acid or (3R)-3-cyclopropyl-3-(3-(((2-((1S)-2,2-dimethylcyclopentyl)-2',6-difluoro-5'-(methyloxy)-1,1'-biphenyl-4-yl)methyl)oxy)-2-fluorophenyl)propanoic acid (83.24). The alkylation and hydrolysis were conducted in an analogous manner to Example 66.6 (using 83.B and 83.24A derived from peak two from the chiral separation of 83.20B on the OJ-column, described herein) to yield 83.24. $^1$H NMR (500 MHz, CDCl$_3$) δ ppm 7.23 (1H, s), 7.12 (1H, dd, J=9.7, 1.6 Hz), 7.07 (1H, t, J=8.8 Hz), 7.03 (1H, m), 6.93 (3H, m), 6.78 (1H, dd, J=5.5, 3.1 Hz), 5.19 (2H, m), 3.79 (3H, s), 2.86 (2H, d, J=7.3 Hz), 2.76 (2H, m), 2.19 (1H, m), 2.04 (1H, m), 1.86 (1H, m), 1.71 (1H, m), 1.57 (1H, m), 1.43 (1H, m), 1.20 (1H, m), 0.73 (3H, s), 0.65 (4H, m), 0.46 (1H, m), 0.34 (1H, dq, J=9.8, 4.8 Hz), 0.20 (1H, dq, J=9.6, 4.9 Hz). MS ESI (neg.) m/e: 551.1 (M–H)$^+$.

Example 83.25

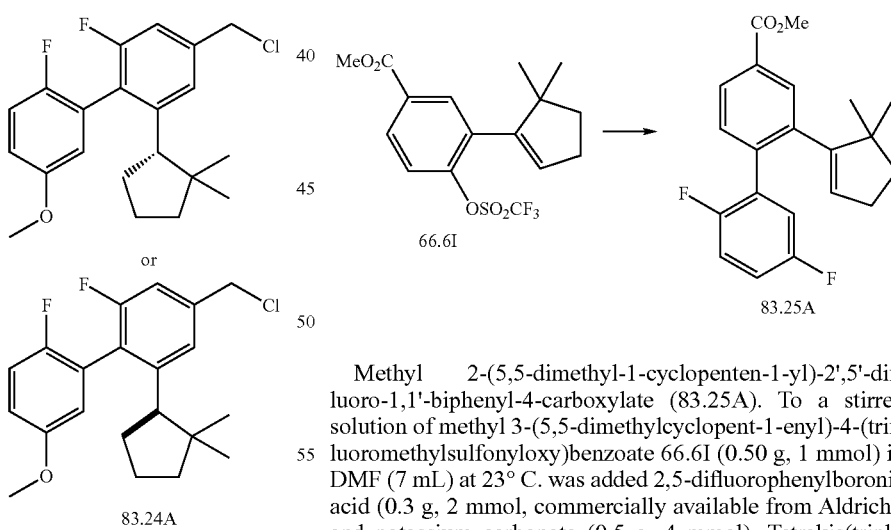

Methyl 2-(5,5-dimethyl-1-cyclopenten-1-yl)-2',5'-difluoro-1,1'-biphenyl-4-carboxylate (83.25A). To a stirred solution of methyl 3-(5,5-dimethylcyclopent-1-enyl)-4-(trifluoromethylsulfonyloxy)benzoate 66.6I (0.50 g, 1 mmol) in DMF (7 mL) at 23° C. was added 2,5-difluorophenylboronic acid (0.3 g, 2 mmol, commercially available from Aldrich), and potassium carbonate (0.5 g, 4 mmol). Tetrakis(triphenylphosphine)palladium (0.2 g, 0.1 mmol) was then added to the mixture. The mixture was heated to 90° C. and the reaction was further stirred for 23 hours. The reaction was then cooled to room temperature, diluted with brine and extracted three times with EtOAc. After drying over anhydrous magnesium sulfate and filtering, the organic solvent was removed under reduced pressure and the product was purified on silica gel (0-10% EtOAc in hexanes) to yield 83.25A as a colorless oil (0.42 g, 93% yield).

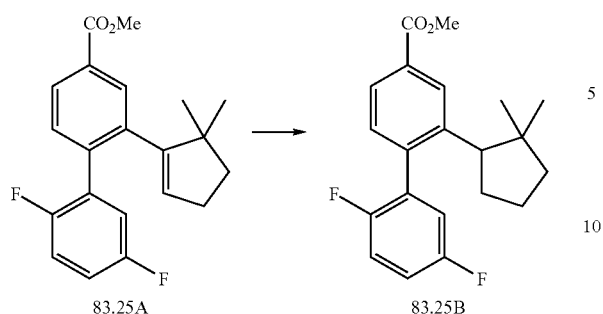

Methyl 2-(2,2-dimethylcyclopentyl)-2',5'-difluoro-1,1'-biphenyl-4-carboxylate (83.25B). To a stirred solution of 83.25A (0.420 g, 1 mmol) in MeOH (5 mL) at 23° C. was added palladium on carbon (0.1 g). The reaction was placed under an atmosphere of hydrogen and stirred for 18 hours. The reaction mixture was then filtered and concentrated in vacuo. The product was purified on silica gel (0-10% EtOAc in hexanes) to yield 83.25B as a colorless oil (0.420 g, 99% yield)

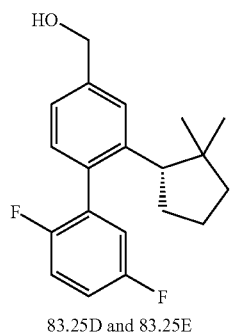

(2-((1R)-2,2-Dimethylcyclopentyl)-2',5'-difluoro-1,1'-biphenyl-4-yl)methanol and (2-((1S)-2,2-dimethylcyclopentyl)-2',5'-difluoro-1,1'-biphenyl-4-yl)methanol (83.25D and 83.25E). To a stirred solution of 83.25B (0.420 g, 1.2 mmol) in THF (10.00 mL) at 0° C. was added LAH (2.4 mL, 2.4 mmol, 1.0M). The reaction was stirred for one hour and then 1N NaOH(aq) was added to quench the reaction. The reaction was extracted three times with EtOAc. After drying over anhydrous magnesium sulfate and filtering, the organic solvent was removed under reduced pressure and the product was purified on silica gel (0-20% EtOAc in hexanes) to yield 83.25C as a colorless oil (0.380 g, 98% yield). Chiral separation of 83.25C was accomplished on Chiracel-OD (4% IPA in hexane) to provide 83.25D (peak one) and 83.25E (peak two). Both enantiomers were used to synthesize example compounds, and both enantiomers gave active example compounds. However, the enantiomer corresponding to peak 2 provided the most active example compounds.

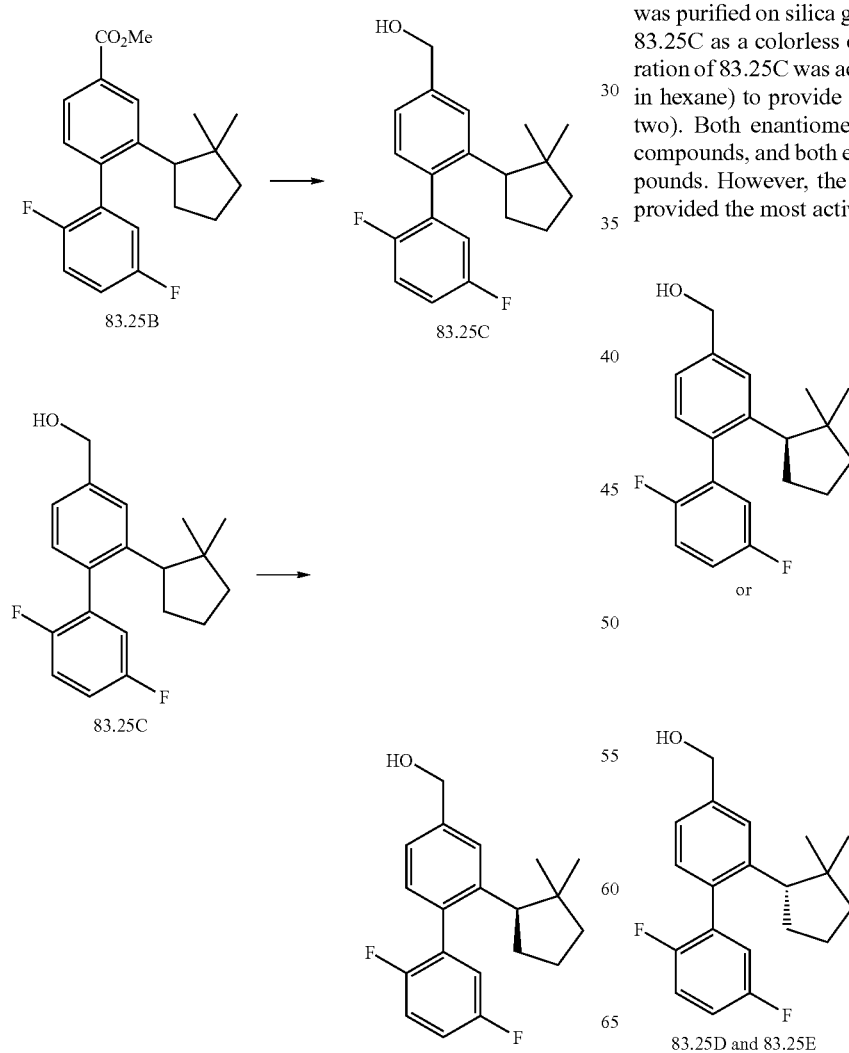

-continued

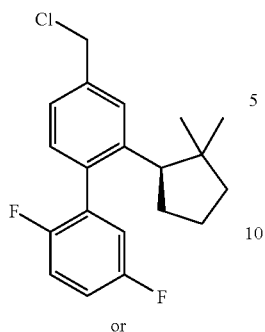

or

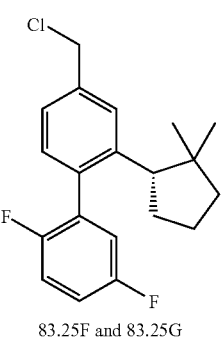

83.25F and 83.25G 4-(Chloromethyl)-2-((1R)-2,2-dimethylcyclopentyl)-2',5'-difluoro-1,1'-biphenyl or 4-(chloromethyl)-2-((1R)-2,2-dimethylcyclopentyl)-2',5'-difluoro-1,1'-biphenyl (83.25F or 83.25G). To a stirred solution of 83.25D or 83.25E (0.170 g, 0.54 mmol) in DCM (2.7 mL) and DMF (0.0042 mL) at 0° C. was added thionyl chloride (0.078 mL, 1.1 mmol). Stirring was continued at room temperature for 1.5 hours. The reaction mixture was then concentrated in vacuo. The product was then purified on silica gel (0-10% EtOAc in hexanes) to yield 83.25F or 83.25G as a colorless oil (0.150 g, 83% yield).

(3S)-3-Cyclopropyl-3-(3-(((2-((1R)-2,2-dimethylcyclopentyl)-2',5'-difluoro-1,1'-biphenyl-4-yl)methyl)oxy)-2-fluorophenyl)propanoic acid or (3S)-3-cyclopropyl-3-(3-(((2-((1S)-2,2-dimethylcyclopentyl)-2',5'-difluoro-1,1'-biphenyl-4-yl)methyl)oxy)-2-fluorophenyl)propanoic acid or (3R)-3-cyclopropyl-3-(3-(((2-((1R)-2,2-dimethylcyclopentyl)-2',5'-difluoro-1,1'-biphenyl-4-yl)methyl)oxy)-2-fluorophenyl)propanoic acid or (3R)-3-cyclopropyl-3-(3-(((2-((1S)-2,2-dimethylcyclopentyl)-2',5'-difluoro-1,1'-biphenyl-4-yl)methyl)oxy)-2-fluorophenyl)propanoic acid (83.25). The alkylation and hydrolysis were conducted in an analogous manner to Example 66.6 (using 83.B and 83.25F or 83.25G derived from peak two from the chiral separation of 83.25C from the OD-column, described herein) to yield 83.25 (0.0464 g, 84% yield over the two steps). MS ESI (neg.) m/e: 521.2 (M−H)+.

Example 83.26

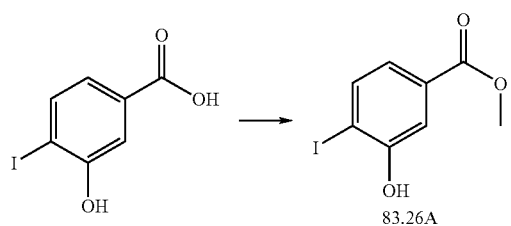

Methyl 3-hydroxy-4-iodobenzoate (83.26A). To a round bottom flask containing 3-hydroxy-4-iodobenzoic acid (1.0346 g, 3.92 mmol, commercially available from Aldrich) was added a cold solution of MeOH (15 mL) and sulfuric acid (0.5 mL). The mixture was heated to 80° C. and monitored with TLC. After 20.5 hours, the solvent was removed and the residue was diluted with EtOAc. The organic phase was washed carefully two times with saturated aqueous NaHCO₃, once with brine, and then dried over anhydrous sodium sulfate. After filtration, the organic solvent was removed in vacuo to afford 83.26A as a white solid (1.0938 g, 100% yield). $^1$H NMR (400 MHz, CDCl₃) δ ppm 7.76 (1H, d, J=8.2 Hz), 7.64 (1H, d, J=2.0 Hz), 7.34 (1H, dd, J=8.2, 2.0 Hz), 3.92 (3H, s).

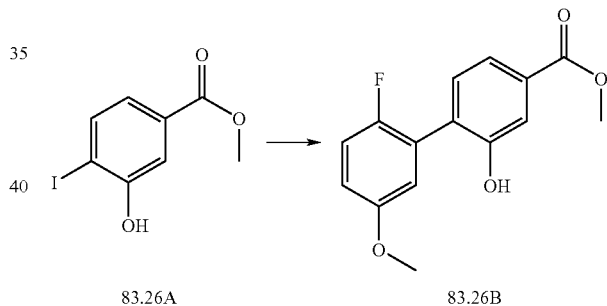

Methyl 2'-fluoro-2-hydroxy-5'-(methyloxy)-1,1'-biphenyl-4-carboxylate (83.26B). To a round bottom flask containing 83.26A (1.0938 g, 3.93 mmol) and 2-fluoro-5-methoxyphenylboronic acid (0.7053 g, 4.15 mmol) (commercially available from Aldrich) was added a premixed solution of 1:1 isopropanol (6 mL) and water (6 mL). After stirring at room temperature for 5 minutes, sodium carbonate (0.5526 g, 5.21 mmol) and palladium, 10 wt % on activated carbon (0.0725 g, 0.0681 mmol) were added, and the reaction was then heated to 65° C. After 17 hours, the reaction was cooled to room temperature and then filtered through Celite. The filtrate was concentrated and then saturated aqueous ammonium chloride was added. After extracting three times with EtOAc, the organic solvent was removed under reduced pressure. The residue was purified by silica gel flash chromatography (0-40% EtOAc/hexane) to afford 83.26B (834.3 mg, 77% yield). $^1$H NMR (500 MHz, CDCl₃) δ ppm 7.69 (2H, td, J=7.7, 1.7 Hz), 7.33 (1H, d, J=7.8 Hz), 7.14 (1H, t, J=9.0 Hz), 6.94 (1H, dt, J=9.0, 3.5 Hz), 6.89 (1H, dd, J=5.9, 3.2 Hz), 5.42 (1H, s), 3.94 (3H, s), 3.82 (3H, s).

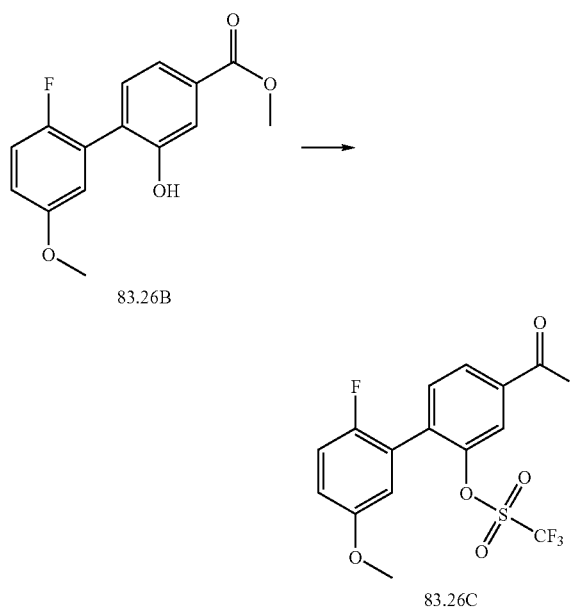

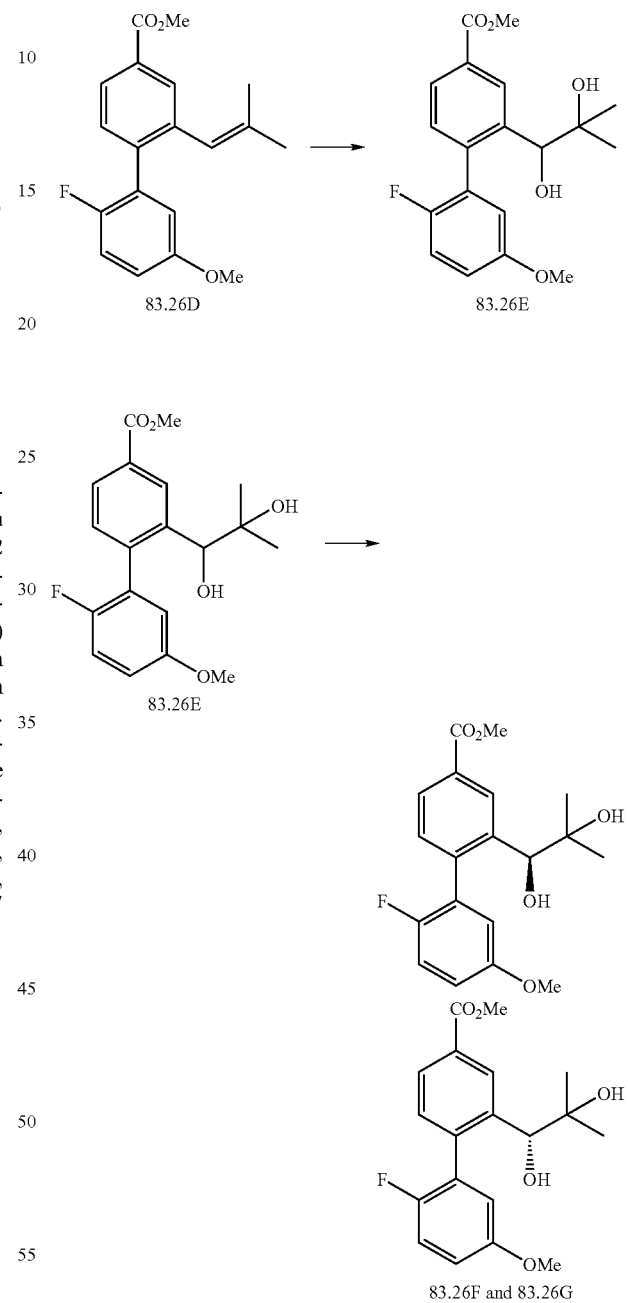

diluted with brine and extracted three times with EtOAc. After drying over anhydrous magnesium sulfate and filtering, the organic solvent was removed under reduced pressure and the product was then purified on silica gel (0-10% EtOAc in hexanes) to yield 83.26D as a colorless oil (0.280 g, 73% yield).

Methyl 2'-fluoro-5'-(methyloxy)-2-(((trifluoromethyl)sulfonyl)oxy)-1,1'-biphenyl-4-carboxylate (83.26C). To a stirred solution of 83.26B (0.8343 g, 3 mmol) in dry DCM (12 mL) was added TEA (0.85 mL, 6 mmol) and 4-dimethylaminopyridine (0.0378 g, 0.3 mmol). After 20 minutes, N-phenyl-bis(trifluoromethanesulfonimide) (1.3097 g, 4 mmol) was added in portions. Upon complete addition, the solution was stirred at room temperature. After 3 hours, the reaction was diluted with brine and extracted three times with DCM. After drying over anhydrous magnesium sulfate and filtration, the organic solvent was removed under reduced pressure and the residue was then purified by silica gel flash chromatography (0-25% EtOAc/hexane) to afford 83.26C (1.0238 g, 83% yield). $^1$H NMR (500 MHz, CDCl$_3$) δ ppm 8.14 (1H, dd, J=8.1, 1.7 Hz), 8.06 (1H, d, J=1.7 Hz), 7.57 (1H, d, J=8.1 Hz), 7.13 (1H, t, J=9.2 Hz), 6.97 (1H, ddd, J=8.7, 3.9, 3.5 Hz), 6.87 (1H, dd, J=5.7, 3.1 Hz), 3.99 (3H, s), 3.83 (3H, s).

Methyl 2'-fluoro-5'-(methyloxy)-2-(2-methyl-1-propenyl)-1,1'-biphenyl-4-carboxylate (83.26D). To a stirred solution of 83.26C (0.500 g, 1.2 mmol) in DMF (6.1 mL) at 23° C. was added 2-methylprop-1-enylboronic acid (0.24 g, 2.4 mmol, commercially available from Synthonix), and potassium carbonate (0.51 g, 3.7 mmol). Tetrakis(triphenylphosphine)palladium (0.071 g, 0.061 mmol) was then added to the mixture. The mixture was heated to 90° C. and stirred for 15 hours. The reaction was then cooled to room temperature, Methyl 2-((1S)-1,2-dihydroxy-2-methylpropyl)-2'-fluoro-5'-(methyloxy)-1,1'-biphenyl-4-carboxylate and Methyl 2-((1R)-1,2-dihydroxy-2-methylpropyl)-2'-fluoro-5'-(methyloxy)-1,1'-biphenyl-4-carboxylate (83.26F and 83.26G). To a stirred solution of 83.26D (0.270 g, 0.86 mmol) in propan-2-one (10.00 mL) at 23° C. was added 4-methylmorpholine n-oxide monohydrate (0.12 g, 0.86 mmol), followed by osmium tetroxide (0.027 mL, 0.086 mmol). The reaction was then stirred for six hours and then concentrated in vacuo.

The product was purified on silica gel (0-10% EtOAc in hexanes) to yield 83.26E as a colorless oil (0.250 g, 84% yield). Chiral separation of 83.26E was accomplished on Chiracel-OD (5% IPA in hexane) to provide 83.26F (peak one) and 83.26G (peak two). Both enantiomers were used to synthesize example compounds, and both enantiomers gave active example compounds. However, the enantiomer corresponding to peak one provided the most active example compounds.

1.2 mmol). The reaction was then stirred at 50° C. for 16 hours and then cooled to room temperature. The reaction was diluted with brine and extracted three times with EtOAc. After drying over anhydrous magnesium sulfate and filtering, the organic solvent was removed under reduced pressure and the product was then purified on silica gel (0-10% EtOAc in hexanes) to yield 83.26H or 83.26I as a colorless oil (0.079 g, 70% yield).

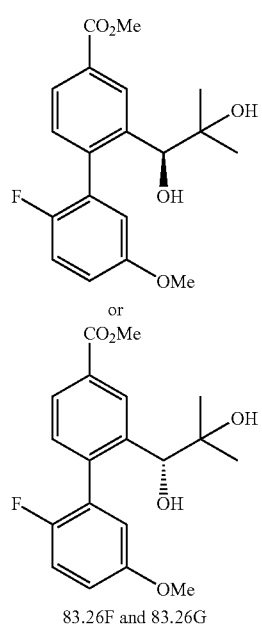

83.26F and 83.26G

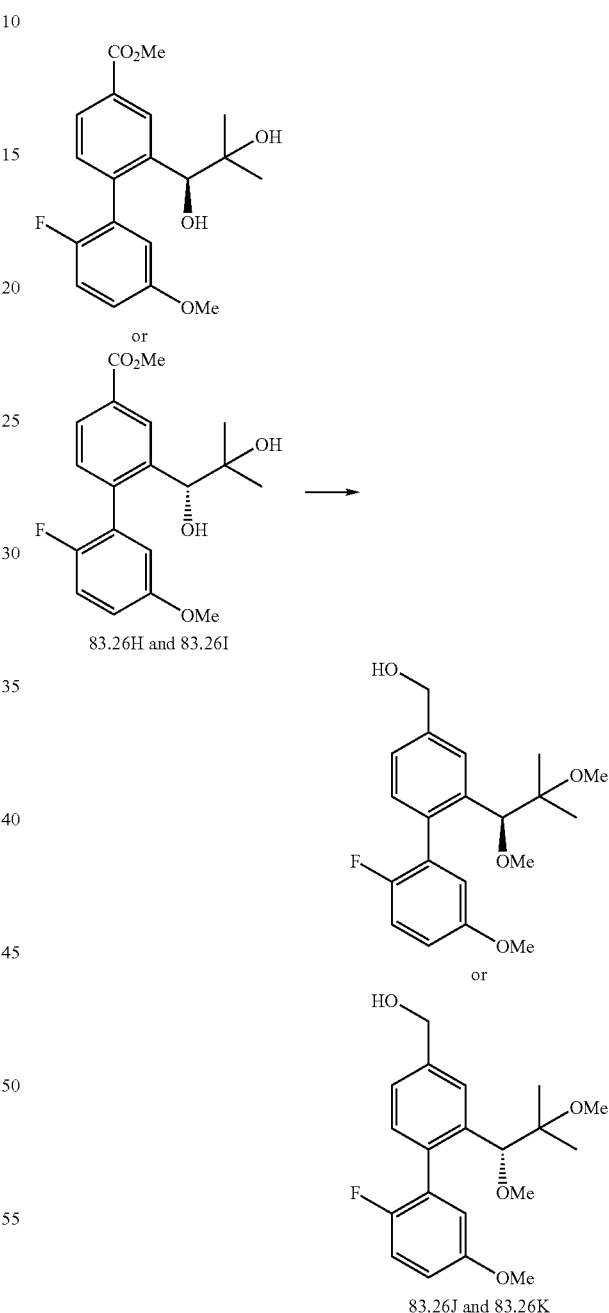

Methyl 2'-fluoro-2-((1S)-2-methyl-1,2-bis(methyloxy)propyl)-5'-(methyloxy)-1,1'-biphenyl-4-carboxylate or methyl 2'-fluoro-2-((1R)-2-methyl-1,2-bis(methyloxy)propyl)-5'-(methyloxy)-1,1'-biphenyl-4-carboxylate (83.26H and 83.26I). To a stirred solution of 83.26F or 83.26G (peak one from the chiral separation of 83.26E) (0.104 g, 0.30 mmol) in DMF (3.0 mL) at 23° C. was added iodomethane (0.074 mL, 1.2 mmol), followed by sodium hydride (0.029 g, (2'-Fluoro-2-((1S)-2-methyl-1,2-bis(methyloxy)propyl)-5'-(methyloxy)-1,1'-biphenyl-4-yl)methanol or (2'-fluoro-2-((1R)-2-methyl-1,2-bis(methyloxy)propyl)-5'-(methyloxy)-1,1'-biphenyl-4-yl)methanol (83.26J) or 83.26K. To a stirred solution of 83.26H or 83.26I (0.079 g, 0.21 mmol) in THF (3.00 mL, 0.21 mmol) at 0° C. was added LAH (0.42 mL, 0.42 mmol). The reaction was then stirred for two hours. Next, 1N NaOH(aq) was added to quench the reaction. The reaction was extracted three times with EtOAc. After drying over anhydrous magnesium sulfate and filtering, the organic solvent was removed under reduced pressure and the product was then purified on silica gel (0-20% EtOAc in hexanes) to yield 83.26J or 83.26K as a colorless oil (0.058 g, 79% yield).

(3S)-3-Cyclopropyl-3-(2-fluoro-3-(((2'-fluoro-2-((1S)-2-methyl-1,2-bis(methyloxy)propyl)-5'-(methyloxy)-1,1'-biphenyl-4-yl)methyl)oxy)phenyl)propanoic acid or (3S)-3-cyclopropyl-3-(2-fluoro-3-(((2'-fluoro-2-((1R)-2-methyl-1,2-bis(methyoxy)propyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((1S)-2-methyl-1,2-bis(methyloxy)propyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((1R)-2-methyl-1,2-bis(methyloxy)propyl)-5'-(methyloxy)-1,1'-biphenyl-4-yl)methyl)oxy)phenyl)propanoic acid (83.26). The Mitsunobu reaction and hydrolysis were conducted in an analogous manner to Example 69.14 (using 83B and 83.26J or 83.26K derived from peak one from the chiral separation of 83.26E from the OD-column, described herein) to yield 83.26 (0.0681 g, 68% yield). MS ESI (neg.) m/e: 553.3 (M−H)+.

Example 83.27

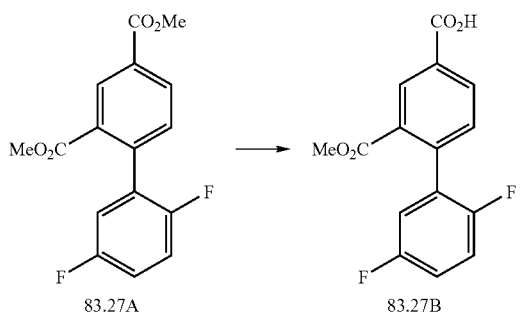

2',5'-Difluoro-2-((methyloxy)carbonyl)-1,1'-biphenyl-4-carboxylic acid (83.27B). To a stirred solution of 83.27A (0.800 g, 2.6 mmol) in THF (7.00 mL) and MeOH (7.00 mL) at 0° C. was slowly added potassium hydroxide (1.4 mL, 2.9 mmol) to maintain the temperature below 6° C. The reaction mixture was then allowed to warm to room temperature and stirred for 19 hours. The reaction was then acidified with 1N HCl and extracted three times with EtOAc. After drying over anhydrous magnesium sulfate and filtering, the organic solvent was removed under reduced pressure to yield 83.27B as a colorless solid (0.76 g, 100% yield).

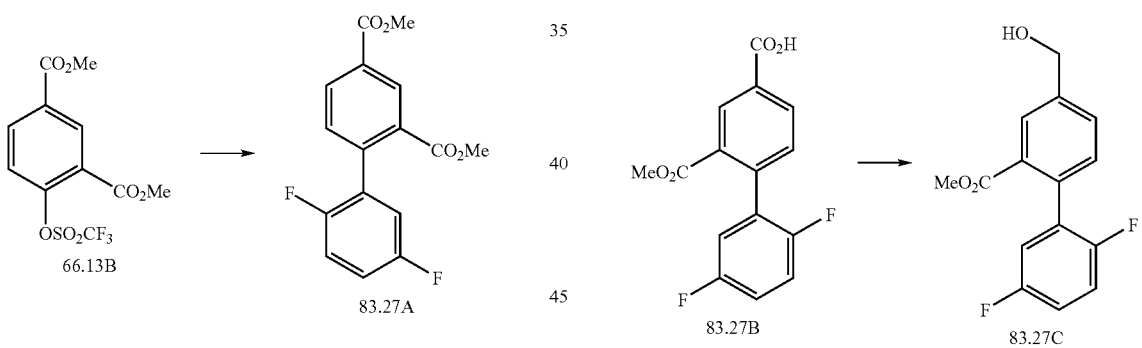

Dimethyl 2',5'-difluoro-1,1'-biphenyl-2,4-dicarboxylate (83.27A). To a stirred solution of dimethyl 4-(trifluoromethylsulfonyloxy)isophthalate 66.13B (1.00 g, 2.9 mmol) in DMF (5.8 mL) at 23° C. was added 2,5-difluorophenylboronic acid (0.69 g, 4.4 mmol) (commercially available from Aldrich), and potassium carbonate (1.2 g, 8.8 mmol). Tetrakis(triphenylphosphine)palladium (0.24 g, 0.20 mmol) was then added to the mixture. The mixture was heated to 90° C. and was stirred for 17 hours. The reaction was then cooled to room temperature, diluted with brine and extracted three times with EtOAc. After drying over anhydrous magnesium sulfate and filtering, the organic solvent was removed under reduced pressure and the product was then purified on silica gel (0-10% EtOAc in hexanes) to yield 83.27A as a colorless oil (0.800 g, 89% yield).

Methyl 2',5'-difluoro-4-(hydroxymethyl)-1,1'-biphenyl-2-carboxylate (83.27C). To a stirred solution of 83.27B (0.585 g, 2 mmol) in THF (20 mL) at 0° C. was added borane-THF (4 mL, 4 mmol, 1.0M). The reaction was warmed to 23° C. and stirring was continued for four hours. The reaction mixture was then concentrated in vacuo. The reaction was diluted with 1N HCl and extracted three times with EtOAc. After drying over anhydrous magnesium sulfate and filtering, the organic solvent was removed under reduced pressure and the product was then purified on silica gel (0-40% EtOAc in hexanes) to yield 83.27C as a colorless oil (0.485 g, 87% yield).

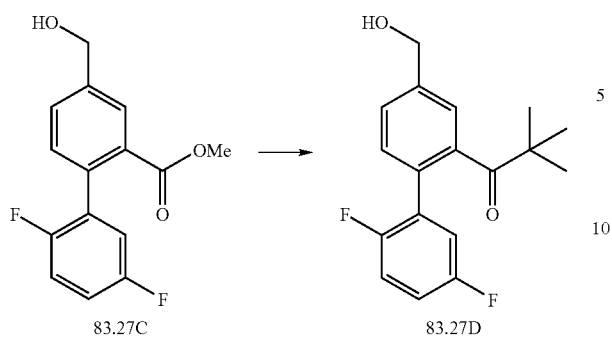

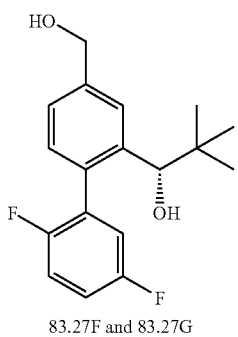

1-(2',5'-Difluoro-4-(hydroxymethyl)-1,1'-biphenyl-2-yl)-2,2-dimethyl-1-propanone (83.27D). To a stirred solution of 83.27C (0.485 g, 2 mmol) in THF (17 mL) at −78° C. was added tert butyl lithium (3 mL, 5 mmol, 1.7 M). The reaction was then stirred for 1.5 hours and then quenched with a saturated solution of ammonium chloride and extracted three times with EtOAc. After drying over anhydrous magnesium sulfate and filtering, the organic solvent was removed under reduced pressure and the product was then purified on silica gel (0-40% EtOAc in hexanes) to yield 83.27D as a colorless oil (0.450 g, 85% yield).

(1R)-1-(2',5'-Difluoro-4-(hydroxymethyl)-1,1'-biphenyl-2-yl)-2,2-dimethyl-1-propanol and (1S)-1-(2',5'-difluoro-4-(hydroxymethyl)-1,1'-biphenyl-2-yl)-2,2-dimethyl-1-propanol (83.27F and 83.27G). To a stirred solution of 83.27D (0.286 g, 0.9 mmol) in THF (5 mL) at 0° C. was added LAH (1 mL, 1 mmol, 1.0 M). The reaction was then stirred for 3 hours. 1N NaOH(aq) was added to quench the reaction, and the mixture was extracted three times with EtOAc. After drying over anhydrous magnesium sulfate and filtering, the organic solvent was removed under reduced pressure and the product was then purified on silica gel (0-20% EtOAc in hexanes) to yield 83.27E as a colorless oil (0.250 g, 87% yield). Chiral separation of 83.27E was accomplished on Chiracel-OD (4% IPA in hexane) to provide 83.27F (peak one-20.4 mins) and 83.27G (peak two-26.1 mins). Both enantiomers were used to synthesize example compounds, and both enantiomers gave active example compounds. However, the enantiomer corresponding to peak 2 provided the most active example compounds.[1]

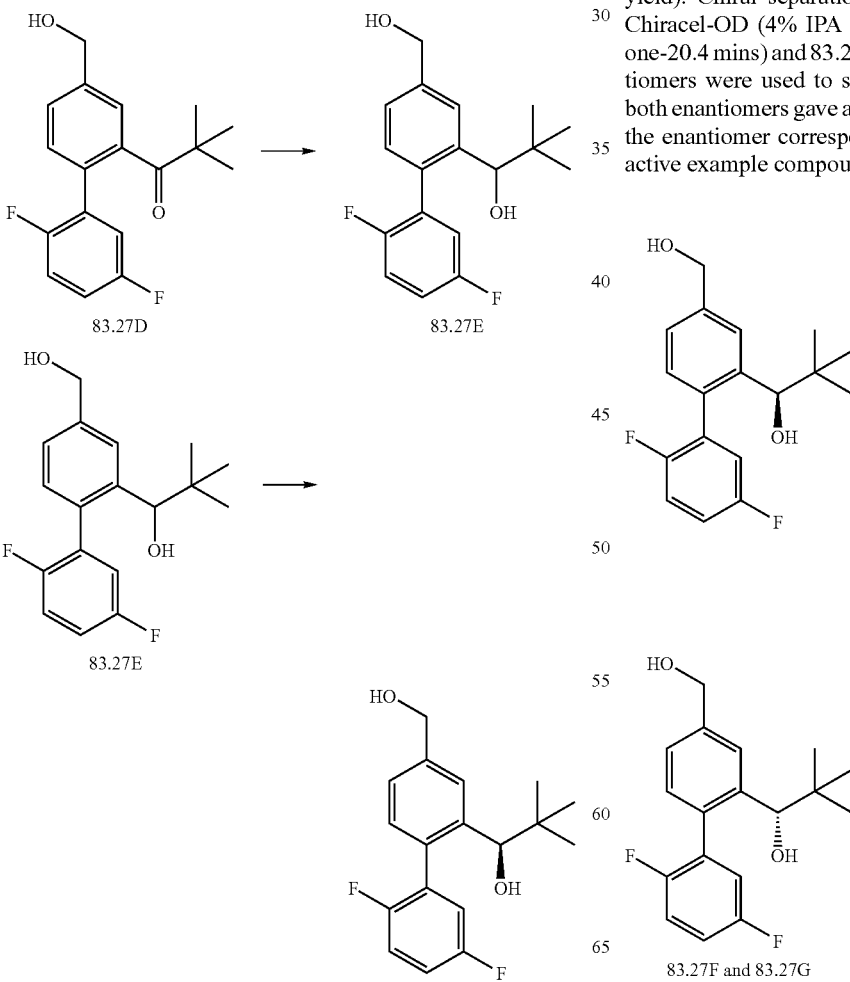

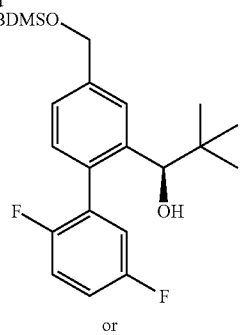

or

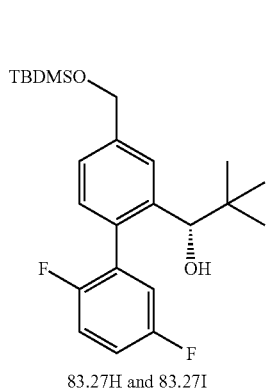

83.27H and 83.27I (1R)-1-(4-((((1,1-Dimethylethyl)(dimethyl)silyl)oxy)methyl)-2',5'-difluoro-1,1'-biphenyl-2-yl)-2,2-dimethyl-1-propanol or (1S)-1-(4-((((1,1-dimethylethyl)(dimethyl)silyl)oxy)methyl)-2',5'-difluoro-1,1'-biphenyl-2-yl)-2,2-dimethyl-1-propanol (83.27H or 83.27I). To a stirred solution of 83.27F or 83.27G (0.097 g, 0.3 mmol) in DCM (3 mL) at 23° C. was added tert-butyldimethylsilyl chloride (0.06 mL, 0.4 mmol), followed by TEA (0.05 mL, 0.4 mmol) and DMAP (0.004 g, 0.03 mmol). The reaction was then stirred for 24 hours and then concentrated in vacuo. The reaction was extracted three times with EtOAc. After drying over anhydrous magnesium sulfate and filtering, the organic solvent was removed under reduced pressure and the product was then purified on silica gel (0-20% EtOAc in hexanes) to yield 83.27H or 83.27G as a colorless oil (0.130 g, 98% yield).

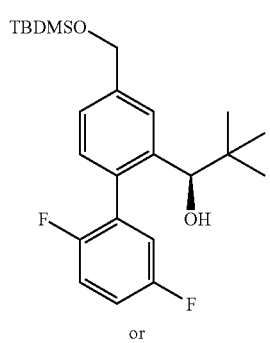

or

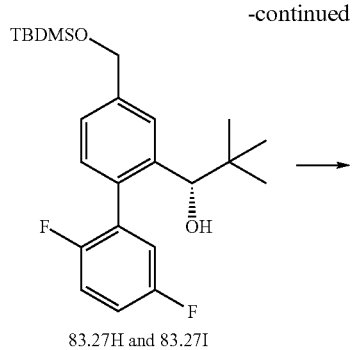

83.27H and 83.27I

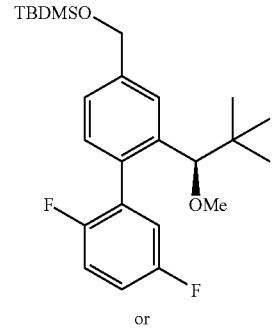

or

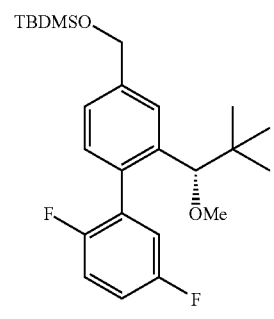

83.27J and 83.27K (1,1-Dimethylethyl)(((2-((1R)-2,2-dimethyl-1-(methyloxy)propyl)-2',5'-difluoro-1,1'-biphenyl-4-yl)methyl)oxy)dimethylsilane or (1,1-dimethylethyl)(((2-((1S)-2,2-dimethyl-1-(methyloxy)propyl)-2',5'-difluoro-1,1'-biphenyl-4-yl)methyl)oxy)dimethylsilane (83.27J or 83.27K). To a stirred solution of 83.27H or 83.27I (0.130 g, 0.31 mmol) in DMF (3.1 mL) at 23° C. was added iodomethane (0.038 mL, 0.62 mmol), followed by sodium hydride (0.015 g, 0.62 mmol). The reaction was then stirred at 50° C. for 16 hours, diluted with water and extracted three times with EtOAc. After drying over anhydrous magnesium sulfate and filtering, the organic solvent was removed under reduced pressure and the product was then purified on silica gel (0-5% EtOAc in hexanes) to yield 83.27J or 83.27K as a colorless oil (0.125 g, 93% yield).

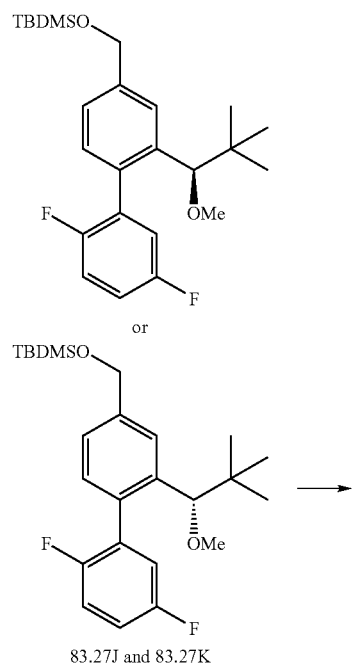

83.27J and 83.27K

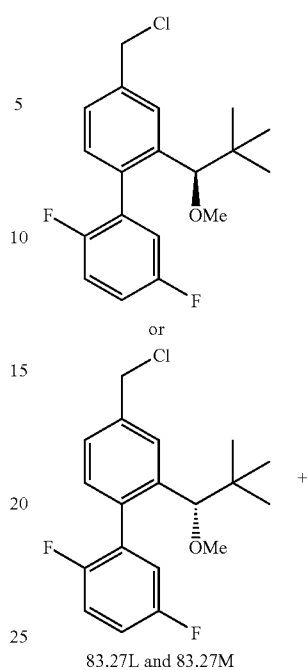

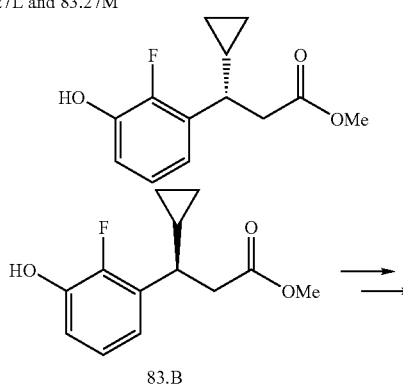

83.27L and 83.27M 4-(Chloromethyl)-2-((1R)-2,2-dimethyl-1-(methyloxy)propyl)-2',5'-difluoro-1,1'-biphenyl or 4-(chloromethyl)-2-((1S)-2,2-dimethyl-1-(methyloxy)propyl)-2',5'-difluoro-1,1'-biphenyl (83.27L or 83.27M). To a stirred solution of 83.27J or 83.27K (0.125 g, 0.29 mmol) in DCM (2.9 mL) and DMF (0.022 mL) at 0° C. was added thionyl chloride (0.042 mL, 0.58 mmol). The reaction was then stirred at room temperature for three hours. The reaction mixture was then concentrated in vacuo, and the product was then purified on silica gel (0-10% EtOAc in hexanes) to yield 83.27L or 83.27M as a colorless oil (0.097 g, 100% yield).

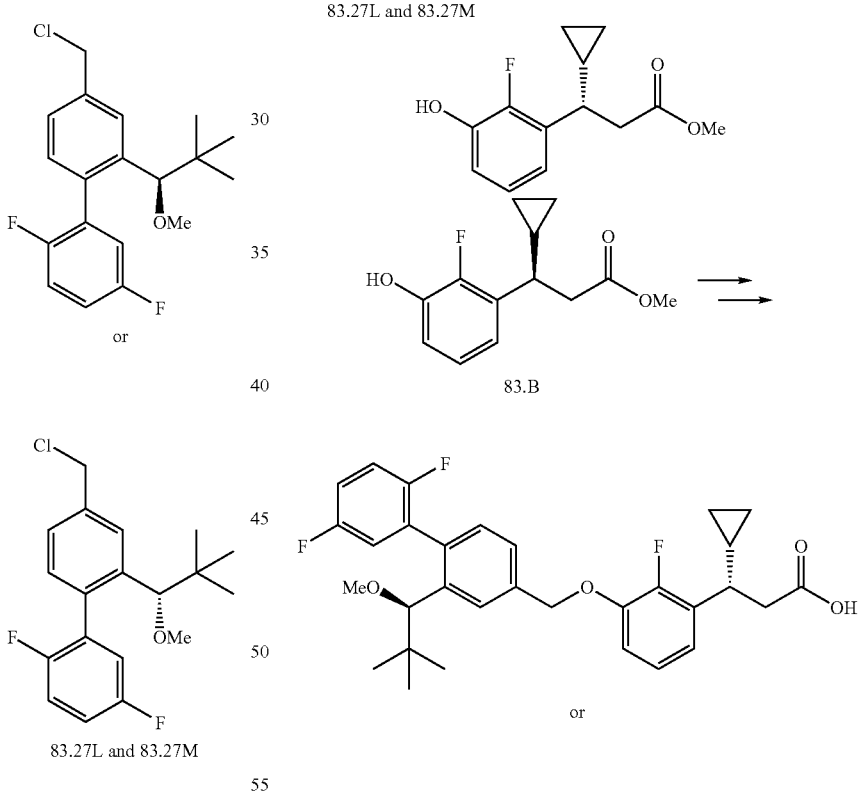

83.B

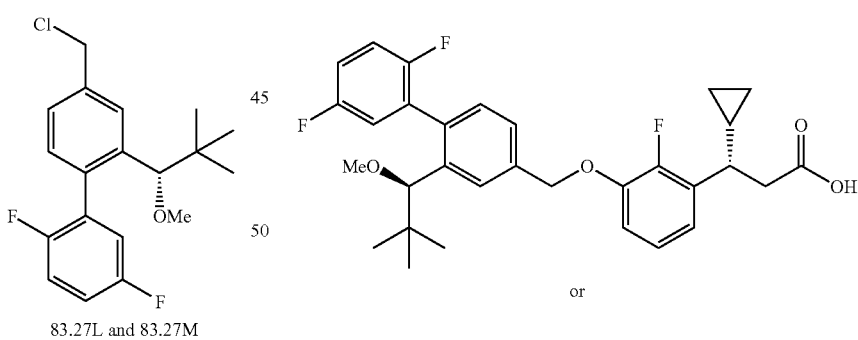

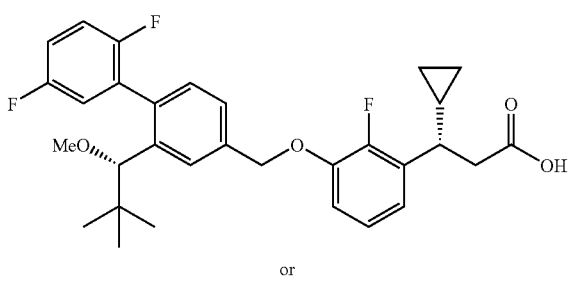

-continued

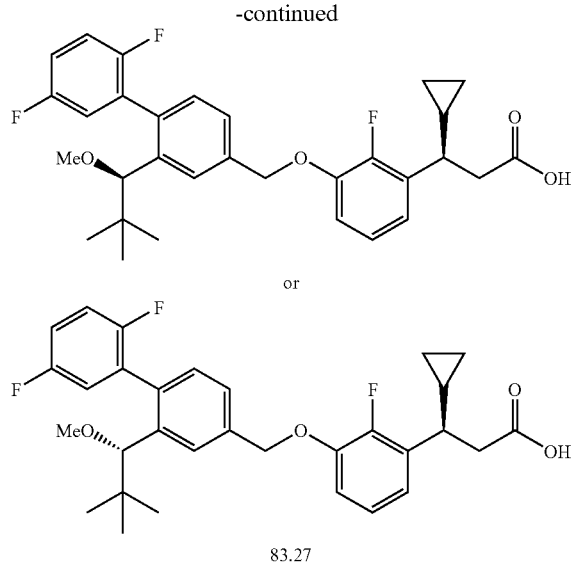

83.27

(3S)-3-cyclopropyl-3-(3-(((2-((1R)-2,2-dimethyl-1-(methyloxy)propyl)-2',5'-difluoro-1,1'-biphenyl-4-yl)methyl)oxy)-2-fluorophenyl)propanoic acid or (3S)-3-cyclopropyl-3-(3-(((2-((1S)-2,2-dimethyl-1-(methyloxy)propyl)-2',5'-difluoro-1,1'-biphenyl-4-yl)methyl)oxy)-2-fluorophenyl)propanoic acid or (3R)-3-cyclopropyl-3-(3-(((2-((1R)-2,2-dimethyl-1-(methyloxy)propyl)-2',5'-difluoro-1,1'-biphenyl-4-yl)methyl)oxy)-2-fluorophenyl)propanoic acid or (3R)-3-cyclopropyl-3-(3-(((2-((1S)-2,2-dimethyl-1-(methyloxy)propyl)-2',5'-difluoro-1,1'-biphenyl-4-yl)methyl)oxy)-2-fluorophenyl)propanoic acid (83.27). The alkylation and hydrolysis were conducted in an analogous manner to Example 66.6 (using 83.B and 83.27L or 83.27M derived from peak two from the chiral separation of 83.27E from the OD-column, described herein) to yield 83.27N or 83.27O (0.0377 g, 68% yield). MS ESI (neg.) m/e: 525.3 (M−H)⁺.

Example 83.28

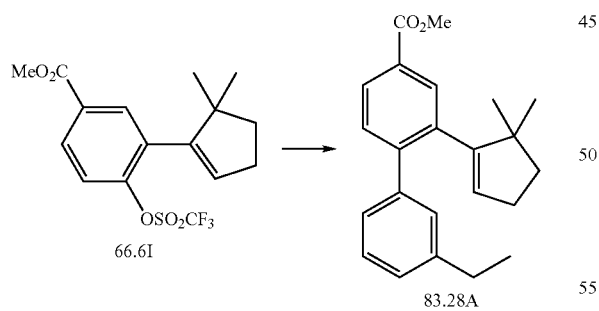

Methyl 2-(5,5-dimethyl-1-cyclopenten-1-yl)-3'-ethyl-1,1'-biphenyl-4-carboxylate (83.28A). To a stirred solution of methyl 3-(5,5-dimethylcyclopent-1-enyl)-4-(trifluoromethylsulfonyloxy)benzoate 66.6I (0.50 g, 1 mmol) in DMF (7 mL) at 23° C. was added 3-ethylphenylboronic acid (0.3 g, 2 mmol) (commercially available from Aldrich), and potassium carbonate (0.5 g, 4 mmol). Tetrakis(triphenylphosphine)palladium (0.2 g, 0.1 mmol) was then added to the mixture. The mixture was heated to 90° C. and the reaction was stirred for 24 hours. The reaction was then cooled to room temperature, diluted with brine and extracted three times with EtOAc. After drying over anhydrous magnesium sulfate and filtering, the organic solvent was removed under reduced pressure and the product was then purified on silica gel (0-10% EtOAc in hexanes) to yield 83.28A as a colorless oil (0.41 g, 93% yield).

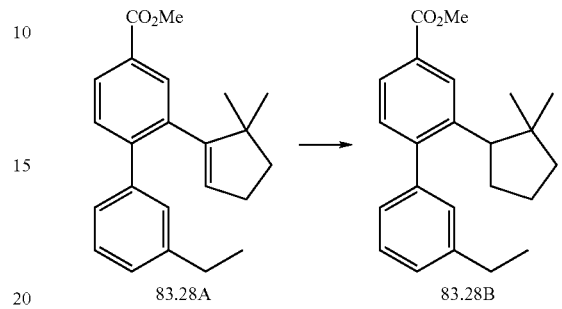

Methyl 2-(2,2-dimethylcyclopentyl)-3'-ethyl-1,1'-biphenyl-4-carboxylate (83.28B). To a stirred solution of 83.28A (0.410 g, 1 mmol) in MeOH (5 mL) at 23° C. was added palladium on carbon (0.1 g, 1 mmol). The reaction was placed under an atmosphere of hydrogen and stirred for 18 hours. The reaction mixture was then filtered and the filtrate was concentrated in vacuo. The product was purified on silica gel (0-10% EtOAc in hexanes) to yield 83.28B as a colorless oil (0.410 g, 99% yield).

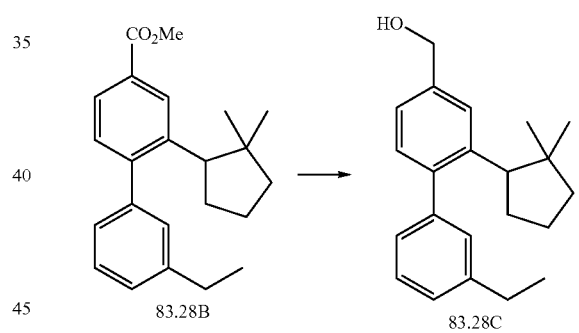

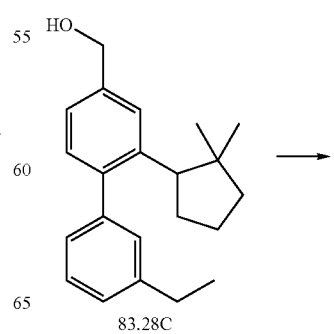

-continued

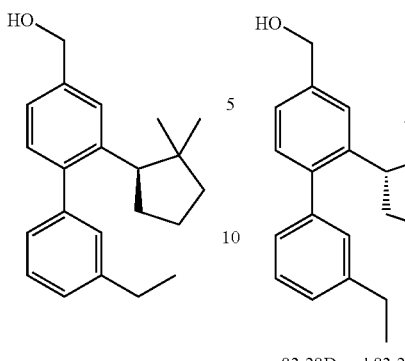

83.28D and 83.28E

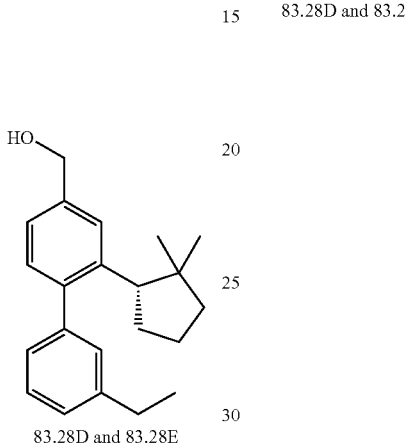

83.28D and 83.28E (2-((1R)-2,2-Dimethylcyclopentyl)-3'-ethyl-1,1'-biphenyl-4-yl)methanol and (2-((1S)-2,2-dimethylcyclopentyl)-3'-ethyl-1,1'-biphenyl-4-yl)methanol (83.28D and 83.28E). To a stirred solution of 83.28B (0.410 g, 1.2 mmol) in THF (10.00 mL) at 0° C. was added LAH (2.4 mL, 2.4 mmol, 1.0M). The reaction was then stirred for 1.5 hours. 1 N NaOH (aq) was added to quench the reaction. The mixture was extracted three times with EtOAc. After drying over anhydrous magnesium sulfate and filtering, the organic solvent was removed under reduced pressure and the product was then purified on silica gel (0-20% EtOAc in hexanes) to yield 83.28C as a colorless oil (0.300 g, 80% yield). Chiral separation of 83.28C was accomplished on Chiracel-OD (4% IPA in hexane) to provide 83.28D (peak one) and 83.28E (peak two). Both enantiomers were used to synthesize example compounds, and both enantiomers gave active example compounds. However, the enantiomer corresponding to peak 2 provided the most active example compounds.

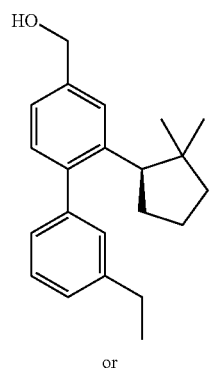

or

-continued

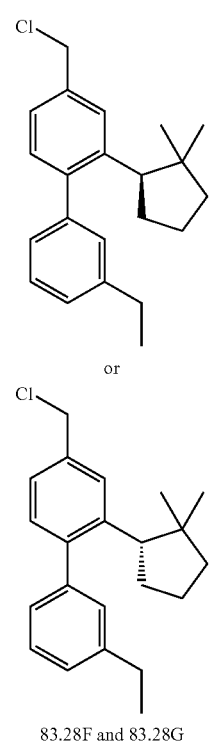

83.28F and 83.28G 4-(Chloromethyl)-2-((1R)-2,2-dimethylcyclopentyl)-3'-ethyl-1,1'-biphenyl or 4-(chloromethyl)-2-((1S)-2,2-dimethylcyclopentyl)-3'-ethyl-1,1'-biphenyl (83.28F or 83.28G). To a stirred solution of 83.28D or 83.28E (0.130 g, 0.42 mmol) in DCM (2.1 mL) and DMF (0.0033 mL) at 0° C. was added thionyl chloride (0.062 mL, 0.84 mmol). The reaction was then stirred at room temperature for 1.5 hours and then concentrated in vacuo. The resulting product was purified on silica gel (0-10% EtOAc in hexanes) to yield 83.28F or 83.28G as a colorless oil (0.120 g, 87% yield).

(3S)-3-cyclopropyl-3-(3-(((2-((1R)-2,2-dimethylcyclopentyl)-3'-ethyl-1,1'-biphenyl-4-yl)methyl)oxy)-2-fluorophenyl)propanoic acid or (3S)-3-cyclopropyl-3-(3-(((2-((1S)-2,2-dimethylcyclopentyl)-3'-ethyl-1,1'-biphenyl-4-yl)methyl)oxy)-2-fluorophenyl)propanoic acid or (3S)-3-cyclopropyl-3-(3-(((2-((1R)-2,2-dimethylcyclopentyl)-3'-ethyl-1,1'-biphenyl-4-yl)methyl)oxy)-2-fluorophenyl)propanoic acid or (3S)-3-cyclopropyl-3-(3-(((2-((1S)-2,2-dimethylcyclopentyl)-3'-ethyl-1,1'-biphenyl-4-yl)methyl)oxy)-2-fluorophenyl)propanoic acid (83.28). The alkylation and hydrolysis were conducted in an analogous manner to Example 66.6 (using 83.B and 83.28F or 83.28G derived from peak two from the chiral separation of 83.28C from the OD-column, described herein) to yield 83.28 (0.0411 g, 76% yield over the two steps). MS ESI (neg.) m/e: 513.3 (M−H)⁺.

(3S)-3-(3-(((2-(1-Azepanylmethyl)-2'-fluoro-5'-(methyloxy)-1,1'-biphenyl-4-yl)methyl)oxy)-2-fluorophenyl)-3-cyclopropylpropanoic acid or (3R)-3-(3-(((2-(1-Azepanylmethyl)-2'-fluoro-5'-(methyloxy)-1,1'-biphenyl-4-yl)methyl)oxy)-2-fluorophenyl)-3-cyclopropylpropanoic acid (83.29). The alkylation and hydrolysis were conducted in an analogous manner to Example 66.6 (using 83.B and 66.73C described herein) to yield 83.29. After removing solvent, 83.29 was obtained as TFA salt (51 mg). MS ESI (neg.) m/e: 544 (M−H)⁺. ¹H NMR (400 MHz, DMSO-d6) δ ppm 9.40 (m, 1H), 7.91 (m, 1H), 7.64-7.66 (m, 1H), 7.44 (m, 1H), 7.27-7.32 (m, 1H), 7.06-7.15 (m, 3H), 6.86-7.00 (m, 2H), 5.23 (s, 2H), 4.04-4.36 (m, 1H), 3.78 (s, 3H), 3.14 (m, 1H), 2.90 (m, 1H), 2.86 (m, 1H), 2.70 (m, 2H), 2.65 (m, 1H), 1.49 (m, 8H), 1.05 (m, 1H), 0.53 (m, (3S)-3-(3-(4-(5-Fluoro-2-methoxypyridin-4-yl)-3-(1-(methoxymethyl)cyclopentyl)benzyloxy)-2-fluorophenyl)-3-cyclopropylpropanoic acid or (3R)-3-(3-(4-(5-fluoro-2-methoxypyridin-4-yl)-3-(1-(methoxymethyl)cyclopentyl)benzyloxy)-2-fluorophenyl)-3-cyclopropylpropanoic acid (83.30). The alkylation and hydrolysis were conducted in an analogous manner to Example 66.6 (using 83.B and 77.12C, described herein) to yield 83.30. ¹H NMR (400 MHz, CDCl₃) δppm 7.77 (1H, s), 7.04-7.14 (1H, m), 7.03 (1H, s), 6.71-6.81 (2H, m), 6.57-6.71 (2H, m), 6.49 (1H, d, J=4.7 Hz), 4.87-4.97 (2H, m), 3.71 (3H, s), 2.97-3.11 (2H, m), 2.98 (3H, s), 2.52-2.70 (3H, m), 2.33-2.52 (1H, m), 1.66-1.80 (1H, m), 1.44-1.59 (2H, m), 1.23-1.44 (4H, m), 0.89 (1H, dd, J=8.2, 3.5 Hz), 0.28-0.43 (1H, m), 0.17 (1H, td, J=8.7, 4.5 Hz), 0.09 (1H, dd, J=9.2, 4.5 Hz), −0.08-0.04 (1H, m). MS ESI (pos.) m/e: 552.2 (M+H)⁺.

Example 83.31

(3S)-3-Cyclopropyl-3-(2-fluoro-3-(((2'-fluoro-2-((R)-(1-methylcyclopropyl)(methyloxy)methyl)-5'-(methyloxy)-1,1'-biphenyl-4-yl)methyl)oxy)phenyl)propanoic acid or (3S)-3-vyclopropyl-3-(2-fluoro-3-(((2'-fluoro-2-((S)-(1-methylcyclopropyl)(methyloxy)methyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((R)-(1-methylcyclopropyl)(methyloxy)methyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((S)-(1-methylcyclopropyl)(methyloxy)methyl)-5'-(methyloxy)-1,1'-biphenyl-4-yl)methyl)oxy)phenyl)propanoic acid (83.31). 83.31 was prepared from 83.18I according to the analogous methods described in Example 83.22. MS ESI (neg.) m/e: 535.2 (M−H)⁺.

(3S)-3-Cyclopropyl-3-(3-(((3-((1R)-2,2-dimethyl-1-(methyloxy)propyl)-4-(5-fluoro-2-(methyloxy)-4-pyridinyl)phenyl)methyl)oxy)-2-fluorophenyl)propanoic acid or (3S)-3-cyclopropyl-3-(3-(((3-((1S)-2,2-dimethyl-1-(methyloxy)propyl)-4-(5-fluoro-2-(methyloxy)-4-pyridinyl)phenyl)methyl)oxy)-2-fluorophenyl)propanoic acid or (3R)-3-cyclopropyl-3-(3-(((3-((1R)-2,2-dimethyl-1-(methyloxy)propyl)-4-(5-fluoro-2-(methyloxy)-4-pyridinyl)phenyl)methyl)oxy)-2-fluorophenyl)propanoic acid or (3R)-3-cyclopropyl-3-(3-(((3-((1S)-2,2-dimethyl-1-(methyloxy)propyl)-4-(5-fluoro-2-(methyloxy)-4-pyridinyl)phenyl)methyl)oxy)-2-fluorophenyl)propanoic acid (83.32). The alkylation and hydrolysis were conducted in an analogous manner to Example 66.6 (using 83.B and 83.21L or 83.21M derived from peak one from the chiral separation of 83.21E from the OD-column, described herein) to yield 83.32 (0.0252 g, 48% yield over the two steps). MS ESI (neg.) m/e: 538.2 (M−H)⁺.

(3S)-3-Cyclopropyl-3-(2-fluoro-3-(((2'-fluoro-2-((1S)-2-methyl-1,2-bis(methyloxy)propyl)-5'-(methyloxy)-1,1'-biphenyl-4-yl)methyl)oxy)phenyl)propanoic acid or (3S)-3-cyclopropyl-3-(2-fluoro-3-(((2'-fluoro-2-((1R)-2-methyl-1,2-bis(methyloxy)propyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((1S)-2-methyl-1,2-bis(methyloxy)propyl)-5'-(methyloxy)-1,1'-biphenyl-4-yl)methyl)oxy)phenyl)propanoic acid or (3R)-3-cyclopropyl-3-(2-fluoro-3-(((2'-fluoro-2-((1R)-2-methyl-1,2-bis(methyloxy)propyl)-5'-(methyloxy)-1,1'-biphenyl-4-yl)methyl)oxy)phenyl)propanoic acid (83.33). The Mitsunobu reaction and hydrolysis were conducted in an analogous manner to Example 69.14 (using 83.B and 83.26J or 83.26K peak two from the chiral separation of 83.26E from the OD-column, described herein) to yield 83.33A or 83.33B. (MS ESI (neg.) m/e: 553.2 (M−H)⁺.

Example 83.34

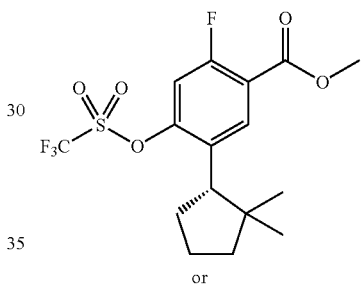

or

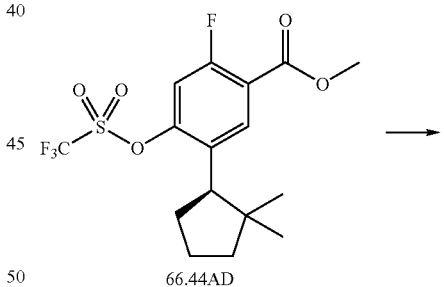

66.44AD

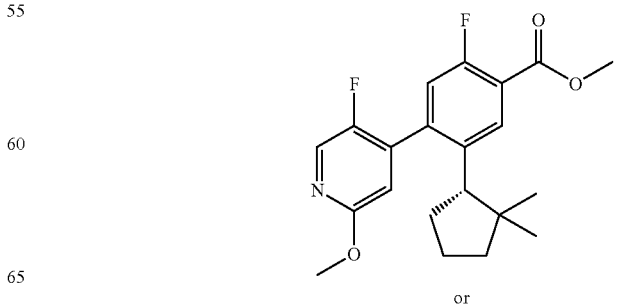

or

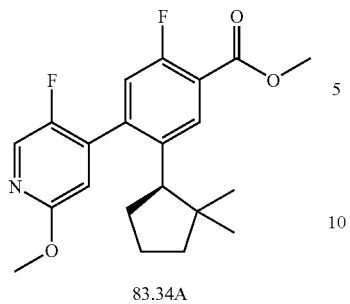

83.34A

Methyl 5-((1S)-2,2-dimethylcyclopentyl)-2-fluoro-4-(5-fluoro-2-(methyloxy)-4-pyridinyl)benzoate or methyl 5-((1R)-2,2-dimethylcyclopentyl)-2-fluoro-4-(5-fluoro-2-(methyloxy)-4-pyridinyl)benzoate (83.34A). To a stirred solution of 66.44AD (0.7937 g, 1.992 mmol) in DMF (4 mL) at 23° C. was added 5-fluoro-2-methoxypyridine boronic acid (commercially available from Asymchem) (0.5115 g, 2.992 mmol) and potassium carbonate (0.8279 g, 5.990 mmol) followed by tetrakis(triphenylphosphine)palladium (0.2374 g, 0.2054 mmol). The mixture was heated to 90° C. After 2 hours, LCMS-showed the reaction was complete. The mixture was cooled to room temperature and then diluted with water. After extracting three times with EtOAc, the mixture was concentrated in vacuo and then purified on silica gel (0%-20% EtOAc/hexane) to afford 83.34A (601.2 mg, 80% yield). MS ESI (pos.) m/e: 376.1 (M+H)$^+$.

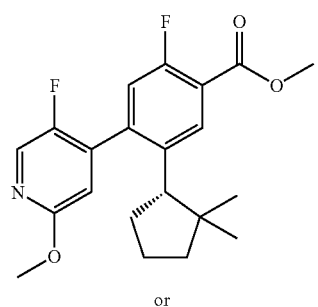

or

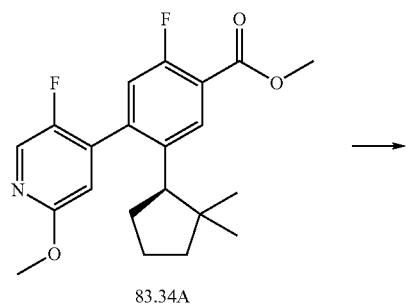

83.34A

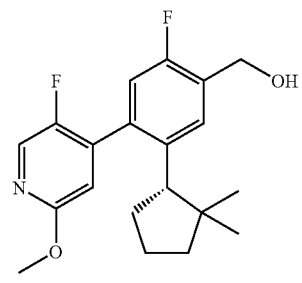

or

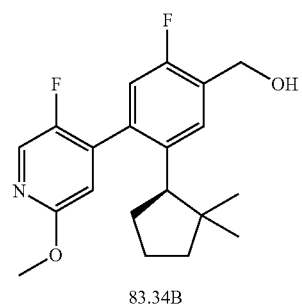

83.34B (5-((1S)-2,2-Dimethylcyclopentyl)-2-fluoro-4-(5-fluoro-2-(methyloxy)-4-pyridinyl)phenyl)methanol or (5-((1R)-2,2-dimethylcyclopentyl)-2-fluoro-4-(5-fluoro-2-(methyloxy)-4-pyridinyl)phenyl)methanol (83.34B). To a cooled solution of 83.34A (0.6012 g, 1.601 mmol) in dry THF (15 mL) at 0° C. was added LAH (1.0M in THF) (3.2 mL, 3.2 mmol) dropwise. Upon complete addition, the reaction was maintained at 0° C. and was monitored by TLC and LCMS. After 45 minutes, 1N NaOH was added to quench the reaction. Gas evolved. The resulting solution was extracted three times with EtOAc. After drying over anhydrous magnesium sulfate, filtration, and concentration, the residue was purified on silica gel (0%-20% EtOAc/hexane) to afford 83.34B (449.9 mg, 81% yield). MS ESI (pos.) m/e: 348.1 (M+H)$^+$.

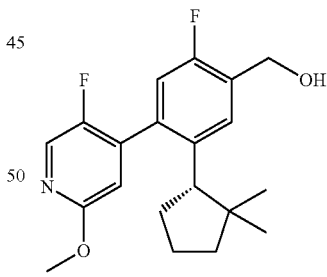

or

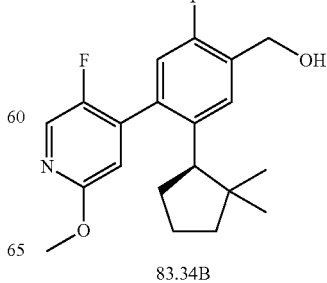

83.34B

-continued

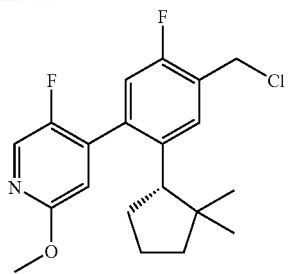

or

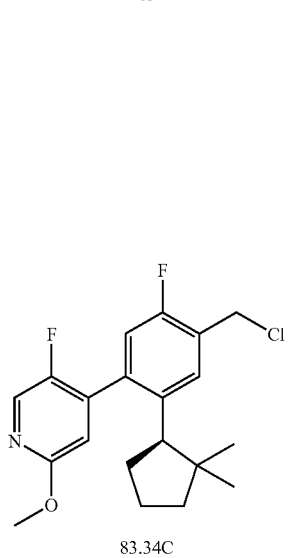

83.34C 4-(4-(Chloromethyl)-2-((1S)-2,2-dimethylcyclopentyl)-5-fluorophenyl)-5-fluoro-2-(methyloxy)pyridine or 4-(4-(chloromethyl)-2-((1R)-2,2-dimethylcyclopentyl)-5-fluorophenyl)-5-fluoro-2-(methyloxy)pyridine (83.34C). To a solution of 83.34B (0.4463 g, 1.285 mmol) in dry DCM (17 mL) and dry DMF (0.12 mL) was added thionyl chloride (0.19 mL, 2.605 mmol) at 0° C. The resulting solution was warmed to room temperature and monitored with TLC and LCMS. After 1.5 hours, the reaction was concentrated. The residue was diluted with EtOAc and washed once with saturated aqueous NaHCO$_3$ solution and once with brine. The organic layer was subsequently dried over anhydrous sodium sulfate, filtered, concentrated, and purified by silica gel flash chromatography (0-15% EtOAc/hexane) to afford 83.34C (446.9 mg, 95% yield). MS ESI (pos.) m/e: 366.1 (M+H)$^+$.

(3S)-3-Cyclopropyl-3-(3-(((5-((1S)-2,2-dimethylcyclopentyl)-2-fluoro-4-(5-fluoro-2-(methyloxy)-4-pyridinyl)phenyl)methyl)oxy)-2-fluorophenyl)propanoic acid or (3S)-3-cyclopropyl-3-(3-(((5-((1R)-2,2-dimethylcyclopentyl)-2-fluoro-4-(5-fluoro-2-(methyloxy)-4-pyridinyl)phenyl)methyl)oxy)-2-fluorophenyl)propanoic acid or (3R)-3-cyclopropyl-3-(3-(((5-((1S)-2,2-dimethylcyclopentyl)-2-fluoro-4-(5-fluoro-2-(methyloxy)-4-pyridinyl)phenyl)methyl)oxy)-2-fluorophenyl)propanoic acid or (3R)-3-cyclopropyl-3-(3-(((5-((1R)-2,2-dimethylcyclopentyl)-2-fluoro-4-(5-fluoro-2-(methyloxy)-4-pyridinyl)phenyl)methyl)oxy)-2-fluorophenyl)propanoic acid (83.34). The alkylation and hydrolysis were conducted in an analogous manner to Example 66.6 (using 83B and 83.34C derived from 66.44AD, described herein) to yield 83.34. MS ESI (pos.) m/e: 554.2 (M+H)$^+$. MS ESI (neg.) m/e: 552.1 (M-H)$^+$.

Example 84

Synthesis of (R)-methyl 4-cyclopropyl-3-(2-fluoro-3-hydroxyphenyl)butanoate and (S)-methyl 4-cyclopropyl-3-(2-fluoro-3-hydroxyphenyl)butanoate (84.F and 84.4G)

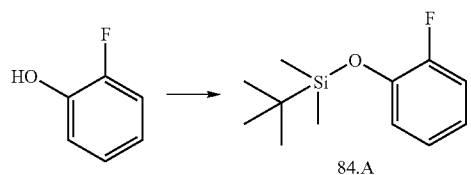

84.A tert-Butyl(2-fluorophenoxy)dimethylsilane (84.A). A 500 mL round bottom flask was charged with tert-butyldimethylchlorosilane (73.9 g, 491 mmol) (available from Aldrich), DMF (220 mL), 2-fluorophenol (41.3 mL, 446 mmol) (available from Aldrich), and imidazole (75.9 g, 1115 mmol). The pale yellow solution was stirred for 1.5 hours at 25° C. and diluted with hexanes (1 L). The organic phase was washed with water (1×300 mL), saturated aqueous NaHCO$_3$ (3×300 mL), water (3×300 mL) and brine (1×300 mL). The organic phase was then dried (MgSO$_4$), and concentrated to afford 84.A (101 g, 100% yield) as a colorless liquid. The crude product was used without further purification.

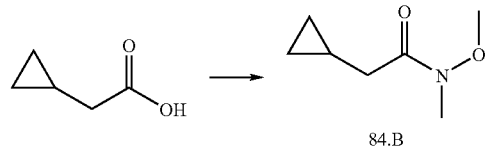

84.B

2-Cyclopropyl-N-methoxy-N-methylacetamide (84.B). A 500 mL round bottom flask was charged with cyclopropylacetic acid (9.87 g, 98.6 mmol) (available from Oakwood) and DCM (200 mL). To the stirred solution was added 1,1'-carbonyldiimidazole (19.2 g, 118 mmol) portionwise (vigorous gas evolution). The yellow solution was stirred for 30 minutes at room temperature, and to it was added N,O-dimethylhydroxylamine hydrochloride (11.5 g, 118 mmol) (available from Aldrich) in one portion. The heterogeneous, white mixture was stirred overnight and diluted with ether (300 mL). The organics were washed with 1 N HCl (2×150 mL), saturated aqueous NaHCO$_3$ (2×150 mL) and brine (1×150 mL), dried (MgSO$_4$), and concentrated to afford 84.B (11.9 g, 84.3% yield) as a colorless liquid. The crude product was used without further purification.

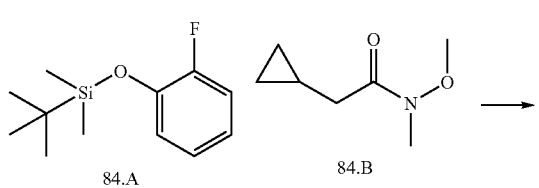

84.A  84.B

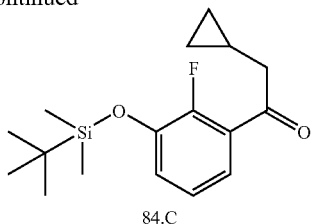

1-(3-(tert-Butyldimethylsilyloxy)-2-fluorophenyl)-2-cyclopropylethanone (84.C). A 1 L round bottom flask was charged with 84.A (17.0 mL, 73.0 mmol) and THF (70 mL) and cooled to −78° C. under N₂. To the cold solution was added sec-butyllithium (1.20 M/cyclohexane) (66.3 mL, 79.6 mmol) dropwise. The mixture was stirred for 30 minutes, and to it was added a solution of 84.B (9.31 mL, 66.3 mmol) in THF (70 mL) dropwise. The final mixture was stirred for 30 minutes at −78° C. The cooling bath was removed, and the mixture was stirred for 30 minutes at ambient temperature. The reaction was quenched with saturated aqueous NH₄Cl (70 mL) and diluted with EtOAc (100 mL). The organic phase was washed with water (100 mL), 1 N HCl (100 mL) and brine (100 mL). The organic phase was then dried (MgSO₄) and concentrated. The residue was purified by silica gel flash chromatography (2% EtOAc/hexane) to afford 84.C (14.9 g, 73% yield) as a yellow oil.

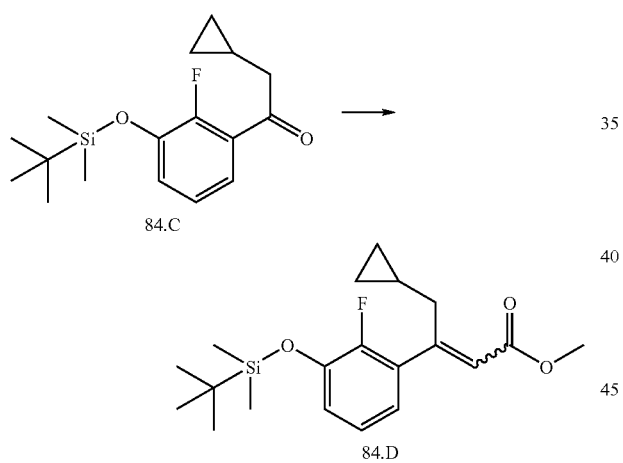

Methyl 3-(3-(tert-butyldimethylsilyloxy)-2-fluorophenyl)-4-cyclopropylbut-2-enoate (84.D). A 25 mL round bottom flask was cooled to −78° C. under N₂ and charged with THF (2 mL) and lithium diisopropylamide (2.0 M in heptane/THF/ethylbenzene) (2.1 mL, 4.1 mmol) (available from Aldrich). To the cold, brown solution was added methyl (trimethylsilyl)acetate (0.61 mL, 3.7 mmol) (available from Aldrich) dropwise. The orange mixture was stirred for 15 minutes, and to it was added a solution of 84.C (0.46 g, 1.5 mmol) in THF (2 mL) dropwise. The mixture was stirred for 30 minutes at −78° C., the cooling bath was removed, and the mixture was stirred for 30 minutes at ambient temperature. The reaction was quenched with saturated aqueous NH₄Cl and diluted with EtOAc. The organic phase was washed with water, 1 N HCl and brine. The organic phase was then dried (MgSO₄) and concentrated. The residue was purified by silica gel flash chromatography (0-2% EtOAc/hexane) to afford 84.D (mixture of geometric isomers) (0.44 g, 81% yield) as a yellow oil.

Methyl 4-cyclopropyl-3-(2-fluoro-3-hydroxyphenyl)butanoate (84.E). A 250 mL round bottom flask was charged with 84.D (4.95 g, 13.6 mmol) and MeOH (60 mL) and flushed with N₂. To the solution were added magnesium turnings (0.990 g, 40.7 mmol) in one portion (a few turnings were fractured by hammering prior to addition to expose clean metallic edges). The gently bubbling mixture was stirred overnight at room temperature. To the mixture was added potassium fluoride (0.789 g, 13.6 mmol). The resulting mixture was stirred for 1 hour, quenched with 1 N HCl (90 mL), and extracted with EtOAc (2×50 mL). The combined organic layers were washed with water (2×50 mL) and brine (1×50 mL), dried (MgSO₄), and concentrated. The residue was purified by silica gel flash chromatography (0-20% EtOAc/hexane) to afford 84.E (2.70 g, 79% yield) as a yellow oil.

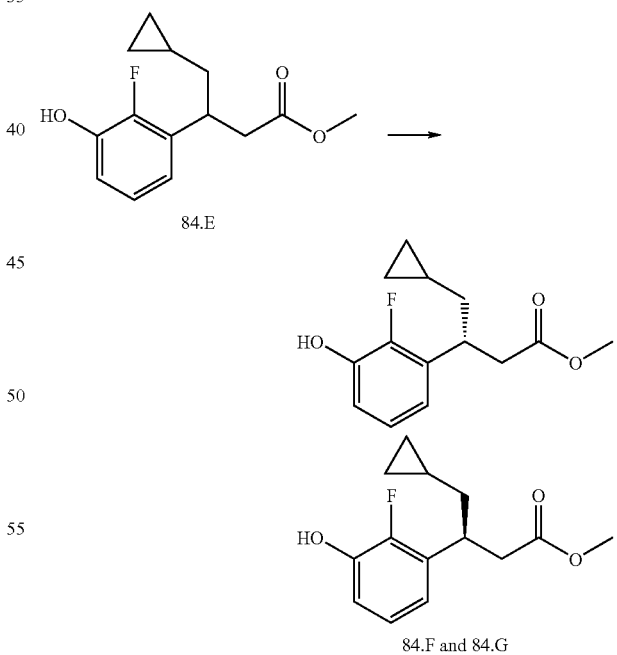

(R)-Methyl 4-cyclopropyl-3-(2-fluoro-3-hydroxyphenyl) butanoate and (S)-methyl 4-cyclopropyl-3-(2-fluoro-3-hydroxyphenyl)butanoate (84.F and 84.G). Racemic 84.E (1.97 g, 7.8 mmol) was resolved by chiral HPLC (Chiralcel OD column, 3% i-PrOH/hexanes, 220 nm, 700 mg/injection) to afford (in order of elution) 84.F (0.98 g, 99% yield) and 84.G (0.96 g, 97% yield) as colorless oils.

The following compounds were prepared from 84.F and the appropriate halomethyl or hydroxymethyl compound according to the methods described herein. Each of the compounds in the following table were prepared using the same enantiomer of the phenol.

TABLE 18

| Compound | TG |
|---|---|
| 84.1 | |
| 84.2 | |

TABLE 18-continued

| | |
|---|---|
| 84.3 | |
| 84.4 | |
| 84.5 | | but not the same one as 84.1

TABLE 18-continued 84.6
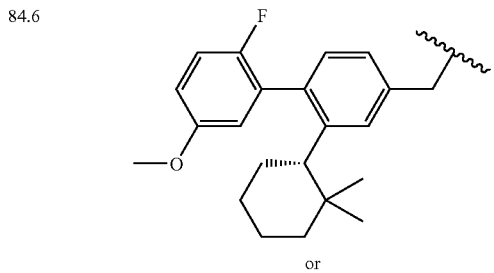
or
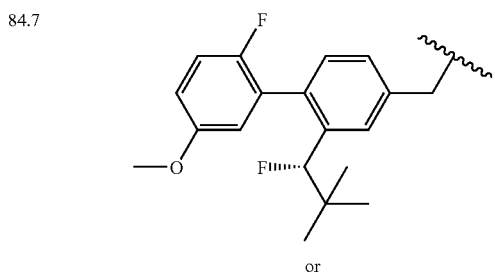

84.7
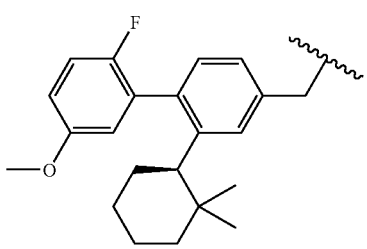
or
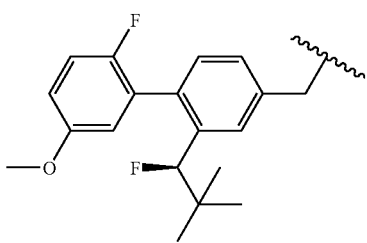

84.8
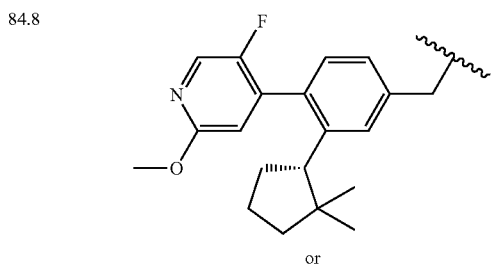
or
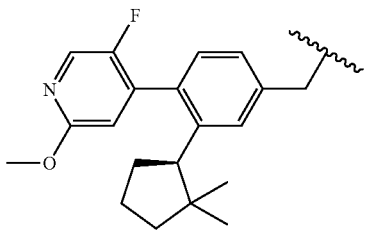

TABLE 18-continued 84.9
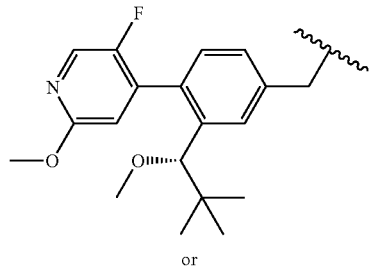
or
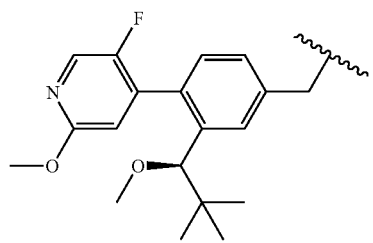

(R)-4-Cyclopropyl-3-{3-[2-((S)-2,2-dimethyl-cyclopentyl)-2'-fluoro-5'-methoxy-biphenyl-4-ylmethoxy]-2-fluoro-phenyl}-butyric acid or (R)-4-cyclopropyl-3-{3-[2-((R)-2,2-dimethyl-cyclopentyl)-2'-fluoro-5'-methoxy-biphenyl-4-ylmethoxy]-2-fluoro-phenyl}-butyric acid or (S)-4-cyclopropyl-3-{3-[2-((S)-2,2-dimethyl-cyclopentyl)-2'-fluoro-5'-methoxy-biphenyl-4-ylmethoxy]-2-fluoro-phenyl}-butyric acid or (S)-4-cyclopropyl-3-{3-[2-((R)-2,2-dimethyl-cyclopentyl)-2'-fluoro-5'-methoxy-biphenyl-4-ylmethoxy]-2-fluoro-phenyl}-butyric acid (84.1). MS ESI (pos.) m/e: 566.3 $(M+H_2O)^+$.

(R)-4-Cyclopropyl-3-{2-fluoro-3-[2'-fluoro-5'-methoxy-2-((S)-1-methoxy-2,2-dimethyl-propyl)-biphenyl-4-ylmethoxy]-phenyl}-butyric acid or (R)-4-cyclopropyl-3-{2-fluoro-3-[2'-fluoro-5'-methoxy-2-((R)-1-methoxy-2,2-dimethyl-propyl)-biphenyl-4-ylmethoxy]-phenyl}-butyric acid or (S)-4-cyclopropyl-3-{2-fluoro-3-[2'-fluoro-5'-methoxy-2-((S)-1-methoxy-2,2-dimethyl-propyl)-biphenyl-4-ylmethoxy]-phenyl}-butyric acid or (S)-4-cyclopropyl-3-{2-fluoro-3-[2'-fluoro-5'-methoxy-2-((R)-1-methoxy-2,2-dimethyl-propyl)-biphenyl-4-ylmethoxy]-phenyl}-butyric acid (84.2). MS ESI (neg.) m/e: 551.2 $(M-H)^+$.

(3R)-4-Cyclopropyl-3-(3-(((2-((1S)-2,2-dimethylcyclopentyl)-2'-fluoro-5'-(methyloxy)-1,1'-biphenyl-4-yl)methyl)oxy)-2-fluorophenyl)butanoic acid or (3R)-4-cyclopropyl-3-(3-(((2-((1R)-2,2-dimethylcyclopentyl)-2'-fluoro-5'-(methyloxy)-1,1'-biphenyl-4-yl)methyl)oxy)-2-fluorophenyl)butanoic acid or (3S)-4-cyclopropyl-3-(3-(((2-((1S)-2,2-dimethylcyclopentyl)-2'-fluoro-5'-(methyloxy)-1,1'-biphenyl-4-yl)methyl)oxy)-2-fluorophenyl)butanoic acid or (3S)-4-cyclopropyl-3-(3-(((2-((1R)-2,2-dimethylcyclopentyl)-2'-fluoro-5'-(methyloxy)-1,1'-biphenyl-4-yl)methyl)oxy)-2-fluorophenyl)butanoic acid (84.3). MS ESI (pos.) m/e: 566.3 $(M+H_2O)^+$.

(3R)-4-Cyclopropyl-3-(3-(((2-((1S)-2,2-dimethylcyclopentyl)-2',5-difluoro-5'-(methyloxy)-1,1'-biphenyl-4-yl)methyl)oxy)-2-fluorophenyl)butanoic acid or (3R)-4-cyclopropyl-3-(3-(((2-((1R)-2,2-dimethylcyclopentyl)-2',5-difluoro-5'-(methyloxy)-1,1'-biphenyl-4-yl)methyl)oxy)-2-fluorophenyl)butanoic acid or (3S)-4-cyclopropyl-3-(3-(((2-((1S)-2,2-dimethylcyclopentyl)-2',5-difluoro-5'-(methyloxy)-1,1'-biphenyl-4-yl)methyl)oxy)-2-fluorophenyl)butanoic acid or (3S)-4-cyclopropyl-3-(3-(((2-((1R)-2,2-dimethylcyclopentyl)-2',5-difluoro-5'-

(methyloxy)-1,1'-biphenyl-4-yl)methyl)oxy)-2-fluorophenyl)butanoic acid (84.4). MS ESI (neg.) m/e: 565.3 (M–H)⁺.

(3R)-4-Cyclopropyl-3-(3-(((2-(5,5-dimethyl-1-cyclopenten-1-yl)-2'-fluoro-5'-(methyloxy)-1,1'-biphenyl-4-yl)methyl)oxy)-2-fluorophenyl)butanoic acid or (3S)-4-cyclopropyl-3-(3-(((2-(5,5-dimethyl-1-cyclopenten-1-yl)-2'-fluoro-5'-(methyloxy)-1,1'-biphenyl-4-yl)methyl)oxy)-2-fluorophenyl)butanoic acid (84.5). MS ESI (neg.) m/e: 545.2 (M–H)⁺.

(3R)-4-Cyclopropyl-3-(3-(((2-((1S)-2,2-dimethylcyclohexyl)-2'-fluoro-5'-(methyloxy)-1,1'-biphenyl-4-yl)methyl)oxy)-2-fluorophenyl)butanoic acid or (3R)-4-cyclopropyl-3-(3-(((2-((1R)-2,2-dimethylcyclohexyl)-2'-fluoro-5'-(methyloxy)-1,1'-biphenyl-4-yl)methyl)oxy)-2-fluorophenyl)butanoic acid or (3S)-4-cyclopropyl-3-(3-(((2-((1S)-2,2-dimethylcyclohexyl)-2'-fluoro-5'-(methyloxy)-1,1'-biphenyl-4-yl)methyl)oxy)-2-fluorophenyl)butanoic acid or (3S)-4-Cyclopropyl-3-(3-(((2-((1R)-2,2-dimethylcyclohexyl)-2'-fluoro-5'-(methyloxy)-1,1'-biphenyl-4-yl)methyl)oxy)-2-fluorophenyl)butanoic acid (84.6). MS ESI (neg.) m/e: 561.3 (M–H)⁺.

(3R)-4-Cyclopropyl-3-(2-fluoro-3-(((2'-fluoro-2-((1S)-1-fluoro-2,2-dimethylpropyl)-5'-(methyloxy)-1,1'-biphenyl-4-yl)methyl)oxy)phenyl)butanoic acid or (3R)-4-cyclopropyl-3-(2-fluoro-3-(((2'-fluoro-2-((1R)-1-fluoro-2,2-dimethylpropyl)-5'-(methyloxy)-1,1'-biphenyl-4-yl)methyl)oxy)phenyl)butanoic acid or (3S)-4-cyclopropyl-3-(2-fluoro-3-(((2'-fluoro-2-((1S)-1-fluoro-2,2-dimethylpropyl)-5'-(methyloxy)-1,1'-biphenyl-4-yl)methyl)oxy)phenyl)butanoic acid or (3S)-4-cyclopropyl-3-(2-fluoro-3-(((2'-fluoro-2-((1R)-1-fluoro-2,2-dimethylpropyl)-5'-(methyloxy)-1,1'-biphenyl-4-yl)methyl)oxy)phenyl)butanoic acid (84.7). MS ESI (neg.) m/e: 539.2 (M–H)⁺.

(3R)-4-Cyclopropyl-3-(3-(((3-((1S)-2,2-dimethylcyclopentyl)-4-(5-fluoro-2-(methyloxy)-4-pyridinyl)phenyl)methyl)oxy)-2-fluorophenyl)butanoic acid or (3R)-4-cyclopropyl-3-(3-(((3-((1R)-2,2-dimethylcyclopentyl)-4-(5-fluoro-2-(methyloxy)-4-pyridinyl)phenyl)methyl)oxy)-2-fluorophenyl)butanoic acid or (3S)-4-cyclopropyl-3-(3-(((3-((1S)-2,2-dimethylcyclopentyl)-4-(5-fluoro-2-(methyloxy)-4-pyridinyl)phenyl)methyl)oxy)-2-fluorophenyl)butanoic acid or (3S)-4-cyclopropyl-3-(3-(((3-((1R)-2,2-dimethylcyclopentyl)-4-(5-fluoro-2-(methyloxy)-4-pyridinyl)phenyl)methyl)oxy)-2-fluorophenyl)butanoic acid (84.8). MS ESI (neg.) m/e: 548.2 (M–H)⁺.

(3R)-4-Cyclopropyl-3-(3-(((3-((1S)-2,2-dimethyl-1-(methyloxy)propyl)-4-(5-fluoro-2-(methyloxy)-4-pyridinyl)phenyl)methyl)oxy)-2-fluorophenyl)butanoic acid or (3R)-4-cyclopropyl-3-(3-(((3-((1R)-2,2-dimethyl-1-(methyloxy)propyl)-4-(5-fluoro-2-(methyloxy)-4-pyridinyl)phenyl)methyl)oxy)-2-fluorophenyl)butanoic acid or (3S)-4-cyclopropyl-3-(3-(((3-((1S)-2,2-dimethyl-1-(methyloxy)propyl)-4-(5-fluoro-2-(methyloxy)-4-pyridinyl)phenyl)methyl)oxy)-2-fluorophenyl)butanoic acid or (3S)-4-cyclopropyl-3-(3-(((3-((1R)-2,2-dimethyl-1-(methyloxy)propyl)-4-(5-fluoro-2-(methyloxy)-4-pyridinyl)phenyl)methyl)oxy)-2-fluorophenyl)butanoic acid (84.9). (MS ESI (pos.) m/e: 554.2 (M+H).

Example 85

Synthesis of methyl 3-(3-hydroxyphenyl)-3-methylbutanoate (85)

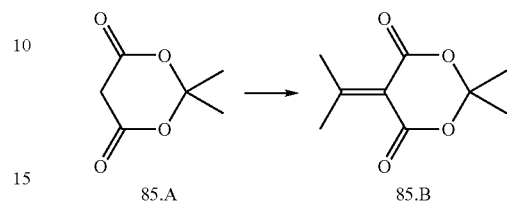

2,2-Dimethyl-5-(propan-2-ylidene)-1,3-dioxane-4,6-dione (85.B). The 2,2-dimethyl-5-(propan-2-ylidene)-1,3-dioxane-4,6-dione (85.B) was prepared from 2,2-dimethyl-1,3-dioxane-4,6-dione 85.A (commercially available from Aldrich) via the same procedure described in Vogt, P. F.; et. al.; Synthetic Communications; 2001, (5); pp. 679-684.

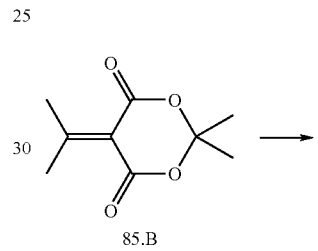

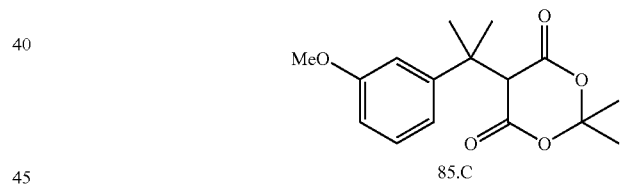

5-(2-(3-Methoxyphenyl)propan-2-yl)-2,2-dimethyl-1,3-dioxane-4,6-dione (85.C). The 5-(2-(3-methoxyphenyl)propan-2-yl)-2,2-dimethyl-1,3-dioxane-4,6-dione (85.C) was prepared via the procedure described in Huang, X.; et. al.; Tetrahedron Letters; 1982, (1); pp. 75-76. from (3-methoxyphenyl)magnesium bromide (1.0 M in THF solution from Aldrich) and 85.B. ¹H NMR (400 MHz, CDCl₃) δppm 7.26 (1H, t, J=8.0 Hz), 6.94 (1H, d, J=7.8 Hz), 6.89 (1H, t, J=2.2 Hz), 6.79 (1H, dd, J=8.2, 2.3 Hz), 3.81 (3H, s), 3.62 (1H, s), 1.67 (6H, s), 1.66 (3H, s), 1.34 (3H, s).

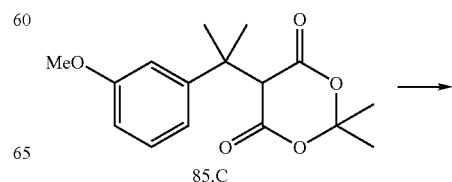

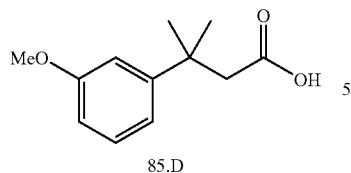

85.D 3-(3-Methoxyphenyl)-3-methylbutanoic acid (85.D). The 5-(2-(3-methoxyphenyl)propan-2-yl)-2,2-dimethyl-1,3-dioxane-4,6-dione 85.C (0.313 g, 1.1 mmol) was dissolved in DMF (1.50 mL, 19 mmol). To the solution was added water (0.15 mL, 8.3 mmol). The resulting solution was then heated to 100° C. and stirred for four hours. The reaction was cooled to room temperature and then diluted with water. The mixture was extracted with EtOAc (2×50 mL). The combined organic layers were then washed with 1N lithium chloride solution (1×20 mL) and brine (1×20 mL) and dried over magnesium sulfate. The filtrate was then concentrated to give crude 3-(3-methoxyphenyl)-3-methylbutanoic acid 85.D (0.247 g, 111% yield) that was used directly in the following reaction. MS ESI (pos.) m/e: 226.1 (M+H$_2$O)$^+$.

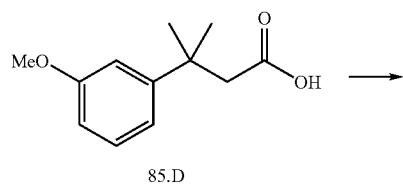

85.D

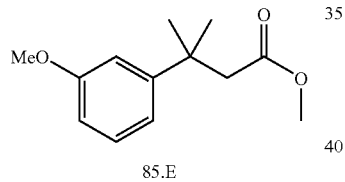

85.E

Methyl 3-(3-methoxyphenyl)-3-methylbutanoate (85.E). 3-(3-Methoxyphenyl)-3-methylbutanoic acid 85.D (0.22 g, 1.1 mmol) was dissolved in MeOH (11 mL) and a catalytic amount (~5 drops) of sulfuric acid was added. The solution was heated to reflux and stirred overnight. The reaction was cooled to room temperature and saturated sodium bicarbonate was added to neutralize the reaction. The mixture was then concentrated and the residue taken up in EtOAc and washed with water (2×30 mL), 1M lithium chloride solution (1×30 mL) and brine (1×30 mL) and dried over magnesium sulfate to give the desired product methyl 3-(3-methoxyphenyl)-3-methylbutanoate 85.E (0.227 g, 97% yield). MS ESI (pos.) m/e: 240.1 (M+H$_2$O)$^+$.

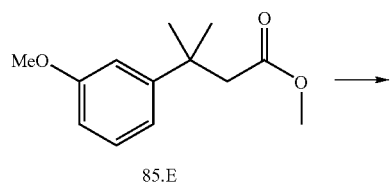

85.E

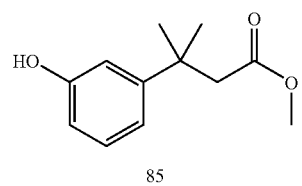

85

Methyl 3-(3-hydroxyphenyl)-3-methylbutanoate (85). To a solution of methyl 3-(3-methoxyphenyl)-3-methylbutanoate 85.E (0.227 g, 1.02 mmol) in 1,2-dichloroethane (10 mL) was added 1,2-ethanedithiol (1.37 mL, 16.3 mmol) followed by aluminum chloride (1.09 g, 8.17 mmol) at 0° C. The reaction mixture was allowed to slowly warm to room temperature over four hours and was then quenched with saturated Rochelle's salt (potassium sodium tartrate) solution. The mixture was extracted (2×50 mL) with DCM. The combined organic layers were washed with water (1×40 mL) and brine (1×40 mL) and dried over magnesium sulfate. The filtrate was concentrated and the residue was purified by medium pressure chromatography (silica, 0 to 30% EtOAc:hexanes) to give methyl 3-(3-hydroxyphenyl)-3-methylbutanoate 85 (0.209 g, 98.3% yield). MS ESI (pos.) m/e: 226.0 (M+H$_2$O)$^+$.

The following compounds were prepared from methyl 3-(3-hydroxyphenyl)-3-methylbutanoate (85) and the appropriate halomethyl or hydroxymethyl compound according to the methods described herein. Each of the compounds in the following table were prepared using the same enantiomer of the phenol.

TABLE 19

| Compound | TG |
|---|---|
| 85.1 | ![F-substituted biphenyl with tert-butyl and methoxy] |
| 85.2 | ![F-substituted biphenyl with dimethylcyclopentenyl and methoxy] |

TABLE 19-continued

[Structure: TG-O-phenyl-C(CH3)2-CH2-C(=O)-O-CH3]

| Compound | TG |
|---|---|
| 85.3 | [structures] |
| 85.4 | [structures] |
| 85.5 | [structures] |
| 85.6 | [structures] |

3-[3-(2-tert-Butyl-2'-fluoro-5'-methoxy-biphenyl-4-yl-methoxy)-phenyl]-3-methyl-butyric acid (85.1). MS ESI (pos.) m/e: 482.2 (M+H$_2$O)$^+$.

3-{3-[2-(5,5-Dimethyl-cyclopent-1-enyl)-2'-fluoro-5'-methoxy-biphenyl-4-ylmethoxy]-phenyl}-3-methyl-butyric acid (85.2). MS ESI (pos.) m/e: 520.2 (M+H$_2$O)$^+$.

3-(3-(((2-((1R)-2,2-Dimethylcyclopentyl)-2'-fluoro-5'-(methyloxy)-1,1'-biphenyl-4-yl)methyl)oxy)phenyl)-3-methylbutanoic acid or 3-(3-(((2-((1S)-2,2-dimethylcyclopentyl)-2'-fluoro-5'-(methyloxy)-1,1'-biphenyl-4-yl)methyl)oxy)phenyl)-3-methylbutanoic acid (85.3). The alkylation and hydrolysis were conducted in an analogous manner to Example 66.6 (using 85 and 66.6M or 66.6N derived from peak two from the chiral separation of 66.6L from the OD-column, described herein) to yield 85.3 (0.0516 g, 84% yield over the two steps). MS ESI (neg.) m/e: 503.2 (M−H)$^+$.

3-{3-[3-((S)-2,2-Dimethyl-cyclopentyl)-4-(5-fluoro-2-methoxy-pyridin-4-yl)-benzyloxy]-phenyl}-3-methyl-butyric acid or 3-{3-[3-((R)-2,2-dimethyl-cyclopentyl)-4-(5-fluoro-2-methoxy-pyridin-4-yl)-benzyloxy]-phenyl}-3-methyl-butyric acid (85.4). MS ESI (neg.) m/e: 504.2 (M–H)⁻.

3-(3-(((5-((1S)-2,2-Dimethylcyclopentyl)-2-fluoro-4-(5-fluoro-2-(methyloxy)-4-pyridinyl)phenyl)methyl)oxy)phenyl)-3-methylbutanoic acid or 3-(3-(((5-((1R)-2,2-dimethylcyclopentyl)-2-fluoro-4-(5-fluoro-2-(methyloxy)-4-pyridinyl)phenyl)methyl)oxy)phenyl)-3-methylbutanoic acid (85.5). The alkylation and hydrolysis were conducted in an analogous manner to Example 66.6 (using 85 and 83.34C derived from 66.44AD, described herein) to yield 85.5. MS ESI (pos.) m/e: 524.2 (M+H)⁺. MS ESI (neg.) m/e: 522.1 (M–H)⁺.

3-(3-(((3-((1S)-2,2-Dimethyl-1-(methyloxy)propyl)-4-(5-fluoro-2-(methyloxy)-4-pyridinyl)phenyl)methyl)oxy)phenyl)-3-methylbutanoic acid or 3-(3-(((3-((1R)-2,2-dimethyl-1-(methyloxy)propyl)-4-(5-fluoro-2-(methyloxy)-4-pyridinyl)phenyl)methyl)oxy)phenyl)-3-methylbutanoic acid (85.6). MS ESI (pos.) m/e: 510.2 (M+H)⁺.

Example 86

Synthesis of methyl (3R)-3-(4-fluoro-3-hydroxyphenyl)pentanoate (86)

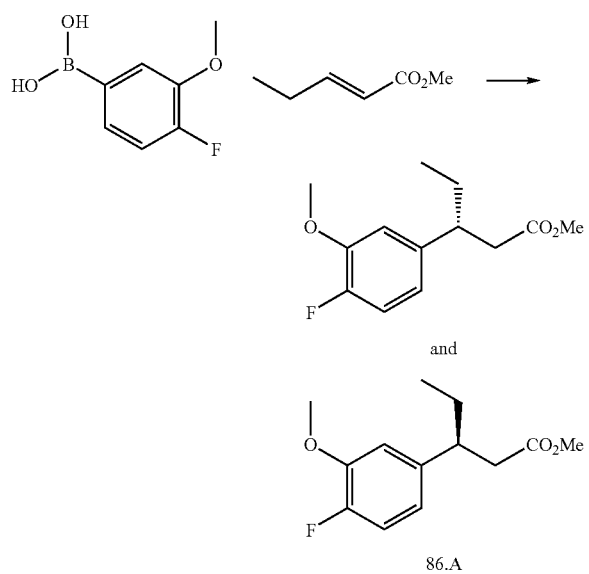

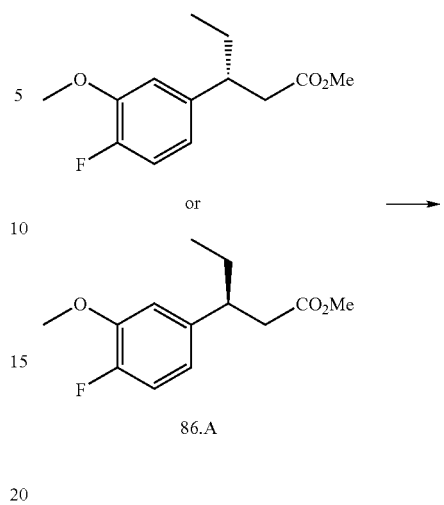

Methyl (3R)-3-(4-fluoro-3-(methyloxy)phenyl)pentanoate and methyl (3S)-3-(4-fluoro-3-(methyloxy)phenyl)pentanoate (86.A). Dioxane/water: 10/1 (22 mL) was added to a flask charged with hydroxy[(S)-BINAP]-rhodium(I) dimer (0.260 g, 0.175 mmol), and 4-fluoro-3-methoxyphenylboronic acid (3.72 g, 21.9 mmol) (commercially available from Combi-Blocks) and flushed with nitrogen and (E)-methyl pent-2-enoate (0.500 g, 4.38 mmol) (commercially available from Acros). The resulting mixture was then stirred at 40° C. overnight. The reaction was diluted with EtOAc and washed with saturated sodium bicarbonate, brine, dried over sodium sulfate, filtered, and concentrated. The residue was purified by silica gel chromatography (0 to 20% EtOAc/Hexanes) to provide 86.A (0.800 g, 76.0% yield).

Methyl (3R)-3-(4-fluoro-3-hydroxyphenyl)pentanoate or methyl (3S)-3-(4-fluoro-3-hydroxyphenyl)pentanoate (86). To a solution of 86.A (0.80 g, 3330 µmol) in DCE (15 mL) was added 1,2-ethanedithiol (4463 µL, 53273 µmol) followed by aluminum chloride (1456 µL, 26637 µmol) at 0° C. The reaction mixture was allowed to slowly warm to room temperature over four hours and was then quenched with saturated Rochelle's salt solution. The mixture was extracted (2×50 mL) with DCM. The combined organic layers were washed with water (1×40 mL) and brine (1×40 mL) and dried over magnesium sulfate. The filtrate was concentrated and the residue was purified by chromatography (silica, 0 to 30% EtOAc:hexanes) to give 86 (533 mg, 70.8% yield). The enantiomeric excess of 86 was increased to >99% by purification by chiral HPLC (Chiralcel OD-H column, 3% IPA/hexane, 220 nm).

The following compounds were prepared from 86 and the appropriate halomethyl or hydroxymethyl compound according to the methods described herein. Each of the compounds in the following table were prepared using the same enantiomer of the phenol.

TABLE 20

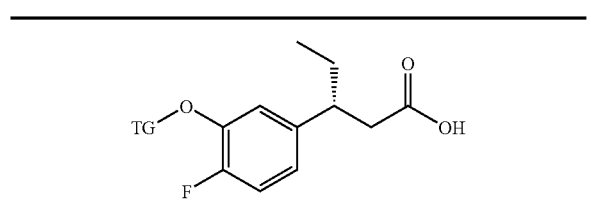

| Compound | TG |
|---|---|
| 86.1 | 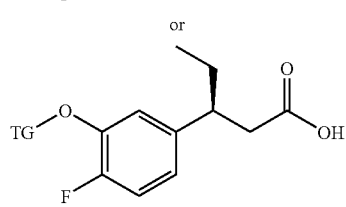 |
| 86.2 | |

(3R)-3-(3-(((2-(5,5-Dimethyl-1-cyclopenten-1-yl)-2'-fluoro-5'-(methyloxy)-1,1'-biphenyl-4-yl)methyl)oxy)-4-fluorophenyl)pentanoic acid or (3S)-3-(3-(((2-(5,5-dimethyl-1-cyclopenten-1-yl)-2'-fluoro-5'-(methyloxy)-1,1'-biphenyl-4-yl)methyl)oxy)-4-fluorophenyl)pentanoic acid (86.1). MS ESI (pos.) m/e: 519.2 (M−H).

(3R)-3-(3-(((2-(1,1-Dimethylethyl)-2'-fluoro-5'-(methyloxy)-1,1'-biphenyl-4-yl)methyl)oxy)-4-fluorophenyl)pentanoic acid or (3S)-3-(3-(((2-(1,1-dimethylethyl)-2'-fluoro-5'-(methyloxy)-1,1'-biphenyl-4-yl)methyl)oxy)-4-fluorophenyl)pentanoic acid (86.2). MS ESI (pos.) m/e: 481.1 (M−H).

Example 87

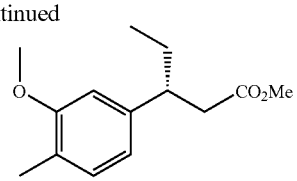

Methyl (3R)-3-(4-methyl-3-(methyloxy)phenyl)pentanoate and methyl (3S)-3-(4-methyl-3-(methyloxy)phenyl) pentanoate (87.1). Dioxane/water: 10/1 (220 mL) was added to a flask charged with hydroxy[(S)-BINAP]-rhodium(I) dimer (0.325 g, 0.219 mmol), 3-methoxy-4-methylphenylboronic acid (3.64 g, 21.9 mmol) (commercially available from Combi-Blocks) and flushed with nitrogen. Next, (E)-methyl pent-2-enoate (0.500 g, 4.38 mmol) (commercially available from Acros) was added. The resulting mixture was then stirred at 40° C. overnight. The reaction was diluted with EtOAc and washed with saturated aqueous NaHCO$_3$, brine, dried over sodium sulfate, filtered, and concentrated. The residue was purified by silica gel chromatography (0 to 20% EtOAc/Hexanes) to provide 87.1 (0.945 g, 91.3% yield).

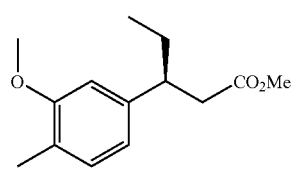

Methyl (3R)-3-(3-hydroxy-4-methylphenyl)pentanoate or methyl (3S)-3-(3-hydroxy-4-methylphenyl)pentanoate (87.2). To a solution of 87.1 (0.612 g, 2.59 mmol) in DCE (15 mL) was added 1,2-ethanedithiol (3.47 mL, 41.4 mmol) followed by aluminum chloride (1.13 mL, 20.7 mmol) at 0° C. The reaction mixture was allowed to slowly warm to room temperature over four hours and was then quenched with saturated Rochelle's salt solution. The mixture was extracted (2×50 mL) with DCM. The combined organic layers were washed with water (1×40 mL) and brine (1×40 mL) and dried over magnesium sulfate. The filtrate was concentrated and the residue was purified by chromatography (silica, 0 to 30% EtOAc:hexanes) to give 87.2. The enantiomeric excess of 87.2 was increased to >99% by purification by chiral HPLC (Chiralcel OD-H column, 3% IPA/hexane, 220 nm).

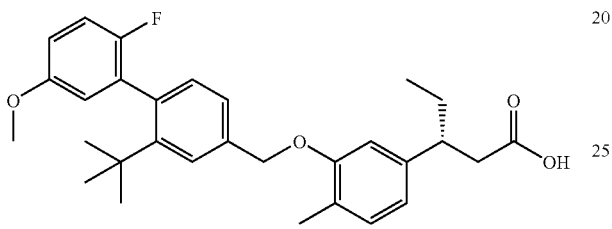

or

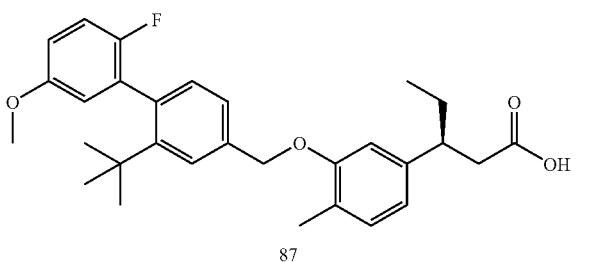

87

(3R)-3-(3-(((2-(5,5-Dimethyl-1-cyclopenten-1-yl)-2'-fluoro-5'-(methyloxy)-1,1'-biphenyl-4-yl)methyl)oxy)-4-methylphenyl)pentanoic acid or (3S)-3-(3-(((2-(5,5-dimethyl-1-cyclopenten-1-yl)-2'-fluoro-5'-(methyloxy)-1,1'-biphenyl-4-yl)methyl)oxy)-4-methylphenyl)pentanoic acid (87). 87 was synthesized analogous to the method for compound 7 from 87.2 and 8.10. MS ESI (pos.) m/e: 496.3 $(M+H_2O)^+$.

Example 88

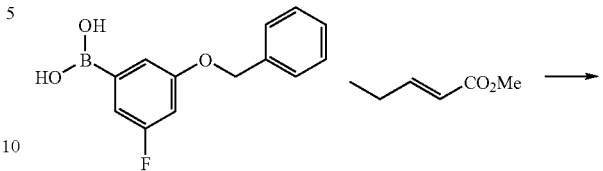

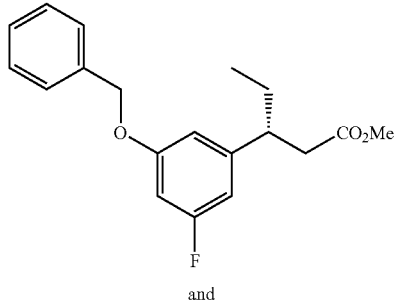

and

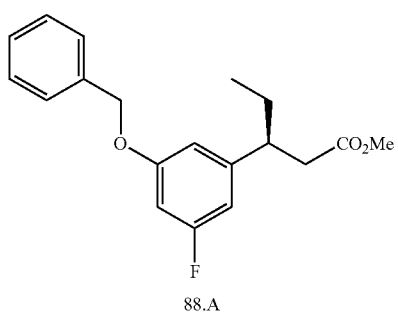

88.A

Methyl (3R)-3-(3-fluoro-5-((phenylmethyl)oxy)phenyl)pentanoate and methyl (3S)-3-(3-fluoro-5-((phenylmethyl)oxy)phenyl)pentanoate (88.A). THF (8 mL) was added to a flask charged with hydroxy[(S)-BINAP]-rhodium(I) dimer (79.2 mg, 87.6 μmol) and 3-(benzyloxy)-5-fluorophenylboronic acid (2156 mg, 8761 μmol) (commercially available from Combi-Block) and then sparged with nitrogen. To the resulting solution was added TEA (1462 μL, 10513 μmol), water (473 μL, 26283 μmol), and (E)-methyl pent-2-enoate (0.2000 g, 1752 μmol) (commercially available from Acros). The resulting mixture was then stirred at 60° C. for 3 hours. After evaporation of the solvent, the residue was dissolved in EtOAc. The solution was washed with saturated aqueous sodium bicarbonate and dried over anhydrous $Na_2SO_4$. Chromatography on silica gel (hexane:EtOAc 1:1) gave 88.A (490 mg, 88.4% yield) as a colorless oil.

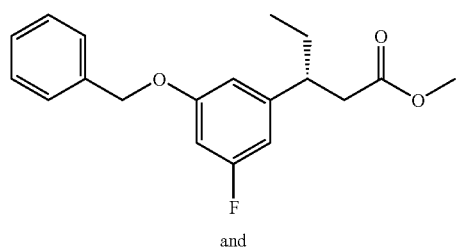

and

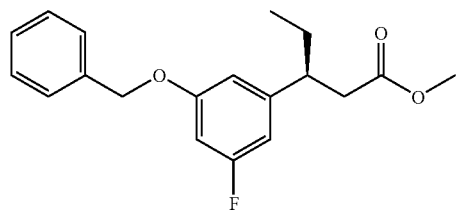

88.A

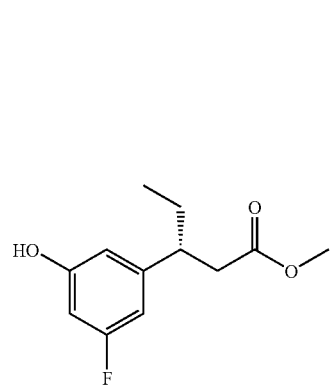

and

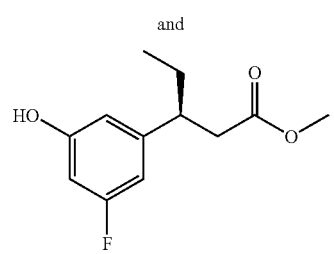

88

Methyl (3R)-3-(3-fluoro-5-hydroxyphenyl)pentanoate and methyl (3S)-3-(3-fluoro-5-hydroxyphenyl)pentanoate (88). To a flask containing 88.A (490 mg, 1549 µmol) under $N_2$ gas was added 10% Pd/C (100 mg, 940 µmol) and sealed with a rubber septum. To this system was added EtOAc (5 mL) then vacuum was applied followed by $H_2$ gas (3×) then left over a balloon of $H_2$ overnight. The reaction was filtered, concentrated, and purified by silica gel chromatography (0 to 20% EtOAc/hexanes) to afford 88 (330 mg, 94.2% yield). The enantiomeric excess of 88 was increased to >99% by purification by chiral HPLC (Chiralcel OD-H column, 3% IPA/hexane, 220 nm).

The following compounds were prepared from 88 and the appropriate halomethyl or hydroxymethyl compound according to the methods described herein. Each of the compounds in the following table were prepared using the same enantiomer of the phenol.

TABLE 21

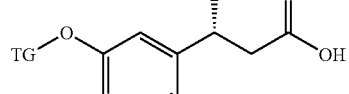

or

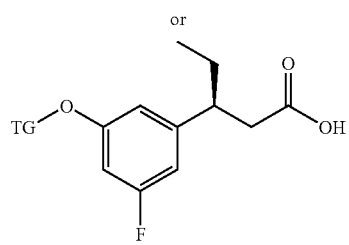

| Compound | TG |
|---|---|
| 88.1 | 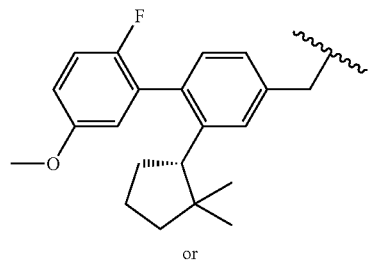 or 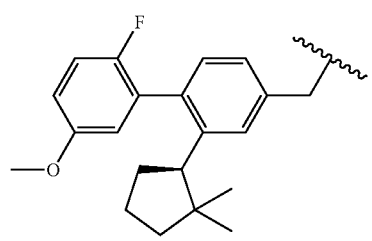 |
| 88.2 | 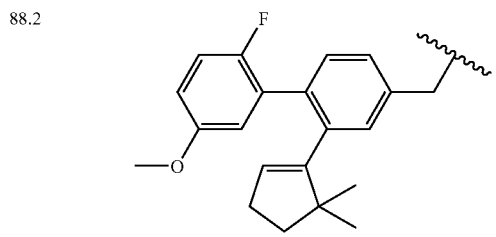 |

TABLE 21-continued 88.3

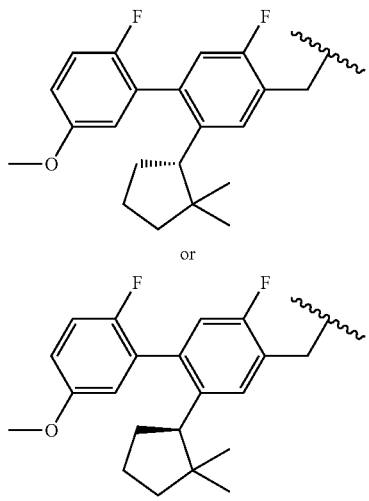

or 88.4

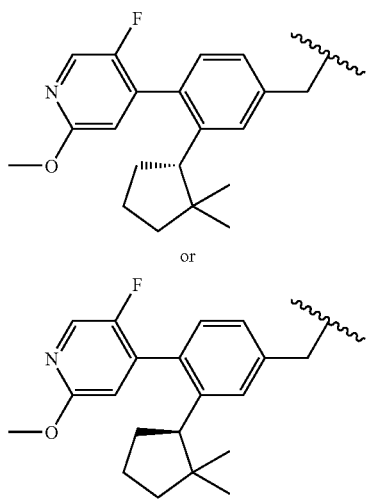

or (3R)-3-(3-(((2-((1S)-2,2-Dimethylcyclopentyl)-2'-fluoro-5'-(methyloxy)-1,1'-biphenyl-4-yl)methyl)oxy)-5-fluorophenyl)pentanoic acid or (3R)-3-(3-(((2-((1R)-2,2-dimethylcyclopentyl)-2'-fluoro-5'-(methyloxy)-1,1'-biphenyl-4-yl)methyl)oxy)-5-fluorophenyl)pentanoic acid or (3S)-3-(3-(((2-((1S)-2,2-dimethylcyclopentyl)-2'-fluoro-5'-(methyloxy)-1,1'-biphenyl-4-yl)methyl)oxy)-5-fluorophenyl)pentanoic acid or (3S)-3-(3-(((2-((1R)-2,2-dimethylcyclopentyl)-2'-fluoro-5'-(methyloxy)-1,1'-biphenyl-4-yl)methyl)oxy)-5-fluorophenyl)pentanoic acid (88.1). Example 88.1 was synthesized analogous to the method for compound 7 from 88 and 66.6O. MS ESI (pos.) m/e: 521.2 (M–H).

(3R)-3-(3-(((2-(5,5-Dimethyl-1-cyclopenten-1-yl)-2'-fluoro-5'-(methyloxy)-1,1'-biphenyl-4-yl)methyl)oxy)-5-fluorophenyl)pentanoic acid or (3S)-3-(3-(((2-(5,5-dimethyl-1-cyclopenten-1-yl)-2'-fluoro-5'-(methyloxy)-1,1'-biphenyl-4-yl)methyl)oxy)-5-fluorophenyl)pentanoic acid (88.2). Example 88.2 was synthesized analogous to the method for compound 7 from 88 and 14.5. MS ESI (pos.) m/e: 519.2 (M–H).

(3R)-3-(3-(((2-((1S)-2,2-Dimethylcyclopentyl)-2',5-difluoro-5'-(methyloxy)-1,1'-biphenyl-4-yl)methyl)oxy)-5-fluorophenyl)pentanoic acid or (3R)-3-(3-(((2-((1R)-2,2-dimethylcyclopentyl)-2',5-difluoro-5'-(methyloxy)-1,1'-biphenyl-4-yl)methyl)oxy)-5-fluorophenyl)pentanoic acid or (3S)-3-(3-(((2-((1S)-2,2-dimethylcyclopentyl)-2',5-difluoro-5'-(methyloxy)-1,1'-biphenyl-4-yl)methyl)oxy)-5-fluorophenyl)pentanoic acid or (3S)-3-(3-(((2-((1R)-2,2-dimethylcyclopentyl)-2',5-difluoro-5'-(methyloxy)-1,1'-biphenyl-4-yl)methyl)oxy)-5-fluorophenyl)pentanoic acid (88.3). Example 88.3 was synthesized using a method analogous to the method used for compound 7 using 88 and 66.44D. MS ESI (pos.) m/e: 539.2 (M–H).

(3R)-3-(3-(((3-((1S)-2,2-Dimethylcyclopentyl)-4-(5-fluoro-2-(methyloxy)-4-pyridinyl)phenyl)methyl)oxy)-5-fluorophenyl)pentanoic acid or (3R)-3-(3-(((3-((1R)-2,2-dimethylcyclopentyl)-4-(5-fluoro-2-(methyloxy)-4-pyridinyl)phenyl)methyl)oxy)-5-fluorophenyl)pentanoic acid or (3S)-3-(3-(((3-((1S)-2,2-dimethylcyclopentyl)-4-(5-fluoro-2-(methyloxy)-4-pyridinyl)phenyl)methyl)oxy)-5-fluorophenyl)pentanoic acid or (3S)-3-(3-(((3-((1R)-2,2-dimethylcyclopentyl)-4-(5-fluoro-2-(methyloxy)-4-pyridinyl)phenyl)methyl)oxy)-5-fluorophenyl)pentanoic acid (88.4). MS ESI (pos.) m/e: 524.2 (M–H).

Example 89

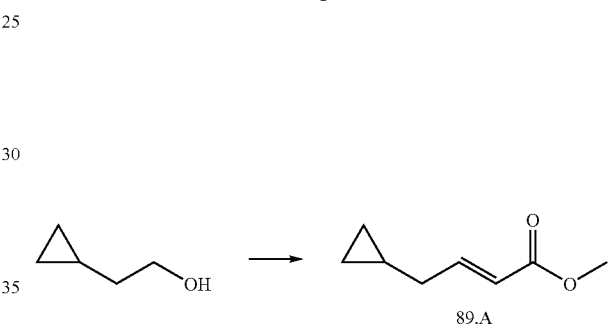

Methyl (2E)-4-cyclopropyl-2-butenoate (89.A). To a solution of 2-cyclopropylethanol (20.72 g, 240.6 mmol) (commercially available from Alfa Aesar) in 5:1 ACN/DCM (480 mL) were added TEMPO (1.879 g, 12.03 mmol) (commercially available from Aldrich) and iodobenzene diacetate (81.36 g, 252.6 mmol) (commercially available from Aldrich) as solids. The resulting slurry was stirred overnight at room temperature to afford a homogeneous solution. The reaction mixture was used directly in the next step. To a suspension of lithium chloride (15.30 g, 360.9 mmol) in ACN (400 mL) were added methyl 2-(diethoxyphosphoryl)acetate (48.04 mL, 288.7 mmol) (commercially available from Aldrich) and DBU (115.1 mL, 769.9 mmol) (commercially available from Aldrich) at room temperature. The mixture was cooled to 0° C., and to it was added 2-cyclopropylacetaldehyde (20.24 g, 240.6 mmol) solution dropwise. The resulting cloudy mixture was warmed to room temperature and stirred overnight. The mixture was partitioned between water and EtOAc. The layers were separated, and the aqueous phase was extracted with additional EtOAc. The combined organics were washed with water and brine, dried (MgSO$_4$), and concentrated. The crude product was purified by silica gel flash chromatography (0-10% EtOAc/hexane) to afford 89.A as a colorless liquid.

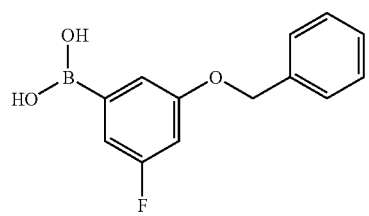

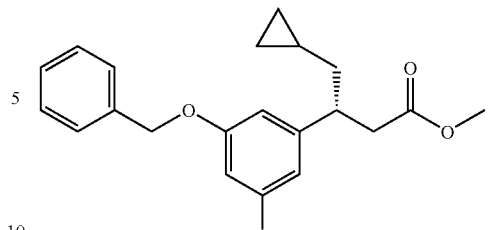

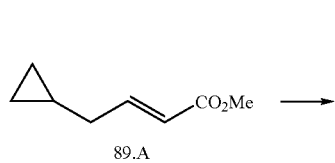

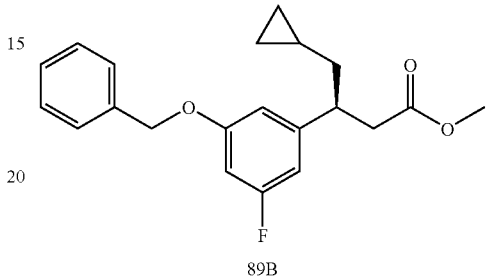

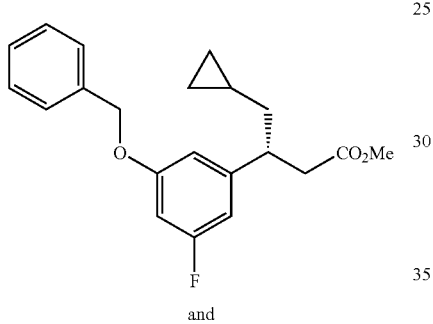

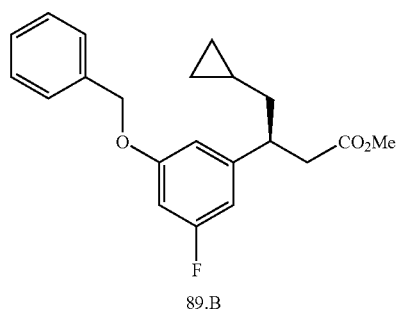

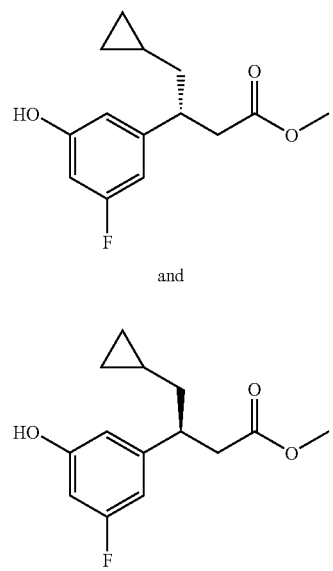

Methyl (3R)-4-cyclopropyl-3-(3-fluoro-5-((phenylmethyl)oxy)phenyl)butanoate and methyl (3S)-4-cyclopropyl-3-(3-fluoro-5-((phenylmethyl)oxy)phenyl)butanoate (89.B). THF (8 mL) was added to a flask charged with hydroxy[(S)-BINAP]-rhodium(I) dimer (64.5 mg, 71.3 μmol) and 3-(benzyloxy)-5-fluorophenylboronic acid (1053 mg, 4280 μmol (commercially available from Combi-Blocks) and then sparged with nitrogen. To the resulting solution was added TEA (1191 μL, 8560 μmol), water (386 μL, 21401 μmol), and (E)-methyl 4-cyclopropylbut-2-enoate (200.0 mg, 1427 μmol). The resulting mixture was then stirred at 60° C. for 3 hours. After removal of the solvent, the residue was dissolved in EtOAc. The solution was washed with 1 N HCl, brine, and dried over anhydrous $Na_2SO_4$. Chromatography on silica gel (hexane:EtOAc 1:1) gave 89.B (450 mg, 92.1% yield) as a colorless oil.

Methyl (3R)-4-cyclopropyl-3-(3-fluoro-5-hydroxyphenyl)butanoate or methyl (3S)-4-cyclopropyl-3-(3-fluoro-5-hydroxyphenyl)butanoate (89). To a flask containing 89.B (450 mg, 1314 μmol) under $N_2$ gas was added 10% Pd/C (100 mg, 940 μmol), and the flask was sealed with a rubber septum. To this system was added EtOAc (20 mL). A vacuum was applied followed by $H_2$ gas and the process was repeated three times. The reaction was then left under a balloon of $H_2$ overnight. The reaction was filtered, concentrated, and purified by combiflash (0 to 20% EtOAc/hexanes) and then purified by Chiral HPLC on an OD column (3% IPA/Hexane) to afford a 89 (280 mg, 84.4% yield).

The following compounds were prepared from 89 and the appropriate halomethyl or hydroxymethyl compound according to the methods described herein. Each of the compounds in the following table were prepared using the same enantiomer of the phenol.

TABLE 22

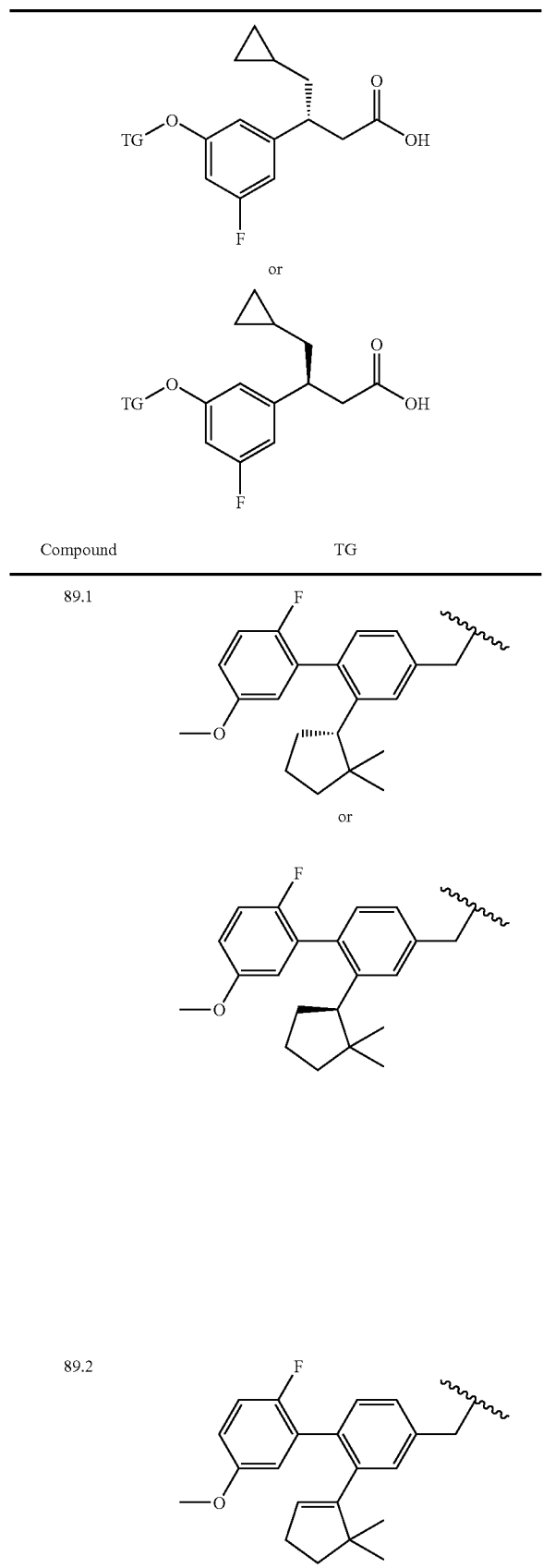

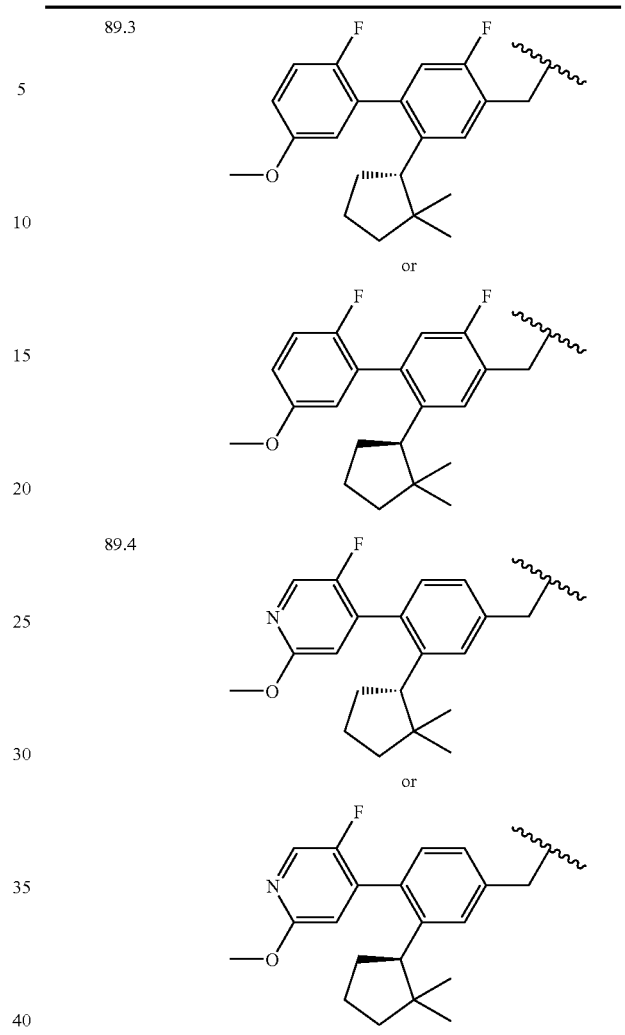

(3R)-4-Cyclopropyl-3-(3-(((2-((1S)-2,2-dimethylcyclopentyl)-2'-fluoro-5'-(methyloxy)-1,1'-biphenyl-4-yl)methyl)oxy)-5-fluorophenyl)butanoic acid or (3R)-4-cyclopropyl-3-(3-(((2-((1R)-2,2-dimethylcyclopentyl)-2'-fluoro-5'-(methyloxy)-1,1'-biphenyl-4-yl)methyl)oxy)-5-fluorophenyl)butanoic acid or (3S)-4-cyclopropyl-3-(3-(((2-((1S)-2,2-dimethylcyclopentyl)-2'-fluoro-5'-(methyloxy)-1,1'-biphenyl-4-yl)methyl)oxy)-5-fluorophenyl)butanoic acid or (3S)-4-cyclopropyl-3-(3-(((2-((1R)-2,2-dimethylcyclopentyl)-2'-fluoro-5'-(methyloxy)-1,1'-biphenyl-4-yl)methyl)oxy)-5-fluorophenyl)butanoic acid (89.1). MS ESI (pos.) m/e: 547.3 (M−H).

(3R)-4-Cyclopropyl-3-(3-(((2-(5,5-dimethyl-1-cyclopenten-1-yl)-2'-fluoro-5'-(methyloxy)-1,1'-biphenyl-4-yl)methyl)oxy)-5-fluorophenyl)butanoic acid or (3S)-4-cyclopropyl-3-(3-(((2-(5,5-dimethyl-1-cyclopenten-1-yl)-2'-fluoro-5'-(methyloxy)-1,1'-biphenyl-4-yl)methyl)oxy)-5-fluorophenyl)butanoic acid (89.2). MS ESI (pos.) m/e: 545.2 (M−H).

(3R)-4-Cyclopropyl-3-(3-(((2-((1S)-2,2-dimethylcyclopentyl)-2',5-difluoro-5'-(methyloxy)-1,1'-biphenyl-4-yl)methyl)oxy)-5-fluorophenyl)butanoic acid or (3R)-4-cyclopropyl-3-(3-(((2-((1R)-2,2-dimethylcyclopentyl)-2',5-difluoro-5'-(methyloxy)-1,1'-biphenyl-4-yl)methyl)oxy)-5-fluorophenyl)butanoic acid or (3S)-4-cyclopropyl-3-(3-(((2-

((1S)-2,2-dimethylcyclopentyl)-2',5-difluoro-5'-(methyloxy)-1,1'-biphenyl-4-yl)methyl)oxy)-5-fluorophenyl)butanoic acid or (3S)-4-cyclopropyl-3-(3-(((2-((1R)-2,2-dimethylcyclopentyl)-2',5-difluoro-5'-(methyloxy)-1,1'-biphenyl-4-yl)methyl)oxy)-5-fluorophenyl)butanoic acid (89.3). MS ESI (pos.) m/e: 565.3 (M–H).

(3R)-4-Cyclopropyl-3-(3-(((3-((1S)-2,2-dimethylcyclopentyl)-4-(5-fluoro-2-(methyloxy)-4-pyridinyl)phenyl)methyl)oxy)-5-fluorophenyl)butanoic acid or (3R)-4-cyclopropyl-3-(3-(((3-((1R)-2,2-dimethylcyclopentyl)-4-(5-fluoro-2-(methyloxy)-4-pyridinyl)phenyl)methyl)oxy)-5-fluorophenyl)butanoic acid or (3S)-4-cyclopropyl-3-(3-(((3-((1S)-2,2-dimethylcyclopentyl)-4-(5-fluoro-2-(methyloxy)-4-pyridinyl)phenyl)methyl)oxy)-5-fluorophenyl)butanoic acid or (3S)-4-cyclopropyl-3-(3-(((3-((1R)-2,2-dimethylcyclopentyl)-4-(5-fluoro-2-(methyloxy)-4-pyridinyl)phenyl)methyl)oxy)-5-fluorophenyl)butanoic acid (89.4). MS ESI (pos.) m/e: 550.3 (M–H).

Example 90

Synthesis of (R)-methyl 3-(2,5-difluoro-3-hydroxyphenyl)pentanoate (90.I) and (S)-methyl 3-(2,5-difluoro-3-hydroxyphenyl)pentanoate (90.H).

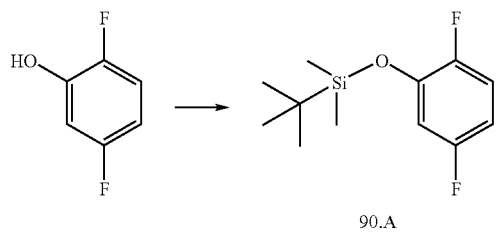

90.A tert-Butyl(2,5-difluorophenoxy)dimethylsilane (90.A). 90.A was prepared from 2,5-difluorophenol (commercially available from Aldrich) according to the analogous method described in Example 84.

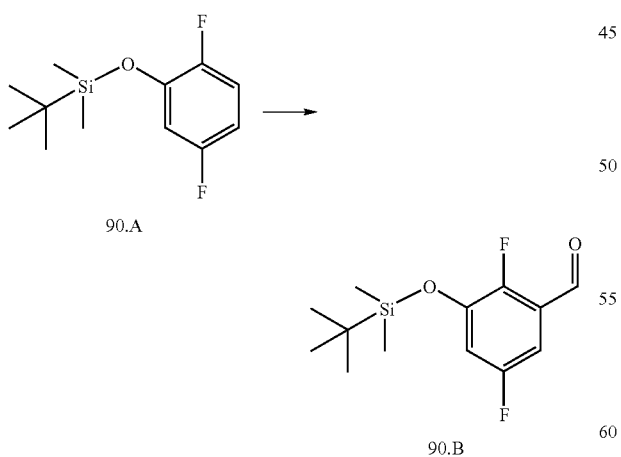

90.A

90.B 3-(tert-Butyldimethylsilyloxy)-2,5-difluorobenzaldehyde (90.B). A 500 mL round bottom flask was charged with 90.A (8.60 g, 35.2 mmol) and THF (70 mL) and cooled to –78° C. under N$_2$. To the cold solution was added sec-butyllithium (1.4 M in cyclohexane) (available from Aldrich) (27.7 mL, 38.7 mmol) dropwise. The mixture was stirred for 30 minutes, and to it was added DMF (4.09 mL, 52.8 mmol) dropwise. The mixture was stirred for 30 minutes at –78° C., warmed to room temperature over 30 minutes, quenched with 1 N HCl, and diluted with EtOAc. The organic layers were washed with water and brine, dried (MgSO$_4$), and concentrated. The crude product was purified by silica gel flash chromatography (0-5% EtOAc/hexane) to afford 90.B (5.71 g, 59.6% yield) as a colorless oil.

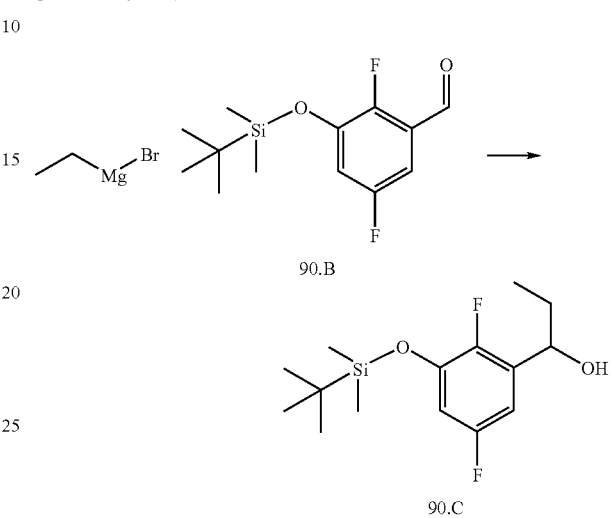

90.B

90.C 1-(3-(tert-Butyldimethylsilyloxy)-2,5-difluorophenyl)propan-1-ol (90.C). A 200 mL round bottom flask was charged with 90.B (1.38 g, 5.1 mmol) and THF (10 mL) and cooled to –78° C. under N$_2$. To the cold solution was added ethylmagnesium bromide (3.0 M in ether) (commercially available from Aldrich) (5.1 mL, 15 mmol) dropwise. The mixture was stirred for 30 minutes at –78° C. The cooling bath was removed, and the mixture was stirred for 30 minutes at ambient temperature. The reaction was quenched with saturated aqueous ammonium chloride and diluted with EtOAc. The organic layers were washed with water and brine, dried (MgSO$_4$), and concentrated. The crude product was purified by silica gel flash chromatography (0-15% EtOAc/hexane) to afford 90.C (0.48 g, 31% yield) as a colorless oil.

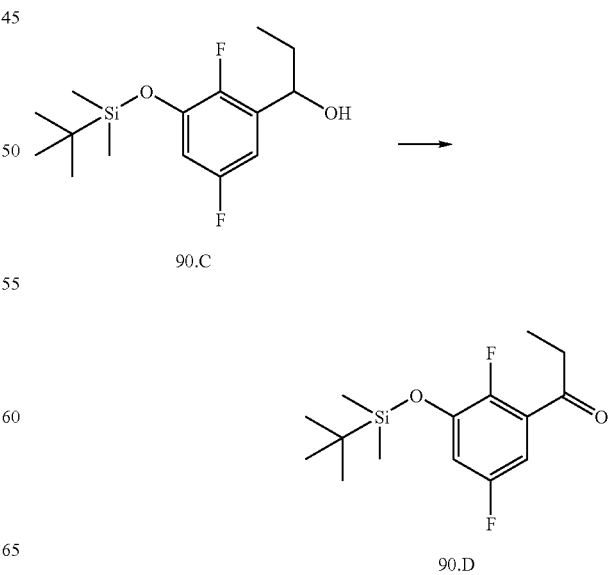

90.C

90.D 1-(3-(tert-Butyldimethylsilyloxy)-2,5-difluorophenyl)propan-1-one (90.D). A 200 mL round bottom flask was charged with 90.C (0.48 g, 1.6 mmol), DCM (15 mL), iodobenzene diacetate (0.56 g, 1.7 mmol), and TEMPO (0.012 g, 0.079 mmol). The mixture was stirred overnight at room temperature and diluted with EtOAc. The organics were washed with saturated aqueous sodium thiosulfate, saturated aqueous sodium bicarbonate, and brine, dried (MgSO$_4$), and concentrated. The crude product was purified by silica gel flash chromatography (0-5% EtOAc/hexane) to afford 90.D (0.45 g, 94% yield) as a colorless oil.

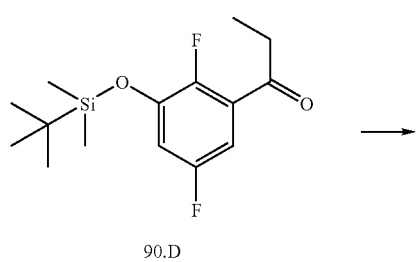

90.D

Methyl 3-(3-(tert-butyldimethylsilyloxy)-2,5-difluorophenyl)pent-2-enoate (90.E). Compound 90.E (mixture of geometric isomers) was prepared from 90.D and methyl (trimethylsilyl)acetate (available from Aldrich) according to the analogous method described in Example 84.

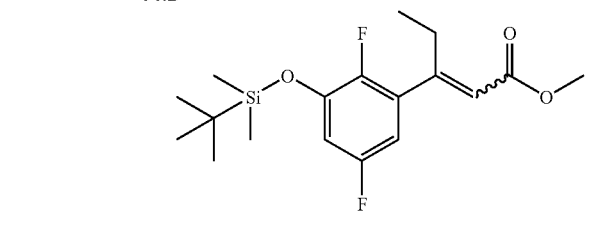

90.E

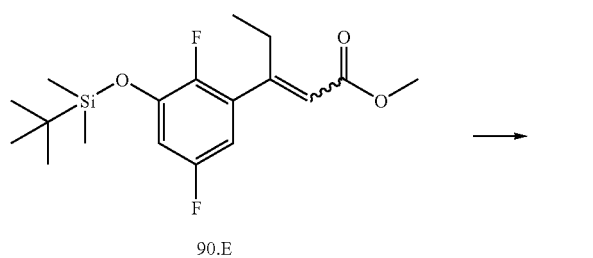

Methyl 3-(3-(tert-butyldimethylsilyloxy)-2,5-difluorophenyl)pentanoate (90.F). A 75 mL pressure tube was charged with 90.E (mixture of geometric isomers) (0.26 g, 0.73 mmol), MeOH (7 mL), and Pd/C (10 wt. %) (0.039 g, 0.036 mmol). The tube was purged 3 times with H$_2$ at 50 psi and sealed. The mixture was stirred for 8 hours at room temperature, filtered through silica gel (EtOAc), and concentrated to afford 90.F (0.23 g, 88% yield) as a colorless oil. The product thus obtained was used without further purification.

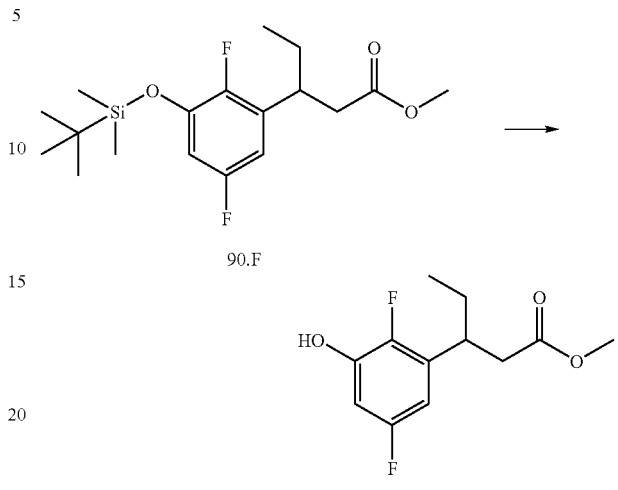

Methyl 3-(2,5-difluoro-3-hydroxyphenyl)pentanoate (90.G). A screw-cap vial was charged with 90.F (0.23 g, 0.64 mmol), DMF (2.5 mL), and potassium fluoride (0.075 g, 1.3 mmol). The mixture was stirred for 5 minutes at room temperature, quenched with 1 N HCl, and diluted with EtOAc. The organics were washed with water and brine, dried (MgSO$_4$), and concentrated. The crude product was purified by silica gel flash chromatography (0-20% EtOAc/hexane) to afford 90.G (0.13 g, 83% yield) as a colorless oil.

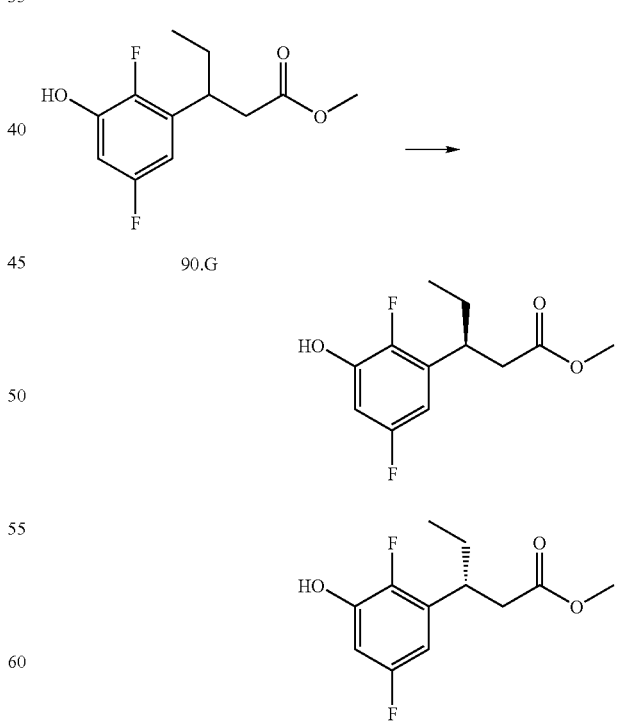

(S)-Methyl 3-(2,5-difluoro-3-hydroxyphenyl)pentanoate and (R)-methyl 3-(2,5-difluoro-3-hydroxyphenyl)pentanoate (90.H and 90.I). Racemic 90.G (0.13 g, 0.53 mmol) was resolved by chiral HPLC (Chiralpak AS column, 3% IPA/hexane, detection at 220 nm) to afford (in order of elution) 90.H (0.057 g, 88% yield, 99% e.e.) and 90.1 (0.055 g, 85% yield, 99% e.e.) as colorless oils.

The following compounds were prepared from 90.I and the appropriate halomethyl or hydroxymethyl compound according to the methods described herein. Each of the compounds in the following table were prepared using the same enantiomer of the phenol.

TABLE 23

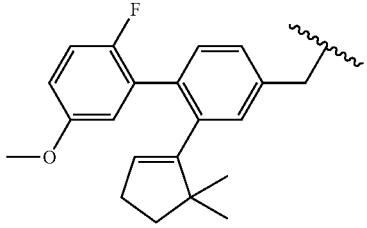

or

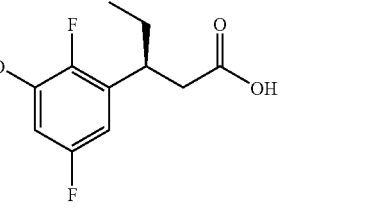

| Compound | TG |
|---|---|
| 90.1 | 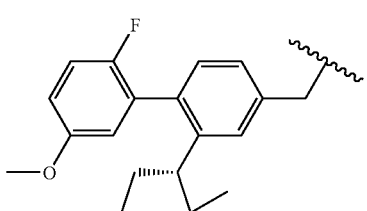 |
| 90.2 | 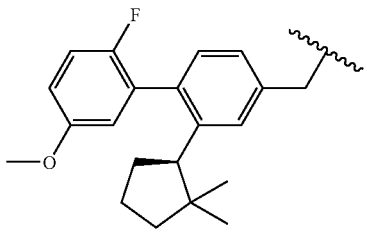 |

TABLE 23-continued

| 90.3 | 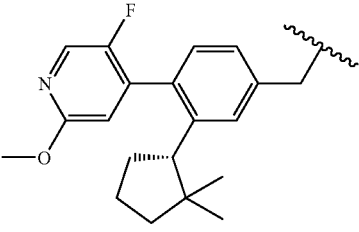 |
|---|---|
|  | or |
|  | 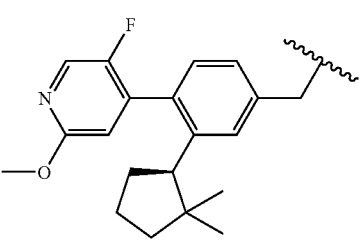 |

(3R)-3-(3-(((2-(5,5-Dimethyl-1-cyclopenten-1-yl)-2'-fluoro-5'-(methyloxy)-1,1'-biphenyl-4-yl)methyl)oxy)-2,5-difluorophenyl)pentanoic acid or (3S)-3-(3-(((2-(5,5-dimethyl-1-cyclopenten-1-yl)-2'-fluoro-5'-(methyloxy)-1,1'-biphenyl-4-yl)methyl)oxy)-2,5-difluorophenyl)pentanoic acid (90.1). MS ESI (neg.) m/e: 537.3 (M–H)⁺.

(3R)-3-(3-(((2-((1S)-2,2-Dimethylcyclopentyl)-2'-fluoro-5'-(methyloxy)-1,1'-biphenyl-4-yl)methyl)oxy)-2,5-difluorophenyl)pentanoic acid or (3R)-3-(3-(((2-((1R)-2,2-dimethylcyclopentyl)-2'-fluoro-5'-(methyloxy)-1,1'-biphenyl-4-yl)methyl)oxy)-2,5-difluorophenyl)pentanoic acid or (3S)-3-(3-(((2-((1S)-2,2-dimethylcyclopentyl)-2'-fluoro-5'-(methyloxy)-1,1'-biphenyl-4-yl)methyl)oxy)-2,5-difluorophenyl)pentanoic acid or (3S)-3-(3-(((2-((1R)-2,2-dimethylcyclopentyl)-2'-fluoro-5'-(methyloxy)-1,1'-biphenyl-4-yl)methyl)oxy)-2,5-difluorophenyl)pentanoic acid (90.2). MS ESI (neg.) m/e: 539.2 (M–H)⁺.

(3R)-3-(3-(((3-((1S)-2,2-Dimethylcyclopentyl)-4-(5-fluoro-2-(methyloxy)-4-pyridinyl)phenyl)methyl)oxy)-2,5-difluorophenyl)pentanoic acid or (3R)-3-(3-(((3-((1R)-2,2-dimethylcyclopentyl)-4-(5-fluoro-2-(methyloxy)-4-pyridinyl)phenyl)methyl)oxy)-2,5-difluorophenyl)pentanoic acid or (3S)-3-(3-(((3-((1S)-2,2-dimethylcyclopentyl)-4-(5-fluoro-2-(methyloxy)-4-pyridinyl)phenyl)methyl)oxy)-2,5-difluorophenyl)pentanoic acid or (3S)-3-(3-(((3-((1R)-2,2-dimethylcyclopentyl)-4-(5-fluoro-2-(methyloxy)-4-

Example 91

Synthesis of (3R)-3-(3-(((2-(5,5-dimethyl-1-cyclopenten-1-yl)-2'-fluoro-5'-(methyloxy)-1,1'-biphenyl-4-yl)methyl)oxy)-5-(trifluoromethyl)phenyl)pentanoic acid or (3S)-3-(3-(((2-(5,5-dimethyl-1-cyclopenten-1-yl)-2'-fluoro-5'-(methyloxy)-1,1'-biphenyl-4-yl)methyl)oxy)-5-(trifluoromethyl)phenyl)pentanoic acid (91)

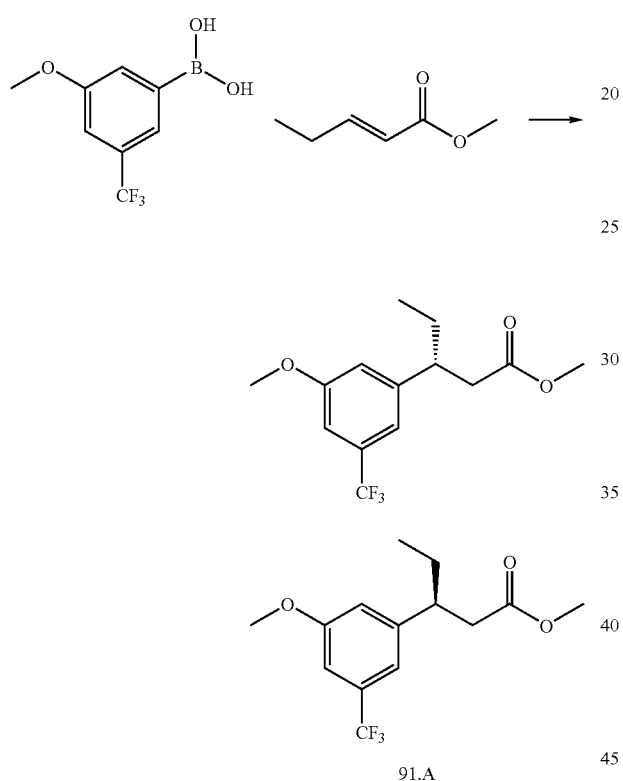

91.A

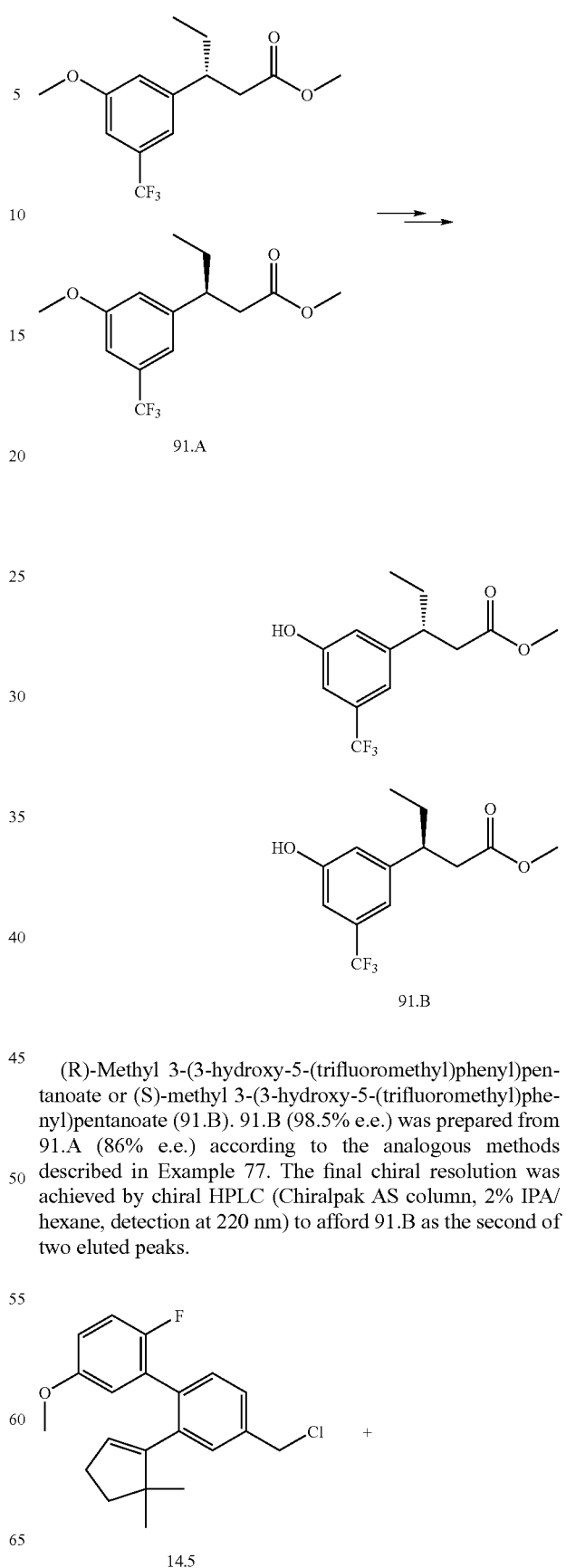

(R)-Methyl 3-(3-methoxy-5-(trifluoromethyl)phenyl)pentanoate and (S)-methyl 3-(3-methoxy-5-(trifluoromethyl)phenyl)pentanoate (91.A). A screw-cap vial was charged with 3-methoxy-5-(trifluoromethyl)benzeneboronic acid (available from Combi-Blocks) (0.98 g, 4.5 mmol), (S)-(−)-2,2'-bis(diphenylphosphino)-1,1'-binaphthalene (available from Aldrich) (0.067 g, 0.11 mmol), acetylacetonatobis(ethylene)rhodium(I) (available from Strem) (0.023 g, 0.089 mmol), and 10:1 1,4-dioxane/water (3.6 mL). The mixture was purged with $N_2$, and to it was added methyl 2-pentenoate (available from Acros) (0.12 mL, 0.89 mmol). The resulting solution was stirred overnight at 100° C. (sealed vial), cooled to room temperature, and diluted with EtOAc. The organics were washed with saturated aqueous sodium bicarbonate, water, and brine, dried ($MgSO_4$), and concentrated. The crude product was purified by silica gel flash chromatography (0-10% EtOAc/hexane) to afford 91.A (0.21 g, 81% yield, 86% e.e.) as a colorless liquid. The major product is believed to be the R enantiomer.

(R)-Methyl 3-(3-hydroxy-5-(trifluoromethyl)phenyl)pentanoate or (S)-methyl 3-(3-hydroxy-5-(trifluoromethyl)phenyl)pentanoate (91.B). 91.B (98.5% e.e.) was prepared from 91.A (86% e.e.) according to the analogous methods described in Example 77. The final chiral resolution was achieved by chiral HPLC (Chiralpak AS column, 2% IPA/hexane, detection at 220 nm) to afford 91.B as the second of two eluted peaks.

-continued


or

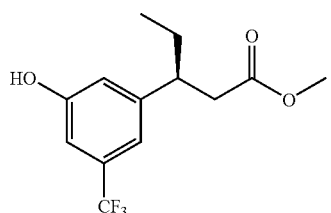

91.B

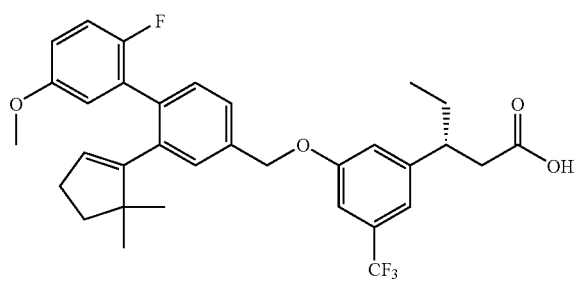

or

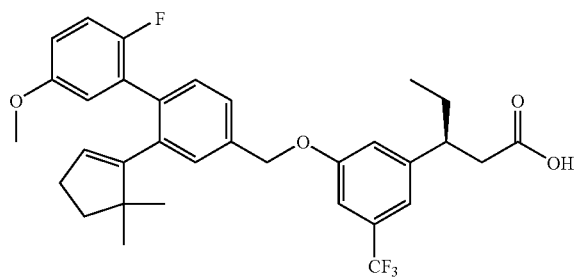

91

(3R)-3-(3-(((2-(5,5-Dimethyl-1-cyclopenten-1-yl)-2'-fluoro-5'-(methyloxy)-1,1'-biphenyl-4-yl)methyl)oxy)-5-(trifluoromethyl)phenyl)pentanoic acid or (3S)-3-(3-(((2-(5,5-dimethyl-1-cyclopenten-1-yl)-2'-fluoro-5'-(methyloxy)-1,1'-biphenyl-4-yl)methyl)oxy)-5-(trifluoromethyl)phenyl)pentanoic acid (91). 91 was prepared from 91.B and 14.5 according to the analogous methods described in Example 7. MS ESI (neg.) m/e: 569.2 (M−H)⁺. The product is believed to be the R enantiomer.

Example 92

Synthesis of (3R)-3-(3-(((2-(1,1-dimethylethyl)-2'-fluoro-5'-(methyloxy)-1,1'-biphenyl-4-yl)methyl)oxy)phenyl)-5-methylhexanoic acid or (3S)-3-(3-(((2-(1,1-dimethylethyl)-2'-fluoro-5'-(methyloxy)-1,1'-biphenyl-4-yl)methyl)oxy)phenyl)-5-methylhexanoic acid (92)

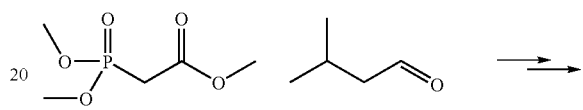

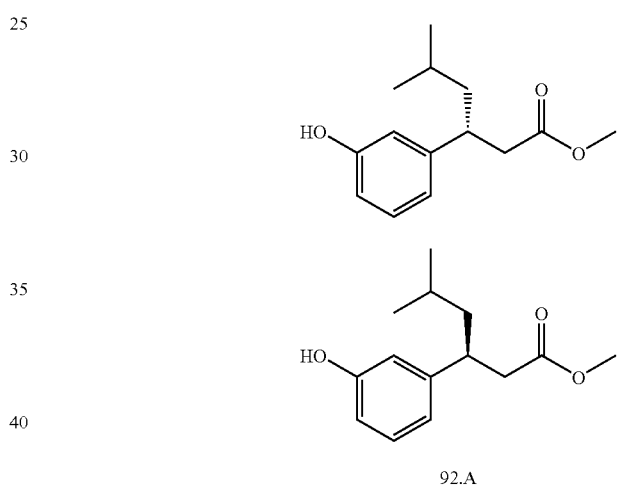

92.A (R)-Methyl 3-(3-hydroxyphenyl)-5-methylhexanoate and (S)-methyl 3-(3-hydroxyphenyl)-5-methylhexanoate (92.A). Example 92.A (99% e.e.) was prepared from trimethyl phosphonoacetate (available from Aldrich) and isovaleraldehyde (available from Aldrich) according to the analogous methods described in Example 68. The final chiral resolution was achieved by chiral HPLC (Chiralcel OD column, 3% IPA/hexane, detection at 220 nm) to afford 92.A as the first of two eluted peaks. The R enantiomer is believed to corresponds to 92.A.

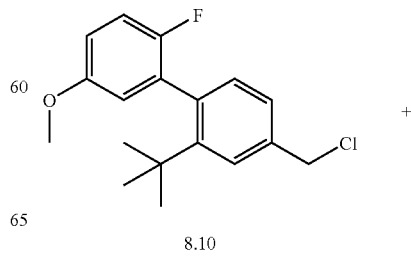

8.10

-continued

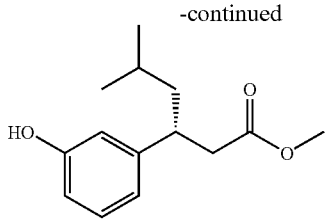

or

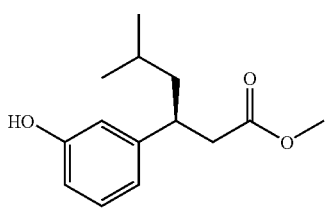

92.A

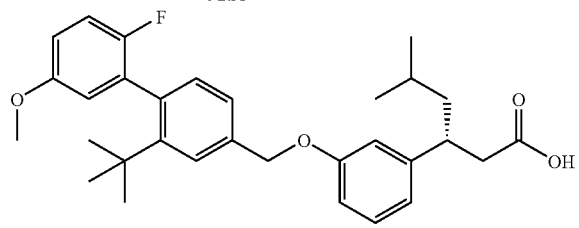

or

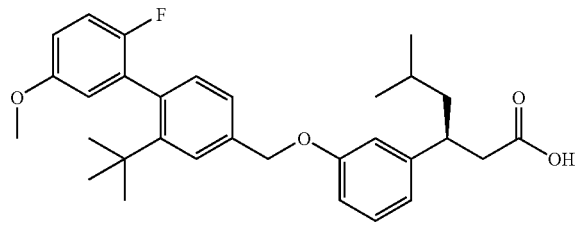

92

(3R)-3-(3-(((2-(1,1-Dimethylethyl)-2'-fluoro-5'-(methyloxy)-1,1'-biphenyl-4-yl)methyl)oxy)phenyl)-5-methylhexanoic acid or (3S)-3-(3-(((2-(1,1-dimethylethyl)-2'-fluoro-5'-(methyloxy)-1,1'-biphenyl-4-yl)methyl)oxy)phenyl)-5-methylhexanoic acid (92). 92 was prepared from 92.A and 8.10 according to the analogous methods described in Example 7. MS ESI (neg.) m/e: 491.2 (M−H)$^+$. The product is believed to be the R enantiomer.

Example 93

Synthesis of (S)-ethyl 3-(3-hydroxyphenyl)-3-((1R, 2R)-2-methylcyclopropyl)propanoate (93.H) and (R)-ethyl 3-(3-hydroxyphenyl)-3-((1R,2R)-2-methylcyclopropyl)propanoate (93.I)

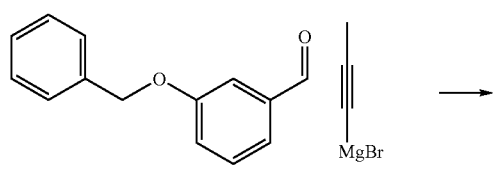

-continued

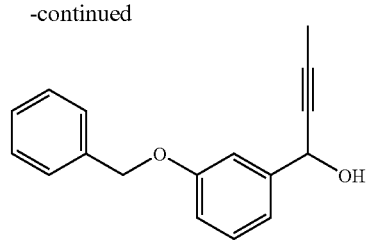

93.A 1-(3-(Benzyloxy)phenyl)but-2-yn-1-ol (93.A). A 1 L round bottom flask was charged with 1-propynylmagnesium bromide (0.5 M in THF) (available from Aldrich) (245 mL, 123 mmol) and cooled to −78° C. To the cold slurry was added a solution of 3-benzyloxybenzaldehyde (available from Aldrich) (20.0 g, 94.2 mmol) in THF (30 mL) over 15 minutes. The mixture was stirred for 30 minutes at −78° C., the cooling bath was removed, and stirring was continued for 1 hour at ambient temperature. The reaction was quenched with saturated aqueous ammonium chloride and diluted with EtOAc. The organics were washed with water and brine, dried (MgSO$_4$), and concentrated. The crude product was purified by silica gel flash chromatography (0-30% EtOAc/hexane) to afford 93.A (23.1 g, 97% yield) as a pale yellow oil.

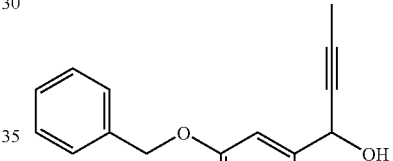

93.A

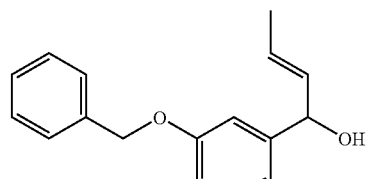

93.B (E)-1-(3-(Benzyloxy)phenyl)but-2-en-1-ol (93.B). To a cold solution of sodium bis(2-methoxyethoxy)aluminum hydride (65+ wt. % in toluene) (available from Aldrich) (14.8 mL, 49.1 mmol) in ether (60 mL) was added a solution of 93.A (6.20 g, 24.6 mmol) in ether (30 mL) dropwise under nitrogen at 0° C. The mixture was stirred for 5 minutes at 0° C., the cooling bath was removed, and stirring was continued for 3 hours at room temperature. The reaction was carefully quenched at 0° C. with EtOAc, diluted with saturated aqueous Rochelle salt, and extracted with additional EtOAc. The combined organics were washed with water and brine, dried (MgSO$_4$), and concentrated. The crude product was purified by silica gel flash chromatography (0-20% EtOAc/hexane) to afford 93.B (5.37 g, 86% yield) as a colorless oil.

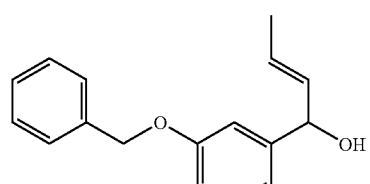

93.B

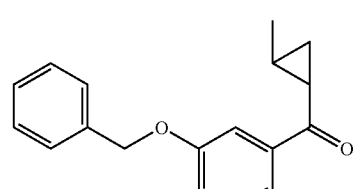

93.D

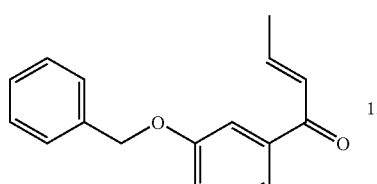

93.C (E)-1-(3-(Benzyloxy)phenyl)but-2-en-1-one (93.C). 93.C was prepared from 93.B via oxidation with TEMPO and iodobenzene diacetate according to the analogous method described in Example 90.

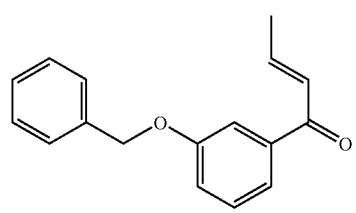

93.C

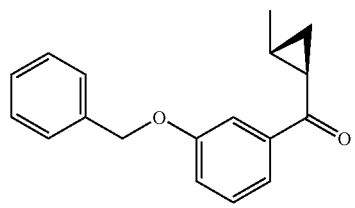

93.E and 93.F (3-(Benzyloxy)phenyl)((1R,2R)-2-methylcyclopropyl)methanone and (3-(benzyloxy)phenyl)((1S,2S)-2-methylcyclopropyl)methanone (93.E and 93.F). Racemic 93.D (2.04 g, 7.66 mmol) was resolved by chiral HPLC (Chiralcel OD column, 1% IPA/hexane, detection at 220 nm) to afford (in order of elution) 93.E (0.842 g, 82.5% yield, 99% e.e.) and 93.F (0.864 g, 84.7% yield, 99% e.e.) as pale yellow oils.

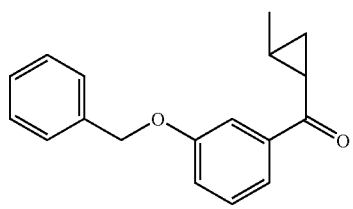

93.D

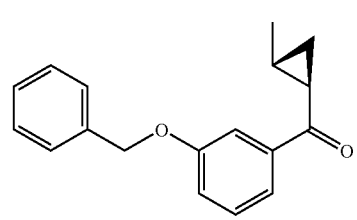

or

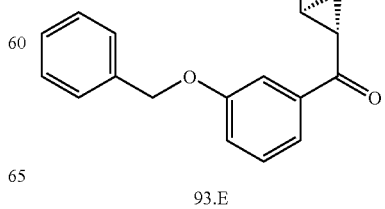

93.E (3-(Benzyloxy)phenyl)(2-methylcyclopropyl)methanone (93.D). To a solution of 93.C (5.33 g, 21.1 mmol) in ACN (200 mL) were added trimethylsulfoxonium iodide (available from Aldrich) (5.58 g, 25.3 mmol) and DBU (4.11 mL, 27.5 mmol). The mixture was stirred overnight at 60° C. under $N_2$, cooled to room temperature, and concentrated. The crude product was purified by silica gel flash chromatography (0-10% EtOAc/hexane) to afford 93.D (2.04 g, 36% yield) as a colorless oil.

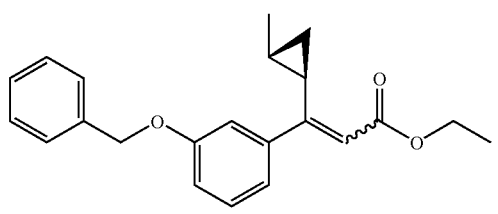

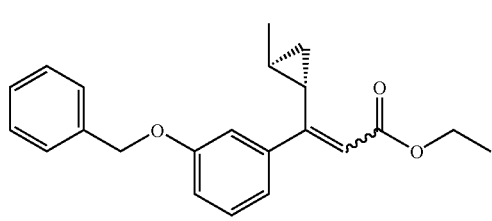

93.G

Ethyl 3-(3-(benzyloxy)phenyl)-3-((1R,2R)-2-methylcyclopropyl)acrylate or ethyl 3-(3-(benzyloxy)phenyl)-3-((1S,2S)-2-methylcyclopropyl)acrylate (93.G). 93.G (mixture of geometric isomers) was prepared from 93.E and ethyl (trimethylsilyl)acetate (available from Aldrich) according to the analogous method described in Example 84.

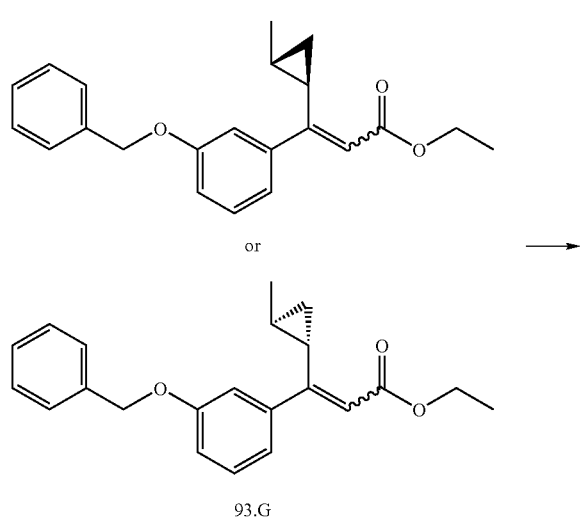

93.G

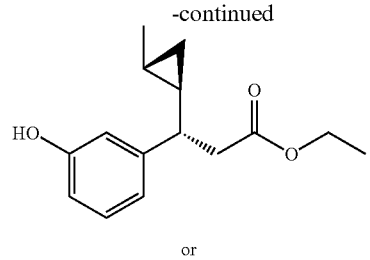

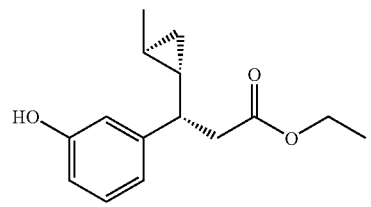

93.H and 93.I

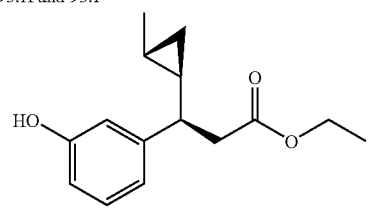

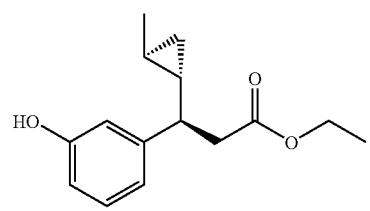

(S)-Ethyl 3-(3-hydroxyphenyl)-3-((1R,2R)-2-methylcyclopropyl)propanoate and (R)-ethyl 3-(3-hydroxyphenyl)-3-((1R,2R)-2-methylcyclopropyl)propanoate or (R)-Ethyl 3-(3-hydroxyphenyl)-3-((1S,2S)-2-methylcyclopropyl)propanoate and (S)-ethyl 3-(3-hydroxyphenyl)-3-((1S,2S)-2-methylcyclopropyl)propanoate (93.H and 93.I). To a solution of 93.G (0.201 g, 0.60 mmol) in EtOH (6 mL) was added platinum(IV) oxide (0.014 g, 0.060 mmol). The mixture was purged with $H_2$ and stirred for 48 hours under a $H_2$ balloon. $H_2$ was expelled from the mixture by purging with $N_2$, and Pd/C (10 wt. %) (0.032 g, 0.030 mmol) was added. The final mixture was purged with $H_2$, stirred for 2 hours under a $H_2$ balloon, filtered through silica gel (EtOAc), and concentrated. The crude product was purified by silica gel flash chromatography (0-25% EtOAc/hexane) and subsequently by reverse-phase HPLC (40-80% ACN/water) to afford a mixture of 93.H and 93.I. The epimers were resolved by chiral HPLC (Chiralcel OD column, 3% IPA/hexane, detection at 220 nm) to afford (in order of elution) 93.H (0.030 g, 20% yield, 99% d.e.) and 93.I (0.032 g, 22% yield, 99% d.e.) as colorless oils.

The following compounds were prepared from 93.H and the appropriate halomethyl or hydroxymethyl compound according to the methods described herein. Each of the compounds in the following table were prepared using the same enantiomer of the phenol.

TABLE 24

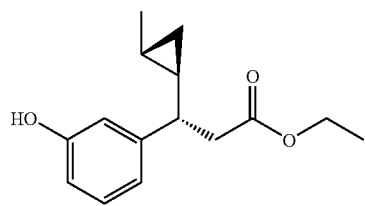

or

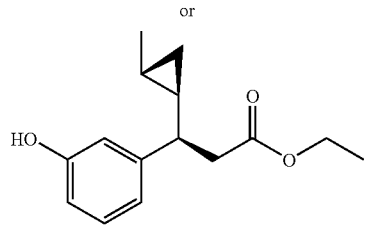

or

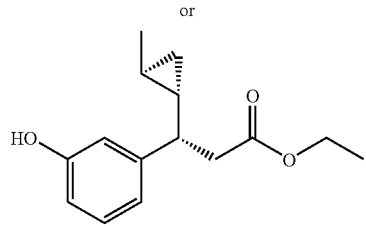

or

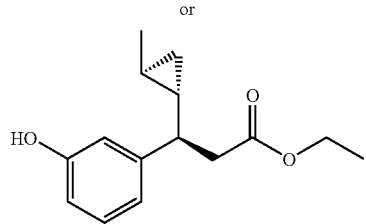

| Compound | TG |
|---|---|
| 93.1 | 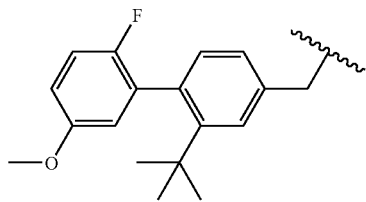 |
| 93.2 | 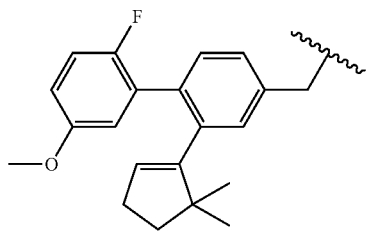 |

(3S)-3-(3-(((2-(1,1-Dimethylethyl)-2'-fluoro-5'-(methyloxy)-1,1'-biphenyl-4-yl)methyl)oxy)phenyl)-3-((1R,2R)-2-methylcyclopropyl)propanoic acid or (3R)-3-(3-(((2-(1,1-dimethylethyl)-2'-fluoro-5'-(methyloxy)-1,1'-biphenyl-4-yl)methyl)oxy)phenyl)-3-((1R,2R)-2-methylcyclopropyl)propanoic acid or (3S)-3-(3-(((2-(1,1-dimethylethyl)-2'-fluoro-5'-(methyloxy)-1,1'-biphenyl-4-yl)methyl)oxy)phenyl)-3-((1S,2S)-2-methylcyclopropyl)propanoic acid or (3R)-3-(3-(((2-(1,1-Dimethylethyl)-2'-fluoro-5'-(methyloxy)-1,1'-biphenyl-4-yl)methyl)oxy)phenyl)-3-((1S,2S)-2-methylcyclopropyl)propanoic acid (93.1). MS ESI (pos.) m/e: 508.3 (M+H$_2$O)$^+$.

(3S)-3-(3-(((2-(5,5-Dimethyl-1-cyclopenten-1-yl)-2'-fluoro-5'-(methyloxy)-1,1'-biphenyl-4-yl)methyl)oxy)phenyl)-3-((1R,2R)-2-methylcyclopropyl)propanoic acid or (3R)-3-(3-(((2-(5,5-dimethyl-1-cyclopenten-1-yl)-2'-fluoro-5'-(methyloxy)-1,1'-biphenyl-4-yl)methyl)oxy)phenyl)-3-((1R,2R)-2-methylcyclopropyl)propanoic acid or (3S)-3-(3-(((2-(5,5-dimethyl-1-cyclopenten-1-yl)-2'-fluoro-5'-(methyloxy)-1,1'-biphenyl-4-yl)methyl)oxy)phenyl)-3-((1S,2S)-2-methylcyclopropyl)propanoic acid or (3R)-3-(3-(((2-(5,5-dimethyl-1-cyclopenten-1-yl)-2'-fluoro-5'-(methyloxy)-1,1'-biphenyl-4-yl)methyl)oxy)phenyl)-3-((1S,2S)-2-methylcyclopropyl)propanoic acid (93.2). MS ESI (pos.) m/e: 546.3 (M+H$_2$O)$^+$.

Example 94

Synthesis of methyl (3R)-3-(3-hydroxyphenyl)-3-(3-isoxazolyl)propanoate (94.1F))

Example 94.1

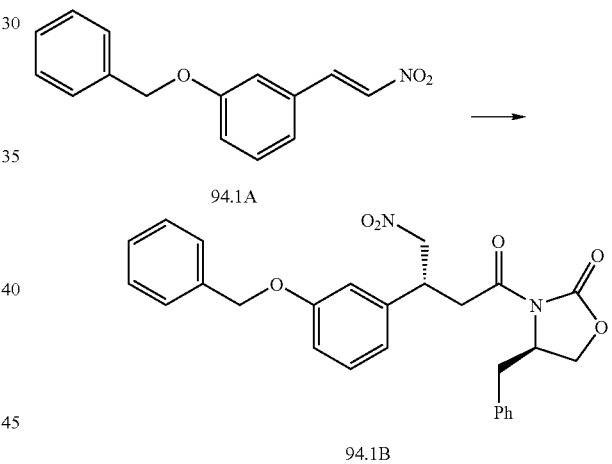

(4R)-3-((3R)-4-Nitro-3-(3-((phenylmethyl)oxy)phenyl) butanoyl)-4-(phenylmethyl)-1,3-oxazolidin-2-one (94.1B). At −78° C., titanium(iv) chloride (1.0 M solution in DCM) (17.8 mL, 17.8 mmol) was added slowly to a solution of (R)-3-acetyl-4-benzyloxazolidin-2-one (available from Aldrich) (3.55 g, 16.2 mmol) in DCM (80 mL), followed by slow addition of diisopropylethyl amine (3.38 mL, 19.4 mmol). The mixture was stirred at −78° C. for 30 minutes and then a solution of (E)-1-(((3-(2-nitrovinyl)phenoxy)methyl)benzene (94.1A) (4.13 g, 16.2 mmol) (commercially available from Aldrich) in DCM (17 mL) was added dropwise (over 15 minutes). Then TiCl$_4$ (16 mL, 1.0 M solution in DCM) was added slowly to the reaction. The mixture was stirred at −78° C. for 2 hours and then quenched with NH$_4$Cl solution. The mixture was extracted with EtOAc (350 mL) and the organic phase was washed with sodium bicarbonate solution and brine, dried over anhydrous Na$_2$SO$_4$. After removing solvent, the residue was recrystallized from MeOH, 94.1B (727 mg), white solid was obtained. MS ESI (np0s.) m/e: 475 (M+H)$^+$.

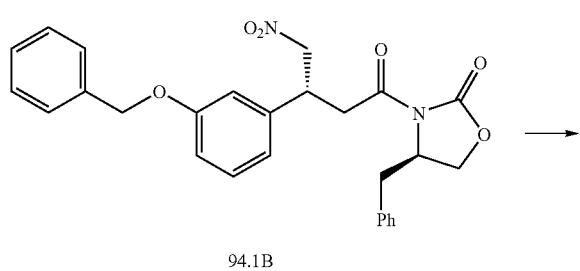

94.1B

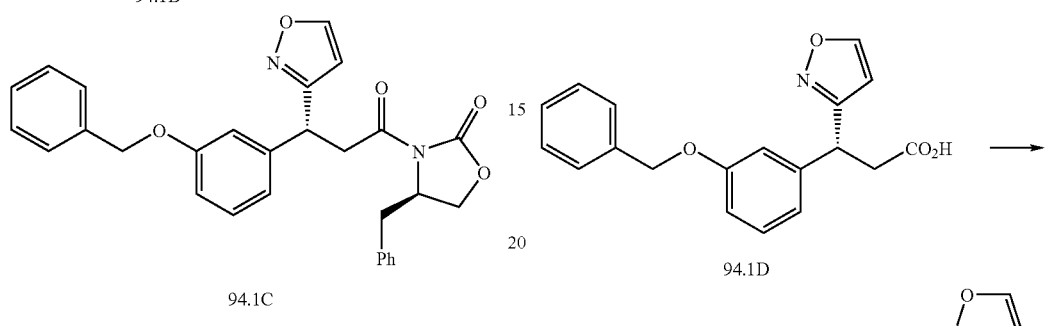

94.1C (4R)-3-((3R)-3-(3-Isoxazolyl)-3-(3-((phenylmethyl)oxy)phenyl)propanoyl)-4-(phenylmethyl)-1,3-oxazolidin-2-one (94.1C). At room temperature, di-t-butyl dicarbonate (0.502 g, 2.30 mmol) was added to a solution of (R)-4-benzyl-3-((R)-3-(3-(benzyloxy)phenyl)-4-nitrobutanoyl)oxazolidin-2-one (94.1B) (0.727 g, 1.53 mmol), vinyl bromide, (1.0 M solution in THF (16.9 mL, 16.9 mmol), N,N-dimethylpyridin-4-amine (DMAP) (0.0187 g, 0.153 mmol) and TEA (0.256 mL, 1.84 mmol). The mixture was stirred at room temperature for 24 hours. The reaction was then diluted with EtOAc (200 mL) and washed with sodium bicarbonate solution and brine. The organic phase was dried over anhydrous sodium sulfate. After removing solvent, the residue was purified by flash chromatography (silica gel, 1:2 EtOAc/hexane) and gave 558 mg of 94.1C.

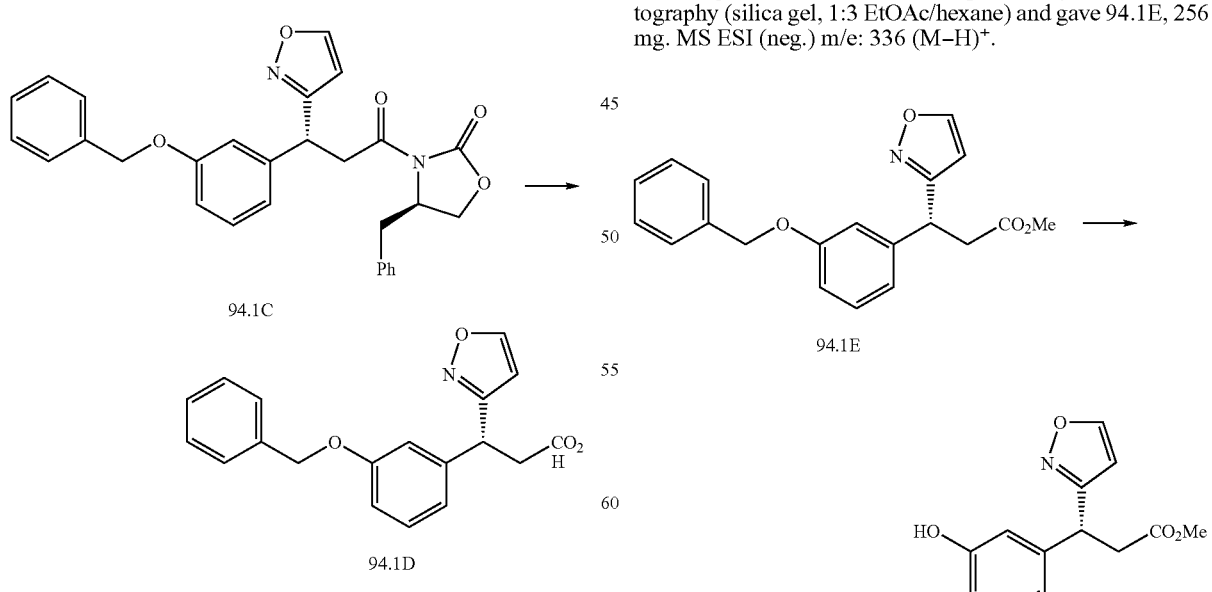

(3R)-3-(3-Isoxazolyl)-3-(3-((phenylmethyl)oxy)phenyl)propanoic acid (94.1D). A solution of (R)-4-benzyl-3-((R)-3-(3-(benzyloxy)phenyl)-3-(isoxazol-3-yl)propanoyl)ox-azolidin-2-one (94.1C) (0.558 g, 1.16 mmol) in THF (12 mL) was cooled to 0° C. $H_2O_2$ (30% w/w, 0.50 mL) was added, and was followed by addition of LiOH, monohydrate (0.0643 mL, 2.31 mmol) in water (4 mL). The resulting mixture was stirred at 0° C. for 2 hours. The organic solvent was blown away by nitrogen, and the aqueous mixture was acidified with 1N HCl to pH 3-5. The mixture was extracted with EtOAc (100 mL). The organic phase was washed with brine, dried over anhydrous $Na_2SO_4$. After removing solvent, crude product (94.1D) (491 mg) was obtained.

Methyl (3R)-3-(3-isoxazolyl)-3-(3-((phenylmethyl)oxy)phenyl)propanoate ((94.1E). A mixture of (R)-3-(3-(benzyloxy)phenyl)-3-(isoxazol-3-yl)propanoic acid (94.1D) (0.49 g, 1.5 mmol), iodomethane (0.65 g, 4.5 mmol) and cesium carbonate (0.99 g, 3.0 mmol) in DMF (10 mL) was stirred at room temperature for 1 hour. The mixture was diluted with EtOAc (140 mL) and the organic phase was washed with water, brine and dried over anhydrous sodium sulfate. After removing solvent, the residue was purified by flash chromatography (silica gel, 1:3 EtOAc/hexane) and gave 94.1E, 256 mg. MS ESI (neg.) m/e: 336 (M–H)$^+$.

Methyl (3R)-3-(3-hydroxyphenyl)-3-(3-isoxazolyl)propanoate ((94.1F). At 0° C., trichloroborane-dimethy sulfide (2.0 M in DCM) (2.19 mL, 4.38 mmol) was added to a solution of (R)-methyl 3-(3-(benzyloxy)phenyl)-3-(isoxazol-3-yl)propanoate (94.1F) (0.246 g, 0.729 mmol) in DCM (5 mL). After addition, the ice bath was removed and the mixture was stirred at room temperature for 3 hours. The flask was cooled by an ice bath and quenched by adding NaHCO$_3$ solution to pH 7-8. The mixture was diluted with EtOAc (120 mL), washed with brine, and dried over anhydrous sodium sulfate. After removing solvent, the residue was purified by flash chromatography (silica gel, 1:1 EtOAc/hexane) and gave 94.1F, 122 mg. MS ESI (pos.) m/e: 248 (M+H)$^+$.

The compounds in the following table were prepared from methyl (3R)-3-(3-hydroxyphenyl)-3-(3-isoxazolyl)propanoate (94.1F) and the appropriate halomethyl or hydroxymethyl compound according to the methods described herein.

TABLE 25

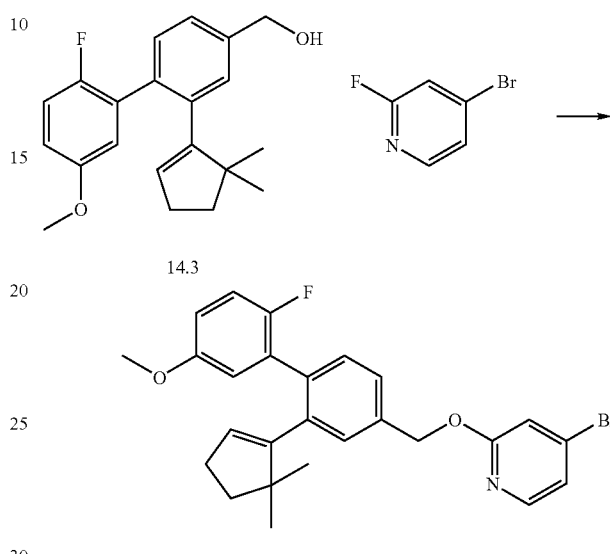

| Compound | TG |
|---|---|
| 94.1 | (2-fluoro-5-methoxy-biphenyl with 5,5-dimethyl-cyclopentenyl group) |
| 94.2 | (2-fluoro-5-methoxy-biphenyl with tert-butyl group) |

(3R)-3-(3-(((2-(5,5-Dimethyl-1-cyclopenten-1-yl)-2'-fluoro-5'-(methyloxy)-1,1'-biphenyl-4-yl)methyl)oxy)phenyl)-3-(3-isoxazolyl)propanoic acid (94.1). The alkylation and hydrolysis were conducted in an analogous manner to Example 66.6 (using 94.1F and 14.4 described herein) to yield 94.1. MS ESI (neg.) m/e: 540 (M–H)$^+$. $^1$H NMR (400 MHz, DMSO-d6) δ ppm 8.75 (m, 1H), 7.39-7.42 (m, 1H), 7.21-7.30 (m, 3H), 7.08-7.12 (m, 1H), 6.99 (m, 1H), 6.87-6.91 (m, 3H), 6.84 (m, 1H), 6.52 (m, 1H), 5.50 (m, 1H), 5.13 (s, 2H), 4.51 (m, 1H), 3.70 (s, 3H), 3.06-3.10 (m, 1H), 2.87-2.93 (m, 1H), 2.20 (m, 2H), 1.59 (m, 2H), 0.77 (s, 6H).

(3R)-3-(3-(((2-(1,1-Dimethylethyl)-2'-fluoro-5'-(methyloxy)-1,1'-biphenyl-4-yl)methyl)oxy)phenyl)-3-(3-isoxazolyl)propanoic acid (94.2). The alkylation and hydrolysis were conducted in an analogous manner to Example 66.6 (using 94.1F and 8.10 described herein) to yield 94.2. MS ESI (neg.) m/e: 502 (M–H)$^+$. $^1$H NMR (400 MHz, DMSO-d6) δ ppm 8.76 (m, 1H), 7.22-7.30 (m, 2H), 7.14-7.18 (m, 1H), 6.88-7.00 (m, 5H), 6.81 (m, 1H), 6.53 (m, 1H), 5.10 (s, 2H), 4.53 (m, 1H), 3.74 (s, 3H), 3.07-3.10 (m, 1H), 2.92-2.94 (m, 1H), 1.14-1.17 (m, 9H).

Example 95

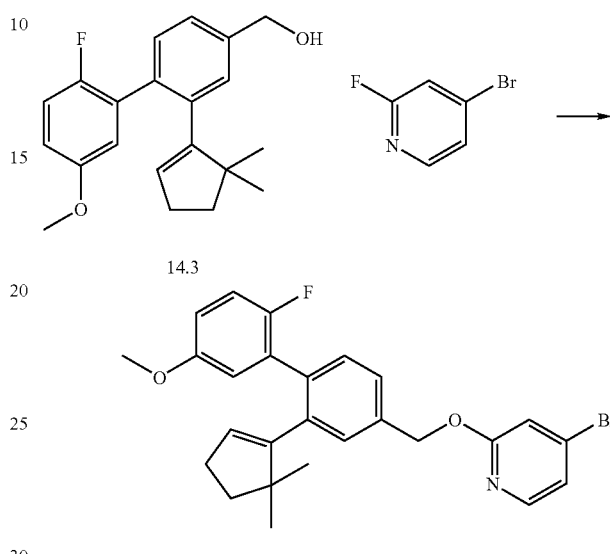

4-Bromo-2-(((2-(5,5-dimethyl-1-cyclopenten-1-yl)-2'-fluoro-5'-(methyloxy)-1,1'-biphenyl-4-yl)methyl)oxy)pyridine (95.A). A dry round bottom flask containing 14.3 (0.0937 g, 0.287 mmol) in dry DMF (1 mL) was cooled in an ice bath. After 10 minutes, sodium hydride (60% wt. in oil) (15.4 mg, 0.385 mmol) was added carefully, and the mixture was stirred at 0° C. After 10 minutes, 4-bromo-2-fluoropyridine (commercially available from Synthonix Corporation) (0.0511 g, 0.290 mmol) was added. The reaction was allowed to stir overnight at room temperature. After 18 hours, the reaction was diluted with water and extracted five times with EtOAc. The combined organic layers were then washed one time with brine and dried over anhydrous magnesium sulfate. The solid was filtered off, and the solvent was concentrated. The residue was purified by silica gel flash chromatography (0-45% EtOAc/hexane) to afford 95.A (105.9 mg, 76% yield). $^1$H NMR (400 MHz) (CDCl$_3$) δ ppm 8.02 (1H, d, J=4.7 Hz), 7.41 (1H, m), 7.35 (2H, m), 7.08 (2H, m), 7.00 (1H, m), 6.79 (2H, dt, J=5.1, 2.5 Hz), 5.52 (1H, s), 5.42 (2H, s), 3.76 (3H, s), 2.25 (2H, td, J=6.9, 2.5 Hz), 1.67 (2H, t, J=7.0 Hz), 0.87 (6H, s).

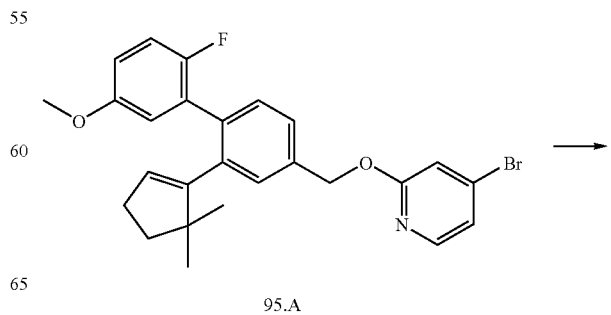

95.A

-continued

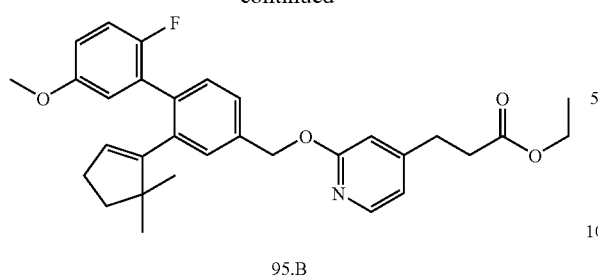

95.B

Ethyl 3-(2-(((2-(5,5-dimethyl-1-cyclopenten-1-yl)-2'-fluoro-5'-(methyloxy)-1,1'-biphenyl-4-yl)methyl)oxy)-4-pyridinyl)propanoate (95.B). To a sealed tube containing 95.A (0.1059 g, 0.22 mmol), bis(dibenzylideneacetone)palladium (0.0068 g, 0.012 mmol), and CTC-Q-Phos (commercially available from Strem Chemicals) (0.0079 g, 0.011 mmol) was added dry THF (2.1 mL). After 5 minutes, 3-ethoxy-3-oxopropylzinc bromide, 0.5 M solution in THF (0.9 mL, 0.45 mmol) was added dropwise. After 1 hour, the mixture was heated to 80° C. and monitored with TLC and LC-MS. After 16.5 hours, the reaction was cooled to room temperature, and then the organic solvent was removed under reduced pressure. The solid was filtered off, and the solvent was concentrated. The residue was purified by silica gel flash chromatography (0-40% EtOAc/hexane) to afford 95.B (86.2 mg, 78% yield). $^1$H NMR (500 MHz) (CDCl$_3$) δ ppm 8.10 (1H, d, J=5.4 Hz), 7.41 (1H, dd, J=7.9, 1.8 Hz), 7.33 (2H, dd, J=4.6, 1.5 Hz), 6.98 (1H, m), 6.81 (3H, m), 6.70 (1H, s), 5.52 (1H, t, J=2.0 Hz), 5.42 (2H, s), 4.15 (2H, q, J=7.1 Hz), 3.76 (3H, s), 2.93 (2H, t, J=7.7 Hz), 2.66 (2H, m), 2.25 (2H, td, J=7.0, 2.4 Hz), 1.66 (2H, t, J=7.0 Hz), 1.25 (3H, t, J=7.1 Hz), 0.86 (6H, s).

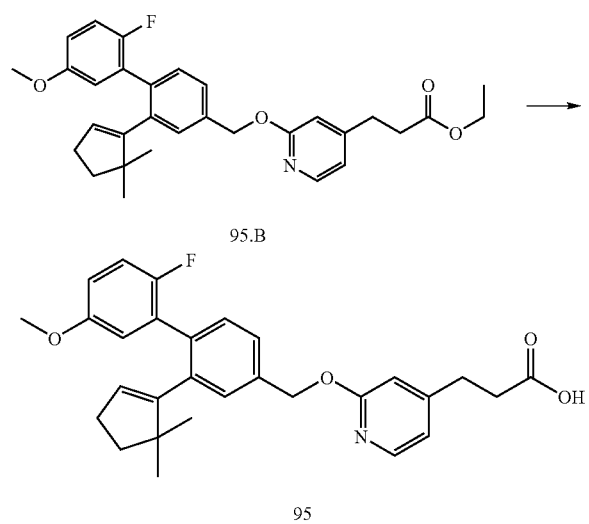

95.B

95

3-(2-(((2-(5,5-Dimethyl-1-cyclopenten-1-yl)-2'-fluoro-5'-(methyloxy)-1,1'-biphenyl-4-yl)methyl)oxy)-4-pyridinyl)propanoic acid (95). The hydrolysis was conducted in an analogous manner to Example 66.6 (using 95.B described herein) to yield 95. $^1$H NMR (400 MHz) (CDCl$_3$) δ ppm 8.12 (1H, d, J=5.3 Hz), 7.44 (1H, m), 7.36 (2H, m), 7.00 (1H, m), 6.82 (3H, m), 6.71 (1H, s), 5.54 (1H, m), 5.40 (2H, s), 3.76 (3H, s), 2.94 (2H, t, J=7.6 Hz), 2.71 (2H, t, J=7.6 Hz), 2.25 (2H, td, J=7.0, 2.3 Hz), 1.67 (2H, t, J=7.0 Hz), 0.87 (6H, s).

Example 96

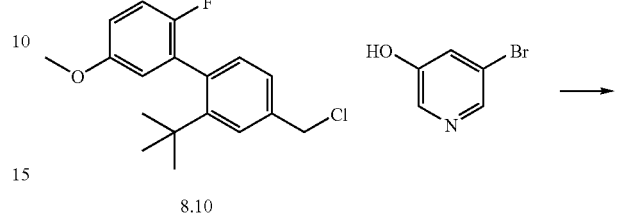

8.10

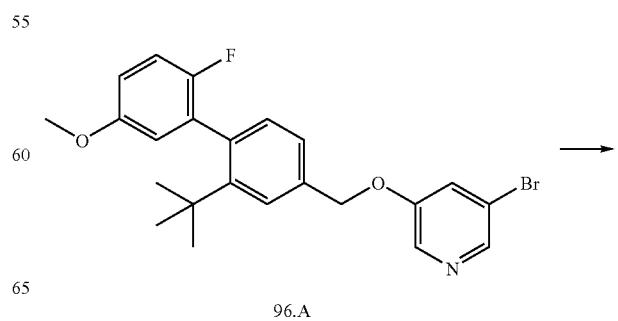

96.A

3-Bromo-5-(((2-(1,1-dimethylethyl)-2'-fluoro-5'-(methyloxy)-1,1'-biphenyl-4-yl)methyl)oxy)pyridine (96.A). A dry round bottom flask containing 3-bromo-5-hydroxypyridine (0.1304 g, 0.749 mmol) (commercially available from Aldrich) in dry DMF (2 mL) was cooled in an ice bath. After 10 minutes, sodium hydride (0.0361 g, 0.903 mmol) (60% wt in oil) was added carefully, and the mixture was stirred at 0° C. After 10 minutes, 8.10 (0.2301 g, 0.750 mmol) was added. The reaction was allowed to stir overnight at room temperature. After 18 hours, the reaction was diluted with water and then extracted five times with EtOAc. The combined organic layers wee then washed one time with brine and dried over anhydrous magnesium sulfate. The solid was filtered off, and the solvent was concentrated. The residue was purified by silica gel flash chromatography (0-25% EtOAc/hexane) to afford 96.A (203.4 mg, 61% yield). $^1$H NMR (400 MHz, CDCl$_3$) δ ppm 8.36 (2H, dd, J=13.1, 2.2 Hz), 7.62 (1H, d, J=1.6 Hz), 7.57 (1H, m), 7.29 (1H, dd, J=7.6, 1.8 Hz), 7.10 (1H, d, J=7.4 Hz), 7.02 (1H, t, J=8.8 Hz), 6.95 (2H, m), 5.14 (2H, s), 3.80 (3H, s), 1.27 (9H, s).

96.A

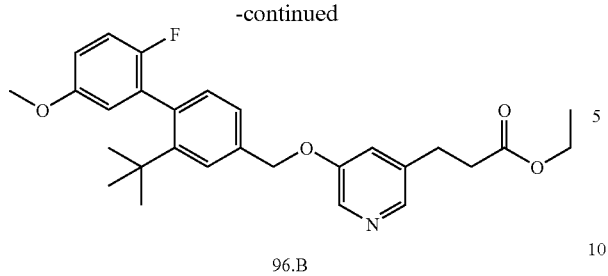

96.B

Ethyl 3-(5-(((2-(1,1-dimethylethyl)-2'-fluoro-5'-(methyloxy)-1,1'-biphenyl-4-yl)methyl)oxy)-3-pyridinyl)propanoate (96.B). To a sealed tube containing 96.A (0.2020 g, 0.455 mmol), bis(dibenzylideneacetone)palladium(0) (0.0141 g, 0.0245 mmol), and CTC-Q-Phos (0.0168 g, 0.0236 mmol) was added dry THF (3 mL). After 5 minutes, 3-ethoxy-3-oxopropylzinc bromide (2.0 mL, 1.00 mmol) (0.5 M solution in THF) was added. After 1 hour, the mixture was heated to 80° C. and monitored with TLC and LC-MS. After 16.5 hours, the reaction was cooled to room temperature, and the organic solvent was removed under reduced pressure. The residue was purified by silica gel flash chromatography (0-40% EtOAc/hexane) to afford 96.B which was used without further purification (129.1 mg, 61% yield). MS ESI (pos.) m/e: 466.3 (M+H)$^+$.

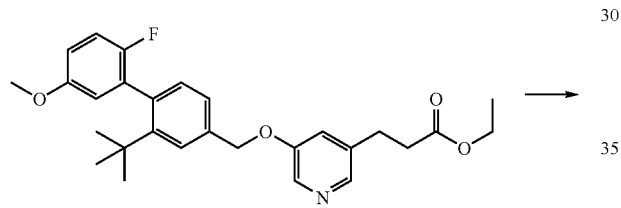

96.B

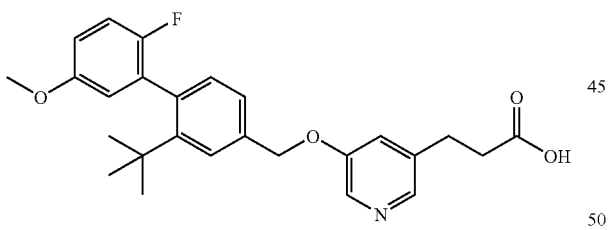

96.1

3-(5-(((2-(1,1-Dimethylethyl)-2'-fluoro-5'-(methyloxy)-1,1'-biphenyl-4-yl)methyl)oxy)-3-pyridinyl)propanoic acid (96). The hydrolysis of 96.B was conducted in an analogous manner to Example 66.6 using 96.B to yield 96. MS ESI (pos.) m/e: 438.3 (M+H)$^+$.

Example 97

The following compounds were prepared from (8.5) and the appropriate halomethyl or hydroxymethyl compound according to the methods described herein. Each of the compounds in the following table were prepared using the same enantiomer of the phenol.

TABLE 26

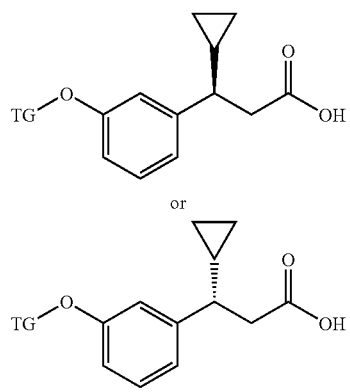

or

Compound | TG
--- | ---
97.1 | 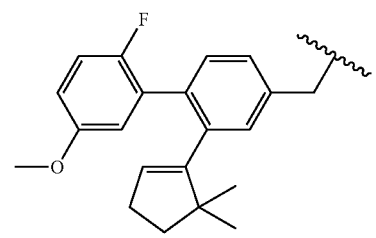
97.2 | 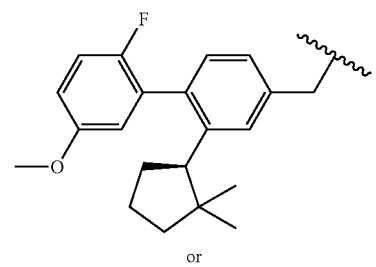
 | or
 | 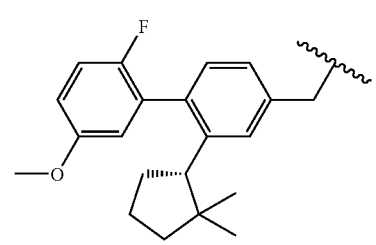

TABLE 26-continued 97.3

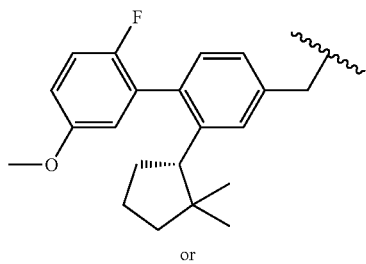

or

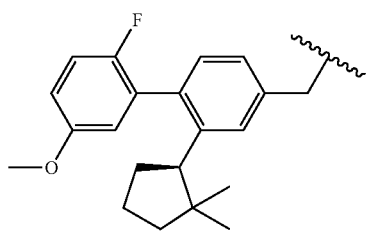

but not the same one as 97.2

(3R)-3-Cyclopropyl-3-(3-(((2-(5,5-dimethyl-1-cyclo-penten-1-yl)-2'-fluoro-5'-(methyloxy)-1,1'-biphenyl-4-yl)methyl)oxy)phenyl)propanoic acid or (3S)-3-cyclopropyl-3-(3-(((2-(5,5-dimethyl-1-cyclopenten-1-yl)-2'-fluoro-5'-(methyloxy)-1,1'-biphenyl-4-yl)methyl)oxy)phenyl)propanoic acid (97.1). 97.1 was synthesized analogous to the method for compound 7 from 8.5 and 14.5. MS ESI (pos.) m/e: 513.3 (M–H).

(3R)-3-Cyclopropyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3R)-3-cyclopropyl-3-(3-(((2-((1S)-2,2-dimethylcyclopentyl)-2'-fluoro-5'-(methyloxy)-1,1'-biphenyl-4-yl)methyl)oxy)phenyl)propanoic acid or (3S)-3-cyclopropyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3S)-3-cyclopropyl-3-(3-(((2-((1S)-2,2-dimethylcyclopentyl)-2'-fluoro-5'-(methyloxy)-1,1'-biphenyl-4-yl)methyl)oxy)phenyl)propanoic acid (97.2). The alkylation and hydrolysis were conducted in an analogous manner to Example 66.6 (using 8.5 and 66.6M or 66.6N derived from peak one from the chiral separation of 66.6L from the OD-column, described herein) to yield 97.2 (0.0471 g, 81% yield over the two steps). MS ESI (neg.) m/e: 515.2 (M–H)+.

(3R)-3-Cyclopropyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3R)-3-cyclopropyl-3-(3-(((2-((1S)-2,2-dimethylcyclopentyl)-2'-fluoro-5'-(methyloxy)-1,1'-biphenyl-4-yl)methyl)oxy)phenyl)propanoic acid or (3S)-3-cyclopropyl-3-(3-(((2-((1R)-2,2-dimethylcyclopentyl)-2'-fluoro-5'-(methyloxy)-1,1'-biphenyl-4-yl)methyl)oxy)phenyl)propanoic acid or (3S)-3-cyclopropyl-3-(3-(((2-((1S)-2,2-dimethylcyclopentyl)-2'-fluoro-5'-(methyloxy)-1,1'-biphenyl-4-yl)methyl)oxy)phenyl)propanoic acid (97.3). The alkylation and hydrolysis were conducted in an analogous manner to Example 66.6 (using 8.5 and 66.6M or 66.6N derived from peak two from the chiral separation of 66.6L from the OD-column, described herein) to yield 97.3 (0.0502 g, 85% yield). MS ESI (neg.) m/e: 515.2 (M–H)+.

Example 98

Synthesis of methyl (3S)-3-(3-hydroxyphenyl)pentanoate (98)

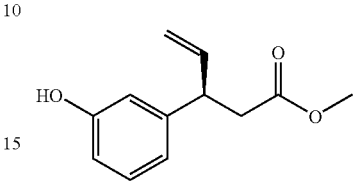

or

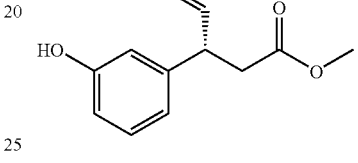

15.4

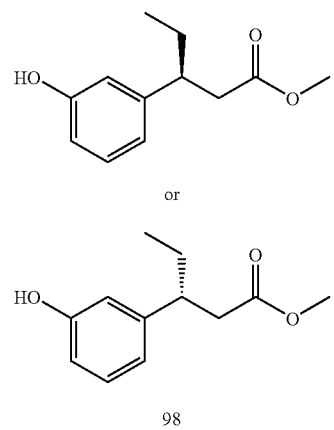

Methyl (3S)-3-(3-hydroxyphenyl)pentanoate (98). A 50 mL flask containing a solution of 15.4 (100 mg, 485 µmol) in EtOAc (10 mL) was purged with N₂. To the flask was added palladium, 10 wt. % (dry), on carbon powder, wet (103 mg, 97.0 µmol). The flask was then purged with H₂ and the contents were stirred overnight under a H₂ balloon. The black mixture was filtered through a pad of Celite and concentrated to afford a pink oil. The crude product was purified by combiflash (0 to 10% EtOAc/hexanes) yielding 98. It is believed that this is the S enantiomer.

The following compounds were prepared from 98 and the appropriate halomethyl or hydroxymethyl compound according to the methods described herein. Each of the compounds in the following table were prepared using the same enantiomer of the phenol.

TABLE 27

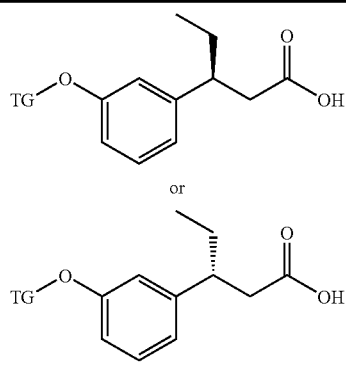

| Compound | TG |
| --- | --- |
| 98.1 | (2-fluoro-5-methoxy-biphenyl with (1S or 1R)-2,2-dimethylcyclopentyl) |
| 98.2 | (2-fluoro-5-methoxy-biphenyl with 2,2-dimethylcyclopentyl, but not the same one as 98.1) |

(3S)-3-(3-(((2-((1S)-2,2-Dimethylcyclopentyl)-2'-fluoro-5'-(methyloxy)-1,1'-biphenyl-4-yl)methyl)oxy)phenyl)pentanoic acid or (3S)-3-(3-(((2-((1R)-2,2-dimethylcyclopentyl)-2'-fluoro-5'-(methyloxy)-1,1'-biphenyl-4-yl)methyl)oxy)phenyl)pentanoic acid or (3R)-3-(3-(((2-((1S)-2,2-dimethylcyclopentyl)-2'-fluoro-5'-(methyloxy)-1,1'-biphenyl-4-yl)methyl)oxy)phenyl)pentanoic acid or (3R)-3-(3-(((2-((1R)-2,2-dimethylcyclopentyl)-2'-fluoro-5'-(methyloxy)-1,1'-biphenyl-4-yl)methyl)oxy)phenyl)pentanoic acid (98.1). Example 98.1 was synthesized analogous to the method for compound 7 from 98 and 66.6P. MS ESI (pos.) m/e: 503.2 (M−H).

(3S)-3-(3-(((2-((1R)-2,2-Dimethylcyclopentyl)-2'-fluoro-5'-(methyloxy)-1,1'-biphenyl-4-yl)methyl)oxy)phenyl)pentanoic acid or (3S)-3-(3-(((2-((1S)-2,2-dimethylcyclopentyl)-2'-fluoro-5'-(methyloxy)-1,1'-biphenyl-4-yl)methyl)oxy)phenyl)pentanoic acid or (3R)-3-(3-(((2-((1R)-2,2-dimethylcyclopentyl)-2'-fluoro-5'-(methyloxy)-1,1'-biphenyl-4-yl)methyl)oxy)phenyl)pentanoic acid or (3R)-3-(3-(((2-((1S)-2,2-dimethylcyclopentyl)-2'-fluoro-5'-(methyloxy)-1,1'-biphenyl-4-yl)methyl)oxy)phenyl)pentanoic acid (98.2). MS ESI (neg.) m/e: 503.2 (M−H)+.

Example 99

The following compounds were prepared from 83.C and the appropriate halomethyl or hydroxymethyl compound according to the methods described herein. Each of the compounds in the following table were prepared using the same enantiomer of the phenol.

TABLE 28

| Compound | TG |
| --- | --- |
| 99.1 | (2-fluoro-5-methoxy-biphenyl with 2,2-dimethylcyclopentenyl) |
| 99.2 | (2-fluoro-5-methoxy-biphenyl with 2,2-dimethylcyclopentyl) |

TABLE 28-continued

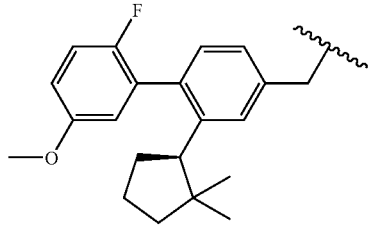

99.3

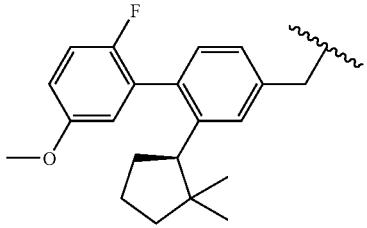

or

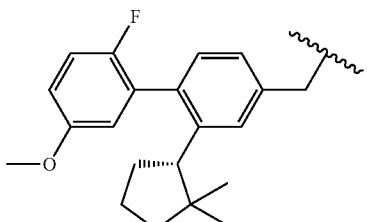

but not the same one as 99.2

(3R)-3-Cyclopropyl-3-(3-(((2-(5,5-dimethyl-1-cyclopenten-1-yl)-2'-fluoro-5'-(methyloxy)-1,1'-biphenyl-4-yl)methyl)oxy)-2-fluorophenyl)propanoic acid or (3S)-3-cyclopropyl-3-(3-(((2-(5,5-dimethyl-1-cyclopenten-1-yl)-2'-fluoro-5'-(methyloxy)-1,1'-biphenyl-4-yl)methyl)oxy)-2-fluorophenyl)propanoic acid (99.1). MS ESI (pos.) m/e: 550.3 (M+H$_2$O)$^+$, 555.2 (M+Na)$^+$.

(3R)-3-Cyclopropyl-3-(3-(((2-((1S)-2,2-dimethylcyclopentyl)-2'-fluoro-5'-(methyloxy)-1,1'-biphenyl-4-yl)methyl)oxy)-2-fluorophenyl)propanoic acid or (3R)-3-cyclopropyl-3-(3-(((2-((1R)-2,2-dimethylcyclopentyl)-2'-fluoro-5'-(methyloxy)-1,1'-biphenyl-4-yl)methyl)oxy)-2-fluorophenyl)propanoic acid or (3S)-3-cyclopropyl-3-(3-(((2-((1S)-2,2-dimethylcyclopentyl)-2'-fluoro-5'-(methyloxy)-1,1'-biphenyl-4-yl)methyl)oxy)-2-fluorophenyl)propanoic acid or (3S)-3-cyclopropyl-3-(3-(((2-((1R)-2,2-dimethylcyclopentyl)-2'-fluoro-5'-(methyloxy)-1,1'-biphenyl-4-yl)methyl)oxy)-2-fluorophenyl)propanoic acid (99.2). MS ESI (pos.) m/e: 535.2 (M+H)$^+$, 552.2 (M+H$_2$O)$^+$, 557.2 (M+Na)$^+$.

(3R)-3-Cyclopropyl-3-(3-(((2-((1S)-2,2-dimethylcyclopentyl)-2'-fluoro-5'-(methyloxy)-1,1'-biphenyl-4-yl)methyl)oxy)-2-fluorophenyl)propanoic acid or (3R)-3-cyclopropyl-3-(3-(((2-((1R)-2,2-dimethylcyclopentyl)-2'-fluoro-5'-(methyloxy)-1,1'-biphenyl-4-yl)methyl)oxy)-2-fluorophenyl)propanoic acid or (3S)-3-cyclopropyl-3-(3-(((2-((1S)-2,2-dimethylcyclopentyl)-2'-fluoro-5'-(methyloxy)-1,1'-biphenyl-4-yl)methyl)oxy)-2-fluorophenyl)propanoic acid or (3S)-3-cyclopropyl-3-(3-(((2-((1R)-2,2-dimethylcyclopentyl)-2'-fluoro-5'-(methyloxy)-1,1'-biphenyl-4-yl)methyl)oxy)-2-fluorophenyl)propanoic acid (99.3). MS ESI (neg.) m/e: 533.2 (M−H)$^+$.

Example 100

The following compounds were prepared from 77.H and the appropriate halomethyl or hydroxymethyl compound according to the methods described herein.

TABLE 29

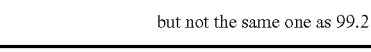

or

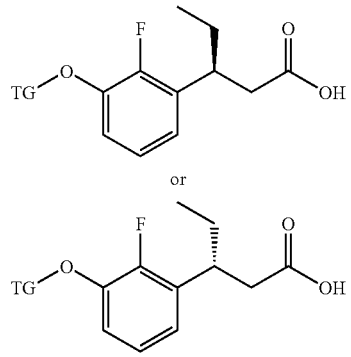

| Compound | TG |
|---|---|
| 100.1 | 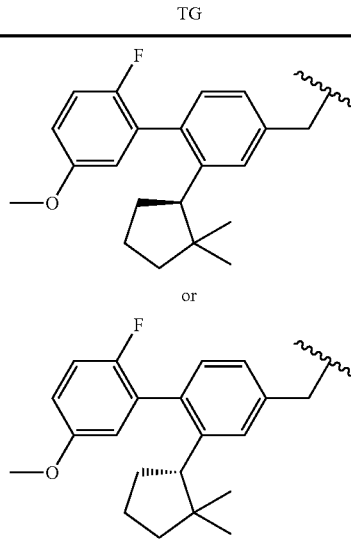<br>or<br>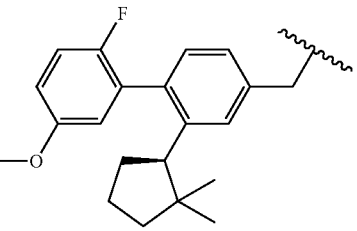 |
| 100.2 | 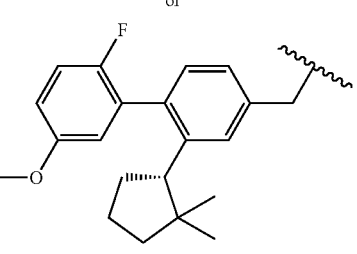<br>or<br>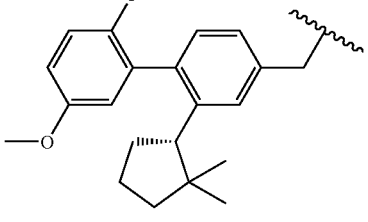<br>or<br>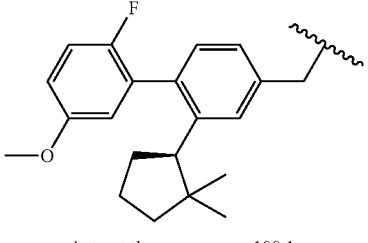<br>but not the same one as 100.1 |

(3S)-3-(3-(((2-((1R)-2,2-Dimethylcyclopentyl)-2'-fluoro-5'-(methyloxy)-1,1'-biphenyl-4-yl)methyl)oxy)-2-fluorophenyl)pentanoic acid or (3S)-3-(3-(((2-((1S)-2,2-dimethylcyclopentyl)-2'-fluoro-5'-(methyloxy)-1,1'-biphenyl-4-yl)methyl)oxy)-2-fluorophenyl)pentanoic acid or (3R)-3-(3-(((2-((1R)-2,2-dimethylcyclopentyl)-2'-fluoro-5'-(methyloxy)-1,1'-biphenyl-4-yl)methyl)oxy)-2-fluorophenyl)pentanoic acid or (3R)-3-(3-(((2-((1S)-2,2-dimethylcyclopentyl)-2'-fluoro-5'-(methyloxy)-1,1'-biphenyl-4-yl)methyl)oxy)-2-fluorophenyl)pentanoic acid (100.1). Example 100.1 was synthesized analogous to the method for compound 7 from 77.H and 66.6P. MS ESI (pos.) m/e: 521.2 (M–H).

(3S)-3-(3-(((2-((1S)-2,2-Dimethylcyclopentyl)-2'-fluoro-5'-(methyloxy)-1,1'-biphenyl-4-yl)methyl)oxy)-2-fluorophenyl)pentanoic acid or (3S)-3-(3-(((2-((1R)-2,2-dimethylcyclopentyl)-2'-fluoro-5'-(methyloxy)-1,1'-biphenyl-4-yl)methyl)oxy)-2-fluorophenyl)pentanoic acid or (3R)-3-(3-(((2-((1S)-2,2-dimethylcyclopentyl)-2'-fluoro-5'-(methyloxy)-1,1'-biphenyl-4-yl)methyl)oxy)-2-fluorophenyl)pentanoic acid or (3R)-3-(3-(((2-((1R)-2,2-dimethylcyclopentyl)-2'-fluoro-5'-(methyloxy)-1,1'-biphenyl-4-yl)methyl)oxy)-2-fluorophenyl)pentanoic acid (100.2). 100.2 was synthesized analogous to the method for compound 7 from 77.H and 66.6O. MS ESI (pos.) m/e: 521.2 (M–H).

Example 101

The following compounds were prepared from 90.H and the appropriate halomethyl or hydroxymethyl compound according to the methods described herein.

TABLE 30

| Compound | TG |
|---|---|
| 101.1 | 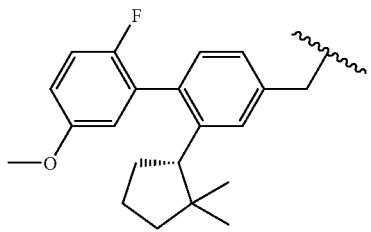 |
| 101.2 | 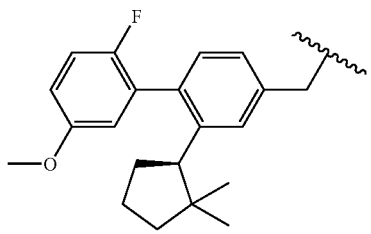 |

(3S)-3-(3-(((2-(5,5-Dimethyl-1-cyclopenten-1-yl)-2'-fluoro-5'-(methyloxy)-1,1'-biphenyl-4-yl)methyl)oxy)-2,5-difluorophenyl)pentanoic acid or (3R)-3-(3-(((2-(5,5-dimethyl-1-cyclopenten-1-yl)-2'-fluoro-5'-(methyloxy)-1,1'-biphenyl-4-yl)methyl)oxy)-2,5-difluorophenyl)pentanoic acid (101.1). MS ESI (neg.) m/e: 537.3 (M–H)⁺.

(3S)-3-(3-(((2-((1S)-2,2-Dimethylcyclopentyl)-2'-fluoro-5'-(methyloxy)-1,1'-biphenyl-4-yl)methyl)oxy)-2,5-difluorophenyl)pentanoic acid or (3S)-3-(3-(((2-((1R)-2,2-dimethylcyclopentyl)-2'-fluoro-5'-(methyloxy)-1,1'-biphenyl-4-yl)methyl)oxy)-2,5-difluorophenyl)pentanoic acid or (3R)-3-(3-(((2-((1S)-2,2-dimethylcyclopentyl)-2'-fluoro-5'-(methyloxy)-1,1'-biphenyl-4-yl)methyl)oxy)-2,5-difluorophenyl)pentanoic acid or (3R)-3-(3-(((2-((1R)-2,2-dimethylcyclopentyl)-2'-fluoro-5'-(methyloxy)-1,1'-biphenyl-4-yl)methyl)oxy)-2,5-difluorophenyl)pentanoic acid (101.2). MS ESI (neg.) m/e: 539.2 (M–H)⁺.

Example 102

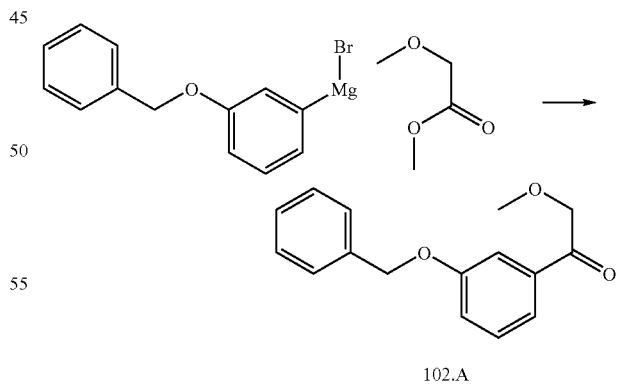

1-(3-(Benzyloxy)phenyl)-2-methoxyethanone (102.A). To a solution of methyl methoxyacetate (available from Aldrich) (0.48 mL, 4.8 mmol) in ether (20 mL) was added 3-benzyloxyphenylmagnesium bromide (1.0 M in THF) (available from Aldrich) (5.0 mL, 5.0 mmol) dropwise at –78° C. The mixture was warmed to room temperature overnight, quenched with 1 N HCl, and diluted with EtOAc. The organic layers were washed with water and brine, dried (MgSO$_4$), and concentrated. The crude product was purified by silica gel flash chromatography (0-20% EtOAc/hexane) to afford 102.A (0.17 g, 14% yield) as a pale yellow oil.

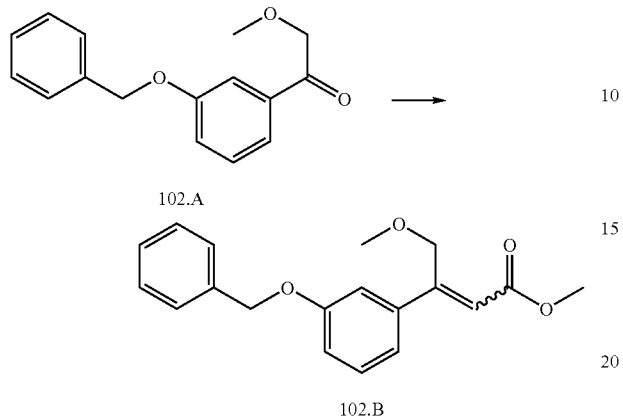

Methyl 3-(3-(benzyloxy)phenyl)-4-methoxybut-2-enoate (102.B). To a solution of 102.A (0.17 g, 0.66 mmol) in benzene (7 mL) was added methyl (triphenylphosphoranylidene)acetate (available from Aldrich) (2.2 g, 6.6 mmol) at room temperature. The mixture was stirred for 72 hours at reflux (100° C.), cooled to room temperature, filtered through silica gel (EtOAc), and concentrated. The crude product was purified by silica gel flash chromatography (0-20% EtOAc/hexane) to afford 102.B (mixture of geometric isomers) (0.11 g, 53% yield) as a pale yellow oil.

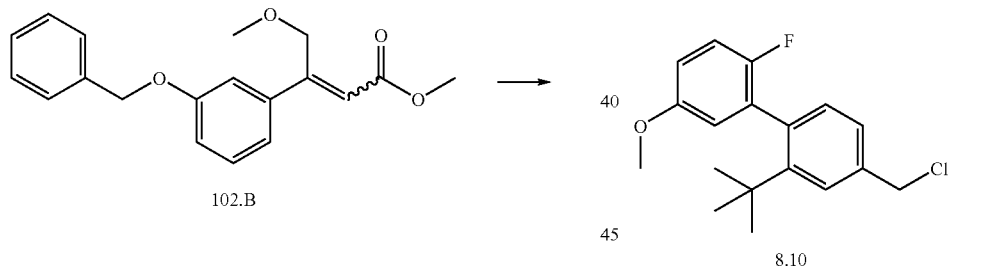

Methyl 3-(3-hydroxyphenyl)-4-methoxybutanoate (102.C). To a solution of 102.B (mixture of geometric isomers) (0.11 g, 0.35 mmol) in EtOAc (2 mL) was added Pd/C (10 wt. %) (0.019 g, 0.018 mmol) under N$_2$. The mixture was purged with H$_2$, stirred overnight under a H$_2$ balloon, filtered through silica gel (EtOAc), and concentrated. The crude product was purified by silica gel flash chromatography (10-40% EtOAc/hexane) to afford 102.C (0.060 g, 76%) as a pale yellow oil.

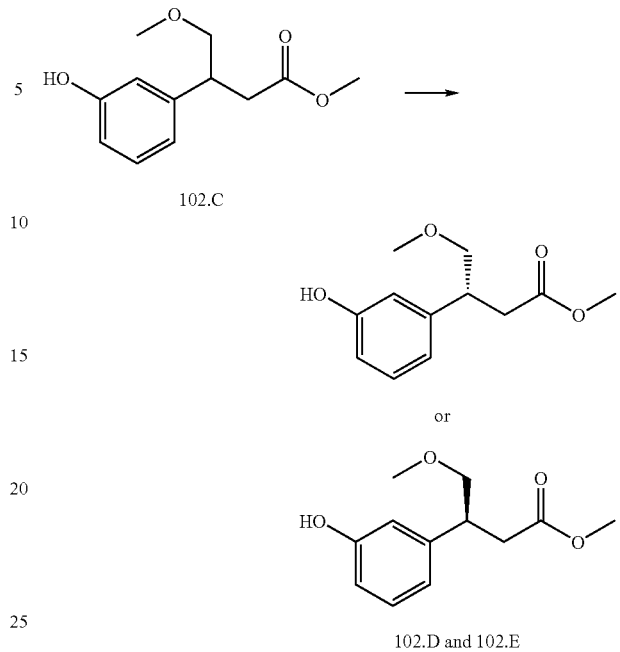

(R)-Methyl 3-(3-hydroxyphenyl)-4-methoxybutanoate and (S)-methyl 3-(3-hydroxyphenyl)-4-methoxybutanoate (102.D and 102.E). Racemic 102.C (0.060 g, 0.27 mmol) was resolved by chiral HPLC (Chiralcel OD column, 3% IPA/hexane, detection at 220 nm) to afford (in order of elution) 102.D (0.030 g, 100% yield, 99% e.e.) and 102.E (99% e.e.) as pale yellow oils.

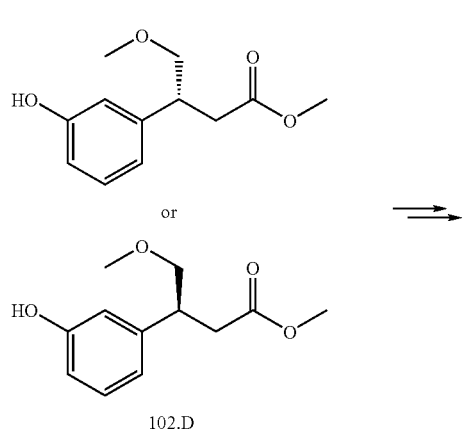

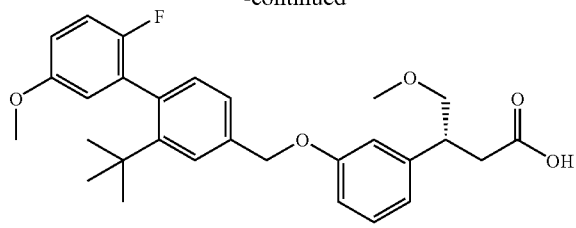

or

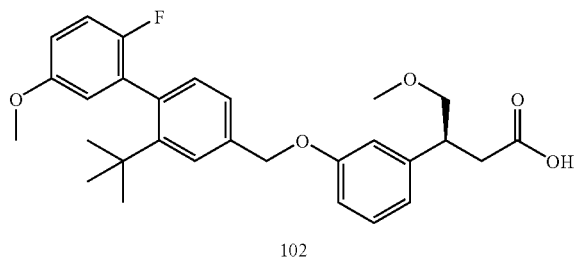
102

(3R)-3-(3-(((2-(1,1-Dimethylethyl)-2'-fluoro-5'-(methyloxy)-1,1'-biphenyl-4-yl)methyl)oxy)phenyl)-4-(methyloxy)butanoic acid or (3S)-3-(3-(((2-(1,1-dimethylethyl)-2'-fluoro-5'-(methyloxy)-1,1'-biphenyl-4-yl)methyl)oxy)phenyl)-4-(methyloxy)butanoic acid (102). 102 was prepared from 102.D and 8.10 according to the analogous methods described in Example 7. MS ESI (pos.) m/e: 481.1 (M+H)$^+$, 498.2 (M+H$_2$O)$^+$, 503.2 (M+Na)$^+$.

Example 103

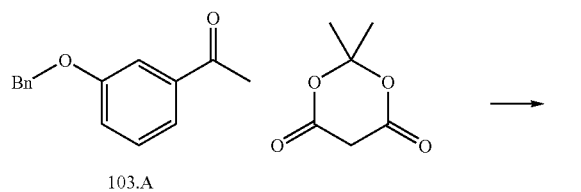
103.A

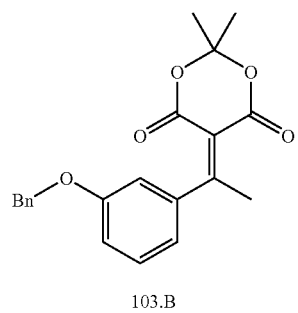
103.B 2,2-Dimethyl-5-(1-(3-((phenylmethyl)oxy)phenyl)ethylidene)-1,3-dioxane-4,6-dione (103.B). A 1.0M solution of titanium tetrachloride in DCM (9.3 mL, 9.3 mmol) was injected dropwise to THF (15 mL) cooled to 0° C. A solution of 1-(3-(benzyloxy)phenyl)ethanone (1.0 g, 4.42 mmol) (commercially available from Aldrich) and 2,2-dimethyl-1,3-dioxane-4,6-dione (701 mg, 4.86 mmol) (commercially available from Aldrich) in THF (5 mL) was then injected dropwise into the flask followed by dropwise addition of pyridine (1.8 mL, 22.1 mmol). The reaction temperature was allowed to warm to room temperature and the mixture was stirred overnight. The reaction was then quenched with water, extracted with EtOAc, dried over MgSO$_4$, and filtered. The solvent was removed and the resulting crude mixture was purified by silica gel flash chromatography (hexane:EtOAc=4:1 to 1:1) to afford 5-(1-(3-(benzyloxy)phenyl)ethylidene)-2,2-dimethyl-1,3-dioxane-4,6-dione 103.B (855 mg, 55% yield).

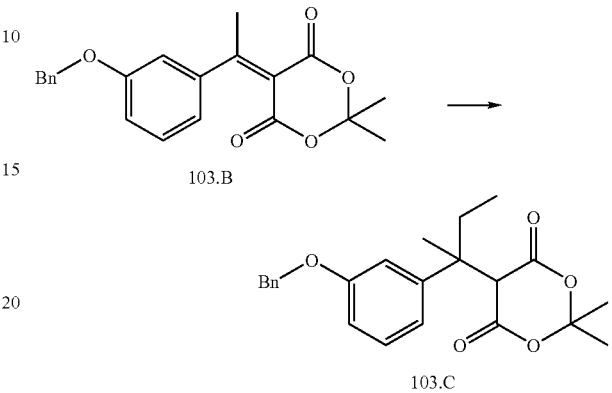

2,2-Dimethyl-5-(1-methyl-1-(3-((phenylmethyl)oxy)phenyl)propyl)-1,3-dioxane-4,6-dione (103.C). Into a solution of 5-(1-(3-(benzyloxy)phenyl)ethylidene)-2,2-dimethyl-1,3-dioxane-4,6-dione 103.B (325 mg, 922 µmol) in anhydrous THF (2 mL) was injected ethylmagnesium bromide (769 µL, 2306 µmol) at 0° C. The reaction was stirred for 20 minutes before raising the temperature to room temperature. The reaction mixture was then stirred for 3 hours. The reaction was then quenched with 6N HCl (0.383 mL), extracted with DCM and washed with a saturated NaHCO$_3$ solution. The resulting crude mixture was purified by silica gel flash chromatography (hexane:EtOAc=2:1) to afford 5-(2-(3-(benzyloxy)phenyl)butan-2-yl)-2,2-dimethyl-1,3-dioxane-4,6-dione 103.C (209 mg, 59% yield).

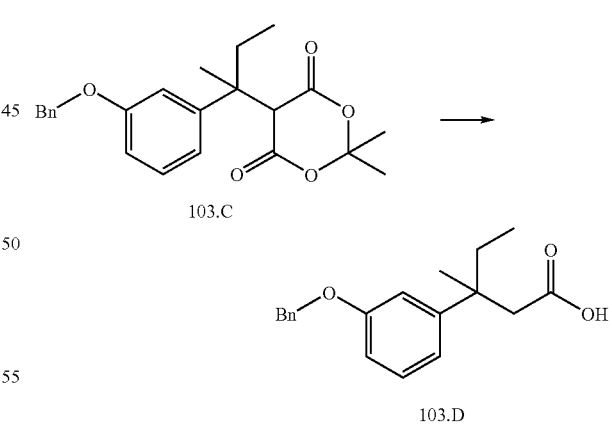

3-Methyl-3-(3-((phenylmethyl)oxy)phenyl)pentanoic acid (103.D). A solution of 5-(2-(3-(benzyloxy)phenyl)butan-2-yl)-2,2-dimethyl-1,3-dioxane-4,6-dione 103.C (209 mg, 546 µmol) in DMF (2 mL) and H$_2$O (0.2 mL) was heated to 90° C. overnight. The reaction was then diluted with 0.2N HCl, extracted with EtOAc, dried over MgSO$_4$, filtered, stripped, and purified by silica gel chromatography to afford 3-(3-(benzyloxy)phenyl)-3-methylpentanoic acid 103.D (106.4 mg, 65.3% yield).

Methyl 3-methyl-3-(3-((phenylmethyl)oxy)phenyl)pentanoate (103.E). Into a solution of 3-(3-(benzyloxy)phenyl)-3-methylpentanoic acid 103.D (184 mg, 617 µmol) in MeOH (3 mL) was injected H₂SO₄ (3.29 µL, 61.7 µmol), and the mixture was heated at 60° C. overnight. The reaction was quenched with saturated NaHCO₃ solution, extracted with DCM, dried over Na₂SO₄, filtered, stripped, and purified by silica gel chromatography to afford methyl 3-(3-(benzyloxy)phenyl)-3-methylpentanoate 103.E (177 mg, 91.9% yield).

Methyl 3-(3-hydroxyphenyl)-3-methylpentanoate (103.F). Into a solution of methyl 3-(3-(benzyloxy)phenyl)-3-methylpentanoate 103.E (100 mg, 320 µmol) in MeOH (5 mL) was added palladium on carbon (34.1 mg, 320 µmol). The reaction was charged with H₂ to 50 psi and stirred for 3 hours. The reaction was then filtered through Celite, washed with DCM, stripped, and purified by silica gel chromatography to afford methyl 3-(3-hydroxyphenyl)-3-methylpentanoate 103.F (65.3 mg, 91.8% yield).

Methyl 3-(3-(((2-((1S)-2,2-dimethylcyclopentyl)-2'-fluoro-5'-(methyloxy)-1,1'-biphenyl-4-yl)methyl)oxy)phenyl)-3-methylpentanoate or methyl 3-(3-(((2-((1R)-2,2-dimethylcyclopentyl)-2'-fluoro-5'-(methyloxy)-1,1'-biphenyl-4-yl)methyl)oxy)phenyl)-3-methylpentanoate (103.G). Into a solution of 66.P (102 mg, 294 µmol) and 103.F (65.3 mg, 294 µmol) in DMF was added cesium carbonate (287 mg, 881 µmol) at room temperature. The mixture was then stirred overnight at room temperature. The reaction was quenched with water, extracted with EtOAc, dried over MgSO₄, filtered, stripped, and purified by silica gel chromatography to afford 103.G (130 mg, 83% yield).

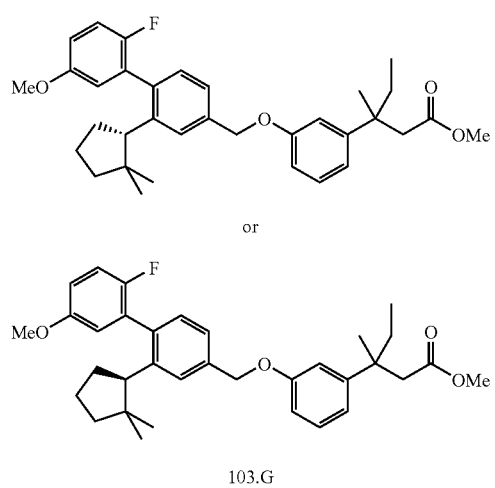

103.G

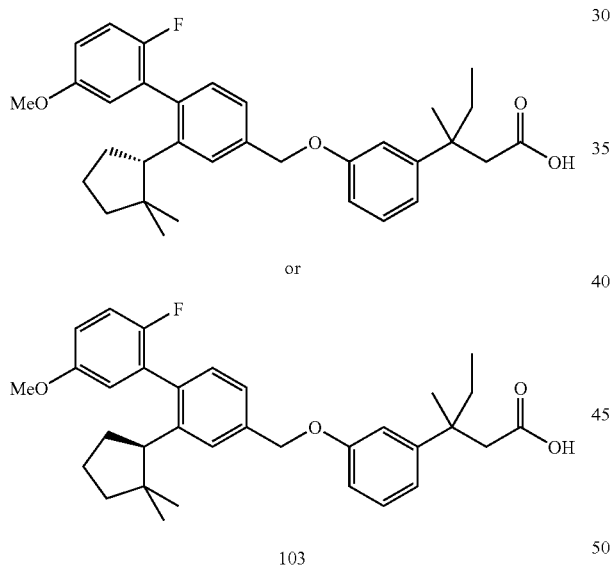

103

3-(3-(((2-((1S)-2,2-Dimethylcyclopentyl)-2'-fluoro-5'-(methyloxy)-1,1'-biphenyl-4-yl)methyl)oxy)phenyl)-3-methylpentanoic acid or 3-(3-(((2-((1R)-2,2-dimethylcyclopentyl)-2'-fluoro-5'-(methyloxy)-1,1'-biphenyl-4-yl)methyl)oxy)phenyl)-3-methylpentanoic acid (103). Into a solution of 103.G (130 mg, 244 μmol) in THF (2 mL) and EtOH (2 mL) was injected a 4 N solution of LiOH (610 μL, 2440 μmol). The reaction mixture was then stirred overnight at 50° C. The reaction was quenched with 410 μL of 6 N HCl, and extracted with EtOAc. The organic layers were combined and dried over MgSO$_4$, filtered, and stripped. The crude mixture was then purified by silica gel chromatography to afford carboxylic acid 103 (100 mg, 79% yield). MS ESI (neg.) m/e: 517.3 (M–H).

Example 104

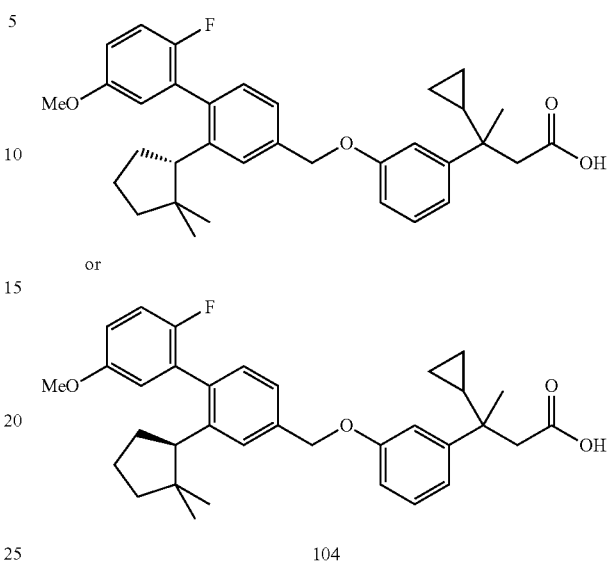

104

3-Cyclopropyl-3-(3-(((2-((1S)-2,2-dimethylcyclopentyl)-2'-fluoro-5'-(methyloxy)-1,1'-biphenyl-4-yl)methyl)oxy)phenyl)butanoic acid or 3-cyclopropyl-3-(3-(((2-((1R)-2,2-dimethylcyclopentyl)-2'-fluoro-5'-(methyloxy)-1,1'-biphenyl-4-yl)methyl)oxy)phenyl)butanoic acid (104). 104 was synthesized by a method analogous to that used to prepare compound 103. (MS ESI (neg.) m/e: 529.3 (M–H).

Example 105

Synthesis of methyl 2-(1-(3-hydroxyphenyl)cyclohexyl)acetate (105)

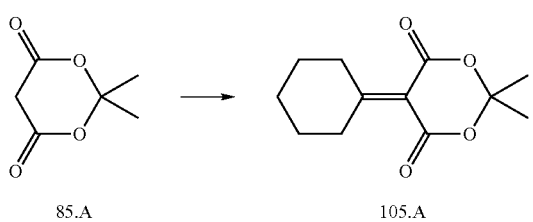

85.A     105.A

5-Cyclohexylidene-2,2-dimethyl-1,3-dioxane-4,6-dione (105.A). A titanium tetrachloride solution (36.0 mL, 36.0 mmol) (1M solution in DCM) was added slowly to a cooled (0° C.) round bottom flask containing dry THF (75 mL). To the resulting yellow slurry was slowly added the 2,2-dimethyl-1,3-dioxane-4,6-dione (2.50 g, 17.0 mmol) (commercially available from Aldrich) and cyclohexanone (1.80 mL, 17.0 mmol) (commercially available from Aldrich) dissolved in THF (25 mL). Pyridine (7.0 mL, 87.0 mmol) was then added and the resulting mixture was allowed to warm to room temperature and stirred overnight. The reaction was then quenched with water (200 mL) and the mixture was extracted with ether (2×300 mL). The combined organic layers were washed with saturated sodium bicarbonate solution (2×150 mL) and brine (1×100 mL) and dried over magnesium sulfate. The filtrate was concentrated, and the residue was recrystallized using ether and hexanes to give 5-cyclohexylidene-2,2-dimethyl-1,3-dioxane-4,6-dione (1.86 g, 48% yield). MS ESI (neg.) m/e: 223.1 (M−H)⁻.

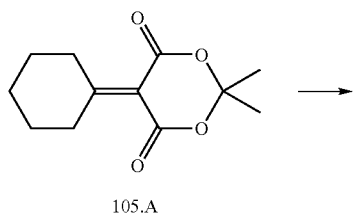

105.A

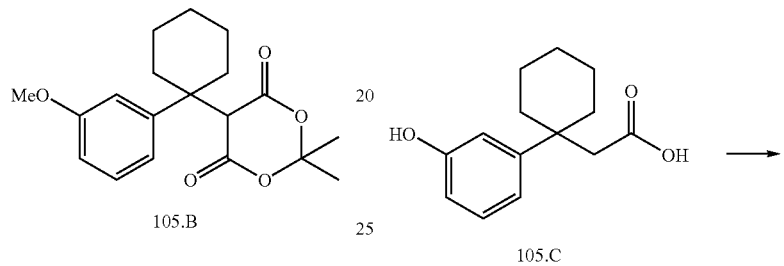

5-(1-(3-Methoxyphenyl)cyclohexyl)-2,2-dimethyl-1,3-dioxane-4,6-dione (105.B). 5-(2-(3-Methoxyphenyl)propan-2-yl)-2,2-dimethyl-1,3-dioxane-4,6-dione (105.B) was prepared from 105.A and (3-methoxyphenyl)magnesium bromide (1.0 M in THF solution from Aldrich) using a procedure described in Huang, X.; et. al.; Tetrahedron Letters; 1982, (1); pp. 75-76. MS ESI (neg.) m/e: 331.1 (M−H)⁻.

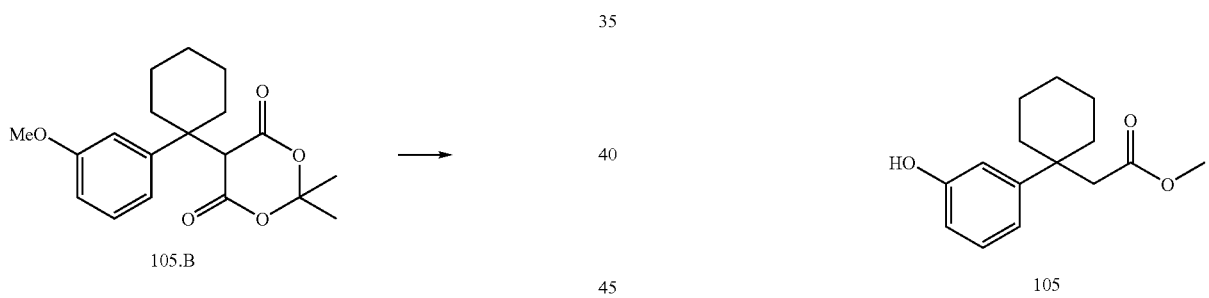

2-(1-(3-Hydroxyphenyl)cyclohexyl)acetic acid (105.C). 5-(1-(3-Methoxyphenyl)cyclohexyl)-2,2-dimethyl-1,3-dioxane-4,6-dione (105.B) (985 mg, 2.96 mmol) was dissolved in N-methylpyrrolidinone (6.0 mL) and water (53.4 µL, 2.96 mmol) was added. The solution was heated at 120° C. for three hours and LCMS indicated conversion to the anisole carboxylic acid intermediate. The reaction was cooled and NaOH (530 mg, 13.3 mmol) and commercially available dodecane-1-thiol (2.47 mL, 10.4 mmol) were added and the mixture was reheated to 120° C. and stirred for 2.5 days. The reaction was cooled and then diluted with water (75 mL). The mixture was extracted with ether (2×75 mL). The aqueous layer was then acidified with hydrochloric acid and extracted with EtOAc (3×75 mL). The combined EtOAc layers were washed with water (2×100 mL) and brine (1×75 mL) and dried over magnesium sulfate. The filtrate was concentrated to give 2-(1-(3-hydroxyphenyl)cyclohexyl)acetic acid 105.C (1.01 g, 145% yield) with acceptable purity (contains residual N-methylpyrrolidone) to take to the next reaction. MS ESI (neg.) m/e: 233.1 (M−H)⁻.

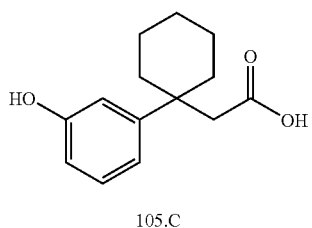

Methyl 2-(1-(3-hydroxyphenyl)cyclohexyl)acetate (105). The crude 2-(1-(3-hydroxyphenyl)cyclohexyl)acetic acid 105.C (1.01 g) was dissolved in MeOH (15 mL) and a catalytic (~10 drops) amount of concentrated sulfuric acid was added. The mixture was then refluxed for 16 hours and then cooled to room temperature. The reaction was then made basic with saturated sodium bicarbonate solution and concentrated to dryness. The residue was then dissolved in EtOAc and water and the layers were separated. The aqueous layer was extracted (2×75 mL) with EtOAc. The combined organic layers were then washed with brine (1×75 mL) and dried over magnesium sulfate. The crude product was purified by medium pressure chromatography (silica, 0 to 15% EtOAc: DCM) to give methyl 2-(1-(3-hydroxyphenyl)cyclohexyl)acetate 105 (560 mg, 52% yield). MS ESI (pos.) m/e: 266.2 (M+H₂O)⁺.

The following compounds were prepared from methyl 2-(1-(3-hydroxyphenyl)cyclohexyl)acetate (105) and the appropriate halomethyl or hydroxymethyl compound according to the methods described herein.

TABLE 31

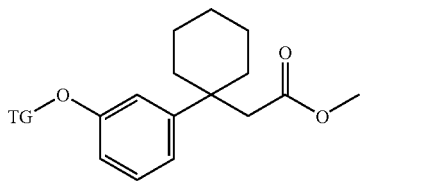

| Compound | TG |
|---|---|
| 105.1 | 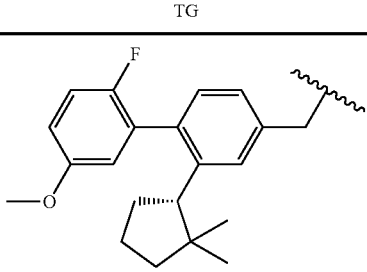 or <br> |
| 105.2 | 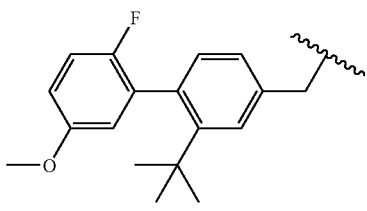 |

(1-{3-[2-((S)-2,2-Dimethyl-cyclopentyl)-2'-fluoro-5'-methoxy-biphenyl-4-ylmethoxy]-phenyl}-cyclohexyl)-acetic acid or (1-{3-[2-((R)-2,2-dimethyl-cyclopentyl)-2'-fluoro-5'-methoxy-biphenyl-4-ylmethoxy]-phenyl}-cyclohexyl)-acetic acid (105.1). MS ESI (neg.) m/e: 543.2 (M−H)⁻.

{1-[3-(2-tert-Butyl-2'-fluoro-5'-methoxy-biphenyl-4-ylmethoxy)-phenyl]-cyclohexyl}-acetic acid (105.2). MS ESI (neg.) m/e: 503.2 (M−H)⁻.

Biological Activity

The GPR40 agonist compounds described herein possess unique, surprising, and highly advantageous properties that are distinct from previously described GPR40 agonists. Unexpectedly, compounds of the present invention have been found to bind to a different site compared to other GPR40 agonists and in general have greater activity than previously described GPR40 agonists in functional assays. For example, compounds of the present invention were found to possess activity on the GPR40 receptor that was similar to the fatty acid natural ligands, indicating that they were full agonists. These results indicate that previously described GPR40 agonists and those of the present invention are pharmacologically distinct.

Competition binding assays were performed on A9 membranes expressing GPR40. The membranes were incubated with different concentrations of Comparative Compound 1, Example 14, or Example 9 in the presence of 5 nM [³H] labeled Comparative Compound 1 for 4 hours at room temperature. [³H] labeled Comparative Compound 1 was displaced completely by the unlabeled Comparative Compound 1 exhibiting homologous competition such that the unlabeled Comparative Compound 1 competes for the same site on the receptor as does the [³H] labeled compound. However, surprisingly and unexpectedly, Example 14 and Example 9 did not displace the bound [³H] labeled Comparative Compound 1. Rather, even more surprisingly, addition of Example 9 or Example 14 enhanced the binding of the radioligand (Comparative Compound 1) to the receptor. The non-competitive behavior displayed shows positive allostery of these compounds in the presence of Comparative Compound 1. The positive cooperativity of these compounds is greater than 1 when the receptor is bound to Comparative Compound 1. Thus, competition binding assays show that the compounds of the present invention agonists bind to a distinct site on the GPR40 receptor compared to other GPR40 agonists.

Figure 1:
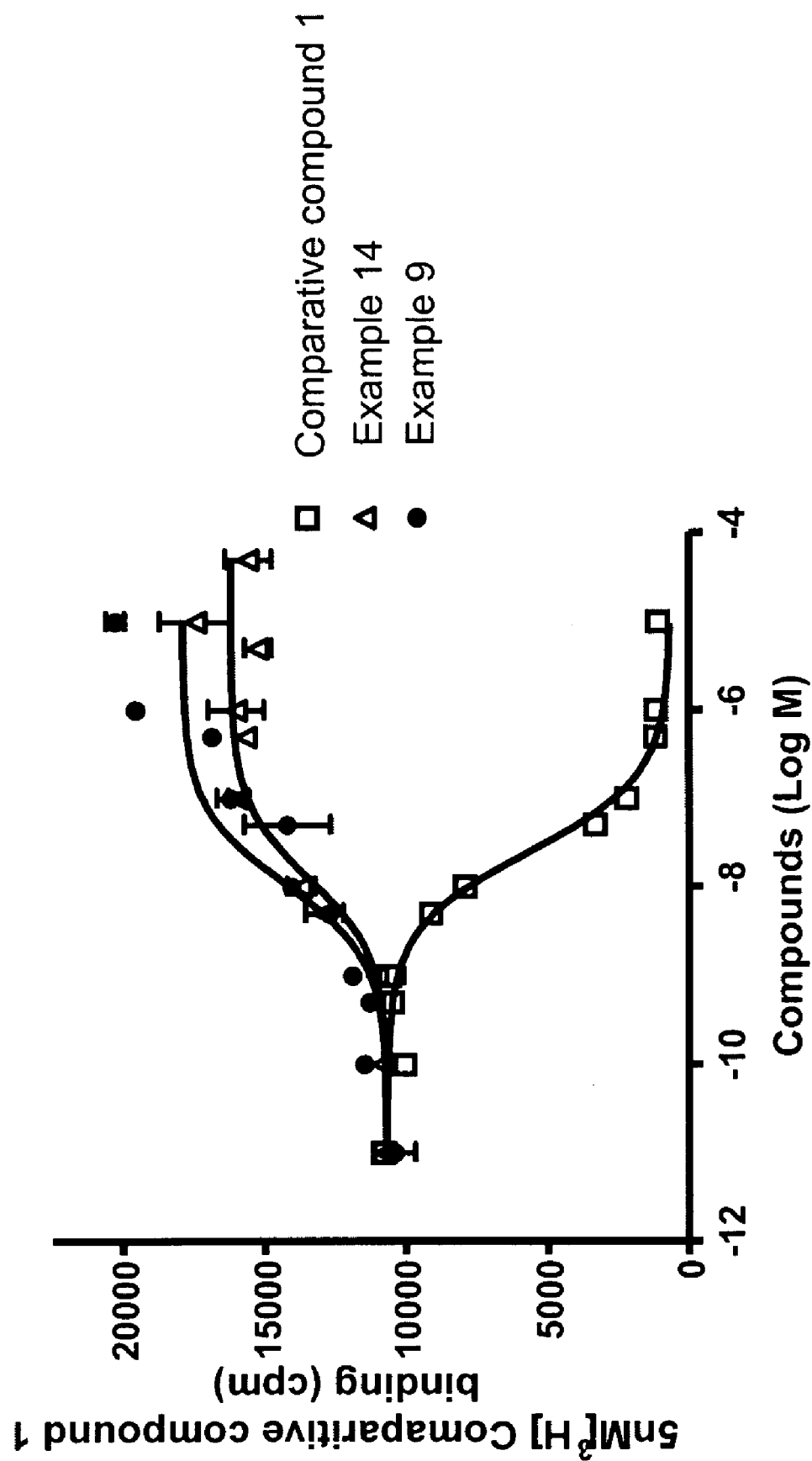
Figure 2:
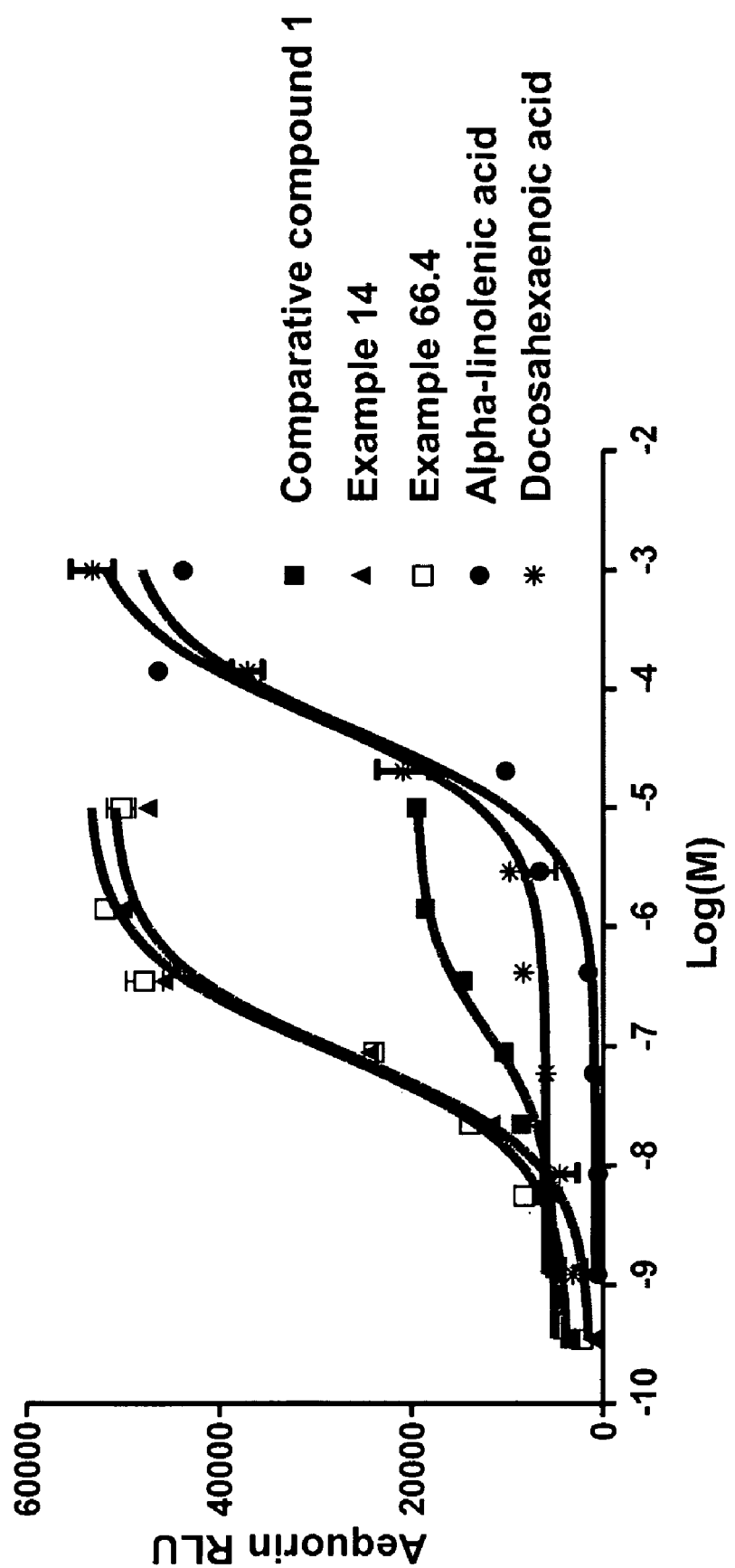
FIG. 2 is a graph showing Aequorin luminescence in response to various compounds as a function of concentration. This graph shows that Examples 14 and 66.4 have activity which is equivalent to naturally occurring fatty acid ligands such as α-linolenic acid and docosahexaenoic acid.
Figure 3:
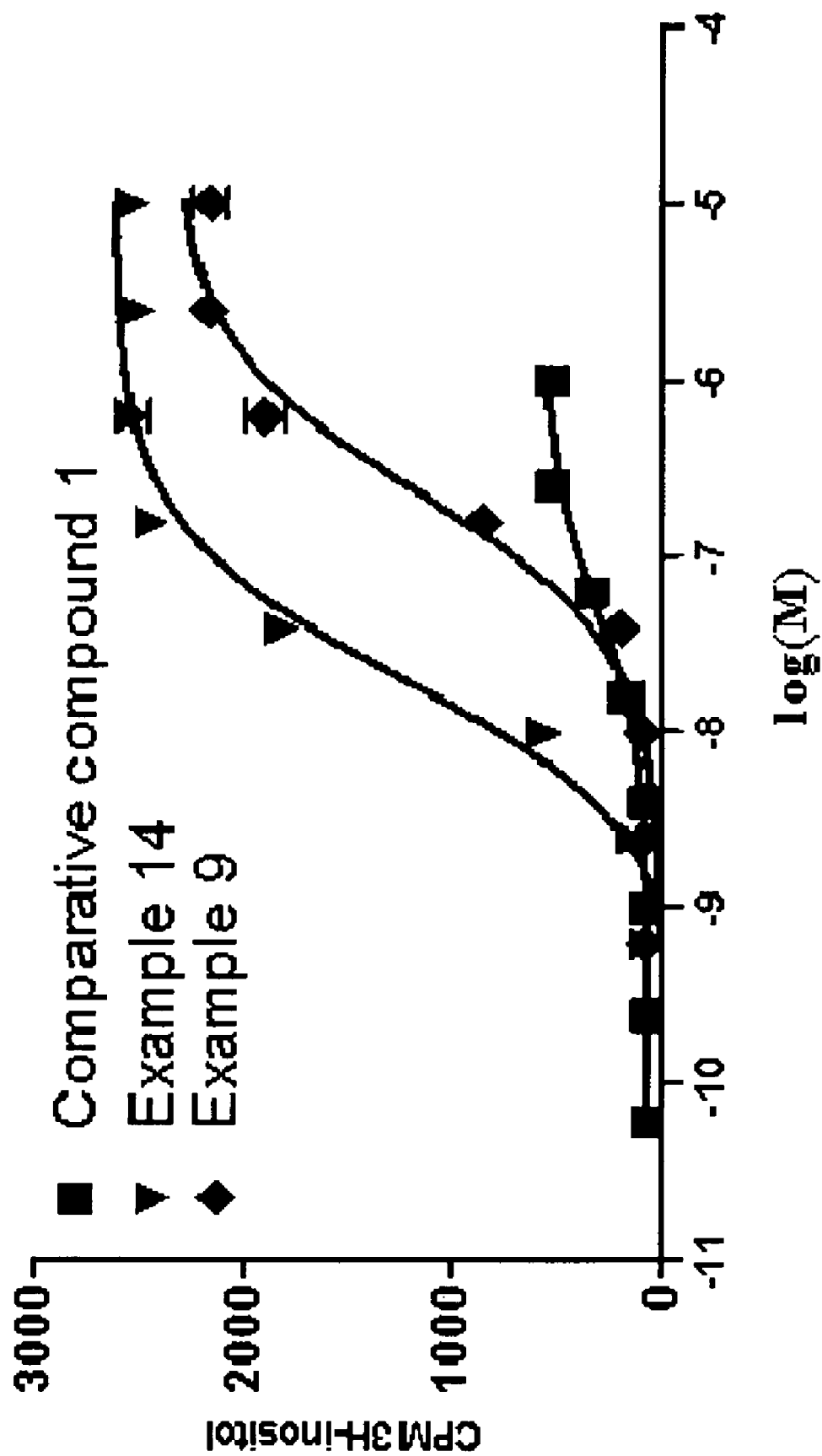
FIG. 3 is a graph showing inositol phosphate accumulation in response to various compounds as a function of concentration. This graph shows that Examples 9 and 14 have activity which is greater than Comparative Compound 1.

In GPR40 cell signaling assays, the compounds of the present invention displayed surprisingly enhanced activity compared with previously described GPR40 agonists. In aequorin assays, using a cell lines stably expressing GPR40, the $E_{max}$ of the compounds of the present invention was greater than that of previously described GPR40 agonists and similar to that of the GPR40 natural ligands, fatty acids (FIG. 2). Thus, the compounds of the present invention appear to be full agonists while the previously described GPR40 compounds were partial agonists. Briefly, the Aequorin assays were performed on doubly stable CHO cells expressing GPR40 and Aequorin DNA. Ligand-induced calcium mobilization was observed as indicated by an increase in the Aequorin luminescence which is in proportion to the calcium released upon activation of the receptor. The luminescence was recorded over a period of 20 seconds with a Microlumat luminometer (Berthold). Example 14 and Example 66.4 were found to be potent full agonists as compared with endogenous full agonists α-linolenic acid and docosahexaenoic acid. The efficacy of the compound of the present invention was surprisingly and unexpectedly improved over Comparative Compound 1. The enhanced activity of the compounds of the present invention compared to previously described GPR40 agonists was also demonstrated in inositol phosphate accumulation assays (FIG. 3). The inositol phosphate assay was performed on an A9 cell line stably transfected with GPR40 (A9_GPR40). The cells were incubated with different concentrations of compounds and [³H] inositol accumulation was measured after 1 hour. Example 14 and Example 9 compounds were found to activate the GPR40 receptor as potent full agonists as compared with Comparative Compound 1 which acted as a partial agonist.

Figure 4:
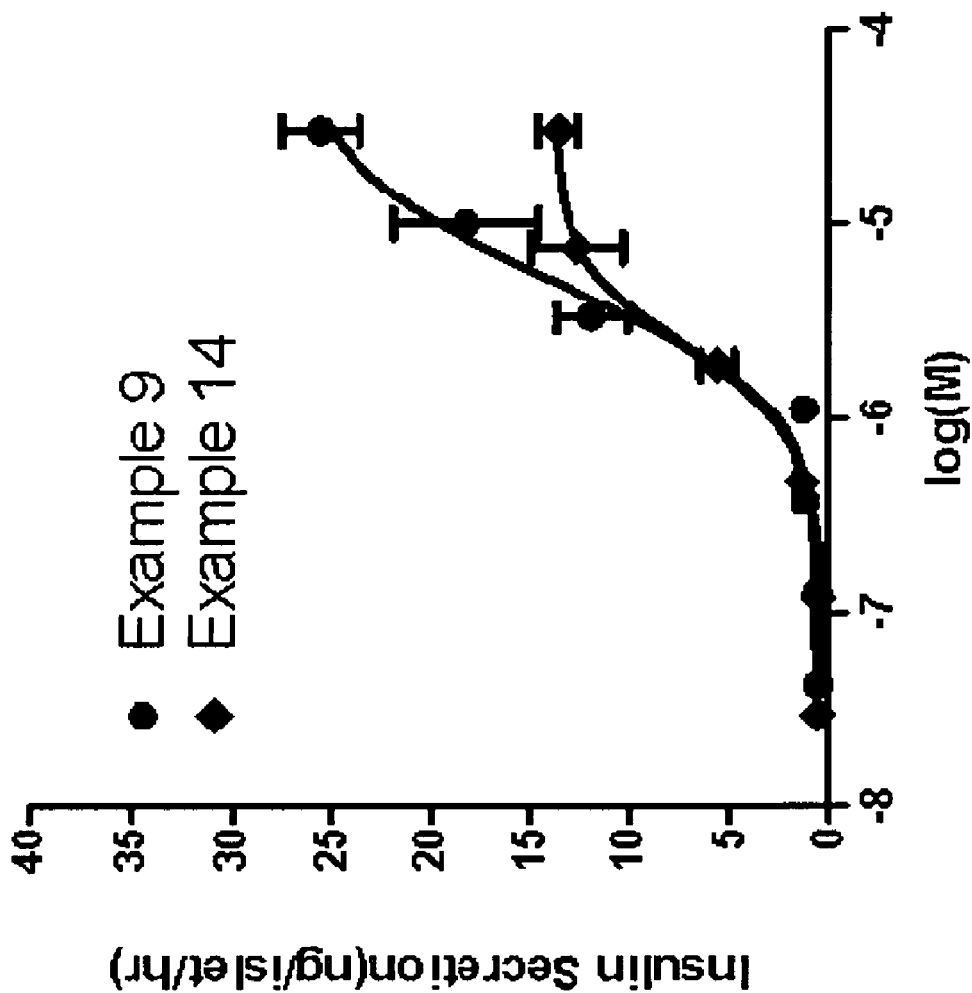
FIG. 4 is a graph showing insulin secretion from C57/B16 mouse islets as a function of concentration of Examples 9 and 14.

The enhanced activity of the compounds of the present invention was also observed in primary cell culture experiments. Islets were isolated from rodents and insulin secretion in response to the compounds of the present invention and certain previously described GPR40 agonists was measured. More specifically, islets were isolated from the pancreas of mice using collagenase digestion followed by purification on a histopaque gradient. Islets were hand-picked and then incubated for one hour in KRBH medium containing 16.7 mM dextrose, 0.1% human serum albumin, and test compounds diluted to a specified concentration. Insulin secreted into the culture supernatant was measured using an insulin ELISA. Dose response plots were graphed using Graphpad Prism software. The compounds of the present invention secreted unexpectedly greater levels of insulin compared with the previously described GPR40 agonists (FIG. 4) tested. The enhanced activity of the compounds of the present invention indicates that these compounds are more effective than previously described GPR40 agonists in treating type 2 diabetes, metabolic syndrome, and other conditions where enhanced GPR40 activity may result in therapeutic utility. With respect to FIGS. 1-4, the structure of Comparative Compound 1 is shown below.

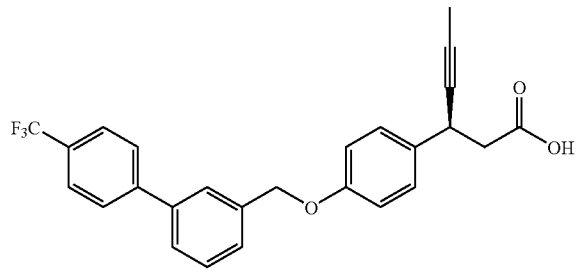

Comparative Compound 1

The synthesis of Comparative Compound 1 is set forth in Example 2 of US Patent Publication No. US2006/0004012 which is hereby incorporated herein by reference.

Cell-Based Aequorin Assay

Cell-based aequorin assays were employed to characterize the modulatory activity of compounds on the GPR40 signaling pathway. In an exemplary assay, CHO cells were stably transfected with both GPR40 and Aequorin (Euroscreen). Cells were detached from the tissue culture dish with 2 mL of trypsin (0.25%(w/v)). Trypsinization was halted with 28 mL of Hanks Buffered Salt Solution containing 20 mM Hepes (H/HBSS) and 0.01% fatty acid-free human serum albumin (HSA). Coelantrazine is added to 1 ug/mL, and the cells were incubated for 2 hours at room temperature. Compounds were dissolved in DMSO for preparation of 10 mM stock solutions. Compounds were diluted in H/HBSS containing 0.01% HSA. Serial dilutions of the test compounds were prepared to determine dose response.

Aequorin luminescence measurements were made using an EG&G Berthold 96-well luminometer, and the response was measured over a 20 second interval after cells and compounds were mixed. The maximum relative light units was plotted to determine dose response. The $EC_{50}$ (effective concentration to reach 50% maximal response) was determined from the dose response plot.

Table 32 presents representative data ($EC_{50}$ values) obtained for exemplary compounds of the invention for the activation of human GPR40.

Inositol Phosphate Accumulation Assay

An A9 cell line stably transfected with GPR40 (A9_GPR40) was used in IP accumulation assays. A9_GPR40 cells were plated in 96-well plates containing 20,000 cells/well in DMEM containing 10% FBS. After the cells attached to the well surface, the media was replaced with inositol free DMEM containing 10% dialyzed FBS and 1 µCi, mL $^3$H-inositol and incubated for 16 hours. Compounds were diluted in HBSS/10 mM LiCl containing a desired amount of HSA and added directly to cells. Following 1 hour incubation at 37° C., the media was replaced with 100 µL of 20 mM formic acid to quench the reaction. 50 µL of the extract was then added to 100 µL of SPA beads, incubated overnight, and measured on a TopCount the following day.

The stereoisomers in Table 32 are as specified, i.e., S-enantiomers or R-enantiomers, and if not specified, or if shown with wavy bonds, are mixtures of S-enantiomers and R-enantiomers. In addition, the present invention provides the S-enantiomers, the R-enantiomers, and mixtures of both S-enantiomers and R-enantiomers including racemates of each compound prepared according to the synthetic methods described herein or adapted with the necessary minor modifications from these methods.

Insulin Secretion Assay

Human islets were isolated from cadaveric donors. Islets were treated with trypsin (0.25%(w/v) and cells were seeded in 96-well plates containing 3,000 cells per well. Cells were cultured in Roswell Park Memorial Institute (RMPI) media containing 10% fetal bovine serum.

For determination of insulin secretion, media was removed from islet cells and replaced with Krebs-Ringer bicarbonate buffer containing 10 mM HEPES (KRBH) and 2 mM glucose. After one hour incubation, media was replaced with KRBH containing 11.2 mM glucose and test compounds. Insulin released into the medium from the islet cells was measured using a scintillation proximity assay (SPA).

For determination of insulin secretion from rodent islets, C57/B16 mice were euthanized with carbon dioxide gas. The pancreatic bile duct was clamped proximal to the duodenum and then cannulated. H/HBSS containing 0.75 mg/mL collagenase XI (Sigma) was then infused into the pancreas through the cannula. The pancreas was excised and then incubated at 37° C. for 13 minutes to complete enzymatic digestion. The collagenase digestion was quenched in H/HBSS containing 1% BSA and washed once in the same buffer. Islets can be purified using density gradient centrifugation using Histopaque (Sigma) and were hand-picked under a stereomicroscope.

Islets were cultured overnight in Roswell Park Memorial Institute (RMPI) media containing 10% fetal bovine serum and 50 uM beta-mercaptoethanol. Following overnight culture, islets were incubated in KRBH containing 2.8 mM glucose for one hour.

For determination of insulin secretion, islets were incubated in DMEM containing 12.5 mM glucose and test compounds for one hour. Insulin released into the culture medium from the islets was measured using an insulin ELISA.

GLP-1 Secretion Experiments

In Vitro GLP-1 Secretion in Primary Cell Cultures

Pregnant Wistar rats were obtained from Harlan (Indianapolis). Fetal rat intestinal cells (FRIC) were isolated from E19 rat embryos following a protocol published by Brubaker and Vranic, Endocrinology 120(5):1976-85, 1987 which is hereby incorporated by reference in its entirety and for all purposes as if specifically set forth herein. Briefly, female Wistar rats were euthanized at day 19 of pregnancy and fetuses were excised. The small intestine was harvested from each fetus, minced, and washed with modified Hank's Buffered Salt Solution (HBSS) (Sigma-Aldrich). Cells were dispersed by two sequential 20 minute rounds of digestion in collagenase buffer (0.5 mg/mL type H SigmaBlend collagenase, 0.5 mg/mL hyaluronidase, 0.05 mg/mL DNase I) at 37° C. Dispersed cells were washed twice with HBSS, and cultured in poly-D-lysine coated 96-well plates in Clonetics BEGM epithelial growth medium. After 24 hours, cells were incubated for 2 hours with dilutions of small molecule GPR40 modulators prepared from a 10 mM DMSO stock solution in HBSS. Secreted active GLP-1 (7-36 amide) and GLP-1 (7-37) was measured in culture media using an ELISA kit (Linco Research, St. Charles, Mich.). The experiments demonstrate that the example compounds significantly increase GLP-1 secretion.

In Vivo GLP-1 Secretion in C57B16 Mice

Male, 12 week old, C57B16 mice were obtained from The Jackson Laboratory (Bar Harbor, Me.). All mice were group-housed in a humidity and temperature-controlled room with a 12 hour light/dark cycle and ad libitum access to chow (Teklad 2018S) and water. The animals were assigned into vehicle or treatment groups. The experiments were conducted under overnight fasted or non-fasted conditions. Blood samples were taken at 0, 15, 30, 60 and 120 minutes after the dose. Plasma active form GLP-1 concentrations were measured using GLP-1 ELISA kits (Linco Research, St. Charles, Mich.). These experiments demonstrate that the example compounds significantly increased plasma levels of GLP-1 in normal mice after administration in both the fasted and non-fasted states.

In Vivo GLP-1 Secretion in Diabetic Mice

Male, 4 week old, C57B16 mice were obtained from The Jackson Laboratory (Bar Harbor, Me.). All mice were group-housed in a humidity and temperature-controlled room with a 12 hour light/dark cycle and ad libitum access to a 35% w/w fat-enriched diet (Bioserv) and water. The diabetic condition was established by 4 weeks of fat-enriched diet feeding and a dose of streptozotocin (Sigma Aldrich) at 95 mg/kg i.p. injection. The animals were assigned into vehicle or treatment groups. The experiments were conducted under non-fasted conditions. Blood samples were taken at 0, 15, 30, 60, 120 and 240 minutes after the dose. Plasma active form GLP-1 concentrations were measured using GLP-1 ELISA kits (Linco Research, St. Charles, Mich.). These experiments demonstrate that the example compounds significantly increased plasma levels of GLP-1 in diabetic mice after administration in the non-fasted state.

All publications and patent applications cited in this specification are hereby incorporated by reference as if each individual publication or patent application were specifically and individually indicated to be incorporated by reference. Each publication and patent application cited herein is incorporated in its entirety as if fully set forth herein. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 32

Assay Data For Human GPR40

| No. | Structure[a] | AequorinEC$_{50}$[b,c] | IP3 EC$_{50}$[c,d] |
|---|---|---|---|
| 1 | [structure: 3-methoxybiphenyl with methyl substituent, linked via CH$_2$O to phenyl propanoic acid] | ++ | ND[e] |
| 2 | [structure: 3-methoxy-2'-fluorobiphenyl with methyl substituent, linked via CH$_2$O to phenyl propanoic acid] | +++ | ND |
| 3 | [structure: 3-methylthiobiphenyl with tert-butyl substituent, linked via CH$_2$O to phenyl (R)-propanoic acid] or [structure: 3-methylthiobiphenyl with tert-butyl substituent, linked via CH$_2$O to phenyl (S)-propanoic acid] | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 4 | 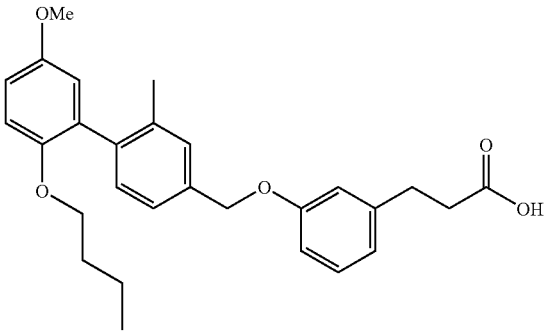 | ++ | ND |
| 5 |   or   | +++ | +++ |
| 6 |   or   | ++ | +/++ |

TABLE 32-continued
Assay Data For Human GPR40
| No. | Structure[a] | AequorinEC$_{50}$[b,c] | IP3 EC$_{50}$[c,d] |
|---|---|---|---|
| 7 | 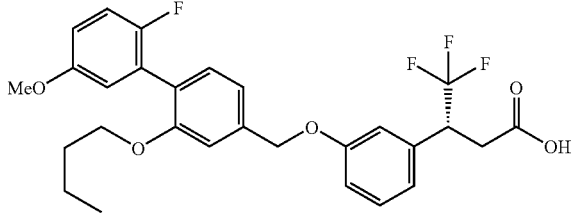 or 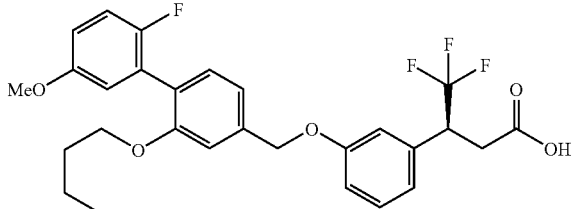 | ++ | ++ |
| 8 | 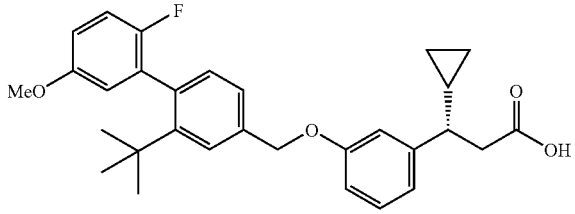 or 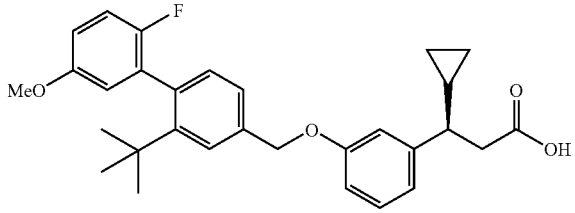 | +++ | +++ |
| 9 | 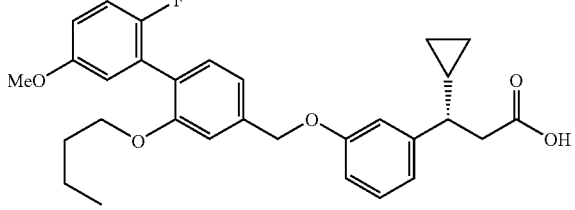 or 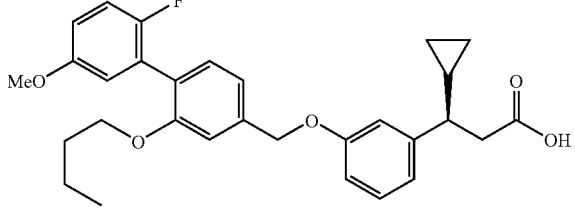 | +++ | +++ |
| 10 | Enantiomer of 8 | ++ | ND |
| 11 | Enantiomer of 9 | ++ | ND |

TABLE 32-continued
| | | Assay Data For Human GPR40 | |
|---|---|---|---|
| No. | Structure[a] | AequorinEC$_{50}$[b,c] | IP3 EC$_{50}$[c,d] |
| 12 | 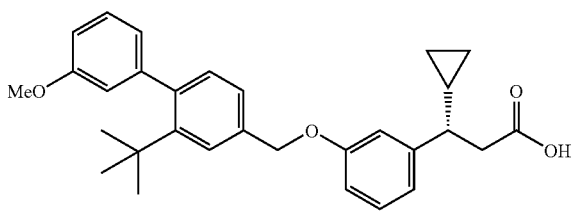 or 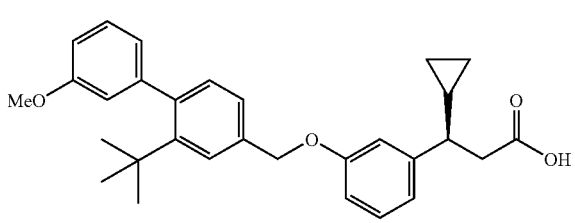 | +++ | +++ |
| 13 | 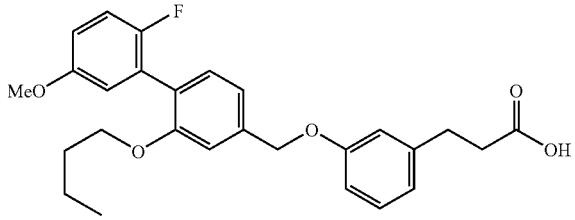 | ++ | ND |
| 14 | 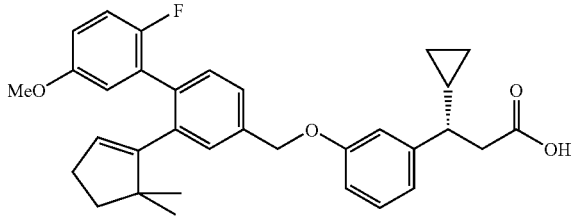 or 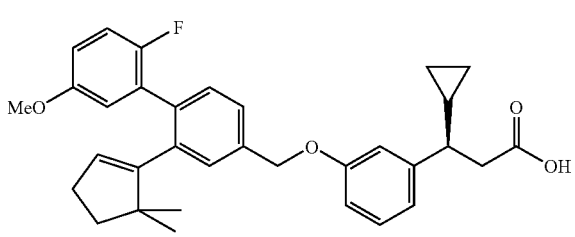 | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 15 | 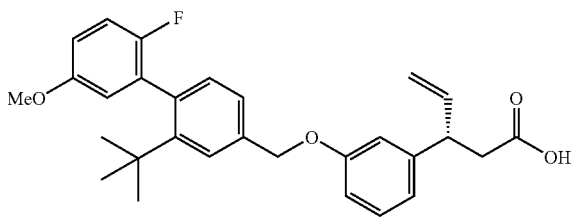 | ++ | ND |
| 16 | 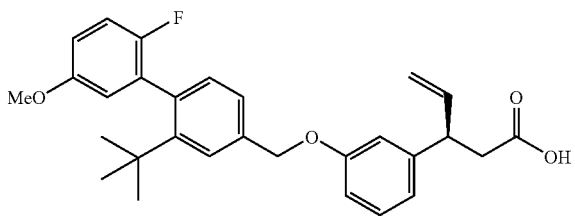 | ++ | ND |
| 17 | 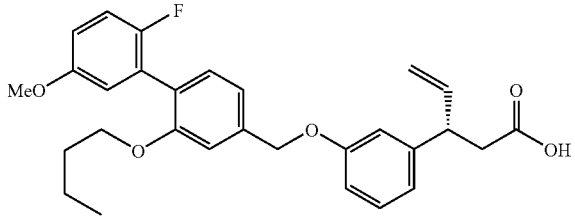 | +++ | +++ |

TABLE 32-continued
Assay Data For Human GPR40
| No. | Structure[a] | AequorinEC$_{50}$[b,c] | IP3 EC$_{50}$[c,d] |
|---|---|---|---|
| 18 | 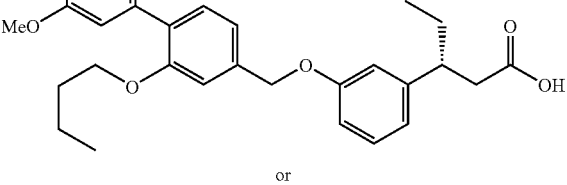<br>or<br>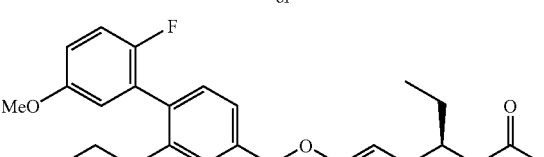 | +++ | +++ |
| 19 | Enantiomer of 15 | ++ | ND |
| 20 | 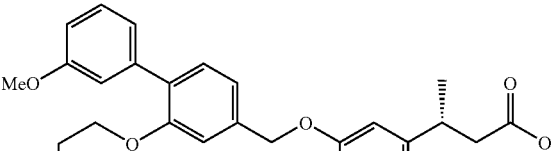<br>or<br>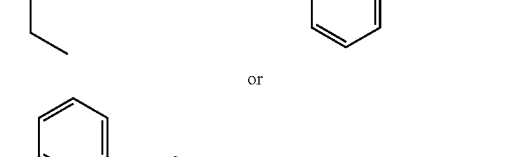 | +++ | +++ |
| 21 | 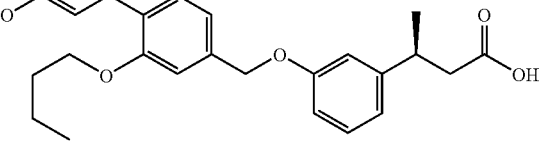<br>or<br>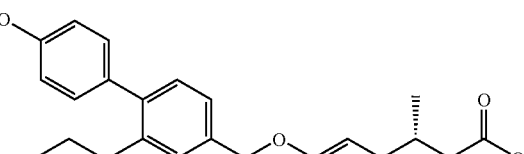 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 22 | 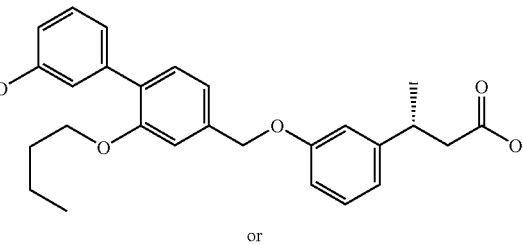 or | ++ | ND |
| 23 | 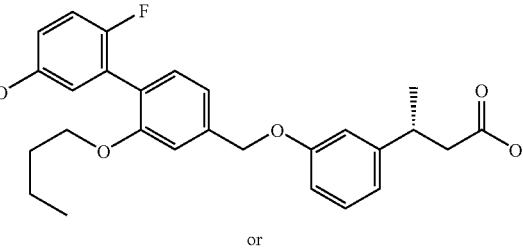 or | ++ | ND |
| 24 | 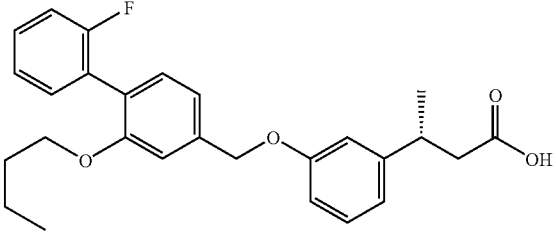 or | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 25 | 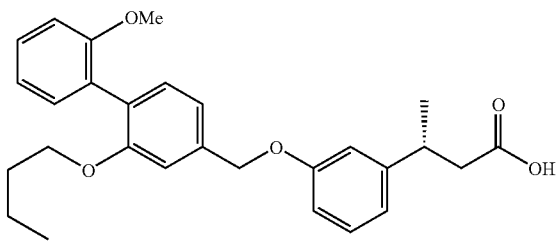<br>or<br>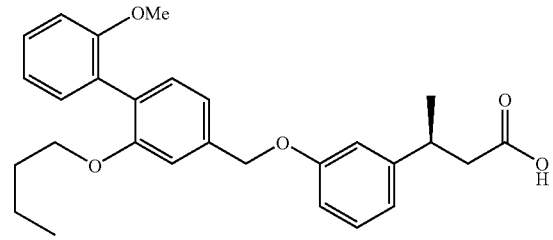 | + | ND |
| 26 | 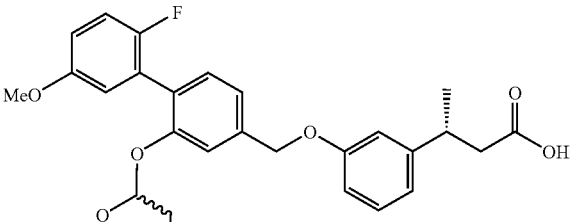<br>or<br>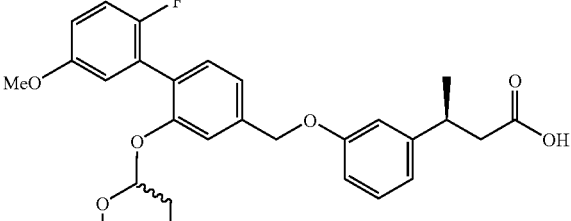 | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 27 | 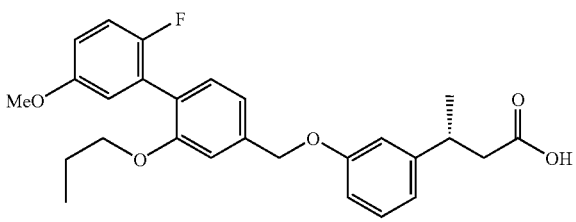 or 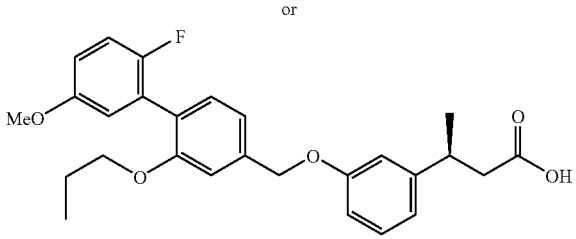 | ++ | ND |
| 28 | 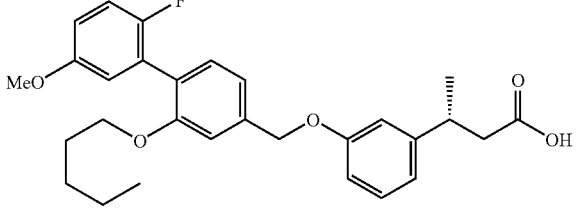 or 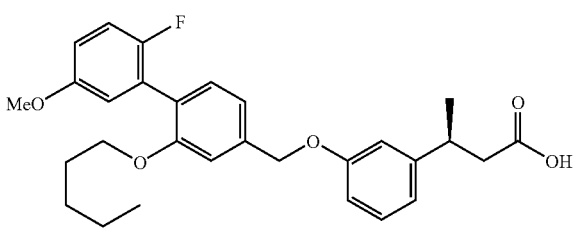 | +++ | ND |
| 29 | 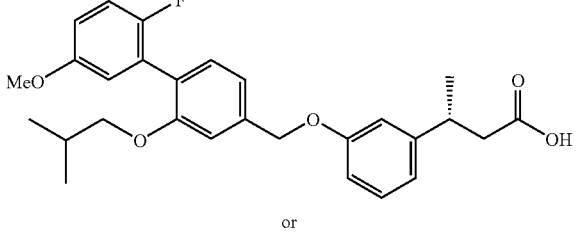 or 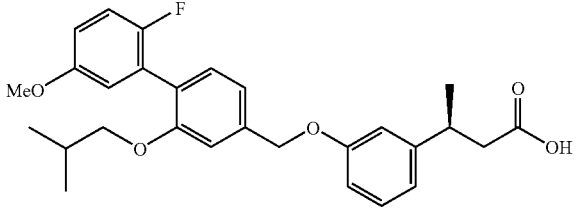 | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 30 | 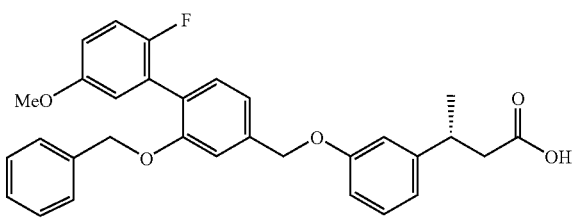 or 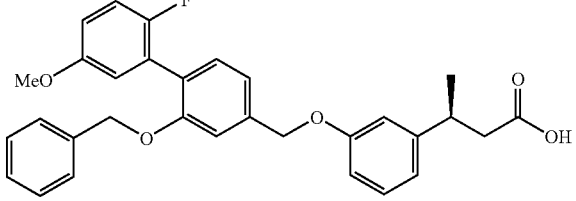 | ++ | ND |
| 31 | 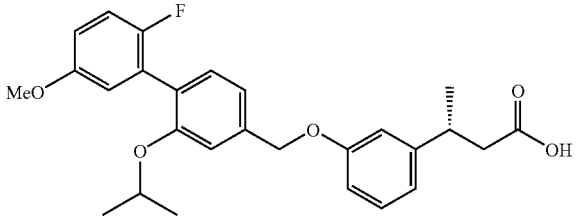 or 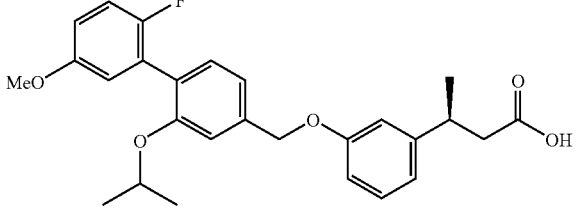 | +++ | ND |
| 32 | 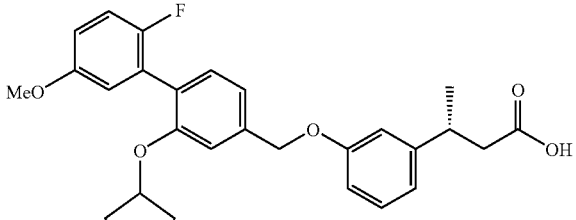 or 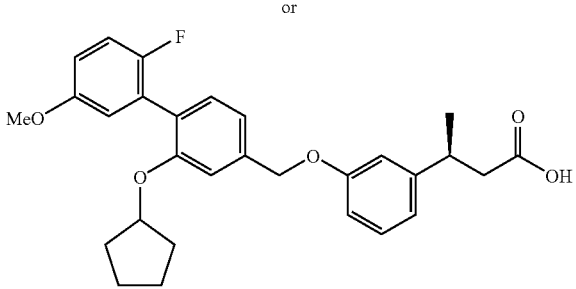 | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 33 | 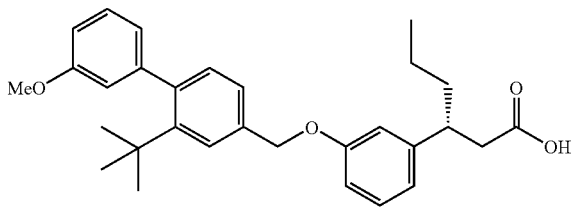 or 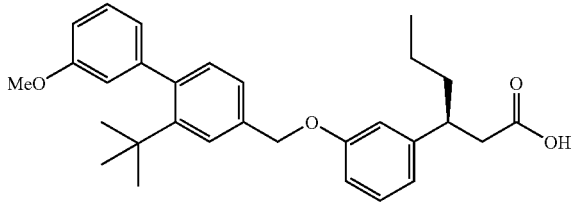 | +++ | +++ |
| 34 | 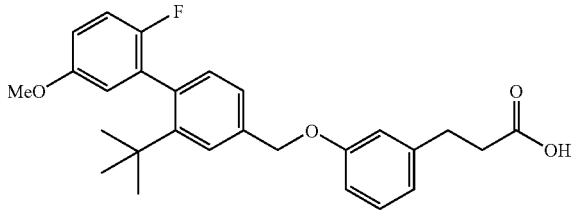 | +++ | +++ |
| 35 | 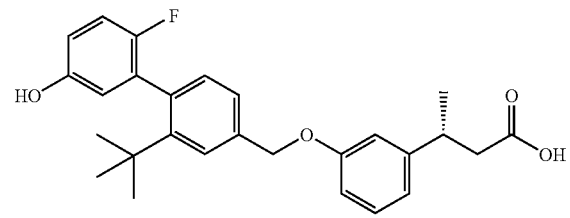 or 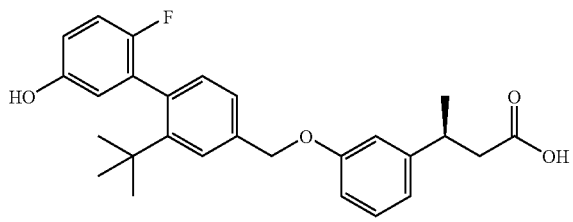 | +++ | +++ |
| 36 | 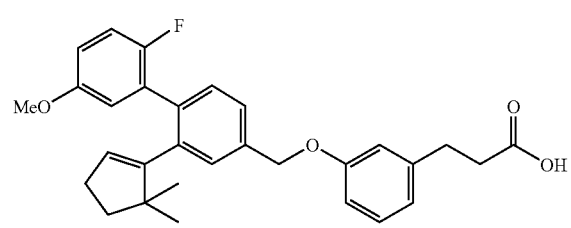 | +++ | +++ |

TABLE 32-continued

Assay Data For Human GPR40

| No. | Structure | AequorinEC$_{50}$$^{b,c}$ | IP3 EC$_{50}$$^{c,d}$ |
|---|---|---|---|
| 37 | | +++ | +/++ |
| 38 | | +++ | ++ |
| 39 | | ++ | +++ |
| 40 | | +++ | ND |
| 41 | | ++ | ND |
| 42 | | +++ | ++ |

TABLE 32-continued
Assay Data For Human GPR40
| No. | Structure[a] | AequorinEC$_{50}$[b,c] | IP3 EC$_{50}$[c,d] |
|---|---|---|---|
| 43 | 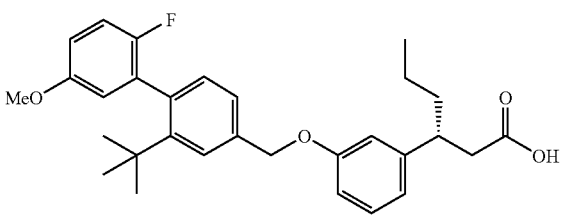 or 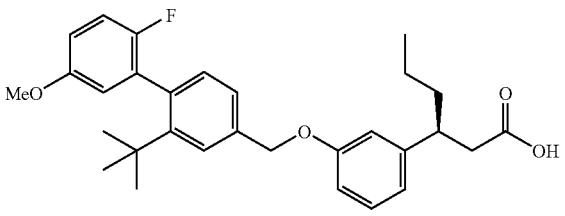 | +++ | +++ |
| 44 | Enantiomer of 43 | +++ | +++ |
| 45 | Enantiomer of 42 | ++ | ++ |
| 46 | 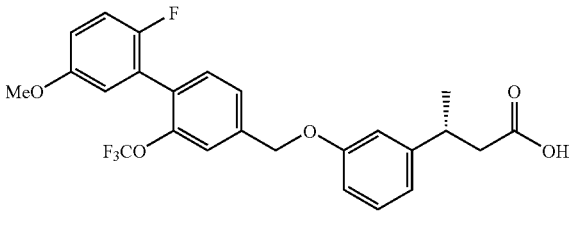 or 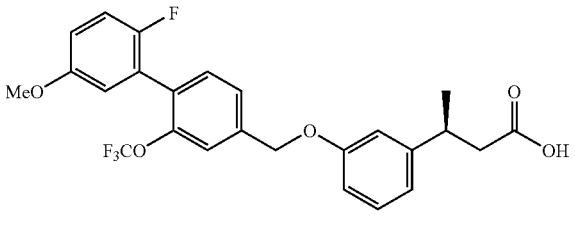 | +++ | ++ |
| 47 | 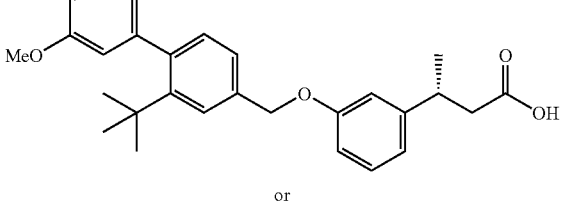 or 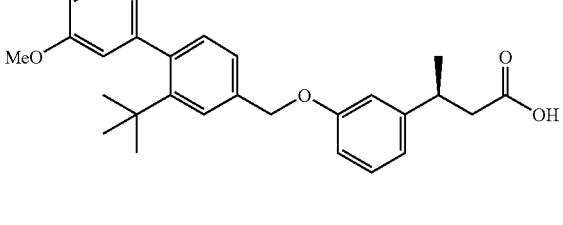 | +++ | +++ |

TABLE 32-continued

Assay Data For Human GPR40

| No. | Structure[a] | AequorinEC$_{50}$[b,c] | IP3 EC$_{50}$[c,d] |
|---|---|---|---|
| 48 | [structure: 2'-F, 5'-MeO, 2-tBu biphenyl-CH2-O-phenyl-CH(isopropenyl)-CH2-COOH] or [enantiomer structure shown] | ++ | ND |
| 49 | Enantiomer of 48 | +++ | +++ |
| 50 | [structure: 2'-F, 5'-MeO biphenyl with 2-butoxy, -CH2-O-phenyl-CH(isopropenyl)-CH2-COOH] or [enantiomer structure shown] | ++ | ++ |
| 51 | [structure: 2'-F, 5'-MeO, 2-tBu biphenyl-CH2-O-phenyl-CH(allyl)-CH2-COOH] or [enantiomer structure shown] | +++ | +++ |

TABLE 32-continued
Assay Data For Human GPR40
| No. | Structure[a] | AequorinEC$_{50}$[b,c] | IP3 EC$_{50}$[c,d] |
|---|---|---|---|
| 52 | 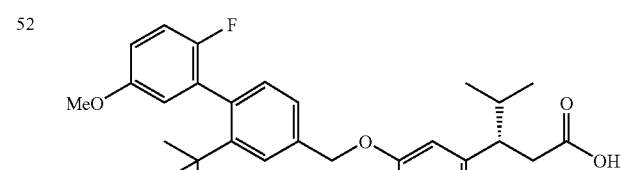 or 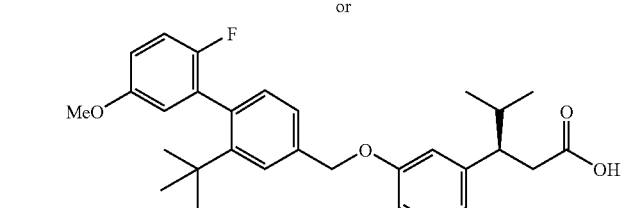 | ++ | ND |
| 53 | 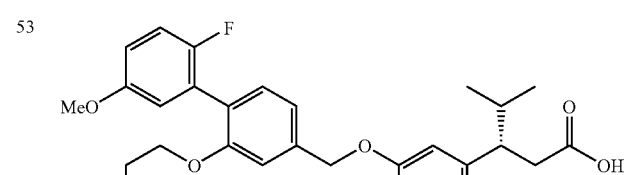 or 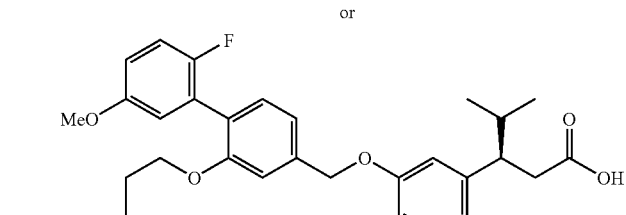 | ++ | ND |
| 54 | 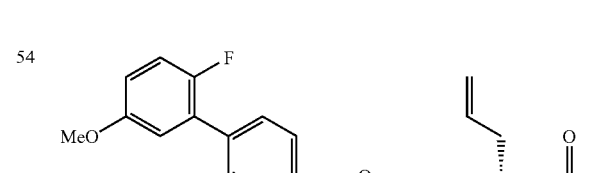 or 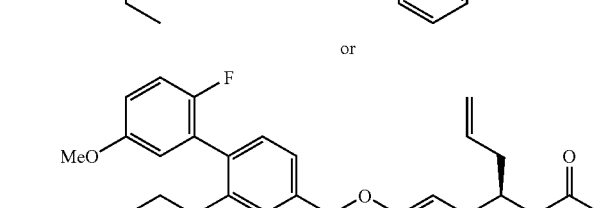 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 55 | 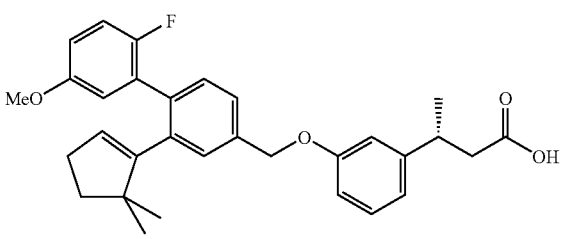 or 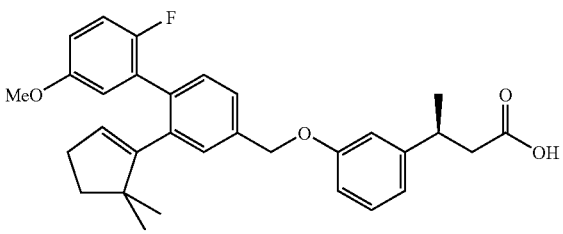 | +++ | ++++ |
| 56 | 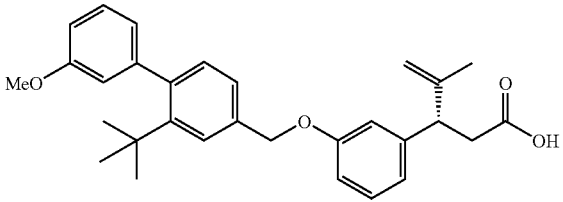 or 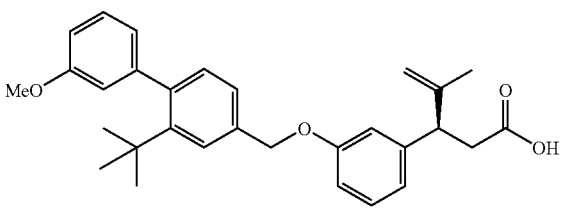 | +++ | +++ |
| 57 | 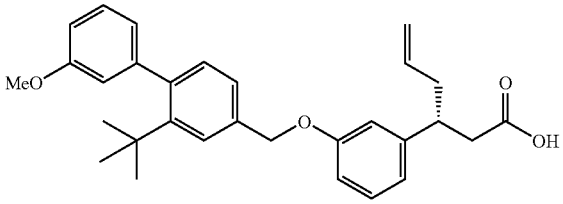 or 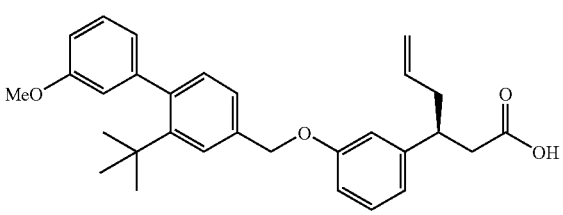 | +++ | +++ |

TABLE 32-continued
Assay Data For Human GPR40
| No. | Structure[a] | AequorinEC$_{50}$[b,c] | IP3 EC$_{50}$[c,d] |
|---|---|---|---|
| 58 | 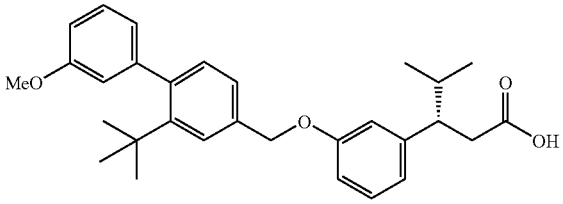<br>or<br>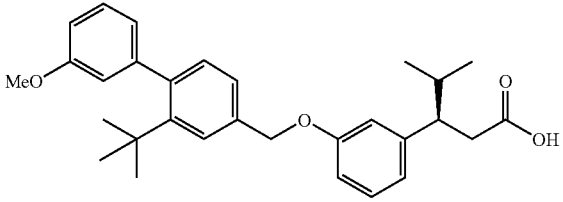 | ++ | ND |
| 59 | 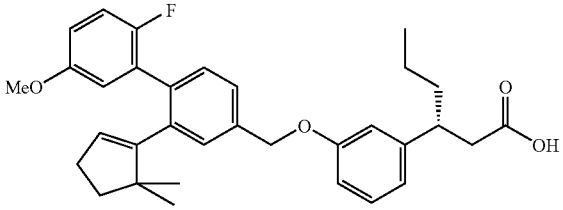<br>or<br>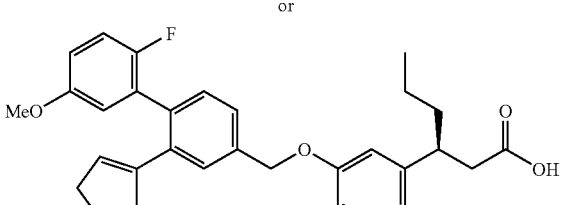 | +++ | ++++ |
| 60 | 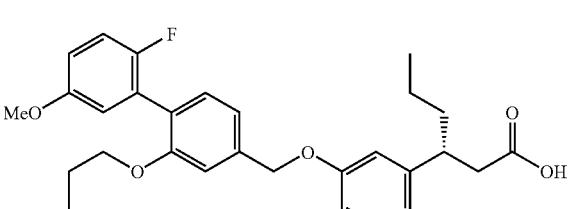<br>or<br>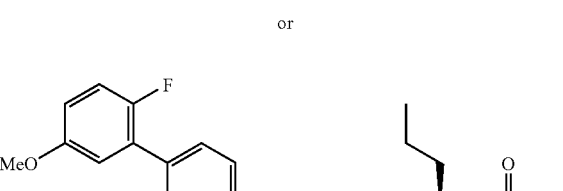 | +++ | +++ |

TABLE 32-continued

Assay Data For Human GPR40

| No. | Structure[a] | AequorinEC$_{50}$[b,c] | IP3 EC$_{50}$[c,d] |
|---|---|---|---|
| 61.1 | | +++ | ND |
| 61.2 | | ++ | ND |
| 61.3 | | +++ | ND |
| 61.4 | | ++ | ND |
| 62.1 | or | +++ | ND |

TABLE 32-continued

Assay Data For Human GPR40

| No. | Structure | AequorinEC$_{50}$$^{b,c}$ | IP3 EC$_{50}$$^{c,d}$ |
|---|---|---|---|
| 62.2 | *structure shown* | +++ | ND |
| 63.1 | Enantiomer of 62.1 | +++ | ND |
| 63.2 | *structure shown* | +++ | ND |
| 64.1 | *structure shown* | +++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 64.2 | | ++ | ND |
| 64.3 | | ++ | ND |
| 64.4 | | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 64.5 | 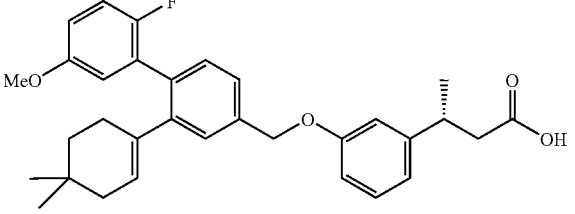<br>or<br>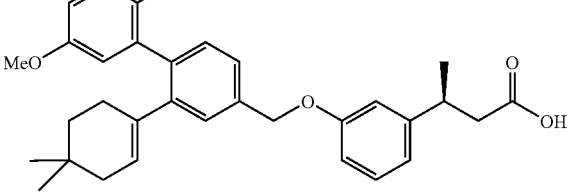 | +++ | ++++ |
| 64.6 | 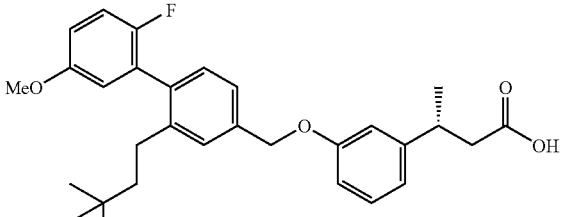<br>or<br>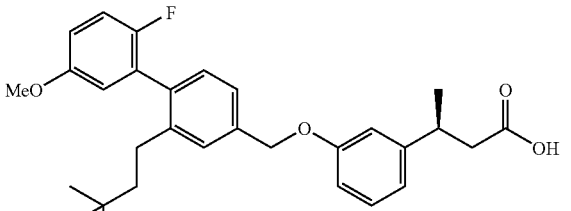 | +++ | ++++ |
| 64.7 | 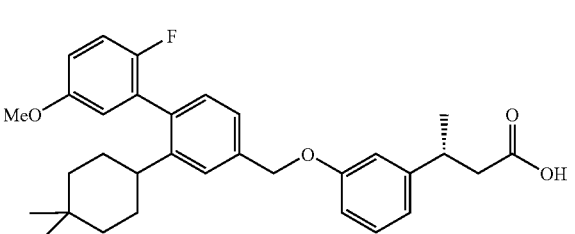<br>or<br>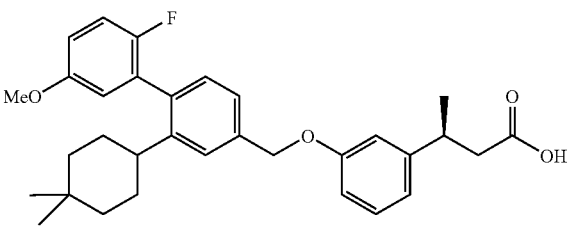 | +++ | ++++ |

TABLE 32-continued
Assay Data For Human GPR40
| No. | Structure | AequorinEC$_{50}$[b,c] | IP3 EC$_{50}$[c,d] |
|---|---|---|---|
| 64.8 | 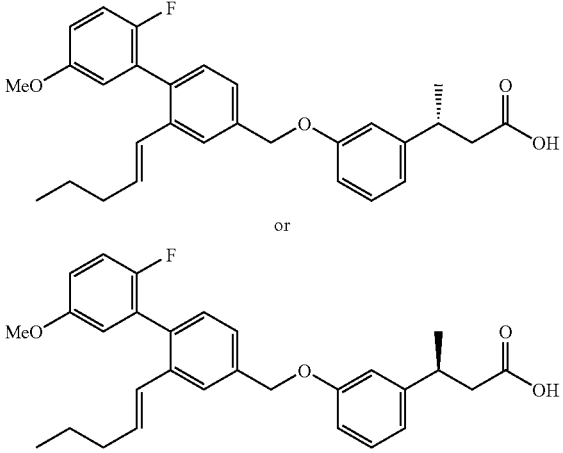 or 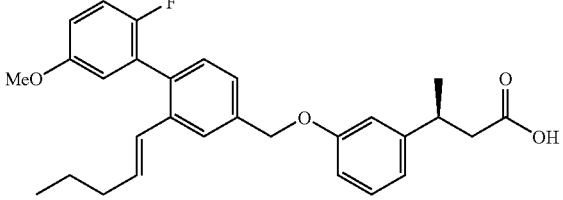 | +++ | ND |
| 64.9 | 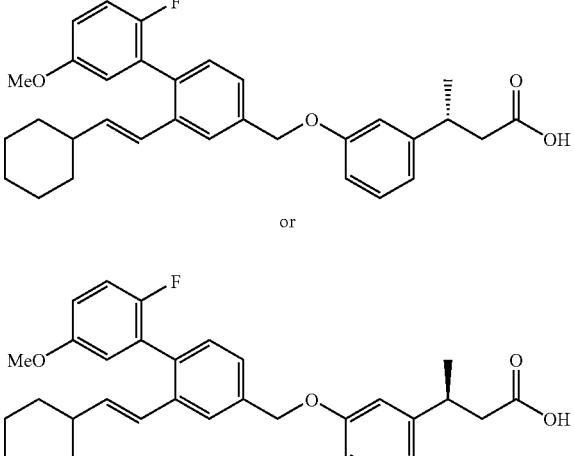 or 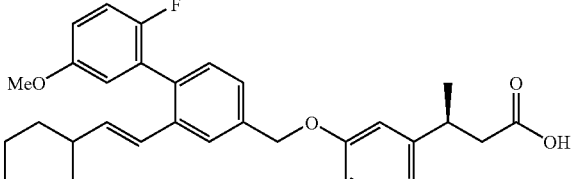 | +++ | ND |
| 64.10 | 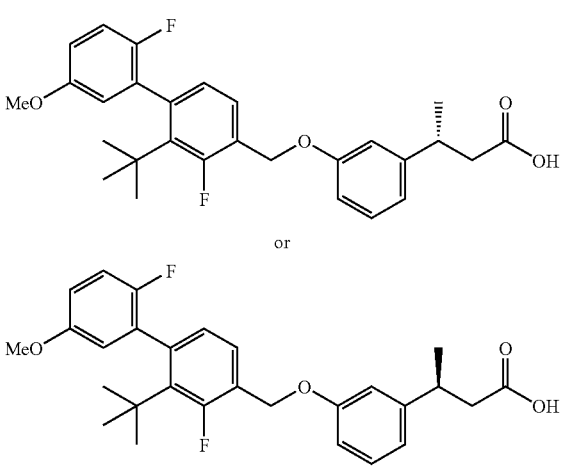 or 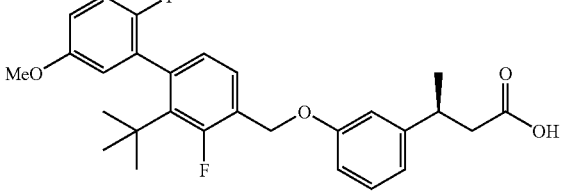 | +++ | +++ |

TABLE 32-continued
Assay Data For Human GPR40
| No. | Structure[a] | AequorinEC$_{50}$[b,c] | IP3 EC$_{50}$[c,d] |
|---|---|---|---|
| 64.11 | 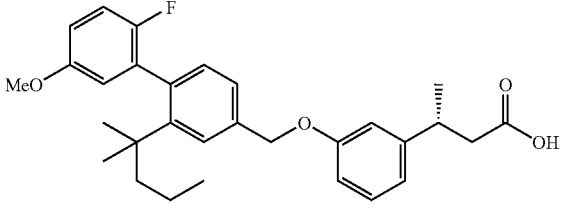 or 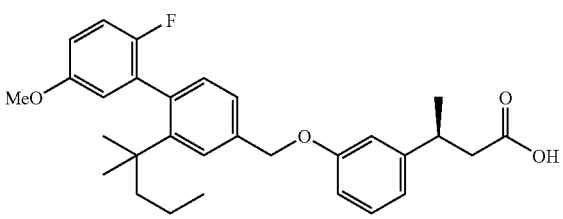 | +++ | +++ |
| 64.12 | 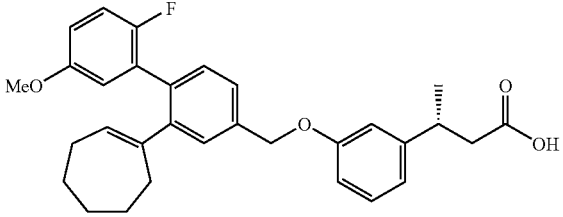 or 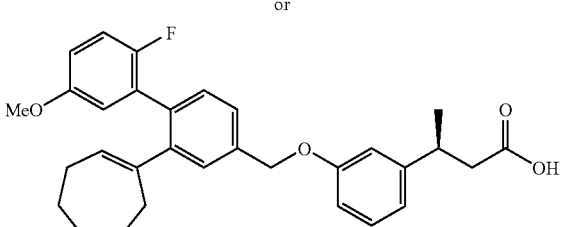 | +++ | ++++ |
| 64.13 | 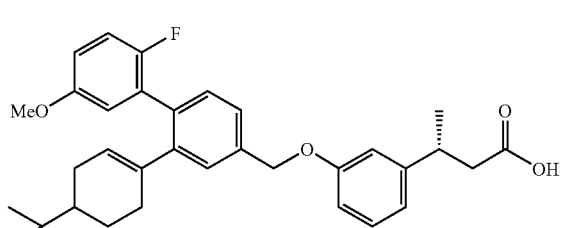 or 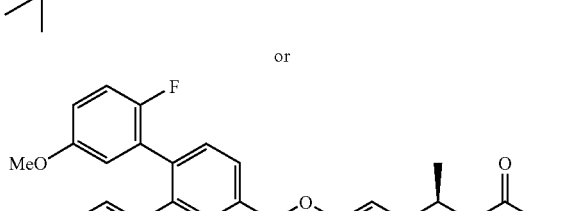 | +++ | ++++ |

TABLE 32-continued

Assay Data For Human GPR40

| No. | Structure$^a$ | AequorinEC$_{50}$$^{b,c}$ | IP3 EC$_{50}$$^{c,d}$ |
|---|---|---|---|
| 64.14 | | +++ | +++ |
| 64.15 | | +++ | ++++ |
| 64.16 | | +++ | ++++ |

TABLE 32-continued
Assay Data For Human GPR40
| No. | Structure | AequorinEC$_{50}$[b,c] | IP3 EC$_{50}$[c,d] |
|---|---|---|---|
| 64.17 | 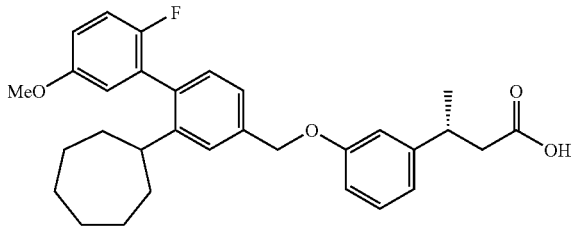 or 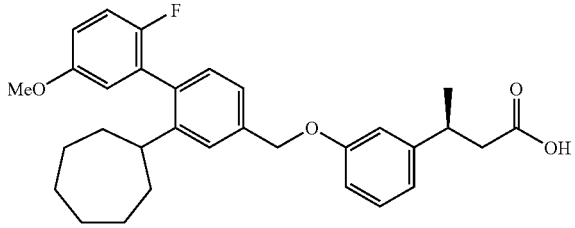 | +++ | ++++ |
| 64.18 | 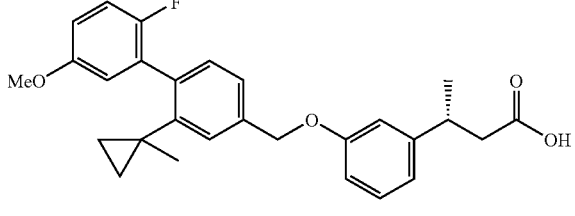 or 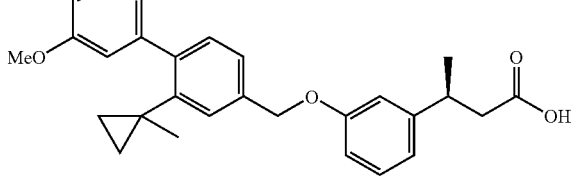 | +++ | +++ |
| 64.19 | 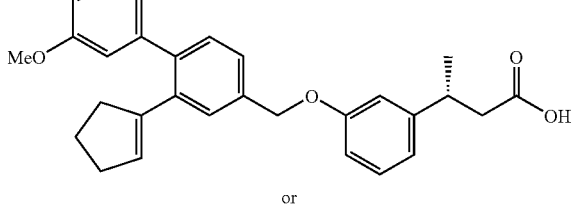 or 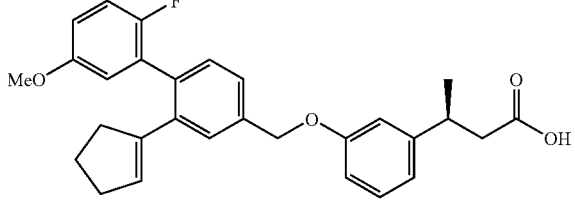 | +++ | +++ |

TABLE 32-continued
Assay Data For Human GPR40
| No. | Structure[a] | AequorinEC$_{50}$[b,c] | IP3 EC$_{50}$[c,d] |
|---|---|---|---|
| 64.20 | 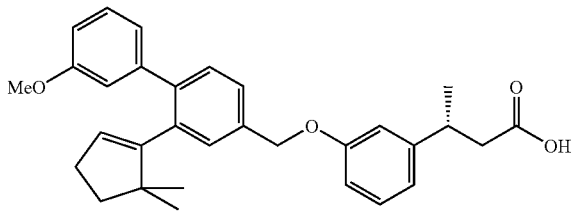 or 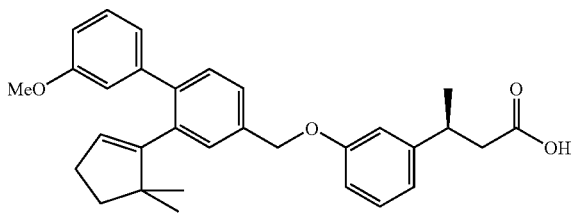 | +++ | ++++ |
| 64.21 | 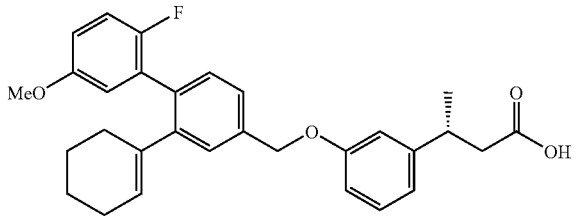 or 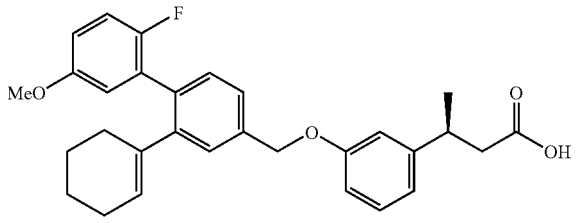 | +++ | ++++ |
| 64.22 | 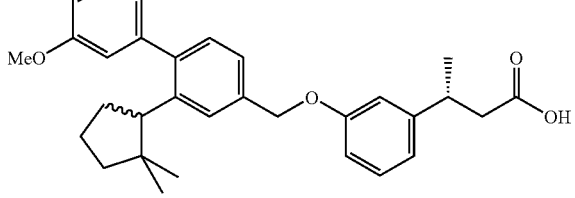 or 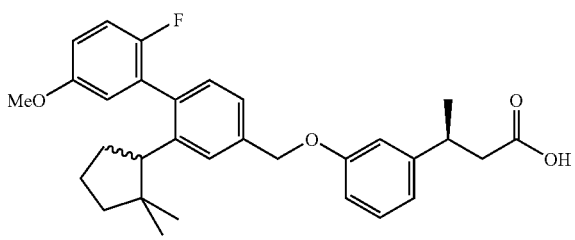 | +++ | ++++ |

TABLE 32-continued

Assay Data For Human GPR40

| No. | Structure[a] | AequorinEC$_{50}$[b,c] | IP3 EC$_{50}$[c,d] |
|---|---|---|---|
| 64.23 | | ++ | ND |
| 64.24 | | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 64.25 | 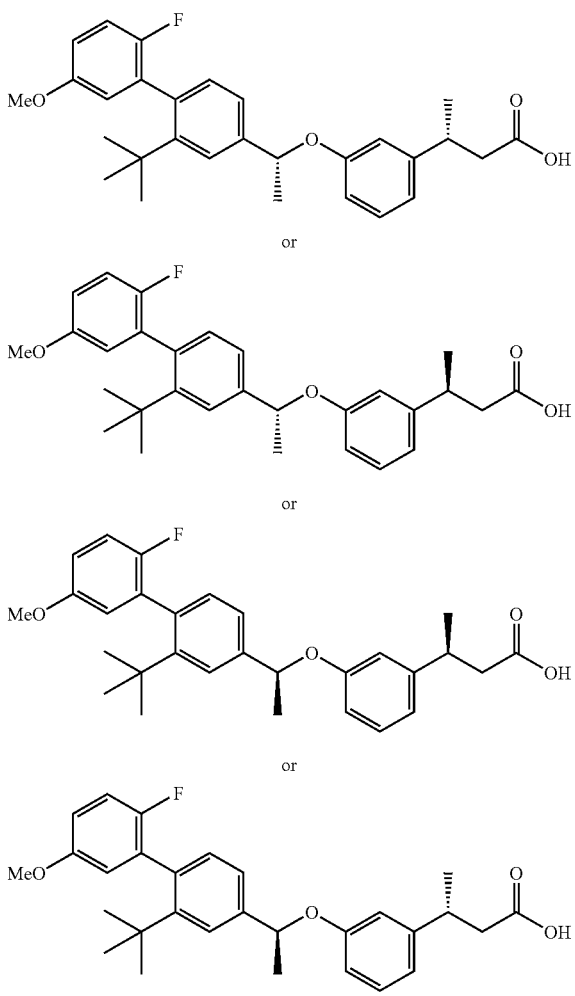 or 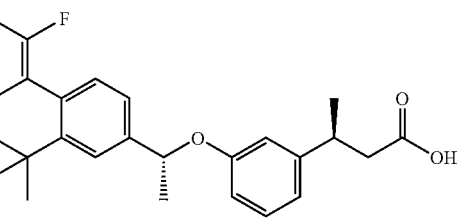 or 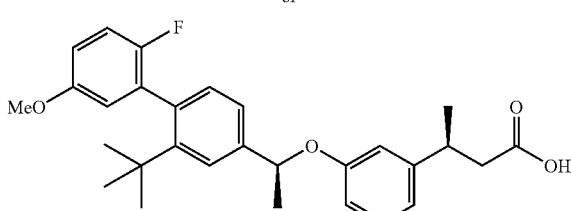 or 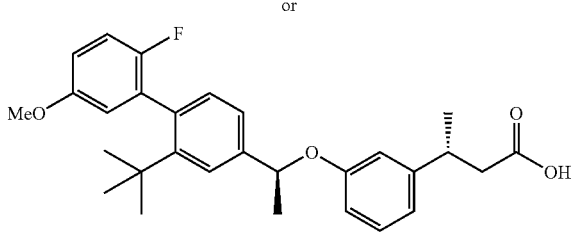 | ++ | ND |
| 64.26 | 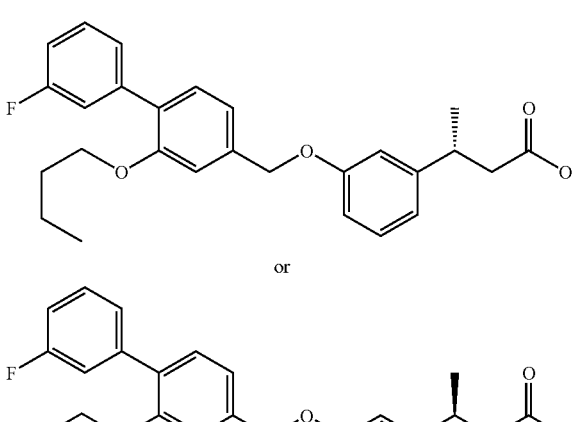 or 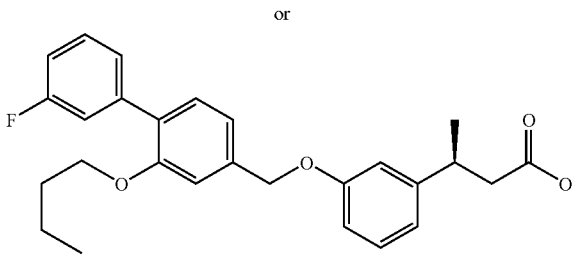 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 65.1 | 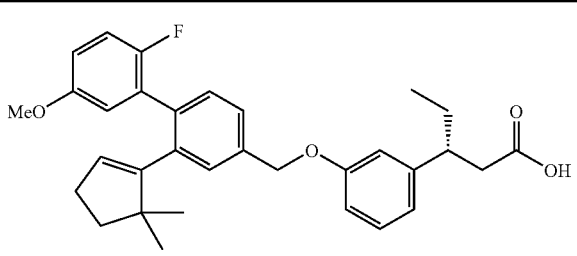 or 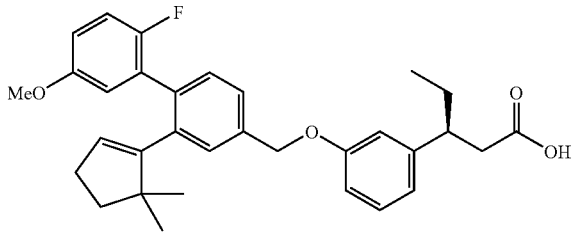 | +++ | ++++ |
| 65.2 | 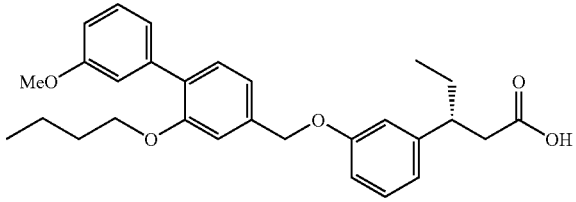 or 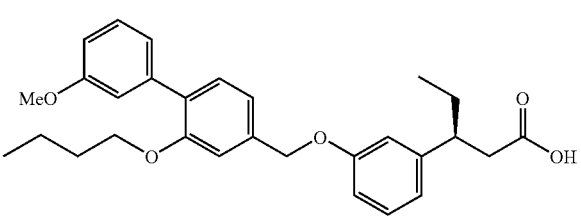 | +++ | ND |
| 66.1 | 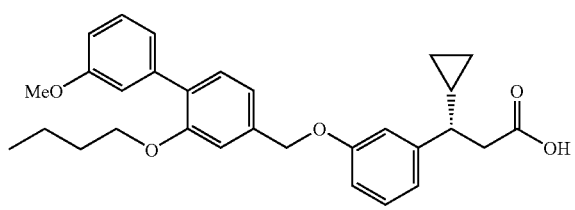 or 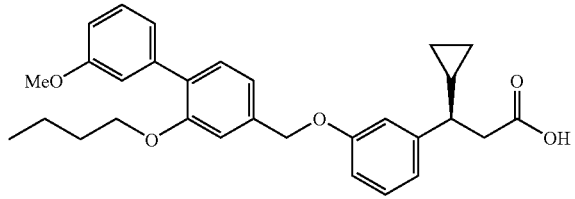 | +++ | ND |

TABLE 32-continued
Assay Data For Human GPR40
| No. | Structure | AequorinEC$_{50}$[b,c] | IP3 EC$_{50}$[c,d] |
|---|---|---|---|
| 66.2 | 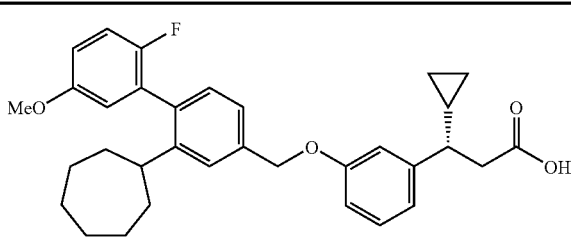 or 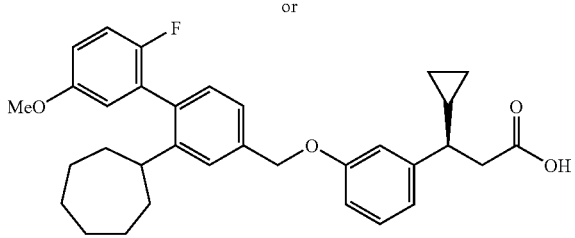 | +++ | ++++ |
| 66.3 | 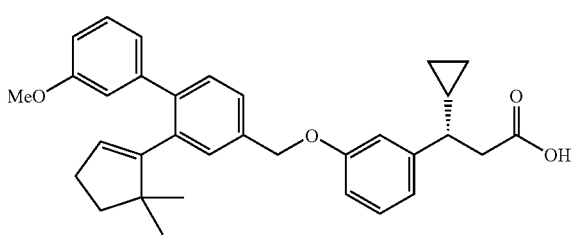 or 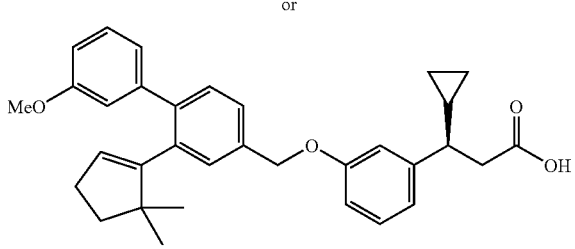 | +++/ ++++ | +++++ |
| 66.4 | 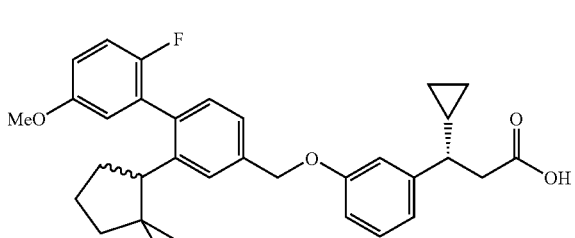 or 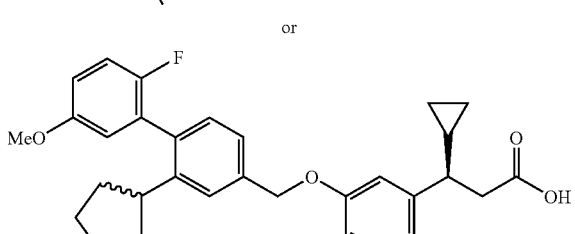 | +++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 66.5 | 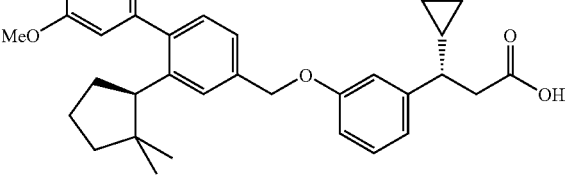 or 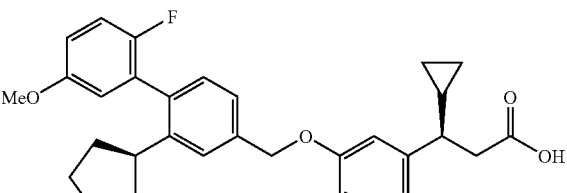 or 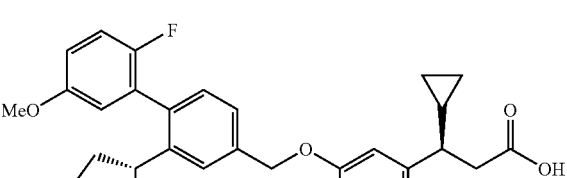 or 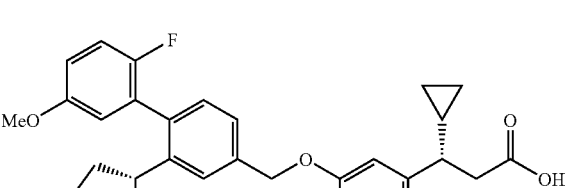 | +++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 66.6 | Diasteromer of 66.5 | ++++ | +++++ |
| 66.7 | (structure shown: four possible stereoisomers connected by "or") | +++ | ND |
| 66.8 | Diastereomer of 66.7 | ++++ | +++++ |
| 66.9 | (structure shown: two possible stereoisomers connected by "or") | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 66.10 | 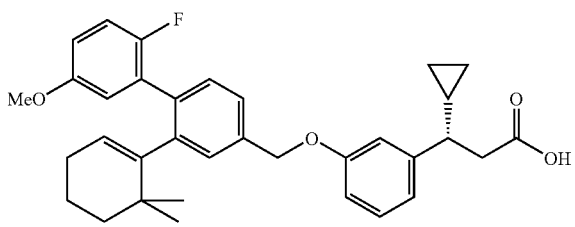<br>or<br>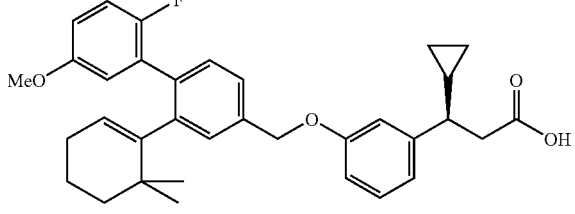 | +++ | +++++ |
| 66.11 | 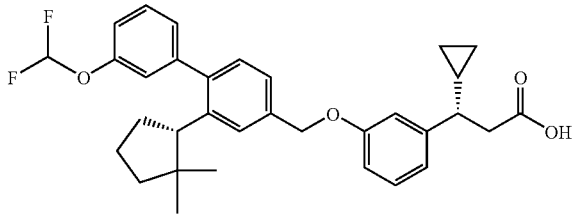<br>or<br>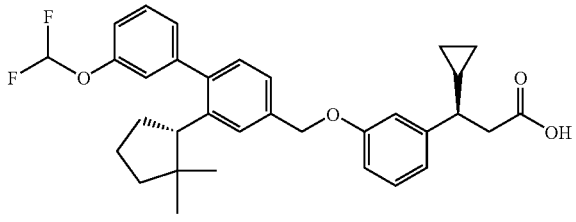<br>or<br>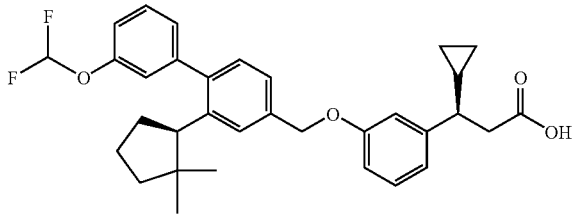<br>or<br>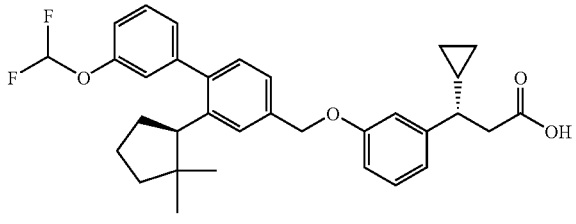 | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 66.12 | 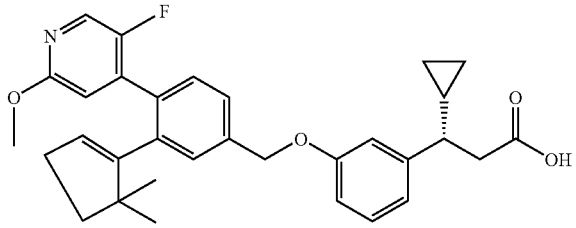<br>or<br>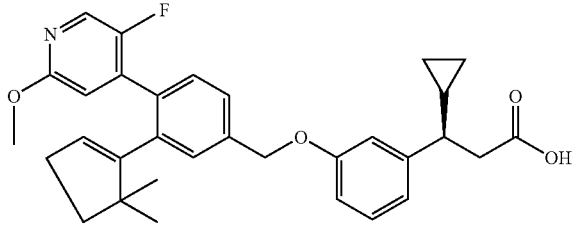 | +++ | ++++ |
| 66.13 | 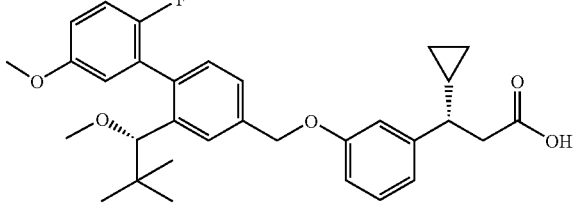<br>or<br>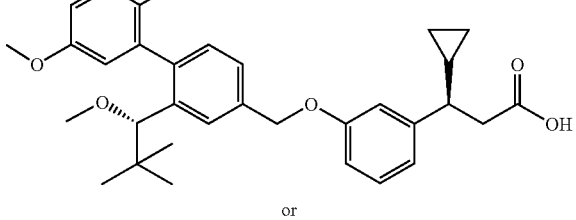<br>or<br>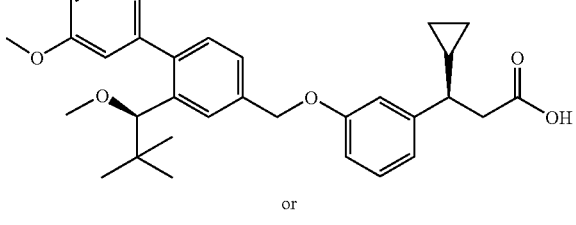<br>or<br>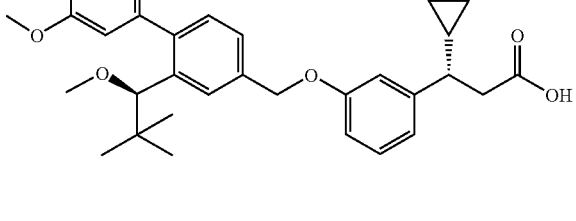 | +++ | +++++ |

TABLE 32-continued
Assay Data For Human GPR40
| No. | Structure | AequorinEC$_{50}$[b,c] | IP3 EC$_{50}$[c,d] |
|---|---|---|---|
| 66.14 | 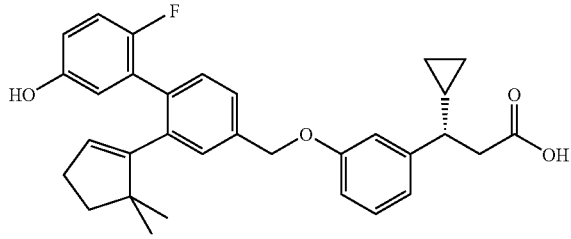<br>or<br>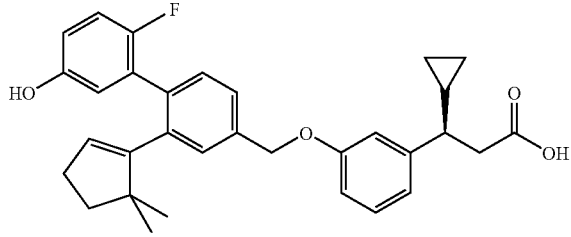 | +++ | ND |
| 66.15 | 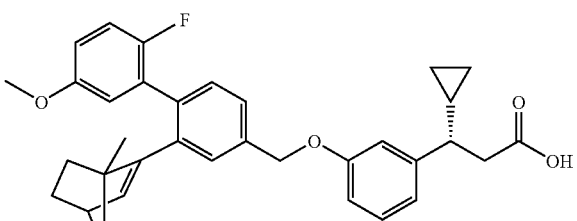<br>or<br>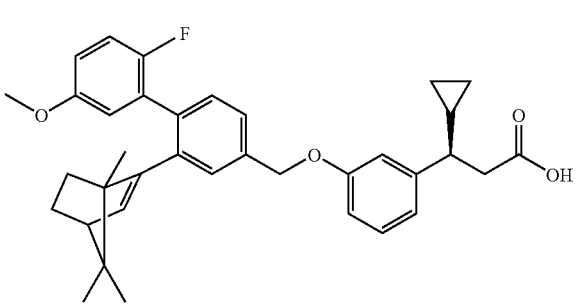 | +++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 66.16 | 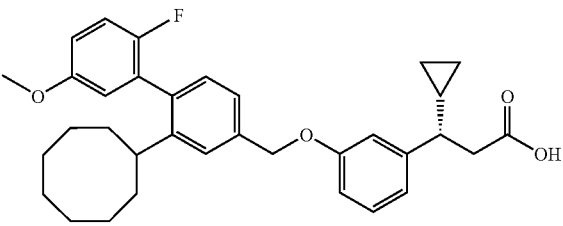 or 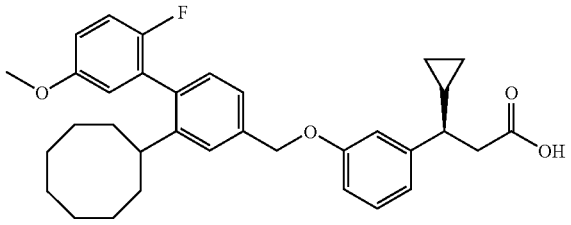 | +++ | ND |
| 66.17 | 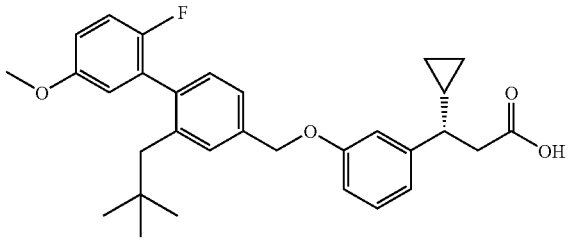 or 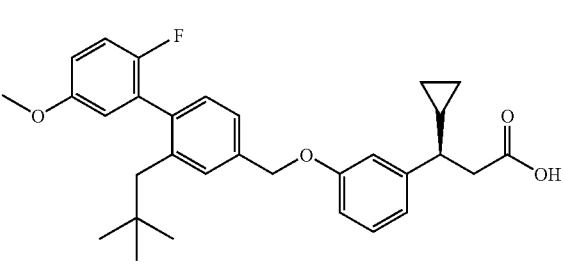 | ++++ | +++++ |

TABLE 32-continued
Assay Data For Human GPR40
| No. | Structure | AequorinEC$_{50}$[b,c] | IP3 EC$_{50}$[c,d] |
|---|---|---|---|
| 66.18 | 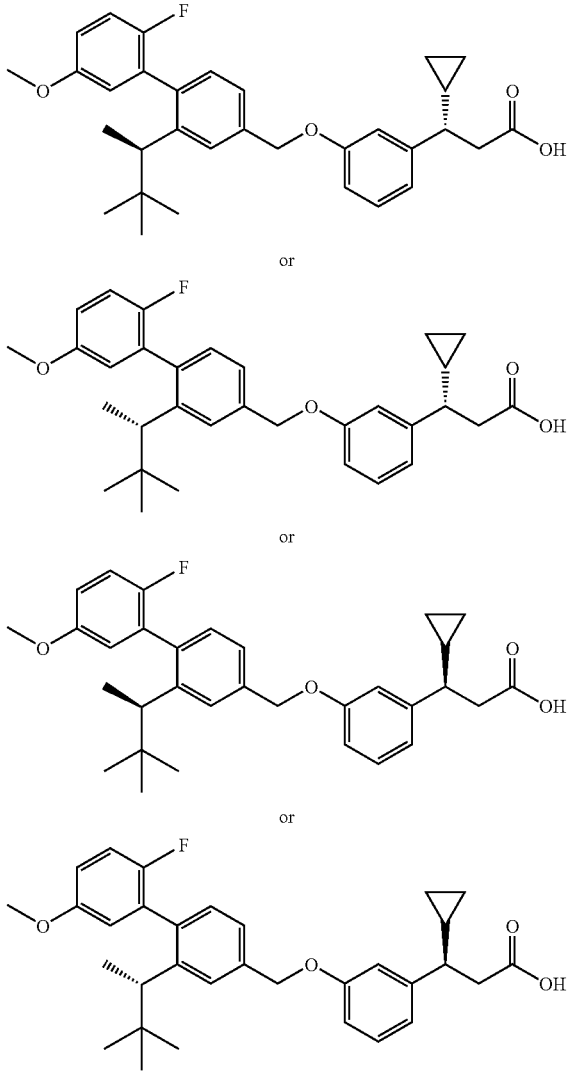 or | +++ | ND |
| 66.19 | Diastereomer of 66.18 | ++++ | +++++ |
| 66.20 | 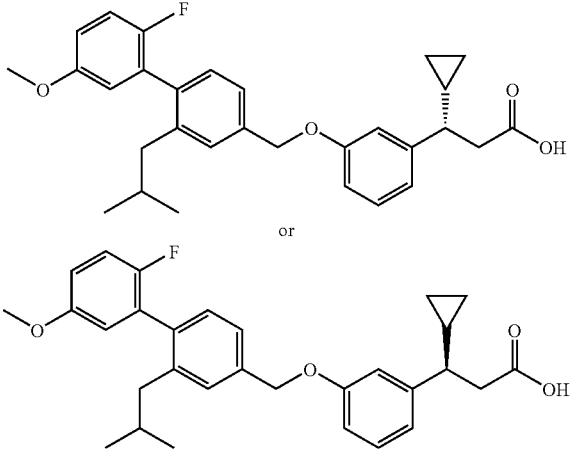 or | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 66.21 | 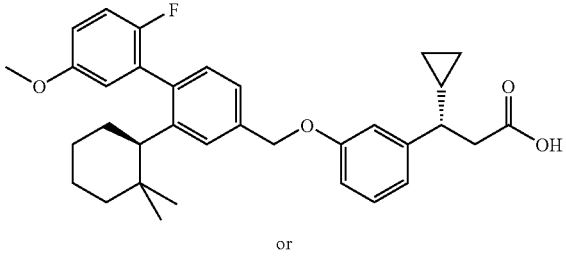<br>or<br>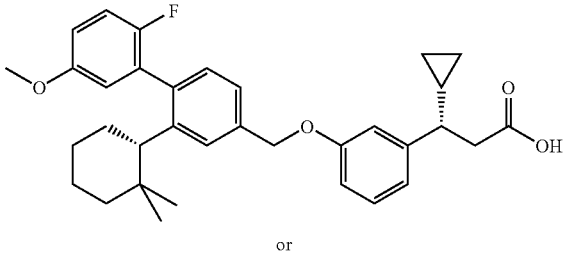<br>or<br>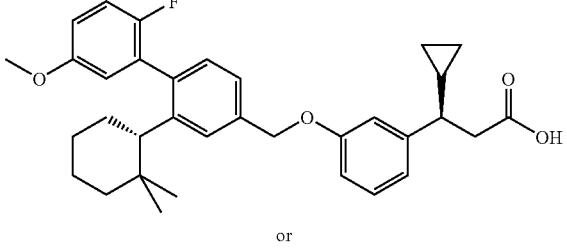<br>or<br>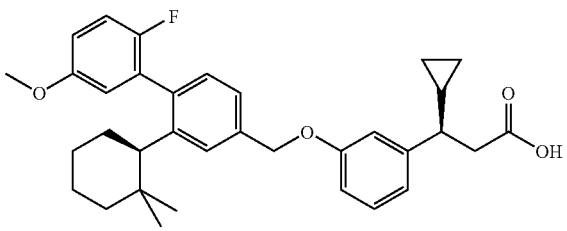 | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.22 | Diastereomer of 66.21 | ++++ | +++++ |
| 66.23 | 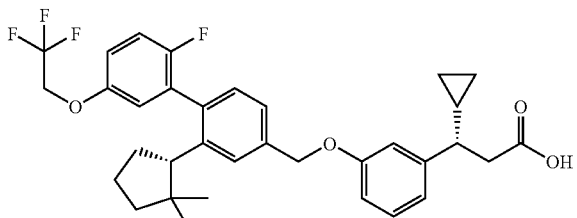<br>or<br>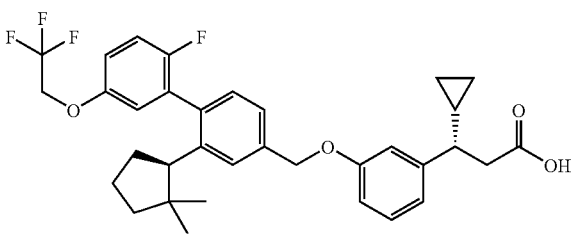<br>or<br>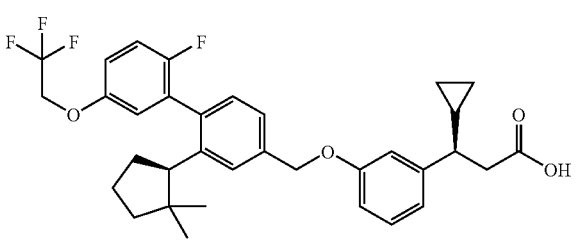<br>or<br>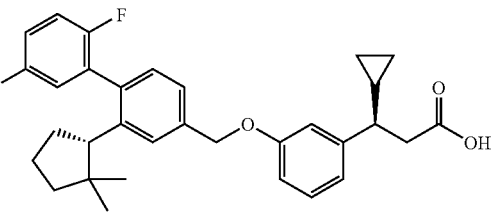 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.24 | Diastereomer of 66.13 | ++ | +++ |
| 66.25 | 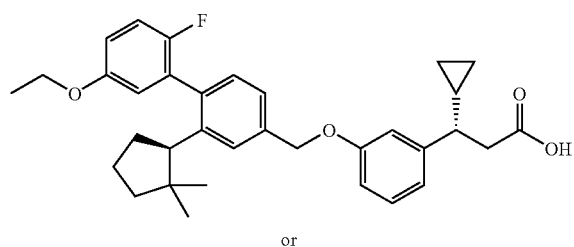 or 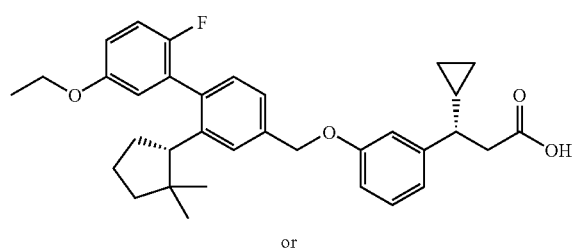 or 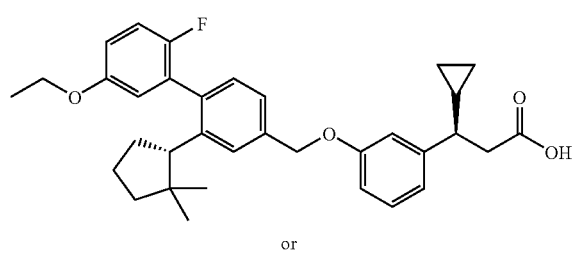 or 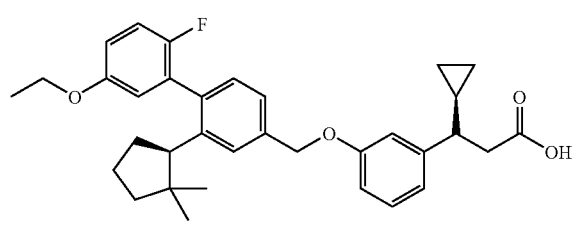 | ++ | ++ |

TABLE 32-continued
Assay Data For Human GPR40
| No. | Structure[a] | AequorinEC$_{50}$[b,c] | IP3 EC$_{50}$[c,d] |
|---|---|---|---|
| 66.26 | Diastereomer of 66.25 | +++ | ++++ |
| 66.27 | | +++ | +++++ |
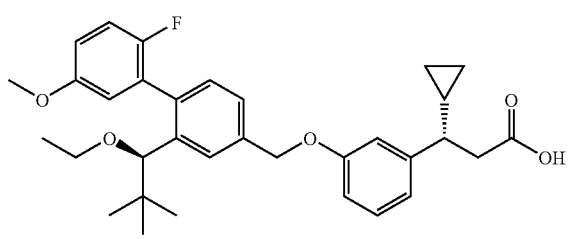
or
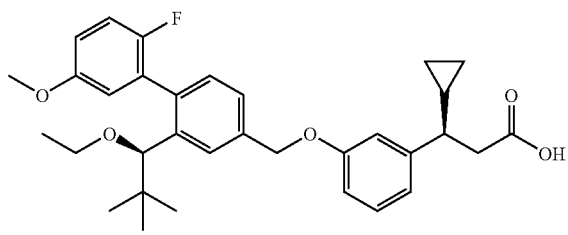
or
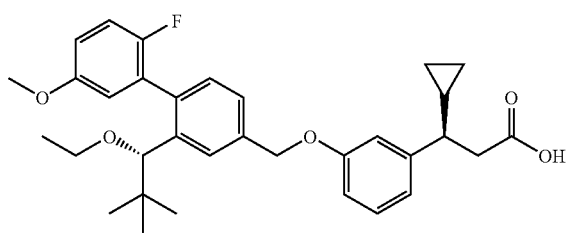
or TABLE 32-continued Assay Data For Human GPR40

| No. | Structure[a] | AequorinEC$_{50}$[b,c] | IP3 EC$_{50}$[c,d] |
|---|---|---|---|
| 66.28 | | +++ | +++++ | or or or

TABLE 32-continued
Assay Data For Human GPR40
| No. | Structure[a] | AequorinEC$_{50}$[b,c] | IP3 EC$_{50}$[c,d] |
|---|---|---|---|
| 66.29 | 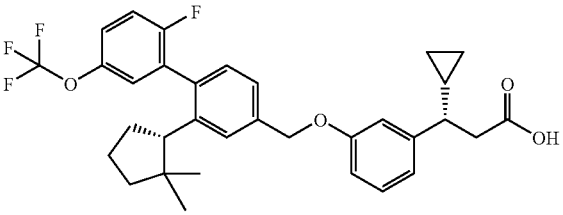 or 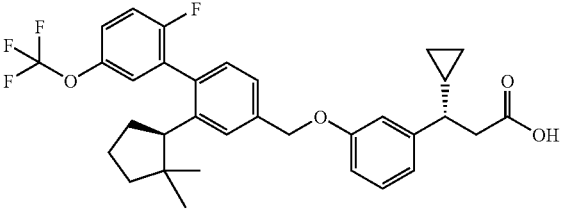 or 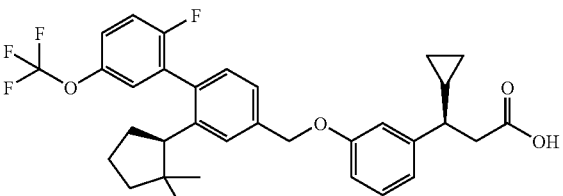 or 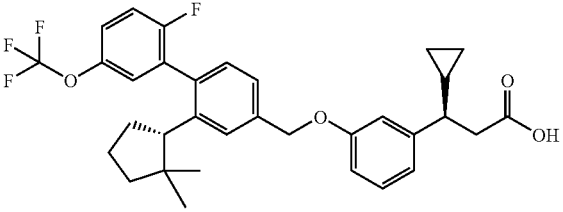 | +++ | ND |

TABLE 32-continued

Assay Data For Human GPR40

| No. | Structure | AequorinEC$_{50}$[b,c] | IP3 EC$_{50}$[c,d] |
|---|---|---|---|
| 66.30 | | +++ | ND | or or or

TABLE 32-continued
Assay Data For Human GPR40
| No. | Structure | AequorinEC$_{50}$$^{b,c}$ | IP3 EC$_{50}$$^{c,d}$ |
|---|---|---|---|
| 66.31 | Diastereomer of 66.30 | +++ | ++++ |
| 66.32 | 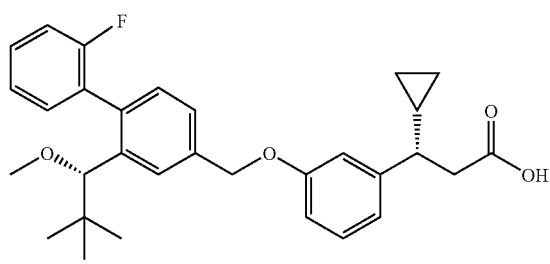<br>or<br>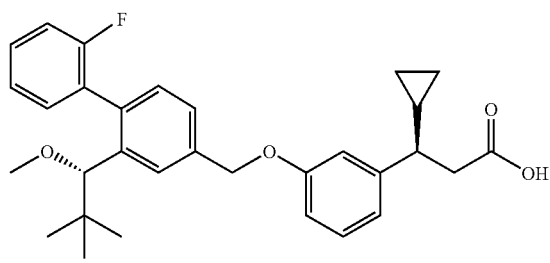<br>or<br>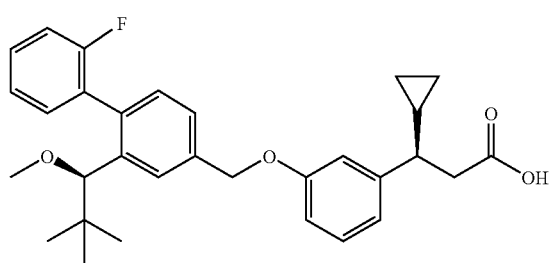 | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.33 | Diastereomer of 66.32 | +++ | ++++ |
| 66.34 | 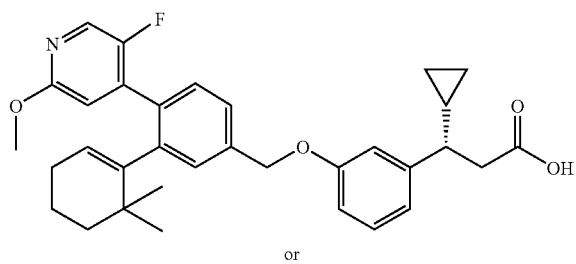or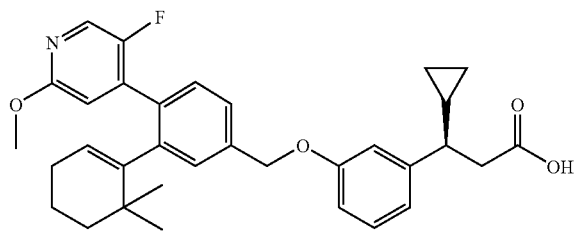 | ++++ | ++++ |
| 66.35 | 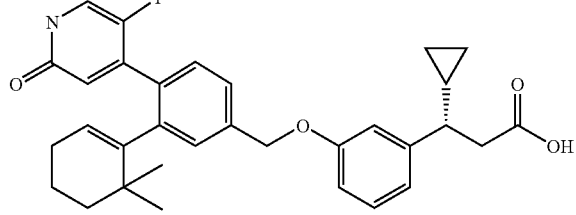or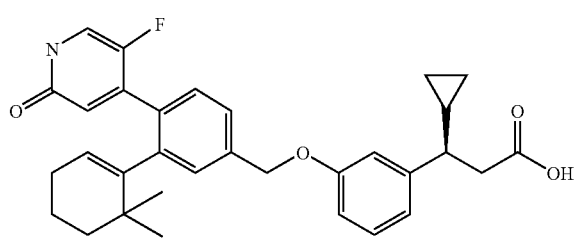 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.36 | 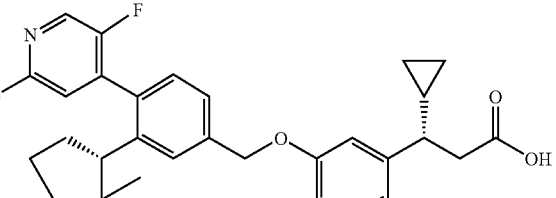 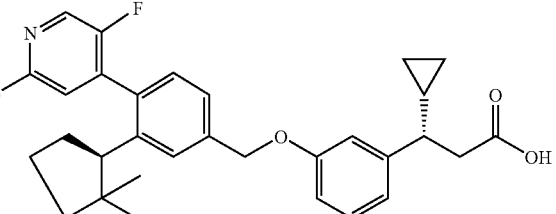 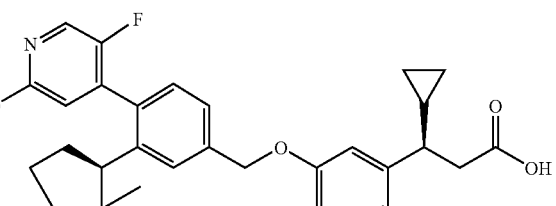 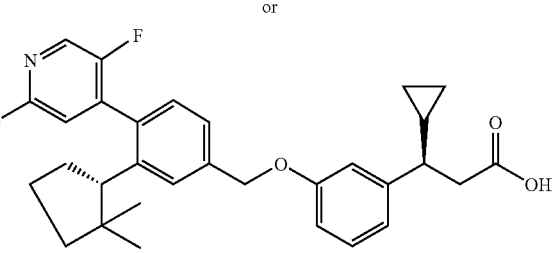 | ++++ | +++++ |
| 66.37 | Diastereomer of 66.36 | +++ | ++++ |
| 66.38 | 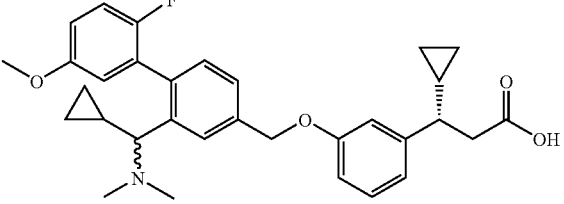 or 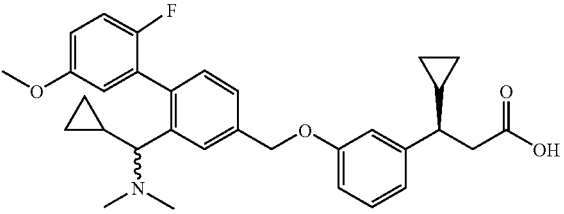 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.39 | No compound associated with this number | | |
| 66.40 | 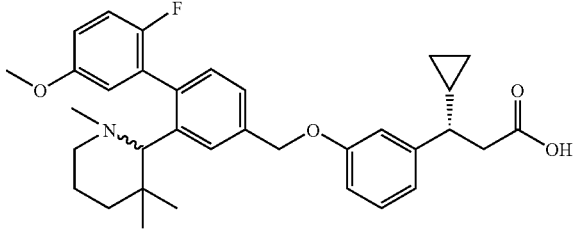 or 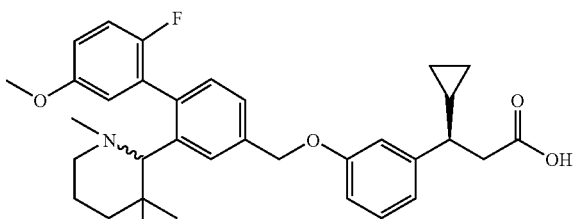 | +++ | ++++ |
| 66.41 | 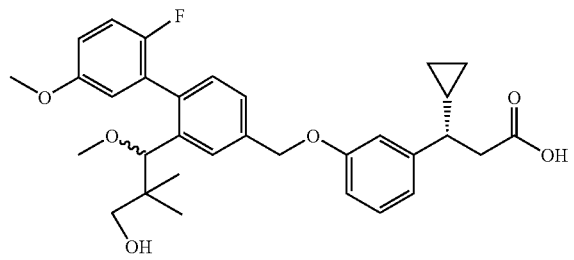 or 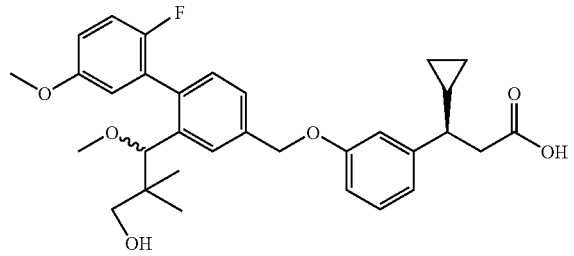 | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.42 | 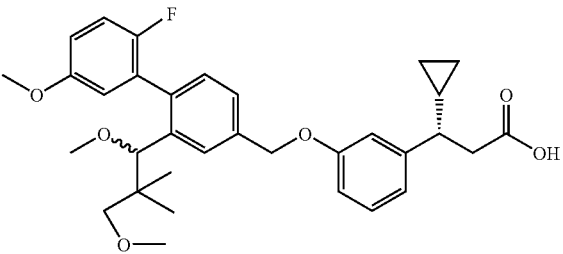 or 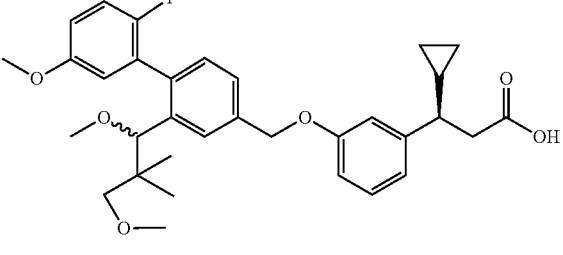 | +++ | ++++ |
| 66.43 | 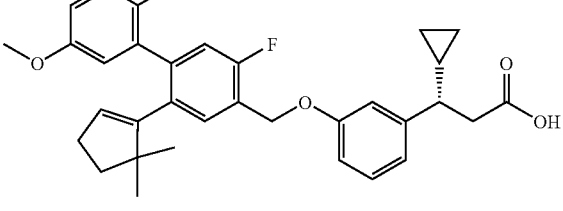 or 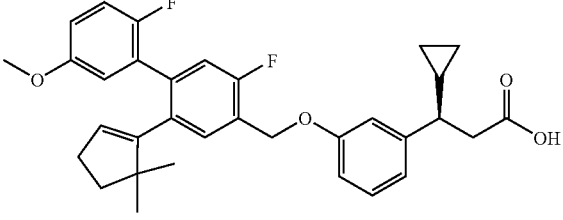 | +++ | +++++ |

TABLE 32-continued

Assay Data For Human GPR40

| No. | Structure[a] | AequorinEC$_{50}$[b,c] | IP3 EC$_{50}$[c,d] |
|---|---|---|---|
| 66.44 | (four stereoisomer structures shown, connected by "or") | ++++ | +++++ |
| 66.45 | Diastereomer of 66.44 | +++ | ND |
| 66.46 | (two structures shown, connected by "or") | ++ | ND |

931
TABLE 32-continued
Assay Data For Human GPR40
| No. | Structure | AequorinEC$_{50}$[b,c] | IP3 EC$_{50}$[c,d] |
|---|---|---|---|
| 66.47 | Diastereomer of 66.11 | +++ | ND |
| 66.48 | 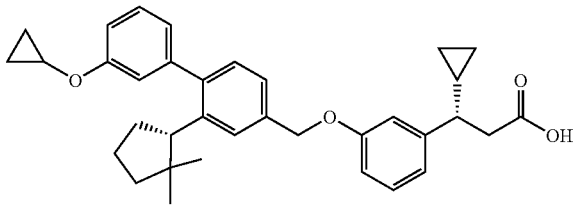 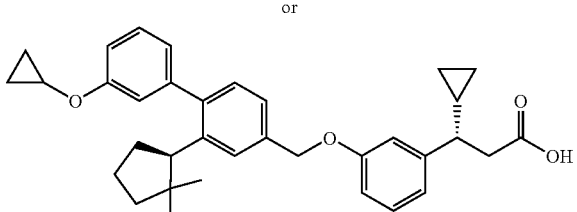 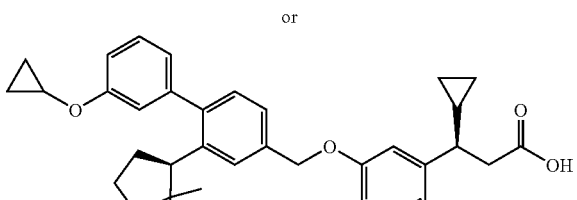 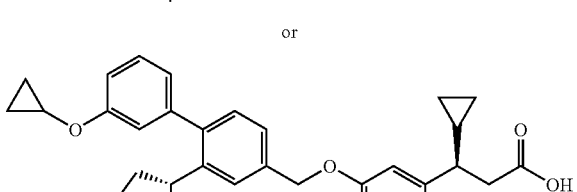 | +++ | ND |
| 66.49 | 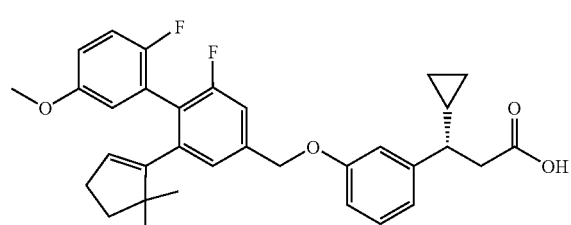 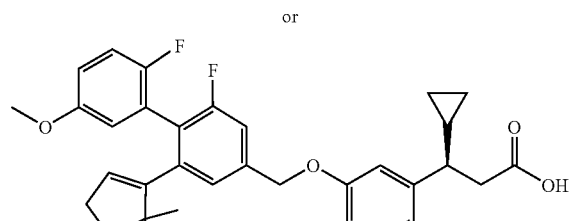 | +++ | ++++ |

TABLE 32-continued

Assay Data For Human GPR40

| No. | Structure[a] | AequorinEC$_{50}$[b,c] | IP3 EC$_{50}$[c,d] |
|---|---|---|---|
| 66.50 | (structure) or (structure) | +++ | +++ |
| 66.51 | (structure) or (structure) or (structure) or (structure) | +++ | ++++ |

TABLE 32-continued

Assay Data For Human GPR40

| No. | Structure[a] | AequorinEC$_{50}$[b,c] | IP3 EC$_{50}$[c,d] |
|---|---|---|---|
| 66.52 | Diastereomer of 66.51 | ++ | ND |
| 66.53 | *(structure)* | ++ | ND |
| 66.54 | *(structure)* | +++ | ++++ |

TABLE 32-continued

Assay Data For Human GPR40

| No. | Structure[a] | AequorinEC$_{50}$[b,c] | IP3 EC$_{50}$[c,d] |
|---|---|---|---|
| 66.55 | Diastereomer of 66.54 | ++ | ND |
| 66.56 | | +++ | ++++ | or or or or or

TABLE 32-continued

Assay Data For Human GPR40

| No. | Structure[a] | AequorinEC$_{50}$[b,c] | IP3 EC$_{50}$[c,d] |
|---|---|---|---|
| 66.57 | Diastereomer of 66.56 | +++ | +++++ |
| 66.58 | Diastereomer of 66.56 and 66.57, | +++ | ND |
| 66.59 | Diastereomer of 66.56, 66.57, and 66.58 | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.60 | 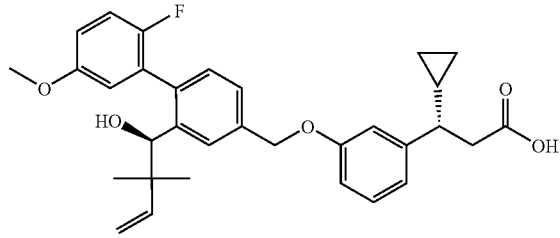 or 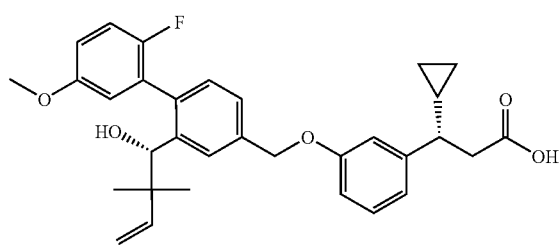 or 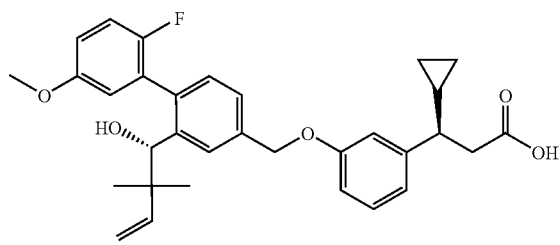 or 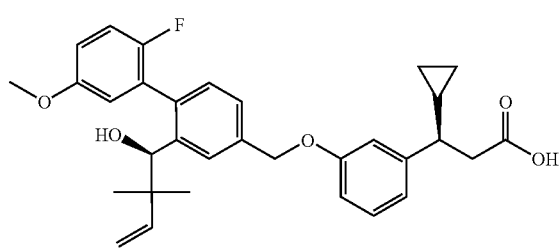 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.61 | Diastereomer of 66.60 | +++ | ND |
| 66.62 | 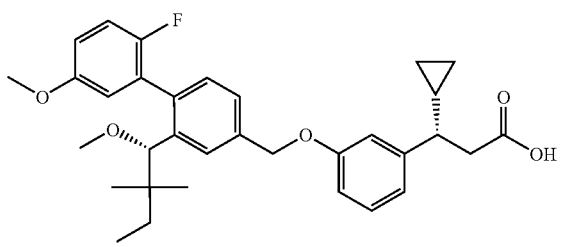<br>or<br>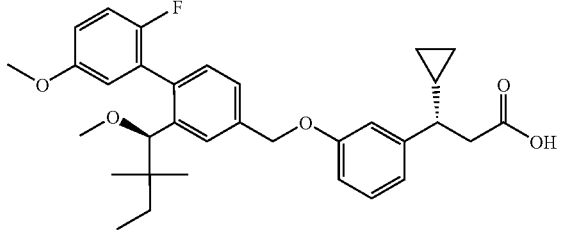<br>or<br>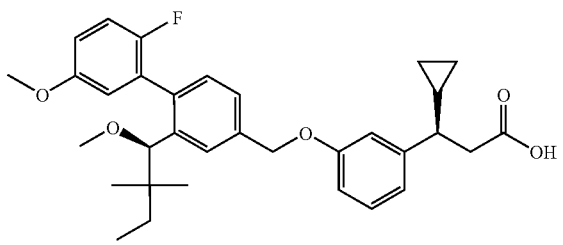<br>or<br>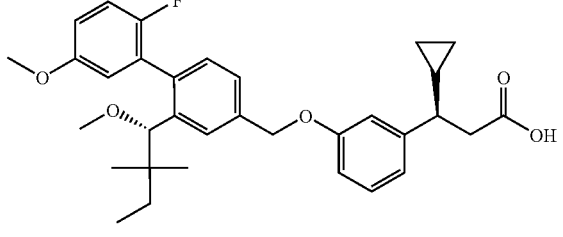 | ++++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 66.63 | 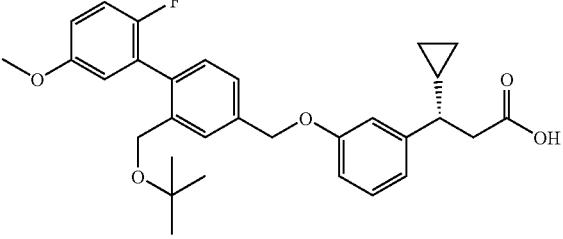 or 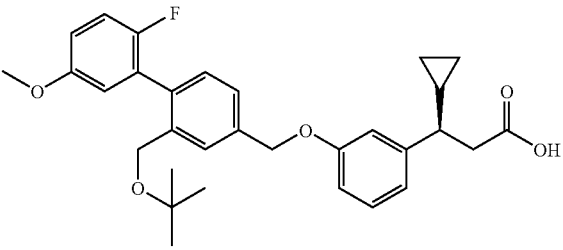 | ++ | ++ |
| 66.64 | 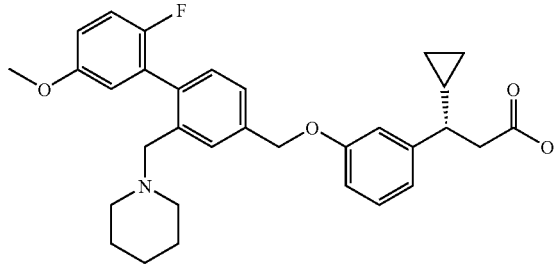 or 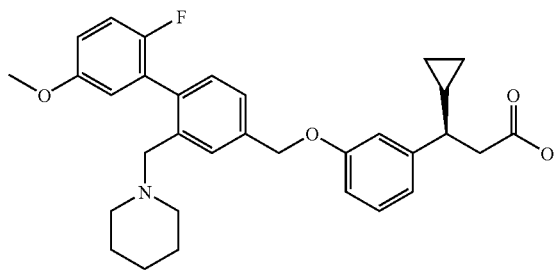 | ++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 66.65 | | ++ | ND |
| 66.66 | | +++ | ++++ |
| 66.67 | | +++ | ++++ |

TABLE 32-continued
Assay Data For Human GPR40
| No. | Structure | AequorinEC$_{50}$[b,c] | IP3 EC$_{50}$[c,d] |
|---|---|---|---|
| 66.68 | 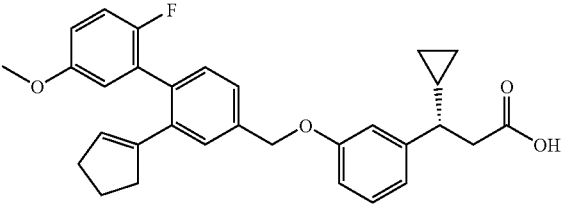 or 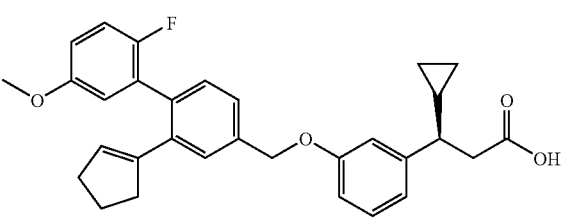 | +++ | ++++ |
| 66.69 | 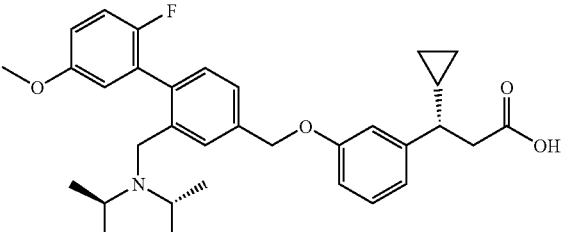 and 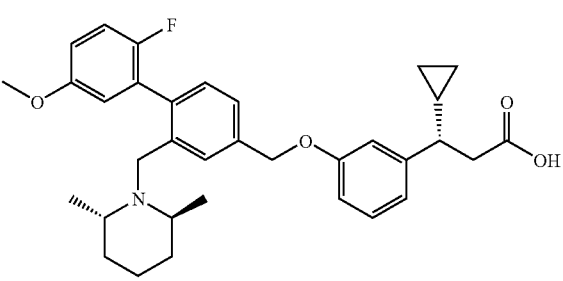 or 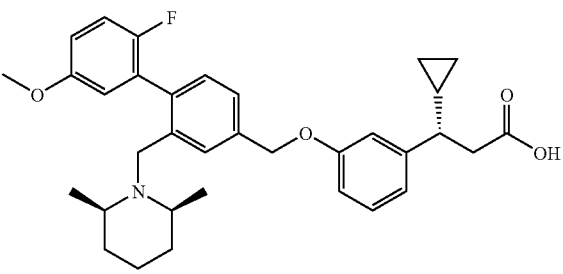 or  | +++ | ++++ |

TABLE 32-continued

Assay Data For Human GPR40

| No. | Structure[a] | AequorinEC$_{50}$[b,c] | IP3 EC$_{50}$[c,d] |
|---|---|---|---|
| | (structure) and (structure) or (structure) | | |
| 66.70 | (structure) and (structure) or | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
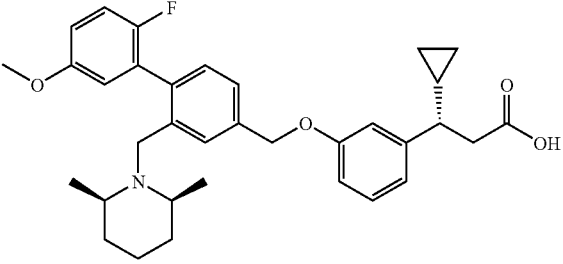
or
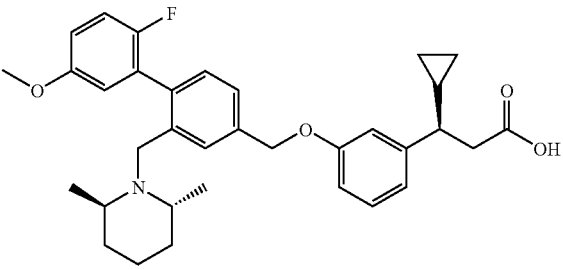
and
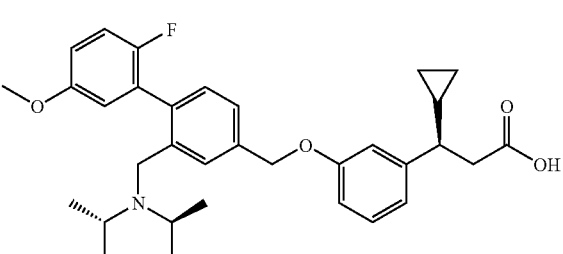
or
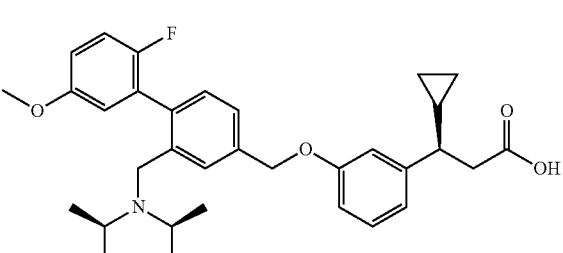
but not the same one as 66.69

TABLE 32-continued
Assay Data For Human GPR40
| No. | Structure | AequorinEC$_{50}$[b,c] | IP3 EC$_{50}$[c,d] |
|---|---|---|---|
| 66.71 | 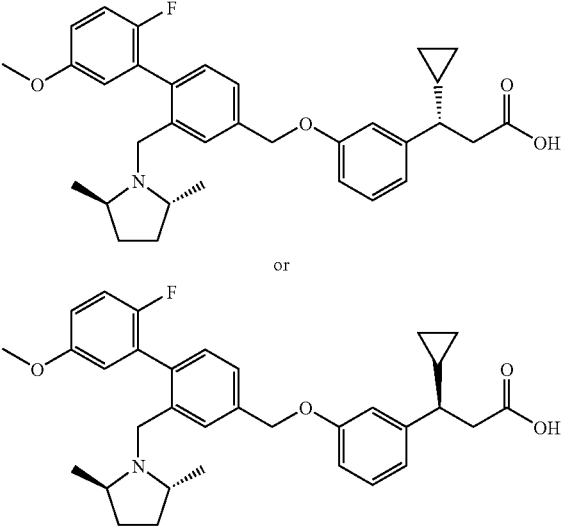 | +++ | +++ |
| 66.72 | 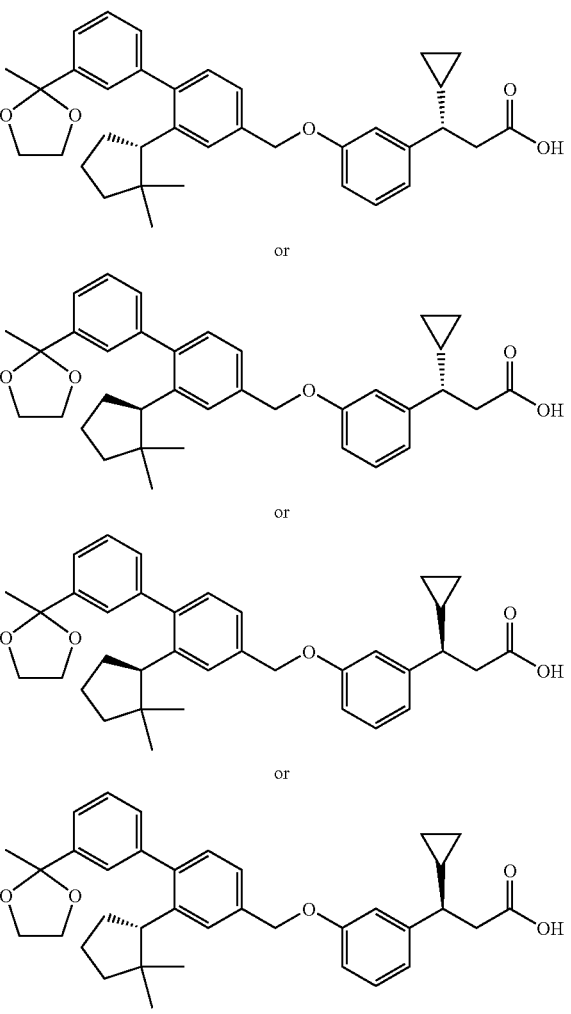 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.73 | 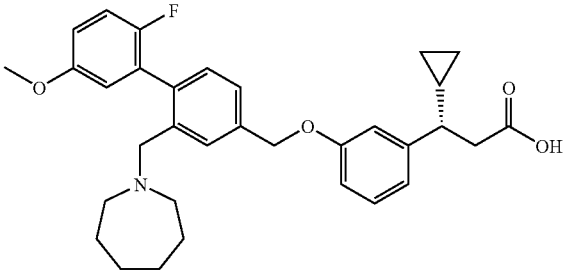<br>or<br>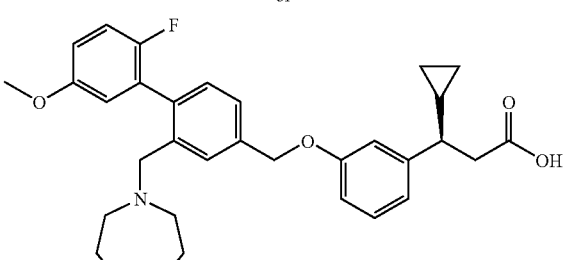 | ++ | ND |
| 66.74 | 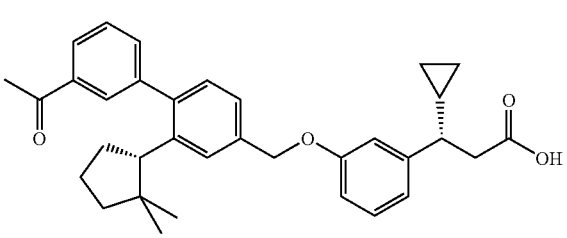<br>or<br>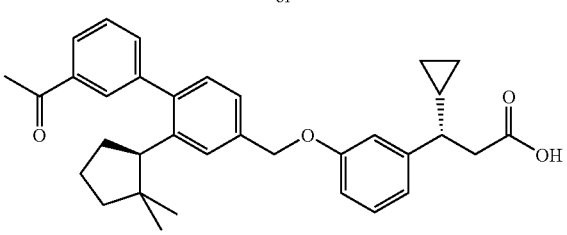<br>or<br>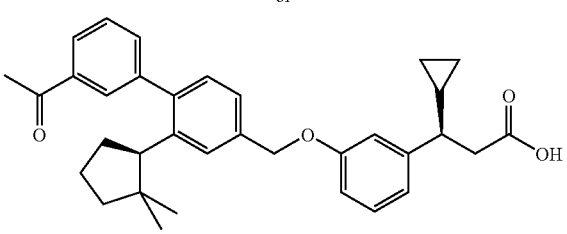<br>or<br>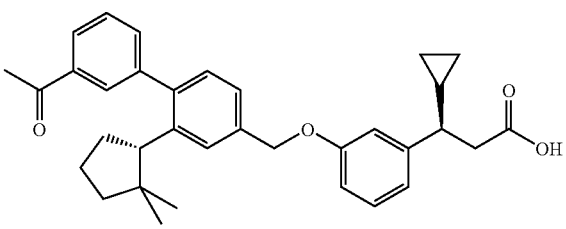 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.75 | 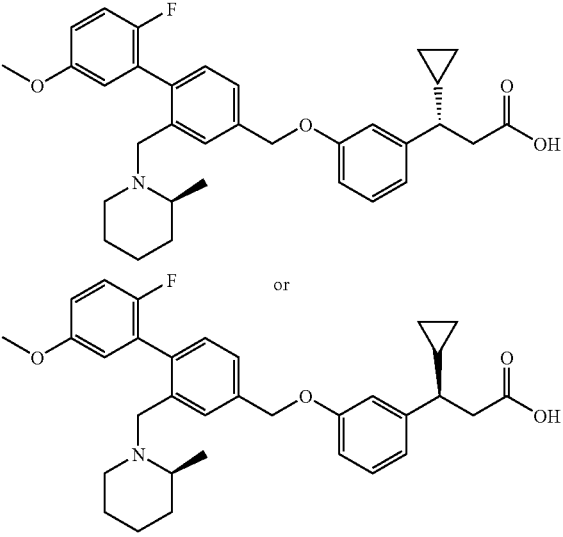 | ++ | ND |
| 66.76 | 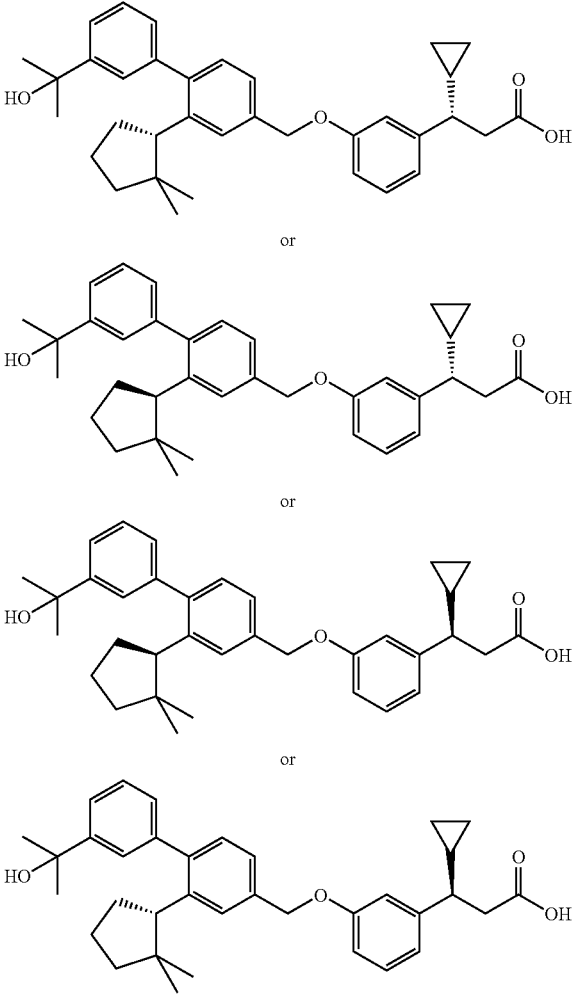 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 66.77 | 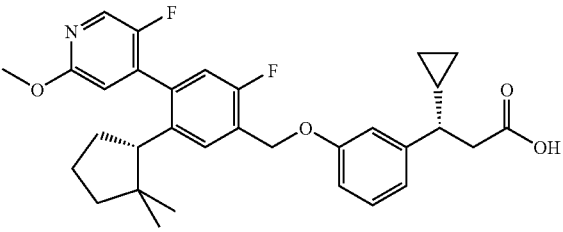 or 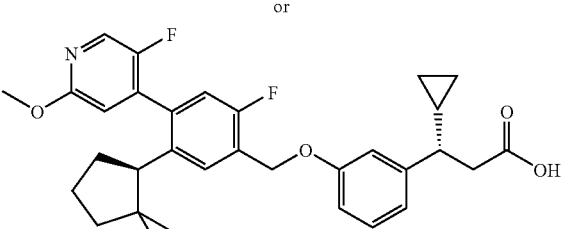 or 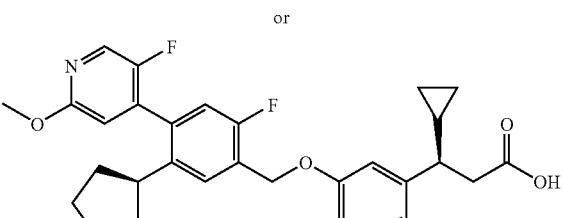 or 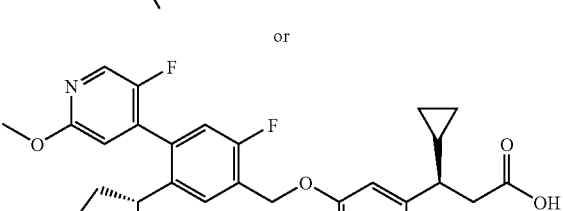 | ++++ | +++++ |
| 67.1 | 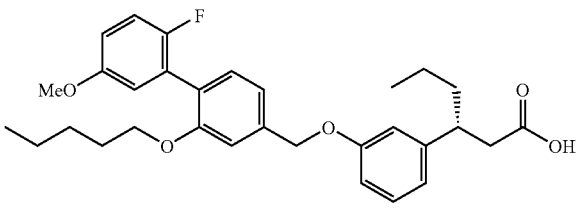 or 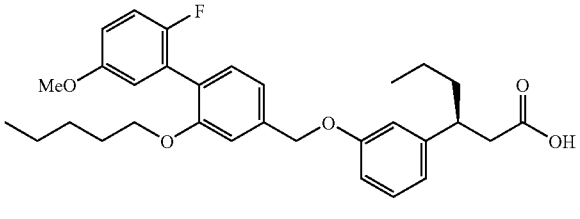 | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 67.2 | 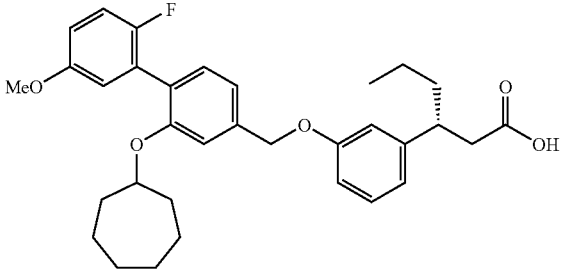 or 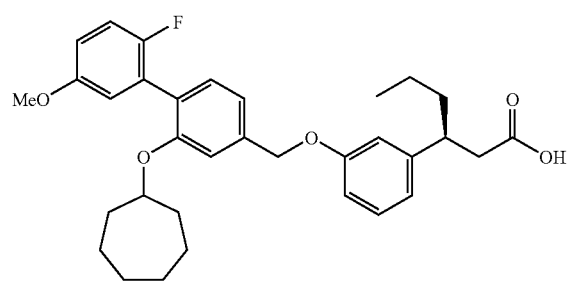 | +++ | +++ |
| 67.3 | 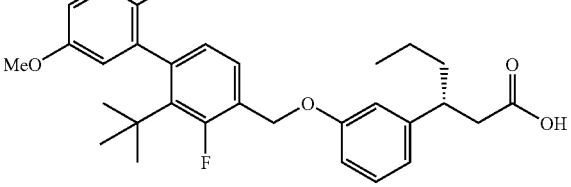 or 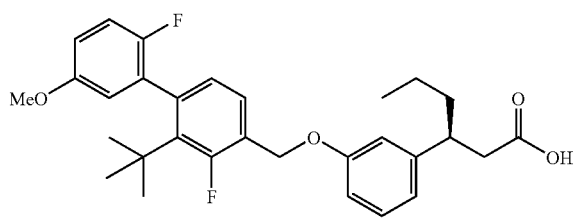 | +++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 67.4 | | +++ | ND |
| 67.5 | | +++ | ND |
| 67.6 | | +++ | ++++ |

TABLE 32-continued
Assay Data For Human GPR40
| No. | Structure | AequorinEC$_{50}$[b,c] | IP3 EC$_{50}$[c,d] |
|---|---|---|---|
| 67.7 | 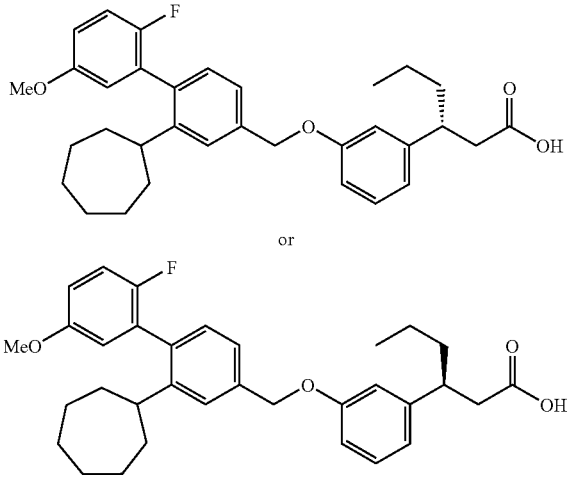 or 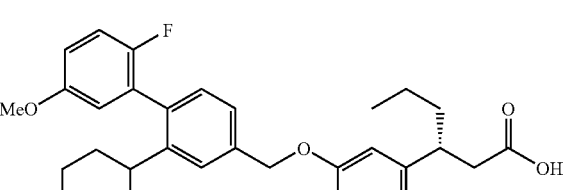 | +++ | ++++ |
| 67.8 | 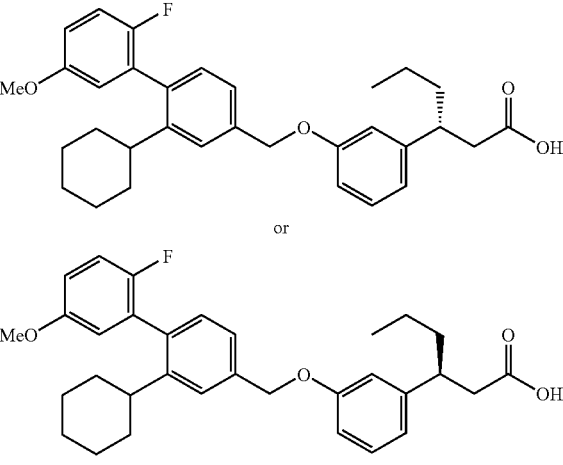 or 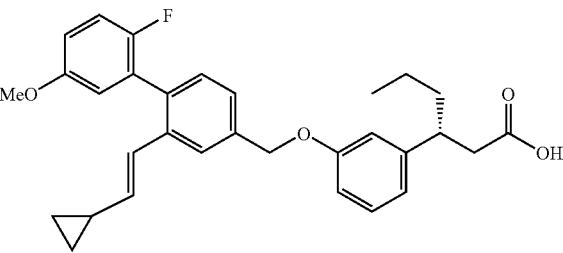 | +++ | ++++ |
| 67.9 | 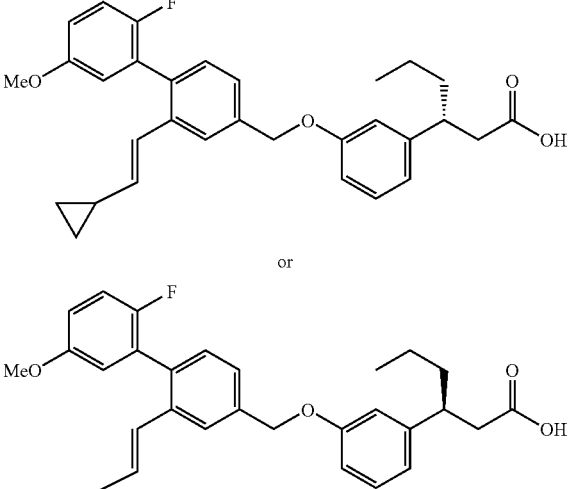 or  | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 67.10 | 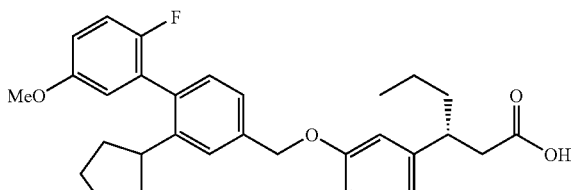 or 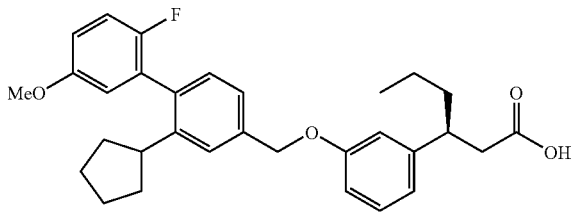 | +++ | ND |
| 67.11 | 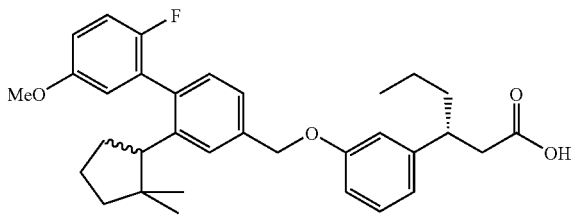 or 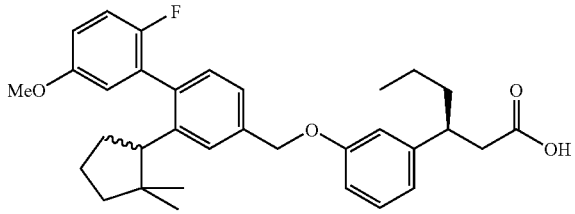 | +++ | ++++ |
| 67.12 | 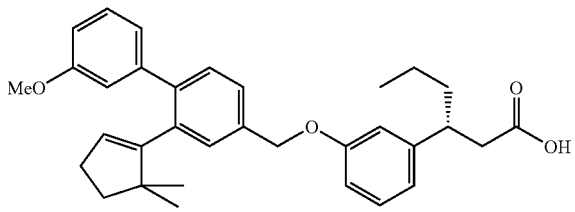 or 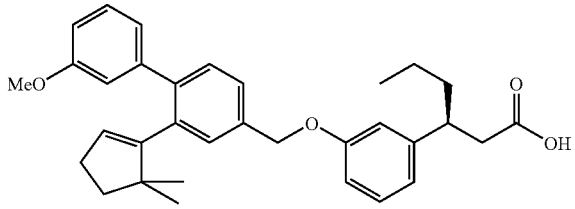 | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 67.13 | 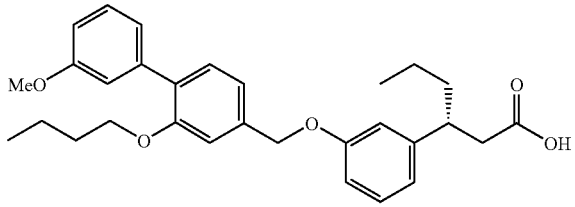 or 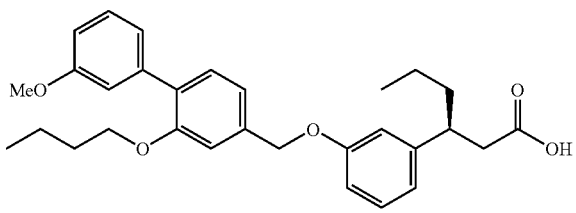 | +++ | ND |
| 67.14 | 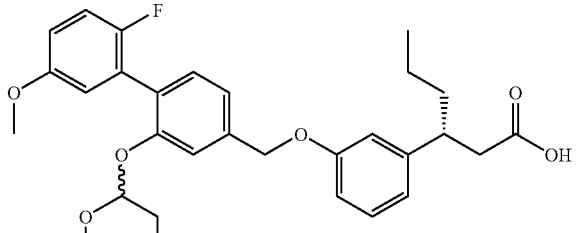 or 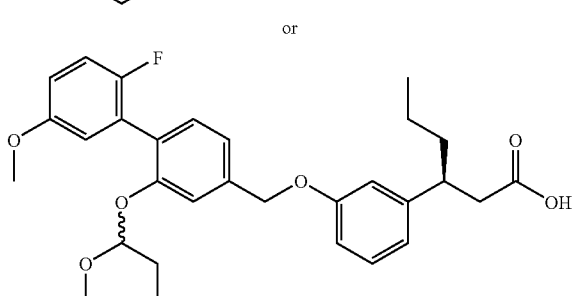 | +++ | ND |
| 67.15 | 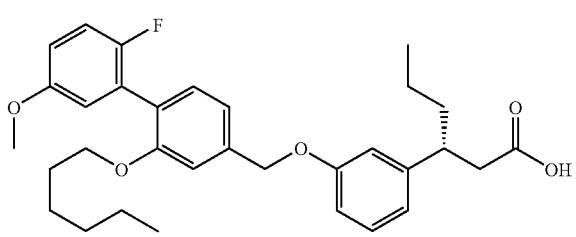 or 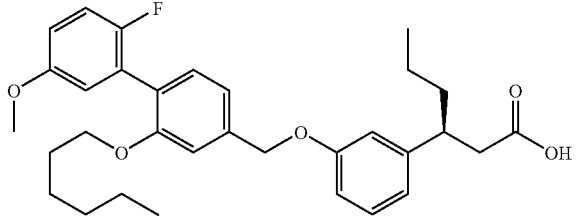 | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 67.16 | 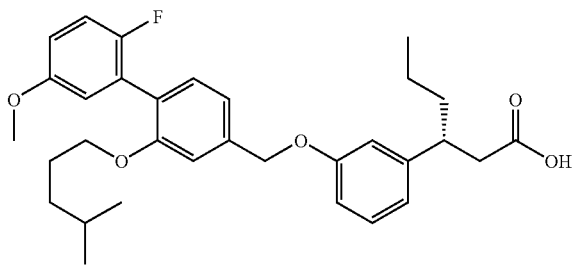 or 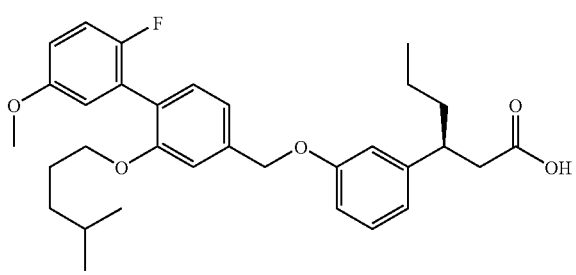 | +++ | ND |
| 67.17 | 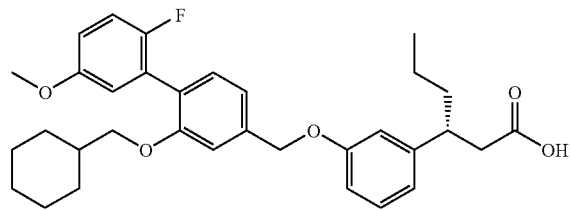 or 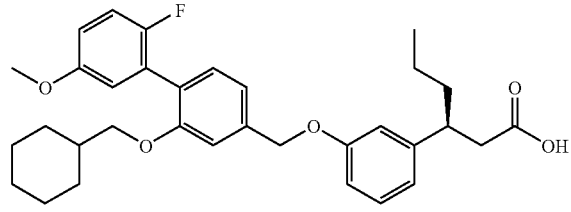 | +++ | ND |
| 67.18 | 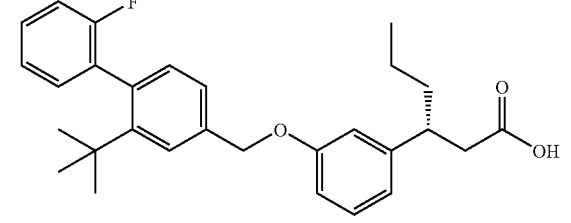 or 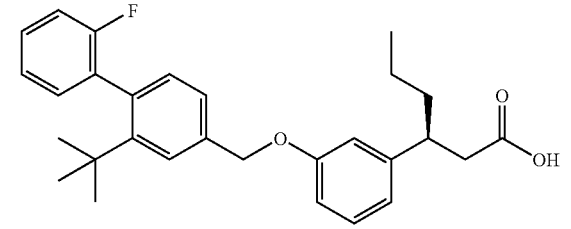 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 67.19 | 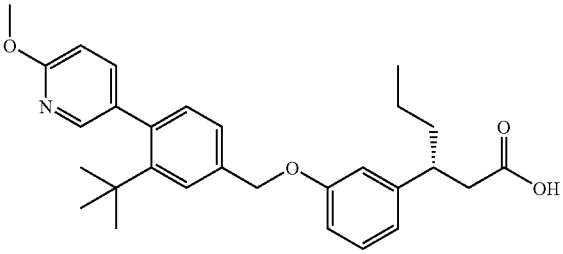 or 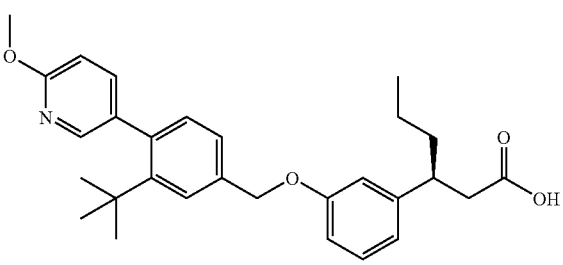 | ++ | ND |
| 67.20 | 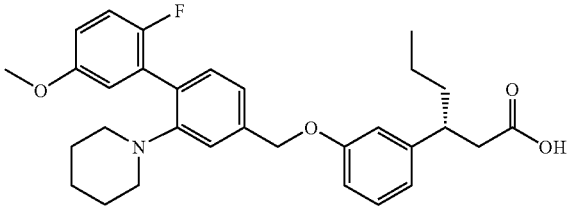 or 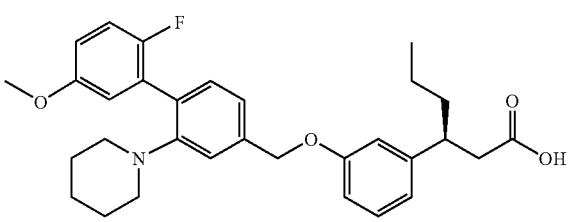 | +++ | ++++ |
| 67.21 | 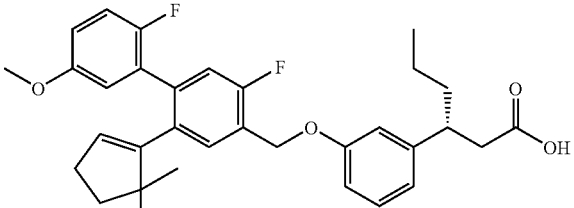 or 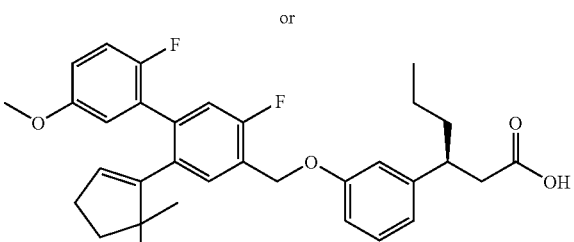 | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 67.22 | 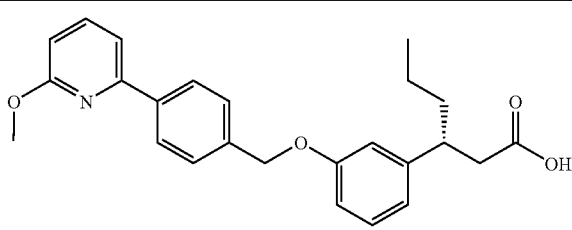 or 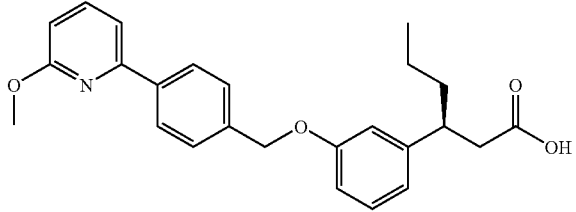 | ++ | ND |
| 67.23 | 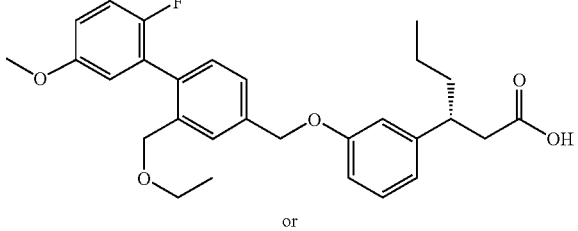 or 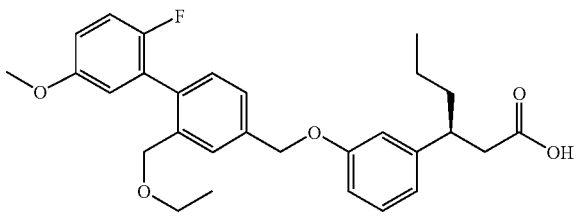 | ++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 67.24 | | +++ | ++++ | or or or

TABLE 32-continued
Assay Data For Human GPR40
| No. | Structure[a] | AequorinEC$_{50}$[b,c] | IP3 EC$_{50}$[c,d] |
|---|---|---|---|
| 67.25 | 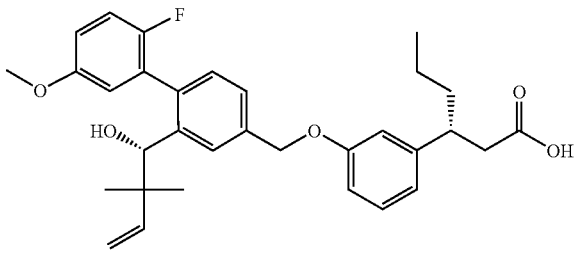 or 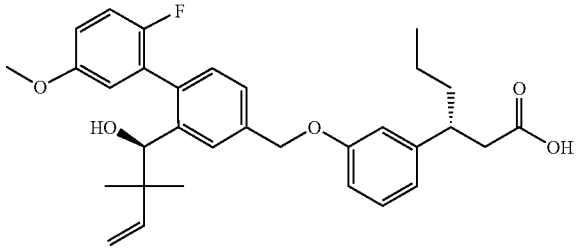 or 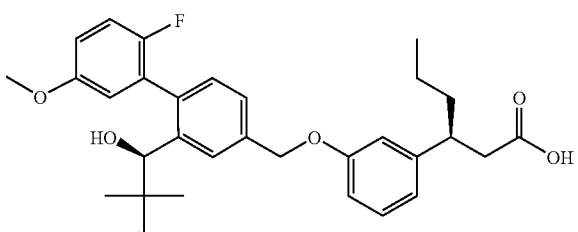 or 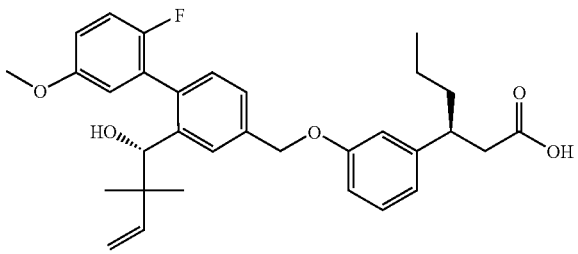 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 67.26 | 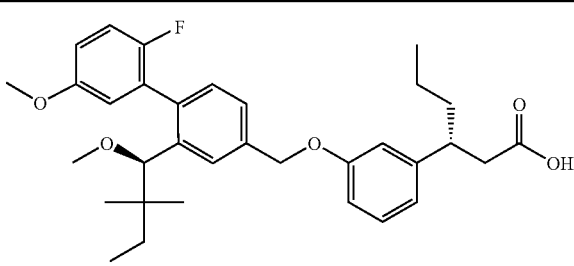<br>or<br>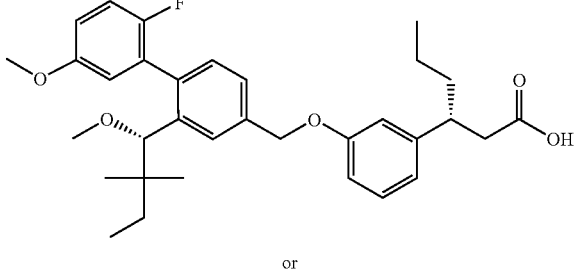<br>or<br>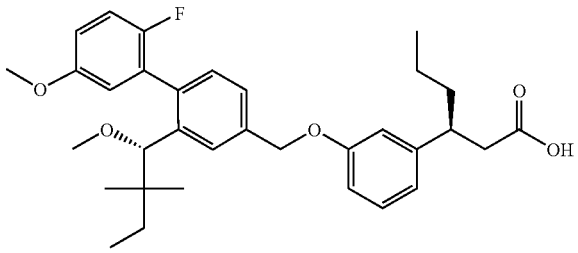<br>or<br>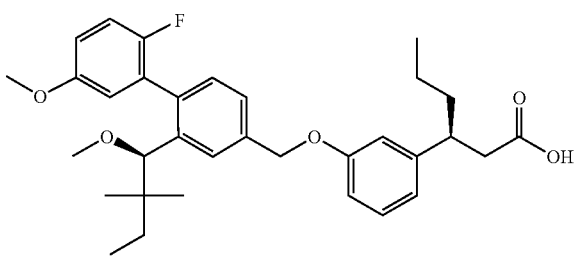 | ++ | ND |

TABLE 32-continued

Assay Data For Human GPR40

| No. | Structure$^a$ | AequorinEC$_{50}$$^{b,c}$ | IP3 EC$_{50}$$^{c,d}$ |
|---|---|---|---|
| 67.27 | | ++ | ND |
| 67.28 | | ++ | ND |
| 68.1 | | +++ | ND |

TABLE 32-continued
Assay Data For Human GPR40
| No. | Structure | AequorinEC$_{50}$$^{b,c}$ | IP3 EC$_{50}$$^{c,d}$ |
|---|---|---|---|
| 68.2 | 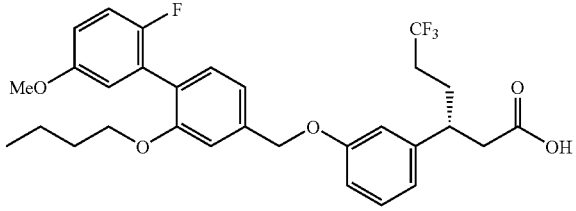 or 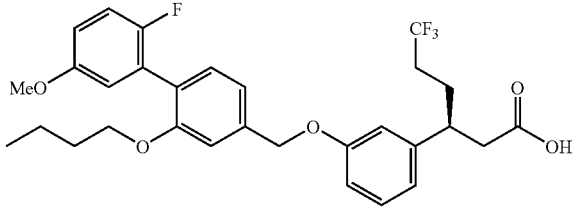 | ++ | ND |
| 69.1 | 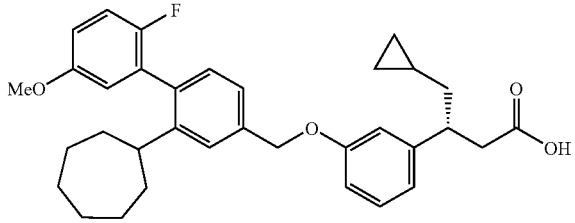 or 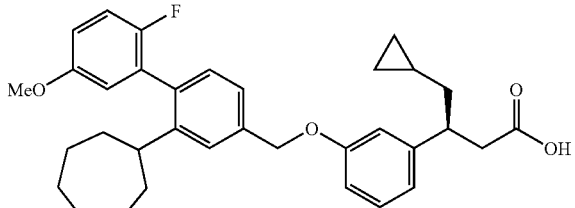 | +++ | +++++ |
| 69.2 | 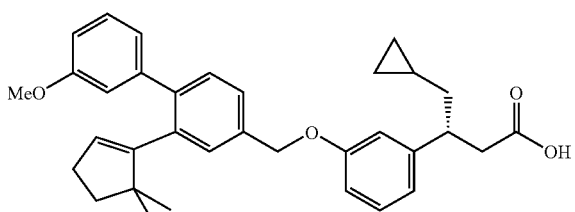 or 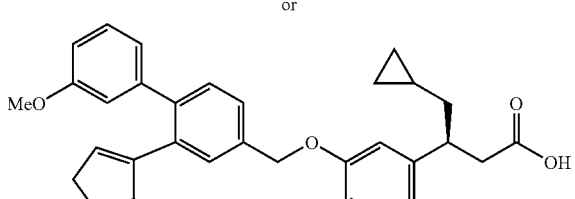 | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 69.3 | 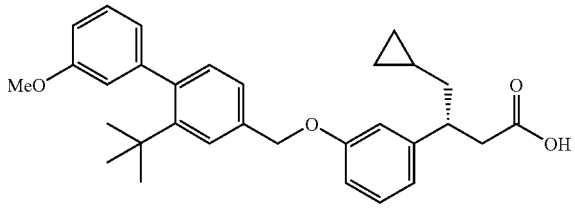 or 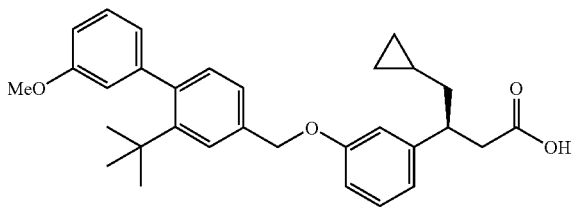 | +++ | ++++ |
| 69.4 | 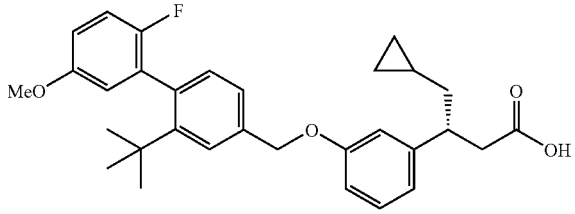 or 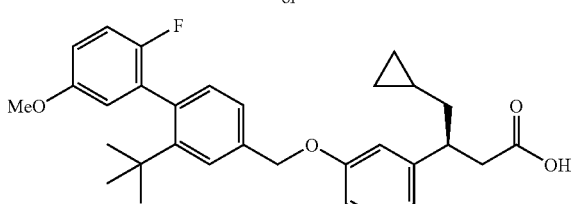 | +++ | ++++ |
| 69.5 | 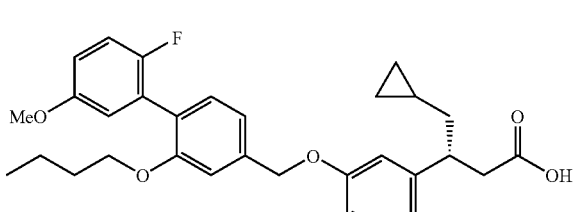 or 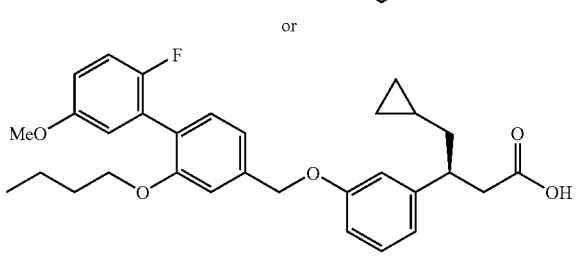 | +++ | ND |

TABLE 32-continued
Assay Data For Human GPR40
| No. | Structure | AequorinEC$_{50}$[b,c] | IP3 EC$_{50}$[c,d] |
|---|---|---|---|
| 69.6 | 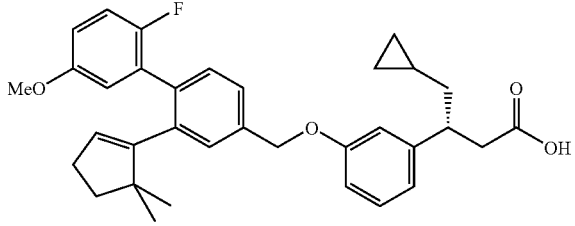 or 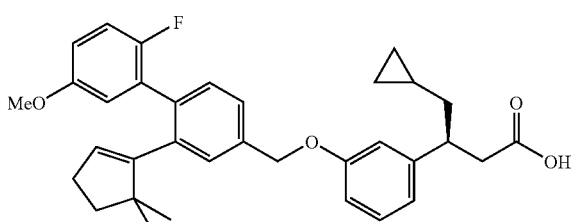 | +++ | ++++ |
| 69.7 | 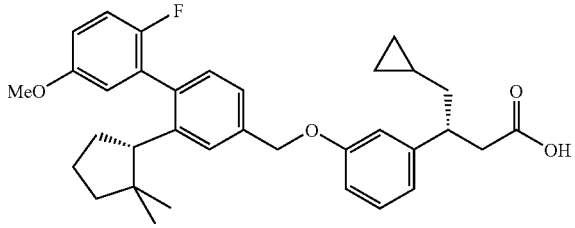 or 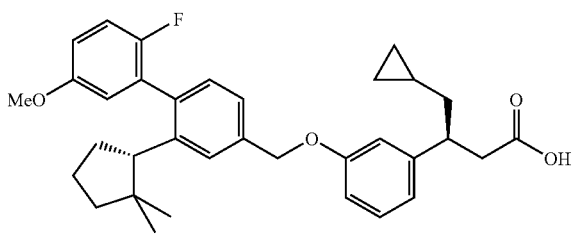 or 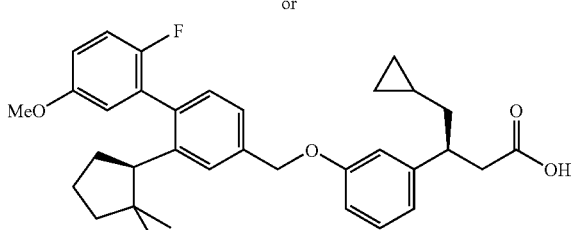 or 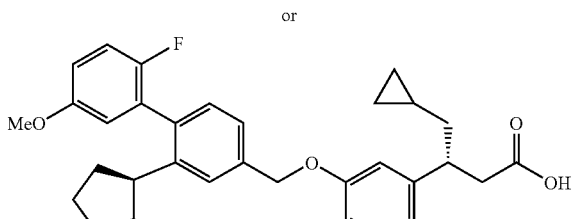 | +++ | ND |

TABLE 32-continued
Assay Data For Human GPR40
| No. | Structure | AequorinEC$_{50}$[b,c] | IP3 EC$_{50}$[c,d] |
|---|---|---|---|
| 69.8 | Diastereomer of 69.7 | ++++ | +++++ |
| 69.9 | 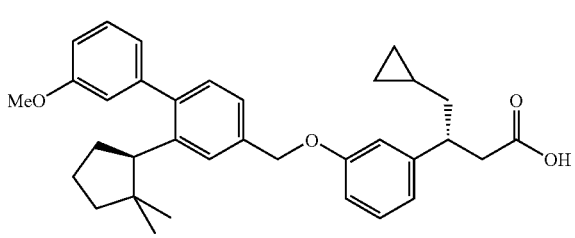<br>or<br>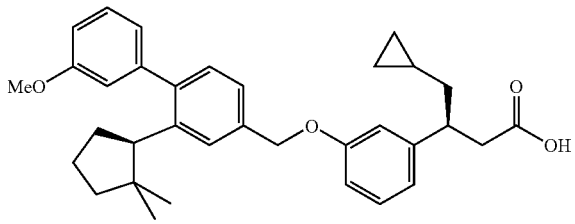<br>or<br>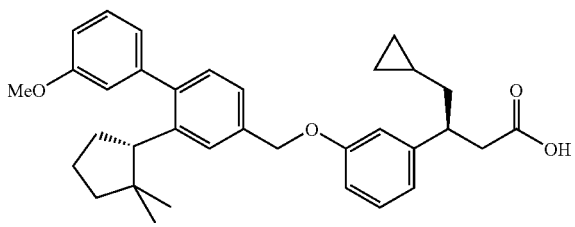<br>or<br>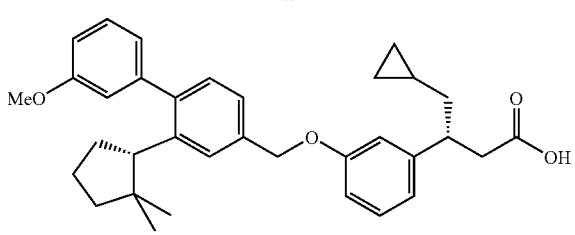 | +++ | ND |
| 69.10 | Diastereomer of 69.9 | ++++ | +++++ |
| 69.11 | 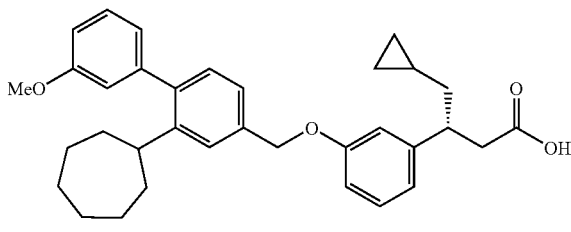<br>or<br>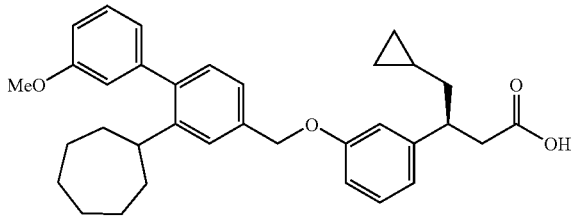 | +++ | ++++ |

TABLE 32-continued
Assay Data For Human GPR40
| No. | Structure | AequorinEC$_{50}$[b,c] | IP3 EC$_{50}$[c,d] |
|---|---|---|---|
| 69.12 | 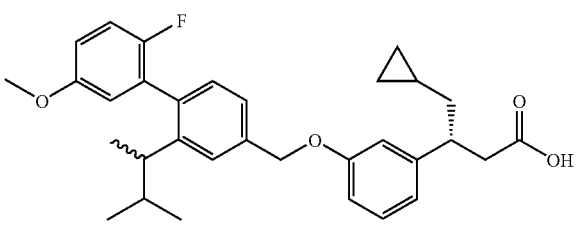 or 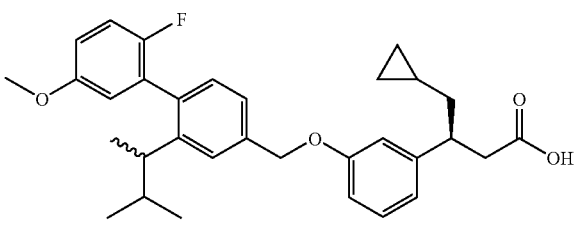 | +++ | +++++ |
| 69.13 | 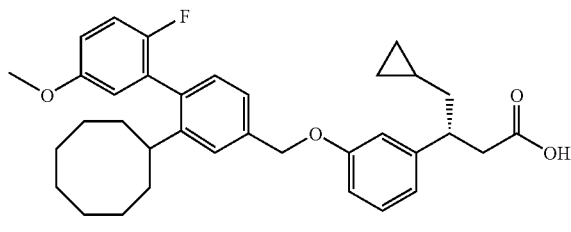 or 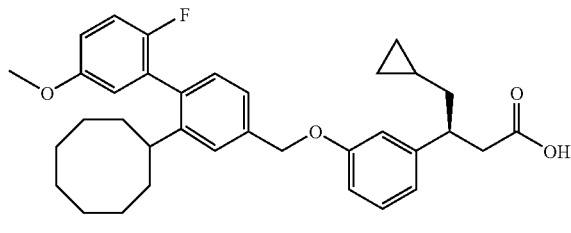 | +++ | +++++ |
| 69.14 | 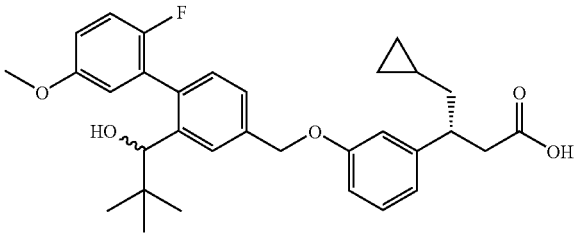 or 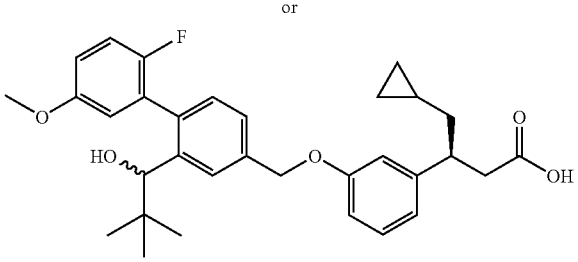 | +++ | +++ |

TABLE 32-continued
Assay Data For Human GPR40
| No. | Structure | AequorinEC$_{50}$$^{b,c}$ | IP3 EC$_{50}$$^{c,d}$ |
|---|---|---|---|
| 69.15 | 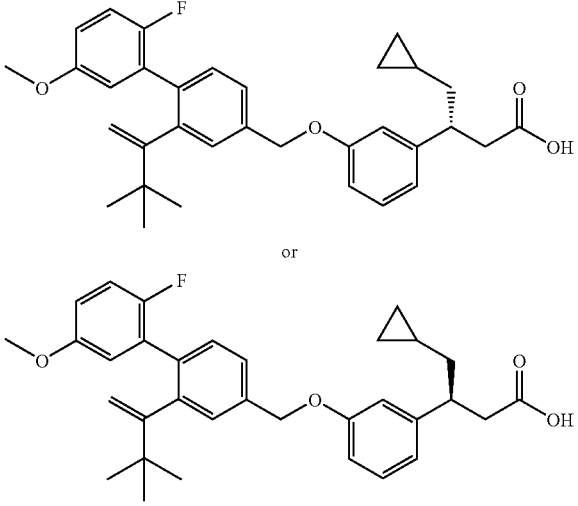 or 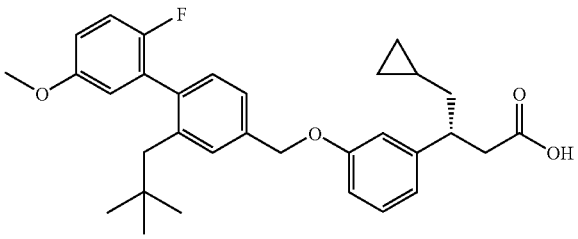 | +++ | ++++ |
| 69.16 | 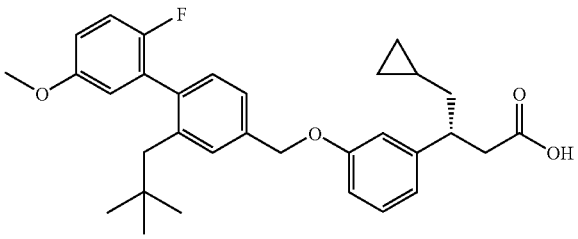 or 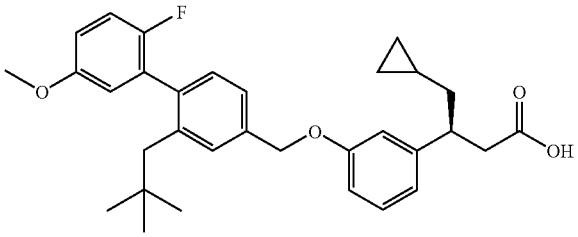 | ++++ | ++++ |
| 69.17 | 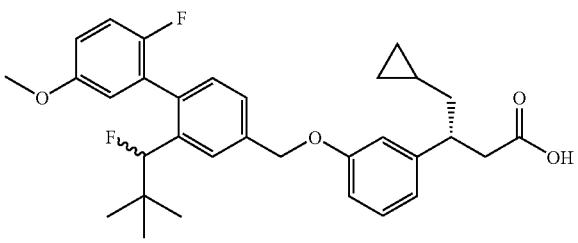 or 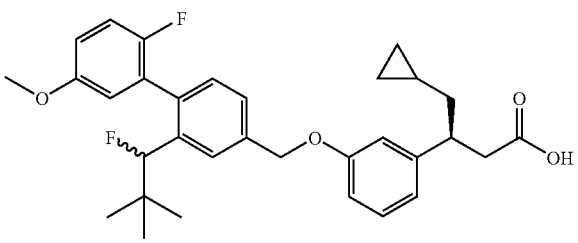 | +++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 69.18 | 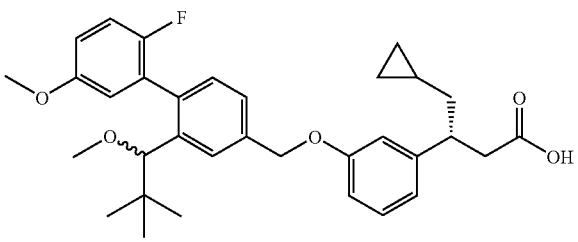 or 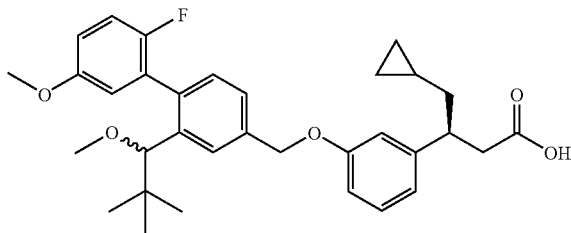 | +++ | +++++ |
| 69.19 | 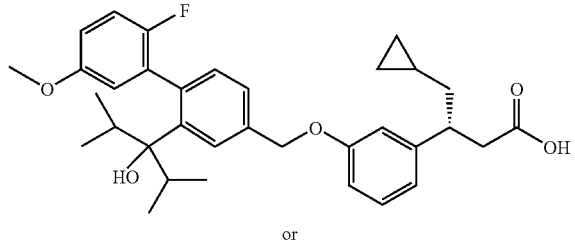 or 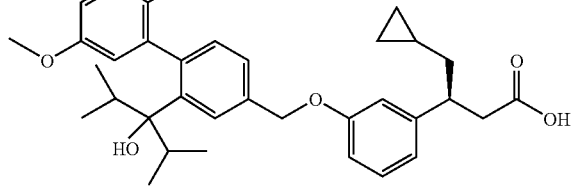 | +++ | +++ |
| 69.20 | 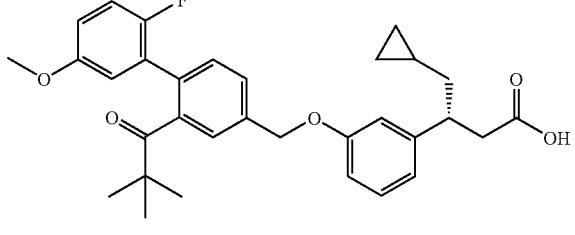 or 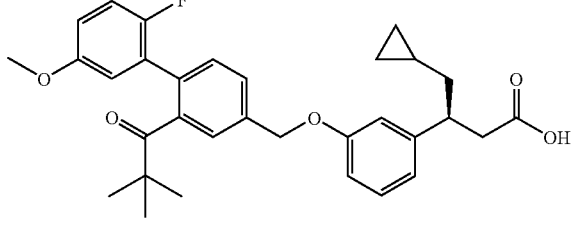 | ++ | ND |

TABLE 32-continued
Assay Data For Human GPR40
| No. | Structure | AequorinEC$_{50}$[b,c] | IP3 EC$_{50}$[c,d] |
|---|---|---|---|
| 69.21 | 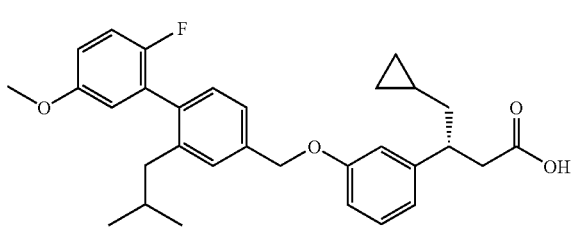<br>or<br>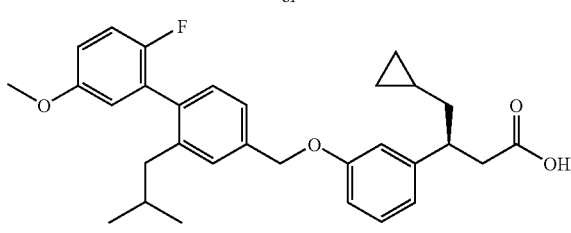 | +++ | ++++ |
| 69.22 | 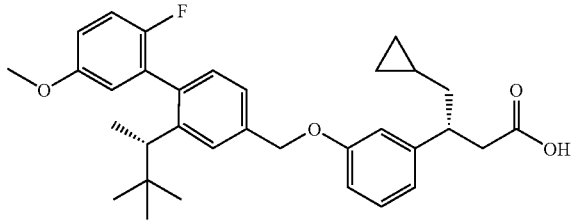<br>or<br>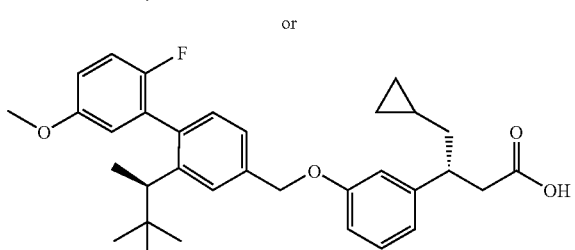<br>or<br>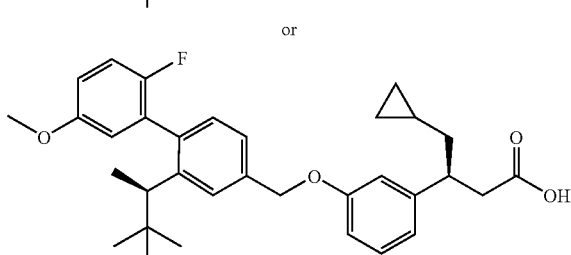<br>or<br>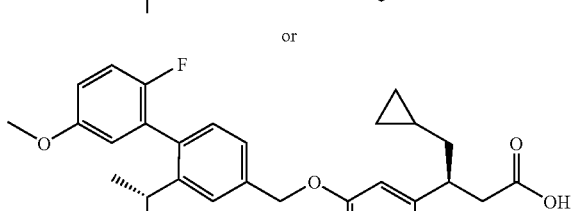 | +++ | +++++ |

TABLE 32-continued
Assay Data For Human GPR40
| No. | Structure$^a$ | AequorinEC$_{50}$$^{b,c}$ | IP3 EC$_{50}$$^{c,d}$ |
|---|---|---|---|
| 69.23 | 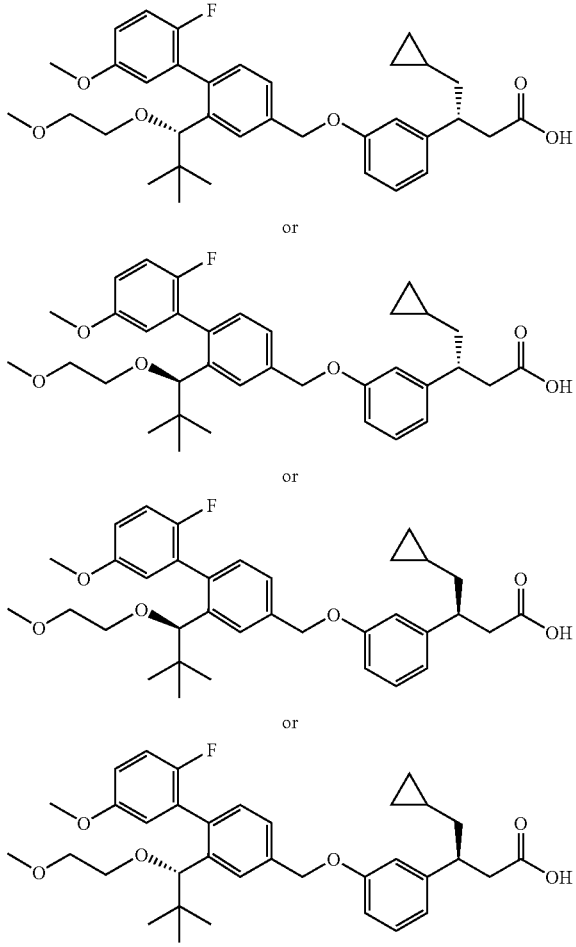 | ++++ | +++++ |
| 69.24 | 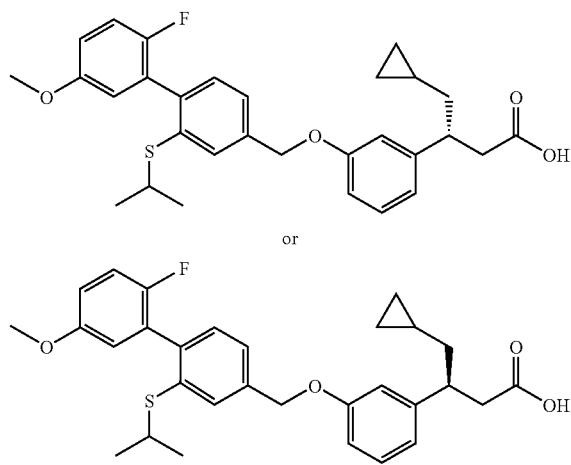 | +++ | ++++ |

TABLE 32-continued
| | Assay Data For Human GPR40 | | |
|---|---|---|---|
| No. | Structure[a] | AequorinEC$_{50}$[b,c] | IP3 EC$_{50}$[c,d] |
| 69.25 | 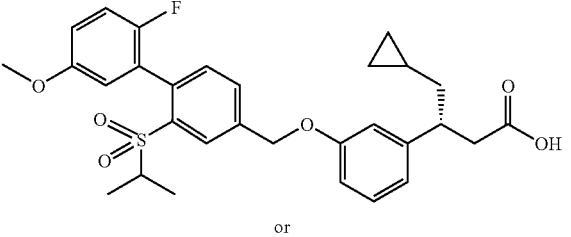 or 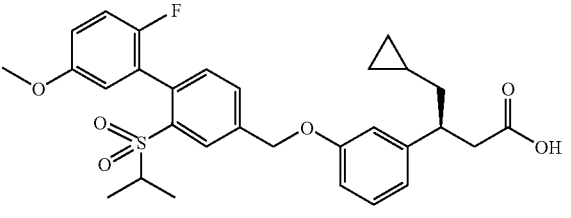 | ++ | ND |
| 69.26 | 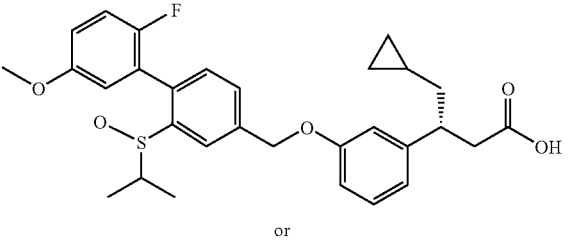 or 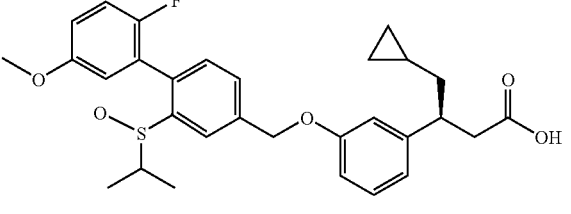 | ++ | ND |
| 69.27 | 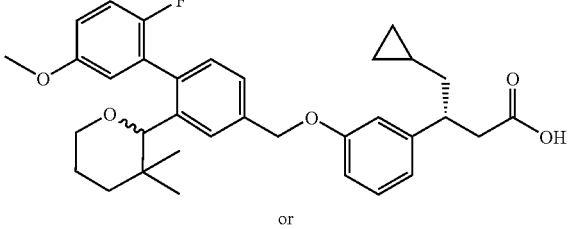 or 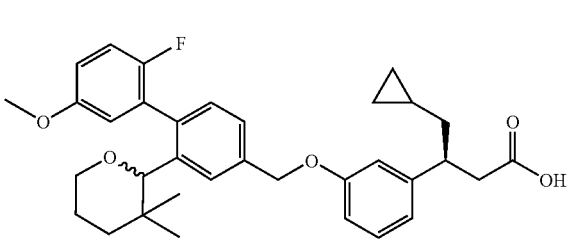 | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 69.28 | 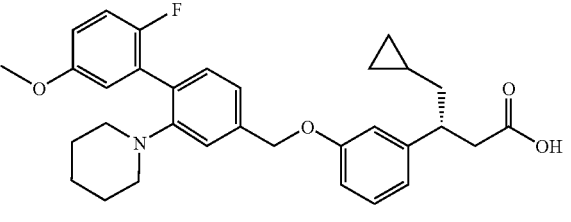<br>or<br>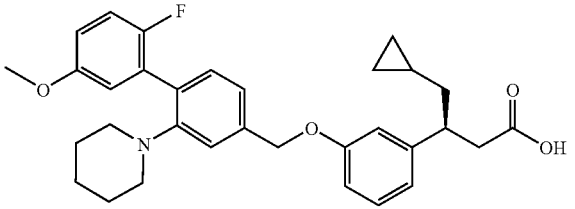 | +++ | ++++ |
| 69.29 | 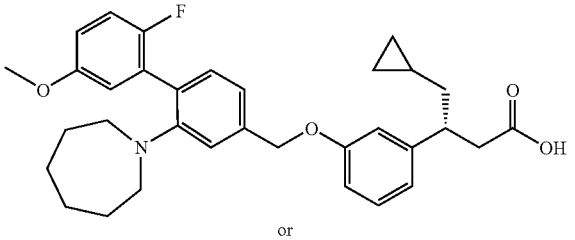<br>or<br>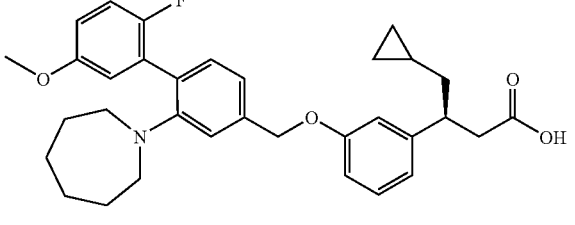 | +++ | +++ |
| 69.30 | 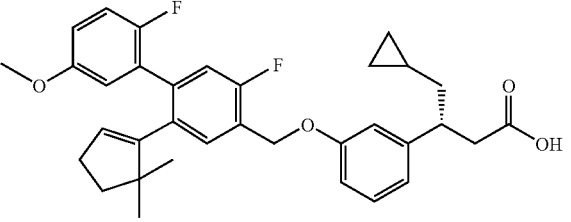<br>or<br>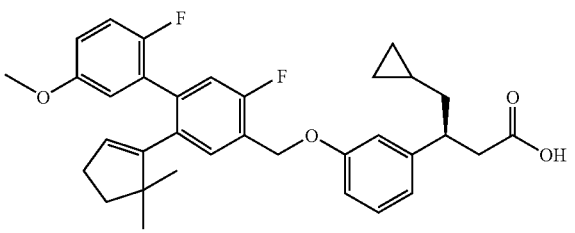 | +++ | +++++ |

TABLE 32-continued

Assay Data For Human GPR40

| No. | Structure | AequorinEC$_{50}$[b,c] | IP3 EC$_{50}$[c,d] |
|---|---|---|---|
| 69.31 | | +++ | ++++ |
| 69.32 | | +++ | ++++ |
| 69.33 | | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 69.34 | 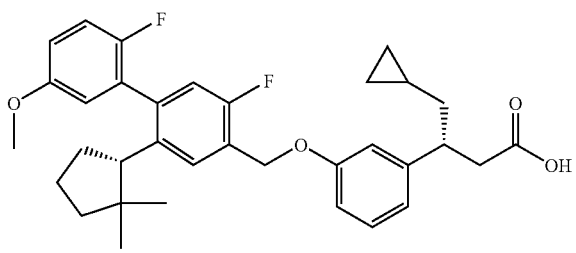or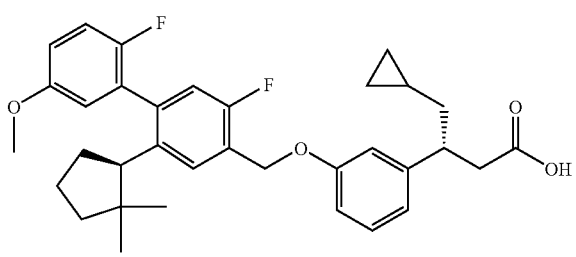or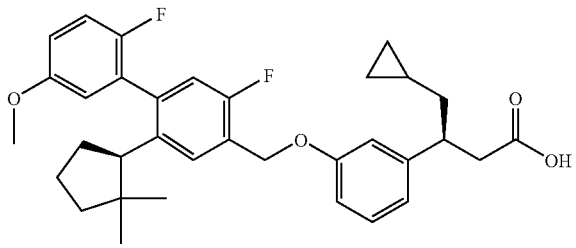or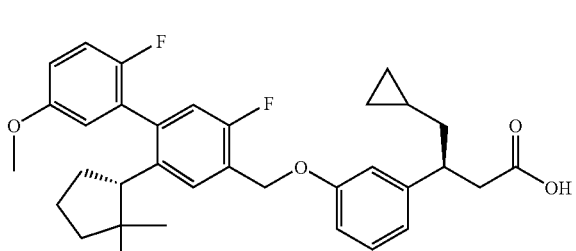 | +++ | +++++ |

TABLE 32-continued

Assay Data For Human GPR40

| No. | Structure[a] | AequorinEC$_{50}$[b,c] | IP3 EC$_{50}$[c,d] |
|---|---|---|---|
| 69.35 | | ++++ | +++++ | or or or

TABLE 32-continued
Assay Data For Human GPR40
| No. | Structure | AequorinEC$_{50}$$^{b,c}$ | IP3 EC$_{50}$$^{c,d}$ |
|---|---|---|---|
| 69.36 | 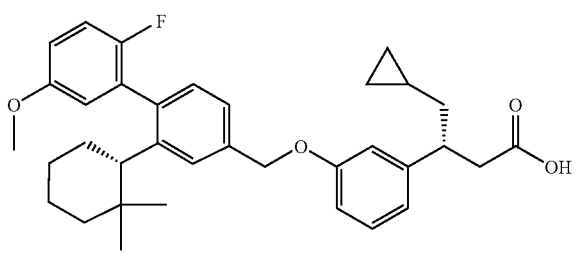<br>or<br>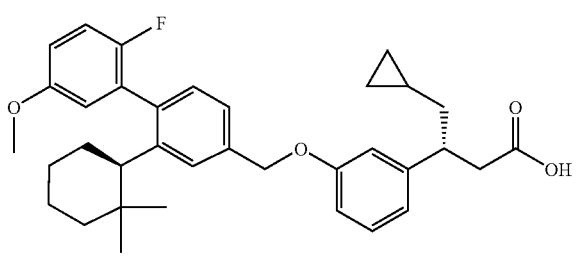<br>or<br>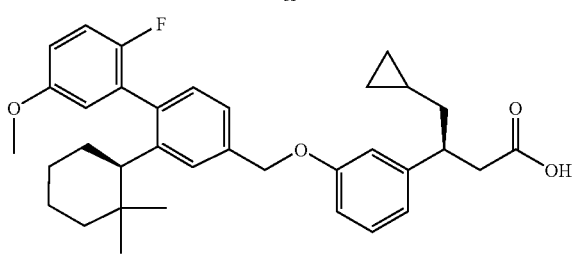<br>or<br>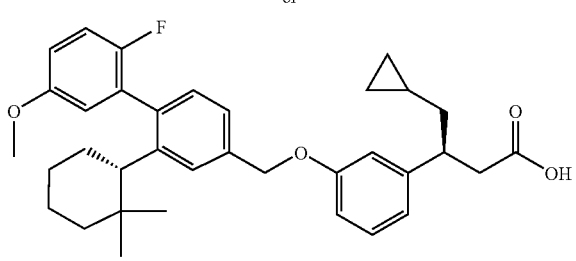 | +++ | +++++ |
| 69.37 | 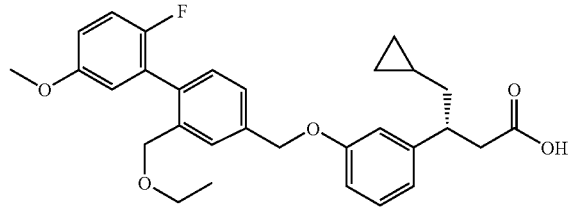<br>or<br>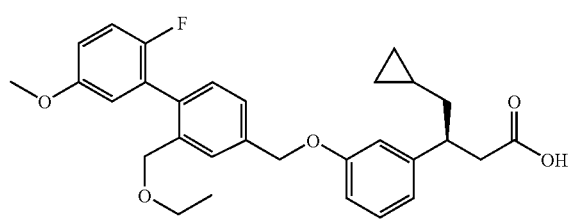 | ++ | ND |

TABLE 32-continued

Assay Data For Human GPR40

| No. | Structure | AequorinEC$_{50}$$^{b,c}$ | IP3 EC$_{50}$$^{c,d}$ |
|---|---|---|---|
| 69.38 | | +++ | +++++ | or or or

TABLE 32-continued
| | Assay Data For Human GPR40 | | |
|---|---|---|---|
| No. | Structure[a] | AequorinEC$_{50}$[b,c] | IP3 EC$_{50}$[c,d] |
| 69.39 | Diastereomer of 69.38 | ++ | ND |
| 69.40 | 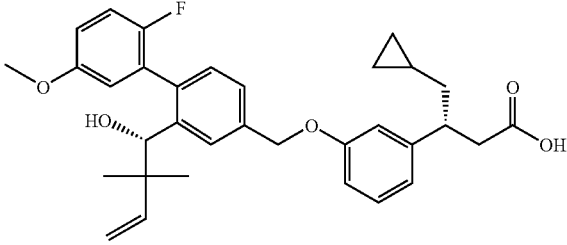<br>or<br>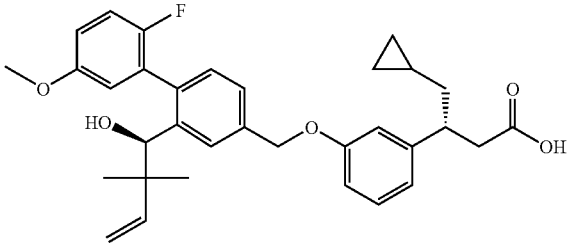<br>or<br>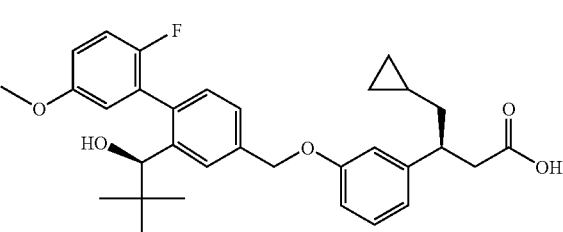<br>or<br>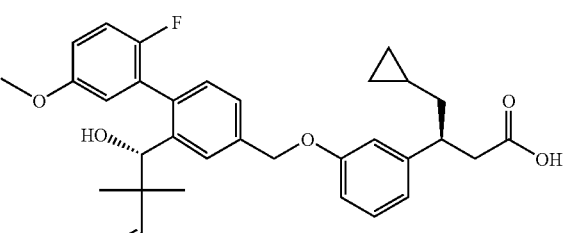 | ++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 69.41 | | +++ | ND | or or or

TABLE 32-continued
Assay Data For Human GPR40
| No. | Structure[a] | AequorinEC$_{50}$[b,c] | IP3 EC$_{50}$[c,d] |
|---|---|---|---|
| 69.42 | Diastereomer of 69.41 | +++ | +++++ |
| 69.43 | 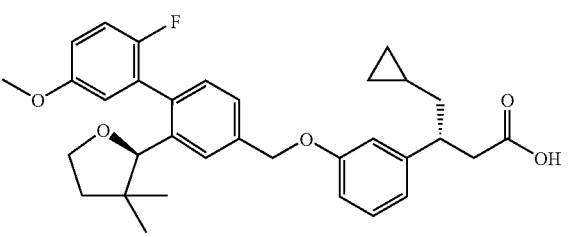<br>or<br>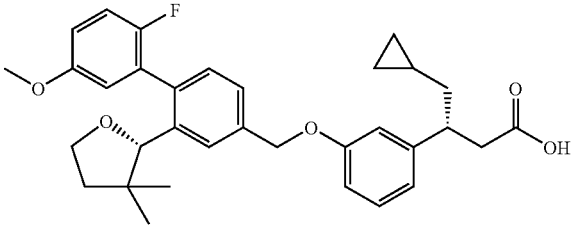<br>or<br>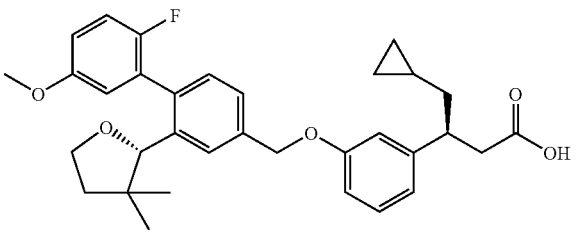<br>or<br>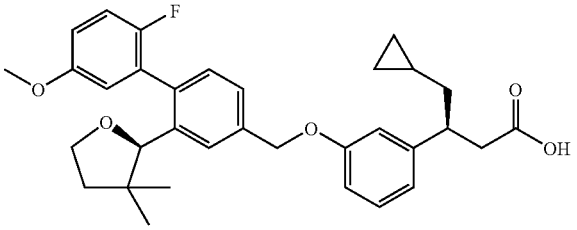 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 69.44 | Diastereomer of 69.43 | +++ | ++++ |
| 69.45 | 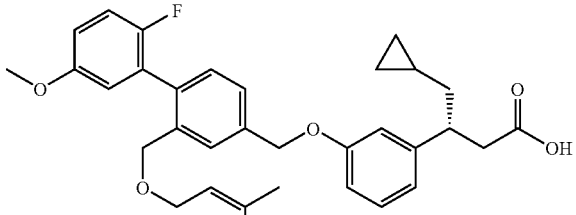 or 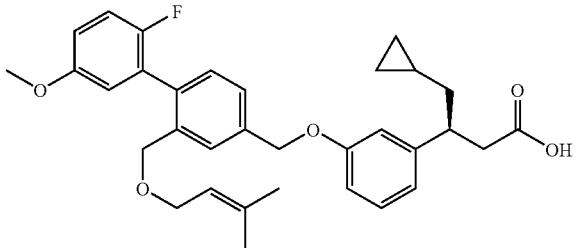 | ++ | ND |
| 69.46 | 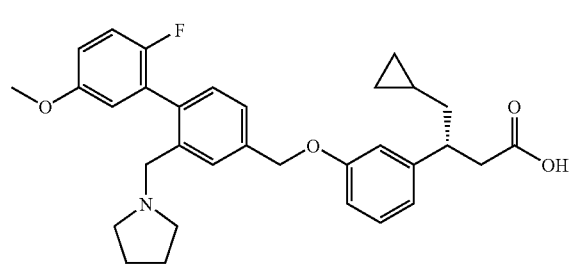 or 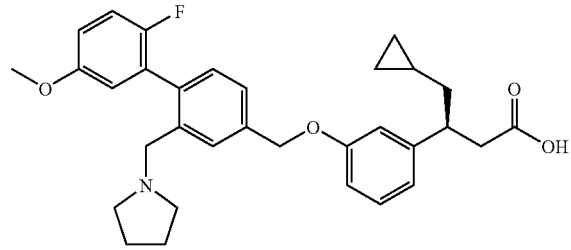 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 69.47 | 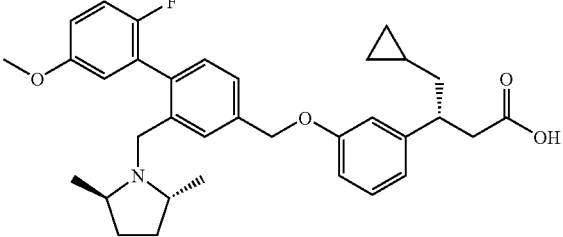 or 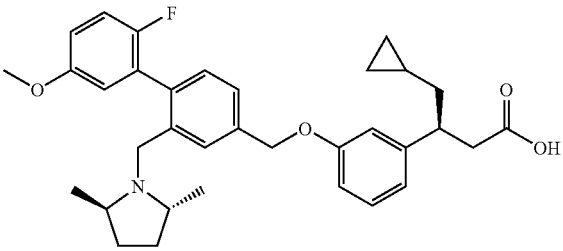 | +++ | ND |
| 69.48 | 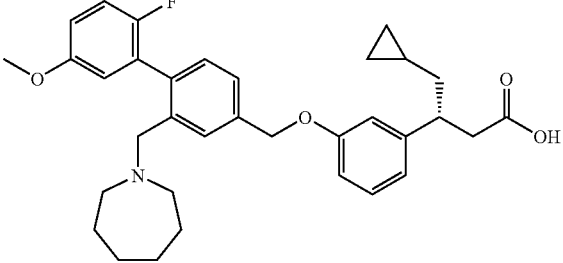 or 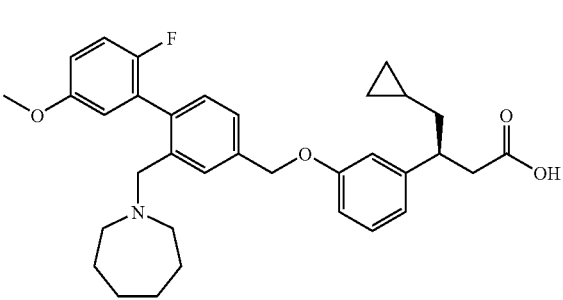 | ++ | ND |

TABLE 32-continued

Assay Data For Human GPR40

| No. | Structure | AequorinEC$_{50}$[b,c] | IP3 EC$_{50}$[c,d] |
|---|---|---|---|
| 70.1 | | +++ | ++++ |
| 70.2 | | +++ | ++++ |
| 70.3 | | +++ | ++++ |

TABLE 32-continued
Assay Data For Human GPR40
| No. | Structure | AequorinEC$_{50}$[b,c] | IP3 EC$_{50}$[c,d] |
|---|---|---|---|
| 70.4 | 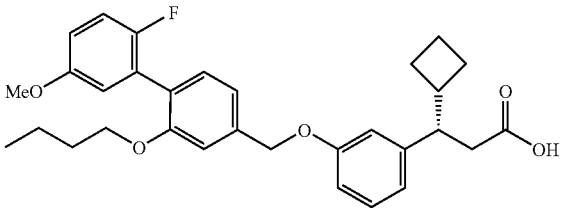 or 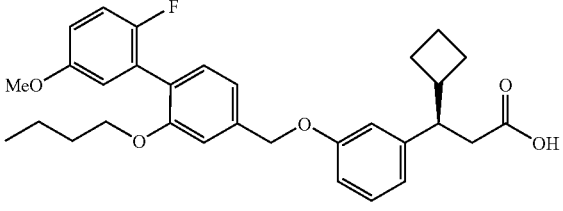 | +++ | +++ |
| 71.1 | 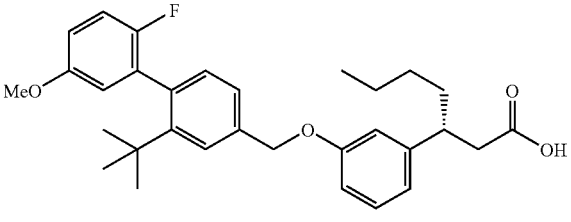 or 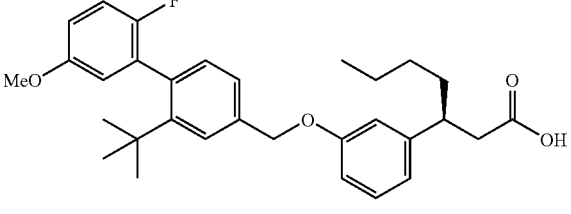 | +++ | ND |
| 71.2 | 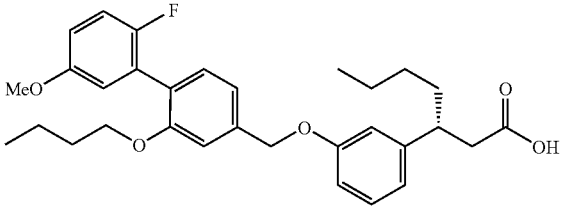 or 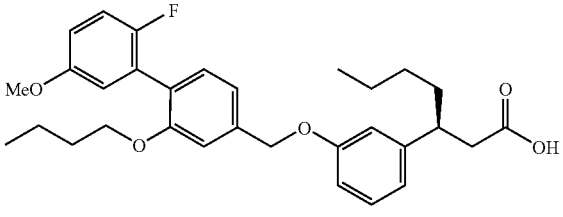 | +++ | +++ |

TABLE 32-continued
Assay Data For Human GPR40
| No. | Structure | AequorinEC$_{50}$[b,c] | IP3 EC$_{50}$[c,d] |
|---|---|---|---|
| 71.3 | 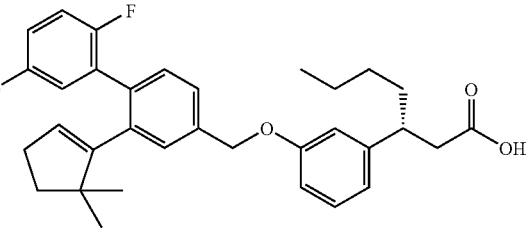 or 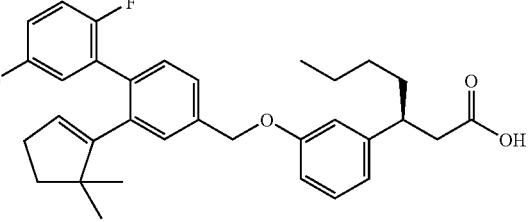 | +++ | ++++ |
| 72 | 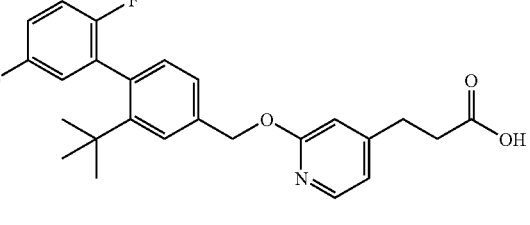 | +++ | ++ |
| 73 | Enantiomer of 51 | ++ | ND |
| 74 | 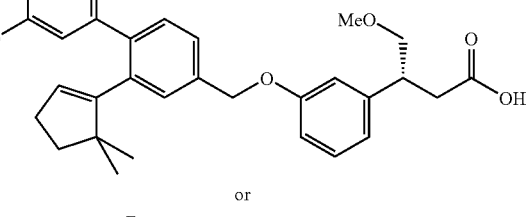 or 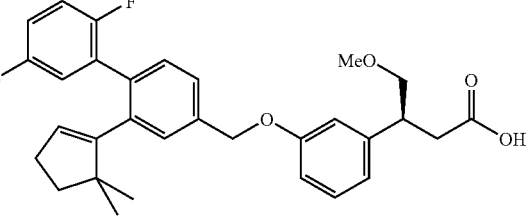 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 75 | 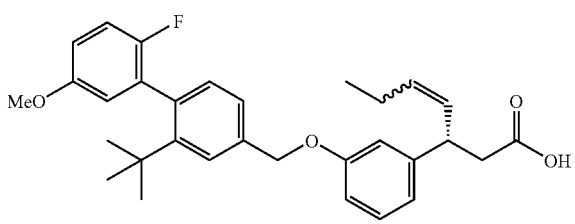 or 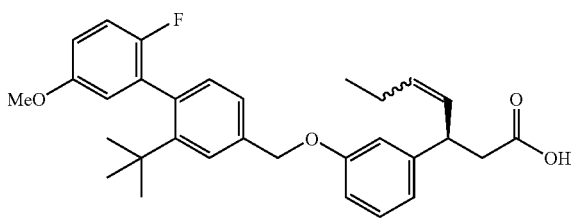 | +++ | ND |
| 76.1 | 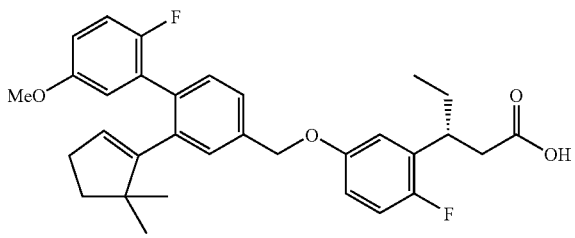 or 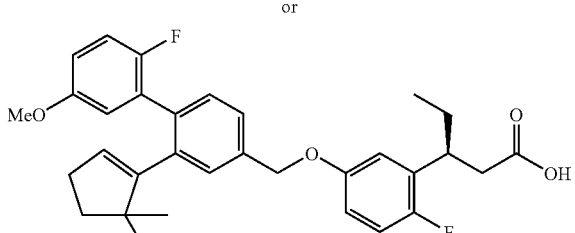 | +++ | ++++ |
| 76.2 | 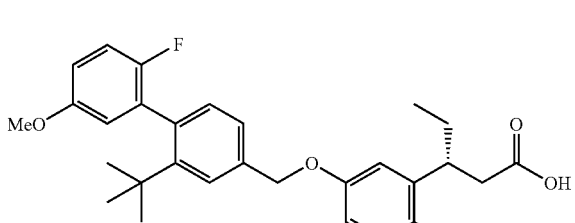 or 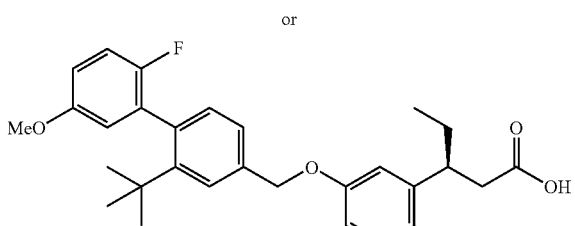 | ++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 76.3 | 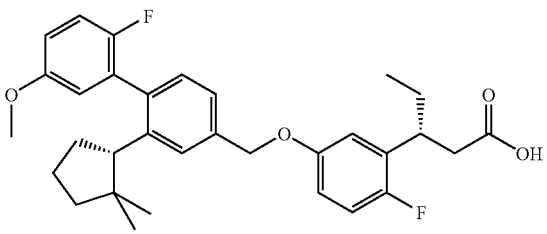 or 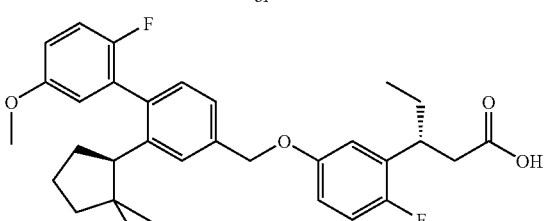 or 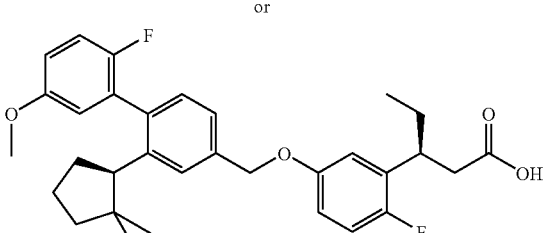 or 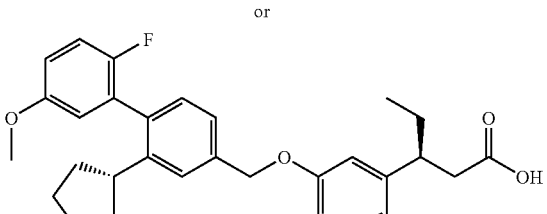 | +++ | ++++ |
| 77.1 | 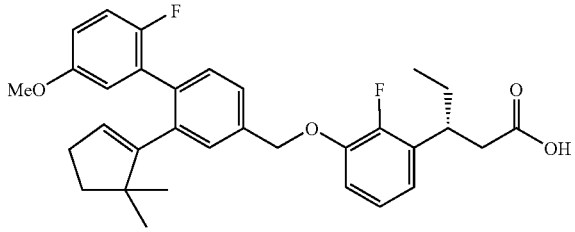 or 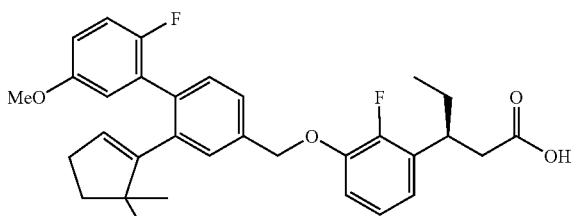 | +++ | ++++ |

TABLE 32-continued

Assay Data For Human GPR40

| No. | Structure | AequorinEC$_{50}$[b,c] | IP3 EC$_{50}$[c,d] |
|-----|-----------|------------------------|---------------------|
| 77.2 | | +++ | +++ |
| 77.3 | | +++ | +++++ |

TABLE 32-continued

Assay Data For Human GPR40

| No. | Structure[a] | AequorinEC$_{50}$[b,c] | IP3 EC$_{50}$[c,d] |
|---|---|---|---|
| 77.4 | | +++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 77.5 | 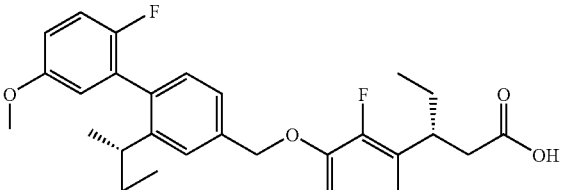 or 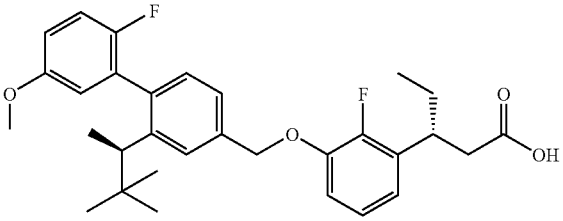 or 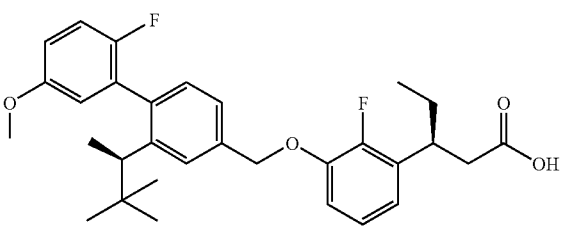 or 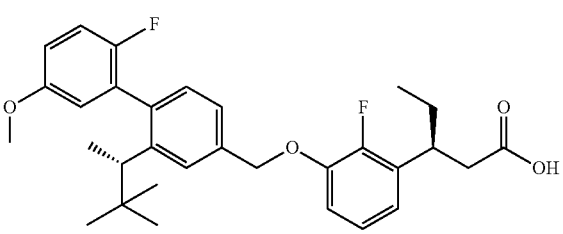 | +++ | +++++ |

TABLE 32-continued

Assay Data For Human GPR40

| No. | Structure[a] | AequorinEC$_{50}$[b,c] | IP3 EC$_{50}$[c,d] |
|---|---|---|---|
| 77.6 | | +++ | +++++ |
| 77.7 | | ++ | +++ |

TABLE 32-continued

Assay Data For Human GPR40

| No. | Structure | AequorinEC$_{50}$[b,c] | IP3 EC$_{50}$[c,d] |
|---|---|---|---|
| 77.8 | | +++ | +++++ | or or or

TABLE 32-continued

Assay Data For Human GPR40

| No. | Structure[a] | AequorinEC$_{50}$[b,c] | IP3 EC$_{50}$[c,d] |
|---|---|---|---|
| 77.9 | | +++ | +++++ | or or or

TABLE 32-continued

Assay Data For Human GPR40

| No. | Structure[a] | AequorinEC$_{50}$[b,c] | IP3 EC$_{50}$[c,d] |
|---|---|---|---|
| 77.10 | | +++ | +++++ |
| 77.11 | | +++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 77.12 | 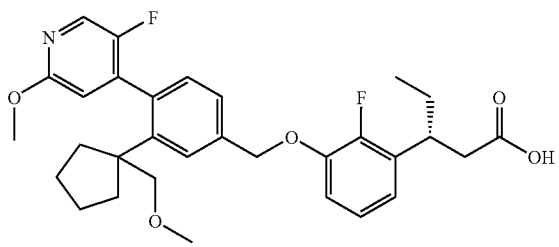 or 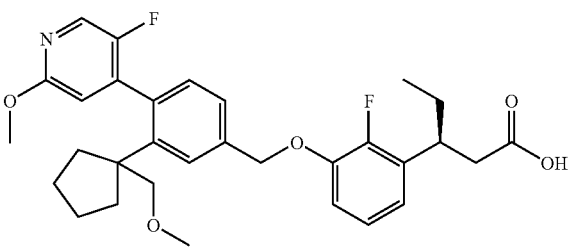 | ++ | ND |
| 78.1 | 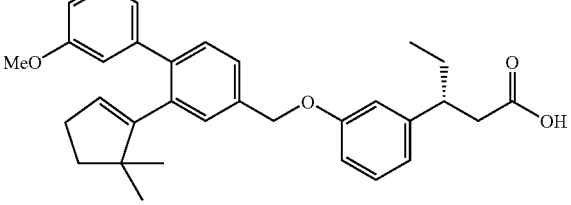 or 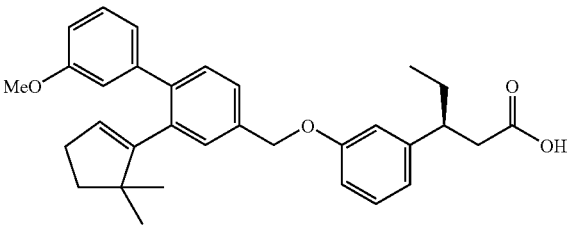 | ND | ND |
| 78.2 | 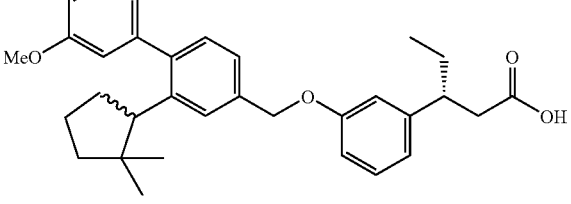 or 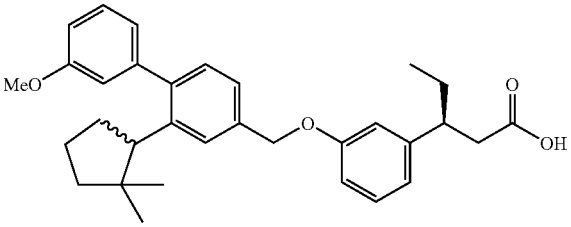 | ND | ND |

TABLE 32-continued
Assay Data For Human GPR40
| No. | Structure[a] | AequorinEC$_{50}$[b,c] | IP3 EC$_{50}$[c,d] |
|---|---|---|---|
| 78.3 | 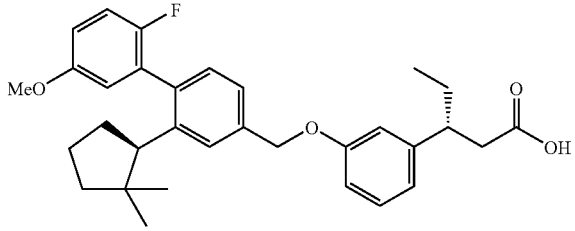or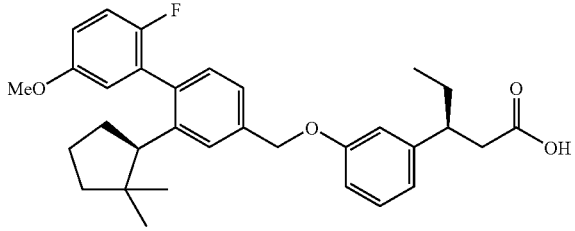or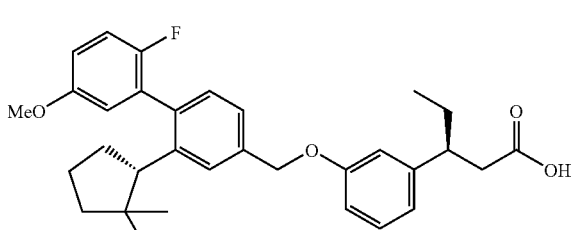or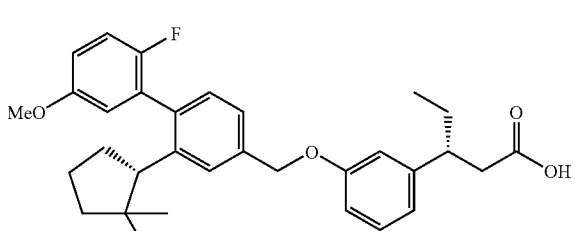 | +++ | ND |

TABLE 32-continued

Assay Data For Human GPR40

| No. | Structure | AequorinEC$_{50}$[b,c] | IP3 EC$_{50}$[c,d] |
|---|---|---|---|
| 78.4 | Diastereomer of 78.3 | ++++ | +++++ |
| 78.5 | | +++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 78.6 | Diastereomer of 78.5 | ++++ | +++++ |
| 78.7 | (structure) or (structure) | +++ | ++++ |
| 78.8 | (structure) or (structure) | +++ | ++++ |
| 78.9 | (structure) or (structure) | +++ | ++++ |

TABLE 32-continued
Assay Data For Human GPR40
| No. | Structure | AequorinEC$_{50}$$^{b,c}$ | IP3 EC$_{50}$$^{c,d}$ |
|---|---|---|---|
| 78.10 | 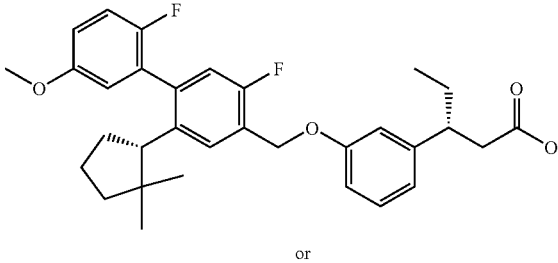 or 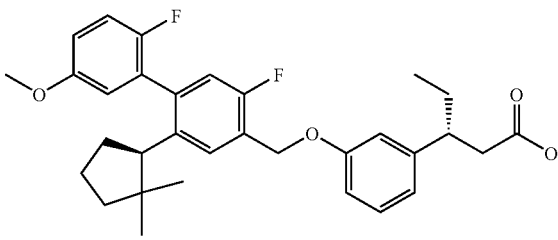 or 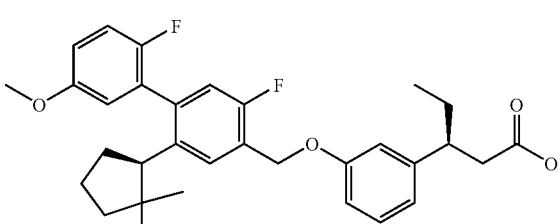 or 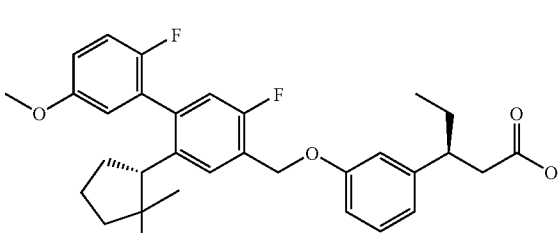 | +++ | +++++ |

TABLE 32-continued
Assay Data For Human GPR40
| No. | Structure | AequorinEC$_{50}$$^{b,c}$ | IP3 EC$_{50}$$^{c,d}$ |
|---|---|---|---|
| 78.11 | 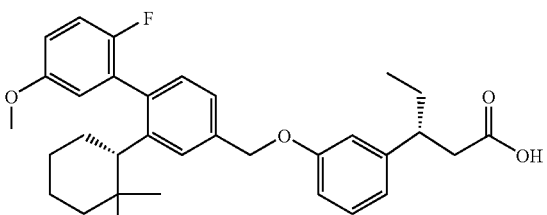 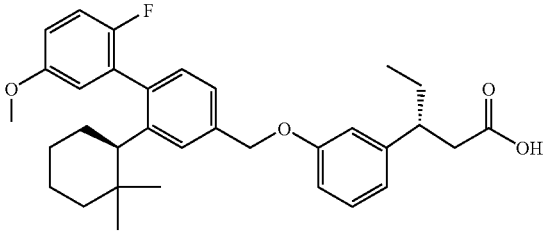 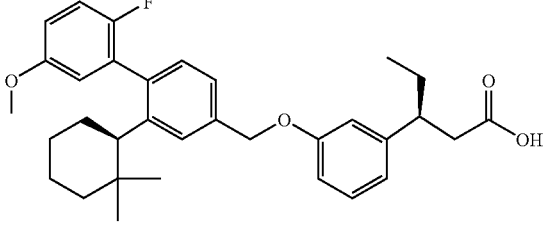 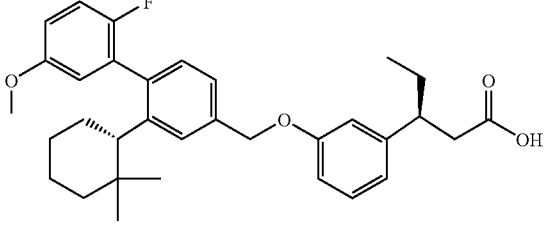 | ++++ | +++++ |
| 78.12 | 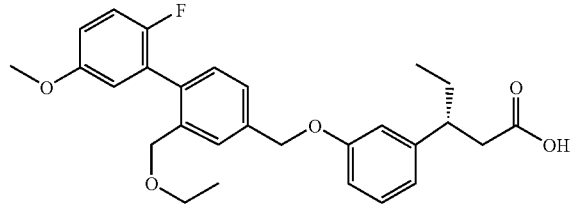 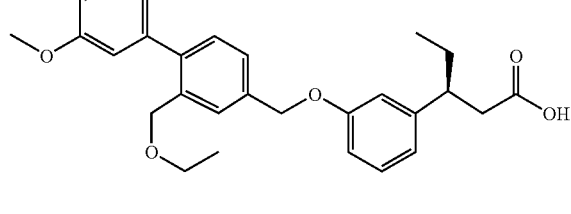 | ++ | ND |

TABLE 32-continued

Assay Data For Human GPR40

| No. | Structure | AequorinEC$_{50}$[b,c] | IP3 EC$_{50}$[c,d] |
|---|---|---|---|
| 78.13 | | ++ | ND | or or or

TABLE 32-continued

Assay Data For Human GPR40

| No. | Structure | AequorinEC$_{50}$[b,c] | IP3 EC$_{50}$[c,d] |
|---|---|---|---|
| 78.14 | | ++++ | +++++ | or or or

TABLE 32-continued
Assay Data For Human GPR40
| No. | Structure[a] | AequorinEC$_{50}$[b,c] | IP3 EC$_{50}$[c,d] |
|---|---|---|---|
| 79.1 | 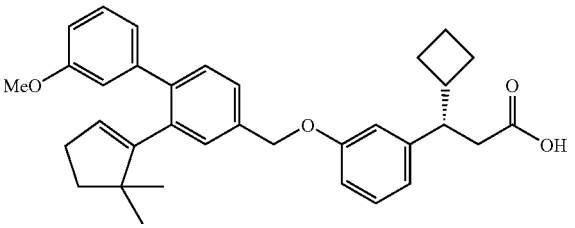<br>or<br>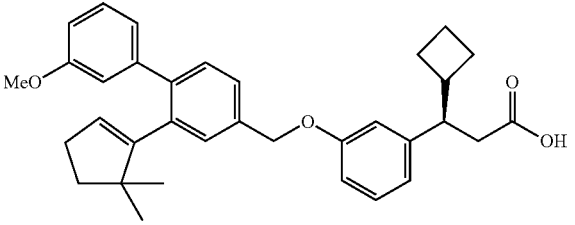 | ND | ND |
| 79.2 | 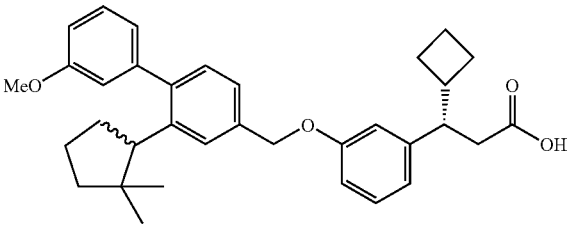<br>or<br>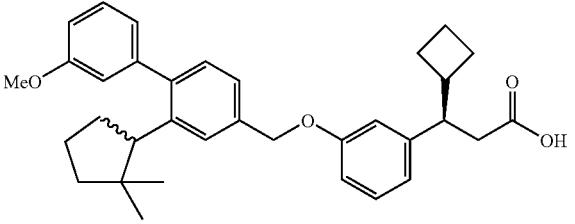 | ND | ND |

TABLE 32-continued

Assay Data For Human GPR40

| No. | Structure | AequorinEC$_{50}$$^{b,c}$ | IP3 EC$_{50}$$^{c,d}$ |
|---|---|---|---|
| 79.3 | | +++ | ++++ |

TABLE 32-continued

Assay Data For Human GPR40

| No. | Structure[a] | AequorinEC$_{50}$[b,c] | IP3 EC$_{50}$[c,d] |
|---|---|---|---|
| 79.4 | Diastereomer of 79.3 | ++++ | +++++ |
| 79.5 | (structure shown) | +++ | ND |
| 79.6 | Diastereomer of 79.5 | +++ | ++++ |
| 79.7 | (structure shown) | +++ | ++++ |

TABLE 32-continued

Assay Data For Human GPR40

| No. | Structure[a] | AequorinEC$_{50}$[b,c] | IP3 EC$_{50}$[c,d] |
|---|---|---|---|
| 79.8 | | +++ | ++++ |
| 80.1 | | +++ | ND |
| 80.2 | | ND | ND |

TABLE 32-continued

Assay Data For Human GPR40

| No. | Structure[a] | AequorinEC$_{50}$[b,c] | IP3 EC$_{50}$[c,d] |
|---|---|---|---|
| 80.3 | | +++ | ND | or or or

TABLE 32-continued

Assay Data For Human GPR40

| No. | Structure[a] | AequorinEC$_{50}$[b,c] | IP3 EC$_{50}$[c,d] |
|---|---|---|---|
| 80.4 | Diastereomer of 80.3 | +++ | +++++ |
| 80.5 | (structure) | +++ | ND |
| 80.6 | Diastereomer of 80.5 | +++ | +++++ |
| 81 | (structure) | +++ | + |

TABLE 32-continued
Assay Data For Human GPR40
| No. | Structure | AequorinEC$_{50}$[b,c] | IP3 EC$_{50}$[c,d] |
|---|---|---|---|
| 82 | 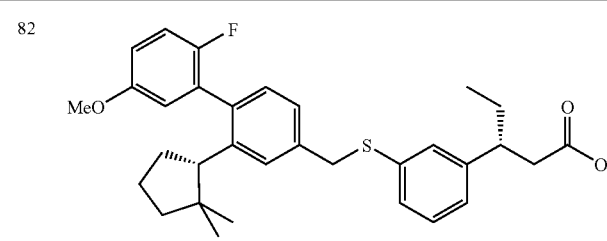<br>or<br>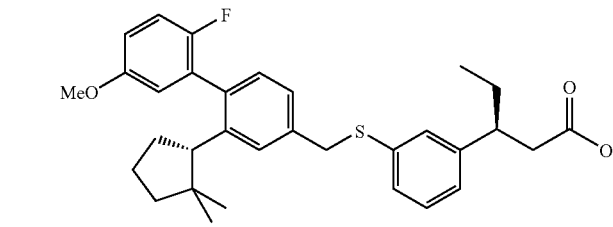<br>or<br>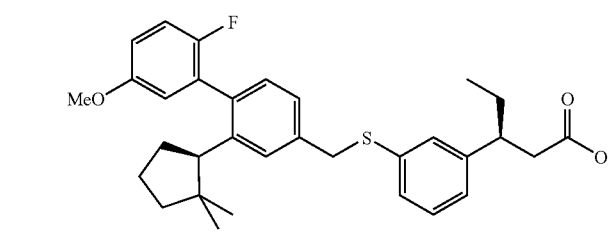<br>or<br>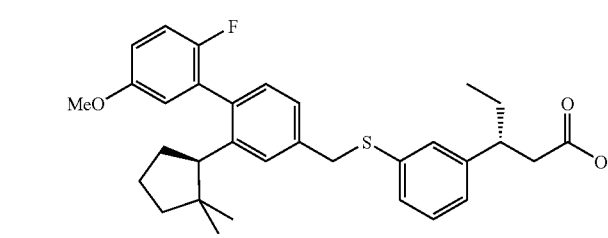 | +++ | ++ |

TABLE 32-continued
Assay Data For Human GPR40
| No. | Structure[a] | AequorinEC$_{50}$[b,c] | IP3 EC$_{50}$[c,d] |
|---|---|---|---|
| 83.1 | 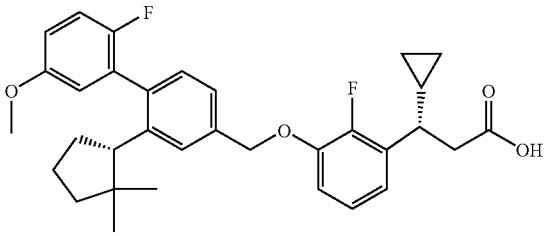<br>or<br>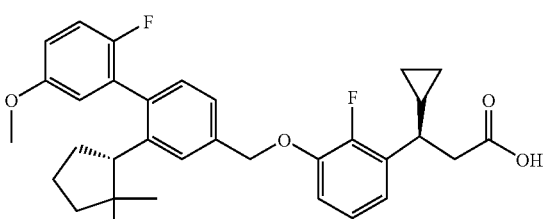<br>or<br>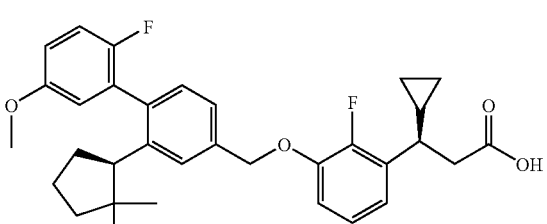<br>or<br>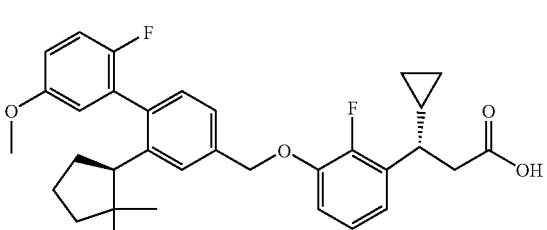 | ++++ | +++++ |

TABLE 32-continued

Assay Data For Human GPR40

| No. | Structure | AequorinEC$_{50}$$^{b,c}$ | IP3 EC$_{50}$$^{c,d}$ |
|---|---|---|---|
| 83.2 | | ++++ | +++++ | or or or

TABLE 32-continued
Assay Data For Human GPR40
| No. | Structure[a] | AequorinEC$_{50}$[b,c] | IP3 EC$_{50}$[c,d] |
|---|---|---|---|
| 83.3 | 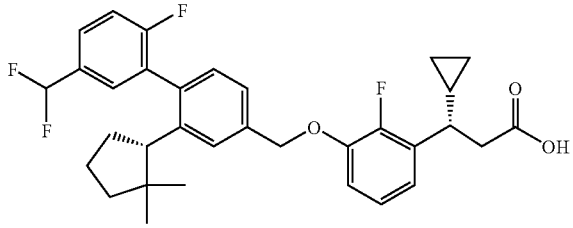 or 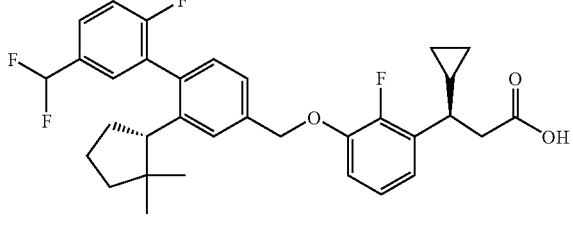 or 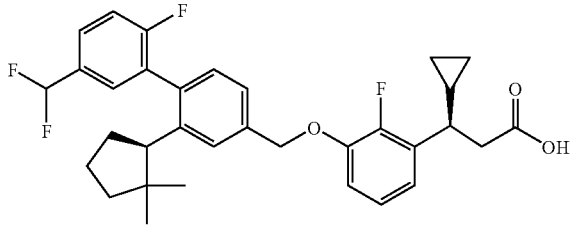 or 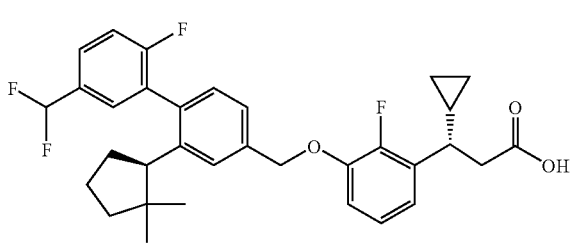 | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 83.4 | 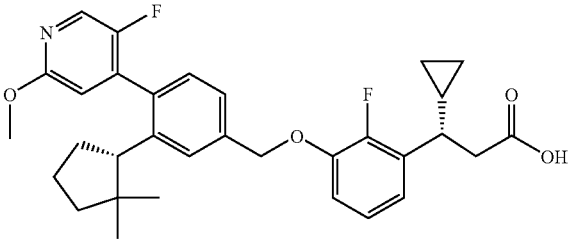 or 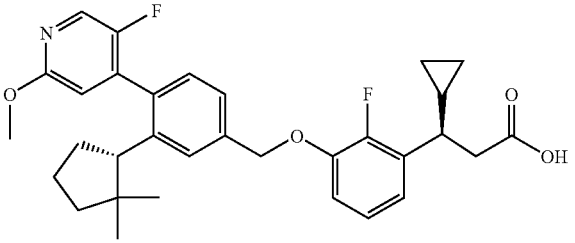 or 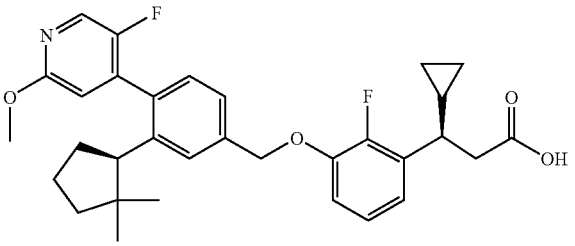 or 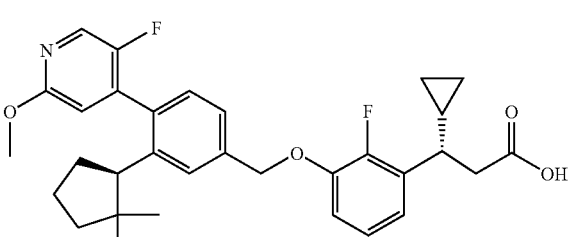 | ++++ | +++++ |

TABLE 32-continued
Assay Data For Human GPR40
| No. | Structure | AequorinEC$_{50}$$^{b,c}$ | IP3 EC$_{50}$$^{c,d}$ |
|---|---|---|---|
| 83.5 | Diastereomer of 83.4 | +++ | ++++ |
| 83.6 | 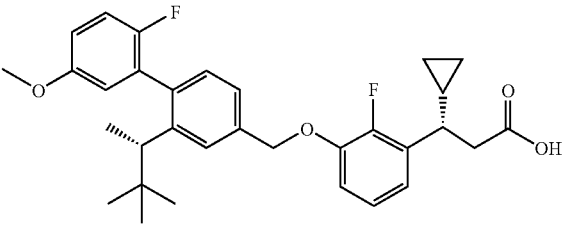 or 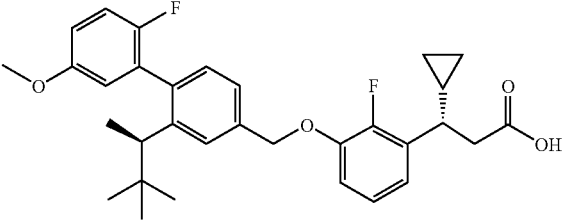 or 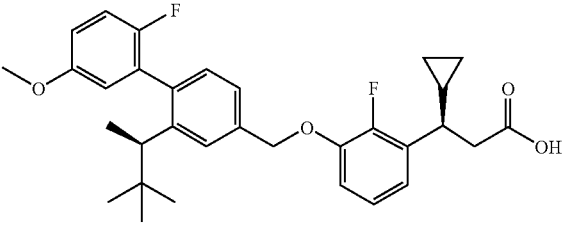 or 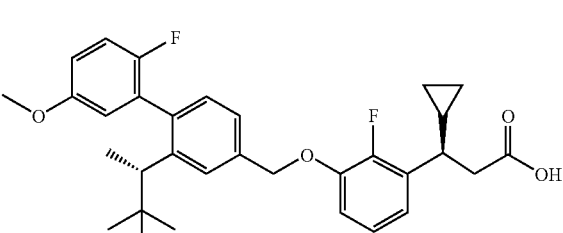 | +++ | +++++ |

TABLE 32-continued

Assay Data For Human GPR40

| No. | Structure[a] | AequorinEC$_{50}$[b,c] | IP3 EC$_{50}$[c,d] |
|---|---|---|---|
| 83.7 | | +++ | +++++ | or or or

TABLE 32-continued

Assay Data For Human GPR40

| No. | Structure | AequorinEC$_{50}$[b,c] | IP3 EC$_{50}$[c,d] |
|---|---|---|---|
| 83.8 | | +++ | +++++ | or or or

TABLE 32-continued
Assay Data For Human GPR40
| No. | Structure | AequorinEC$_{50}$[b,c] | IP3 EC$_{50}$[c,d] |
|---|---|---|---|
| 83.9 | 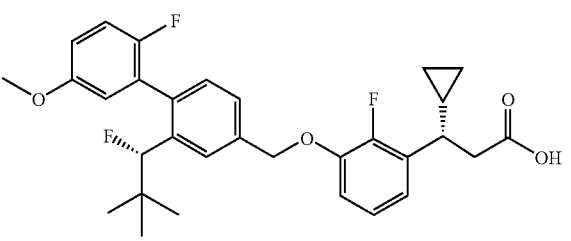<br>or<br>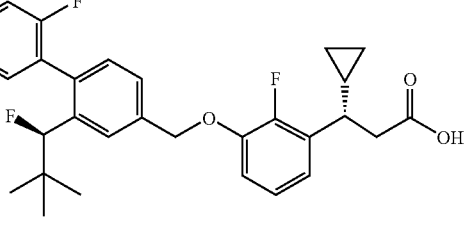<br>or<br>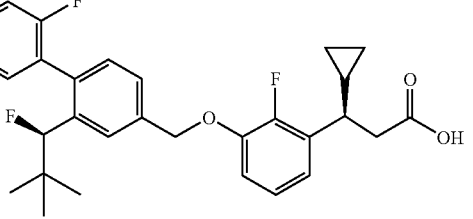<br>or<br>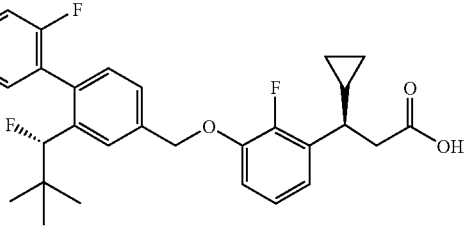 | +++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 83.10 | 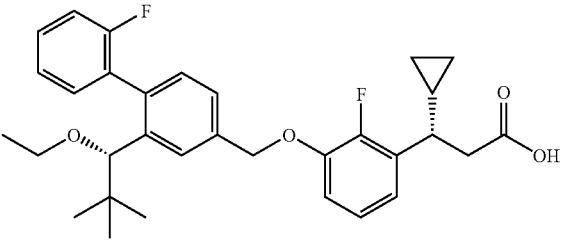 or 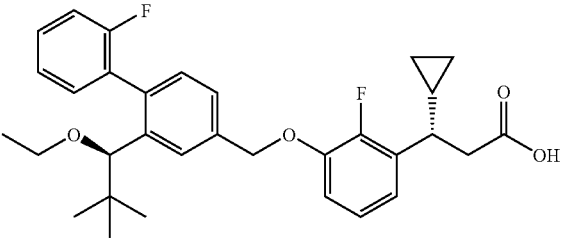 or 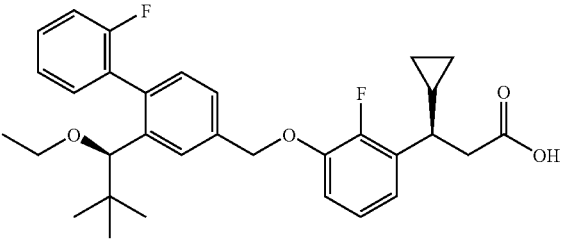 or 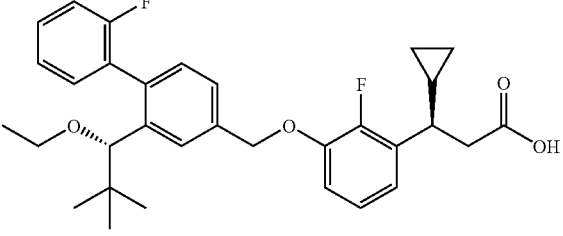 | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 83.11 | 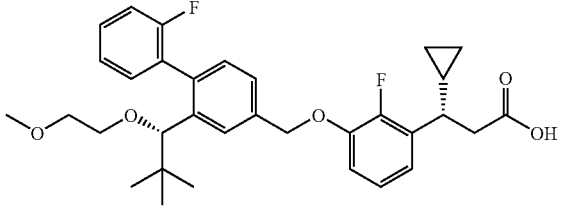 or 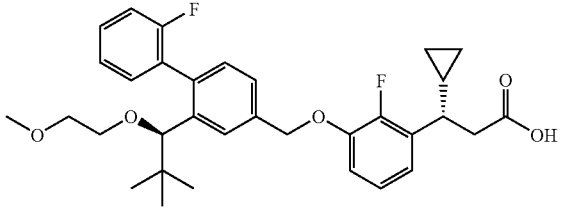 or 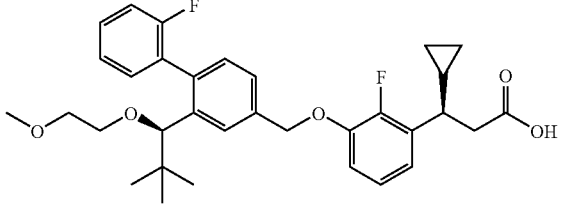 or 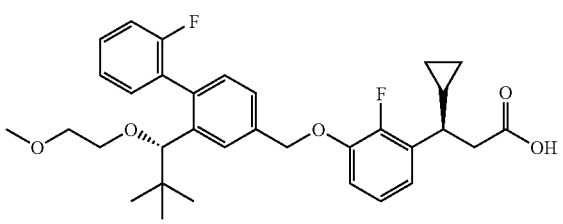 | +++ | ++++ |

TABLE 32-continued
Assay Data For Human GPR40
| No. | Structure | AequorinEC$_{50}$[b,c] | IP3 EC$_{50}$[c,d] |
|---|---|---|---|
| 83.12 | 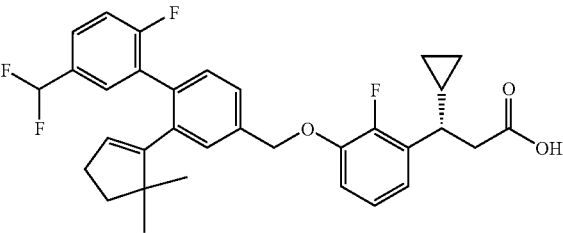 or 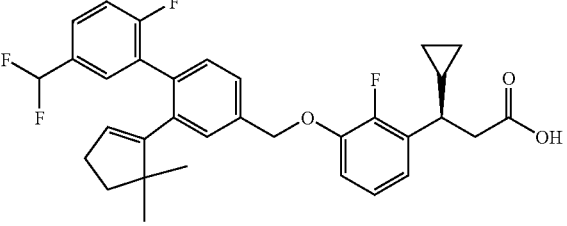 | +++ | ++++ |
| 83.13 | Diastereomer of 83.3 | ++ | ND |
| 83.14 | 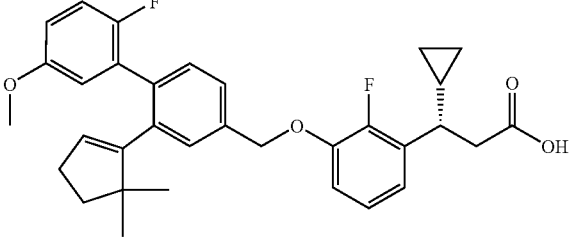 or 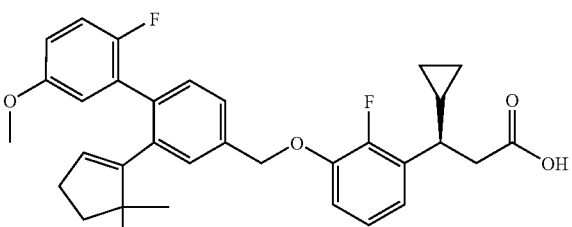 | +++ | +++++ |

//TABLE 32-continued

Assay Data For Human GPR40

| No. | Structure | AequorinEC$_{50}$$^{b,c}$ | IP3 EC$_{50}$$^{c,d}$ |
|---|---|---|---|
| 83.15 | | +++ | +++++ |
| 83.16 | | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 83.17 | Diastereomer of 83.1 | +++ | ND |
| 83.18 | 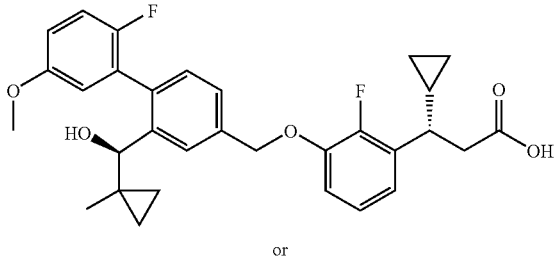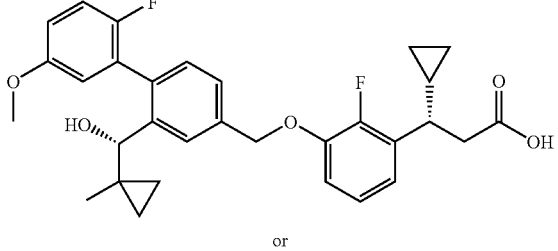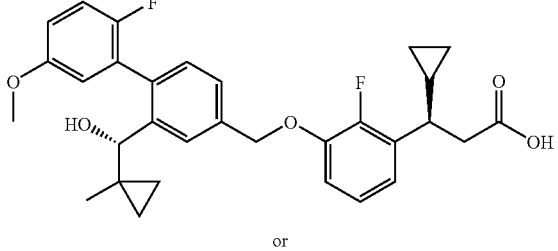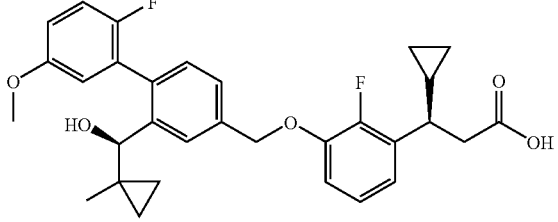 or or or | ++ | ND |

TABLE 32-continued

Assay Data For Human GPR40

| No. | Structure | AequorinEC$_{50}$[b,c] | IP3 EC$_{50}$[c,d] |
|---|---|---|---|
| 83.19 | Diastereomer of 83.18 | ++ | ND |
| 83.20 | | +++ | +++++ | or or or

TABLE 32-continued
Assay Data For Human GPR40
| No. | Structure | AequorinEC$_{50}$[b,c] | IP3 EC$_{50}$[c,d] |
|---|---|---|---|
| 83.21 | 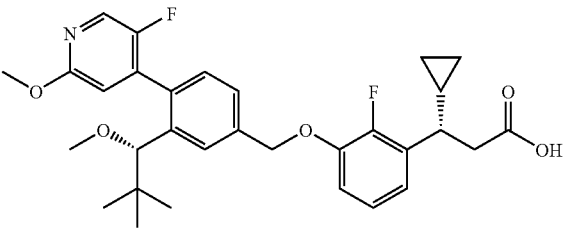 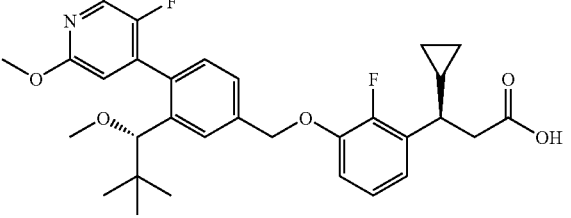 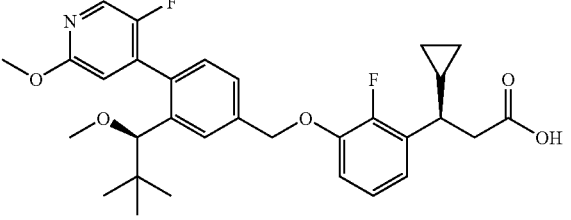 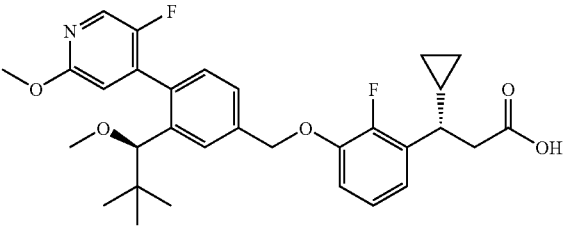 or | ++++ | +++++ |
or
or
or

TABLE 32-continued

Assay Data For Human GPR40

| No. | Structure[a] | AequorinEC$_{50}$[b,c] | IP3 EC$_{50}$[c,d] |
|---|---|---|---|
| 83.22 | | ++++ | +++++ | or or or

TABLE 32-continued

Assay Data For Human GPR40

| No. | Structure | AequorinEC$_{50}$$^{b,c}$ | IP3 EC$_{50}$$^{c,d}$ |
|---|---|---|---|
| 83.23 | | +++ | ND | or or or

TABLE 32-continued
Assay Data For Human GPR40
| No. | Structure | AequorinEC$_{50}$[b,c] | IP3 EC$_{50}$[c,d] |
|---|---|---|---|
| 83.24 | Diastereomer of 83.20 | +++ | ++++ |
| 83.25 | | +++ | ++++ |
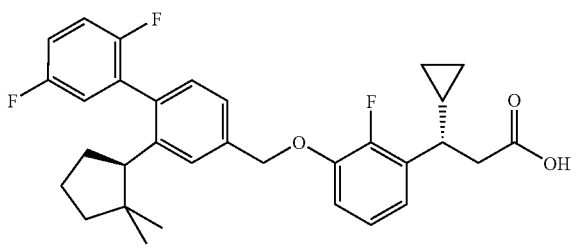
or
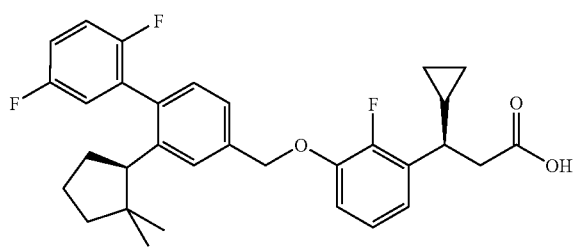
or
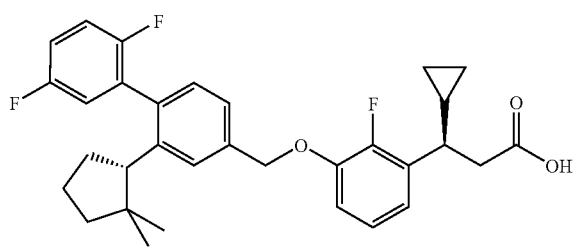

TABLE 32-continued
Assay Data For Human GPR40
| No. | Structure[a] | AequorinEC$_{50}$[b,c] | IP3 EC$_{50}$[c,d] |
|---|---|---|---|
| 83.26 | 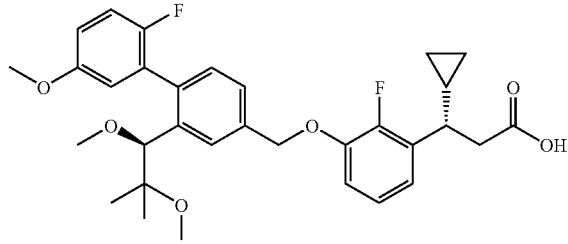
or
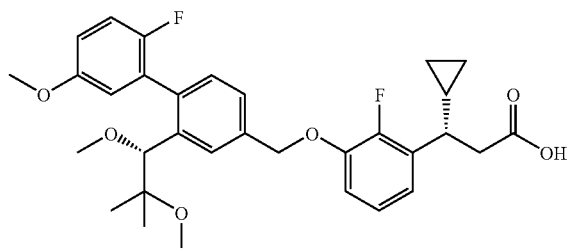
or
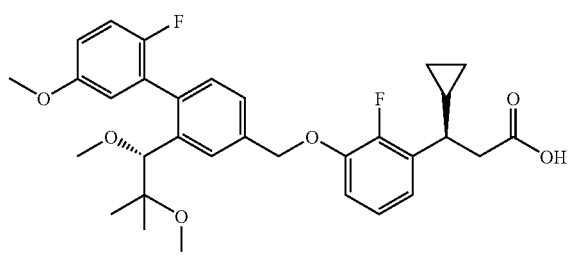
or
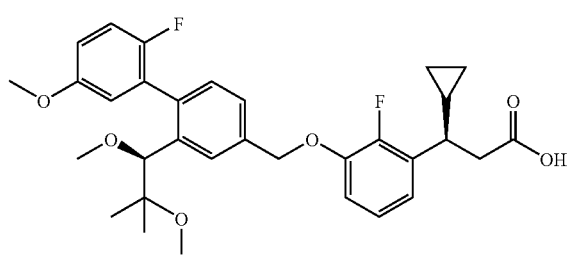 | +++ | ++++ |

TABLE 32-continued

Assay Data For Human GPR40

| No. | Structure[a] | AequorinEC$_{50}$[b,c] | IP3 EC$_{50}$[c,d] |
|---|---|---|---|
| 83.27 | | +++ | ++++ | or or or

TABLE 32-continued
Assay Data For Human GPR40
| No. | Structure | AequorinEC$_{50}$[b,c] | IP3 EC$_{50}$[c,d] |
|---|---|---|---|
| 83.28 |  or  or  or  | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 83.29 | 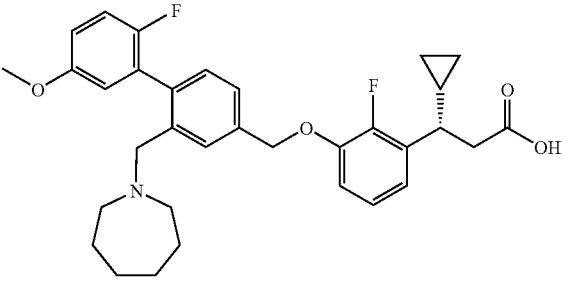<br>Or<br>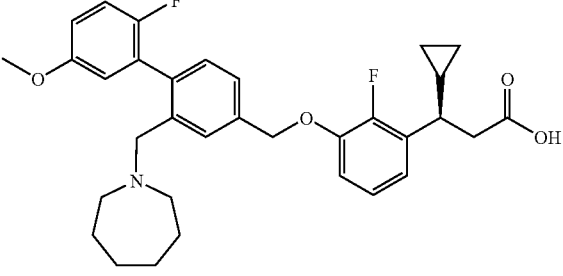 | ++ | +++ |
| 83.30 | 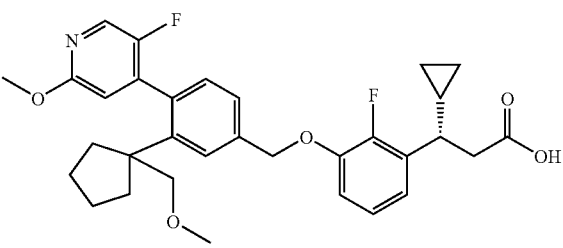<br>or<br>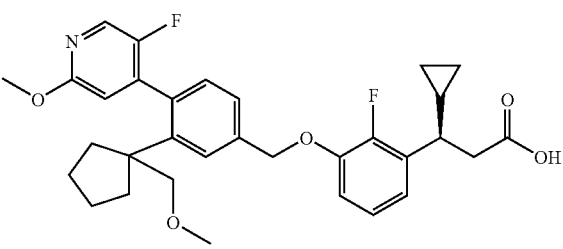 | ++ | ND |
| 83.31 | Diastereomer of 83.22 | ++ | ND |
| 83.32 | Diastereomer of 83.21 | ++ | ND |
| 83.33 | Diastereomer of 83.26 | ++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 83.34 | | ++++ | +++++ | or or or

TABLE 32-continued
Assay Data For Human GPR40
| No. | Structure[a] | AequorinEC$_{50}$[b,c] | IP3 EC$_{50}$[c,d] |
|---|---|---|---|
| 84.1 | 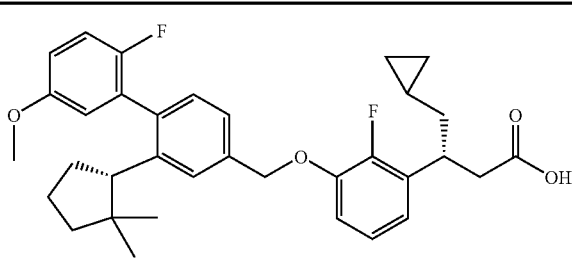 or 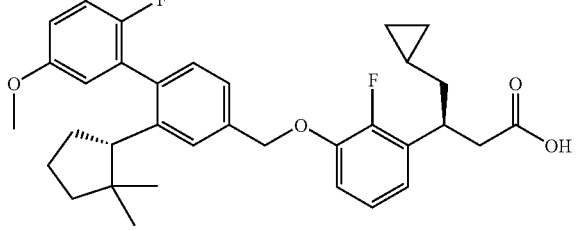 or 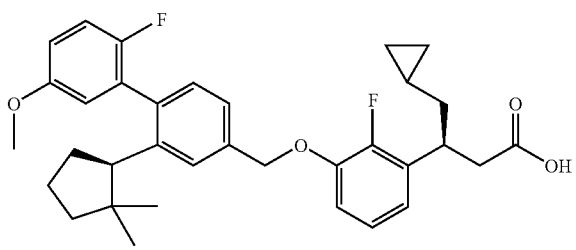 or 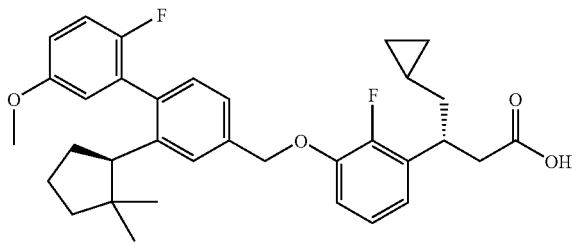 or | +++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 84.2 | 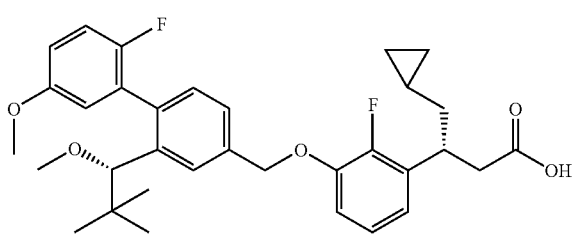 or 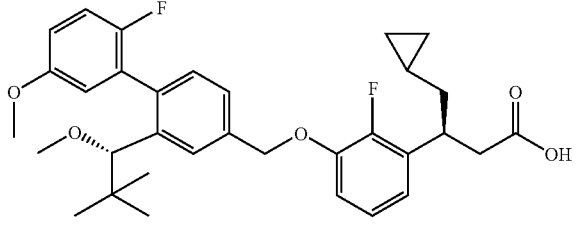 or 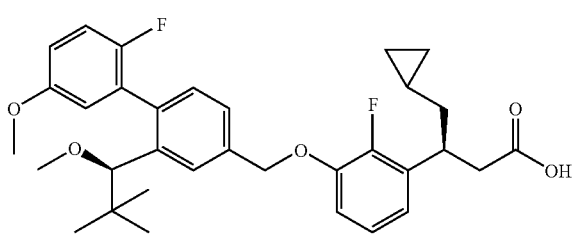 or 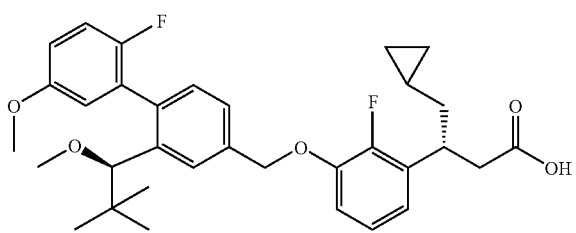 | +++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 84.3 | 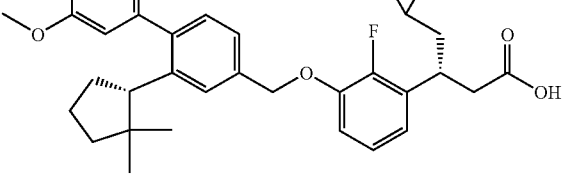 or  or 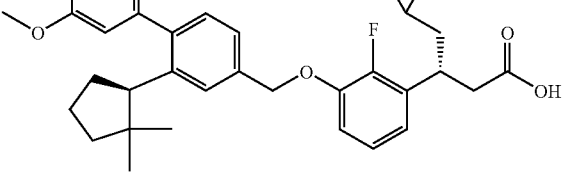 or  | +++ | +++++ |

TABLE 32-continued
Assay Data For Human GPR40
| No. | Structure | AequorinEC$_{50}$[b,c] | IP3 EC$_{50}$[c,d] |
|---|---|---|---|
| 84.4 | 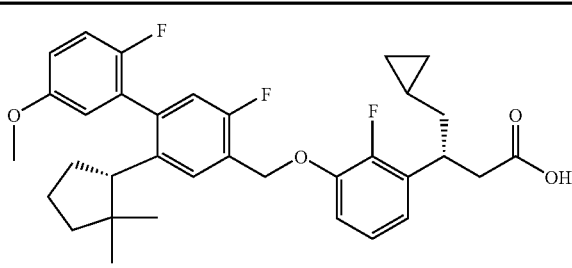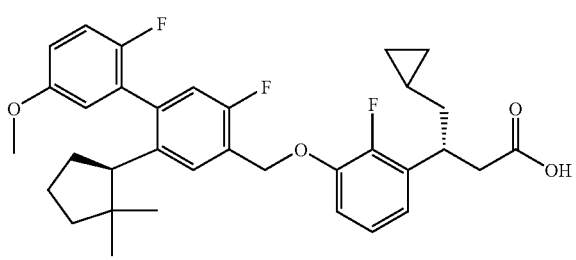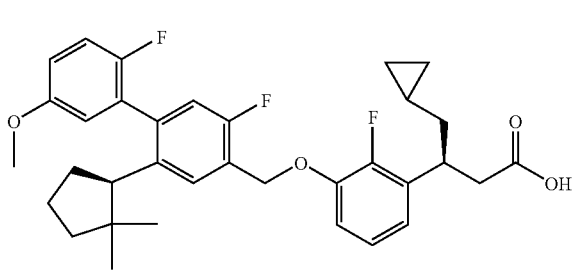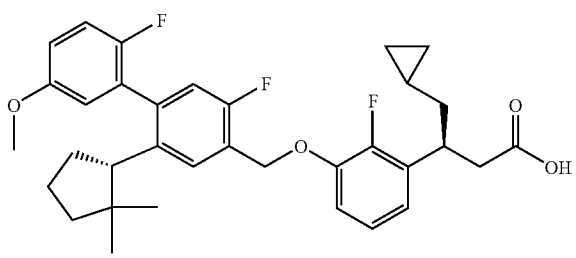 or ... or ... or | +++ | +++++ |

TABLE 32-continued

Assay Data For Human GPR40

| No. | Structure[a] | AequorinEC$_{50}$[b,c] | IP3 EC$_{50}$[c,d] |
|---|---|---|---|
| 84.5 | | +++ | ++++ |
| 84.6 | | +++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 84.7 | 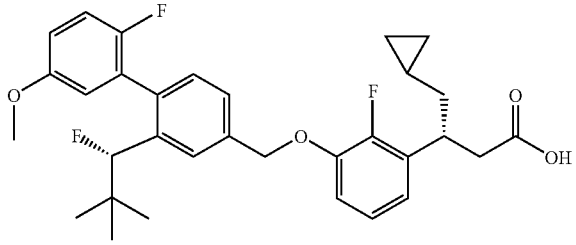 or 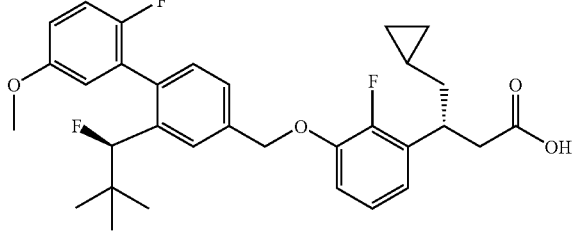 or 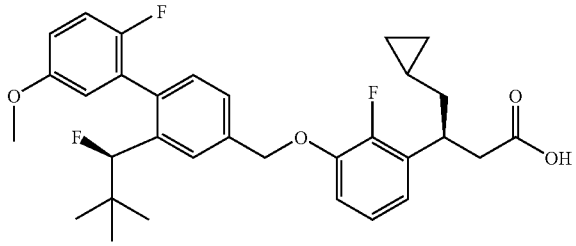 or 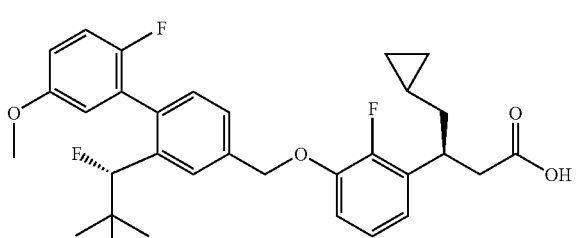 | ++++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 84.8 | 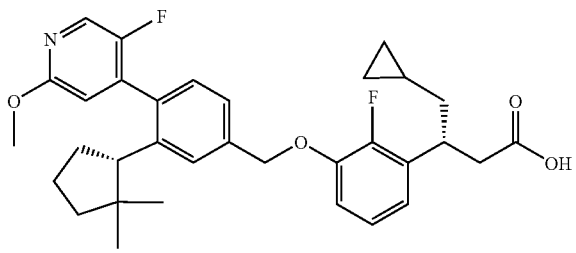<br>or<br>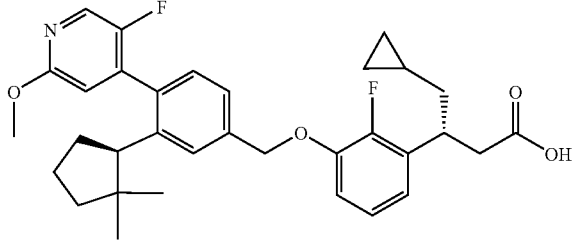<br>or<br>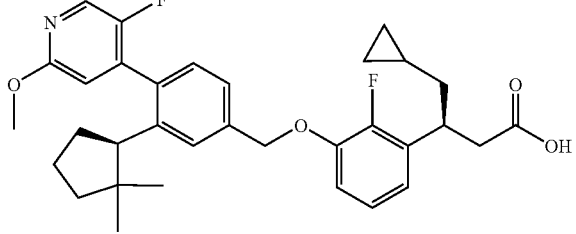<br>or<br>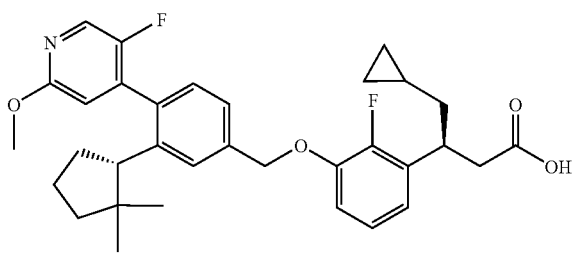 | +++ | +++++ |

TABLE 32-continued

Assay Data For Human GPR40

| No. | Structure[a] | AequorinEC$_{50}$[b,c] | IP3 EC$_{50}$[c,d] |
|---|---|---|---|
| 84.9 | | +++ | +++++ |
| | or | | |
| | or | | |
| | or | | |
| | | | |
| 85.1 | | +++ | +++ |

TABLE 32-continued

Assay Data For Human GPR40

| No. | Structure[a] | AequorinEC$_{50}$[b,c] | IP3 EC$_{50}$[c,d] |
|---|---|---|---|
| 85.2 | | +++ | ++++ |
| 85.3 | | +++ | ++++ |
| | | | |
| 85.4 | or | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 85.5 | 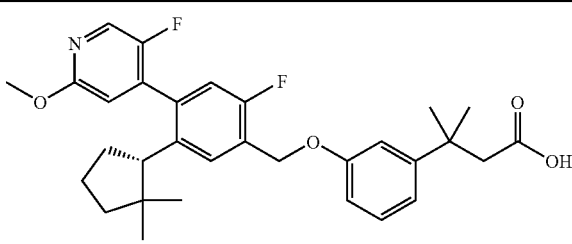 or 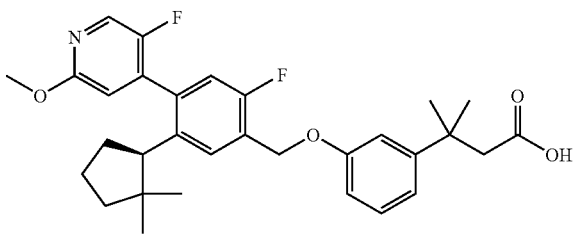 | +++ | ++++ |
| 85.6 | 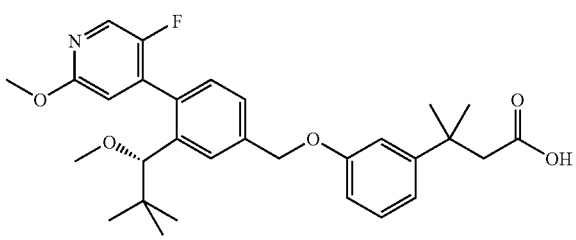 or 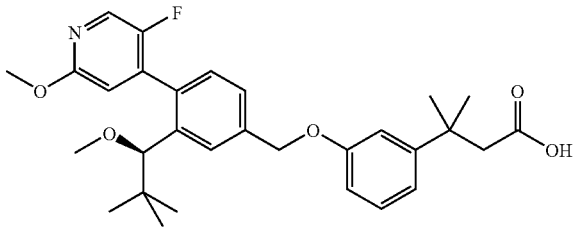 | +++ | ++++ |
| 86.1 | 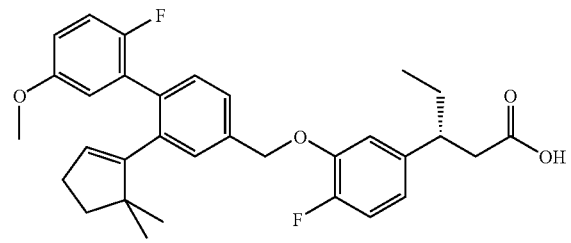 or 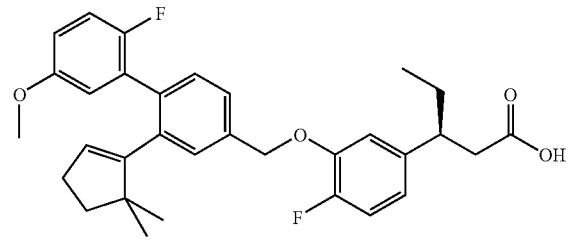 | +++ | +++ |

TABLE 32-continued
Assay Data For Human GPR40
| No. | Structure[a] | AequorinEC$_{50}$[b,c] | IP3 EC$_{50}$[c,d] |
|---|---|---|---|
| 86.2 | 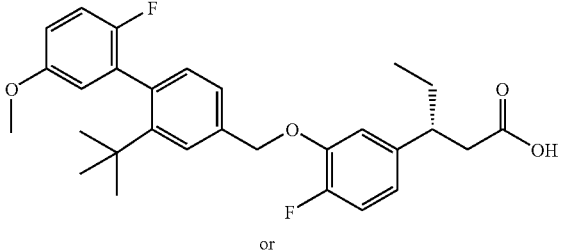 or 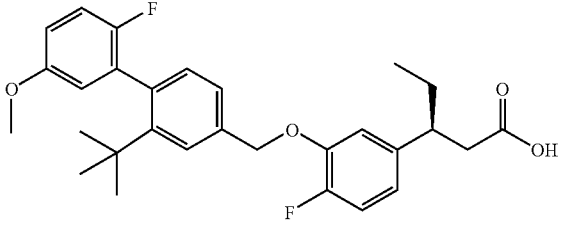 | ++ | ND |
| 87 | 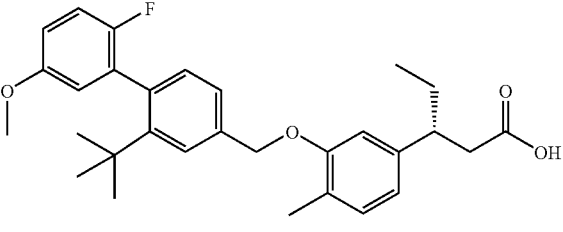 or 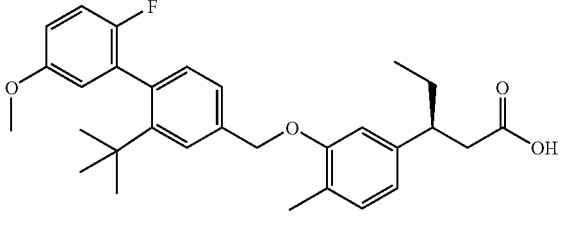 | +++ | +++ |

TABLE 32-continued
Assay Data For Human GPR40
| No. | Structure[a] | AequorinEC$_{50}$[b,c] | IP3 EC$_{50}$[c,d] |
|---|---|---|---|
| 88.1 | 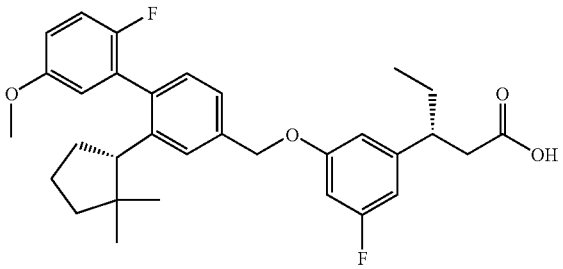<br>or<br>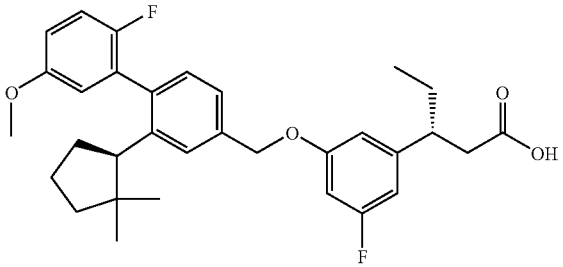<br>or<br>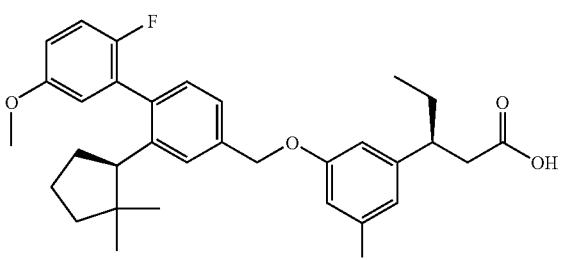<br>or<br>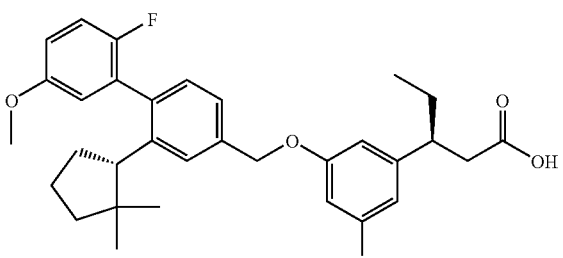 | ++++ | +++++ |

TABLE 32-continued

Assay Data For Human GPR40

| No. | Structure[a] | AequorinEC$_{50}$[b,c] | IP3 EC$_{50}$[c,d] |
|---|---|---|---|
| 88.2 | (structures) | +++ | ++++ |
| 88.3 | (structures) | +++ | +++++ |

TABLE 32-continued

Assay Data For Human GPR40

| No. | Structure[a] | AequorinEC$_{50}$[b,c] | IP3 EC$_{50}$[c,d] |
|---|---|---|---|
| 88.4 | | +++ | +++++ | or or or

TABLE 32-continued
Assay Data For Human GPR40
| No. | Structure[a] | AequorinEC$_{50}$[b,c] | IP3 EC$_{50}$[c,d] |
|---|---|---|---|
| 89.1 | 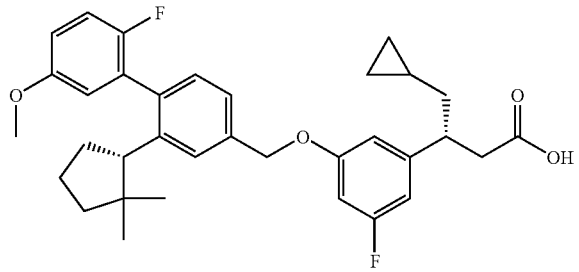 or 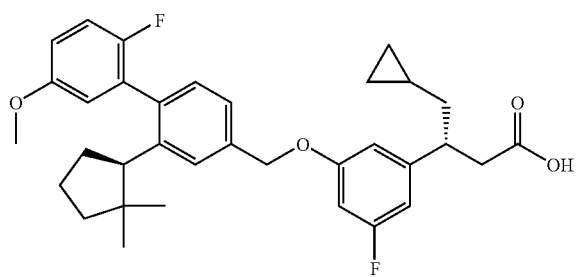 or 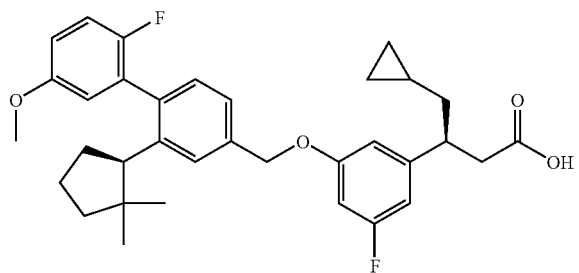 or 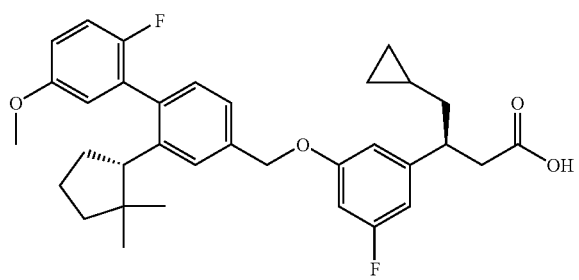 | ++++ | +++++ |

TABLE 32-continued
Assay Data For Human GPR40
| No. | Structure[a] | AequorinEC$_{50}$[b,c] | IP3 EC$_{50}$[c,d] |
|---|---|---|---|
| 89.2 | 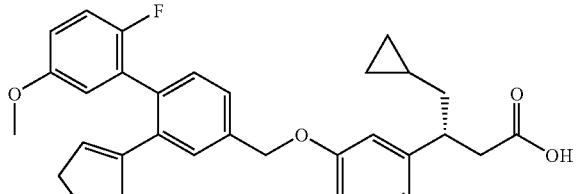 or 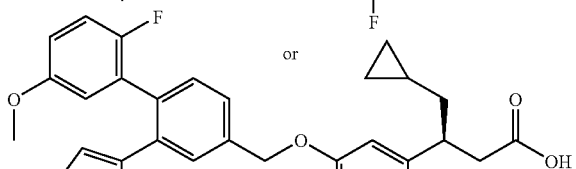 | +++ | ++++ |
| 89.3 | 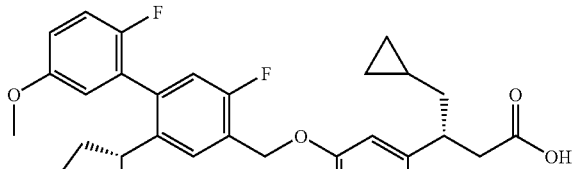 or 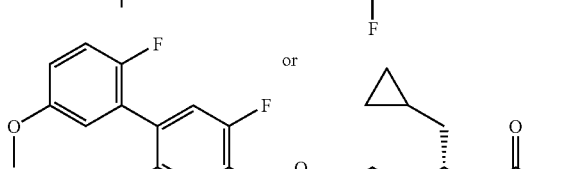 or 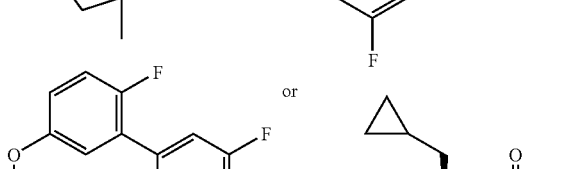 or 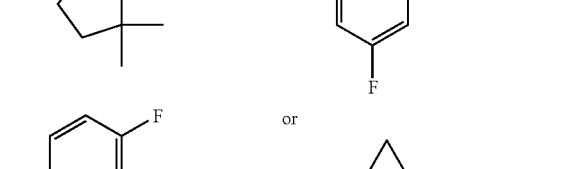 | +++ | +++++ |

TABLE 32-continued
Assay Data For Human GPR40
| No. | Structure | AequorinEC$_{50}$[b,c] | IP3 EC$_{50}$[c,d] |
|---|---|---|---|
| 89.4 | 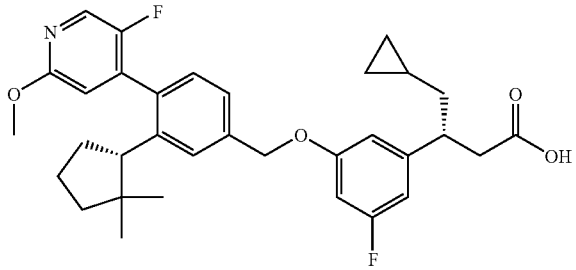<br>or<br>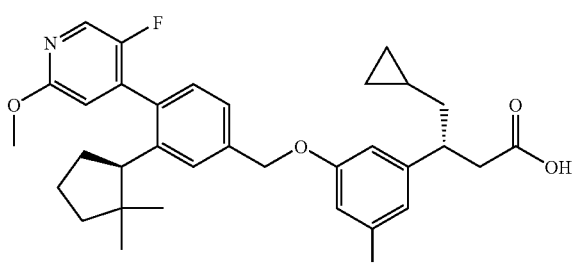<br>or<br>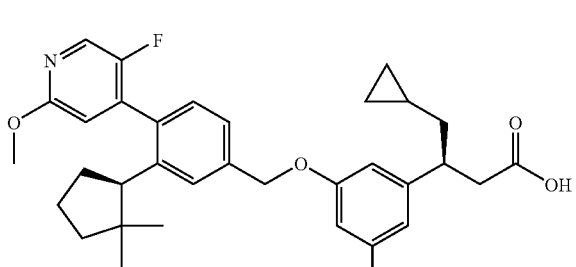<br>or<br>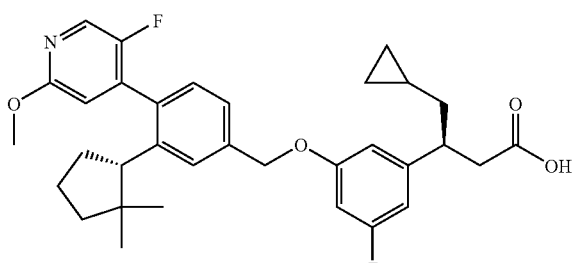 | +++ | +++++ |

TABLE 32-continued
Assay Data For Human GPR40
| No. | Structure | AequorinEC$_{50}$[b,c] | IP3 EC$_{50}$[c,d] |
|---|---|---|---|
| 90.1 | 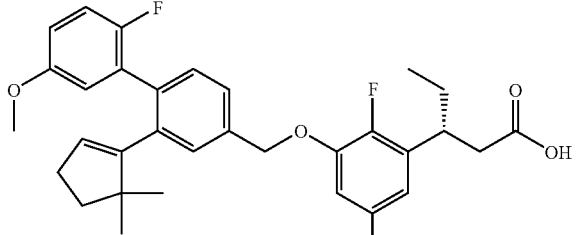 or 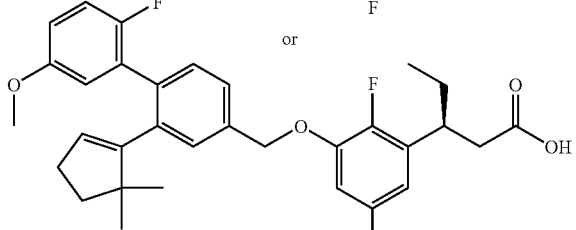 | +++ | ++++ |
| 90.2 | 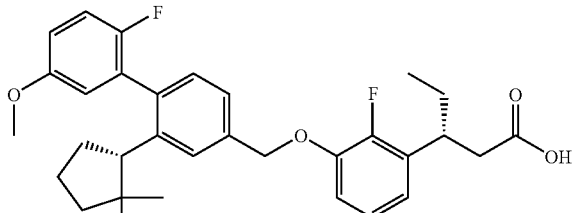 or 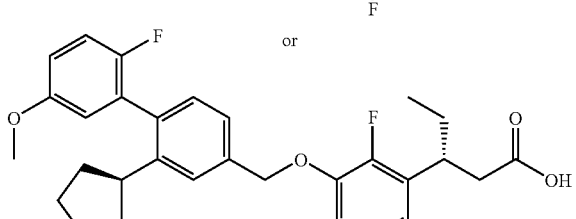 or 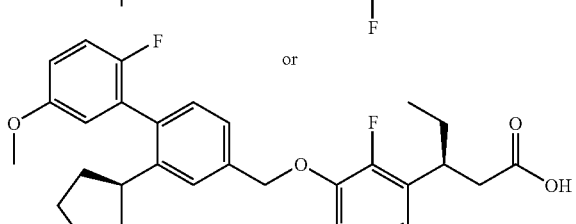 or 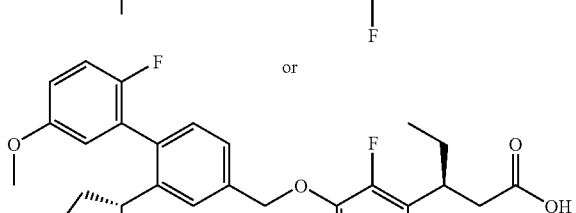 | +++ | +++++ |

TABLE 32-continued
Assay Data For Human GPR40
| No. | Structure | AequorinEC$_{50}$$^{b,c}$ | IP3 EC$_{50}$$^{c,d}$ |
|---|---|---|---|
| 90.3 | 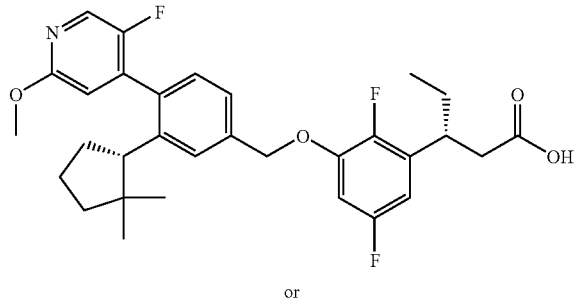<br>or<br>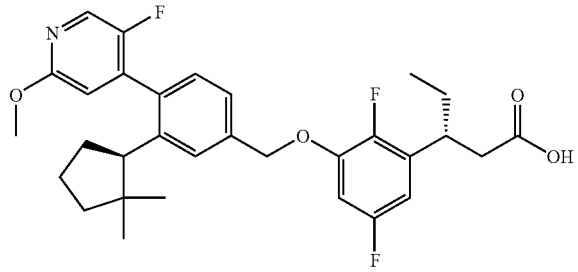<br>or<br>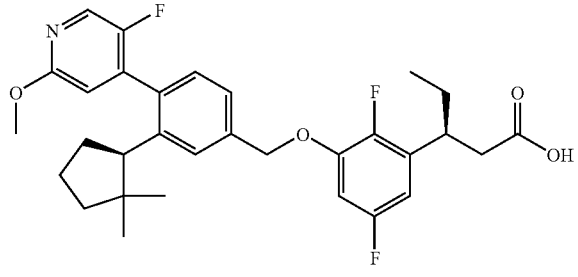<br>or<br>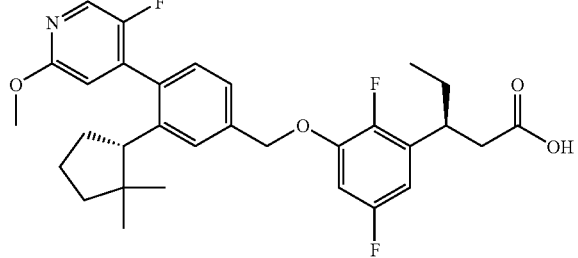 | +++ | +++++ |

TABLE 32-continued
Assay Data For Human GPR40
| No. | Structure | AequorinEC$_{50}$$^{b,c}$ | IP3 EC$_{50}$$^{c,d}$ |
|---|---|---|---|
| 91 | 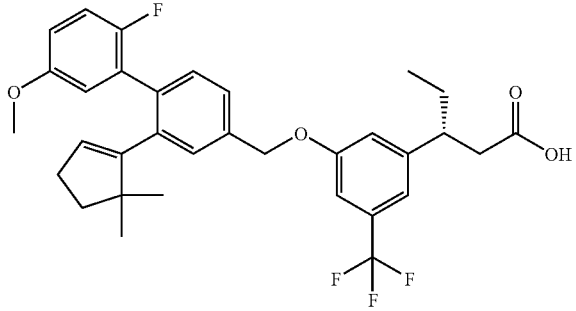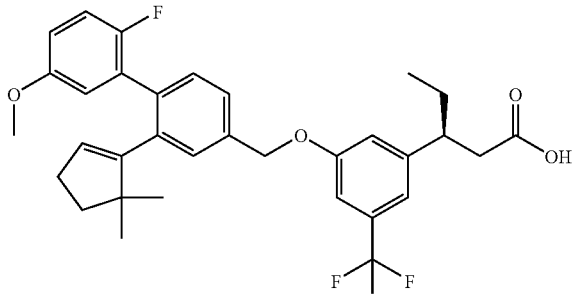or | +++ | ++++ |
| 92 | 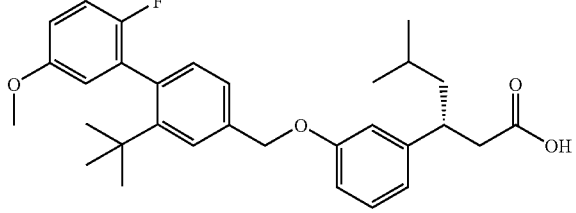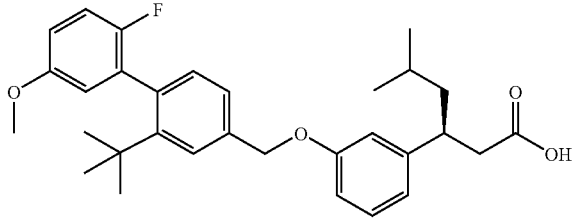or | ++ | ND |

TABLE 32-continued
Assay Data For Human GPR40
| No. | Structure | AequorinEC$_{50}$[b,c] | IP3 EC$_{50}$[c,d] |
|---|---|---|---|
| 93.1 | 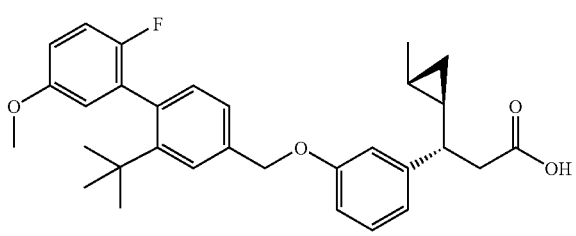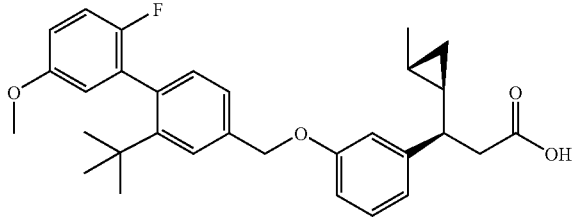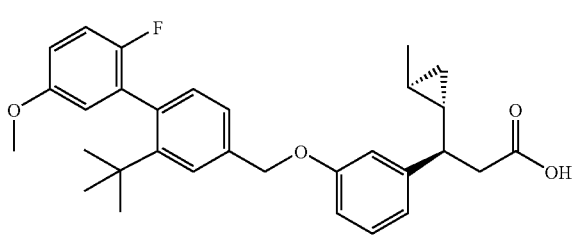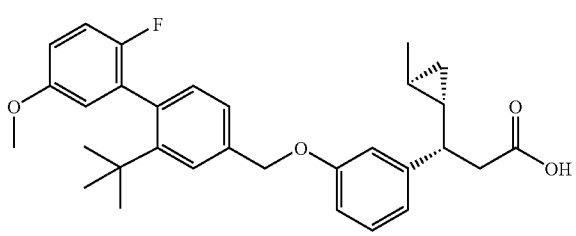 or ... or ... or ... | +++ | ++++ |

TABLE 32-continued
Assay Data For Human GPR40
| No. | Structure[a] | AequorinEC$_{50}$[b,c] | IP3 EC$_{50}$[c,d] |
|---|---|---|---|
| 93.2 | 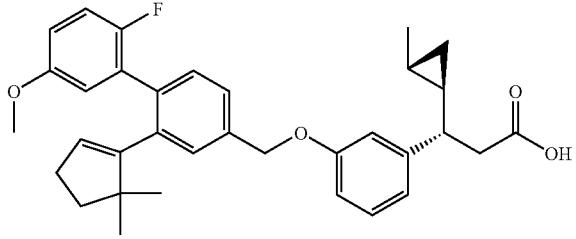 or 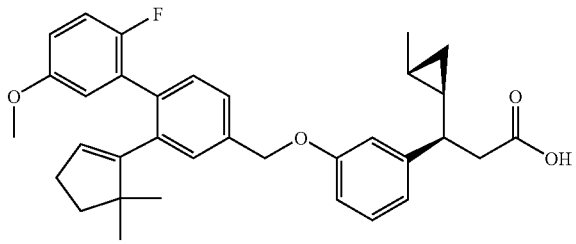 or 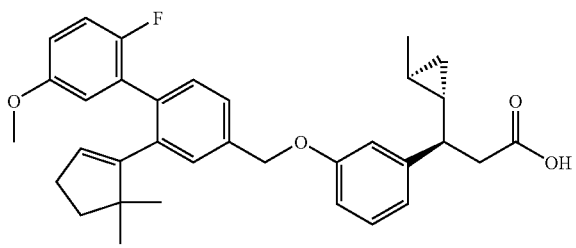 or 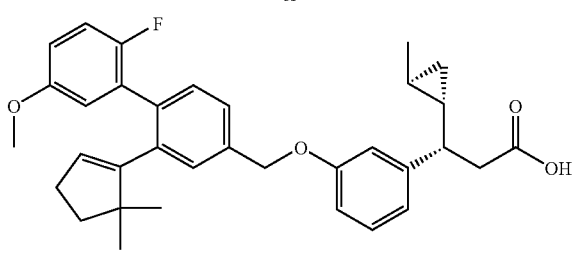 | +++ | ++++ |
| 94.1 | 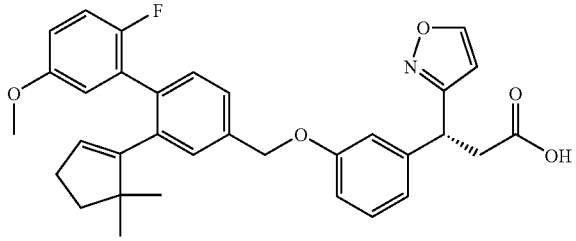 | ++ | ND |
| 94.2 | 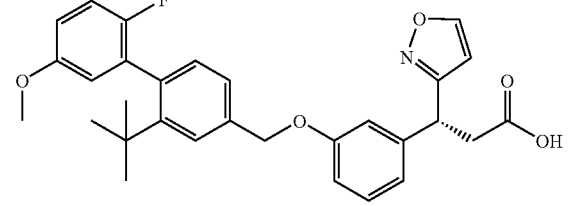 | ++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 95 | | +++ | +++ |
| 96 | | ++ | ND |
| 97.1 | Enantiomer of 14 | ++ | ND |
| 97.2 | | ++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 97.3 | Diastereomer of 97.2 | +++ | ++++ |
| 98.1 | (four possible stereoisomer structures shown, connected by "or") | +++ | ND |

TABLE 32-continued
Assay Data For Human GPR40
| No. | Structure[a] | AequorinEC$_{50}$[b,c] | IP3 EC$_{50}$[c,d] |
|---|---|---|---|
| 98.2 | Diastereomer of 98.1 | ++ | ND |
| 99.1 | 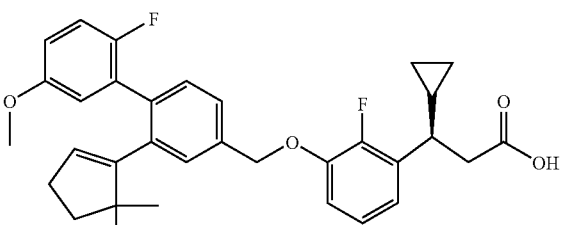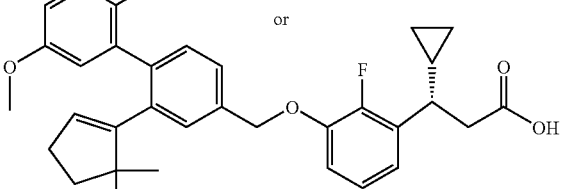 | ++ | ND |
| 99.2 | 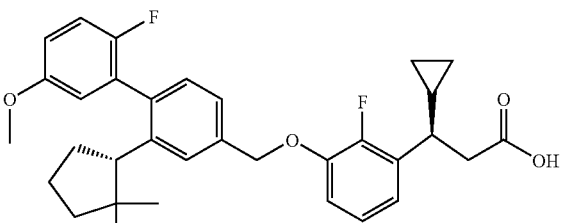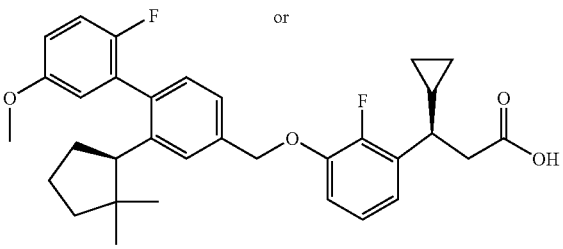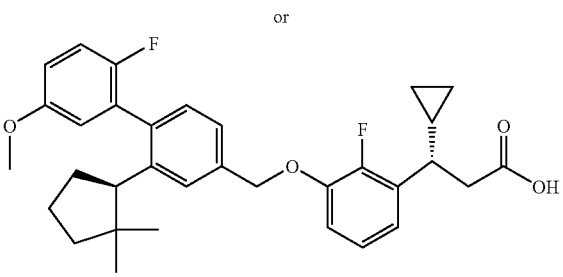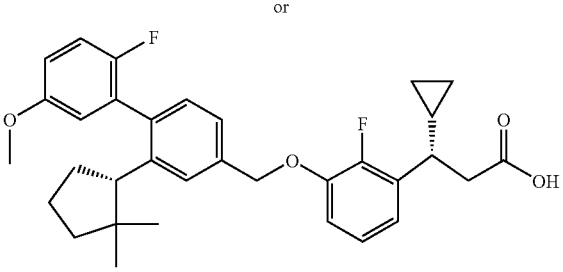 | +++ | ++++ |
or
or
or TABLE 32-continued Assay Data For Human GPR40

| No. | Structure | AequorinEC$_{50}$[b,c] | IP3 EC$_{50}$[c,d] |
|---|---|---|---|
| 99.3 | Diastereomer of 99.2 | ++ | ND |
| 100.1 | (structure) | ++ | ND |

TABLE 32-continued

Assay Data For Human GPR40

| No. | Structure[a] | AequorinEC$_{50}$[b,c] | IP3 EC$_{50}$[c,d] |
|---|---|---|---|
| 100.2 | Diastereomer of 100.1 | +++ | ND |
| 101.1 | *(structure)* | ++ | ND |
| 101.2 | *(structure)* | +++ | ND |

TABLE 32-continued
Assay Data For Human GPR40
| No. | Structure | AequorinEC$_{50}$$^{b,c}$ | IP3 EC$_{50}$$^{c,d}$ |
|---|---|---|---|
| 102 | 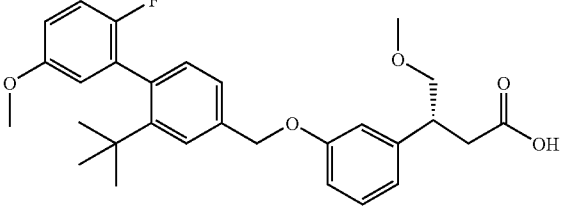 or 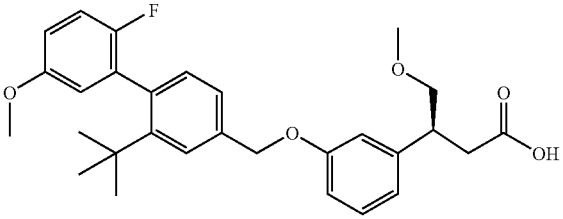 | +++ | ND |
| 103 | 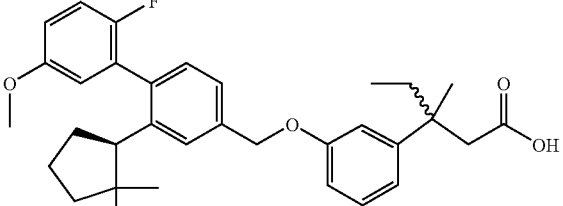 or 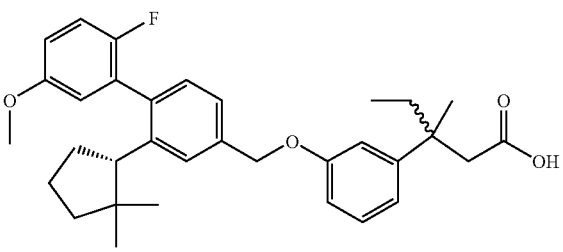 | +++ | ++++ |
| 104 | 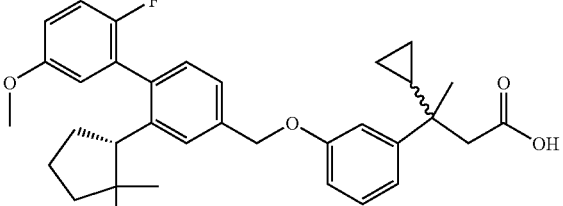 or 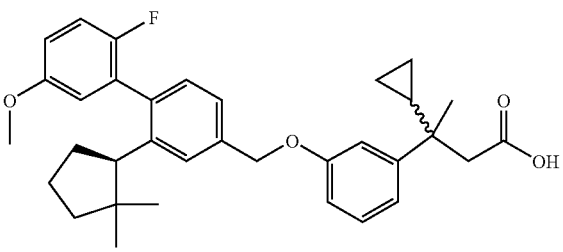 | +++ | ++++ |

TABLE 32-continued

Assay Data For Human GPR40

| No. | Structure[a] | AequorinEC$_{50}$[b,c] | IP3 EC$_{50}$[c,d] |
|---|---|---|---|
| 105.1 | 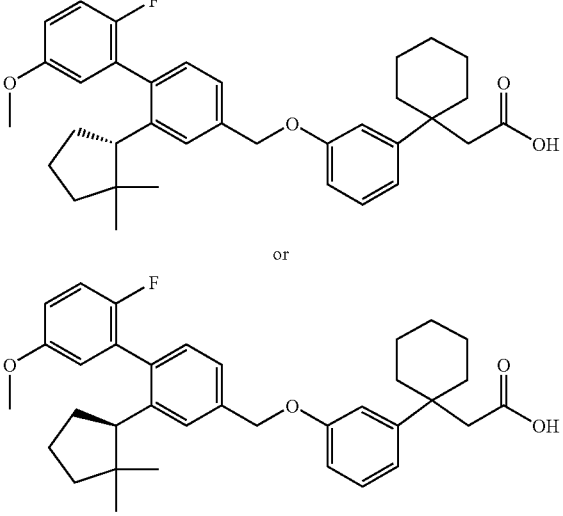 or 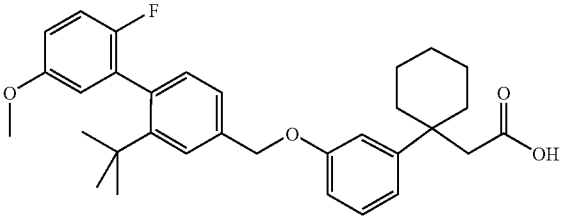 | +++ | ++++ |
| 105.2 | 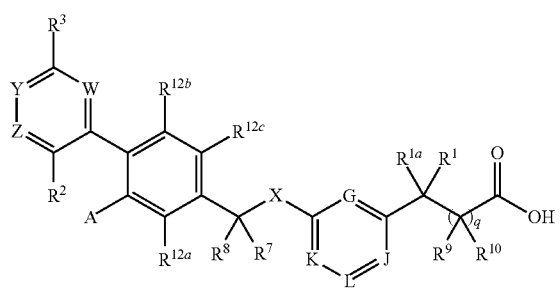 | ++ | ND |

[a]When present, the "〰" bond indicates a mixture of stereoisomers are present in the exemplary compound or indicates a mixture of cis and trans isomers when attached to a double bond.
[b]Aequorin assay data
[c]EC$_{50}$ Ranges:
+ EC$_{50}$ > 10 μM
++ 1 μM ≤ EC$_{50}$ ≤ 10 μM
+++ 0.1 μM ≤ EC$_{50}$ < 1 μM
++++ 0.01 μM ≤ EC$_{50}$ < 0.1 μM
+++++ EC$_{50}$ < 0.01 μM
[d]Inositol phosphate assay data
[e]ND means not determined

What is claimed:

1. A compound of formula I:

I or a pharmaceutically acceptable salt, stereoisomer, $C_1$-$C_6$ alkyl ester, or a mixture thereof, wherein
G is selected from N or $CR^{11a}$;
J is selected from N or $CR^{11b}$;
L is selected from N or $CR^{11c}$;
K is selected from N or $CR^{11d}$;
wherein 0 or 1 of G, J, L, and K is N;
A is selected from —($C_1$-$C_{12}$)alkyl; —($C_2$-$C_{12}$)alkenyl; —($C_1$-$C_{12}$)alkyl-O—($C_1$-$C_4$)alkyl; —($C_1$-$C_{12}$)alkyl-OH; —($C_1$-$C_{12}$)alkyl-O—($C_2$-$C_4$)alkenyl; —($C_2$-$C_{12}$)alkenyl-O—($C_1$-$C_4$)alkyl; —($C_2$-$C_{12}$)alkenyl-OH; —($C_2$-$C_{12}$)alkenyl-O—($C_2$-$C_4$)alkenyl; —O—($C_1$-$C_{12}$)alkyl; —O—($C_2$-$C_{12}$)alkenyl; —O—($C_1$-$C_4$)alkyl-aryl; —S—($C_1$-$C_{12}$)alkyl; —S—($C_2$-$C_{12}$)alkenyl; —S(O)—($C_1$-$C_{12}$)alkyl; —S(O)—($C_2$-$C_{12}$)alkenyl; —S(O)$_2$—($C_1$-$C_{12}$)alkyl; —S(O)$_2$—($C_2$-$C_{12}$)alkenyl; a heterocycle comprising 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$)alkyl groups; a —($C_1$-$C_4$)alkyl-heterocyclyl wherein the heterocyclyl of the —($C_1$-$C_4$)alkyl-heterocyclyl comprises 4 to 7 ring members of which 1 or 2 are heteroatoms selected from N, O, or S wherein the heterocycle has 0 or 1 double bond between ring members and is unsubstituted or is substituted with from 1 to 4 ($C_1$-$C_2$)alkyl groups; or a —O-heterocyclyl wherein the heterocyclyl of the —O-heterocyclyl comprises 4 to 7 ring members of which 1 or 2 are heteroatoms selected from N, O, or S, wherein the heterocycle has 0 or 1 double bond between ring members and is unsubstituted or is substituted with from 1 to 4 ($C_1$-$C_2$) alkyl groups; further wherein the alkyl and alkenyl groups of —($C_1$-$C_{12}$)alkyl, —($C_2$-$C_{12}$)alkenyl, —($C_1$-$C_{12}$)alkyl-O—($C_1$-$C_4$)alkyl, —($C_1$-$C_{12}$)alkyl-O—H, —($C_1$-$C_{12}$)alkyl-O—($C_2$-$C_4$)alkenyl, —($C_2$-$C_{12}$)alkenyl-O—($C_1$-$C_4$)alkyl, —($C_2$-$C_{12}$)alkenyl-OH, —($C_2$-$C_{12}$)alkenyl-O—($C_2$-$C_4$)alkenyl, —O—($C_1$-$C_{12}$)alkyl, —O—($C_2$-$C_{12}$)alkenyl, and —O—($C_1$-$C_4$)alkyl-aryl are unsubstituted or are substituted with from 1 to 4 substituents selected from —F, —Cl, —OH, (=O), —$NH_2$, NH($C_1$-$C_4$)alkyl, —N(($C_1$-$C_4$)alkyl)$_2$, aryl, unsubstituted —($C_1$-$C_2$)alkyl, or unsubstituted —O—($C_1$-$C_2$)alkyl;

X is O, S, or $NR^a$ wherein $R^a$ is selected from —H or —($C_1$-$C_6$) alkyl groups;

W, Y, and Z are selected from N or $CR^{13}$; wherein 0, 1, or 2 of W, Y, and Z is N; and further wherein Z is not N if $R^2$ is —F;

$R^1$ is selected from —H, —($C_1$-$C_6$)alkyl, —($C_2$-$C_6$)alkenyl, —($C_2$-$C_6$)alkynyl, —($C_1$-$C_4$)alkyl-O—($C_1$-$C_4$) alkyl, heterocyclyl, aryl, or heteroaryl;

$R^{1a}$ is selected from —H and —($C_1$-$C_4$)alkyl;

or $R^1$ and $R^{1a}$ may join together to form a 3 to 7 membered ring with 0, 1, or 2 heteroatoms selected from O, N, or S;

$R^2$ is selected from —H, —F, —$CF_3$, or —O—($C_1$-$C_6$) alkyl;

$R^3$ is —H, —F, —Cl, —OH, —($C_1$-$C_4$)alkyl, —O—($C_1$-$C_3$)alkyl, or —S—($C_1$-$C_2$)alkyl;

$R^7$ and $R^8$ are independently selected from —H and —($C_1$-$C_4$)alkyl;

$R^9$ and $R^{10}$ are independently selected from —H and —($C_1$-$C_4$)alkyl;

each of $R^{11a}$, $R^{11b}$, $R^{11c}$, and $R^{11d}$ is independently selected from —H, —F, —Cl, —($C_1$-$C_4$)alkyl, or —O($C_1$-$C_4$)alkyl; and $R^{11a}$ is absent if G is N; $R^{11b}$ is absent if J is N, $R^{11c}$ is absent if L is N; or $R^{11d}$ is absent if K is N;

each of $R^{12a}$, $R^{12b}$, and $R^{12c}$ is independently selected from —H, —F, —Cl, —($C_1$-$C_4$)alkyl, or —O($C_1$-$C_4$)alkyl;

$R^{13}$ is selected from —H, —F, —($C_1$-$C_4$)alkyl, and —O—($C_1$-$C_4$)alkyl; and q is 1 or 2.

2. The compound of claim 1, wherein X is O.

3. The compound of claim 1, wherein G is $CR^{11a}$; J is $CR^{11b}$; L is $CR^{11c}$; and K is $CR^{11d}$.

4. The compound of claim 1, wherein $R^3$ is selected from —OH, —O($C_1$-$C_2$)alkyl, or —S($C_1$-$C_2$)alkyl.

5. The compound of claim 4, wherein $R^3$ is methoxy.

6. The compound of claim 1, wherein $R^3$ is selected from —F, —Cl, —$OCHF_2$, —$OCH_2CF_3$, —$OCF_3$, —O-cyclopropyl, —$CF_3$, or —$CHF_2$.

7. The compound of claim 1, wherein $R^2$ is selected from —F, —$CF_3$, or ($C_1$-$C_6$)alkoxy.

8. The compound of claim 1, wherein q is 1.

9. The compound of claim 1, wherein $R^{1a}$ is H.

10. The compound of claim 1, wherein W, Y, and Z are all C—H; or W and Z are C—H and Y is N.

11. The compound of claim 1, wherein A is selected from ($C_3$-$C_{10}$)alkyl or ($C_4$-$C_{10}$)alkenyl.

12. The compound of claim 1, wherein A is a group of formula A'

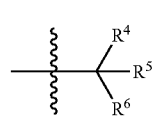

where the wavy line indicates the point of attachment; and $R^4$, $R^5$, and $R^6$ are independently selected from H, F, and ($C_1$-$C_4$)alkyl, wherein at least two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring.

13. The compound of claim 1, wherein A is selected from —($C_4$-$C_{12}$)alkyl, —($C_4$-$C_{12}$)alkenyl, —($C_3$-$C_{12}$)alkyl-O—($C_1$-$C_4$)alkyl, —($C_3$-$C_{12}$)alkyl-OH, —($C_3$-$C_{12}$)alkenyl-O—($C_1$-$C_4$)alkyl, —($C_3$-$C_{12}$)alkenyl-OH, —O—($C_4$-$C_{12}$)alkyl, —O—($C_4$-$C_{12}$)alkenyl, a heterocycle comprising 4 to 7 ring members of which 1 or 2 are heteroatoms selected from N or O, wherein the heterocycle has 0 or 1 double bond between ring members and is unsubstituted or is substituted with from 1 to 4 ($C_1$-$C_2$)alkyl groups, a —($C_1$-$C_4$)alkyl-heterocyclyl wherein the heterocyclyl of the —($C_1$-$C_4$)alkyl-heterocyclyl comprises 4 to 7 ring members of which 1 or 2 are heteroatoms selected from N or O, wherein the heterocycle has 0 or 1 double bond between ring members and is unsubstituted or is substituted with from 1 to 4 ($C_1$-$C_2$)alkyl groups, or a —O-heterocyclyl wherein the heterocyclyl of the —O-heterocyclyl comprises 4 to 7 ring members of which 1 or 2 are heteroatoms selected from N or O, wherein the heterocycle has 0 or 1 double bond between ring members and is unsubstituted or is substituted with from 1 to 4 ($C_1$-$C_2$)alkyl groups, further wherein the alkyl and alkenyl groups of —($C_4$-$C_{12}$) alkyl, —($C_4$-$C_{12}$)alkenyl, —($C_3$-$C_{12}$)alkyl-O—($C_1$-$C_4$) alkyl, —($C_3$-$C_{12}$)alkyl-O—H, —($C_3$-$C_{12}$)alkenyl-O—($C_1$-$C_4$)alkyl, —($C_3$-$C_{12}$)alkenyl-OH, —O—($C_4$-$C_{12}$)alkyl, or —O—($C_4$-$C_{12}$)alkenyl are unsubstituted or are substituted with from 1 to 4 substituents selected from —F, —Cl, —OH, (=O), —$NH_2$, NH($C_1$-$C_4$)alkyl, —N(($C_1$-$C_4$)alkyl)$_2$, aryl, unsubstituted —O—($C_1$-$C_2$)alkyl, unsubstituted —($C_1$-$C_2$) alkyl.

14. The compound of claim 13, wherein A is a —($C_4$-$C_8$) alkyl-O—($C_1$-$C_2$)alkyl, —($C_4$-$C_8$)alkyl-OH, —($C_4$-$C_8$)alkenyl-O—($C_1$-$C_2$)alkyl, or —($C_4$-$C_8$)alkenyl-OH and each of the alkyl and alkenyl groups of —($C_4$-$C_8$)alkyl-O—($C_1$-$C_2$) alkyl, —($C_4$-$C_8$)alkyl-OH, —($C_4$-$C_8$)alkenyl-O—($C_1$-$C_2$) alkyl, or —($C_4$-$C_8$)alkenyl-OH are unsubstituted or are substituted with 1 to 4 substituents selected from —OH, unsubstituted —O—($C_1$-$C_2$)alkyl, or unsubstituted —($C_1$-$C_2$)alkyl.

15. The compound of claim 1, wherein A is selected from

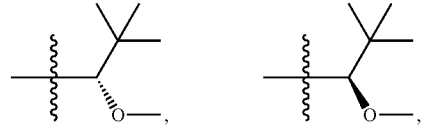

1191
-continued

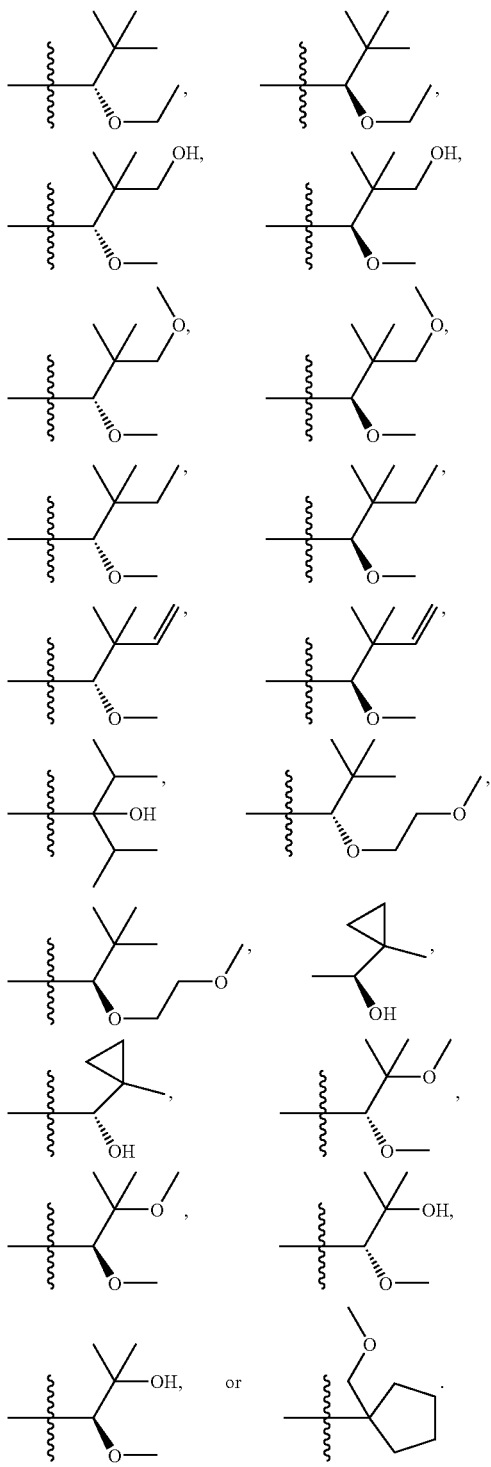

16. The compound of claim 1, wherein A is

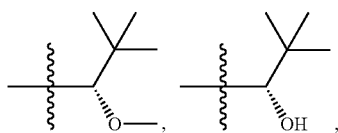

1192
-continued

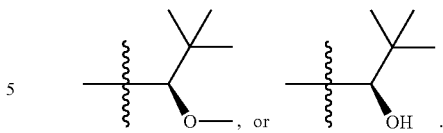

17. The compound of claim 1, wherein A is a ($C_5$-$C_7$) cycloalkyl group or a ($C_5$-$C_7$)cycloalkenyl group optionally substituted with 1, 2, 3, or 4 methyl groups.

18. The compound of claim 1, wherein A has the formula

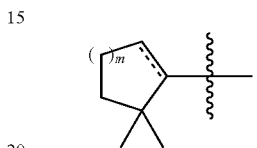

wherein m is 1, 2, or 3, and the dashed line indicates a single or double bond.

19. The compound of claim 18, wherein A has the formula

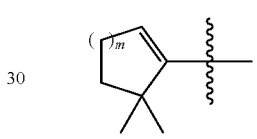

wherein m is 1, 2, or 3.

20. The compound of claim 18, wherein A is selected from

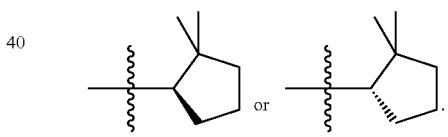

21. The compound of claim 1, wherein $R^2$ is F.

22. The compound of claim 1, wherein $R^7$ and $R^8$ are both H.

23. The compound of claim 1, wherein $R^9$ and $R^{10}$ are both H.

24. The compound of claim 1, wherein $R^1$ is a ($C_1$-$C_4$) alkyl.

25. The compound of claim 24, wherein $R^1$ is a methyl, an ethyl or a propyl.

26. The compound of claim 1, wherein $R^1$ is a —$CH_2$-cyclopropyl, or a cyclopropyl or a cyclobutyl group that is optionally substituted with one or two methyl groups.

27. The compound of claim 1, wherein $R^1$ is a ($C_2$-$C_4$) alkenyl.

28. The compound of claim 1, wherein G is $CR^{11a}$; J is $CR^{11b}$; L is $CR^{11c}$; K is $CR^{11d}$; $R^{11a}$, $R^{11b}$, $R^{11c}$, $R^{11d}$, $R^{12a}$, $R^{12b}$, and $R^{12c}$ are all H; $R^{1a}$ is H; W is C—H; Y, is C—H; Z is C—H; $R^2$ is F; $R^3$ is methoxy; $R^7$ is H; $R^8$ is H; $R^9$ is H; $R^{10}$ is H; X is O, and q is 1.

29. The compound of claim 1, wherein the compound has the formula II

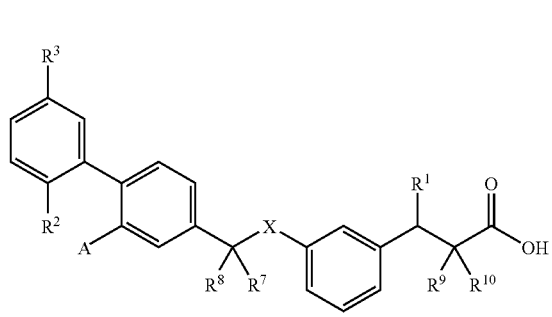

or a pharmaceutically acceptable salt, stereoisomer, $C_1$-$C_6$ alkyl ester, or a mixture thereof.

30. The compound of claim 1, wherein K is N; G is $CR^{11a}$; J is $CR^{11b}$; and L is $CR^{11c}$.

31. The compound of claim 1, wherein G is $CR^{11a}$; J is $CR^{11b}$; L is $CR^{11c}$; K is $CR^{11d}$; $R^{11a}$ is H or F; $R^{11b}$, $R^{11c}$, and $R^{11d}$ are H; $R^{1a}$ is H; W is C—H; Z is C—H; $R^2$ is F; $R^3$ is methoxy; $R^7$ is H; $R^8$ is H; $R^9$ is H; $R^{10}$ is H; X is O; q is 1; and two of $R^{12a}$, $R^{12b}$, and $R^{12c}$ are H and the other of $R^{12a}$, $R^{12b}$, and $R^{12c}$ is F.

32. The compound of claim 1, wherein the compound has the formula III

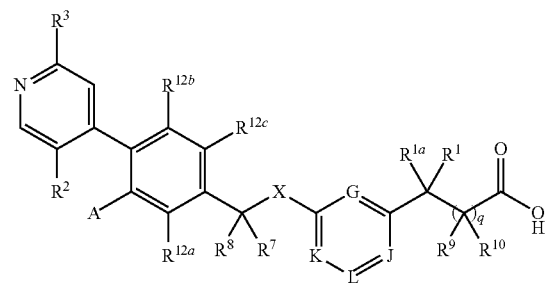

or a pharmaceutically acceptable salt, stereoisomer, $C_1$-$C_6$ alkyl ester, or a mixture thereof.

33. The compound of claim 1, wherein the compound has the formula III'

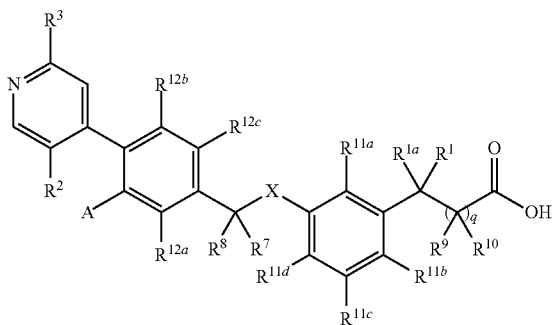

or a pharmaceutically acceptable salt, stereoisomer, $C_1$-$C_6$ alkyl ester, or a mixture thereof.

34. The compound of claim 1, wherein the compound has the formula III"

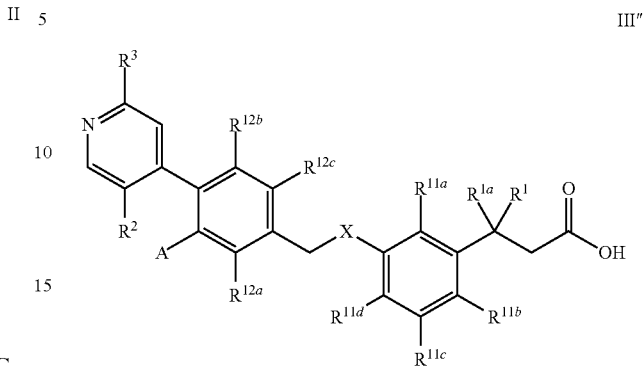

or a pharmaceutically acceptable salt, stereoisomer, $C_1$-$C_6$ alkyl ester, or a mixture thereof.

35. The compound of claim 34, wherein $R^3$ is methoxy.

36. The compound of claim 35, wherein $R^2$ is F.

37. The compound of claim 36, wherein $R^{11a}$ is F, $R^{11b}$ is H, $R^{11c}$ is H, and $R^{11d}$ is H.

38. The compound of claim 36, wherein $R^{11a}$ is H, $R^{11b}$ is H, $R^{11c}$ is H, and $R^{11d}$ is H.

39. The compound of claim 36, wherein $R^{12c}$ is H.

40. The compound of claim 36, wherein $R^{12c}$ is F.

41. The compound of claim 36, wherein $R^{12a}$ is H and $R^{12b}$ is H.

42. The compound of claim 1, wherein the compound is a salt.

43. A pharmaceutical composition, comprising: a pharmaceutically acceptable carrier, diluent, or excipient, and the compound of claim 1.

44. A method for treating a disease or condition, comprising: administering to a subject in need thereof, a therapeutically effective amount of the compound of claim 1, wherein the disease or condition is selected from the group consisting of type II diabetes and hyperglycemia.

45. The method of claim 44, wherein the disease or condition is type II diabetes.

46. The method of claim 44, wherein the compound is administered in combination with a second therapeutic agent.

47. The method of claim 46, wherein the second therapeutic agent is metformin, is a thiazolidinedione, or is a DPP-IV inhibitor.

48. The compound of claim 1, wherein the compound does not displace a compound of the following formula that is bound to the GPR40 receptor:

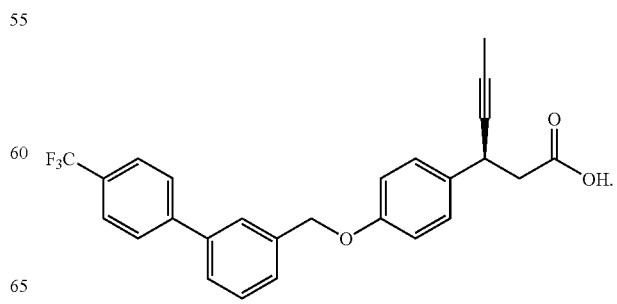

49. A compound of formula I:

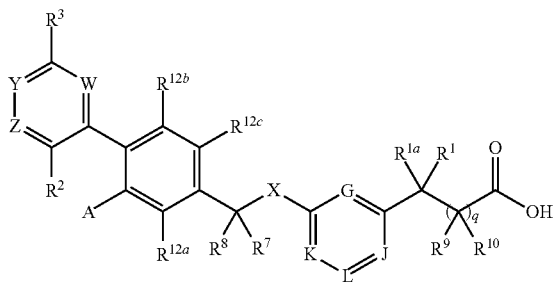

or a pharmaceutically acceptable salt, stereoisomer, $C_1$-$C_6$ alkyl ester, or a mixture thereof,
wherein
G is selected from N or $CR^{11a}$;
J is selected from N or $CR^{11b}$;
L is selected from N or $CR^{11c}$;
K is selected from N or $CR^{11d}$;
wherein 0 or 1 of G, J, L, and K is N;
A is selected from ($C_1$-$C_{12}$)alkyl, ($C_2$-$C_{12}$)alkenyl, —O—($C_1$-$C_{12}$)alkyl, —O—($C_2$-$C_{12}$)alkenyl, —O—($C_1$-$C_4$) alkyl-aryl, or a heterocycle comprising 4 to 7 ring members of which 1 or 2 are heteroatoms selected from N or O, wherein the heterocycle has 0 or 1 double bond between ring members;
X is O or S;
W, Y, and Z are selected from N or $CR^{13}$; wherein 0 or 1 of W, Y, and Z is N; and further wherein Z is not N if $R^2$ is F;
$R^1$ is selected from H, ($C_1$-$C_6$)alkyl, ($C_2$-$C_6$)alkenyl, ($C_2$-$C_6$)alkynyl, —($C_1$-$C_4$)alkyl-O—($C_1$-$C_4$)alkyl, heterocyclyl, aryl, or heteroaryl;
$R^{1a}$ is selected from H and ($C_1$-$C_4$)alkyl;
$R^2$ is selected from H, F, $CF_3$, or ($C_1$-$C_6$)alkoxy;
$R^3$ is H, —OH, —O—($C_1$-$C_2$)alkyl, or —S—($C_1$-$C_2$) alkyl;
$R^7$ and $R^8$ are independently selected from H and ($C_1$-$C_4$) alkyl;
$R^9$ and $R^{10}$ are independently selected from H and ($C_1$-$C_4$) alkyl;
Each of $R^{11a}$, $R^{11b}$, $R^{11c}$, and $R^{11d}$ is independently selected from H, F, Cl, ($C_1$-$C_4$)alkyl, or ($C_1$-$C_4$)alkoxy; and $R^{11a}$ is absent if G is N; $R^{11b}$ is absent if J is N, $R^{11c}$ is absent if L is N; or $R^{11d}$ is absent if K is N;
Each of $R^{12a}$, $R^{12b}$, and $R^{12c}$ is independently selected from H, F, Cl, ($C_1$-$C_4$)alkyl, or ($C_1$-$C_4$)alkoxy;
$R^{13}$ is selected from H, F, ($C_1$-$C_4$)alkyl, and —O—($C_1$-$C_4$) alkyl; and
q is 1 or 2.

50. The compound of claim 49, wherein G is $CR^{11a}$; J is $CR^{11b}$; L is $CR^{11c}$; and K is $CR^{11d}$.

51. The compound of claim 49, wherein $R^3$ is selected from —OH, —O($C_1$-$C_2$)alkyl, or —S($C_1$-$C_2$)alkyl.

52. The compound of claim 49, wherein $R^2$ is selected from F, $CF_3$, or ($C_1$-$C_6$)alkoxy.

53. The compound of claim 49, wherein each of $R^{11}$, $R^{11b}$, $R^{11c}$, $R^{11d}$, $R^{12a}$, $R^{12b}$, and $R^{12c}$ is H.

54. The compound of claim 49, wherein q is 1.

55. The compound of claim 49, wherein $R^{1a}$ is H.

56. The compound of claim 49, wherein W, Y, and Z are all C—H.

57. The compound of claim 49, wherein A is selected from ($C_3$-$C_{10}$)alkyl or ($C_4$-$C_{10}$)alkenyl.

58. The compound of claim 49, wherein A is a group of formula A'

where the wavy line indicates the point of attachment; and
$R^4$, $R^5$, and $R^6$ are independently selected from H, F, ($C_1$-$C_4$)alkyl, wherein at least two of $R^4$, $R^5$, and $R^6$ are other than H; or two or three of $R^4$, $R^5$, and $R^6$ join together to form an optionally substituted saturated or partially unsaturated 3-8 membered monocyclic or bicyclic ring.

59. The compound of claim 49, wherein $R^2$ is F.

60. The compound of claim 49, wherein $R^3$ is methoxy.

61. The compound of claim 49, wherein X is O.

62. The compound of claim 49, wherein $R^7$ and $R^8$ are both H.

63. The compound of claim 49, wherein $R^9$ and $R^{10}$ are both H.

64. The compound of claim 49, wherein $R^1$ is a ($C_1$-$C_4$) alkyl.

65. The compound of claim 64, wherein $R^1$ is a methyl, an ethyl or a propyl.

66. The compound of claim 49, wherein $R^1$ is a cyclopropyl or a cyclobutyl group that is optionally substituted.

67. The compound of claim 49, wherein $R^1$ is a ($C_2$-$C_4$) alkenyl.

68. The compound of claim 49, wherein G is $CR^{11a}$; J is $CR^{11b}$; L is $CR^{11c}$; K is $CR^{11d}$; $R^{11a}$, $R^{11b}$, $R^{11c}$, $R^{11d}$, $R^{12a}$, $R^{12b}$, and $R^{12c}$ are all H; $R^{1a}$ is H; W is C—H; Y, is C—H; Z is C—H; $R^2$ is F; $R^3$ is methoxy; $R^7$ is H; $R^8$ is H; $R^9$ is H; $R^{10}$ is H; X is O, and q is 1.

69. The compound of claim 68, wherein A is a branched chain ($C_4$-$C_8$)alkyl group.

70. The compound of claim 69, wherein A is a t-butyl group.

71. The compound of claim 49, wherein A is an optionally substituted ($C_5$-$C_7$)cycloalkyl group or an optionally substituted ($C_5$-$C_7$)cycloalkenyl group.

72. The compound of claim 49, wherein the ($C_5$-$C_7$)cycloalkyl group or the ($C_5$-$C_7$)cycloalkenyl group is substituted with 1, 2, 3, or 4 methyl groups.

73. The compound of claim 49, wherein A has the formula

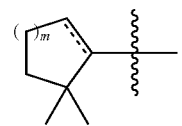

wherein m is 1, 2, or 3, and the dashed line indicates a single or double bond.

74. The compound of claim 73, wherein A has the formula

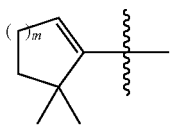

wherein m is 1, 2, or 3.

75. The compound of claim 49, wherein A is —O—($C_3$-$C_{10}$)alkyl or —O—($C_3$-$C_{10}$)alkenyl.

76. The compound of claim 49, wherein the compound has the formula II

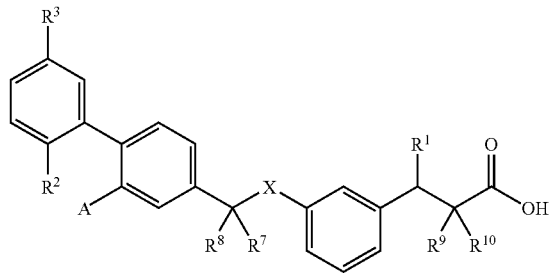

or a pharmaceutically acceptable salt, $C_1$-$C_6$ alkyl ester, or a mixture thereof.

77. The compound of claim 49, wherein G is $CR^{11a}$; J is $CR^{11b}$; L is $CR^{11c}$; K is $CR^{11d}$; $R^{11a}$, $R^{11b}$, $R^{11c}$, and $R^{11d}$ are H; $R^{1a}$ is H; W is C—H; Z is C—H; $R^2$ is F; $R^3$ is methoxy; $R^7$ is H; $R^8$ is H; $R^9$ is H; $R^{10}$ is H; X is O; q is 1; and two of $R^{12a}$, $R^{12b}$, and $R^{12c}$ are H and the other of $R^{12a}$, $R^{12b}$, and $R^{12c}$ is F.

78. The compound of claim 49, wherein the compound has the formula III

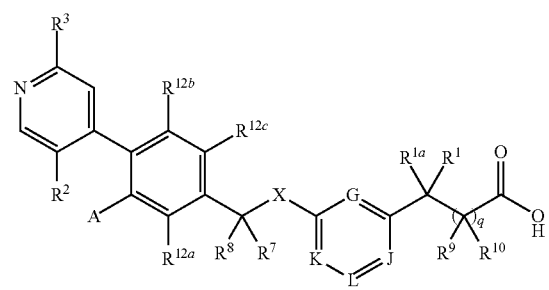

or a pharmaceutically acceptable salt, stereoisomer, $C_1$-$C_6$ alkyl ester, or a mixture thereof.

79. The compound of claim 78, wherein the compound has the formula III'

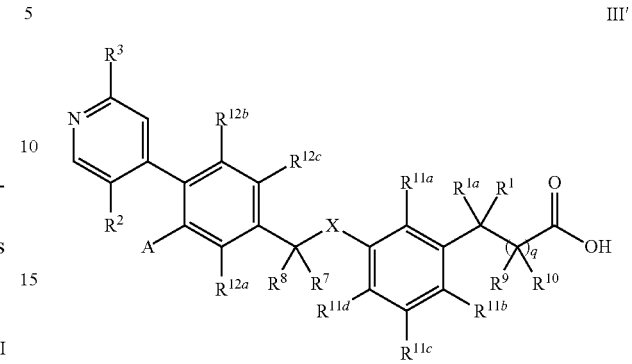

or a pharmaceutically acceptable salt, stereoisomer, $C_1$-$C_6$ alkyl ester, or a mixture thereof.

80. The compound of claim 78, wherein the compound has the formula III"

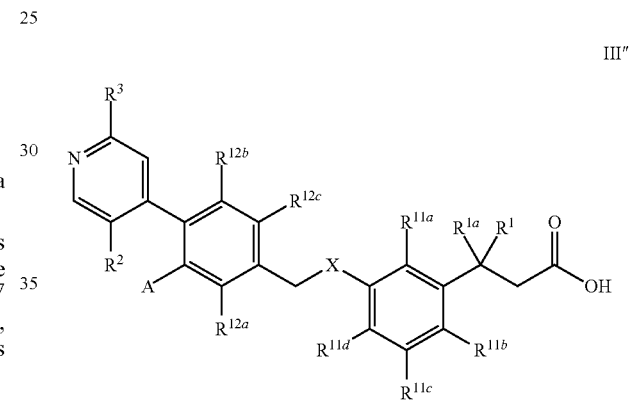

or a pharmaceutically acceptable salt, stereoisomer, $C_1$-$C_6$ alkyl ester, or a mixture thereof.

81. The compound of claim 80, wherein $R^3$ is methoxy.

82. The compound of claim 81, wherein $R^2$ is F.

83. The compound of claim 82, wherein $R^{11a}$ is F, $R^{11b}$ is H, $R^{11c}$ is H, and $R^{11d}$ is H.

84. The compound of claim 82, wherein $R^{12c}$ is F.

85. The compound of claim 82, wherein $R^{12a}$ is H and $R^{12b}$ is H.

86. The compound of claim 49, wherein the compound is a salt.

87. A pharmaceutical composition, comprising: a pharmaceutically acceptable carrier, diluent, or excipient, and the compound of claim 49.

88. A method for treating a disease or condition, comprising: administering to a subject in need thereof, a therapeutically effective amount of the compound of claim 49, wherein the disease or condition is selected from the group consisting of type II diabetes and hyperglycemia.

89. The method of claim 88, wherein the disease or condition is type II diabetes.

90. The method of claim 88, wherein the compound is administered in combination with a second therapeutic agent.

91. The method of claim 90, wherein the second therapeutic agent is metformin, is a thiazolidinedione, or is a DPP-IV inhibitor.

92. The compound of claim 49, wherein the compound does not displace a compound of the following formula that is bound to the GPR40 receptor:

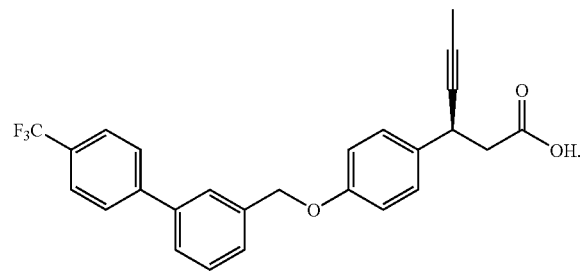

93. A method for increasing GLP-1 levels in the blood plasma of a subject, comprising: administering the compound of claim 49 to the subject.

94. The method of claim 93, wherein the subject is a diabetic patient.

95. A method for increasing GLP-1 levels in the blood plasma of a subject, comprising: administering the compound of claim 1 to the subject.

96. The method of claim 95, wherein the subject is a diabetic patient.

* * * * *